US012465643B2

(12) United States Patent
Koltun et al.

(10) Patent No.: US 12,465,643 B2

(45) **Date of Patent: *Nov. 11, 2025**

(54) RAS INHIBITORS

(71) Applicant: Revolution Medicines, Inc., Redwood City, CA (US)

(72) Inventors: Elena S. Koltun, Foster City, CA (US); James Cregg, Belmont, CA (US); Yang Liu, Foster City, CA (US); Adrian L. Gill, Atherton, CA (US)

(73) Assignee: Revolution Medicines, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/068,133

(22) Filed: Mar. 3, 2025

(65) Prior Publication Data

US 2025/0242029 A1 Jul. 31, 2025

Related U.S. Application Data

(63) Continuation of application No. 18/188,966, filed on Mar. 23, 2023, now Pat. No. 12,280,113, which is a continuation of application No. 17/476,269, filed on Sep. 15, 2021, now Pat. No. 11,690,915.

(60) Provisional application No. 63/192,775, filed on May 25, 2021, provisional application No. 63/184,412, filed on May 5, 2021, provisional application No. 63/129,231, filed on Dec. 22, 2020, provisional application No. 63/078,802, filed on Sep. 15, 2020.

(51) Int. Cl.

| | |
|---|---|
| ***A61K 45/06*** | (2006.01) |
| ***A61P 35/00*** | (2006.01) |
| ***C07D 417/14*** | (2006.01) |

(52) U.S. Cl.

CPC .............. *A61K 45/06* (2013.01); *A61P 35/00* (2018.01); *C07D 417/14* (2013.01)

(58) Field of Classification Search

CPC .. A61K 45/06; A61K 31/5025; C07D 47/122; C07D 487/12; C07D 519/00; C07D 513/22; C07D 498/18; C07D 498/22

USPC .......................................................... 514/248

See application file for complete search history.

(56) References Cited

U.S. PATENT DOCUMENTS

| | | | |
|---|---|---|---|
| 6,183,965 | B1 | 2/2001 | Verdine et al. |
| 6,372,712 | B1 | 4/2002 | Briesewitz et al. |
| 6,686,454 | B1 | 2/2004 | Yatscoff et al. |
| 6,713,607 | B2 | 3/2004 | Caggiano et al. |
| 7,220,552 | B1 | 5/2007 | Crabtree et al. |
| 7,396,660 | B2 | 7/2008 | Huang et al. |
| 7,851,183 | B2 | 12/2010 | Zotchev et al. |
| 8,664,186 | B2 | 3/2014 | Aigle et al. |
| 9,119,853 | B2 | 9/2015 | Moss et al. |
| 9,211,291 | B2 | 12/2015 | Berkenblit et al. |
| 9,250,237 | B2 | 2/2016 | Liu et al. |
| 9,260,484 | B2 | 2/2016 | Briesewitz et al. |
| 9,428,845 | B1 | 8/2016 | Verdine et al. |
| 9,989,535 | B2 | 6/2018 | Verdine et al. |
| 10,023,588 | B2 | 7/2018 | Ostrem et al. |
| 10,039,839 | B2 | 8/2018 | Verdine et al. |
| 10,203,323 | B2 | 2/2019 | Verdine et al. |
| 10,466,249 | B2 | 11/2019 | Verdine et al. |
| 10,533,016 | B2 | 1/2020 | Verdine et al. |
| 10,800,787 | B2 | 10/2020 | Bodhuri et al. |
| 10,948,495 | B2 | 3/2021 | Verdine et al. |
| 10,989,710 | B2 | 4/2021 | Verdine et al. |
| 11,008,334 | B2 | 5/2021 | Ostrem et al. |
| 11,059,830 | B2 | 7/2021 | Verdine et al. |
| 11,566,007 | B2 | 1/2023 | Koltun et al. |
| 11,608,346 | B2 | 3/2023 | Koltun et al. |
| 11,644,460 | B2 | 5/2023 | Verdine et al. |
| 11,690,915 | B2 | 7/2023 | Aay et al. |
| 11,739,074 | B2 | 8/2023 | Aggen et al. |
| 11,952,352 | B2 | 4/2024 | Gill et al. |
| 11,987,590 | B2 | 5/2024 | Verdine et al. |
| 12,202,845 | B2 | 1/2025 | Knox et al. |
| 12,252,497 | B2 | 3/2025 | Burnett et al. |
| 2002/0110874 | A1 | 8/2002 | Khosla et al. |
| 2002/0147133 | A1 | 10/2002 | Briesewitz et al. |
| 2003/0153053 | A1 | 8/2003 | Reid |
| 2003/0175901 | A1 | 9/2003 | Reeves et al. |
| 2004/0087496 | A1 | 5/2004 | Kim et al. |
| 2004/0157768 | A1 | 8/2004 | Or et al. |
| 2005/0233431 | A1 | 10/2005 | Ashley et al. |
| 2007/0203168 | A1 | 8/2007 | Zhao |
| 2007/0218502 | A1 | 9/2007 | Hahn et al. |
| 2007/0265333 | A1 | 11/2007 | Fu et al. |
| 2011/0117606 | A1 | 5/2011 | Jorgensen et al. |
| 2012/0208720 | A1 | 8/2012 | Kashiwagi et al. |
| 2012/0270800 | A1 | 10/2012 | Verdine et al. |
| 2013/0072439 | A1 | 3/2013 | Nash et al. |
| 2013/0344030 | A1 | 12/2013 | Steadman et al. |

(Continued)

FOREIGN PATENT DOCUMENTS

| | | | |
|---|---|---|---|
| EP | 0194972 | A2 | 9/1986 |
| EP | 0393934 | A1 | 10/1990 |

(Continued)

OTHER PUBLICATIONS

"On Target to Outsmart Cancer™," Revolution Medicines (Jan. 11, 2022) (33 pages).

(Continued)

*Primary Examiner* — Yevgeny Valenrod

(74) *Attorney, Agent, or Firm* — Clark & Elbing LLP

(57) ABSTRACT

The disclosure features macrocyclic compounds, and pharmaceutical compositions and protein complexes thereof, capable of inhibiting Ras proteins, and their uses in the treatment of cancers.

2 Claims, 39 Drawing Sheets

Specification includes a Sequence Listing.

(56) References Cited

U.S. PATENT DOCUMENTS

| | | | |
|---|---|---|---|
| 2014/0256717 | A1 | 9/2014 | Fernandez et al. |
| 2014/0316104 | A1 | 10/2014 | Fischer et al. |
| 2015/0250896 | A1 | 9/2015 | Zhao |
| 2015/0307855 | A1 | 10/2015 | Yuzawa et al. |
| 2016/0083373 | A1 | 3/2016 | Xu |
| 2016/0296528 | A1 | 10/2016 | Pastor Fernández et al. |
| 2017/0190734 | A1 | 7/2017 | Aciro et al. |
| 2018/0318434 | A1 | 11/2018 | Verdine et al. |
| 2020/0197391 | A1 | 6/2020 | Jin et al. |
| 2020/0199102 | A1 | 6/2020 | Mulvihill et al. |
| 2021/0285955 | A1 | 9/2021 | Mulvihill et al. |
| 2021/0405060 | A1 | 12/2021 | Verdine et al. |
| 2022/0143202 | A1 | 5/2022 | Verdine et al. |
| 2023/0002412 | A1 | 1/2023 | Canales et al. |
| 2023/0100838 | A1 | 3/2023 | Pitzen et al. |
| 2023/0106174 | A1 | 4/2023 | Koltun et al. |
| 2023/0212152 | A1 | 7/2023 | Arnold et al. |
| 2023/0226186 | A1 | 7/2023 | Aay et al. |
| 2023/0233569 | A1 | 7/2023 | Singh et al. |
| 2023/0374035 | A1 | 11/2023 | Koltun et al. |
| 2024/0084305 | A1 | 3/2024 | Liu et al. |
| 2024/0108630 | A1 | 4/2024 | Corcoran et al. |
| 2024/0139185 | A1 | 5/2024 | Jin et al. |
| 2024/0262847 | A1 | 8/2024 | Burnett et al. |
| 2024/0277796 | A1 | 8/2024 | Seamon |
| 2024/0352036 | A1 | 10/2024 | Li et al. |
| 2024/0352038 | A1 | 10/2024 | Li et al. |
| 2024/0368190 | A1 | 11/2024 | Li et al. |
| 2024/0383920 | A1 | 11/2024 | Li et al. |
| 2024/0400523 | A1 | 12/2024 | Koltun et al. |
| 2024/0426833 | A1 | 12/2024 | Mulvihill et al. |
| 2025/0009753 | A1 | 1/2025 | Blaj et al. |
| 2025/0041295 | A1 | 2/2025 | Jiang et al. |
| 2025/0049810 | A1 | 2/2025 | Jiang et al. |
| 2025/0051306 | A1 | 2/2025 | Aggen et al. |
| 2025/0074923 | A1 | 3/2025 | Knox et al. |
| 2025/0076289 | A1 | 3/2025 | Verdine et al. |
| 2025/0085291 | A1 | 3/2025 | Verdine et al. |
| 2025/0101031 | A1 | 3/2025 | Verdine et al. |
| 2025/0115551 | A1 | 4/2025 | Li et al. |
| 2025/0121077 | A1 | 4/2025 | Verdine et al. |
| 2025/0129097 | A1 | 4/2025 | Cregg et al. |

FOREIGN PATENT DOCUMENTS

| | | | |
|---|---|---|---|
| EP | 0562853 | A1 | 9/1993 |
| KR | 10-2009-0041971 | A | 4/2009 |
| WO | WO-86/02080 | A1 | 4/1986 |
| WO | WO-95/32294 | A1 | 11/1995 |
| WO | WO-96/20216 | A1 | 7/1996 |
| WO | WO-96/41807 | A1 | 12/1996 |
| WO | WO-98/01546 | A2 | 1/1998 |
| WO | WO-98/07743 | A1 | 2/1998 |
| WO | WO-98/12217 | A1 | 3/1998 |
| WO | WO-00/47724 | A2 | 8/2000 |
| WO | WO-01/36460 | A2 | 5/2001 |
| WO | WO-01/36612 | A1 | 5/2001 |
| WO | WO-01/90070 | A2 | 11/2001 |
| WO | WO-03/033010 | A1 | 4/2003 |
| WO | WO-2008/069824 | A2 | 6/2008 |
| WO | WO-2010/031185 | A1 | 3/2010 |
| WO | WO-2010/034243 | A1 | 4/2010 |
| WO | WO-2010/088573 | A1 | 8/2010 |
| WO | WO-2012/078915 | A1 | 6/2012 |
| WO | WO-2012/131371 | A1 | 10/2012 |
| WO | WO-2012/131377 | A1 | 10/2012 |
| WO | WO-2013/001310 | A1 | 1/2013 |
| WO | WO-2013/022818 | A1 | 2/2013 |
| WO | WO-2013/185090 | A1 | 12/2013 |
| WO | WO-2013/185103 | A1 | 12/2013 |
| WO | WO-2014/009774 | A1 | 1/2014 |
| WO | WO-2014/121942 | A1 | 8/2014 |
| WO | WO-2014/169167 | A1 | 10/2014 |
| WO | WO-2014/176488 | A1 | 10/2014 |
| WO | WO-2014/187959 | A2 | 11/2014 |
| WO | WO-2015/132784 | A1 | 9/2015 |
| WO | WO-2016/008011 | A1 | 1/2016 |
| WO | WO-2016/033486 | A1 | 3/2016 |
| WO | WO-2016/160362 | A1 | 10/2016 |
| WO | WO-2017/058768 | A1 | 4/2017 |
| WO | WO-2017/085198 | A1 | 5/2017 |
| WO | WO-2018/081592 | A2 | 5/2018 |
| WO | WO-2018/091634 | A1 | 5/2018 |
| WO | WO-2018/217651 | A1 | 11/2018 |
| WO | WO-2020/101736 | A1 | 5/2020 |
| WO | WO-2020/106640 | A1 | 5/2020 |
| WO | WO-2021/052499 | A1 | 3/2021 |
| WO | WO-2021/086833 | A1 | 5/2021 |
| WO | WO-2022/060583 | A1 | 3/2022 |
| WO | WO-2022/137085 | A1 | 6/2022 |
| WO | WO-2022/137174 | A1 | 6/2022 |
| WO | WO-2022/139304 | A1 | 6/2022 |
| WO | WO-2022/217053 | A1 | 10/2022 |
| WO | WO-2022/235725 | A1 | 11/2022 |
| WO | WO-2022/235945 | A1 | 11/2022 |
| WO | WO-2022/271658 | A1 | 12/2022 |
| WO | WO-2023/015559 | A1 | 2/2023 |
| WO | WO-2023/025832 | A1 | 3/2023 |
| WO | WO-2023/133543 | A1 | 7/2023 |
| WO | WO-2023/240263 | A1 | 12/2023 |
| WO | WO-2024/081363 | A1 | 4/2024 |
| WO | WO-2024/102421 | A2 | 5/2024 |
| WO | WO-2024/206858 | A1 | 10/2024 |
| WO | WO-2024/211663 | A1 | 10/2024 |
| WO | WO-2024/211712 | A1 | 10/2024 |
| WO | WO-2024/229406 | A1 | 11/2024 |

OTHER PUBLICATIONS

"Registration No. 333-235968: Amendment No. 2 to Form S-1 Registration Statement Under The Securities Act of 1933 for Revolution Medicines, Inc.," United States Securities and Exchange Commission, Washington, D.C., 20549, dated Feb. 11, 2020 (354 pages).

"SMART™ Drugs: Engineering Nature's Solution to the Undruggable Target Challenge," WarpDrive Bio, 2016, available <http://www.warpdrivebio.com/docs/Warp%20Drive%20Bio_SMART%20Drugs%20Platform_2016.pdf> (31 pages).

"*Streptomyces iranensis* regulatory protein LuxR," EBI Database Accession No. CDR13506 (2014) (2 pages).

"*Streptomyces rapamycinicus* NRRL 5491 hypothetical protein," EBI Database Accession No. AGP59507 (2014) (2 pages).

"Substructure Search Report on Specifically Substituted Macrocycles—Substances Only," prepared by Science IP, dated Dec. 17, 2014 (6177 pages).

"Translating Frontier Oncology Targets to Outsmart Cancer™," Corporate Overview Q3-2020, Revolution Medicines, Aug. 20, 2020 (35 pages).

Aebi et al., "Synthesis, Conformation, and Immunosuppressive Activities of Three Analogues of Cyclosporin A Modified in the 1-Position," J Med Chem. 33(3):999-1009 (1990).

Allain et al., "Cyclophilin B mediates cyclosporin A incorporation in human blood T-lymphocytes through the specific binding of complexed drug to the cell surface," Biochem J. 317 (Pt 2):565-70 (1996).

Andrei et al., "Stabilization of protein-protein interactions in drug discovery," Expert Opin Drug Discov. 12(9):925-40 (2017) (17 pages).

Antunes et al., "A mutational analysis defines Vibrio fischeri LuxR binding sites," J Bacteriol. 190(13):4392-7 (2008).

Araujo et al. "Mechanisms of response and tolerance to active RAS inhibition in KRAS-mutant NSCLC," Cancer Discov. (Jul. 2024) (87 pages).

Archibald et al., "Discovery and Evaluation of Potent, Cysteine-based alpha4beta1 Integrin Antagonists," Bioorg Med Chem Lett. 10(9):993-995 (2000).

Baillie, "Targeted Covalent Inhibitors for Drug Design," Covalent Inhibitor Drug Discovery & Development Symposium PBSS, Feb. 7, Foster City, California. (2019) (16 pages).

(56) References Cited

OTHER PUBLICATIONS

Banaszynski et al., "Characterization of the FKBP.rapamycin.FRB ternary complex," J Am Chem Soc. 127(13):4715-21 (2005).
Banteli et al., "A synthesis of the C1—N12 tripeptide fragment of sanglifehrin A," Tetrahedron Letters. 40(11):2109-2112 (Mar. 12, 1999).
Baranasic et al., "Draft Genome Sequence of *Streptomyces rapamycinicus* Strain NRRL 5491, the Producer of the Immunosuppressant Rapamycin," Genome Announc. 1(4):e00581-13 (2013) (2 pages).
Bastin et al., "Salt selection and optimisation procedures for pharmaceutical new chemical entities," Org Process Res Dev 4(5):427-35 (2000).
Bayle et al., "Rapamycin analogs with differential binding specificity permit orthogonal control of protein activity," Chem Biol. 13(1):99-107 (2006).
Bender et al., "Periodate Oxidation of alpha-Keto gamma-Lactams. Enol Oxidation and beta-Lactam Formation. Mechanism of Periodate Hydroxylation Reactions," J Org Chem. 43(17):3354-3362 (1978).
Benjamin et al., "Rapamycin passes the torch: a new generation of mTOR inhibitors," Nat Rev Drug Discov. 10(11):868-80 (2011).
Bhuyan et al., "Antioxidant activity of peptide-based angiotensin converting enzyme inhibitors," Org Biomol Chem. 10(11):2237-47 (2012).
Blodgett et al., "Unusual transformations in the biosynthesis of the antibiotic phosphinothricin tripeptide," Nat Chem Biol. 3(8):480-5 (2007).
Braun et al., "A bifunctional molecule that displays context-dependent cellular activity," J Am Chem Soc. 125(25):7575-80 (Jun. 2003).
Briesewitz et al., "Affinity modulation of small-molecule ligands by borrowing endogenous protein surfaces," Proc Natl Acad Sci U.S.A. 96(5):1953-8 (1999).
Bruce, "In vivo protein complex topologies: sights through a cross-linking lens," Proteomics. 12(10):1565-75 (2012).
Burgess et al., "Controlled translocation of palladium(II) within a 22 ring atom macrocyclic ligand," Dalton Trans. 43(45):17006-16 (2014) (12 pages).
Chaurasia et al., "Molecular insights into the stabilization of protein-protein interactions with small molecule: The FKBP12-rapamycin-FRB case study," Chem Phys Lett. 587:68-74 (2013).
Che et al., "Inducing protein-protein interactions with molecular glues," Bioorg Med Chem Lett. 28(15):2585-92 (Aug. 2018) (18 pages).
Chen et al., "Adaptive and Reversible Resistance to Kras Inhibition in Pancreatic Cancer Cells," Cancer Res. 78(4): 985-1002 (19 pages) (Feb. 2018).
Chen et al., "Emerging strategies to target RAS signaling in human cancer therapy," J Hematol Oncol. 14(1):116 (Jul. 23, 2021) (23 pages).
Chevalier et al., "Straightforward synthesis of bioconjugatable azo dyes. Part 1: Black Hole Quencher-1 (BHQ-1) scaffold," Tetrahedron Lett. 55(50):6759-63 (2014).
Choi et al., "Challenges in Ras therapeutics in pancreatic cancer," Semin Cancer Biol. 54: 101-108 (8 pages) (Feb. 2019).
Ding et al., "Insights into Bacterial 6-Methylsalicylic Acid Synthase and Its Engineering to Orsellinic Acid Synthase for Spirotetronate Generation," Chem Biol. 17(5):495-503 (2010).
Doak et al., "Cyclophilin Succumbs to a Macrocyclic Chameleon," J Med Chem. 61(21):9469-9472 (Nov. 2018).
Dyson et al., Chemistry of synthetic medicines. May's Chemistry of Synthetic Drugs, Fifth Edition. Moscow: Mir. pp. 12-19 (1964) (9 Pages).
Eberle et al., "Preparation of Functionalized Ethers of Cyclosporin A," Tetrahedron Lett. 35(35):6477-6480 (1994).
Findlay et al., "The structure of demethoxyrapamycin," Can J Chem. 60:2046-7 (1982).
Garg et al., "Elucidation of the Cryptic Epimerase Activity of Redox-Inactive Ketoreductase Domains from Modular Polyketide Synthases by Tandem Equilibrium Isotope Exchange," J Am Chem Soc. 136(29):10190-10193 (2014).
Gill et al., "Discovery of Small Molecule Inhibitors of the Oncogenic, GTP-Bound (ON) Form of KRASG12C and KRASG13C," Revolution Medicines (Sep. 2019) (1 page).
Gill, "Discovery of Small Molecule Inhibitors of Oncogenic Mutants of RAS," Revolution Medicines, ACS, Apr. 2, Orlando (2019) (23 pages).
Gordon et al., "A SARS-CoV-2 Protein Interaction Map Reveals Targets for Drug Repurposing," Nature. 583(7816):459-68 (Apr. 2020).
Guerra et al., "LAL regulators SCO0877 and SCO7173 as pleiotropic modulators of phosphate starvation response and actinorhodin biosynthesis in *Streptomyces coelicolor*," PLoS One. 7(2):e31475 (2012) (11 pages).
Guo et al., "Rapamycin-inspired macrocycles with new target specificity," Nat Chem. 11(3):254-263 (Mar. 2019) (13 pages).
Halford, "Covalent drugs go from fringe field to fashionable endeavor: Designing molecules that make bonds with their biological targets is in vogue," Chemical and Engineering News, 98(43) (Nov. 2020) (6 pages).
Hansson et al., "Bioengineering and Semisynthesis of an Optimized Cyclophilin Inhibitor for Treatment of Chronic Viral Infection," Chem Biol. 22(2):285-92 (2015) (24 pages).
He et al., "The LuxR family members GdmRI and GdmRII are positive regulators of geldanamycin biosynthesis in *Streptomyces hygroscopicus* 17997," Arch Microbiol. 189(5):501-10 (2008).
Hoffman, "The origins and evolution of "controlled" drug delivery systems," J Control Release. 132(3):153-63 (Dec. 2008) (Epub Aug. 2008).
Holderfield et al. "Concurrent inhibition of oncogenic and wild-type RAS-GTP for cancer therapy," Nature. 629(8013):919-926 (May 2024) (33 pages) (supplementary information included).
Hong et al., "Evidence for an iterative module in chain elongation on the azalomycin polyketide synthase," Beilstein J Org Chem. 12:2164-2172 (2016).
Horn et al., "Draft Genome Sequence of *Streptomyces iranensis*," Genome Announc. 2(4):e00616-14 (2014) (2 Pages).
Horton et al., "Engineering hybrid genes without the use of restriction enzymes: gene splicing by overlap extension," Gene. 77(1):61-8 (1989).
Hosted et al., "Use of rpsL for dominance selection and gene replacement in *Streptomyces roseosporus*," J Bacteriol. 179(1): 180-6 (1997).
Huang et al., "Conjugation to Albumin-Binding Molecule Tags as a Strategy to Improve Both Efficacy and Pharmacokinetic Properties of the Complement Inhibitor Compstatin," ChemMedChem. 9(10):2223-6 (2014).
Huang et al., "Enhanced rapamycin production in *Streptomyces hygroscopicus* by integrative expression of aveR, a LAL family transcriptional regulator," World J Microbiol Biotechnol. 27:2103-9 (2011).
Hubler et al., "Synthetic routes to NEtXaa4-cyclosporin A derivatives as potential anti-HIV I drugs," Tetrahedron Lett. 41:7193-6 (2000).
International Search Report and Written Opinion for International Patent Application No. PCT/US2021/050454, mailed Dec. 23, 2021 (13 pages).
International Search Report and Written Opinion for International Patent Application No. PCT/US2022/027770, mailed Aug. 12, 2022 (15 pages).
International Search Report and Written Opinion for International Patent Application No. PCT/US2022/027778, mailed Jul. 4, 2022 (12 pages).
Ishizawa et al., "TRAP display: a high-speed selection method for the generation of functional polypeptides," J Am Chem. 135(14):5433-40 (2013).
Janes et al., "Targeting KRAS Mutant Cancers with a Covalent G12C-Specific Inhibitor," Cell., 172(3):578-589.e17 (Jan. 2018) (30 pages).
Jarvis, "Have drug hunters finally cracked KRas?—After decades of failures, researchers see promise in fresh approaches to developing drugs that block cancer's toughest target," Chemical & Engineering

(56) References Cited

OTHER PUBLICATIONS

News. 94(23):28-33. <https://cen.acs.org/articles/94/123/drug-hunters-finally-cracked-KRas.html>, retrieved on Oct. 14, 2018 (2016) (9 pages).
Jiang et al. "Translational and Therapeutic Evaluation of RAS-GTP Inhibition by RMC-6236 in RAS-Driven Cancers," Cancer Discov. 14(6):994-1017 (Jun. 2024) (39 pages) (supplemental information included).
Kawakami et al., "In vitro selection of multiple libraries created by genetic code reprogramming to discover macrocyclic peptides that antagonize VEGFR2 activity in living cells," ACS Chem Biol. 8(6):1205-14 (2013).
Kelsey, "Approaches to Inhibiting RAS-Driven Tumors Beyond KRASG12C," RAS Targeted Drug Development, Revolution Medicines, Sep. 16 2020 (24 pages).
Kelsey, "Discovery and Development of RAS(ON) Inhibitors Beyond KRASG12C," AACR-NCI-EORTC Virtual International Conference on Molecular Targets and Cancer Therapeutics, Oct. 7-10, Redwood City, California (Oct. 2021) (24 pages).
Kendrew et al., "Recombinant strains for the enhanced production of bioengineered rapalogs," Metab Eng. 15:167-73 (2013).
Koltun et al., "Drugging the RAS(ON) Form of Diverse Oncogenic RAS Mutations," 21st RSC / SCI Medicinal Chemistry Symposium, Sep. 15, Cambridge, Massachusetts (Sep. 2021) (35 Pages).
Koltun et al., "First-in-class, orally bioavailable KRASG12V (ON) tri-complex inhibitors, as single agents and in combinations, drive profound anti-tumor activity in preclinical models of KRASG12V mutant cancers," American Association of Cancer Research, Meeting Abstract (Jul. 1, 2021) (1page).
Koltun et al., "First-in-class, orally bioavailable KRASG12V(ON)/RASMULTI(ON) tri-complex inhibitors, as single agents and in combinations, drive profound anti-tumor activity in preclinical models of KRASG12V mutant cancers," American Association of Cancer Research Annual Meeting 2021, Virtual Meeting I ; Apr. 10-15, 2021. Poster 1260 (Apr. 10, 2021) (1 page).
Kuhn et al., "Synthesis of Functional Ras Lipoproteins and Fluorescent Derivatives," J Am Chem Soc. 123(6):1023-35 (2001).
Kummerer, "Pharmaceuticals in the Environment," Annual Review of Environment and Resources. 35:57-75 (Nov. 2010) (Epub Aug. 18, 2010).
Kuramochi et al., "Identification of Small Molecule Binding Molecules by Affinity Purification Using a Specific Ligand Immobilized on PEGA Resin," Bioconjug Chem. 19(12):2417-26 (2008).
Laureti et al., "Identification of a bioactive 51-membered macrolide complex by activation of a silent polyketide synthase in *Streptomyces ambofaciens*," Proc Natl Acad Sci USA. 108(15):6258-63 (2011).
Laureti et al., Supporting Material for "Identification of a bioactive 51-membered macrolide complex by activation of a silent polyketide synthase in *Streptomyces ambofaciens*," Proc Natl Acad Sci U.S.A. 108(15):6258-63 (2011), accessed via <https://www.pnas.org/content/suppl/2011/03/24/1019077108.DCSupplemental> (41 pages).
Lee et al., "Current implications of cyclophilins in human cancers," J Exp Clin Cancer Res. 29(1):97 (2010) (6 pages).
Leskiw et al., "TTA codons in some genes prevent their expression in a class of developmental, antibiotic-negative, *Streptomyces* mutants," Proc Natl Acad Sci USA. 88(6):2461-5 (1991).
Li et al., "A simple and efficient route to the FKBP-binding domain from rapamycin," available in PMC Sep. 28, 2012, published in final edited form as: Tetrahedron Lett. 52(39):5070-2 (2011) (7 pages).
Luengo et al., "Structure-activity studies of rapamycin analogs: evidence that the C-7 methoxy group is part of the effector domain and positioned at the FKBP12-FRAP interface," Chem Biol. 2(7):471-81 (1995).
Mackman et al., "Discovery of a Potent and Orally Bioavailable Cyclophilin Inhibitor Derived from the Sanglifehrin Macrocycle," J Med Chem. 61(21):9473-9499 ( Aug. 2018).
Majumder et al. "Interaction of aryl hydrocarbon receptor-interacting protein-like 1 with the farnesyl moiety," J Biol Chem. 288(29):21320-21328 (2013).
McGregor et al., "Expanding the Scope of Electrophiles Capable of Targeting K-Ras Oncogenes," Biochemistry. 56(25):3178-3183 (2017).
Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012) (10 pages).
Mo et al., "Interspecies Complementation of the LuxR Family Pathway-Specific Regulator Involved in Macrolide Biosynthesis," J Microbiol Biotechnol. 26(1):66-71 (2016).
Moore et al., "RAS-targeted therapies: is the undruggable drugged?" available in PMC Feb. 1, 2021, published in final edited form as: Nat Rev Drug Discov. 19(8):533-52 (Aug. 2020) (43 pages).
Mullard, "Cracking KRAS," Nat Rev Drug Discov. 18(12):887-91 (Nov. 2019) (14 pages).
Murphy et al., "Isolation and characterisation of amphotericin B analogues and truncated polyketide intermediates produced by genetic engineering of *Streptomyces nodosus*," Org Biomol Chem. 8(16):3758-70 (2010).
Ochi et al., "New strategies for drug discovery: activation of silent or weakly expressed microbial gene clusters," Appl Microbiol Biotechnol. 97(1):87-98 (2013).
Ostrem et al., "Direct small-molecule inhibitors of KRAS: from structural insights to mechanism-based design," Nat Rev Drug Discov. 15(11):771-785 (2016).
Ostrem et al., "K-Ras(G12C) inhibitors allosterically control GTP affinity and effector interactions," Nature. 503(7477):548-51 (2013) (14 pages).
Papageorgiou et al., "Improved binding affinity for cyclophilin A by a cyclosporin derivative singly modified at its effector domain," J Med Chem. 37(22):3674-6 (1994).
Pei et al., "Targeting Ras with Macromolecules," Cold Spring Harb Perspect Med. 8(3):a031476 (Mar. 2018) (14 pages).
Pfeifer et al., "Biosynthesis of complex polyketides in a metabolically engineered strain of *E. coli*," Science. 291(5509):1790-2 (2001) (4 pages).
Pollock et al., "Development of Inhibitors of the Activated Form of KRASG12C," AACR Targeting RAS-Driven Cancers, Dec. 9-12, San Diego, California (Dec. 2018) (Abstract Included) (2 pages).
Power et al., "Engineered Synthesis of 7-Oxo- and 15-Deoxy-15-Oxo-Amphotericins: Insights into Structure-Activity Relationships in Polyene Antibiotics," Chem Biol. 15(1):78-86 (2008).
PubChem CID 130196149, <https://pubchem.ncbi.nlm.nih.gov/compound/130196149>, retrieved on Apr. 1, 2020 (10 pages).
Quesniaux et al., "Cyclophilin binds to the region of cyclosporine involved in its immunosuppressive activity," Eur J Immunol. 17(9):1359-65 (1987).
Quesniaux et al., "Study of the conformation of cyclosporine in aqueous medium by means of monoclonal antibodies," Int J Pept Protein Res. 31(2):173-85 (1988).
Ranganathan et al., "Knowledge-based design of bimodular and trimodular polyketide synthases based on domain and module swaps: a route to simple statin analogues," Chem Biol. 6(10):731-41 (1999).
Ray et al., "New Electrophiles and Strategies for Mechanism-Based and Targeted Covalent Inhibitor Design," Biochemistry. 58: 5234-5244 (Dec. 2019).
Reid et al. "A model of structure and catalysis for ketoreductase domains in modular polyketide synthases," Biochemistry. 42(1):72-79 (2003).
Revill et al., "Genetically engineered analogs of ascomycin for nerve regeneration," J Pharmacol Exp Ther. 302(3):1278-85 (2002).
Revolution Medicines, "Corporate Overview Q1 2021," Translating Frontier Oncology Targets to Outsmart Cancer™ (Apr. 30, 2021) (35 pages).
Revolution Medicines, "Corporate Overview Q1 2021," Translating Frontier Oncology Targets to Outsmart Cancer™ (Mar. 2, 2021) (35 pages).
Revolution Medicines, "Corporate Overview Q1-2021," Translating Frontier Oncology Targets to Outsmart Cancer™ (Jan. 12, 2021) (34 pages).
Revolution Medicines, "Corporate Overview Q2 2021," Translating Frontier Oncology Targets to Outsmart Cancer™ (May 10, 2021) (34 pages).

(56) References Cited

OTHER PUBLICATIONS

Revolution Medicines, "Corporate Overview," Translating Frontier Oncology Targets to Outsmart Cancer™ (Aug. 11, 2021) (43 pages).
Revolution Medicines, "Corporate Overview," Translating Frontier Oncology Targets to Outsmart Cancer™ (Feb. 8, 2021) (35 pages).
Revolution Medicines, "Drugging the RAS(ON) Form of Diverse Oncogenic RAS Mutations," RAS Targeted Drug Discovery: Expanding RAS Druggability Beyond G12C (Feb. 2021) (24 pages).
Revolution Medicines, "RMC-6291: Biological Features of Targeting KRASG12C(ON) and Potential Application to Overcoming Drug Resistance in RAS-Addicted Tumors," dated May 26, 2021 (17 pages).
Revolution Medicines, "Translating Frontier Oncology Targets to Outsmart Cancer™: Corporate Overview Q4-2020," dated Nov. 12, 2020 (30 pages).
Ruan et al., "Binding of rapamycin analogs to calcium channels and FKBP52 contributes to their neuroprotective activities," Proc Natl Acad Sci U S A. 105(1):33-8 (2008).
Rudolph, "Covalent Modification in Drug Discovery—A Chemist's Perspective," Pharmaceutical & BioScience Society. Dated Feb. 7, 2019 (39 pages).
Saeidian et al., "Effect of aromaticity and ring strain on proton affinity of aziridine and amidine skeletons: a DFT study," Journal of the Iranian Chemical Society. 17:1731-1741 (Mar. 2020).
Sànchez-Tillò et al., "Cyclophilin A is required for M-CSF-dependent macrophage proliferation," Eur J Immunol. 36(9):2515-24 (2006).
Schulze et al. "Chemical remodeling of a cellular chaperone to target the active state of mutant KRAS," Science. 381(6659):794-799 (Aug. 2023) (79 pages) (supplemental information included).
Schulze et al., "Tri-Complex Inhibitors of the Oncogenic, GTP-Bound Form of KRASG12C Overcome RTK-Mediated Escape Mechanisms and Drive Tumor Regressions in Vivo," Revolution Medicines (Oct. 2019) (1 page).
Schutt, "Safety Considerations for Covalent Inhibitors," Pharmaceutical & BioScience Society. Dated Feb. 7, 2019 (36 pages).
Schwecke et al., "The biosynthetic gene cluster for the polyketide immunosuppressant rapamycin," Proc Natl Acad Sci U S A. 92(17):7839-43 (1995).
Sebastiano et al., "Impact of Dynamically Exposed Polarity on Permeability and Solubility of Chameleonic Drugs Beyond the Rule of 5," J Med Chem. 61:4189-4202 (Apr. 2018).
Shigdel et al., "Genomic discovery of an evolutionarily programmed modality for small-molecule targeting of an intractable protein surface," Proc Natl Acad Sci U S A. 117(29):17195-203 (Jul. 2020).
Sieber et al., "Novel inhibitors of the calcineurin/NFATc hub—alternatives to CsA and FK506?" Cell Commun Signal. 7:25 (2009) (19 pages).
Sieburth et al., "SUR-8, a conserved Ras-binding protein with leucine-rich repeats, positively regulates Ras-mediated signaling in C. elegans," Cell. 94(1):119-30 (Jul. 1998).
Simanshu et al., "RAS Proteins and Their Regulators in Human Disease," available in PMC Jun. 29, 2018, published in final edited form as: Cell. 170(1):17-33 (2017) (34 pages).
Smith, "Translating Frontier Oncology Targets to Outsmart Cancer," RAS-Targeted Drug Discovery Summit, Revolution Medicines, Sep. 19 (2019) (29 pages).
Smulik et al., "Synthesis of cyclosporin A-derived affinity reagents by olefin metathesis," Org Lett. 4(12):2051-4 (2002).
Steadman et al., "Discovery of Potent Cyclophilin Inhibitors Based on the Structural Simplification of Sanglifehrin A," J Med Chem. 60:1000-1017 (2017).
Stewart et al., "Development of Inhibitors of the Activated Form of KRASG12C," AACR Targeting RAS-Driven Cancers, Dec. 9-12, San Diego, California. Poster B37 (2018) (1 page).
STN record of WO 2014/009774, available online Jan. 16, 2014 (4 pages).
STN record of WO 98/12217, available online Mar. 26, 1998 (6 pages).
Sun et al. "Design and structure-based study of new potential FKBP12 inhibitors," Biophys J. 85(5):3194-3201 (2003).
Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).
Takakusagi et al., "Efficient one-cycle affinity selection of binding proteins or peptides specific for a small-molecule using a T7 phage display pool," Bioorg Med Chem. 16(22):9837-46 (2008).
Tanaka et al., "Clinical Acquired Resistance to KRASG12C Inhibition through a Novel KRAS Switch-II Pocket Mutation and Polyclonal Alterations Converging on RAS-MAPK Reactivation," Cancer Discov. 11(8):1913-1922 (Apr. 6, 2021).
Tang et al., "Generation of New Epothilones by Genetic Engineering of a Polyketide Synthase in *Myxococcus xanthus*," J Antibiot (Tokyo). 58(3):178-184 (2005).
UniProtKB Accession No. A0A061A6I8, Sep. 3, 2014, available <http://www.uniprot.org/uniprot/A0A061A6I8>, (12 pages).
UniProtKB Accession No. Q54296, "Polyketide synthase," <https://www.uniprot.org/uniprot/A0A61A6I8.txt?version=14>, retrieved May 29, 2020 (12 pages).
UniProtKB Accession No. Q54296, Nov. 1, 1996, available <http://www.uniprot.org/uniprot/Q54296>, (12 pages).
UniProtKB Accession No. Q54297, Nov. 1, 1996, available <https://www.uniprot.org/uniprot/Q54297.txt>, (3 pages).
Upadhyaya et al., "Direct Ras Inhibitors Identified From a Structurally Rigidified Bicyclic Peptide Library," available in PMC Oct. 21, 2015, published in final edited form as: Tetrahedron. 70(42):7714-7720 (2014) (15 pages).
Vakiti et al., "Stereoselective synthesis of C17—C34 fragment of antascomicin A," Tetrahedron Lett. 55(47):6438-40 (2014).
Vignot et al., "mTOR-targeted therapy of cancer with rapamycin derivatives," Ann Oncol. 16(4):525-37 (2005).
Vocadlo et al. "Mechanistic insights into glycosidase chemistry," Curr Opin Chem Biol. 12:539-555 (2008) (17 pages).
Wagner et al., "New naturally occurring amino acids," Angew Chem Int Ed Engl. 22(11):816-28 (1983).
Wang et al., "Thermodynamic analysis of cyclosporin a binding to cyclophilin a in a lung tumor tissue lysate," Anal Chem. 76(15):4343-8 (2004).
Wasko et al. "Tumour-selective activity of RAS-GTP inhibition in pancreatic cancer," Nature. 629(8013):927-936 (May 2024) (31 pages).
Weissman et al., "Combinatorial biosynthesis of reduced polyketides," Nat Rev Microbiol. 3(12):925-36 (2005).
Weissman, "Genetic engineering of modular PKSs: from combinatorial biosynthesis to synthetic biology," Nat Prod Rep. 33(2):203-230 (2016).
Wildes et al., "Inhibition of the Oncogenic, GTP-Bound Form of KRASG12C by Second Generation, Tri-Complex Inhibitors Overcomes RTK-Mediated Escape Mechanisms," The FASEB Regulation and Function of Small GTPases Conference, Jun. 23-28, Olean, New York (Abstract Included) (Jun. 2019) (2 pages).
Wilson et al., "Comparative X-ray structures of the major binding protein for the immunosuppressant FK506 (tacrolimus) in unliganded form and in complex with FK506 and rapamycin," Acta Cryst. D51:511-21 (1995).
Wright et al., "Multivalent binding in the design of bioactive compounds," Curr Org Chem. 5(11):1107-31 (2001).
Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).
Wu et al., "Inhibition of ras-effector interactions by cyclic peptides," Med Chem Commun. 4(2):378-82 (2013).
Wu et al., "Synthesis of Ketone Analogues of Prolyl and Pipecolyl Ester FKBP12 Ligands," J Med Chem. 45(16):3558-3568 (2002).
Zhang et al., "Bifunctional Small-Molecule Ligands of K-Ras Induce Its Association with Immunophilin Proteins," Angew Chem Int Ed Engl. 131:16460-5 (Nov. 2019).

(56) References Cited

OTHER PUBLICATIONS

Zhou et al., "Biophysical and biochemical characterization of KRASG12C inhibition through a novel modality," AACR Targeting RAS-Driven Cancers, Dec. 9-12, San Diego, California. Poster A06 (2018) (1 page).
U.S. Appl. No. 19/196,483, Cregg et al.

| | G12A | G12C | G12D | G12E | G12F | wt | G12H | G12I | G12K | G12L | G12M | G12N | G12P | G12Q | G12R | G12S | G12T | G12V | G12W | G12Y |
|---|---|---|---|---|---|---|---|---|---|---|---|---|---|---|---|---|---|---|---|---|
| Compound A | 1.72 | 0.00 | 0.23 | 1.62 | 1.60 | 1.44 | 1.02 | 1.20 | 1.47 | 1.40 | 0.87 | 0.88 | 1.00 | 1.39 | 1.33 | 1.04 | 0.78 | 0.70 | 1.39 | 1.54 |

SEQUENCE LISTING

```
Sequence total quantity: 4
SEQ ID NO: 1            moltype = DNA  length = 91
FEATURE                 Location/Qualifiers
source                  1..91
                        mol_type = other DNA
                        organism = synthetic construct
SEQUENCE: 1
gcctgctgaa aatgactgag tataaacttg tgatggttgg agcttgtggc gtaggcaaga  60
gcgccttgac gatacagcta attcagaatc a                                 91

SEQ ID NO: 2            moltype = RNA  length = 20
FEATURE                 Location/Qualifiers
source                  1..20
                        mol_type = other RNA
                        organism = synthetic construct
SEQUENCE: 2
atggttggag ctgatggcgt                                              20

SEQ ID NO: 3            moltype = DNA  length = 20
FEATURE                 Location/Qualifiers
source                  1..20
                        mol_type = other DNA
                        organism = synthetic construct
SEQUENCE: 3
taagtgggag cgccactcca                                              20

SEQ ID NO: 4            moltype = DNA  length = 20
FEATURE                 Location/Qualifiers
source                  1..20
                        mol_type = other DNA
                        organism = synthetic construct
SEQUENCE: 4
ccaaacacca gcatcaagag                                              20
```

RAS INHIBITORS

SEQUENCE LISTING

The instant application contains a Sequence Listing which has been submitted electronically in XML format and is hereby incorporated by reference in its entirety. Said XML copy, created Feb. 28, 2025, is named 51432-0090010_Sequence_Listing_2_28_25 and is 4,454 bytes in size.

BACKGROUND

The vast majority of small molecule drugs act by binding a functionally important pocket on a target protein, thereby modulating the activity of that protein. For example, cholesterol-lowering drugs known as statins bind the enzyme active site of HMG-CoA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates are that only about 10% of all human proteins are targetable by small molecules. Bojadzic and Buchwald, Curr Top Med Chem 18: 674-699 (2019). The other 90% are currently considered refractory or intractable toward above-mentioned small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

It has been well established in literature that Ras proteins (K-Ras, H-Ras and N-Ras) play an essential role in various human cancers and are therefore appropriate targets for anticancer therapy. Indeed, mutations in Ras proteins account for approximately 30% of all human cancers in the United States, many of which are fatal. Dysregulation of Ras proteins by activating mutations, overexpression or upstream activation is common in human tumors, and activating mutations in Ras are frequently found in human cancer. For example, activating mutations at codon 12 in Ras proteins function by inhibiting both GTPase-activating protein (GAP)-dependent and intrinsic hydrolysis rates of GTP, significantly skewing the population of Ras mutant proteins to the "on" (GTP-bound) state (Ras(ON)), leading to oncogenic MAPK signaling. Notably, Ras exhibits a picomolar affinity for GTP, enabling Ras to be activated even in the presence of low concentrations of this nucleotide. Mutations at codons 13 (e.g., G13D) and 61 (e.g., Q61K) of Ras are also responsible for oncogenic activity in some cancers.

Despite extensive drug discovery efforts against Ras during the last several decades, a drug directly targeting the "on" form of Ras is still not approved. Additional efforts are needed to uncover additional medicines for cancers driven by the various Ras mutations.

SUMMARY

Provided herein are Ras inhibitors. These Ras inhibitors target, that is, selectively bind to or inhibit, Ras(ON) (e.g., selective over the GDP-bound, inactive state of Ras). The approach described herein entails formation of a high affinity three-component complex between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex between the Ras protein and the widely expressed cytosolic chaperone, cyclophilin A (CYPA). Without being bound by theory, the inventors believe that one way the inhibitory effect on Ras is effected by compounds of the invention and the complexes they form is by steric occlusion of the interaction site between Ras and downstream effector molecules, such as RAF and PI3K, which are required for propagating the oncogenic signal.

As such, in some embodiments, the disclosure features a compound, or pharmaceutically acceptable salt thereof, of structural Formula Ia:

Formula Ia

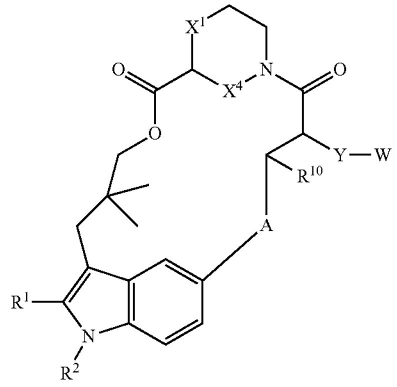

wherein A is optionally substituted 3 to 6-membered cycloalkylene, optionally substituted 3 to 6-membered heterocycloalkylene, optionally substituted 6-membered arylene, optionally substituted 5 to 6-membered heteroarylene, optionally substituted $C_2$-$C_4$ alkylene, or optionally substituted $C_2$-$C_4$ alkenylene;

Y is

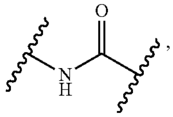, 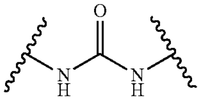,

—NHC(O)— —NHC(O)NH—

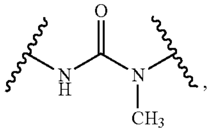, 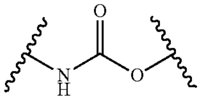,

—$NHC(O)NCH_3$— —NHC(O)O—

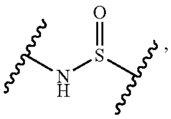, 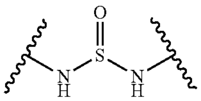,

—NHC(S)— —NHC(S)NH—

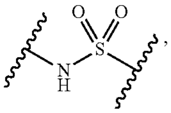, or 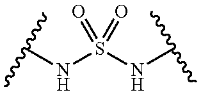;

—$NHC(O)_2$— —$NHC(O)_2NH$—

W is hydrogen, $C_1$-$C_4$ alkyl, optionally substituted $C_1$-$C_3$ heteroalkyl, optionally substituted 3 to 10-membered heterocycloalkyl, optionally substituted 3 to 10-membered cycloalkyl, optionally substituted 6 to 10-membered aryl, or optionally substituted 5 to 10-membered heteroaryl;

$X^1$ and $X^4$ are each, independently, $CH_2$ or NH;

$R^1$ is optionally substituted $C_1$-$C_6$ alkyl, optionally substituted $C_1$-$C_6$ heteroalkyl, optionally substituted 3 to 15-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; and $R^{10}$ is hydrogen, hydroxy, optionally substituted $C_1$-$C_3$ alkyl, or optionally substituted $C_1$-$C_6$ heteroalkyl. In some embodiments, $R^{10}$ is hydrogen.

Also provided are pharmaceutical compositions comprising a compound of Formula Ia, or a pharmaceutically acceptable salt thereof, and a pharmaceutically acceptable excipient.

Also provided is a method of treating cancer in a subject in need thereof, the method comprising administering to the subject a therapeutically effective amount of a compound of the present invention, or a pharmaceutically acceptable salt thereof.

In some embodiments, a method is provided of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

Definitions and Chemical Terms

In this application, unless otherwise clear from context, (i) the term "a" means "one or more"; (ii) the term "or" is used to mean "and/or" unless explicitly indicated to refer to alternatives only or the alternative are mutually exclusive, although the disclosure supports a definition that refers to only alternatives and "and/or"; (iii) the terms "comprising" and "including" are understood to encompass itemized components or steps whether presented by themselves or together with one or more additional components or steps; and (iv) where ranges are provided, endpoints are included.

As used herein, the term "about" is used to indicate that a value includes the standard deviation of error for the device or method being employed to determine the value. In certain embodiments, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1/%, or less in either direction (greater than or less than) of a stated value, unless otherwise stated or otherwise evident from the context (e.g., where such number would exceed 100% of a possible value).

As used herein, the term "adjacent" in the context of describing adjacent atoms refers to bivalent atoms that are directly connected by a covalent bond.

A "compound of the present invention" and similar terms as used herein, whether explicitly noted or not, refers to Ras inhibitors described herein, including compounds of Formula Ia or Formula Ib and subformulae thereof, and compounds of Table 1a or Table 1b, as well as salts (e.g., pharmaceutically acceptable salts), solvates, hydrates, stereoisomers (including atropisomers), and tautomers thereof.

The term "wild-type" refers to an entity having a structure or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

Those skilled in the art will appreciate that certain compounds described herein can exist in one or more different isomeric (e.g., stereoisomers, geometric isomers, atropisomers, tautomers) or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation state having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$ $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substituents are disclosed in groups or in ranges, unless otherwise indicated, the present disclosure is intended to cover individual compounds and groups of compounds (e.g., genera and subgenera) containing each and every individual subcombination of members at each position.

The term "optionally substituted X" (e.g., "optionally substituted alkyl") is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. For example, in the term "optionally substituted $C_1$-$C_6$ alkyl-$C_2$-$C_9$ heteroaryl," the alkyl portion, the heteroaryl portion, or both, may be optionally substituted. Combinations of substituents envisioned by the present disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group may be, independently, deuterium; halogen; —$(CH_2)_{0-4}R^{\circ}$; —$(CH_2)_{0-4}OR^{\circ}$; —$O(CH_2)_{0-4}R^{\circ}$; —O—$(CH_2)_{0-4}C(O)OR$∞; —$(CH_2)_{0-4}CH(OR^{\circ})_2$; —$(CH_2)_{0-4}SR^{\circ}$; —$(CH_2)_{0-4}Ph$, which may be substituted with R∞; —$(CH_2)_{0-4}O(CH_2)_{0-1}Ph$ which may be substituted with R∞; —CH═CHPh, which may be substituted with R∞; —$(CH_2)_{0-4}O(CH_2)_{0-1}$-pyridyl which may be substituted with R∞; 4-11 membered saturated or unsaturated heterocycloalkyl (e.g., 4-8 membered saturated or unsaturated heterocycloalkyl (e.g., pyridyl)) which may be further optionally substituted (e.g., with a methyl); 3-8 membered saturated or unsaturated cycloalkyl (e.g., cyclopropyl, cyclobutyl, or cyclopentyl); —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$, —$(CH_2)_{0-4}C(O)R^{\circ}$; —$C(S)R^{\circ}$; —$(CH_2)_{0-4}C(O)OR^{\circ}$; —$(CH_2)_{0-4}$—C(O)—$N(R^{\circ})_2$; —$(CH_2)_{0-4}$—C(O)—$N(R^{\circ})$—$S(O)_2$—$R^{\circ}$; —$C(NCN)NR^{\circ}_2$; —$(CH_2)_{0-4}C(O)SR^{\circ}$; —$(CH_2)_{0-4}C(O)OSR^{\circ}_3$; —$(CH_2)_{0-4}OC(O)R^{\circ}$; —$OC(O)(CH_2)_{0-4}SR^{\circ}$; —SC(S)SR∞, —$(CH_2)_{0-4}SC(O)R^{\circ}$; —$(CH_2)_{0-4}C(O)NR^{\circ}_2$; —$C(S)NR^{\circ}_2$; —C(S)SR∞, —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$, —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NOR^{\circ})NR^{\circ}O$; —$C(NH)NR^{\circ}_2$; —$P(O)_2R^{\circ}$; —$P(O)R^{\circ}_2$; —$P(O)(OR^{\circ})_2$; —$OP(O)R^{\circ}_2$; —$OP(O)(OR^{\circ})_2$; —$OP(O)(OR^{\circ})R^{\circ}$, —$SiR^{\circ}_3$; —($C_{1-4}$ straight or branched alkylene)O—$N(R^{\circ})_2$; or —($C_{1-4}$ straight or branched alkylene)C(O)O—$N(R^{\circ})_2$, wherein each $R^{\circ}$ may be substituted as defined below and is independently hydrogen, —$C_{1-6}$ aliphatic, —$CH_2Ph$, —$O(CH_2)_{0-1}Ph$, —$CH_2$— (5-6 membered heteroaryl ring), or a 3-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), may be, independently, halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —($C_{1-4}$ straight or branched alkylene)C(O)$OR^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*, =NNHC(O)R*, =NNHC(O)OR*, =NNHS(O)$_2$R*, =NR*, =NOR*, —O(C(R*$_2$))$_{2-3}$O—, or —S(O(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, $C_{1-6}$ aliphatic which may be substituted as defined below, unsubstituted —OPh, or an unsubstituted 3-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on an aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^†$ include =O and =S.

The term "acetyl," as used herein, refers to the group —C(O)CH$_3$.

The term "alkoxy," as used herein, refers to a —O—$C_1$-$C_{20}$ alkyl group, wherein the alkoxy group is attached to the remainder of the compound through an oxygen atom.

The term "alkyl," as used herein, refers to a saturated, straight or branched monovalent hydrocarbon group containing from 1 to 20 (e.g., from 1 to 10 or from 1 to 6) carbons. In some embodiments, an alkyl group is unbranched (i.e., is linear); in some embodiments, an alkyl group is branched. Alkyl groups are exemplified by, but not limited to, methyl, ethyl, n- and iso-propyl, n-, sec-, iso- and tert-butyl, and neopentyl.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like. The term "$C_x$-$C_y$ alkylene" represents alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_1$-$C_6$, $C_1$-$C_{10}$, $C_2$-$C_{20}$, $C_2$-$C_6$, $C_2$-$C_{10}$, or $C_2$-$C_{20}$ alkylene). In some embodiments, the alkylene can be further substituted with 1, 2, 3, or 4 substituent groups as defined herein.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. The term "alkenylene," as used herein, represents a divalent straight or branched chain groups of, unless otherwise specified, from 2 to 20 carbons (e.g., from 2 to 6 or from 2 to 10 carbons) containing one or more carbon-carbon double bonds.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl.

The term "alkynyl sulfone," as used herein, represents a group comprising the structure

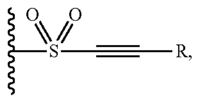

wherein R is any chemically feasible substituent described herein.

The term "amino," as used herein, represents —N(R$^†$)$_2$, e.g., —NH$_2$ and —N(CH$_3$)$_2$.

The term "aminoalkyl," as used herein, represents an alkyl moiety substituted on one or more carbon atoms with one or more amino moieties.

The term "amino acid," as described herein, refers to a molecule having a side chain, an amino group, and an acid group (e.g., —CO$_2$H or —SO$_3$H), wherein the amino acid is attached to the parent molecular group by the side chain, amino group, or acid group (e.g., the side chain). As used herein, the term "amino acid" in its broadest sense, refers to any compound or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. Exemplary amino acids include alanine, arginine, asparagine, aspartic acid, cysteine, glutamic acid, glutamine, glycine, histidine, optionally substituted hydroxylnorvaline, isoleucine, leucine, lysine, methionine, norvaline, ornithine, phenylalanine, proline, pyrrolysine, selenocysteine, serine, taurine, threonine, tryptophan, tyrosine, and valine.

The term "aryl," as used herein, represents a monovalent monocyclic, bicyclic, or multicyclic ring system formed by carbon atoms, wherein the ring attached to the pendant group is aromatic. Examples of aryl groups are phenyl, naphthyl, phenanthrenyl, and anthracenyl. An aryl ring can be attached to its pendant group at any heteroatom or carbon ring atom that results in a stable structure and any of the ring atoms can be optionally substituted unless otherwise specified.

The term "$C_0$," as used herein, represents a bond. For example, part of the term —N(C(O)—($C_0$-$C_5$ alkylene-H)— includes —N(C(O)—($C_0$ alkylene-H)—, which is also represented by —N(C(O)—H)—.

The terms "carbocyclic" and "carbocyclyl," as used herein, refer to a monovalent, optionally substituted $C_3$-$C_{12}$ monocyclic, bicyclic, or tricyclic ring structure, which may be bridged, fused or spirocyclic, in which all the rings are formed by carbon atoms and at least one ring is non-aromatic. Carbocyclic structures include cycloalkyl, cycloalkenyl, and cycloalkynyl groups. Examples of carbocyclyl groups are cyclohexyl, cyclohexenyl, cyclooctynyl, 1,2-dihydronaphthyl, 1,2,3,4-tetrahydronaphthyl, fluorenyl, indenyl, indanyl, decalinyl, and the like. A carbocyclic ring can be attached to its pendant group at any ring atom that results in a stable structure and any of the ring atoms can be optionally substituted unless otherwise specified.

The term "carbonyl," as used herein, represents a C(O) group, which can also be represented as C═O.

The term "carboxyl," as used herein, means —$CO_2$H, (C═O)(OH), COOH, or C(O)OH or the unprotonated counterparts.

The term "cyano." as used herein, represents a —CN group.

The term "cycloalkyl," as used herein, represents a monovalent saturated cyclic hydrocarbon group, which may be bridged, fused or spirocyclic having from three to eight ring carbons, unless otherwise specified, and is exemplified by cyclopropyl, cyclobutyl, cyclopentyl, cyclohexyl, cycloheptyl, and cycloheptyl.

The term "cycloalkenyl," as used herein, represents a monovalent, non-aromatic, saturated cyclic hydrocarbon group, which may be bridged, fused or spirocyclic having from three to eight ring carbons, unless otherwise specified, and containing one or more carbon-carbon double bonds.

The term "diastereomer," as used herein, means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "haloacetyl," as used herein, refers to an acetyl group wherein at least one of the hydrogens has been replaced by a halogen.

The term "haloalkyl," as used herein, represents an alkyl moiety substituted on one or more carbon atoms with one or more of the same of different halogen moieties.

The term "halogen," as used herein, represents a halogen selected from bromine, chlorine, iodine, or fluorine.

The term "heteroalkyl," as used herein, refers to an "alkyl" group, as defined herein, in which at least, one carbon atom has been replaced with (e.g. an O, N, or S atom). The heteroatom may appear in the middle or at the end of the radical.

The term "heteroaryl," as used herein, represents a monovalent, monocyclic or polycyclic ring structure that contains at least one fully aromatic ring: i.e., they contain 4n+2 pi electrons within the monocyclic or polycyclic ring system and contains at least one ring heteroatom selected from N, O, or S in that aromatic ring. Exemplary unsubstituted heteroaryl groups are of 1 to 12 (e.g., 1 to 11, 1 to 10, 1 to 9, 2 to 12, 2 to 11, 2 to 10, or 2 to 9) carbons. The term "heteroaryl" includes bicyclic, tricyclic, and tetracyclic groups in which any of the above heteroaromatic rings is fused to one or more, aryl or carbocyclic rings, e.g., a phenyl ring, or a cyclohexane ring. Examples of heteroaryl groups include, but are not limited to, pyridyl, pyrazolyl, benzooxazolyl, benzoimidazolyl, benzothiazolyl, imidazolyl, thiazolyl, quinolinyl, tetrahydroquinolinyl, and 4-azaindolyl. A heteroaryl ring can be attached to its pendant group at any ring atom that results in a stable structure and any of the ring atoms can be optionally substituted unless otherwise specified. In some embodiment, the heteroaryl is substituted with 1, 2, 3, or 4 substituents groups.

The term "heterocycloalkyl," as used herein, represents a monovalent monocyclic, bicyclic or polycyclic ring system, which may be bridged, fused or spirocyclic, wherein at least one ring is non-aromatic and wherein the non-aromatic ring contains one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocycloalkyl groups are of 1 to 12 (e.g., 1 to 11, 1 to 10, 1 to 9, 2 to 12, 2 to 11, 2 to 10, or 2 to 9) carbons. The term "heterocycloalkyl" also represents a heterocyclic compound having a bridged multicyclic structure in which one or more carbons or heteroatoms bridges two non-adjacent members of a monocyclic ring, e.g., a quinuclidinyl group. The term "heterocycloalkyl" includes bicyclic, tricyclic, and tetracyclic groups in which any of the above heterocyclic rings is fused to one or more aromatic, carbocyclic, heteroaromatic, or heterocyclic rings, e.g., an aryl ring, a cyclohexane ring, a cyclohexene ring, a cyclopentane ring, a cyclopentene ring, a pyridine ring, or a pyrrolidine ring. Examples of heterocycloalkyl groups are pyrrolidinyl, piperidinyl, 1,2,3,4-tetrahydroquinolinyl, decahydroquinolinyl, dihydropyrrolopyridine, and decahydronapthyridinyl. A heterocycloalkyl ring can be attached to its pendant group at any ring atom that results in a stable structure and any of the ring atoms can be optionally substituted unless otherwise specified.

The term "hydroxy," as used herein, represents a —OH group.

The term "hydroxyalkyl," as used herein, represents an alkyl moiety substituted on one or more carbon atoms with one or more —OH moieties.

The term "isomer," as used herein, means any tautomer, stereoisomer, atropiosmer, enantiomer, or diastereomer of any compound of the invention. It is recognized that the compounds of the invention can have one or more chiral centers or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers or conformers of the basic molecular structure, including atropisomers. Some compounds of the present invention may exist in different tautomeric forms, all of the latter being included within the scope of the present invention.

The term "sulfonyl," as used herein, represents an —$S(O)_2$— group.

The term "thiocarbonyl," as used herein, refers to a —C(S)— group.

Those of ordinary skill in the art, reading the present disclosure, will appreciate that certain compounds described herein may be provided or utilized in any of a variety of forms such as, for example, salt forms, protected forms, pro-drug forms, ester forms, isomeric forms (e.g., optical or structural isomers), isotopic forms, etc. In some embodiments, reference to a particular compound may relate to a specific form of that compound. In some embodiments, reference to a particular compound may relate to that compound in any form. In some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form.

BRIEF DESCRIPTION OF THE DRAWINGS

FIG. 5A shows cell surface expression of PD-L1, PVR and CD73 on H358 cells following 48-hour treatment with Compound A in the presence of Interferon gamma (IFNγ), as measured by flow cytometry. Each graph shows mean fluorescence intensity ((MFI), for each respective immune checkpoint protein) vs. log M [Compound A].

FIG. 5B shows cell surface expression of PD-L1, PVR and CD73 on SW900 cells following 48-hour treatment with Compound A in the presence of Interferon gamma (IFNγ), as measured by flow cytometry. Each graph shows mean fluorescence intensity ((MFI), for each respective immune checkpoint protein) vs. log M [Compound A].

FIG. 5C shows cell surface expression of PD-L1, PVR and CD73 on Capan-2 cells following 48-hour treatment with Compound A in the presence of Interferon gamma (IFNγ), as measured by flow cytometry. Each graph shows mean fluorescence intensity ((MFI), for each respective immune checkpoint protein) vs. log M [Compound A].

FIG. 6A is a heatmap representing cellular RAS/RAF disruption assay results regarding various KRAS mutations in the presence of different RAS inhibitors. FIG. 6B shows the IC50 value associated with each colored bar of the heatmap.

DETAILED DESCRIPTION

Compounds

Figure 1A:
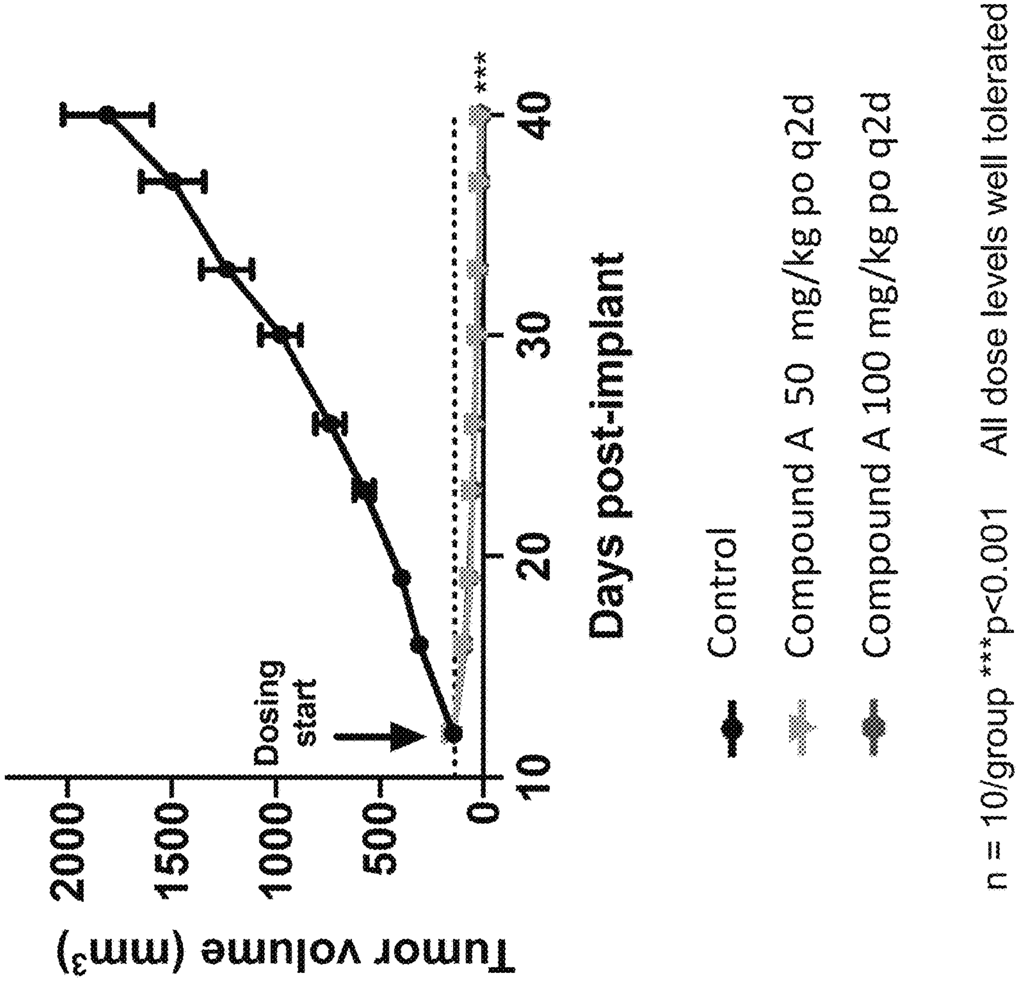
FIG. 1A is a graph demonstrating the in vivo efficacy of Compound A, a Ras inhibitor disclosed herein, in a human pancreatic adenocarcinoma HPAC $KRAS^{G12D/wt}$ xenograft model using female BALB/c nude mice. The graph shows tumor volume ($mm^3$) vs. days post-implant of the mouse xenograft model. Mice were randomized to treatment groups prior to administration of test articles or vehicle. Compound A was administered by oral gavage once every other day.

Provided herein are Ras inhibitors. These Ras inhibitors target, that is, selectively bind to or inhibit, Ras(ON) (e.g., selective over the GDP-bound, inactive state of Ras). As used herein, the term "RAS(ON) inhibitor" refers to an inhibitor that targets, that is, selectively binds to or inhibits, the GTP-bound, active state of RAS (e.g., selective over the GDP-bound, inactive state of RAS). Inhibition of the GTP-bound, active state of RAS includes, for example, the inhibition of oncogenic signaling from the GTP-bound, active state of RAS. In some embodiments, the RAS(ON) inhibitor is an inhibitor that selectively binds to and inhibits the GTP-bound, active state of RAS. In certain embodiments, RAS(ON) inhibitors may also bind to or inhibit the GDP-bound, inactive state of RAS (e.g., with a lower affinity or inhibition constant than for the GTP-bound, active state of RAS). In some embodiments, a RAS(ON) inhibitor has a molecular weight of between 800 and 1100 Da, inclusive. Accordingly, for example, the term "KRAS(ON) inhibitor" refers to any inhibitor that binds to KRAS in its GTP-bound "ON" position. A "KRAS$^{G12C}$(ON) inhibitor" is a KRAS inhibitor that selectively binds to or targets the G12C mutant form of KRAS. Non-limiting examples of RAS(ON) inhibitors, some of which are KRAS$^{G12C}$(ON) inhibitors, are provided in WO 2021091982, WO 2021091967, WO 2021091956, and WO 2020132597.

As used herein, the term "RAS(OFF) inhibitor" refers to an inhibitor that targets, that is, selectively binds to or inhibits the GDP-bound, inactive state of RAS (e.g., selective over the GTP-bound, active state of RAS). Inhibition of the GDP-bound, inactive state of RAS includes, for example, sequestering the inactive state by inhibiting the exchange of GDP for GTP, thereby inhibiting RAS from adopting the active conformation. In certain embodiments, RAS(OFF) inhibitors may also bind to or inhibit the GTP-bound, active state of RAS (e.g., with a lower affinity or inhibition constant than for the GDP-bound, inactive state of RAS). In some embodiments, a RAS(OFF) inhibitor has a molecular weight of under 700 Da. In some embodiments, a RAS(OFF) inhibitor has a molecular weight of under 700 Da. Accordingly, for example, the term "KRAS(OFF) inhibitor" refers to any inhibitor that binds to KRAS in its GDP-bound "OFF" position. A "KRAS$^{G12C}$(OFF) inhibitor" is a KRAS inhibitor that selectively binds to or targets the G12C mutant form of KRAS. KRAS$^{G12C}$(OFF) inhibitors are known in the art and non-limiting examples include adagrasib and sotorasib. Additional KRAS(OFF) inhibitors are provided herein.

The term "inhibitor" means a compound or agent (e.g., peptide, antibody) that prevents a biomolecule, (e.g., a protein) from completing or initiating a reaction. An inhibitor can inhibit a reaction by competitive, uncompetitive, or non-competitive means.

The approach described herein entails formation of a high affinity three-component complex between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex between the Ras protein and the widely expressed cytosolic chaperone, cyclophilin A (CYPA). Without being bound by theory, the inventors believe that one way the inhibitory effect on Ras is effected by compounds of the invention and the complexes they form is by steric occlusion of the interaction site between Ras and downstream effector molecules, such as RAF, which are required for propagating the oncogenic signal.

Without being bound by theory, the inventors postulate that non-covalent interactions of a compound of the present invention with Ras and the chaperone protein (e.g., cyclophilin A) may contribute to the inhibition of Ras activity. For example, van der Waals, hydrophobic, hydrophilic and hydrogen bond interactions, and combinations thereof, may contribute to the ability of the compounds of the present invention to form complexes and act as Ras inhibitors. Accordingly, a variety of Ras proteins may be inhibited by compounds of the present invention (e.g., a wild-type Ras or Ras$^{amp}$, or K-Ras, N-Ras, H-Ras, and mutants thereof at positions 12, 13 and 61, such as G12C, G12D, G12V, G12S, G13C, G13D, and Q61 L, and others described herein, as well as combinations of Ras proteins).

Accordingly, provided herein are compounds, or pharmaceutically acceptable salts thereof, having the structure of Formula Ia:

Formula Ia

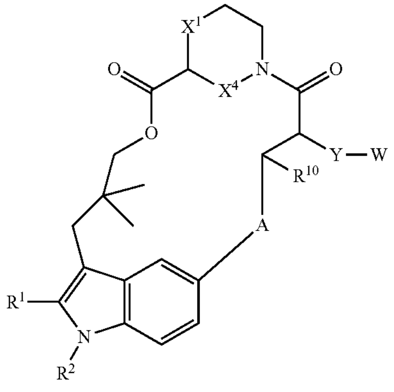

wherein A is optionally substituted 3 to 6-membered cycloalkylene, optionally substituted 3 to 6-membered heterocycloalkylene, optionally substituted 6-membered arylene, optionally substituted 5 to 6-membered heteroarylene, optionally substituted $C_2$-$C_4$ alkylene, or optionally substituted $C_2$-$C_4$ alkenylene;

Y is

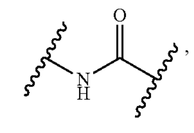, 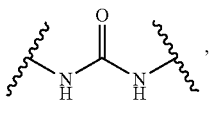,

—NHC(O)— —NHC(O)NH—

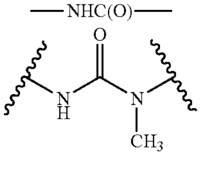, 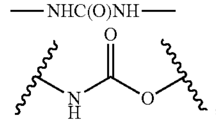,

—NHC(O)NCH3— —NHC(O)O—

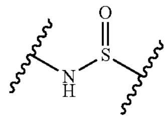, 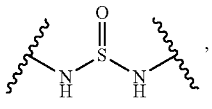,

—NHC(S)— —NHC(S)NH—

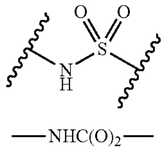, or 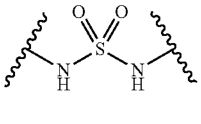;

—NHC(O)2— —NHC(O)2NH—

W is hydrogen, $C_1$-$C_4$ alkyl, optionally substituted $C_1$-$C_3$ heteroalkyl, optionally substituted 3 to 10-membered heterocycloalkyl, optionally substituted 3 to 10-membered cycloalkyl, optionally substituted 6 to 10-membered aryl, or optionally substituted 5 to 10-membered heteroaryl;

$X^1$ and $X^4$ are each, independently, $CH_2$ or NH;

$R^1$ is optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 15-membered heterocycloalkyl, optionally substituted 6 to 10-membered aryl, or optionally substituted 5 to 10-membered heteroaryl; and $R^2$ is hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; and $R^{10}$ is hydrogen, hydroxy, optionally substituted $C_1$-$C_3$ alkyl, or optionally substituted $C_1$-$C_6$ heteroalkyl.

In some embodiments, the compound, or pharmaceutically acceptable salt thereof, has the structure of Formula Ia-2:

Formula Ia-2

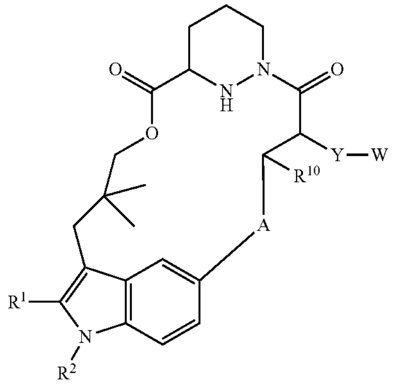

wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

Y is,

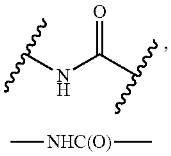, 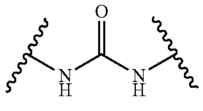,

—NHC(O)— —NHC(O)NH—

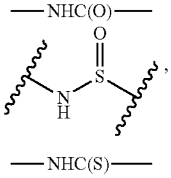, 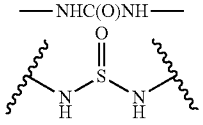,

—NHC(S)— —NHC(S)NH—

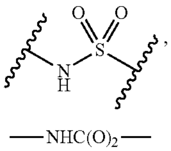, or 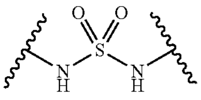;

—NHC(O)2— —NHC(O)2NH—

W is hydrogen, $C_1$-$C_4$ alkyl, optionally substituted 3 to 10-membered heterocycloalkyl, optionally substituted 3 to 10-membered cycloalkyl, optionally substituted 6 to 10-membered aryl, or optionally substituted 5 to 10-membered heteroaryl;

$R^1$ is optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; and $R^{10}$ is hydrogen or optionally substituted $C_1$-$C_6$ heteroalkyl. In some embodiments, $R^{10}$ is hydrogen.

In some embodiments, $R^1$ is optionally substituted 6 to 10-membered aryl or optionally substituted 5 to 10-membered heteroaryl. In some embodiments, $R^1$ is optionally substituted phenyl or optionally substituted pyridine.

In some embodiments, A is optionally substituted thiazole, optionally substituted triazole, optionally substituted morpholino, optionally substituted piperidinyl, optionally substituted pyridine, or optionally substituted phenyl. In some embodiments, A is optionally substituted thiazole, optionally substituted triazole, optionally substituted morpholino, or phenyl. In some embodiments, A is not an optionally substituted phenyl or benzimidazole. In some embodiments, A is not hydroxyphenyl.

In some embodiments, Y is —NHC(O)— or —NHC(O)NH—.

In some embodiments, the compound, or a pharmaceutically acceptable salt thereof, has the structure of Formula IIa:

Formula IIa

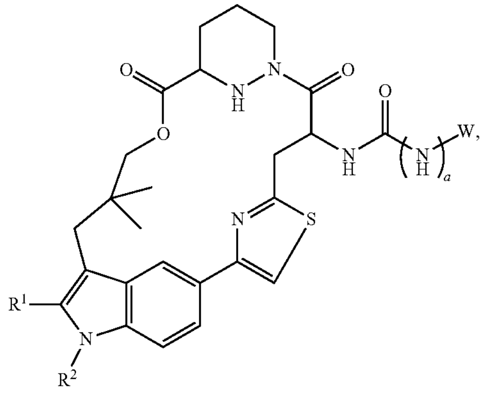

wherein a is 0 or 1.

In some embodiments, the compound, or a pharmaceutically acceptable salt thereof, has the structure of Formula IIa-1:

Formula IIa-1

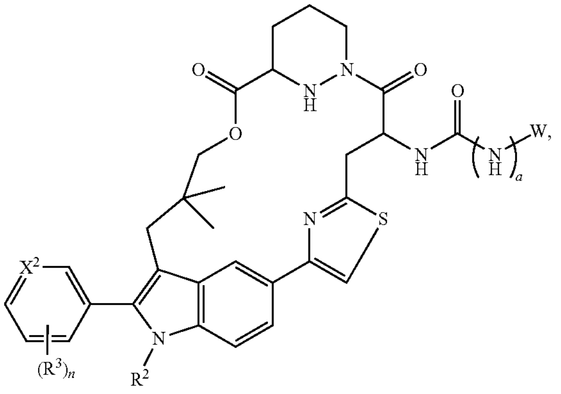

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl; and n is an integer from 1 to 4.

In some embodiments, the compound, or a pharmaceutically acceptable salt thereof, has the structure of Formula IIa-2:

Formula IIa-2

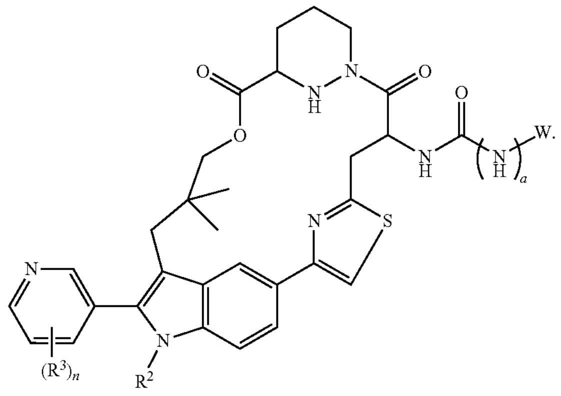

In some embodiments, the compound, or a pharmaceutically acceptable salt thereof, has the structure of Formula IIa-3:

Formula IIa-3

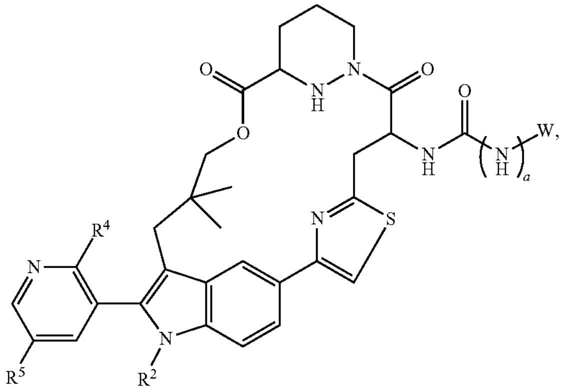

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl.

In some embodiments, the compound, or a pharmaceutically acceptable salt thereof, has the structure of Formula IIa-4:

Formula IIa-4

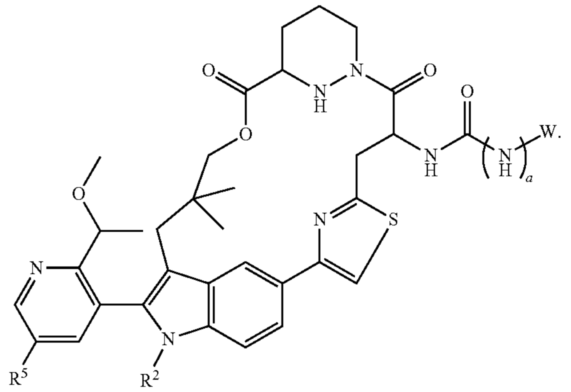

In some embodiments, the compound, or a pharmaceutically acceptable salt thereof, has the structure of Formula IIa-5:

Formula IIa-5

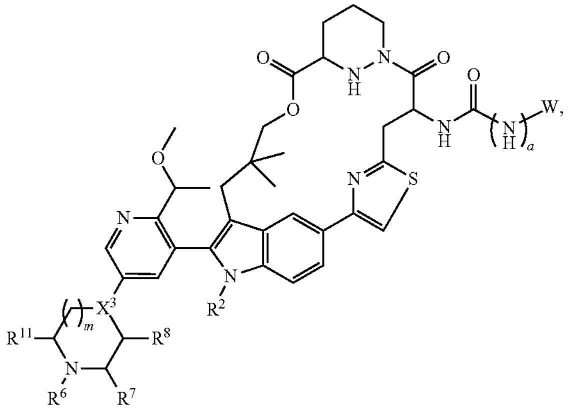

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl. In some embodiments, $X^3$ is N. In some embodiments, m is 1. In some embodiments, $R^{11}$ is H. In some embodiments, $X^3$ is N, m is 1, and $R^{11}$ is H.

In some embodiments, the compound, or a pharmaceutically acceptable salt thereof, has the structure of Formula IIa-6:

Formula IIa-6

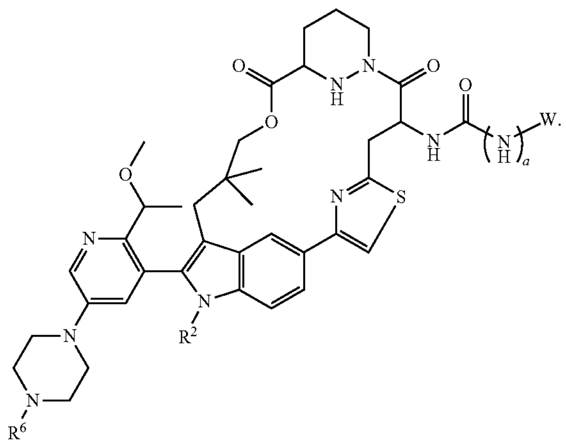

In some embodiments, the compound, or a pharmaceutically acceptable salt thereof, has the structure of Formula IIa-7:

Formula IIa-7

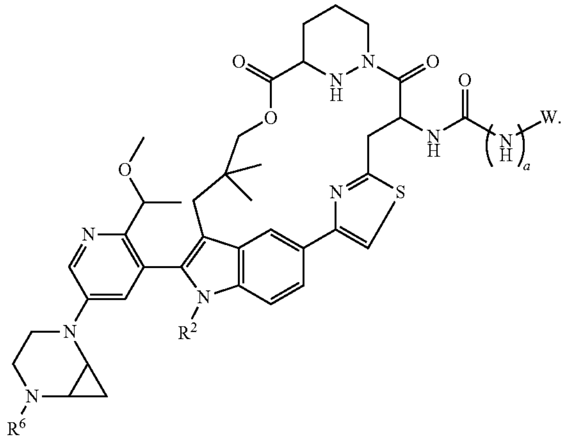

In some embodiments (e.g., of any one of Formulae IIa-6 or IIa-7), $R^6$ is methyl.

In some embodiments, the compound, or a pharmaceutically acceptable salt thereof, has the structure of Formula IIa-8 or Formula IIa-9:

Formula IIa-8

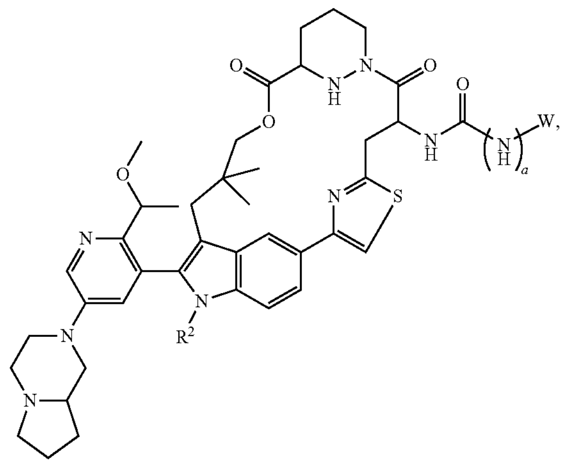

Formula IIa-9

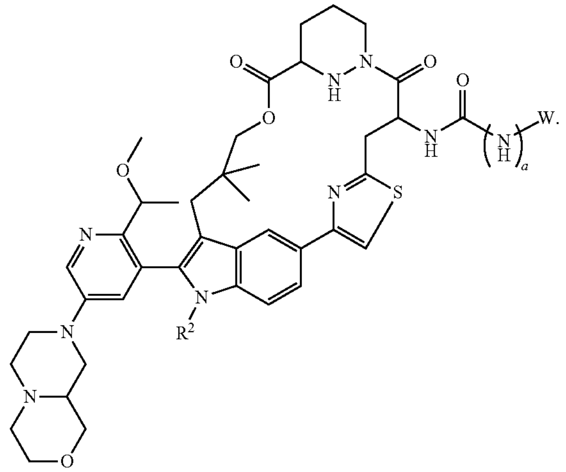

In some embodiments, the compound, or a pharmaceutically acceptable salt thereof, has the structure of Formula IIIa:

Formula IIIa

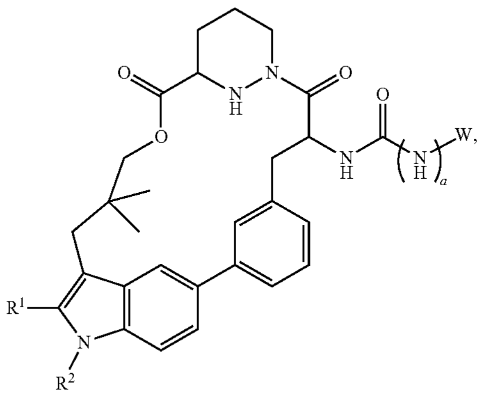

wherein a is 0 or 1.

In some embodiments, the compound, or a pharmaceutically acceptable salt thereof, has the structure of Formula IIIa-1:

wherein $X^2$ is N or CH;

Formula IIIa-1

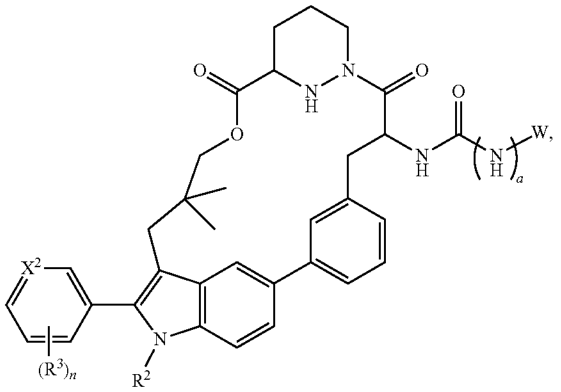

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl; and n is an integer from 1 to 4.

In some embodiments, the compound, or a pharmaceutically acceptable salt thereof, has the structure of Formula IIIa-2:

Formula IIIa-2

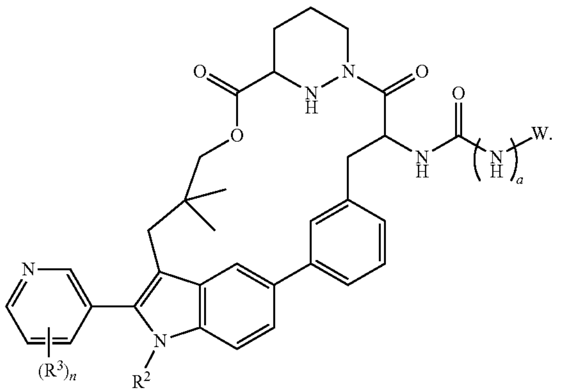

In some embodiments, the compound, or a pharmaceutically acceptable salt thereof, has the structure of Formula IIIa-3:

Formula IIIa-3

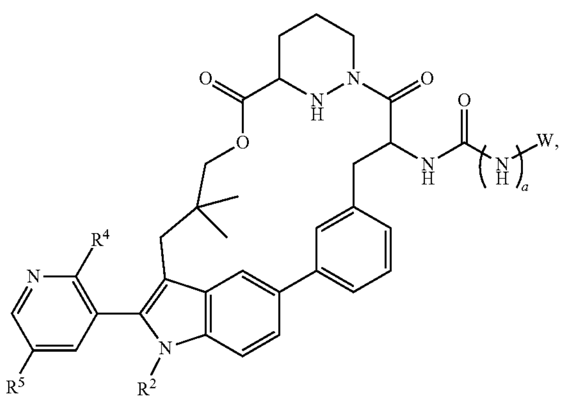

wherein $R^4$ and R, are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl.

In some embodiments, the compound, or a pharmaceutically acceptable salt thereof, has the structure of Formula IIIa-4:

Formula IIIa-4

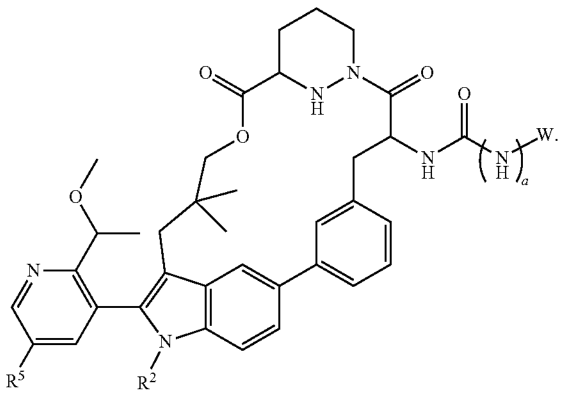

In some embodiments, the compound, or a pharmaceutically acceptable salt thereof, has the structure of Formula IIIa-5:

Formula IIIa-5

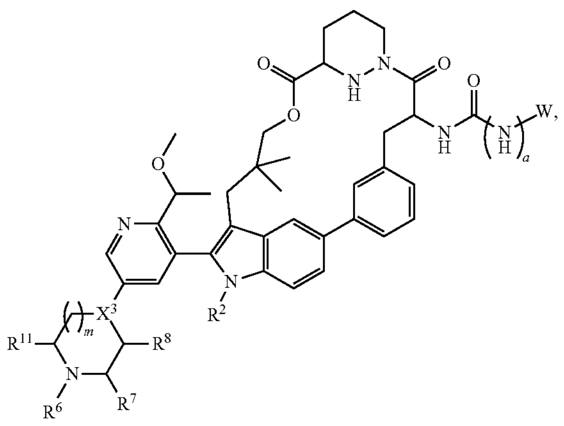

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl. In some embodiments, $X^3$ is N. In some embodiments, m is 1. In some embodiments, $R^1$ is hydrogen. In some embodiments, $X^3$ is N, m is 1, and $R^1$ is H.

In some embodiments, the compound, or a pharmaceutically acceptable salt thereof, has the structure of Formula IIIa-6:

Formula IIIa-6

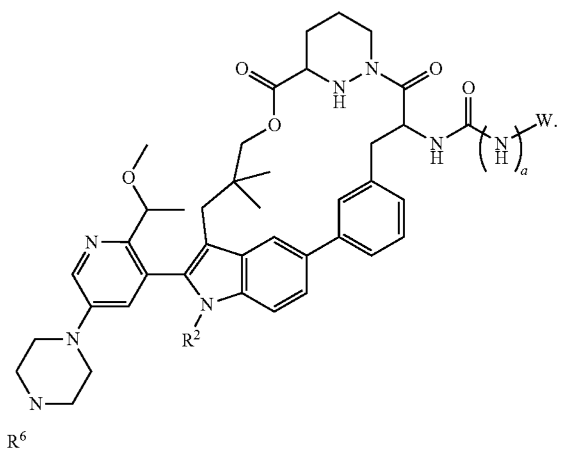

In some embodiments, the compound, or a pharmaceutically acceptable salt thereof has the structure of Formula IIIa-7:

Formula IIIa-7

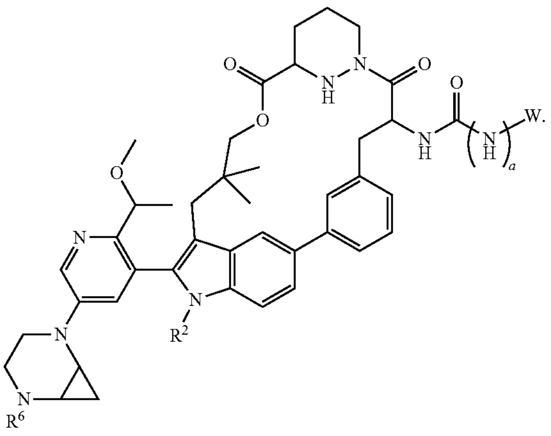

In some embodiments (e.g., of any one of Formulae IIIa-6 or IIIa-7), $R^6$ is methyl.

In some embodiments, the compound, or a pharmaceutically acceptable salt thereof, has the structure of Formula IIIa-8 or Formula IIIa-9:

Formula IIIa-8

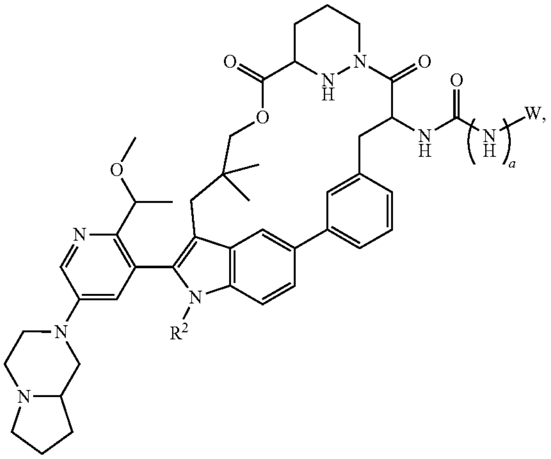

Formula IIIa-9

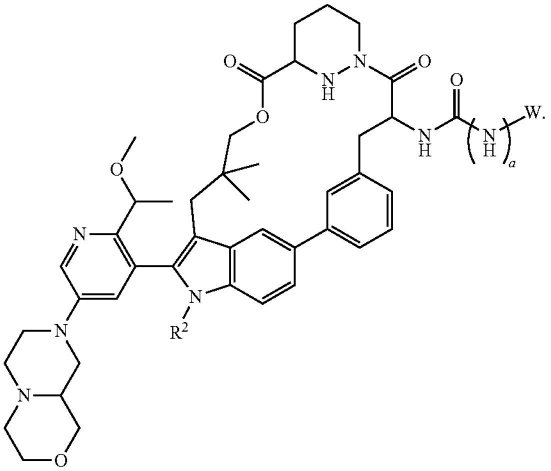

In some embodiments, the compound, or a pharmaceutically acceptable salt thereof, has the structure of Formula IVa:

Formula IVa

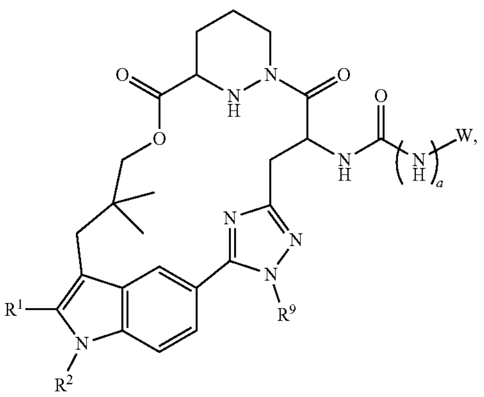

wherein $R^9$ is H or $C_1$-$C_6$, alkyl; and a is 0 or 1.

In some embodiments, the compound, or a pharmaceutically acceptable salt thereof, has the structure of Formula IVa-1:

Formula IVa-1

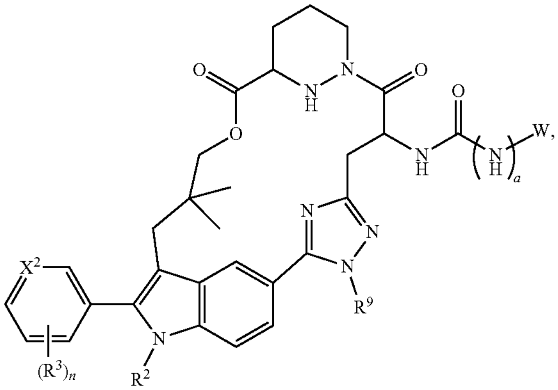

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_3$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl; and n is an integer from 1 to 4.

In some embodiments, the compound, or a pharmaceutically acceptable salt thereof, has the structure of Formula IVa-2:

Formula IVa-2

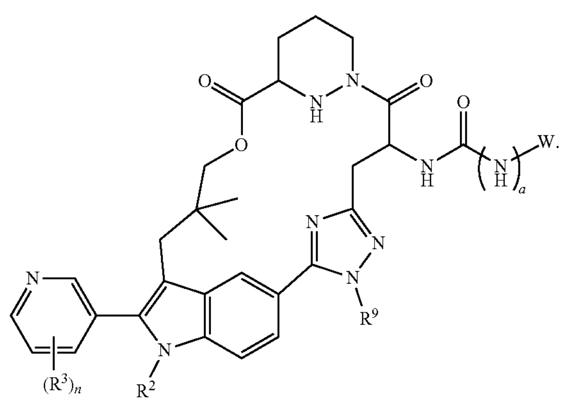

In some embodiments, the compound, or a pharmaceutically acceptable salt thereof, has the structure of Formula IVa-3:

Formula IVa-3

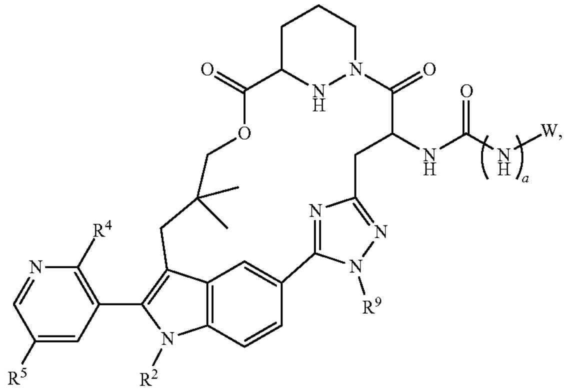

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl.

In some embodiments, the compound, or a pharmaceutically acceptable salt thereof, has the structure of Formula IVa-4:

Formula IVa-4

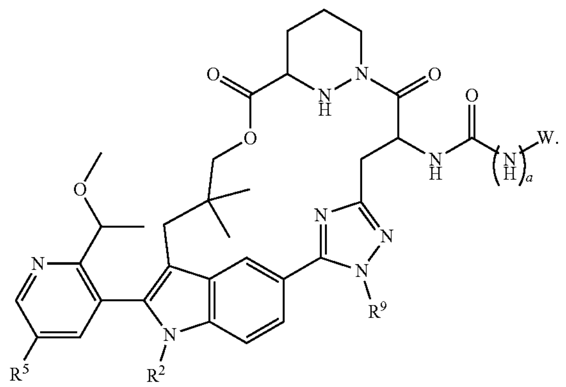

In some embodiments, the compound, or a pharmaceutically acceptable salt thereof, has the structure of Formula IVa-5:

Formula IVa-5

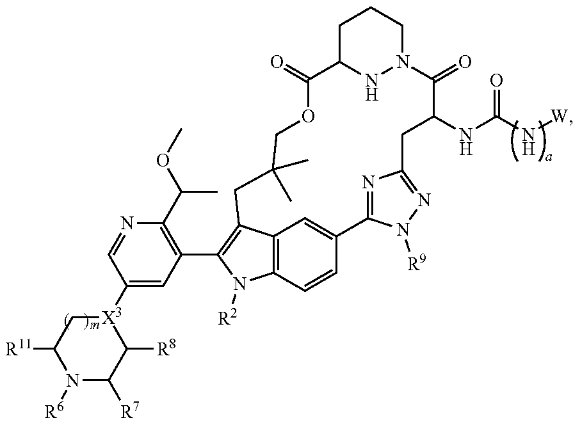

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 6-membered heterocycloalkyl. In some embodiments, $X^3$ is N. In some embodiments, m is 1. In some embodiments, $R^{11}$ is hydrogen. In some embodiments, $X^3$ is N, m is 1, and $R^{11}$ is H.

In some embodiments, the compound, or a pharmaceutically acceptable salt thereof, has the structure of Formula IVa-6:

Formula IVa-6

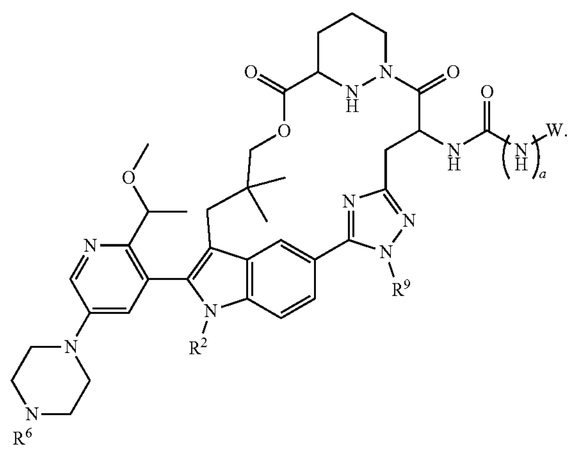

In some embodiments, the compound, or a pharmaceutically acceptable salt thereof, has the structure of Formula IVa-7:

Formula IVa-7

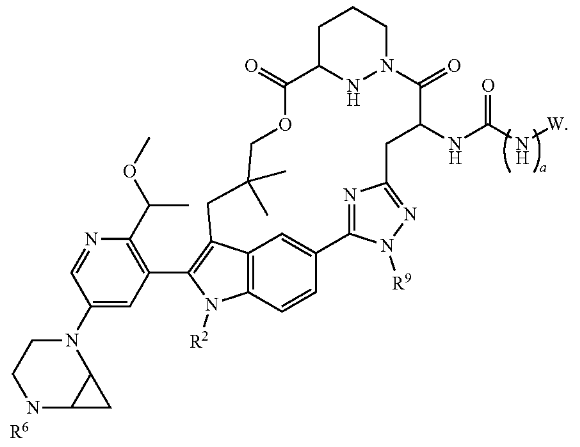

In some embodiments (e.g., of any one of Formulae IVa-6 or IVa-7), $R^6$ is methyl.

In some embodiments, the compound, or a pharmaceutically acceptable salt thereof, has the structure of Formula IVa-8 or Formula IVa-9:

Formula IVa-8

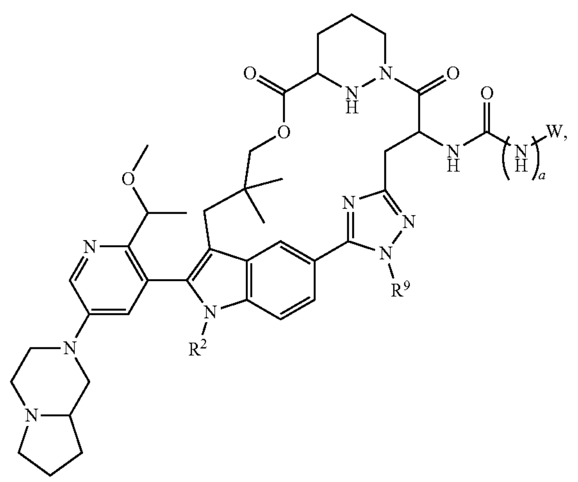

Formula IVa-9

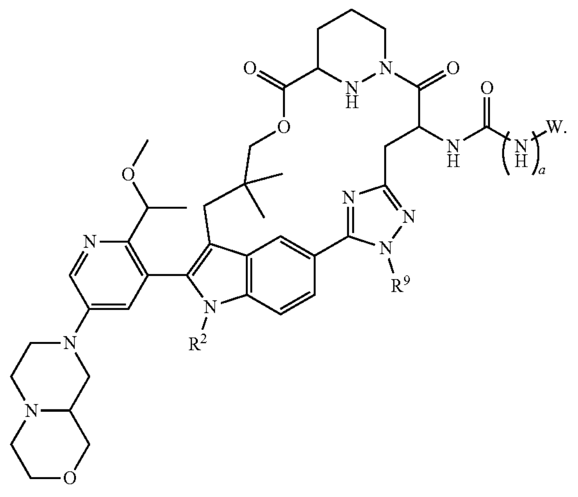

In some embodiments (e.g., of any one of Formulae IVa, IVa-1, IVa-2, IVa-3, IVa-4, IVa-5, IVa-6, IVa-7, IVa-8, or IVa-9), $R^9$ is methyl.

In some embodiments, Y is $—NHS(O)_2—$ or $—NHS(O)_2NH—$.

In some embodiments, the compound, or a pharmaceutically acceptable salt thereof, has the structure of Formula Va:

Formula Va

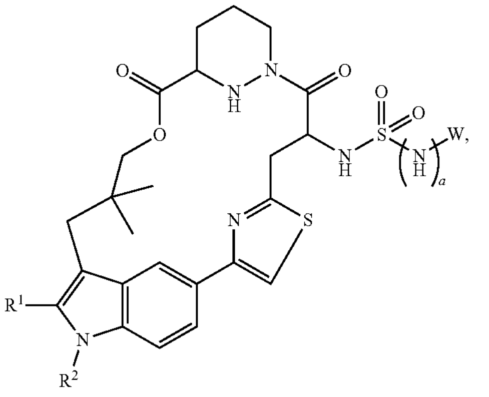

wherein a is 0 or 1.

In some embodiments, the compound, or a pharmaceutically acceptable salt thereof, has the structure of Formula Va-1:

Formula Va-1

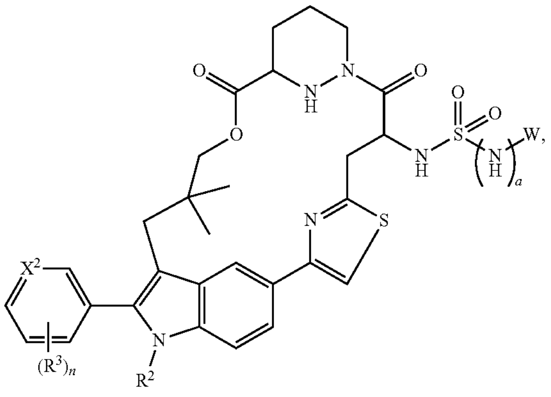

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl; and n is an integer from 1 to 4.

In some embodiments, the compound, or a pharmaceutically acceptable salt thereof, has the structure of Formula Va-2:

Formula Va-2

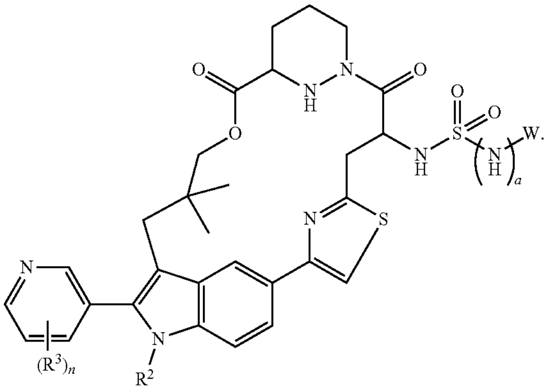

In some embodiments, the compound, or a pharmaceutically acceptable salt thereof, has the structure of Formula Va-3:

Formula Va-3

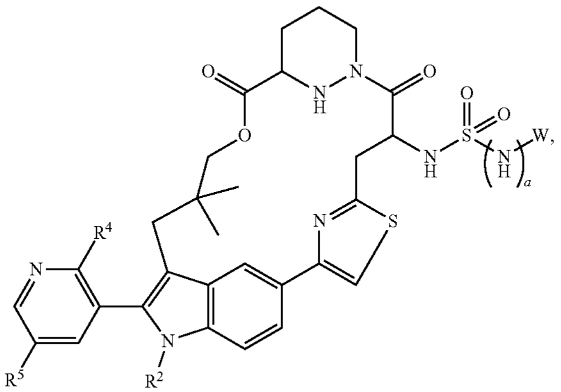

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl.

In some embodiments, the compound, or a pharmaceutically acceptable salt thereof, has the structure of Formula Va-4:

Formula Va-4

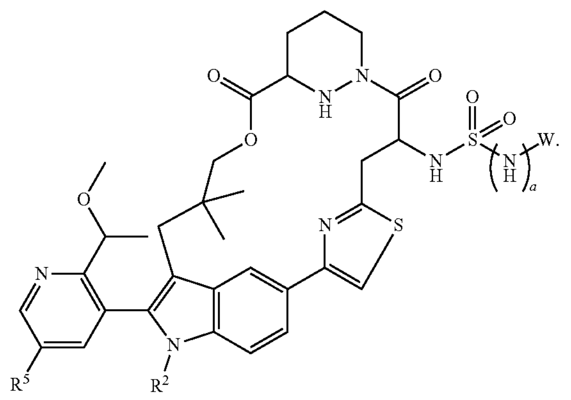

In some embodiments, the compound, or a pharmaceutically acceptable salt thereof, has the structure of Formula Va-5:

Formula Va-5

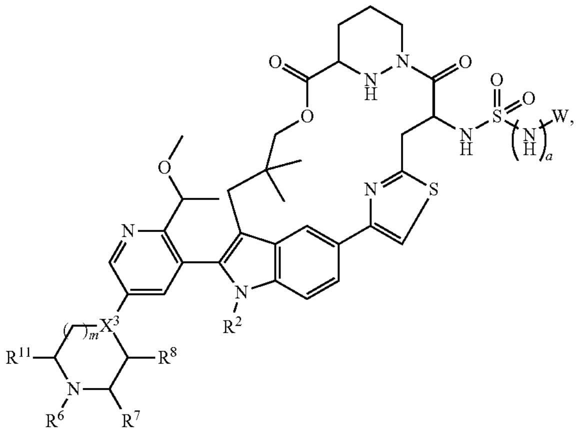

wherein $X^3$ is N or CH;

m is 1 or 2;

$R^6$, $R^7$, $R^8$, and $R^{11}$ are each independently selected from hydrogen, optionally substituted $C_1$-$C_6$, alkyl, optionally substituted $C_1$-$C_6$, heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^3$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl. In some embodiments, $X^3$ is N. In some embodiments, m is 1. In some embodiments, $R^1$ is hydrogen. In some embodiments, $X^3$ is N, m is 1, and $R^1$ is H.

In some embodiments, the compound, or a pharmaceutically acceptable salt thereof, has the structure of Formula VIa:

Formula VIa

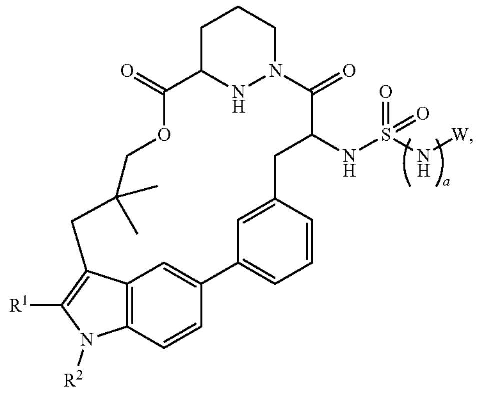

wherein a is 0 or 1.

In some embodiments, the compound, or a pharmaceutically acceptable salt thereof, has the structure of Formula VIa-1:

Formula VIa-1

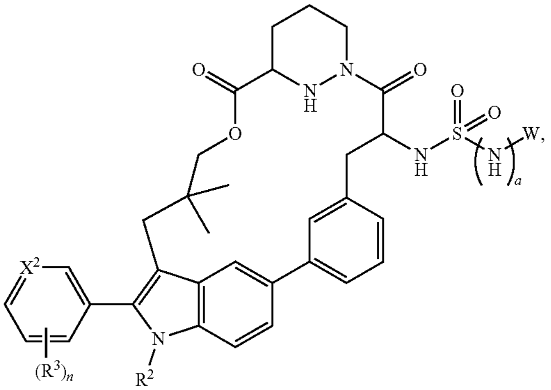

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl; and n is an integer from 1 to 4.

In some embodiments, the compound, or a pharmaceutically acceptable salt thereof, has the structure of Formula VIa-2:

Formula VIa-2

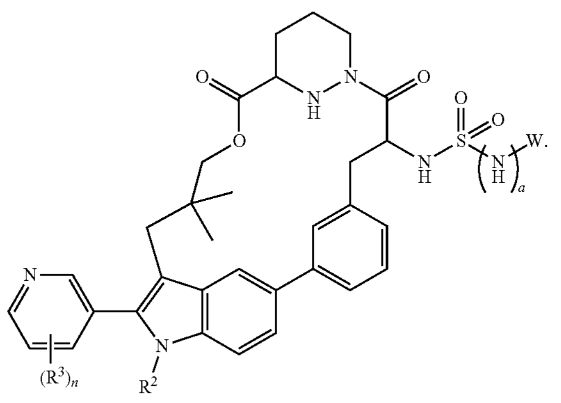

In some embodiments, the compound, or a pharmaceutically acceptable salt thereof, has the structure of Formula VIa-3:

Formula VIa-3

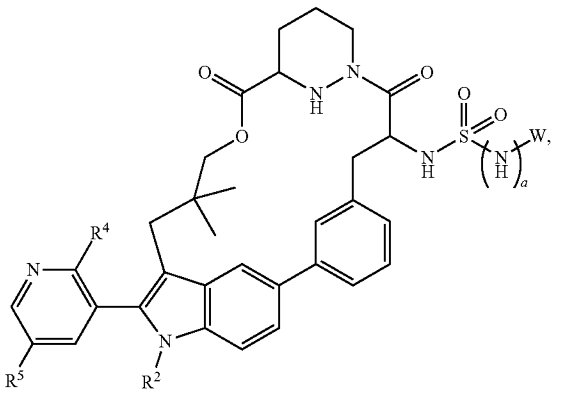

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl.

In some embodiments, the compound, or a pharmaceutically acceptable salt thereof, has the structure of Formula VIa-4:

Formula VIa-4

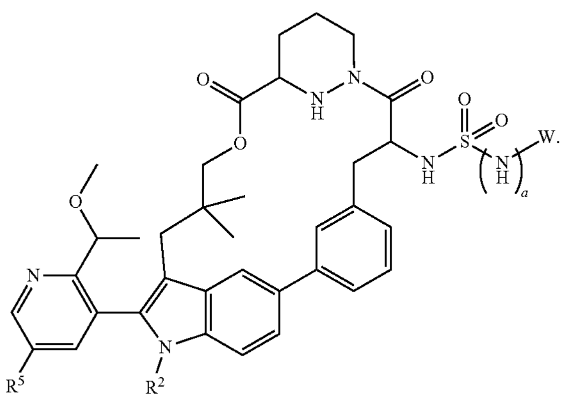

In some embodiments, the compound, or a pharmaceutically acceptable salt thereof, has the structure of Formula VIa-5:

Formula VIa-5

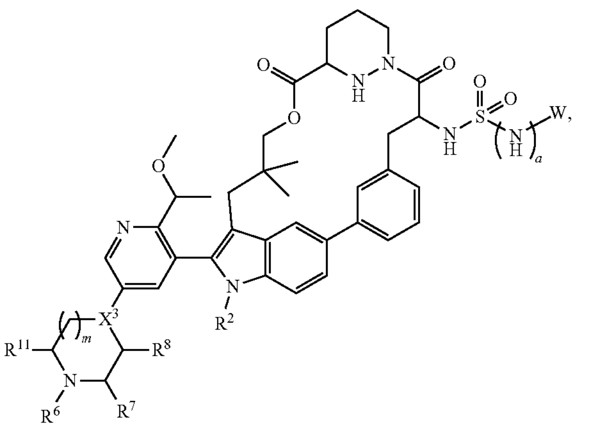

wherein $X^3$ is N or CH;

m is 1 or 2;

$R^6$, $R^7$, $R^8$, and $R^{11}$ are each independently selected from hydrogen, optionally substituted $C_1$-$C_6$alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl. In some embodiments, $X^3$ is N. In some embodiments, m is 1. In some embodiments, $R^1$ is hydrogen. In some embodiments, $X^3$ is N, m is 1, and $R^1$ is H.

In some embodiments, the compound, or a pharmaceutically acceptable salt thereof, has the structure of Formula VIIa:

Formula VIIa

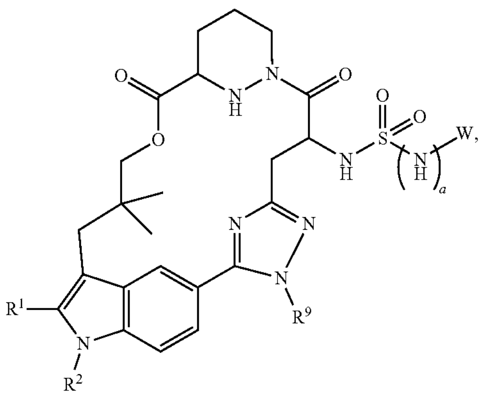

wherein $R^9$ is H or $C_1$-$C_6$ alkyl; and a is 0 or 1.

In some embodiments, the compound, or a pharmaceutically acceptable salt thereof, has the structure of Formula VIIa-1:

Formula VIIa-1

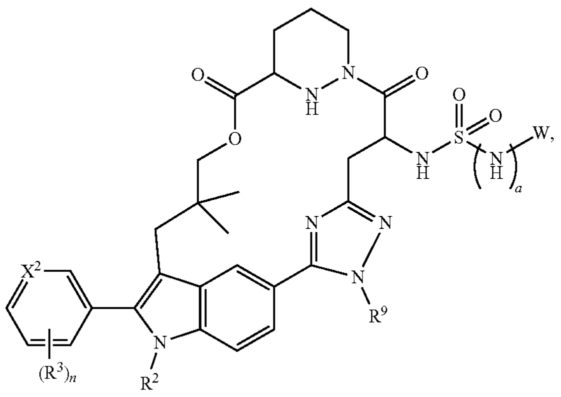

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl; and In some embodiments, the compound, or a pharmaceutically acceptable salt thereof, has the structure of Formula VIIa-2:

Formula VIIa-2

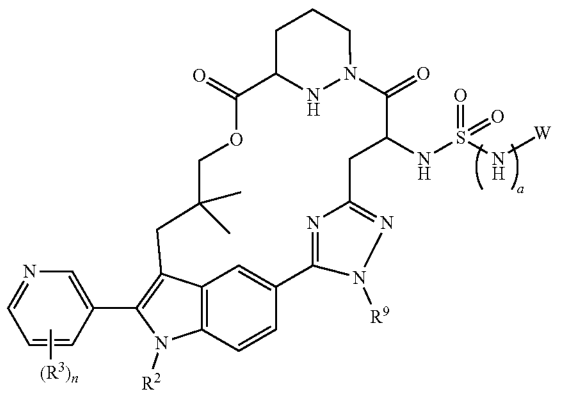

In some embodiments, the compound, or a pharmaceutically acceptable salt thereof, has the structure of Formula VIIa-3:

Formula VIIa-3

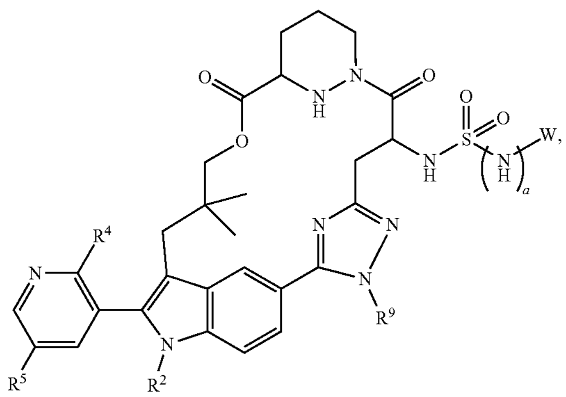

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl.

In some embodiments, the compound, or a pharmaceutically acceptable salt thereof, has the structure of Formula VIIa-4:

Formula VIIa-4

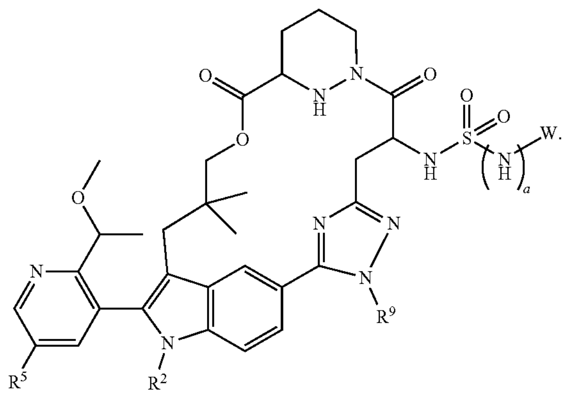

In some embodiments, the compound, or a pharmaceutically acceptable salt thereof, has the structure of Formula VIIa-5:

Formula VIIa-5

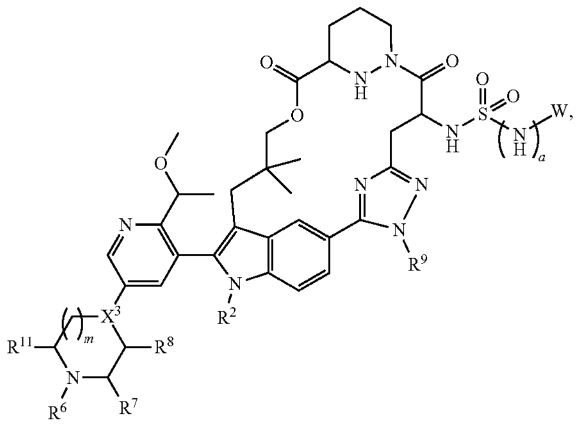

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl. In some embodiments, $X^3$ is N. In some embodiments, m is 1. In some embodiments, $R^1$ is hydrogen. In some embodiments, $X^3$ is N, m is 1, and $R^1$ is H.

In some embodiments (e.g., of any one of Formulae VIIa, VIIa-1, VIIa-2, VIIa-3, VIIa-4, or VIIa-5), $R^9$ is methyl.

In some embodiments, Y is —NHS(O)— or —NHS(O)NH—.

In some embodiments, the compound, or a pharmaceutically acceptable salt thereof, has the structure of Formula VIIIa:

Formula VIIIa

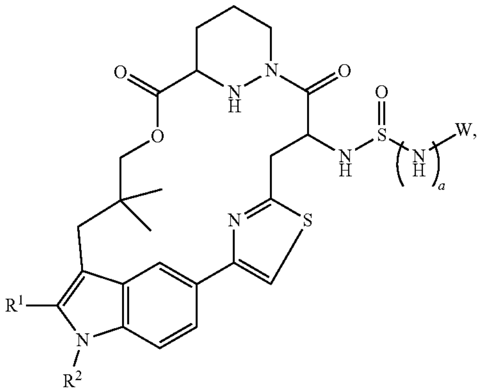

wherein a is 0 or 1.

In some embodiments, the compound, or a pharmaceutically acceptable salt thereof, has the structure of Formula VIIIa-1:

Formula VIIIa-1

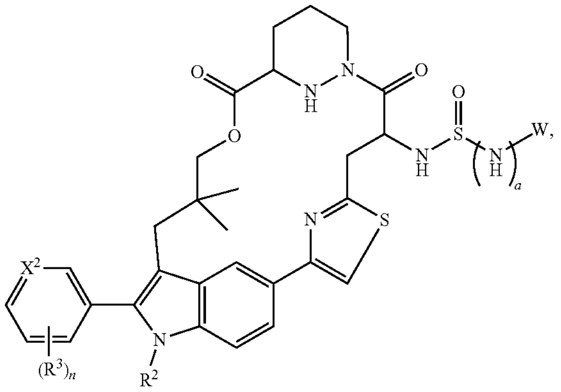

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl; and In some embodiments, the compound, or a pharmaceutically acceptable salt thereof, has the structure of Formula VIIIa-2:

Formula VIIIa-2

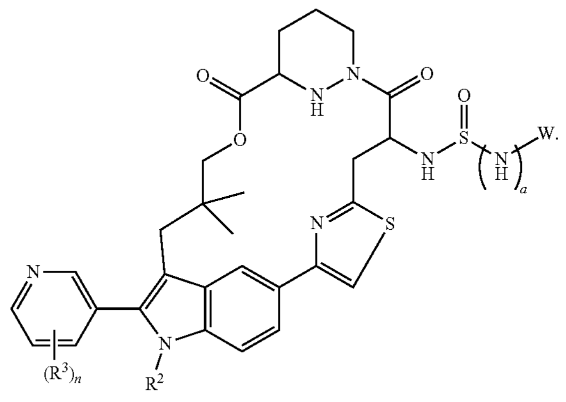

In some embodiments, the compound, or a pharmaceutically acceptable salt thereof, has the structure of Formula VIIIa-3:

Formula VIIIa-3

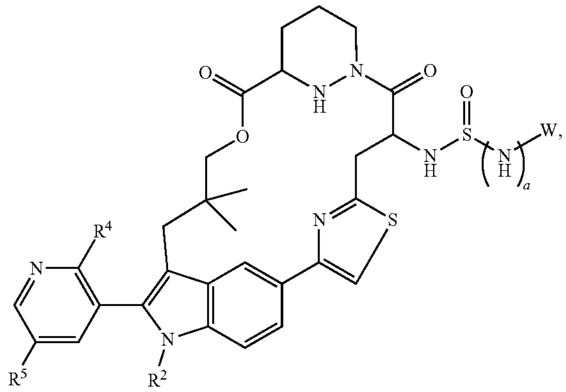

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl.

In some embodiments, the compound, or a pharmaceutically acceptable salt thereof, has the structure of Formula VIIIa-4:

Formula VIIIa-4

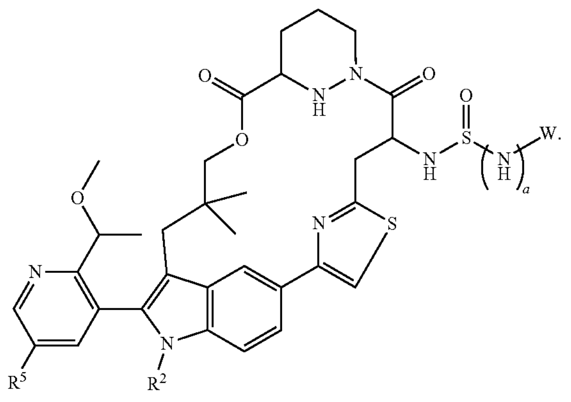

In some embodiments, the compound, or a pharmaceutically acceptable salt thereof, has the structure of Formula VIIIa-5:

Formula VIIIa-5

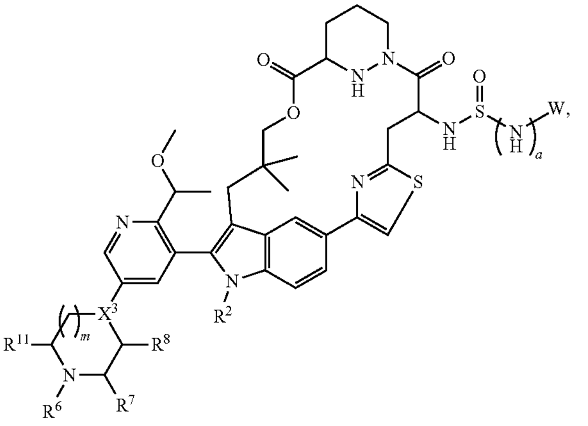

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl. In some embodiments, $X^3$ is N. In some embodiments, m is 1. In some embodiments, $R^1$ is hydrogen. In some embodiments, $X^3$ is N, m is 1, and $R^1$ is H.

In some embodiments, the compound, or a pharmaceutically acceptable salt thereof, has the structure of Formula IXa:

Formula IXa

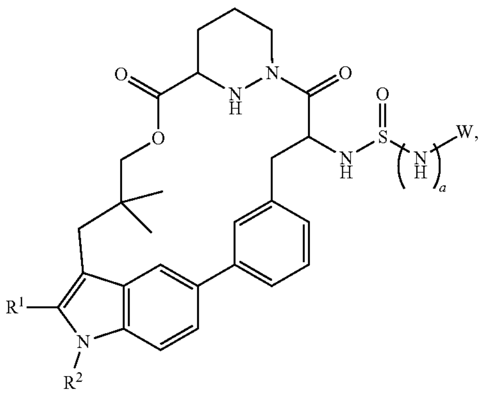

wherein a is 0 or 1.

In some embodiments, the compound, or a pharmaceutically acceptable salt thereof, has the structure of Formula IXa-1:

Formula IXa-1

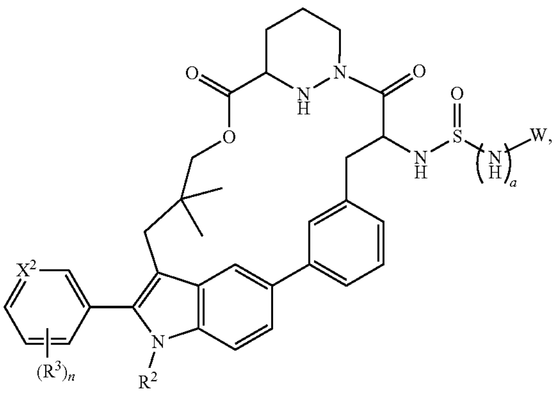

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl; and In some embodiments, the compound, or a pharmaceutically acceptable salt thereof, has the structure of Formula IXa-2:

Formula IXa-2

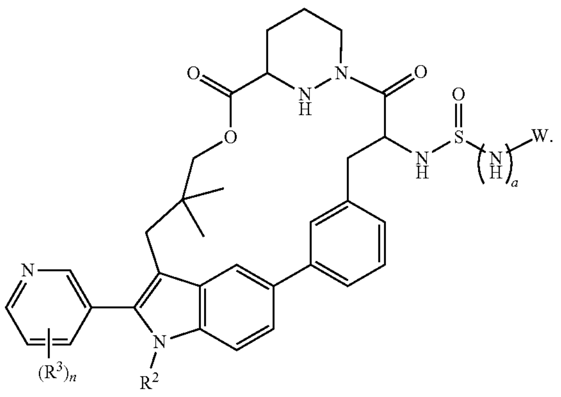

In some embodiments, the compound, or a pharmaceutically acceptable salt thereof, has the structure of Formula IXa-3:

Formula IXa-3

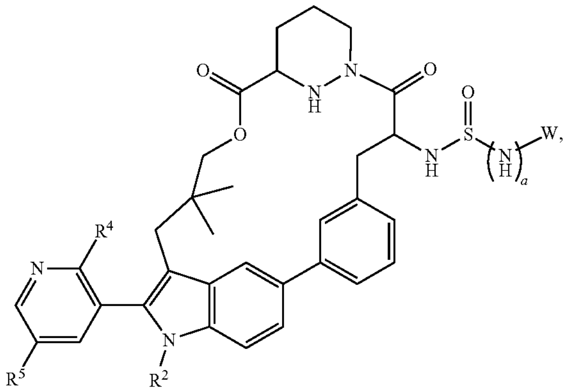

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl.

In some embodiments, the compound, or a pharmaceutically acceptable salt thereof, has the structure of Formula IXa-4:

Formula IXa-4

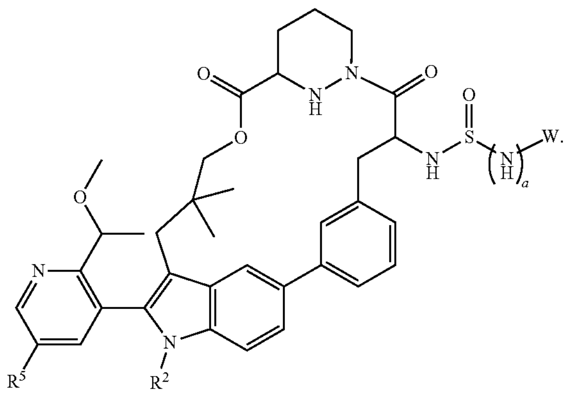

In some embodiments, the compound, or a pharmaceutically acceptable salt thereof, has the structure of Formula IXa-5:

Formula IXa-5

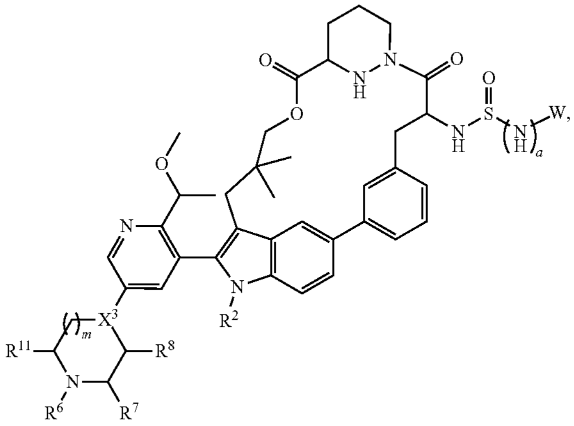

wherein $X^3$ is N or CH;

n is 1 or 2;

$R^6$, $R^7$, $R^8$, and $R^{11}$ are each independently selected from hydrogen, optionally substituted $C_1$-$C_8$alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl. In some embodiments, $X^3$ is N. In some embodiments, m is 1. In some embodiments, $R^1$ is hydrogen. In some embodiments, $X^3$ is N, m is 1, and $R^1$ is H.

In some embodiments, the compound, or a pharmaceutically acceptable salt thereof, has the structure of Formula Xa:

Formula Xa

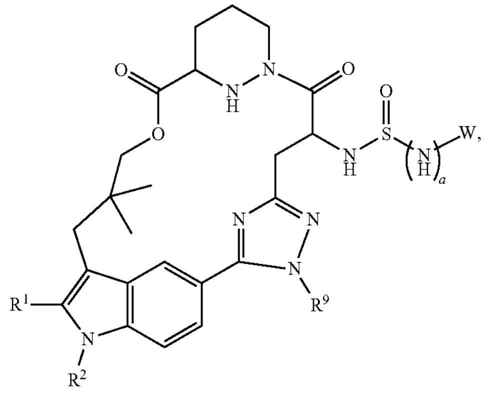

wherein $R^9$ is H or $C_1$-$C_6$ alkyl; and a is 0 or 1.

In some embodiments, the compound, or a pharmaceutically acceptable salt thereof, has the structure of Formula Xa-1:

Formula Xa-1

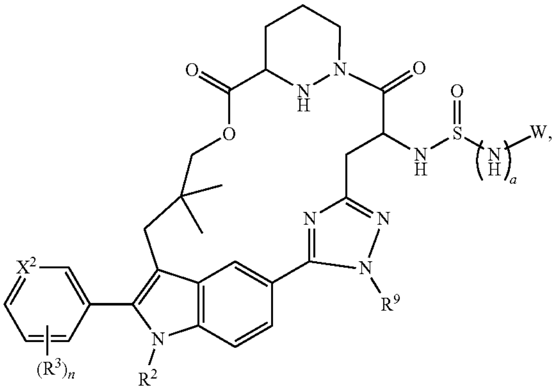

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl; and In some embodiments, the compound, or a pharmaceutically acceptable salt thereof, has the structure of Formula Xa-2:

Formula Xa-2

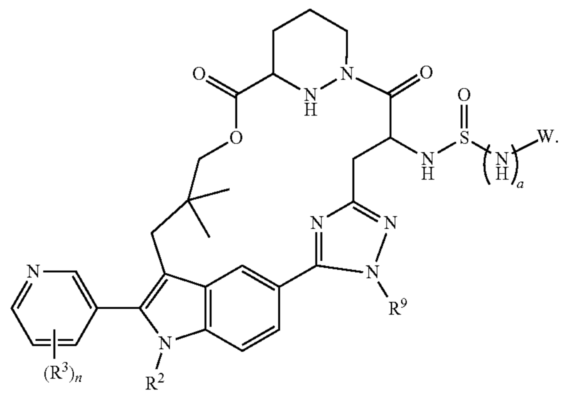

In some embodiments, the compound, or a pharmaceutically acceptable salt thereof, has the structure of Formula Xa-3:

Formula Xa-3

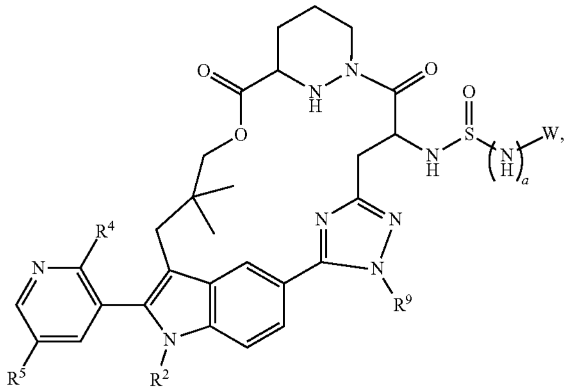

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl (e.g., optionally substituted 3 to 6-membered heterocycloalkyl), optionally substituted 6 to 10-membered aryl, or optionally substituted 5 to 10-membered heteroaryl.

In some embodiments, the compound, or a pharmaceutically acceptable salt thereof, has the structure of Formula Xa-4:

Formula Xa-4

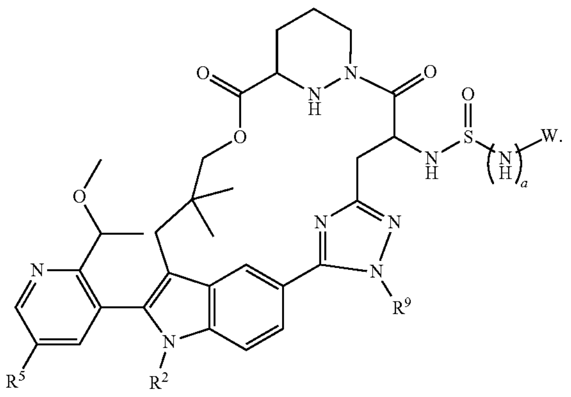

In some embodiments, the compound, or a pharmaceutically acceptable salt thereof, has the structure of Formula Xa-5:

Formula Xa-5

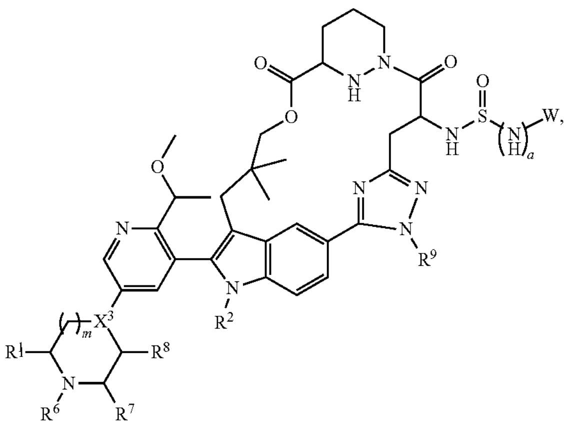

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl. In some embodiments, $X^3$ is N. In some embodiments, m is 1. In some embodiments, $R^1$ is hydrogen. In some embodiments, $X^3$ is N, m is 1, and $R^1$ is H.

In some embodiments (e.g., of any one of Formulae Xa, Xa-1, Xa-2, Xa-3, Xa-4, or Xa-5), $R^9$ is methyl.

In some embodiments of any aspect described herein, a is 0. In some embodiments of any of the above, a is 0.

In some embodiments of any aspect described herein, $R^2$ is optionally substituted $C_1$-$C_6$ alkyl. In some embodiments, $R^2$ is selected from —$CH_2CH_3$ or —$CH_2CF_3$.

In some embodiments of any aspect described herein, W is $C_1$-$C_4$ alkyl. In some embodiments, W is:

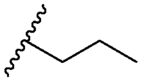 or 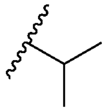.

In some embodiments of any aspect described herein, W is optionally substituted cyclopropyl, optionally substituted cyclobutyl, optionally substituted cyclopentyl, or optionally substituted cyclohexyl, optionally substituted piperidine, optionally substituted piperazine, optionally substituted pyridine, or optionally substituted phenyl.

In some embodiments of any aspect described herein, W is optionally substituted 3 to 10-membered heterocycloalkyl, optionally substituted 3 to 10-membered cycloalkyl, optionally substituted 6 to 10-membered aryl, or optionally substituted 5 to 10-membered heteroaryl.

In some embodiments of any aspect described herein, W is optionally substituted 3 to 10-membered heterocycloalkyl. In some embodiments, W is selected from the following, or a stereoisomer thereof:

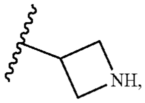 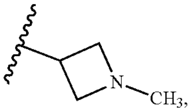 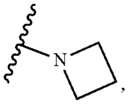,

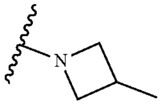, 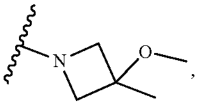, 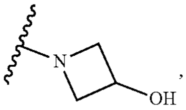,

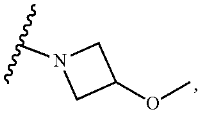, 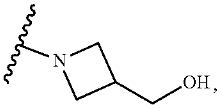,

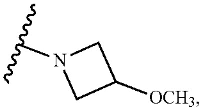 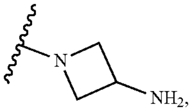

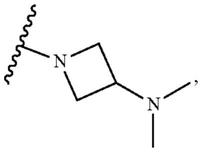, 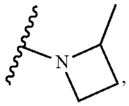, 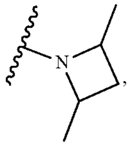,

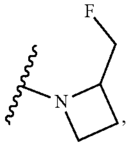, 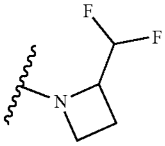, 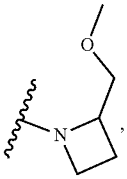,

-continued

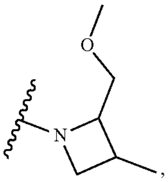, 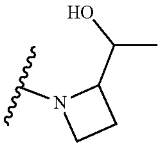, 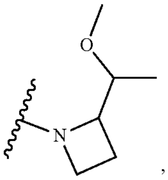,

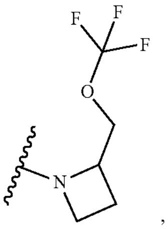, 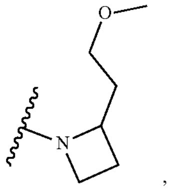, 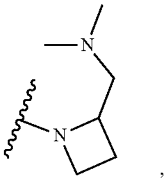,

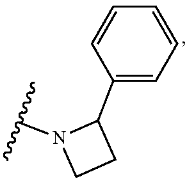, 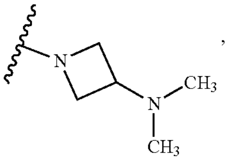,

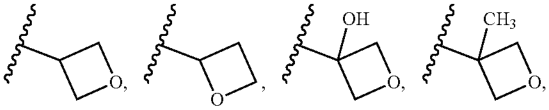

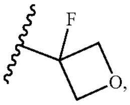 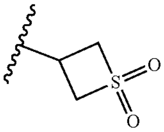, 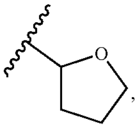

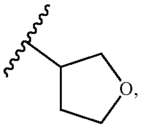 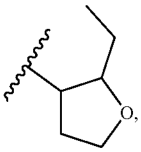 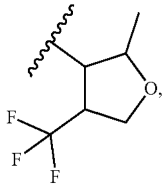

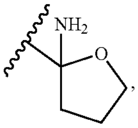 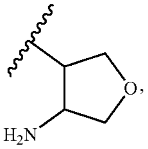 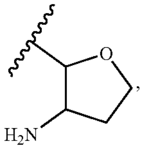

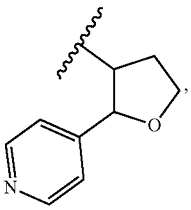, 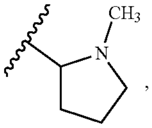, 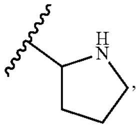

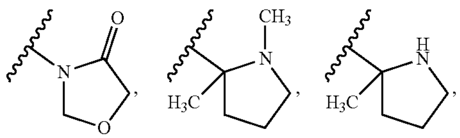

-continued
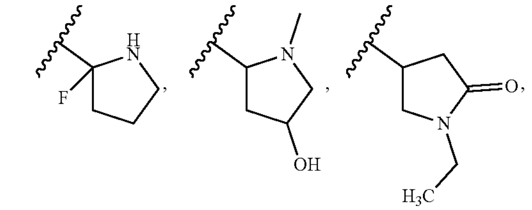
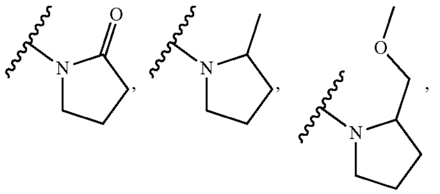
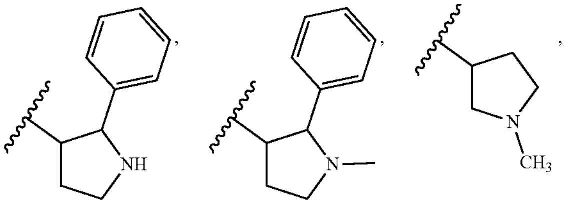
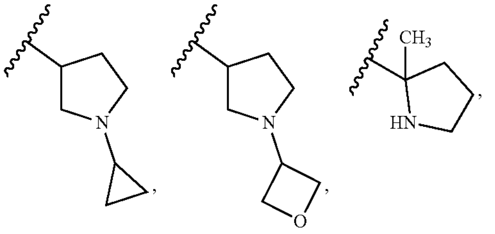
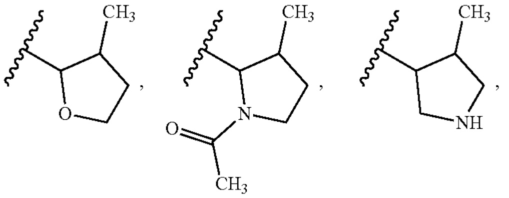
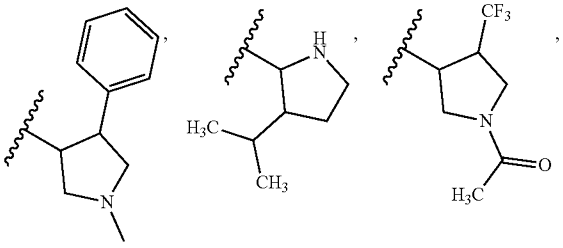
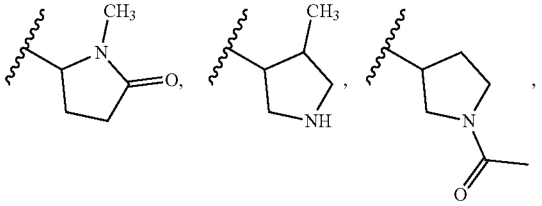
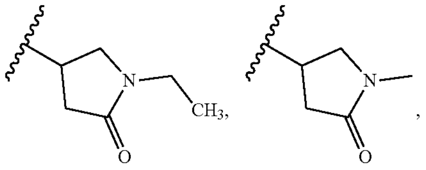
-continued
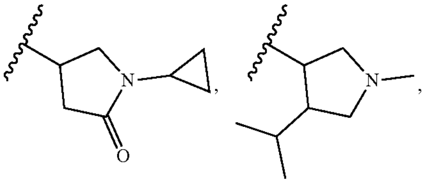
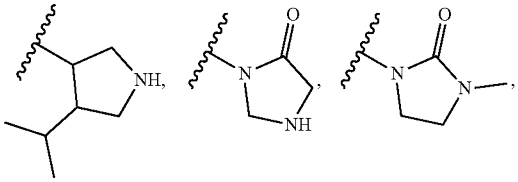
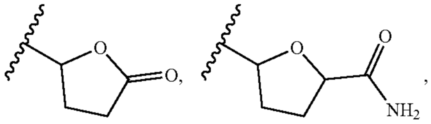
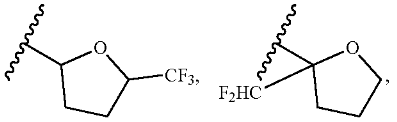
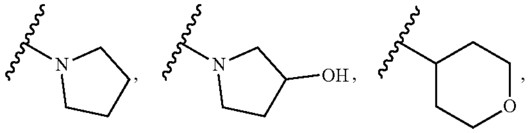
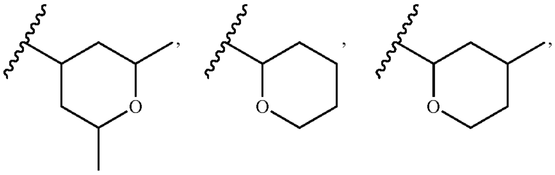
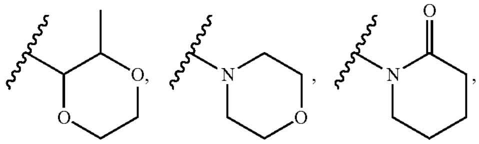
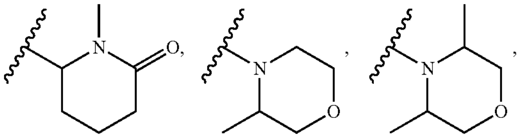
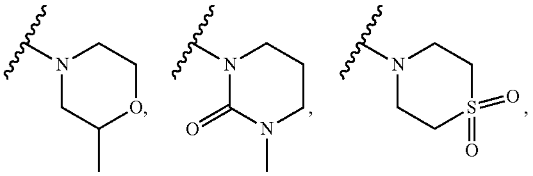
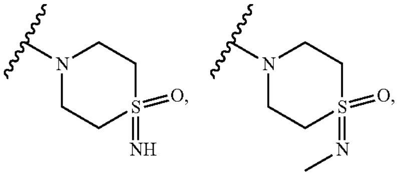
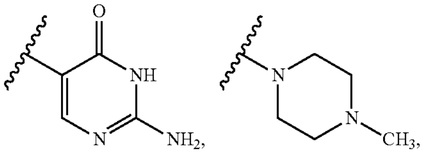

-continued
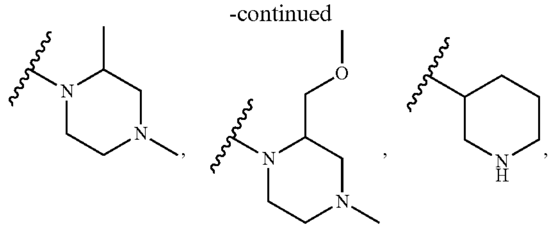
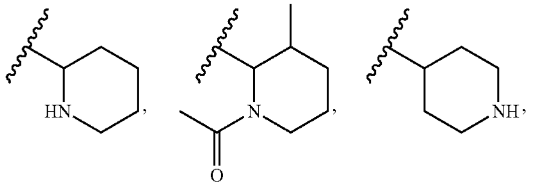
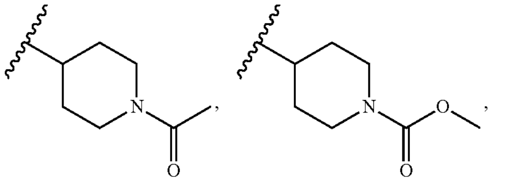
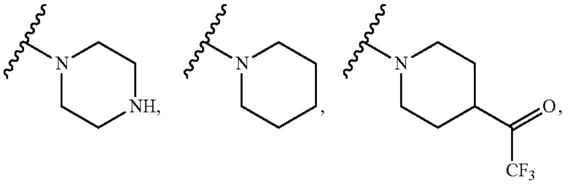
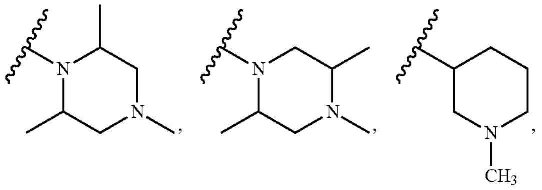
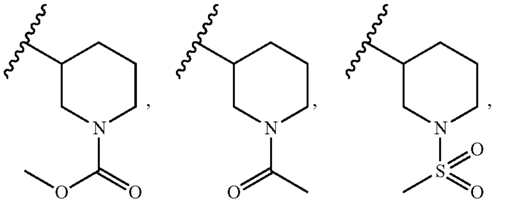
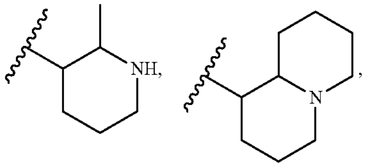
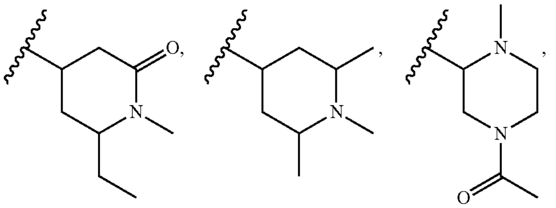
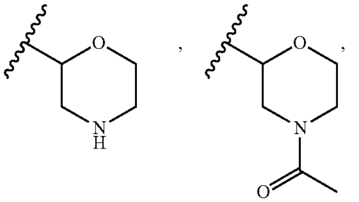
-continued
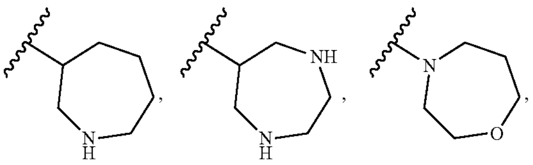
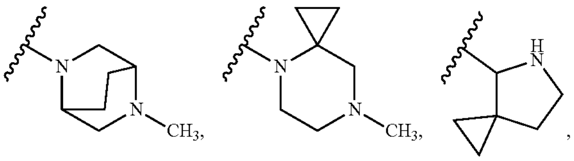
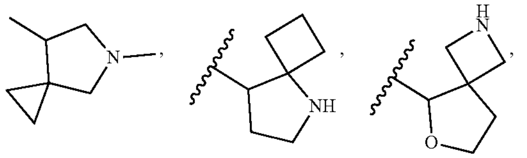
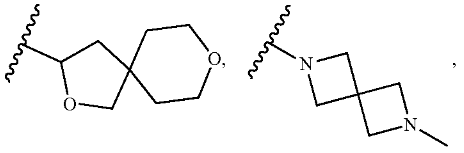
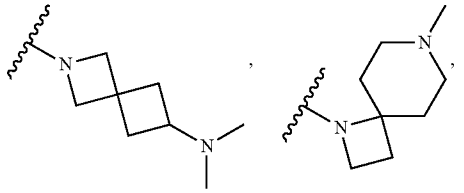
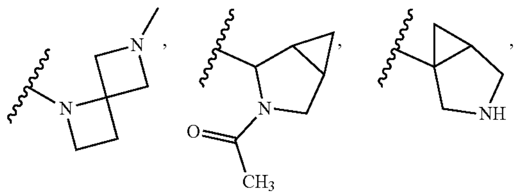
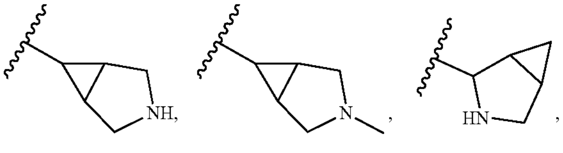
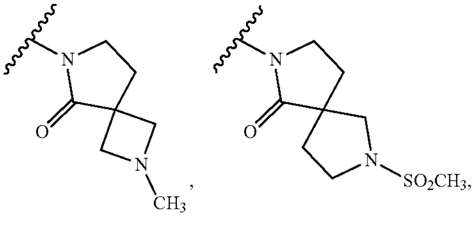
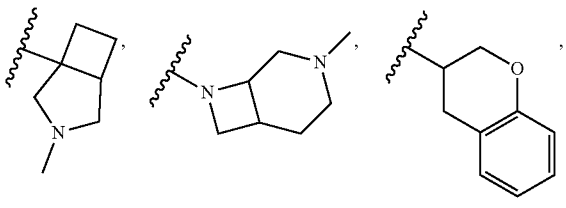

-continued
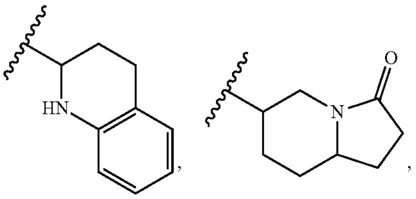
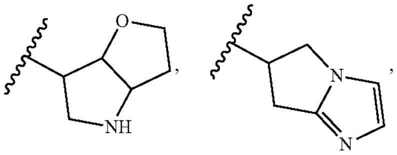
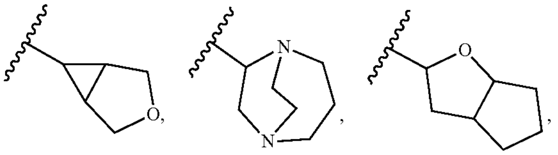
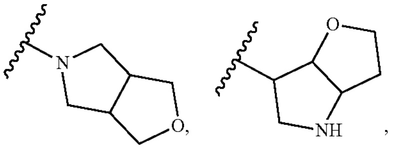
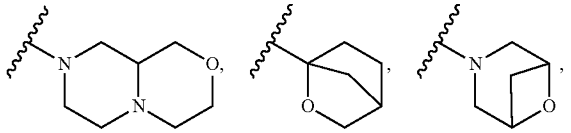
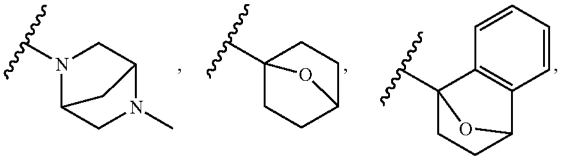
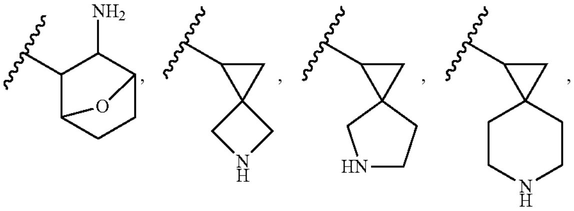
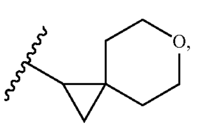
or
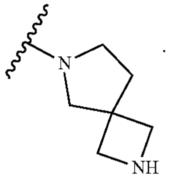
In some embodiments, W is selected from the following, or a stereoisomer thereof:
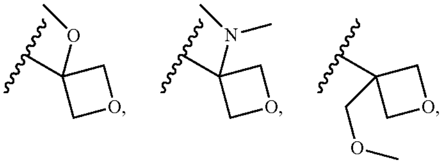
-continued
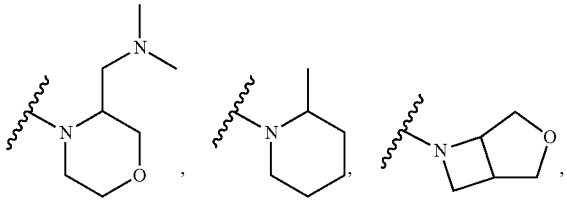
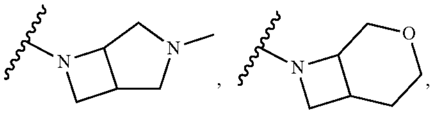
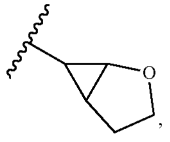
or
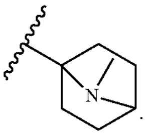
In some embodiments of any aspect described herein, WV is optionally substituted 3 to 10-membered cycloalkyl. In some embodiments, W is selected from the following, or a stereoisomer thereof:
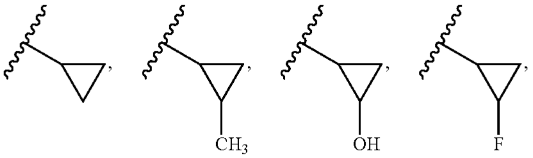
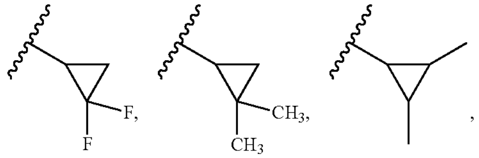
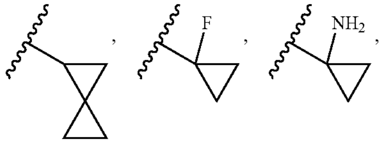
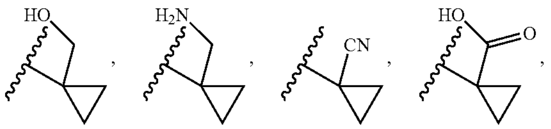
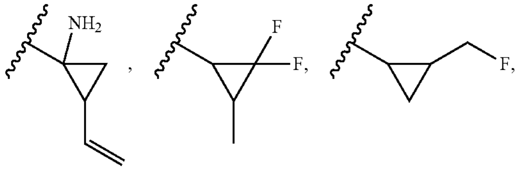
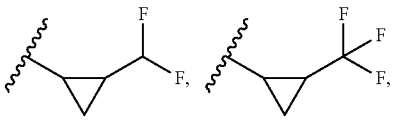
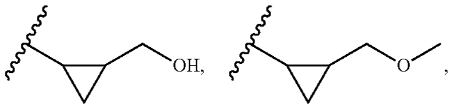

-continued

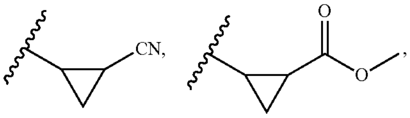

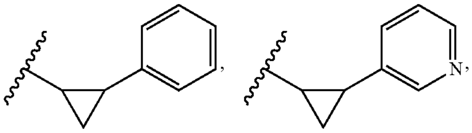

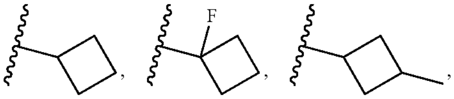

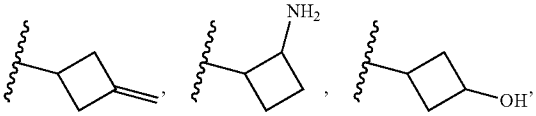

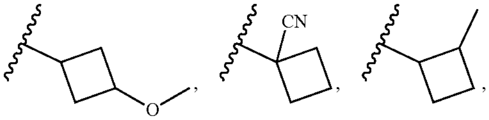

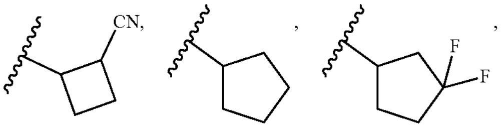

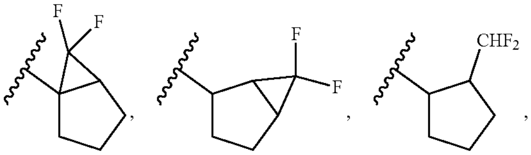

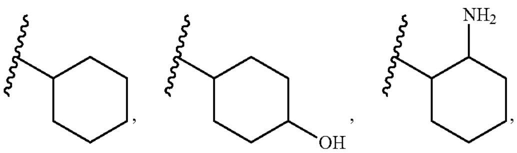

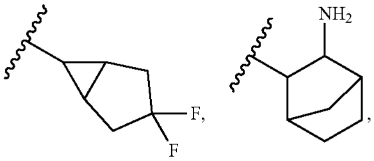

or

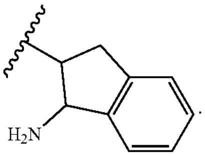

In some embodiments, W is selected from the following, or a stereoisomer thereof:

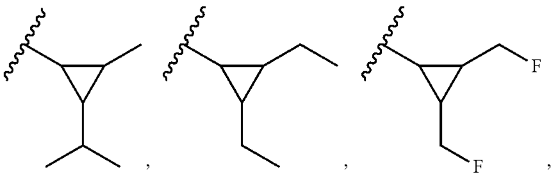

-continued

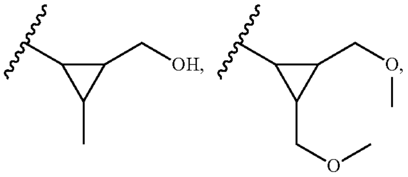

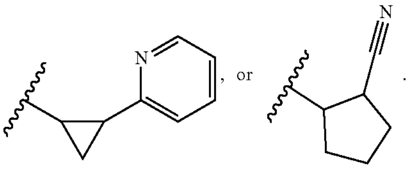

In some embodiments of any aspect described herein, W is optionally substituted 5 to 10-membered heteroaryl. In some embodiments, W is selected from the following, or a stereoisomer thereof:

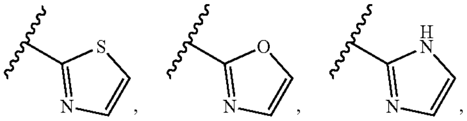

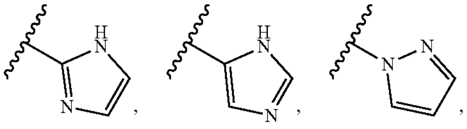

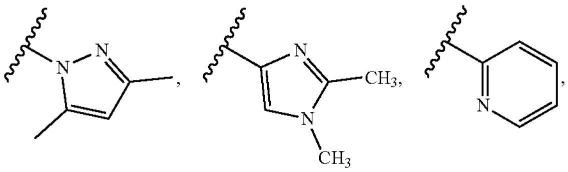

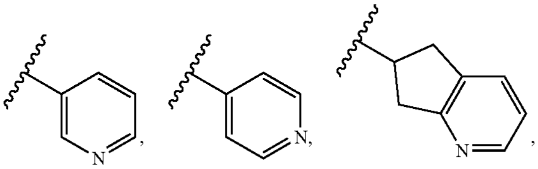

or

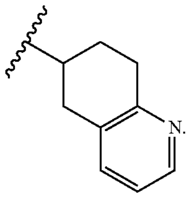

In some embodiments of any aspect described herein, W is optionally substituted 6 to 10-membered aryl. In some embodiments, W is optionally substituted phenyl.

In some embodiments of any aspect described herein, W is optionally substituted $C_1$-$C_3$ heteroalkyl. In some embodiments, W is selected from the following, or a stereoisomer thereof:

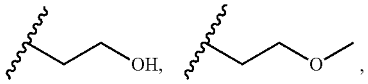

or

-continued

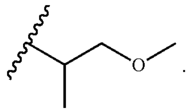

In some embodiments, a compound of the present invention is selected from Table 1a, or a pharmaceutically acceptable salt or stereoisomer thereof. In some embodiments, a compound of the present invention is selected from Table 1a, or a pharmaceutically acceptable salt or atropisomer thereof.

TABLE 1a

| Certain Compounds of the Present Invention | |
|---|---|
| Ex. # | Structure |
| A1 | 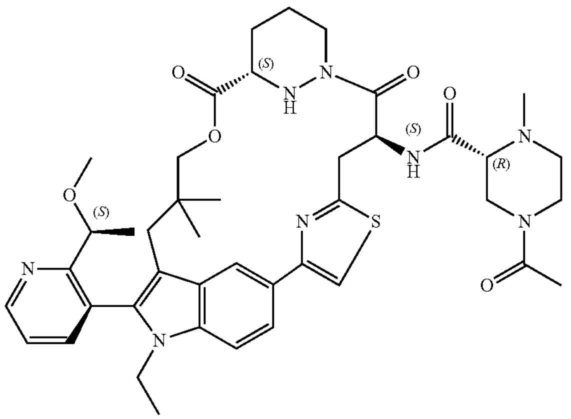 |
| A2 | 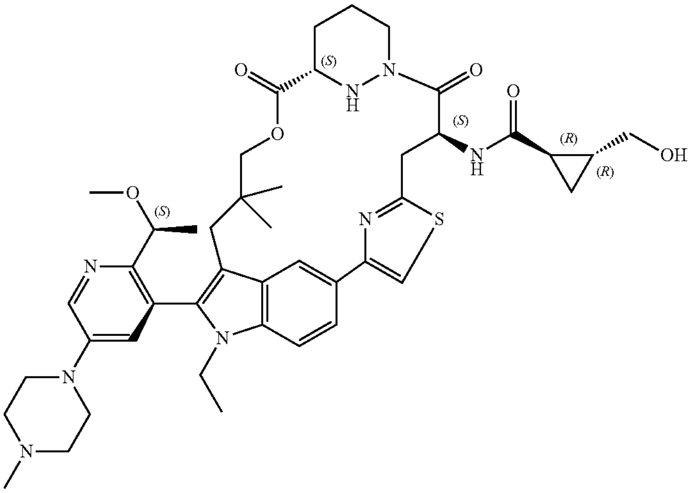 |

TABLE 1a-continued
| Certain Compounds of the Present Invention | |
|---|---|
| Ex. # | Structure |
| A3 | 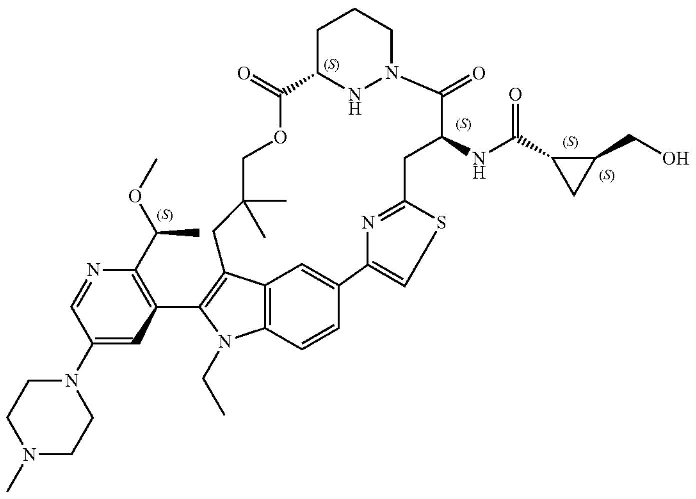 |
| A4 | 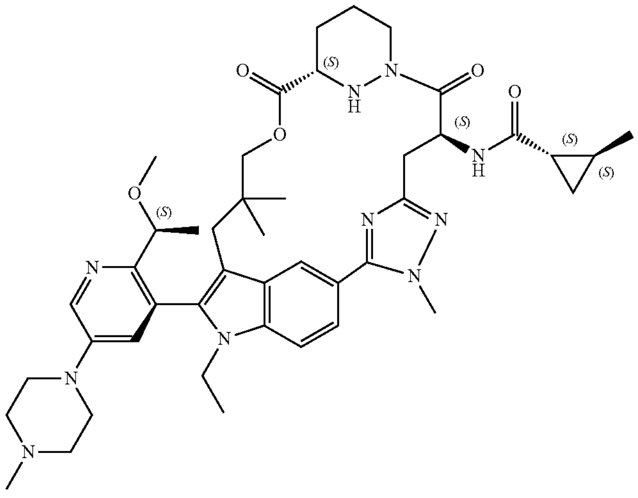 |
| A5 | 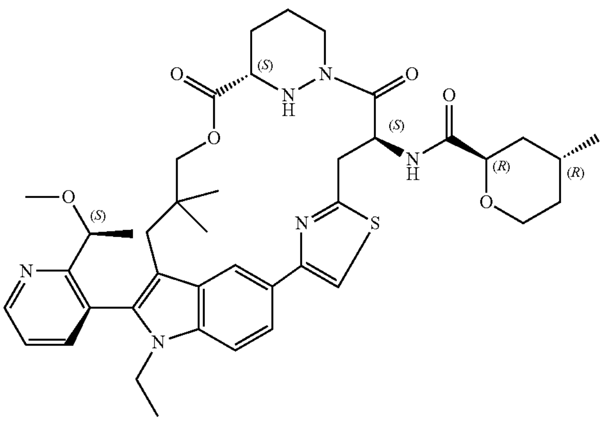 |

TABLE 1a-continued
| Certain Compounds of the Present Invention | |
|---|---|
| Ex. # | Structure |
| A6 | 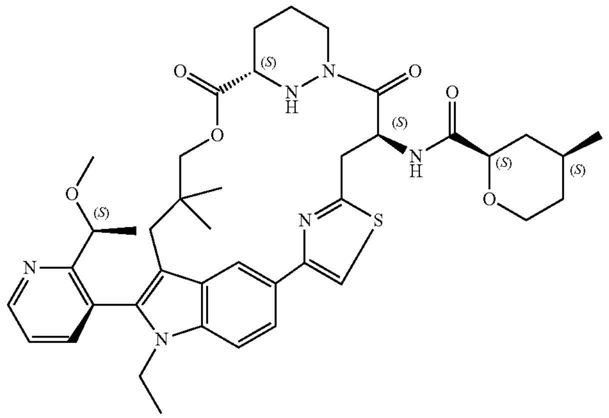 |
| A7 | 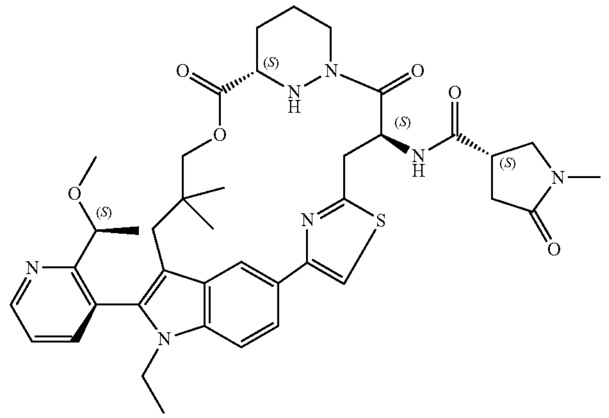 |
| A8 | 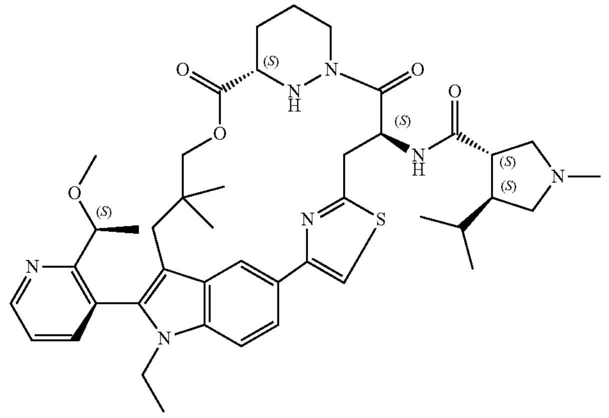 |

TABLE 1a-continued
| Certain Compounds of the Present Invention | |
|---|---|
| Ex. # | Structure |
| A9 | 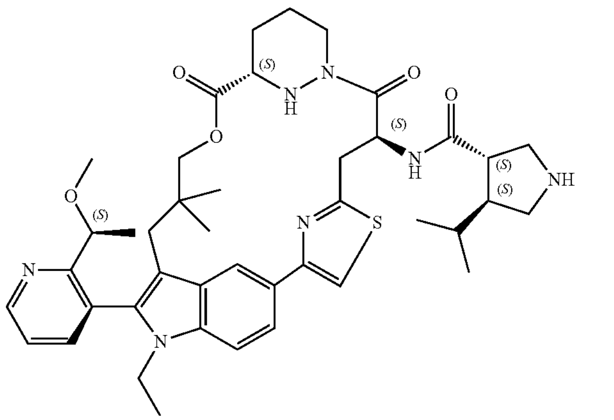 |
| A10 | 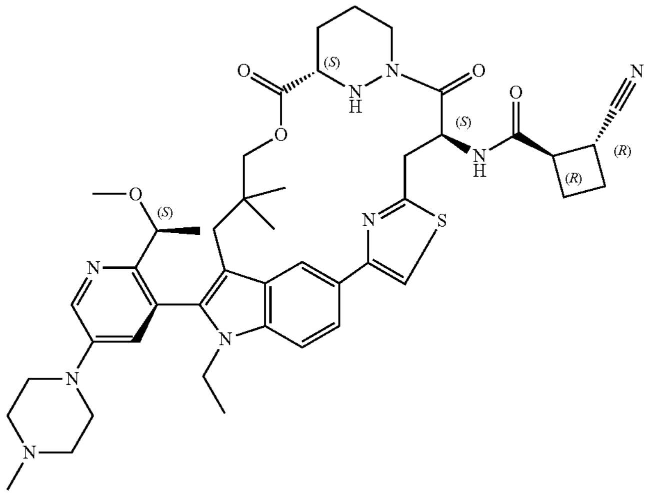 |
| A11 | 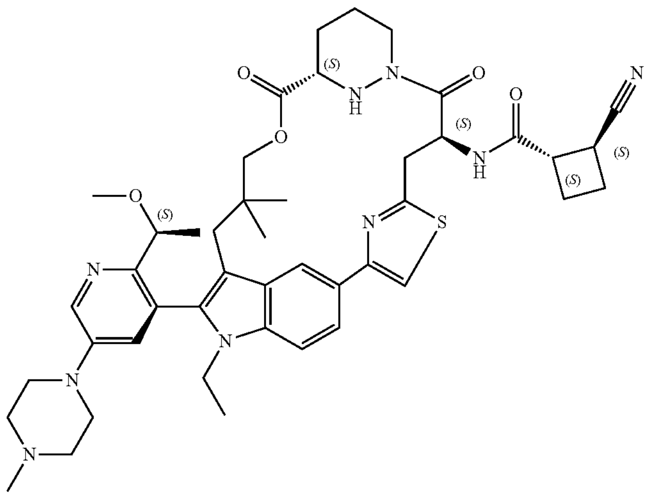 |

TABLE 1a-continued
Certain Compounds of the Present Invention
| Ex. # | Structure |
|---|---|
| A12 | 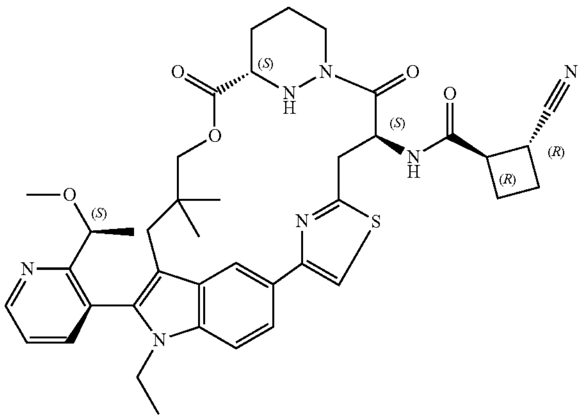 |
| A13 | 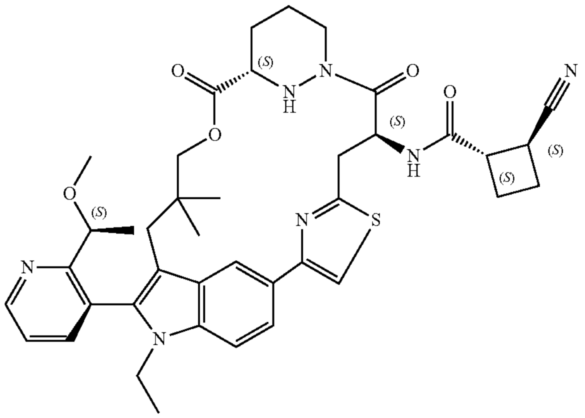 |
| A14 | 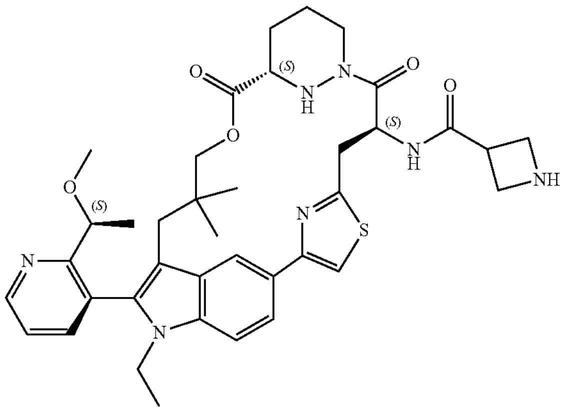 |

TABLE 1a-continued
| Certain Compounds of the Present Invention | |
|---|---|
| Ex. # | Structure |
| A15 | 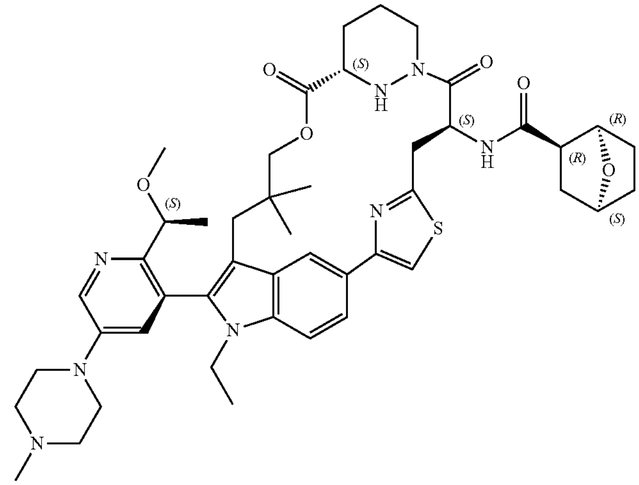 |
| A16 | 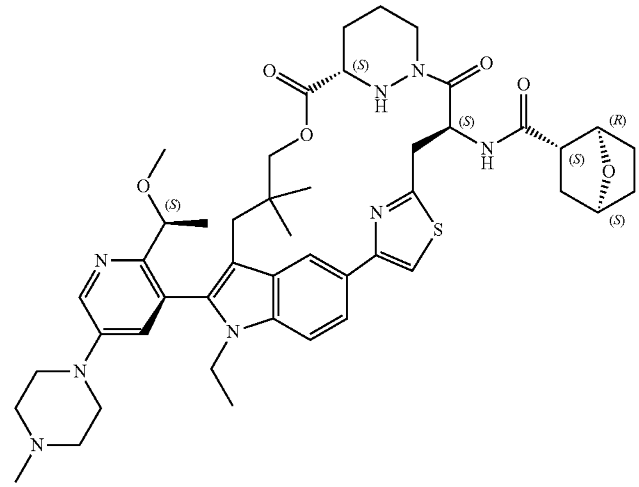 |
| A17 | 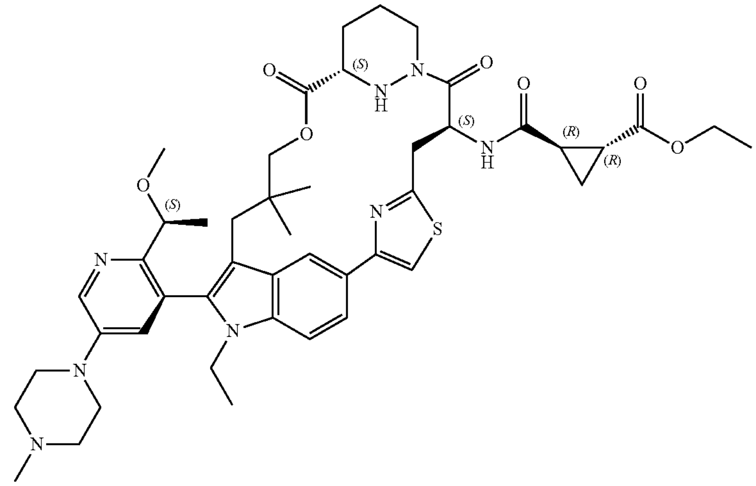 |

TABLE 1a-continued
| Certain Compounds of the Present Invention | |
|---|---|
| Ex. # | Structure |
| A18 | 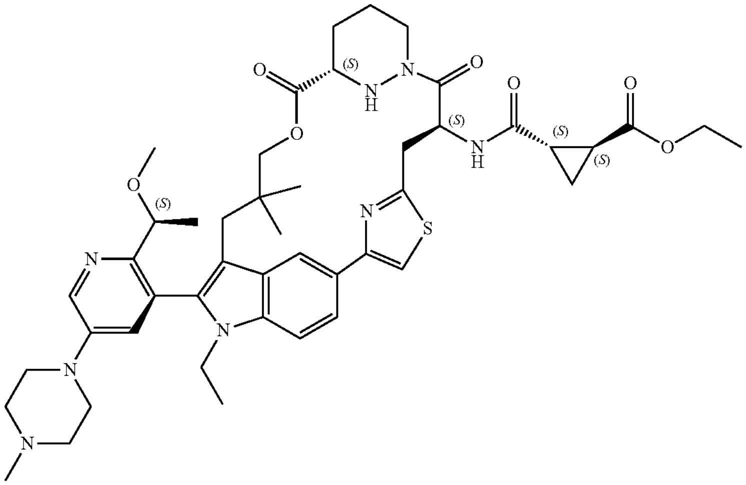 |
| A19 | 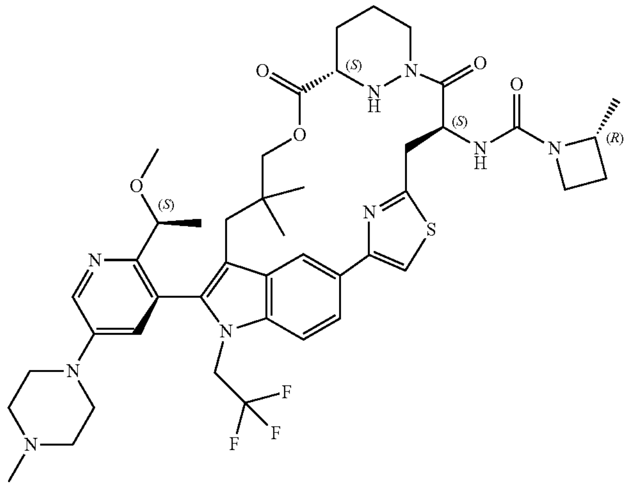 |
| A20 | 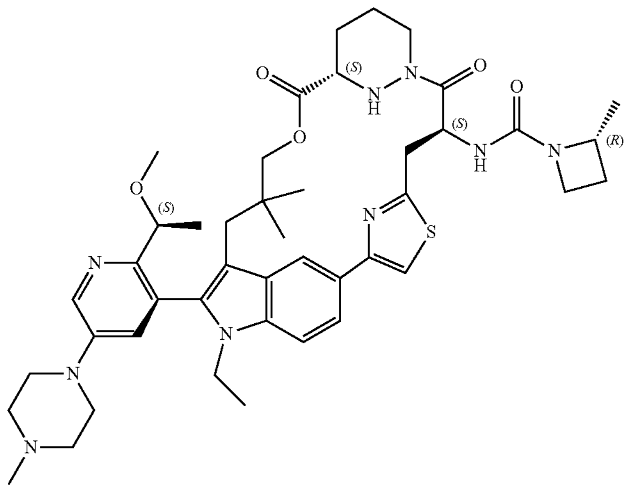 |

TABLE 1a-continued
| Certain Compounds of the Present Invention | |
|---|---|
| Ex. # | Structure |
| A21 | 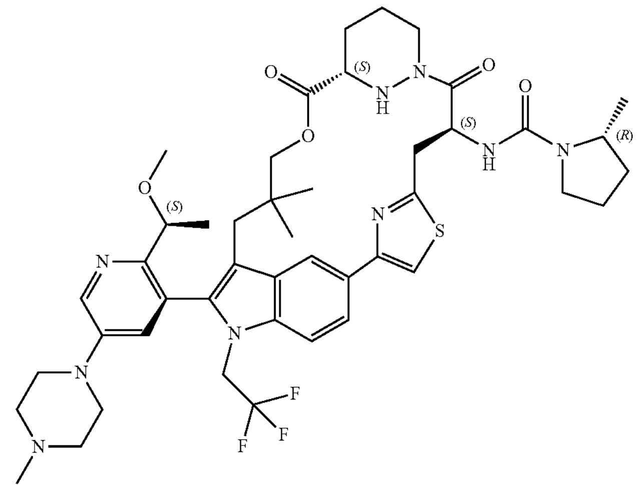 |
| A22 | 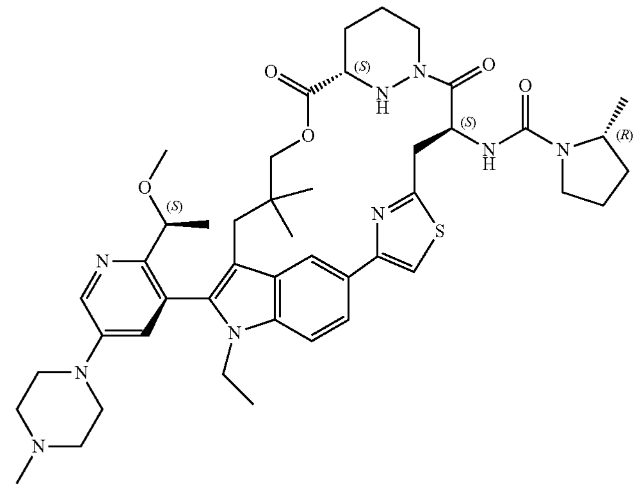 |
| A23 | 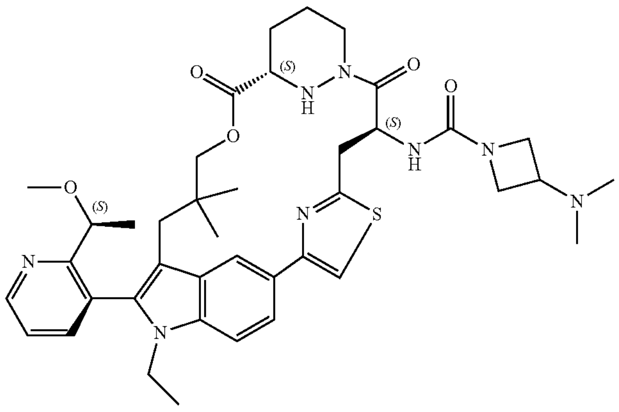 |

TABLE 1a-continued
| Certain Compounds of the Present Invention | |
| --- | --- |
| Ex. # | Structure |
| A24 | 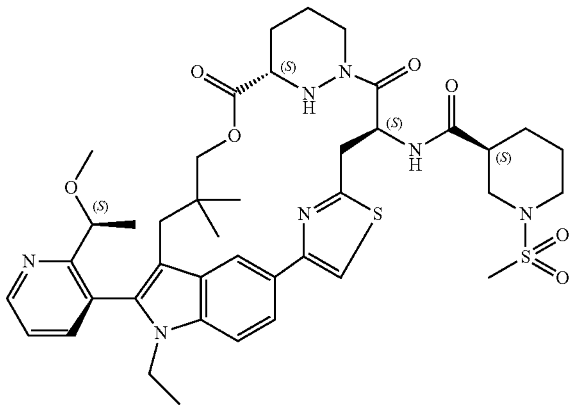 |
| A25 | 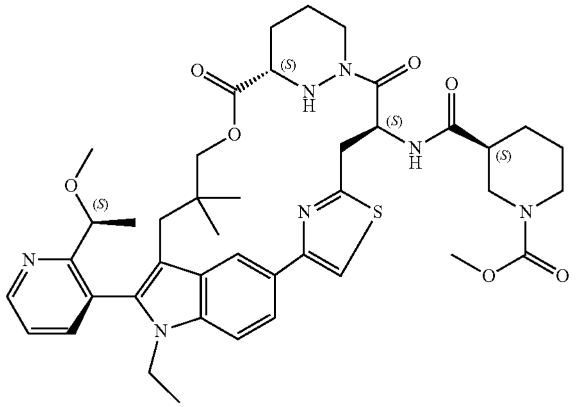 |
| A26 | 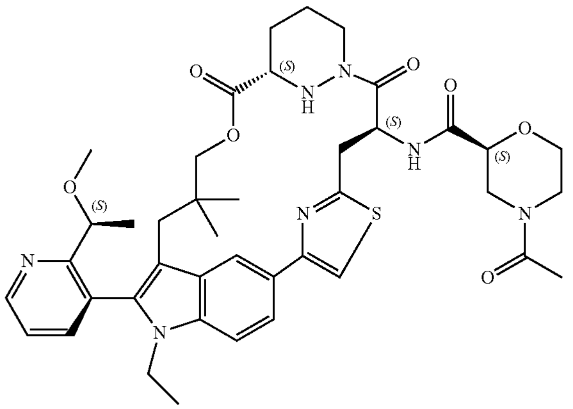 |

TABLE 1a-continued
| Certain Compounds of the Present Invention | |
|---|---|
| Ex. # | Structure |
| A27 | 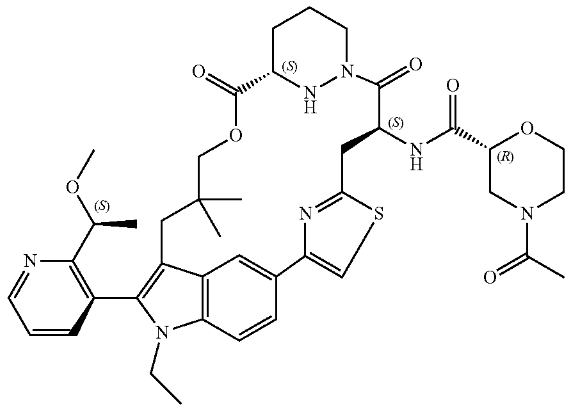 |
| A28 | 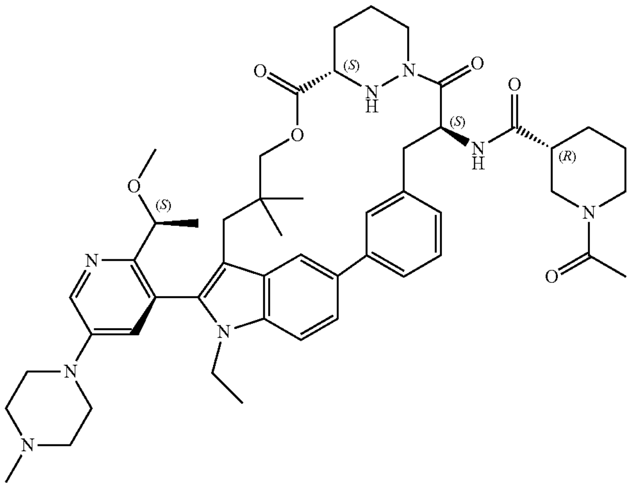 |
| A29 | 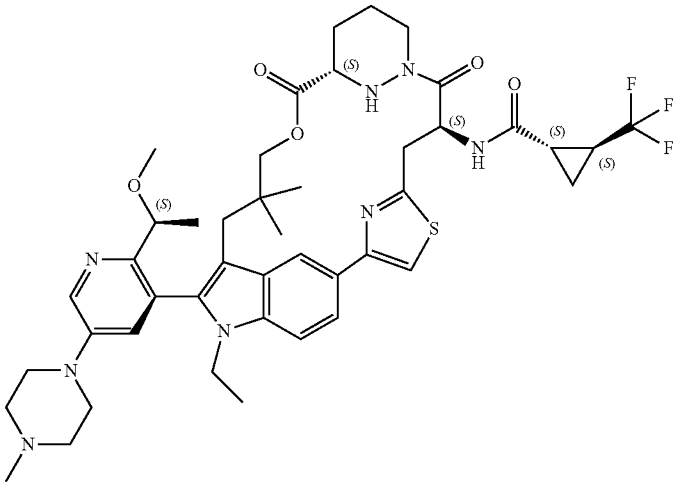 |

TABLE 1a-continued
| Certain Compounds of the Present Invention | |
|---|---|
| Ex. # | Structure |
| A30 | 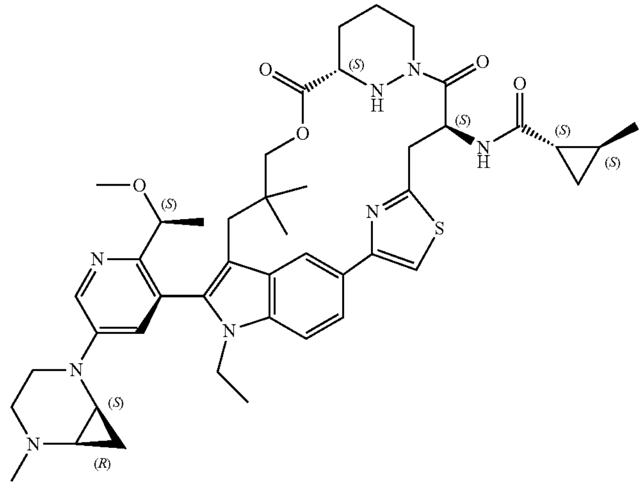 |
| A31 | 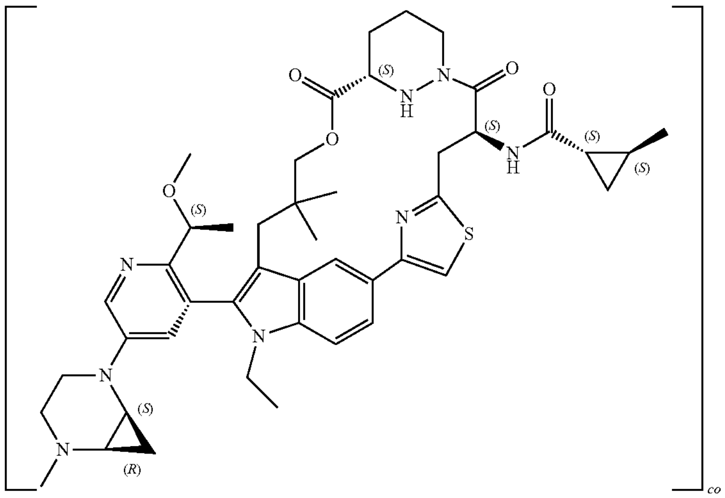 |
| A32 | 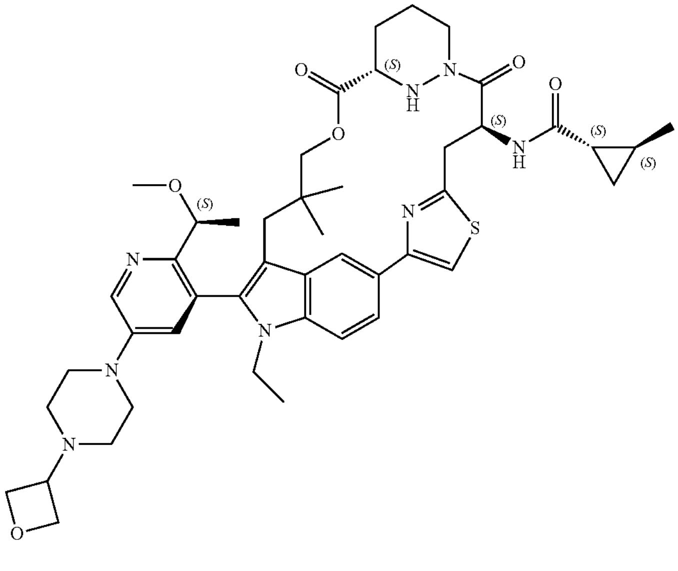 |

TABLE 1a-continued
| Certain Compounds of the Present Invention | |
| --- | --- |
| Ex. # | Structure |
| A33 | 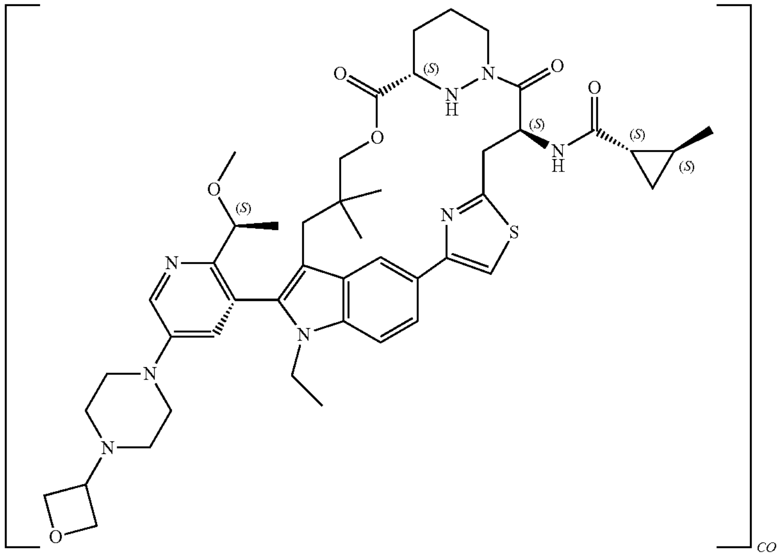 CO |
| A34 | 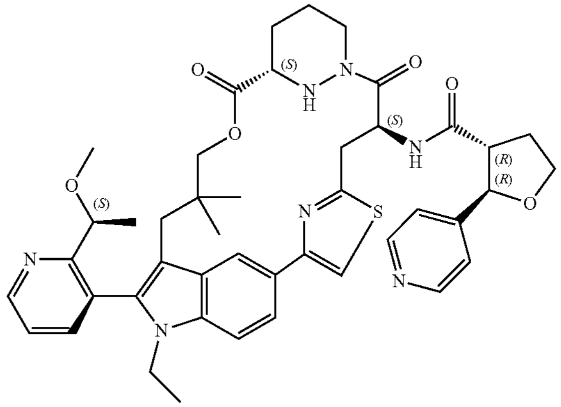 |
| A35 | 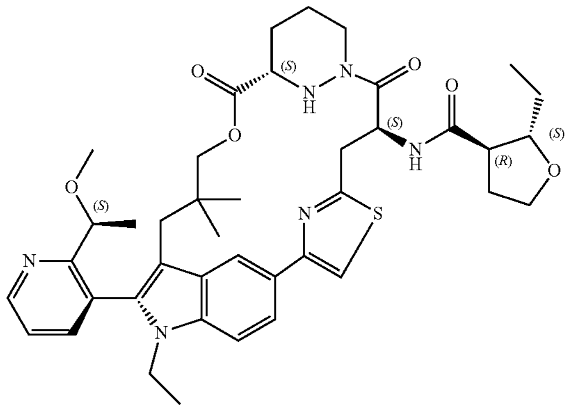 |

TABLE 1a-continued
| Certain Compounds of the Present Invention | |
|---|---|
| Ex. # | Structure |
| A36 | 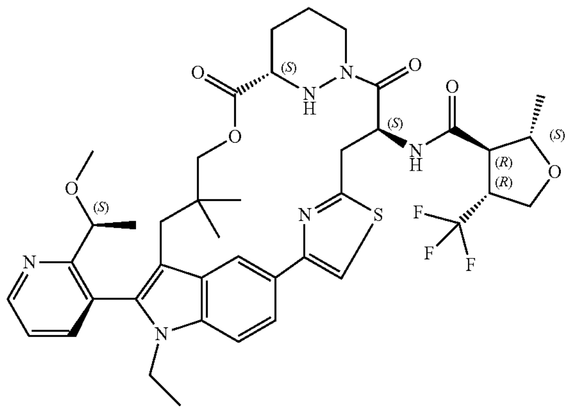 |
| A37 | 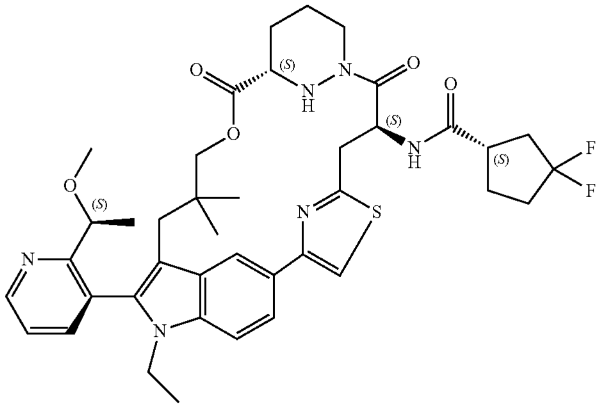 |
| A38 | 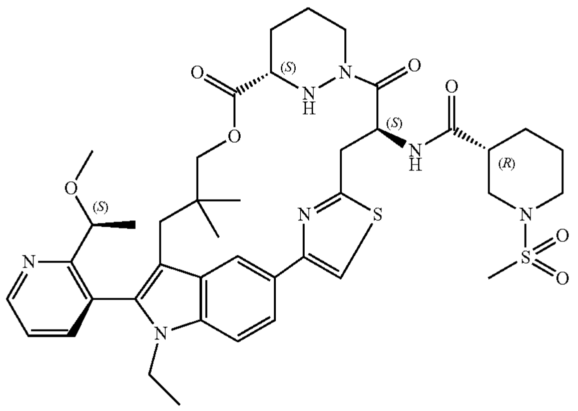 |

TABLE 1a-continued
| Certain Compounds of the Present Invention | |
|---|---|
| Ex. # | Structure |
| A39 | 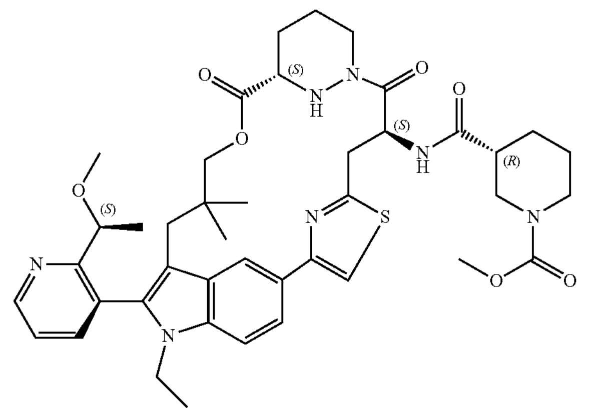 |
| A40 | 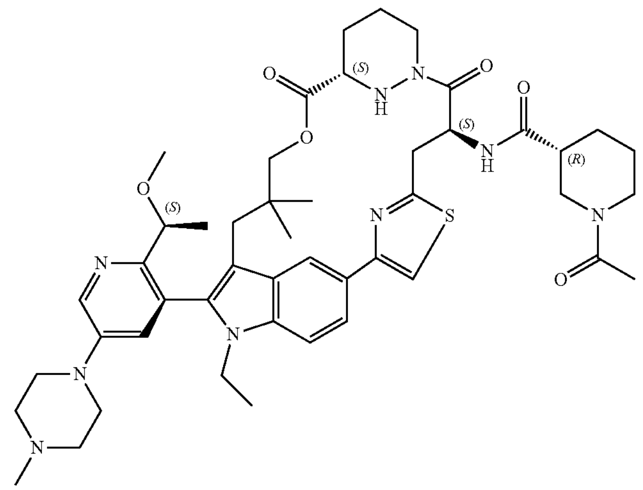 |
| A41 | 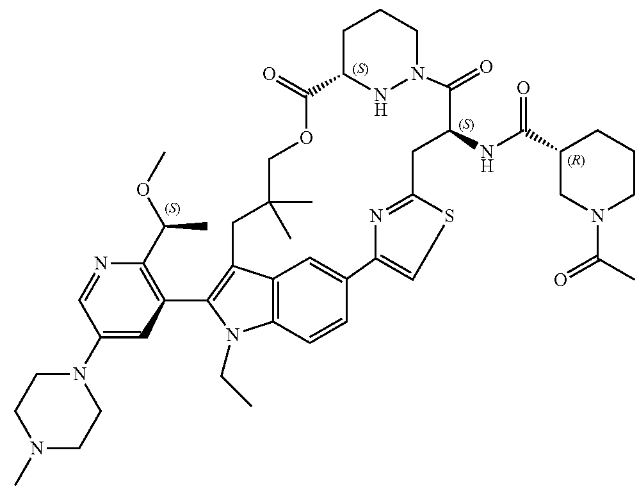 |

TABLE 1a-continued
| Certain Compounds of the Present Invention | |
|---|---|
| Ex. # | Structure |
| A42 | 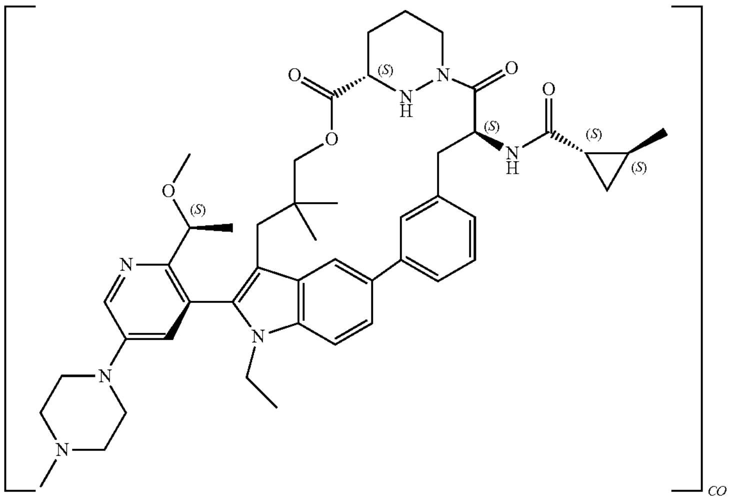 |
| A43 | 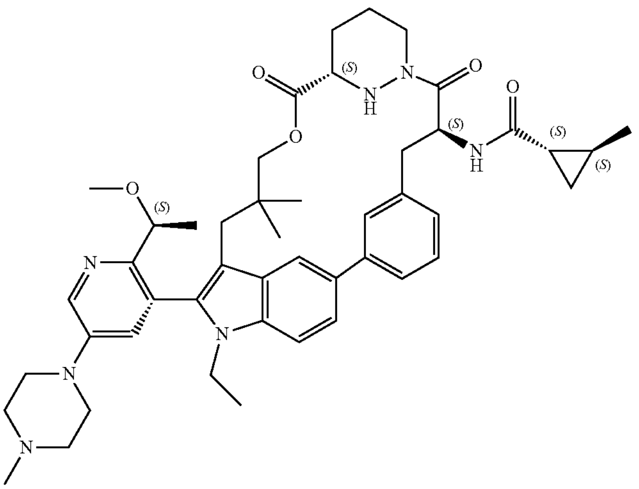 |
| A44 | 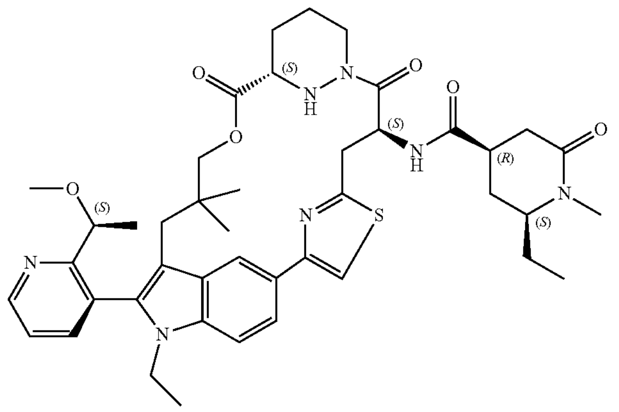 |

TABLE 1a-continued
| Certain Compounds of the Present Invention | |
|---|---|
| Ex. # | Structure |
| A45 | 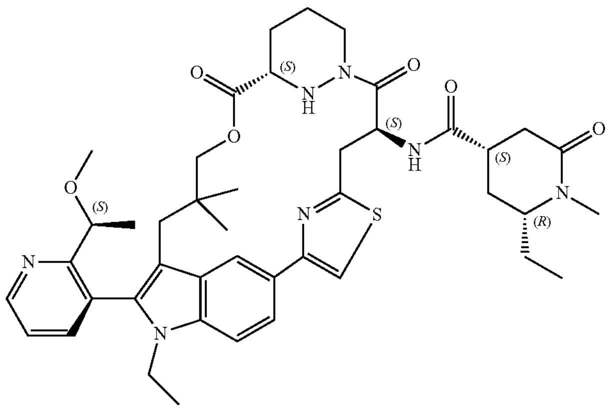 |
| A46 | 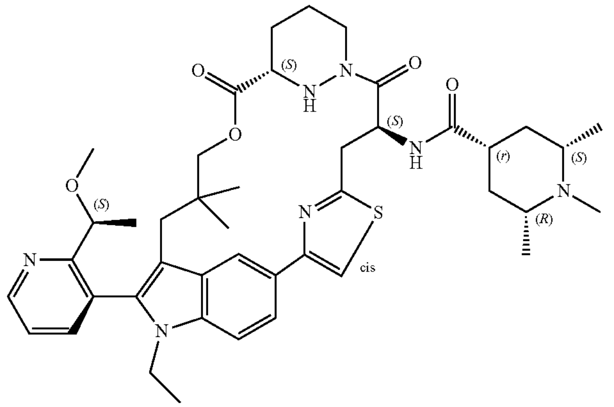 |
| A47 | 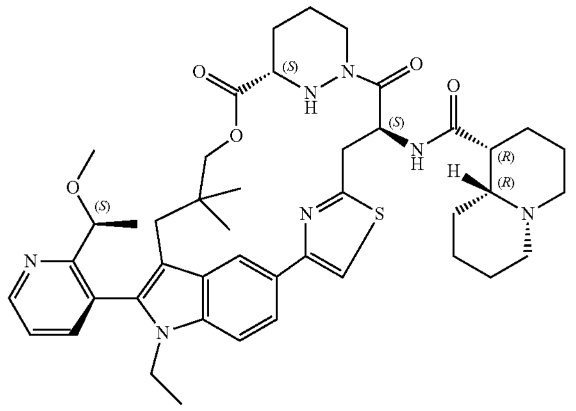 |

TABLE 1a-continued
| Certain Compounds of the Present Invention | |
|---|---|
| Ex. # | Structure |
| A48 | 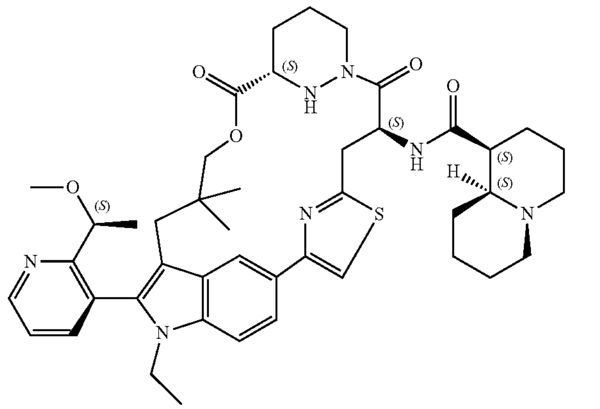 |
| A49 | 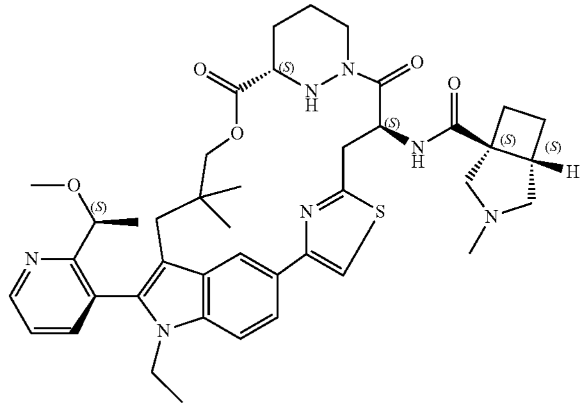 |
| A50 | 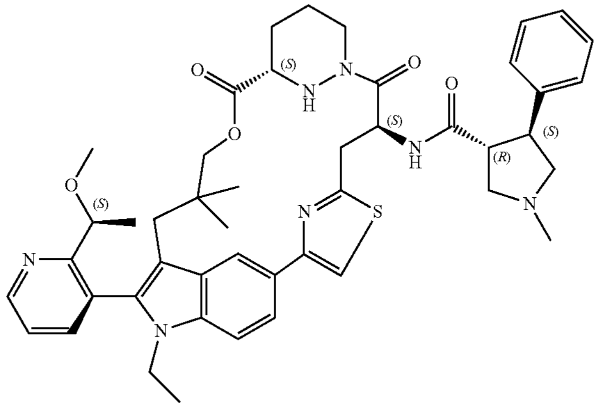 |

TABLE 1a-continued
| Certain Compounds of the Present Invention | |
|---|---|
| Ex. # | Structure |
| A51 | 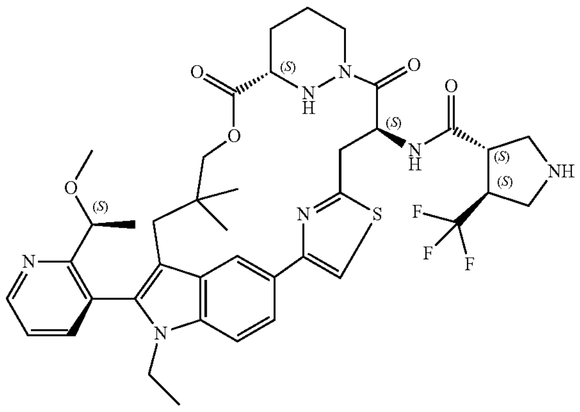 |
| A52 | 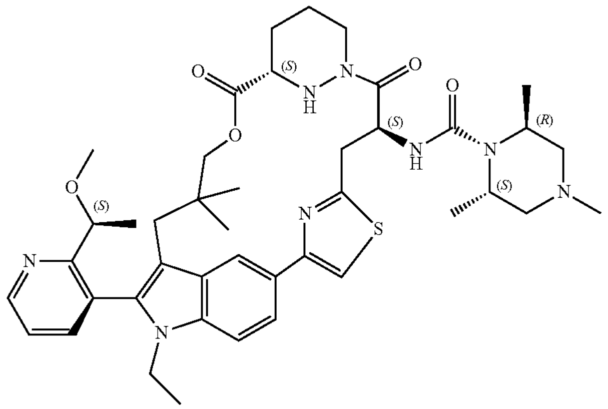 |
| A53 | 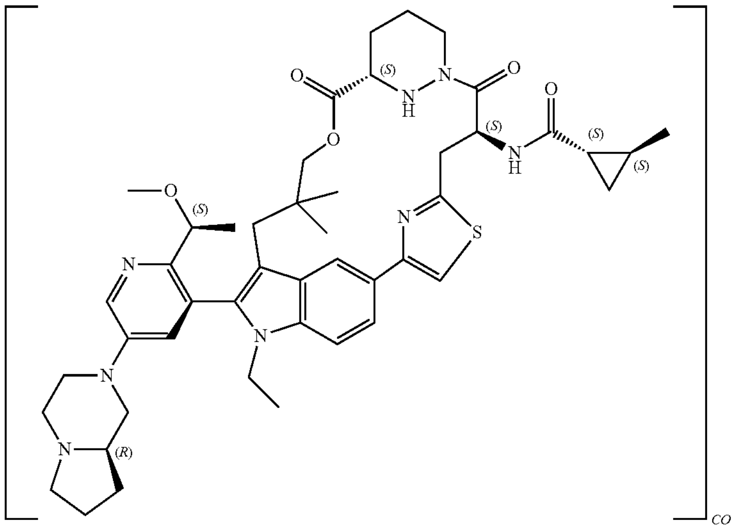 |

TABLE 1a-continued
| Certain Compounds of the Present Invention | |
|---|---|
| Ex. # | Structure |
| A54 | 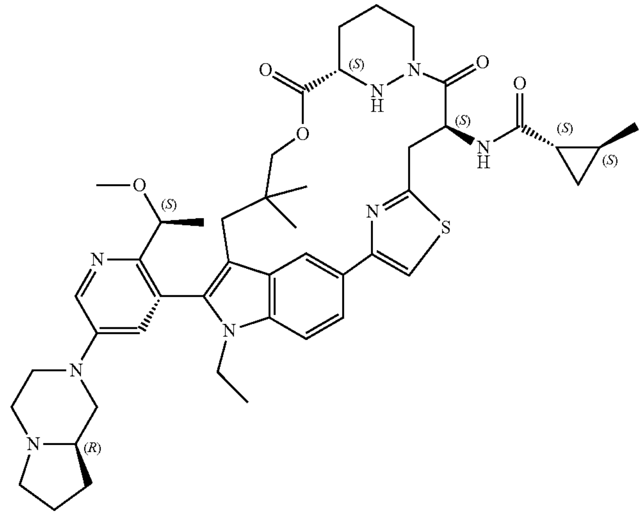 |
| A55 | 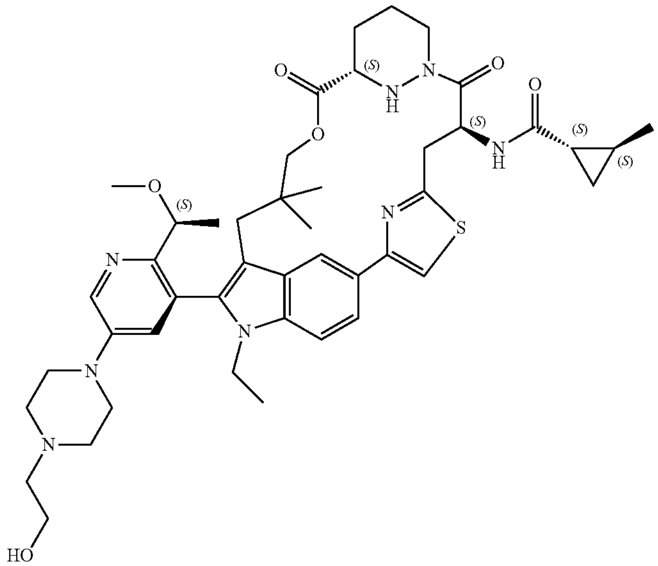 |
| A56 | 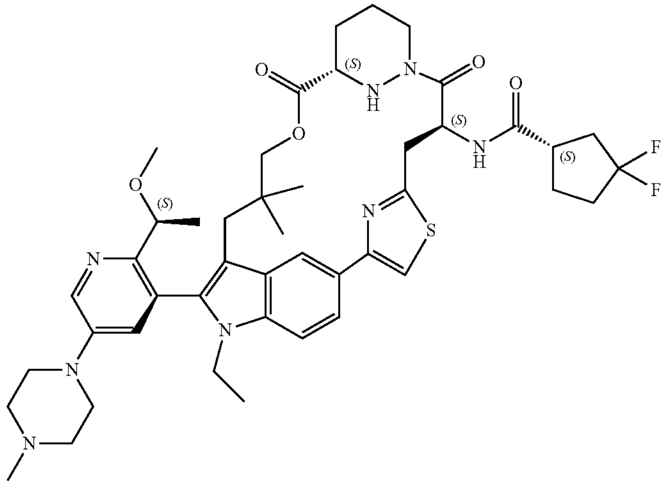 |

TABLE 1a-continued
| Certain Compounds of the Present Invention | |
|---|---|
| Ex. # | Structure |
| A57 | 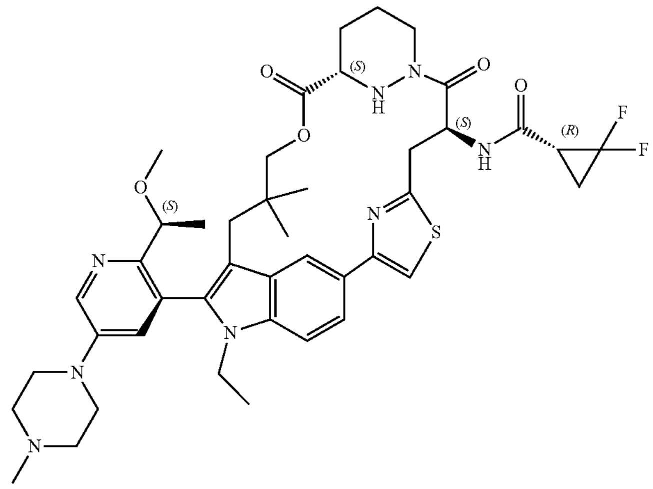 |
| A58 | 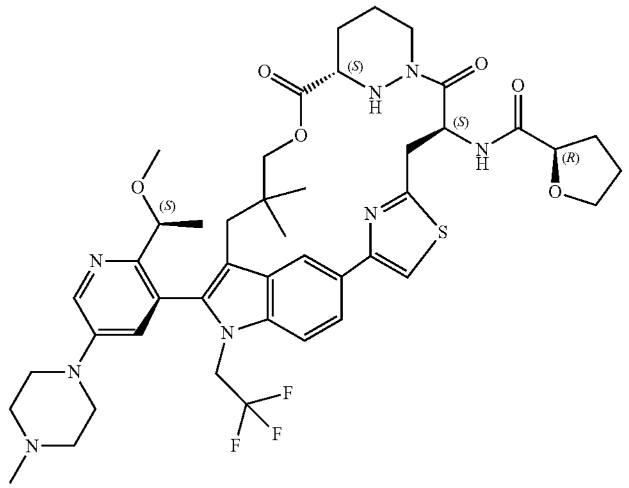 |
| A59 | 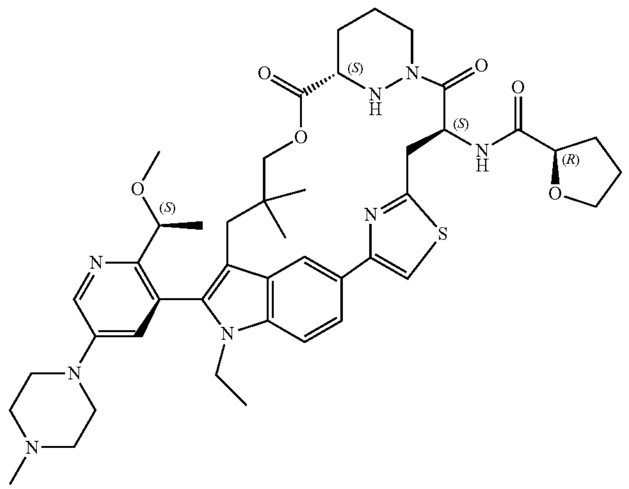 |

TABLE 1a-continued
| Certain Compounds of the Present Invention | |
|---|---|
| Ex. # | Structure |
| A60 | 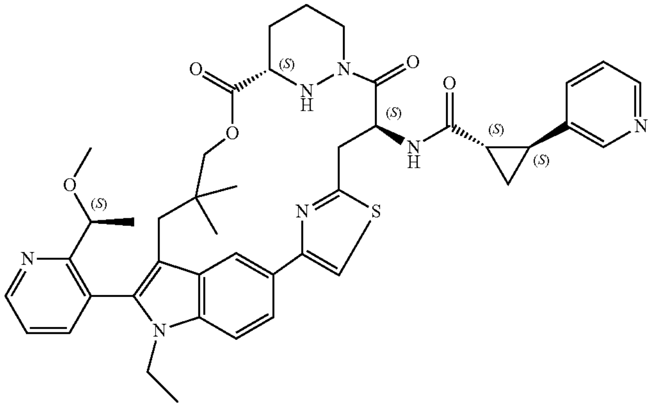 |
| A61 | 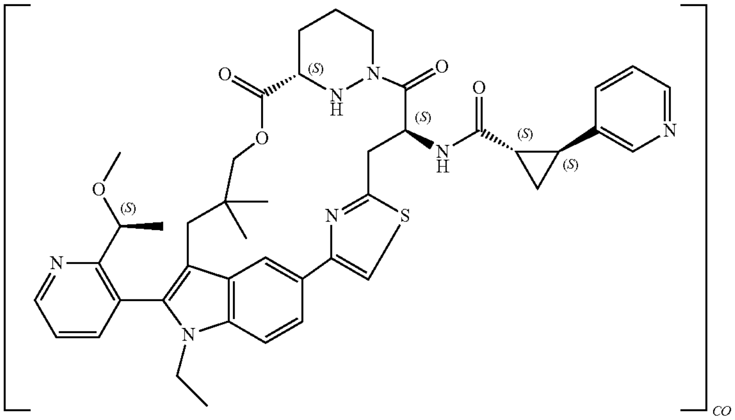 |
| A62 | 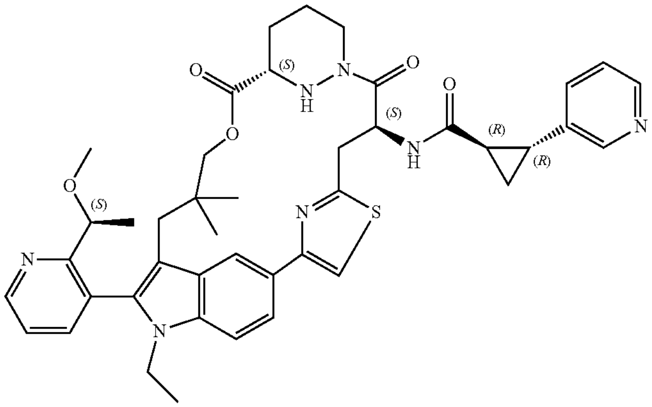 |

TABLE 1a-continued
| Certain Compounds of the Present Invention | |
|---|---|
| Ex. # | Structure |
| A63 | 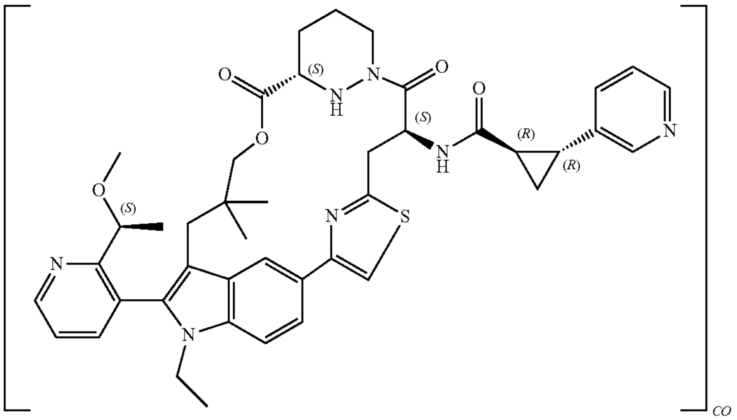 |
| A64 | 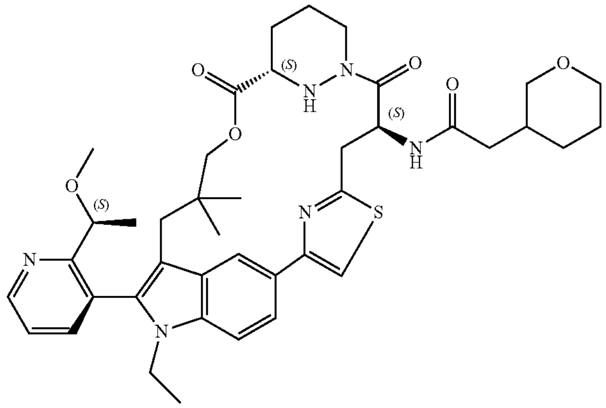 |
| A65 | 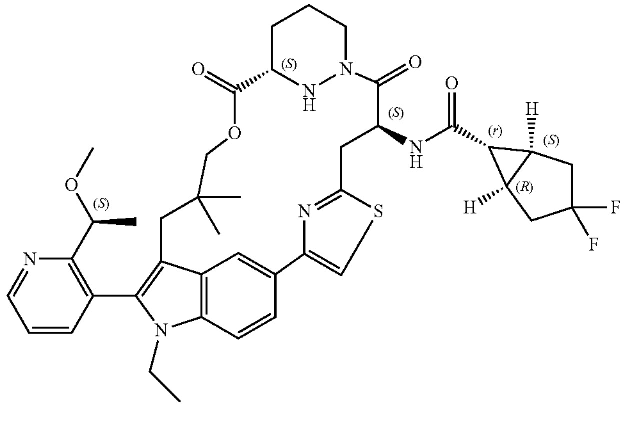 |

TABLE 1a-continued
| Certain Compounds of the Present Invention | |
|---|---|
| Ex. # | Structure |
| A66 | 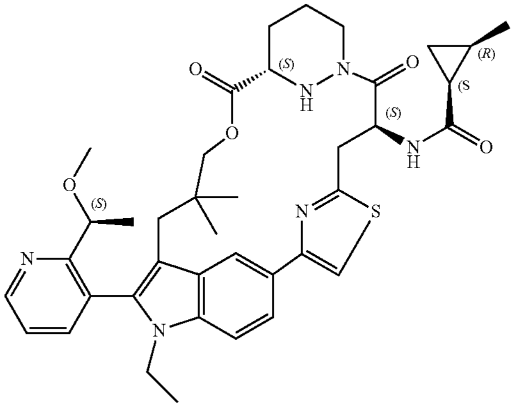 |
| A67 | 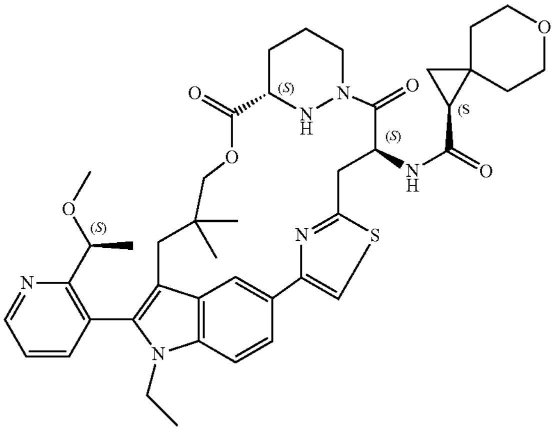 |
| A68 | 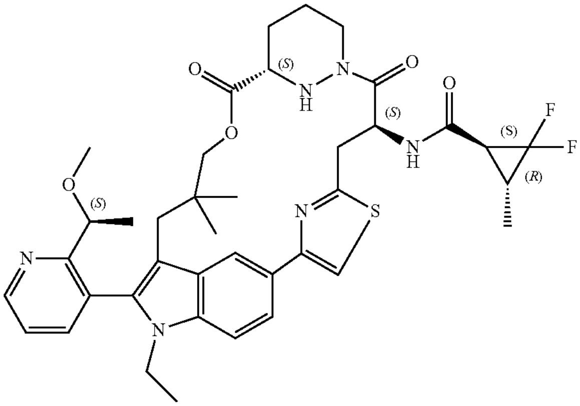 |

TABLE 1a-continued
| Certain Compounds of the Present Invention | |
|---|---|
| Ex. # | Structure |
| A69 | 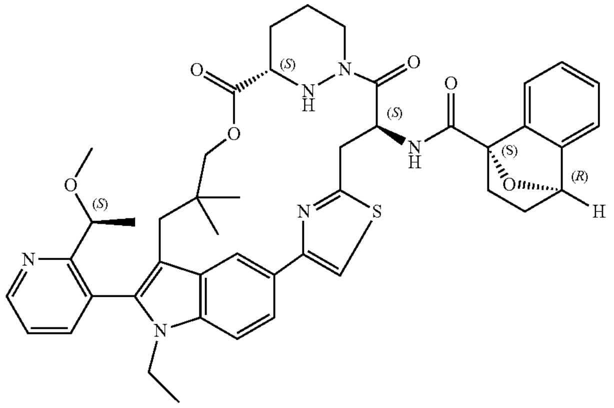 |
| A70 | 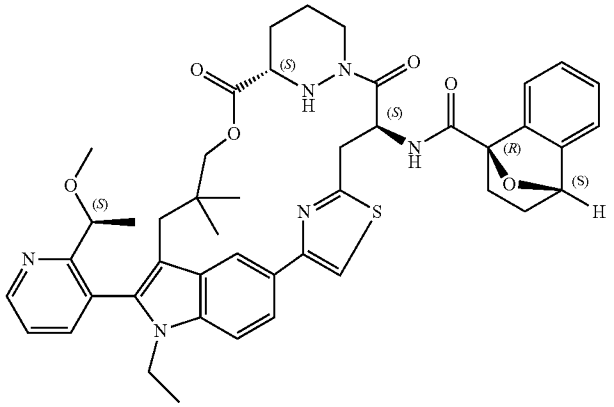 |
| A71 | 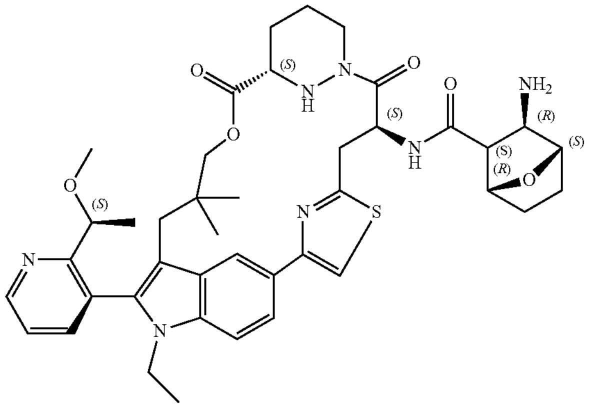 |

TABLE 1a-continued
| Certain Compounds of the Present Invention | |
|---|---|
| Ex. # | Structure |
| A72 | 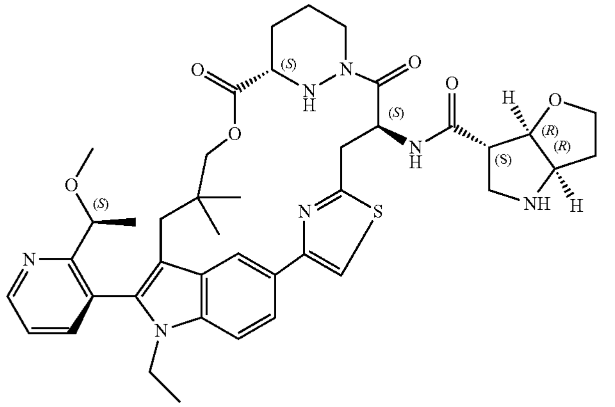 |
| A73 | 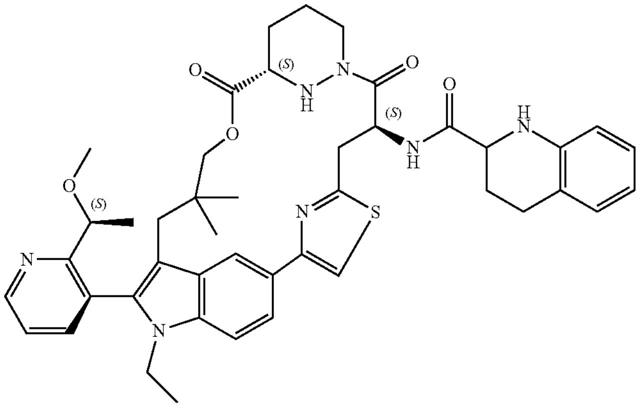 |
| A74 | 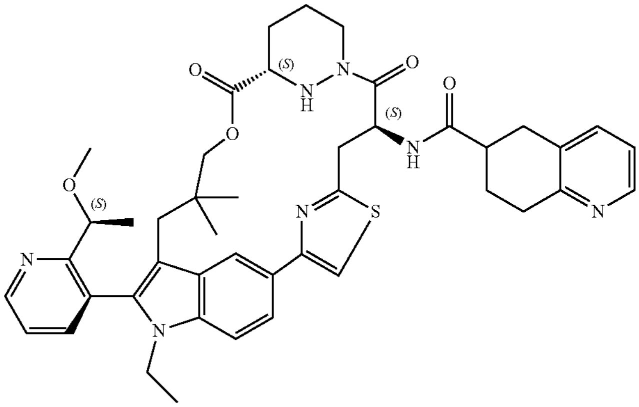 |

TABLE 1a-continued
| Certain Compounds of the Present Invention | |
|---|---|
| Ex. # | Structure |
| A75 | 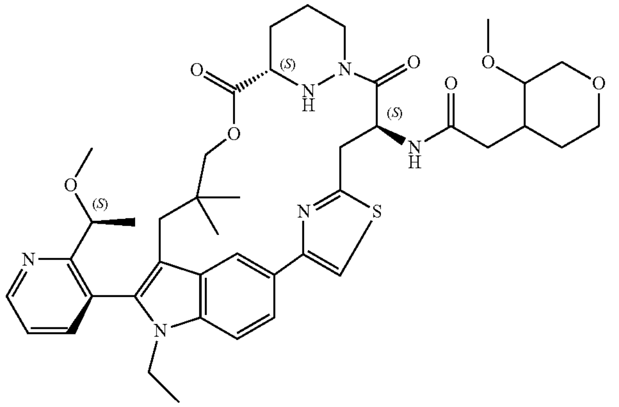 |
| A76 | 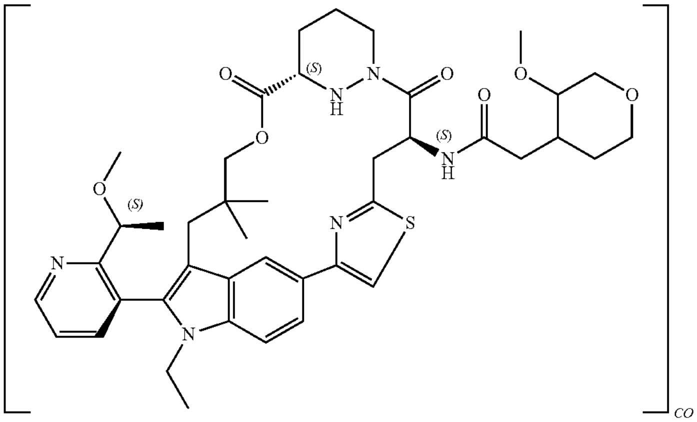 |
| A77 | 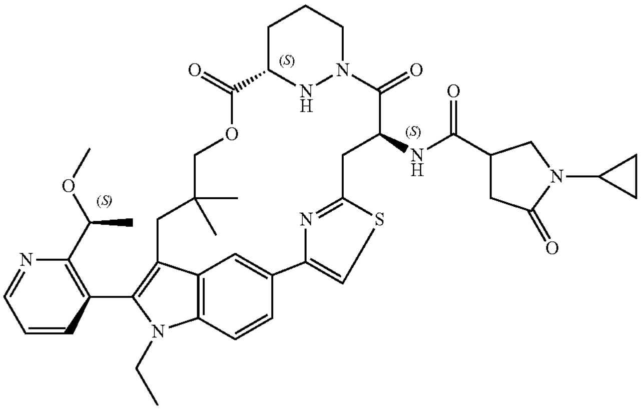 |

TABLE 1a-continued
| Certain Compounds of the Present Invention | |
|---|---|
| Ex. # | Structure |
| A78 | 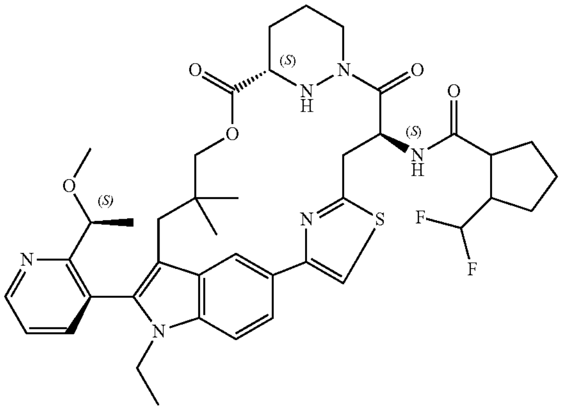 |
| A79 | 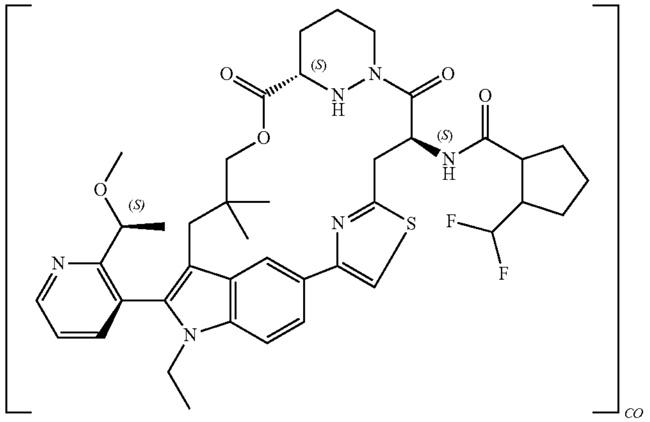 |
| A80 | 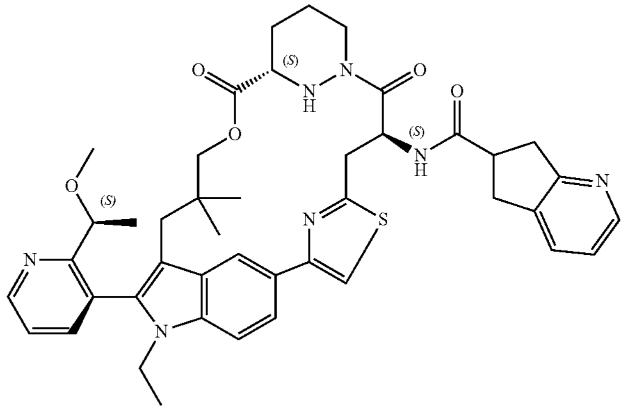 |

TABLE 1a-continued
| Certain Compounds of the Present Invention | |
|---|---|
| Ex. # | Structure |
| A81 | 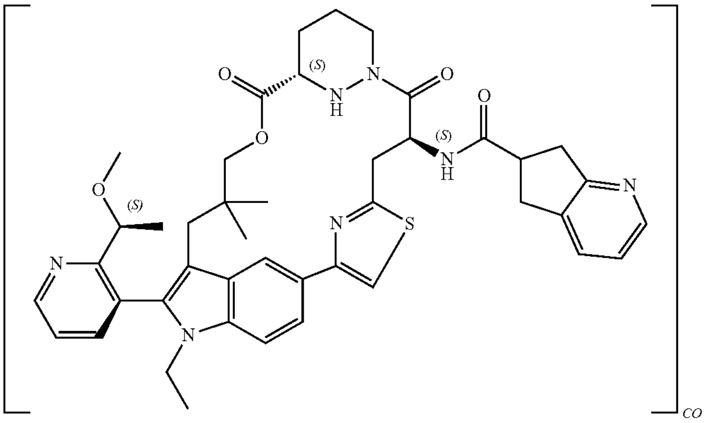 |
| A82 | 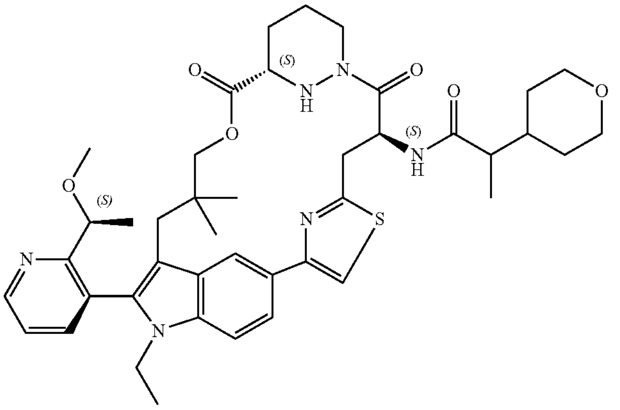 |
| A83 | 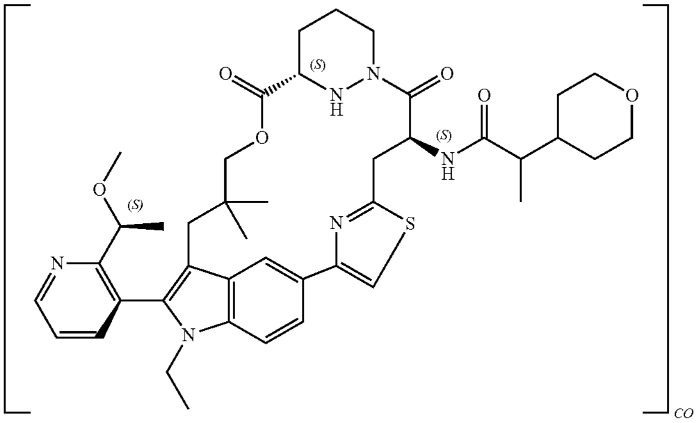 |

TABLE 1a-continued
| Certain Compounds of the Present Invention | |
|---|---|
| Ex. # | Structure |
| A84 | 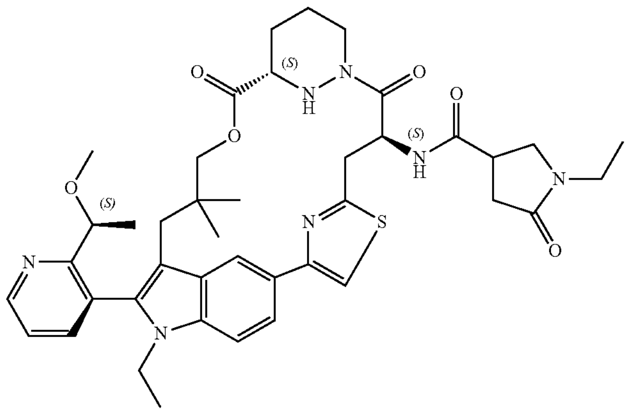 |
| A85 | 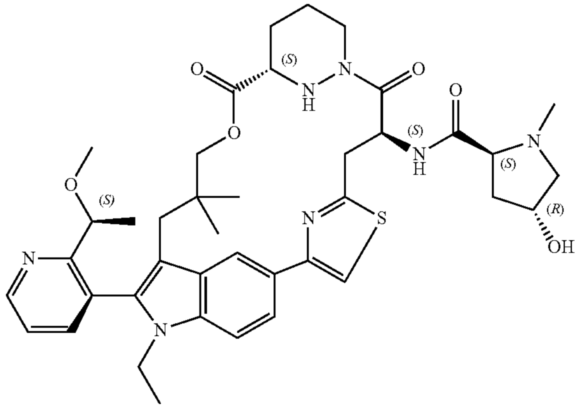 |
| A86 | 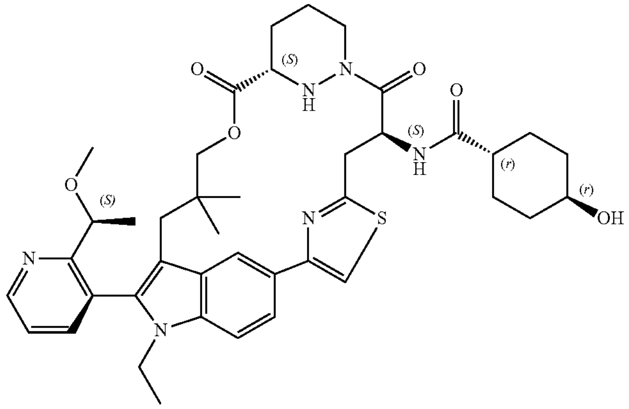 |

TABLE 1a-continued
Certain Compounds of the Present Invention
| Ex. # | Structure |
| --- | --- |
| A87 | 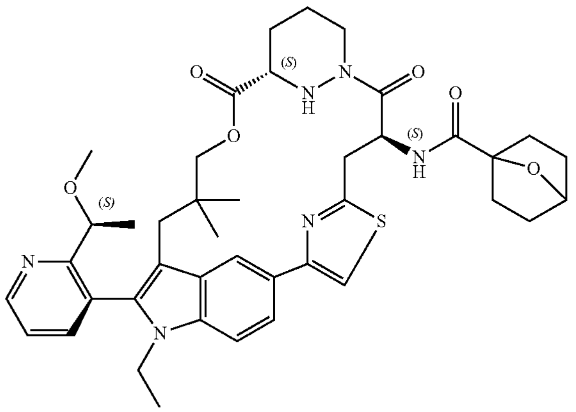 |
| A88 | 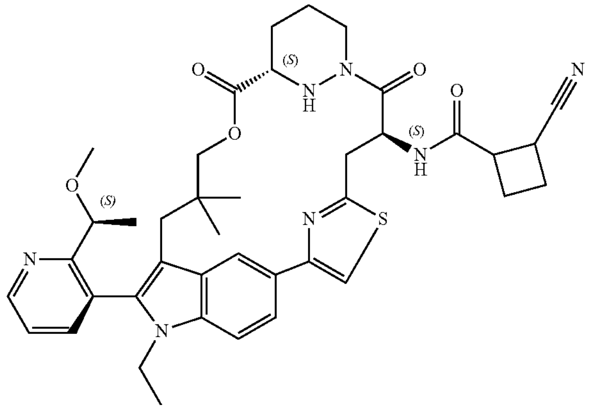 |
| A89 | 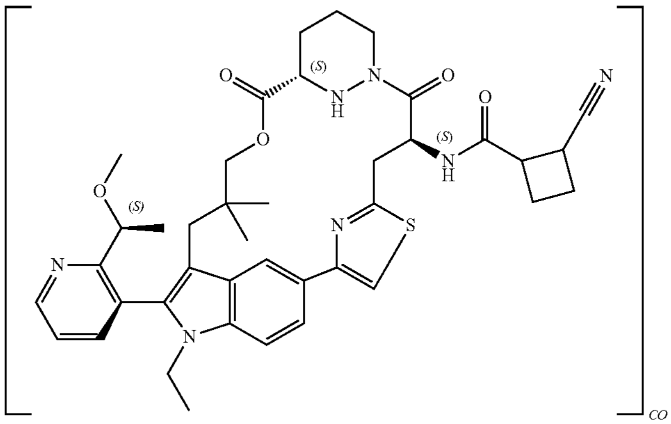 |

TABLE 1a-continued
| Certain Compounds of the Present Invention | |
|---|---|
| Ex. # | Structure |
| A90 | 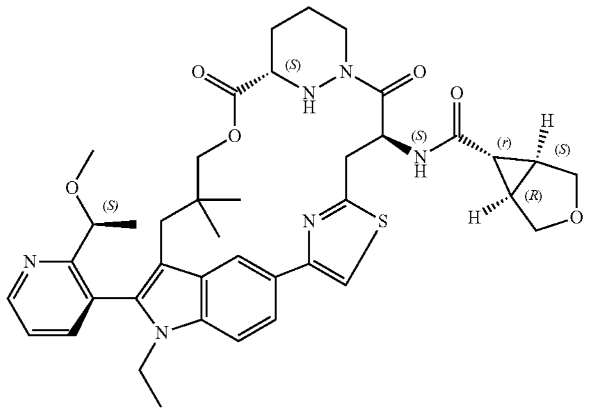 |
| A91 | 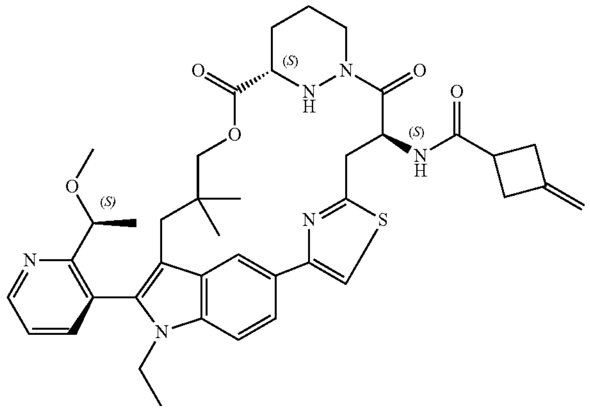 |
| A92 | 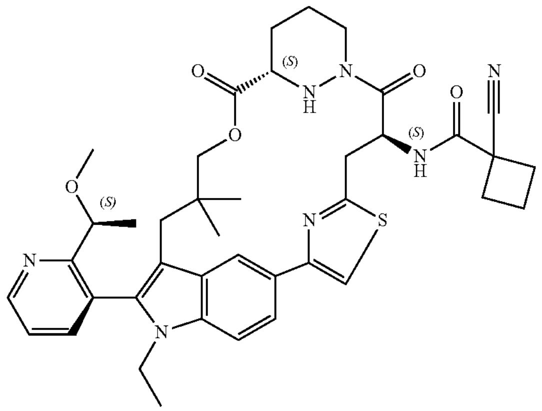 |

TABLE 1a-continued
| Certain Compounds of the Present Invention | |
|---|---|
| Ex. # | Structure |
| A93 | 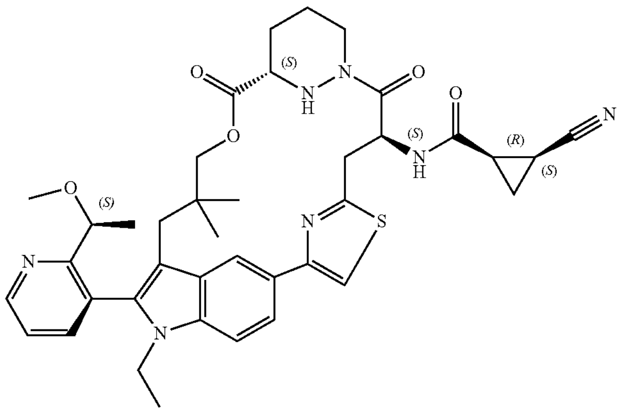 |
| A94 | 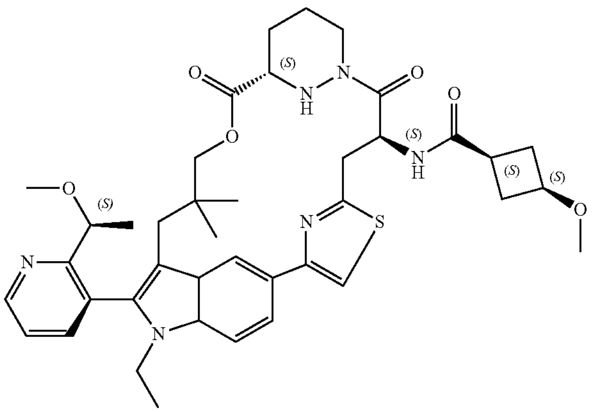 |
| A95 | 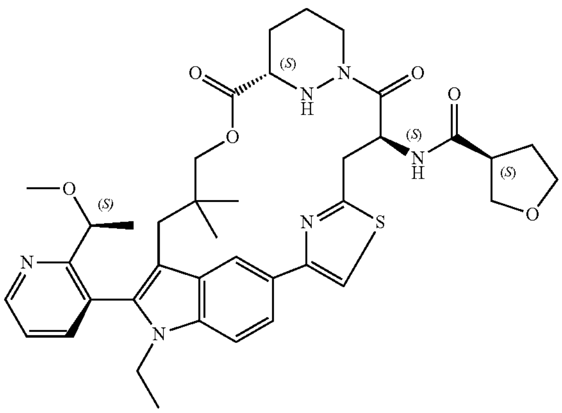 |

TABLE 1a-continued
| Certain Compounds of the Present Invention | |
| --- | --- |
| Ex. # | Structure |
| A96 | 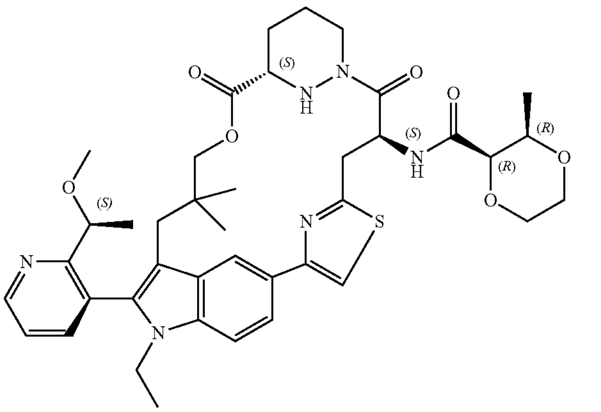 |
| A97 | 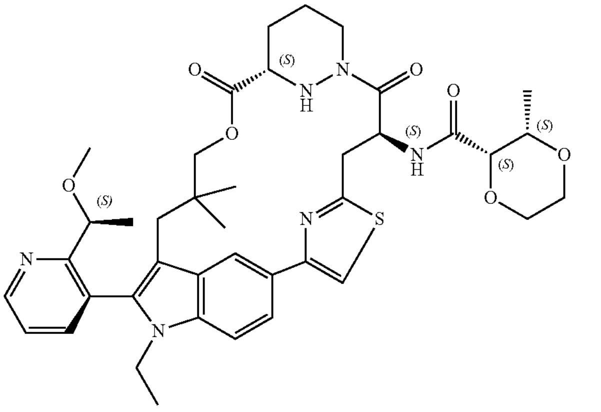 |
| A98 | 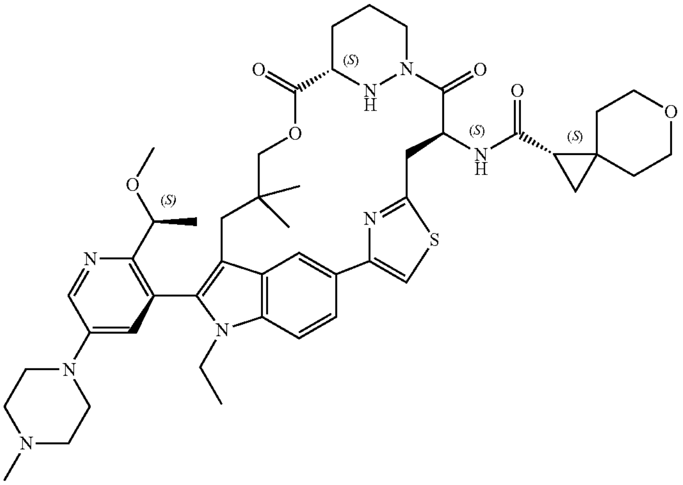 |

TABLE 1a-continued
| Certain Compounds of the Present Invention | |
|---|---|
| Ex. # | Structure |
| A99 | 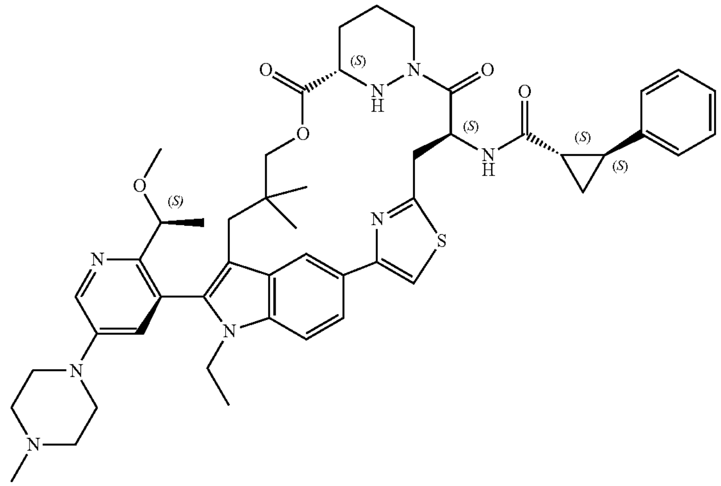 |
| A100 | 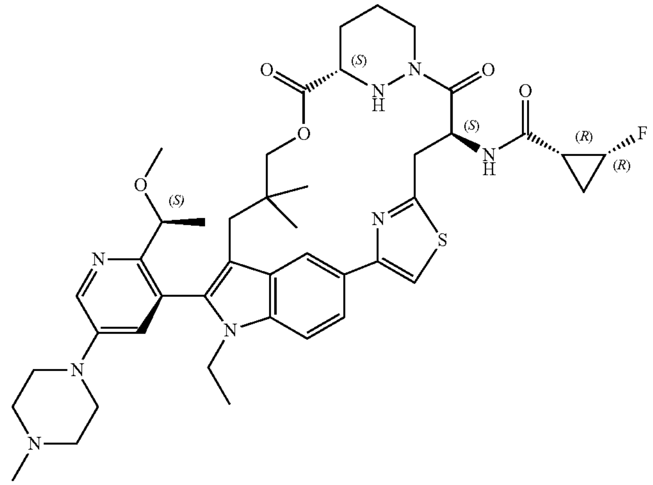 |
| A101 | 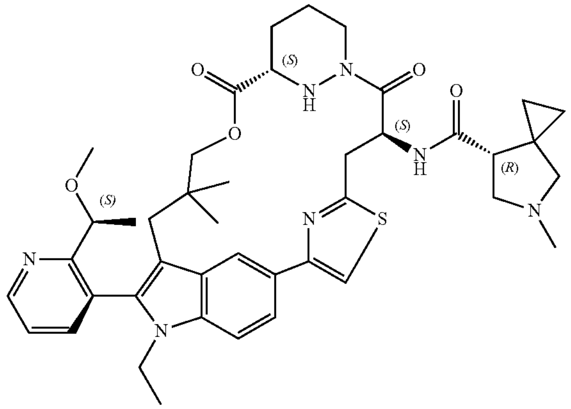 |

TABLE 1a-continued
| Certain Compounds of the Present Invention | |
|---|---|
| Ex. # | Structure |
| A102 | 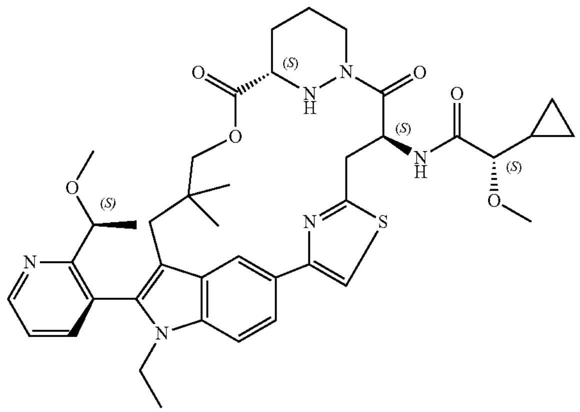 |
| A103 | 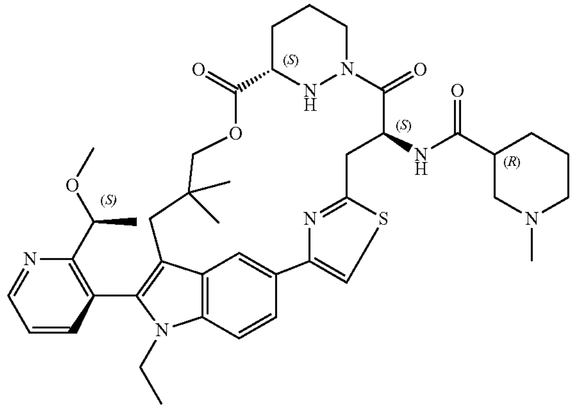 |
| A104 | 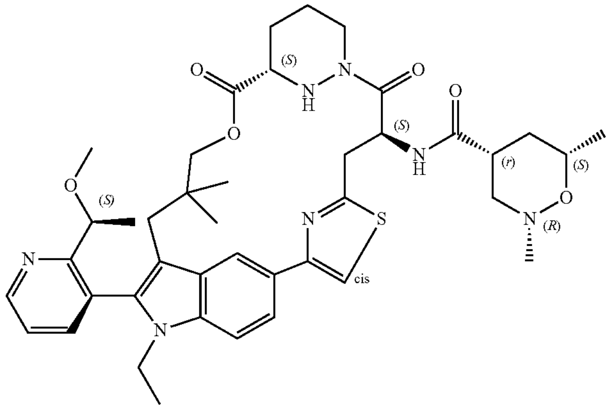 |

TABLE 1a-continued
| Certain Compounds of the Present Invention | |
|---|---|
| Ex. # | Structure |
| A105 | 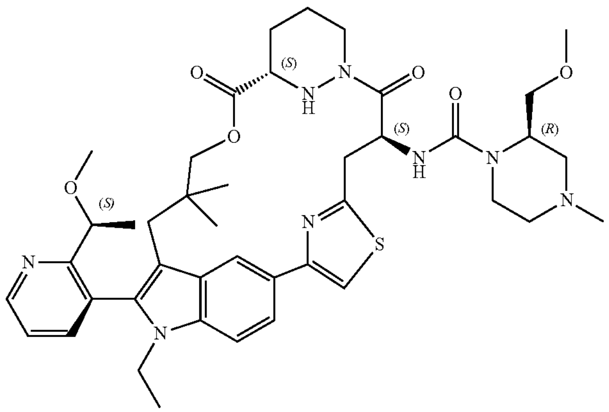 |
| A106 | 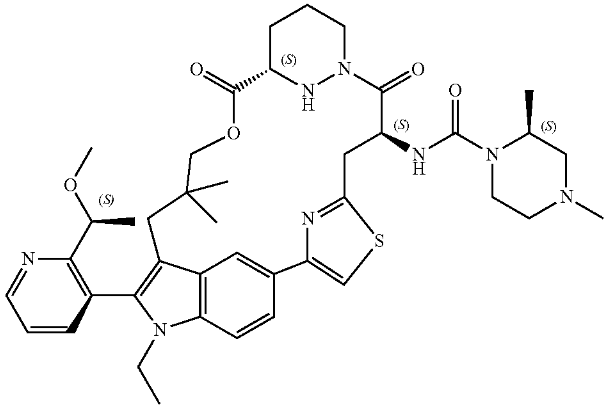 |
| A107 | 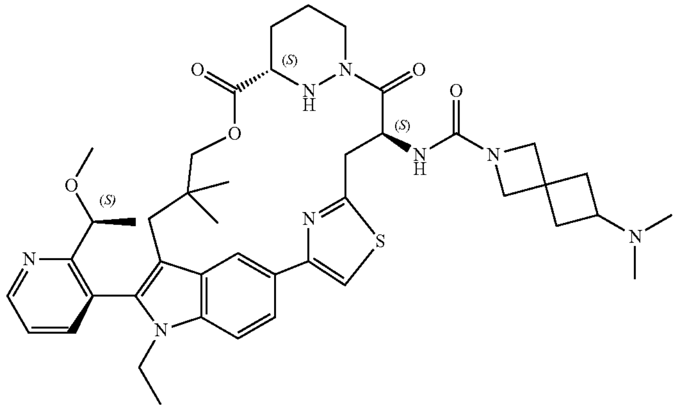 |

TABLE 1a-continued
| Certain Compounds of the Present Invention | |
|---|---|
| Ex. # | Structure |
| A108 | 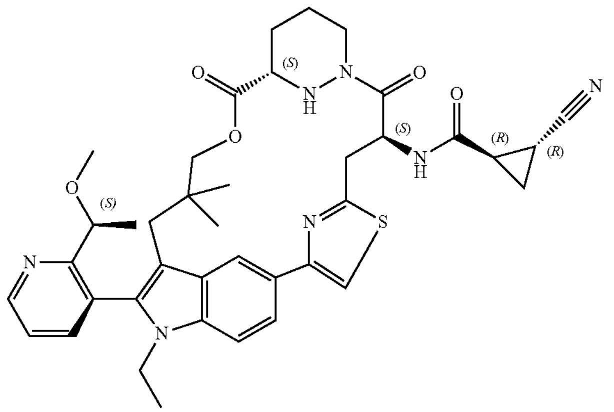 |
| A109 | 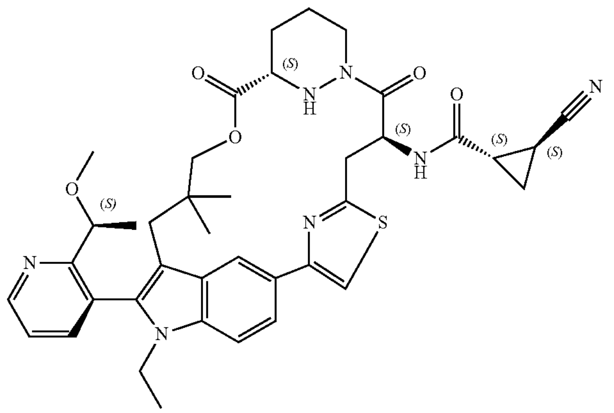 |
| A110 | 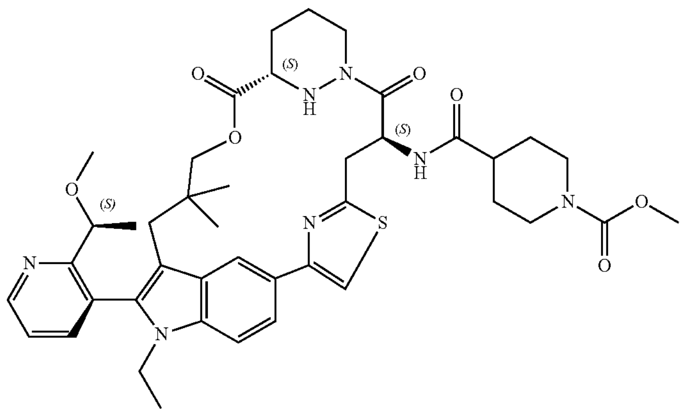 |

TABLE 1a-continued
| Certain Compounds of the Present Invention | |
|---|---|
| Ex. # | Structure |
| A111 | 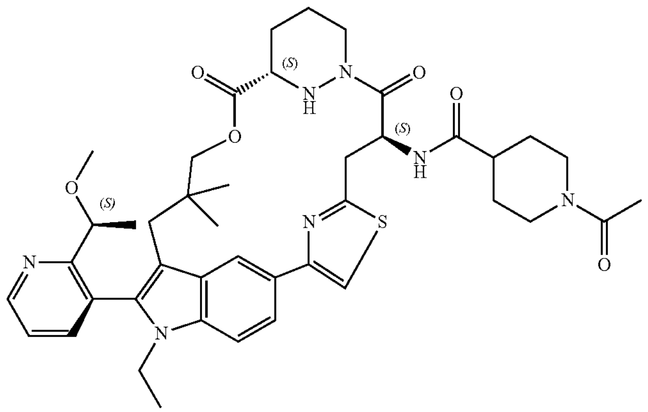 |
| A112 | 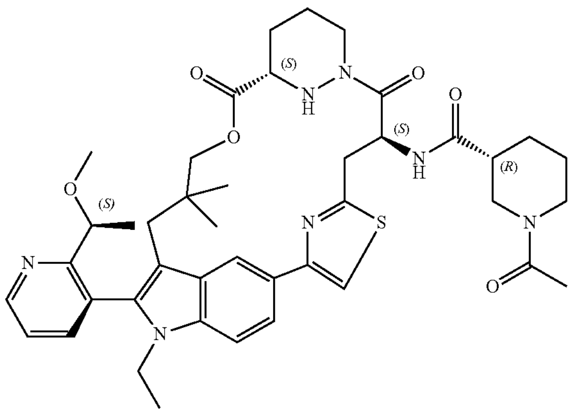 |
| A113 | 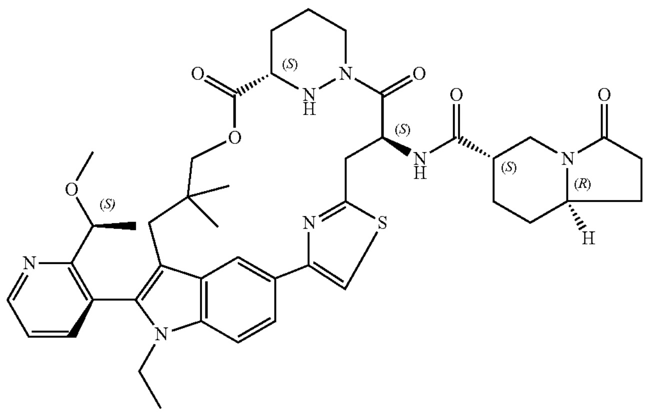 |

TABLE 1a-continued
| Certain Compounds of the Present Invention | |
|---|---|
| Ex. # | Structure |
| A114 | 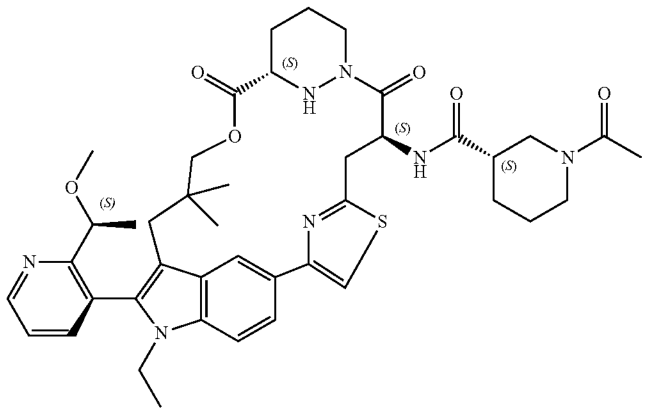 |
| A115 | 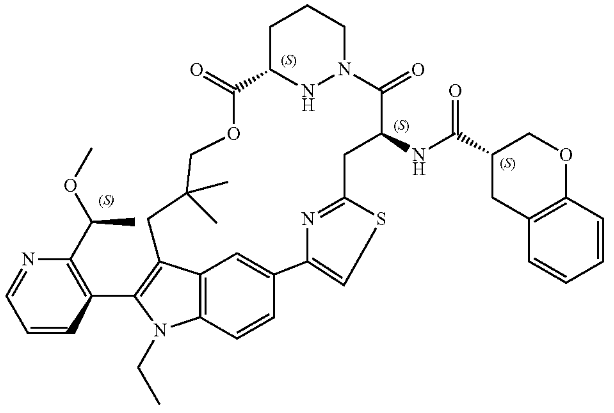 |
| A116 | 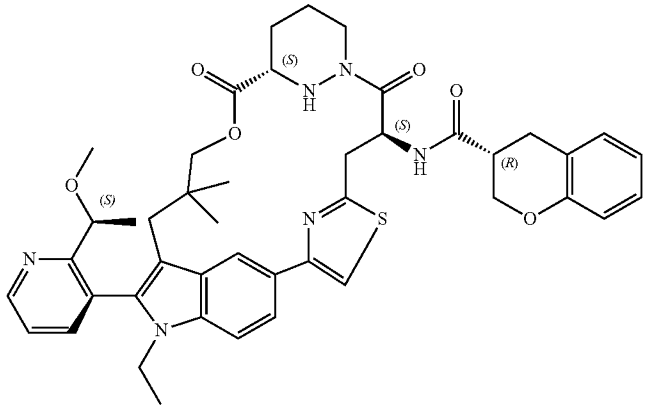 |

TABLE 1a-continued
| Certain Compounds of the Present Invention | |
|---|---|
| Ex. # | Structure |
| A117 | 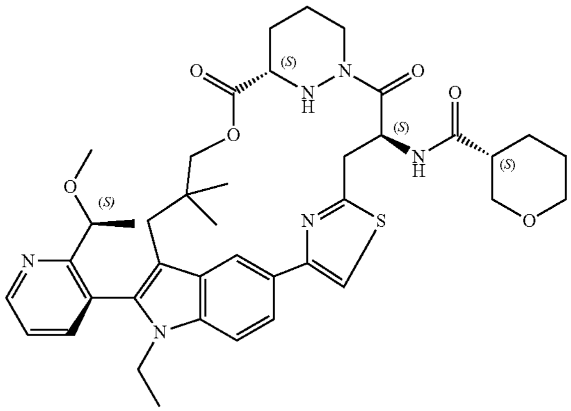 |
| A118 | 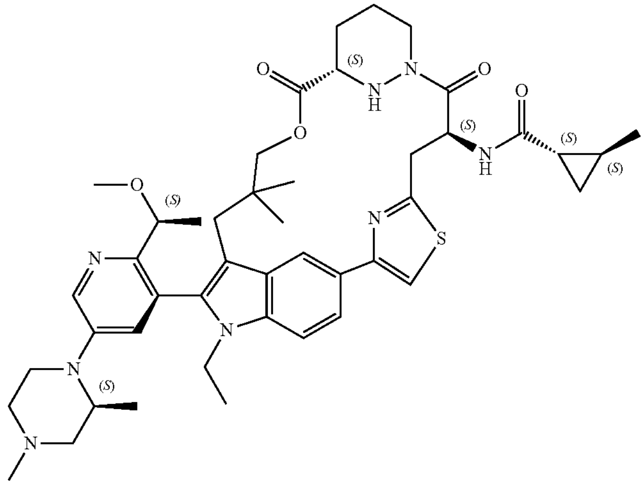 |
| A119 | 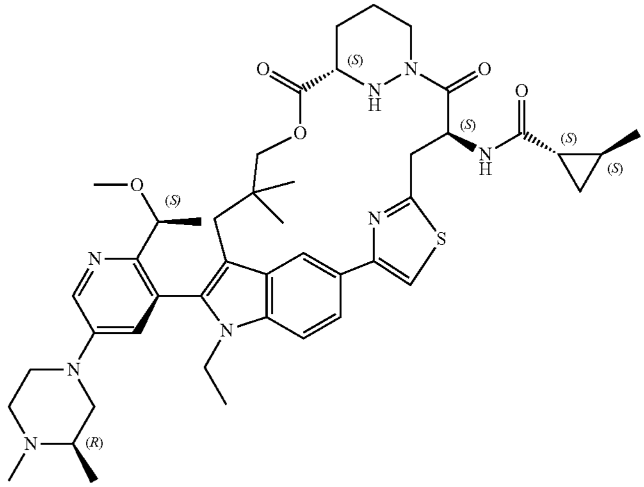 |

TABLE 1a-continued
Certain Compounds of the Present Invention
| Ex. # | Structure |
| --- | --- |
| A120 | 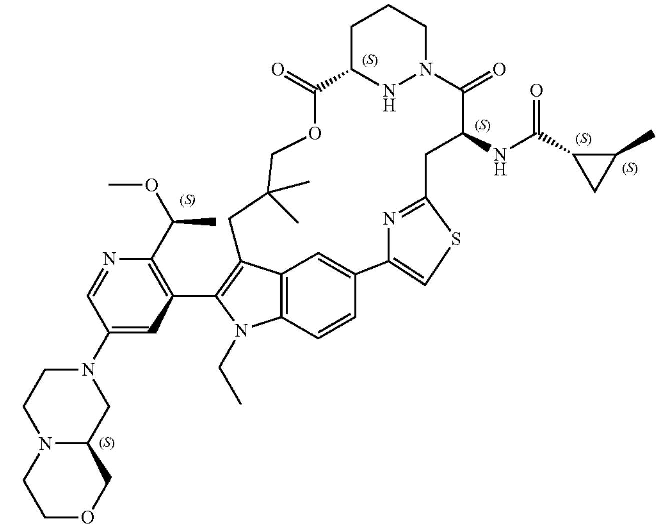 |
| A121 | 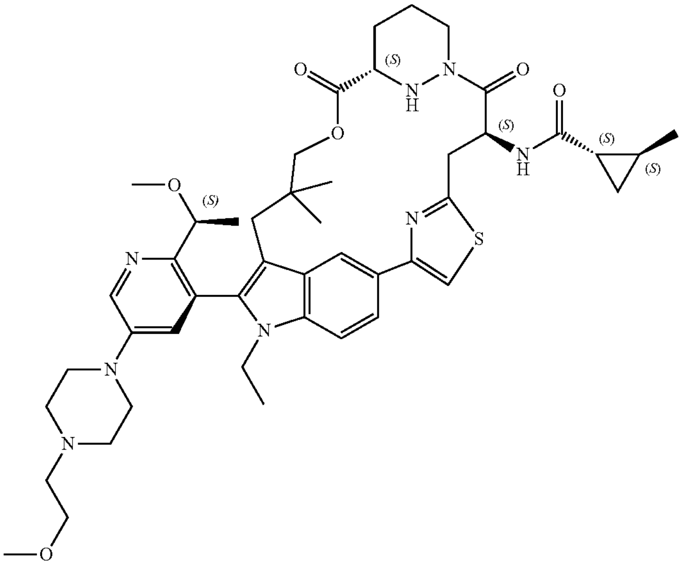 |
| A122 | 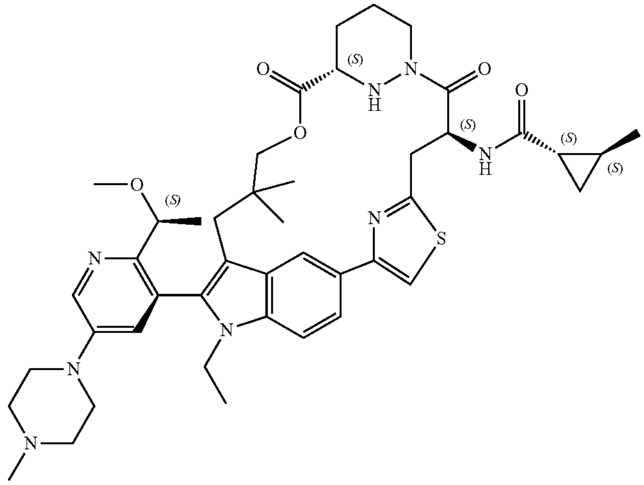 |

TABLE 1a-continued
| Certain Compounds of the Present Invention | |
|---|---|
| Ex. # | Structure |
| A123 | 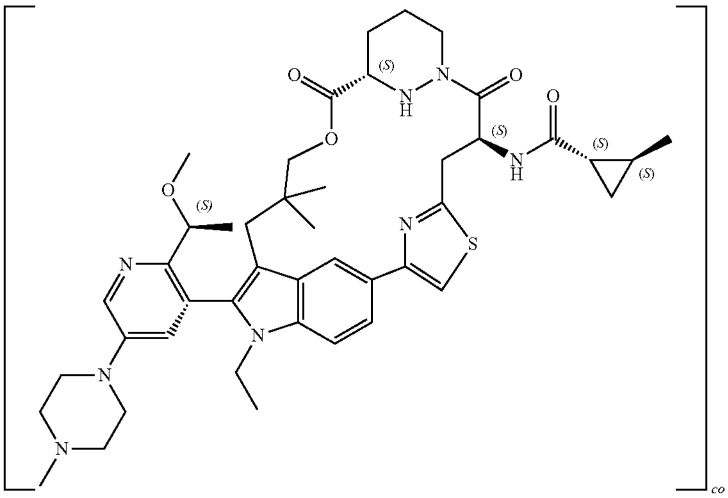 |
| A124 | 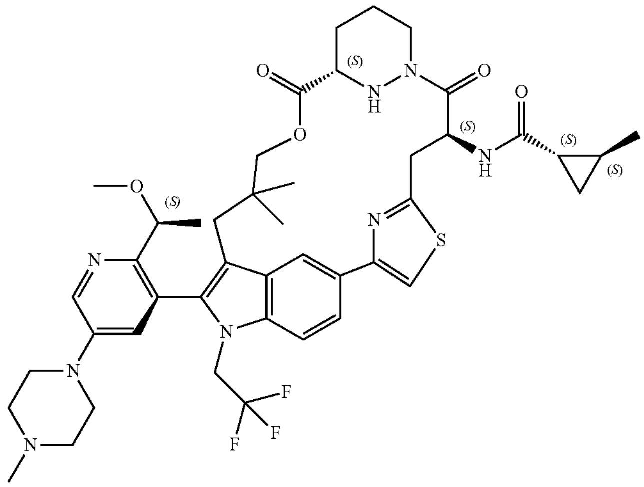 |
| A125 | 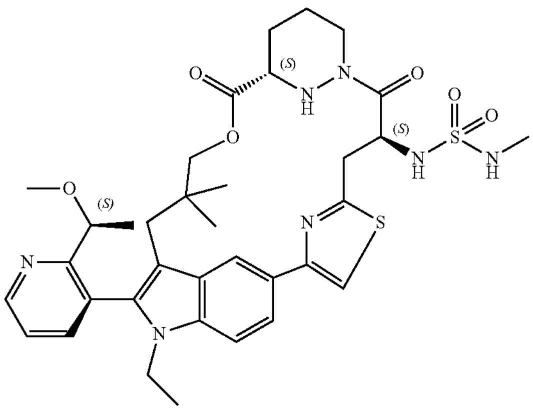 |

TABLE 1a-continued
| Certain Compounds of the Present Invention | |
|---|---|
| Ex. # | Structure |
| A126 | 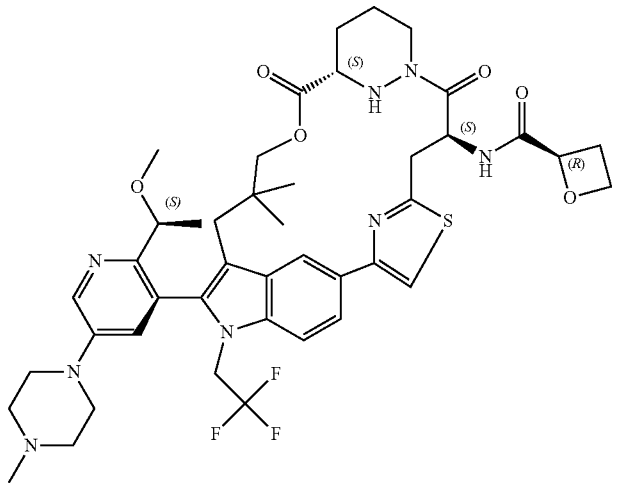 |
| A127 | 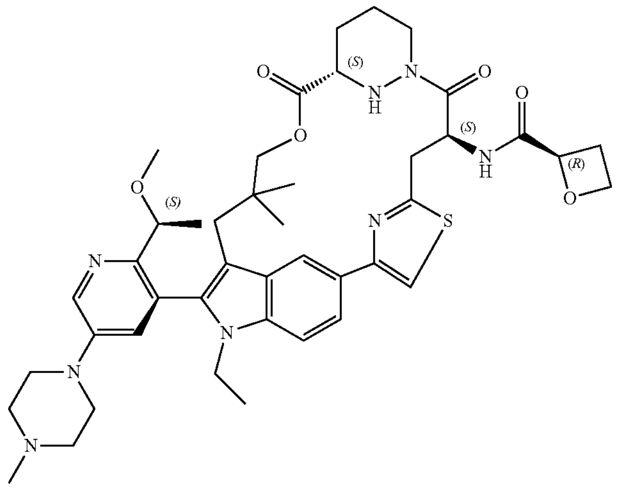 |
| A128 | 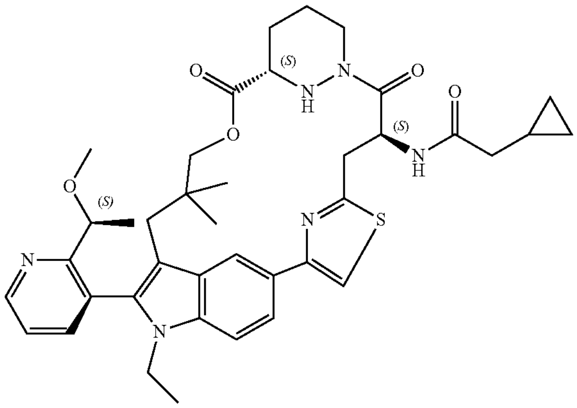 |

TABLE 1a-continued
| Certain Compounds of the Present Invention | |
|---|---|
| Ex. # | Structure |
| A129 | 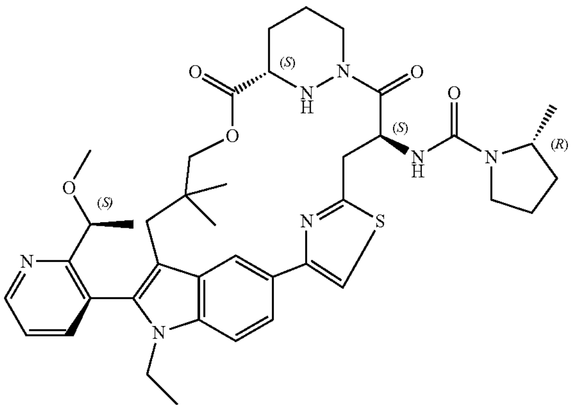 |
| A130 | 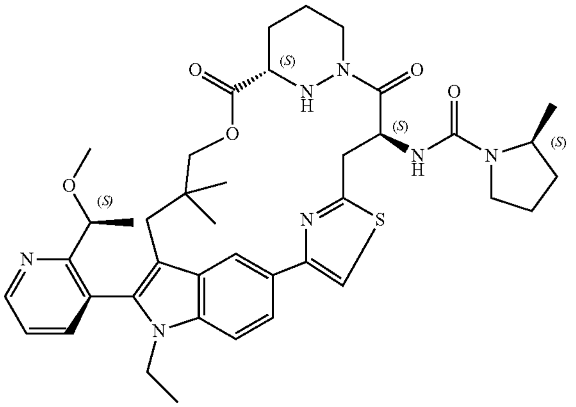 |
| A131 | 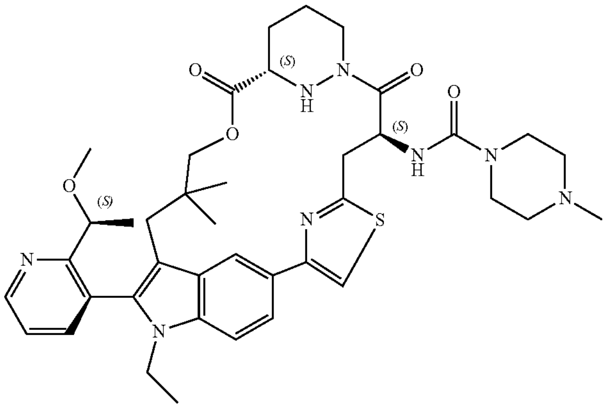 |

TABLE 1a-continued
| Certain Compounds of the Present Invention | |
|---|---|
| Ex. # | Structure |
| A132 | 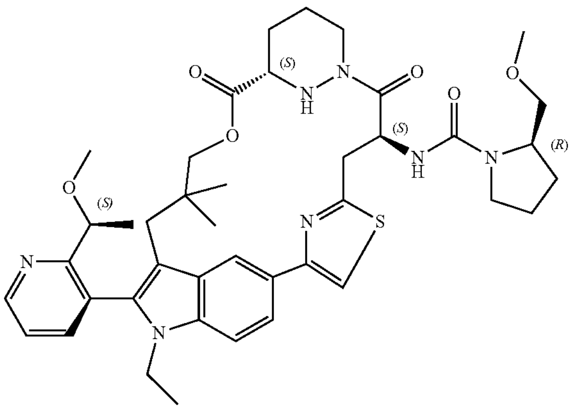 |
| A133 | 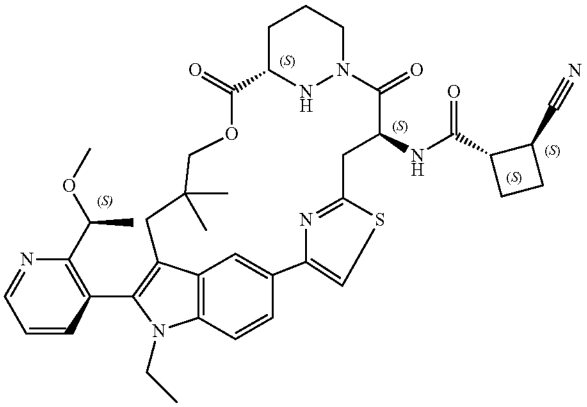 |
| A134 | 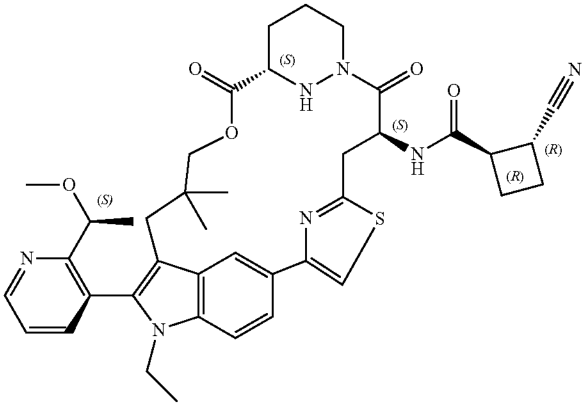 |

TABLE 1a-continued
| Certain Compounds of the Present Invention | |
|---|---|
| Ex. # | Structure |
| A135 | 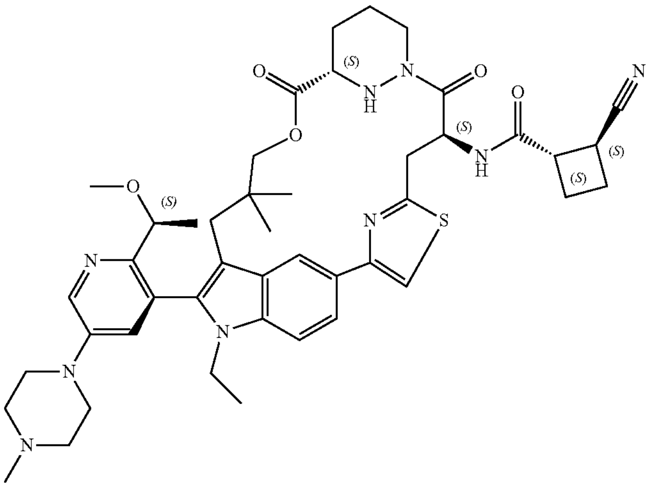 |
| A136 | 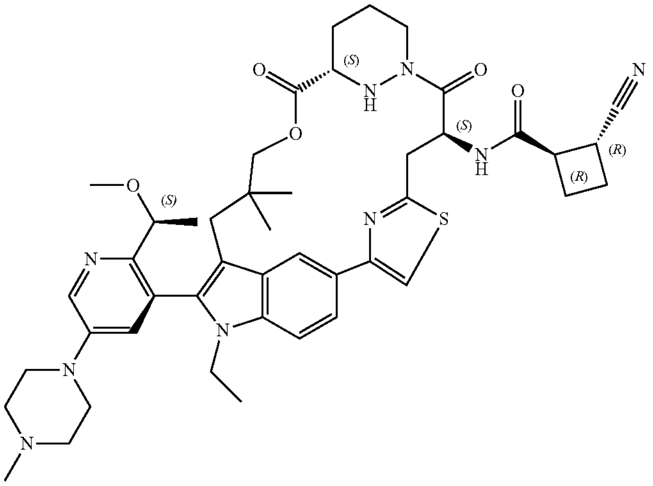 |
| A137 | 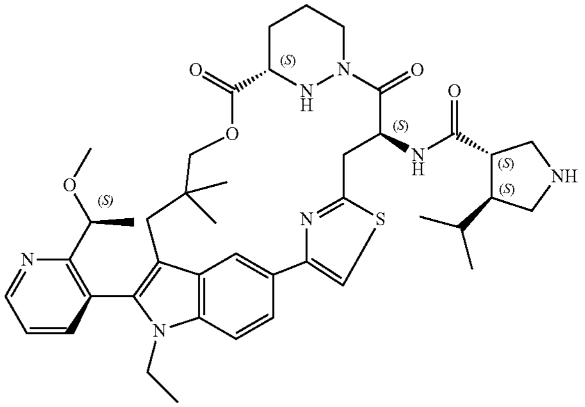 |

TABLE 1a-continued
| Certain Compounds of the Present Invention | |
| --- | --- |
| Ex. # | Structure |
| A138 | 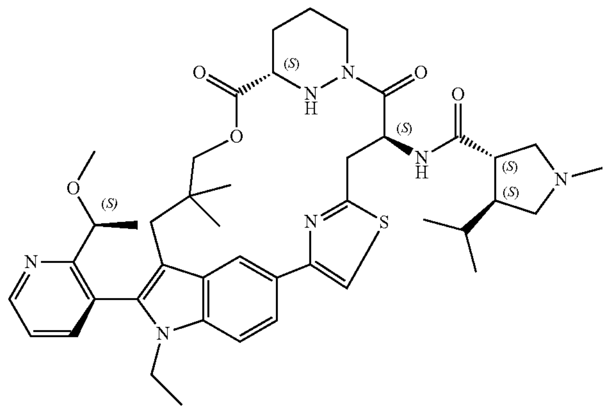 |
| A139 | 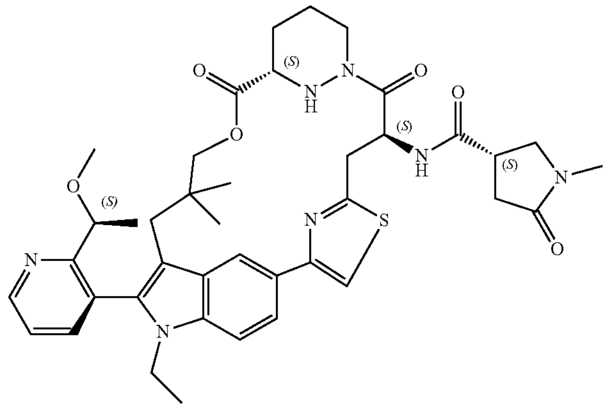 |
| A140 | 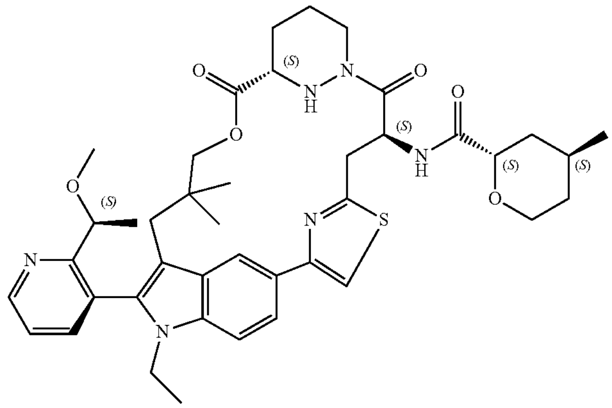 |

TABLE 1a-continued
| Certain Compounds of the Present Invention | |
|---|---|
| Ex. # | Structure |
| A141 | 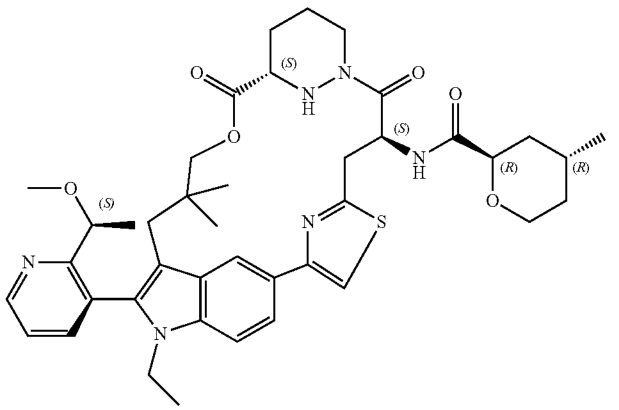 |
| A142 | 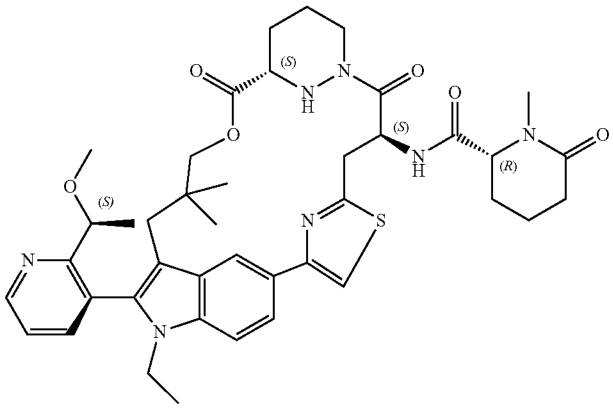 |
| A143 | 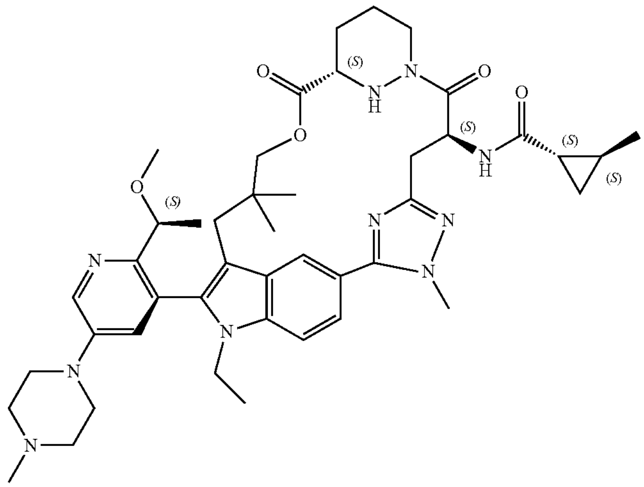 |

TABLE 1a-continued
Certain Compounds of the Present Invention
| Ex. # | Structure |
|---|---|
| A144 | 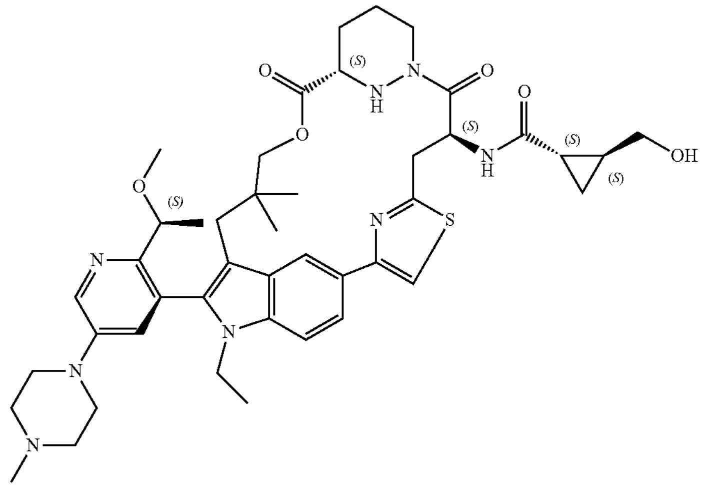 |
| A145 | 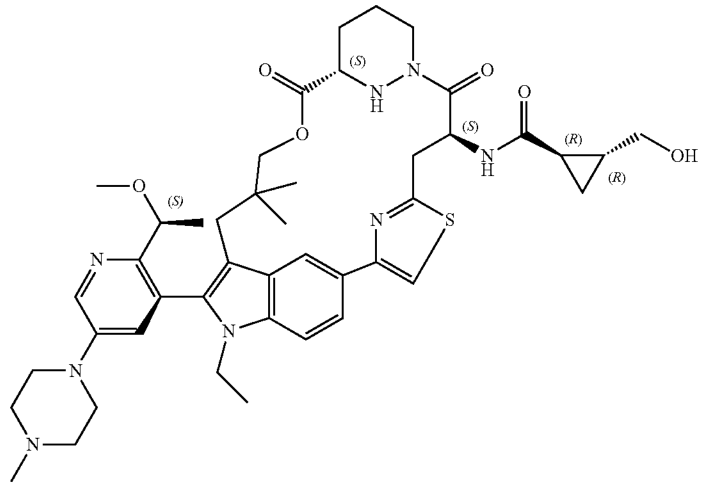 |
| A146 | 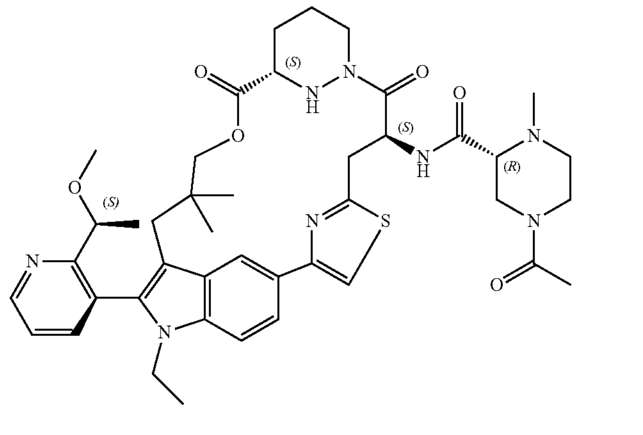 |

TABLE 1a-continued
| Certain Compounds of the Present Invention | |
|---|---|
| Ex. # | Structure |
| A147 | 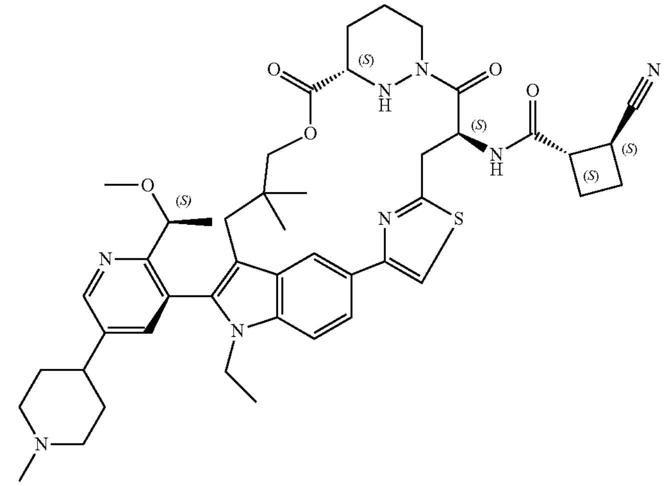 |
| A148 | 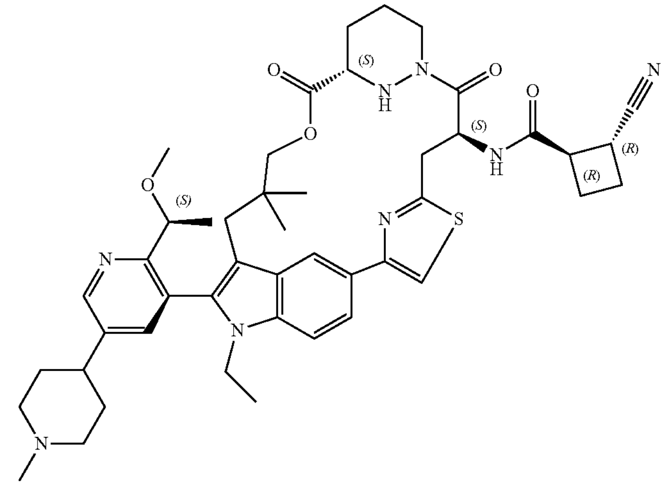 |
| A149 | 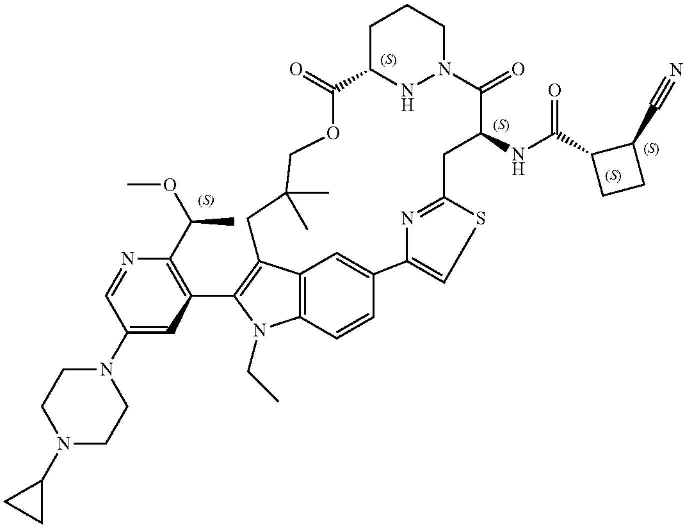 |

TABLE 1a-continued
| Certain Compounds of the Present Invention | |
|---|---|
| Ex. # | Structure |
| A150 | 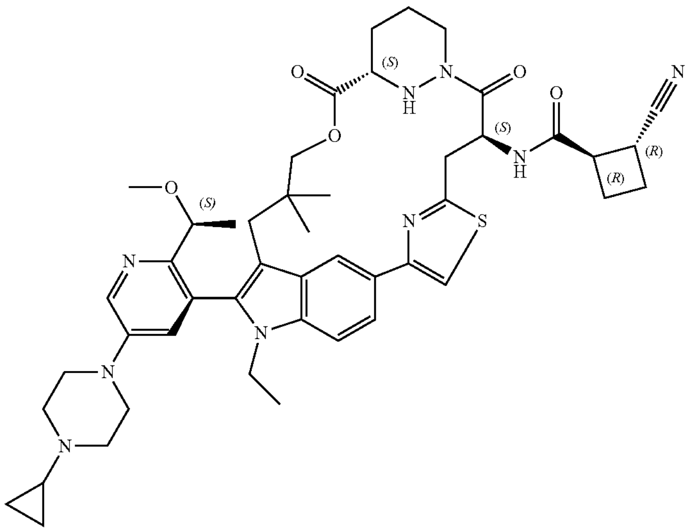 |
| A151 | 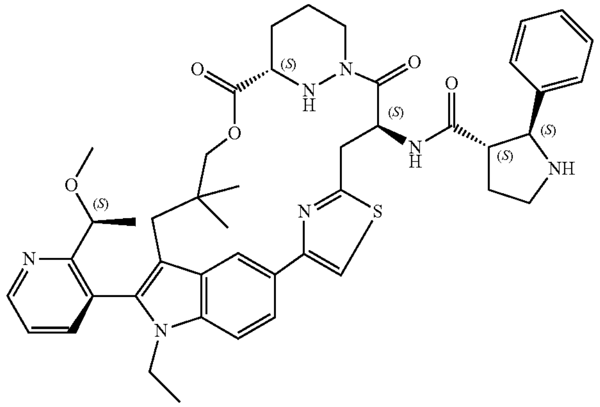 |
| A152 | 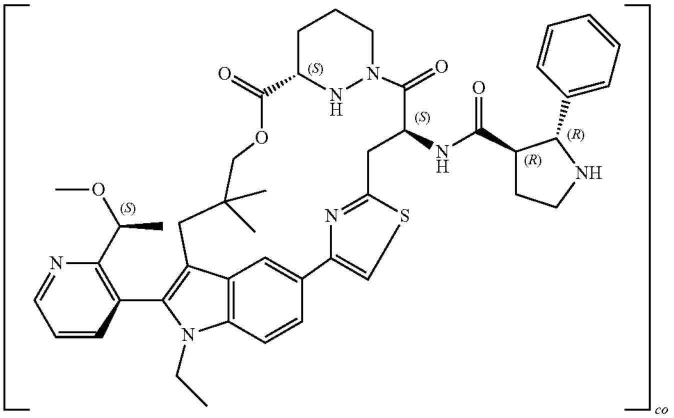 |

TABLE 1a-continued
| Certain Compounds of the Present Invention | |
|---|---|
| Ex. # | Structure |
| A153 | 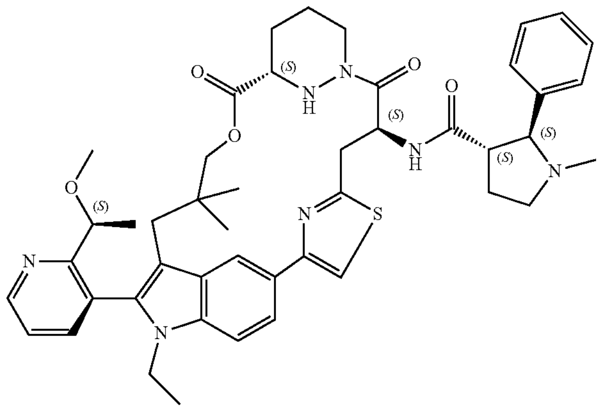 |
| A154 | 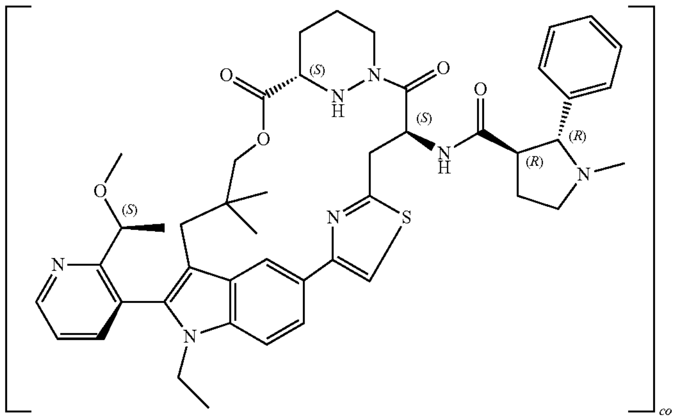 |
| A155 | 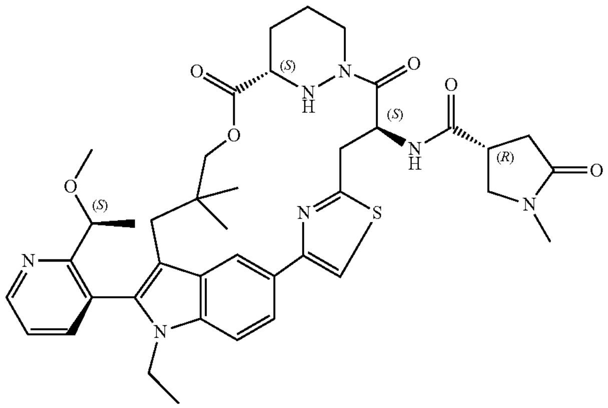 |

TABLE 1a-continued
Certain Compounds of the Present Invention
| Ex. # | Structure |
|---|---|
| A156 | 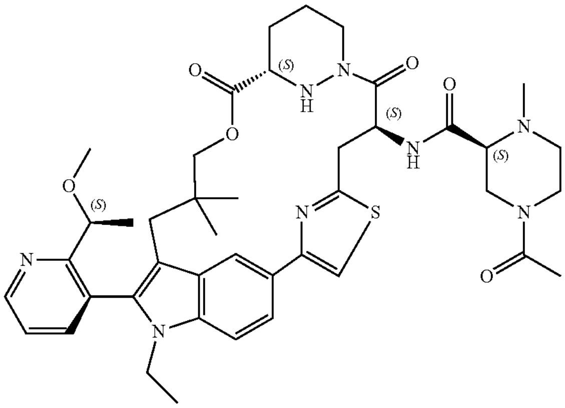 |
| A157 | 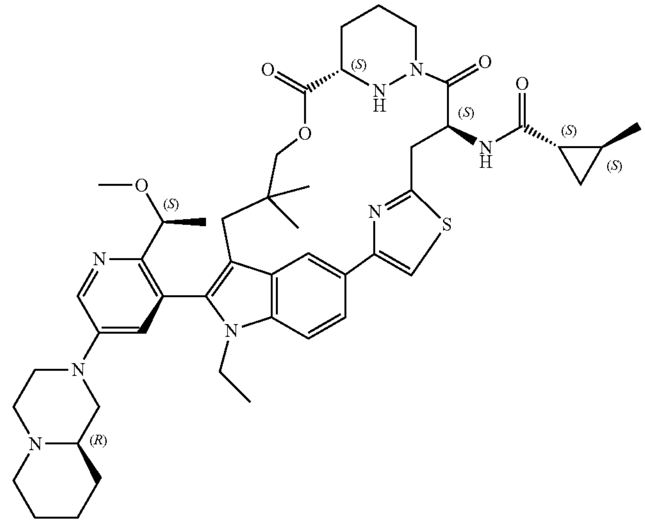 |
| A158 | 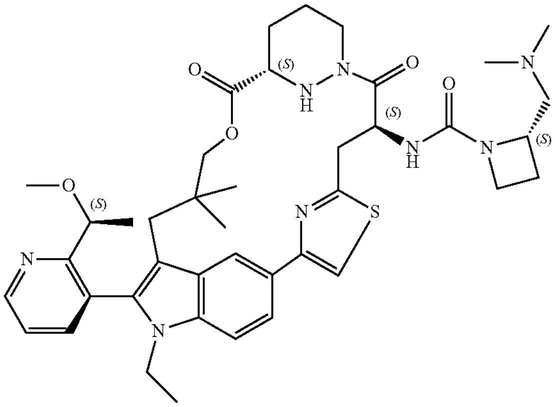 |

TABLE 1a-continued
| Certain Compounds of the Present Invention | |
|---|---|
| Ex. # | Structure |
| A159 | 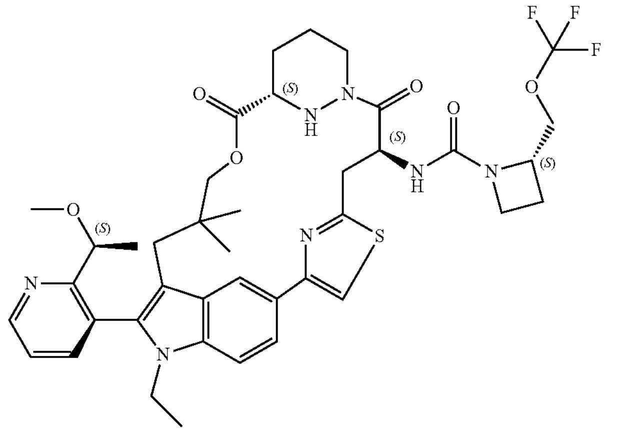 |
| A160 | 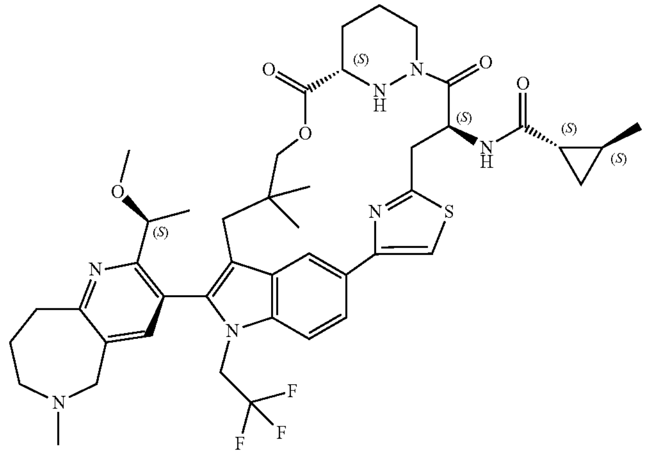 |
| A161 | 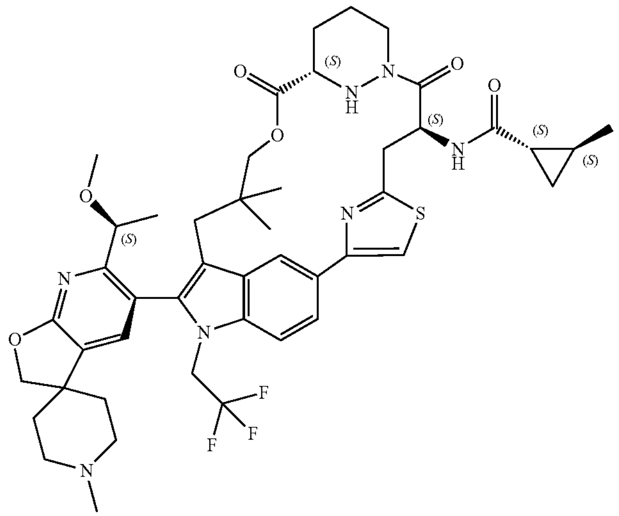 |

TABLE 1a-continued
Certain Compounds of the Present Invention
| Ex. # | Structure |
| --- | --- |
| A162 | 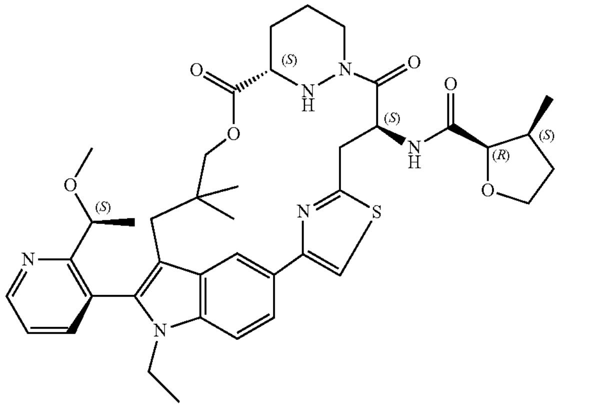 |
| A163 | 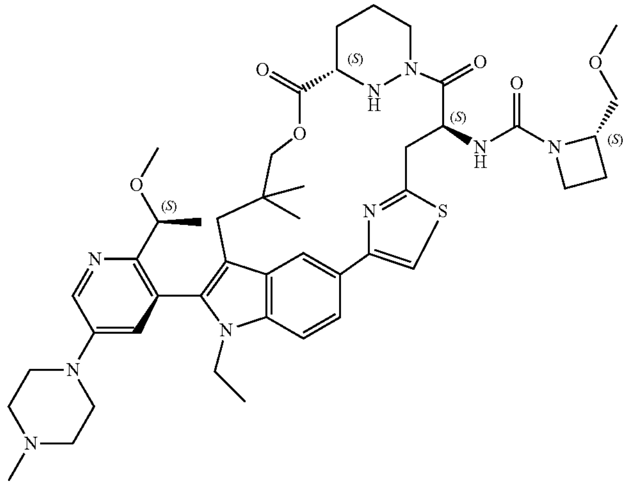 |
| A164 | 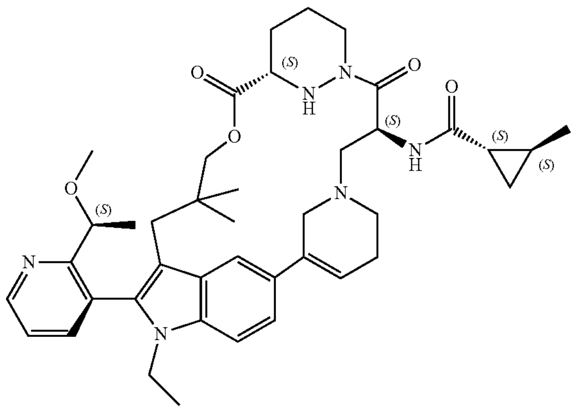 |

TABLE 1a-continued
| Certain Compounds of the Present Invention | |
|---|---|
| Ex. # | Structure |
| A165 | 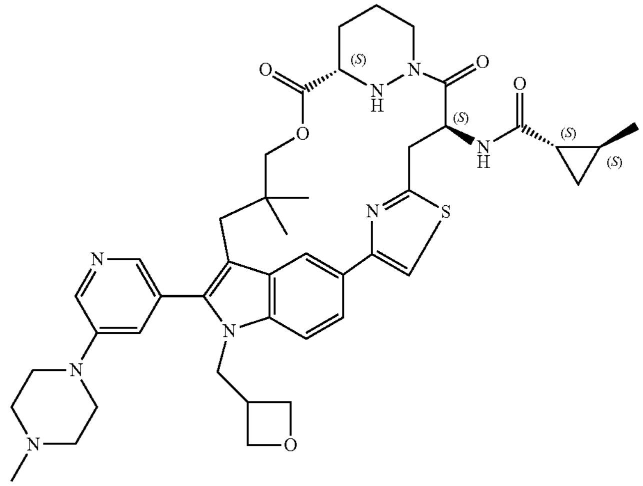 |
| A166 | 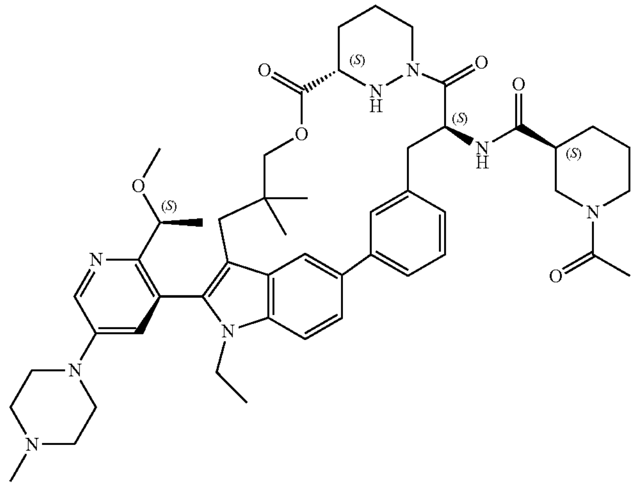 |
| A167 | 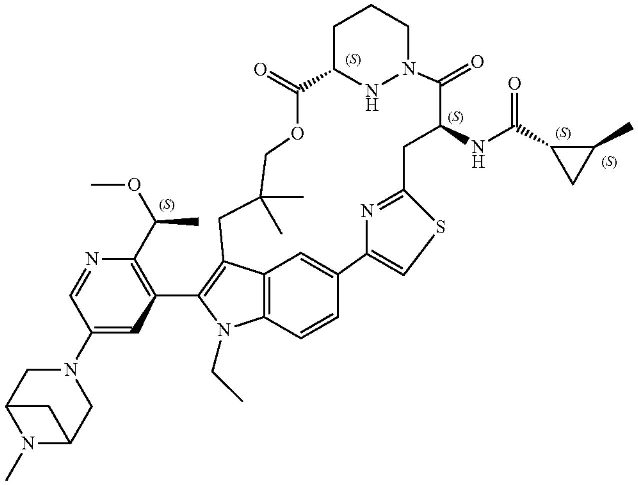 |

TABLE 1a-continued
| Certain Compounds of the Present Invention | |
|---|---|
| Ex. # | Structure |
| A168 | 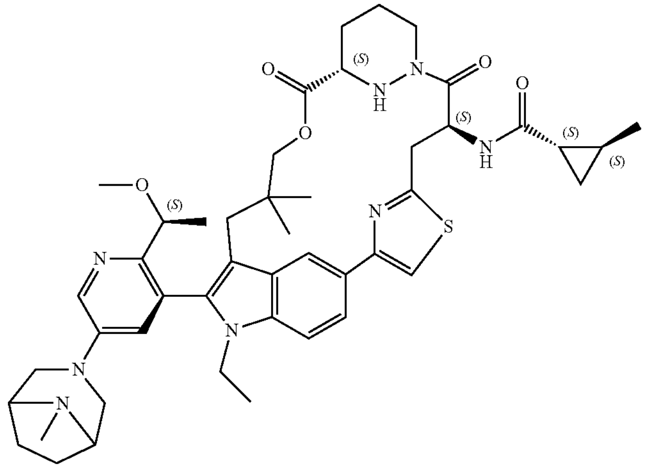 |
| A169 | 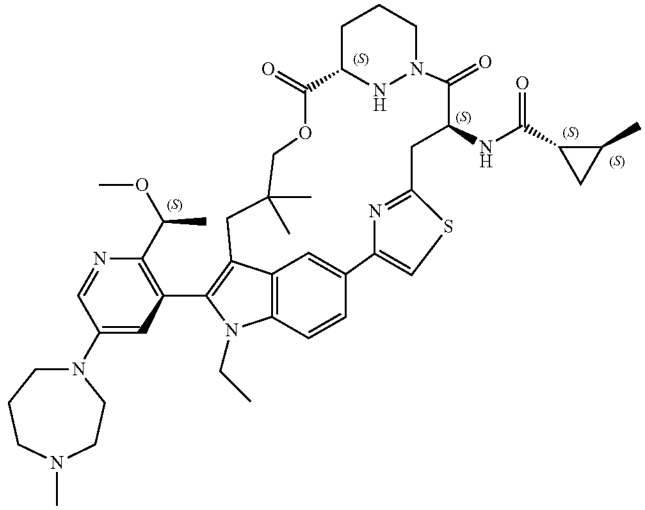 |
| A170 | 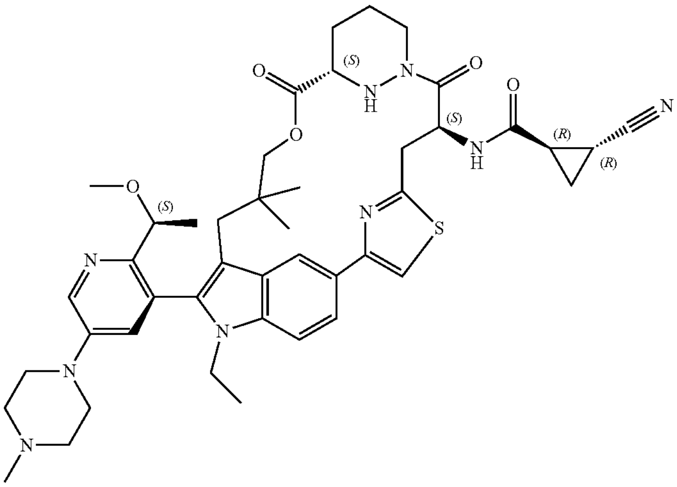 |

TABLE 1a-continued
| Certain Compounds of the Present Invention | |
|---|---|
| Ex. # | Structure |
| A171 | 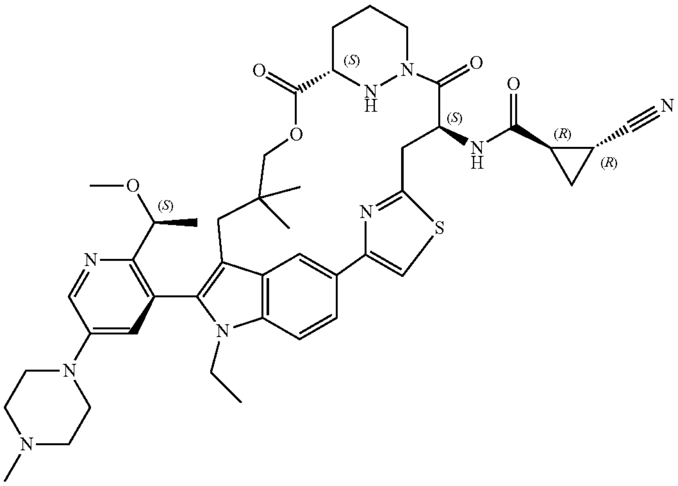 |
| A172 | 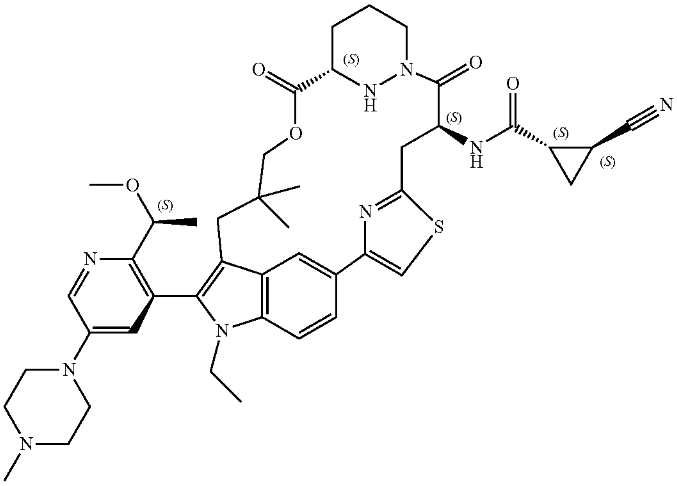 |
| A173 | 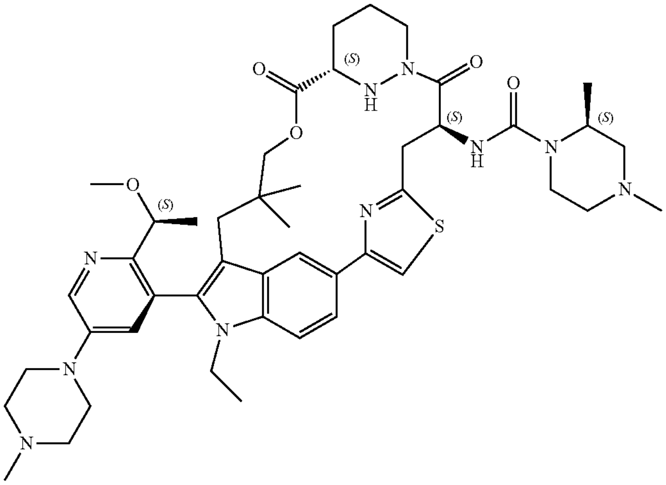 |

TABLE 1a-continued
| Certain Compounds of the Present Invention | |
|---|---|
| Ex. # | Structure |
| A174 | 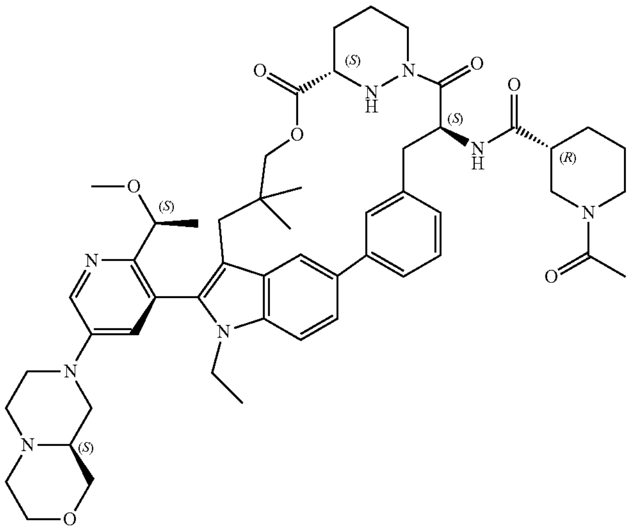 |
| A175 | 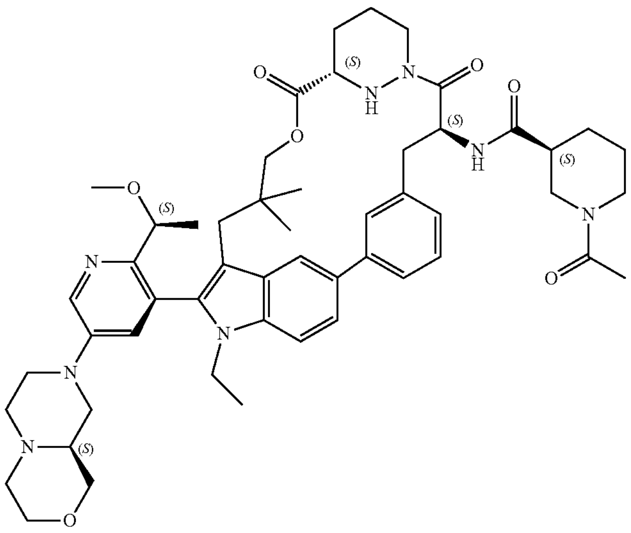 |
| A176 | 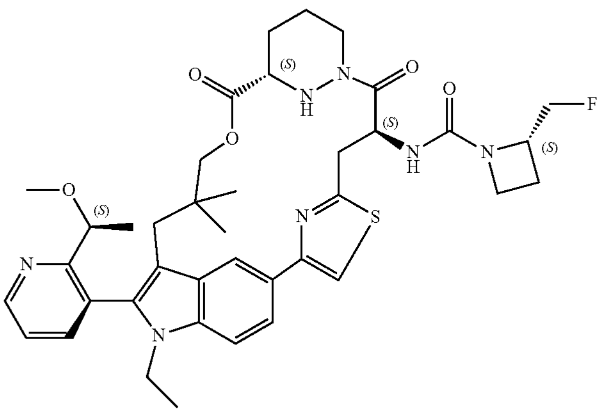 |

TABLE 1a-continued
| Certain Compounds of the Present Invention | |
|---|---|
| Ex. # | Structure |
| A177 | 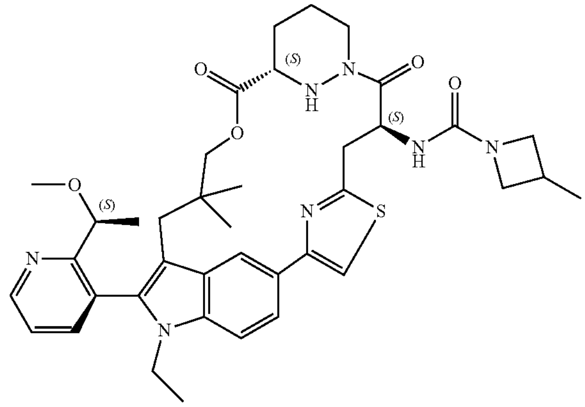 |
| A178 | 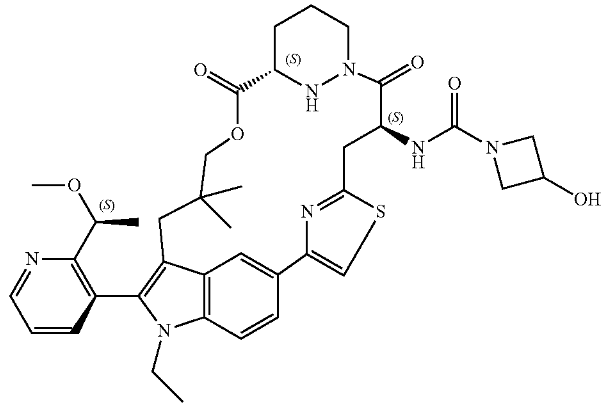 |
| A179 | 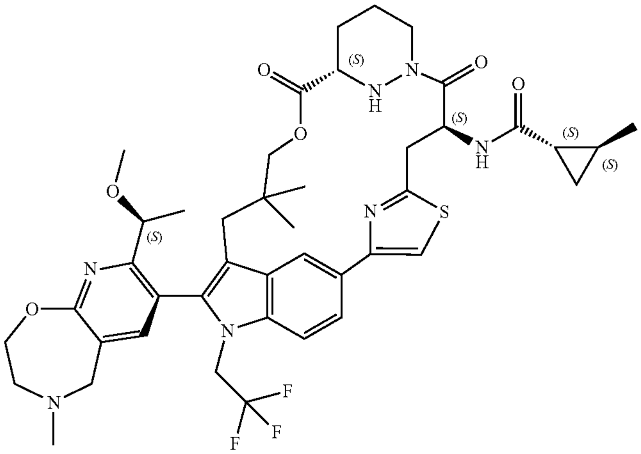 |

TABLE 1a-continued
| Certain Compounds of the Present Invention | |
|---|---|
| Ex. # | Structure |
| A180 | 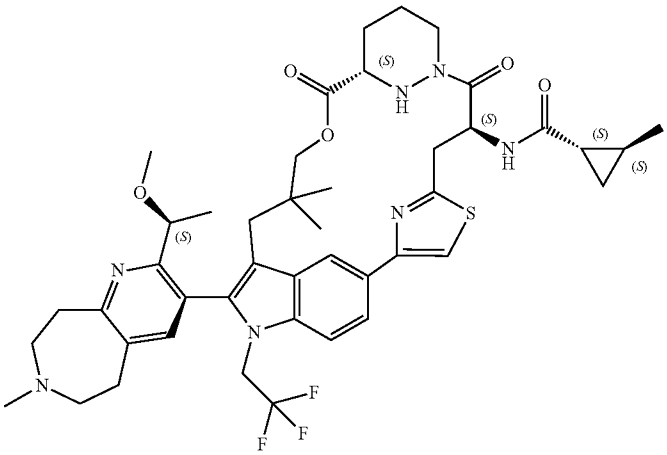 |
| A181 | 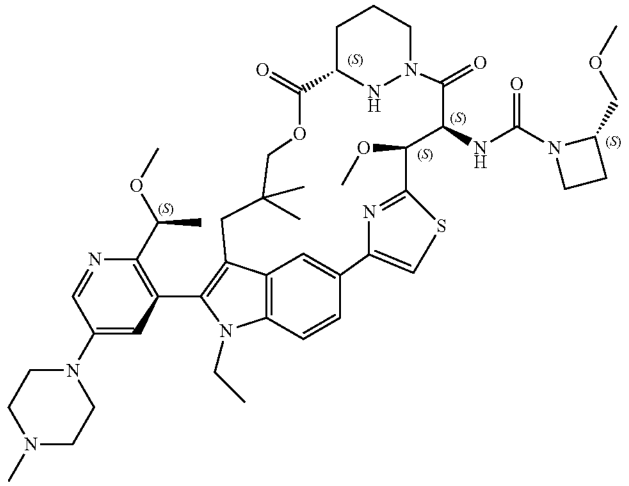 |
| A182 | 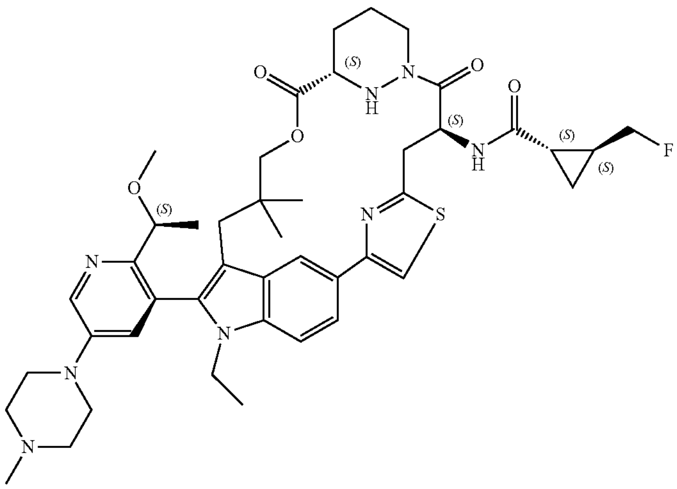 |

TABLE 1a-continued
| Certain Compounds of the Present Invention | |
|---|---|
| Ex. # | Structure |
| A183 | 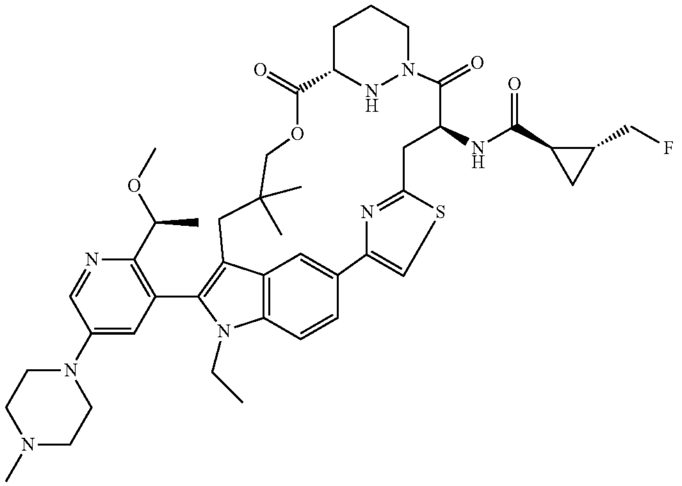 [SMILES: CCn1c(-c2cc(N3CCN(C)CC3)cnc2[C@H](C)OC)c2c3cc(ccc31)-c1csc(n1)C[C@H](NC(=O)[C@@H]1C[C@H]1CF)C(=O)N1CCC[C@H](N1)C(=O)OCC(C)(C)C2] |
| A184 | 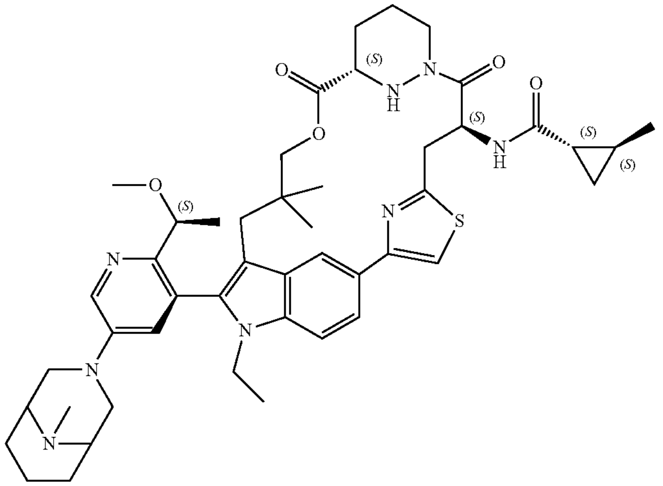 |
| A185 | 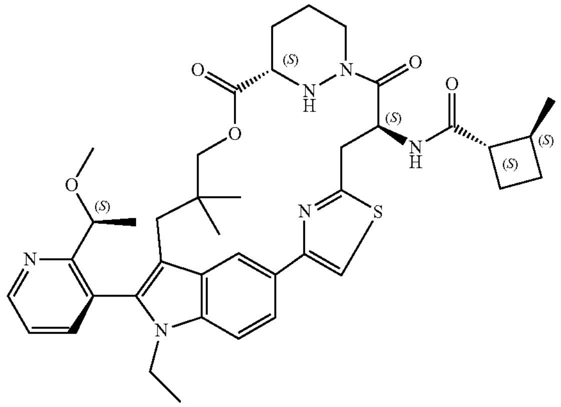 |

TABLE 1a-continued
| Certain Compounds of the Present Invention | |
|---|---|
| Ex. # | Structure |
| A186 | 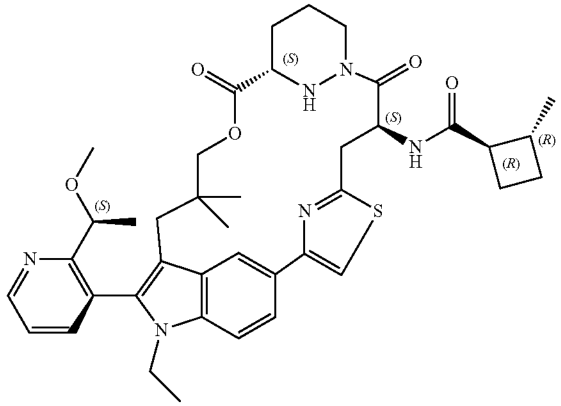 |
| A187 | 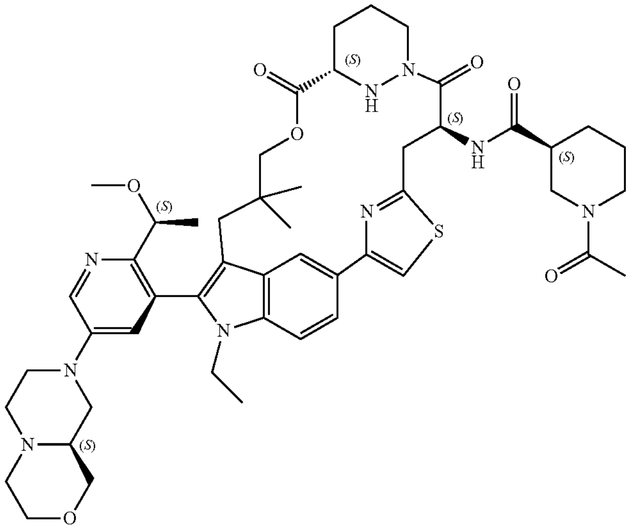 |
| A188 | 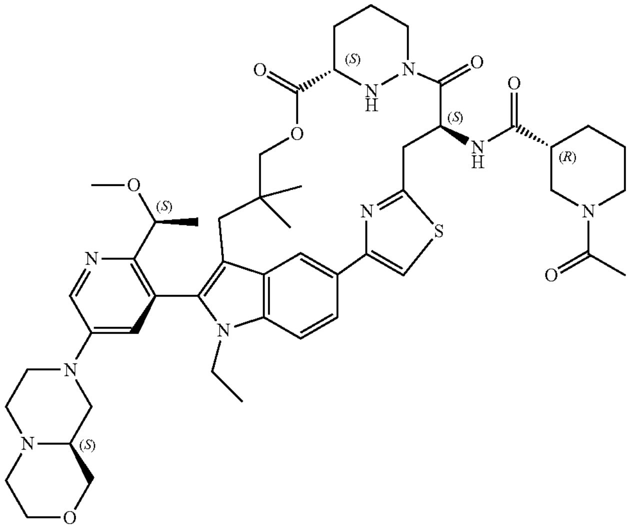 |

TABLE 1a-continued
| Certain Compounds of the Present Invention | |
|---|---|
| Ex. # | Structure |
| A189 | 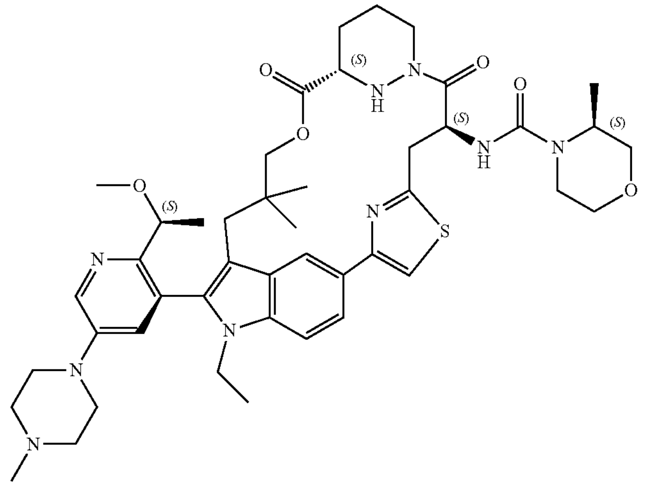 |
| A190 | 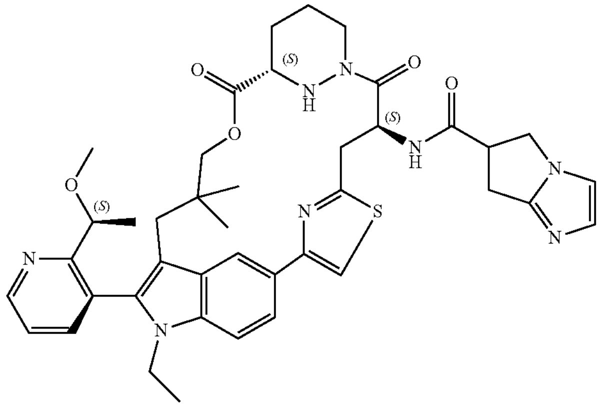 |
| A191 | 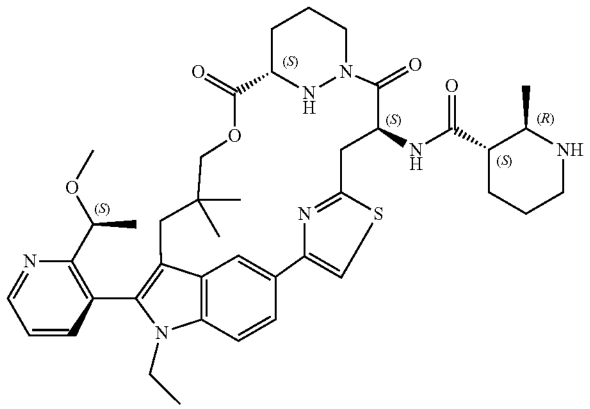 |

TABLE 1a-continued
| Certain Compounds of the Present Invention | |
|---|---|
| Ex. # | Structure |
| A192 | 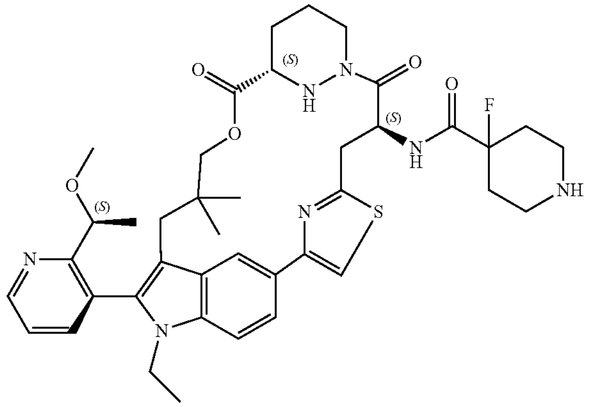 |
| A193 | 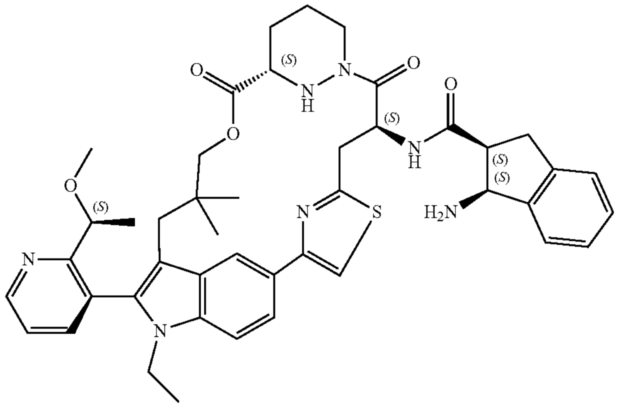 |
| A194 | 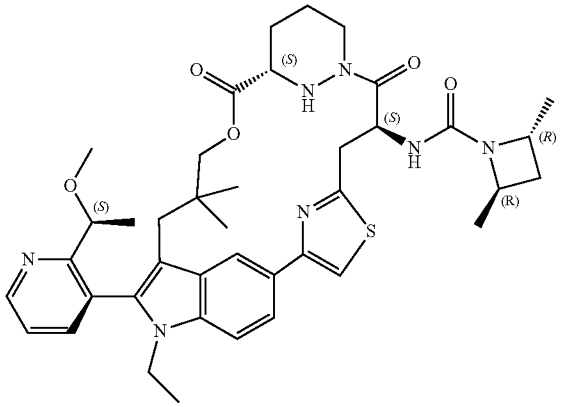 |

TABLE 1a-continued
| Certain Compounds of the Present Invention | |
|---|---|
| Ex. # | Structure |
| A195 | 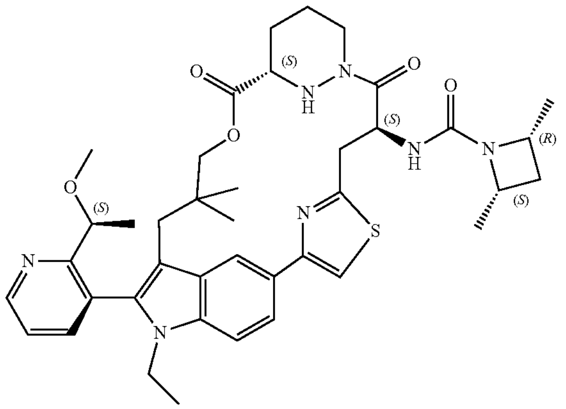 |
| A196 | 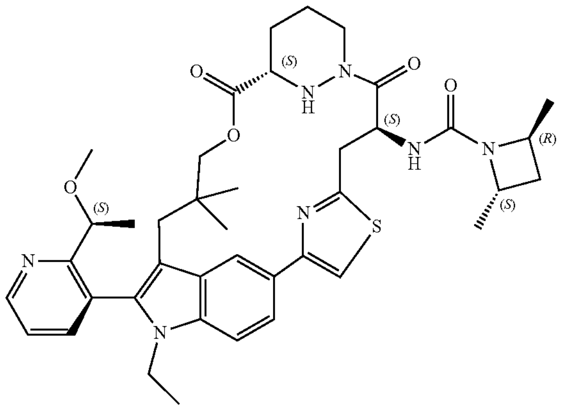 |
| A197 | 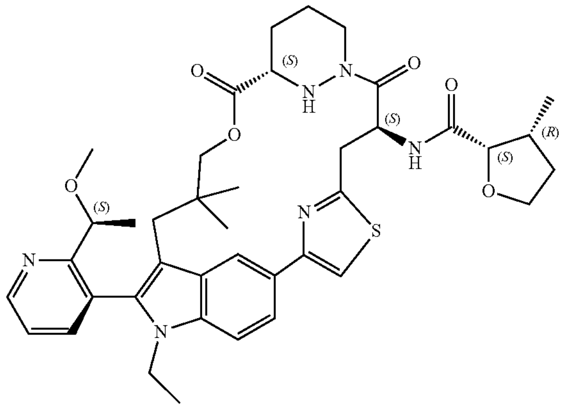 |

TABLE 1a-continued
| Certain Compounds of the Present Invention | |
|---|---|
| Ex. # | Structure |
| A198 | 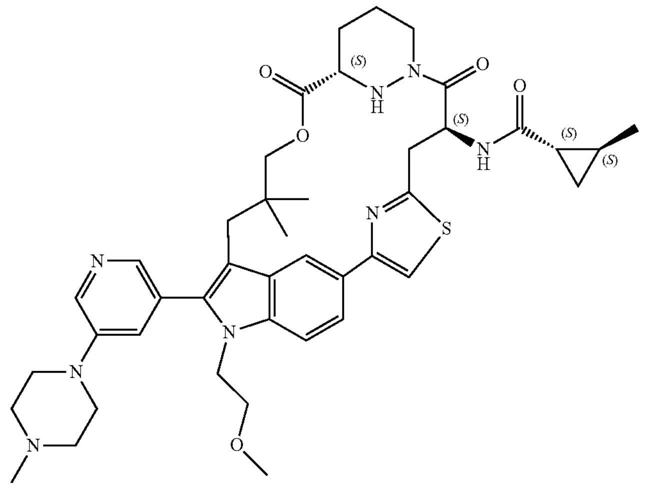 |
| A199 | 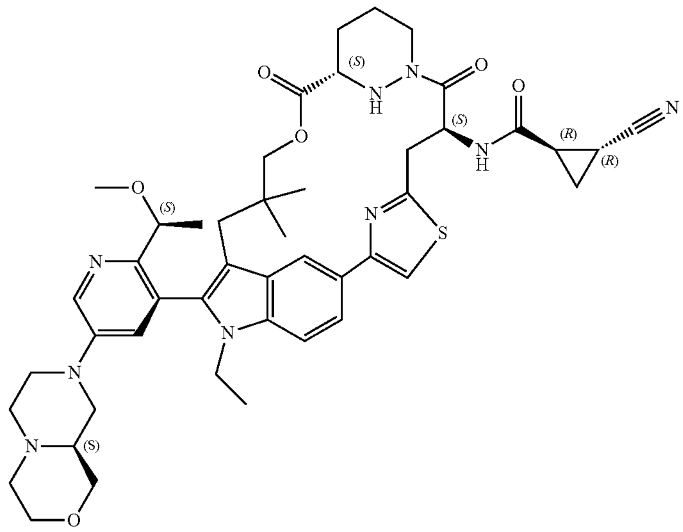 |
| A200 | 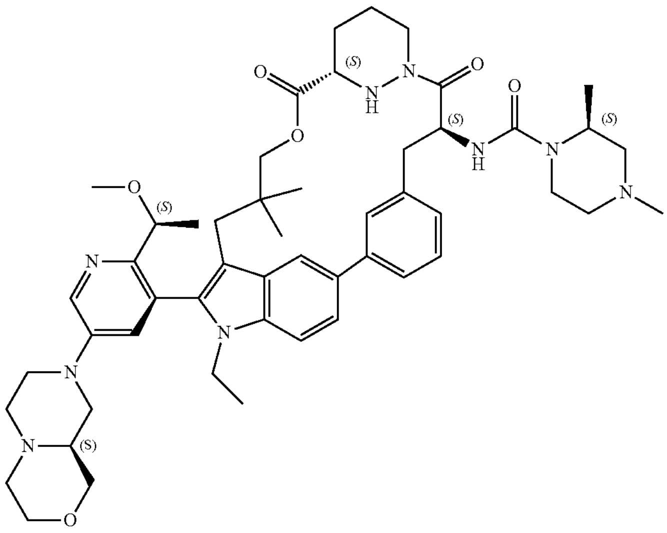 |

TABLE 1a-continued
| Certain Compounds of the Present Invention | |
|---|---|
| Ex. # | Structure |
| A201 | 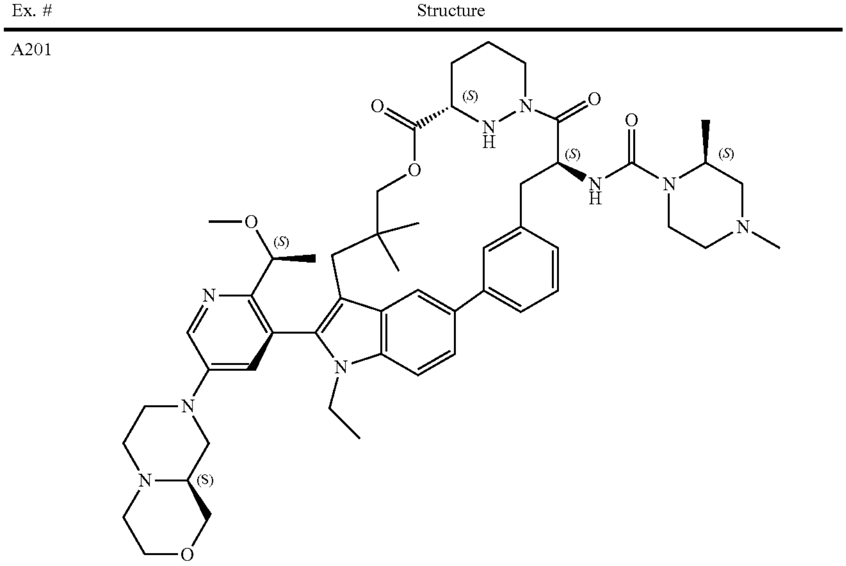 |
| A202 | 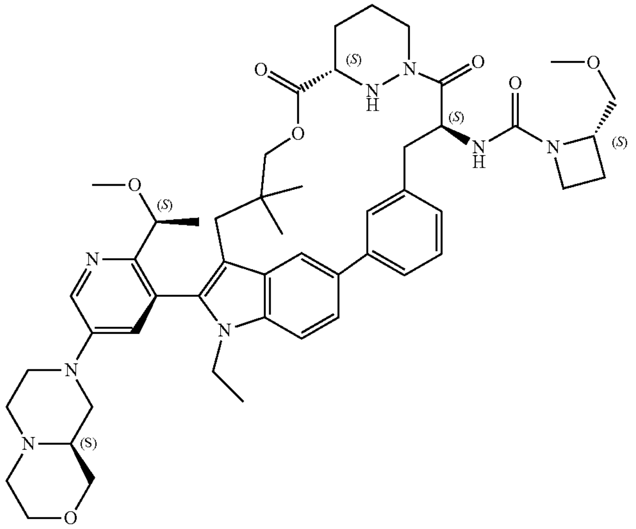 |
| A203 | 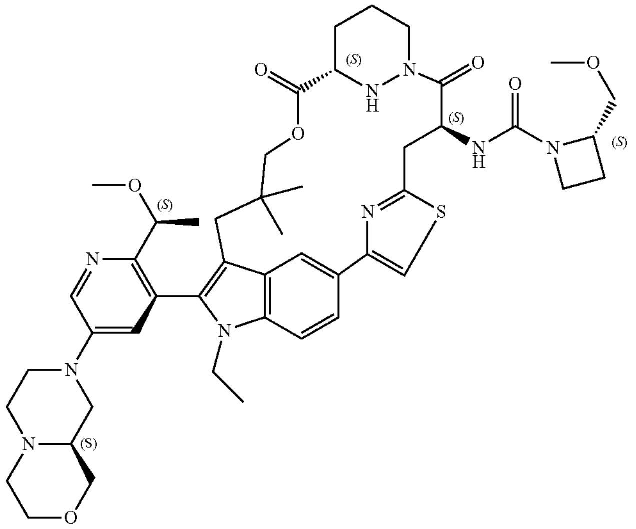 |

TABLE 1a-continued
| Certain Compounds of the Present Invention | |
|---|---|
| Ex. # | Structure |
| A204 | 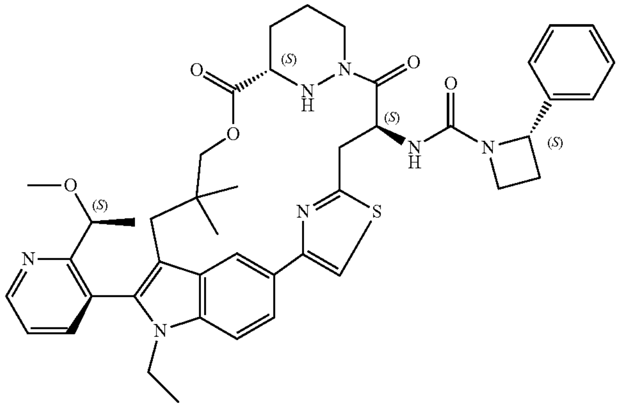 |
| A205 | 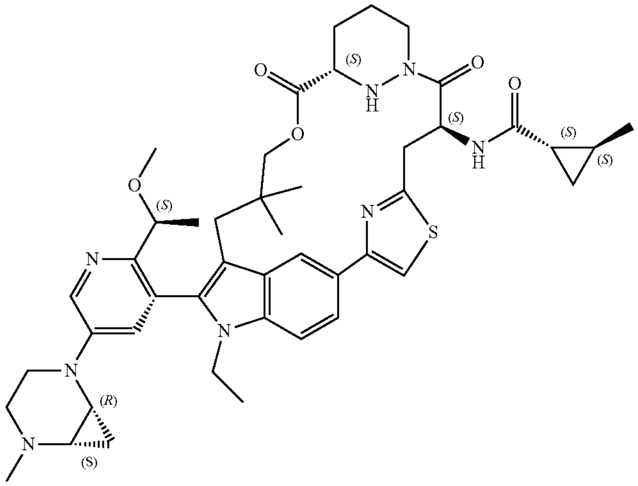 |
| A206 | 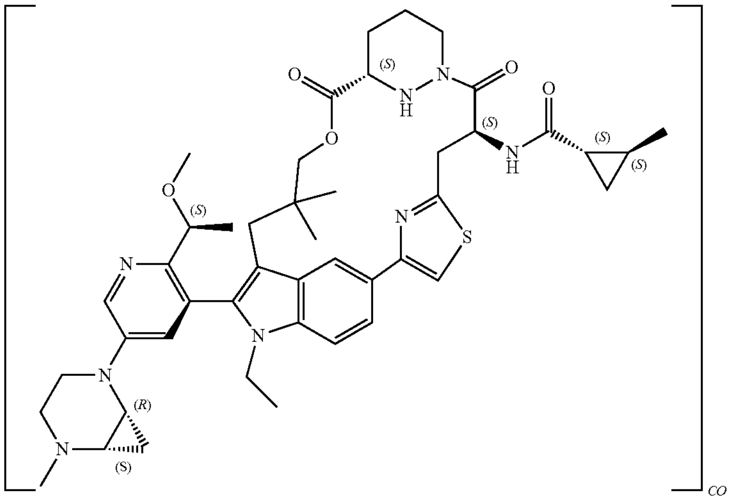 |

TABLE 1a-continued
| Certain Compounds of the Present Invention | |
|---|---|
| Ex. # | Structure |
| A207 | 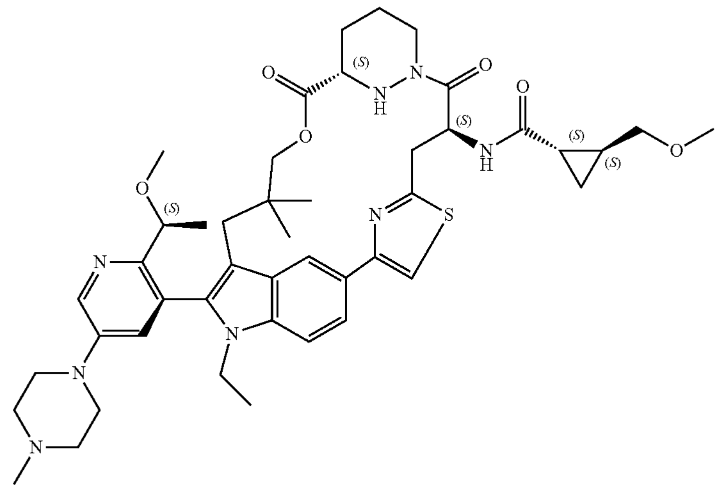 |
| A208 | 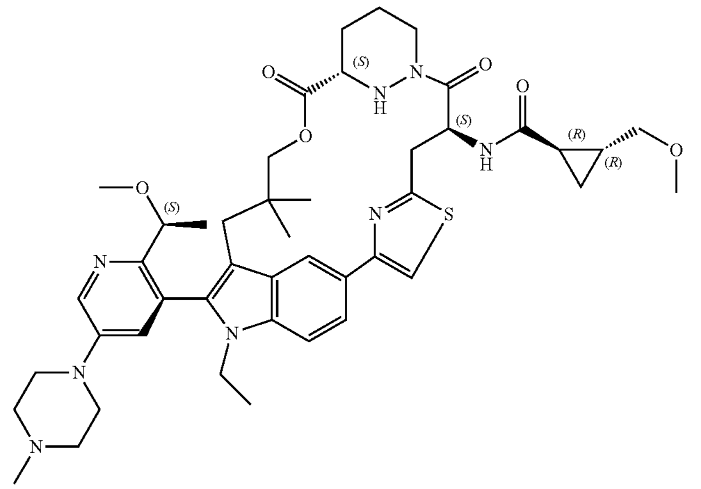 |
| A209 | 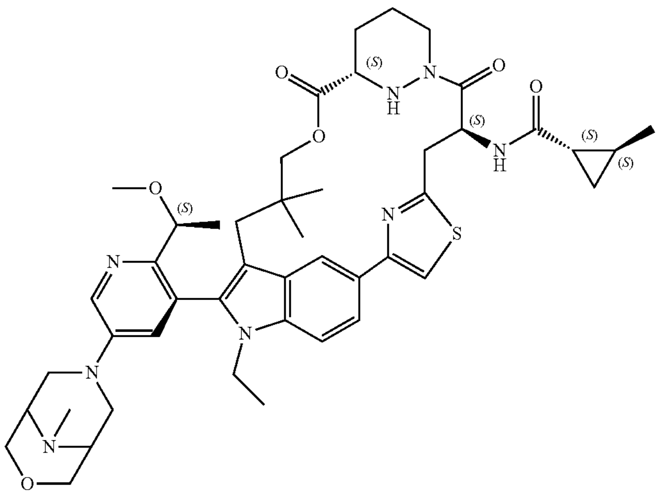 |

TABLE 1a-continued
| Certain Compounds of the Present Invention | |
|---|---|
| Ex. # | Structure |
| A210 | 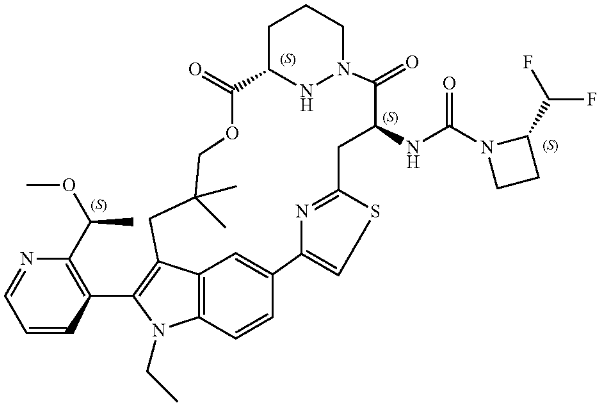 |
| A211 | 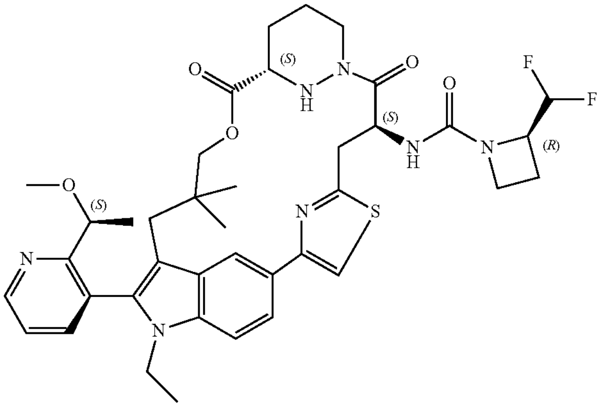 |
| A212 | 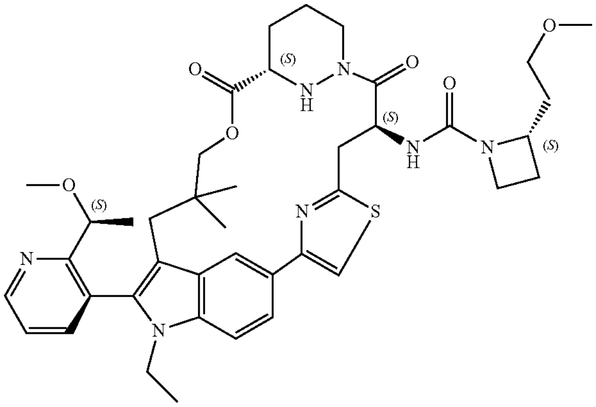 |

TABLE 1a-continued
| Certain Compounds of the Present Invention | |
|---|---|
| Ex. # | Structure |
| A213 | 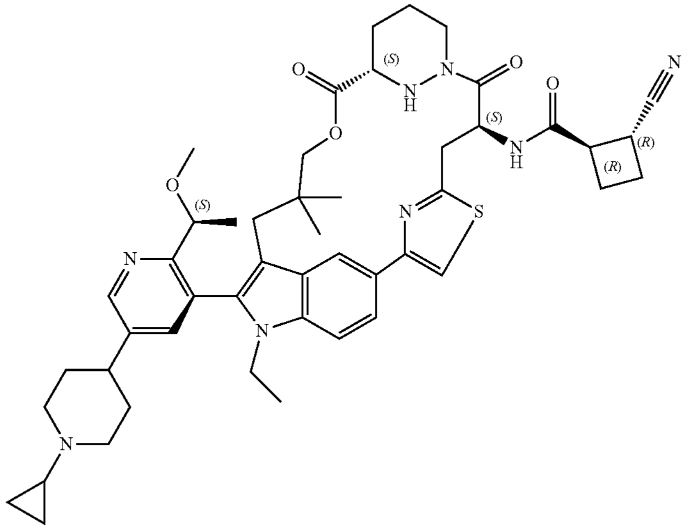 |
| A214 | 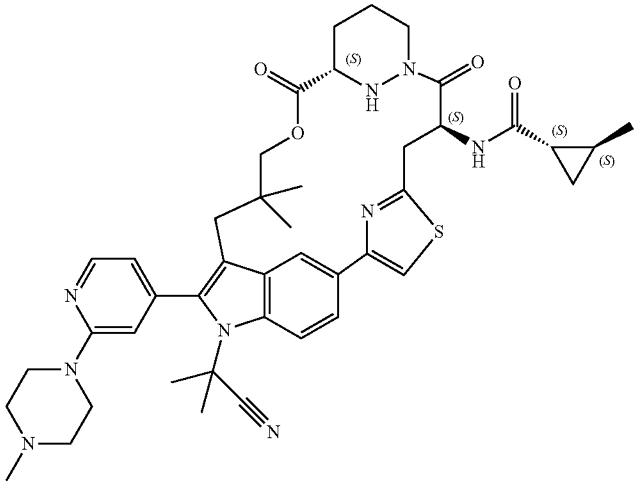 |
| A215 | 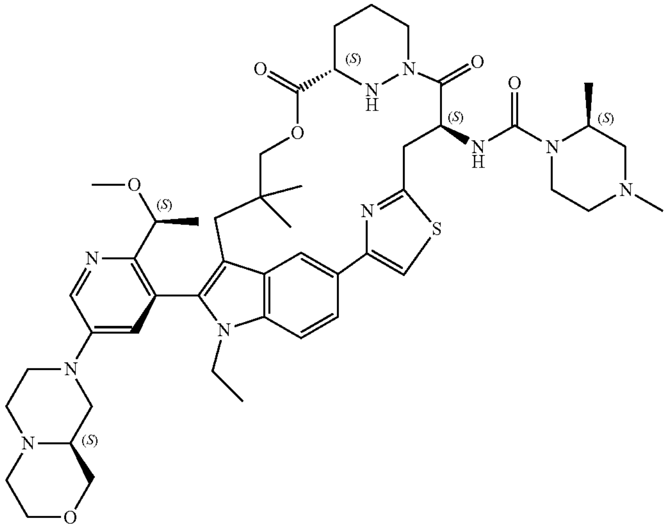 |

TABLE 1a-continued
| Certain Compounds of the Present Invention | |
|---|---|
| Ex. # | Structure |
| A216 | 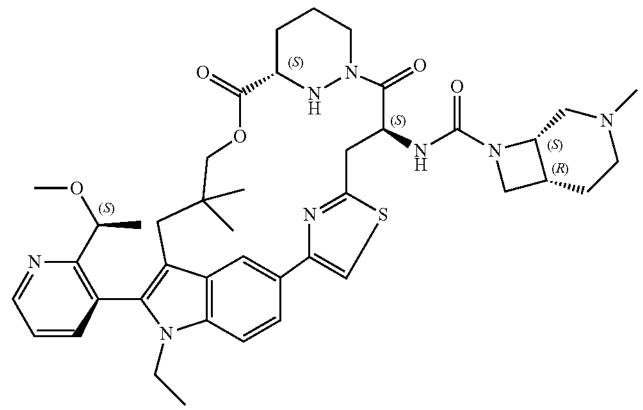 |
| A217 | 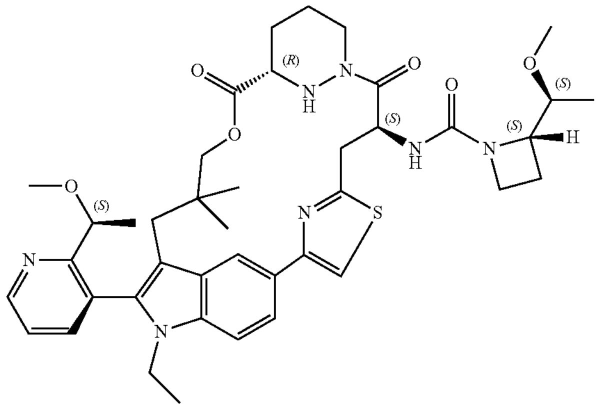 |
| A218 | 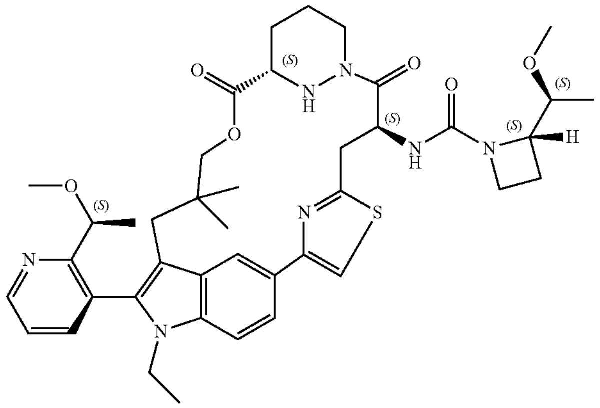 |

TABLE 1a-continued
| Certain Compounds of the Present Invention | |
|---|---|
| Ex. # | Structure |
| A219 | 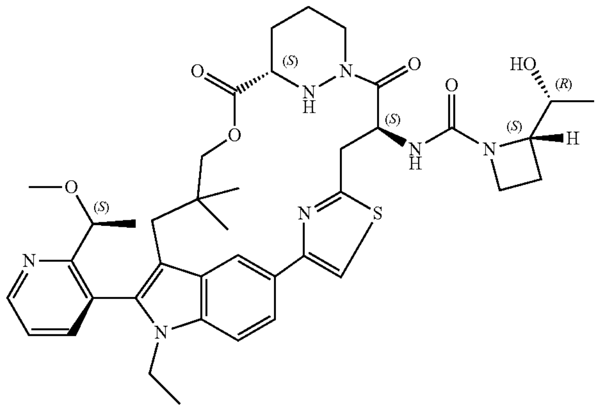 |
| A220 | 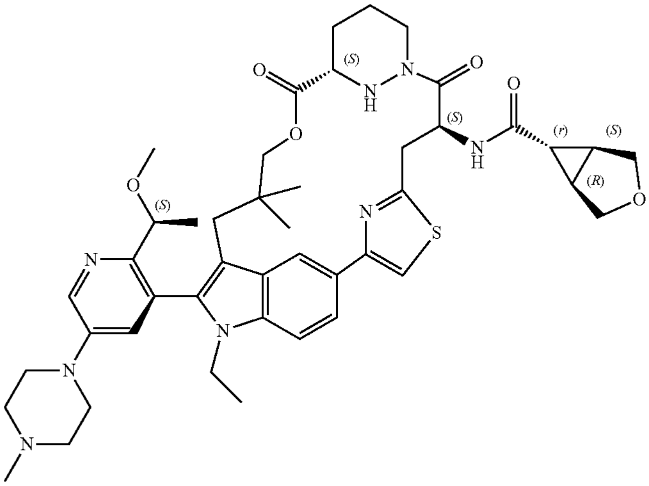 |
| A221 | 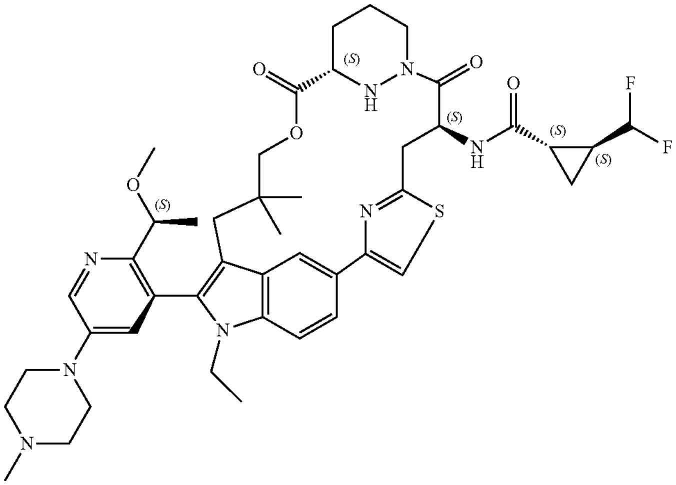 |

TABLE 1a-continued
| Certain Compounds of the Present Invention | |
|---|---|
| Ex. # | Structure |
| A222 | 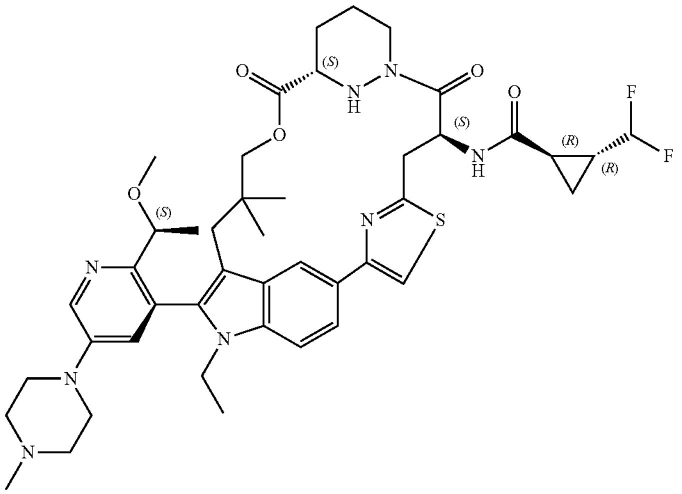 |
| A223 | 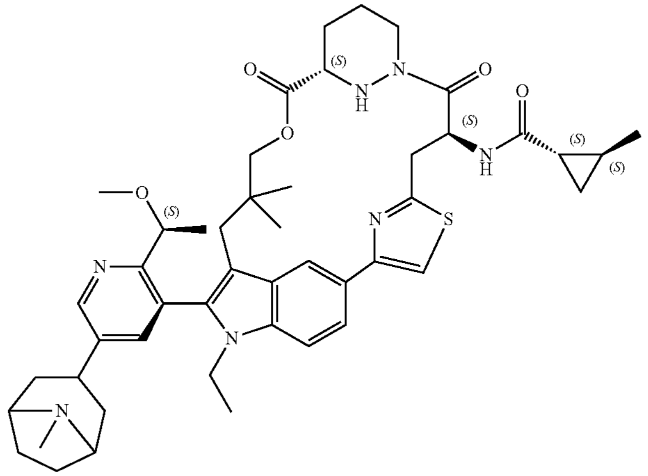 |
| A224 | 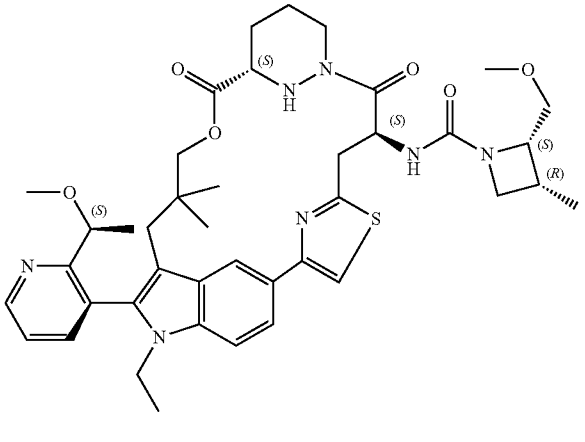 |

TABLE 1a-continued
| Certain Compounds of the Present Invention | |
|---|---|
| Ex. # | Structure |
| A225 | 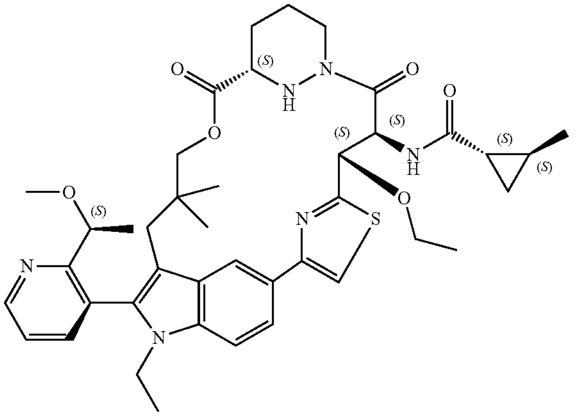 |
| A226 | 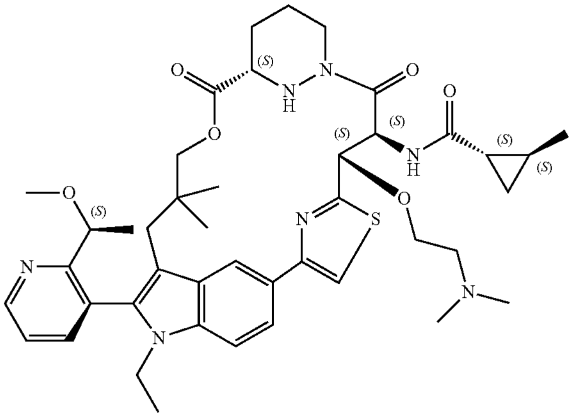 |
| A227 | 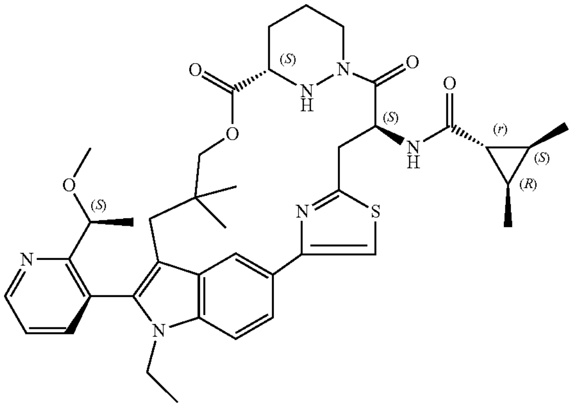 |

TABLE 1a-continued
| Certain Compounds of the Present Invention | |
|---|---|
| Ex. # | Structure |
| A228 | 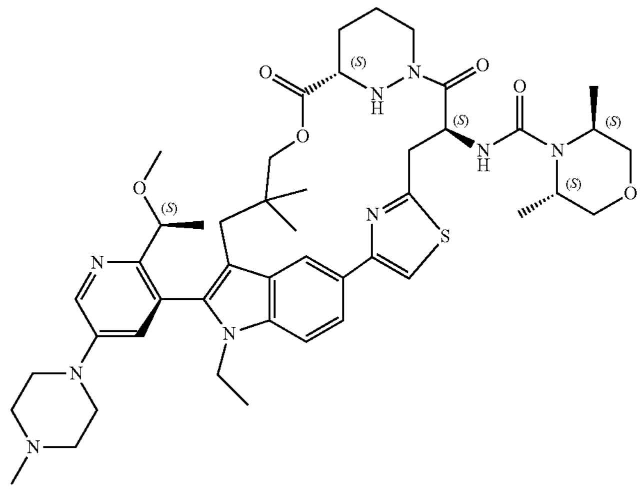 |
| A229 | 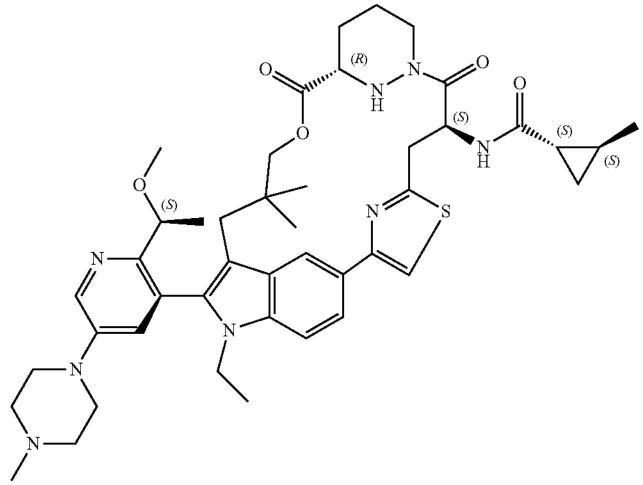 |
| A230 | 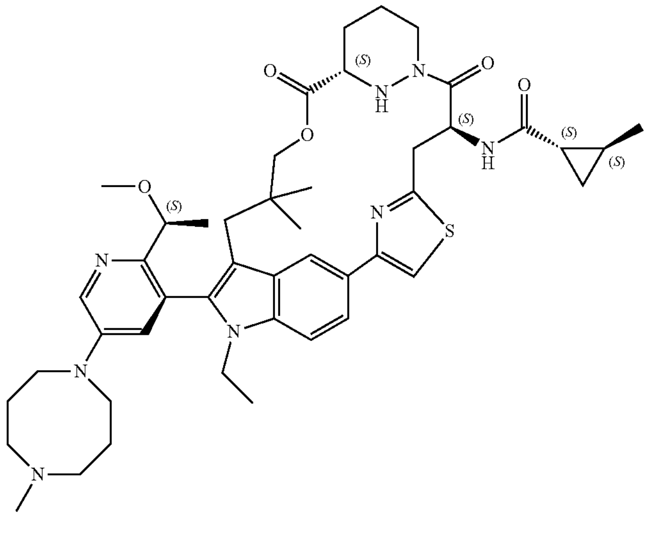 |

TABLE 1a-continued
| Certain Compounds of the Present Invention | |
|---|---|
| Ex. # | Structure |
| A231 | 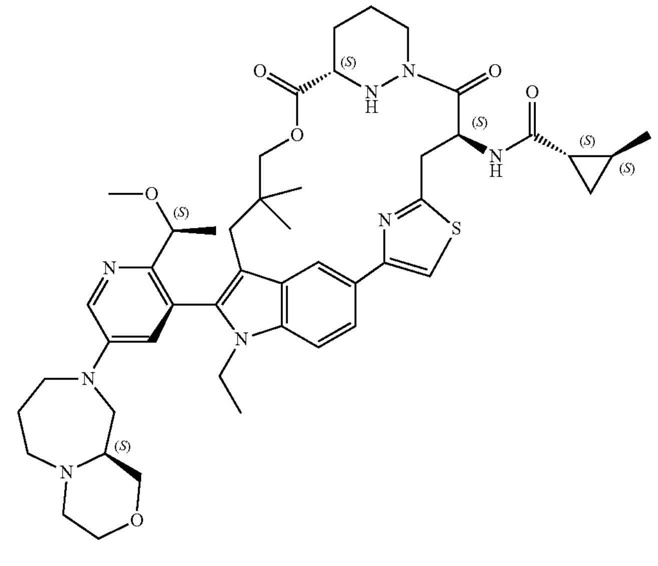 |
| A232 | 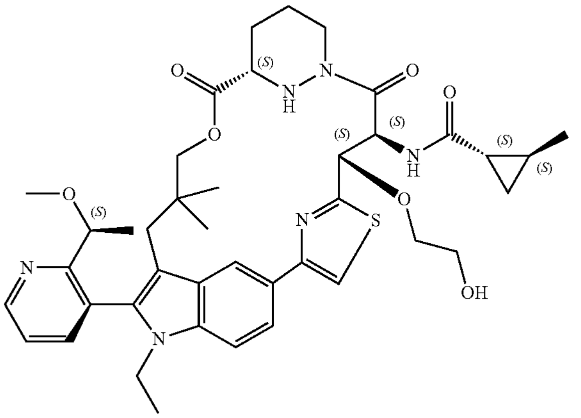 |
| A233 | 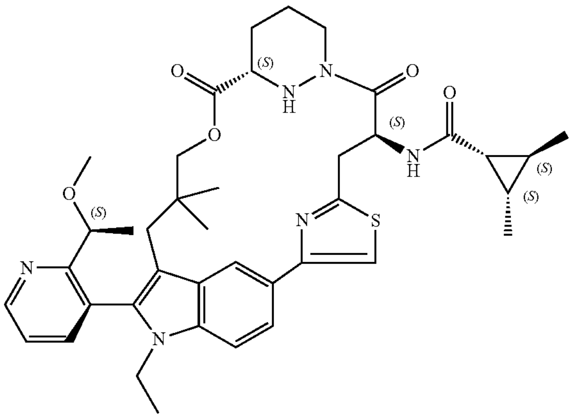 |

TABLE 1a-continued
| Certain Compounds of the Present Invention | |
|---|---|
| Ex. # | Structure |
| A234 | 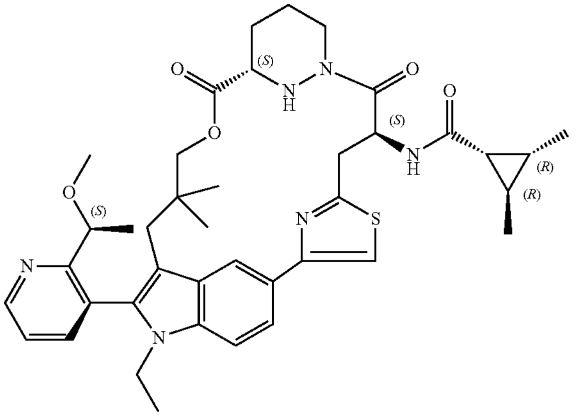 |
| A235 | 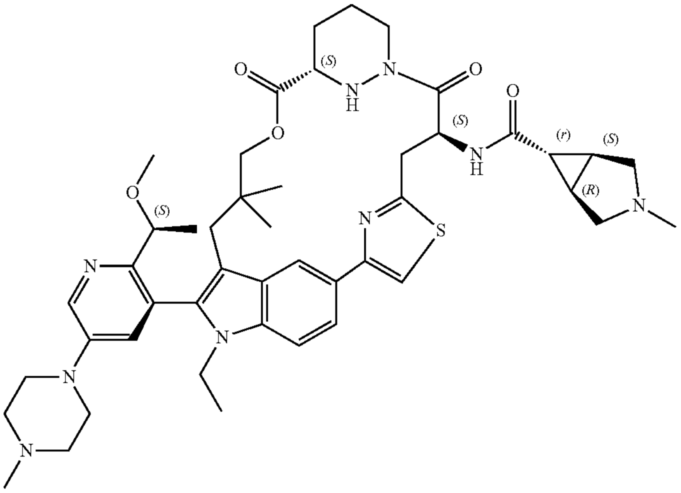 |
| A236 | 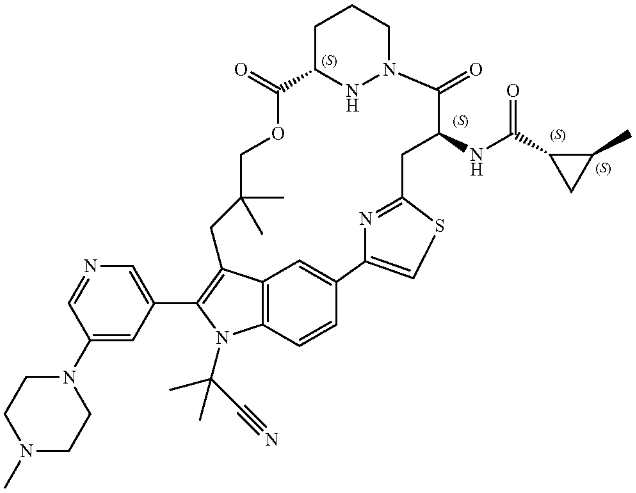 |

TABLE 1a-continued
| Certain Compounds of the Present Invention | |
|---|---|
| Ex. # | Structure |
| A237 | 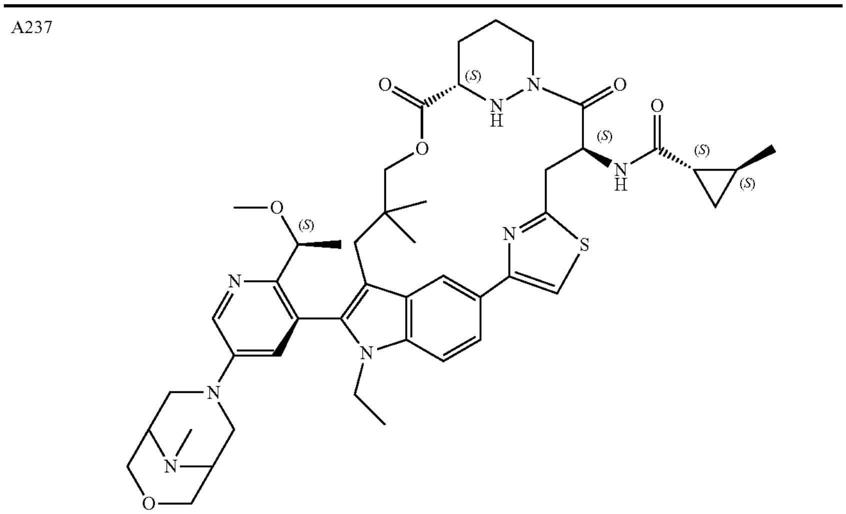 |
| A238 | 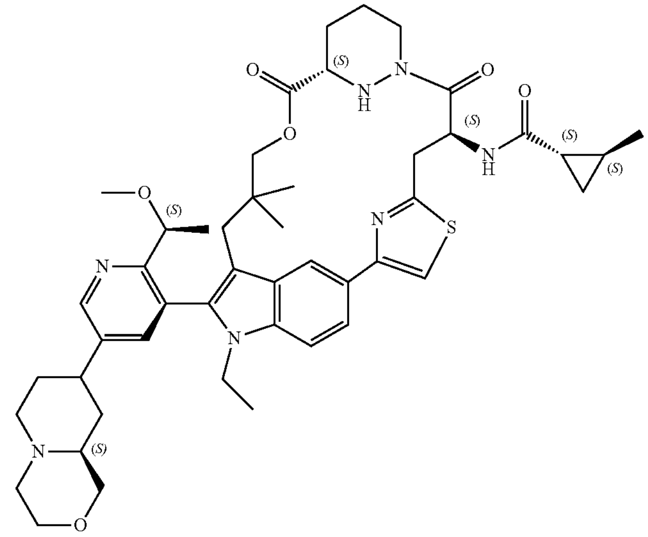 |
| A239 | 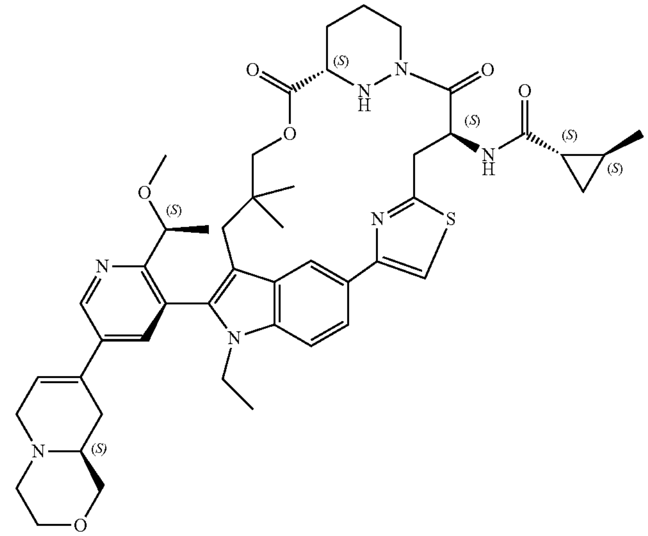 |

TABLE 1a-continued
| Certain Compounds of the Present Invention | |
|---|---|
| Ex. # | Structure |
| A240 | 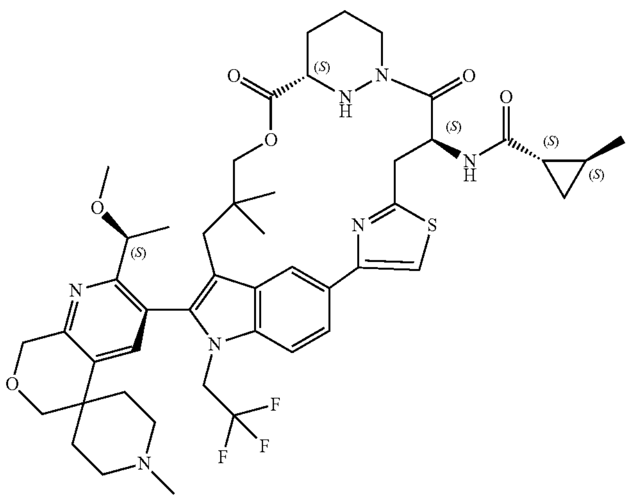 |
| A241 | 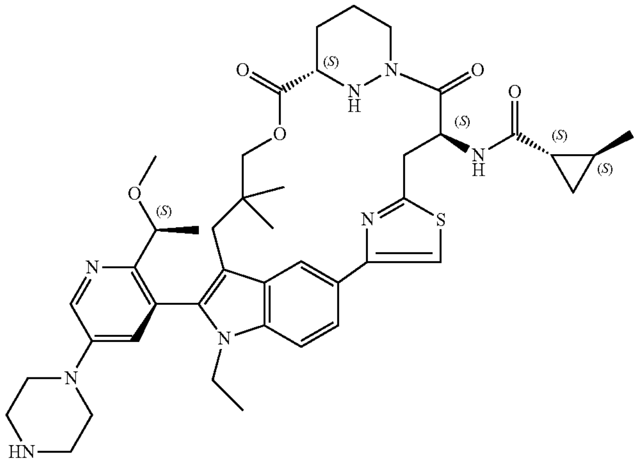 |
| A242 | 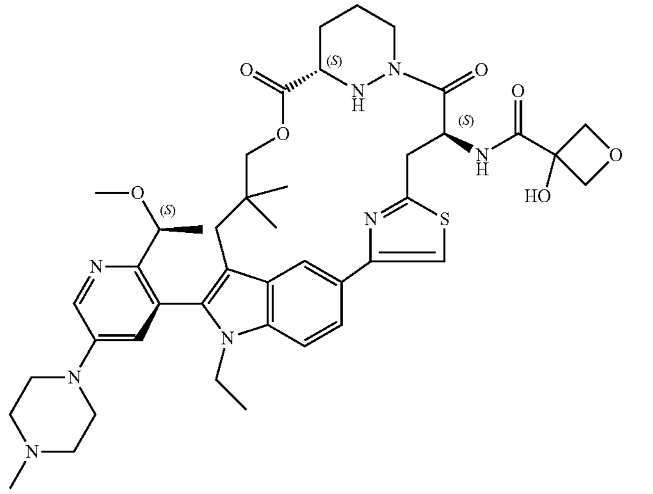 |

TABLE 1a-continued
| Certain Compounds of the Present Invention | |
|---|---|
| Ex. # | Structure |
| A243 | 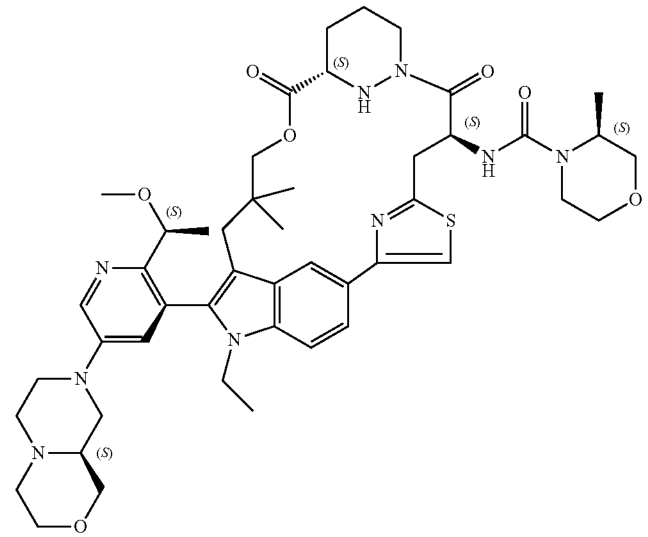 |
| A244 | 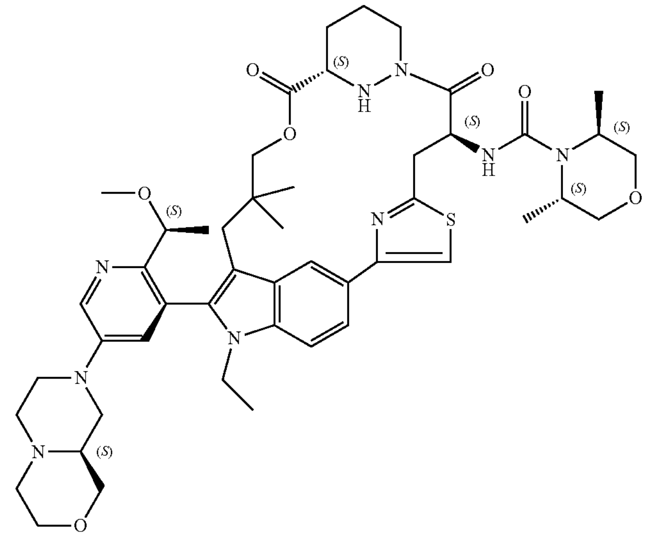 |
| A245 | 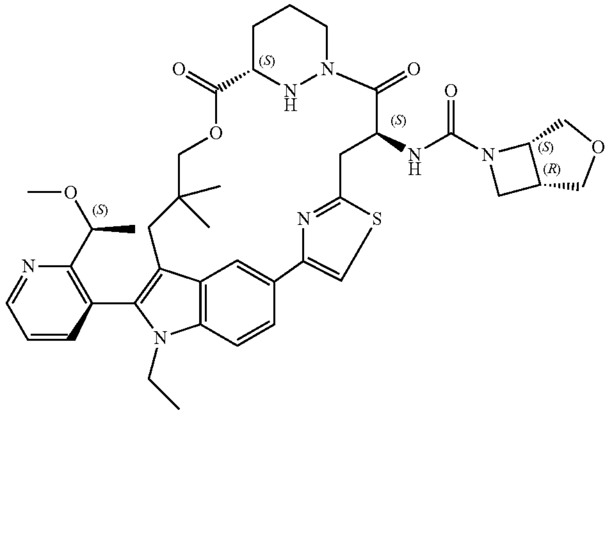 |

TABLE 1a-continued
| Certain Compounds of the Present Invention | |
|---|---|
| Ex. # | Structure |
| A246 | 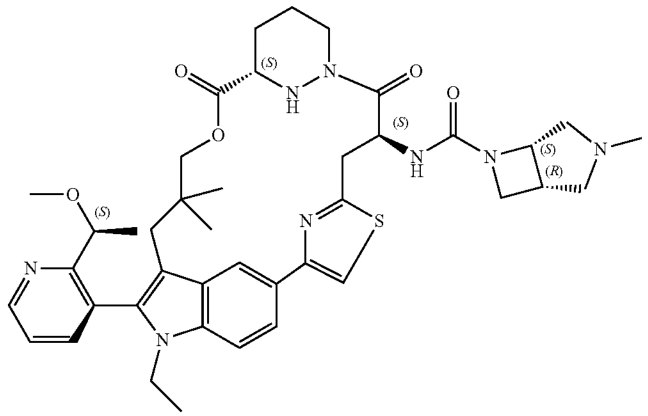 |
| A247 | 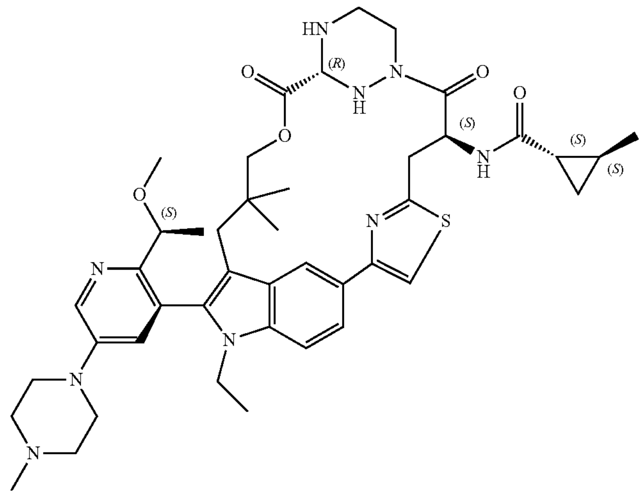 |
| A248 | 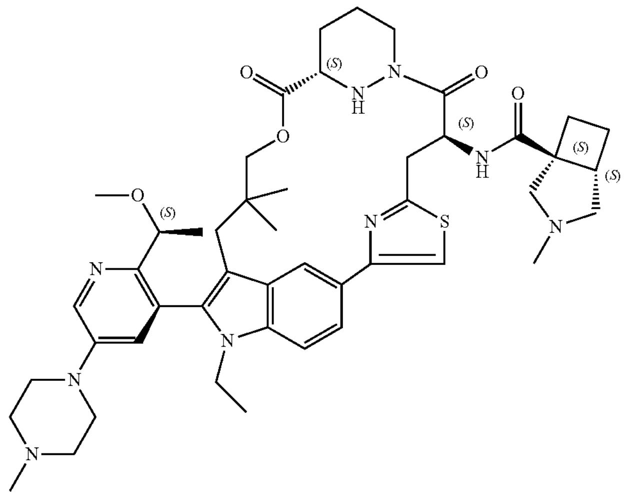 |

TABLE 1a-continued
| Certain Compounds of the Present Invention | |
|---|---|
| Ex. # | Structure |
| A249 | 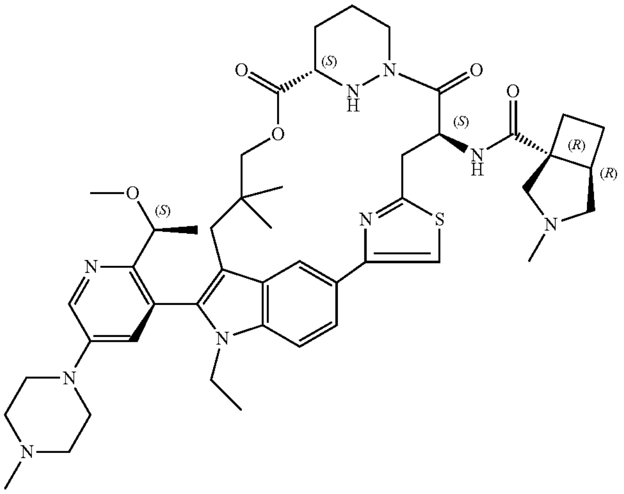 |
| A250 | 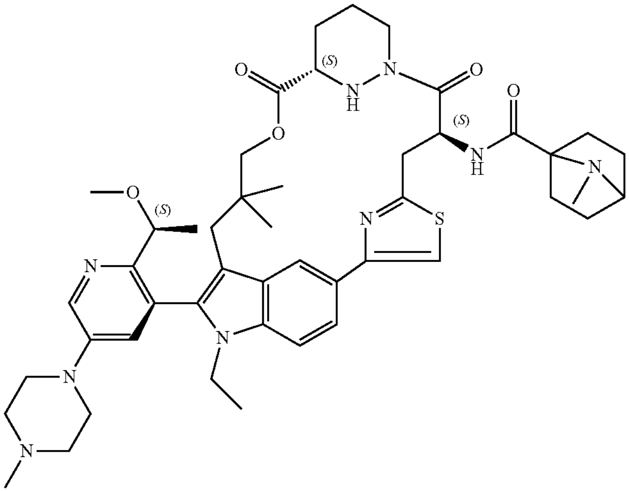 |
| A251 | 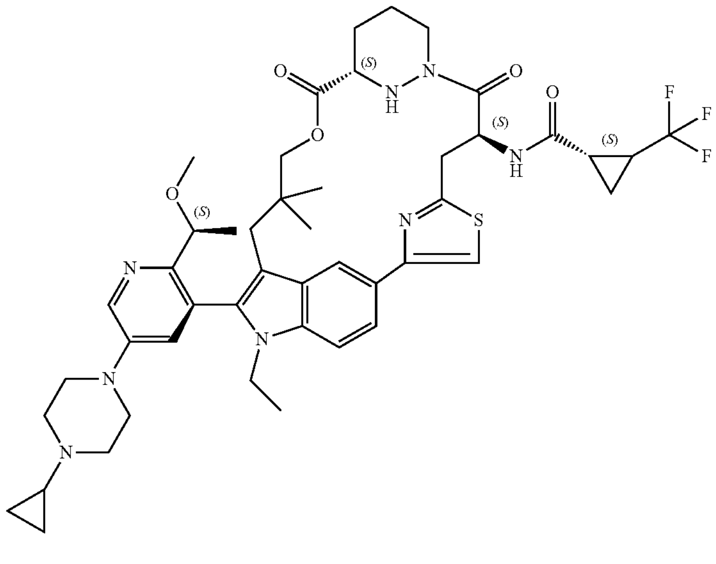 |

TABLE 1a-continued
| Certain Compounds of the Present Invention | |
|---|---|
| Ex. # | Structure |
| A252 | 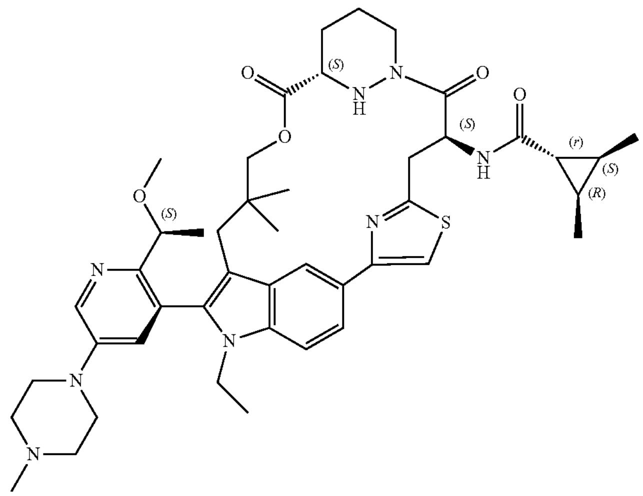 |
| A253 | 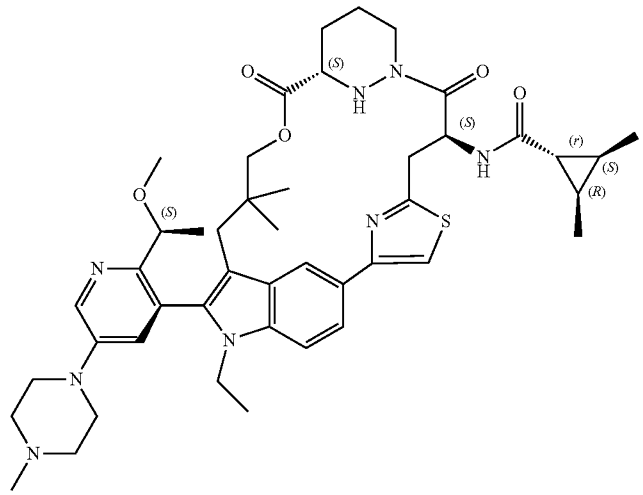 |
| A254 | 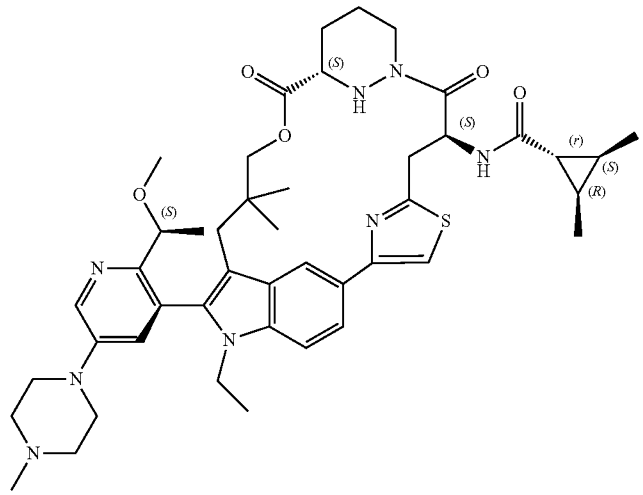 |

TABLE 1a-continued
| Certain Compounds of the Present Invention | |
|---|---|
| Ex. # | Structure |
| A255 | 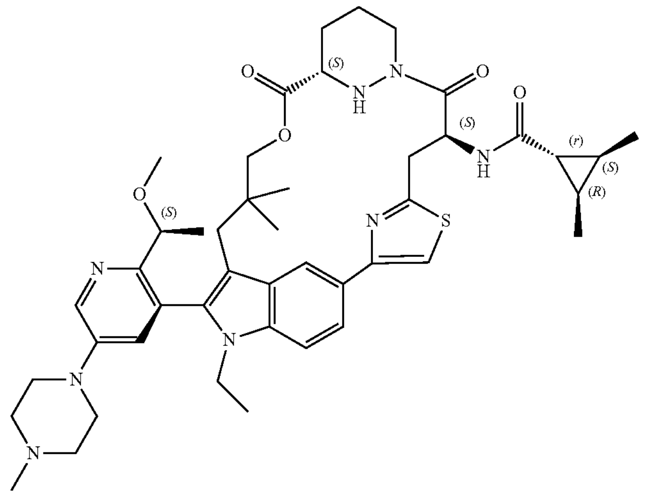 |
| A256 | 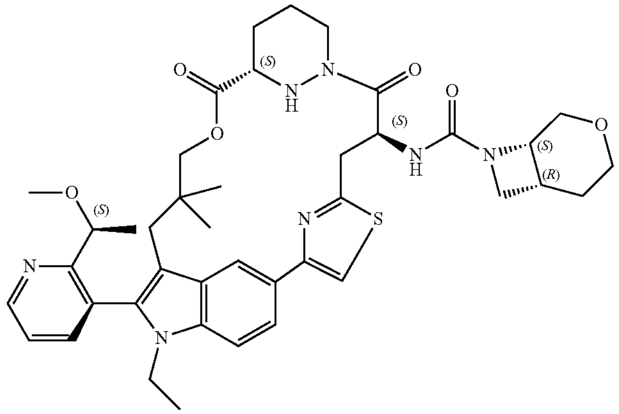 |
| A257 | 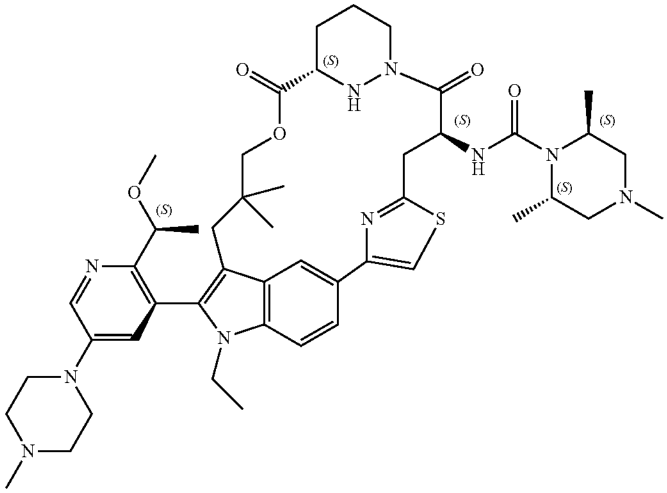 |

TABLE 1a-continued
| Certain Compounds of the Present Invention | |
| --- | --- |
| Ex. # | Structure |
| A258 | 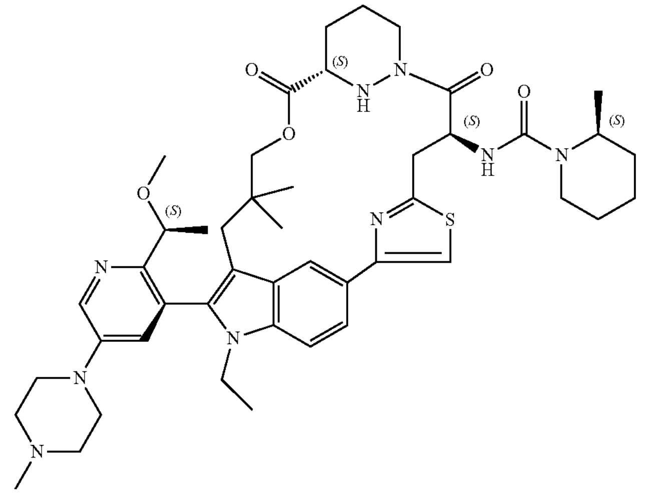 |
| A259 | 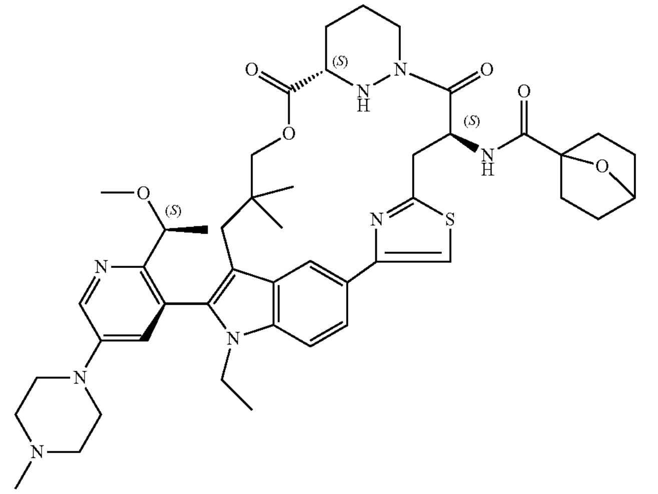 |
| A260 | 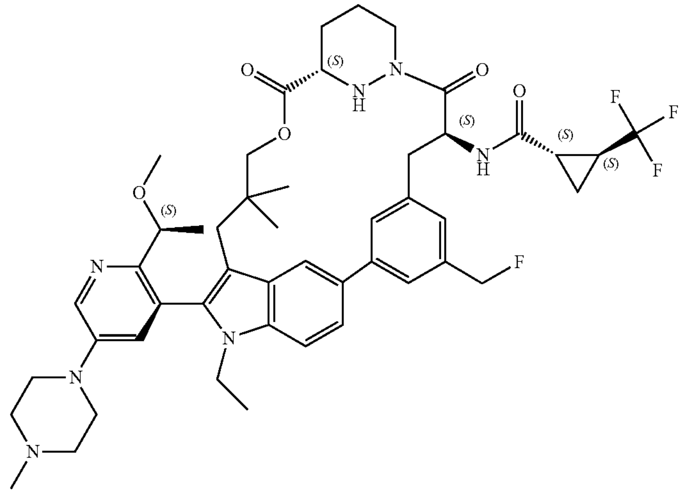 |

TABLE 1a-continued
| Certain Compounds of the Present Invention | |
|---|---|
| Ex. # | Structure |
| A261 | 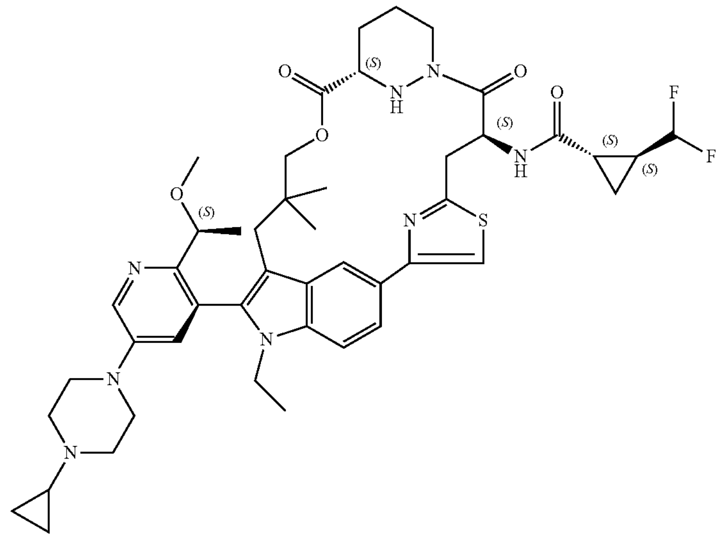 |
| A262 | 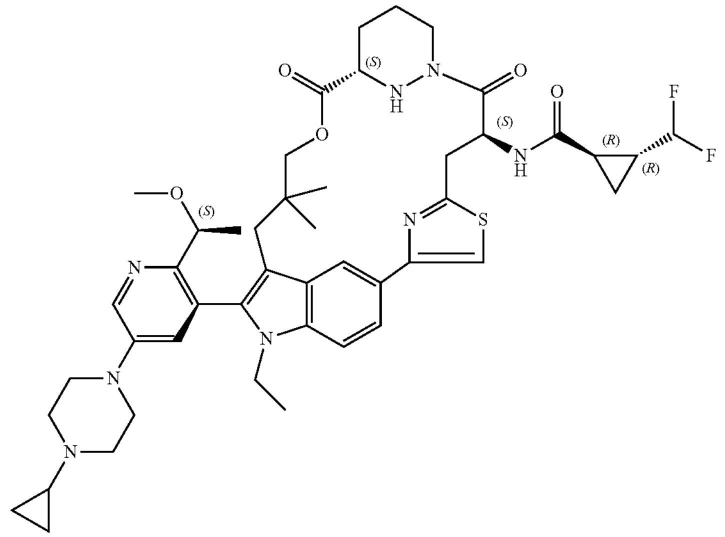 |

TABLE 1a-continued
| Certain Compounds of the Present Invention | |
|---|---|
| Ex. # | Structure |
| A263 | 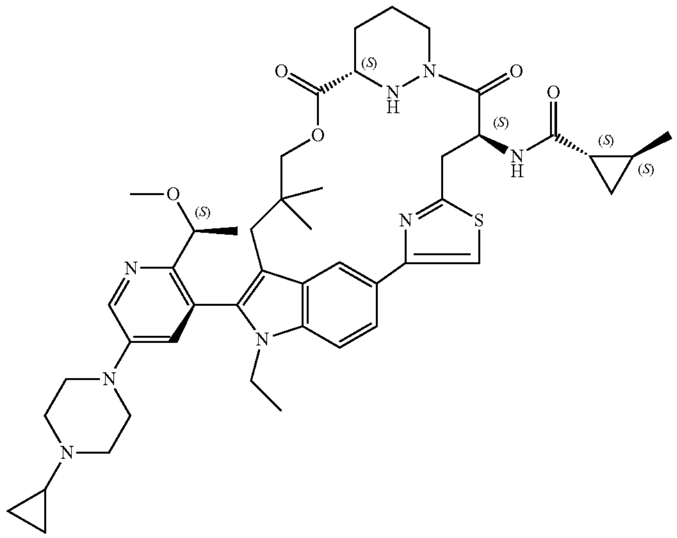 |
| A264 | 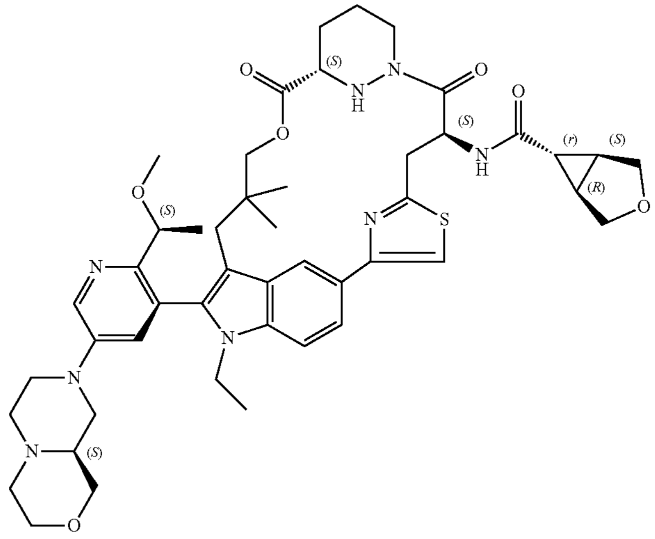 |

TABLE 1a-continued
| Certain Compounds of the Present Invention | |
|---|---|
| Ex. # | Structure |
| A265 | 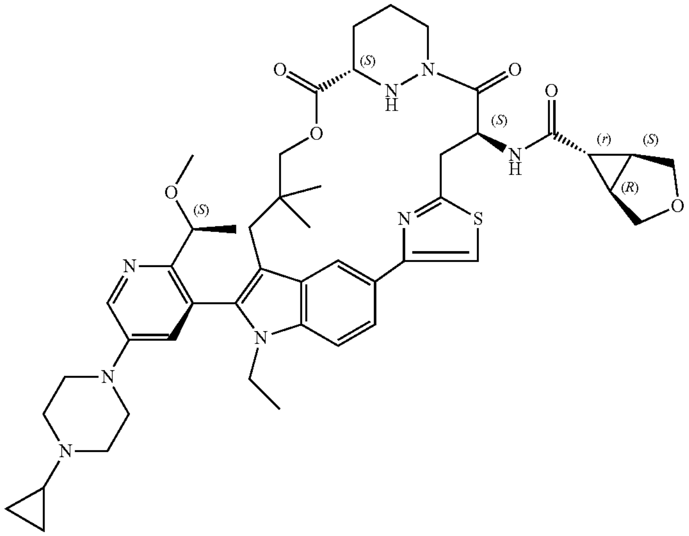 |
| A266 | 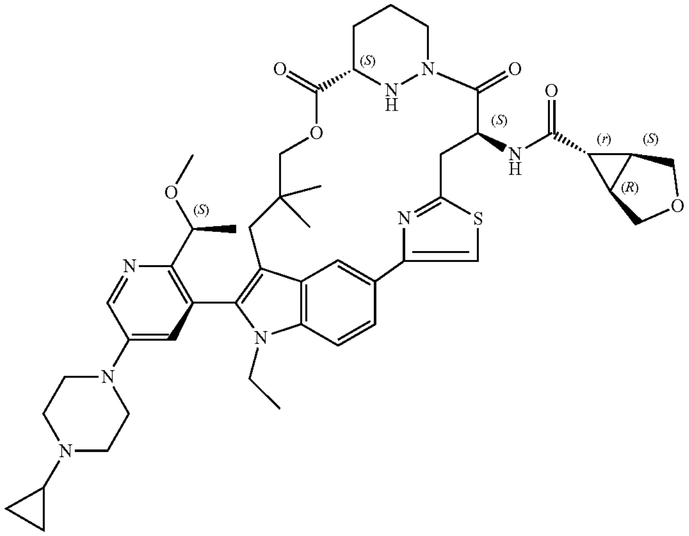 |

TABLE 1a-continued
| Certain Compounds of the Present Invention | |
|---|---|
| Ex. # | Structure |
| A267 | 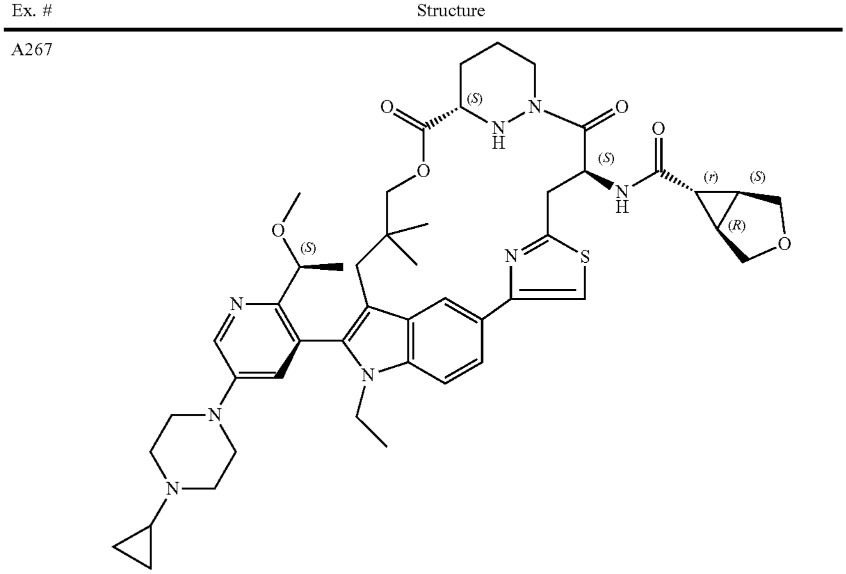 |
| A268 | 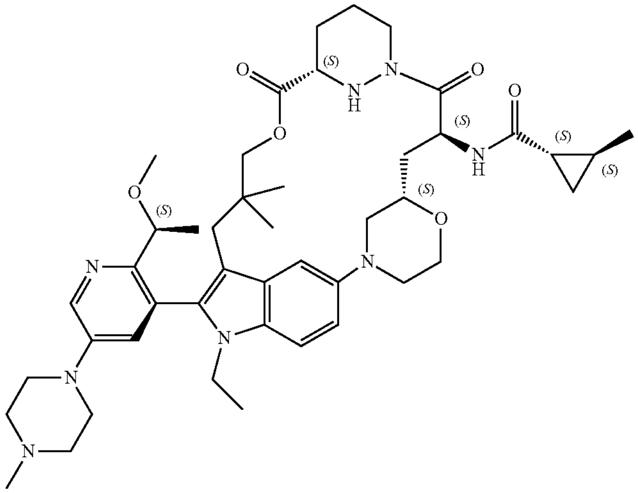 |
| A269 | 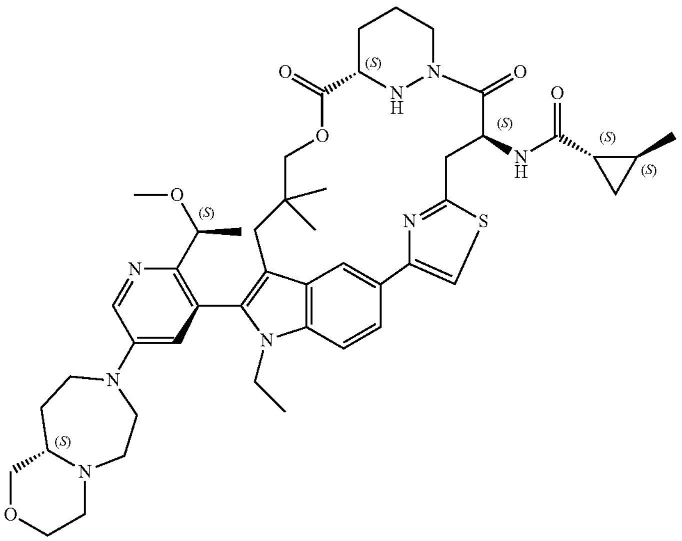 |

TABLE 1a-continued
| Certain Compounds of the Present Invention | |
|---|---|
| Ex. # | Structure |
| A270 | 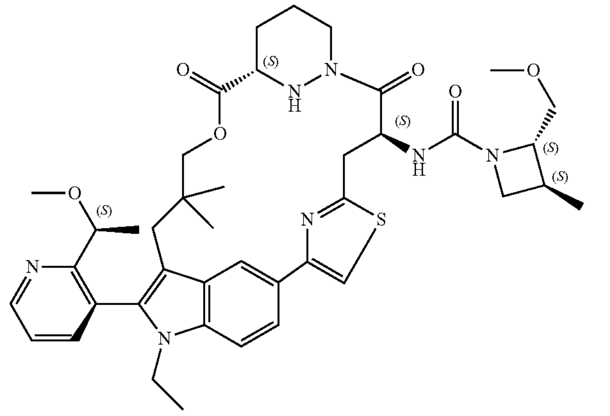 |
| A271 | 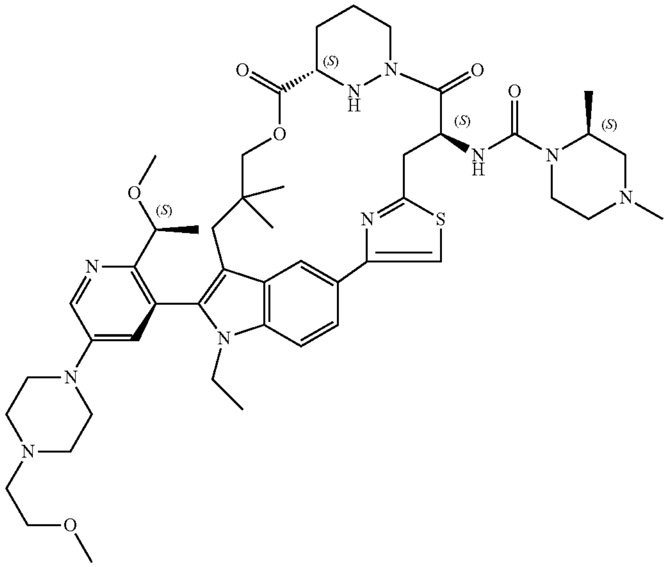 |
| A272 | 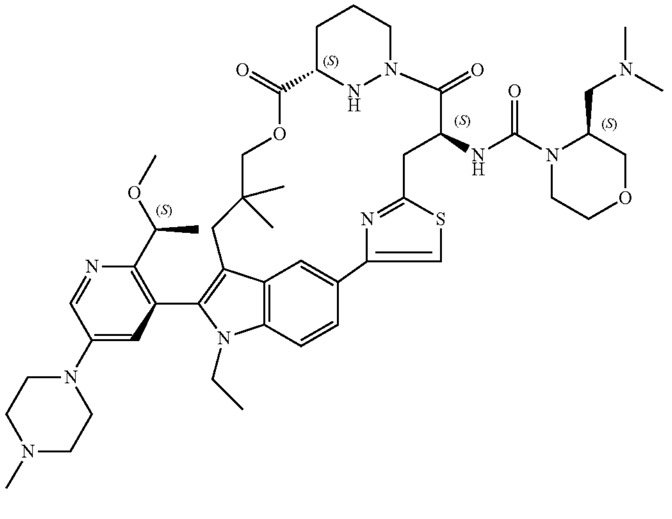 |

TABLE 1a-continued
| Certain Compounds of the Present Invention | |
|---|---|
| Ex. # | Structure |
| A273 | 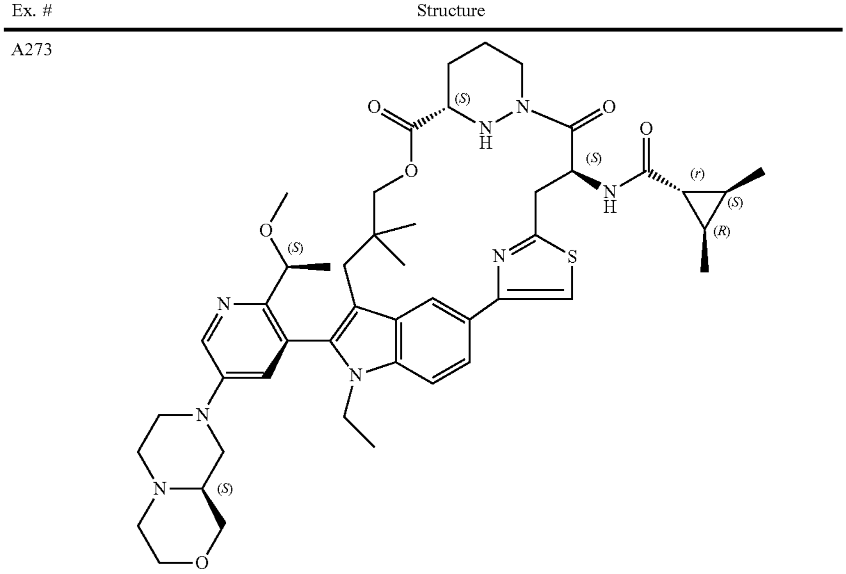 |
| A274 | 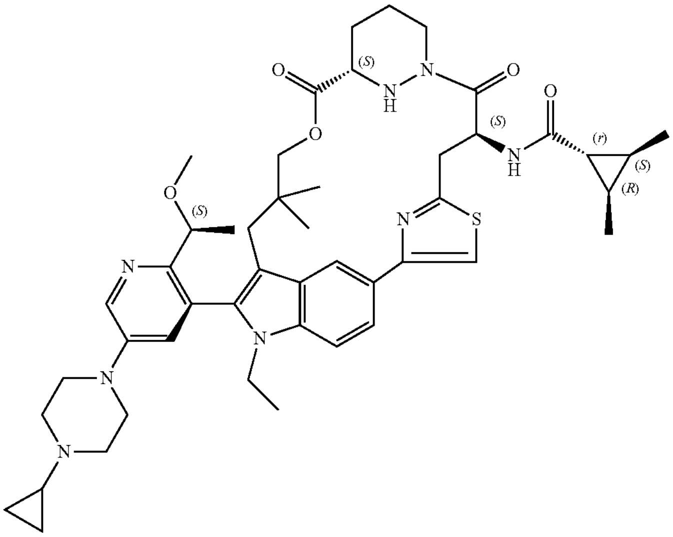 |
| A275 | 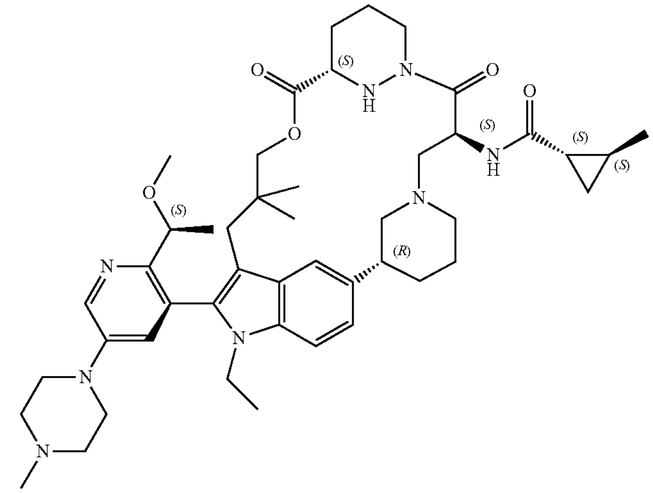 |

TABLE 1a-continued
| Certain Compounds of the Present Invention | |
|---|---|
| Ex. # | Structure |
| A276 | 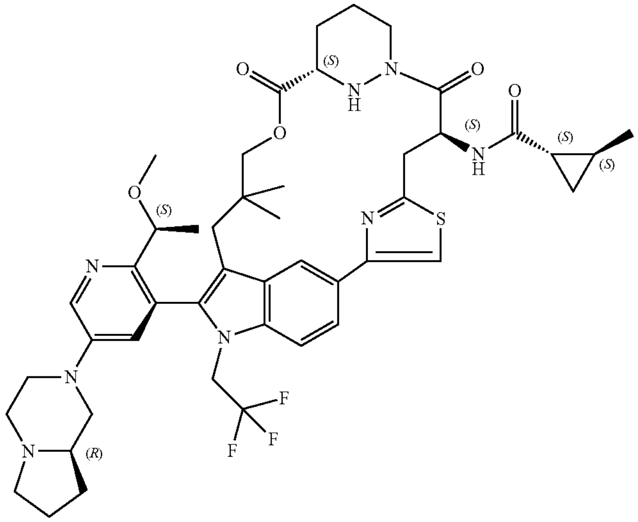 |
| A277 | 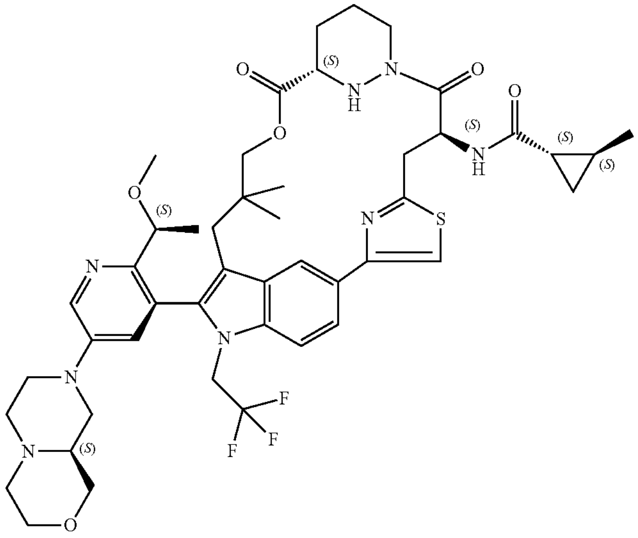 |
| A278 | 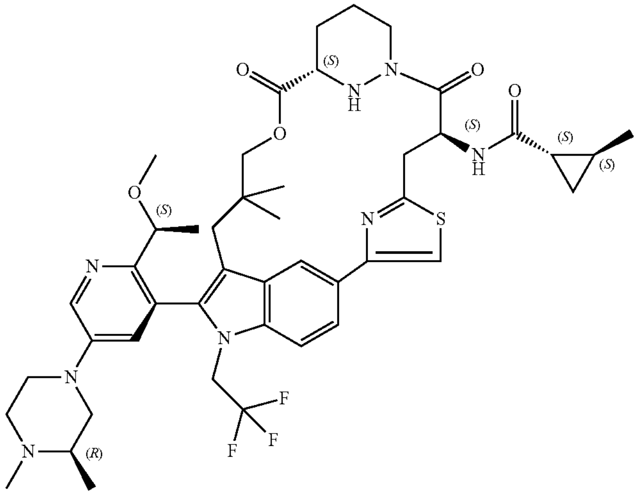 |

TABLE 1a-continued
| Certain Compounds of the Present Invention | |
|---|---|
| Ex. # | Structure |
| A279 | 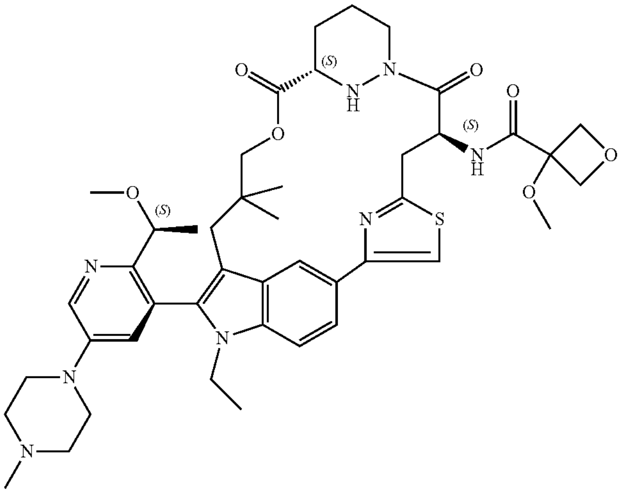 |
| A280 | 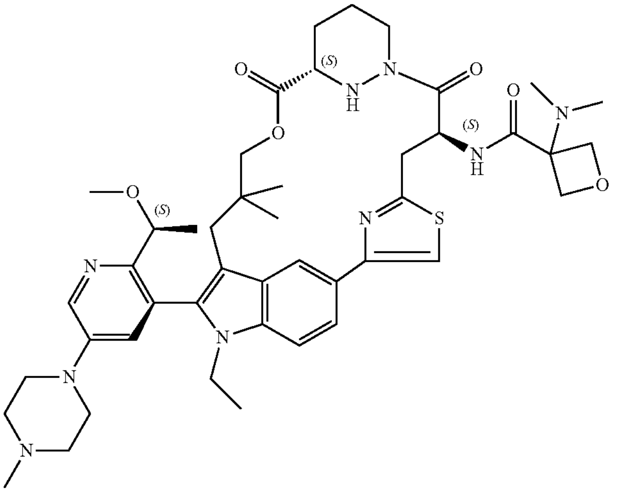 |
| A281 | 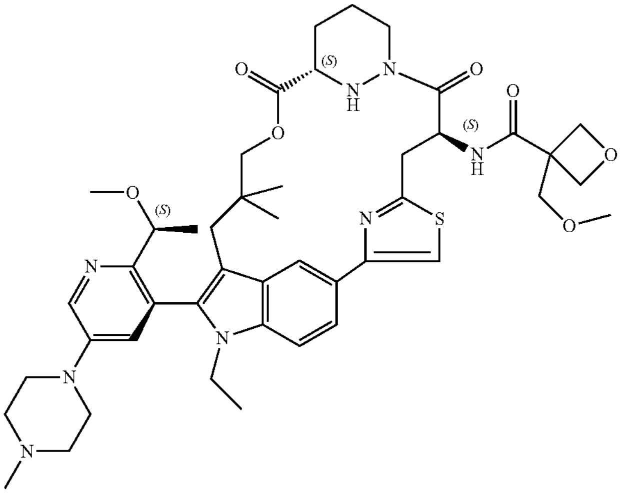 |

TABLE 1a-continued
| Certain Compounds of the Present Invention | |
|---|---|
| Ex. # | Structure |
| A282 | 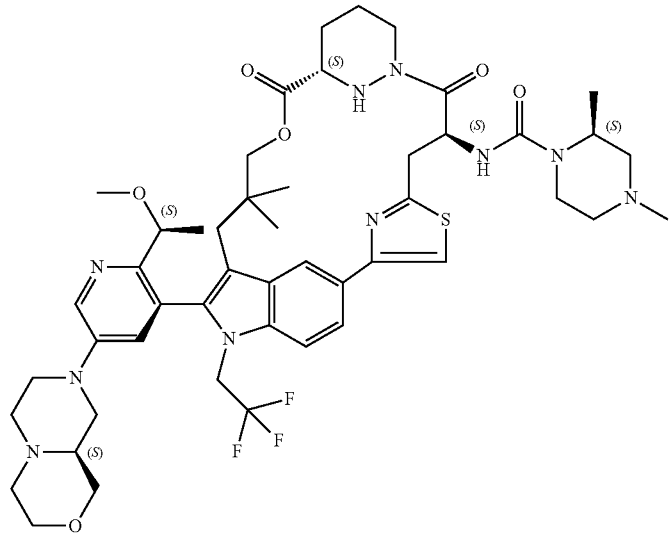 |
| A283 | 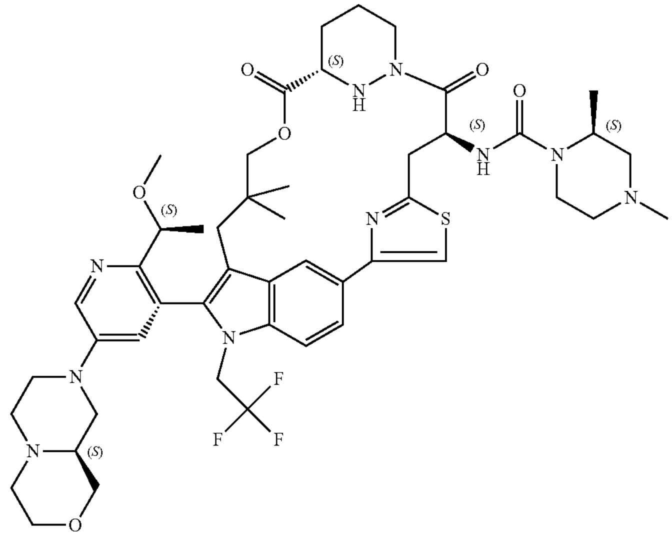 |
| A284 | 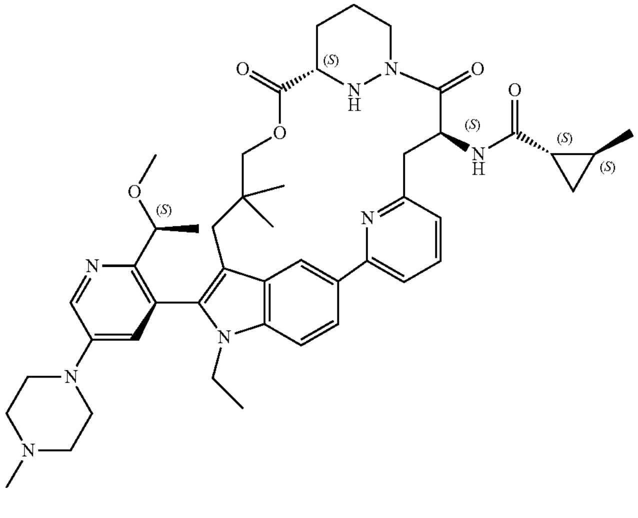 |

TABLE 1a-continued
| Ex. # | Structure |
|---|---|
| | Certain Compounds of the Present Invention |
| A285 | 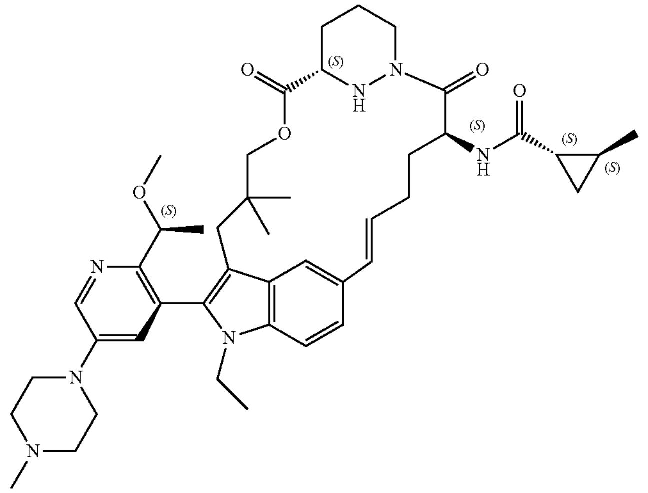 |
| A286 | 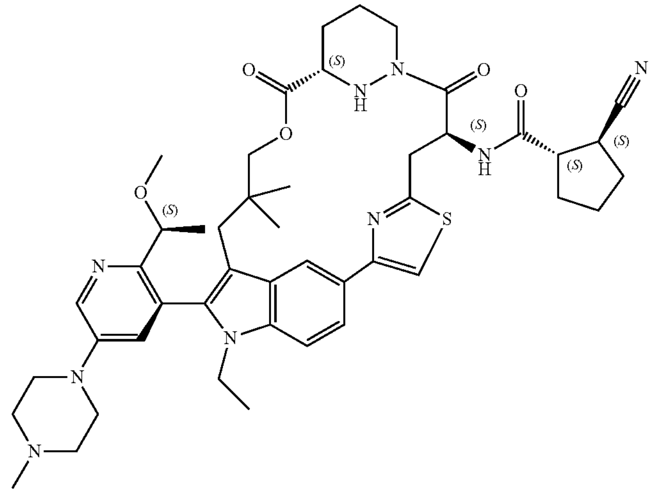 |
| A287 | 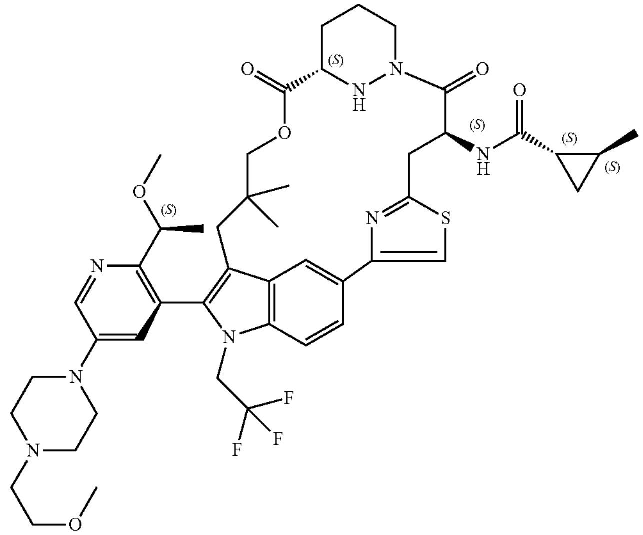 |

TABLE 1a-continued
| Certain Compounds of the Present Invention | |
|---|---|
| Ex. # | Structure |
| A288 | 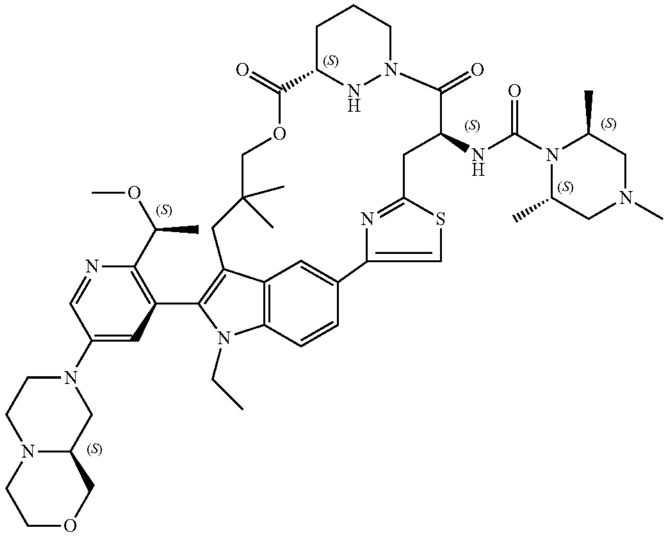 |
| A289 | 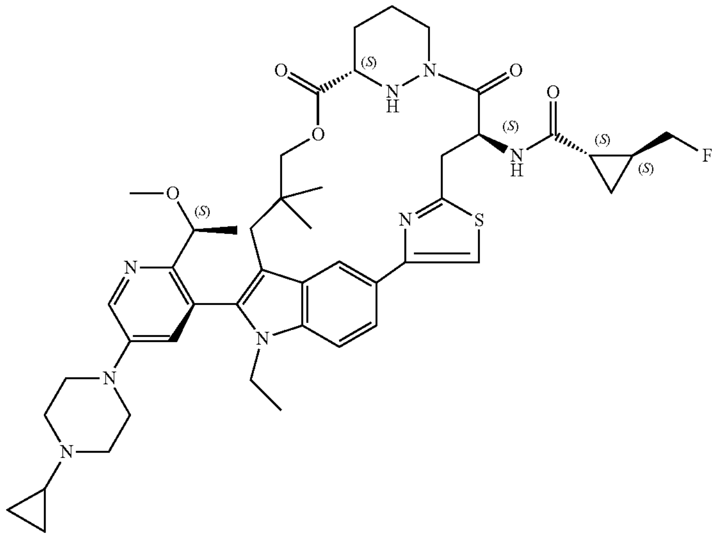 |

TABLE 1a-continued
| Certain Compounds of the Present Invention | |
|---|---|
| Ex. # | Structure |
| A290 | 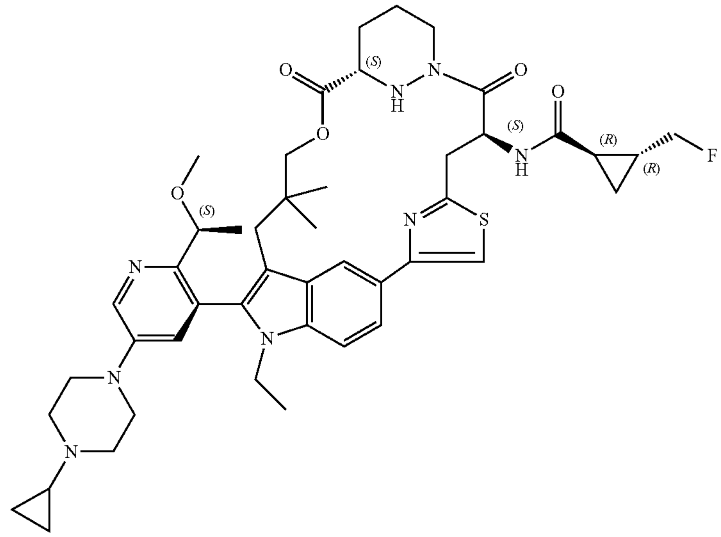 |
| A291 | 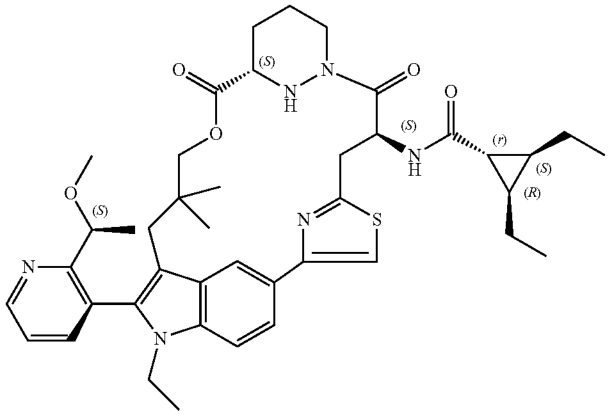 |
| A292 | 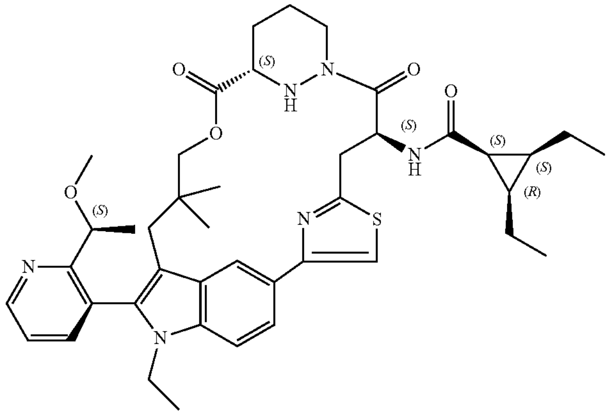 |

TABLE 1a-continued
| Certain Compounds of the Present Invention | |
|---|---|
| Ex. # | Structure |
| A293 | 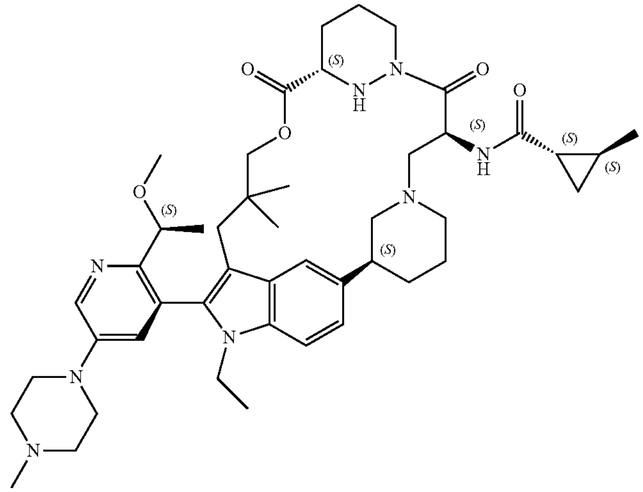 |
| A294 | 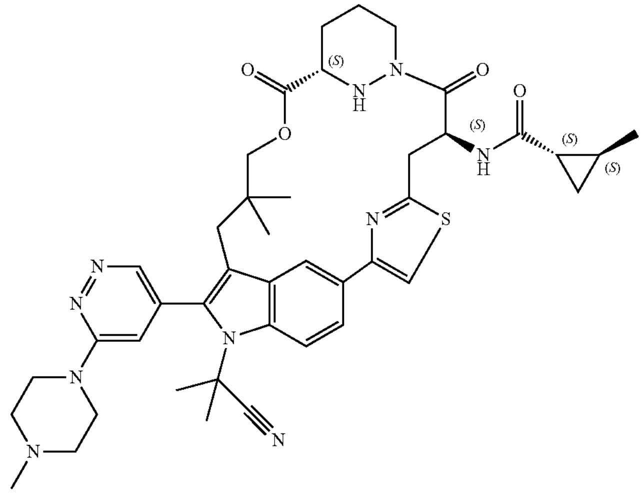 |
| A295 | 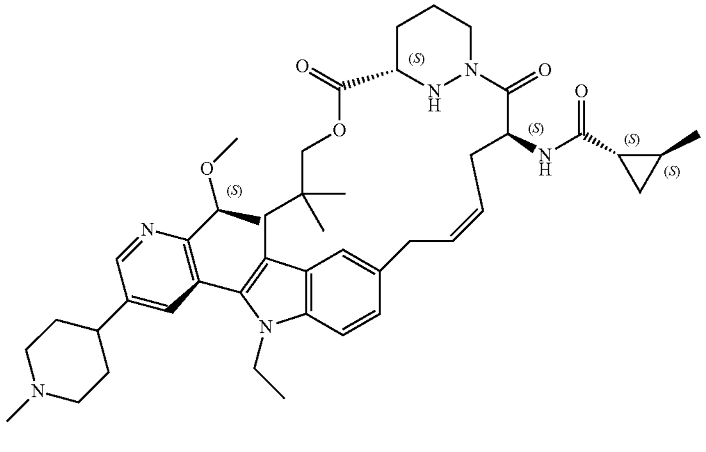 |

TABLE 1a-continued
| Certain Compounds of the Present Invention | |
|---|---|
| Ex. # | Structure |
| A296 | 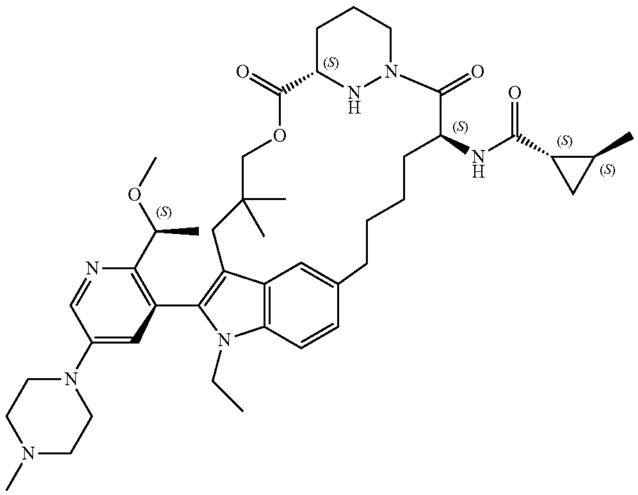 |
| A297 | 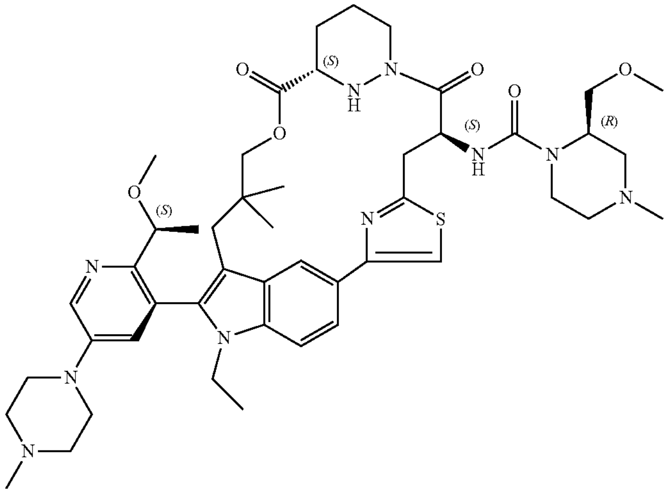 |
| A298 | 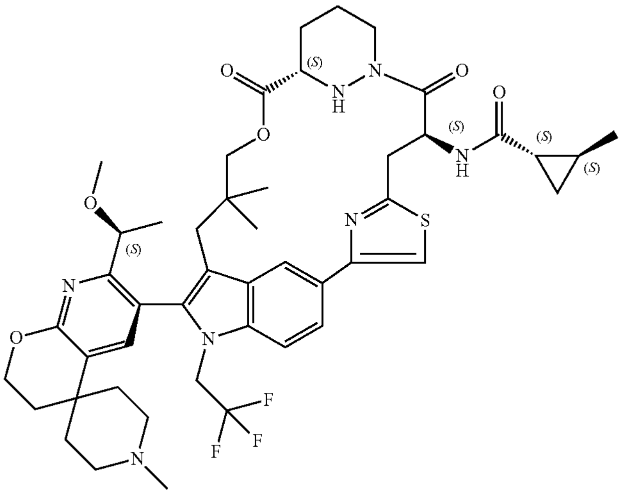 |

TABLE 1a-continued
| Certain Compounds of the Present Invention | |
| --- | --- |
| Ex. # | Structure |
| A299 | 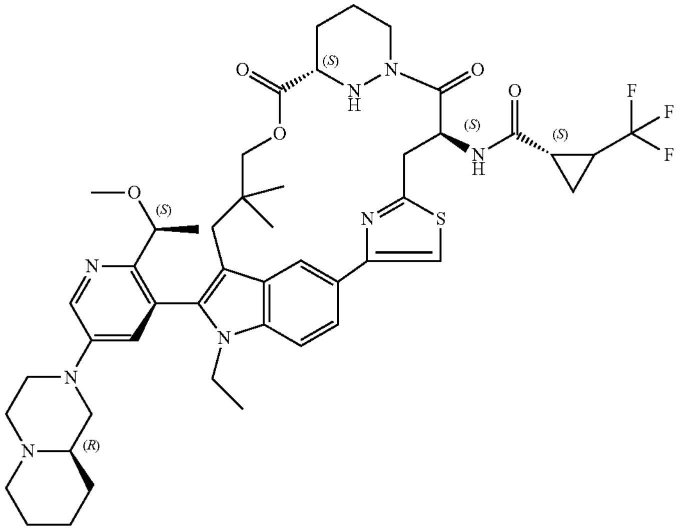 |
| A300 | 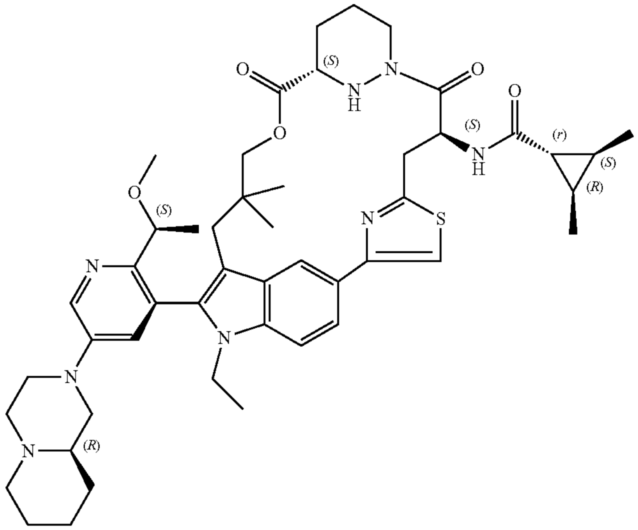 |
| A301 | 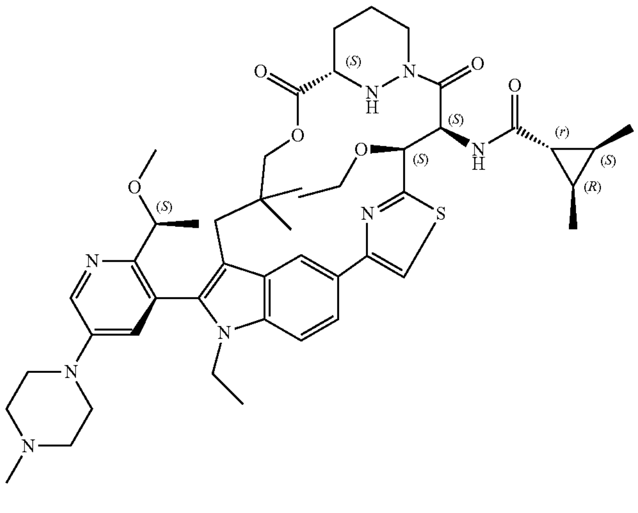 |

TABLE 1a-continued
| Certain Compounds of the Present Invention | |
|---|---|
| Ex. # | Structure |
| A302 | 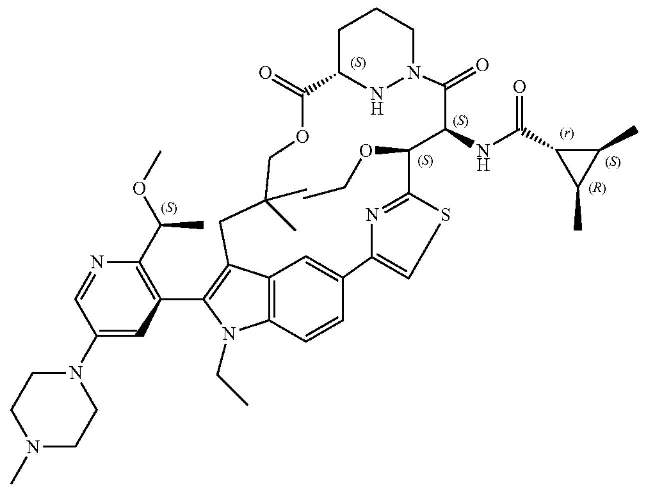 |
| A303 | 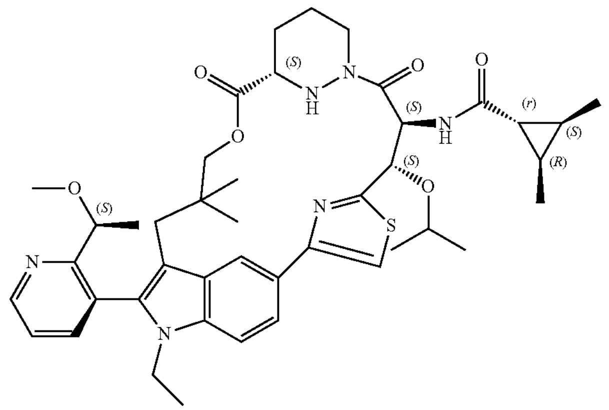 |
| A304 | 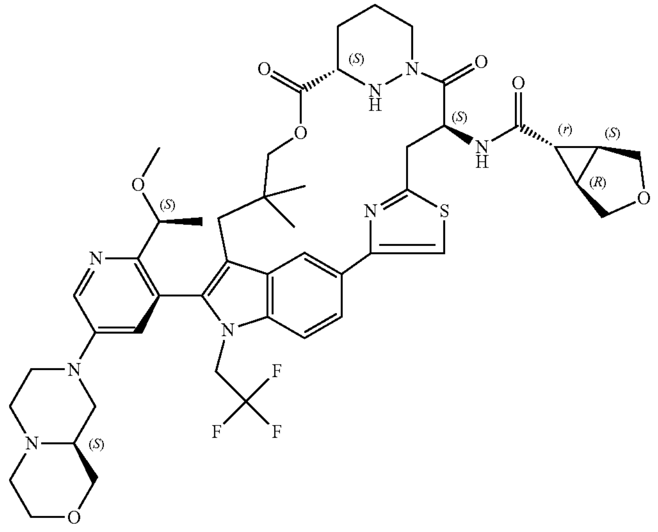 |

TABLE 1a-continued
| Certain Compounds of the Present Invention | |
|---|---|
| Ex. # | Structure |
| A305 | 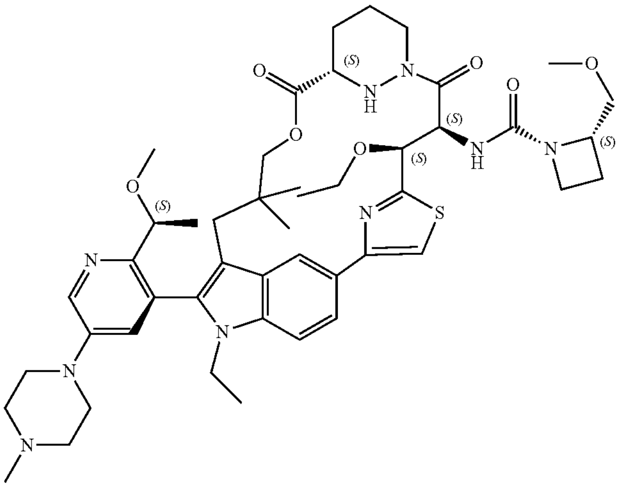 |
| A306 | 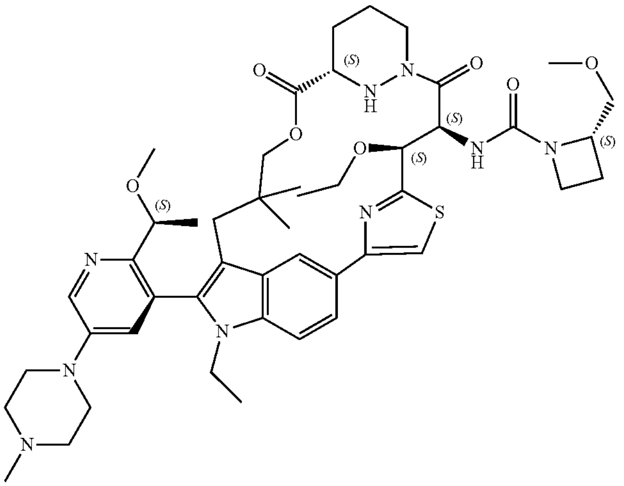 |
| A307 | 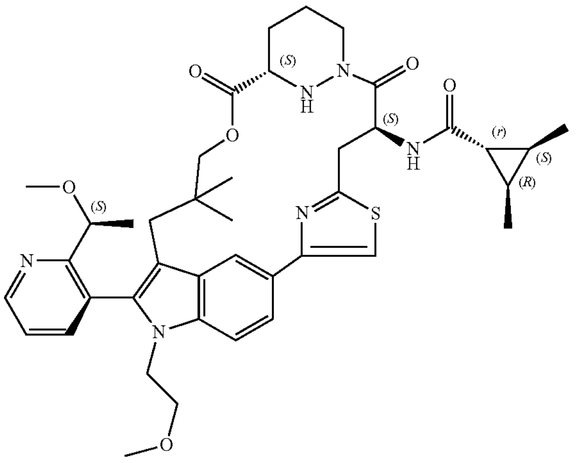 |

TABLE 1a-continued
| Certain Compounds of the Present Invention | |
|---|---|
| Ex. # | Structure |
| A308 | 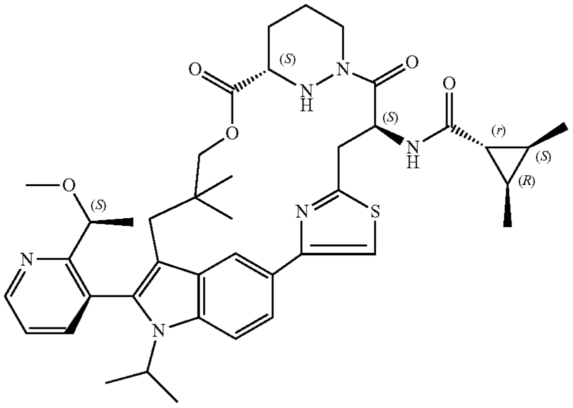 |
| A309 | 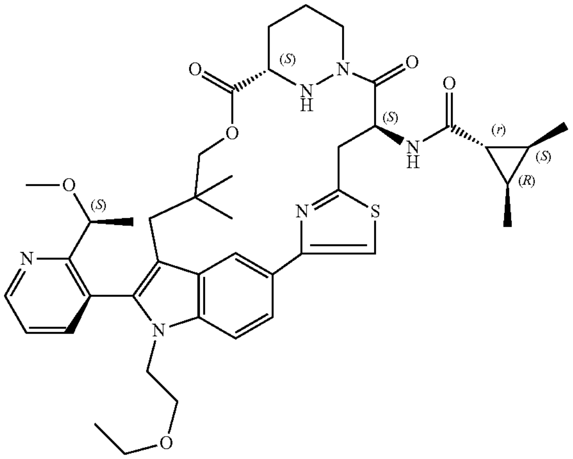 |
| A310 | 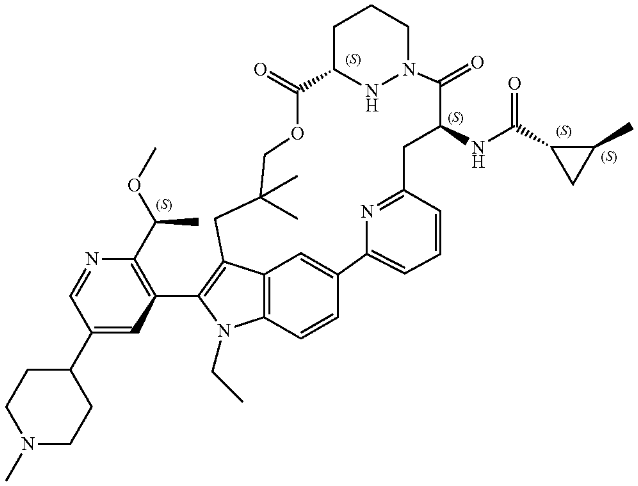 |

TABLE 1a-continued
| Certain Compounds of the Present Invention | |
|---|---|
| Ex. # | Structure |
| A311 | 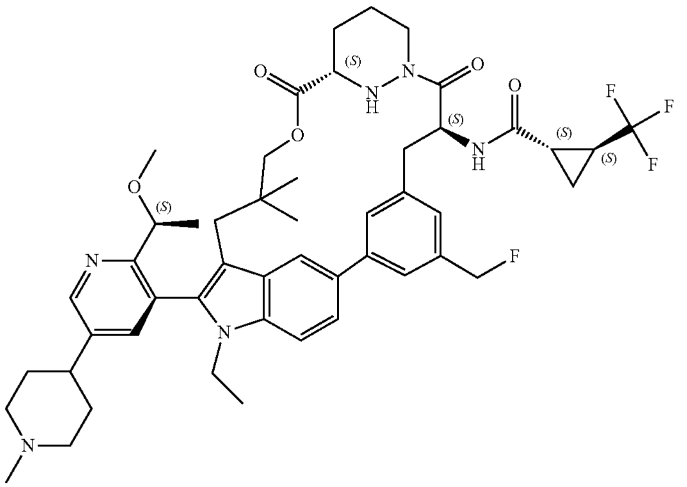 |
| A312 | 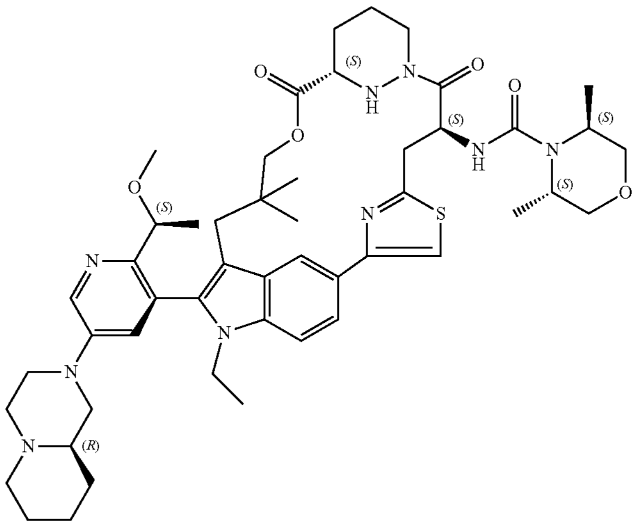 |
| A313 | 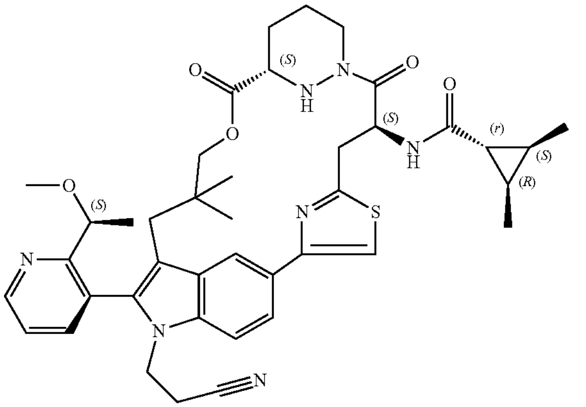 |

TABLE 1a-continued
| Certain Compounds of the Present Invention | |
|---|---|
| Ex. # | Structure |
| A314 | 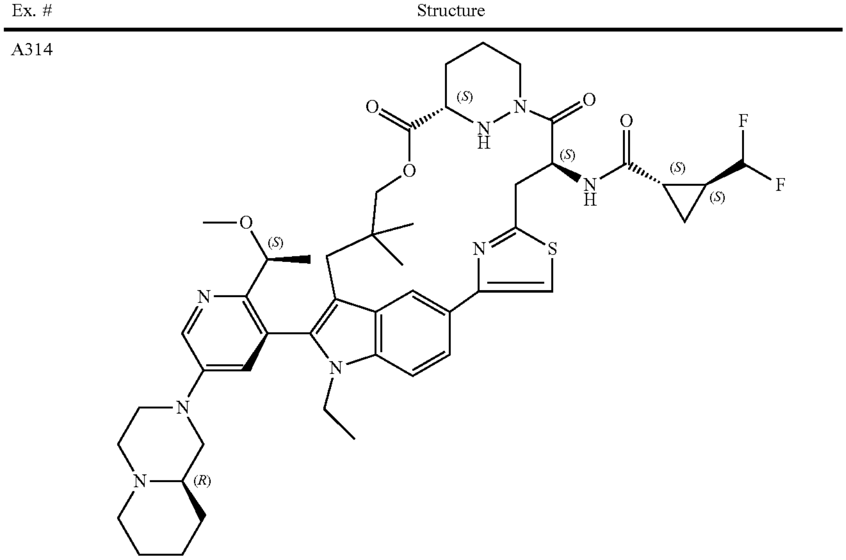 |
| A315 | 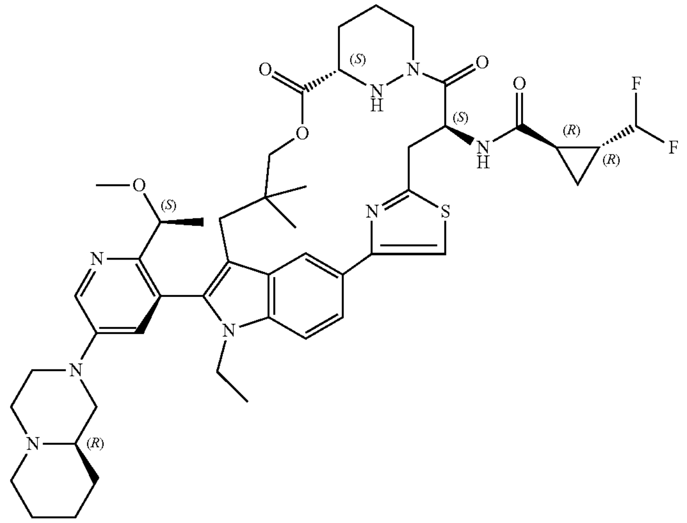 |
| A316 | 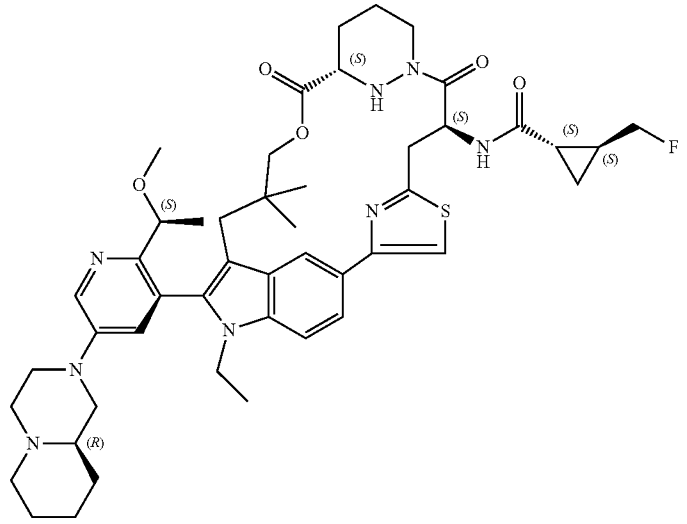 |

TABLE 1a-continued
| Certain Compounds of the Present Invention | |
|---|---|
| Ex. # | Structure |
| A317 | 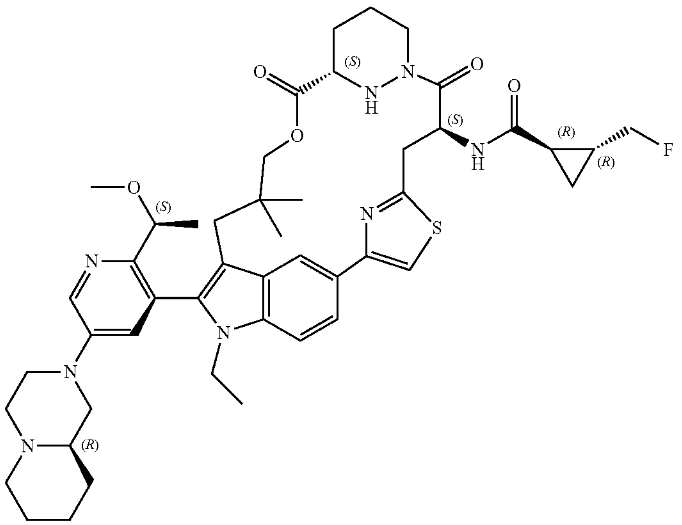 |
| A318 | 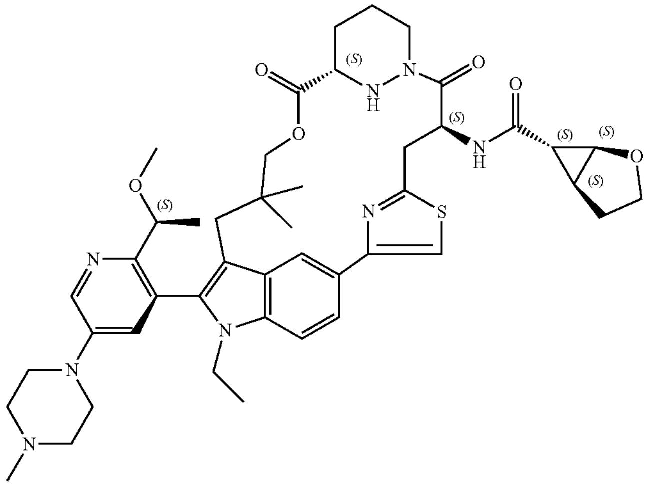 |
| A319 | 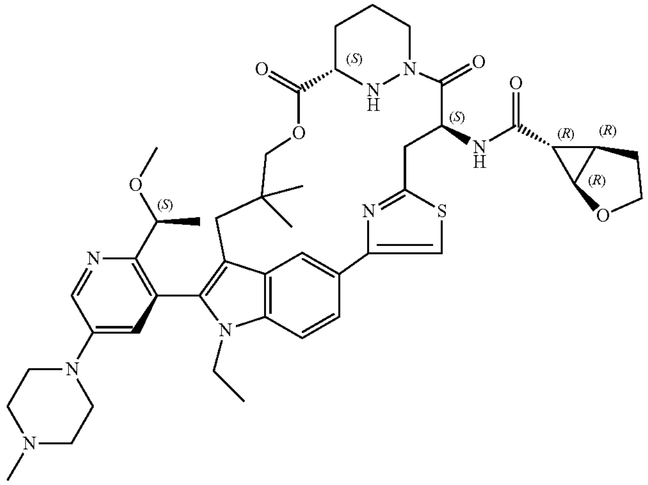 |

TABLE 1a-continued
| Certain Compounds of the Present Invention | |
|---|---|
| Ex. # | Structure |
| A320 | 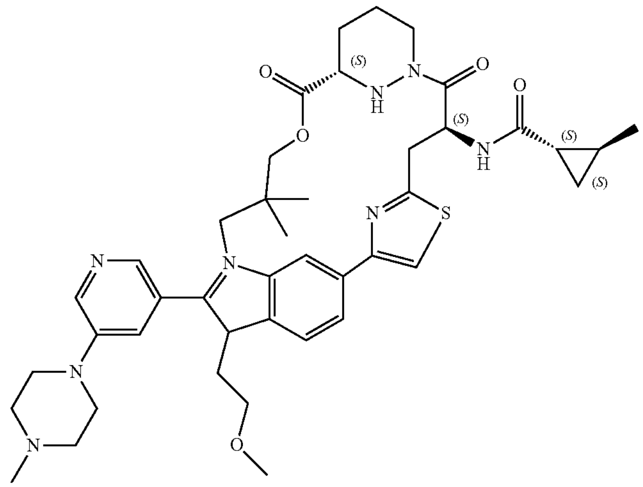 |
| A321 | 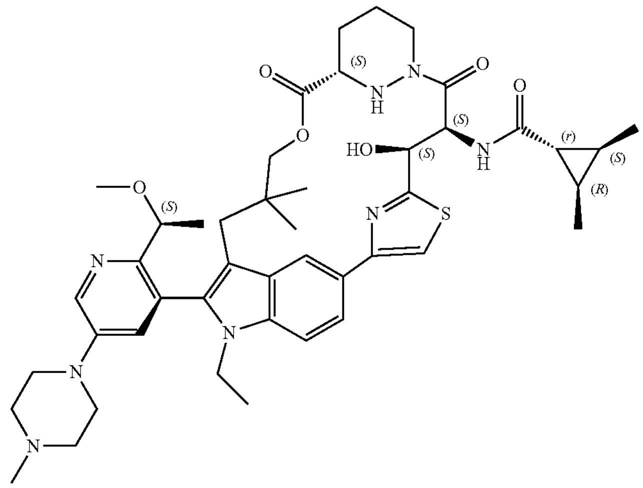 |
| A322 | 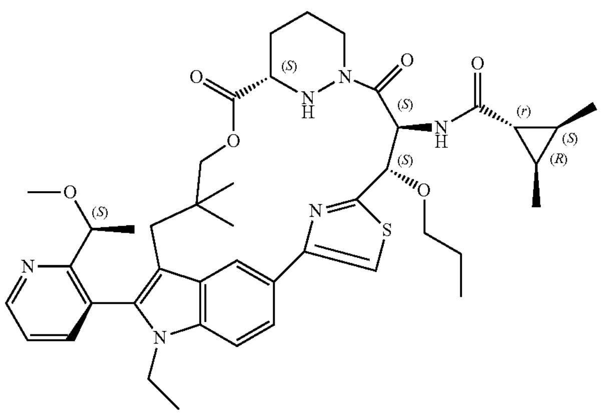 |

TABLE 1a-continued
| Certain Compounds of the Present Invention | |
|---|---|
| Ex. # | Structure |
| A323 | 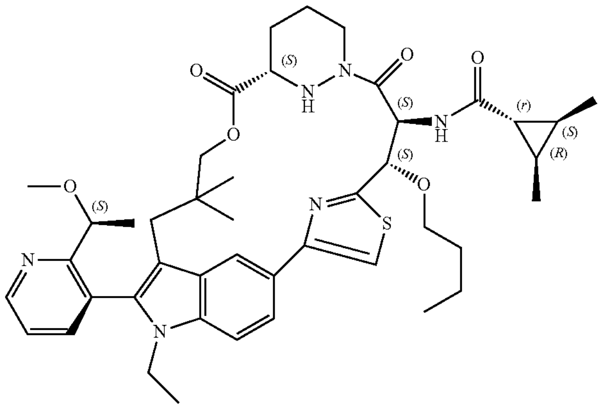 |
| A324 | 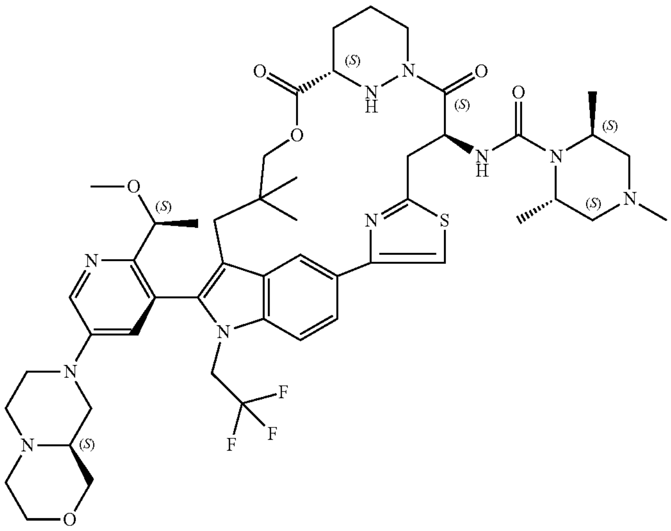 |
| A325 | 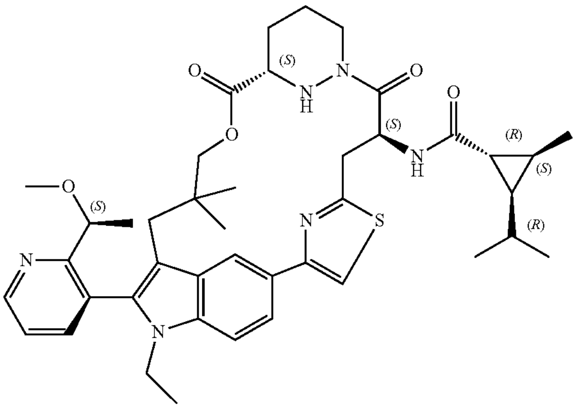 |

TABLE 1a-continued
| Certain Compounds of the Present Invention | |
|---|---|
| Ex. # | Structure |
| A326 | 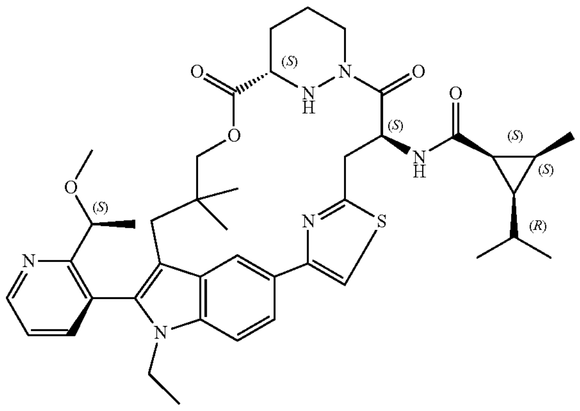 |
| A327 | 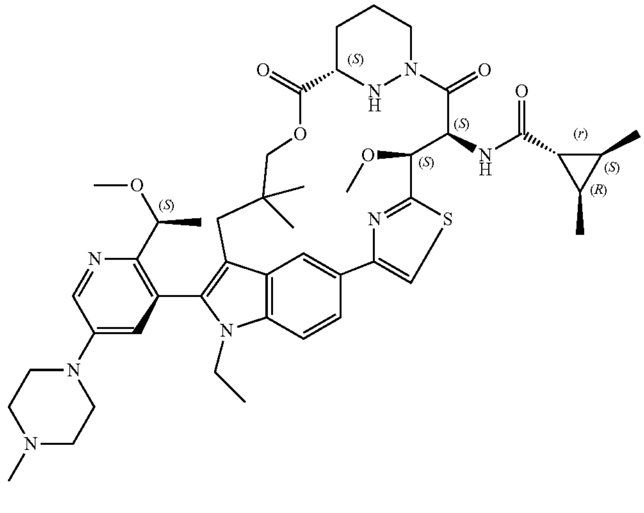 |
| A328 | 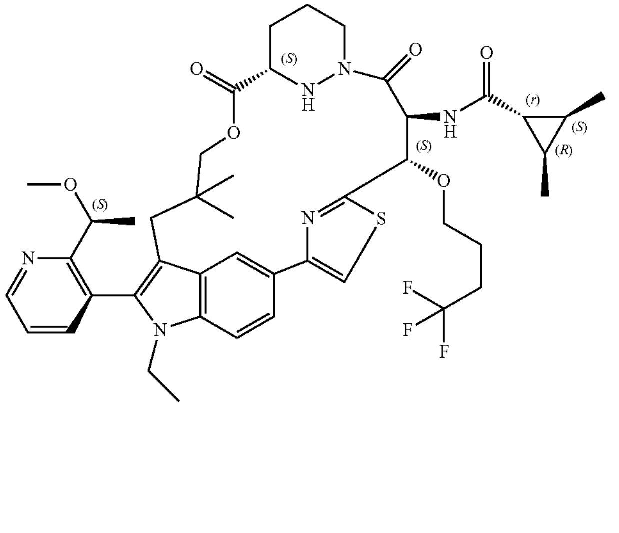 |

TABLE 1a-continued
| Certain Compounds of the Present Invention | |
|---|---|
| Ex. # | Structure |
| A329 | 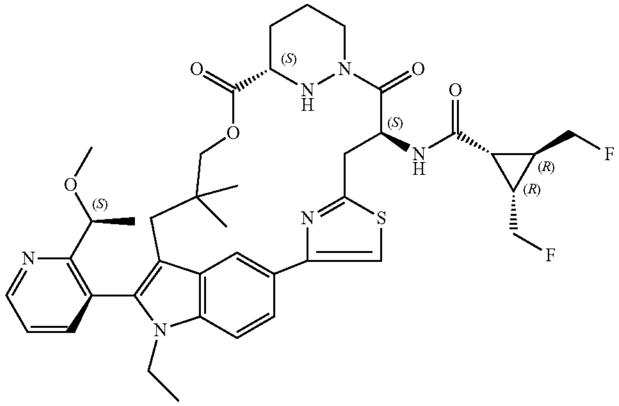 |
| A330 | 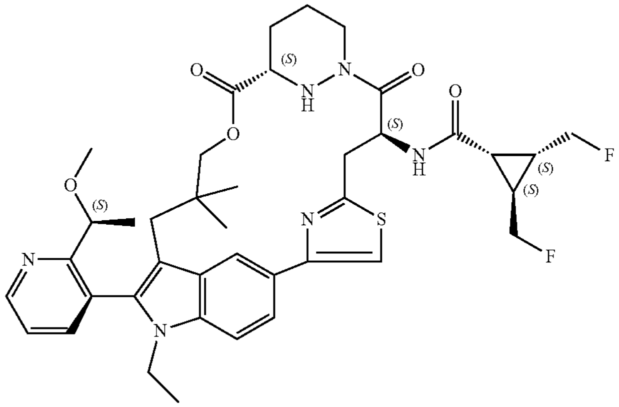 |
| A331 | 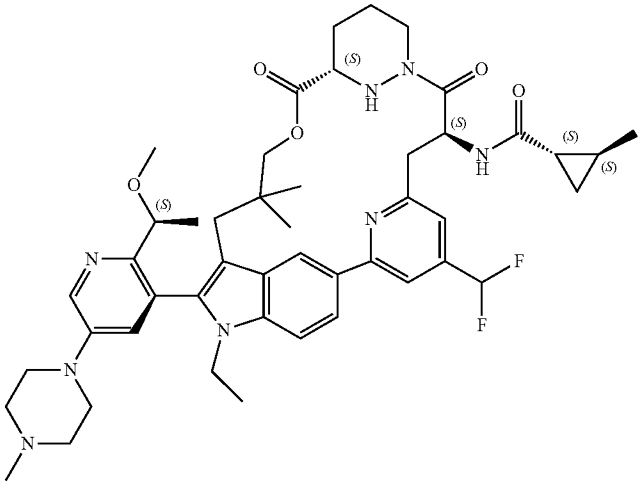 |

TABLE 1a-continued
| Certain Compounds of the Present Invention | |
|---|---|
| Ex. # | Structure |
| A332 | 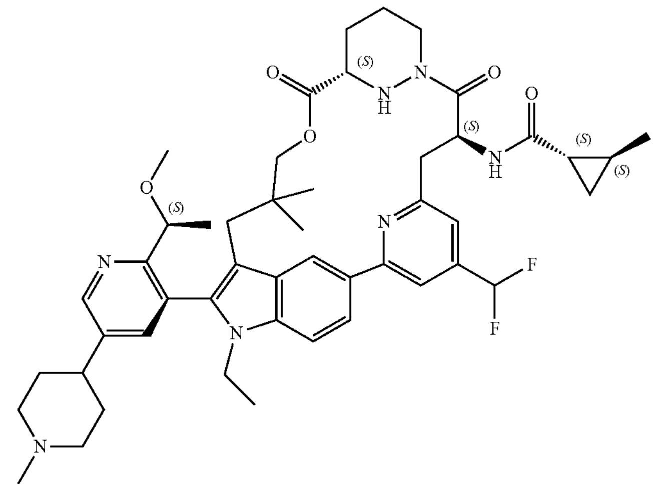 |
| A333 | 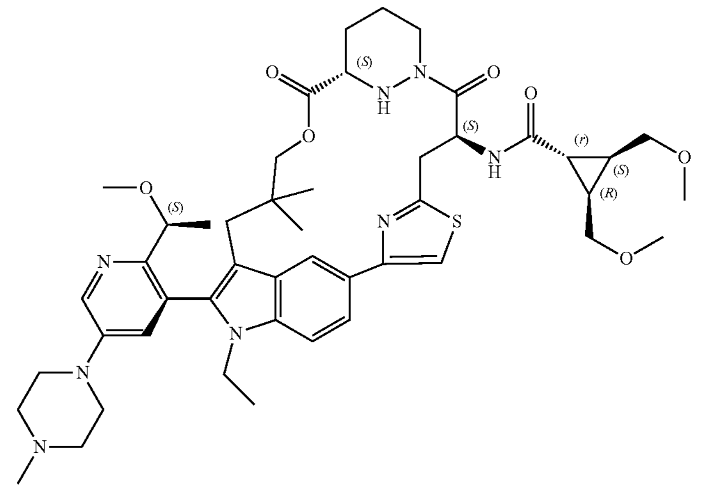 |
| A334 | 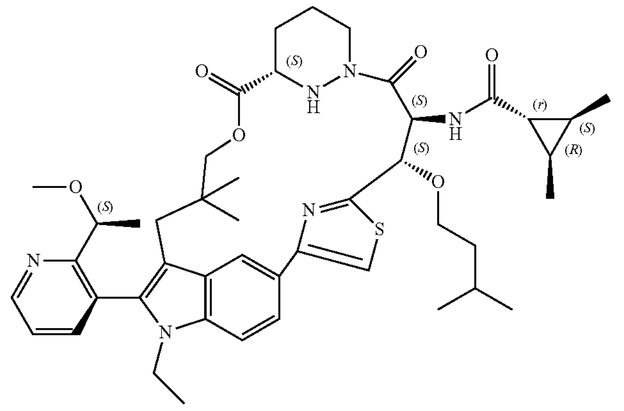 |

TABLE 1a-continued
| Certain Compounds of the Present Invention | |
|---|---|
| Ex. # | Structure |
| A335 | 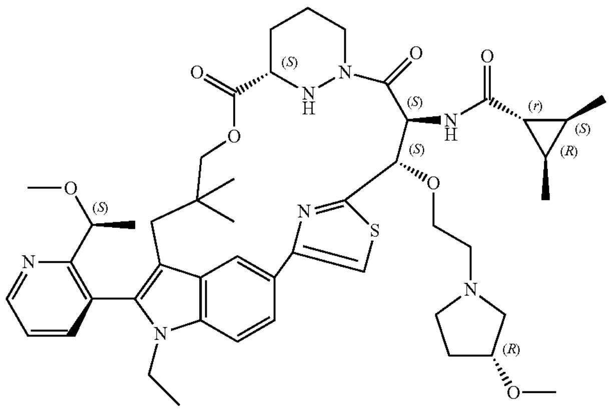 |
| A336 | 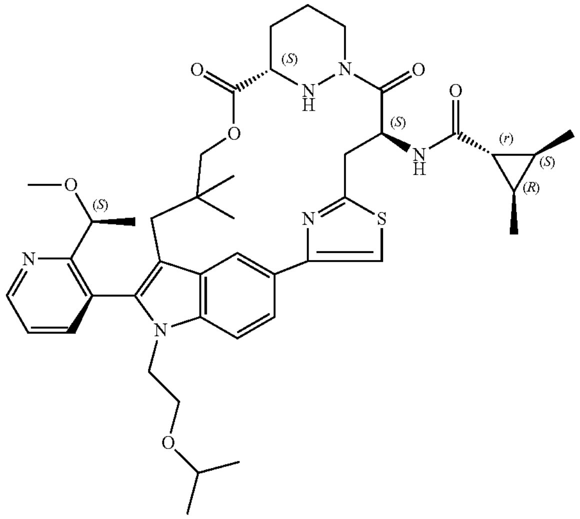 |
| A337 | 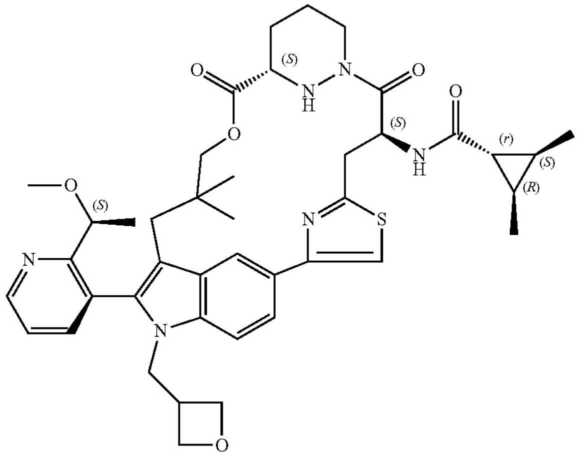 |

TABLE 1a-continued
| Certain Compounds of the Present Invention | |
|---|---|
| Ex. # | Structure |
| A338 | 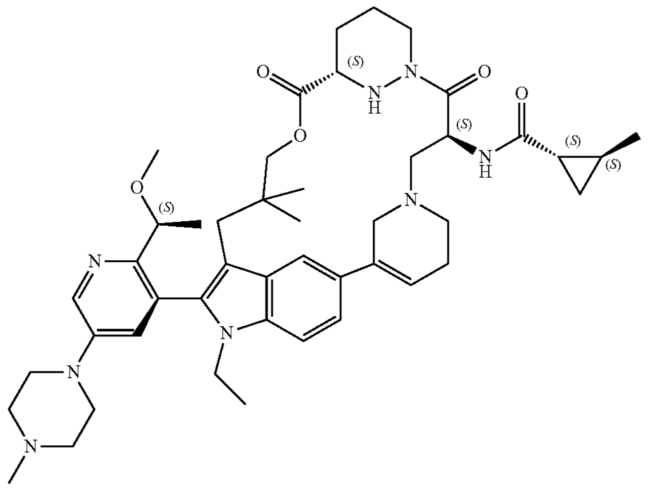 |
| A339 | 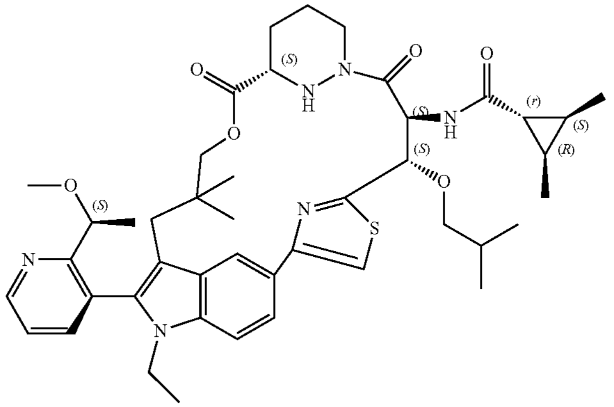 |
| A340 | 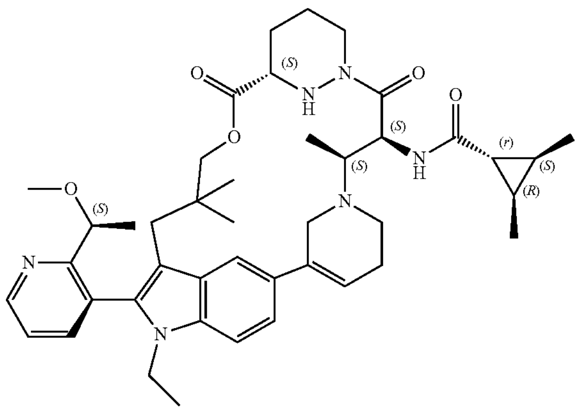 |

TABLE 1a-continued
| Certain Compounds of the Present Invention | |
|---|---|
| Ex. # | Structure |
| A341 | 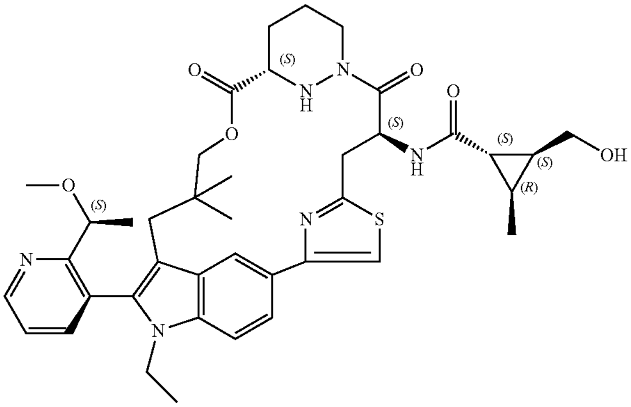 |
| A342 | 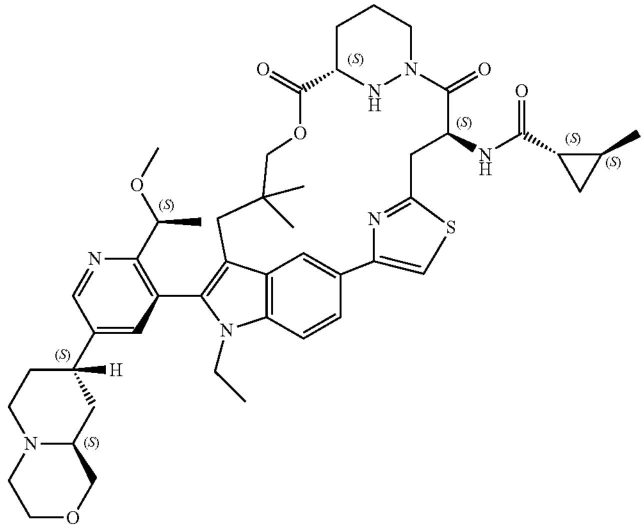 |
| A343 | 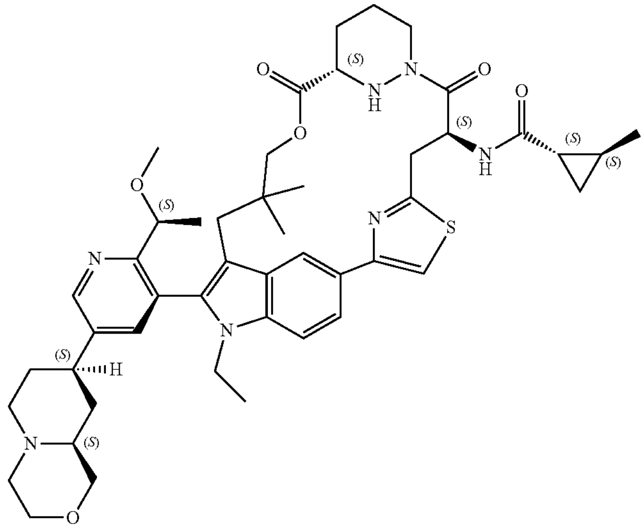 |

TABLE 1a-continued
| Certain Compounds of the Present Invention | |
|---|---|
| Ex. # | Structure |
| A344 | 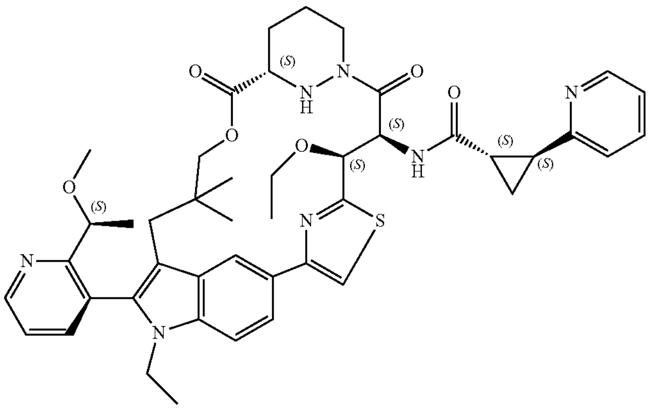 |
| A345 | 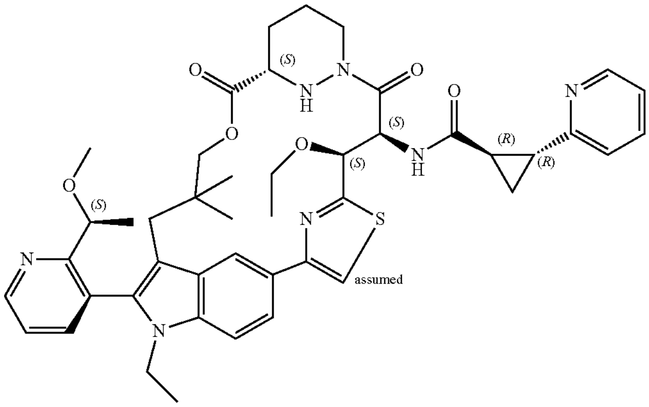 |
| A346 | 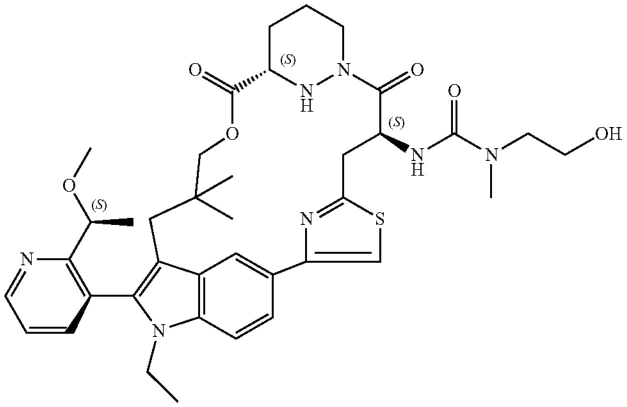 |

TABLE 1a-continued
| Certain Compounds of the Present Invention | |
|---|---|
| Ex. # | Structure |
| A347 | 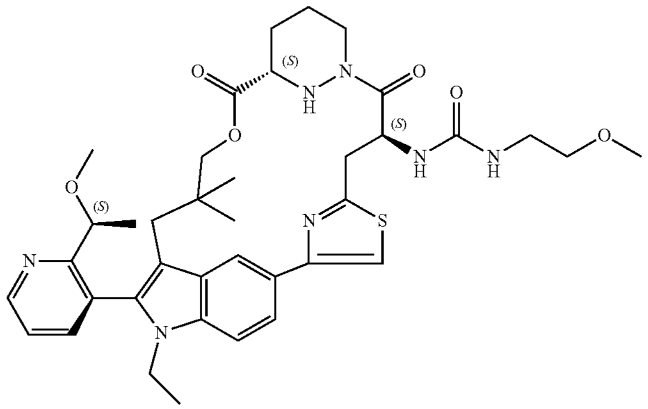 |
| A348 | 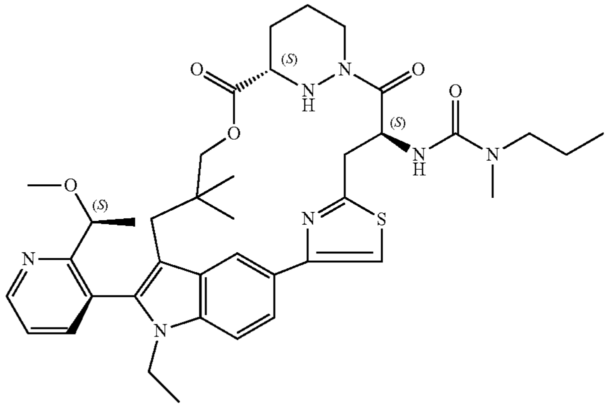 |
| A349 | 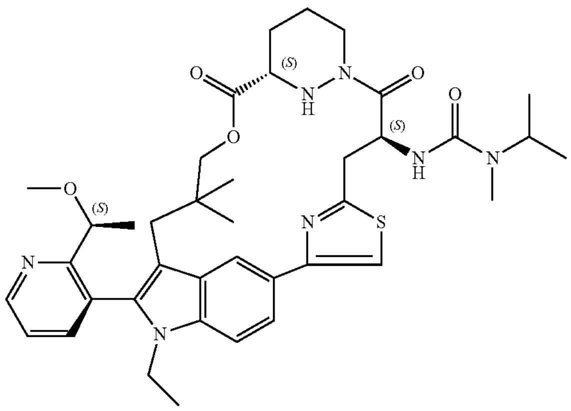 |

TABLE 1a-continued
| Certain Compounds of the Present Invention | |
|---|---|
| Ex. # | Structure |
| A350 | 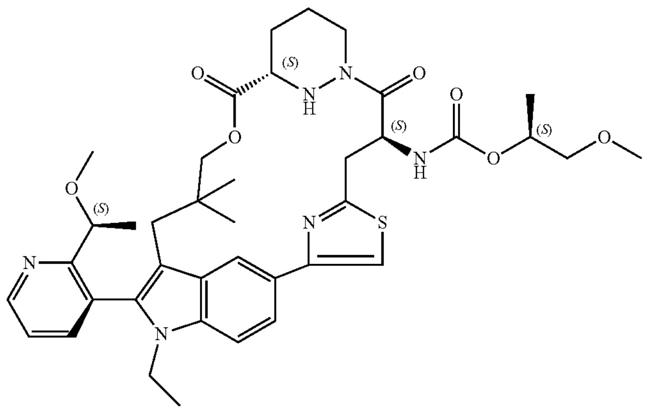 |
| A351 | 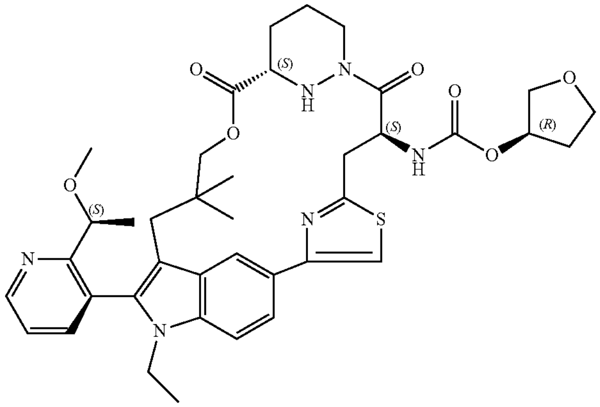 |
| A352 | 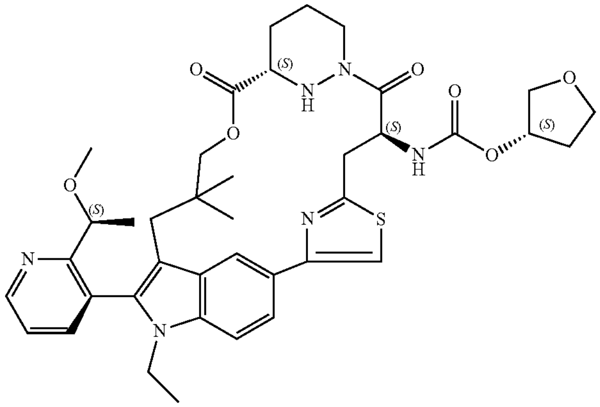 |

TABLE 1a-continued

| Certain Compounds of the Present Invention | |
|---|---|
| Ex. # | Structure |
| A353 | 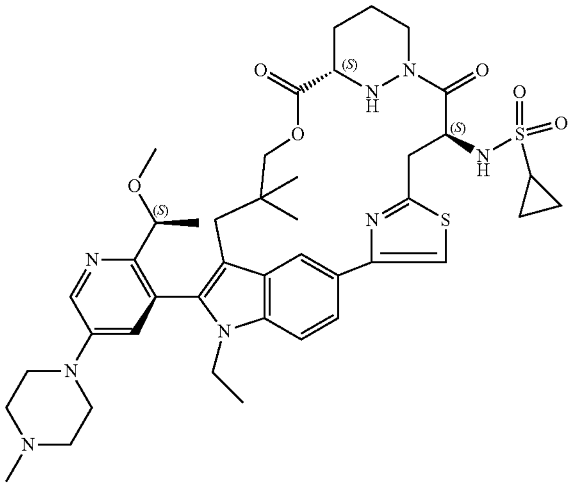 |

Note
that some compounds are shown with bonds as flat or wedged. In some instances, the relative stereochemistry of stereoisomers has been determined; in some instances, the absolute stereochemistry has been determined. All stereoisomers of the compounds of the foregoing table are contemplated by the present invention. In particular embodiments, an atropisomer of a compound of the foregoing table is contemplated. Any compound shown in brackets indicates that the compound is a diastereomer, and the absolute stereochemistry of such diastereomer may not be known.

In some embodiments, a compound of the present invention is selected from Table 1b, or a pharmaceutically acceptable salt or stereoisomer thereof. In some embodiments, a compound of the present invention is selected from Table 1 b, or a pharmaceutically acceptable salt or atropisomer thereof.

TABLE 1b

| Certain Compounds of the Present Invention | |
|---|---|
| Ex. # | Structure |
| A354 | 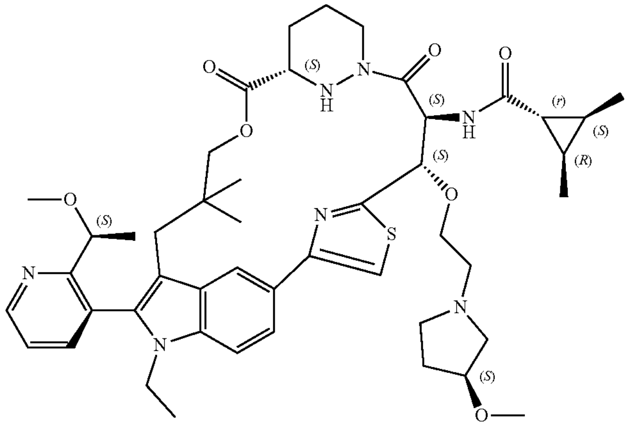 |

TABLE 1b-continued
| Certain Compounds of the Present Invention | |
|---|---|
| Ex. # | Structure |
| A355 | 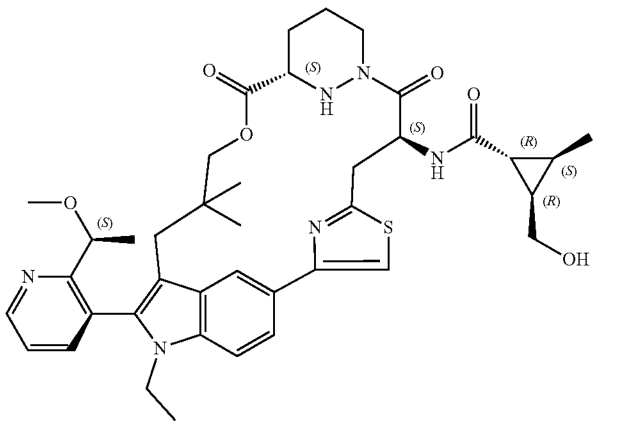 |
| A356 | 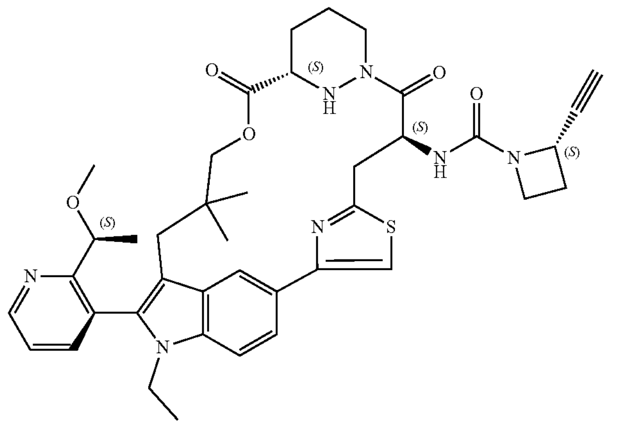 |
| A357 | 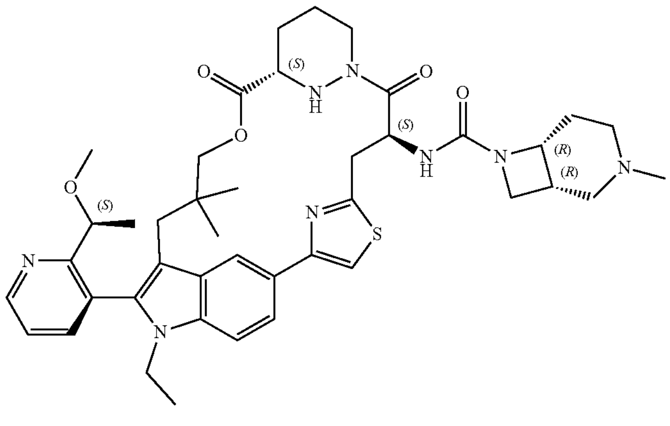 |

TABLE 1b-continued
| Certain Compounds of the Present Invention | |
|---|---|
| Ex. # | Structure |
| A358 | 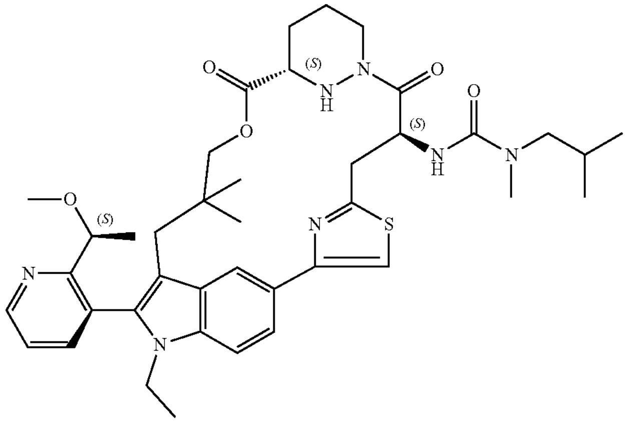 |
| A359 | 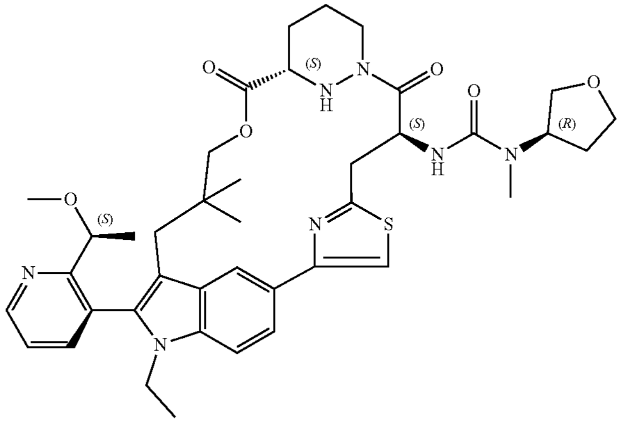 |
| A360 | 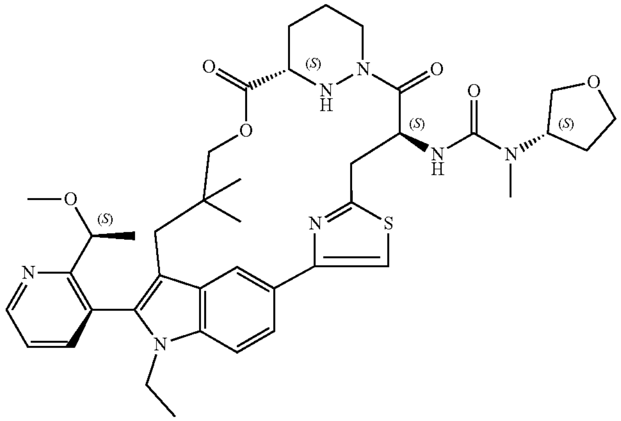 |

TABLE 1b-continued
| Certain Compounds of the Present Invention | |
|---|---|
| Ex. # | Structure |
| A361 | 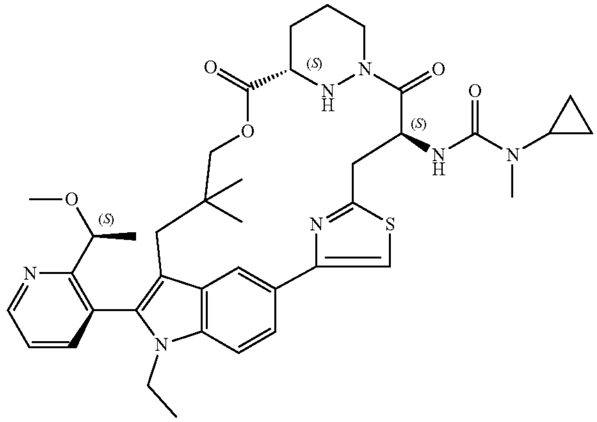 |
| A362 | 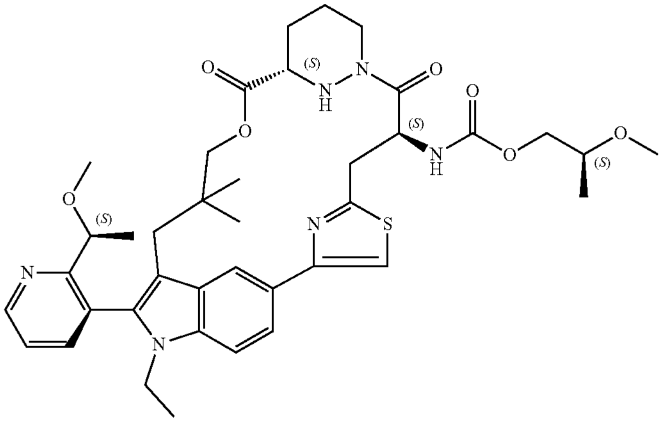 |
| A363 | 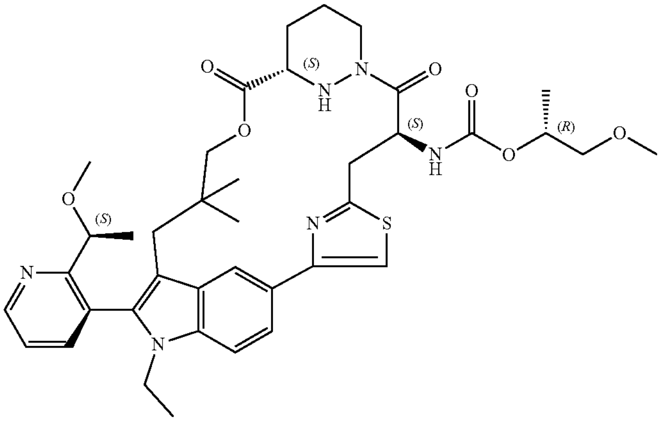 |

TABLE 1b-continued
| Certain Compounds of the Present Invention | |
|---|---|
| Ex. # | Structure |
| A364 | 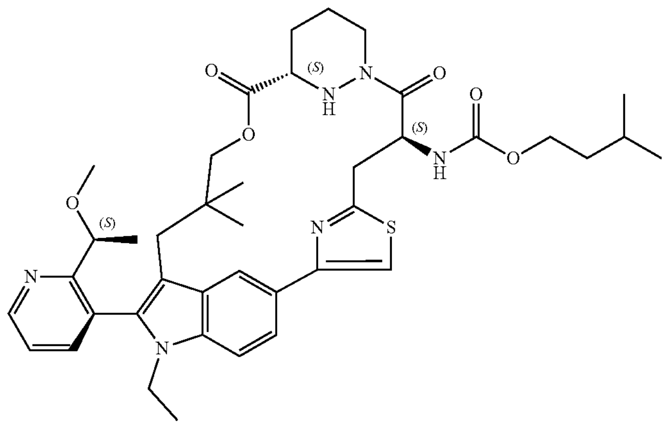 |
| A365 | 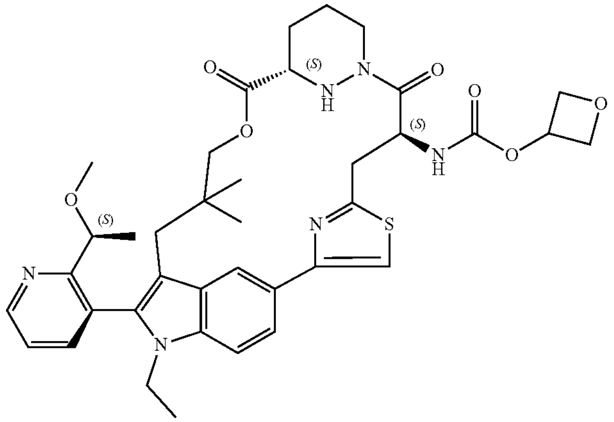 |
| A366 | 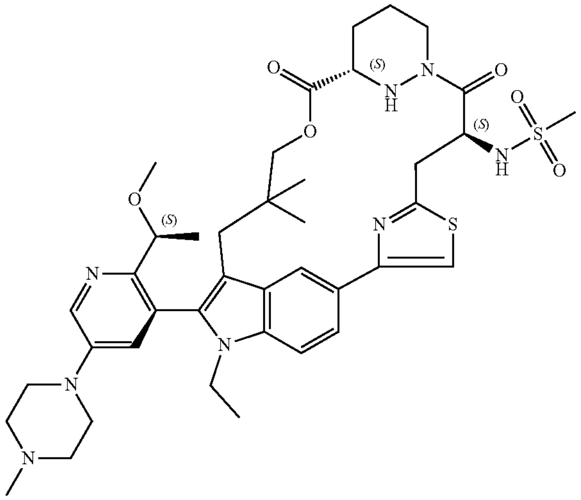 |

TABLE 1b-continued
| Certain Compounds of the Present Invention | |
|---|---|
| Ex. # | Structure |
| A367 | 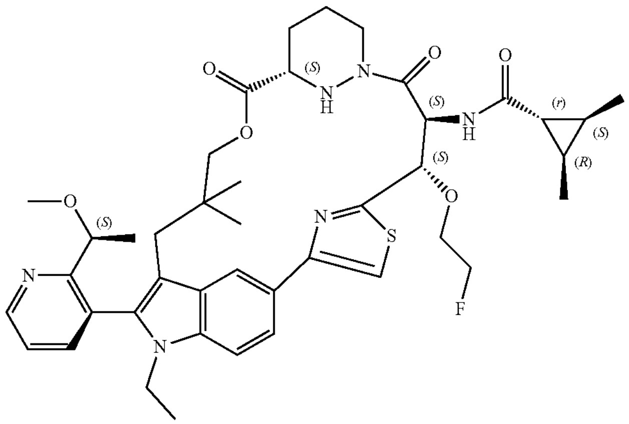 |
| A368 | 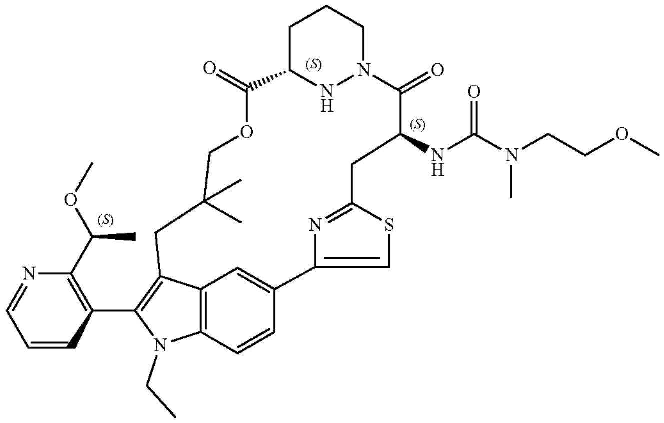 |
| A369 | 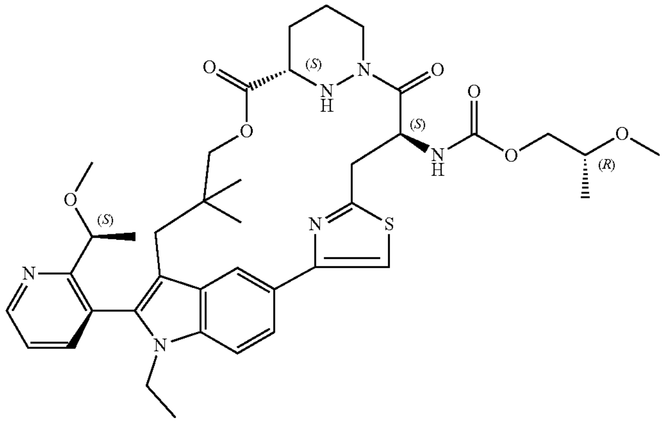 |

TABLE 1b-continued
| Certain Compounds of the Present Invention | |
|---|---|
| Ex. # | Structure |
| A370 | 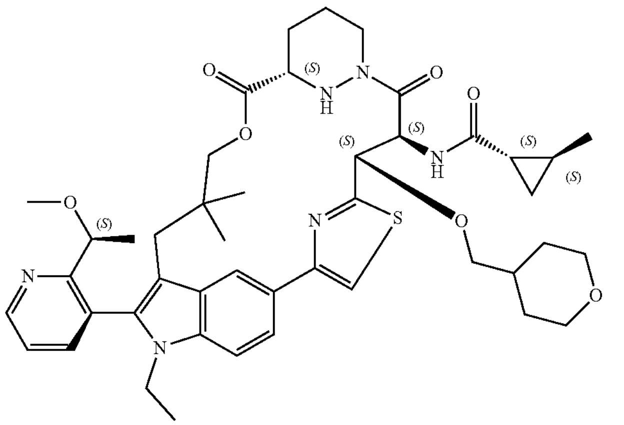 |
| A371 | 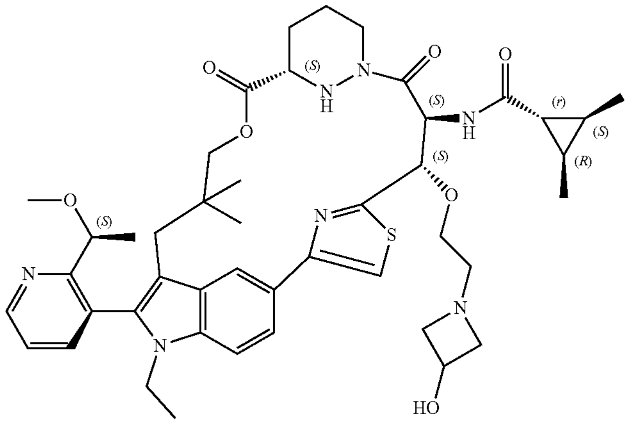 |
| A372 | 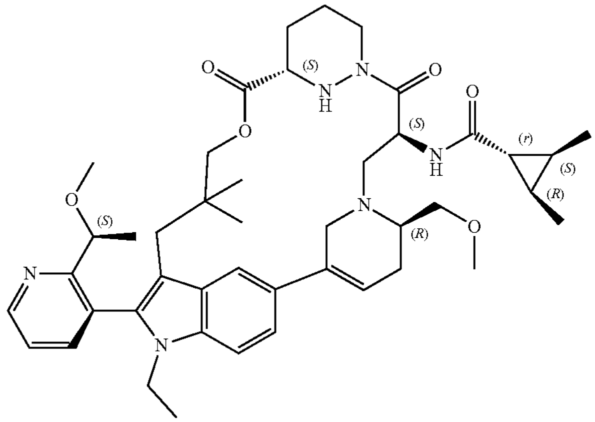 |

TABLE 1b-continued
| Certain Compounds of the Present Invention | |
|---|---|
| Ex. # | Structure |
| A373 | 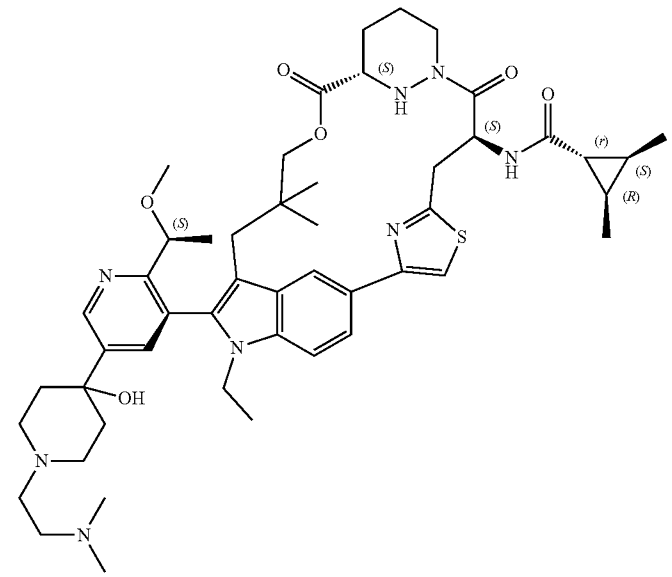 |
| A374 | 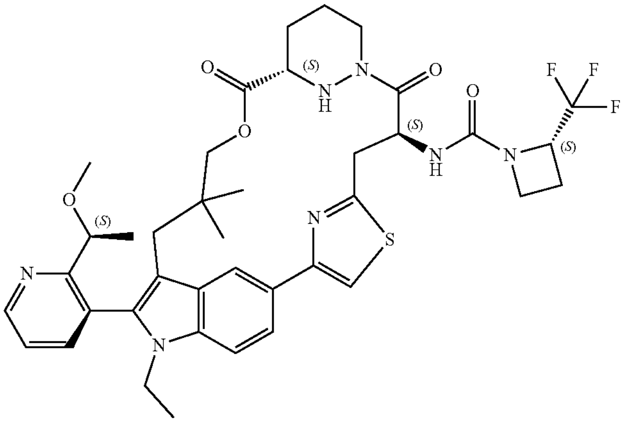 |
| A375 | 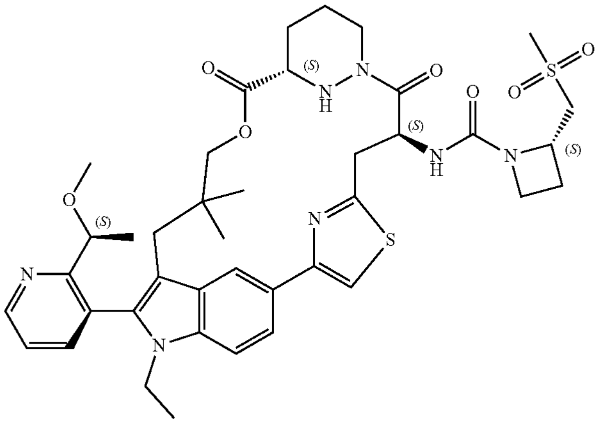 |

TABLE 1b-continued
| Certain Compounds of the Present Invention | |
|---|---|
| Ex. # | Structure |
| A376 | 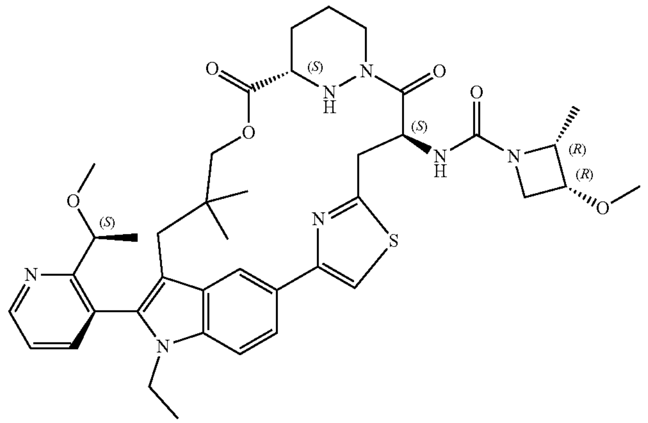 |
| A377 | 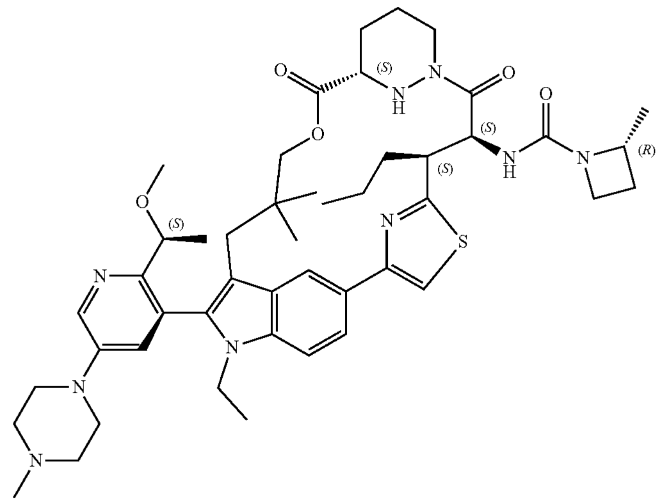 |
| A378 | 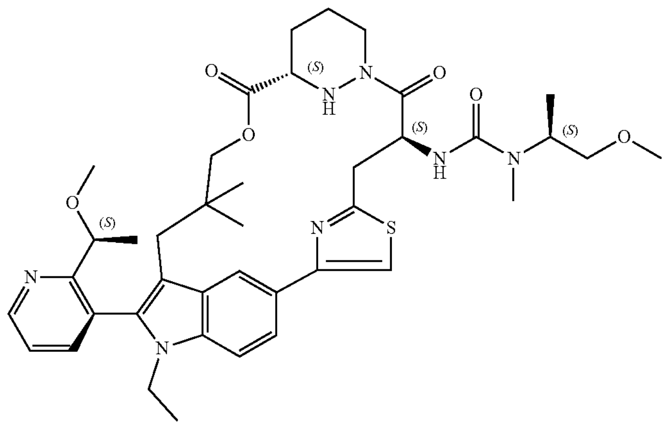 |

TABLE 1b-continued
| Certain Compounds of the Present Invention | |
|---|---|
| Ex. # | Structure |
| A379 | 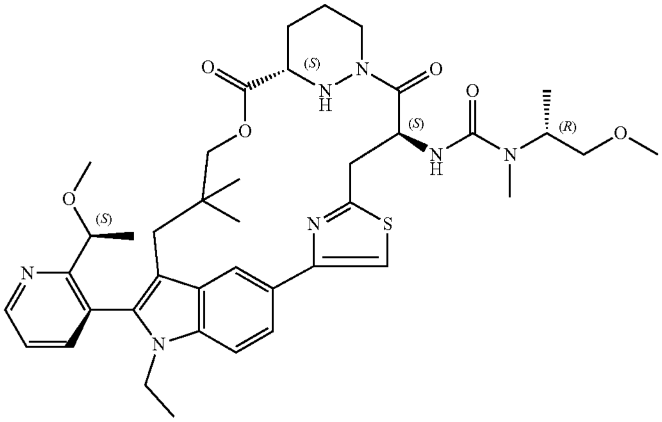 |
| A380 | 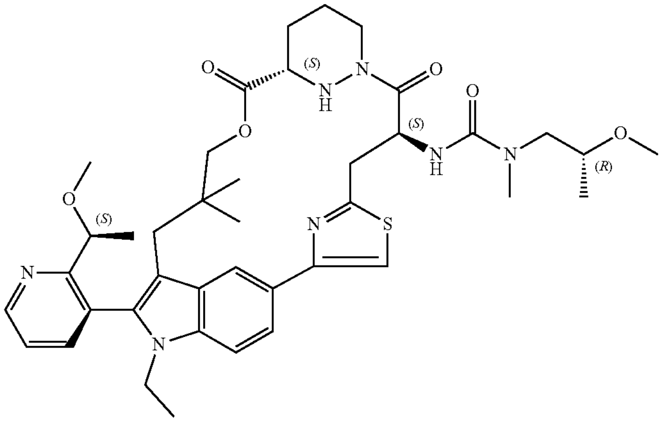 |
| A381 | 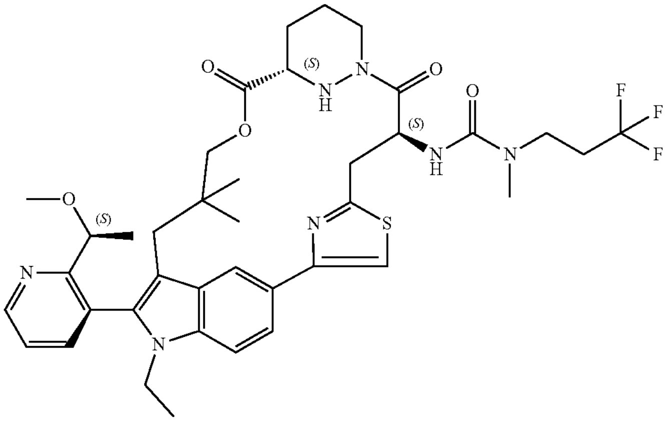 |

TABLE 1b-continued
| Certain Compounds of the Present Invention | |
|---|---|
| Ex. # | Structure |
| A382 | 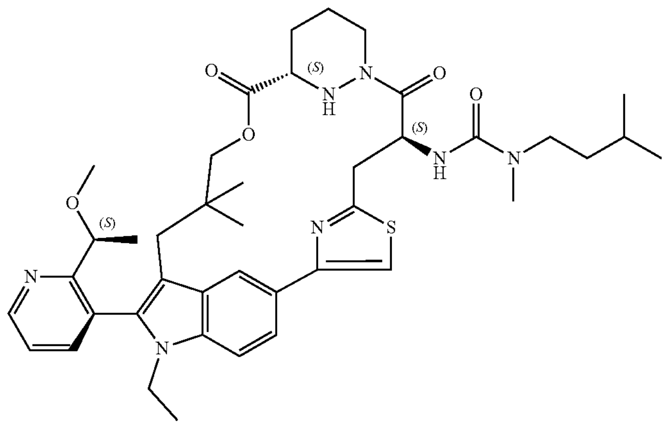 |
| A383 | 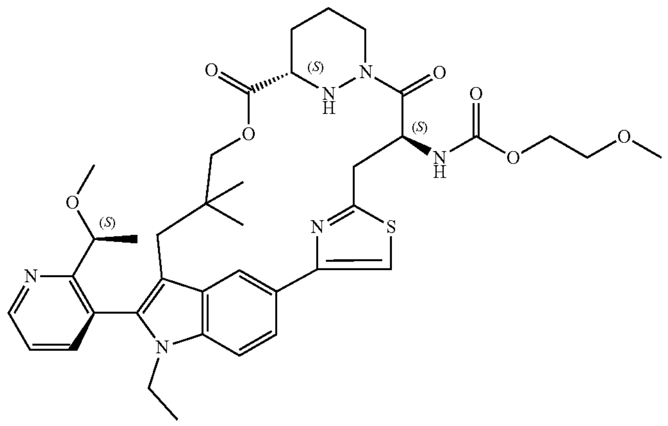 |
| A384 | 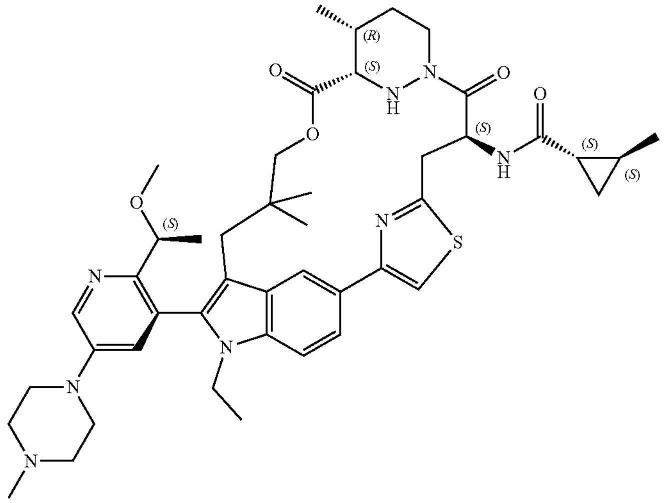 |

TABLE 1b-continued
| Certain Compounds of the Present Invention | |
|---|---|
| Ex. # | Structure |
| A385 | 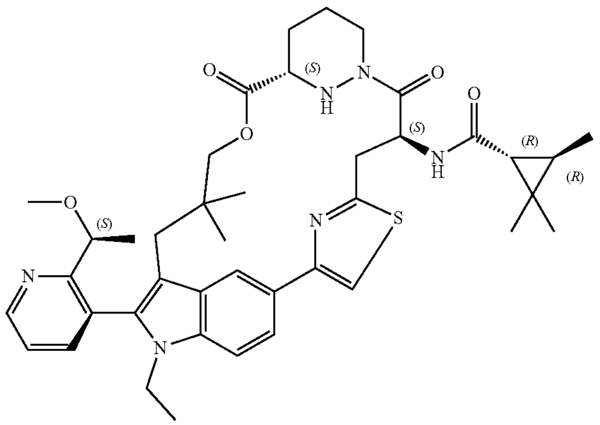 |
| A386 | 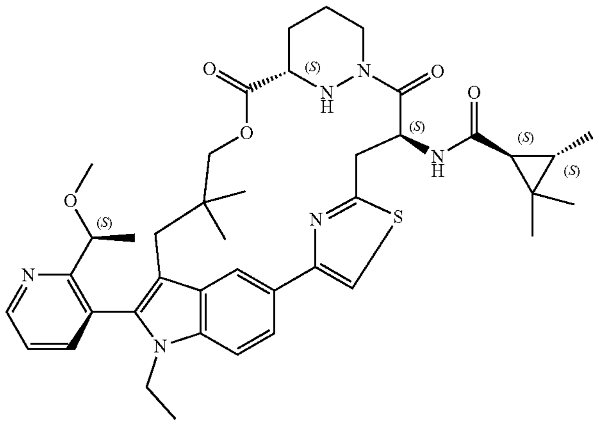 |
| A387 | 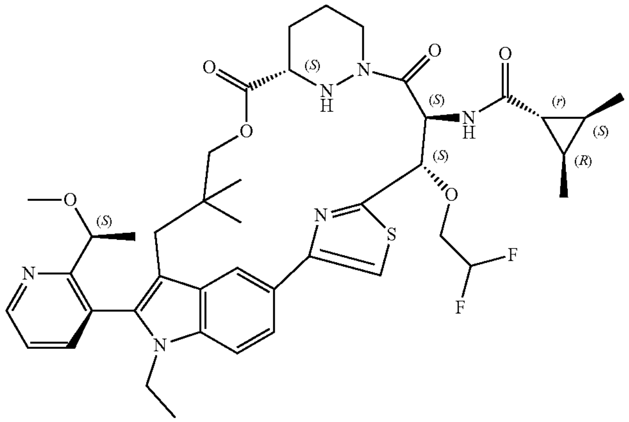 |

TABLE 1b-continued
| Certain Compounds of the Present Invention | |
|---|---|
| Ex. # | Structure |
| A388 | 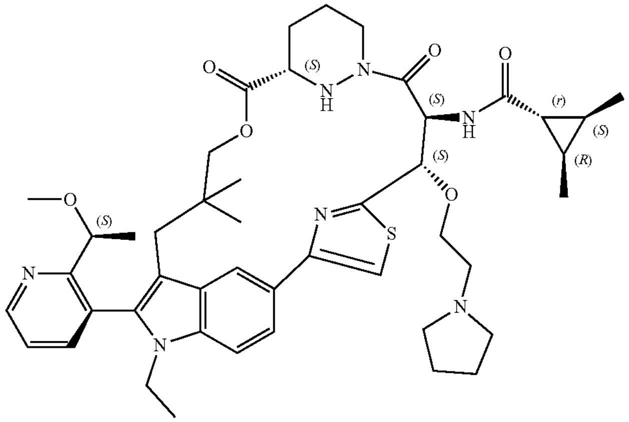 |
| A389 | 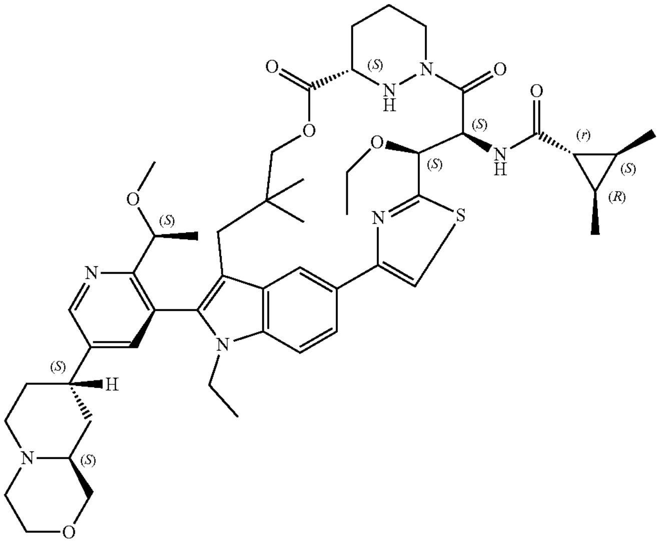 |
| A390 | 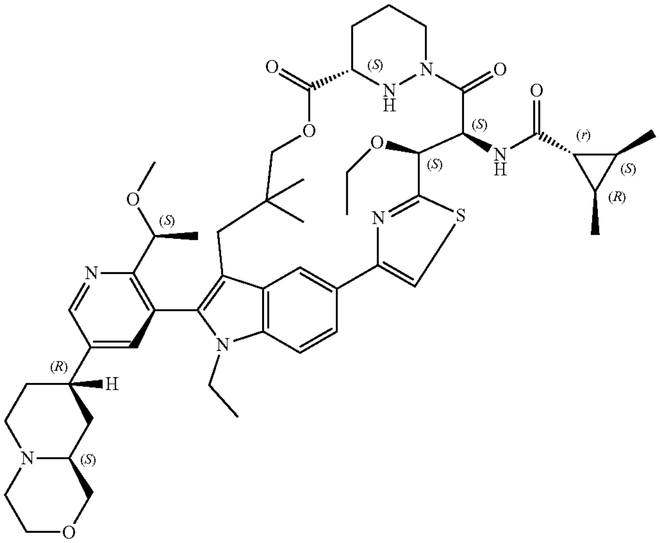 |

TABLE 1b-continued
| Certain Compounds of the Present Invention | |
|---|---|
| Ex. # | Structure |
| A391 | 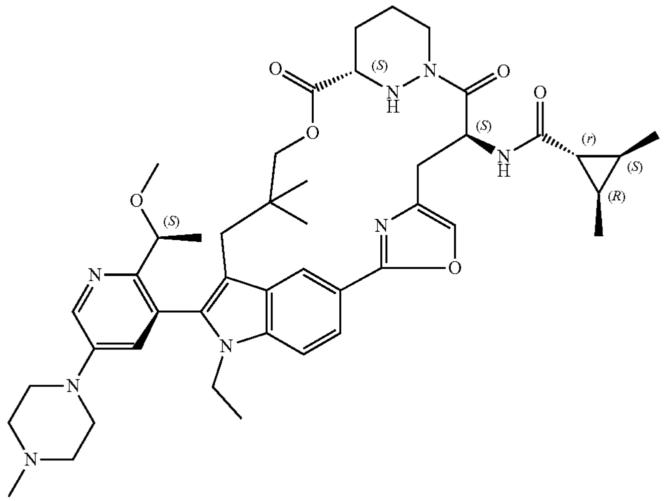 |
| A392 | 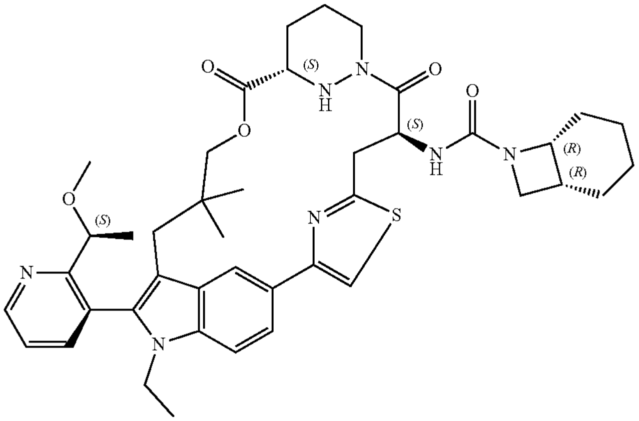 |
| A393 | 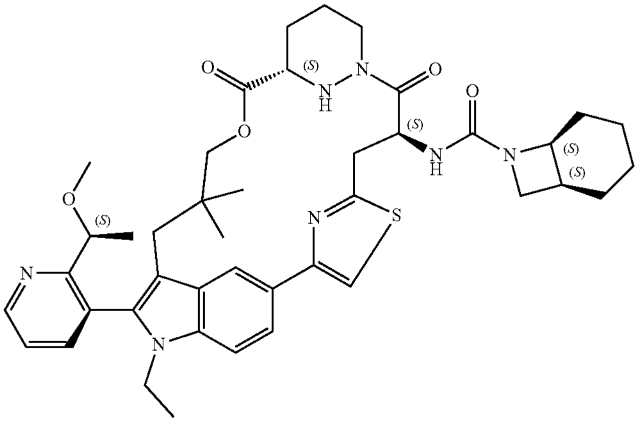 |

TABLE 1b-continued
| Certain Compounds of the Present Invention | |
|---|---|
| Ex. # | Structure |
| A394 | 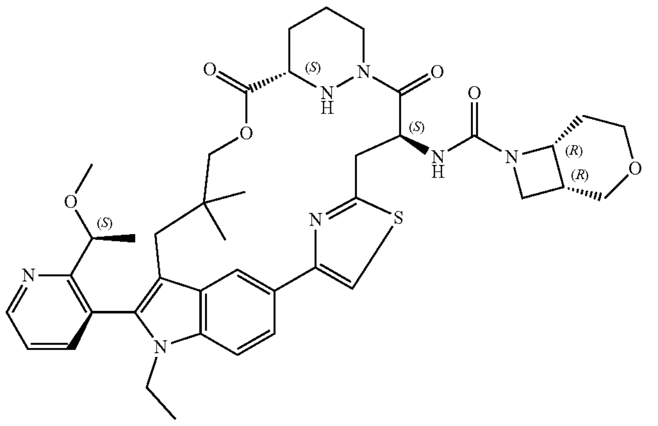 |
| A395 | 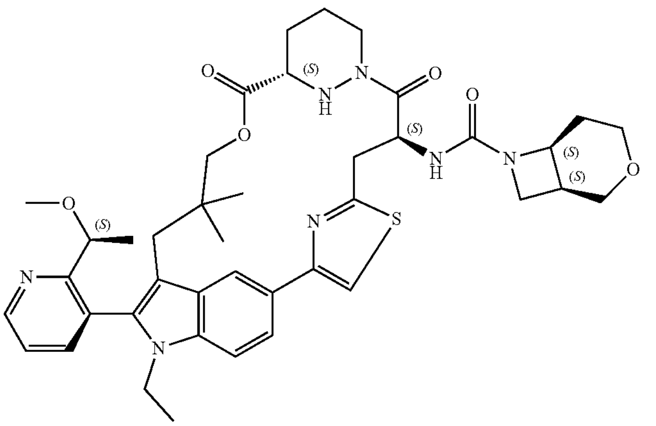 |
| A396 | 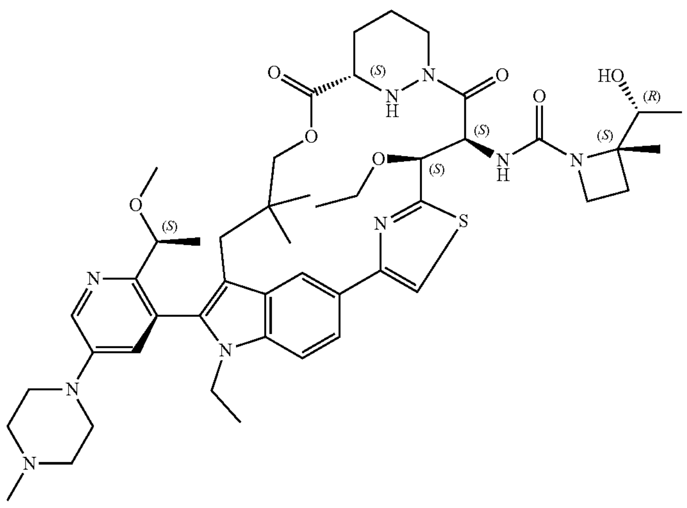 |

TABLE 1b-continued
| Certain Compounds of the Present Invention | |
|---|---|
| Ex. # | Structure |
| A397 | 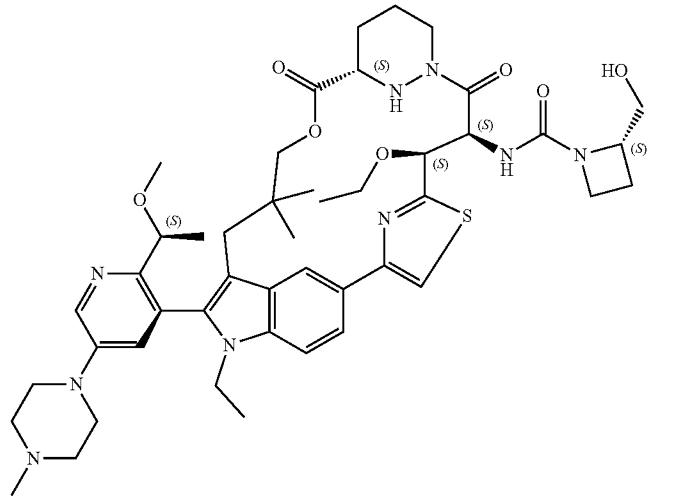 |
| A398 | 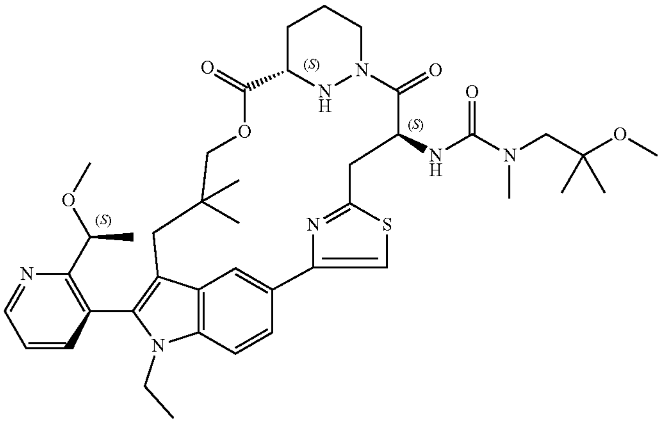 |
| A399 | 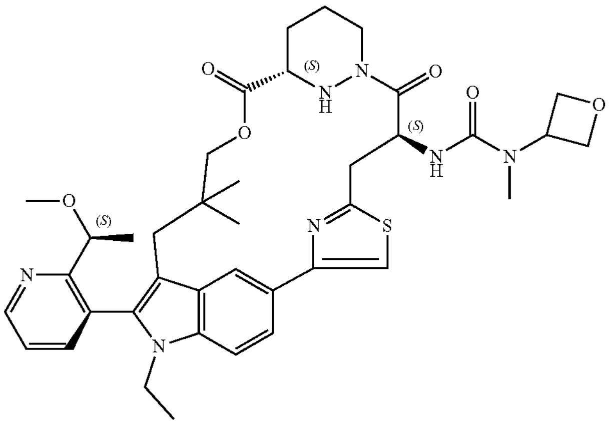 |

TABLE 1b-continued
| Certain Compounds of the Present Invention | |
|---|---|
| Ex. # | Structure |
| A400 | 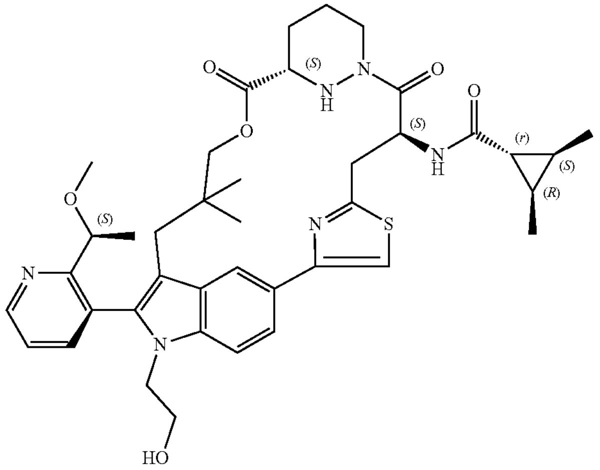 |
| A401 | 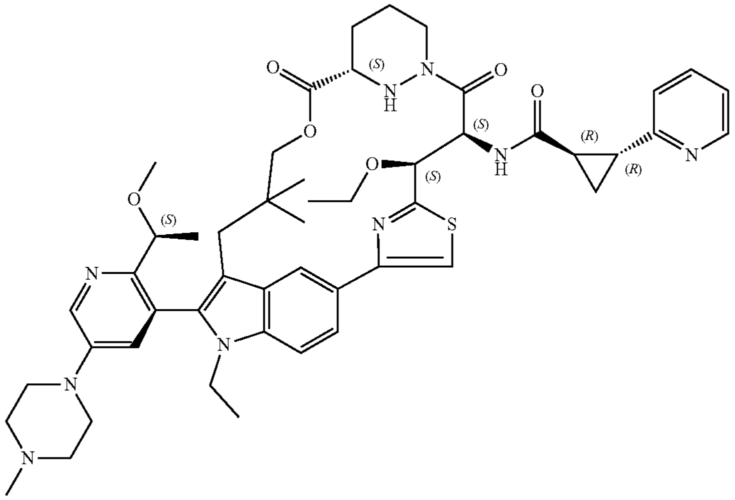 |
| A402 | 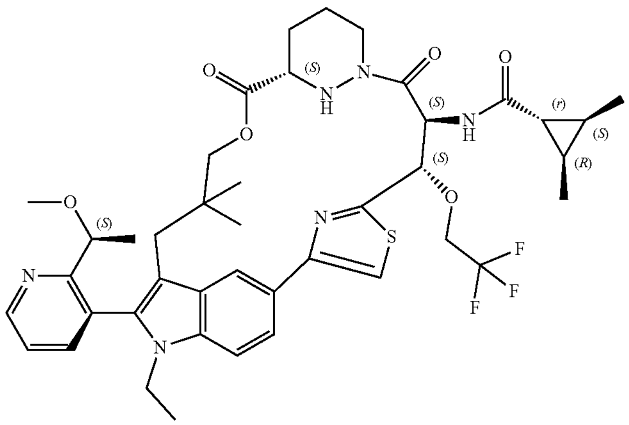 |

TABLE 1b-continued
| Certain Compounds of the Present Invention | |
|---|---|
| Ex. # | Structure |
| A403 | 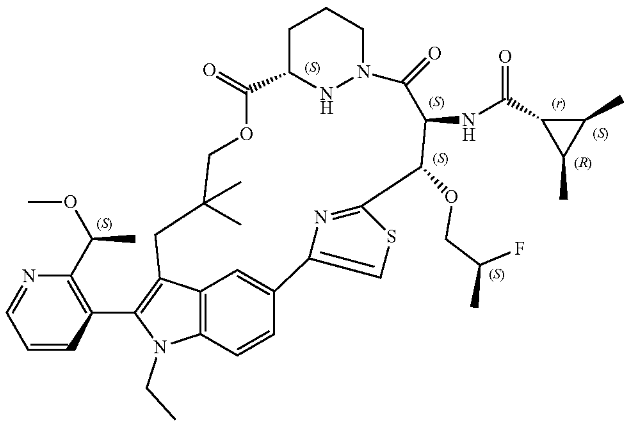 |
| A404 | 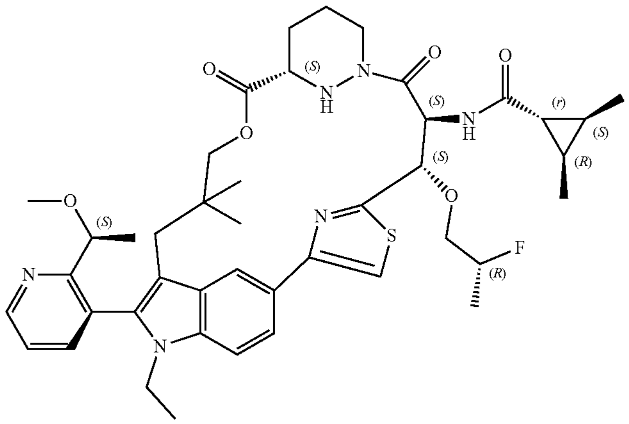 |
| A405 | 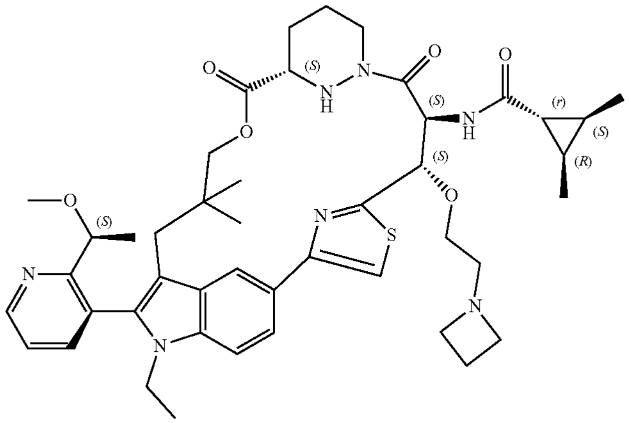 |

TABLE 1b-continued
| Certain Compounds of the Present Invention | |
|---|---|
| Ex. # | Structure |
| A406 | 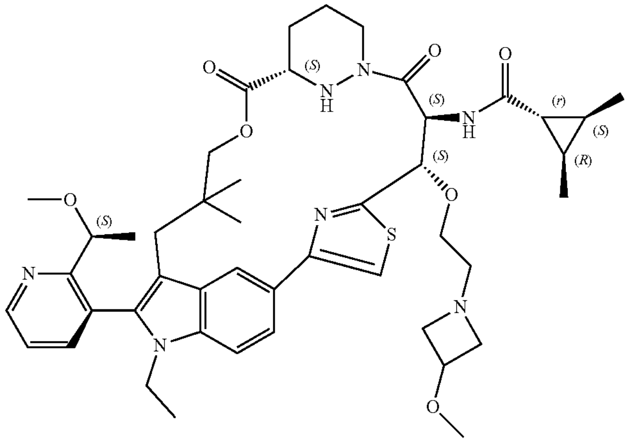 |
| A407 | 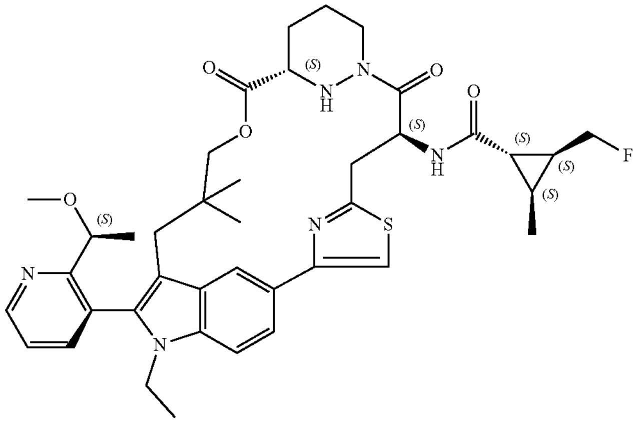 |
| A408 | 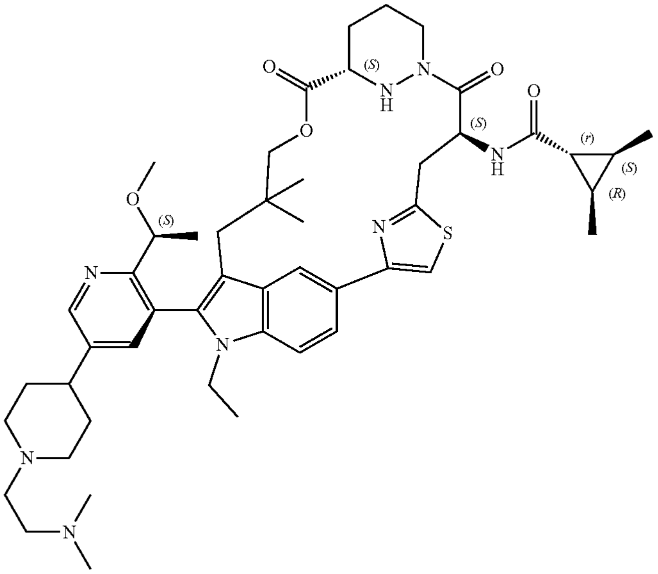 |

TABLE 1b-continued
| Certain Compounds of the Present Invention | |
|---|---|
| Ex. # | Structure |
| A409 | 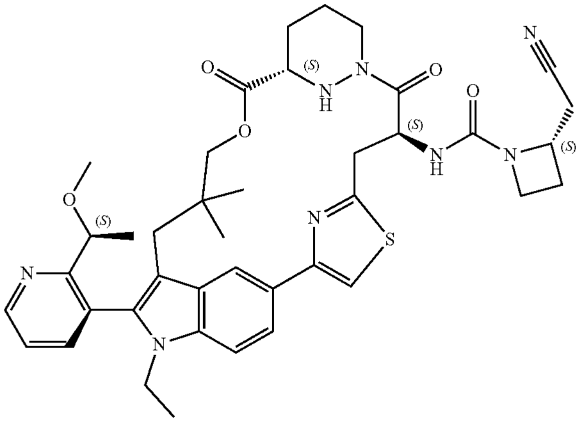 |
| A410 | 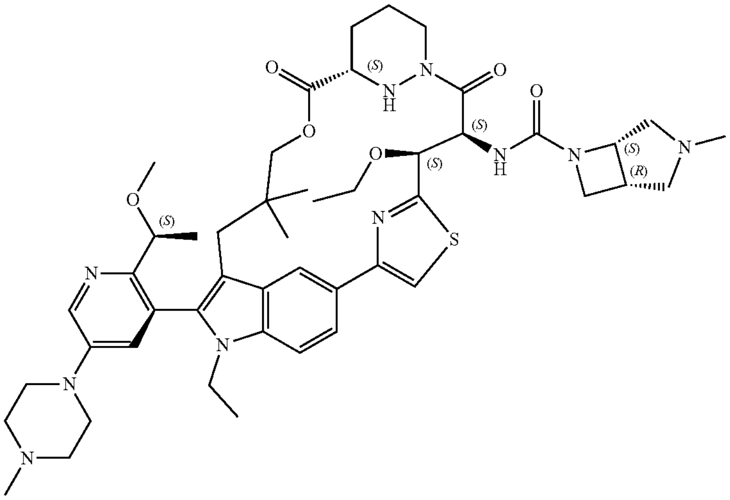 |
| A411 | 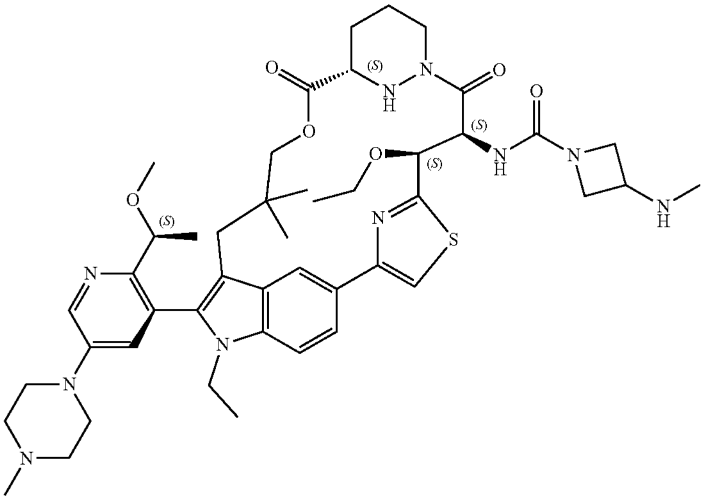 |

TABLE 1b-continued
| Certain Compounds of the Present Invention | |
|---|---|
| Ex. # | Structure |
| A412 | 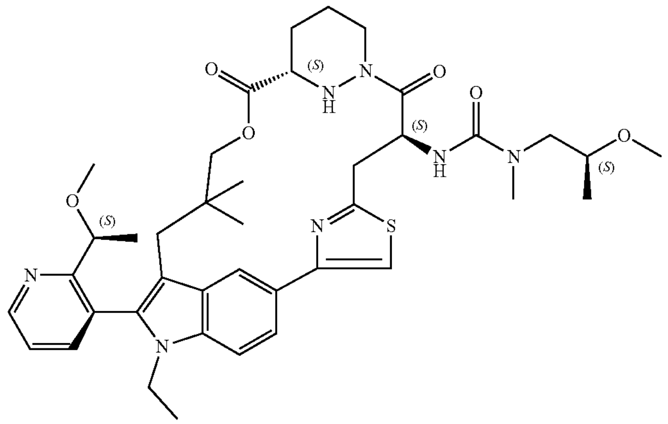 |
| A413 | 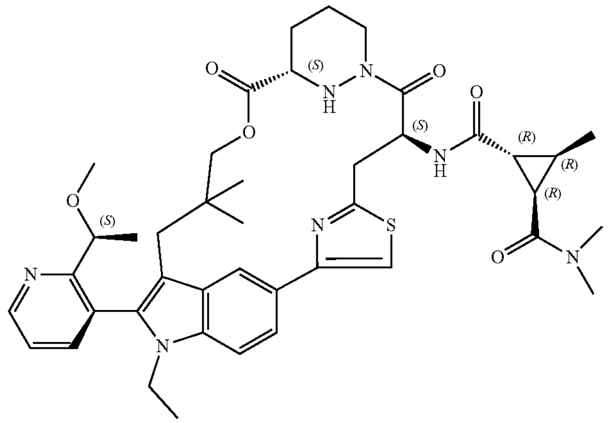 |
| A414 | 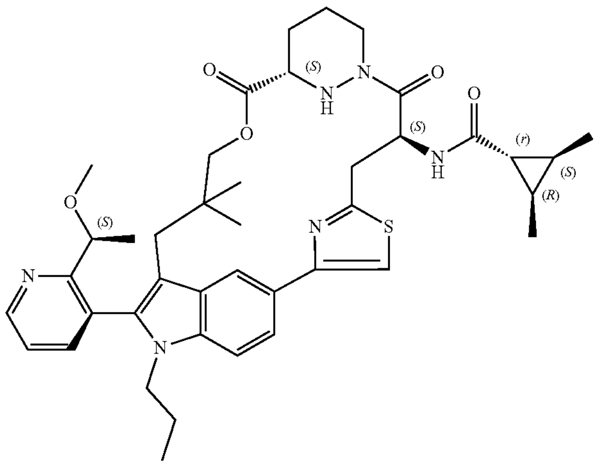 |

TABLE 1b-continued
| Certain Compounds of the Present Invention | |
|---|---|
| Ex. # | Structure |
| A415 | 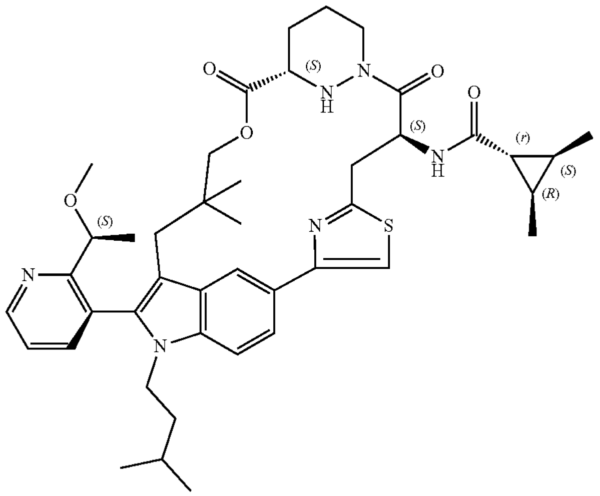 |
| A416 | 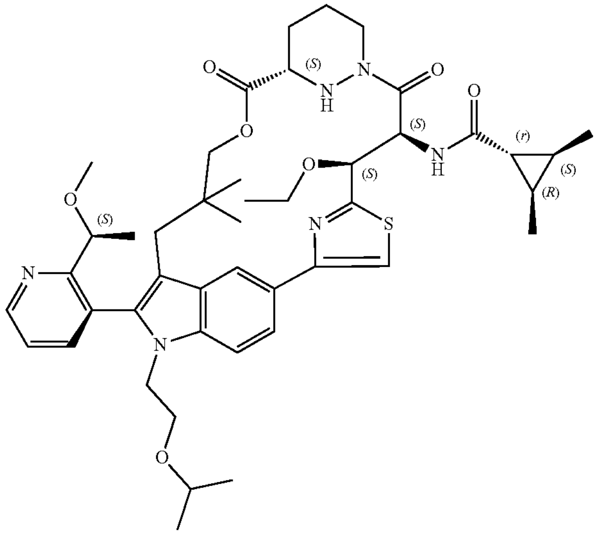 |
| A417 | 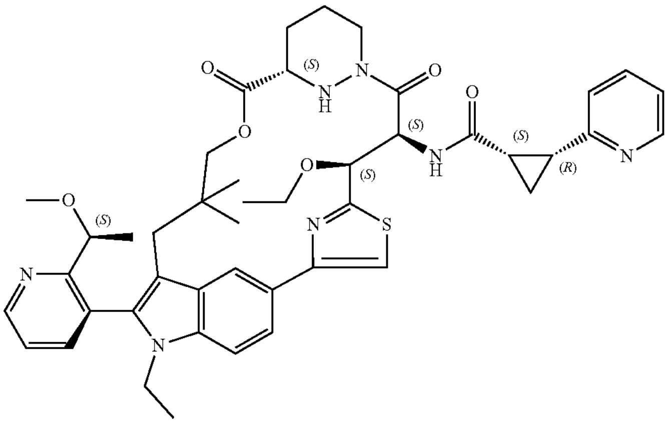 |

TABLE 1b-continued
| Certain Compounds of the Present Invention | |
|---|---|
| Ex. # | Structure |
| A418 | 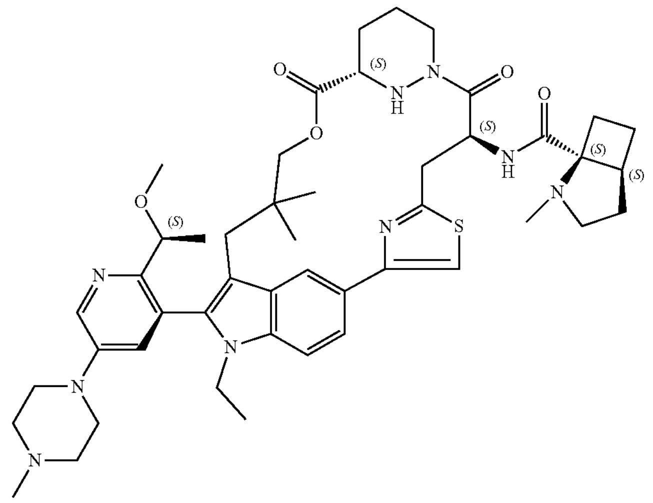 |
| A419 | 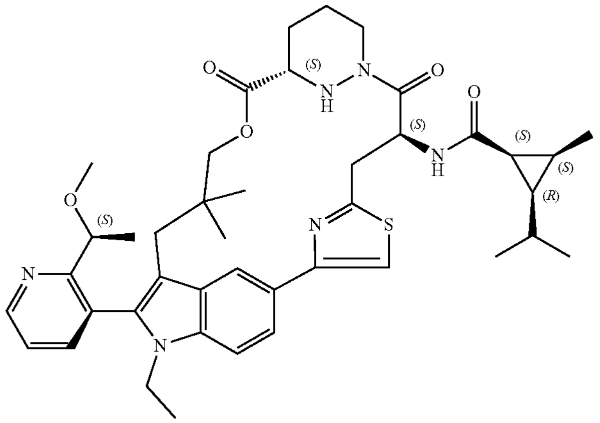 |
| A420 | 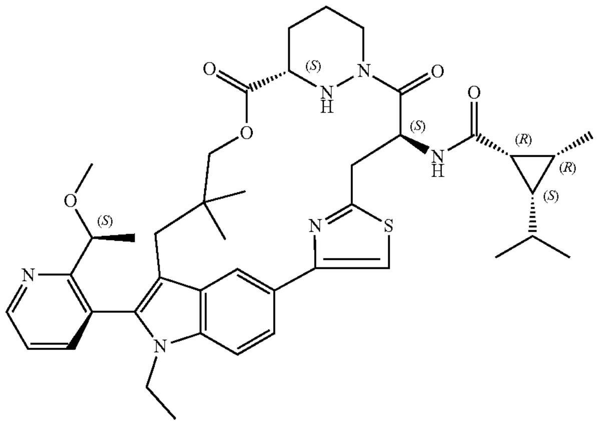 |

TABLE 1b-continued
| Certain Compounds of the Present Invention | |
|---|---|
| Ex. # | Structure |
| A421 | 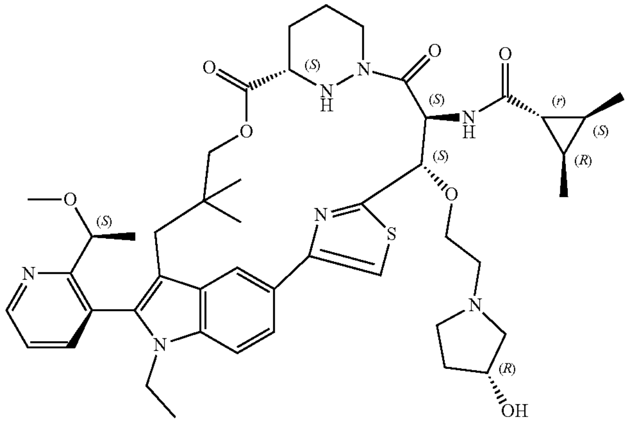 |
| A422 | 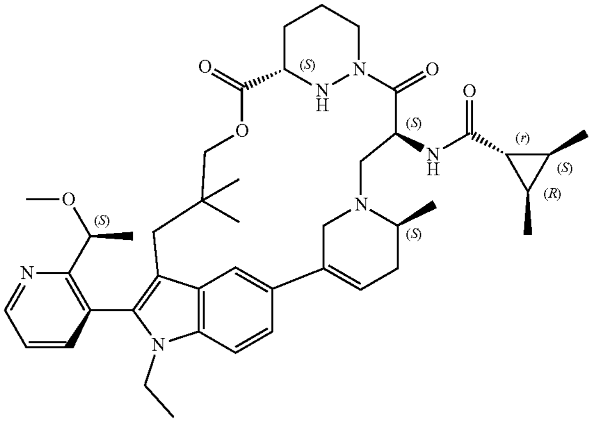 |
| A423 | 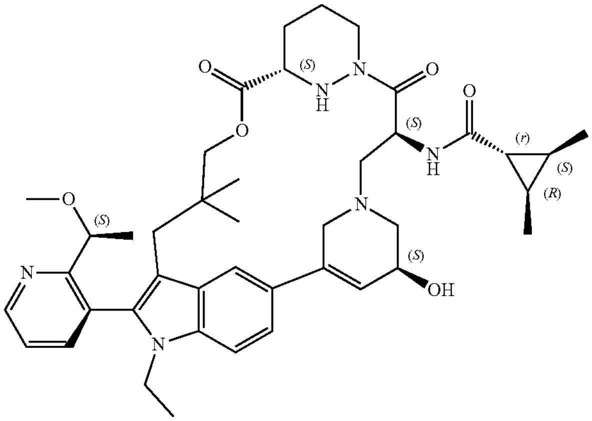 |

TABLE 1b-continued
| Certain Compounds of the Present Invention | |
|---|---|
| Ex. # | Structure |
| A424 | 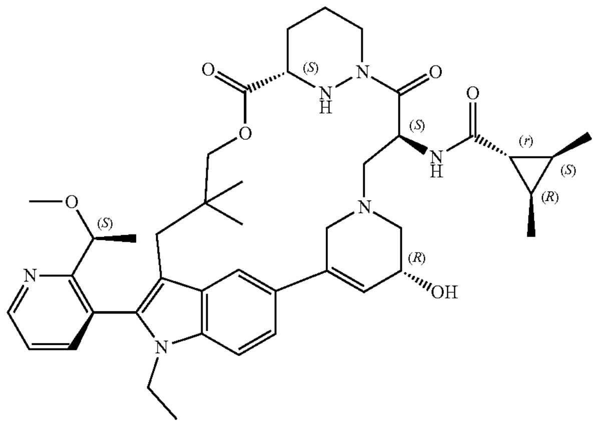 |
| A425 | 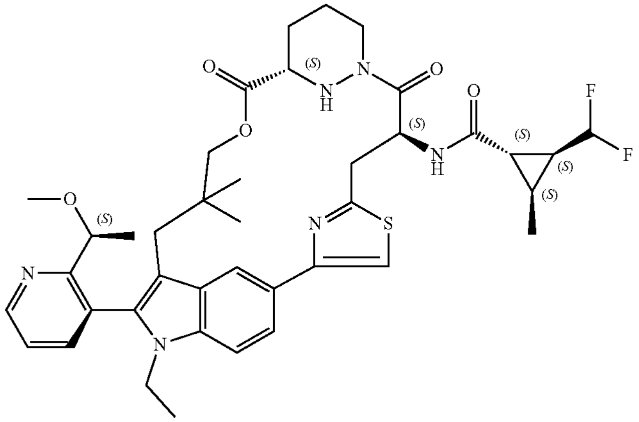 |
| A426 | 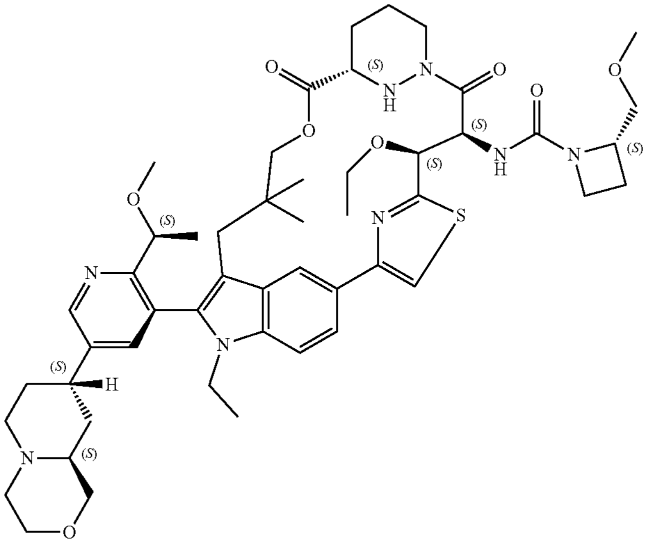 |

TABLE 1b-continued
| Certain Compounds of the Present Invention | |
|---|---|
| Ex. # | Structure |
| A427 | 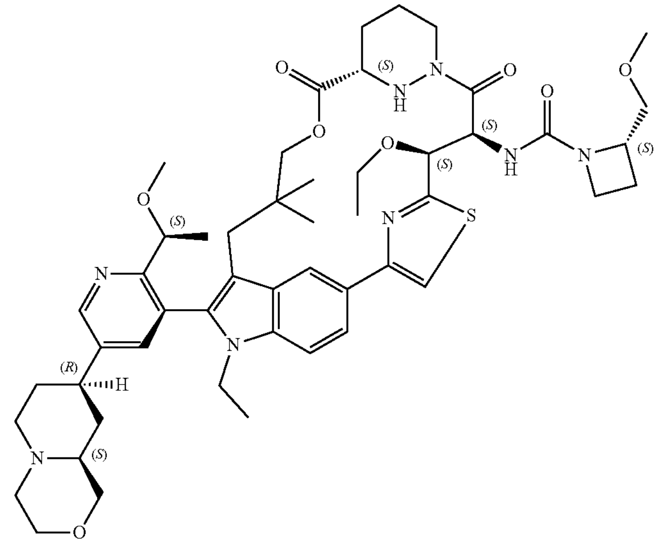 |
| A428 | 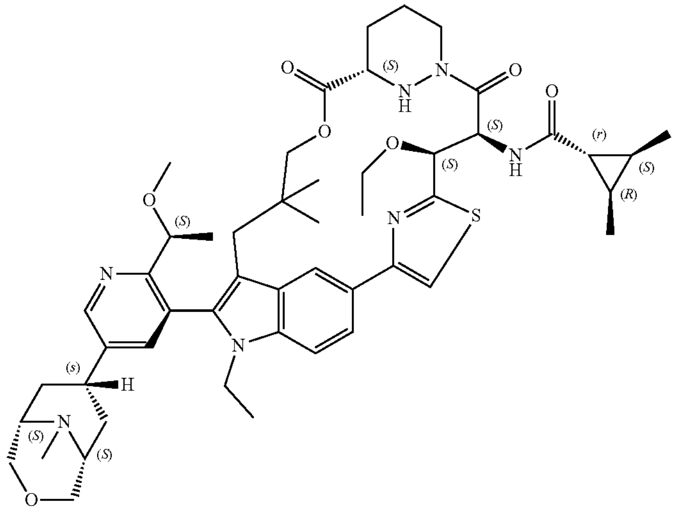 |

TABLE 1b-continued
| Certain Compounds of the Present Invention | |
|---|---|
| Ex. # | Structure |
| A429 | 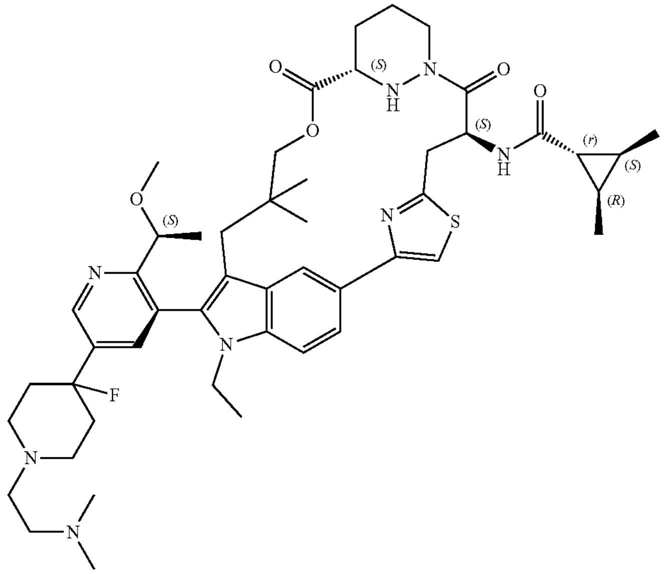 |
| A430 | 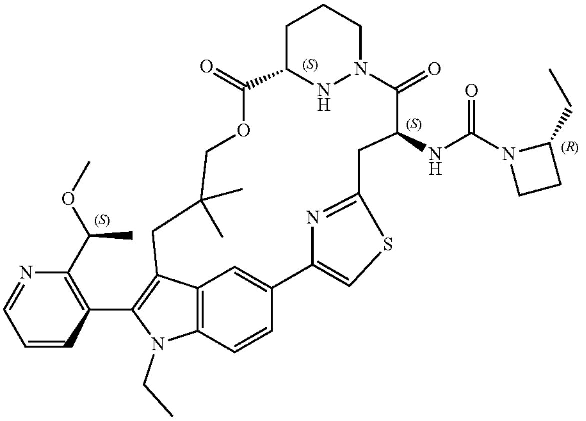 |
| A431 | 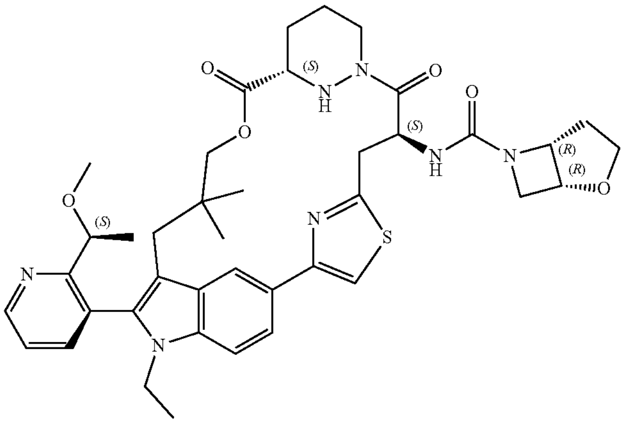 |

TABLE 1b-continued
| Certain Compounds of the Present Invention | |
|---|---|
| Ex. # | Structure |
| A432 | 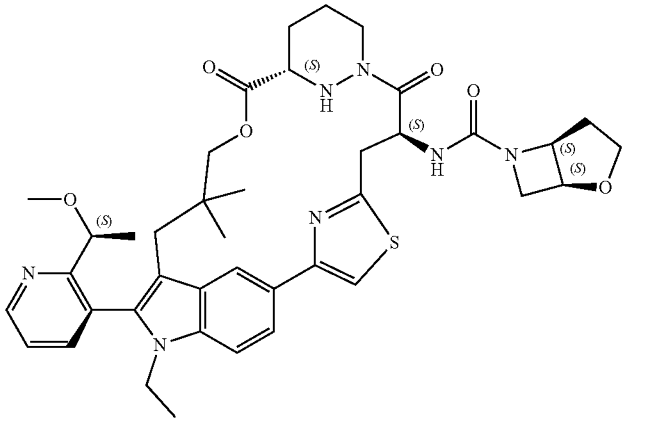 |
| A433 | 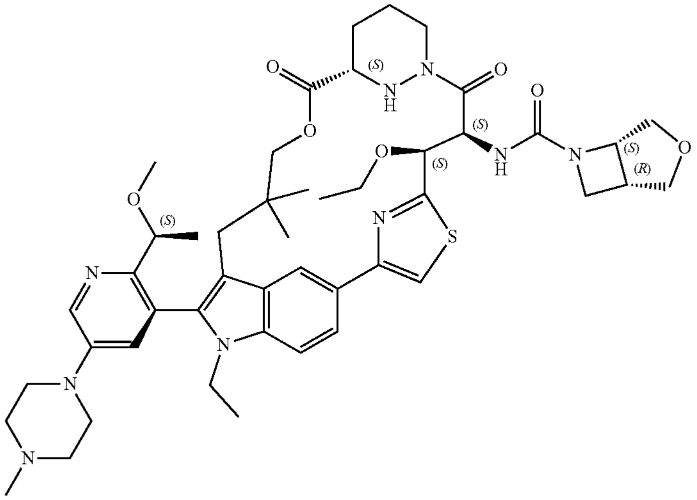 |
| A434 | 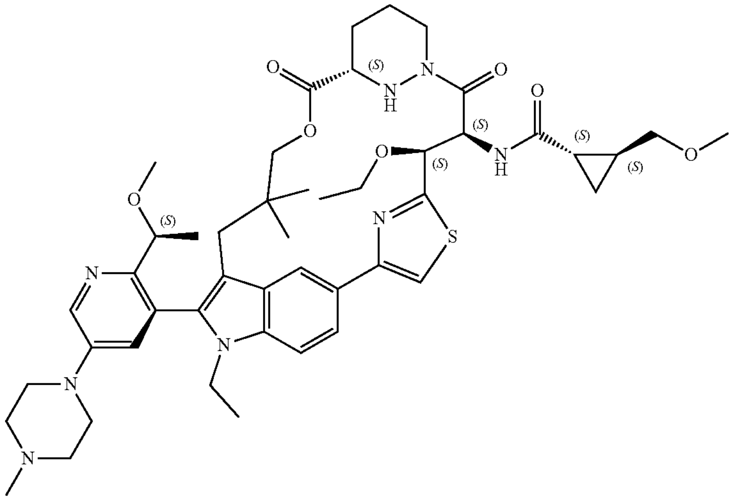 |

TABLE 1b-continued
| Certain Compounds of the Present Invention | |
|---|---|
| Ex. # | Structure |
| A435 | 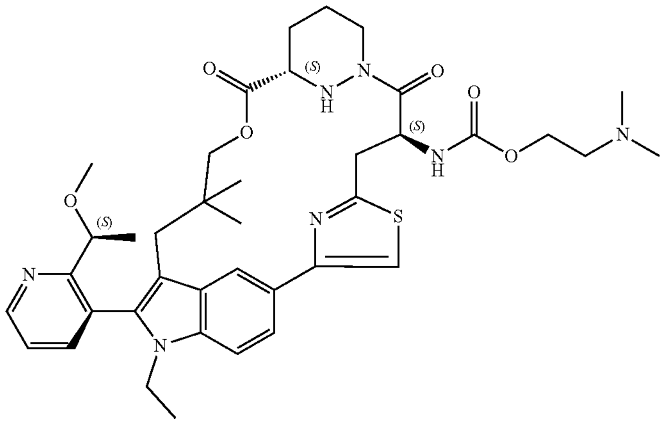 |
| A436 | 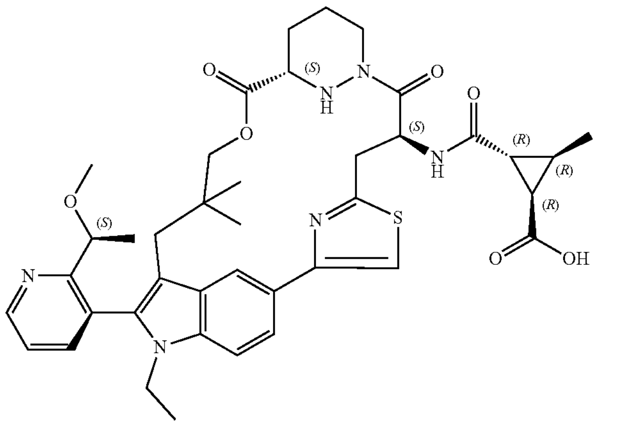 |
| A437 | 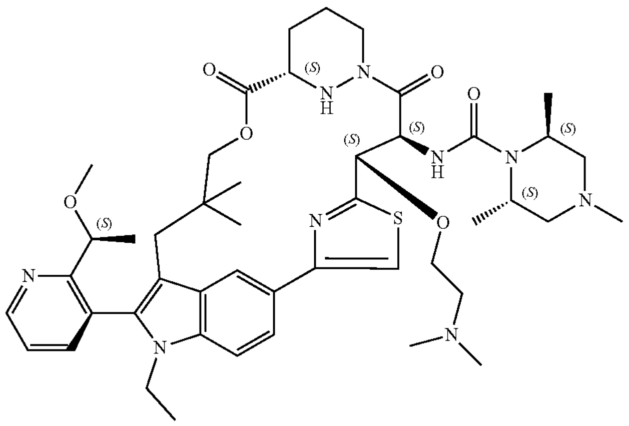 |

TABLE 1b-continued
| Certain Compounds of the Present Invention | |
|---|---|
| Ex. # | Structure |
| A438 | 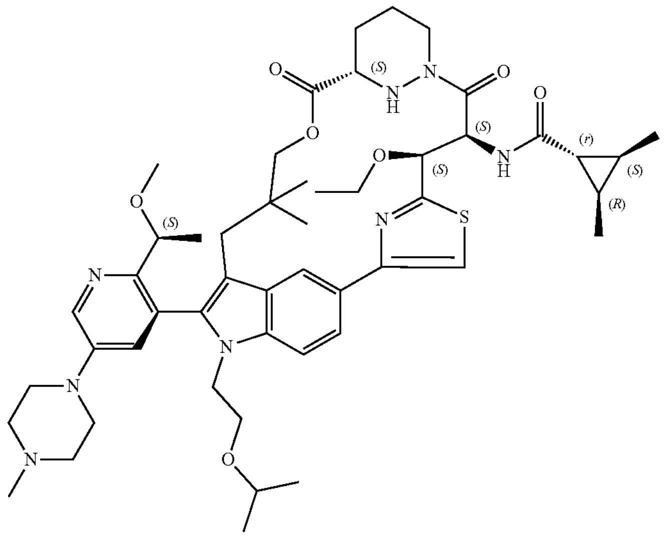 |
| A439 | 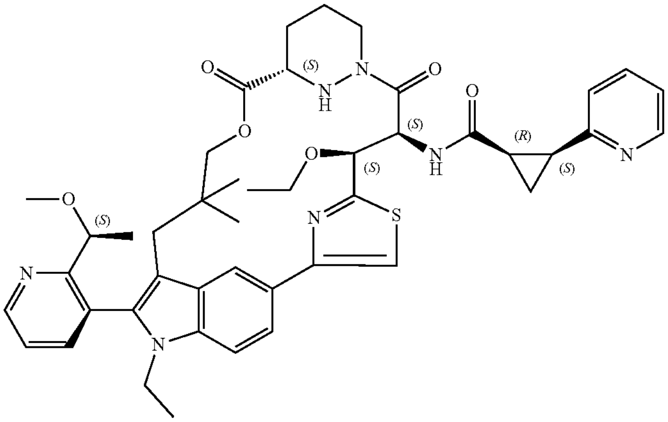 |
| A440 | 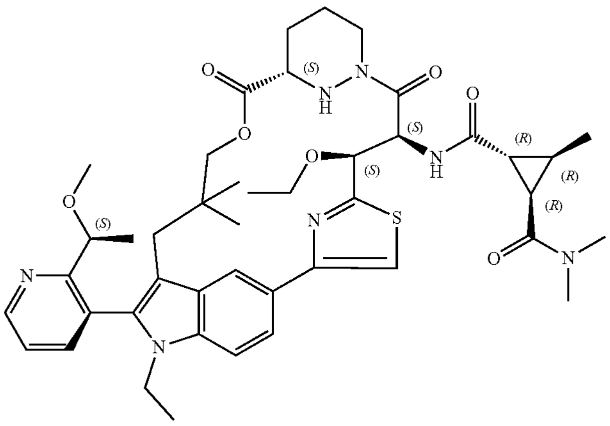 |

TABLE 1b-continued
| Certain Compounds of the Present Invention | |
|---|---|
| Ex. # | Structure |
| A441 | 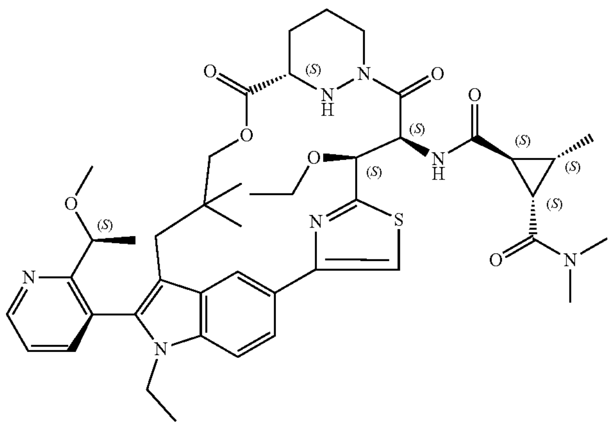 |
| A442 | 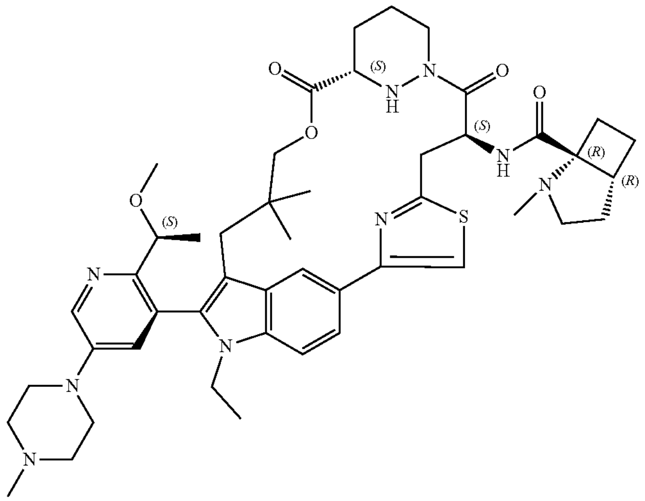 |
| A443 | 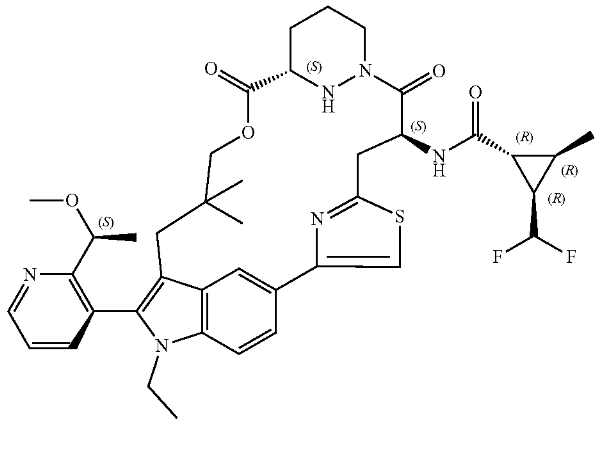 |

TABLE 1b-continued
| Certain Compounds of the Present Invention | |
|---|---|
| Ex. # | Structure |
| A444 | 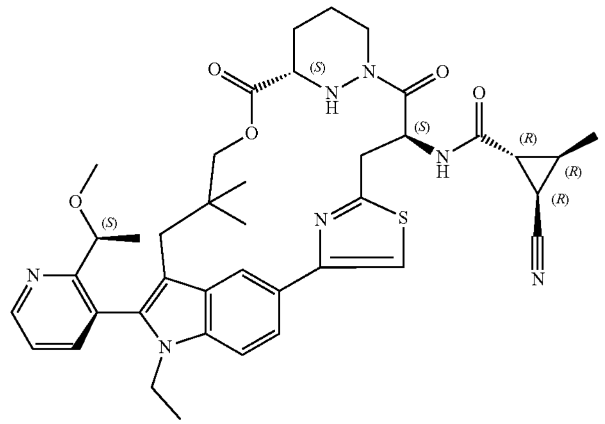 |
| A445 | 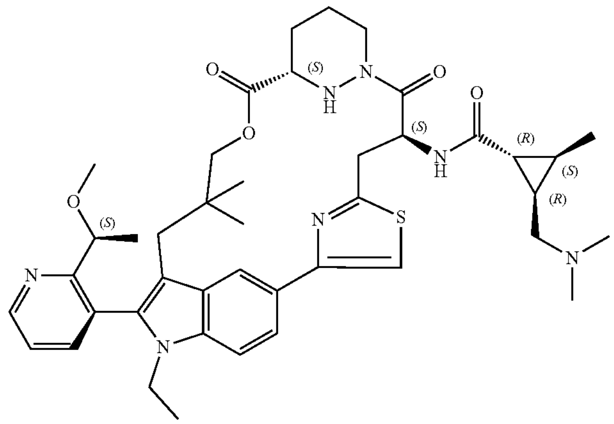 |
| A446 | 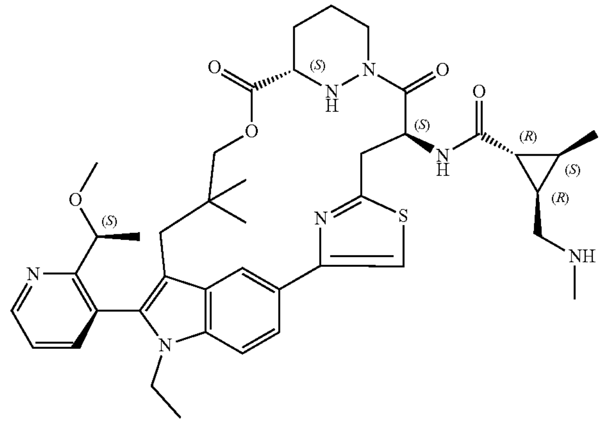 |

TABLE 1b-continued
| Certain Compounds of the Present Invention | |
|---|---|
| Ex. # | Structure |
| A447 | 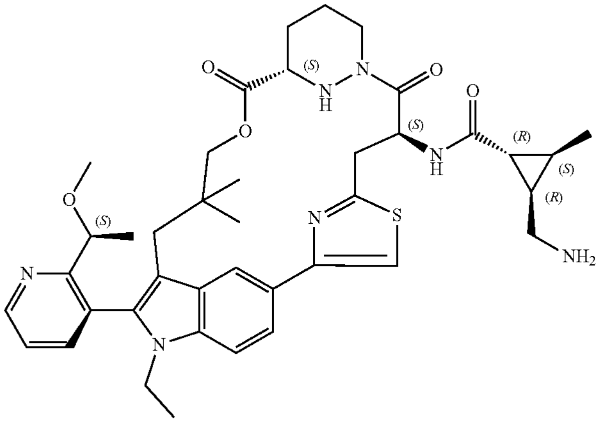 |
| A448 | 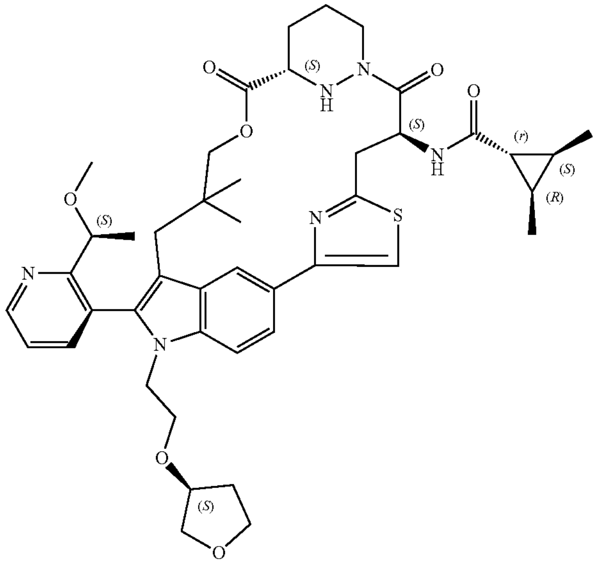 |
| A449 | 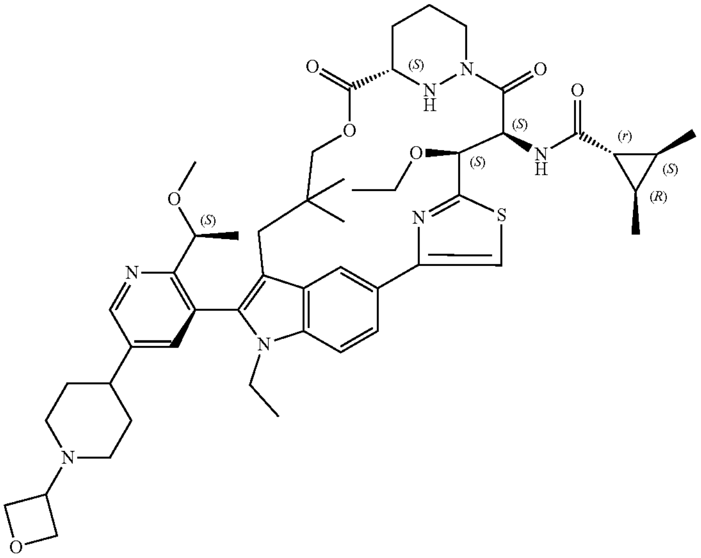 |

TABLE 1b-continued
| Certain Compounds of the Present Invention | |
|---|---|
| Ex. # | Structure |
| A450 | 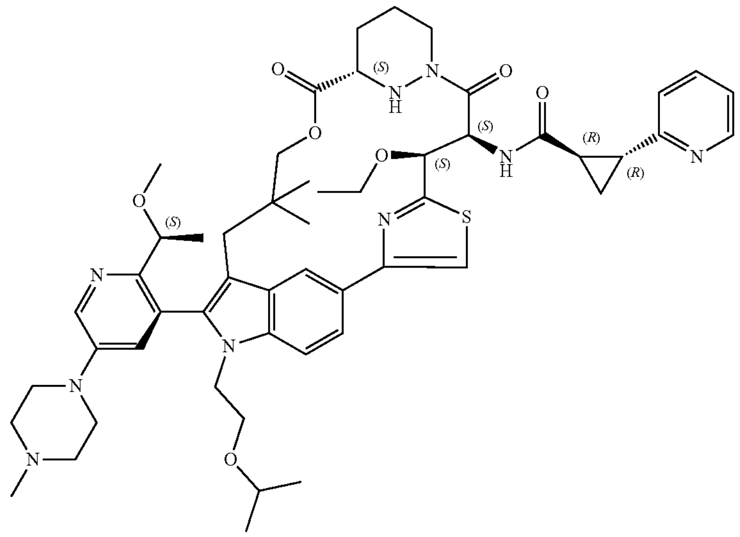 |
| A451 | 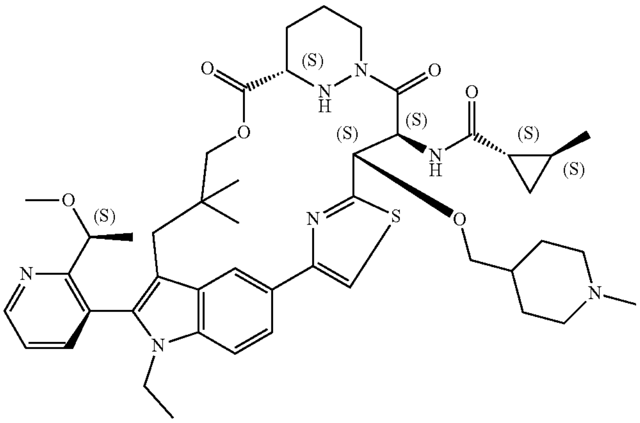 |
| A452 | 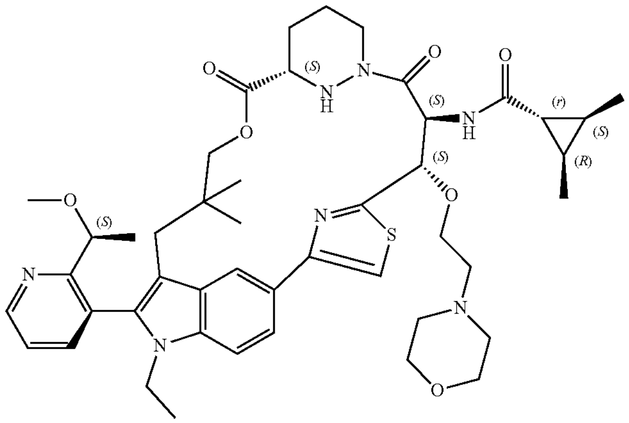 |

TABLE 1b-continued
| Certain Compounds of the Present Invention | |
|---|---|
| Ex. # | Structure |
| A453 | 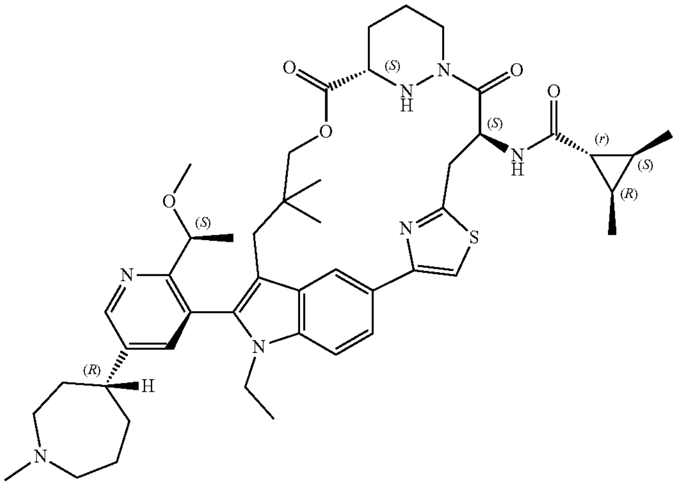 |
| A454 | 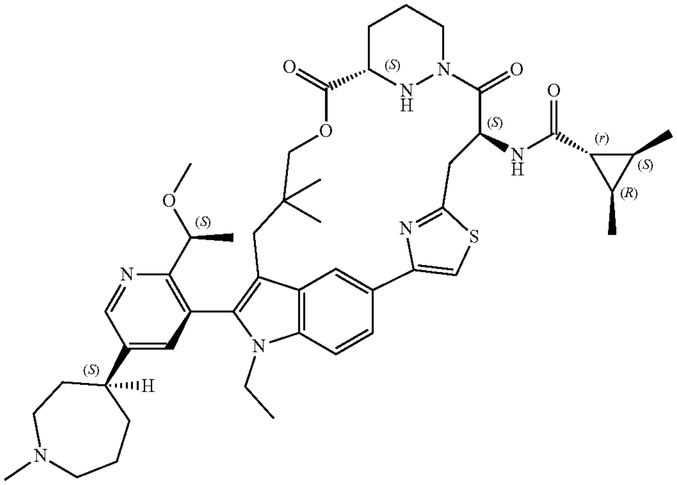 |
| A455 | 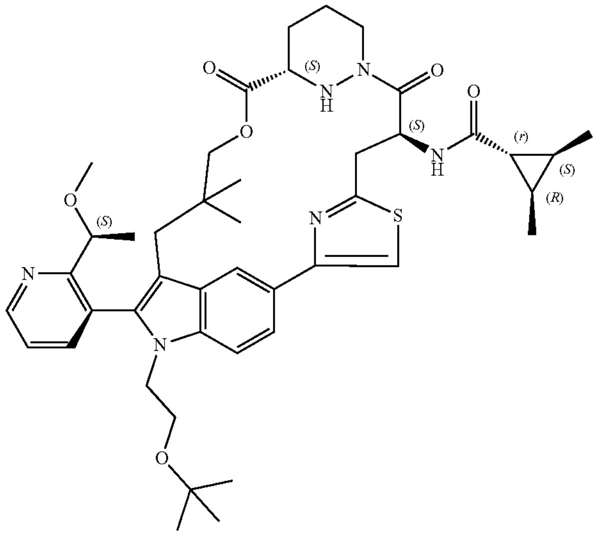 |

TABLE 1b-continued
| Certain Compounds of the Present Invention | |
|---|---|
| Ex. # | Structure |
| A456 | 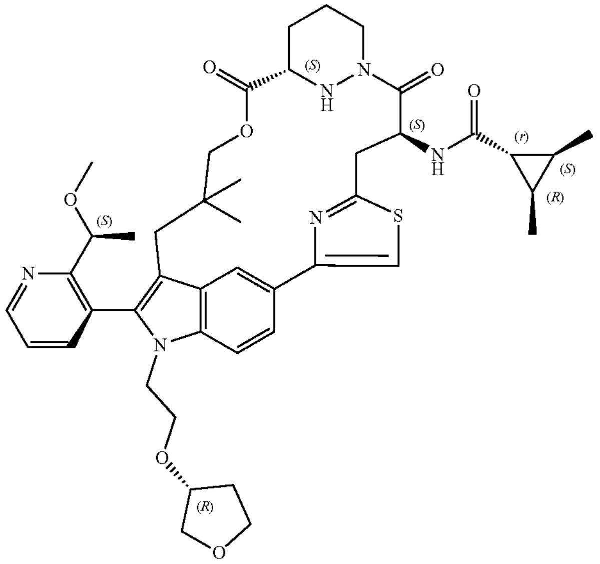 |
| A457 | 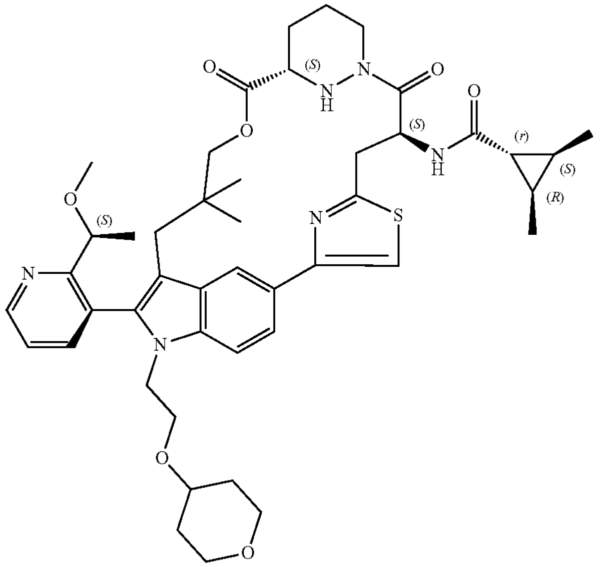 |

TABLE 1b-continued
| Certain Compounds of the Present Invention | |
|---|---|
| Ex. # | Structure |
| A458 | 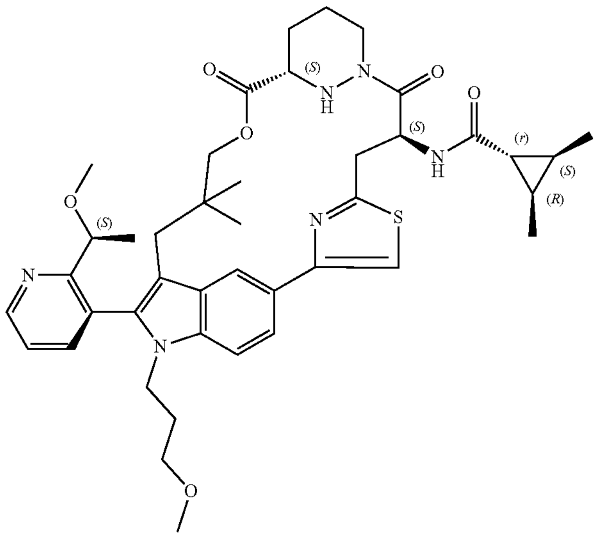 |
| A459 | 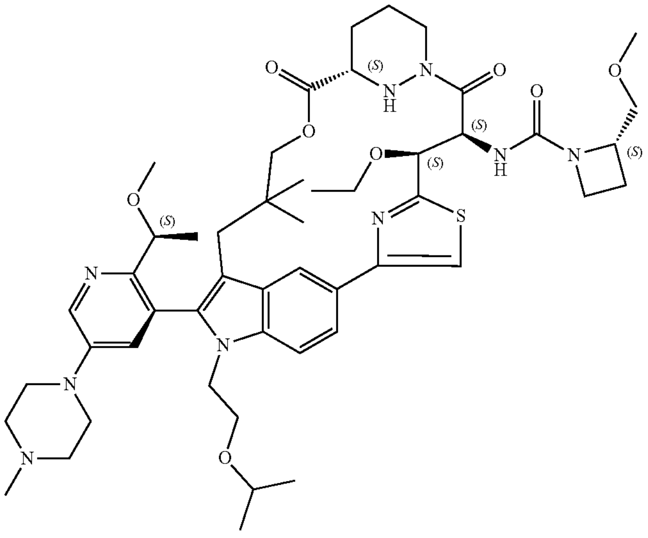 |

TABLE 1b-continued
| Certain Compounds of the Present Invention | |
|---|---|
| Ex. # | Structure |
| A460 | 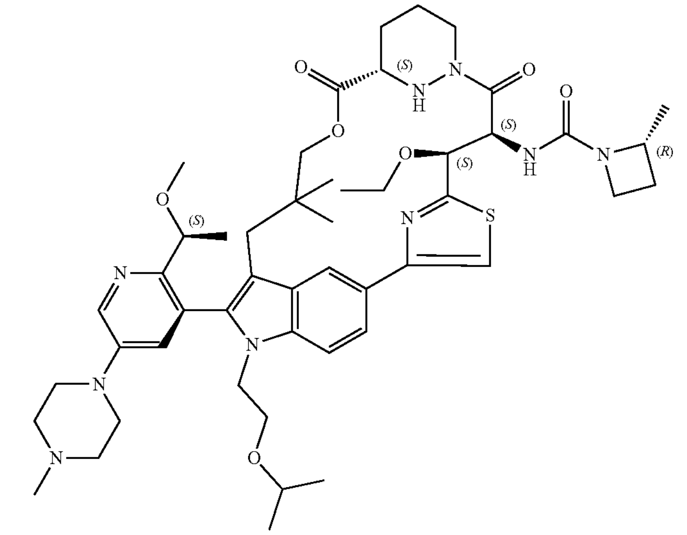 |
| A461 | 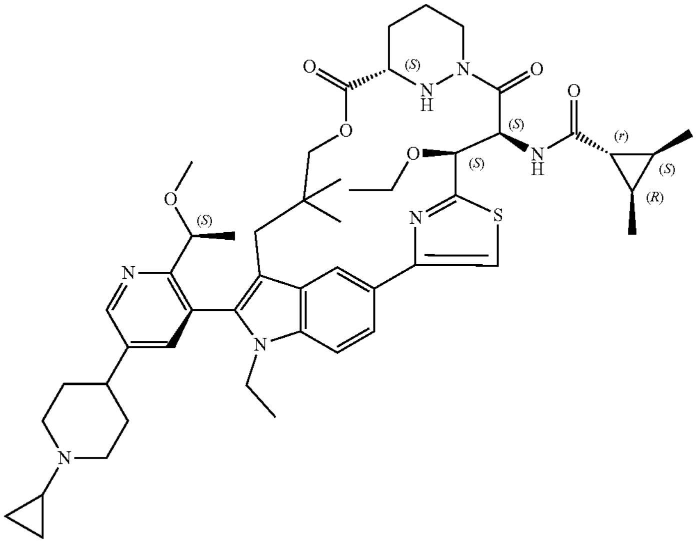 |
| A462 | 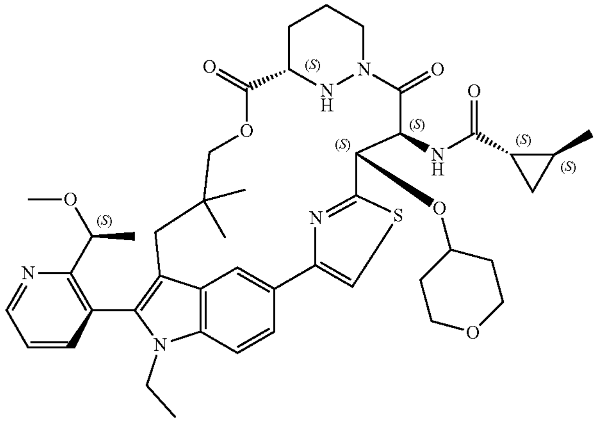 |

TABLE 1b-continued
| Certain Compounds of the Present Invention | |
|---|---|
| Ex. # | Structure |
| A463 | 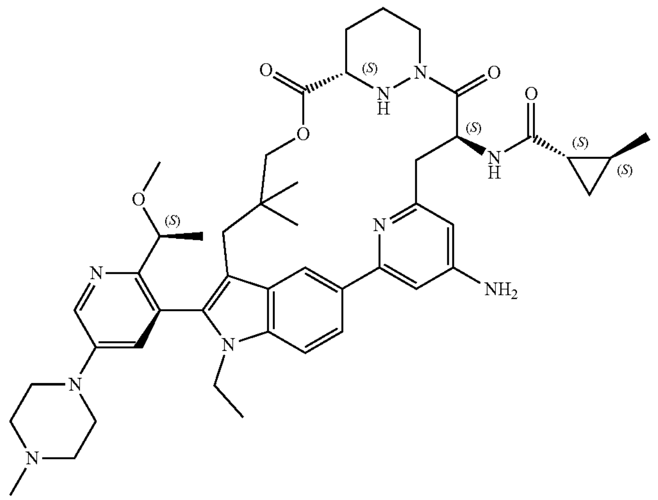 |
| A464 | 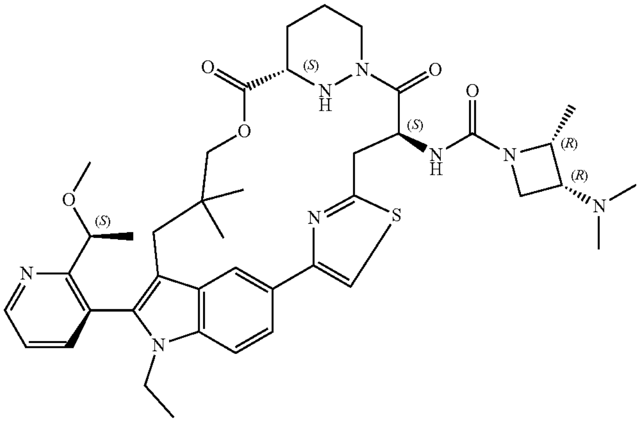 |
| A465 | 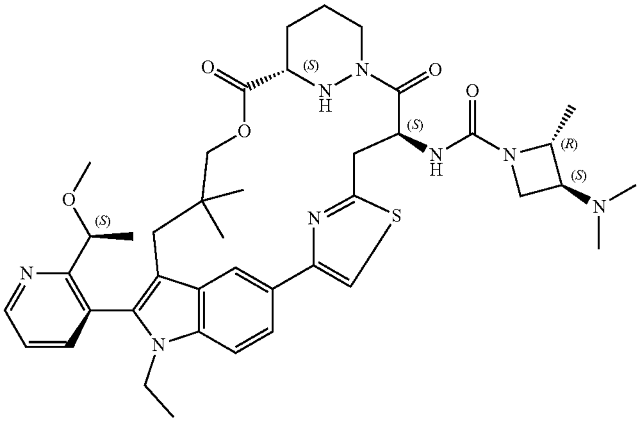 |

TABLE 1b-continued
| Certain Compounds of the Present Invention | |
| --- | --- |
| Ex. # | Structure |
| A466 | 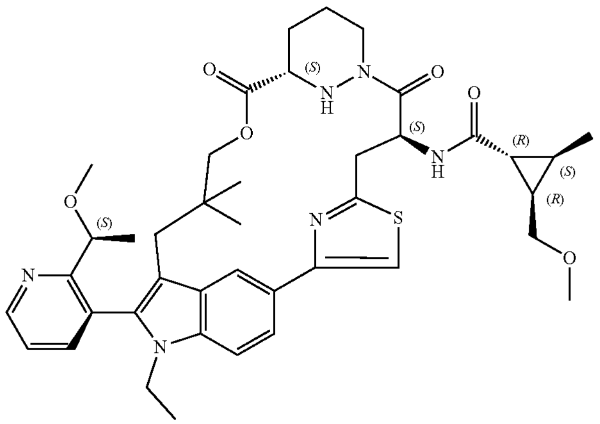 |
| A467 | 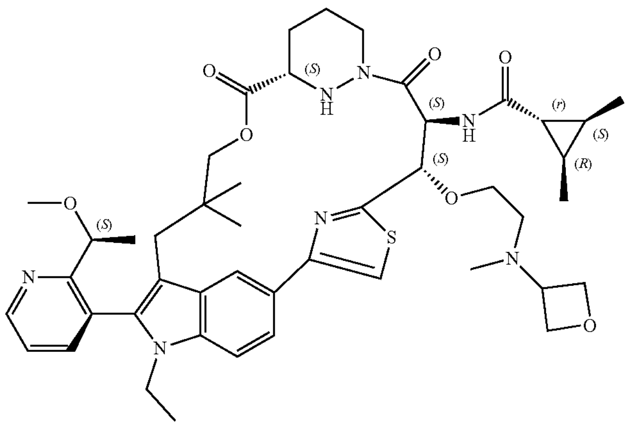 |
| A468 | 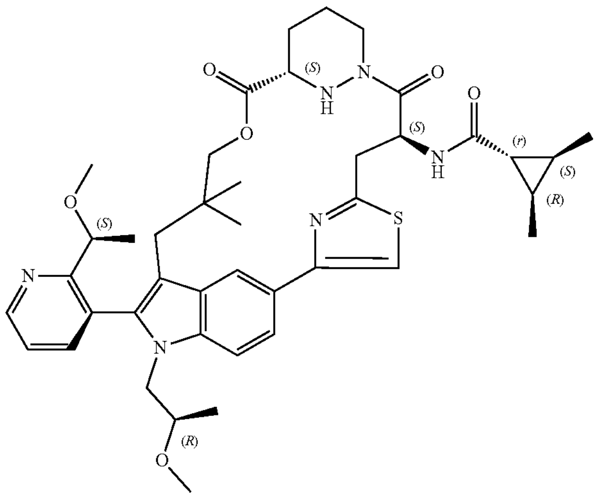 |

TABLE 1b-continued
| Certain Compounds of the Present Invention | |
|---|---|
| Ex. # | Structure |
| A469 | 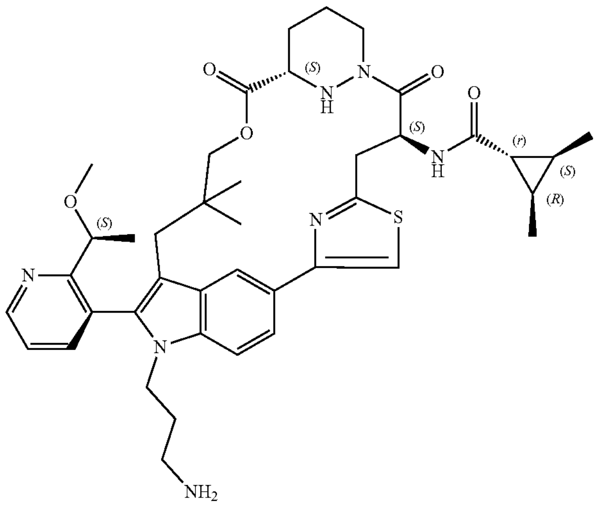 |
| A470 | 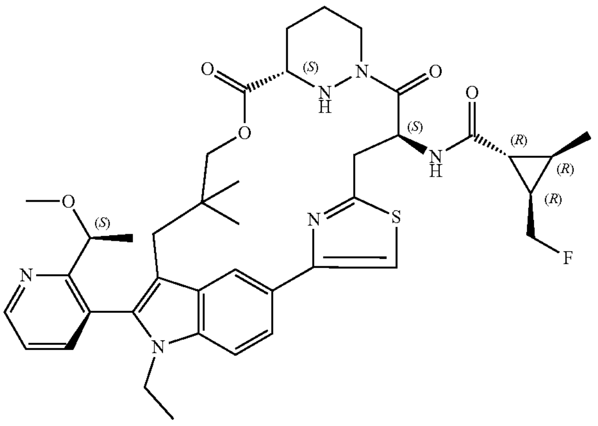 |
| A471 | 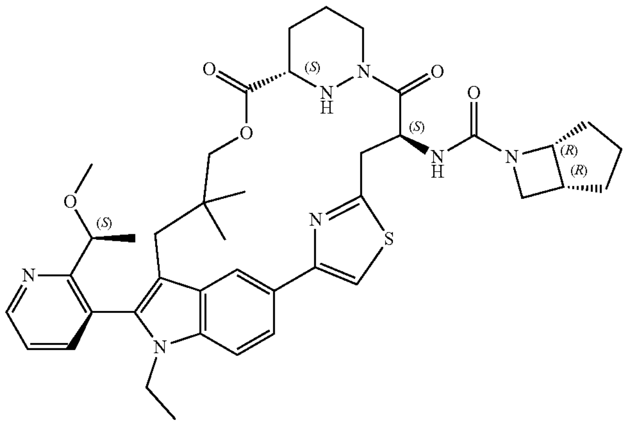 |

TABLE 1b-continued
| Certain Compounds of the Present Invention | |
|---|---|
| Ex. # | Structure |
| A472 | 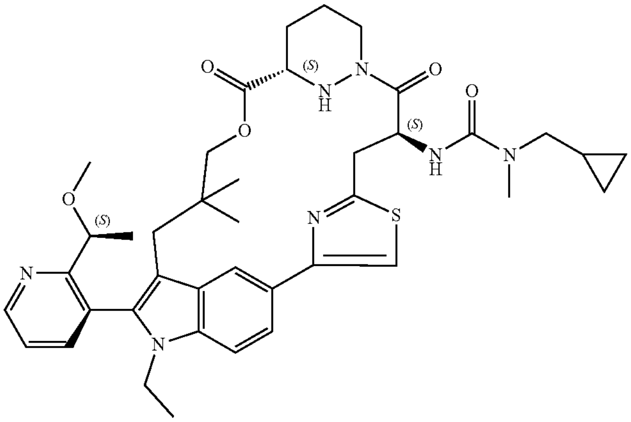 |
| A473 | 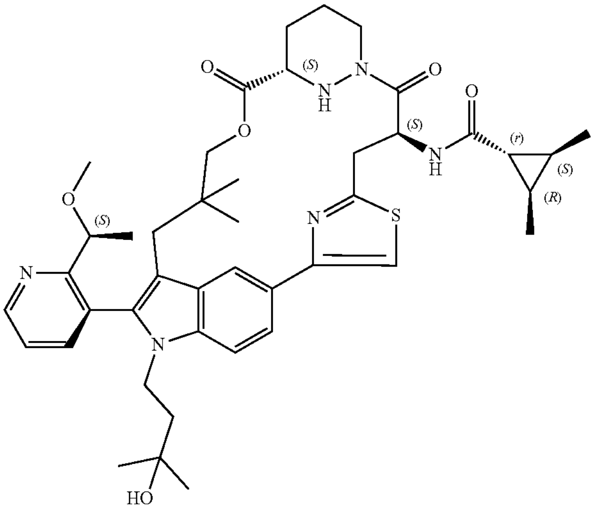 |
| A474 | 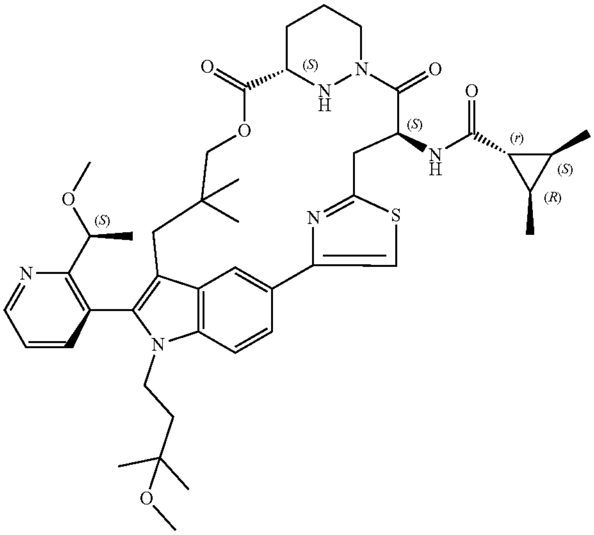 |

TABLE 1b-continued
| Certain Compounds of the Present Invention | |
|---|---|
| Ex. # | Structure |
| A475 | 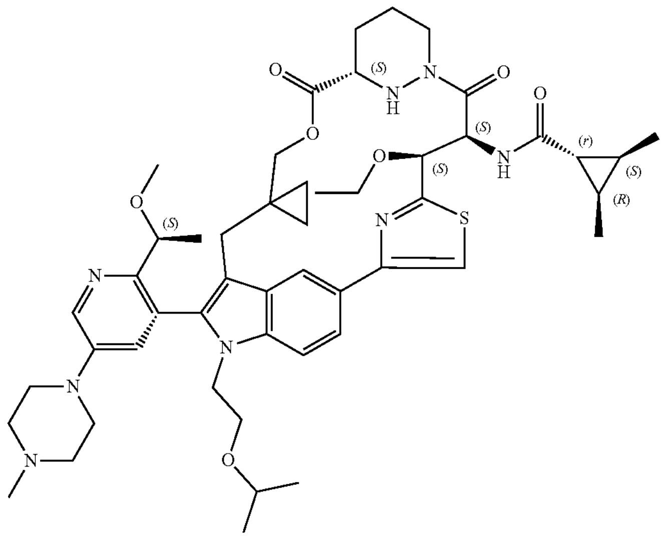 |
| A476 | 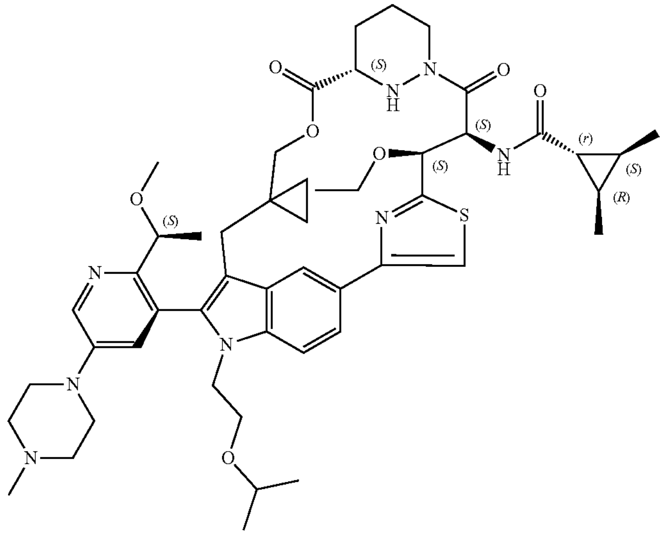 |
| A477 | 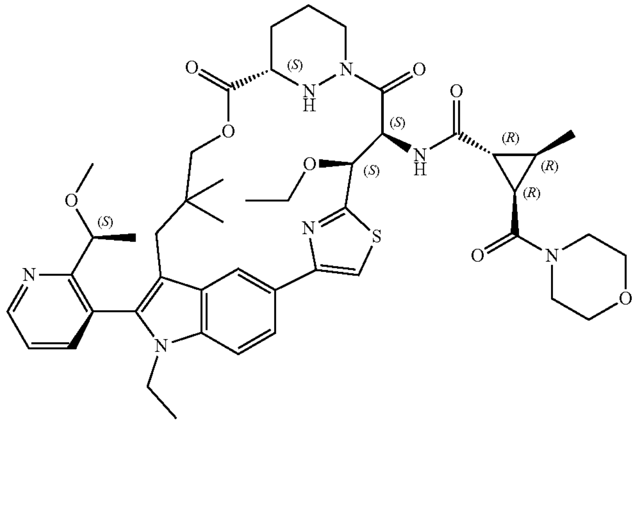 |

TABLE 1b-continued
| Certain Compounds of the Present Invention | |
|---|---|
| Ex. # | Structure |
| A478 | 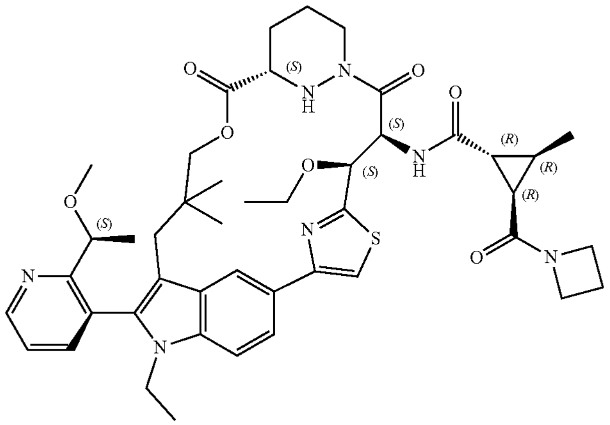 |
| A479 | 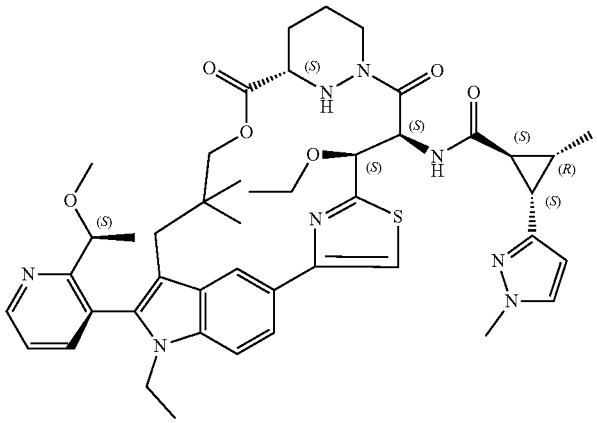 |
| A480 | 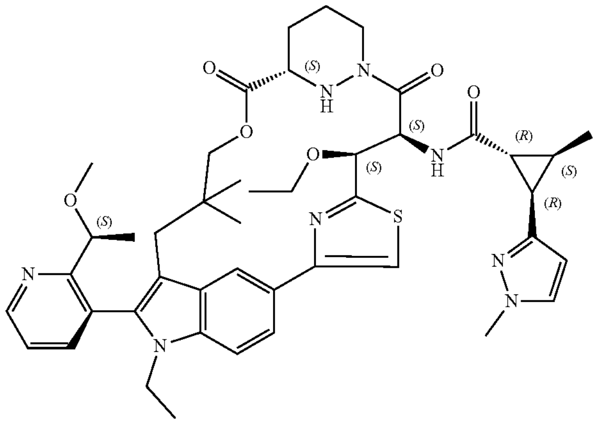 |

TABLE 1b-continued
| Certain Compounds of the Present Invention | |
|---|---|
| Ex. # | Structure |
| A481 | 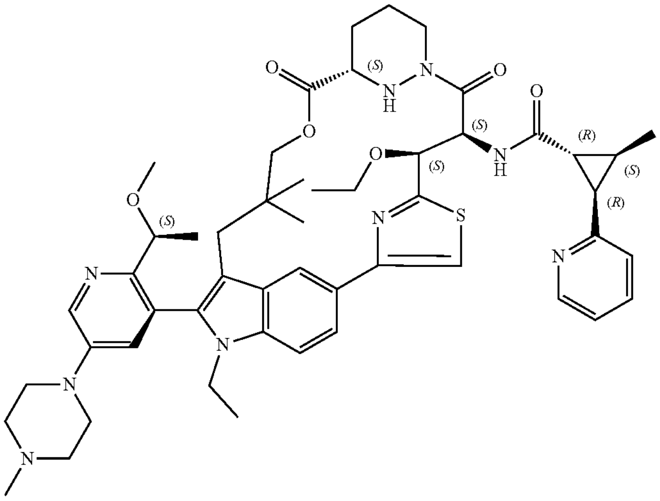 |
| A482 | 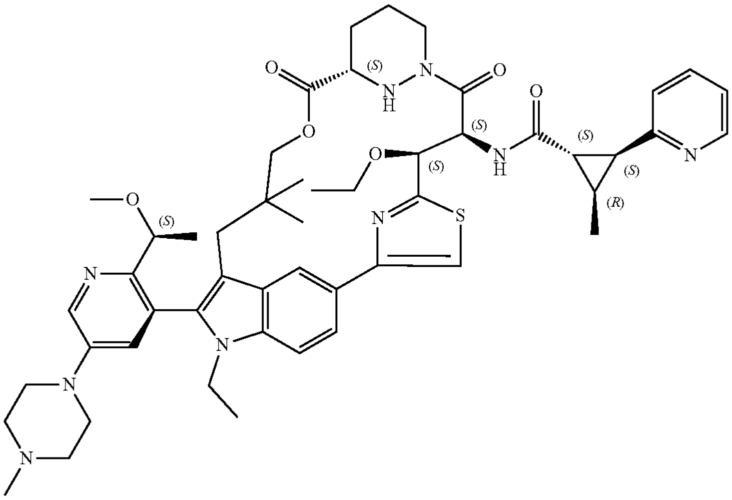 |
| A483 | 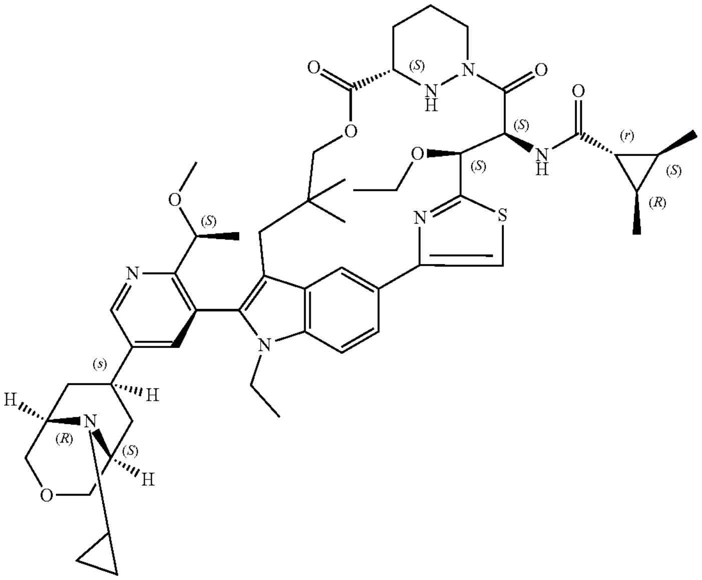 |

TABLE 1b-continued
| Certain Compounds of the Present Invention | |
|---|---|
| Ex. # | Structure |
| A484 | 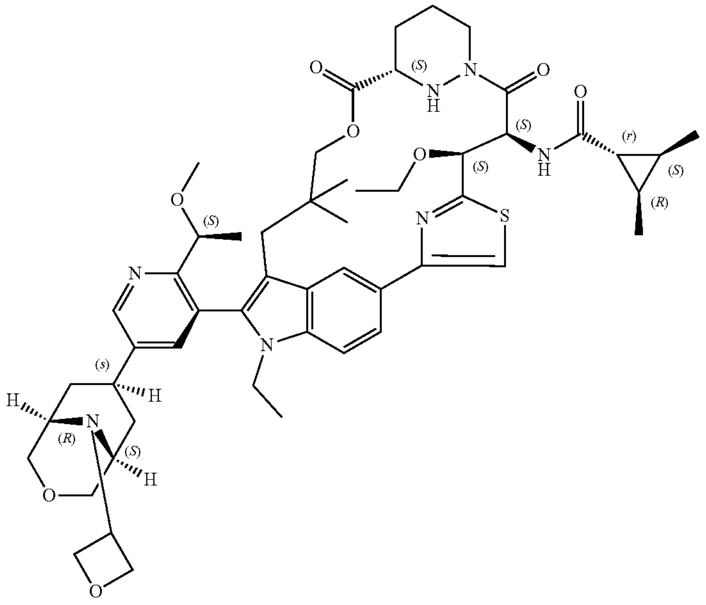 |
| A485 | 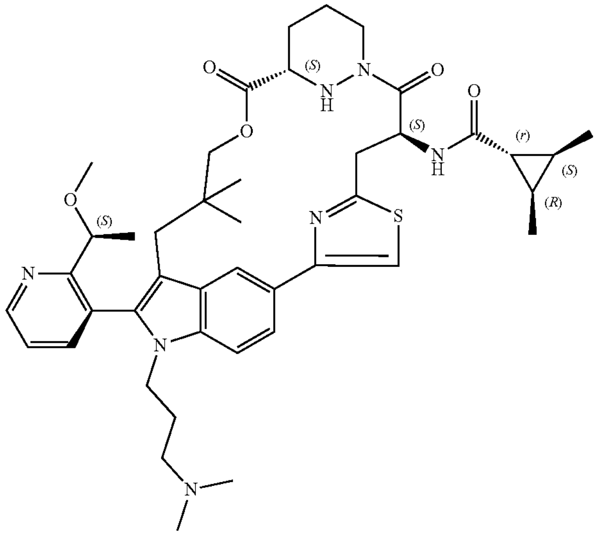 |

TABLE 1b-continued
| Certain Compounds of the Present Invention | |
|---|---|
| Ex. # | Structure |
| A486 | 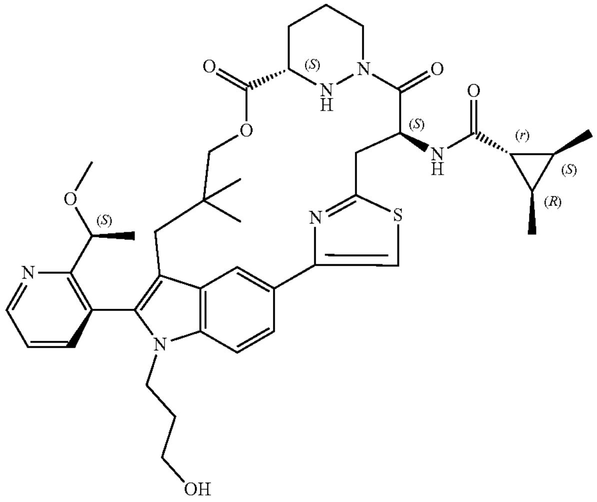 |
| A487 | 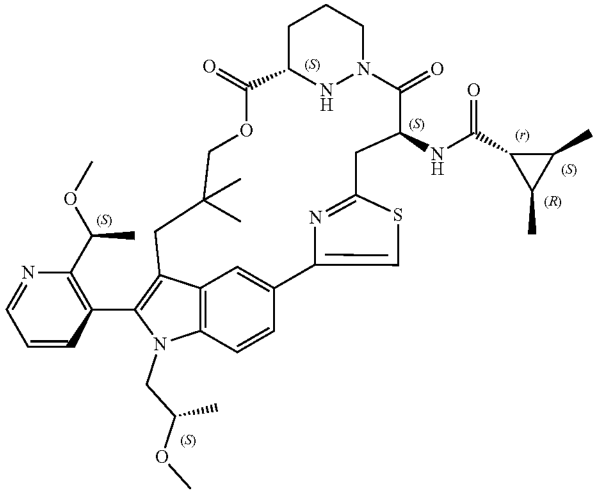 |
| A488 | 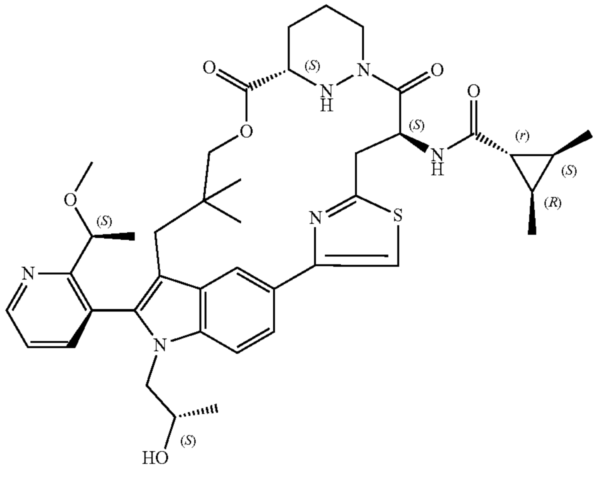 |

TABLE 1b-continued
| Certain Compounds of the Present Invention | |
|---|---|
| Ex. # | Structure |
| A489 | 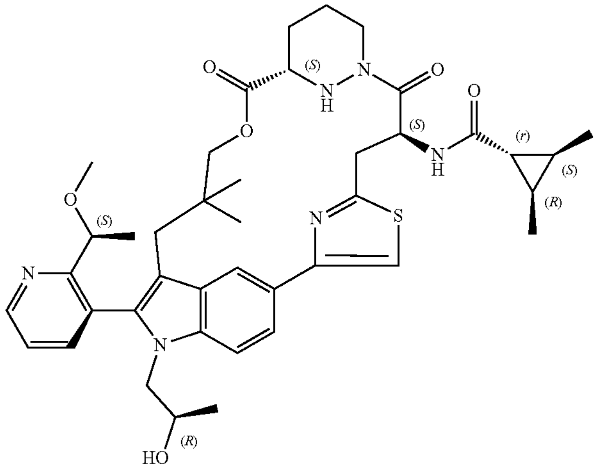 |
| A490 | 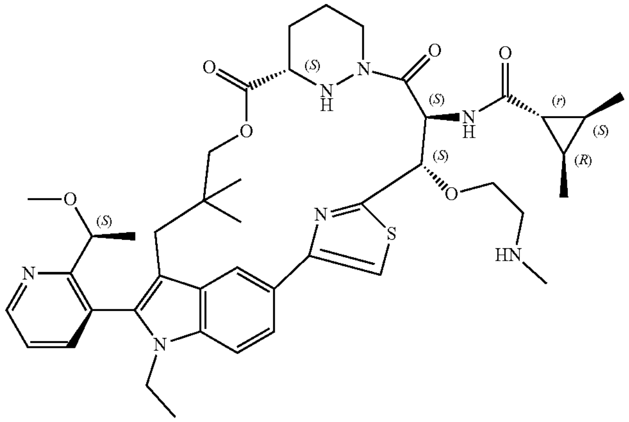 |
| A491 | 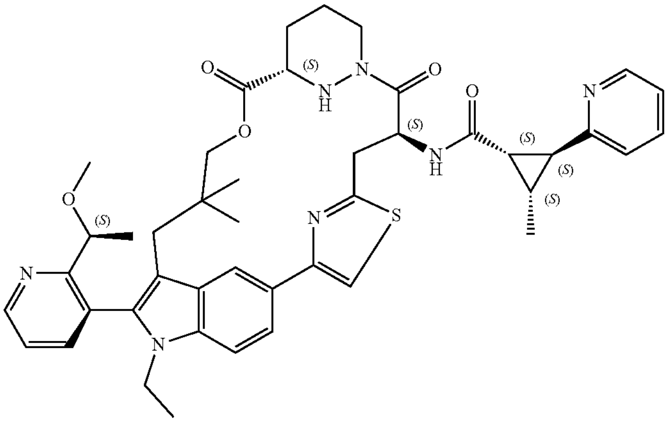 |

TABLE 1b-continued
| Certain Compounds of the Present Invention | |
|---|---|
| Ex. # | Structure |
| A492 | 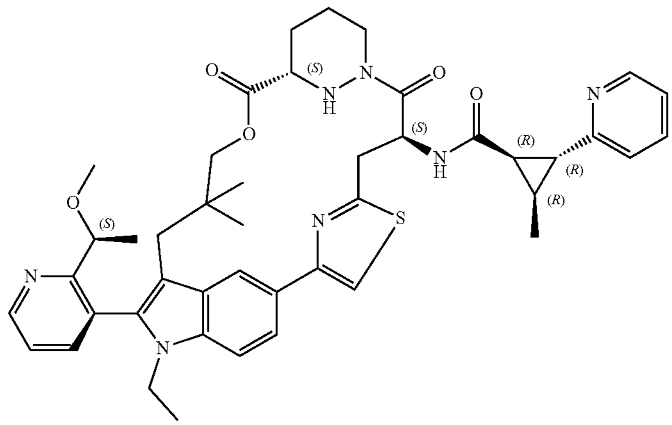 |
| A493 | 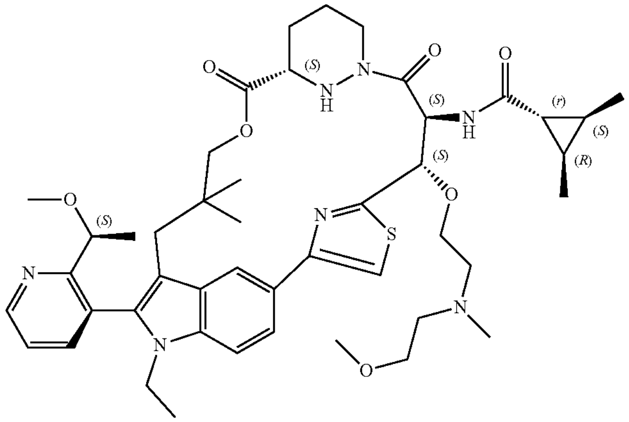 |
| A494 | 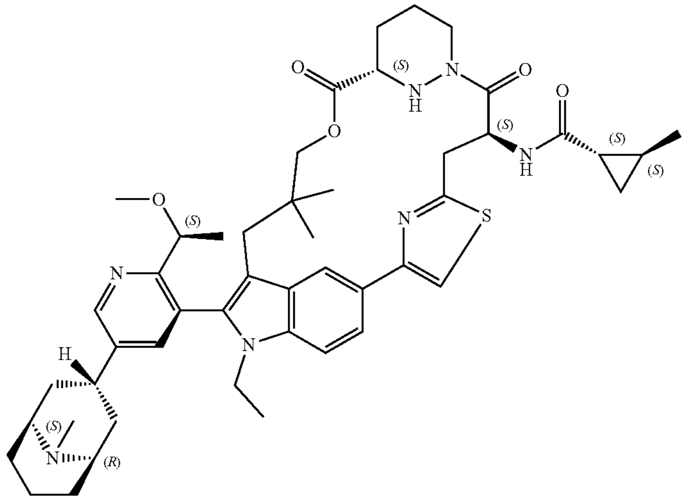 |

TABLE 1b-continued
| Certain Compounds of the Present Invention | |
|---|---|
| Ex. # | Structure |
| A495 | 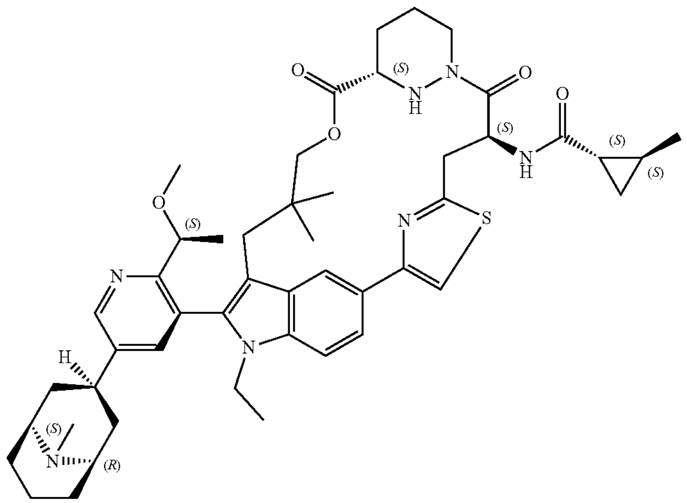 |
| A496 | 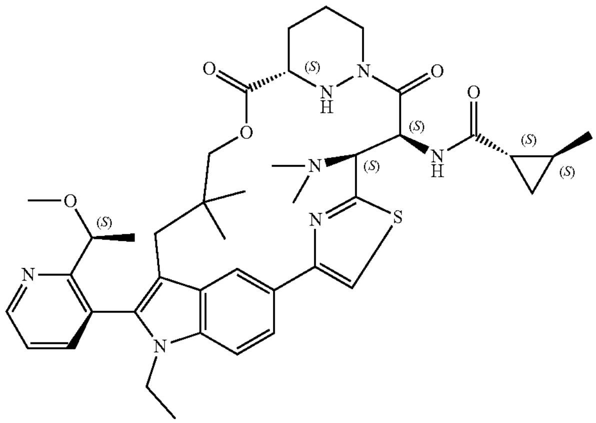 |
| A497 | 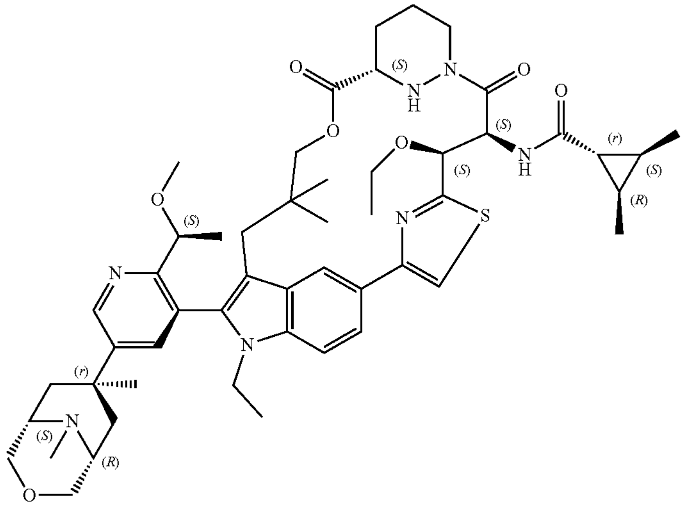 |

TABLE 1b-continued
| Certain Compounds of the Present Invention | |
|---|---|
| Ex. # | Structure |
| A498 | 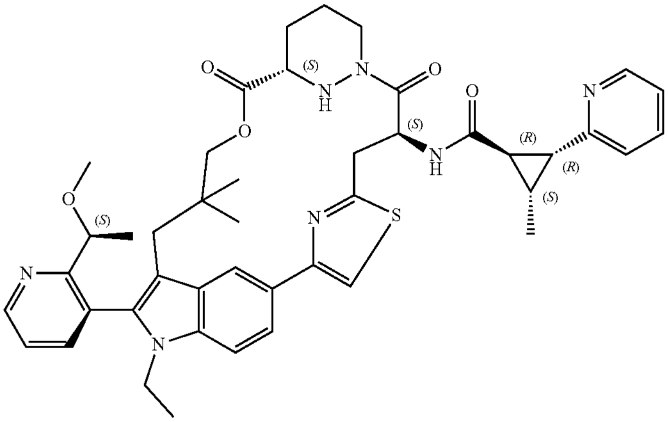 |
| A499 | 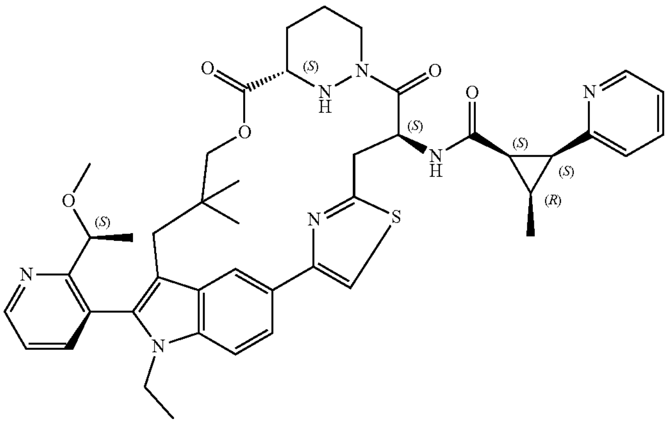 |
| A500 | 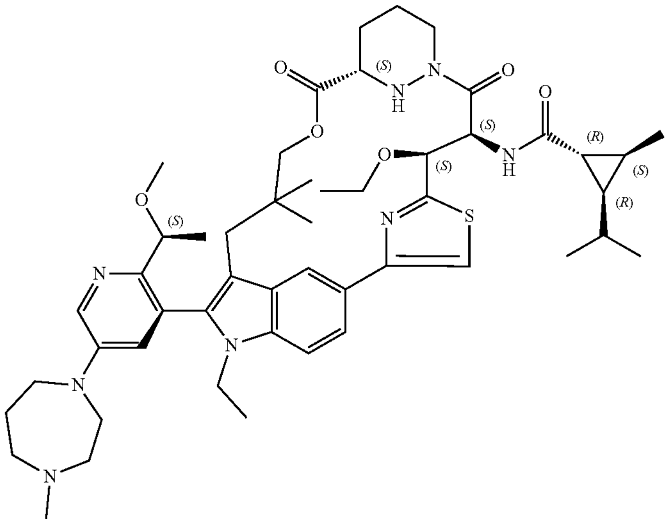 |

TABLE 1b-continued
| Certain Compounds of the Present Invention | |
|---|---|
| Ex. # | Structure |
| A501 | 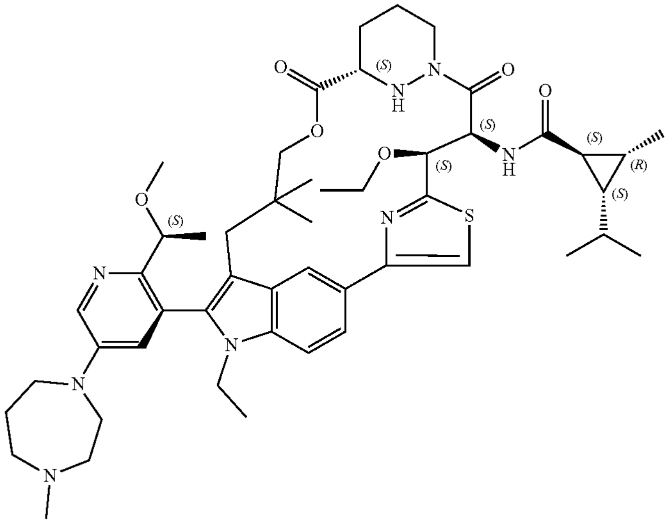 |
| A502 | 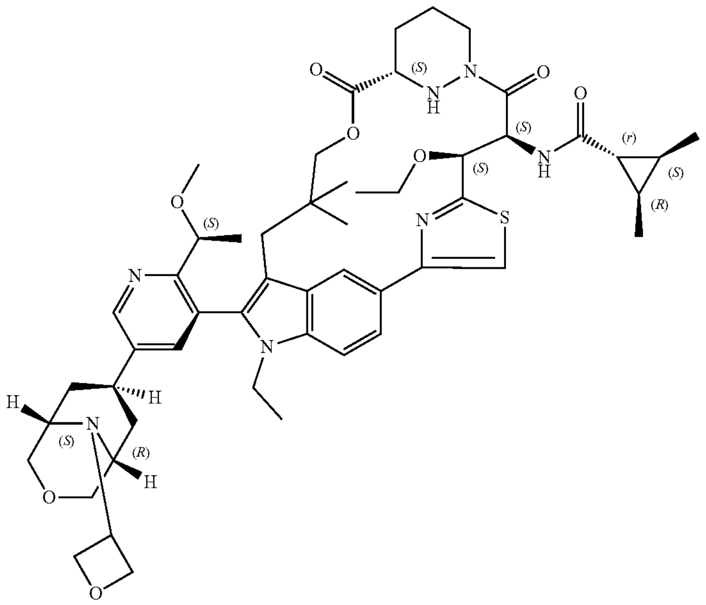 |

TABLE 1b-continued
| Certain Compounds of the Present Invention | |
|---|---|
| Ex. # | Structure |
| A503 | 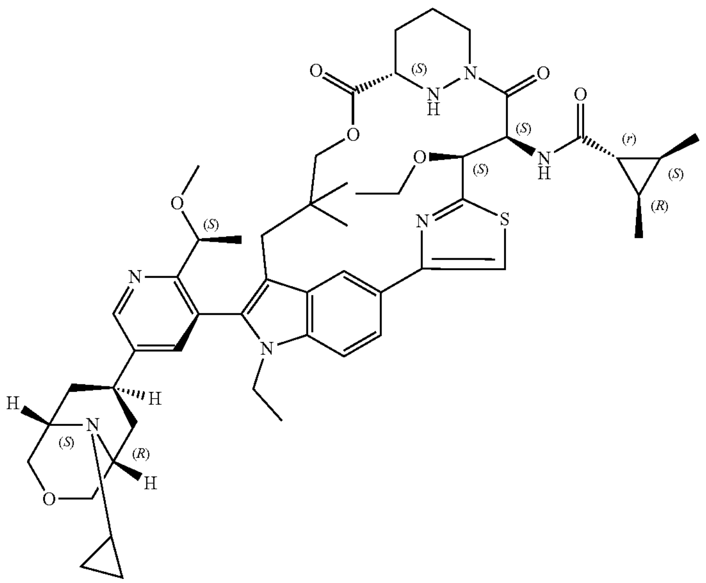 |
| A504 | 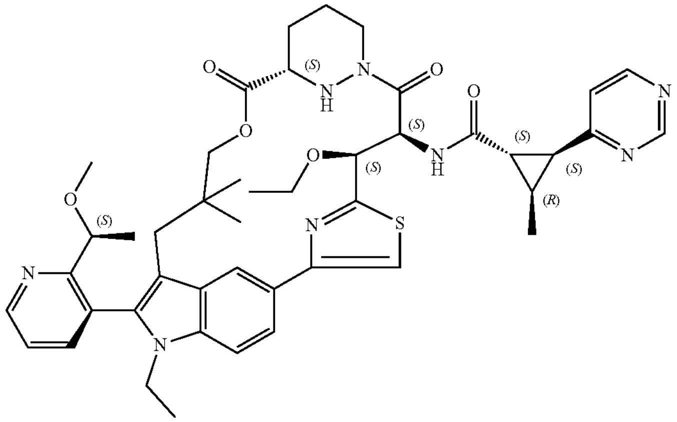 |
| A505 | 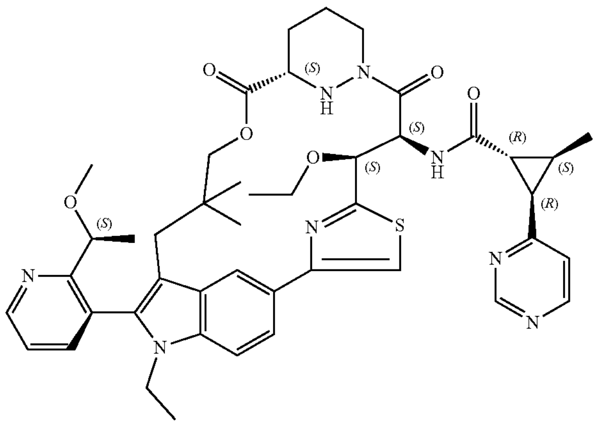 |

TABLE 1b-continued
| Certain Compounds of the Present Invention | |
|---|---|
| Ex. # | Structure |
| A506 | 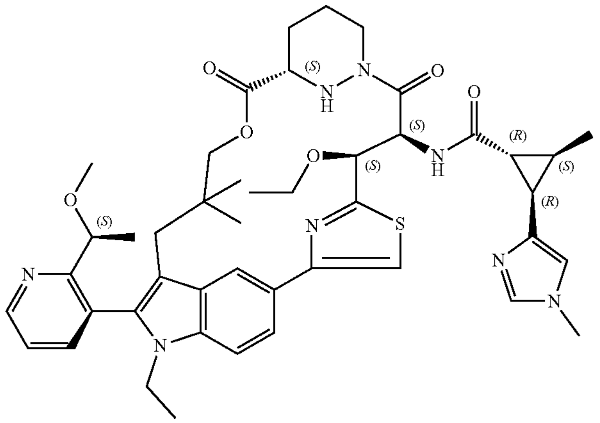 |
| A507 | 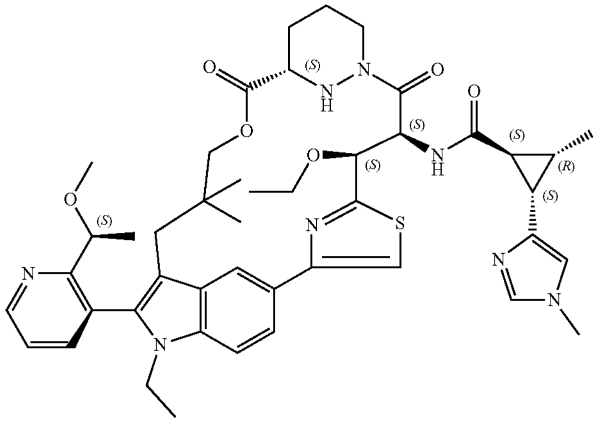 |
| A508 | 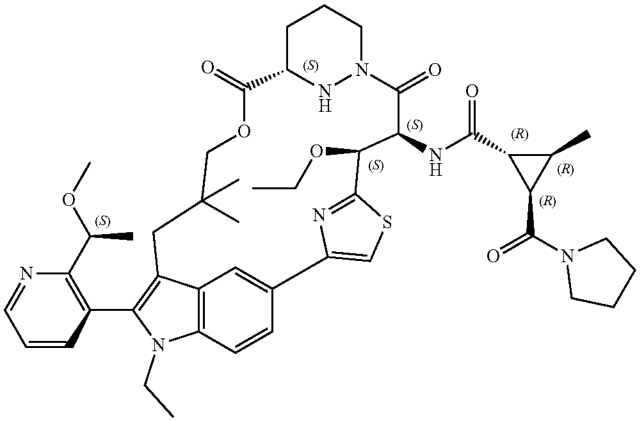 |

TABLE 1b-continued
| Certain Compounds of the Present Invention | |
|---|---|
| Ex. # | Structure |
| A509 | 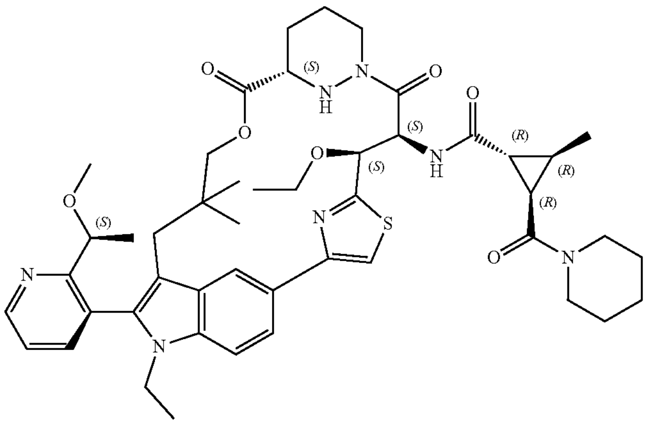 |
| A510 | 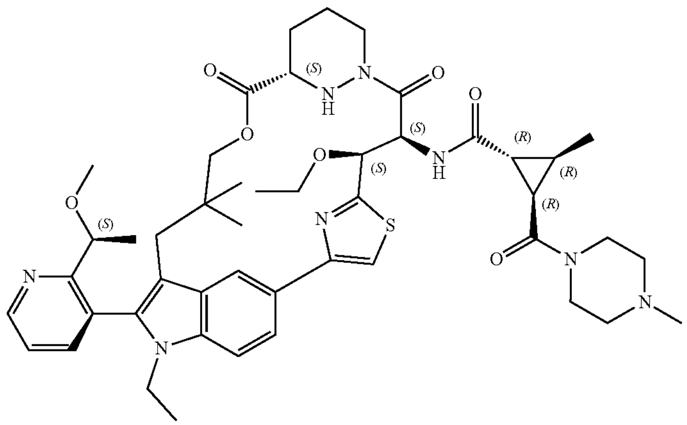 |
| A511 | 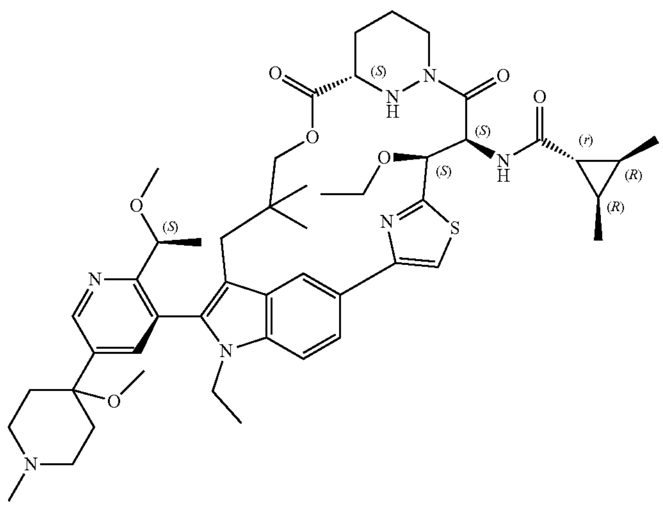 |

TABLE 1b-continued
| Certain Compounds of the Present Invention | |
|---|---|
| Ex. # | Structure |
| A512 | 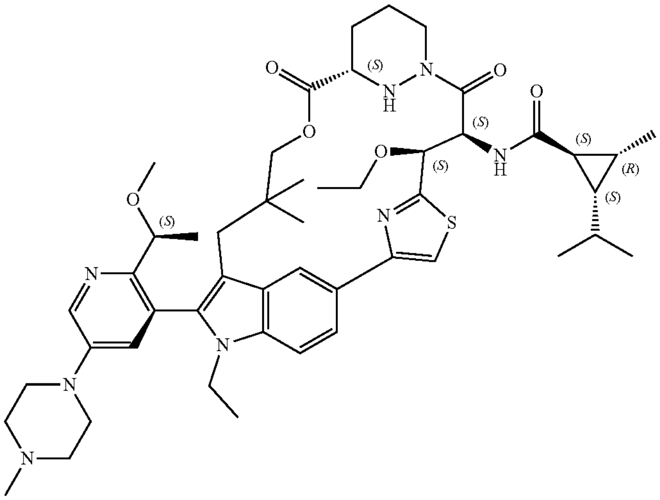 |
| A513 | 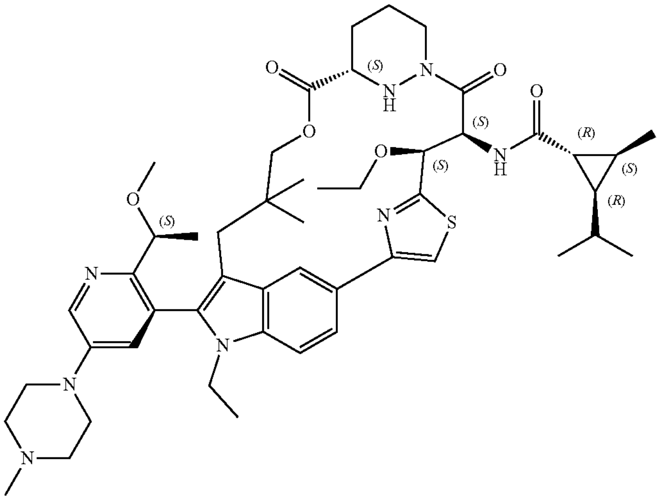 |
| A514 | 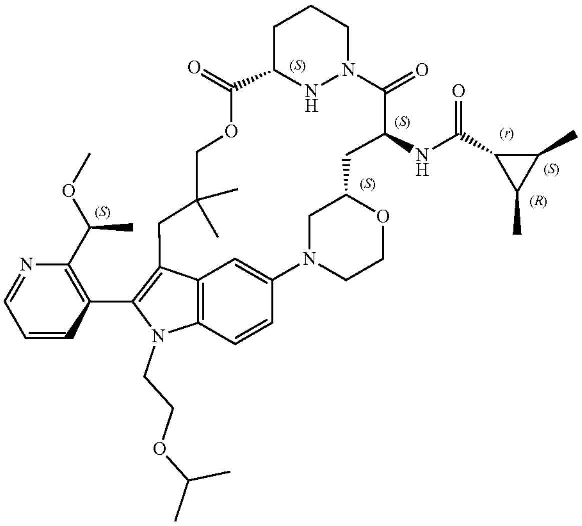 |

TABLE 1b-continued
| Certain Compounds of the Present Invention | |
|---|---|
| Ex. # | Structure |
| A515 | 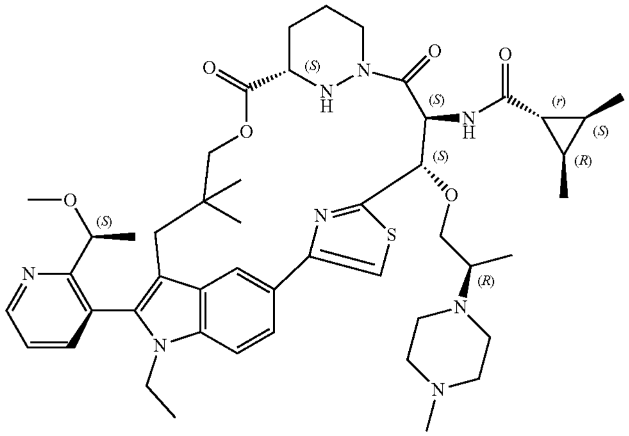 |
| A516 | 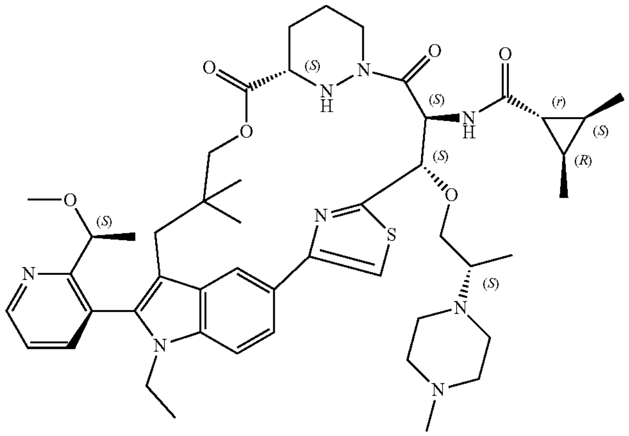 |
| A517 | 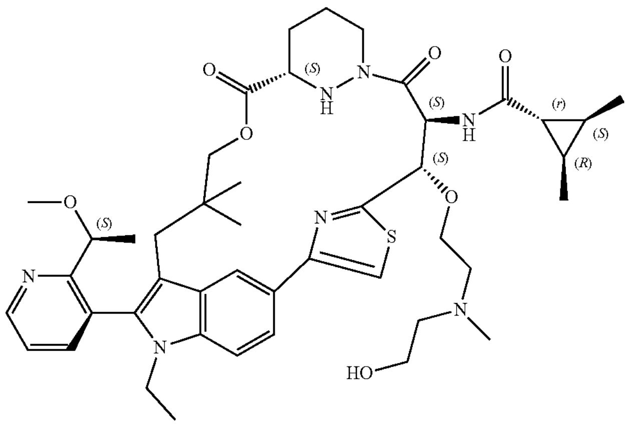 |

TABLE 1b-continued
Certain Compounds of the Present Invention
| Ex. # | Structure |
| --- | --- |
| A518 | 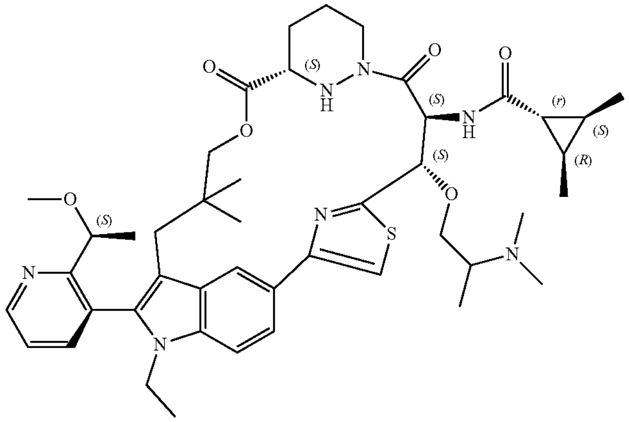 |
| A519 | 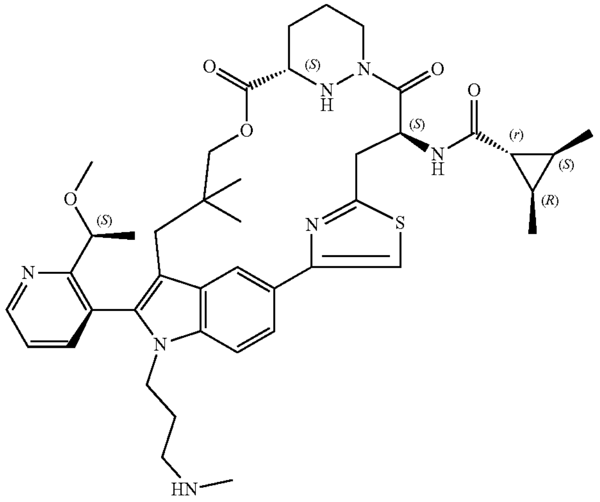 |
| A520 | 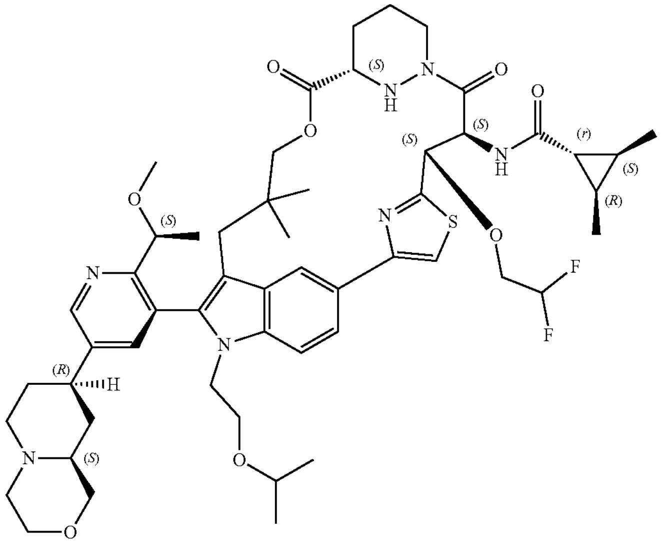 |

TABLE 1b-continued
| Certain Compounds of the Present Invention | |
|---|---|
| Ex. # | Structure |
| A521 | 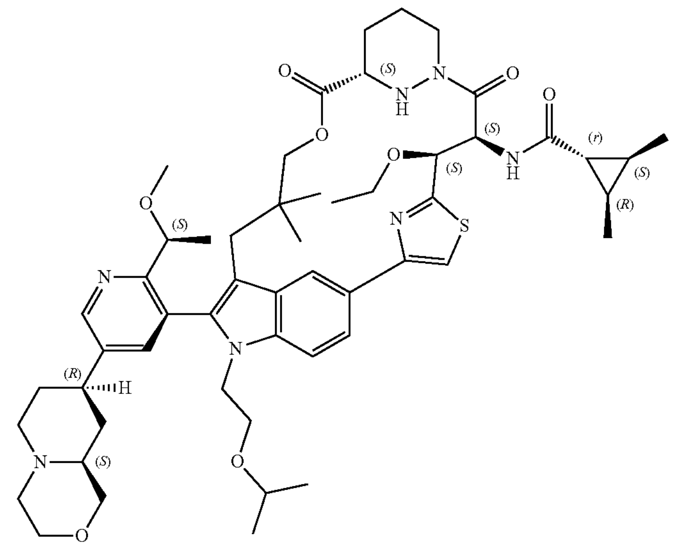 |
| A522 | 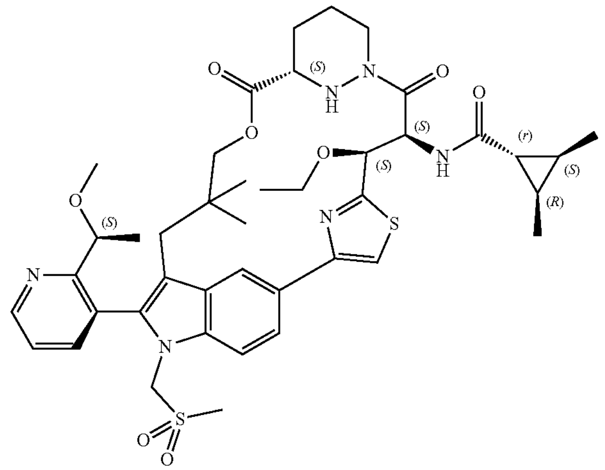 |
| A523 | 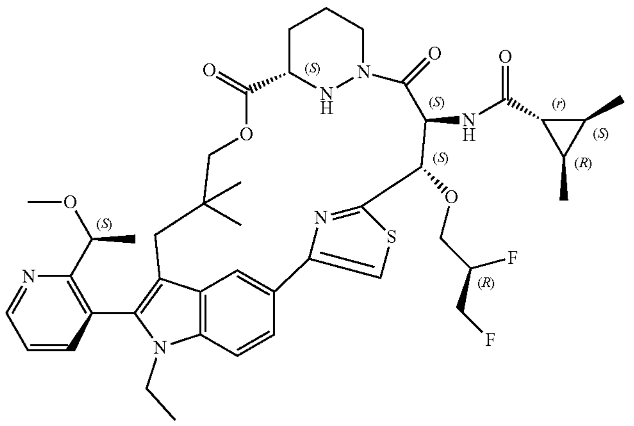 |

TABLE 1b-continued
| Certain Compounds of the Present Invention | |
|---|---|
| Ex. # | Structure |
| A524 | 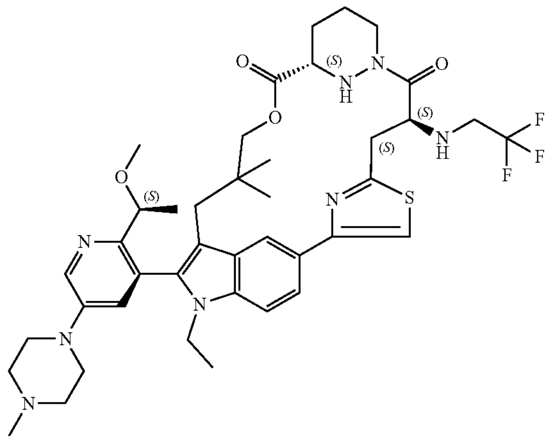 |
| A525 | 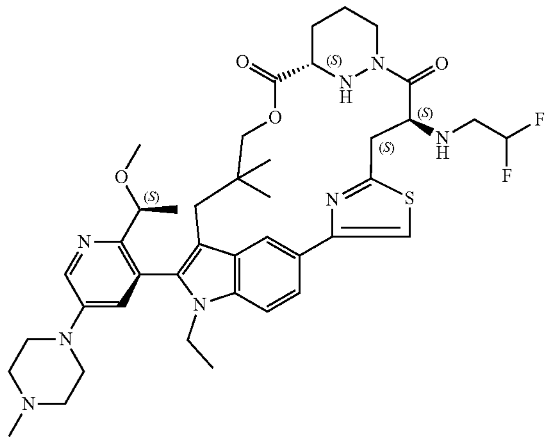 |
| A526 | 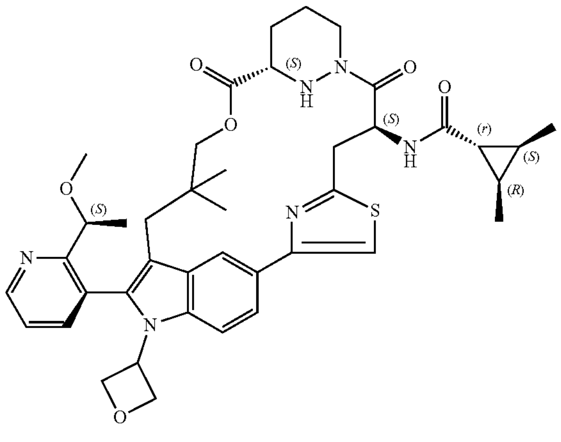 |

TABLE 1b-continued
| Certain Compounds of the Present Invention | |
|---|---|
| Ex. # | Structure |
| A527 | 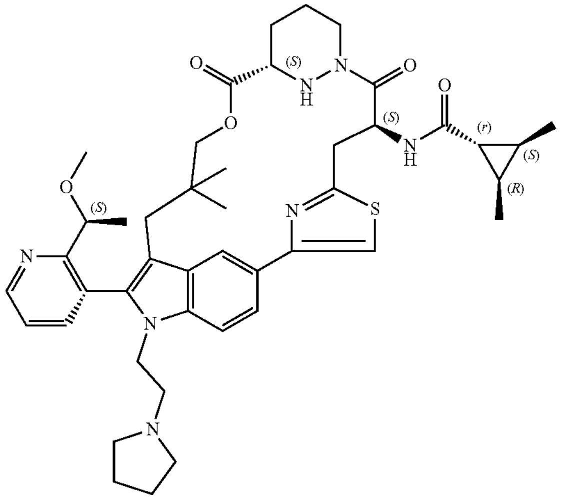 |
| A528 | 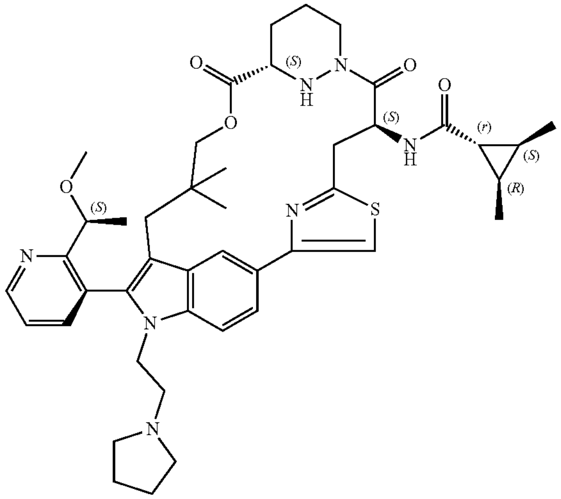 |
| A529 | 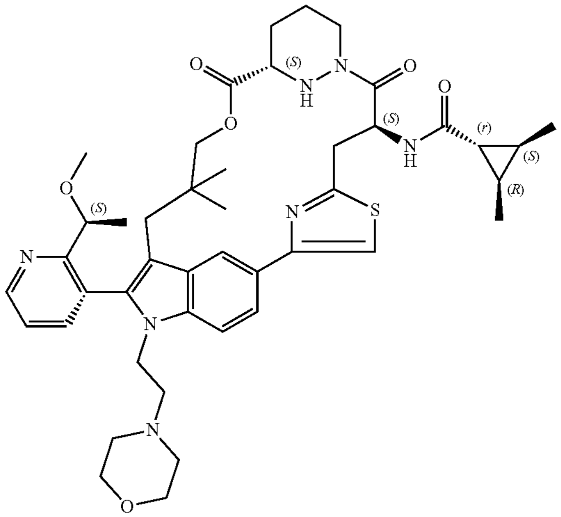 |

TABLE 1b-continued
| Certain Compounds of the Present Invention | |
|---|---|
| Ex. # | Structure |
| A530 | 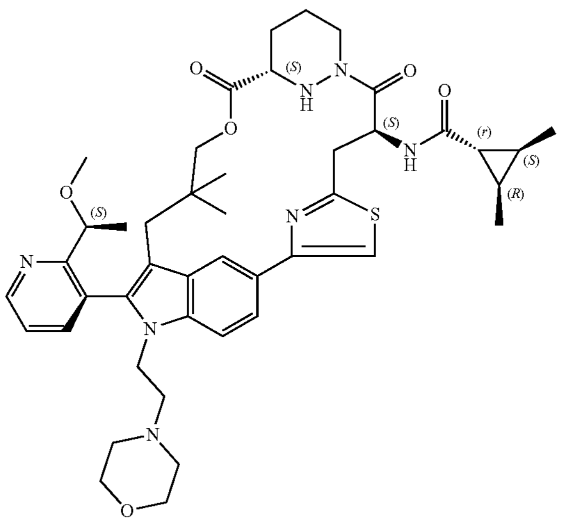 |
| A531 | 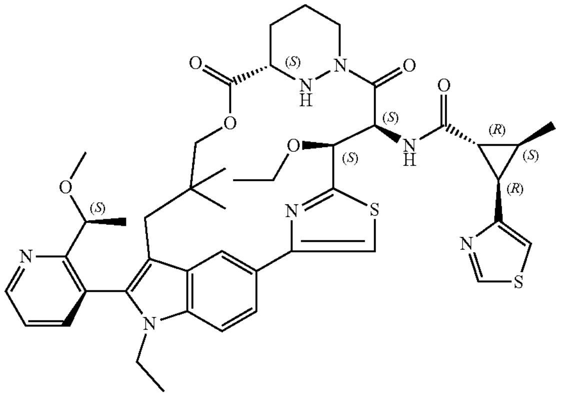 |
| A532 | 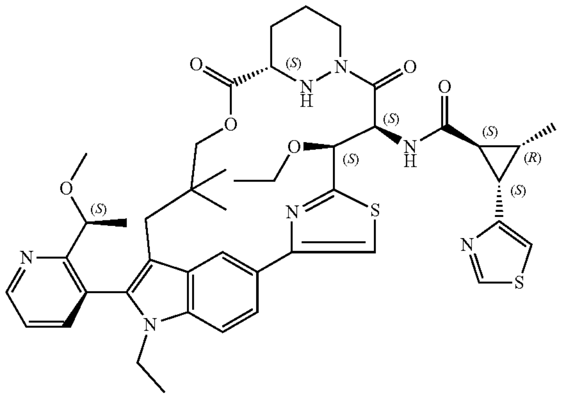 |

TABLE 1b-continued
| Certain Compounds of the Present Invention | |
|---|---|
| Ex. # | Structure |
| A533 | 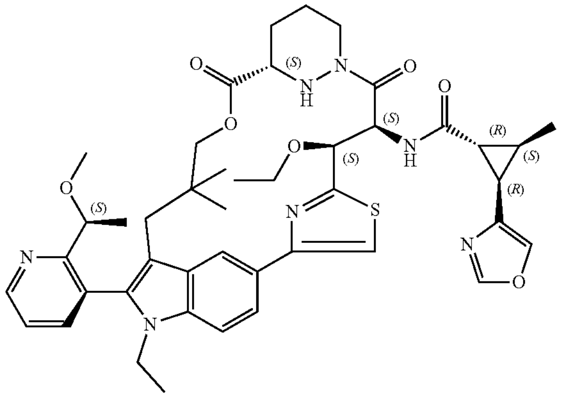 |
| A534 | 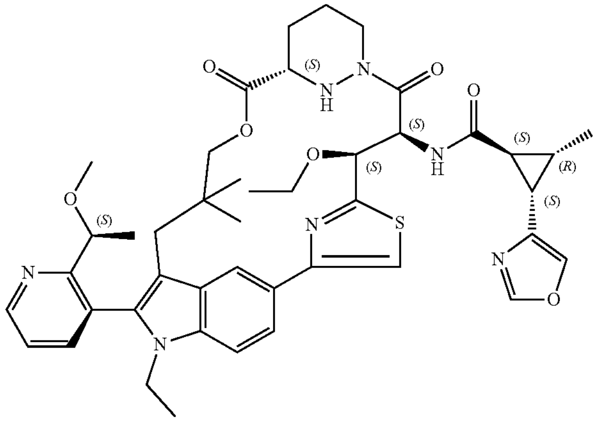 |
| A535 | 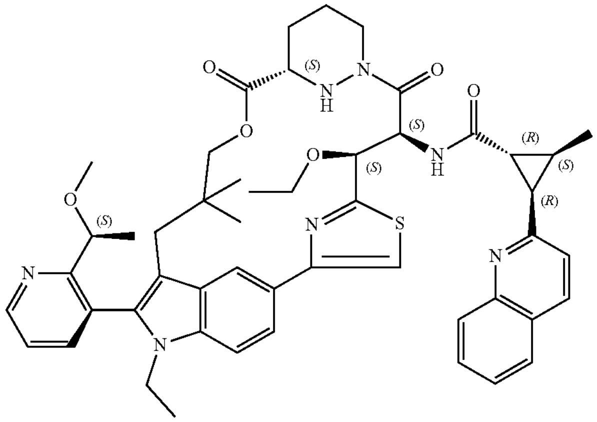 |

TABLE 1b-continued
| Certain Compounds of the Present Invention | |
|---|---|
| Ex. # | Structure |
| A536 | 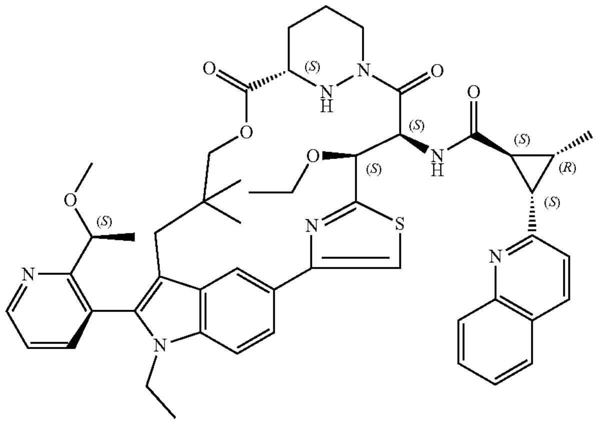 |
| A537 | 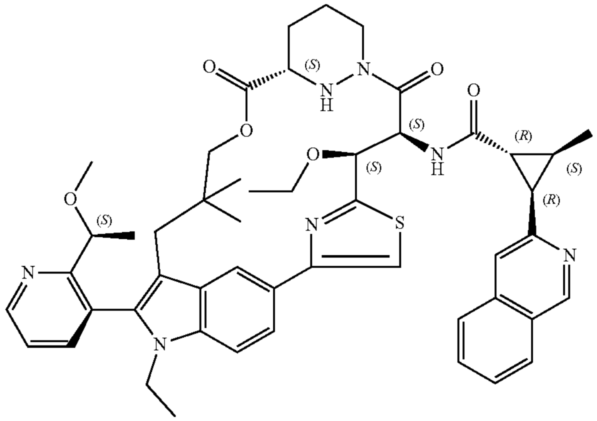 |
| A538 | 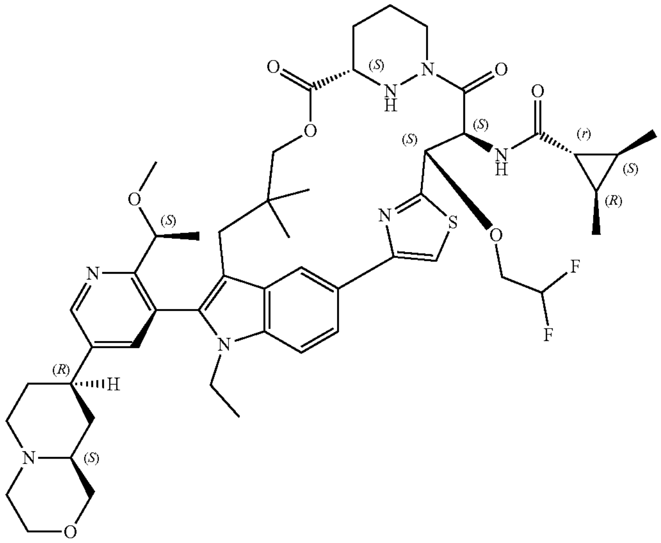 |

TABLE 1b-continued
| Certain Compounds of the Present Invention | |
|---|---|
| Ex. # | Structure |
| A539 | 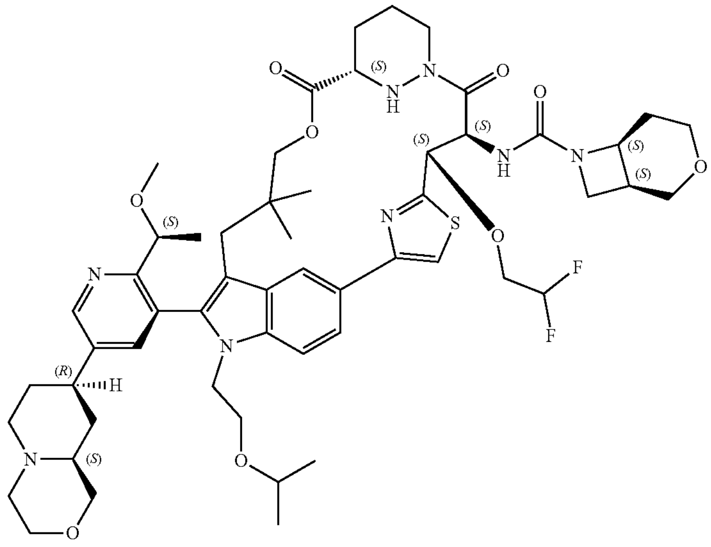 |
| A540 | 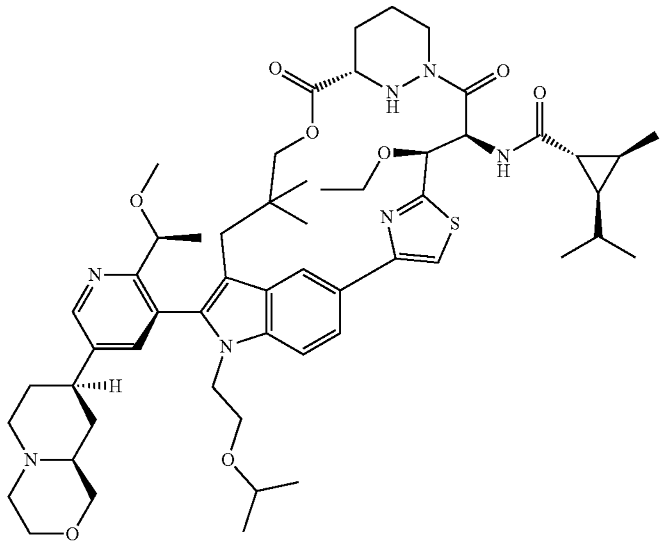 |

TABLE 1b-continued
| Certain Compounds of the Present Invention | |
|---|---|
| Ex. # | Structure |
| A541 | 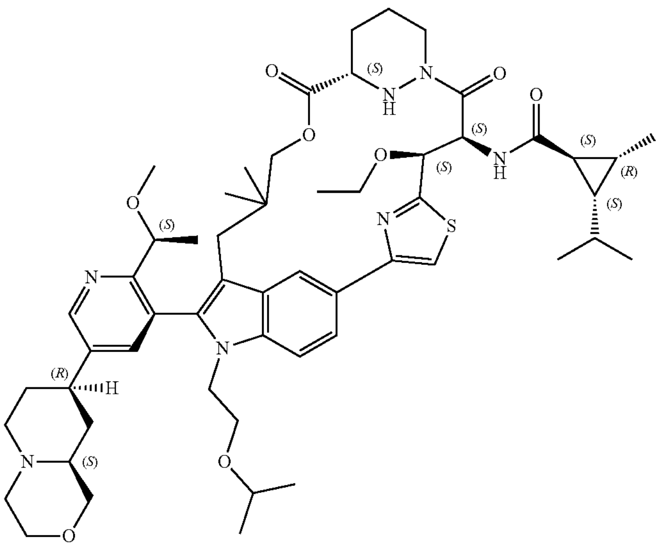 |
| A542 | 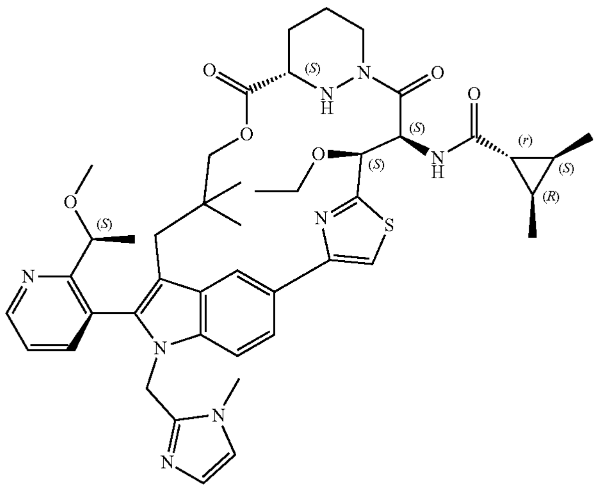 |
| A543 | 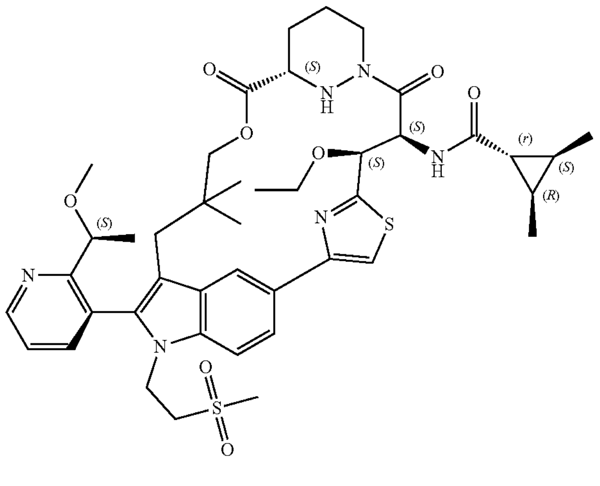 |

TABLE 1b-continued
| Certain Compounds of the Present Invention | |
|---|---|
| Ex. # | Structure |
| A544 | 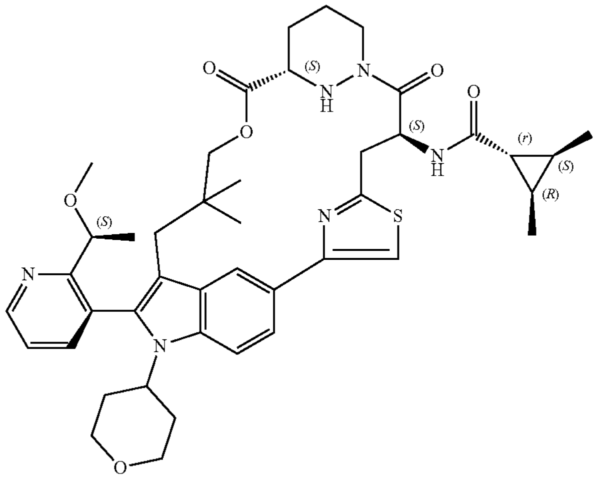 |
| A545 | 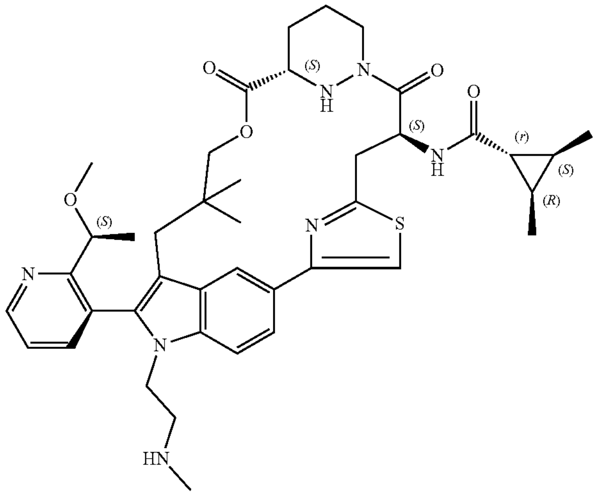 |
| A546 | 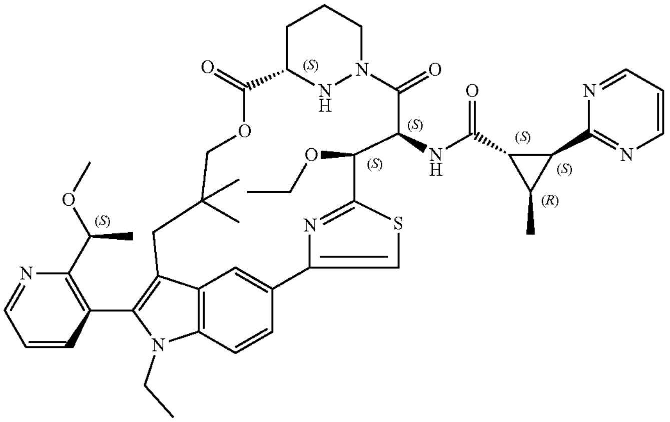 |

TABLE 1b-continued
| Certain Compounds of the Present Invention | |
|---|---|
| Ex. # | Structure |
| A547 | 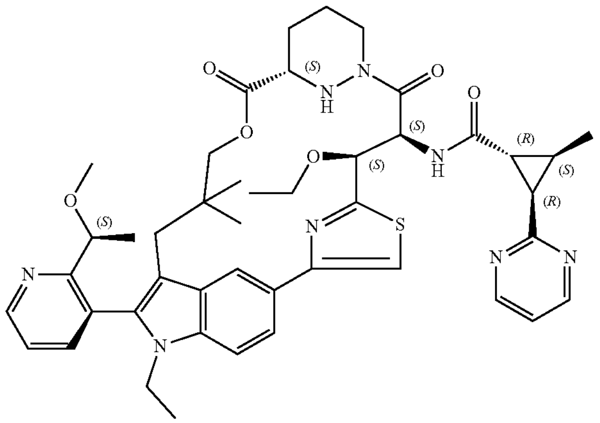 |
| A548 | 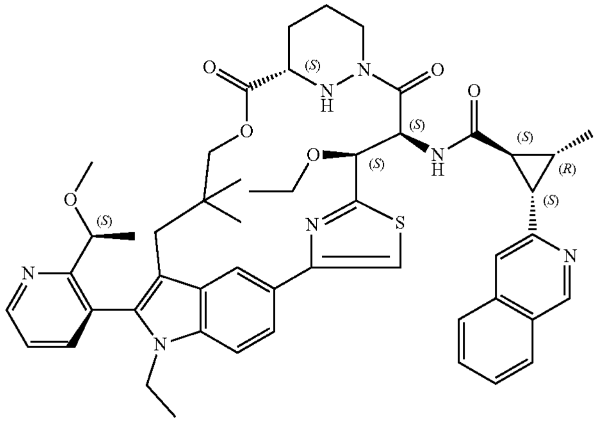 |
| A549 | 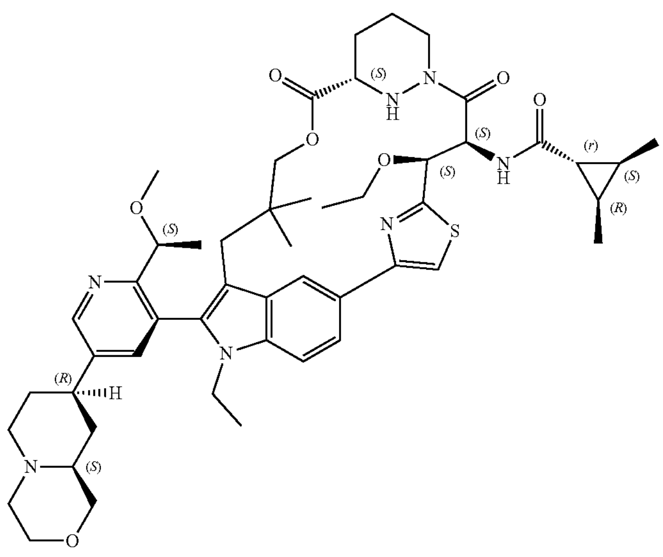 |

TABLE 1b-continued
| Certain Compounds of the Present Invention | |
|---|---|
| Ex. # | Structure |
| A550 | 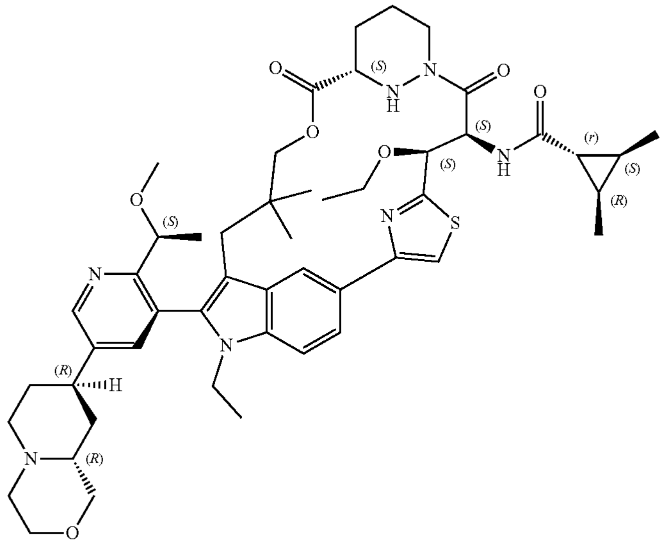 |
| A551 | 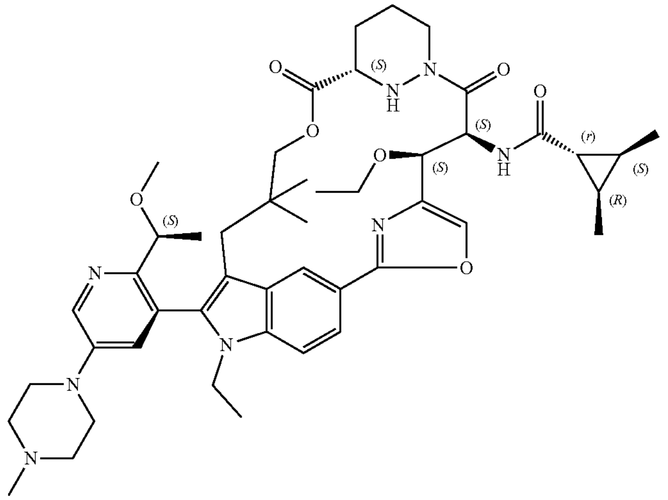 |
| A552 | 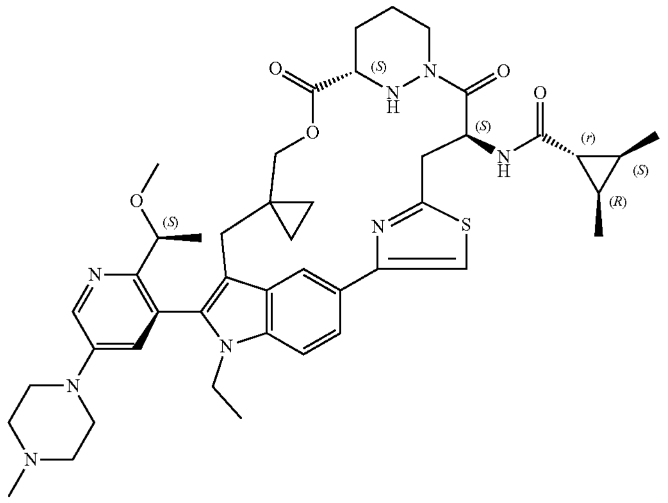 |

TABLE 1b-continued
| Certain Compounds of the Present Invention | |
|---|---|
| Ex. # | Structure |
| A553 | 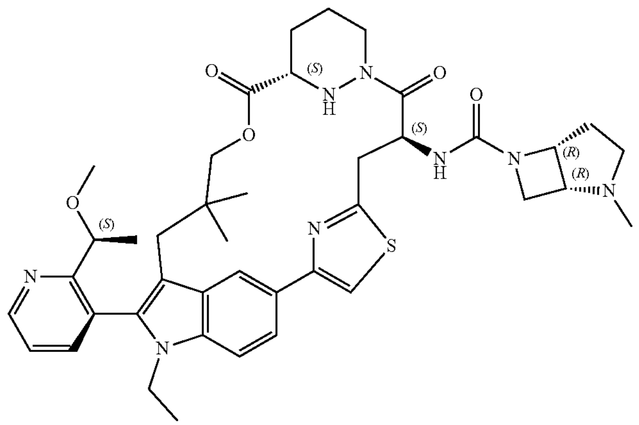 |
| A554 | 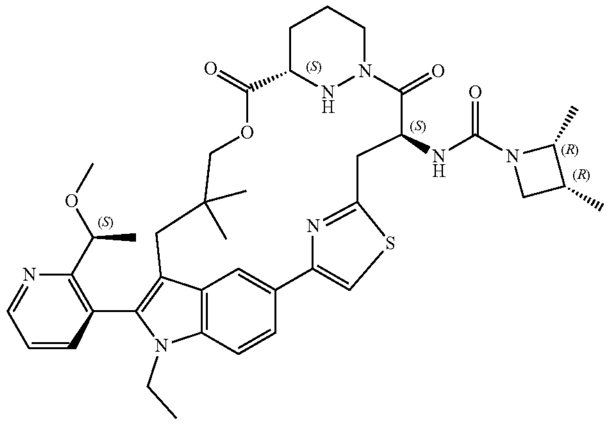 |
| A555 | 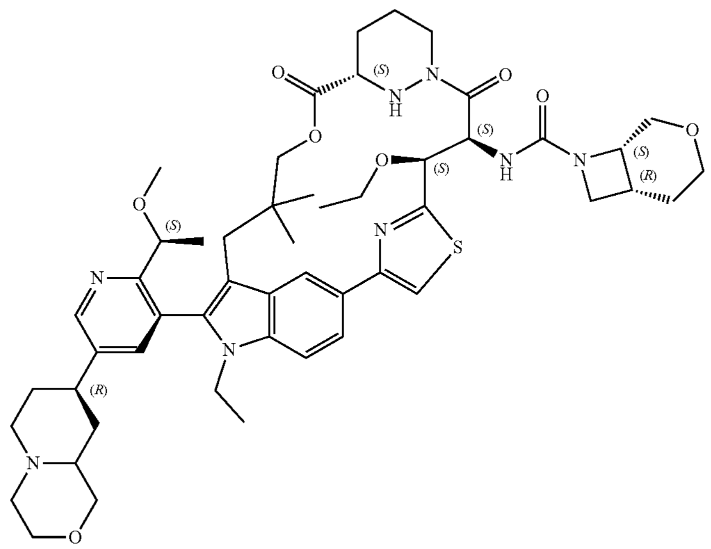 |

TABLE 1b-continued
| Certain Compounds of the Present Invention | |
|---|---|
| Ex. # | Structure |
| A556 | 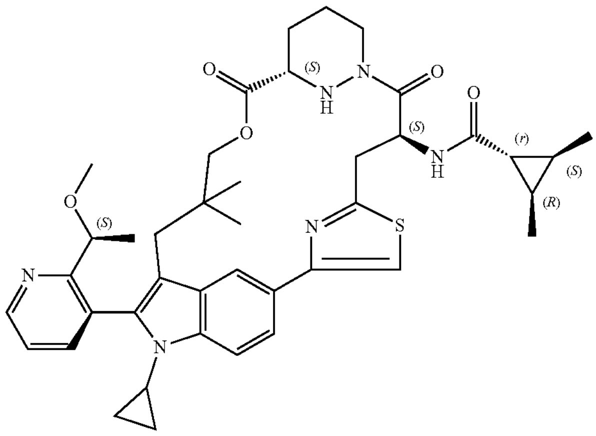 |
| A557 | 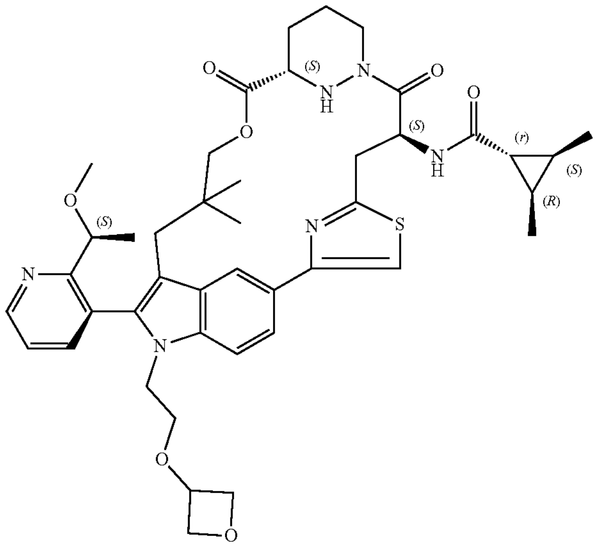 |
| A558 | 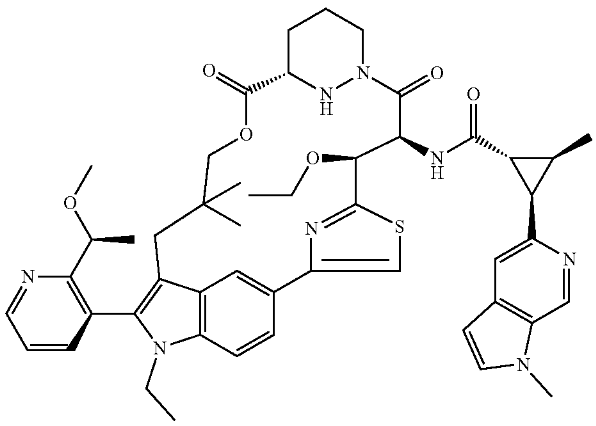 |

TABLE 1b-continued
| Certain Compounds of the Present Invention | |
|---|---|
| Ex. # | Structure |
| A559 | 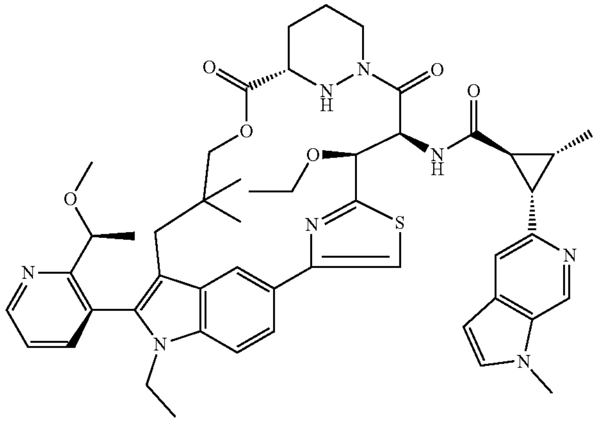 |
| A560 | 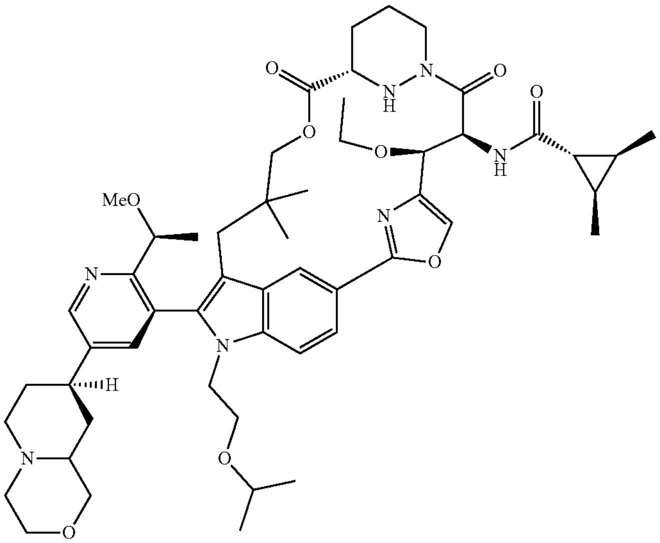 |
| A561 | 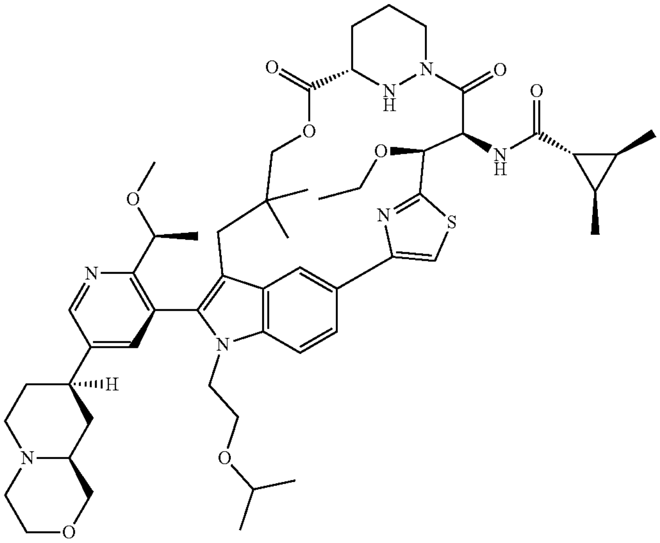 |

TABLE 1b-continued
| Certain Compounds of the Present Invention | |
|---|---|
| Ex. # | Structure |
| A562 | 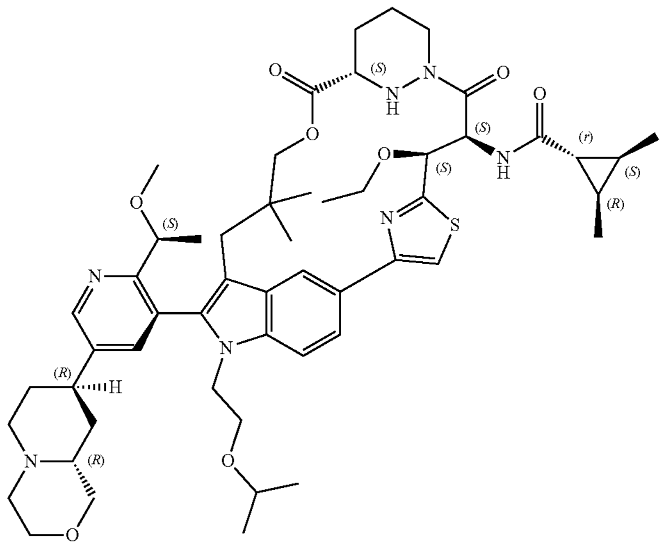 |
| A563 | 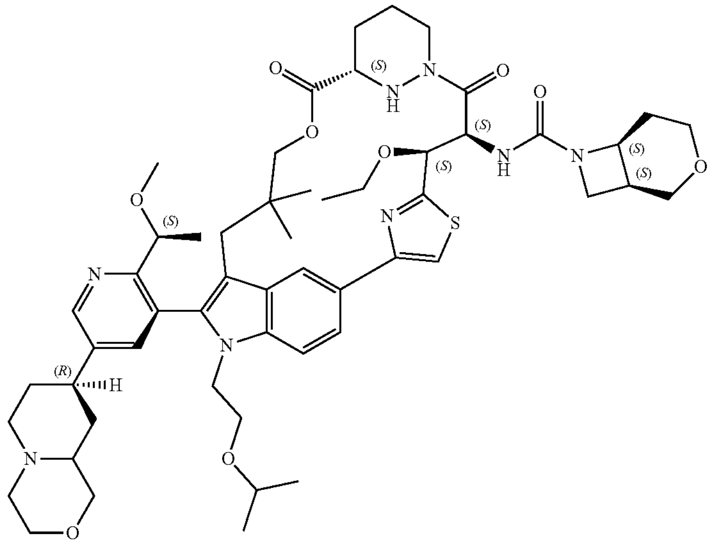 |

TABLE 1b-continued
| Certain Compounds of the Present Invention | |
|---|---|
| Ex. # | Structure |
| A564 | 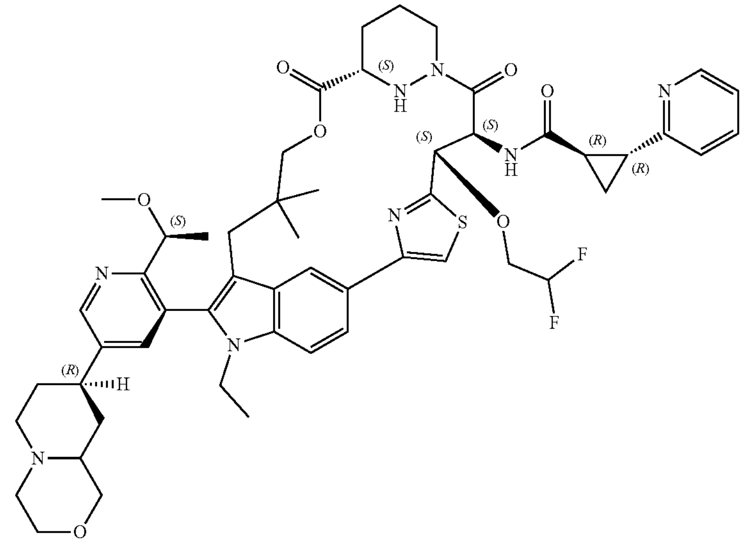 |
| A565 | 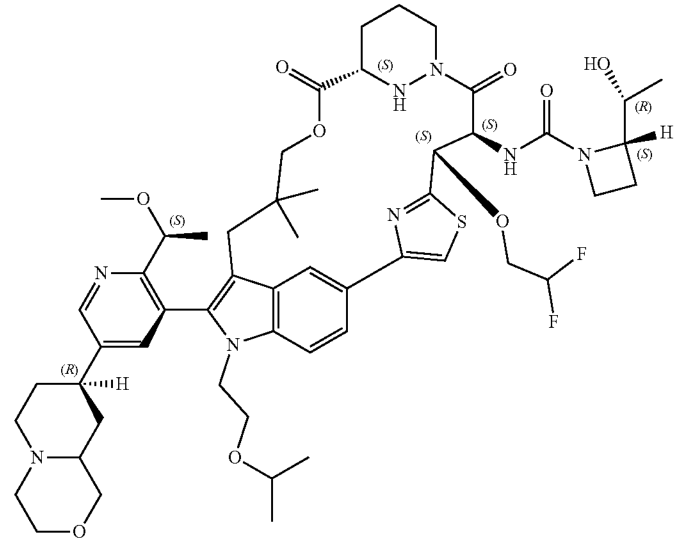 |
| A566 | 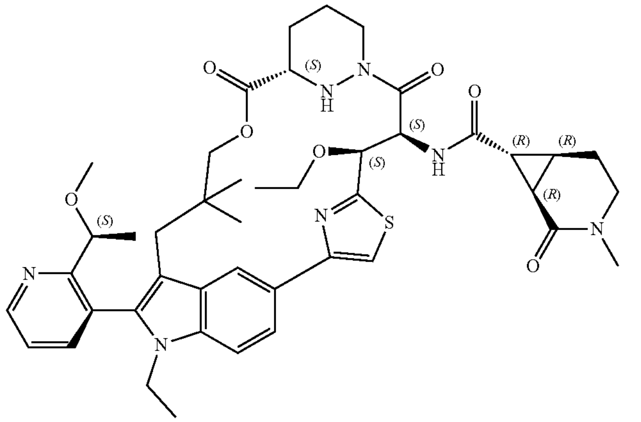 |

TABLE 1b-continued
| Certain Compounds of the Present Invention | |
|---|---|
| Ex. # | Structure |
| A567 | 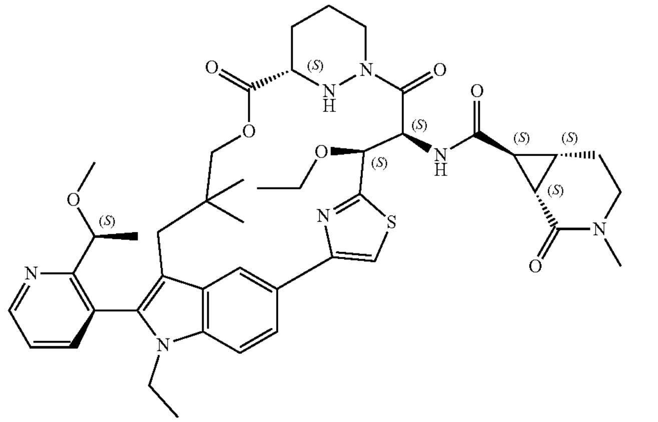 |
| A568 | 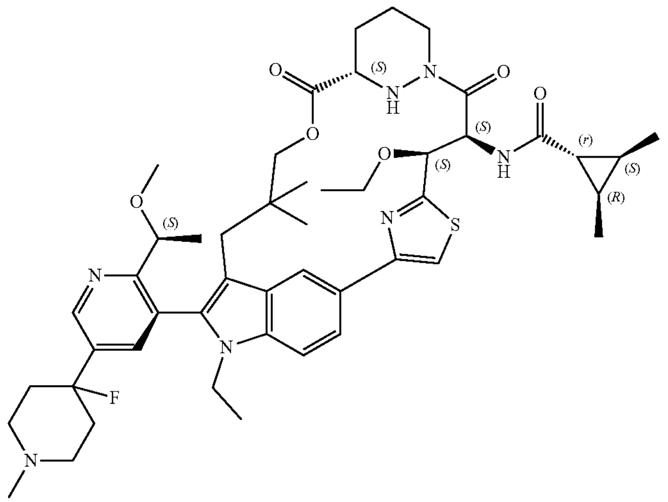 |
| A569 | 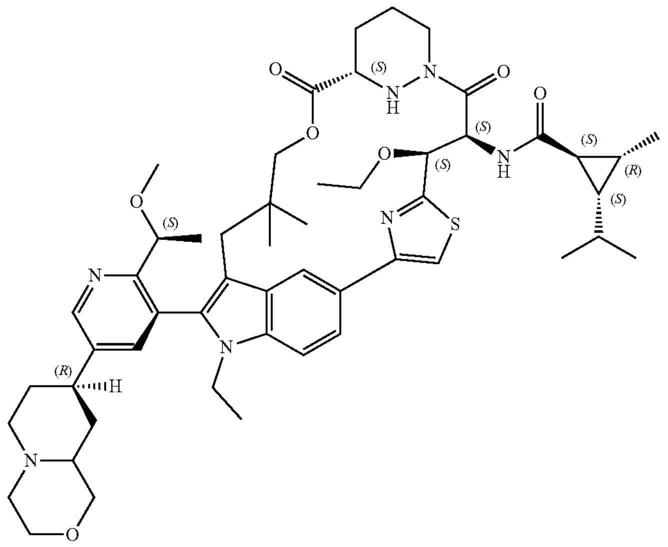 |

TABLE 1b-continued
| Certain Compounds of the Present Invention | |
|---|---|
| Ex. # | Structure |
| A570 | 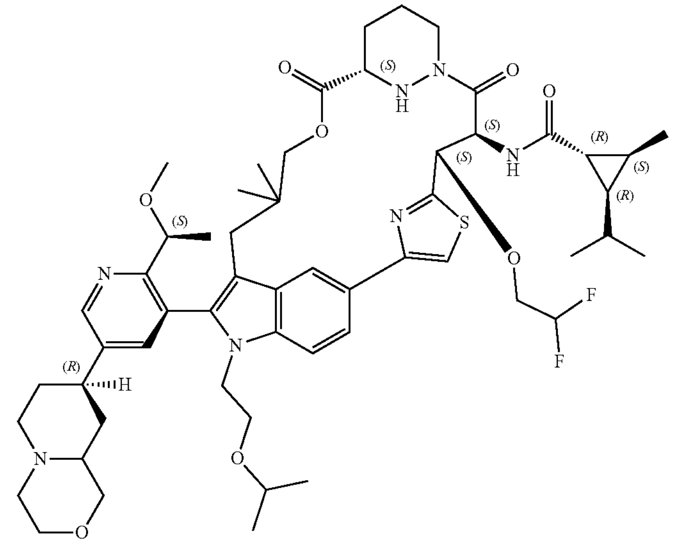 |
| A571 | 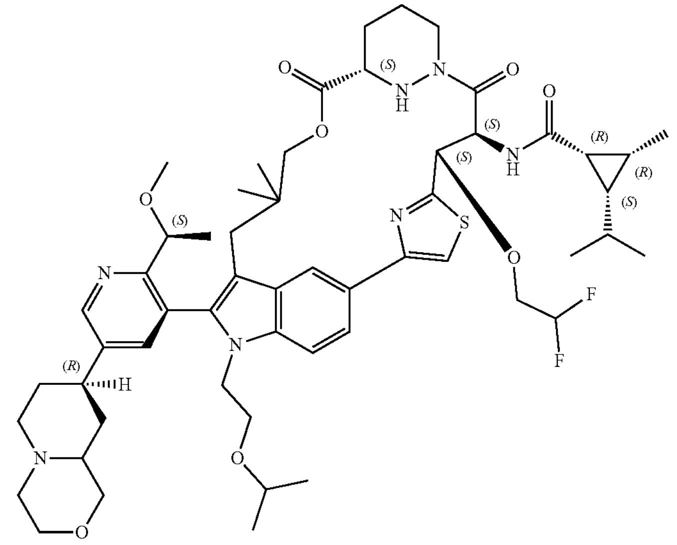 |
| A572 | 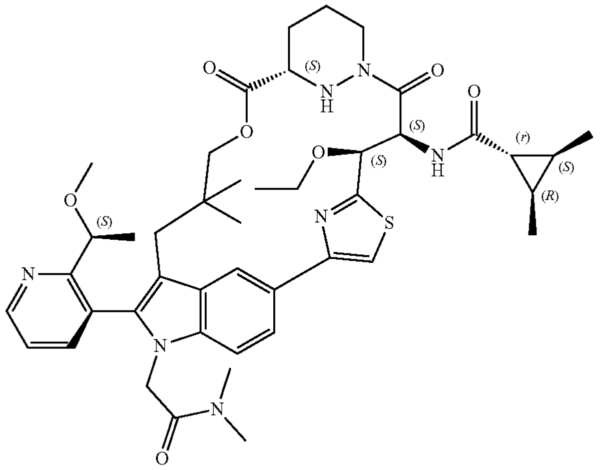 |

TABLE 1b-continued
| Certain Compounds of the Present Invention | |
|---|---|
| Ex. # | Structure |
| A573 | 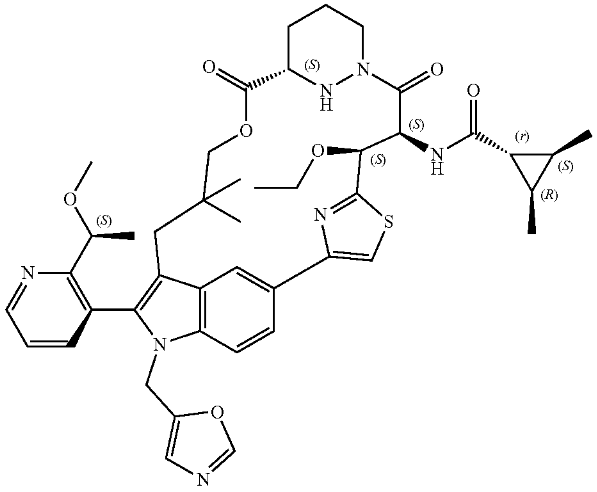 |
| A574 | 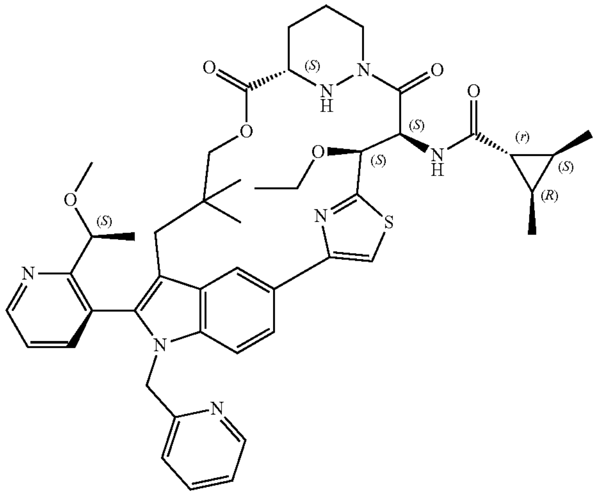 |

TABLE 1b-continued
| Certain Compounds of the Present Invention | |
|---|---|
| Ex. # | Structure |
| A575 | 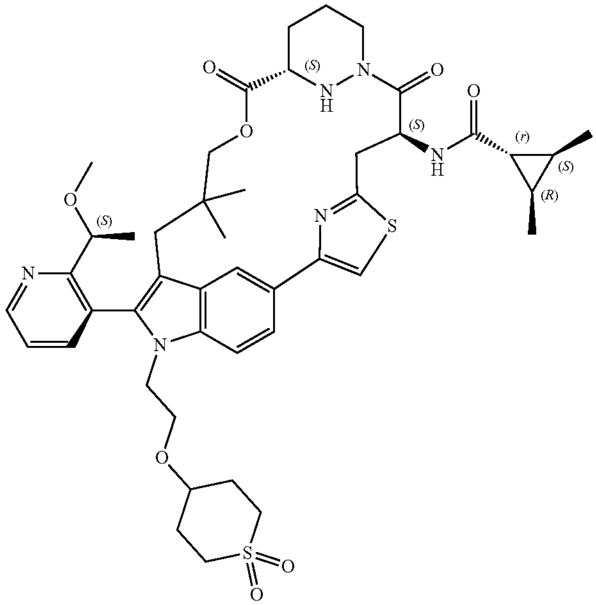 |
| A576 | 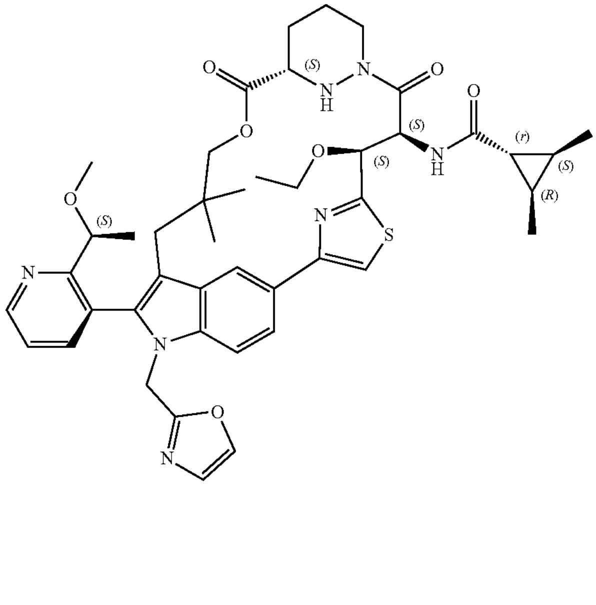 |

TABLE 1b-continued
| Certain Compounds of the Present Invention | |
|---|---|
| Ex. # | Structure |
| A577 | 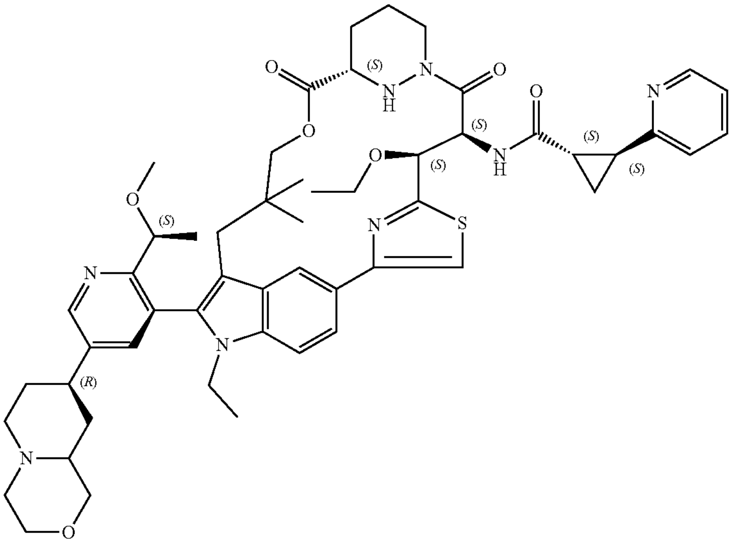 |
| A578 | 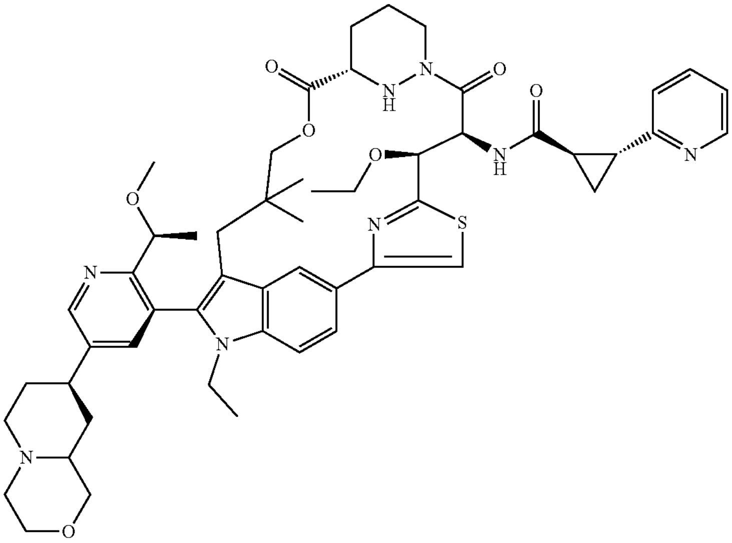 |
| A579 | 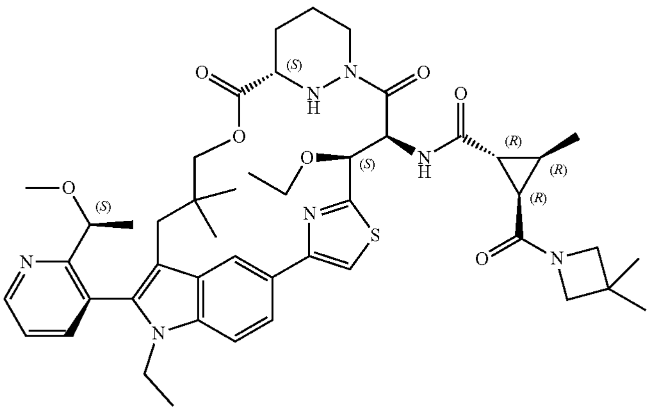 |

TABLE 1b-continued
| Certain Compounds of the Present Invention | |
|---|---|
| Ex. # | Structure |
| A580 | 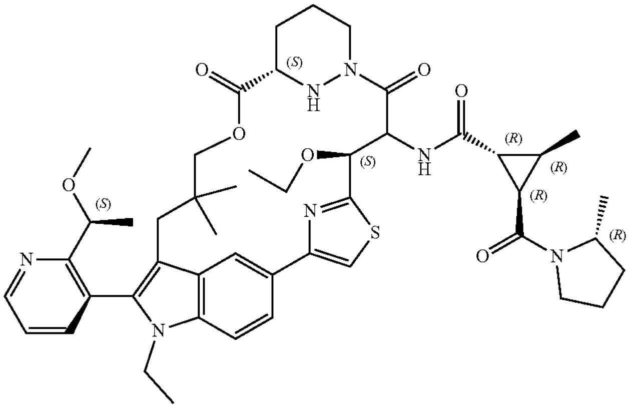 |
| A581 | 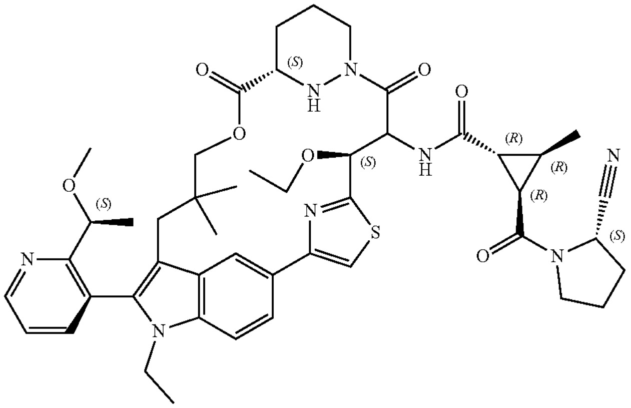 |
| A582 | 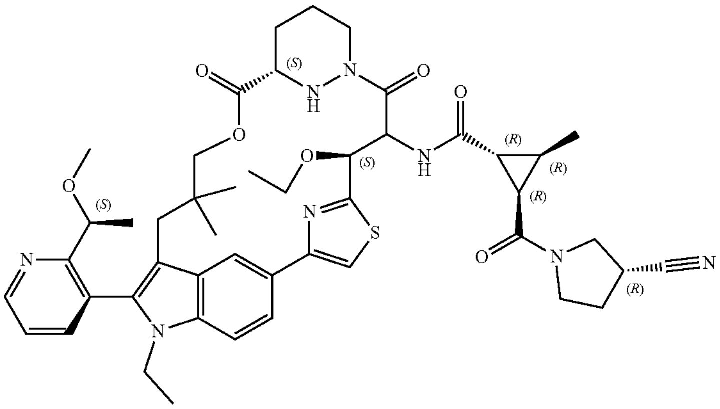 |

TABLE 1b-continued
| Certain Compounds of the Present Invention | |
|---|---|
| Ex. # | Structure |
| A583 | 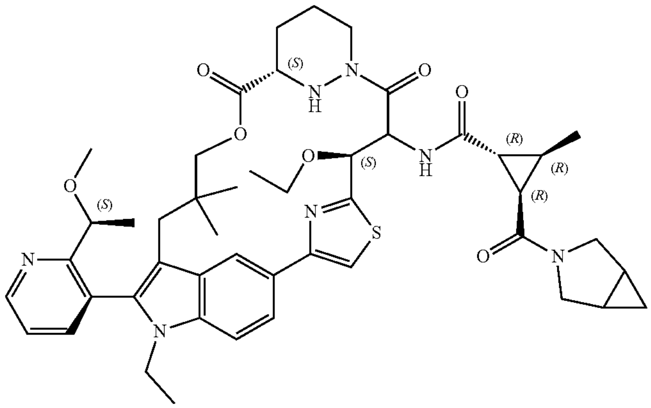 |
| A584 | 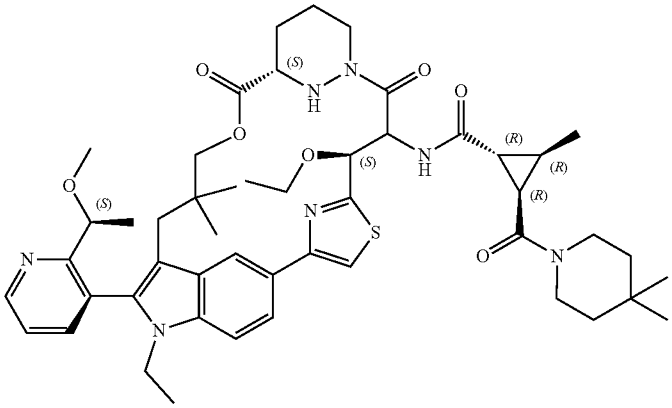 |
| A585 | 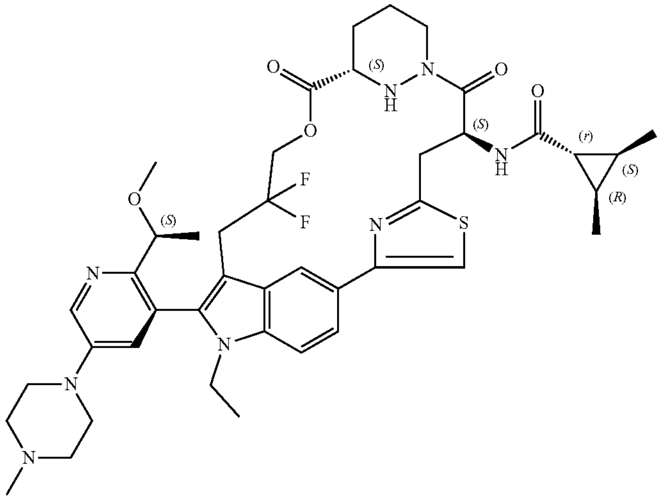 |

TABLE 1b-continued
| Certain Compounds of the Present Invention | |
|---|---|
| Ex. # | Structure |
| A586 | 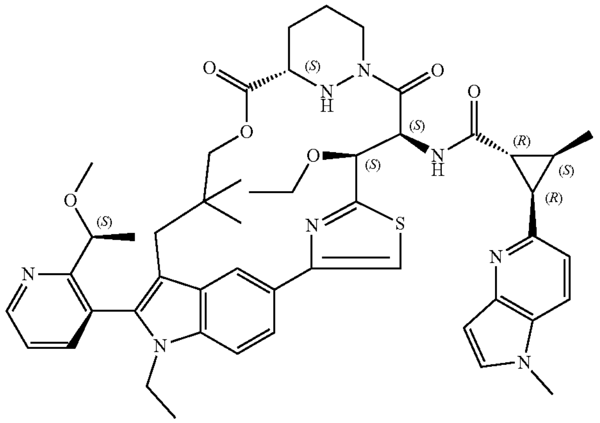 |
| A587 | 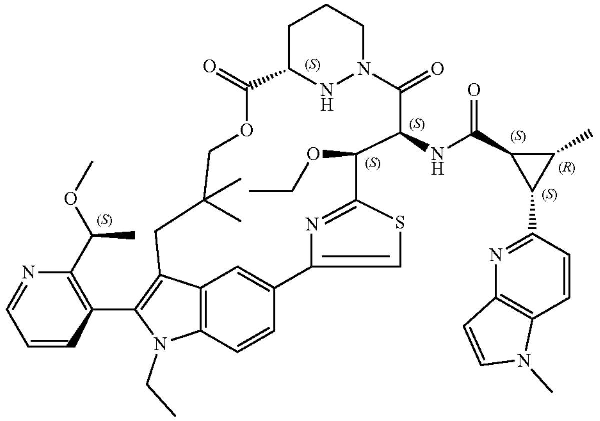 |
| A588 | 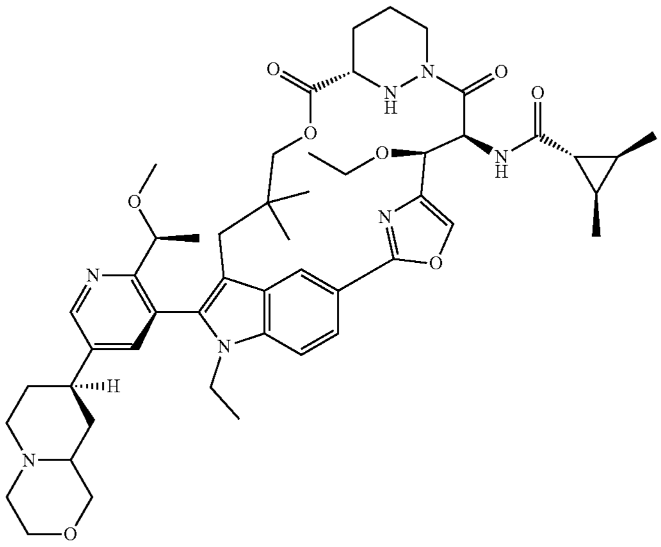 |

TABLE 1b-continued
| Certain Compounds of the Present Invention | |
|---|---|
| Ex. # | Structure |
| A589 | 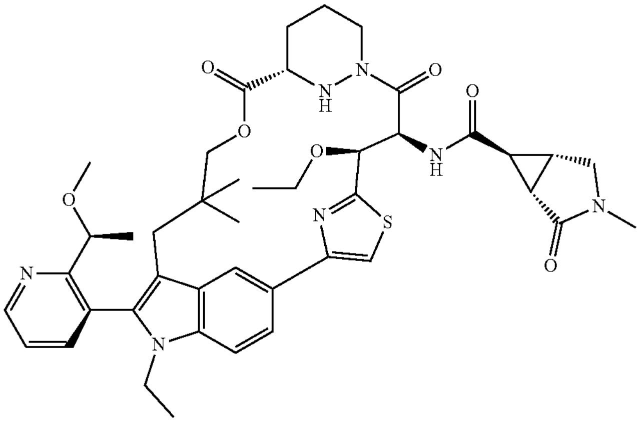 |
| A590 | 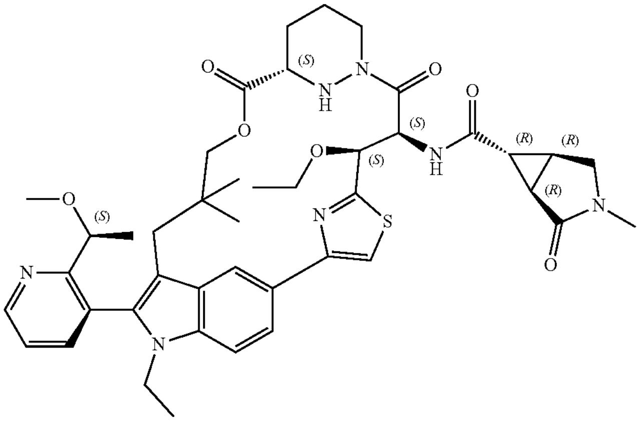 |
| A591 | 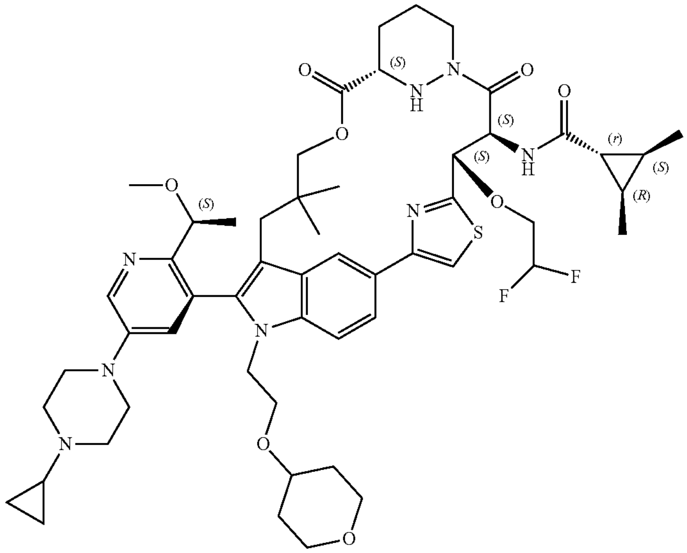 |

TABLE 1b-continued
Certain Compounds of the Present Invention
| Ex. # | Structure |
| --- | --- |
| A592 | 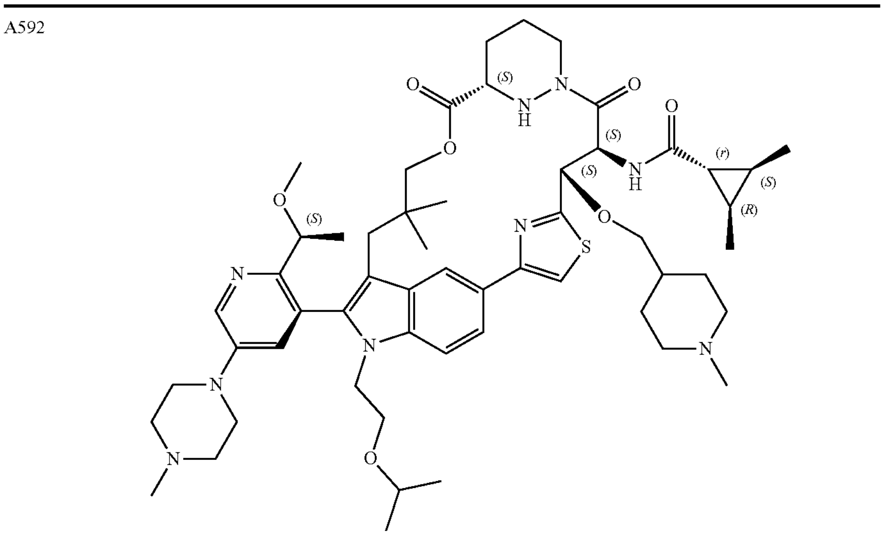 |
| A593 | 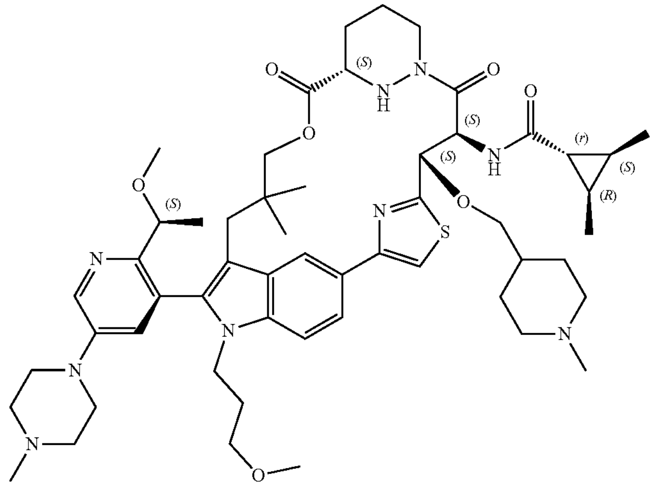 |
| A594 | 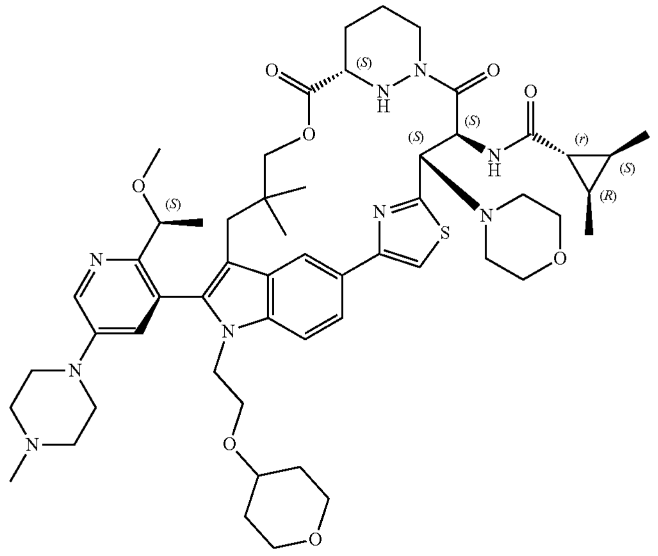 |

TABLE 1b-continued
| Certain Compounds of the Present Invention | |
|---|---|
| Ex. # | Structure |
| A595 | 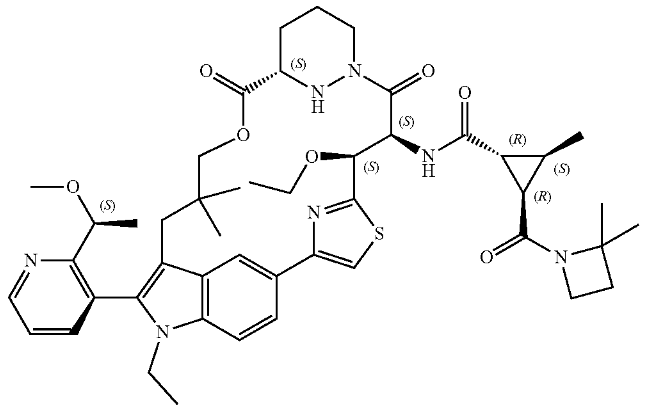 |
| A596 | 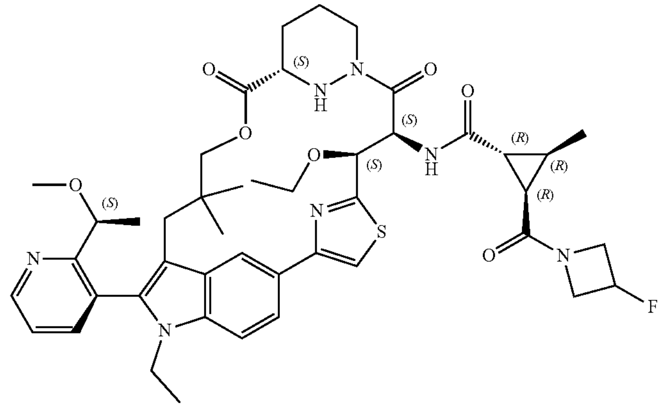 |
| A597 | 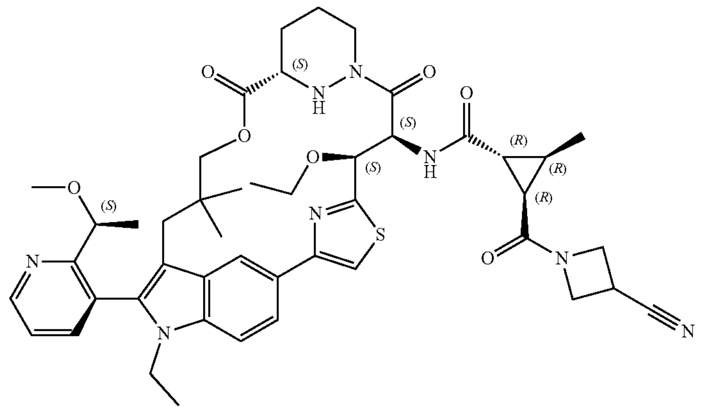 |

TABLE 1b-continued
| Certain Compounds of the Present Invention | |
|---|---|
| Ex. # | Structure |
| A598 | 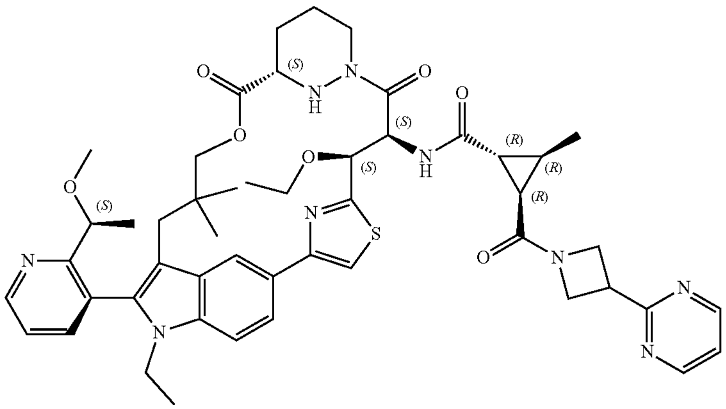 |
| A599 | 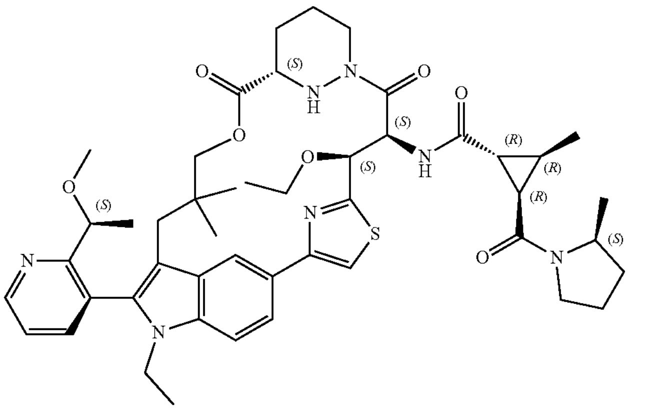 |
| A600 | 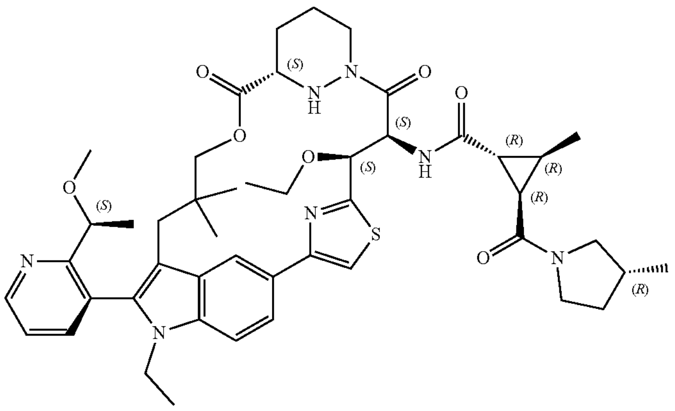 |

TABLE 1b-continued
| Certain Compounds of the Present Invention | |
|---|---|
| Ex. # | Structure |
| A601 | 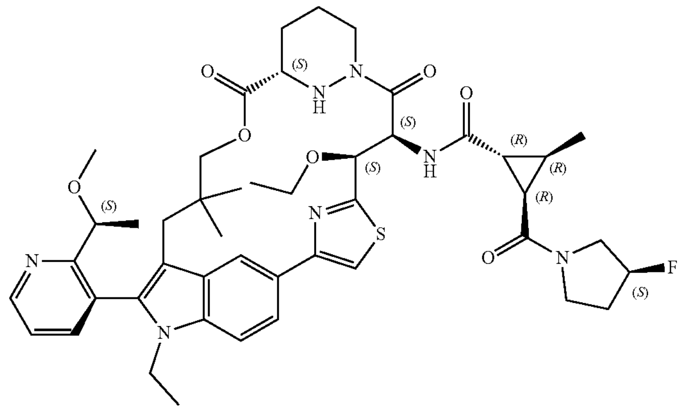 |
| A602 | 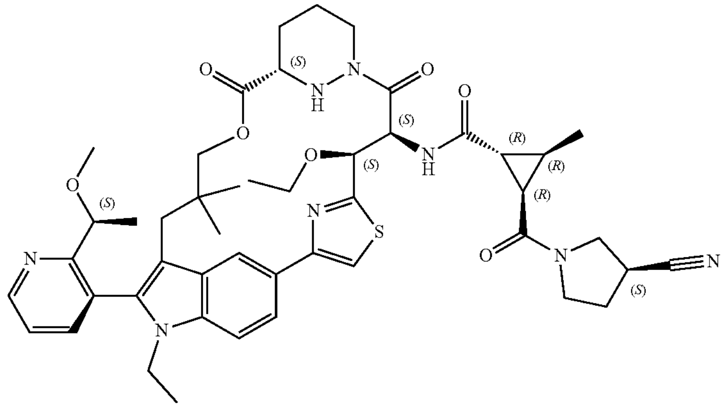 |
| A603 | 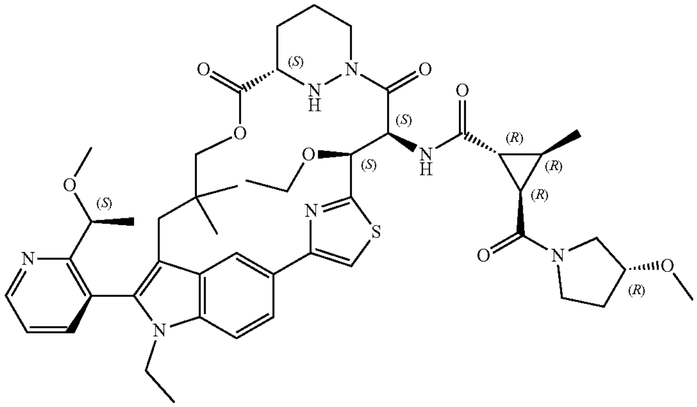 |

TABLE 1b-continued
| Certain Compounds of the Present Invention | |
|---|---|
| Ex. # | Structure |
| A604 | 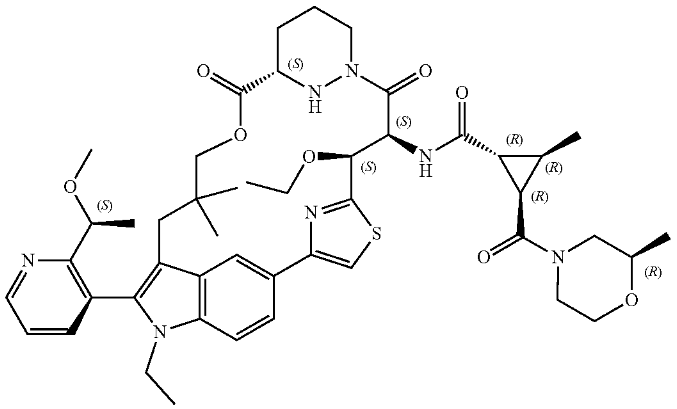 |
| A605 | 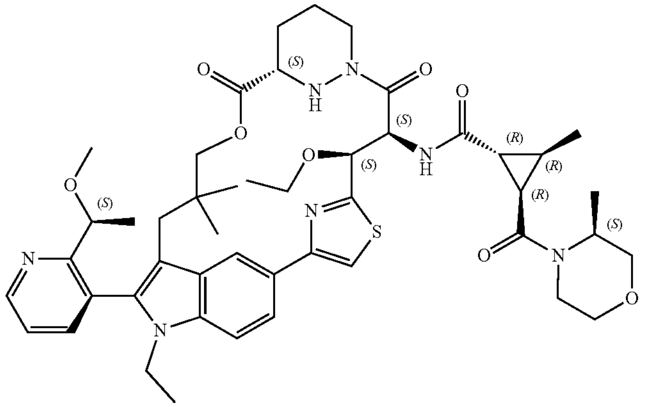 |
| A606 | 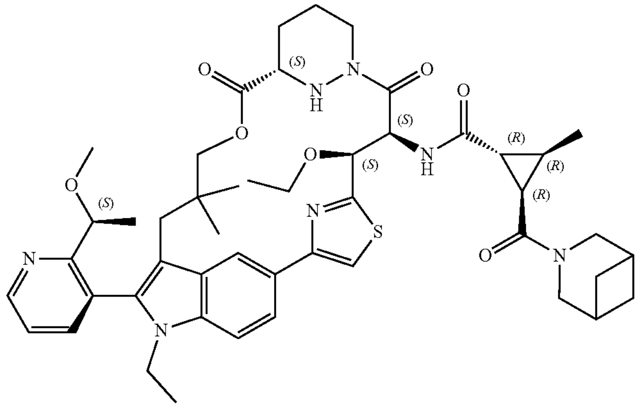 |

TABLE 1b-continued

| Certain Compounds of the Present Invention | |
|---|---|
| Ex. # | Structure |
| A607 | 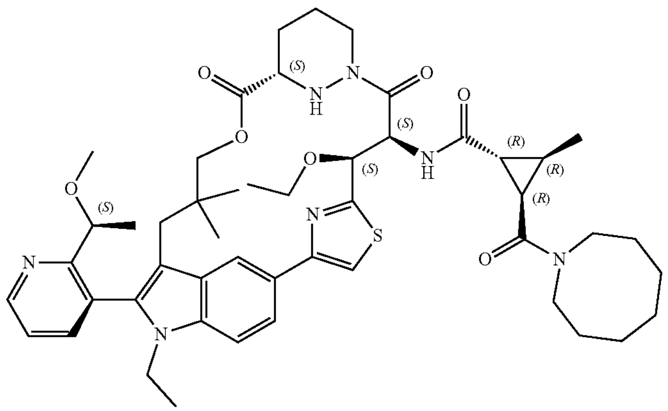 |
| A608 | 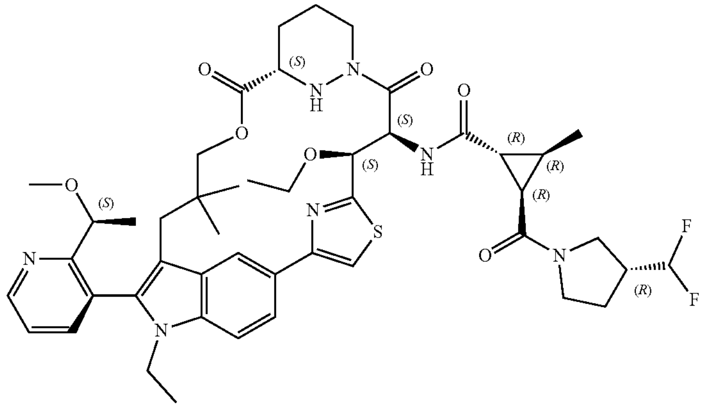 |

Note that some compounds are shown with bonds as flat or wedged. In some instances, the relative stereochemistry of stereoisomers has been determined; in some instances, the absolute stereochemisty has been determined. All stereoisomers of the compounds of the foregoing table are contemplated by the present invention. In particular embodiments, an atropsiomer of a compound of the foregoing table is contemplated. Any compound shown in brackets indicatess that the compound is a diastereomer, and the absolute stereochemistry of such diastereomer may not be known.

In some embodiments, a compound of the present invention is a compound selected from Table 2, or a pharmaceutically acceptable salt or stereoisomer thereof. In some embodiments, a compound of the present invention is a compound selected from Table 2, or a pharmaceutically acceptable salt or atropisomer thereof.

In some embodiments, a compound of the present invention is not a compound selected from Table 2. In some embodiments, a compound of the present invention is not a compound selected from Table 2, or a pharmaceutically acceptable salt or stereoisomer thereof. In some embodiments, a compound of the present invention is not a compound selected from Table 2, or a pharmaceutically acceptable salt or atropisomer thereof.

TABLE 2

| Certain Compounds | |
|---|---|
| Ex. # | Structure |
| B1 | 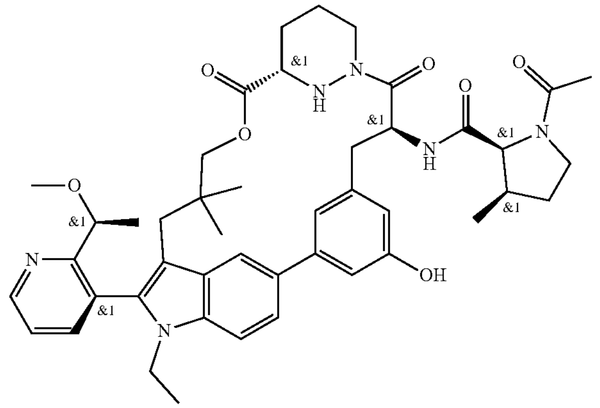 |
| B2 | 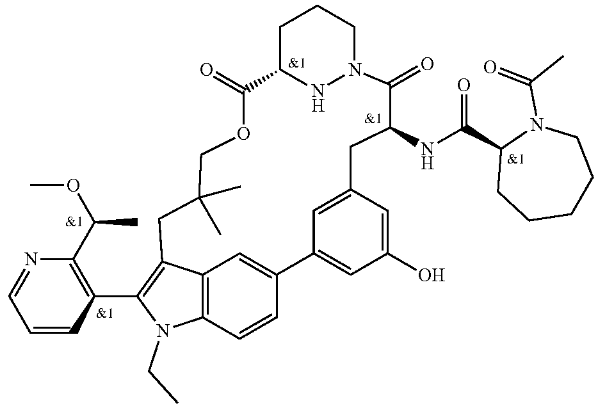 |
| B3 | 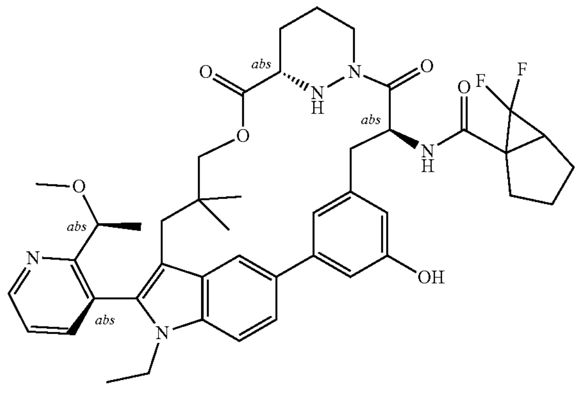 |

TABLE 2-continued
| Certain Compounds | |
|---|---|
| Ex. # | Structure |
| B4 | 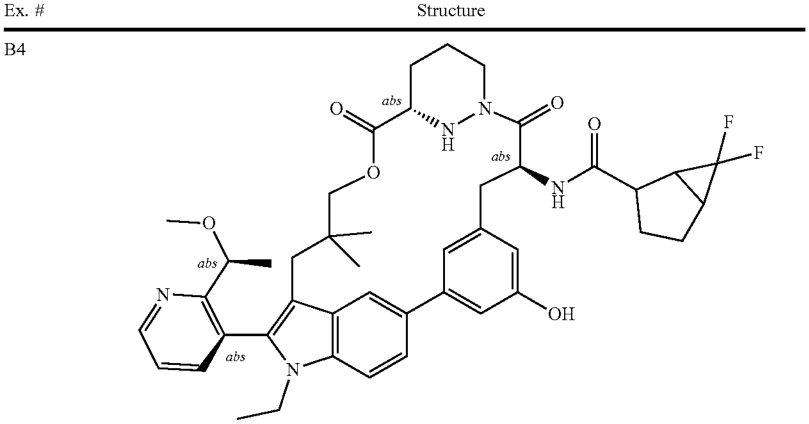 |
| B5 | 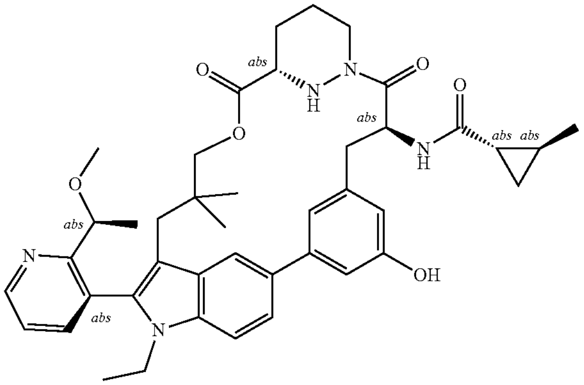 |
| B6 | 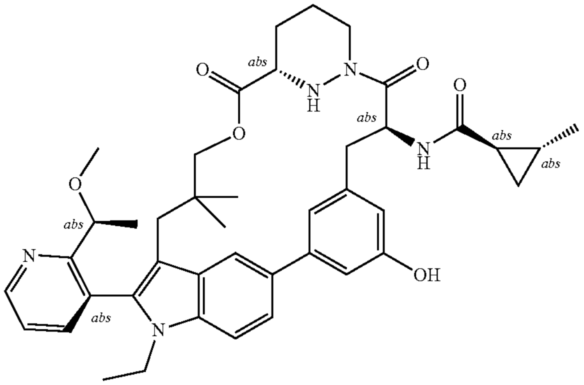 |
| B7 | 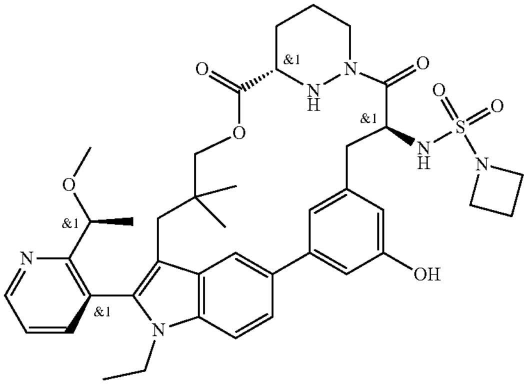 |

TABLE 2-continued
| Certain Compounds | |
|---|---|
| Ex. # | Structure |
| B8 | 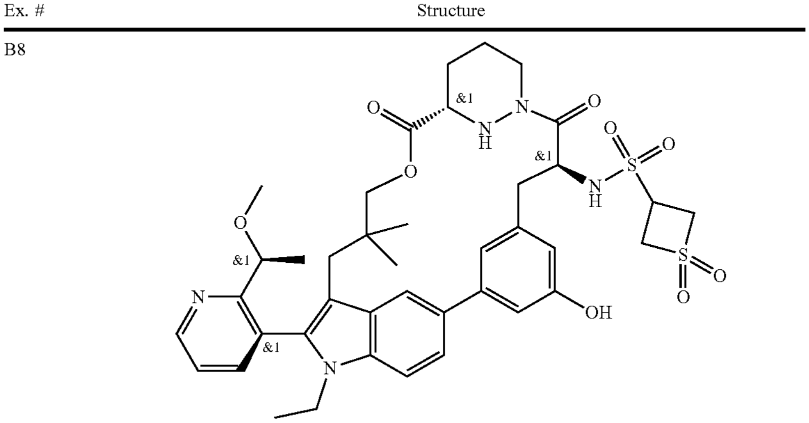 |
| B9 | 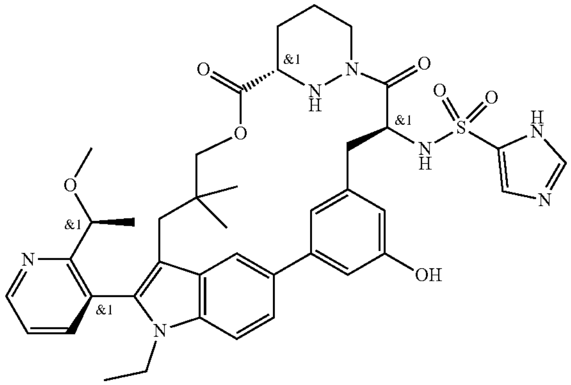 |
| B10 | 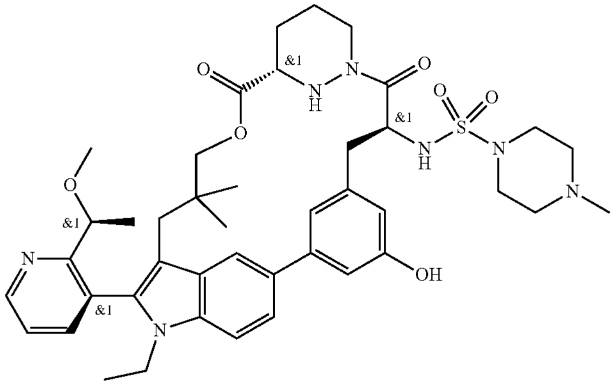 |
| B11 | 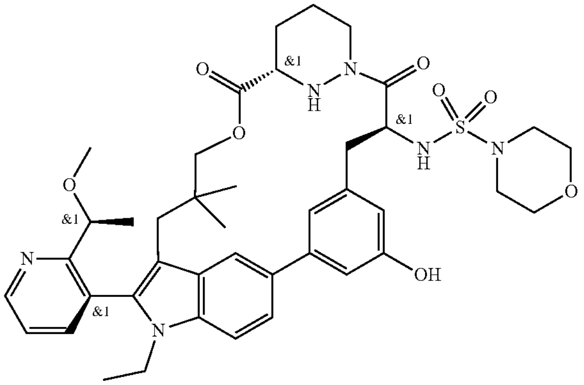 |

TABLE 2-continued
| Certain Compounds | |
|---|---|
| Ex. # | Structure |
| B12 | 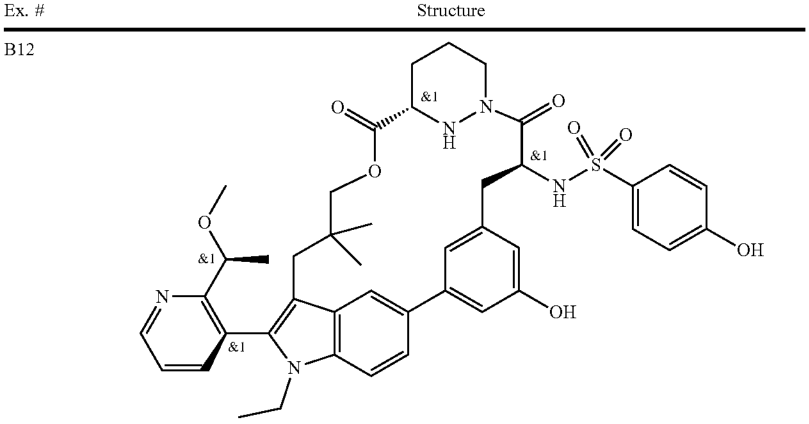 |
| B13 | 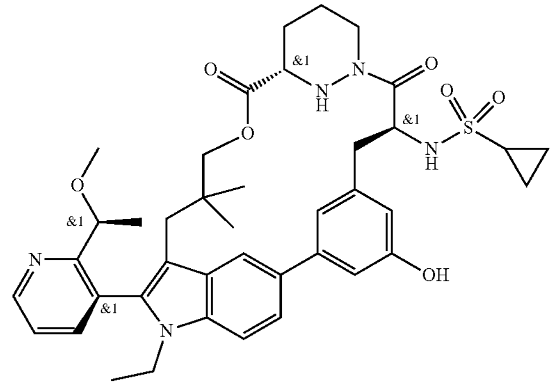 |
| B14 | 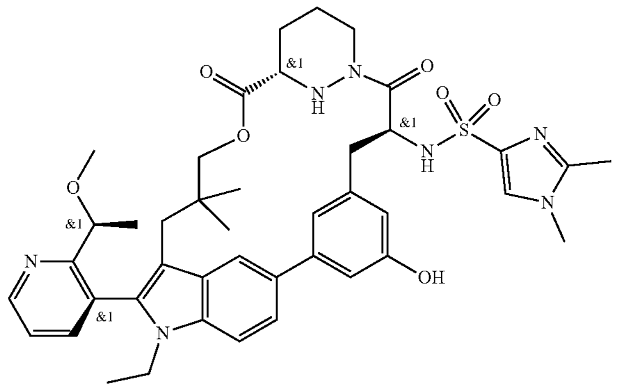 |
| B15 | 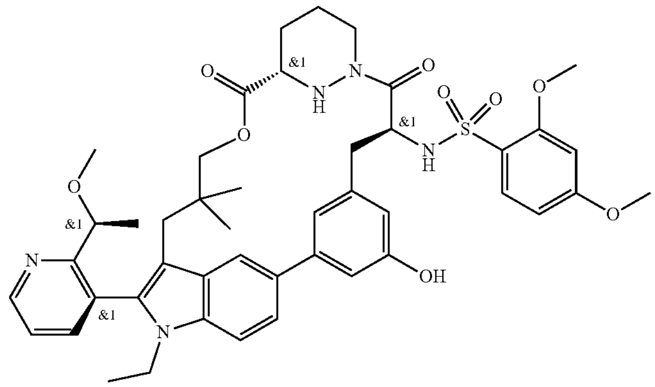 |

TABLE 2-continued
| Certain Compounds | |
|---|---|
| Ex. # | Structure |
| B16 | 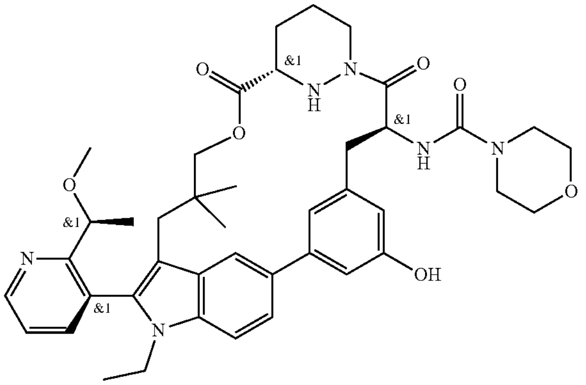 |
| B17 | 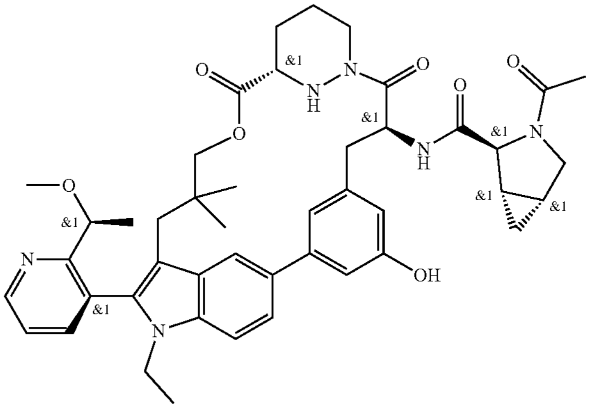 |
| B18 | 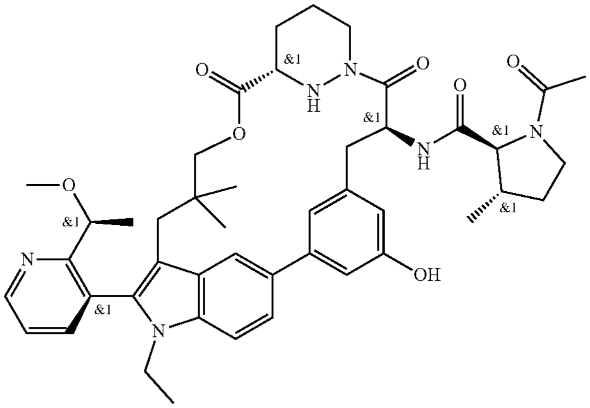 |

TABLE 2-continued
| Certain Compounds | |
| --- | --- |
| Ex. # | Structure |
| B19 | 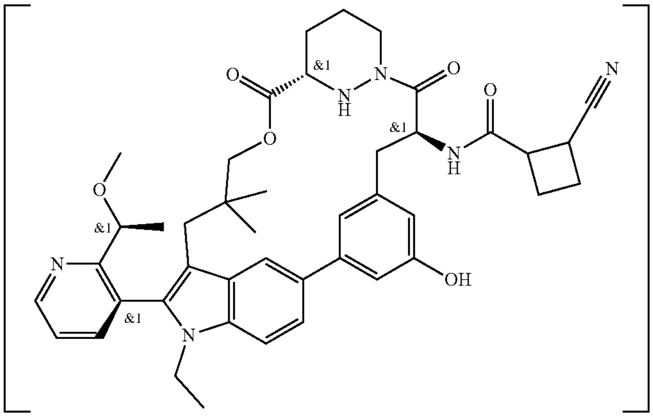 |
| B20 | 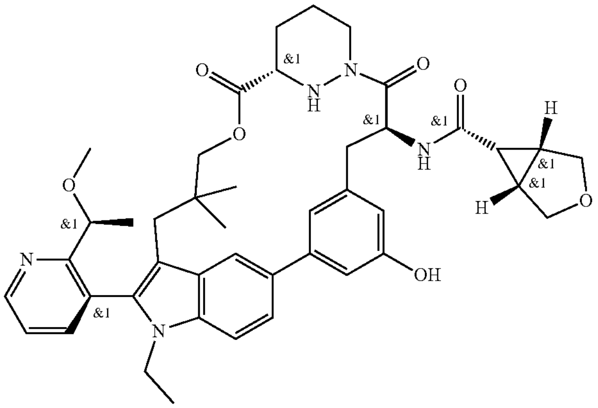 |
| B21 | 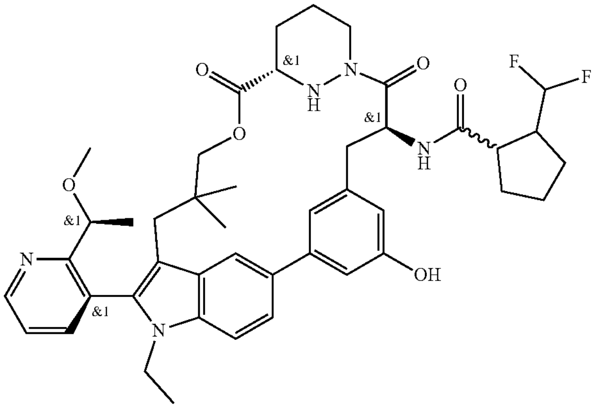 |

TABLE 2-continued
| Certain Compounds | |
|---|---|
| Ex. # | Structure |
| B22 | 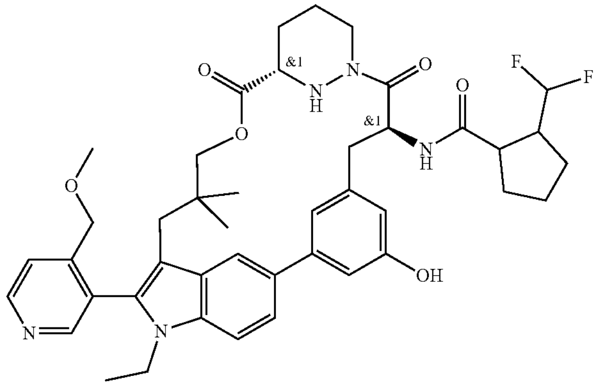 [SMILES: CCn1c(-c2cnccc2COC)c2c3cc(ccc31)-c1cc(O)cc(c1)C[C@H](NC(=O)C1CCCC1C(F)F)C(=O)N1CCC[C@H](N1)C(=O)OCC(C)(C)C2] |
| B23 | 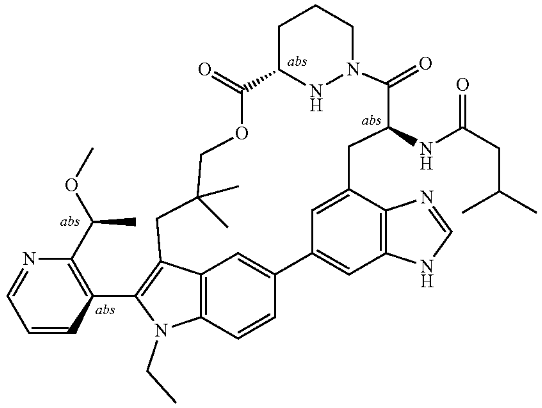 |
| B24 | 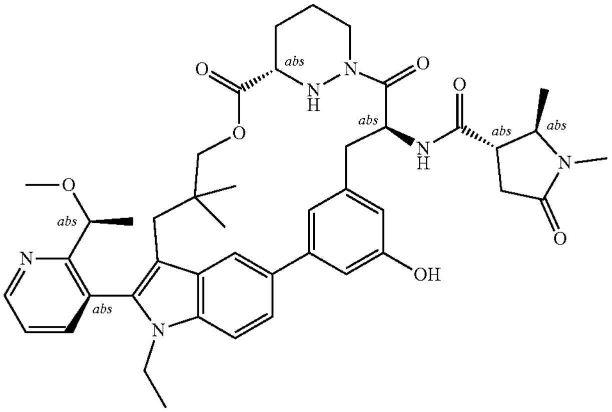 |

TABLE 2-continued

| Certain Compounds | |
|---|---|
| Ex. # | Structure |
| B25 | 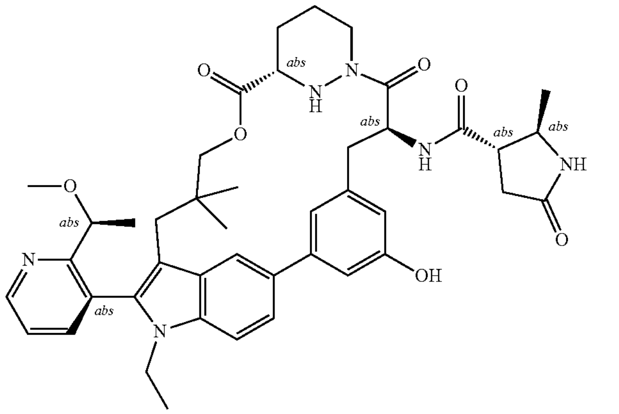 |

In some embodiments, a compound of the present invention is a compound selected from Table 3 (e.g., C1-C20 or C1-C21), or a pharmaceutically acceptable salt or stereoisomer thereof. In some embodiments, a compound of the present invention is a compound selected from Table 3 (e.g., C1-C20 or C1-C21), or a pharmaceutically acceptable salt or atropisomer thereof.

In some embodiments, a compound of the present invention is not a compound selected from Table 3 (e.g., C1-C20 or C1-C21). In some embodiments, a compound of the present invention is not a compound selected from Table 3 (e.g., C1-C20 or C1-C21), or a pharmaceutically acceptable salt or stereoisomer thereof. In some embodiments, a compound of the present invention is not a compound selected from Table 3 (e.g., C1-C20 or C1-C21), or a pharmaceutically acceptable salt or atropisomer thereof.

TABLE 3

| Certain Compounds | |
|---|---|
| Ex. # | Structure |
| C1 | 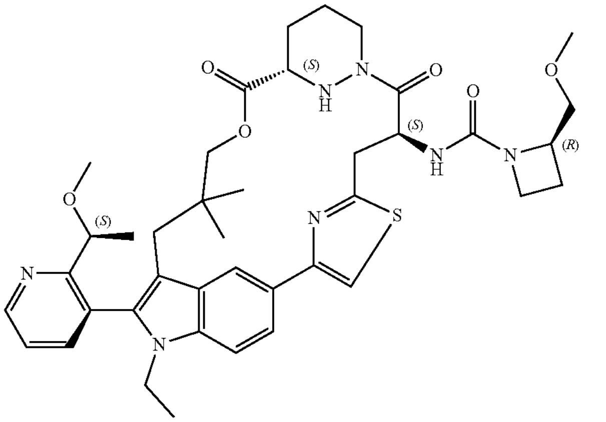 |

TABLE 3-continued
| Certain Compounds | |
|---|---|
| Ex. # | Structure |
| C2 | 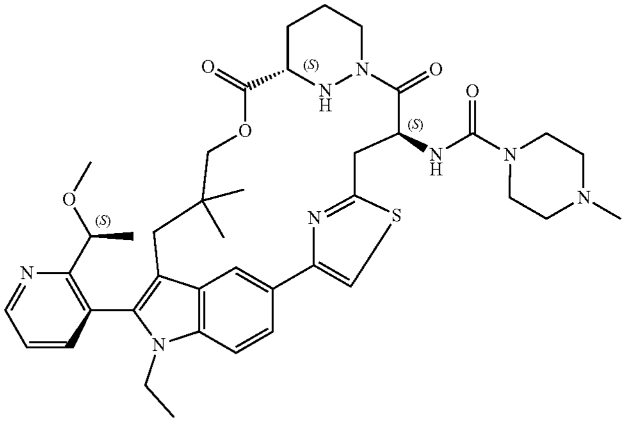 |
| C3 | 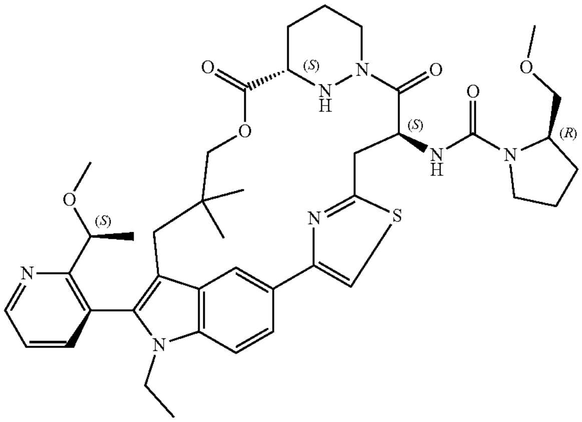 |
| C4 | 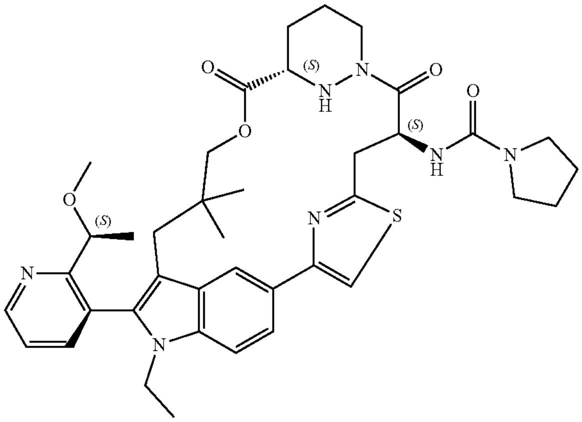 |

TABLE 3-continued
| Certain Compounds | |
|---|---|
| Ex. # | Structure |
| C5 | 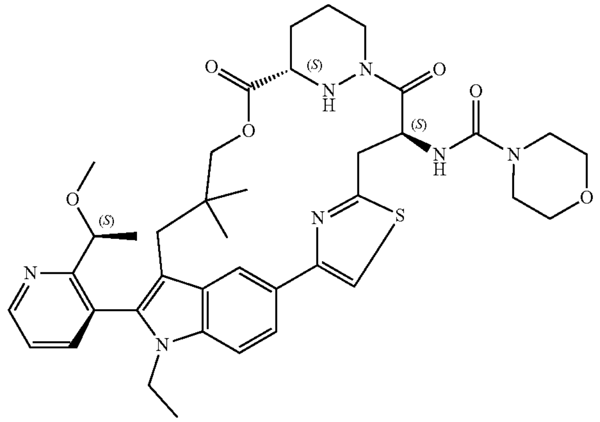 |
| C6 | 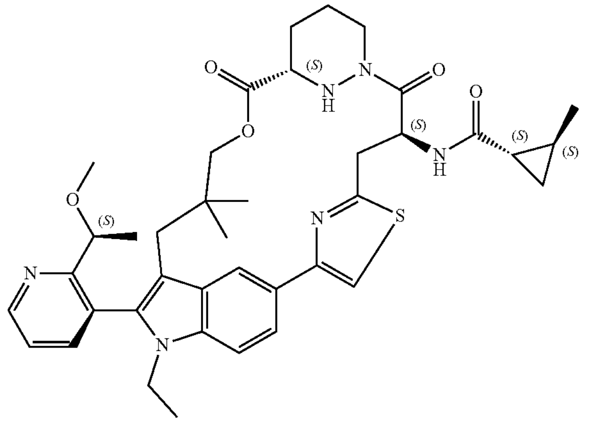 |
| C7 | 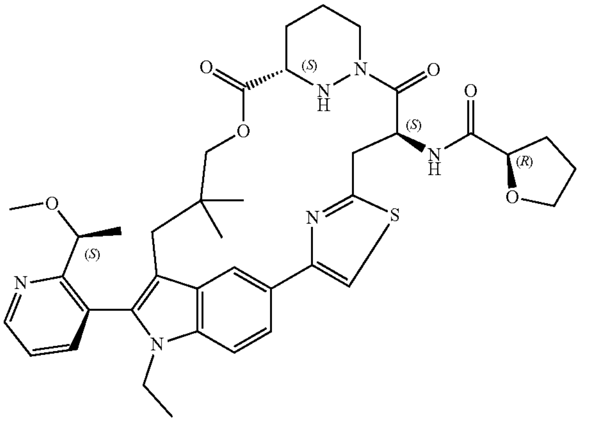 |

TABLE 3-continued
| Certain Compounds | |
|---|---|
| Ex. # | Structure |
| C8 | 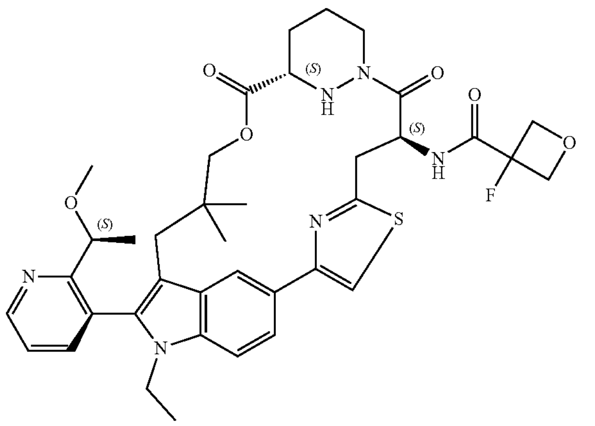 |
| C9 | 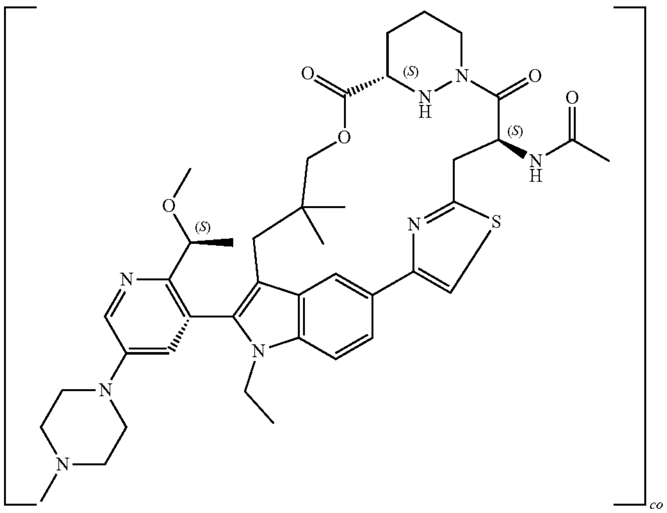 |
| C10 | 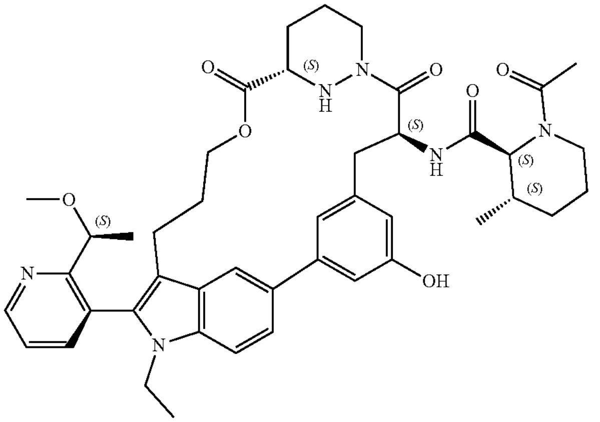 |

TABLE 3-continued
| Certain Compounds | |
|---|---|
| Ex. # | Structure |
| C11 | 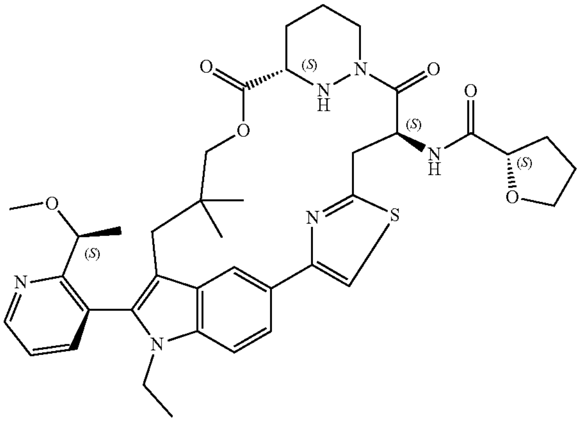 |
| C12 | 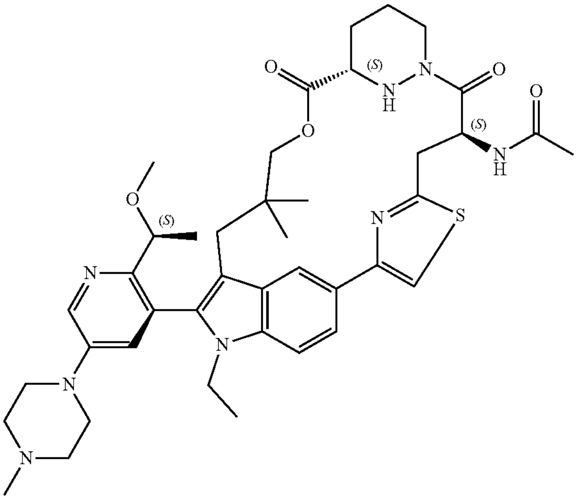 |
| C13 | 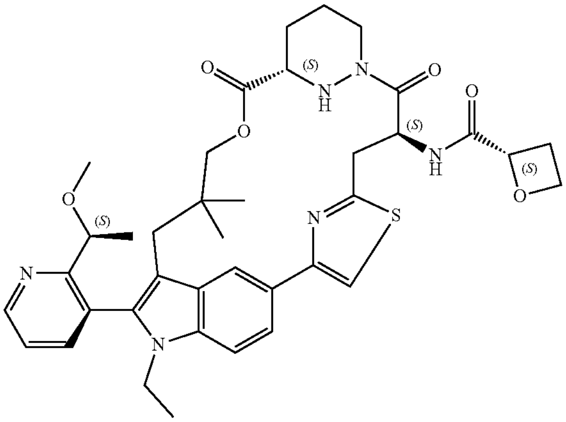 |

TABLE 3-continued
| Certain Compounds | |
|---|---|
| Ex. # | Structure |
| C14 | 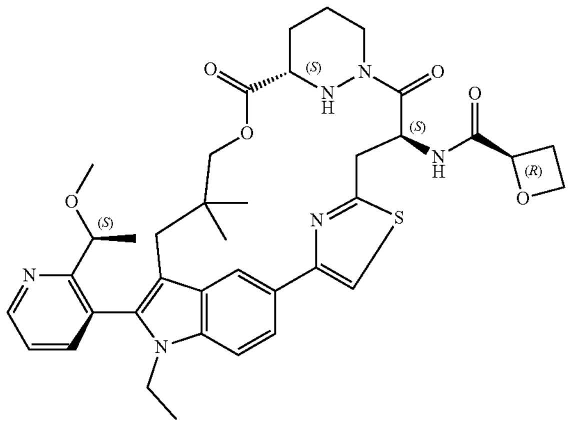 |
| C15 | 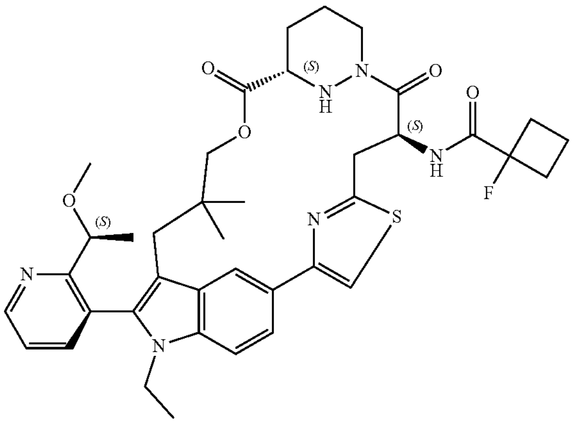 |
| C16 | 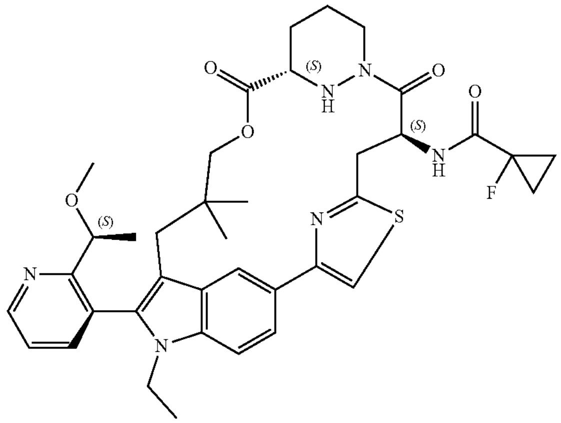 |

TABLE 3-continued
| Certain Compounds | |
|---|---|
| Ex. # | Structure |
| C17 | 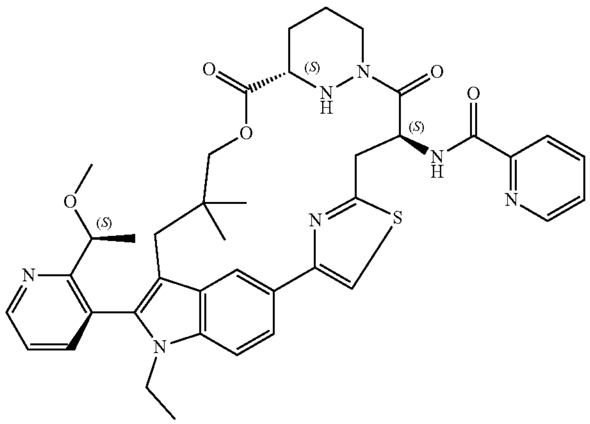 |
| C18 | 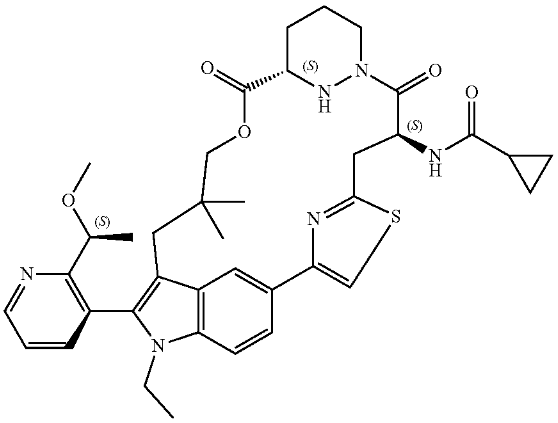 |
| C19 | 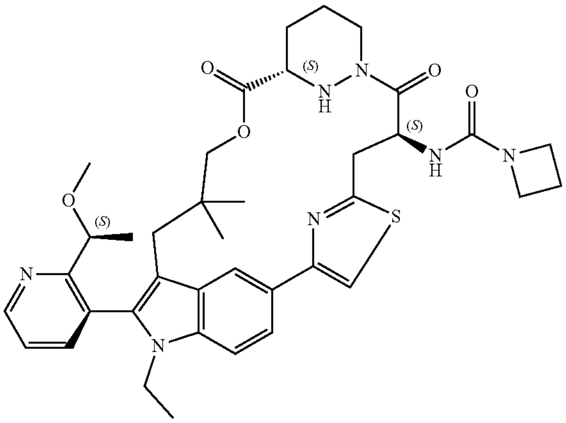 |

TABLE 3-continued

| Certain Compounds | |
|---|---|
| Ex. # | Structure |
| C20 | 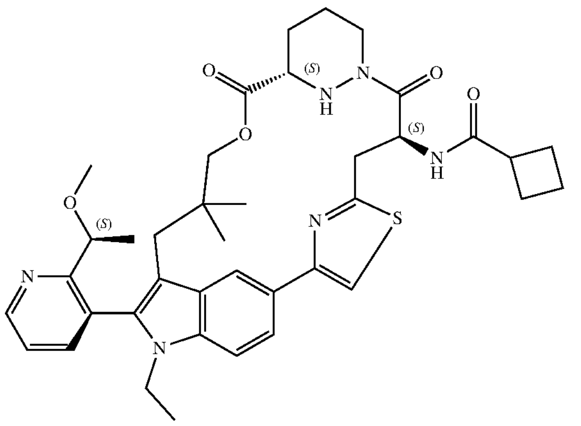 |
| C21 | 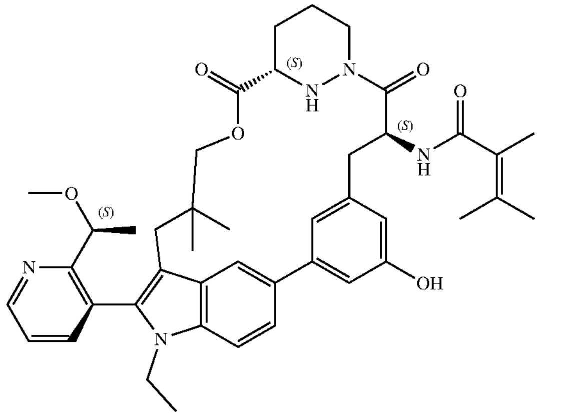 |

In some embodiments, a compound of the present invention has improved oral bioavailability (% F) compared to what is known in the art. Methods of measuring oral bioavailability are known in the art, and one such method is provided below:

Oral bioavailability may be determined in BALB/c mice. Following intravenous (IV) bolus and oral gavage (PO) administration of a test compound, about 30 μL of whole blood samples are collected at designated time points into tubes containing $K_2EDTA$. The blood samples are centrifuged at 4600 rpm at 4° C. for about 5 minutes and plasma samples are stored at −80° C. prior to bioanalysis. Plasma samples are extracted by protein precipitation and analyzed by tandem mass spectrometry (LC MS/MS) on, for example, an API 5500 system using electrospray positive ionization.

All PK parameters may be derived from plasma concentration over time data with noncompartment analysis using WinNonlin. The bioavailability (F %, also % F) is estimated using the following equation:

$$F\ \% = \frac{AUC_{inf,PO}}{AUC_{inf,IV}} \cdot \frac{\text{Dose}_{IV}}{\text{Dose}_{PO}}$$

$AUC_{inf,PO}$ is the area under the plasma concentration over time from time zero to infinity following PO administration.

$AUC_{inf,IV}$ is the area under the plasma concentration over time from time zero to infinity following IV administration.

$Dose_{IV}$ is the total dose of IV administration $Dose_{PO}$ is the total dose of PO administration In general, F % (or % F) values of over 30% are preferred, with values over 50% being more preferred.

In some embodiments, a compound of the present invention is selective for one or more particular Ras mutants over other Ras mutants or wild-type compared to what is known in the art. Methods of measuring such selectivity are known in the art, such as the Ras-Raf binding assay, a protocol for which is provided in the Examples below. Accordingly, in some embodiments, compounds of the present invention are selective for $KRAS^{G12C}$ over other Ras mutants or over wild-type. In some embodiments, compounds of the present invention are selective for $KRAS^{G12D}$ over other Ras mutants or over wild-type. In some embodiments, compounds of the present invention are selective for $KRAS^{G12V}$ over other Ras mutants or over wild-type. In some embodiments, compounds of the present invention are selective for $KRAS^{G12D}$ over other Ras mutants or over wild-type. In some embodiments, compounds of the present invention are selective for $NRAS^{Q61K}$ over other Ras mutants or over wild-type. In some embodiments, compounds of the present invention are selective for $KRAS^{G12D}$ and $KRAS^{G12V}$ over other Ras mutants and wild-type. Compounds of the present invention may also exhibit greater selectivity with respect to other RAS mutants disclosed herein, or combinations thereof. In some embodiments, compounds of the present invention exhibit an IC50 value of less than 30 nm for one or more Ras mutants described herein in the Ras-Raf binding assay described above.

In some embodiments, a compound of the present invention is more potent for one or more particular Ras mutants over other Ras mutants or wild-type compared to what is known in the art. Methods of measuring such potency are known in the art, such as the pERK assay, a protocol for which is provided in the Examples below. Accordingly, in some embodiments, compounds of the present invention exhibit greater potency with respect to $KRAS^{G12D}$ than what is known in the art. In some embodiments, compounds of the present invention exhibit greater potency with respect to $KRAS^{G12V}$ than what is known in the art. In some embodiments, compounds of the present invention exhibit greater potency with respect to $KRAS^{G12C}$ than what is known in the art. In some embodiments, compounds of the present invention exhibit greater potency with respect to both $KRAS^{G12D}$ and $KRAS^{G12V}$ than what is known in the art. Compounds of the present invention may also exhibit greater potency with respect to other RAS mutants disclosed herein, or combinations thereof.

In some embodiments, a compound of the present invention exhibits a greater detrimental effect on cell viability with respect to one or more particular Ras mutants over other Ras mutants or wild-type compared to what is known in the art. Methods of measuring cell viability are known in the art, such as the CellTiter-GloÆCell Viability Assay assay, a protocol for which is provided in the Examples below.

Accordingly, in some embodiments, compounds of the present invention exhibit a greater decrease in cell viability with respect to $KRAS^{G12D}$ compared to what is known in the art. In some embodiments, compounds of the present invention exhibit a greater decrease in cell viability with respect to $KRAS^{G12V}$ compared to what is known in the art. In some embodiments, compounds of the present invention exhibit a greater decrease in cell viability with respect to $KRAS^{G12C}$ compared to what is known in the art. In some embodiments, compounds of the present invention exhibit a greater decrease in cell viability with respect to both $KRAS^{G12D}$ and $KRAS^{G12V}$ compared to what is known in the art. Compounds of the present invention may also exhibit a greater decrease in cell viability respect to other RAS mutants disclosed herein, or combinations thereof.

In some embodiments, a compound of the present invention may exhibit greater metabolic stability, permeability, or solubility, or a combination thereof, versus what is known in the art. Methods for measuring such properties are known in the art. In some embodiments, a compound of the present invention may exhibit improvements with respect to any of the following properties, or a combination thereof, compared to what is known in the art: selectivity, potency, cell viability, metabolic stability, permeability, or solubility.

In some embodiments, a compound of the present invention is or acts as a prodrug, such as with respect to administration to a cell or to a subject in need thereof.

Also provided are pharmaceutical compositions comprising a compound of the present invention, or a pharmaceutically acceptable salt thereof, and a pharmaceutically acceptable excipient.

Further provided is a method of treating cancer in a subject in need thereof, the method comprising administering to the subject a therapeutically effective amount of a compound of the present invention, or a pharmaceutically acceptable salt thereof. The cancer may, for example, be pancreatic cancer, colorectal cancer, non-small cell lung cancer, acute myeloid leukemia, multiple myeloma, thyroid gland adenocarcinoma, a myelodysplastic syndrome, or squamous cell lung carcinoma. In some embodiments, the cancer comprises a Ras mutation, such as K-Ras G12C, K-Ras G12D, K-Ras G12V, K-Ras G12S, K-Ras G13C, K-Ras G13D, K-Ras Q61H, K-Ras Q61R, K-Ras Q61K, or K-Ras Q61L, or a combination thereof. In some embodiments, the cancer comprises a Ras mutation, such as N-Ras G12D, N-Ras Q61R, N-Ras Q61K, N-Ras Q61L, N-Ras Q61H, or N-Ras Q61P, or a combination thereof. Other Ras mutations are described herein.

Further provided is a method of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof. For example, the Ras protein is K-Ras G12C, K-Ras G12D, K-Ras G12V, K-Ras G12S, K-Ras G13C, K-Ras G13D, K-Ras Q61H, K-Ras Q61R, K-Ras 061K, or K-Ras Q61L. The Ras protein may be, for example, N-Ras G12D, N-Ras Q61R, N-Ras Q61K, N-Ras Q61L, N-Ras Q61H, or N-Ras Q61P. Other Ras proteins are described herein. The cell may be a cancer cell, such as a pancreatic cancer cell, a colorectal cancer cell, a lung cancer (e.g., non-small cell lung cancer cell), an acute myeloid leukemia cell, a multiple myeloma cell, a thyroid gland adenocarcinoma cell, a myelodysplastic syndrome cell, a melanoma cell, or a squamous cell lung carcinoma cell. Other cancer types are described herein. The cell may be in vivo or in vitro.

With respect to compounds of the present invention, one stereoisomer may exhibit better inhibition than another stereoisomer. For example, one atropisomer may exhibit inhibition, whereas the other atropisomer may exhibit little or no inhibition.

In some embodiments, a method or use described herein further comprises administering an additional anti-cancer therapy. In some embodiments, the additional anti-cancer therapy is a HER2 inhibitor, an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, or a combination thereof. In some embodiments, the additional anticancer therapy is a SHP2 inhibitor. Other additional anti-cancer therapies are described herein.

Methods of Synthesis

The compounds described herein may be made from commercially available starting materials or synthesized using known organic, inorganic, or enzymatic processes.

The compounds of the present invention can be prepared in a number of ways well known to those skilled in the art of organic synthesis. By way of example, compounds of the present invention can be synthesized using the methods described in the Schemes below, together with synthetic methods known in the art of synthetic organic chemistry, or variations thereon as appreciated by those skilled in the art. These methods include but are not limited to those methods described in the Schemes below, Scheme 1. General synthesis of macrocyclic esters
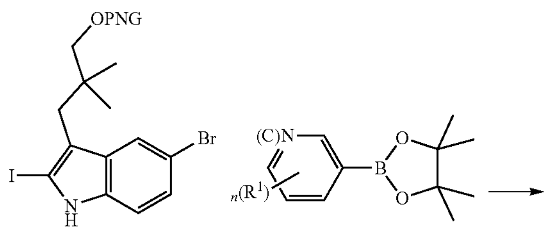
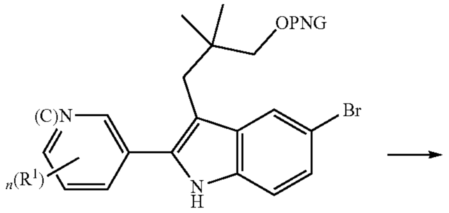
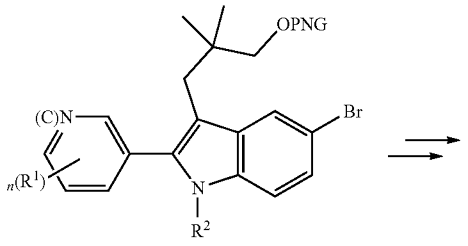
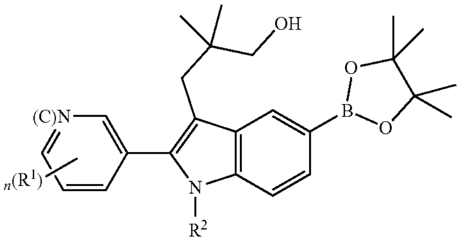
1
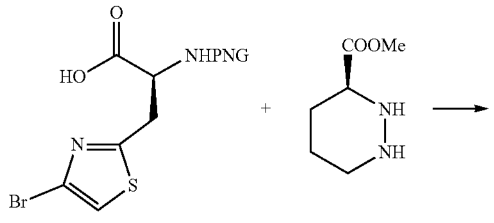
2
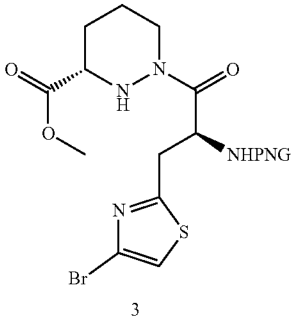
3
-continued
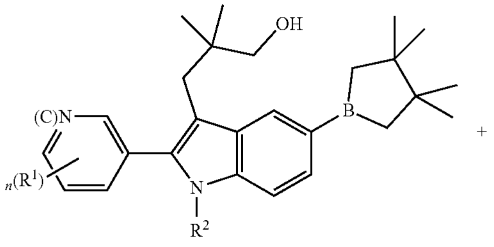
1
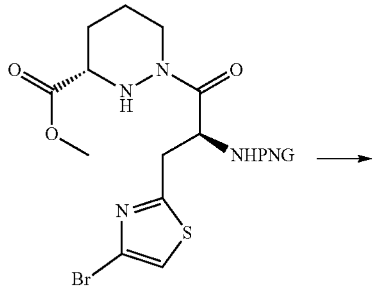
3
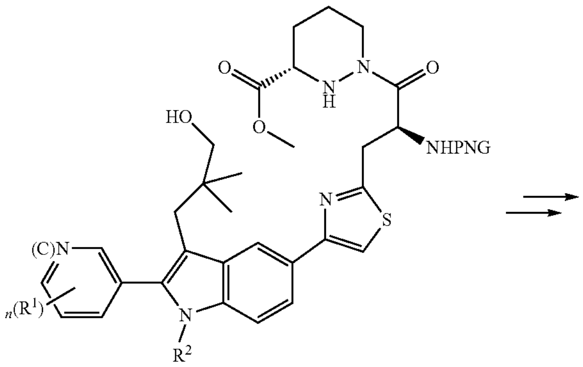
4
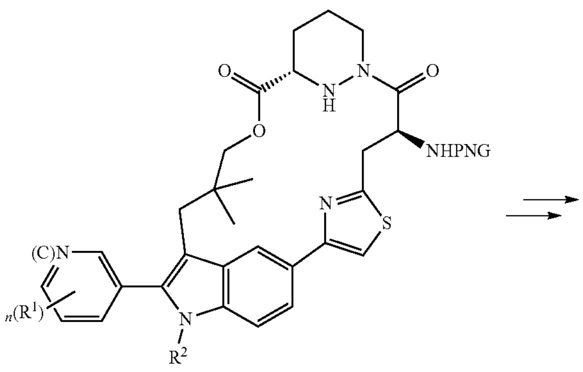
5

-continued

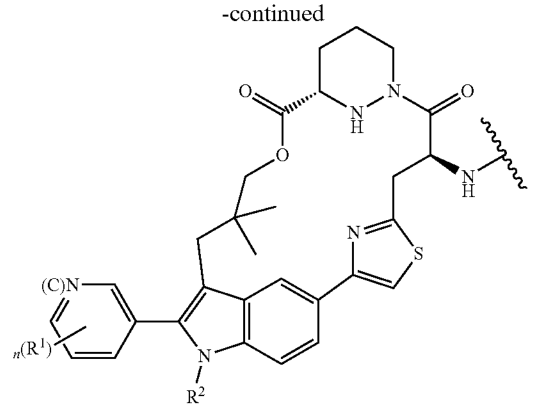

6

Optional Derivatization, e.g.:

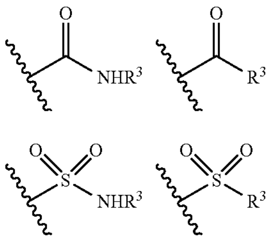

A general synthesis of macrocyclic esters is outlined in Scheme 1. An appropriately substituted indolyl boronic ester (1) can be prepared in four steps starting from protected 3-(5-bromo-2-iodo-1H-indol-3-yl)-2,2-dimethylpropan-1-ol and appropriately substituted boronic acid, including palladium mediated coupling, alkylation, de-protection, and palladium mediated borylation reactions.

Methyl-amino-3-(4-bromothiazol-2-yl)propanoyl)hexahydropyridazine-3-carboxylate (3) can be prepared via coupling of (S)-2-amino-3-(4-bromothiazol-2-yl)propanoic acid (2) with methyl (S)-hexahydropyridazine-3-carboxylate.

The final macrocyclic esters can be made by coupling of methyl-amino-3-(4-bromothiazol-2-yl)propanoyl)hexahydropyridazine-3-carboxylate (3) and an appropriately substituted indolyl boronic ester (1) in the presence of Pd catalyst followed by hydrolysis and macrolactonization steps to result in an appropriately protected macrocyclic intermediate (5). Deprotection and coupling with an appropriately substituted carboxylic acid (or other coupling partner) can result in a macrocyclic product. Additional deprotection or functionalization steps could be required to produce a final compound 6.

Further, with respect to Scheme 1, the thiazole may be replaced with an alternative optionally substituted 5 to 6-membered heteroarylene, or an optionally substituted 3 to 6-membered cycloalkylene, optionally substituted 3 to 6-membered heterocycloalkylene (e.g., morpholino), or optionally substituted 6-membered arylene (e.g., phenyl), Scheme 2. Alternative general synthesis of macrocyclic esters

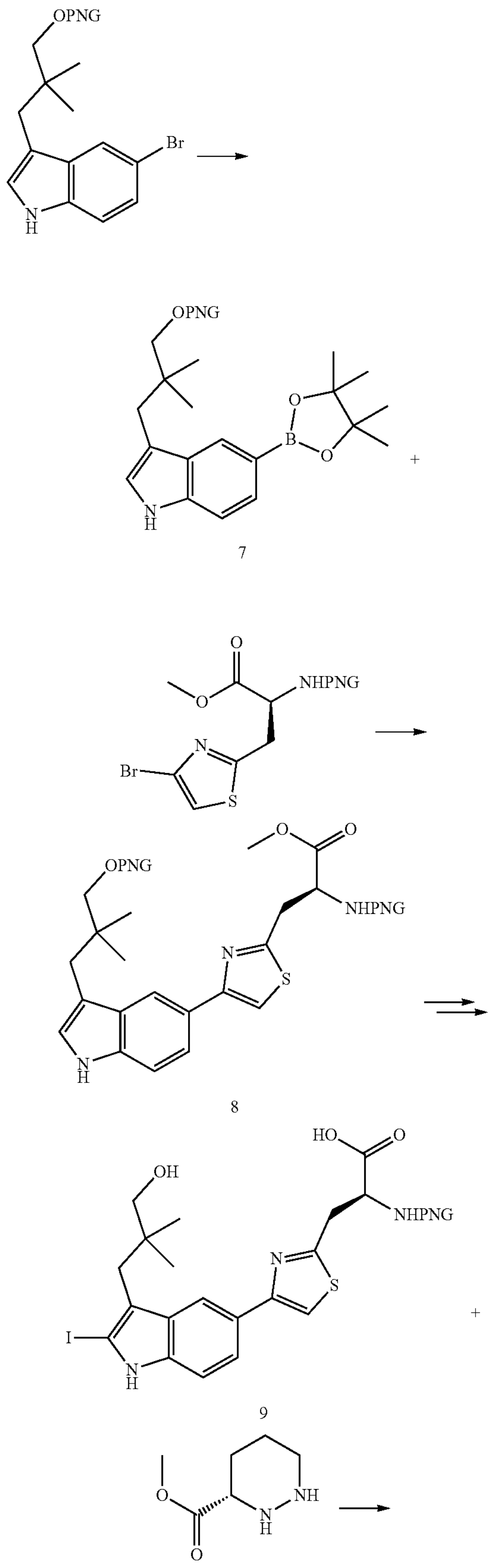

7

8

9

-continued

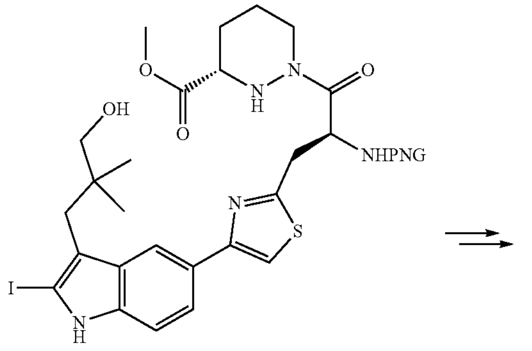

10

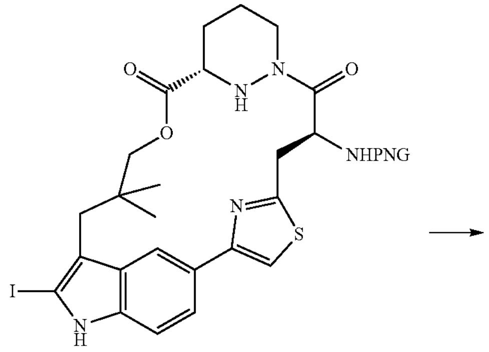

11

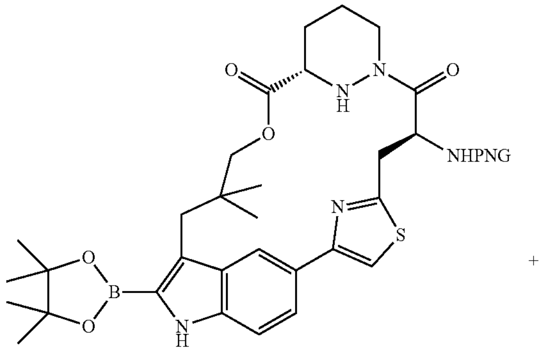

12

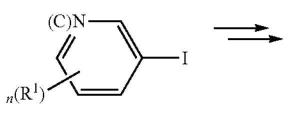

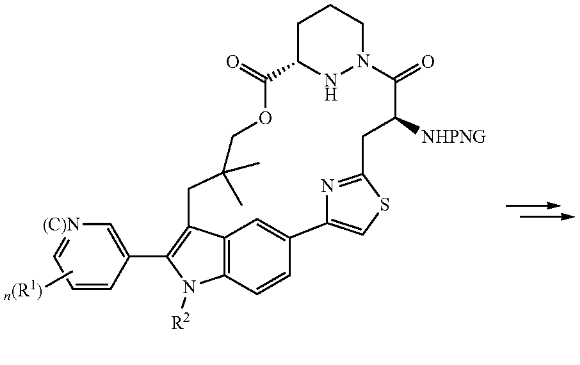

-continued

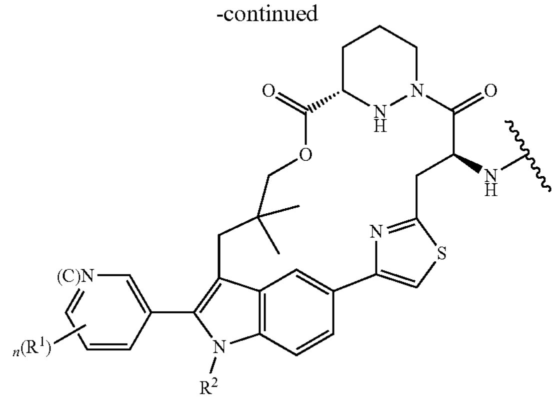

6

Optional Derivatization, e.g.:

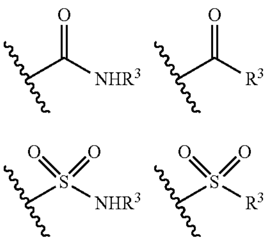

Alternatively, macrocyclic esters can be prepared as described in Scheme 2. An appropriately substituted and protected indolyl boronic ester (7) can be coupled in the presence of Pd catalyst with (S)-2-amino-3-(4-bromothiazol-2-yl)propanoic acid, followed by iodination, deprotection, and ester hydrolysis. Subsequent coupling with methyl (S)-hexahydropyridazine-3-carboxylate, followed by hydrolysis and macrolactonization can result in iodo intermediate (11). Subsequent palladium mediated borylation and coupling in the presence of Pd catalyst with an appropriately substituted iodo aryl or iodo heteroaryl intermediate can yield an appropriately protected macrocyclic intermediate. Alkylation, deprotection and coupling with an appropriately substituted carboxylic acid carboxylic acid (or other coupling partner) results in a macrocyclic product. Additional deprotection or functionalization steps could be required to produce a final compound 6.

Further, with respect to Scheme 2, the thiazole may be replaced with an alternative optionally substituted 5 to 6-membered heteroarylene, or an optionally substituted 3 to 6-membered cycloalkylene, optionally substituted 3 to 6-membered heterocycloalkylene (e.g., morpholino), or optionally substituted 6-membered arylene (e.g., phenyl).

Compounds of Table 1a or Table 1 b herein were prepared using methods disclosed herein or were prepared using methods described herein combined with the knowledge of one of skill in the art.

Pharmaceutical Compositions and Methods of Use

Pharmaceutical Compositions and Methods of Administration

The compounds with which the invention is concerned are Ras inhibitors, and are useful in the treatment of cancer. Accordingly, one embodiment of the present invention provides pharmaceutical compositions containing a compound of the invention or a pharmaceutically acceptable salt thereof, and a pharmaceutically acceptable excipient, as well as methods of using the compounds of the invention to prepare such compositions.

As used herein, the term "pharmaceutical composition" refers to a compound, such as a compound of the present invention, or a pharmaceutically acceptable salt thereof, formulated together with a pharmaceutically acceptable excipient.

In some embodiments, a compound is present in a pharmaceutical composition in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Excipients include, but are not limited to: butylated optionally substituted hydroxyltoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, optionally substituted hydroxylpropyl cellulose, optionally substituted hydroxylpropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients. See, e.g., Ansel, et al., Ansel's Pharmaceutical Dosage Forms and Drug Delivery Systems. Philadelphia: Lippincott, Williams & Wilkins, 2004; Gennaro, et al., Remington: The Science and Practice of Pharmacy. Philadelphia: Lippincott, Williams & Wilkins, 2000; and Rowe, Handbook of Pharmaceutical Excipients. Chicago, Pharmaceutical Press, 2005. In some embodiments, a composition includes at least two different pharmaceutically acceptable excipients.

Compounds described herein, whether expressly stated or not, may be provided or utilized in salt form, e.g., a pharmaceutically acceptable salt form, unless expressly stated to the contrary. The term "pharmaceutically acceptable salt," as use herein, refers to those salts of the compounds described herein that are, within the scope of sound medical judgment, suitable for use in contact with the tissues of humans and other animals without undue toxicity, irritation, allergic response and the like, and are commensurate with a reasonable benefit/risk ratio. Pharmaceutically acceptable salts are well known in the art. For example, pharmaceutically acceptable salts are described in: Berge et al., *J Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention, be prepared from inorganic or organic bases. In some embodiments, the compounds are prepared or used as pharmaceutically acceptable salts prepared as addition products of pharmaceutically acceptable acids or bases. Suitable pharmaceutically acceptable acids and bases are well-known in the art, such as hydrochloric, sulfuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

As used herein, the term "subject" refers to any member of the animal kingdom. In some embodiments, "subject" refers to humans, at any stage of development. In some embodiments, "subject" refers to a human patient. In some embodiments, "subject" refers to non-human animals. In some embodiments, the non-human animal is a mammal (e.g., a rodent, a mouse, a rat, a rabbit, a monkey, a dog, a cat, a sheep, cattle, a primate, or a pig). In some embodiments, subjects include, but are not limited to, mammals, birds, reptiles, amphibians, fish, or worms. In some embodiments, a subject may be a transgenic animal, genetically-engineered animal, or a clone.

As used herein, the term "dosage form" refers to a physically discrete unit of a compound (e.g., a compound of the present invention) for administration to a subject. Each unit contains a predetermined quantity of compound. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms. As used herein, the term "dosing regimen" refers to a set of unit doses (typically more than one) that are administered individually to a subject, typically separated by periods of time. In some embodiments, a given therapeutic compound (e.g., a compound of the present invention) has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., a compound of the present invention) that partially or completely alleviates, ameliorates, relieves, inhibits, delays onset of, reduces severity of, or reduces incidence of one or more symptoms, features, or causes of a particular disease, disorder, or condition. In some embodiments, such treatment may be administered to a subject who does not exhibit signs of the relevant disease, disorder or condition or of a subject who exhibits only early signs of the disease, disorder, or condition. Alternatively, or additionally, in some embodiments, treatment may be administered to a subject who exhibits one or more established signs of the relevant disease, disorder or condition. In some embodiments, treatment may be of a subject who has been diagnosed as suffering from the relevant disease, disorder, or condition. In some embodiments, treatment may be of a subject known to have one or more susceptibility factors that are statistically correlated with increased risk of development of the relevant disease, disorder, or condition.

The term "therapeutically effective amount" means an amount that is sufficient, when administered to a population suffering from or susceptible to a disease, disorder, or condition in accordance with a therapeutic dosing regimen, to treat the disease, disorder, or condition. In some embodiments, a therapeutically effective amount is one that reduces the incidence or severity of, or delays onset of, one or more symptoms of the disease, disorder, or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, a therapeutically effective amount may be formulated or administered in a single dose. In some embodiments, a therapeutically effective amount may be formulated or administered in a plurality of doses, for example, as part of a dosing regimen.

For use as treatment of subjects, the compounds of the invention, or a pharmaceutically acceptable salt thereof, can be formulated as pharmaceutical or veterinary compositions. Depending on the subject to be treated, the mode of administration, and the type of treatment desired, e.g., prevention, prophylaxis, or therapy, the compounds, or a pharmaceutically acceptable salt thereof, are formulated in ways consonant with these parameters. A summary of such techniques may be found in *Remington: The Science and Practice of Pharmacy,* $21^{st}$ Edition, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compositions can be prepared according to conventional mixing, granulating or coating methods, respectively, and the present pharmaceutical compositions can contain from about 0.1% to about 99%, from about 5% to about 90%, or from about 1% to about 20% of a compound of the present invention, or pharmaceutically acceptable salt thereof, by weight or volume. In some embodiments, compounds, or a pharmaceutically acceptable salt thereof, described herein may be present in amounts totaling 1-95% by weight of the total weight of a composition, such as a pharmaceutical composition.

The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

As used herein, the term "administration" refers to the administration of a composition (e.g., a compound, or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal or vitreal.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. A formulation will generally include a diluent as well as, in some cases, adjuvants, buffers, preservatives and the like. Compounds, or a pharmaceutically acceptable salt thereof, can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively noninvasive methods such as the use of suppositories, transdermal patches, transmucosal delivery and intranasal administration. Oral administration is also suitable for compounds of the invention, or a pharmaceutically acceptable salt thereof. Suitable forms include syrups, capsules, and tablets, as is understood in the art.

Each compound, or a pharmaceutically acceptable salt thereof, as described herein, may be formulated in a variety of ways that are known in the art. For example, the first and second agents of the combination therapy may be formulated together or separately. Other modalities of combination therapy are described herein.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds, or a pharmaceutically acceptable salt thereof, may vary in potency as therapy progresses); or the kit may contain multiple doses suitable for administration to multiple subjects ("bulk packaging"). The kit components may be assembled in cartons, blister packs, bottles, tubes, and the like.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, optionally substituted hydroxylpropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion-controlled release can be achieved by appropriate coating of a tablet, capsule, pellet, or granulate formulation of compounds, or by incorporating the compound, or a pharmaceutically acceptable salt thereof, into an appropriate matrix. A controlled release coating may include one or more of the coating substances mentioned above or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-optionally substituted hydroxylmethacrylate, methacrylate hydrogels, 1,3 butylene glycol, ethylene glycol methacrylate, or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, or halogenated fluorocarbon.

The liquid forms in which the compounds, or a pharmaceutically acceptable salt thereof, and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the invention, or a pharmaceutically acceptable salt thereof, will depend on the nature of the compound, and can readily be determined by one skilled in the art. A dosage may be, for example, about 0.001 mg to about 2000 mg per day, about 1 mg to about 1000 mg per day, about 5 mg to about 500 mg per day, about 100 mg to about 1500 mg per day, about 500 mg to about 1500 mg per day, about 500 mg to about 2000 mg per day, or any range derivable therein. In some embodiments, the daily dose range for oral administration, for example, may lie within the range of from about 0.001 mg to about 2000 mg per kg body weight of a human, in single or divided doses. On the other hand, it may be necessary to use dosages outside these limits in some cases.

In some embodiments, the pharmaceutical composition may further comprise an additional compound having anti-proliferative activity. Depending on the mode of administration, compounds, or a pharmaceutically acceptable salt thereof, will be formulated into suitable compositions to permit facile delivery. Each compound, or a pharmaceutically acceptable salt thereof, of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

It will be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics or procedures and the desired therapeutic effect to be achieved. It will also be appreciated that the therapies employed may achieve a desired effect for the same disorder, or they may achieve different effects (e.g., control of any adverse effects).

Administration of each drug in a combination therapy, as described herein, can, independently, be one to four times daily for one day to one year, and may even be for the life of the subject. Chronic, long-term administration may be indicated.

Methods of Use

In some embodiments, the invention discloses a method of treating a disease or disorder that is characterized by aberrant Ras activity due to a Ras mutant. In some embodiments, the disease or disorder is a cancer.

Accordingly, also provided is a method of treating cancer in a subject in need thereof, the method comprising administering to the subject a therapeutically effective amount of a compound of the present invention, or a pharmaceutically acceptable salt thereof, or a pharmaceutical composition comprising such a compound or salt. In some embodiments, the cancer is colorectal cancer, non-small cell lung cancer, small-cell lung cancer, pancreatic cancer, appendiceal cancer, melanoma, acute myeloid leukemia, small bowel cancer, ampullary cancer, germ cell cancer, cervical cancer, cancer of unknown primary origin, endometrial cancer, esophagogastric cancer, GI neuroendocrine cancer, ovarian cancer, sex cord stromal tumor cancer, hepatobiliary cancer, or bladder cancer. In some embodiments, the cancer is appendiceal, endometrial or melanoma. Also provided is a method of treating a Ras protein-related disorder in a subject in need thereof, the method comprising administering to the subject a therapeutically effective amount of a compound of the present invention, or a pharmaceutically acceptable salt thereof, or a pharmaceutical composition comprising such a compound or salt.

In some embodiments, the compounds of the present invention or pharmaceutically acceptable salts thereof, pharmaceutical compositions comprising such compounds or salts, and methods provided herein may be used for the treatment of a wide variety of cancers including tumors such as lung, prostate, breast, brain, skin, cervical carcinomas, testicular carcinomas, etc. More particularly, cancers that may be treated by the compounds or salts thereof, pharmaceutical compositions comprising such compounds or salts, and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. Other cancers include, for example:

Cardiac, for example: sarcoma (angiosarcoma, fibrosarcoma, rhabdomyosarcoma, liposarcoma), myxoma, rhabdomyoma, fibroma, lipoma and teratoma;

Lung, for example: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal, for example: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract, for example: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver, for example: hepatoma (hepatocellular carcinoma), cholangiocarcinoma, hepatoblastoma, angiosarcoma, hepatocellular adenoma, hemangioma;

Biliary tract, for example: gall bladder carcinoma, ampullary carcinoma, cholangiocarcinoma;

Bone, for example: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system, for example: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, neurofibromatosis type 1, meningioma, glioma, sarcoma);

Gynecological, for example: uterus (endometrial carcinoma, uterine carcinoma, uterine corpus endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic, for example: blood (myeloid leukemia (acute and chronic), acute lymphoblastic leukemia, chronic lymphocytic leukemia, myeloproliferative diseases (e.g., myelofibrosis and myeloproliferative neoplasms, multiple myeloma, myelodysplastic syndrome), Hodgkin's disease, non-Hodgkin's lymphoma (malignant lymphoma);

Skin, for example: malignant melanoma, basal cell carcinoma, squamous cell carcinoma, Kaposi's sarcoma, moles dysplastic nevi, lipoma, angioma, dermatofibroma, keloids, psoriasis, and Adrenal glands, for example: neuroblastoma.

In some embodiments, the Ras protein is wild-type. ($Ras^{WT}$). Accordingly, in some embodiments, a compound of the present invention is employed in a method of treating a patient having a cancer comprising a $Ras^{WT}$ (e.g., K-$Ras^{WT}$, H-$Ras^{WT}$ or N-$Ras^{WT}$). In some embodiments, the Ras protein is Ras amplification (e.g., K-$Ras^{amp}$). Accordingly, in some embodiments, a compound of the present invention is employed in a method of treating a patient having a cancer comprising a $Ras^{amp}$ (K-$Ras^{amp}$, H-$Ras^{amp}$ or N-$Ras^{amp}$). In some embodiments, the cancer comprises a Ras mutation, such as a Ras mutation described herein. In some embodiments, a mutation is selected from:

(a) the following K-Ras mutants: G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V, and combinations thereof;

(b) the following H-Ras mutants: Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R, and combinations thereof; and (c) the following N-Ras mutants: Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T, and combinations thereof;

or a combination of any of the foregoing. In some embodiments, the cancer comprises a Ras mutation selected from the group consisting of G12C, G13C, G12A, G12D, G13D, G12S, G13S, G12V and G13V. In some embodiments, the cancer comprises at least two Ras mutations selected from the group consisting of G12C, G13C, G12A, G12D, G13D, G12$, G13S, G12V and G13V. In some embodiments, a compound of the present invention inhibits more than one Ras mutant. For example, a compound may inhibit both K-Ras G12D and K-Ras G12C. In some embodiments, a compound may inhibit both K-Ras G12V and K-Ras G120. In some embodiments, a compound may inhibit both K-Ras G120 and K-Ras G130. In some embodiments, a compound may inhibit both K-Ras G120 and K-Ras G12V. In some embodiments, a compound may inhibit both K-Ras G12V and K-Ras G12S. In some embodiments, the mutation is selected from the group consisting of G12A, G12C, G12D, G12E, G12F, G12H, G121, G12K, G12L, G12M, G12N, G12P, G12Q, G12R, G12S, G12T, G12V, G12W and G12Y, or a combination thereof, of K-Ras, N-Ras or H-Ras. In some embodiments, the mutation is selected from the group consisting of G12H, G121, G12K, G12M, G12N, G12P, G12Q, G12T, G12W, and G12Y, or a combination thereof, of K-Ras, N-Ras or H-Ras. In some embodiments, the compound inhibits wild-type K-Ras, wild-type H-Ras or wild-type N-Ras, and optionally further inhibits a mutated Ras protein containing a mutation as described herein. In some embodiments, the cancer is non-small cell lung cancer and the Ras mutation comprises a K-Ras mutation, such as K-Ras G12C. In some embodiments, the cancer is colorectal cancer and the Ras mutation comprises a K-Ras mutation, such as K-Ras G12C. In some embodiments, the cancer is pancreatic cancer and the Ras mutation comprises an N-Ras mutation, such as N-Ras G12D. In some embodiments, the cancer is non-small cell lung cancer and the Ras protein is K-$Ras^{amp}$.

Additionally, in some embodiments, the cancer comprises a K-Ras mutation selected from the group consisting of G12C, G12D, G13C, G12V, G13D, G12R, G12S, Q61H, 061K and Q61L. In some embodiments, the cancer comprises an N-Ras mutation selected from the group consisting of G12C, Q61H, Q61K, Q61 L, Q61P and Q61R. In some embodiments, the cancer comprises an H-Ras mutation selected from the group consisting of Q61H and Q61 L. In some embodiments, the cancer comprises a Ras mutation selected from the group consisting of G12C, G13C, G12A, G12D, G13D, G12S, G13S, G12V and G13V. In some embodiments, the cancer comprises at least two Ras mutations selected from the group consisting of G12C, G13C, G12A, G12D, G13D, G12S, G13S, G12V and G13V. In some embodiments, a compound of the present invention inhibits more than one Ras mutant. For example, a compound may inhibit both K-Ras G12C and K-Ras G13C. A compound may inhibit both N-Ras G12C and K-Ras 0120. In some embodiments, a compound may inhibit both K-Ras 0120 and K-Ras G12D.

In some embodiments, a compound may inhibit both K-Ras G12V and K-Ras G120. In some embodiments, a compound may inhibit both K-Ras G12V and K-Ras G12S. In some embodiments, a compound of the present invention inhibits $Ras^{WT}$ in addition to one or more additional Ras mutations (e.g., K-, H- or N-$Ras^{WT}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K-, H- or N-$Ras^{WT}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K-, H- or N-$Ras^{WT}$ and N-Ras Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T). In some embodiments, a compound of the present invention inhibits $Ras^{amp}$, in addition to one or more additional Ras mutations (e.g., K-, H- or N-$Ras^{amp}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K-, H- or N-$Ras^{amp}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K-, H- or N-Rasa-r and N-Ras Q61R, Q61K, G12D, Q61L, Q61H, G13R, G13D, G12S, G12C, G12V, G12A, G13V, G12R, P185S, G13C, A146T, G60E, 061P, A59D, E132K, E49K, T50I, A146V, or A59T).

Methods of detecting Ras mutations are known in the art. Such means include, but are not limited to direct sequencing, and utilization of a high-sensitivity diagnostic assay (with CE-IVD mark), e.g., as described in Domagala, et al., Pol J Pathol 3:145-164 (2012), incorporated herein by reference in its entirety, including TheraScreen PCR; AmoyDx; PNA-Clamp; RealQuality; EntroGen; LightMix; StripAssay; Hybcell plexA; Devyser; Surveyor; Cobas; and TheraScreen Pyro. See, also, e.g., WO 20201106640.

In some embodiments, the cancer is non-small cell lung cancer and the Ras mutation comprises a K-Ras mutation, such as K-Ras G12C, K-Ras G12V or K-Ras G12D. In some embodiments, the cancer is colorectal cancer and the Ras mutation comprises a K-Ras mutation, such as K-Ras G12C, K-Ras G12V or K-Ras G12D. In some embodiments, the cancer is pancreatic cancer and the Ras mutation comprises an K-Ras mutation, such as K-Ras G12D or K-Ras G12V. In some embodiments, the cancer is pancreatic cancer and the Ras mutation comprises an N-Ras mutation, such as N-Ras G12D. In some embodiments, the cancer is melanoma and the Ras mutation comprises an N-Ras mutation, such as N-Ras Q61R or N-Ras Q61K. In some embodiments, the cancer is non-small cell lung cancer and the Ras protein is K-$Ras^{amp}$. In any of the foregoing if not already specified, a compound may inhibit $Ras^{WT}$ (e.g., K-, H- or N-$Ras^{WT}$) or $Ras^{amp}$ (e.g., K-, H- or N-$Ras^{amp}$) as well.

In some embodiments, a cancer comprises a Ras mutation and an $STK11^{LOF}$, a KEAP1, an EPHA5 or an NF1 mutation, or a combination thereof. In some embodiments, the cancer is non-small cell lung cancer and comprises a K-Ras G12C mutation. In some embodiments, the cancer is non-small cell lung cancer and comprises a K-Ras G12C mutation, an STK11 LOF mutation, and a KEAP1 mutation.

In some embodiments, the cancer is non-small cell lung cancer and comprises a K-Ras G12C mutation and an $STK11^{LOF}$ mutation. In some embodiments, the cancer is non-small cell lung cancer and comprises a K-Ras G12C mutation and an $STK11^{LOF}$ mutation. In some embodiments, a cancer comprises a K-Ras G13C Ras mutation and an $STK11^{LOF}$a KEAP1, an EPHA5 or an NF1 mutation. In some embodiments, the cancer is non-small cell lung cancer and comprises a K-Ras G12D mutation. In some embodiments, the cancer is non-small cell lung cancer and comprises a K-Ras G12V mutation. In some embodiments, the cancer is colorectal cancer and comprises a K-Ras G12C mutation. In some embodiments, the cancer is pancreatic cancer and comprises a K-Ras G12D mutation. In some embodiments, the cancer is pancreatic cancer and comprises a K-Ras G12V mutation. In some embodiments, the cancer is endometrial cancer and comprises a K-Ras G12C mutation. In some embodiments, the cancer is gastric cancer and comprises a K-Ras G12C mutation. In any of the foregoing, a compound may inhibit $Ras^{WT}$ (e.g., K-, H- or N-$Ras^{WT}$) or $Ras^{amp}$ (e.g., K-, H- or N-$Ras^{amp}$) as well.

Also provided is a method of inhibiting a Ras protein in a cell, the method comprising contacting the cell with an effective amount of a compound of the present invention, or a pharmaceutically acceptable salt thereof. A compound, or a pharmaceutically acceptable salt thereof, may inhibit more than one type of Ras protein in a cell. A method of inhibiting RAF-Ras binding, the method comprising contacting the cell with an effective amount of a compound of the present invention, or a pharmaceutically acceptable salt thereof, is also provided. The cell may be a cancer cell. The cancer cell may be of any type of cancer described herein. The cell may be in vivo or in vitro, Combination Therapy The methods of the invention may include a compound of the invention used alone or in combination with one or more additional therapies (e.g., non-drug treatments or therapeutic agents). The dosages of one or more of the additional therapies (e.g., non-drug treatments or therapeutic agents) may be reduced from standard dosages when administered alone. For example, doses may be determined empirically from drug combinations and permutations or may be deduced by isobolographic analysis (e.g., Black et al., *Neurology* 65:S3-S6 (2005)).

A compound of the present invention may be administered before, after, or concurrently with one or more of such additional therapies. When combined, dosages of a compound of the invention and dosages of the one or more additional therapies (e.g., non-drug treatment or therapeutic agent) provide a therapeutic effect (e.g., synergistic or additive therapeutic effect) A compound of the present invention and an additional therapy, such as an anti-cancer agent, be administered together, such as in a unit pharmaceutical composition, or separately and, when administered separately, this may occur simultaneously or sequentially. Such sequential administration may be close or remote in time.

In some embodiments, the additional therapy is the administration of side-effect limiting agents (e.g., agents intended to lessen the occurrence or severity of side effects of treatment. For example, in some embodiments, the compounds of the present invention can also be used in combination with a therapeutic agent that treats nausea. Examples of agents that can be used to treat nausea include: dronabinol, granisetron, metoclopramide, ondansetron, and prochlorperazine, or pharmaceutically acceptable salts thereof.

In some embodiments, the one or more additional therapies includes a non-drug treatment (e.g., surgery or radiation therapy). In some embodiments, the one or more additional therapies includes a therapeutic agent (e.g., a compound or biologic that is an anti-angiogenic agent, signal transduction inhibitor, antiproliferative agent, glycolysis inhibitor, or autophagy inhibitor). In some embodiments, the one or more additional therapies includes a non-drug treatment (e.g., surgery or radiation therapy) and a therapeutic agent (e.g., a compound or biologic that is an anti-angiogenic agent, signal transduction inhibitor, antiproliferative agent, glycolysis inhibitor, or autophagy inhibitor). In other embodiments, the one or more additional therapies includes two therapeutic agents. In still other embodiments, the one or more additional therapies includes three therapeutic agents. In some embodiments, the one or more additional therapies includes four or more therapeutic agents.

In this Combination Therapy section, all references are incorporated by reference for the agents described, or a pharmaceutically acceptable salt, solvate, isomer (e.g., stereoisomer), prodrug, or tautomer thereof, whether explicitly stated as such or not.

Non-Drug Therapies

Examples of non-drug treatments include, but are not limited to, radiation therapy, cryotherapy, hyperthermia, surgery (e.g., surgical excision of tumor tissue), and T cell adoptive transfer (ACT) therapy.

In some embodiments, the compounds of the invention may be used as an adjuvant therapy after surgery. In some embodiments, the compounds of the invention may be used as a neo-adjuvant therapy prior to surgery.

Radiation therapy may be used for inhibiting abnormal cell growth or treating a hyperproliferative disorder, such as cancer, in a subject (e.g., mammal (e.g., human)). Techniques for administering radiation therapy are known in the art. Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachy therapy." as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide (s), e.g., a solution of I-125 or I-131, or a radioactive fluid can be produced using a slurry of a suitable fluid containing small particles of solid radionuclides, such as Au-198, or Y-90. Moreover, the radionuclide(s) can be embodied in a gel or radioactive micro spheres.

In some embodiments, the compounds of the present invention can render abnormal cells more sensitive to treatment with radiation for purposes of killing or inhibiting the growth of such cells. Accordingly, this invention further relates to a method for sensitizing abnormal cells in a mammal to treatment with radiation which comprises administering to the mammal an amount of a compound of the present invention, which amount is effective to sensitize abnormal cells to treatment with radiation. The amount of the compound in this method can be determined according to the means for ascertaining effective amounts of such compounds described herein. In some embodiments, the compounds of the present invention may be used as an adjuvant therapy after radiation therapy or as a neo-adjuvant therapy prior to radiation therapy.

In some embodiments, the non-drug treatment is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 7,572,631; 5,883,223; 6,905,874; 6,797,514; and 6,867,041.

Therapeutic Agents

A therapeutic agent may be a compound used in the treatment of cancer or symptoms associated therewith.

For example, a therapeutic agent may be a steroid. Accordingly, in some embodiments, the one or more additional therapies includes a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof.

Further examples of therapeutic agents that may be used in combination therapy with a compound of the present invention include compounds described in the following patents: U.S. Pat. Nos. 6,258,812, 6,630,500, 6,515,004, 6,713,485, 5,521,184, 5,770,599, 5,747,498, 5,990,141, 6,235,764, and 8,623,885, and International Patent Applications WO01/37820, WO01/32651, WO02/68406, WO02/66470, WO02/55501, WO04/05279, WO04/07481, WO04/07458, WO04/09784, WO02/59110, WO99/45009, WO00/59509, WO99/61422, WO00/12089, and WO00/102871.

A therapeutic agent may be a biologic (e.g., cytokine (e.g., interferon or an interleukin such as IL-2)) used in treatment of cancer or symptoms associated therewith. In some embodiments, the biologic is an immunoglobulin-based biologic, e.g., a monoclonal antibody (e.g., a humanized antibody, a fully human antibody, an Fc fusion protein, or a functional fragment thereof) that agonizes a target to stimulate an anti-cancer response or antagonizes an antigen important for cancer. Also included are antibody-drug conjugates.

A therapeutic agent may be a T-cell checkpoint inhibitor. In one embodiment, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein.

In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PD-L1. In some embodiments, the checkpoint inhibitor is an inhibitor or antagonist (e.g., an inhibitory antibody or Fc fusion or small molecule inhibitor) of PD-L2 (e.g., a PD-L2/Ig fusion protein). In some embodiments, the checkpoint inhibitor is an inhibitor or antagonist (e.g., an inhibitory antibody or small molecule inhibitor) of B7-H3, B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the checkpoint inhibitor is pembrolizumab, nivolumab, PDR001 (NVS), REGN2810 (Sanofi/Regeneron), a PD-L1 antibody such as, e.g., avelumab, durvalumab, atezolizumab, pidilizumab, JNJ-63723283 (JNJ), BGB-A317 (BeiGene & Celgene) or a checkpoint inhibitor disclosed in Preusser, M. et al. (2015) Nat. Rev. Neurol., including, without limitation, ipilimumab, tremelimumab, nivolumab, pembrolizumab, AMP224, AMP514/MED10680, BMS936559, MED14736, MPDL3280A, MSB0010718C, BMS986016, IMP321, lirilumab, IPH2101, 1-7F9, and KW-6002.

A therapeutic agent may be an anti-TIGIT antibody, such as MBSA43, BMS-986207, MK-7684, COM902, AB154, MTIG7192A or OMP-313M32 (etigilimab).

A therapeutic agent may be an agent that treats cancer or symptoms associated therewith (e.g., a cytotoxic agent, non-peptide small molecules, or other compound useful in the treatment of cancer or symptoms associated therewith, collectively, an "anti-cancer agent"). Anti-cancer agents can be, e.g., chemotherapeutics or targeted therapy agents.

Anti-cancer agents include mitotic inhibitors, intercalating antibiotics, growth factor inhibitors, ceil cycle inhibitors, enzymes, topoisomerase inhibitors, biological response modifiers, alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Further anti-cancer agents include leucovorin (LV), irenotecan, oxaliplatin, capecitabine, paclitaxel, and doxetaxel. In some embodiments, the one or more additional therapies includes two or more anti-cancer agents. The two or more anti-cancer agents can be used in a cocktail to be administered in combination or administered separately. Suitable dosing regimens of combination anti-cancer agents are known in the art and described in, for example, Saltz et al. *Proc. Am. Soc. Clin. Oncol.* 18:233a (1999), and Douillard et al., *Lancet* 355(9209):1041-1047 (2000).

Other non-limiting examples of anti-cancer agents include GleevecÆ (Imatinib Mesylate); KyprolisÆ (carfilzomib); VelcadeÆ (borezoib); Casodex (bicalutamide); IressaÆ (gefitinib); alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin A; spongistatin; nitrogen mustards such as chlorambucil, chlornaphazine, cholophosphamide, estramustine, ifosfamide, mechlorethaniine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gammall and calicheamicin omegall (see, e.g., *Agnew, Chem. Intl. Ed Engl.* 33:183-186 (1994)); dynemicin such as dynemicin A; bisphosphonates such as clodronate; an esperamicin; neocarzinostatin chromophore and related chromoprotein enediyne antibiotic chromophores, aclacinomysins, actinomycin, authramycin, azaserine, bleomycins, cactinomycin, calicheamicin, carabicin, caminomycin, caminomycin, carzinophilin, chromomycins, dactinomycin, daunorubicin, detorubicin, 6-diazo-5-oxo-L-norleucine, adriamycin (doxorubicin), morpholino-doxorubicin, cyanomorpholino-doxorubicin, 2-pyrrolino-doxorubicin, deoxydoxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptiniurn acetate; an epothilone such as epothilone B; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSKÆ polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethane; vindesine; dacarbazine; mannomustine; mitobronitol; mitolactol; pipobroman; gacytosine; arabinoside ("Ara-C"); cyclophosphamide; thiotepa; taxoids, e.g., TaxolÆ (paclitaxel), AbraxaneÆ (cremophor-free, albumin-engineered nanoparticle formulation of paclitaxel), and TaxotereÆ (doxetaxel); chloranbucil; tamoxifen (Nolvadex™); raloxifene; aromatase inhibiting 4(5)-imdazoles; 4-hydroxytamoxifen; trioxifene; keoxifene; LY 117018; onapristone; toremifene (FarestonÆ); flutamide, nilutamide, bicalutamide, leuprolide, goserelin; chlorambucil; GemzarÆgemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; NavelbineÆ (vinorelbine); novantrone; teniposide; edatrexate; daunomycin; aminopterin; ibandronate; irinotecan (e.g., CPT-11); topoisomerase inhibitor RFS 2000; difluoromethylomithine (DMFO); retinoids such as retinoic acid; esperamicins; capecitabine (e.g., XelodaÆ); and pharmaceutically acceptable salts of any of the above.

Additional non-limiting examples of anti-cancer agents include trastuzumab (HerceptinÆ), bevacizumab (AvastinÆ), cetuximab (ErbituxÆ), rituximab (RituxanÆ), TaxolÆ, ArimidexÆ, ABVD, avicine, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastics (e.g., cell-cycle nonspecific antineoplastic agents, and other antineoplastics described herein), antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, dichloroacetic acid, discodermolide, elsamitrucin, enocitabine, eribulin, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitors, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

Further non-limiting examples of anti-cancer agents include natural products such as vinca alkaloids (e.g., vinblastine, vincristine, and vinorelbine), epidipodophyllotoxins (e.g., etoposide and teniposide), antibiotics (e.g., dactinomycin (actinomycin D), daunorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., a CDK4/6 inhibitor such as abemaciclib, ribociclib, palbociclib; seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs, pyrimidine analogs (e.g., fluorouracil, floxuridine, and cytarabine), purine analogs and related inhibitors (e.g., mercaptopurine, thioguanine, pentostatin, and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTOR inhibitors (e.g., vistusertib, temsirolimus, everolimus, ridaforolimus, and sirolimus), KSP (Eg5) inhibitors (e.g., Array 520). DNA binding agents (e.g., ZalypsisÆ), PI3K inhibitors such as PI3K delta inhibitor (e.g., GS-1101 and TGR-1202). PI3K delta and gamma inhibitor (e.g., CAL-130), copanlisib, alpelisib and idelalisib; multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CSI (e.g., elotuzumab), HSP90 inhibitors (e.g., 17 AAG and KOS 953), PI3K/Akt inhibitors (e.g., perifosine), Akt inhibitors (e.g., GSK-2141795), PKC inhibitors (e.g., enzastaurin), FTIs (e.g., Zamestra™), anti-CD138 (e.g., BT062), Torcl/2 specific kinase inhibitors (e.g., INK128), ER/UPR targeting agents (e.g., MKC-3946), cFMS inhibitors (e.g., ARRY-382), JAK1/2 inhibitors (e.g., CYT387), PARP inhibitors (e.g., olaparib and veliparib (ABT-888)), and BCL-2 antagonists.

In some embodiments, an anti-cancer agent is selected from mechlorethamine, camptothecin, ifosfamide, tamoxifen, raloxifene, gemcitabine, Navelbine, sorafenib, or any analog or derivative variant of the foregoing.

In some embodiments, the anti-cancer agent is a HER2 inhibitor. Non-limiting examples of HER2 inhibitors include monoclonal antibodies such as trastuzumab (HerceptinÆ) and pertuzumab (PerjetaÆ); small molecule tyrosine kinase inhibitors such as gefitinib (IressaÆ), erlotinib (TarcevaÆ), pilitinib, CP-654577, CP-724714, canertinib (CI 1033), HKI-272, lapatinib (GW-572016; TykerbÆ), PKI-166, AEE788, BMS-599626, HKI-357, BIBW 2992, ARRY-334543, and JNJ-26483327.

In some embodiments, an anti-cancer agent is an ALK inhibitor. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO 05016894.

In some embodiments, an anti-cancer agent is an inhibitor of a member downstream of a Receptor Tyrosine Kinase (RTK)/Growth Factor Receptor (e.g., a SHP2 inhibitor (e.g., SHP099, TNO155, RMC-4550, RMC-4630, JAB-3068, JAB-3312, RLY-1971, ERAS-601, SH3809, PF-07284892, or BBP-398, or a pharmaceutically acceptable salt, solvate, isomer (e.g., stereoisomer), prodrug, or tautomer thereof), a SOS1 inhibitor (e.g., B1-1701963, BI-3406, SDR5, BAY-293, or RMC-5845, or a pharmaceutically acceptable salt, solvate, isomer (e.g., stereoisomer), prodrug, or tautomer thereof), a Raf inhibitor, a MEK inhibitor, an ERK inhibitor, a PI3K inhibitor, a PTEN inhibitor, an AKT inhibitor, or an mTOR inhibitor (e.g., mTORC1 inhibitor or mTORC2 inhibitor). In some embodiments, the anti-cancer agent is JAB-3312.

In some embodiments, an anti-cancer agent is a SOS1 inhibitor. In some embodiments, the SOS1 inhibitor is selected from those disclosed in WO 2021173524, WO 2021130731, WO 2021127429, WO 2021092115, WO 2021105960, WO 2021074227, WO 2020180768, WO 2020180770, WO 2020173935, WO 2020146470, WO 2019201848, WO 2019122129, WO 2018172250, and WO 2018115380, or a pharmaceutically acceptable salt, solvate, isomer (e.g., stereoisomer), prodrug, or tautomer thereof.

In some embodiments, an anti-cancer agent is an additional Ras inhibitor or a Ras vaccine, or another therapeutic modality designed to directly or indirectly decrease the oncogenic activity of Ras. In some embodiments, an anti-cancer agent is an additional Ras inhibitor. In some embodiments, the Ras inhibitor targets Ras in its active, or GTP-bound state. In some embodiments, the Ras inhibitor targets Ras in its inactive, or GDP-bound state. In some embodiments, the Ras inhibitor is, such as an inhibitor of K-Ras G12C, such as AMG 510 (sotorasib), MRTX1257, MRTX849 (adagrasib), JNJ-74699157, LY3499446, ARS-1620, ARS-853, BPI-421286, LY3537982, JDQ443, JAB-21000, RMC-6291 or GDC-6036, or a pharmaceutically acceptable salt, solvate, isomer (e.g., stereoisomer), prodrug, or tautomer thereof. In some embodiments, the Ras inhibitor is an inhibitor of K-Ras G12D, such as MRTX1133 or JAB-22000, or a pharmaceutically acceptable salt, solvate, isomer (e.g., stereoisomer), prodrug, or tautomer thereof. In some embodiments, the Ras inhibitor is a K-Ras G12V inhibitor, such as JAB-23000, or a pharmaceutically acceptable salt, solvate, isomer (e.g., stereoisomer), prodrug, or tautomer thereof. In some embodiments, the Ras inhibitor is RMC-6236, or a pharmaceutically acceptable salt, solvate, isomer (e.g., stereoisomer), prodrug, or tautomer thereof. In some embodiments, the Ras inhibitor is selected from a Ras(ON) inhibitor disclosed in the following, incorporated herein by reference in their entireties, or a pharmaceutically acceptable salt, solvate, isomer (e.g., stereoisomer), prodrug, or tautomer thereof: WO 2021091982, WO 2021091967, WO 2021091956 and WO 2020132597. Other examples of Ras inhibitors that may be combined with a Ras inhibitor of the present invention are provided in the following, incorporated herein by reference in their entireties: WO 2021173923, WO 2021169990, WO 2021169963, WO 2021168193, WO 2021158071, WO 2021155716, WO 2021152149, WO 2021150613, WO 2021147967, WO 2021147965, WO 2021143693, WO 2021142252, WO 2021141628, WO 2021139748, WO 2021139678, WO 2021129824, WO 2021129820, WO 2021127404, WO 2021126816, WO 2021126799, WO 2021124222, WO 2021121371, WO 2021121367, WO 2021121330, WO 2020050890, WO 2020047192, WO 2020035031, WO 2020028706, WO 2019241157, WO 2019232419, WO 2019217691, WO 2019217307, WO 2019215203, WO 2019213526, WO 2019213516, WO 2019155399, WO 2019150305, WO 2019110751, WO 2019099524, WO 2019051291, WO 2018218070, WO 2018217651, WO 2018218071, WO 2018218069, WO 2018206539, WO 2018143315, WO 2018140600, WO 2018140599, WO 2018140598, WO 2018140514, WO 2018140513, WO 2018140512, WO 2018119183, WO 2018112420, WO 2018068017, WO 2018064510, WO 2017201161, WO 2017172979, WO 2017100546, WO 2017087528, WO 2017058807, WO 2017058805, WO 2017058728, WO 2017058902, WO 2017058792, WO 2017058768, WO 2017058915, WO 2017015562, WO 2016168540, WO 2016164675, WO 2016049568, WO 2016049524, WO 2015054572, WO 2014152588, WO 2014143659, and WO 2013155223, or a pharmaceutically acceptable salt, solvate, isomer (e.g., stereoisomer), prodrug, or tautomer thereof.

In some embodiments, a therapeutic agent that may be combined with a compound of the present invention is an inhibitor of the MAP kinase (MAPK) pathway (or "MAPK inhibitor"). MAPK inhibitors include, but are not limited to, one or more MAPK inhibitor described in Cancers (Basel) 2015 September; 7(3): 1758-1784. For example, the MAPK inhibitor may be selected from one or more of trametinib, binimetinib, selumetinib, cobimetinib, LErafAON (NeoPharm), ISIS 5132; vemurafenib, pimasertib, TAK733, R04987655 (CH4987655); CI-1040; PD-0325901; CH5126766; MAP855; AZD6244; refametinib (RDEA 119/BAY 86-9766); GDC-0973/XL581; AZD8330 (ARRY-424704/ARRY-704); R05126766 (Roche, described in PLoS One. 2014 Nov. 25; 9(11)); and GSK1120212 (or JTP-74057, described in Clin Cancer Res. 2011 Mar. 1; 17(5): 989-1000). The MAPK inhibitor may be PLX8394, LXH254, GDC-5573, or LY3009120.

In some embodiments, an anti-cancer agent is a disrupter or inhibitor of the RAS-RAF-ERK or PI3K-AKT-TOR or PI3K-AKT signaling pathways. The PI3K/AKT inhibitor may include, but is not limited to, one or more PI3K/AKT inhibitor described in Cancers (Basel) 2015 September; 7(3): 1758-1784. For example, the PI3K/AKT inhibitor may be selected from one or more of NVP-6EZ235; BGT226; XL765/SAR245409; SF1126; GDC-0980; PI-103; PF-04691502; PKI-587; GSK2126458.

In some embodiments, an anti-cancer agent is a PD-1 or PD-L1 antagonist.

In some embodiments, additional therapeutic agents include ALK inhibitors, HER2 inhibitors, EGFR inhibitors, IGF-1R inhibitors, MEK inhibitors, PI3K inhibitors, AKT inhibitors, TOR inhibitors, MCL-1 inhibitors, BCL-2 inhibitors, SHP2 inhibitors, proteasome inhibitors, and immune therapies. In some embodiments, a therapeutic agent may be a pan-RTK inhibitor, such as afatinib.

IGF-1R inhibitors include linsitinib, or a pharmaceutically acceptable salt thereof.

EGFR inhibitors include, but are not limited to, small molecule antagonists, antibody inhibitors, or specific antisense nucleotide or siRNA. Useful antibody inhibitors of EGFR include cetuximab (ErbituxÆ), paniturnumab (VectibixÆ), zalutumumab, nimotuzumab, and matuzumab. Further antibody-based EGFR inhibitors include any anti-EGFR antibody or antibody fragment that can partially or completely block EGFR activation by its natural ligand. Non-limiting examples of antibody-based EGFR inhibitors include those described in Modjtahedi et al., Br. J. Cancer 1993, 67:247-253; Teramoto et al., Cancer 1996, 77:639-645; Goldstein et al., Clin. Cancer Res. 1995, 1:1311-1318; Huang et al., 1999, Cancer Res. 15:59(8):1935-40; and Yang et al., Cancer Res. 1999, 59:1236-1243. The EGFR inhibitor can be monoclonal antibody Mab E7.6.3 (Yang, 1999 supra), or Mab C225 (ATCC Accession No. HB-86508), or an antibody or antibody fragment having the binding specificity thereof.

Small molecule antagonists of EGFR include gefitinib (IressaÆ), erlotinib (TarcevaÆ), and lapatinib (TykerBÆ). See, e.g., Yan et al., Pharmacogenetics and Pharmacogenomics In Oncology Therapeutic Antibody Development, BioTechniques 2005, 39(4):565-8; and Paez et al., EGFR Mutations In Lung Cancer Correlation With Clinical Response To Gefitinib Therapy, Science 2004, 304(5676): 1497-500. In some embodiments, the EGFR inhibitor is osimertinib (TagrissoÆ). Further non-limiting examples of small molecule EGFR inhibitors include any of the EGFR inhibitors described in the following patent publications, and all pharmaceutically acceptable salts of such EGFR inhibitors: EP 0520722; EP 0566226; WO96/33980; U.S. Pat. No. 5,747,498; WO96/30347; EP 0787772; WO97/30034; WO97/30044; WO97/38994; WO97/49688; EP 837063; WO98/02434; WO97/38983; WO95/19774; WO95/19970: WO97/13771; WO98/02437; WO98/02438; WO97/32881; DE 19629652; WO98/33798; WO97/32880; WO97/32880; EP 682027; WO97/02266; WO97/27199; WO98/07726; WO97/34895; WO96/31510; WO98/14449; WO98/14450; WO98/14451; WO95/09847; WO97/19065; WO98/17662; U.S. Pat. Nos. 5,789,427; 5,650,415; 5,656,643; WO99/35146; WO99/35132; WO99/07701; and WO92/20642. Additional non-limiting examples of small molecule EGFR inhibitors include any of the EGFR inhibitors described in Traxler et al., Exp. Opin. Ther. Patents 1998, 8(12):1599-1625. In some embodiments, an EGFR inhibitor is an ERBB inhibitor. In humans, the ERBB family contains HER1 (EGFR, ERBB1), HER2 (NEU, ERBB2), HER3 (ERBB3), and HER (ERBB4).

MEK inhibitors include, but are not limited to, pimasertib, selumetinib, cobimetinib (CotellicÆ), trametinib (MekinistÆ), and binimetinib (MektoviÆ). In some embodiments, a MEK inhibitor targets a MEK mutation that is a Class I MEK1 mutation selected from D67N; P124L; P124S; and L177V. In some embodiments, the MEK mutation is a Class II MEK1 mutation selected from ΔE51-Q58; ΔF53-Q58; E203K; L177M; C121S; F53L; K57E; Q56P; and K57N.

PI3K inhibitors include, but are not limited to, wortmannin; 17-hydroxywortmannin analogs described in WO06/044453; 4-[2-(1H-Indazol-4-yl)-6-[[4-(methylsulfonyl)piperazin-1-yl]methyl]thieno[3,2-d]pyrimidin-4-yl]morpholine (also known as pictilisib or GDC-0941 and described in WO09/036082 and WO09/055730); 2-methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in WO06/122806); (S)-I-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in WO08/070740); LY294002 (2-(4-morpholinyl)-8-phenyl-4H-I-benzopyran-4-one (available from Axon Medchem); PI 103 hydrochloride (3-[4-(4-morpholinylpyrido-[3',2':4,5]furo[3,2-d]pyrimidin-2-yl]phenol hydrochloride (available from Axon Medchem); PIK 75 (2-methyl-5-nitro-2-[(6-bromoimidazo[1,2-a]pyridin-3-yl)methylene]-1-methylhydrazide-benzenesulfonic acid, monohydrochloride) (available from Axon Medchem); PIK 90 (N-(7,8-dimethoxy-2,3-dihydro-imidazo[1,2-c]quinazolin-5-yl)-nicotinamide (available from Axon Medchem); AS-252424 (5-[l-[5-(4-fluoro-2-hydroxy-phenyl)-furan-2-yl]-meth-(Z)-ylidene]-thiazolidine-2,4-dione rapalogs, e.g., as disclosed in WO98/02441 and WO01/14387, e.g. AP23464 and AP23841; 40-(2-hydroxyethyl) rapamycin; 40-[3-hydroxy(hydroxymethyl) methylpropanoate]-rapamycin (also known as CC1779); 40-epi-(tetrazolyt)-rapamycin (also called ABT578); 32-deoxorapamycin; 16-pentynyloxy-32(S)-dihydrorapanycin; derivatives disclosed in WO05/005434; derivatives disclosed in U.S. Pat. Nos. 5,258,389, 5,118,677, 5,118,678, 5,100,883, 5,151,413, 5,120,842, and 5,256,790, and in WO94/090101, WO92/05179, WO93/111130, WO94/02136, WO94/02485, WO95/14023, WO94/02136, WO95/16691, WO96/41807, WO96/41807, and WO2018204416; and phosphorus-containing rapamycin derivatives (e.g., WO05/016252). In some embodiments, the mTOR inhibitor is a bisteric inhibitor (see, e.g., WO2018204416, WO2019212990 and WO2019212991), such as RMC-5552, having the structure

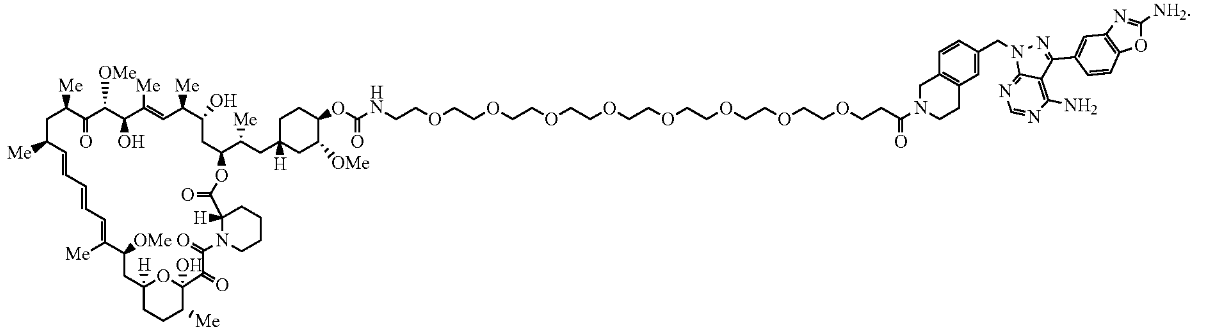 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]

(available from Axon Medchem): TGX-221 (7-methyl-2-(4-morpholinyl)-9-[1-(phenylamino)ethyl]-4H-pyrido-[1,2-a]pyrimidin-4-one (available from Axon Medchem): XL-765; and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits AktI) (Barnett et al., Biochem. J. 2005, 385(Pt. 2): 399-408); Akt-1-1,2 (inhibits AkI and 2) (Barnett et al., Biochem. J. 2005, 385(Pt. 2): 399-408); API-59CJ-Ome (e.g., Jin et al., Br. J. Cancer 2004, 91:1808-12): 1-H-imidazo[4,5-c]pyridinyl compounds (e.g., WO 05/011700); indole-3-carbinol and derivatives thereof (e.g., U.S. Pat. No. 6,656,963; Sarkar and Li J Nutr. 2004, 134(12 Suppl): 3493S-3498S); perifosine (e.g., interferes with Akt membrane localization; Dasmahapatra et al. Clin. Cancer Res. 2004, 10(15):5242-52); phosphatidylinositol ether lipid analogues (e.g., Gills and Dennis Expert. Opin. Investig. Drugs 2004, 13:787-97); and triciribine (TCN or API-2 or NCI identifier: NSC 154020; Yang et al., Cancer Res. 2004, 64:4394-9).

mTOR inhibitors include, but are not limited to, ATP-competitive mTORC1/mTORC2 inhibitors, e.g., PI-103, PP242, PP30; Torin 1; FKBP12 enhancers; 4H-1-benzopyran-4-one derivatives; and rapamycin (also known as sirolimus) and derivatives thereof, including: temsirolimus (ToriselÆ); everolimus (AfinitorÆ); WO94/09010); ridaforolimus (also known as deforolimus or AP23573);

BRAF inhibitors that may be used in combination with compounds of the invention include, for example, vemurafenib, dabrafenib, and encorafenib. A BRAF may comprise a Class 3 BRAF mutation. In some embodiments, the Class 3 BRAF mutation is selected from one or more of the following amino acid substitutions in human BRAF: D287H; P367R; V459L; G466V; G466E; G466A; S467L; G469E; N581 S; N581I; D594N; D594G; D594A; D594H; F595L; G596D; G596R and A762E.

MCL-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

In some embodiments, the additional therapeutic agent is a SHP2 inhibitor. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung and colon. Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian and breast cancer). Thus, combination therapy involving a SHP2 inhibitor with a RAS pathway inhibitor could be a general strategy for preventing tumor resistance in a wide range of malignancies.

Non-limiting examples of such SHP2 inhibitors that are known in the art, include: Chen et al. *Mol Pharmacol.* 2006, 70, 562; Sarver et al., *J. Med. Chem.* 2017, 62, 1793; Xie et al., *J. Med. Chem.* 2017, 60, 113734; and Igbe et al., *Oncotarget,* 2017, 8, 113734; and PCT applications: WO 2021149817, WO 2021148010, WO 2021147879, WO 2021143823, WO 2021143701, WO 2021143680, WO 2021121397, WO 2021119525, WO 2021115286, WO 2021110796, WO 2021088945, WO 2021073439, WO 2021061706, WO 2021061515, WO 2021043077, WO 2021033153, WO 2021028362, WO 2021033153, WO 2021028362, WO 2021018287, WO 2020259679, WO 2020249079, WO 2020210384, WO 2020201991, WO 2020181283, WO 2020177653, WO 2020165734, WO 2020165733, WO 2020165732, WO 2020156243, WO 2020156242, WO 2020108590, WO 2020104635, WO 2020094104, WO 2020094018, WO 2020081848, WO 2020073949, WO 2020073945, WO 2020072656, WO 2020065453, WO 2020065452, WO 2020063760, WO 2020061103, WO 2020061101, WO 2020033828, WO 2020033286, WO 2020022323, WO 2019233810, WO 2019213318, WO 2019183367, WO 2019183364, WO 2019182960, WO 2019167000, WO 2019165073, WO 2019158019, WO 2019152454, WO 2019051469, WO 2019051084, WO 2018218133, WO 2018172984, WO 2018160731, WO 2018136265, WO 2018136264, WO 2018130928, WO 2018129402, WO 2018081091, WO 2018057884, WO 2018013597, WO 2017216706, WO 2017211303, WO 2017210134, WO 2017156397, WO 2017100279, WO 2017079723, WO 2017078499, WO 2016203406, WO 2016203405, WO 2016203404, WO 2016196591, WO 2016191328, WO 2015107495, WO 2015107494, WO 2015107493, WO 2014176488, WO 2014113584, US 20210085677, U.S. Ser. No. 10/858,359, U.S. Ser. No. 10/934,302, U.S. Ser. No. 10/954,243, U.S. Ser. No. 10/988,466, U.S. Ser. No. 11/001,561, U.S. Ser. No. 11/033,547, U.S. Ser. No. 11/034,705, or U.S. Ser. No. 11/044,675, or a pharmaceutically acceptable salt, solvate, isomer (e.g., stereoisomer), prodrug, or tautomer thereof, each of which is incorporated herein by reference.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue (C333) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TNO155, having the structure

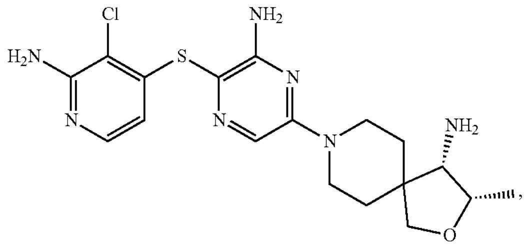 [SMILES: C[C@@H]1OCC2(CCN(c3cnc(Sc4ccnc(N)c4Cl)c(N)n3)CC2)[C@@H]1N]

or a pharmaceutically acceptable salt, solvate, isomer (e.g., stereoisomer), prodrug, or tautomer thereof.

In some embodiments, the SHP2 inhibitor is RMC-4550, having the structure

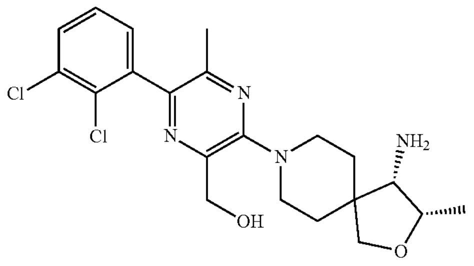 [SMILES: Cc1nc(N2CCC3(CC2)CO[C@@H](C)[C@H]3N)c(CO)nc1-c1cccc(Cl)c1Cl]

or a pharmaceutically acceptable salt, solvate, isomer (e.g., stereoisomer), prodrug, or tautomer thereof. In some embodiments, the SHP2 inhibitor is RMC-4630, having the structure:

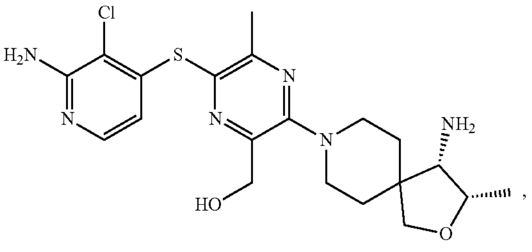 [SMILES: Cc1nc(N2CCC3(CC2)CO[C@@H](C)[C@H]3N)c(CO)nc1Sc1ccnc(N)c1Cl]

or a pharmaceutically acceptable salt, solvate, isomer (e.g., stereoisomer), prodrug, or tautomer thereof. In some embodiments, the SHP2 inhibitor is JAB-3068, having the structure

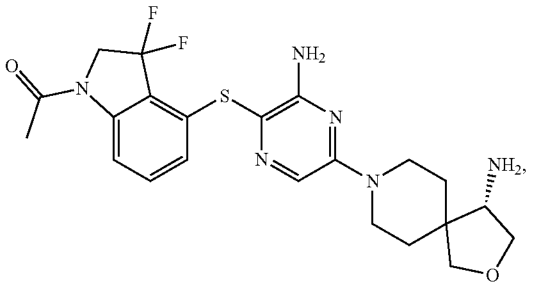 [SMILES: CC(=O)N1CC(F)(F)c2c(Sc3ncc(N4CCC5(CC4)COC[C@H]5N)nc3N)cccc21]

or a pharmaceutically acceptable salt, solvate, isomer (e.g., stereoisomer), prodrug, or tautomer thereof. In some embodiments, the SHP2 inhibitor is JAB-3312. In some embodiments, the SHP2 inhibitor is the following compound,

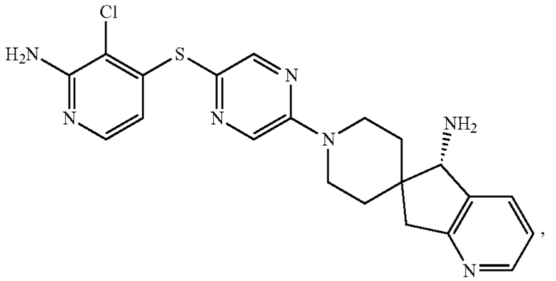 [SMILES: Nc1nccc(Sc2cnc(N3CCC4(CC3)Cc3ncccc3[C@H]4N)cn2)c1Cl]

or a pharmaceutically acceptable salt, solvate, isomer (e.g., stereoisomer), prodrug, or tautomer thereof. In some embodiments, the SHP2 inhibitor is RLY-1971, having the structure

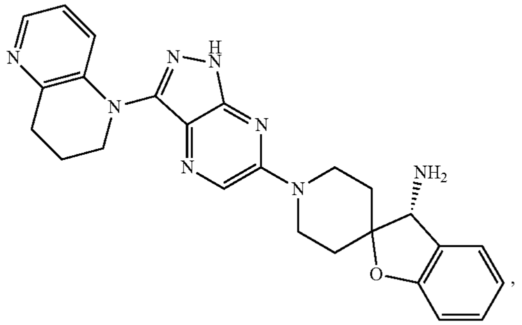 [SMILES: N[C@@H]1c2ccccc2OC12CCN(c1cnc3c(N4CCCc5ncccc54)n[nH]c3n1)CC2]

or a pharmaceutically acceptable salt, solvate, isomer (e.g., stereoisomer), prodrug, or tautomer thereof. In some embodiments, the SHP2 inhibitor is ERAS-601, or a pharmaceutically acceptable salt, solvate, isomer (e.g., stereoisomer), prodrug, or tautomer thereof. In some embodiments, the SHP2 inhibitor is BBP-398, or a pharmaceutically acceptable salt, solvate, isomer (e.g., stereoisomer), prodrug, or tautomer thereof. In some embodiments, the SHP2 inhibitor is SH3809. In some embodiments, the SHP2 inhibitor is PF-07284892, or a pharmaceutically acceptable salt, solvate, isomer (e.g., stereoisomer), prodrug, or tautomer thereof.

In some embodiments, the additional therapeutic agent is selected from the group consisting of a MEK inhibitor, HER2 inhibitor, a SHP2 inhibitor, CDK4/6 inhibitor, an mTOR inhibitor, a SOS1 inhibitor, and a PD-L1 inhibitor. In some embodiments, the additional therapeutic agent is selected from the group consisting of a MEK inhibitor, a SHP2 inhibitor, and a PD-L1 inhibitor. See, e.g., Hallin et al., Cancer Discovery, DOI: 10.1158/2159-8290 (Oct. 28, 2019) and Canon et al., Nature, 575:217 (2019). In some embodiments, a Ras inhibitor of the present invention is used in combination with a MEK inhibitor and a SOS1 inhibitor. In some embodiments, a Ras inhibitor of the present invention is used in combination with a PD-L1 inhibitor and a SOS1 inhibitor. In some embodiments, a Ras inhibitor of the present invention is used in combination with a PD-L1 inhibitor and a SHP2 inhibitor. In some embodiments, a Ras inhibitor of the present invention is used in combination with a MEK inhibitor and a SHP2 inhibitor. In some embodiments, the cancer is colorectal cancer and the treatment comprises administration of a Ras inhibitor of the present invention in combination with a second or third therapeutic agent.

Proteasome inhibitors include, but are not limited to, carfilzomib (KyprolisÆ), bortezomib (VelcadeÆ), and oprozomib.

Immune therapies include, but are not limited to, monoclonal antibodies, immunomodulatory imides (IMiDs), GITR agonists, genetically engineered T-cells (e.g., CAR-T cells), bispecific antibodies (e.g., BiTEs), and anti-PD-1, anti-PD-L1, anti-CTLA4, anti-LAGI, and anti-OX40 agents).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 2007, 110(1):186-192; Thompson et al., Clin. Cancer Res. 2007, 13(6):1757-1761; and WO06/121168 A1), as well as described elsewhere herein.

GITR agonists include, but are not limited to, GITR fusion proteins and anti-GITR antibodies (e.g., bivalent anti-GITR antibodies), such as, a GITR fusion protein described in U.S. Pat. Nos. 6,111,090, 8,586,023, WO2010/003118 and WO2011/090754; or an anti-GITR antibody described, e.g., in U.S. Pat. No. 7,025,962, EP 1947183, U.S. Pat. Nos. 7,812,135, 8,388,967, 8,591,886, 7,618,632, EP 1866339, and WO2011/028683, WO2013/039954, WO05/007190, WO07/133822, WO05/055808, WO99/40196, WO01/03720, WO99/20758, WO06/083289, WO/05115451, and WO2011/051726.

Another example of a therapeutic agent that may be used in combination with the compounds of the invention is an anti-angiogenic agent. Anti-angiogenic agents are inclusive of, but not limited to, in vitro synthetically prepared chemical compositions, antibodies, antigen binding regions, radionuclides, and combinations and conjugates thereof. An anti-angiogenic agent can be an agonist, antagonist, allosteric modulator, toxin or, more generally, may act to inhibit or stimulate its target (e.g., receptor or enzyme activation or inhibition), and thereby promote cell death or arrest cell growth. In some embodiments, the one or more additional therapies include an anti-angiogenic agent.

Anti-angiogenic agents can be MMP-2 (matrix-metalloproteinase 2) inhibitors, MMP-9 (matrix-metalloprotienase 9) inhibitors, and COX-II (cyclooxygenase 11) inhibitors. Non-limiting examples of anti-angiogenic agents include rapamycin, temsirolimus (CCI-779), everolimus (RAD001), sorafenib, sunitinib, and bevacizumab. Examples of useful COX-II inhibitors include alecoxib, valdecoxib, and rofecoxib.

Examples of useful matrix metalloproteinase inhibitors are described in WO96/33172, WO96/27583, WO98/07697, WO98/03516, WO98/34918, WO98/34915, WO98/33768, WO98/30566, WO90/05719, WO99/52910, WO99/52889, WO99/29667, WO99007675, EP0606046, EP0780386, EP1786785, EP1181017, EP0818442, EP1004578, and US20090012085, and U.S. Pat. Nos. 5,863,949 and 5,861, 510. Preferred MMP-2 and MMP-9 inhibitors are those that have little or no activity inhibiting MMP-1. More preferred, are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Further exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF (e.g., bevacizumab), or soluble VEGF receptors or a ligand binding region thereof) such as VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as VectibixÆ (panitumumab), erlotinib (TarcevaÆ), anti-AngI and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic agents include: SD-7784 (Pfizer, USA); cilengitide (Merck KGaA, Germany, EPO 0770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892, 112); emaxanib, (Pfizer, USA, U.S. Pat. No. 5,792,783); vatalanib, (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands), DACantiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 0970070); ARGENT technology (Ariad, USA); YIGSR-Stealth (Johnson & Johnson, USA); fibrinogen-E fragment (BioActa, UK); angiogenic inhibitor (Trigen, UK); TBC-1635 (Encysive Pharmaceuticals, USA); SC-236 (Pfizer, USA); ABT-567 (Abbott, USA); Metastatin (EntreMed, USA); maspin (Sosei, Japan); 2-methoxyestradiol (Oncology Sciences Corporation, USA); ER-68203-00 (IV AX, USA); BeneFin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); bevacizumab (pINN) (Genentech, USA); angiogenic inhibitors (SUGEN, USA); XL 784 (Exelixis, USA); XL 647 (Exelixis, USA); MAb, alpha5beta3 integrin, second generation (Applied Molecular Evolution, USA and Medimmune, USA); enzastaurin hydrochloride (Lilly, USA); CEP 7055 (Cephalon, USA and Sanofi-Synthelabo, France); BC 1 (Genoa Institute of Cancer Research, Italy); rBPI 21 and BPI-derived antiangiogenic (XOMA, USA); PI 88 (Progen, Australia); cilengitide (Merck KGaA, German; Munich Technical University, Germany, Scripps Clinic and Research Foundation, USA); AVE 8062 (Ajinomoto, Japan); AS 1404 (Cancer Research Laboratory, New Zealand); SG 292, (Telios, USA); Endostatin (Boston Childrens Hospital, USA); ATN 161 (Attenuon, USA); 2-methoxyestradiol (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenic, (EntreMed, USA); urokinase plasminogen activator inhibitor, (Dendreon, USA); oglufanide (pINN), (Melmotte, USA); HIF-Ialfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol; anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors; SU 11248 (Pfizer, USA and SUGEN USA); ABT 518, (Abbott, USA); YH16 (Yantai Rongchang, China); S-3APG (Boston Childrens Hospital, USA and EntreMed, USA); MAb, KDR (ImClone Systems, USA); MAb, alpha5 beta (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); irsogladine, (Nippon Shinyaku, Japan); RG 13577 (Aventis, France); WX 360 (Wilex, Germany); squalamine, (Genaera, USA); RPI 4610 (Sirna, USA); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VE-cadherin-2 antagonists (ImClone Systems, USA); Vasostatin (National Institutes of Health, USA); Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Further examples of therapeutic agents that may be used in combination with compounds of the invention include agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor, c-Met.

Another example of a therapeutic agent that may be used in combination with compounds of the invention is an autophagy inhibitor. Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used. In some embodiments, the one or more additional therapies include an autophagy inhibitor.

Another example of a therapeutic agent that may be used in combination with compounds of the invention is an anti-neoplastic agent. In some embodiments, the one or more additional therapies include an anti-neoplastic agent. Non-limiting examples of anti-neoplastic agents include acemannan, aclarubicin, aldesleukin, alemtuzumab, alitretinoin, altretamine, amifostine, aminolevulinic acid, amrubicin, amsacrine, anagrelide, anastrozole, ancer, ancestim, arglabin, arsenic trioxide, BAM-002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon-1, interferon alpha, natural, interferon beta, interferon beta-Ia, interferon beta-Ib, interferon gamma, natural interferon gamma-Ia, interferon gamma-Ib, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levarnisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, or zoledronic acid; abarelix; AE 941 (Aeterna), ambamustine, antisense oligonucleotide, bcl-2 (Genta), APC 8015 (Dendreon), decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Additional examples of therapeutic agents that may be used in combination with compounds of the invention include ipilimurnab (YervoyÆ); tremelimumab; galiximab; nivolumab, also known as BMS-936558 (OpdivoÆ); pembrolizumab (KeytrudaÆ); avelumab (BavencioÆ); AMP224; BMS-936559; MPDL3280A, also known as RG7446; MEDI-570; AMG557; MGA271; IMP321; BMS-663513: PF-05082566; CDX-1127; anti-OX40 (Providence Health Services); huMAbOX40L; atacicept; CP-870893; lucatumumab; dacetuzumab; muromonab-CD3; ipilumumab; MED14736 (ImfinziÆ); MSB0010718C; AMP 224; adalimumab (HumiraÆ); ado-trastuzumab emtansine (KadcylaÆ); aflibercept (EyleaÆ); alemtuzumab (CampathÆ); basiliximab (SimulectÆ); belimumab (BenlystaÆ);

basiliximab (SimulectÆ); belimumab (BenlystaÆ); brentuximab vedotin (AdcetrisÆ); canakinumab (IlarisÆ); certolizumab pegol (CimziaÆ); daclizumab (ZenapaxÆ); daratumumab (DarzalexÆ); denosumab (ProliaÆ); eculizumab (SolirisÆ); efalizumab (RaptivaÆ); gemtuzumab ozogamicin (MylotargÆ); golimumab (SimponiÆ); ibritumomab tiuxetan (ZevalinÆ); infliximab (RemicadeÆ); motavizumab (NumaxÆ); natalizumab (TysabriÆ); obinutuzumab (GazyvaÆ); ofatumumab (ArzerraÆ); omalizumab (XolairÆ); palivizumab (SynagisÆ); pertuzumab (PerjetaÆ); pertuzumab (PerjetaÆ); ranibizumab (LucentisÆ); raxibacumab (AbthraxÆ); tocilizumab (ActemraÆ); tositumomab; tositumomab-i-131; tositumomab and tositumomab-i-131 (BexxarÆ); ustekinumab (StelaraÆ); AMG 102; AMG 386; AMG 479; AMG 655; AMG 706; AMG 745; and AMG 951.

The compounds described herein can be used in combination with the agents disclosed herein or other suitable agents, depending on the condition being treated. Hence, in some embodiments the one or more compounds of the disclosure will be co-administered with other therapies as described herein. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described herein can be formulated together in the same dosage form and administered simultaneously. Alternatively, a compound of the invention and any of the therapies described herein can be simultaneously administered, wherein both the agents are present in separate formulations. In another alternative, a compound of the present disclosure can be administered and followed by any of the therapies described herein, or vice versa. In some embodiments of the separate administration protocol, a compound of the invention and any of the therapies described herein are administered a few minutes apart, or a few hours apart, or a few days apart.

In some embodiments of any of the methods described herein, the first therapy (e.g., a compound of the invention) and one or more additional therapies are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours, up to 24 hours, or up to 1-7, 1-14, 1-21 or 1-30 days before or after the one or more additional therapies.

The invention also features kits including (a) a pharmaceutical composition including an agent (e.g., a compound of the invention) described herein, and (b) a package insert with instructions to perform any of the methods described herein. In some embodiments, the kit includes (a) a pharmaceutical composition including an agent (e.g., a compound of the invention) described herein, (b) one or more additional therapies (e.g., non-drug treatment or therapeutic agent), and (c) a package insert with instructions to perform any of the methods described herein.

As one aspect of the present invention contemplates the treatment of the disease or symptoms associated therewith with a combination of pharmaceutically active compounds that may be administered separately, the invention further relates to combining separate pharmaceutical compositions in kit form. The kit may comprise two separate pharmaceutical compositions: a compound of the present invention, and one or more additional therapies. The kit may comprise a container for containing the separate compositions such as a divided bottle or a divided foil packet. Additional examples of containers include syringes, boxes, and bags. In some embodiments, the kit may comprise directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

NUMBERED EMBODIMENTS

[1] A compound, or pharmaceutically acceptable salt thereof, having the structure of Formula Ia:

Formula Ia

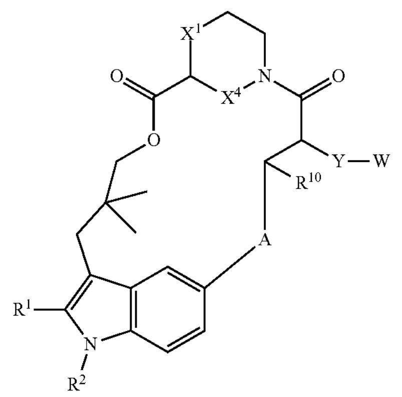

wherein A is optionally substituted 3 to 6-membered cycloalkylene, optionally substituted 3 to 6-membered heterocycloalkylene, optionally substituted 6-membered arylene, optionally substituted 5 to 6-membered heteroarylene, optionally substituted $C_2$-$C_4$ alkylene, or optionally substituted $C_2$-$C_4$ alkenylene;

Y is

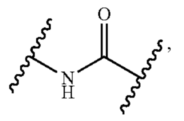

—NHC(O)—

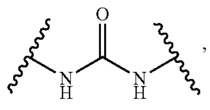

—NHC(O)NH—

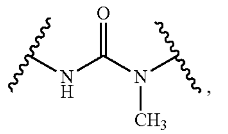

—$NHC(O)NCH_3$—

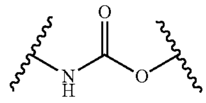

—NHC(O)O—

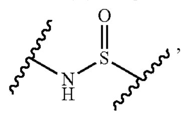

—NHC(S)—

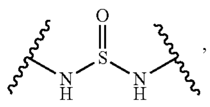

—NHC(S)NH—

-continued

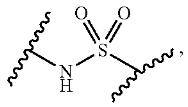, or 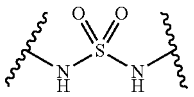;

—NHS(O)2— —NHS(O)2NH—

W is hydrogen, $C_1$-$C_4$ alkyl, optionally substituted $C_1$-$C_3$ heteroalkyl, optionally substituted 3 to 10-membered heterocycloalkyl, optionally substituted 3 to 10-membered cycloalkyl, optionally substituted 6 to 10-membered aryl, or optionally substituted 5 to 10-membered heteroaryl;

$X^1$ and $X^4$ are each, independently, $CH_2$ or NH;

$R^1$ is optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 15-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; and $R^{10}$ is hydrogen, hydroxy, optionally substituted $C_1$-$C_3$ alkyl, or optionally substituted $C_1$-C6 heteroalkyl.

[2] The compound of paragraph [1], or pharmaceutically acceptable salt thereof, wherein $R^1$ is optionally substituted 6 to 10-membered aryl or optionally substituted 5 to 10-membered heteroaryl.

[3] The compound of paragraph [2], or pharmaceutically acceptable salt thereof, wherein $R^1$ is optionally substituted phenyl or optionally substituted pyridine.

[4] The compound of any one of paragraphs [1]-[3], or pharmaceutically acceptable salt thereof, wherein A is optionally substituted thiazole, optionally substituted triazole, optionally substituted morpholino, optionally substituted piperidinyl, optionally substituted pyridine, or optionally substituted phenyl.

[5] The compound of any one of paragraphs [1]-[3], or pharmaceutically acceptable salt thereof, wherein A is not an optionally substituted phenyl or benzimidazole.

[6] The compound of paragraph 5, or pharmaceutically acceptable salt thereof, wherein A is not hydroxyphenyl.

[7] The compound of any one of paragraphs [1]-[6], or pharmaceutically acceptable salt thereof, wherein the compound is not a compound of Table 2.

[8] The compound of any one of paragraphs [1]-[7], or pharmaceutically acceptable salt thereof, wherein the compound is not a compound of Table 3.

[9] The compound of any one of paragraphs [1]-[8], or pharmaceutically acceptable salt thereof, wherein Y is —NHC(O)— or —NHC(O)NH—.

[10] The compound of paragraph [9] or pharmaceutically acceptable salt thereof, having the structure of Formula IIa:

Formula IIa

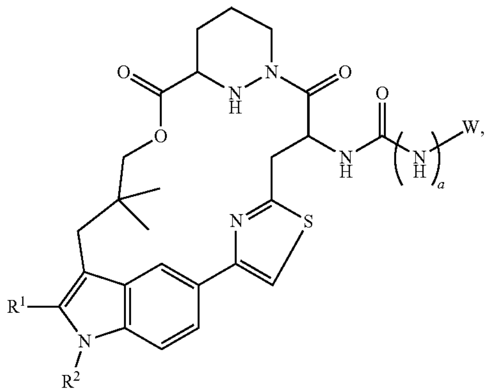

wherein a is 0 or 1.

[11] The compound of paragraph [10], or pharmaceutically acceptable salt thereof, having the structure of Formula I1-1a:

Formula II-1a

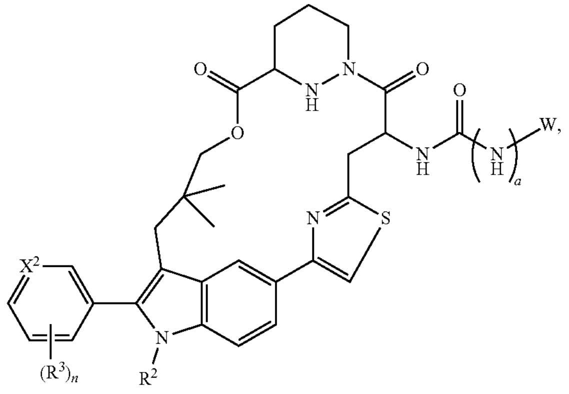

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[12] The compound of paragraph [11], or pharmaceutically acceptable salt thereof, having the structure of Formula IIa-2:

Formula IIa-2

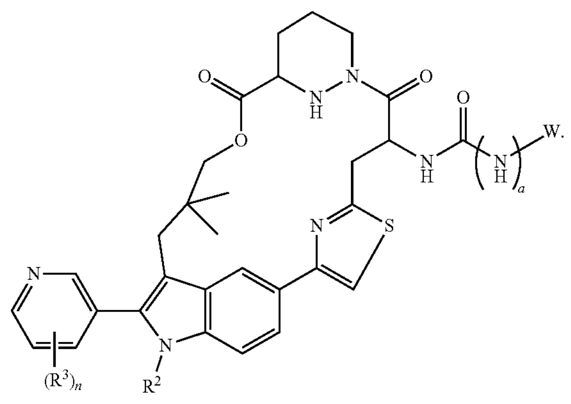

[13] The compound of paragraph [12], or pharmaceutically acceptable salt thereof, having the structure of Formula IIa-3:

Formula IIa-3

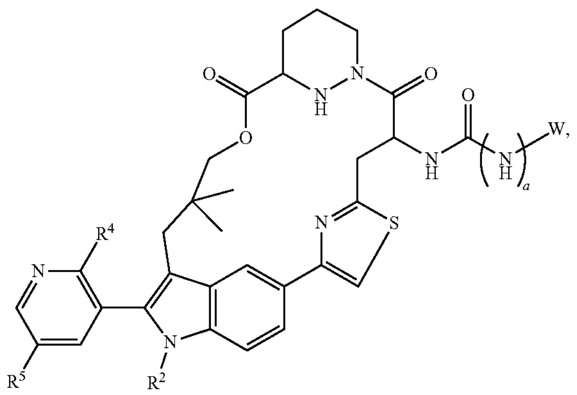

wherein $R^4$ and R are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl.

[14] The compound of paragraph [13] or pharmaceutically acceptable salt thereof, having the structure of Formula IIa-4:

Formula IIa-4

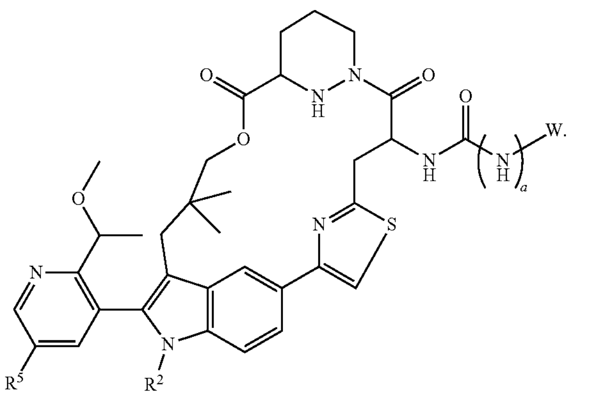

[15] The compound of paragraph [14] or pharmaceutically acceptable salt thereof, having the structure of Formula IIa-5:

Formula IIa-5

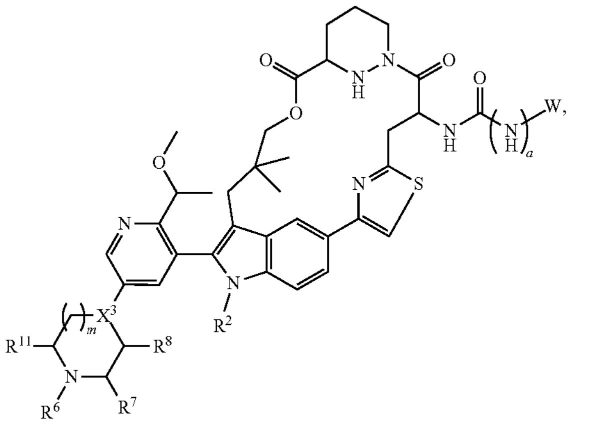

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[16] The compound of paragraph [15], or pharmaceutically acceptable salt thereof, having the structure of Formula IIa-6:

Formula IIa-6

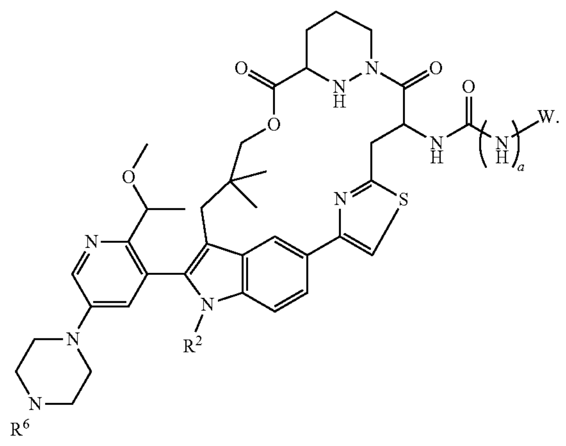

[17] The compound of paragraph [15], or pharmaceutically acceptable salt thereof, having the structure of Formula IIa-7:

Formula IIa-7

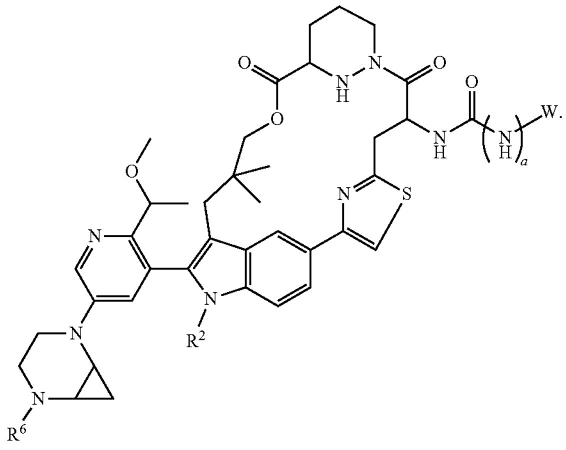

[18] The compound of paragraph [16] or [17], wherein $R^3$ is methyl.

[19] The compound of paragraph [15], or pharmaceutically acceptable salt thereof, having the structure of Formula IIa-8 or Formula IIa-9:

Formula IIa-8

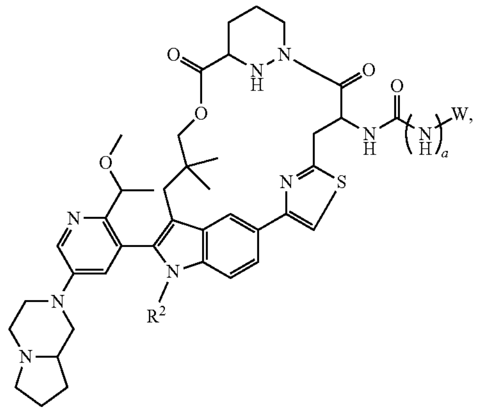

Formula IIa-9

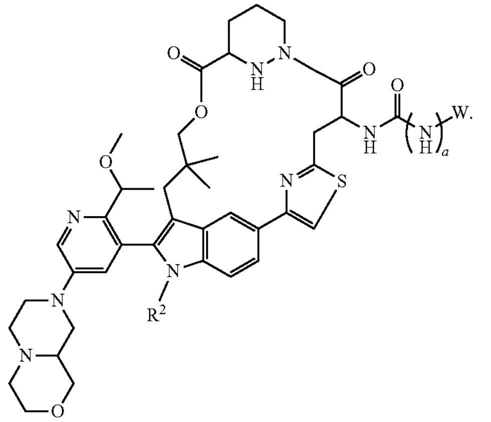

[20] The compound of paragraph [9], or pharmaceutically acceptable salt thereof, having the structure of Formula IIIa:

Formula IIIa

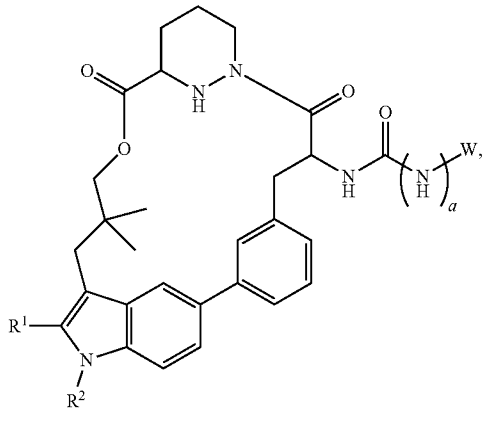

wherein a is 0 or 1.

[21] The compound of paragraph [20], or pharmaceutically acceptable salt thereof, having the structure of Formula IIIa-1:

Formula IIIa-1

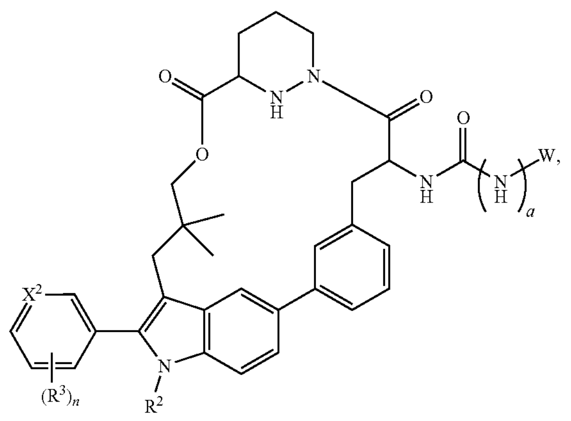

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[22] The compound of paragraph [21], or pharmaceutically acceptable salt thereof, having the structure of Formula IIIa-2:

Formula IIIa-2

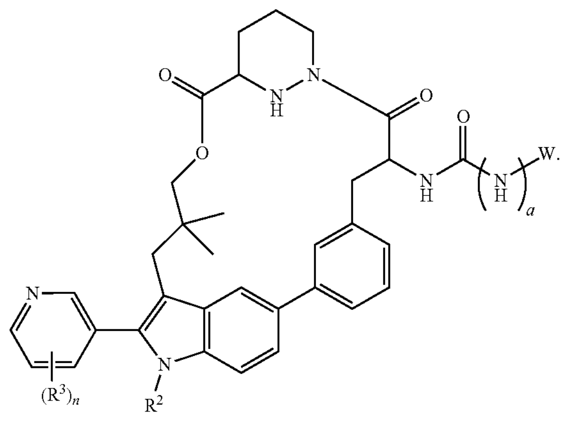

[23]. The compound of paragraph [22], or pharmaceutically acceptable salt thereof, having the structure of Formula IIIa-3:

Formula IIIa-3

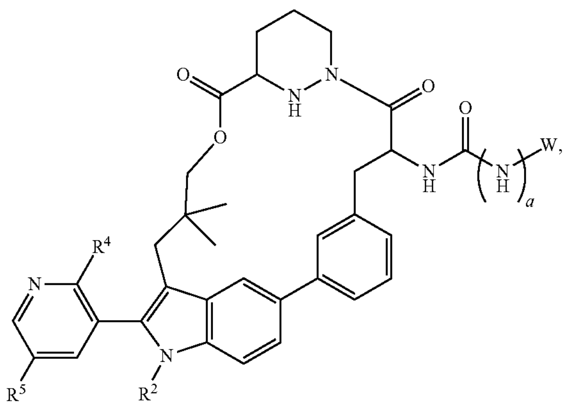

wherein $R^4$ and $R^5$ are each independently selected from halogen, cyano, hydroxy, optionally substituted amine, optionally substituted amido, optionally substituted $C_1$-$C_5$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl.

[24] The compound of paragraph [23], or pharmaceutically acceptable salt thereof, having the structure of Formula IIIa-4:

Formula IIIa-4

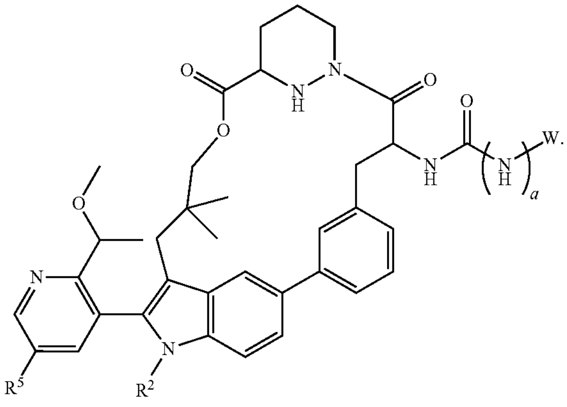

[25] The compound of paragraph [24], or pharmaceutically acceptable salt thereof, having the structure of Formula IIIa-5:

Formula IIIa-5

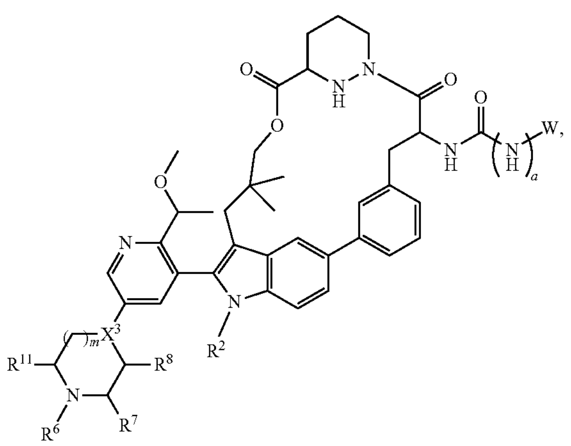

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[26] The compound of paragraph [25], or pharmaceutically acceptable salt thereof, having the structure of Formula IIIa-6:

Formula IIIa-6

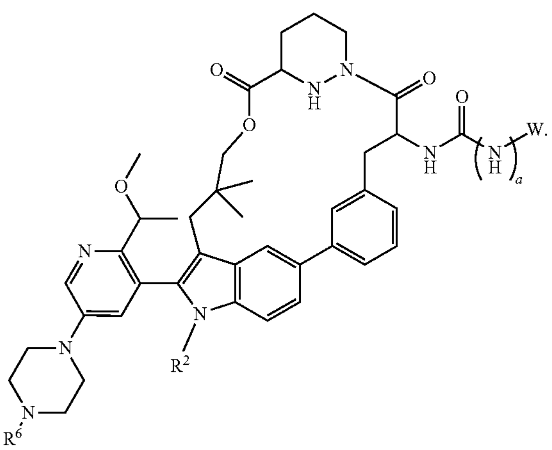

[27] The compound of paragraph [25], or pharmaceutically acceptable salt thereof, having the structure of Formula IIIa-7:

Formula IIIa-7

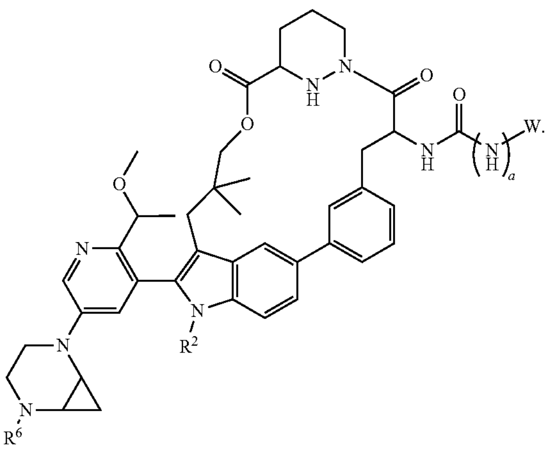

[28] The compound of paragraph [26] or [27], wherein $R^3$ is methyl.

[29] The compound of paragraph [25], or pharmaceutically acceptable salt thereof, having the structure of Formula IIIa-8 or Formula IIIa-9:

Formula IIIa-8

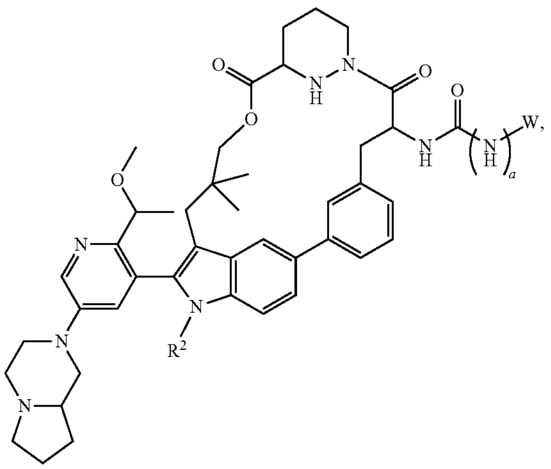

-continued

Formula IIIa-9

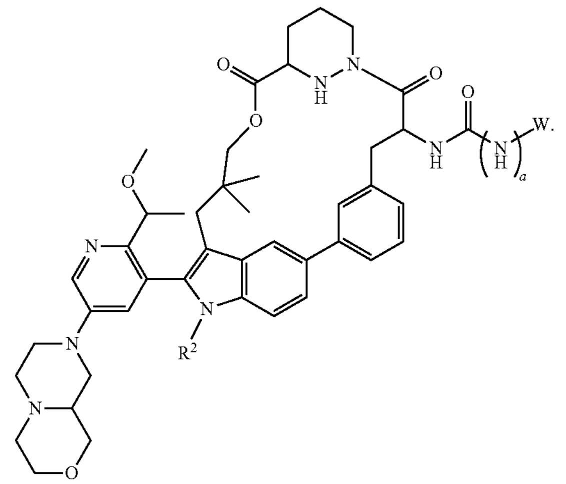

[30] The compound of paragraph [9], or pharmaceutically acceptable salt thereof, having the structure of Formula IVa:

Formula IVa

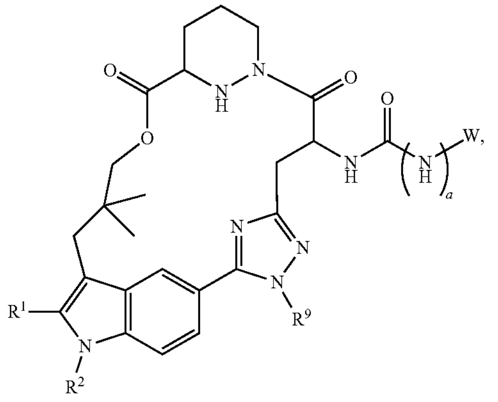

wherein $R^9$ is H or $C_1$-$C_6$ alkyl; and a is 0 or 1.

[31] The compound of paragraph [30], or pharmaceutically acceptable salt thereof, having the structure of Formula IVa-1:

Formula IVa-1

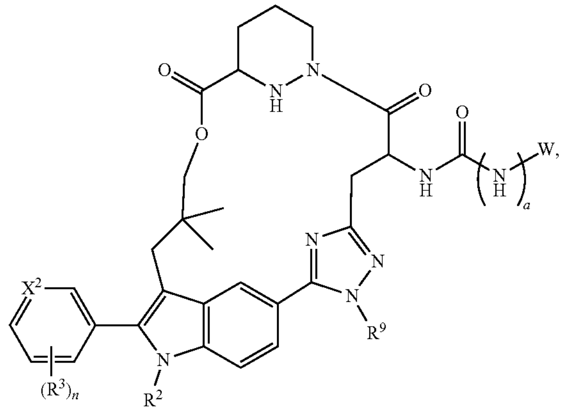

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[32] The compound of paragraph [31], or pharmaceutically acceptable salt thereof, having the structure of Formula IVa-2:

Formula IVa-2

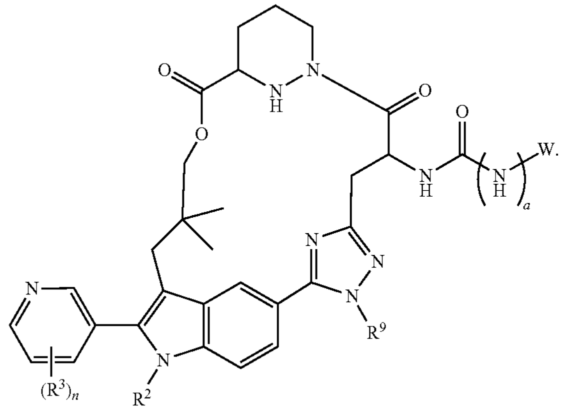

[33] The compound of paragraph [32], or pharmaceutically acceptable salt thereof, having the structure of Formula IVa-3:

Formula IVa-3

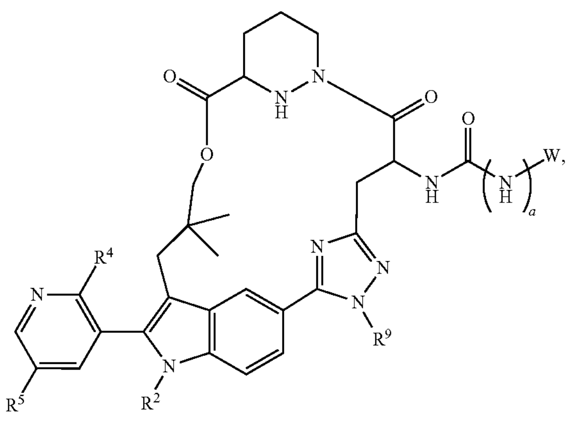

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl.

[34] The compound of paragraph [33], or pharmaceutically acceptable salt thereof, having the structure of Formula IVa-4:

Formula IVa-4

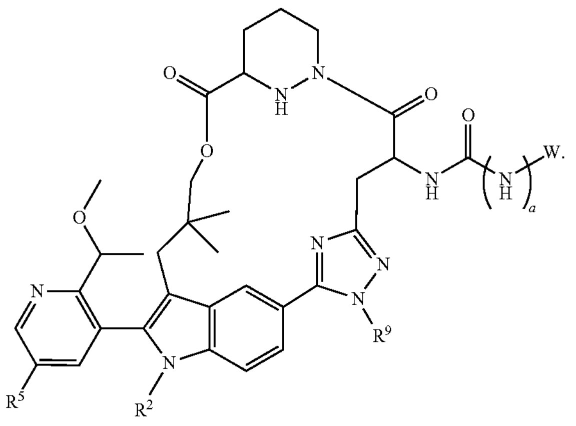

[35] The compound of paragraph [34], or pharmaceutically acceptable salt thereof, having the structure of Formula IVa-5:

Formula IVa-5

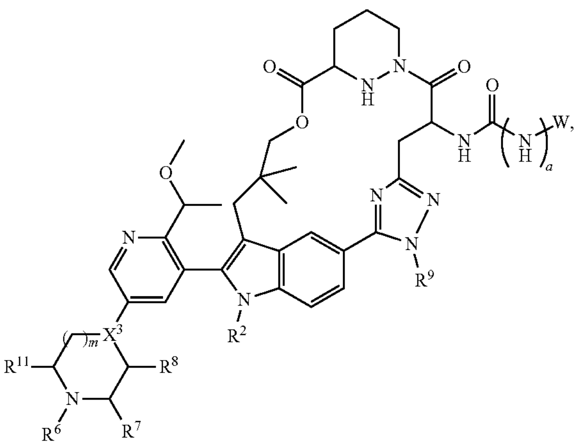

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted C1-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[36] The compound of paragraph [35], or pharmaceutically acceptable salt thereof, having the structure of Formula IVa-6:

Formula IVa-6

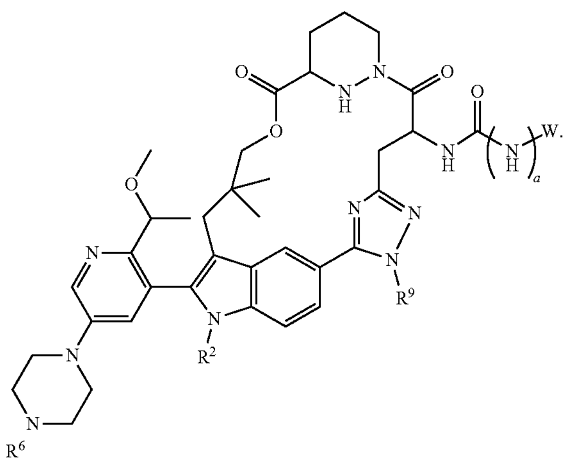

[37] The compound of paragraph [35], or pharmaceutically acceptable salt thereof, having the structure of Formula IVa-7:

Formula IVa-7

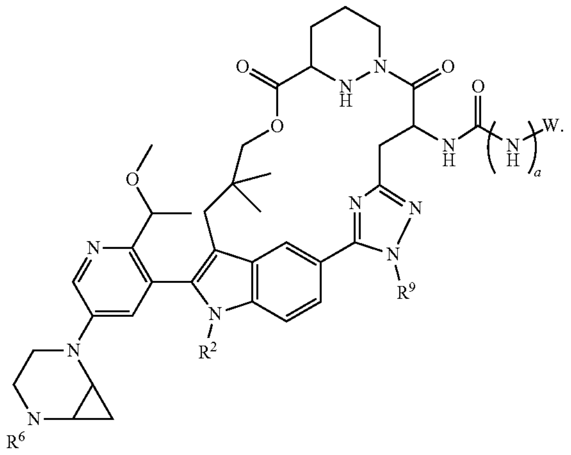

[38] The compound of paragraph [36] or [37], wherein $R^3$ is methyl.

[39] The compound of paragraph [35], or pharmaceutically acceptable salt thereof, having the structure of Formula IVa-8 or Formula IVa-9:

Formula IVa-8

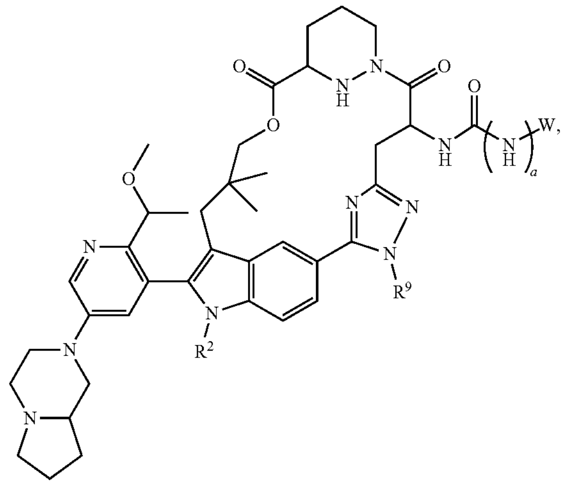

-continued

Formula IVa-9

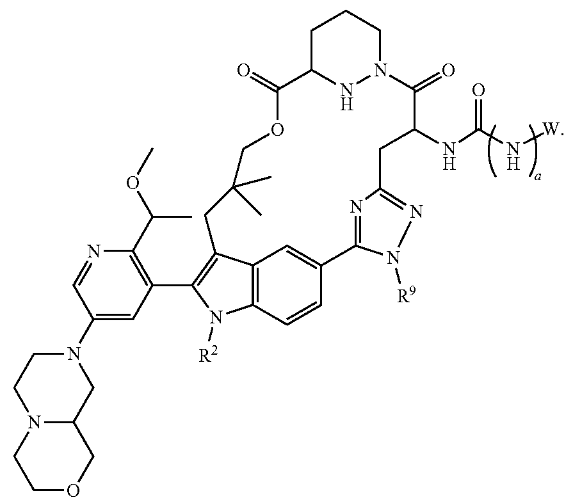

[40] The compound of any one of paragraphs [30]-[39], or pharmaceutically acceptable salt thereof, wherein $R^9$ is methyl.

[41] The compound of any one of paragraphs [1]-[8], or pharmaceutically acceptable salt thereof, wherein Y is $—NHS(O)_2—$ or $—NHS(O)_2NH—$.

[42] The compound of paragraph [41], or pharmaceutically acceptable salt thereof, having the structure of Formula Va:

Formula Va

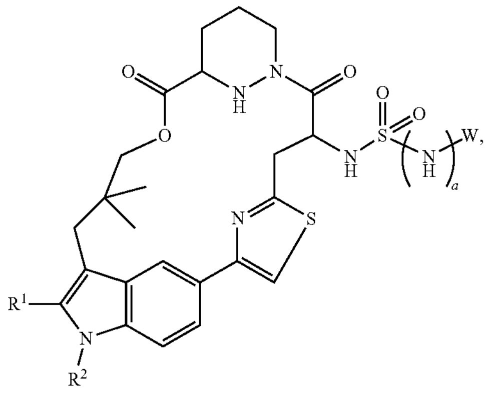

wherein a is 0 or 1.

[43] The compound of paragraph [42], or pharmaceutically acceptable salt thereof, having the structure of Formula Va-1:

Formula Va-1

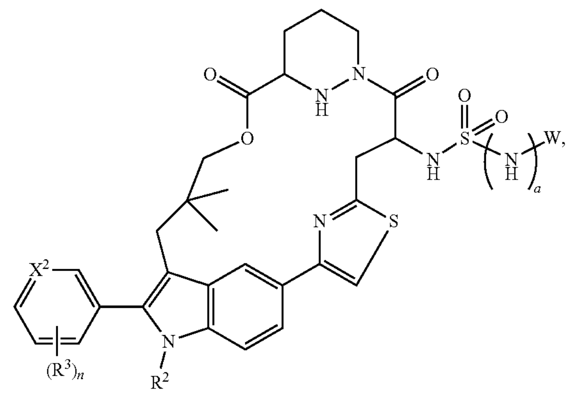

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[44] The compound of paragraph [43], or pharmaceutically acceptable salt thereof, having the structure of Formula Va-2:

Formula Va-2

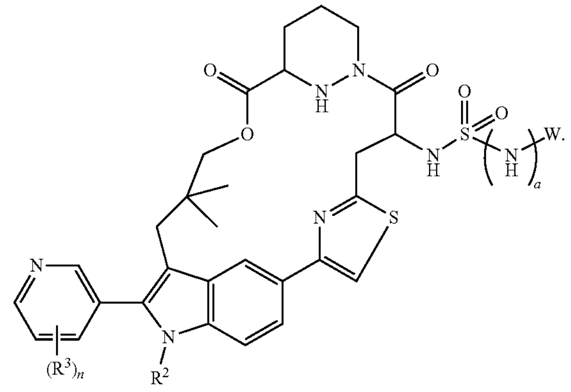

[45] The compound of paragraph [44], or pharmaceutically acceptable salt thereof, having the structure of Formula Va-3:

Formula Va-3

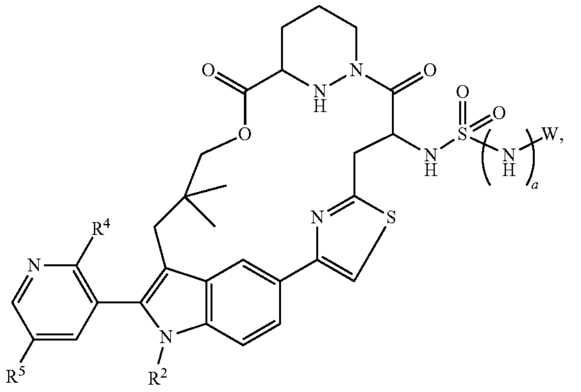

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl.

[46] The compound of paragraph [45], or pharmaceutically acceptable salt thereof, having the structure of Formula Va-4:

Formula Va-4

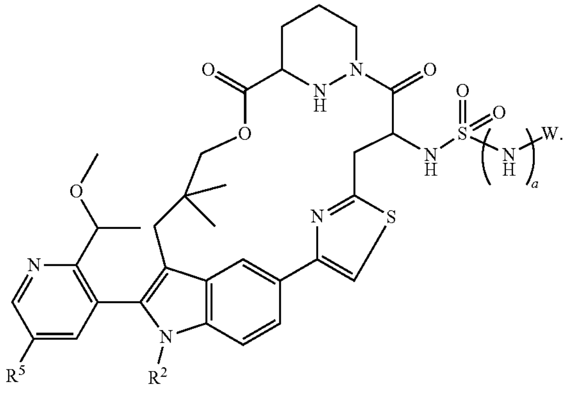

[47] The compound of paragraph [46], or pharmaceutically acceptable salt thereof, having the structure of Formula Va-5:

Formula Va-5

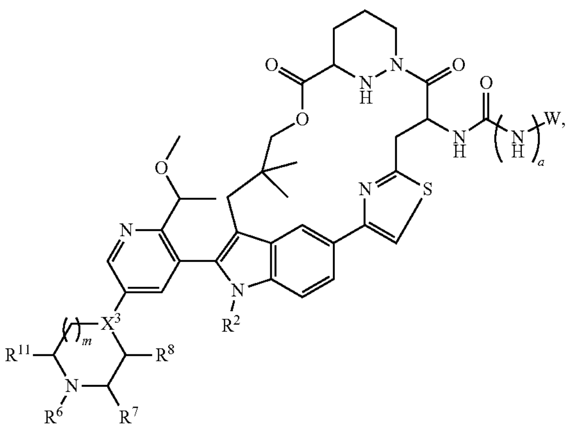

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[48] The compound of paragraph [41], or pharmaceutically acceptable salt thereof, having the structure of Formula VIa:

Formula VIa

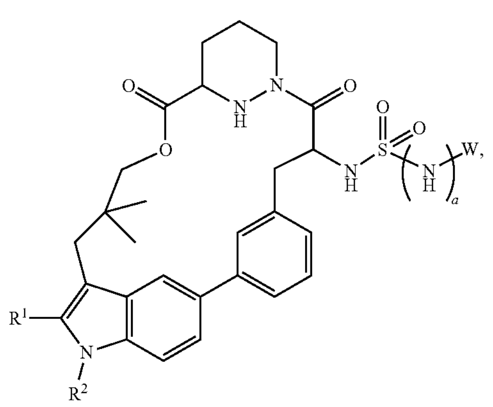

wherein a is 0 or 1.

[49] The compound of paragraph [48], or pharmaceutically acceptable salt thereof, having the structure of Formula VIa-1:

Formula VIa-1

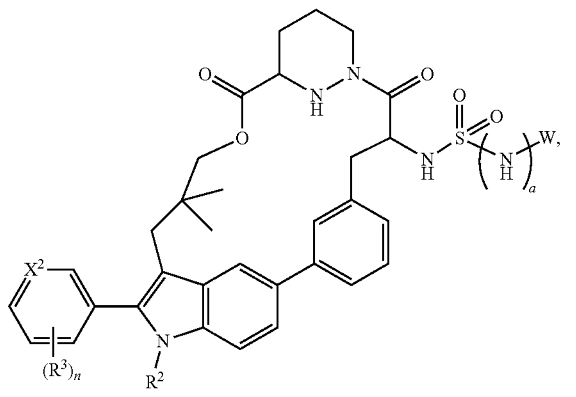

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[50] The compound of paragraph [49], or pharmaceutically acceptable salt thereof, having the structure of Formula VIa-2:

Formula VIa-2

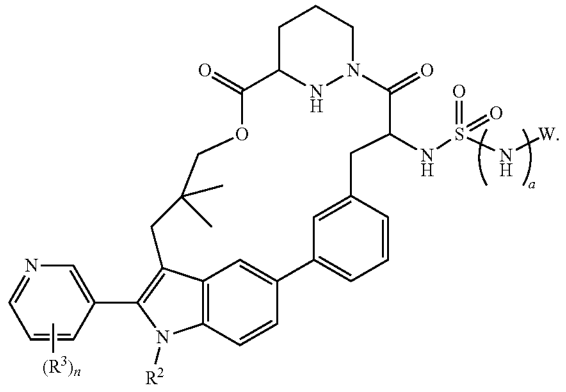

[51] The compound of paragraph [50], or pharmaceutically acceptable salt thereof, having the structure of Formula VIa-3:

Formula VIa-3

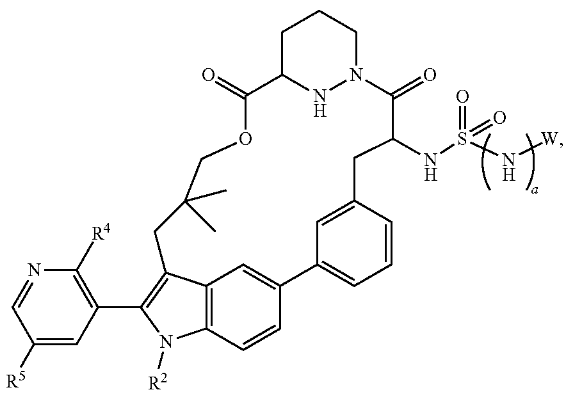

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl.

[52] The compound of paragraph [51], or pharmaceutically acceptable salt thereof, having the structure of Formula VIa-4:

Formula VIa-4

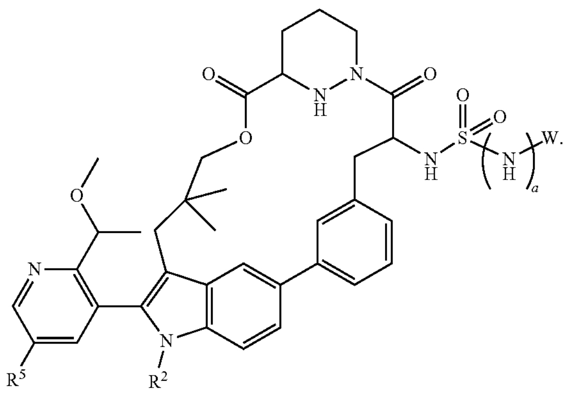

[53] The compound of paragraph [52], or pharmaceutically acceptable salt thereof, having the structure of Formula VIa-5:

Formula VIa-5

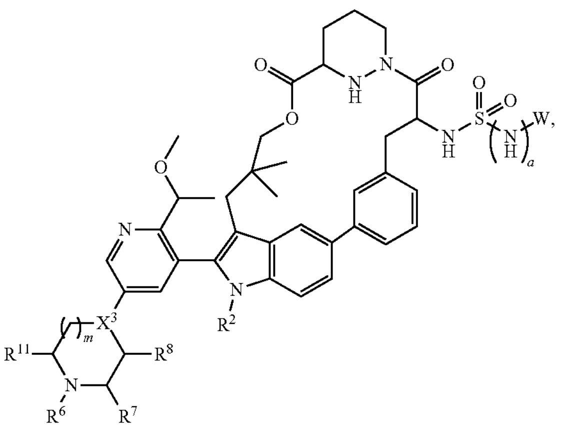

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[54] The compound of paragraph [41], or pharmaceutically acceptable salt thereof, having the structure of Formula VIIa:

Formula VIIa

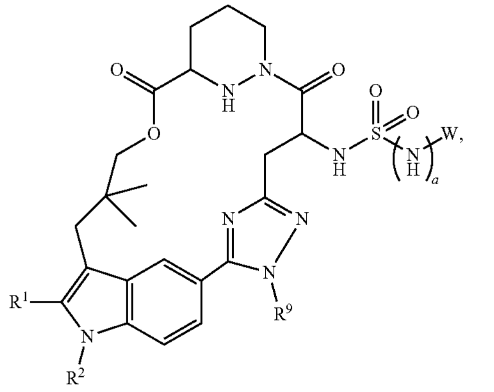

wherein $R^9$ is H or $C_1$-$C_6$ alkyl; and a is 0 or 1.

[55] The compound of paragraph [54], or pharmaceutically acceptable salt thereof, having the structure of Formula VIIa-1:

Formula VIIa-1

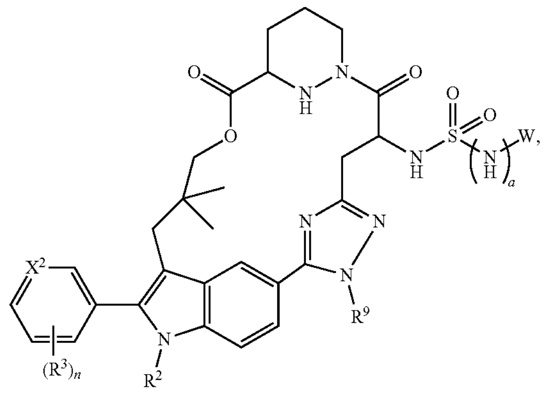

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[56] The compound of paragraph [55], or pharmaceutically acceptable salt thereof, having the structure of Formula VIIa-2:

Formula VIIa-2

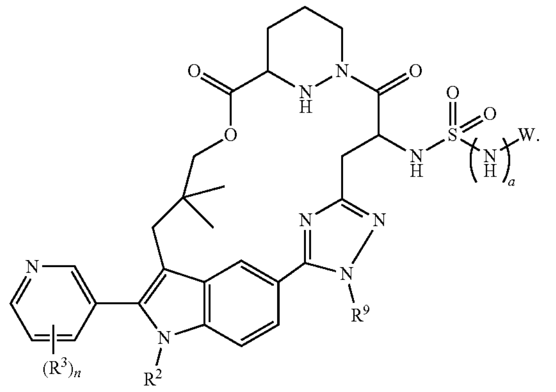

[57] The compound of paragraph [56], or pharmaceutically acceptable salt thereof, having the structure of Formula VIIa-3:

Formula VIIa-3

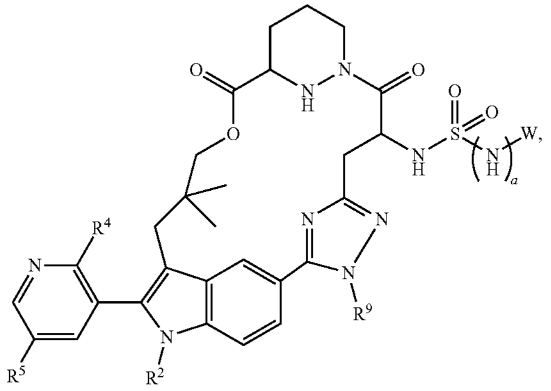

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl.

[58] The compound of paragraph [57], or pharmaceutically acceptable salt thereof, having the structure of Formula VIIa-4:

Formula VIIa-4

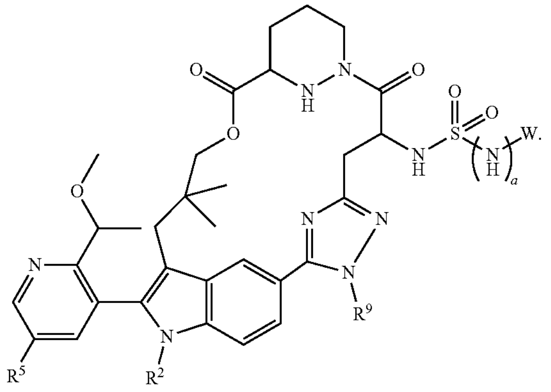

[59] The compound of paragraph [58], or pharmaceutically acceptable salt thereof, having the structure of Formula VIIa-5:

Formula VIIa-5

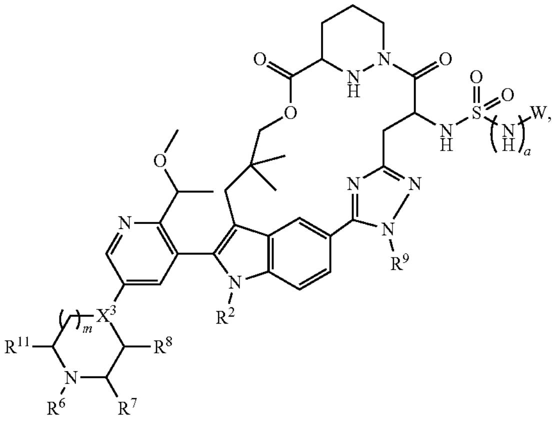

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[60] The compound of any one of paragraphs [54]-[59], or pharmaceutically acceptable salt thereof, wherein $R^9$ is methyl.

[61] The compound of any one of paragraphs [1]-[8], or pharmaceutically acceptable salt thereof, wherein Y is —NHS(O)— or —NHS(O)NH—.

[62] The compound of paragraph [61], or pharmaceutically acceptable salt thereof, having the structure of Formula VIIIa:

Formula VIIIa

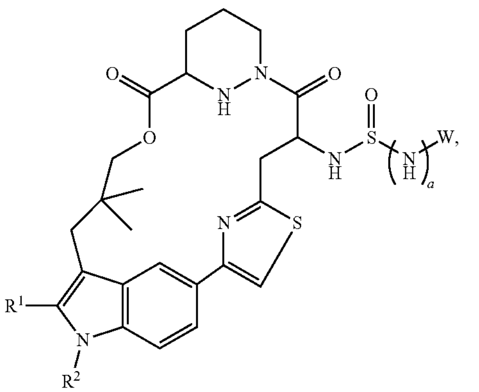

wherein a is 0 or 1.

[63] The compound of paragraph [62], or pharmaceutically acceptable salt thereof, having the structure of Formula VIIIa-1:

Formula VIIIa-1

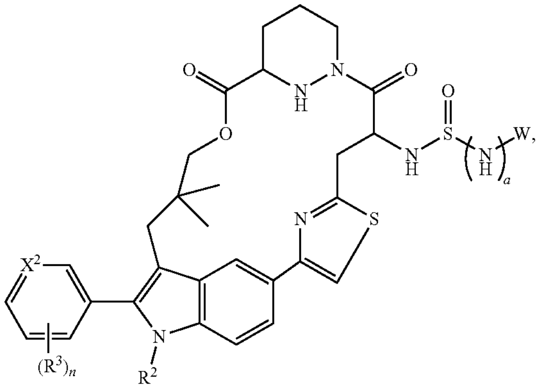

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[64] The compound of paragraph [63], or pharmaceutically acceptable salt thereof, having the structure of Formula VIIIa-2:

Formula VIIIa-2

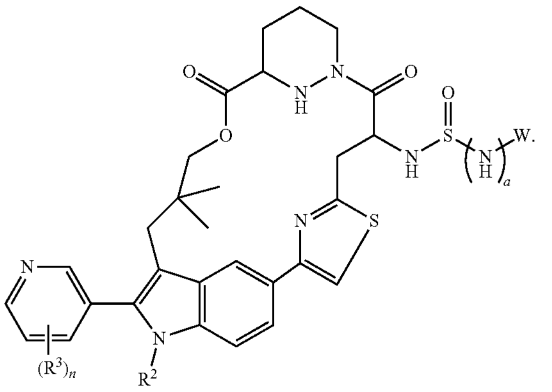

[65] The compound of paragraph [64], or pharmaceutically acceptable salt thereof, having the structure of Formula VIIIa-3:

Formula VIIIa-3

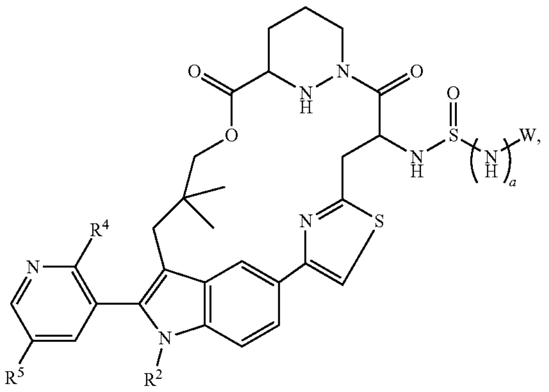

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl.

[66] The compound of paragraph [65], or pharmaceutically acceptable salt thereof, having the structure of Formula VIIIa-4:

Formula VIIIa-4

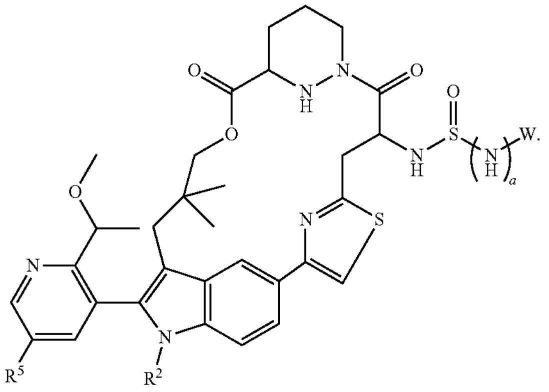

[67] The compound of paragraph [66], or pharmaceutically acceptable salt thereof, having the structure of Formula VIIIa-5:

Formula VIIIa-5

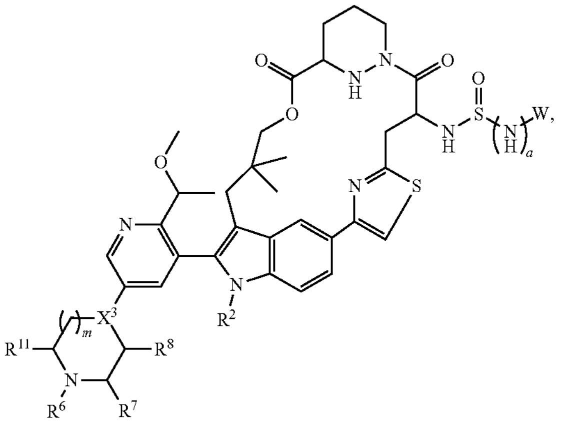

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[68] The compound of paragraph [61], or pharmaceutically acceptable salt thereof, having the structure of Formula IXa:

Formula IXa

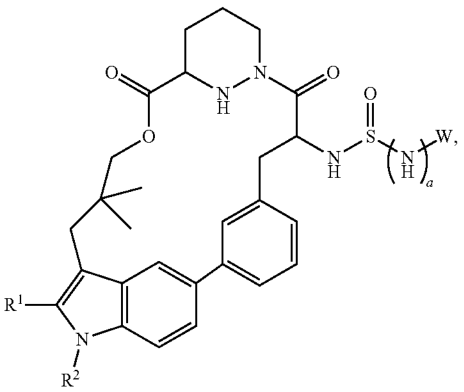

wherein a is 0 or 1.

[69] The compound of paragraph [68], or pharmaceutically acceptable salt thereof, having the structure of Formula IXa-1:

Formula IXa-1

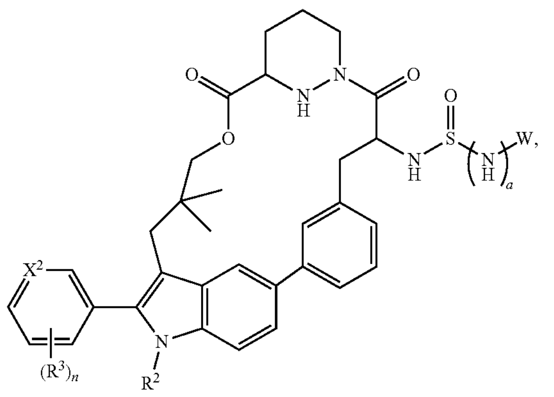

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[70] The compound of paragraph [69], or pharmaceutically acceptable salt thereof, having the structure of Formula IXa-2:

Formula IXa-2

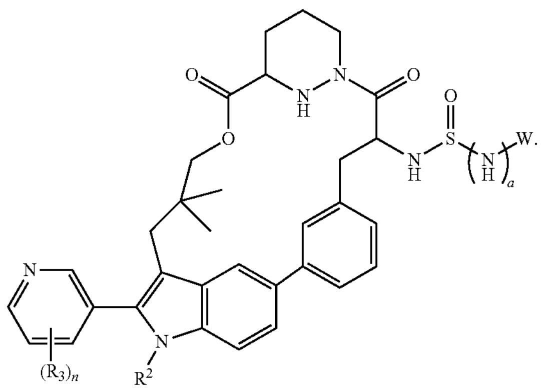

[71] The compound of paragraph [70], or pharmaceutically acceptable salt thereof, having the structure of Formula IXa-3:

Formula IXa-3

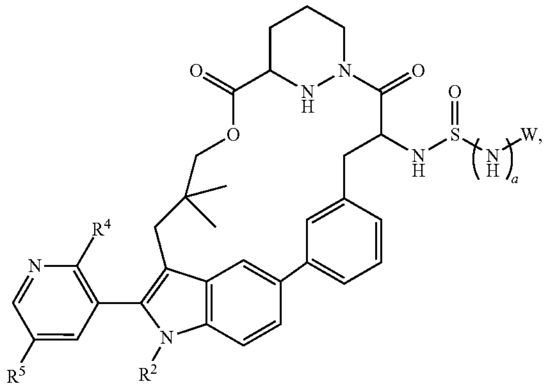

wherein $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl.

[72] The compound of paragraph [71], or pharmaceutically acceptable salt thereof, having the structure of Formula IXa-4:

Formula IXa-4

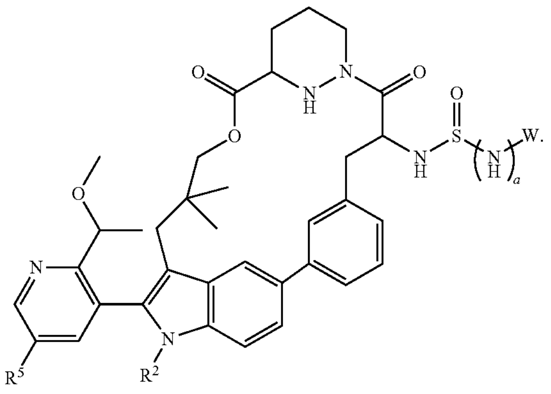

[73] The compound of paragraph [72], or pharmaceutically acceptable salt thereof, having the structure of Formula IXa-5:

Formula IXa-5

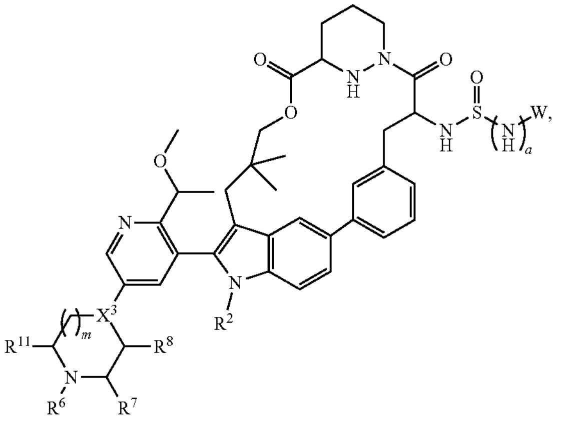

wherein X is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[74] The compound of paragraph [61], or pharmaceutically acceptable salt thereof, having the structure of Formula Xa:

Formula Xa

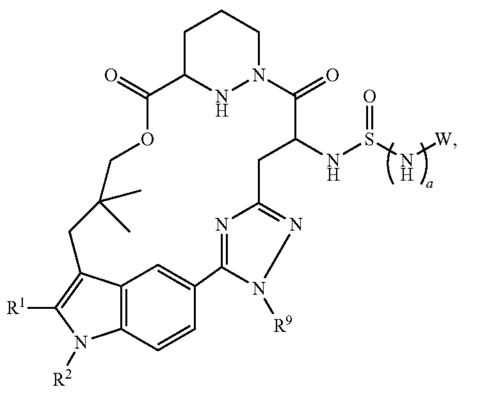

wherein $R^9$ is H or $C_1$-$C_6$ alkyl; and a is 0 or 1.

[75] The compound of paragraph [74], or pharmaceutically acceptable salt thereof, having the structure of Formula Xa-1:

Formula Xa-1

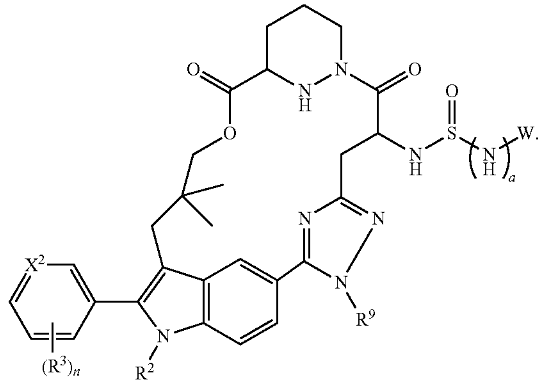

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[76] The compound of paragraph [75], or pharmaceutically acceptable salt thereof, having the structure of Formula Xa-2:

Formula Xa-2

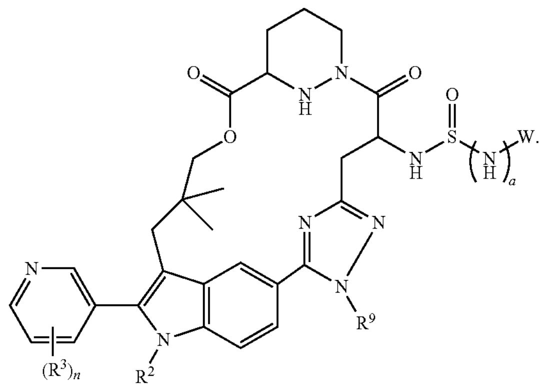

[77] The compound of paragraph [76], or pharmaceutically acceptable salt thereof, having the structure of Formula Xa-3:

Formula Xa-3

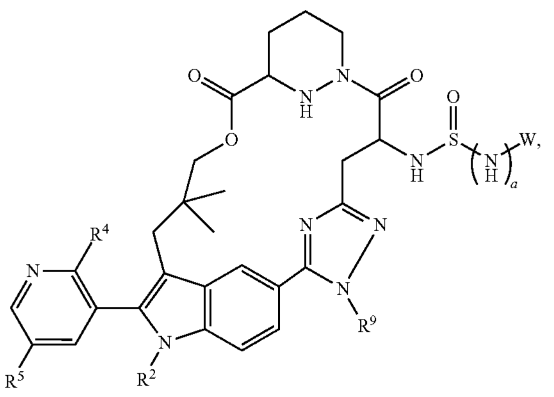

wherein $R^4$ and R are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl.

[78] The compound of paragraph [77] or pharmaceutically acceptable salt thereof, having the structure of Formula Xa-4:

Formula Xa-4

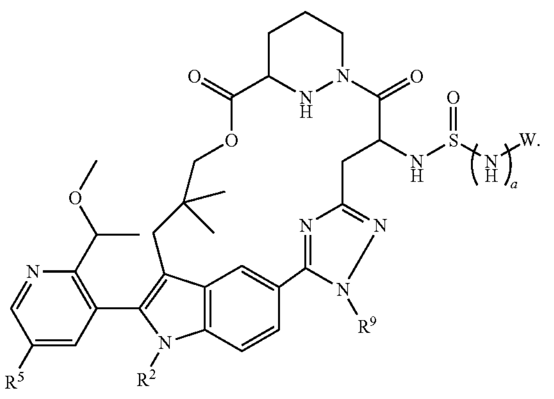

[79] The compound of paragraph [78], or pharmaceutically acceptable salt thereof, having the structure of Formula Xa-5:

Formula Xa-5

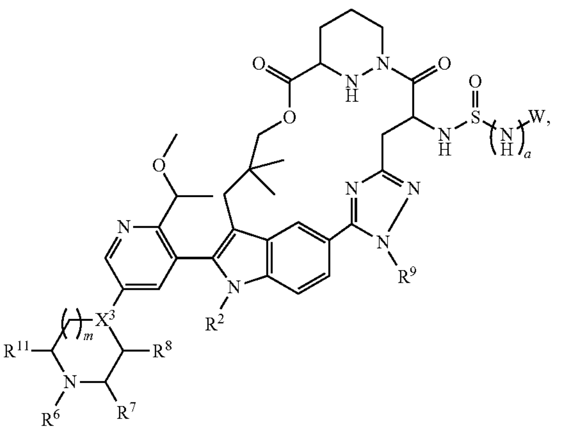

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[80] The compound of any one of paragraphs [74]-[79], or pharmaceutically acceptable salt thereof, wherein $R^9$ is methyl.

[81] The compound of any one of paragraphs [10]-[40], [42]-[60], or [62]-[80], or pharmaceutically acceptable salt thereof, wherein a is 0.

[82] The compound of any one of paragraphs [10]-[40], [42]-[60], or [62]-[80], or pharmaceutically acceptable salt thereof, wherein a is 1.

[83] The compound of any one of paragraphs [1]-[82], or pharmaceutically acceptable salt thereof, wherein $R^2$ is optionally substituted $C_1$-$C_6$ alkyl.

[84] The compound of paragraph [83], or pharmaceutically acceptable salt thereof, wherein $R^2$ is selected from $—CH_2CH_3$ or $—CH_2CF_3$.

[85] The compound of any one of paragraphs [1]-[84], or pharmaceutically acceptable salt thereof, wherein W is $C_1$-$C_4$ alkyl.

[86] The compound of any one of paragraphs [1]-[84], or pharmaceutically acceptable salt thereof, wherein W is optionally substituted cyclopropyl, optionally substituted cyclobutyl, optionally substituted cyclopentyl, or optionally substituted cyclohexyl, optionally substituted piperidine, optionally substituted piperazine, optionally substituted pyridine, or optionally substituted phenyl.

[87] The compound of any one of paragraphs [1]-[84], or pharmaceutically acceptable salt thereof, wherein W is optionally substituted 3 to 10-membered heterocycloalkyl, optionally substituted 3 to 10-membered cycloalkyl, optionally substituted 6 to 10-membered aryl, or optionally substituted 5 to 10-membered heteroaryl.

[88] The compound of any one of paragraphs [1]-[84], or pharmaceutically acceptable salt thereof, wherein W is optionally substituted 3 to 10-membered heterocycloalkyl.

[89] The compound of paragraph [88], or pharmaceutically acceptable salt thereof, wherein W is selected from the following, or a stereoisomer thereof:

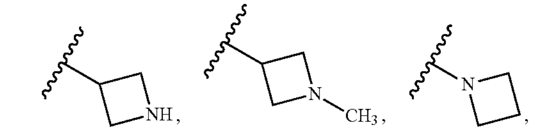
, , ,

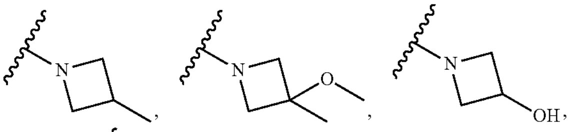
, , ,

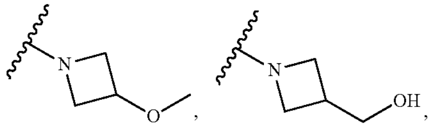
, ,

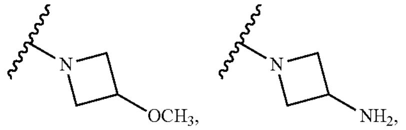
, ,

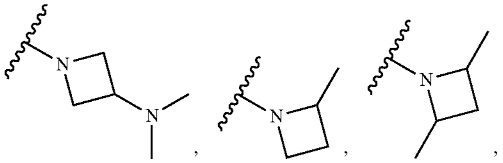
, , ,

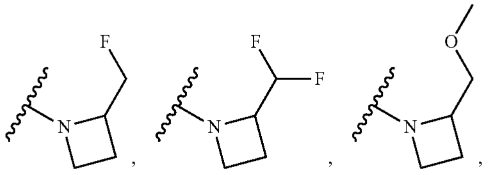
, , ,

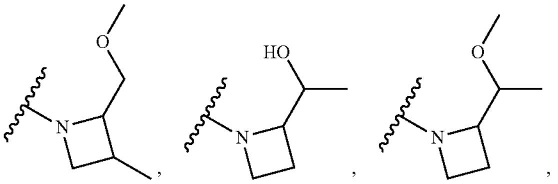
, , ,

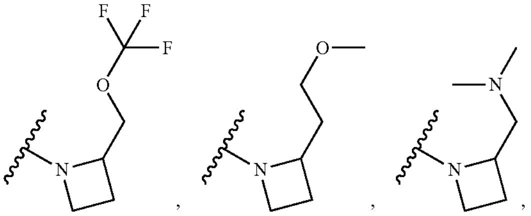
, , ,

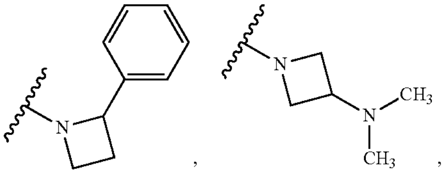
, ,

-continued

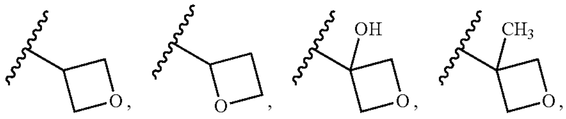
, , , ,

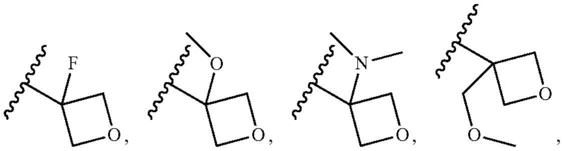
, , , ,

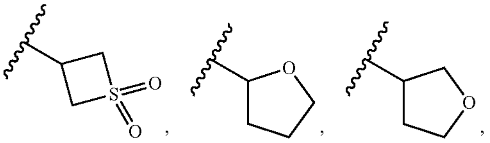
, , ,

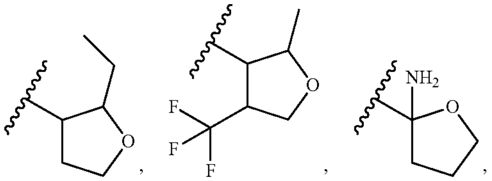
, , ,

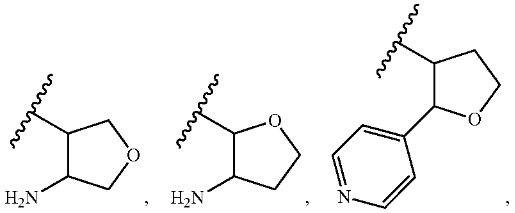
, , ,

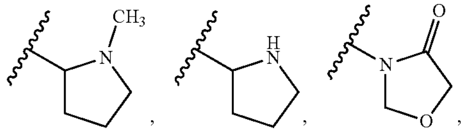
, , ,

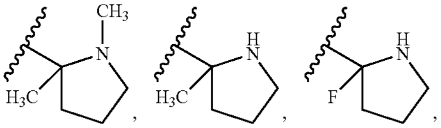
, , ,

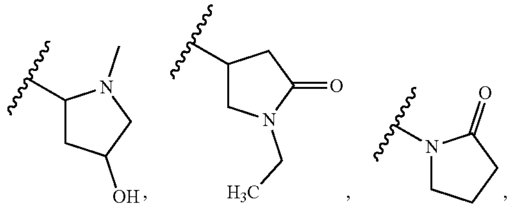
, , ,

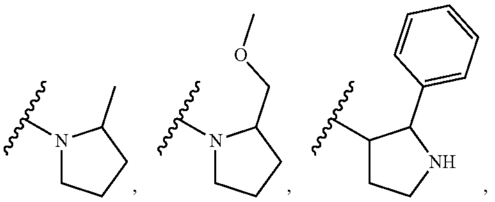
, , ,

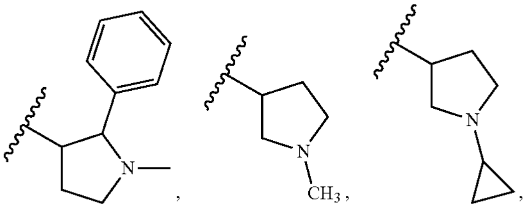
, , ,

-continued
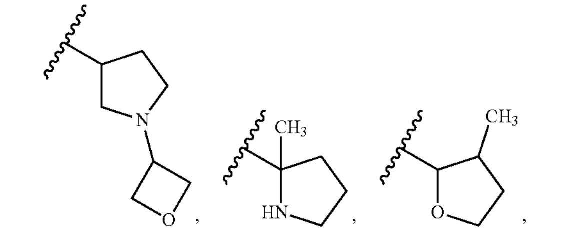
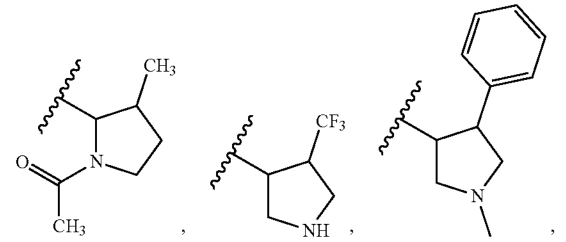
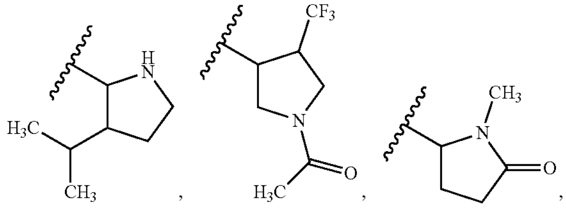
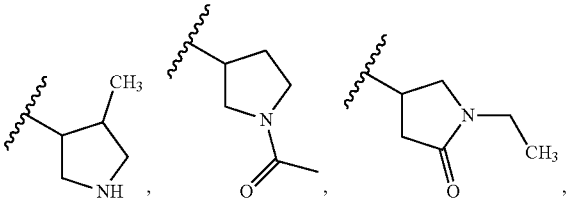
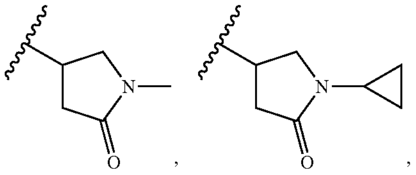
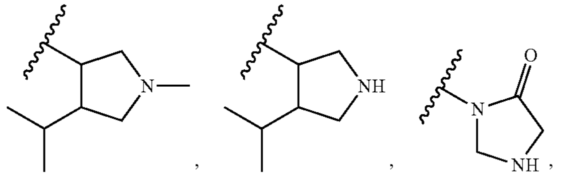
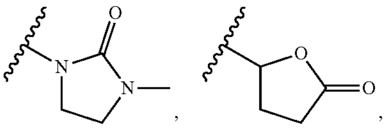
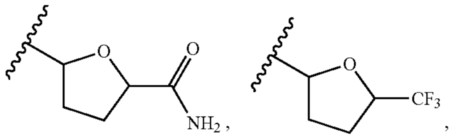
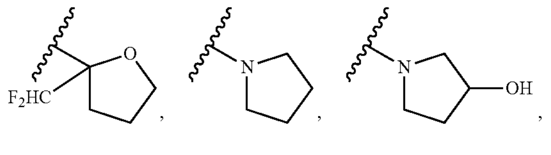
-continued
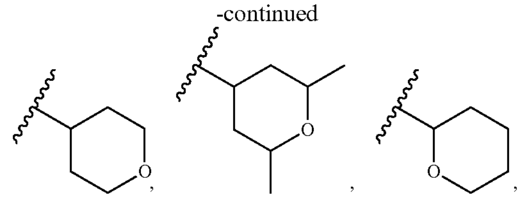
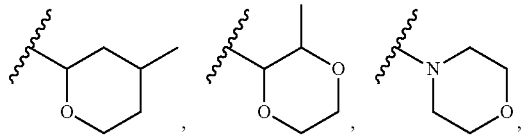
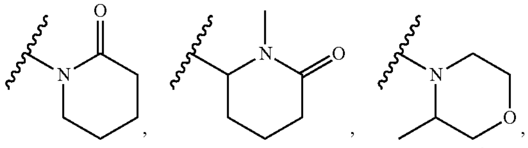
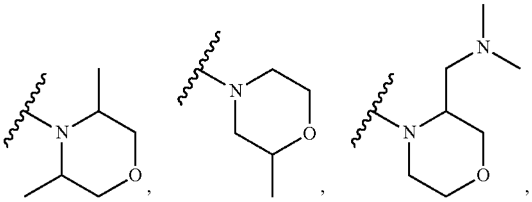
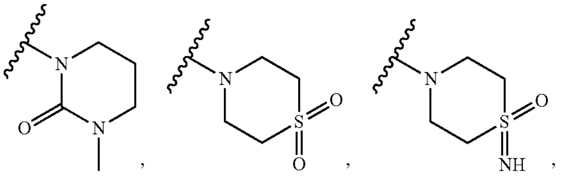
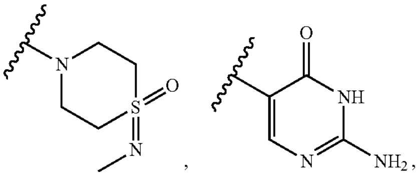
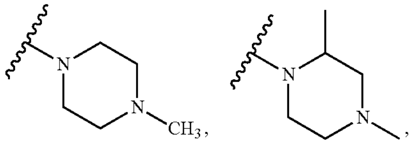
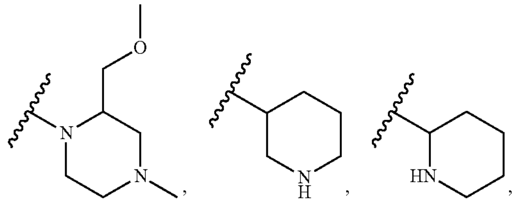
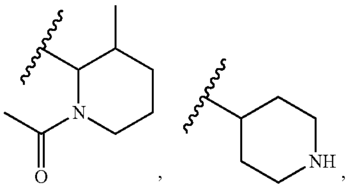
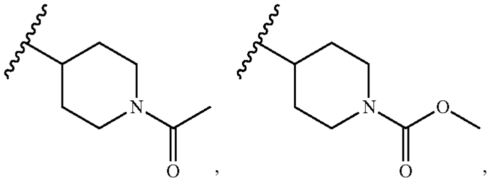

-continued
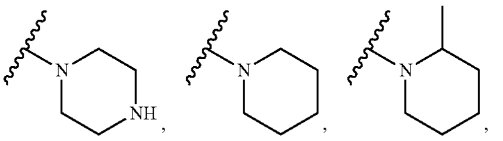
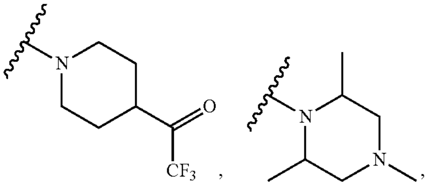
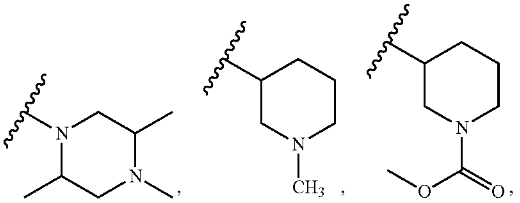
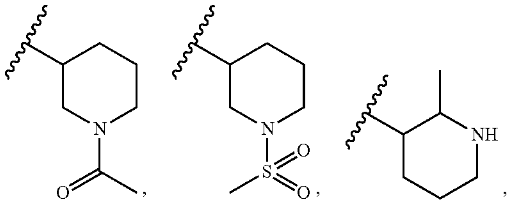
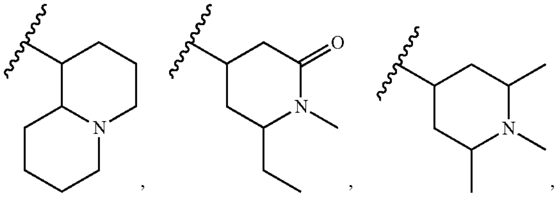
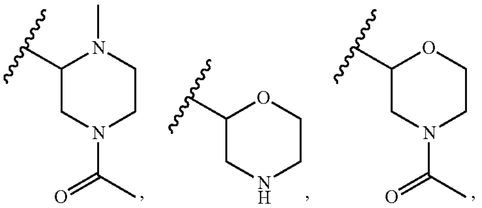
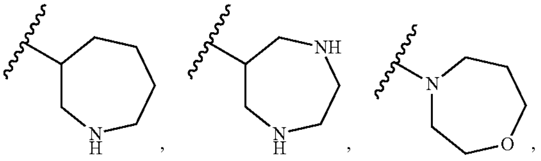
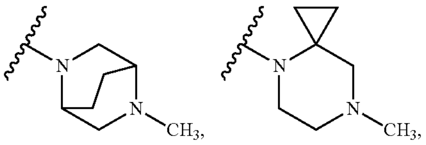
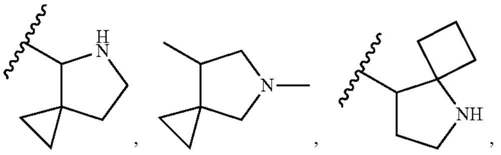
-continued
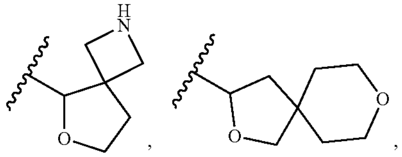
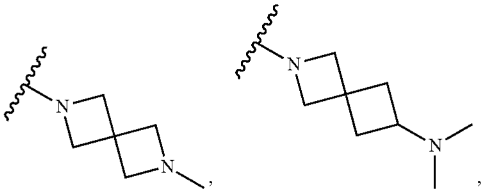
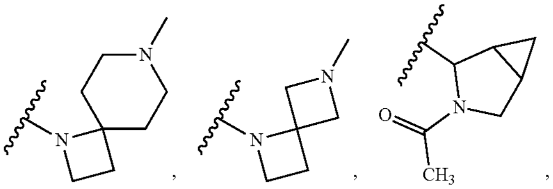
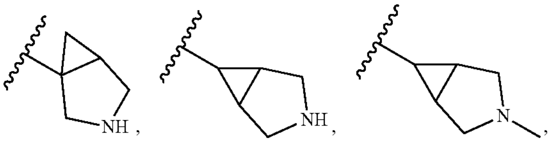
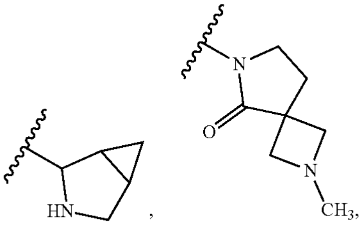
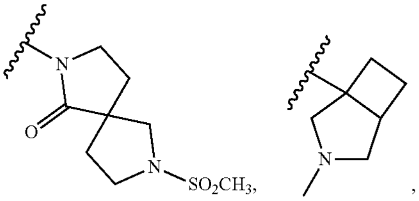
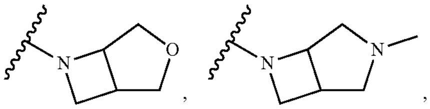
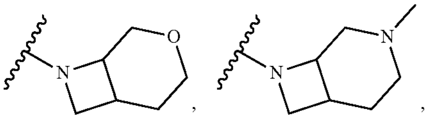
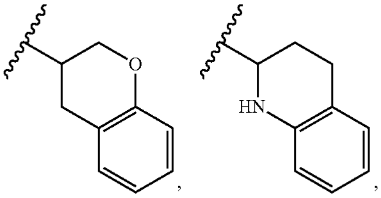
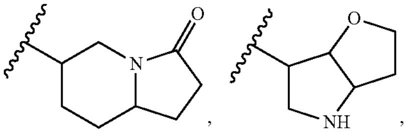

-continued
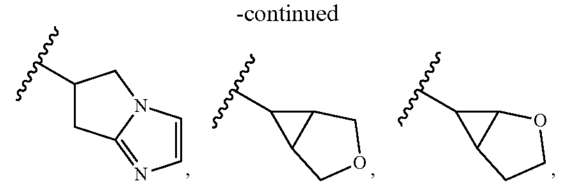
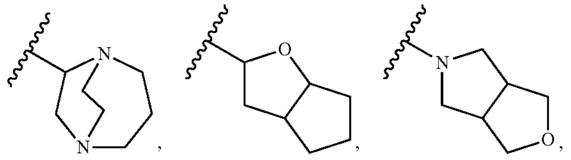
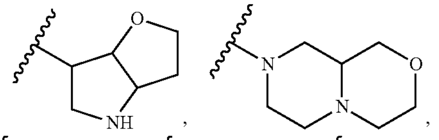
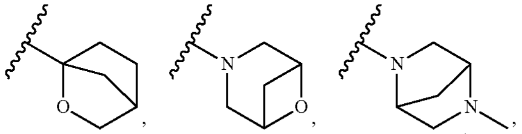
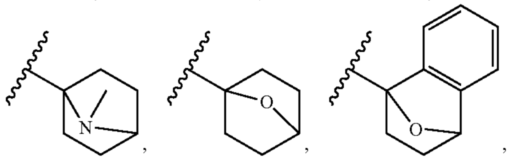
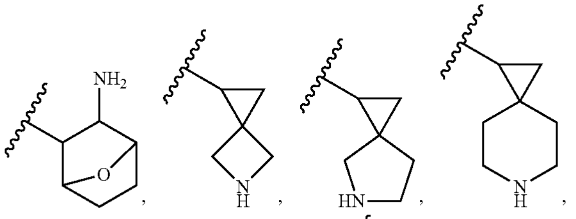
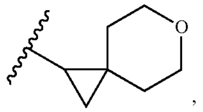
or
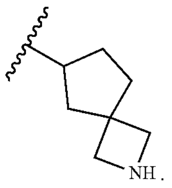
[90] The compound of any one of paragraphs [1]-[84], or pharmaceutically acceptable salt thereof, wherein W is optionally substituted 3 to 10-membered cycloalkyl.
[91] The compound of paragraph [90], or, pharmaceutically acceptable salt thereof, wherein W is selected from the following, or a stereoisomer thereof:
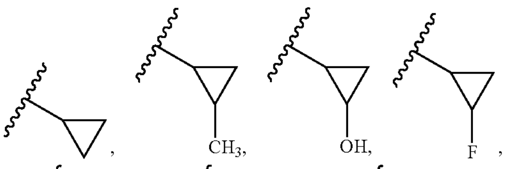
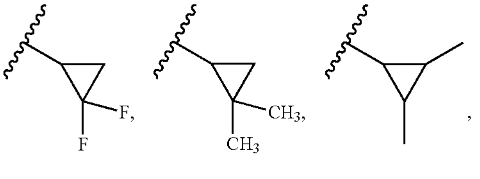
-continued
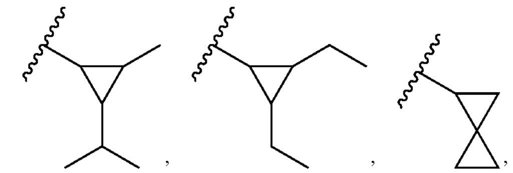
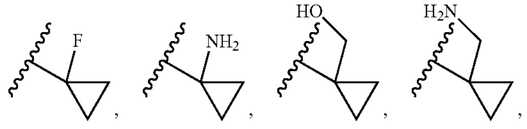
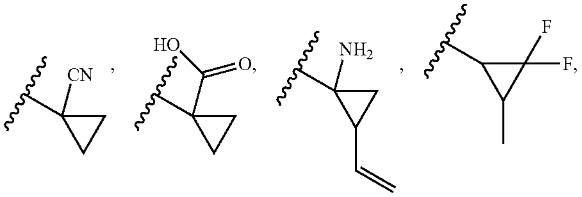
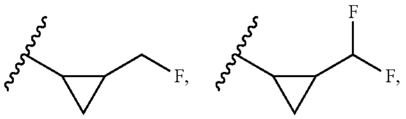
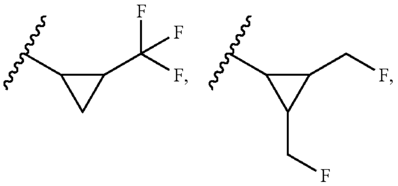
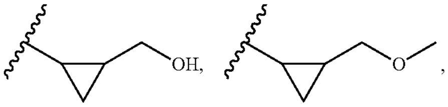
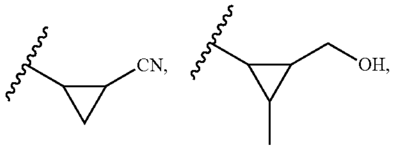
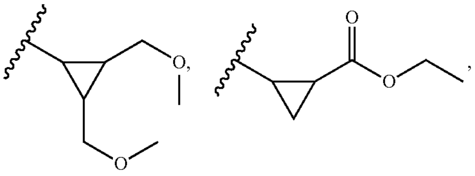
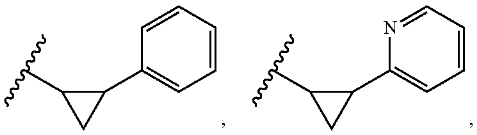
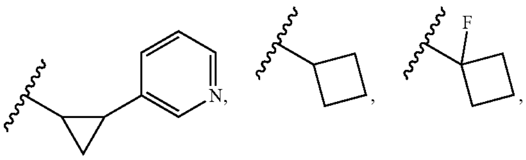
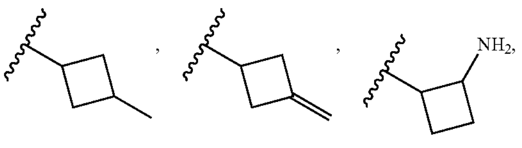

-continued

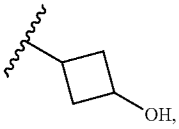 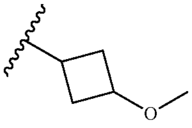 , 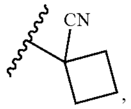 ,

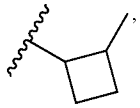 , 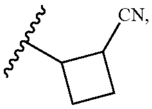 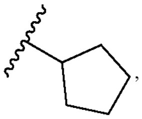 ,

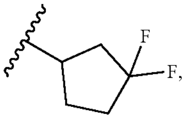 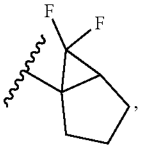 , 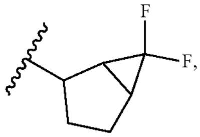

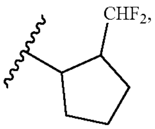 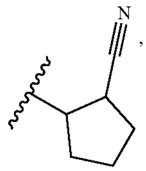 , 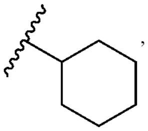 ,

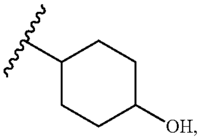 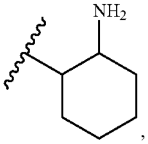 , 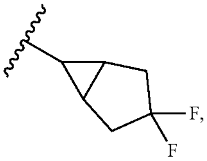

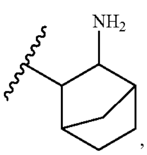 , or 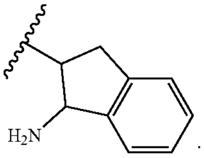 .

[92] The compound of any one of paragraphs [1]-[84], or pharmaceutically acceptable salt thereof, wherein W is optionally substituted 5 to 10-membered heteroaryl.

[93] The compound of paragraph [92], or pharmaceutically acceptable salt thereof, wherein W is selected from the following, or a stereoisomer thereof:

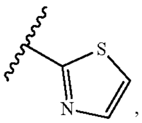 , 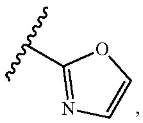 , 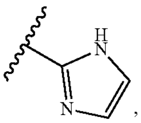 ,

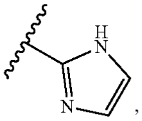 , 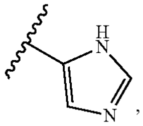 , 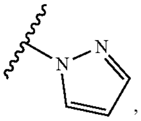 ,

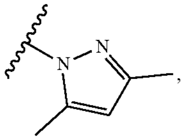 , 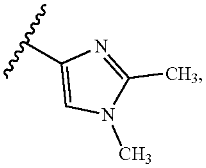 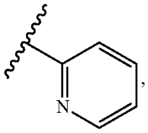 ,

-continued

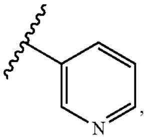 , 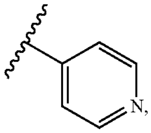 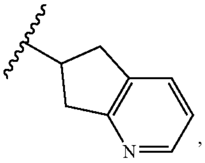 , or

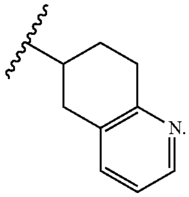

[94] The compound of any one of paragraphs [1]-[84], or pharmaceutically acceptable salt thereof, wherein W is optionally substituted 6 to 10-membered aryl.

[95] The compound of paragraph [94], or pharmaceutically acceptable salt thereof, wherein W is optionally substituted phenyl.

[96] The compound of any one of paragraphs [1]-[84], or pharmaceutically acceptable salt thereof, wherein W is optionally substituted $C_1$-$C_3$ heteroalkyl.

[97] The compound of paragraph [96], or pharmaceutically acceptable salt thereof, wherein W is selected from the following, or a stereoisomer thereof:

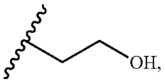 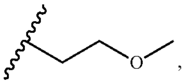 , or

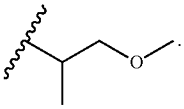

[98] The compound of paragraph [85], or pharmaceutically acceptable salt thereof, wherein W is selected from the following:

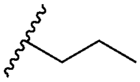 or 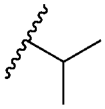 .

[99]A compound, or a pharmaceutically acceptable salt thereof, of Table 1a.

[100]A compound, or a pharmaceutically acceptable salt thereof, of Table 1b.

[101]A compound, or a pharmaceutically acceptable salt thereof, having the structure of Formula Ib:

Formula Ib

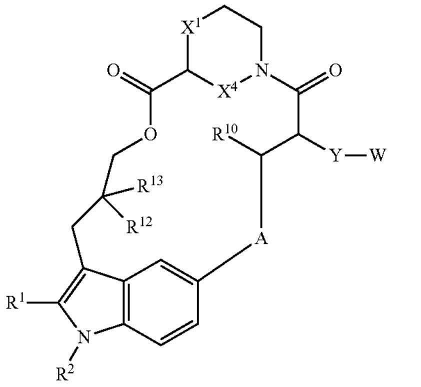

wherein A is optionally substituted 3 to 6-membered cycloalkylene, optionally substituted 3 to 6-membered heterocycloalkylene, optionally substituted 6-membered arylene, optionally substituted 5 to 6-membered heteroarylene, optionally substituted $C_2$-$C_4$ alkylene, or optionally substituted $C_2$-$C_4$ alkenylene;

Y is

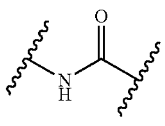

—NHC(O)— ,

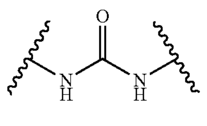

—NHC(O)NH— ,

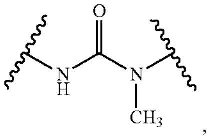

—NHC(O)NCH$_3$— ,

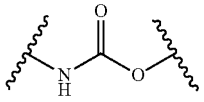

—NHC(O)O— ,

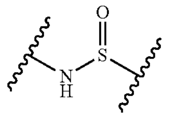

—NHC(S)— ,

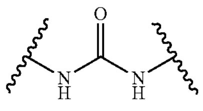

—NHC(S)NH— ,

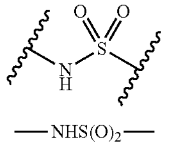

—NHS(O)$_2$— ,

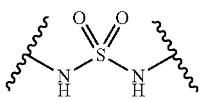

—NHS(O)$_2$NH— ;

W is hydrogen, $C_1$-$C_4$ alkyl, optionally substituted $C_1$-$C_3$ heteroalkyl, optionally substituted 3 to 10-membered heterocycloalkyl, optionally substituted 3 to 10-membered cycloalkyl, optionally substituted 6 to 10-membered aryl, or optionally substituted 5 to 10-membered heteroaryl; or W is —$R^{14}C(=O)R^{15}$ where $R^{14}$ is 3 to 10-membered cycloalkylene and $R^{15}$ is selected from optionally substituted 3 to 10-membered cycloalkyl, optionally substituted 6 to 10-membered aryl, or optionally substituted 5 to 10-membered heteroaryl;

$X^1$ and $X^4$ are each, independently, $CH_2$, $CH(CH_3)$ or NH;

$R^1$ is optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 15-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl;

$R^{10}$ is hydrogen, hydroxy, optionally substituted $C_1$-$C_6$ alkoxy, optionally substituted $C_1$-$C_3$ alkyl, optionally substituted $C_1$-$C_6$ heteroalkyl, or optionally substituted 3 to 7-membered heterocycloalkyl; and $R^{12}$ and $R^{13}$ are each, independently, selected from F or $CH_3$, or $R^{12}$ and $R^{13}$ combine with the atoms to which they are attached to make a 3-membered cycloalkyl.

[102] The compound of paragraph [101], or pharmaceutically acceptable salt thereof, wherein $R^1$ is optionally substituted 6 to 10-membered aryl or optionally substituted 5 to 10-membered heteroaryl.

[103] The compound of paragraph [102], or pharmaceutically acceptable salt thereof, wherein $R^1$ is optionally substituted phenyl or optionally substituted pyridine.

[104] The compound of any one of paragraphs [101]-[103], or pharmaceutically acceptable salt thereof, wherein A is optionally substituted thiazole, optionally substituted triazole, optionally substituted morpholino, optionally substituted piperidinyl, optionally substituted pyridine, or optionally substituted phenyl.

[105] The compound of any one of paragraphs [101]-[103], or pharmaceutically acceptable salt thereof, wherein A is not an optionally substituted phenyl or benzimidazole.

[106] The compound of paragraph [105], or pharmaceutically acceptable salt thereof, wherein A is not hydroxyphenyl.

[107] The compound of any one of paragraphs [101]-[106], or pharmaceutically acceptable salt thereof, wherein the compound is not a compound of Table 2.

[108] The compound of any one of paragraphs [101]-[107], or pharmaceutically acceptable salt thereof, wherein the compound is not a compound of Table 3.

[109] The compound of any one of paragraphs [101]-[108], or pharmaceutically acceptable salt thereof, wherein Y is —NHC(O)— or —NHC(O)NH—.

[110] The compound of paragraph [109], or pharmaceutically acceptable salt thereof, having the structure of Formula IIb:

Formula IIb

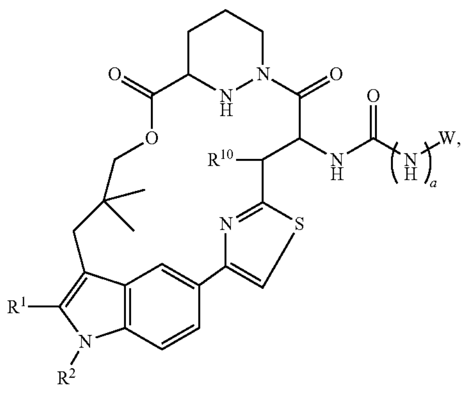

wherein a is 0 or 1.

[111] The compound of paragraph [110], or pharmaceutically acceptable salt thereof, having the structure of Formula Ib-1:

Formula IIb-1

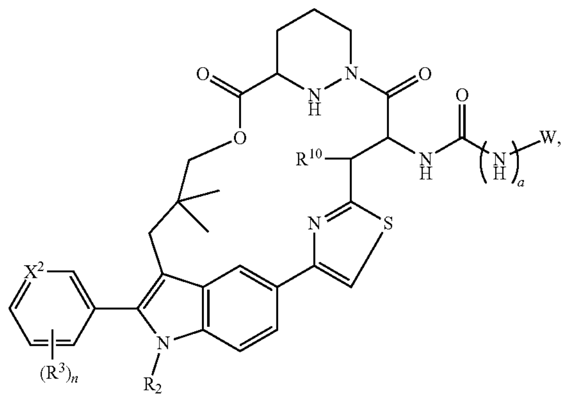

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[112] The compound of paragraph [111], or pharmaceutically acceptable salt thereof, having the structure of Formula IIb-2:

Formula IIb-2

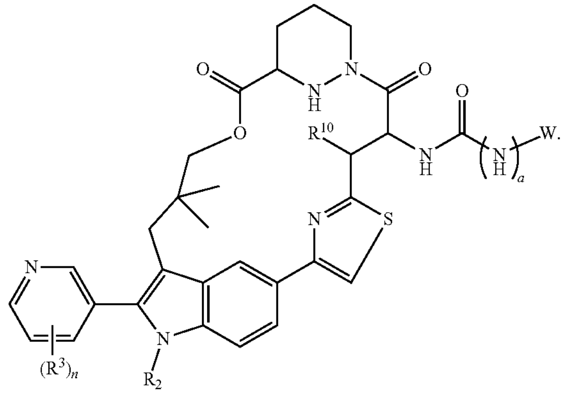

[113] The compound of paragraph [112], or pharmaceutically acceptable salt thereof having the structure of Formula IIb-3:

Formula IIb-3

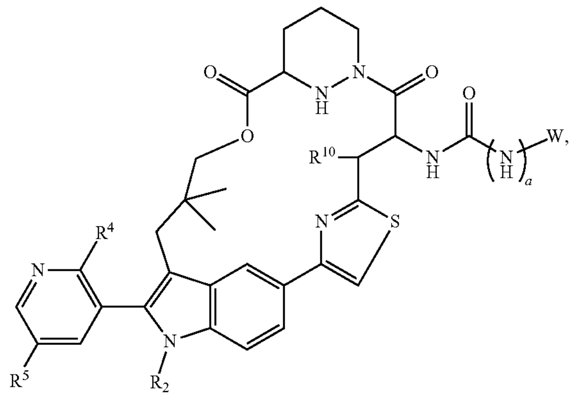

wherein $R^4$ and $R^5$ are each independently selected from hydrogen, halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl. In some embodiments, $R^4$ and $R^5$ are not hydrogen.

In some embodiments, the compound, or pharmaceutically acceptable salt thereof, has the structure of Formula Ib-3, wherein W is optionally substituted 3 to 10-membered heterocycloalkyl, optionally substituted 3 to 10-membered cycloalkyl, optionally substituted 6 to 10-membered aryl, or optionally substituted 5 to 10-membered heteroaryl; or W is —$R^{14}C(=O)R^{15}$ where $R^{14}$ is 3 to 10-membered cycloalkyl and $R^{15}$ is selected from optionally substituted 3 to 10-membered cycloalkyl, optionally substituted 6 to 10-membered aryl, or optionally substituted 5 to 10-membered heteroaryl; $R^2$ is hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^4$ and $R^5$ are each independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and $R^{10}$ is hydrogen, hydroxy, optionally substituted $C_1$-$C_6$ alkoxy, optionally substituted $C_1$-$C_3$alkyl, optionally substituted $C_1$-$C_6$ heteroalkyl, or optionally substituted 3 to 7-membered heterocycloalkyl.

[114] The compound of paragraph [113], or pharmaceutically acceptable salt thereof, having the structure of Formula IIb-4:

Formula IIb-4

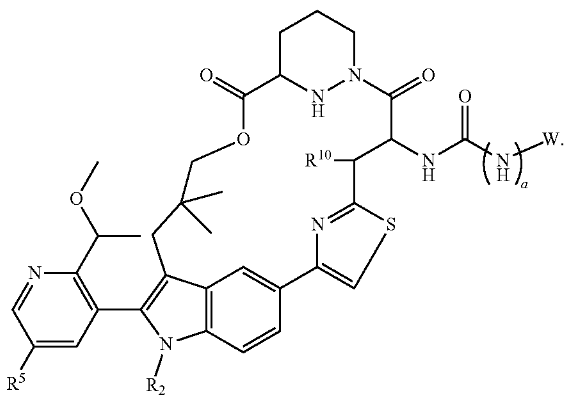

In some embodiments, the compound, or pharmaceutically acceptable salt thereof, has the structure of Formula IIb-4, wherein W is optionally substituted 3 to 10-membered heterocycloalkyl, optionally substituted 3 to 10-membered cycloalkyl, optionally substituted 6 to 10-membered aryl, or optionally substituted 5 to 10-membered heteroaryl; or W is —$R^{14}C(=O)R^{15}$ where $R^{14}$ is 3 to 10-membered cycloalkyl and $R^{15}$ is selected from optionally substituted 3 to 10-membered cycloalkyl, optionally substituted 6 to 10-membered aryl, or optionally substituted 5 to 10-membered heteroaryl; $R^2$ is hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^5$ is selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and $R^{10}$ is hydrogen, hydroxy, optionally substituted $C_1$-$C_6$ alkoxy, optionally substituted $C_1$-$C_3$ alkyl, optionally substituted $C_1$-$C_6$ heteroalkyl, or optionally substituted 3 to 7-membered heterocycloalkyl.

[115] The compound of paragraph [114], or pharmaceutically acceptable salt thereof, having the structure of Formula IIb-5:

Formula IIb-5

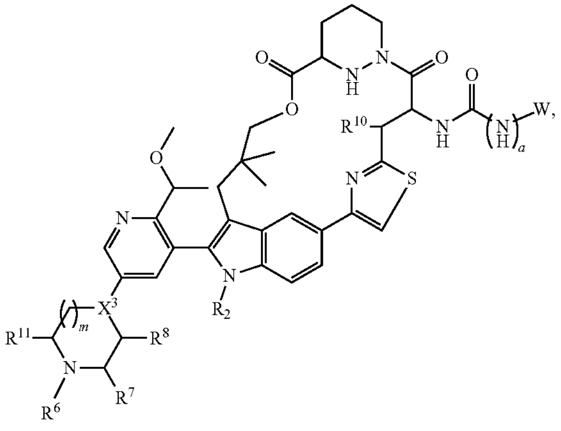

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[116] The compound of paragraph [115], or pharmaceutically acceptable salt thereof, having the structure of Formula IIb-6:

Formula IIb-6

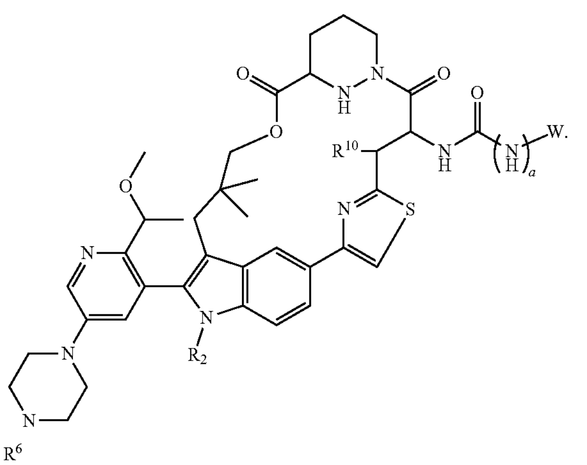

[117] The compound of paragraph [115], or pharmaceutically acceptable salt thereof, having the structure of Formula IIb-7:

Formula IIb-7

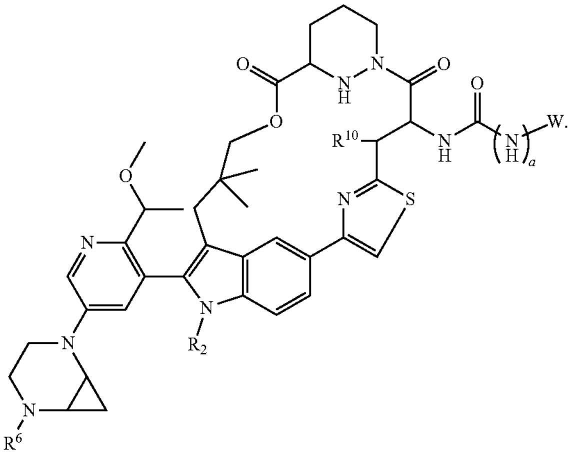

[118] The compound of paragraph [116] or [117], wherein $R^6$ is methyl.

[119] The compound of paragraph [115], or pharmaceutically acceptable salt thereof, having the structure of Formula IIb-8 or Formula IIb-9:

Formula IIb-8

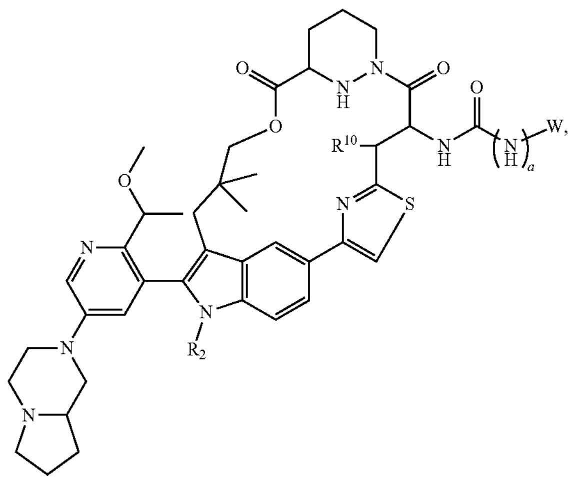

Formula IIb-9

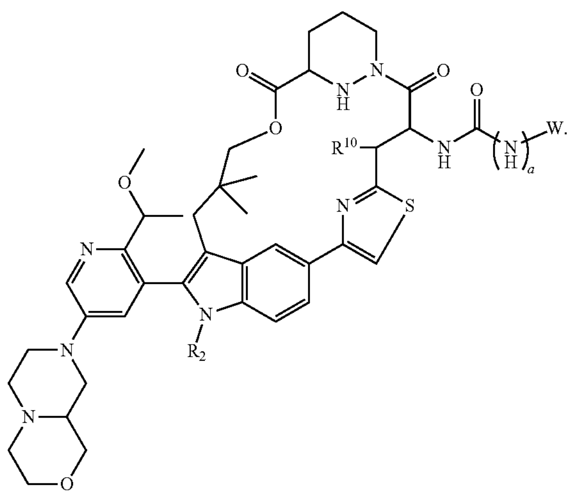

[120] The compound of paragraph [109], or pharmaceutically acceptable salt thereof, having the structure of Formula IIIb:

Formula IIIb

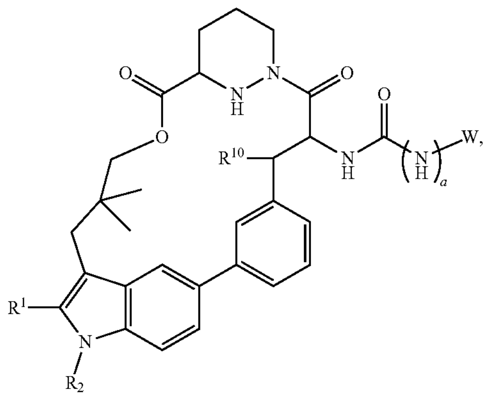

wherein a is 0 or 1.

[121] The compound of paragraph [120], or pharmaceutically acceptable salt thereof, having the structure of Formula IIIb-1:

Formula IIIb-1

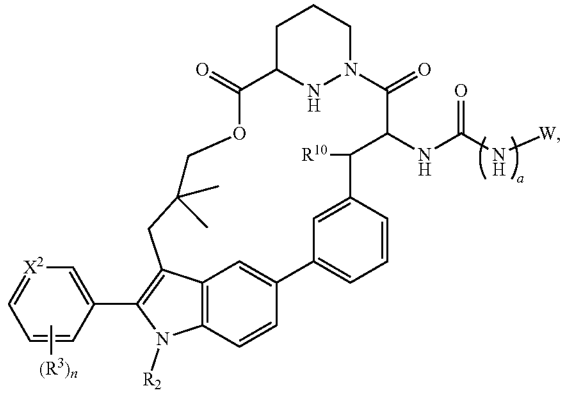

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[122] The compound of paragraph [121], or pharmaceutically acceptable salt thereof, having the structure of Formula IIIb-2:

Formula IIIb-2

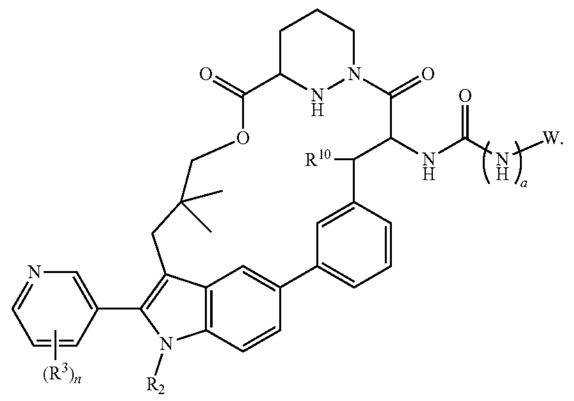

[123] The compound of paragraph [122], or pharmaceutically acceptable salt thereof, having the structure of Formula IIIb-3:

Formula IIIb-3

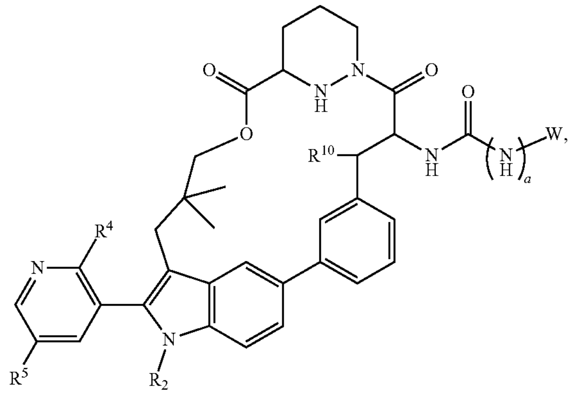

wherein $R^4$ and R are each independently selected from hydrogen, halogen, cyano, hydroxy, optionally substituted amine, optionally substituted amido, optionally substituted $C_1$-$C_6$alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl. In some embodiments, $R^4$ and $R^5$ are not hydrogen.

[124] The compound of paragraph [123], or pharmaceutically acceptable salt thereof, having the structure of Formula IIIb-4:

Formula IIIb-4

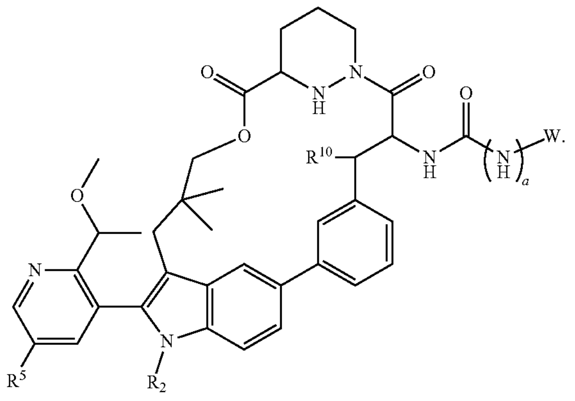

[125] The compound of paragraph [124], or pharmaceutically acceptable salt thereof, having the structure of Formula IIIb-5:

Formula IIIb-5

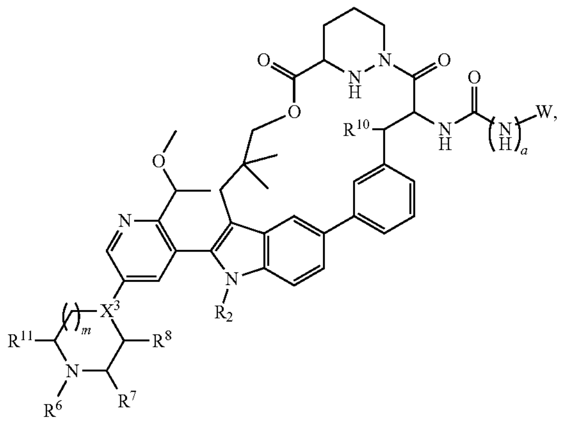

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[126] The compound of paragraph [125], or pharmaceutically acceptable salt thereof, having the structure of Formula IIIb-6:

Formula IIIb-6

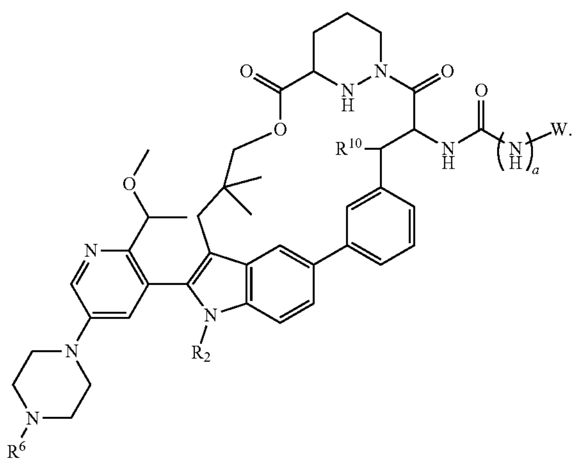

[127] The compound of paragraph [125], or pharmaceutically acceptable salt thereof, having the structure of Formula IIIb-7:

Formula IIIb-7

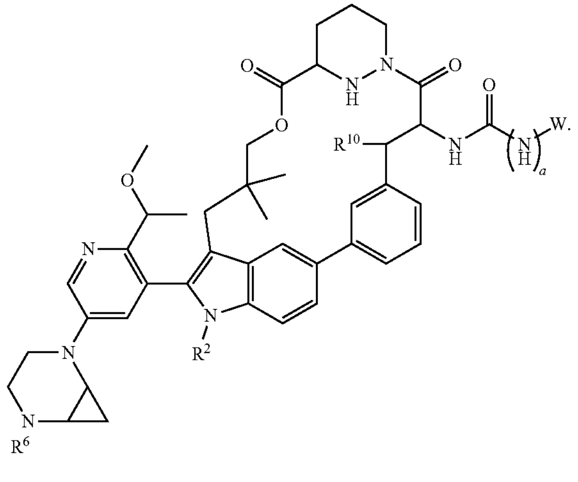

[128] The compound of paragraph [126] or [127], wherein $R^6$ is methyl.

[129] The compound of paragraph [125], or pharmaceutically acceptable salt thereof, having the structure of Formula IIIb-8 or Formula IIIb-9:

Formula IIIb-8

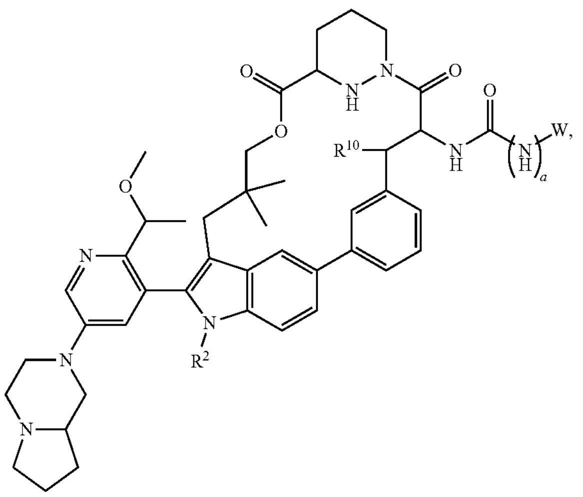

Formula IIIb-9

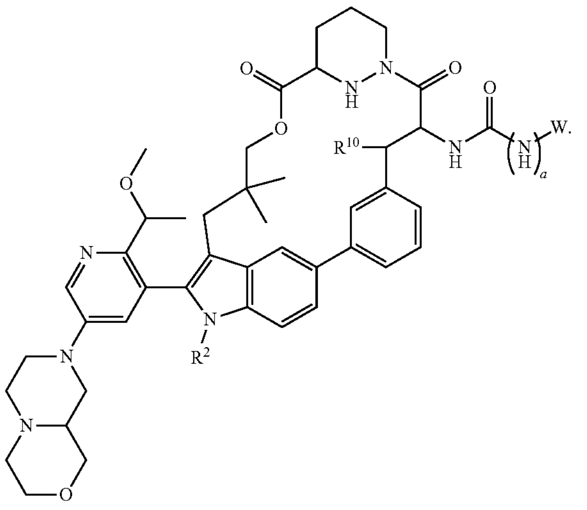

[130] The compound of paragraph [109], or pharmaceutically acceptable salt thereof, having the structure of Formula IVb:

Formula IVb

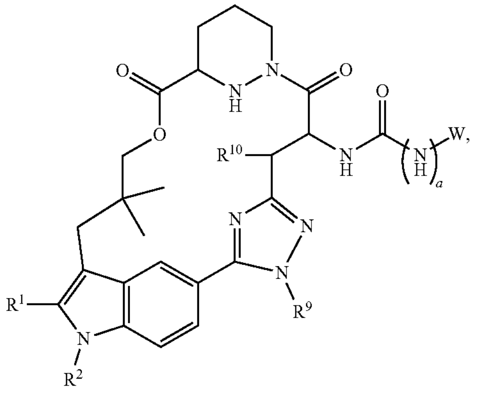

wherein $R^9$ is H or $C_1$-$C_6$ alkyl; and a is 0 or 1.

[131] The compound of paragraph [130], or pharmaceutically acceptable salt thereof, having the structure of Formula IVb-1:

Formula IVb-1

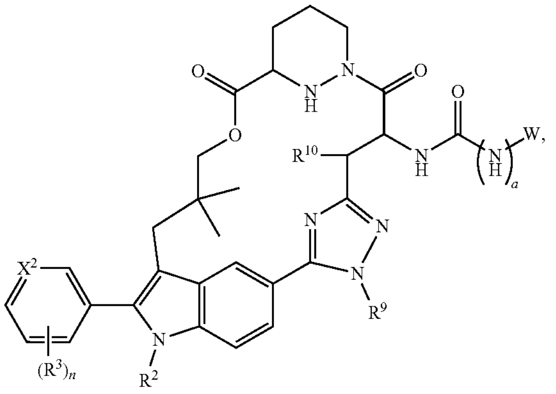

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[132] The compound of paragraph [131], or pharmaceutically acceptable salt thereof, having the structure of Formula IVb-2:

Formula IVb-2

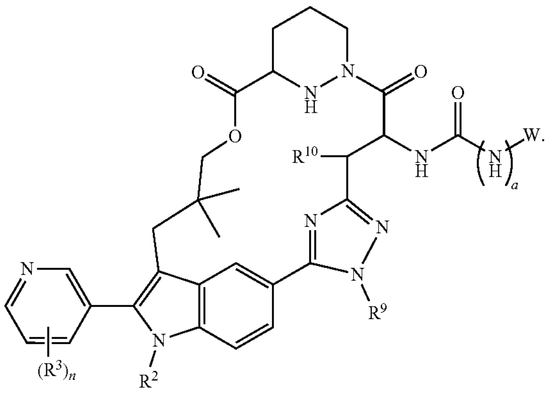

[133] The compound of paragraph [132], or pharmaceutically acceptable salt thereof, having the structure of Formula IVb-3:

Formula IVb-3

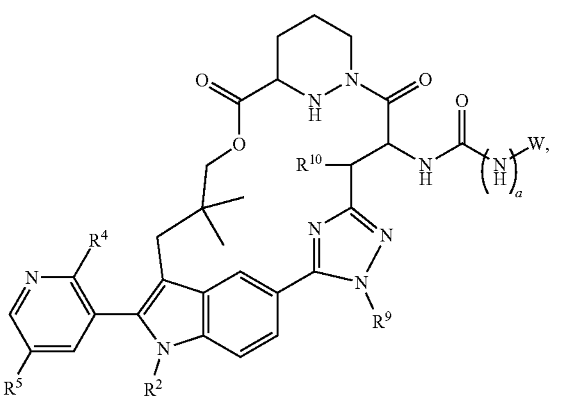

wherein $R^4$ and $R^5$ are each independently selected from hydrogen, halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl. In some embodiments, $R^4$ and $R^5$ are not hydrogen.

[134] The compound of paragraph [133], or pharmaceutically acceptable salt thereof, having the structure of Formula IVb-4:

Formula IVb-4

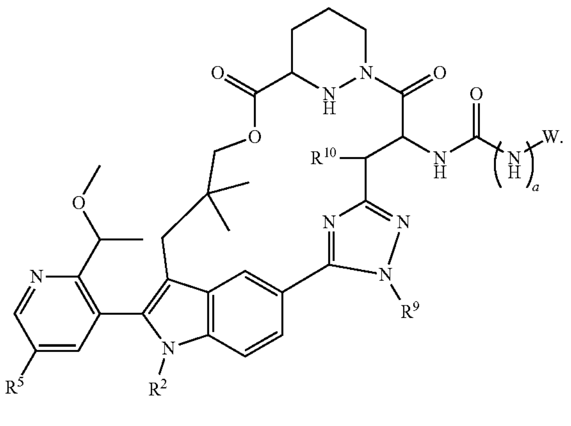

[135] The compound of paragraph [134], or pharmaceutically acceptable salt thereof, having the structure of Formula IVb-5:

Formula IVb-5

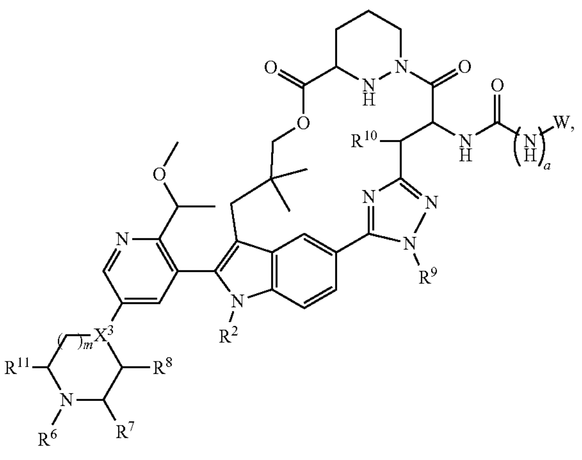

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 6-membered cycloalkyl or an optionally substituted 3 to 8-membered heterocycloalkyl; or $R^7$ and $R^8$ combine with the atoms to which they are attached to form an optionally substituted 3 to 6-membered heterocycloalkyl; or $R^7$ and $R^{11}$ combine with the atoms to which they are attached to form an optionally substituted 4 to 6-membered heterocycloalkyl.

[136] The compound of paragraph [135], or pharmaceutically acceptable salt thereof, having the structure of Formula IVb-6:

Formula IVb-6

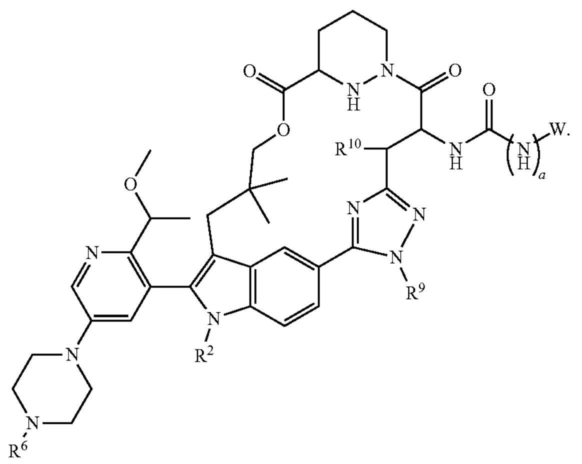

[137] The compound of paragraph [135], or pharmaceutically acceptable salt thereof, having the structure of Formula IVb-7:

Formula IVb-7

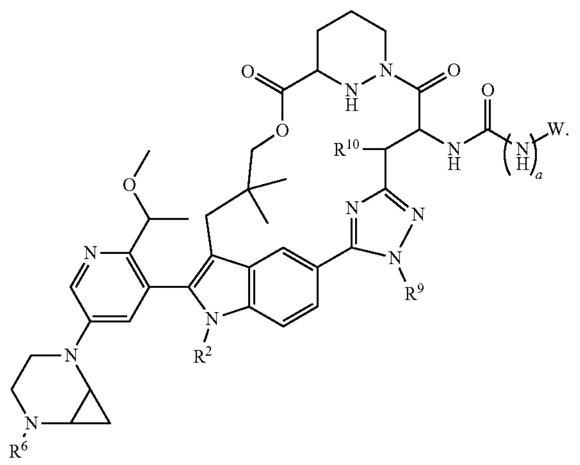

[138] The compound of paragraph [136] or [137], wherein $R^6$ is methyl.

[139] The compound of paragraph [135], or pharmaceutically acceptable salt thereof, having the structure of Formula IVb-8 or Formula IVb-9:

Formula IVb-8

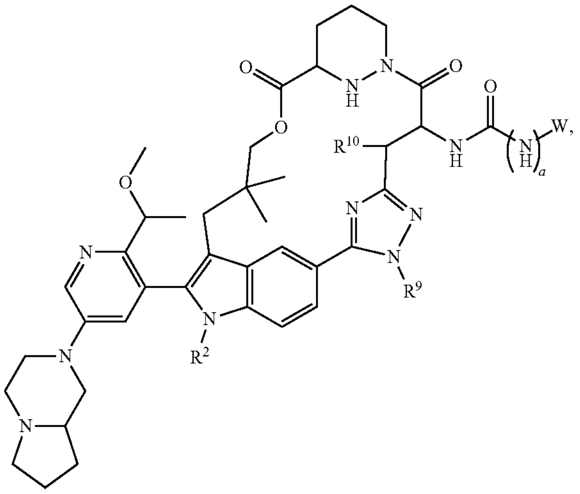

-continued

Formula IVb-9

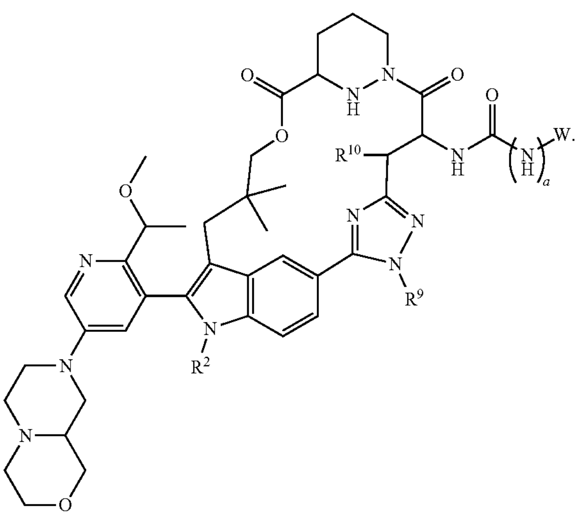

[140] The compound of any one of paragraphs [130]-[139], or pharmaceutically acceptable salt thereof, wherein $R^9$ is methyl.

[141] The compound of any one of paragraphs [101]-[108], or pharmaceutically acceptable salt thereof, wherein Y is —$NHS(O)_2$— or —$NHS(O)_2NH$—.

[142] The compound of paragraph [141], or pharmaceutically acceptable salt thereof, having the structure of Formula Vb:

Formula Vb

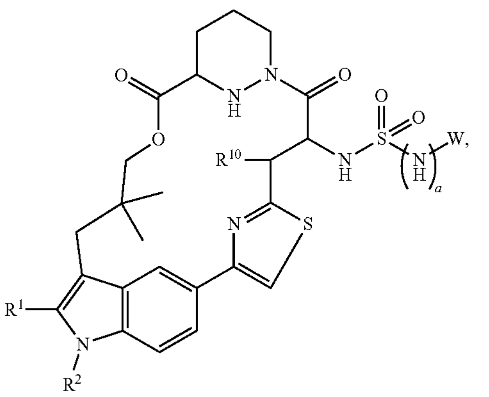

wherein a is 0 or 1.

[143] The compound of paragraph [142], or pharmaceutically acceptable salt thereof, having the structure of Formula Vb-1:

Formula Vb-1

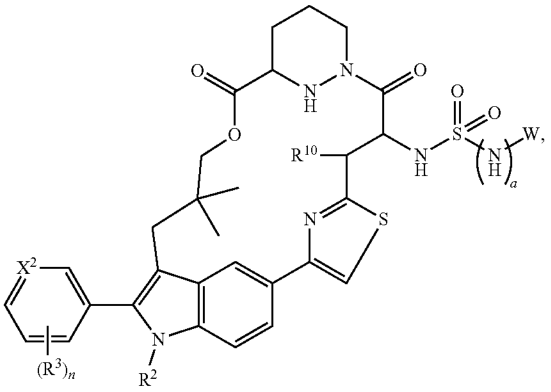

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and n is an integer from 1 to 4.

[144] The compound of paragraph [143], or pharmaceutically acceptable salt thereof, having the structure of Formula Vb-2:

Formula Vb-2

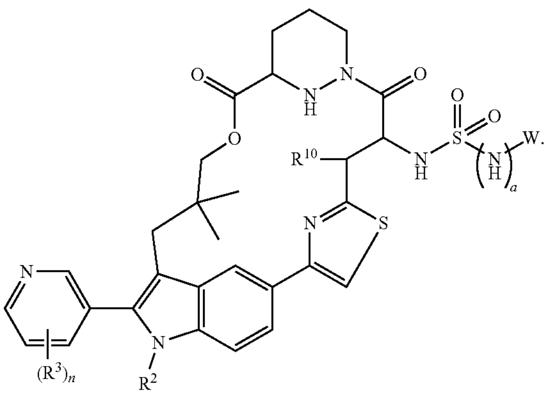

[145] The compound of paragraph [144], or pharmaceutically acceptable salt thereof, having the structure of Formula Vb-3:

Formula Vb-3

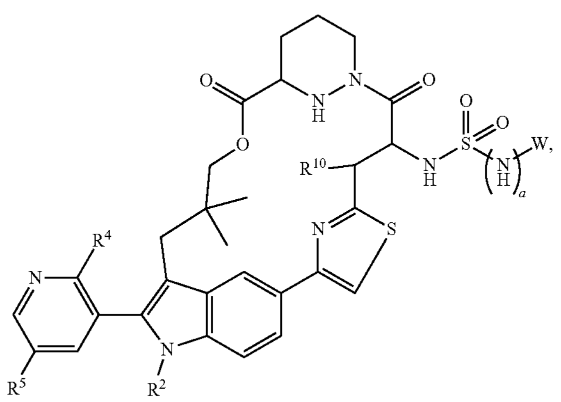

wherein $R^4$ and $R^5$ are each independently selected from hydrogen, halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl. In some embodiments, $R^4$ and $R^5$ are not hydrogen.

[146] The compound of paragraph [145], or pharmaceutically acceptable salt thereof, having the structure of Formula Vb-4:

Formula Vb-4

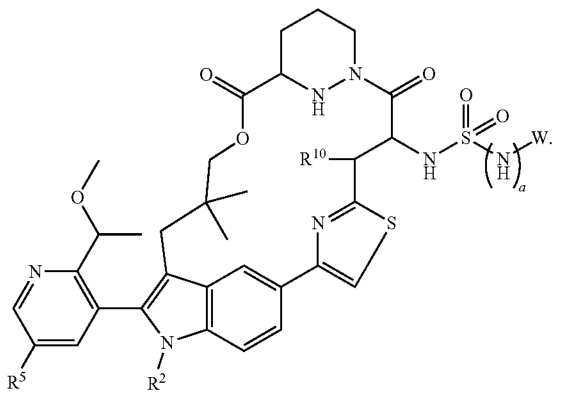

[147] The compound of paragraph [146], or pharmaceutically acceptable salt thereof, having the structure of Formula Vb-5:

Formula Vb-5

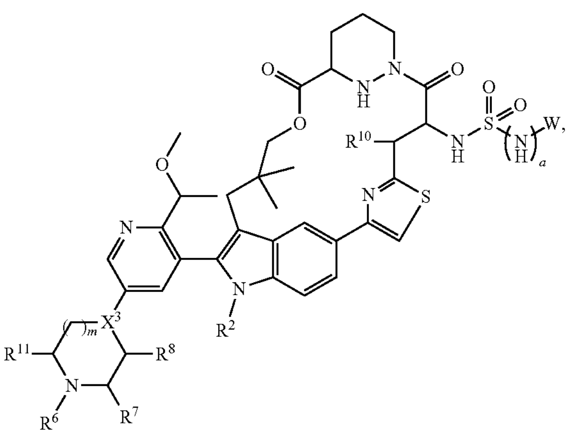

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[148] The compound of paragraph [141], or pharmaceutically acceptable salt thereof, having the structure of Formula VIb:

Formula VIb

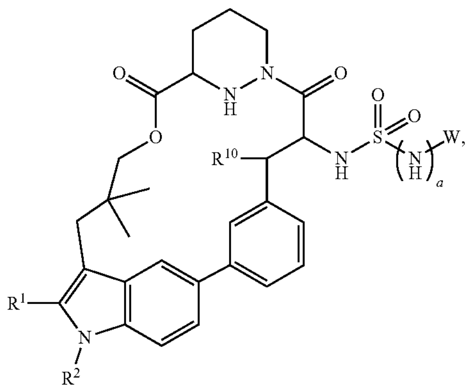

wherein a is 0 or 1.

[149] The compound of paragraph [148], or pharmaceutically acceptable salt thereof, having the structure of Formula VIb-1:

Formula VIb-1

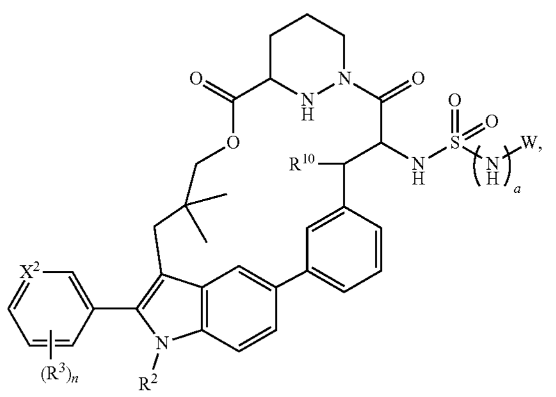

wherein $X^2$ is N or OH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and

[150] The compound of paragraph [149], or pharmaceutically acceptable salt thereof, having the structure of Formula VIb-2:

Formula VIb-2

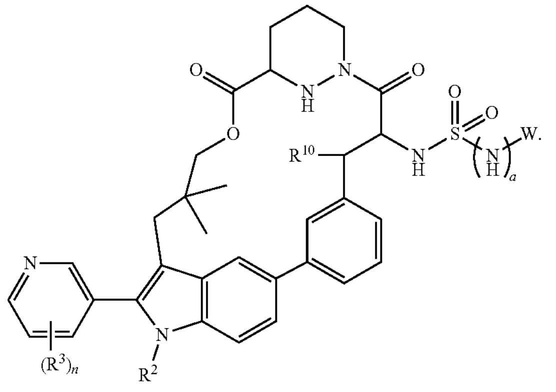

[151] The compound of paragraph [150], or pharmaceutically acceptable salt thereof, having the structure of Formula VIb-3:

Formula VIb-3

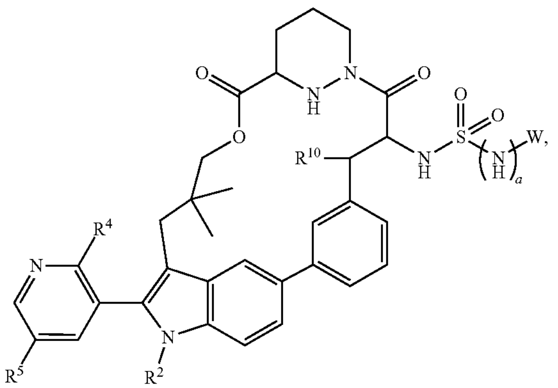

wherein $R^4$ and $R^5$ are each independently selected from hydrogen, halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl. In some embodiments, $R^4$ and $R^5$ are not hydrogen.

[152] The compound of paragraph [151], or pharmaceutically acceptable salt thereof, having the structure of Formula VIb-4:

Formula VIb-4

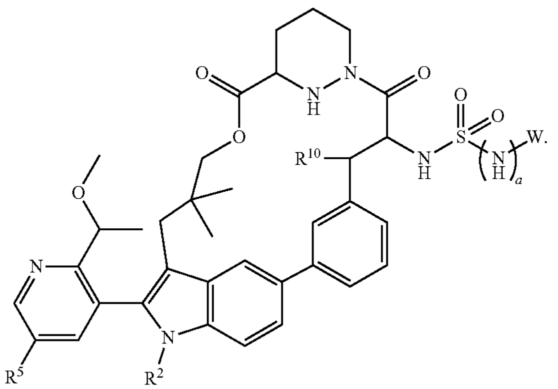

[153] The compound of paragraph [152], or pharmaceutically acceptable salt thereof, having the structure of Formula VIb-5:

Formula VIb-5

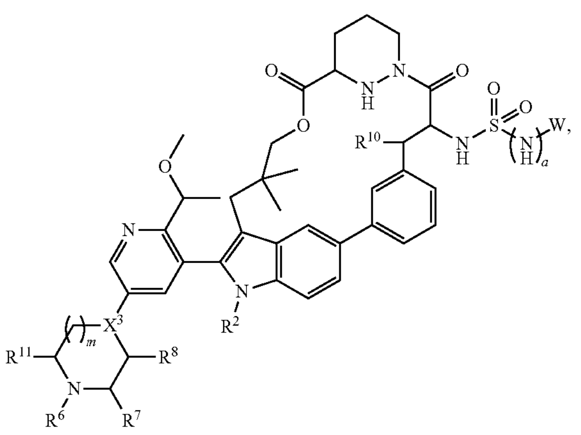

wherein $X^3$ is N or CH;

m is 1 or 2

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[154] The compound of paragraph [141], or pharmaceutically acceptable salt thereof, having the structure of Formula VIIb:

Formula VIIb

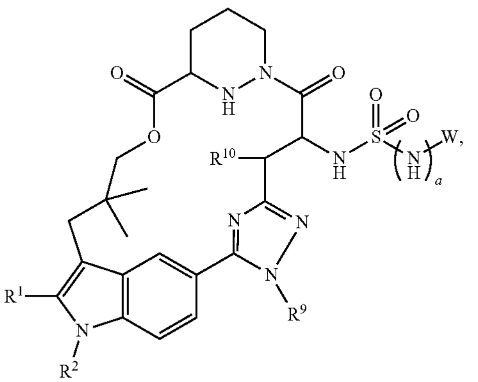

wherein $R^9$ is H or $C_1$-$C_6$ alkyl; and a is 0 or 1.

[155] The compound of paragraph [154], or pharmaceutically acceptable salt thereof, having the structure of Formula VIIb-1:

Formula VIIb-1

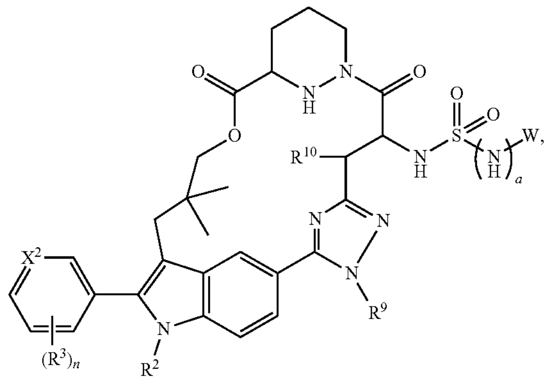

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and

[156] The compound of paragraph [155], or pharmaceutically acceptable salt thereof, having the structure of Formula VIIb-2:

Formula VIIb-2

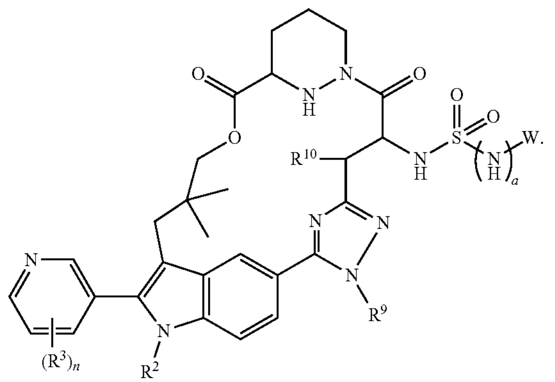

[157] The compound of paragraph [156], or pharmaceutically acceptable salt thereof, having the structure of Formula VIIb-3:

Formula VIIb-3

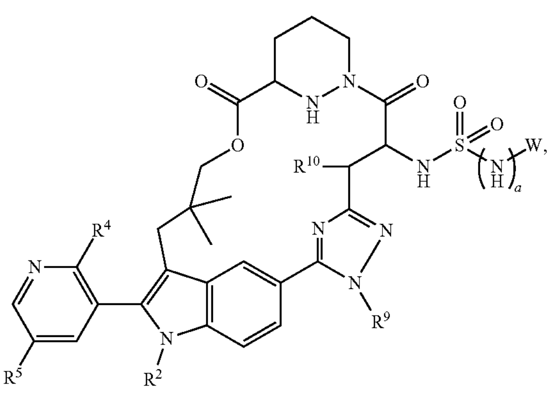

wherein $R^4$ and $R^5$ are each independently selected from hydrogen, halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl. In some embodiments, $R^4$ and $R^5$ are not hydrogen.

[158] The compound of paragraph [157], or pharmaceutically acceptable salt thereof, having the structure of Formula VIIb-4:

Formula VIIb-4

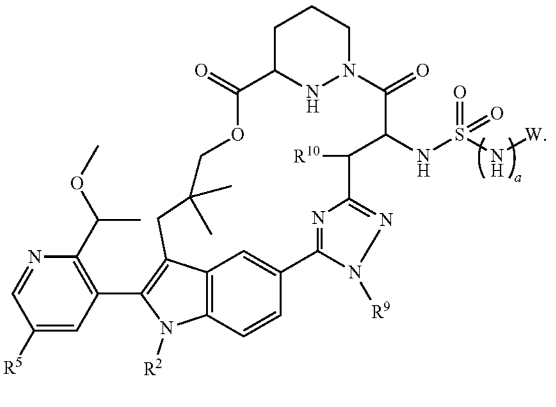

[159] The compound of paragraph [158], or pharmaceutically acceptable salt thereof, having the structure of Formula VIIb-5:

Formula VIIb-5

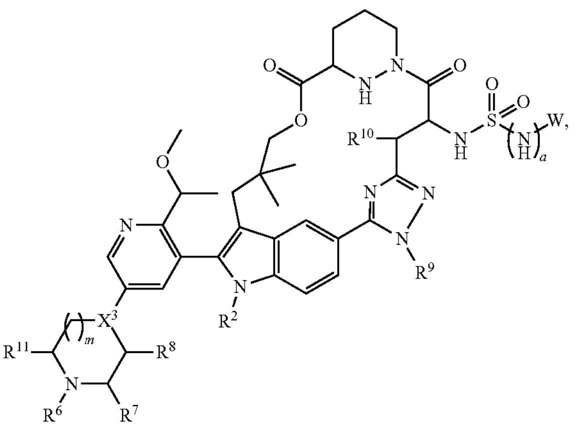

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[160] The compound of any one of paragraphs [154]-[159], or pharmaceutically acceptable salt thereof, wherein $R^9$ is methyl.

[161] The compound of any one of paragraphs [101]-[108], or pharmaceutically acceptable salt thereof, wherein Y is —NHS(O)— or —NHS(O)NH—.

[162] The compound of paragraph [161], or pharmaceutically acceptable salt thereof, having the structure of Formula VIIIb:

Formula VIIIb

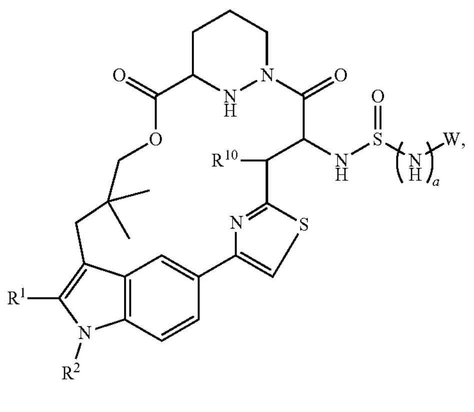

wherein a is 0 or 1.

[163] The compound of paragraph [162], or pharmaceutically acceptable salt thereof, having the structure of Formula VIIIb-1:

Formula VIIIb-1

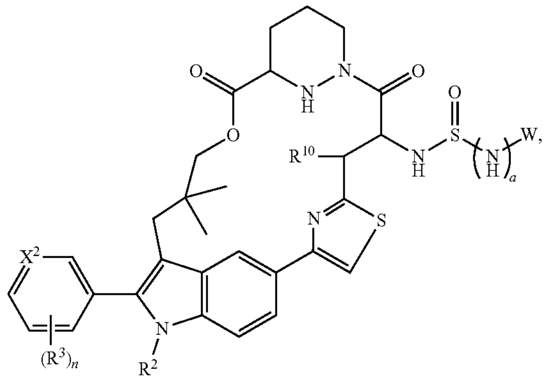

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and

[164] The compound of paragraph [163], or pharmaceutically acceptable salt thereof, having the structure of Formula VIIIb-2:

Formula VIIIb-2

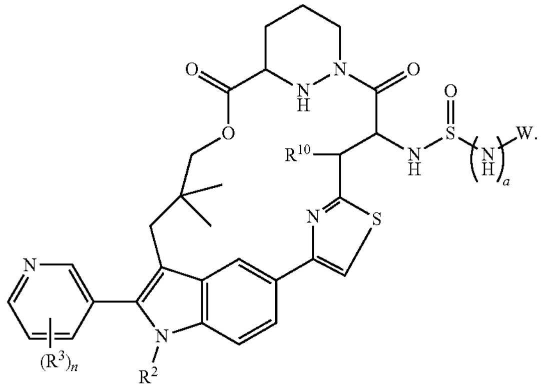

[165] The compound of paragraph [164], or pharmaceutically acceptable salt thereof, having the structure of Formula VIIIb-3:

Formula VIIIb-3

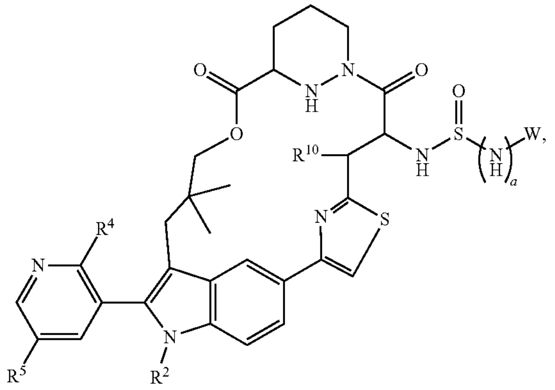

wherein $R^4$ and R are each independently selected from hydrogen, halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl. In some embodiments, $R^4$ and $R^5$ are not hydrogen.

[166] The compound of paragraph [165], or pharmaceutically acceptable salt thereof, having the structure of Formula VIIIb-4:

Formula VIIIb-4

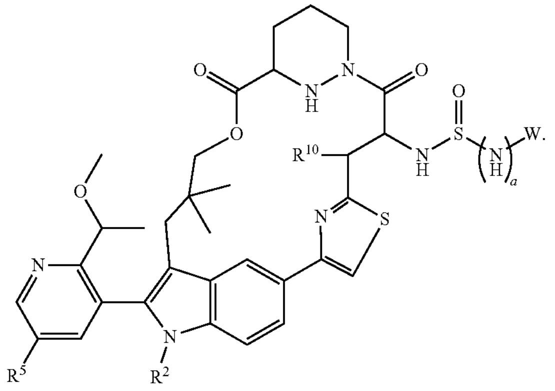

[167] The compound of paragraph [166], or pharmaceutically acceptable salt thereof, having the structure of Formula VIIIb-5:

Formula VIIIb-5

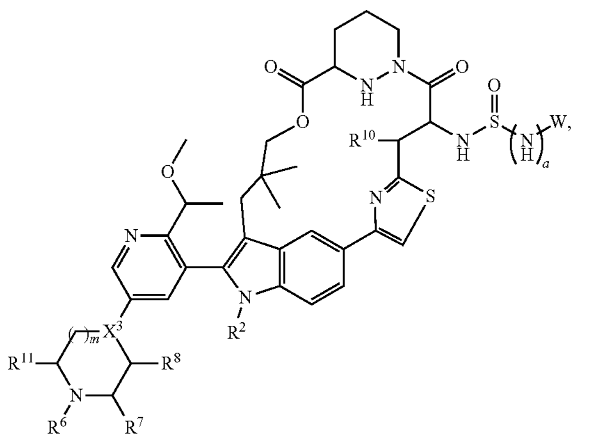

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[168] The compound of paragraph [161], or pharmaceutically acceptable salt thereof, having the structure of Formula IXb:

Formula IXb

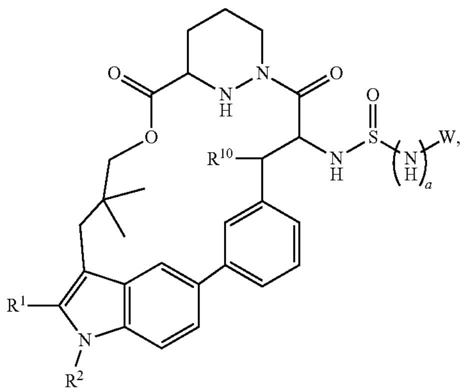

wherein a is 0 or 1.

[169]. The compound of paragraph [168], or pharmaceutically acceptable salt thereof, having the structure of Formula IXb-1:

Formula IXb-1

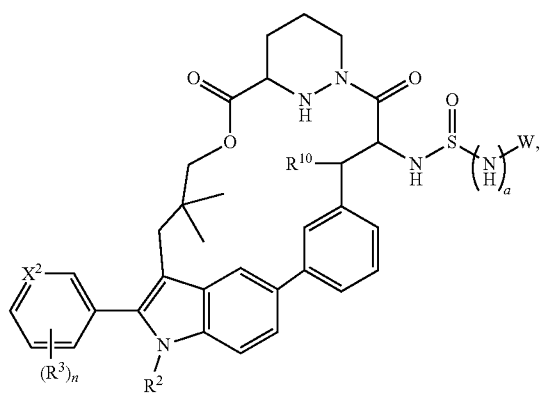

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and

[170] The compound of paragraph [169], or pharmaceutically acceptable salt thereof, having the structure of Formula IXb-2:

Formula IXb-2

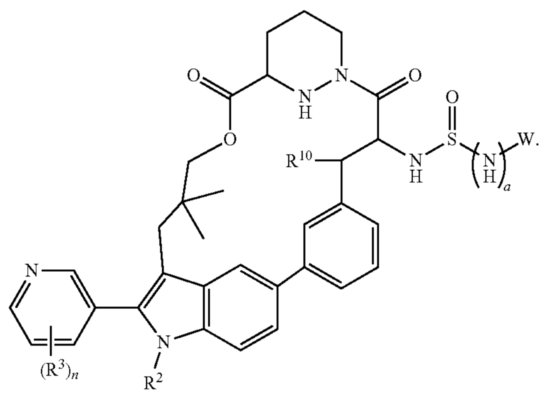

[171] The compound of paragraph [170], or pharmaceutically acceptable salt thereof, having the structure of Formula IXb-3:

Formula IXb-3

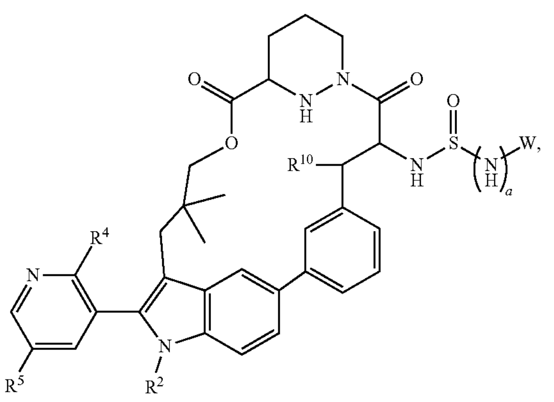

wherein $R^4$ and $R^5$ are each independently selected from hydrogen, halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl. In some embodiments, $R^4$ and $R^5$ are not hydrogen.

[172] The compound of paragraph [171], or pharmaceutically acceptable salt thereof, having the structure of Formula IXb-4:

Formula IXb-4

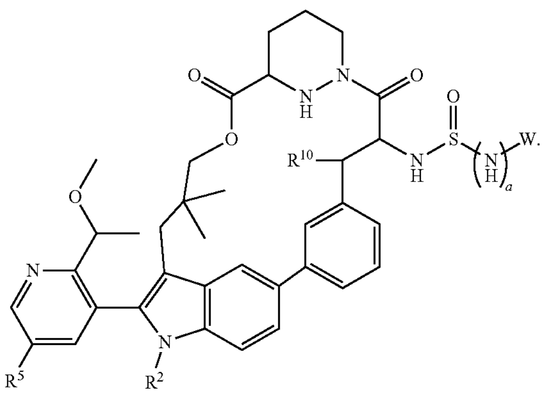

[173] The compound of paragraph [172], or pharmaceutically acceptable salt thereof, having the structure of Formula IXb-5:

Formula IXb-5

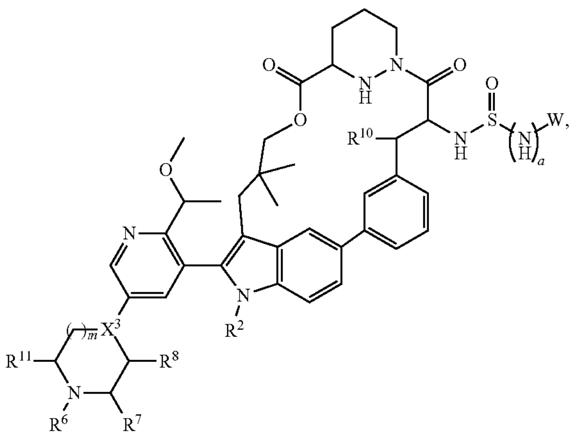

wherein $X^3$ is N or CH;

m is 1 or 2;

$R^6$, $R^7$, $R^8$, and $R^{11}$ are each independently selected from hydrogen, optionally substituted $C_1$-$C_5$ alkyl, optionally substituted $C_1$-$C_5$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[174] The compound of paragraph [161], or pharmaceutically acceptable salt thereof, having the structure of Formula Xb:

Formula Xb

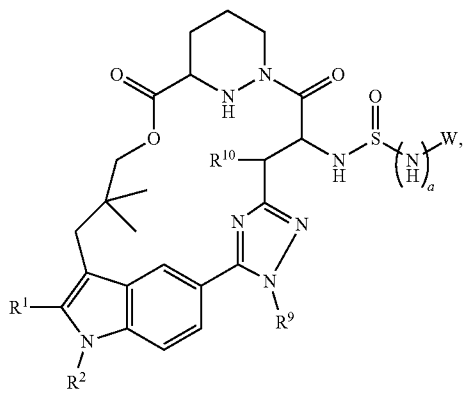

wherein $R^9$ is H or $C_1$-$C_6$ alkyl; and a is 0 or 1.

[175] The compound of paragraph [174], or pharmaceutically acceptable salt thereof, having the structure of Formula Xb-1:

Formula Xb-1

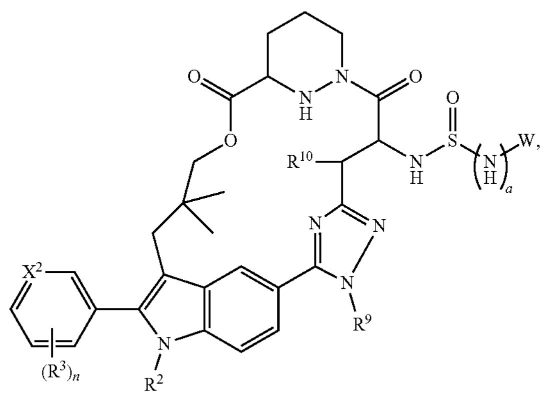

wherein $X^2$ is N or CH;

each $R^3$ is independently selected from halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl; and

[176] The compound of paragraph [175], or pharmaceutically acceptable salt thereof, having the structure of Formula Xb-2:

Formula Xb-2

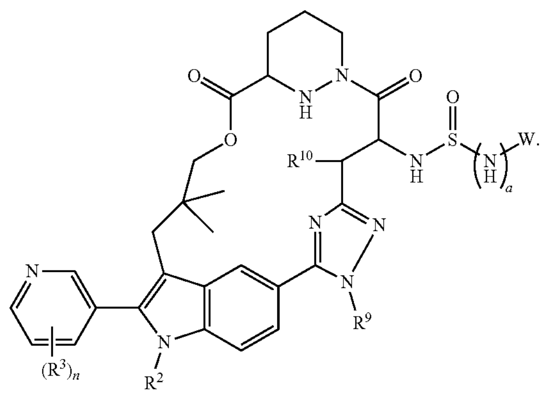

[177] The compound of paragraph [176], or pharmaceutically acceptable salt thereof, having the structure of Formula Xb-3:

Formula Xb-3

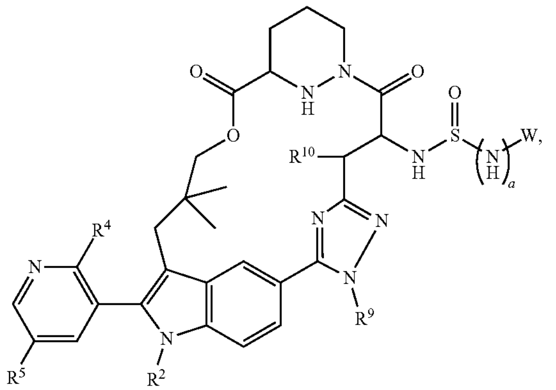

wherein $R^4$ and $R^5$ are each independently selected from hydrogen, halogen, cyano, hydroxy, optionally substituted amine, optionally substituted amido, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 11-membered heterocycloalkyl, optionally substituted 6 to 10-membered aryl, or optionally substituted 5 to 10-membered heteroaryl. In some embodiments, $R^4$ and $R^5$ are not hydrogen.

[178] The compound of paragraph [177], or pharmaceutically acceptable salt thereof, having the structure of Formula Xb-4:

Formula Xb-4

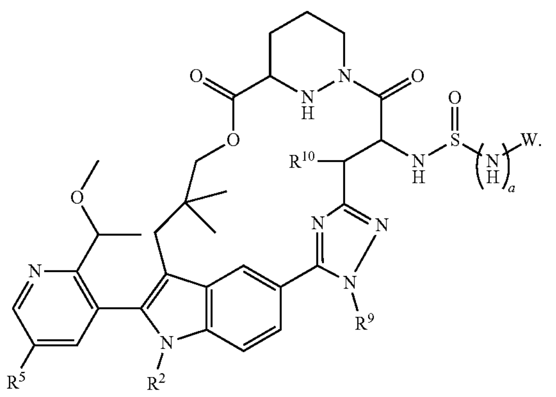

[179] The compound of paragraph [178], or pharmaceutically acceptable salt thereof, having the structure of Formula Xb-5:

Formula Xb-5

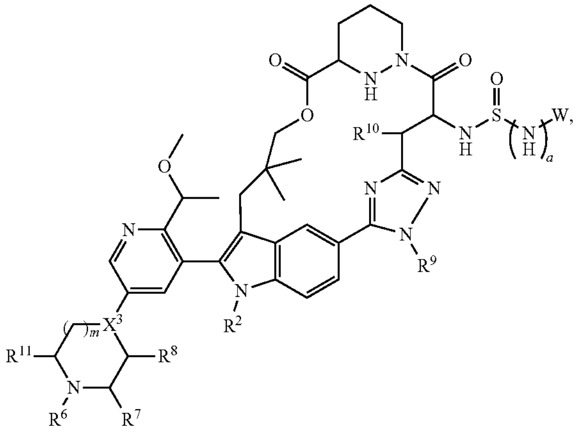

wherein $X^3$ is N or CH;

m is 1 or 2;

$R^6$, $R^7$, $R^8$, and $R^{11}$ are each independently selected from hydrogen, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl; or $R^6$ and $R^7$ combine with the atoms to which they are attached to form an optionally substituted 3 to 8-membered cycloalkyl or an optionally substituted 3 to 8-membered heterocycloalkyl; or $R^7$ and $R^8$ combine with the atoms to which they are attached to form an optionally substituted 3 to 8-membered heterocycloalkyl; or $R^7$ and $R^{11}$ combine with the atoms to which they are attached to form an optionally substituted 4 to 8-membered heterocycloalkyl.

[180] The compound of any one of paragraphs [174]-[179], or pharmaceutically acceptable salt thereof, wherein $R^9$ is methyl.

[181] The compound of any one of paragraphs [110]-[140], [142]-[160], or [162]-[180], or pharmaceutically acceptable salt thereof, wherein a is 0.

[182] The compound of any one of paragraphs [110]-[140], [142]-[160], or [162]-[180], or pharmaceutically acceptable salt thereof, wherein a is 1.

[183] The compound of any one of paragraphs [101]-[182], or pharmaceutically acceptable salt thereof, wherein $R^2$ is optionally substituted $C_1$-$C_6$ alkyl.

[184] The compound of paragraph [183], or pharmaceutically acceptable salt thereof, wherein $R^2$ is selected from $-CH_2CH_3$ or $-CH_2CF_3$.

[185] The compound of any one of paragraphs [101]-[184], or pharmaceutically acceptable salt thereof, wherein $R^{10}$ is hydrogen.

[186] The compound of any one of paragraphs [101]-[184], or pharmaceutically acceptable salt thereof, wherein $R^{10}$ is hydroxy, optionally substituted $C_1$-$C_6$ alkoxy, optionally substituted $C_1$-$C_3$ alkyl, optionally substituted $C_1$-$C_6$ heteroalkyl, or optionally substituted 3 to 7-membered heterocycloalkyl.

[187] The compound of paragraph [186], or pharmaceutically acceptable salt thereof, wherein $R^{10}$ is optionally substituted ethoxy.

[188] The compound of paragraph [186], or pharmaceutically acceptable salt thereof, wherein $R^{10}$ is selected from the following, or a stereoisomer thereof:

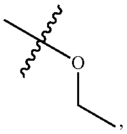,
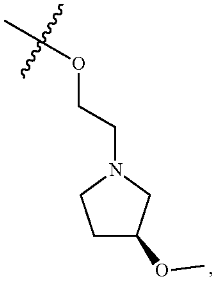,
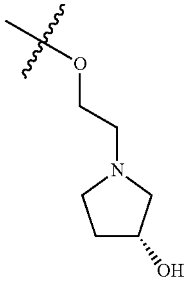,
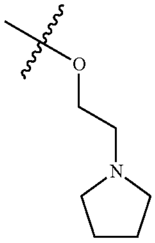,
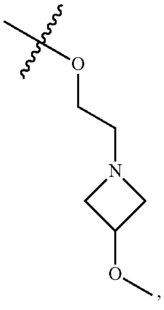,
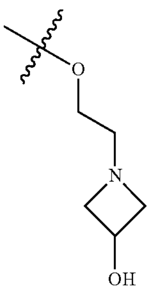,
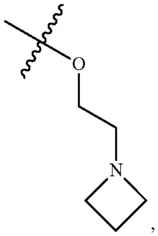,
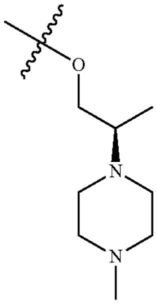,
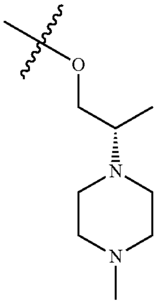,
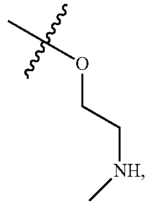,
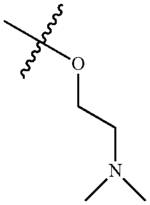,
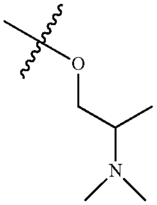,
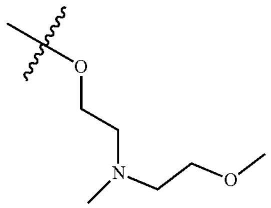,
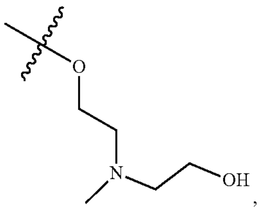,
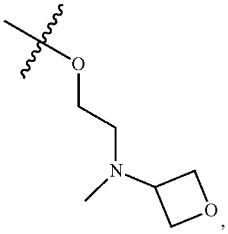,
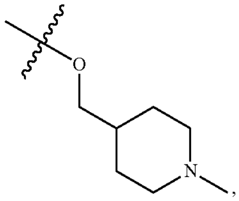, -continued

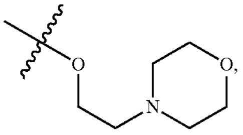 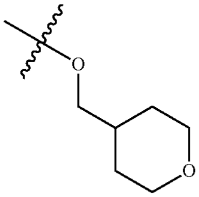 ,
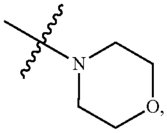 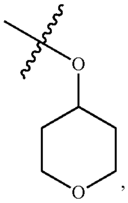 , 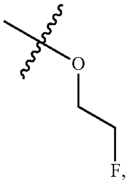
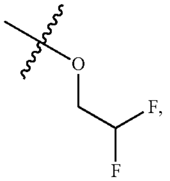 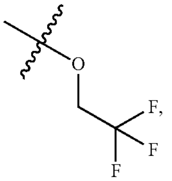 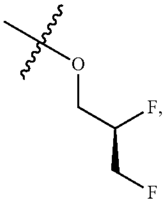
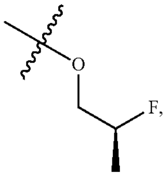 or 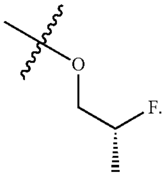

[189] The compound of any one of paragraphs [101]-[188], or pharmaceutically acceptable salt thereof wherein W is CC4 alkyl.

[190] The compound of any one of paragraphs [101]-[188], or pharmaceutically acceptable salt thereof wherein W is optionally substituted cyclopropyl, optionally substituted cyclobutyl, optionally substituted cyclopentyl, or optionally substituted cyclohexyl, optionally substituted piperidine, optionally substituted piperazine, optionally substituted pyridine, or optionally substituted phenyl.

[191] The compound of any one of paragraphs [101]-[188], or pharmaceutically acceptable salt thereof, wherein W is optionally substituted 3 to 10-membered heterocycloalkyl, optionally substituted 3 to 10-membered cycloalkyl, optionally substituted 6 to 10-membered aryl, or optionally substituted 5 to 10-membered heteroaryl.

[192] The compound of any one of paragraphs [101]-[188], or pharmaceutically acceptable salt thereof, wherein W is optionally substituted 3 to 10-membered heterocycloalkyl.

[193] The compound of paragraph [192], or pharmaceutically acceptable salt thereof, wherein W is selected from the following, or a stereoisomer thereof:

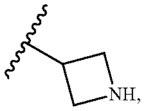 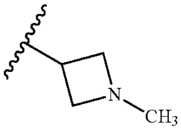 , 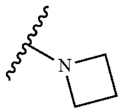 ,
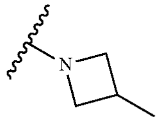 , 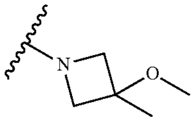 ,

-continued

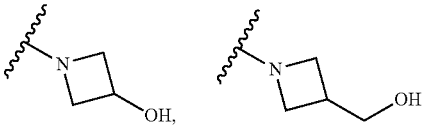 ,
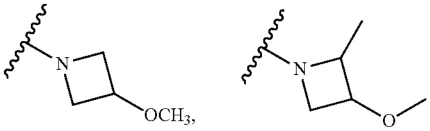 ,
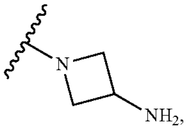 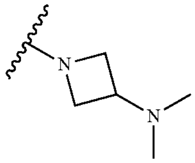 , 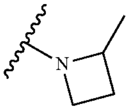 ,
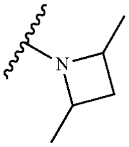 , 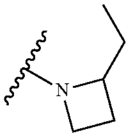 , 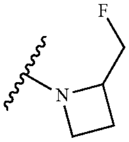 ,
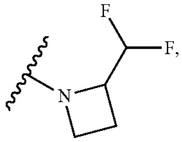 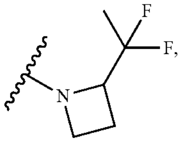 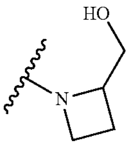 ,
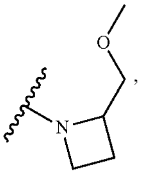 , 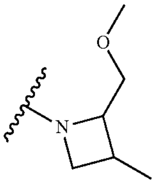 , 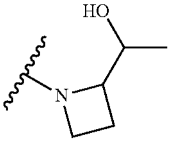 ,
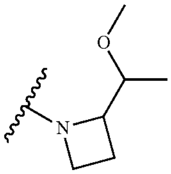 , 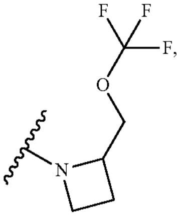 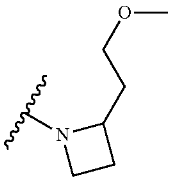
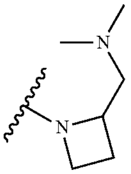 , 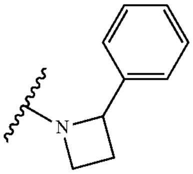 , 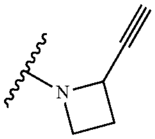 ,
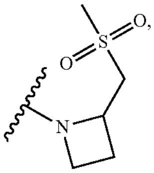 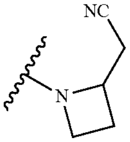 , 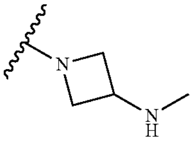 ,
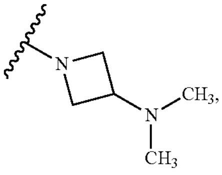 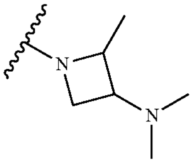 , -continued
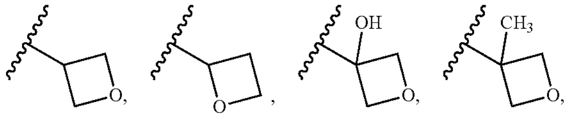
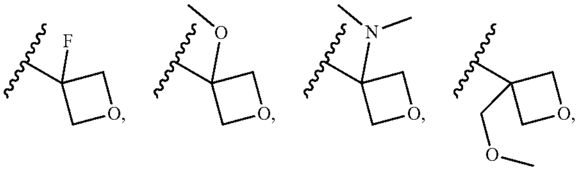
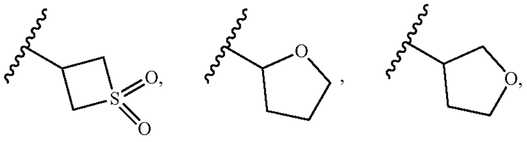
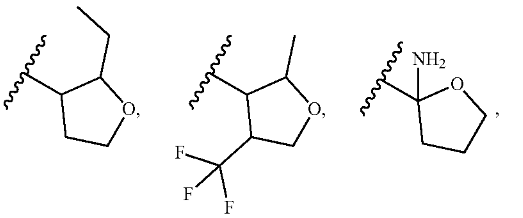
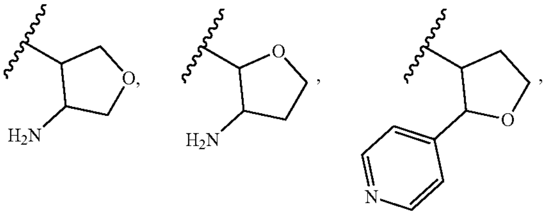
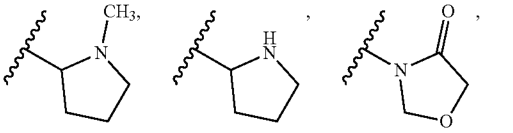
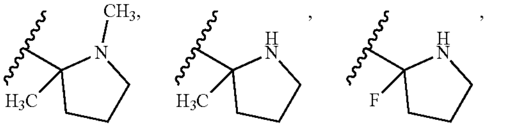
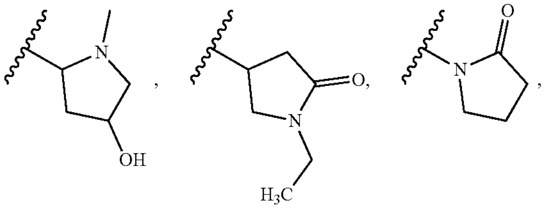
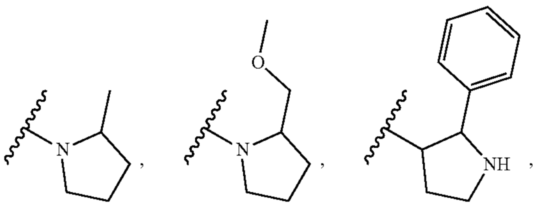
-continued
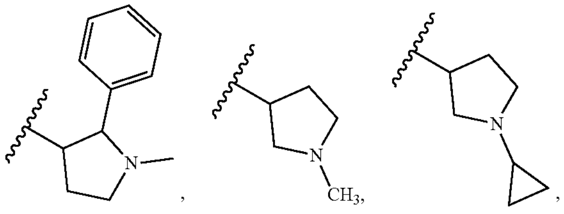
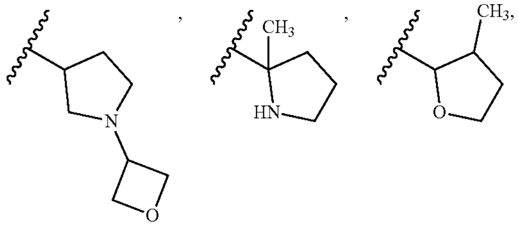
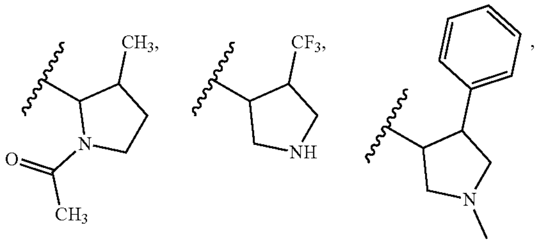
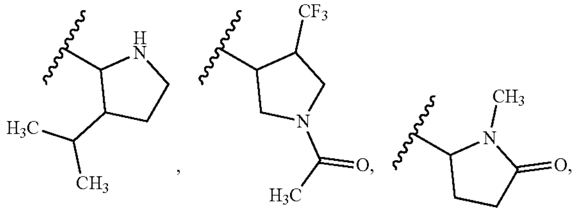
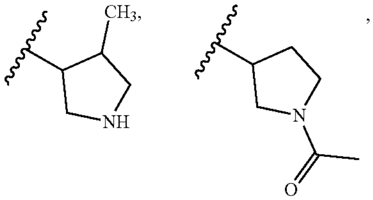
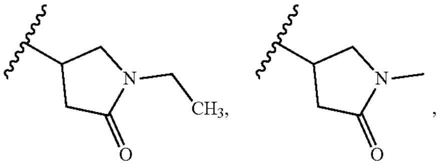
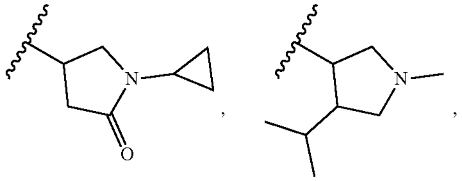
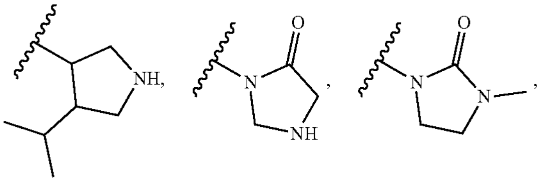

-continued
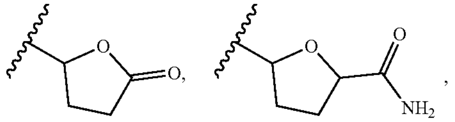
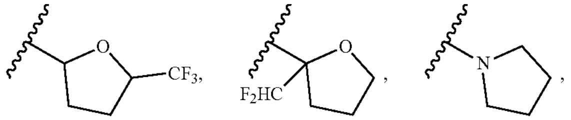
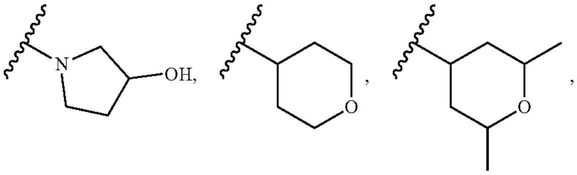
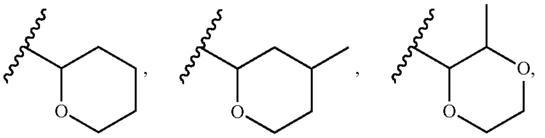
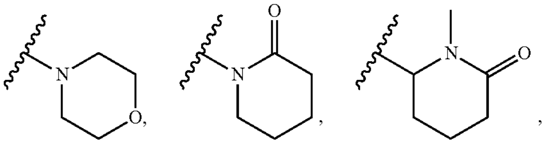
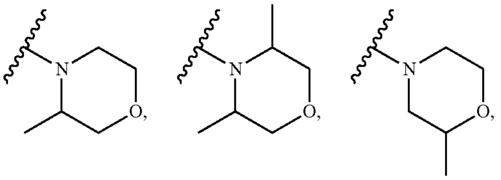
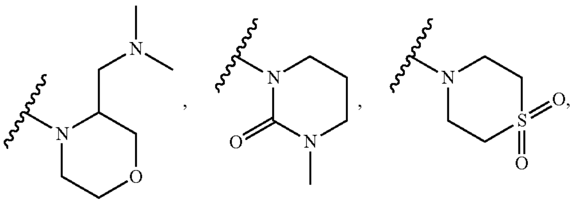
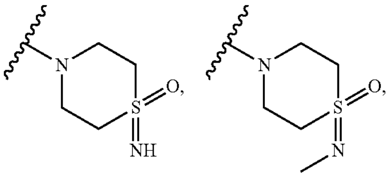
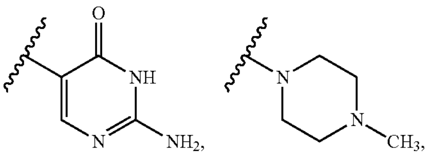
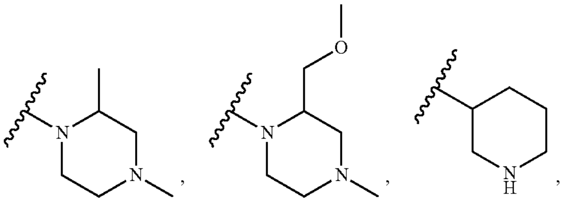
-continued
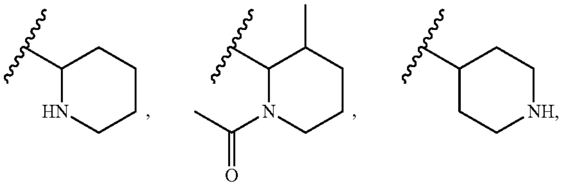
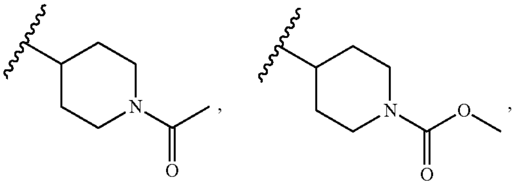
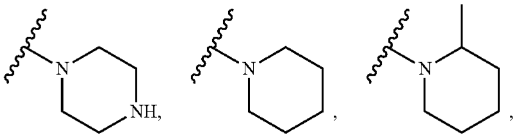
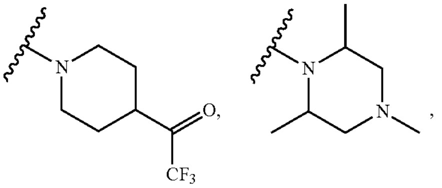
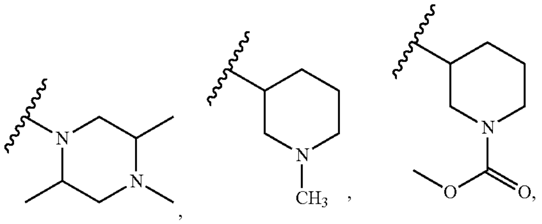
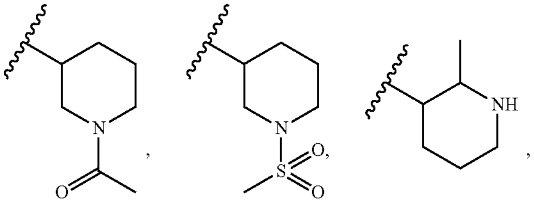
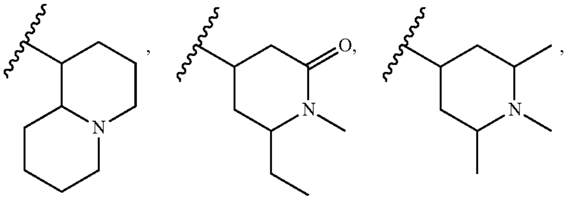
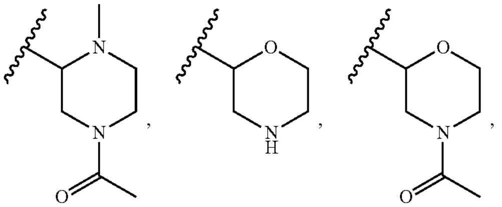
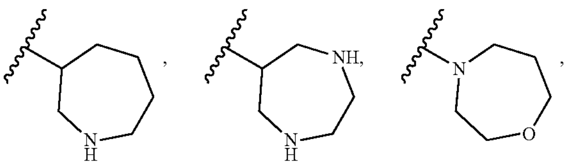

-continued
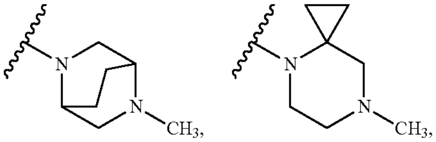
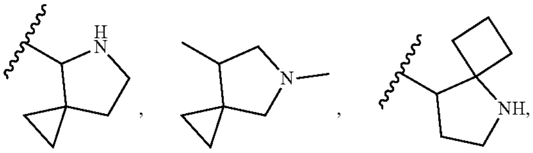
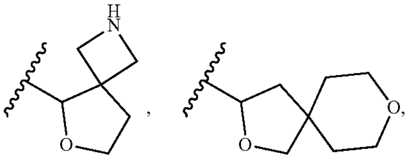
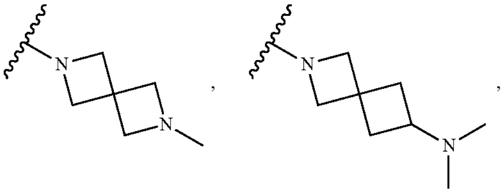
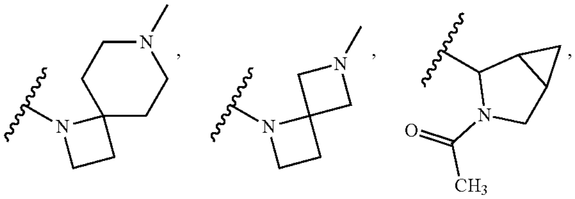
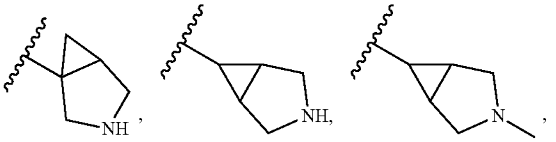
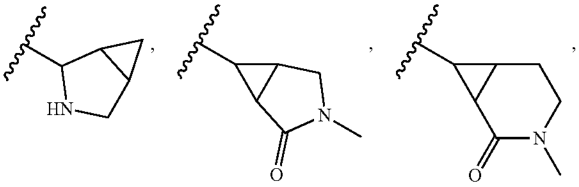
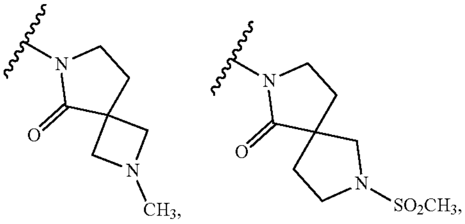
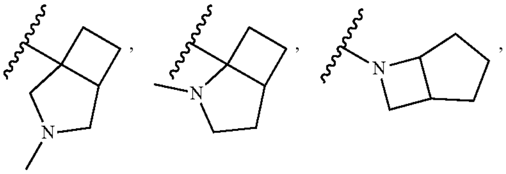
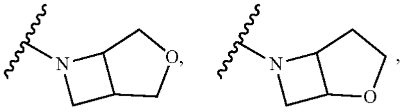
-continued
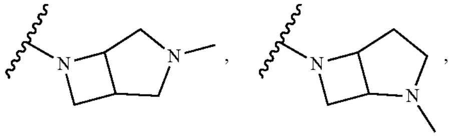
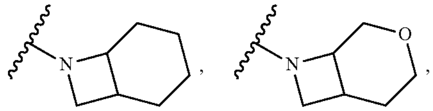
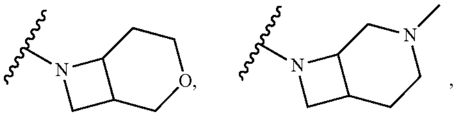
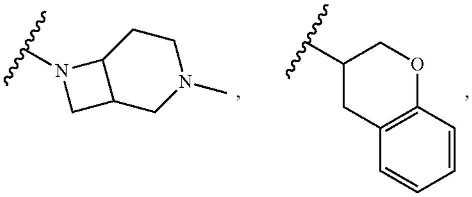
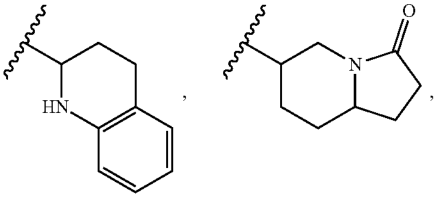
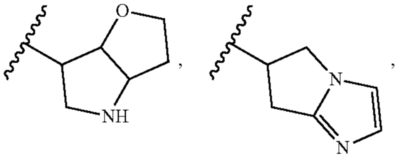
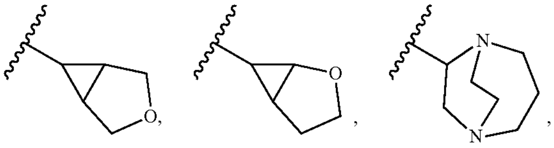
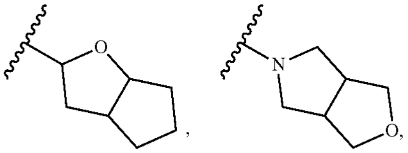
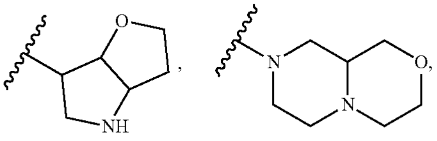
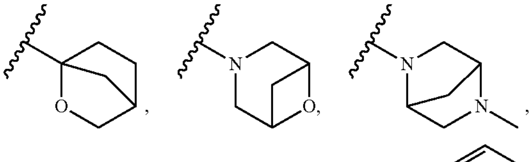
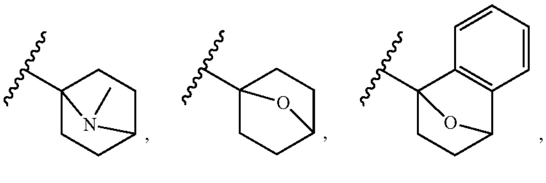

-continued
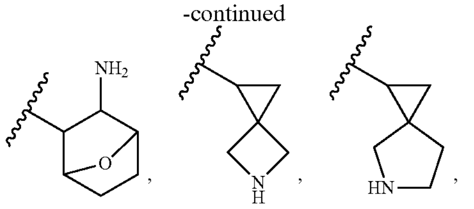
or
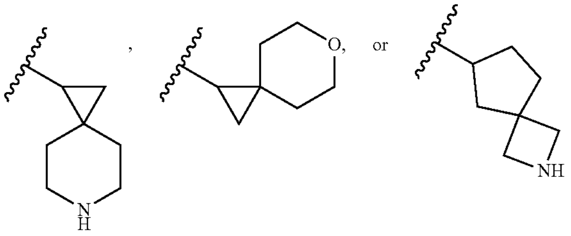
[194] The compound of any one of paragraphs [101]-[188], or pharmaceutically acceptable salt thereof, wherein W is optionally substituted 3 to 10-membered cycloalkyl.
[195] The compound of paragraph [194], or pharmaceutically acceptable salt thereof, wherein W is selected from the following, or a stereoisomer thereof:
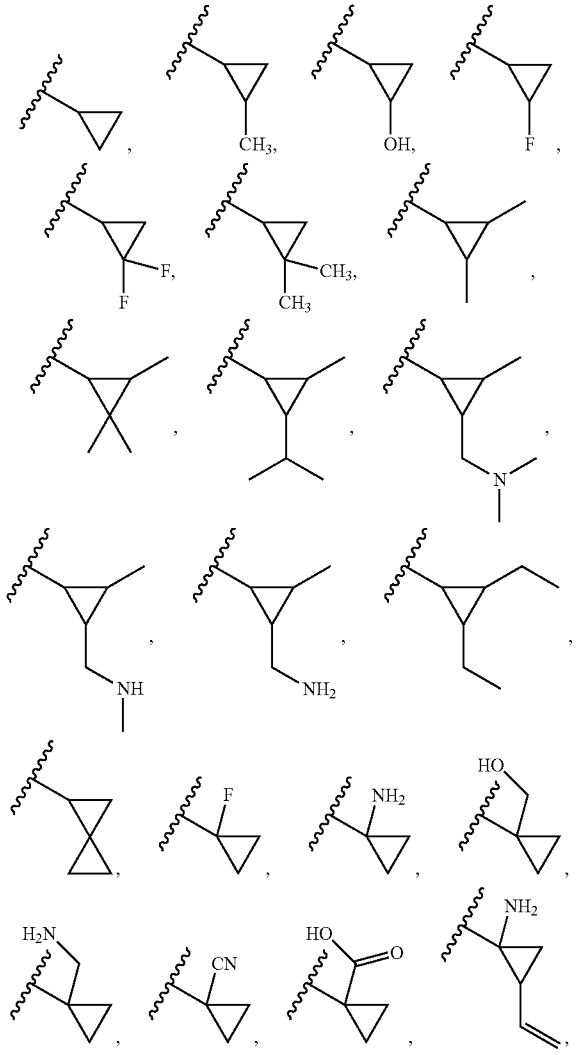
-continued
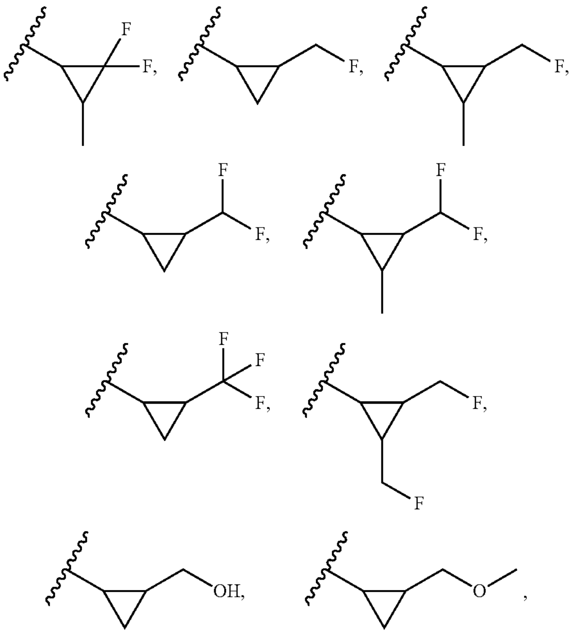
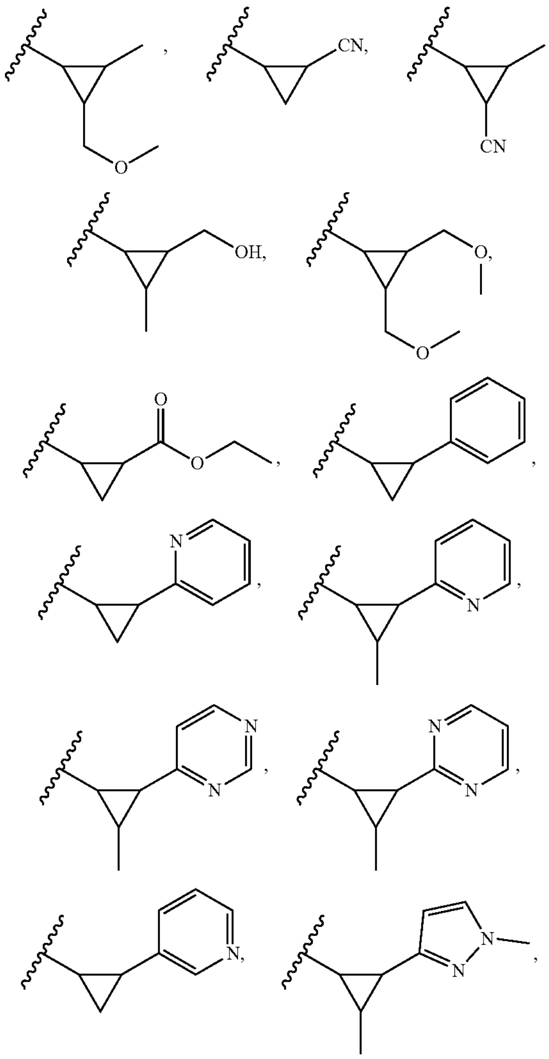

-continued

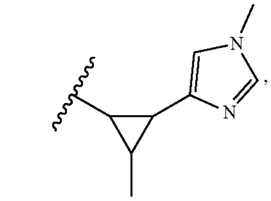,
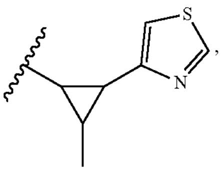,
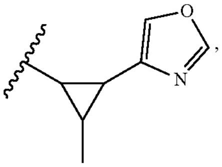,
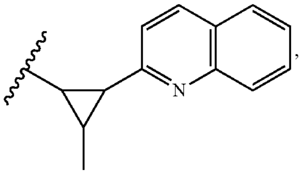,
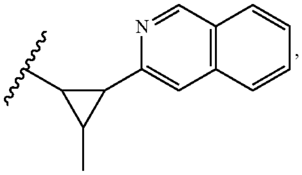,
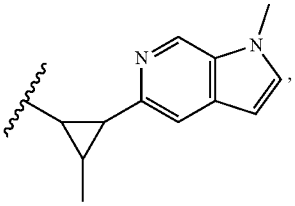,
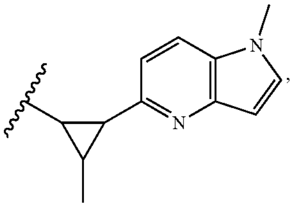,
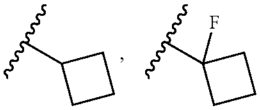,
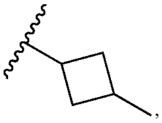,
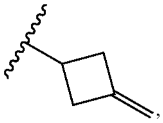,
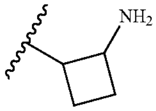,
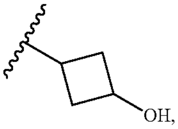
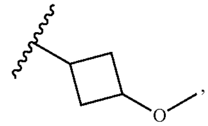,
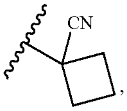,
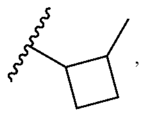,
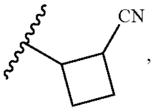,
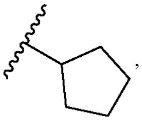,
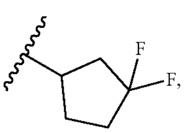
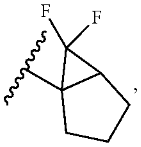,
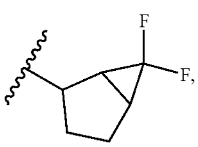
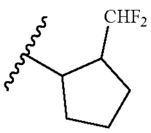,
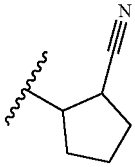,
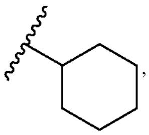, -continued

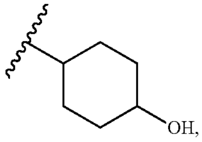
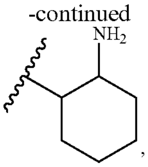,
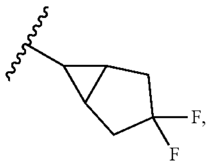
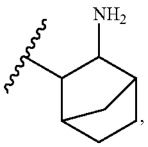, or 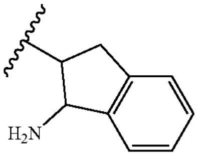.

[196] The compound of any one of paragraphs [101]-[188], or pharmaceutically acceptable salt thereof, wherein W is optionally substituted 5 to 10-membered heteroaryl.

[197] The compound of paragraph [196], or pharmaceutically acceptable salt thereof, wherein W is selected from the following, or a stereoisomer thereof:

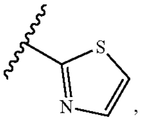,
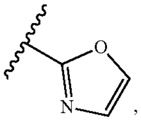,
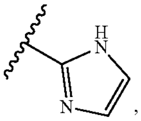,
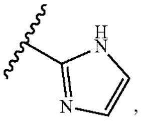,
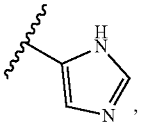,
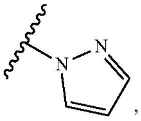,
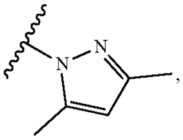,
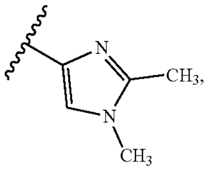
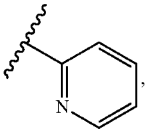,
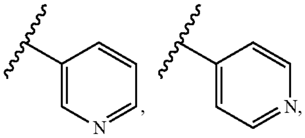
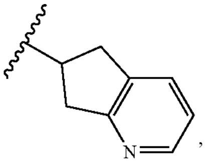, or
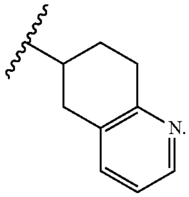

[198] The compound of any one of paragraphs [101]-[188], or pharmaceutically acceptable salt thereof, wherein W is optionally substituted 6 to 10-membered aryl.

[199] The compound of paragraph [198], or pharmaceutically acceptable salt thereof, wherein W is optionally substituted phenyl.

[200] The compound of any one of paragraphs [101]-[188], or pharmaceutically acceptable salt thereof, wherein W is optionally substituted $C_1$-$C_3$ heteroalkyl.

[201] The compound of paragraph [200], or pharmaceutically acceptable salt thereof, wherein W is selected from the following, or a stereoisomer thereof:

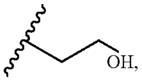 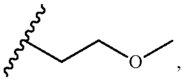, 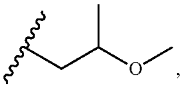,

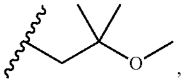, or 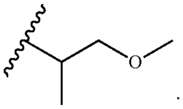.

[202] The compound of paragraph [189], or pharmaceutically acceptable salt thereof, wherein W is selected from the following:

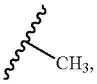 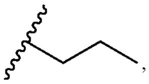, 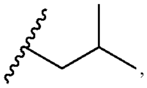,

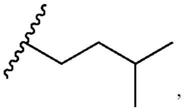, 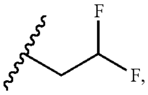 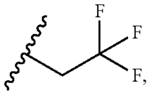

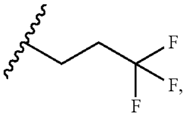 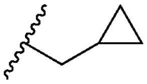 or 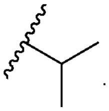.

[203] The compound of any one of paragraphs [101]-[188], or pharmaceutically acceptable salt thereof, wherein W is —$R^{14}C(=O)R^{15}$ where $R^{14}$ is 3 to 10-membered cycloalkylene and $R^{15}$ is selected from optionally substituted 3 to 10-membered cycloalkyl, optionally substituted 6 to 10-membered aryl, or optionally substituted 5 to 10-membered heteroaryl.

[204] The compound of paragraph [203], or pharmaceutically acceptable salt thereof, wherein W is selected from the following, or a stereoisomer thereof:

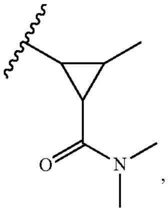, 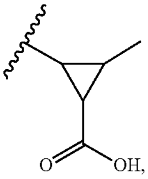 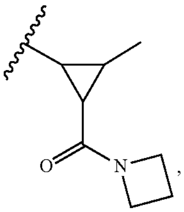,

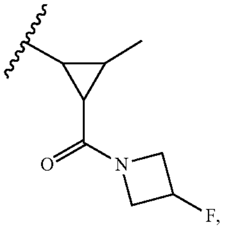 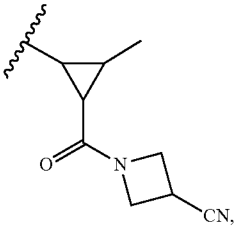

-continued

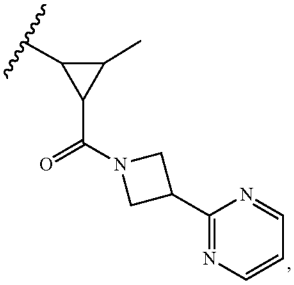, 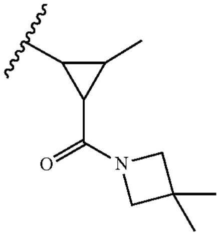,

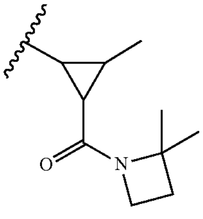, 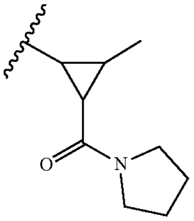,

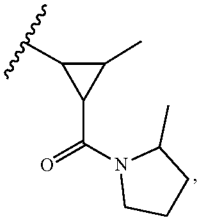, 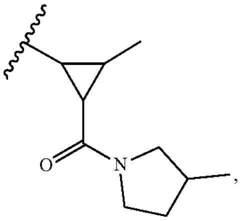,

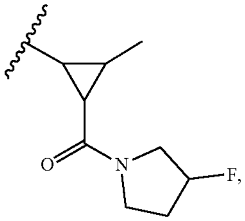 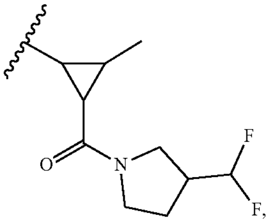

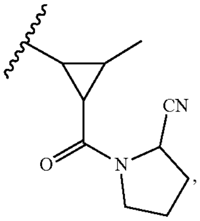, 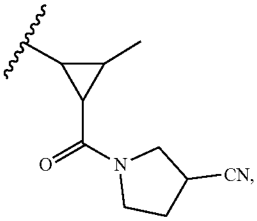

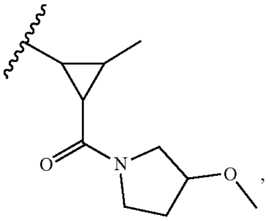, 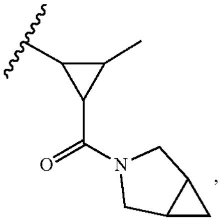,

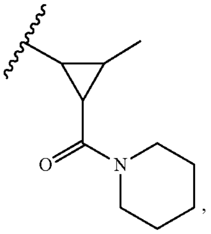, 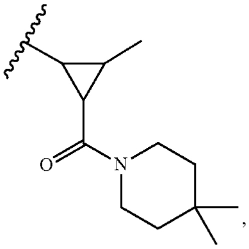,

-continued

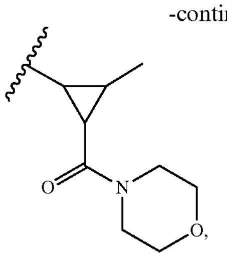 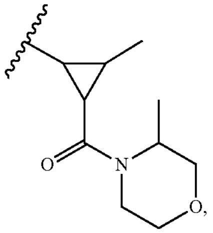

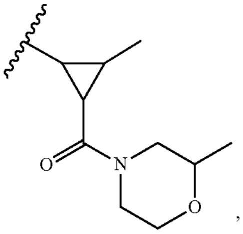, 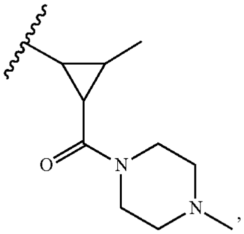,

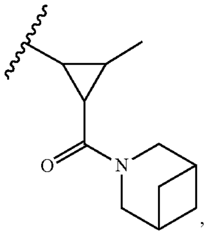, or 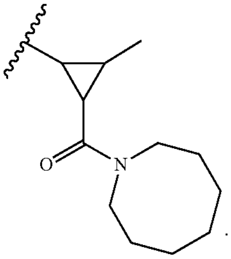.

[205]A compound, or a pharmaceutically acceptable salt thereof, of Table 1a or Table 1b.

[206]A pharmaceutical composition comprising a compound, or a pharmaceutically acceptable salt thereof, of any one of paragraphs [1]-[205] and a pharmaceutically acceptable excipient.

[207]A method of treating cancer in a subject in need thereof, the method comprising administering to the subject a therapeutically effective amount of a compound, or a pharmaceutically acceptable salt thereof, of any one of paragraphs [1]-[205] or a pharmaceutical composition of paragraph [206].

[208] The method of paragraph [207], wherein the cancer comprises a Ras mutation.

[209] The method of paragraph [208], wherein the Ras mutation is at position 12, 13 or 61. In some embodiments, the Ras mutation is at position 12.

[210] The method of paragraph [209], wherein the Ras mutation is at a position selected from the group consisting of G12C, G12D, G12V, G12R, G13C, G13D, and Q61K, or a combination thereof.

[211] The method of paragraph [210], wherein the Ras mutation is at a position selected from the group consisting of G12D, G12V and G12R, or a combination thereof.

[212] The method of paragraph [211], wherein the Ras mutation is at a position selected from the group consisting of G12D and G12V, or a combination thereof.

[213] The method of any one of paragraphs [207]-[212], wherein the cancer is pancreatic cancer.

[214] The method of any one of paragraphs [207]-[212], wherein the cancer is lung cancer.

[215] The method of any one of paragraphs [207]-[212], wherein the cancer is colorectal cancer.

[216]A method of treating a Ras protein-related disorder in a subject in need thereof, the method comprising administering to the subject a therapeutically effective amount of a compound, or a pharmaceutically acceptable salt thereof, of any one of paragraphs [1]-[205] or a pharmaceutical composition of paragraph [206].

[217]A method of inhibiting a Ras protein in a cell, the method comprising contacting the cell with an effective amount of a compound, or a pharmaceutically acceptable salt thereof, of any one of paragraphs [1]-[205] or a pharmaceutical composition of paragraph [206].

[218] The method of paragraph [217], wherein more than one Ras protein is inhibited in the cell.

[219] The method of [217] or [218], wherein the cell is a cancer cell.

[220] The method of paragraph [219], wherein the cancer cell is a pancreatic cancer cell.

[221] The method of paragraph [219], wherein the cancer cell is a lung cancer cell.

[222] The method of paragraph [219], wherein the cancer cell is a colorectal cancer cell.

[223] The method of any one of paragraphs [207]-[222], wherein the Ras protein is KRAS.

[224] The method or use of any one of paragraphs [207]-[223], wherein the method further comprises administering an additional anticancer therapy.

[225] The method of paragraph [224], wherein the additional anticancer therapy is an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, a HER2 inhibitor, or a combination thereof.

[226] The method of paragraph [224] or [225], wherein the additional anticancer therapy is a SHP2 inhibitor.

[227] The method of paragraph [224] or [225], wherein the additional anticancer therapy comprises a SHP2 inhibitor and a PD-L1 inhibitor.

[228] The method of paragraph [224] or [225], wherein the additional therapy comprises a second Ras inhibitor and a PD-L1 inhibitor.

[229] The method of paragraph [225] or [228], wherein the second Ras inhibitor is a $KRAS^{G12}C$ inhibitor.

[230] The method of paragraph [228] or [229], wherein the second Ras inhibitor is a $KRAS^{G12}C(ON)$ inhibitor.

[231] The method of paragraph [228] or [229], wherein the second Ras inhibitor is a $KRAS^{G12C}(OFF)$ inhibitor.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure or scope of the appended claims.

Chemical Syntheses

Definitions used in the following examples and elsewhere herein are:

| | |
|---|---|
| $B_2pin_2$ | Bis(pinacolato)diboron |
| BINAP | 2,2'-Bis(diphenylphosphino)-1,1'-binaphthyl |

-continued

| | |
|---|---|
| $CH_2CL$, DCM | Methylene chloride, Dichloromethane |
| $CH_3CN$, MeCN | Acetonitrile |
| CuI | Copper (1) iodide |
| DIPEA, DIEA | Diisopropylethyl amine |
| DMF | N,N-Dimethylformamide |
| EA | Ethyl acetate |
| EDCl | N-Ethyl-N'-carbodiimide hydrochloride |
| EtOAc | Ethyl acetate |
| h | hour |
| $H_2O$ | Water |
| HCl | Hydrochloric acid |
| HOBt | Hydroxybenzotriazole |
| $K_3PO_4$ | Potassium phosphate (tribasic) |
| MeOH | Methanol |
| $Na_2SO_4$ | Sodium sulfate |
| NMM | N-methylmorpholine |
| NMP | N-methyl pyrrolidone |
| $Pd(dppf)Cl_2$ | [1,1'-Bis(diphenylphosphino)ferrocene]dichloropalladium(II) |
| PE | Petroleum ether |
| rt | Room temperature |
| TFA | Trifluoroacetic acid |

Instrumentation

Mass spectrometry data collection took place with a Shimadzu LCMS-2020, an Agilent 1260LC-6120/6125MSD, a Shimadzu LCMS-2010EV, or a Waters Acquity UPLC, with either a QDa detector or SQ Detector 2. Samples were injected in their liquid phase onto a C-18 reverse phase. The compounds were eluted from the column using an acetonitrile gradient and fed into the mass analyzer. Initial data analysis took place with either Agilent ChemStation, Shimadzu LabSolutions, or Waters MassLynx. NMR data was collected with either a Bruker AVANCE III HD 400 MHz, a Bruker Ascend 500 MHz instrument, or a Varian 400 MHz, and the raw data was analyzed with either TopSpin or Mestrelab Mnova.

Synthesis of Intermediates

Intermediate 1. Synthesis of 3-(5-bromo-1-ethyl-2-[2-[(1S)-1-methoxyethyl]pyridin-3-yl]indol-3-yl)-2,2-dimethylpropan-1-ol

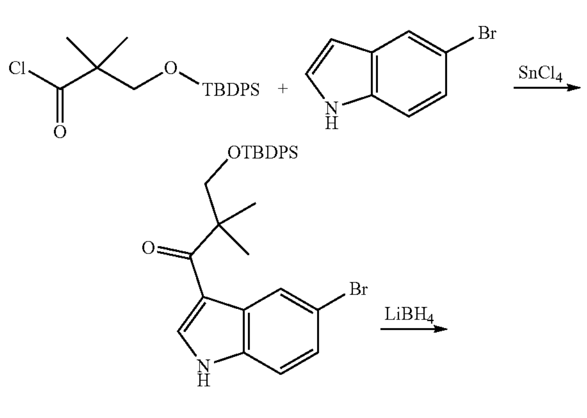

-continued

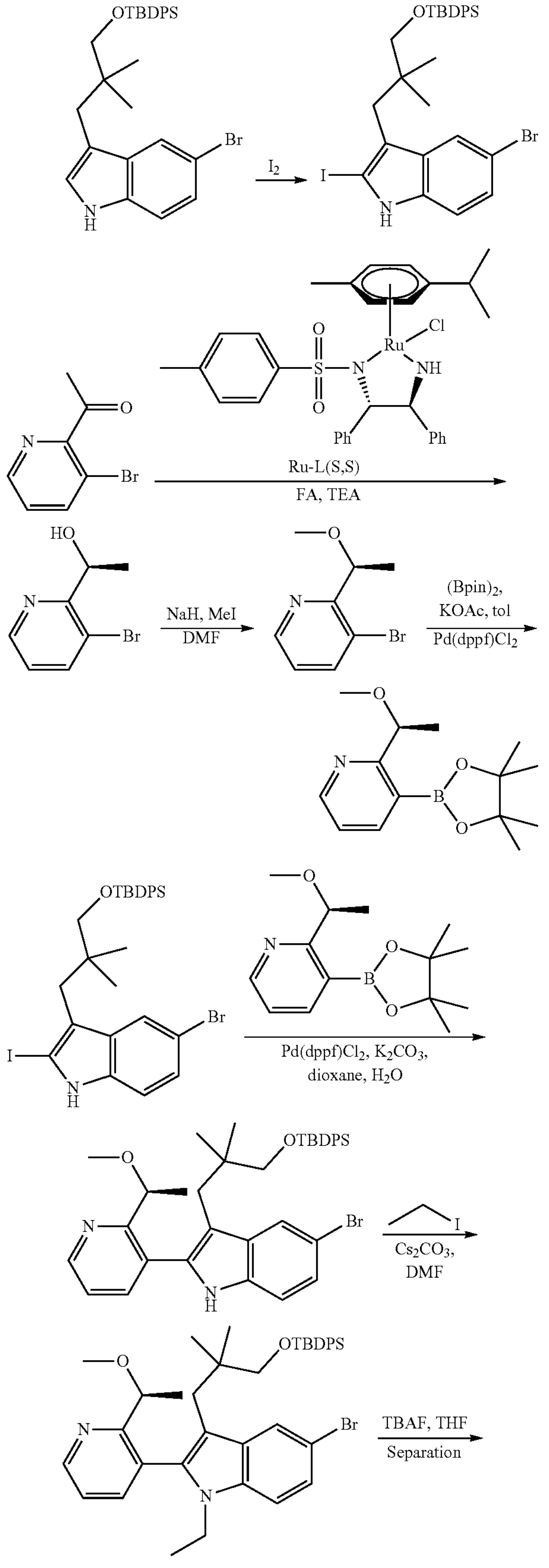

-continued

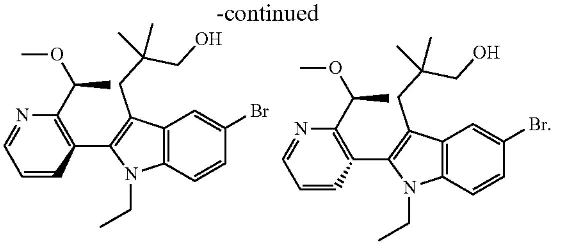

Intermediate 1

Step 1

To a mixture of 3-((tert-butyldiphenylsilyl)oxy)-2,2-dimethylpropanoyl chloride (65 g, 137 mmol, crude) in DCM (120 mL) at 0° C. under an atmosphere of N2 was added 1M $SnCl_4$ in DCM (137 mL, 137 mmol) slowly. The mixture was stirred at 0° C. for 30 min, then a solution of 5-bromo-1H-indole (26.8 g, 137 mmol) in DCM (40 mL) was added dropwise. The mixture was stirred at 0° C. for 45 min, then diluted with EtOAc (300 mL), washed with brine (400 mL), dried over $Na_2SO_4$ and filtered. The filtrate was concentrated under reduced pressure and the residue was purified by silica gel column chromatography to give 1-(5-bromo-1H-indol-3-yl)-3-((tert-butyldiphenylsilyl)oxy)-2,2-dimethylpropan-1-one (55 g, 75% yield). LCMS (ESI): m/z [M+Na] calc'd for $C_{29}H_{32}BrNO_2SiNa$ 556.1. found 556.3.

Step 2

To a mixture of 1-(5-bromo-1H-indol-3-yl)-3-((tert-butyldiphenylsilyl)oxy)-2,2-dimethylpropan-1-one (50 g, 93.6 mmol) in THF (100 mL) at 0° C. under an atmosphere of N2 was added $LiBH_4$ (6.1 g, 281 mmol). The mixture was heated to 60° C. and stirred for 20 h, then MeOH (10 mL) and EtOAc (100 mL) were added and the mixture washed with brine (50 mL), dried over $Na_2SO_4$, filtered and the filtrate concentrated under reduced pressure. The residue was diluted with DCM (50 mL), cooled to 10° C. and diludine (9.5 g, 37.4 mmol) and TsOH. $H_2O$ (890 mg, 4.7 mmol) added. The mixture was stirred at 10° C. for 2 h, filtered, the filtrate concentrated under reduced pressure and the residue was purified by silica gel column chromatography to give 1-(5-bromo-1H-indol-3-yl)-3-((tert-butyldiphenylsilyl)oxy)-2,2-dimethylpropan-1-one (41 g, 84% yield). LCMS (ESI): m/z [M+H] calc'd for $C_{29}H_{34}BrNOSi$ 519.2. found 520.1; $^1H$ NMR (400 MHz, $CDCl_3$) δ 7.96 (s, 1H), 7.75-7.68 (m, 5H), 7.46-7.35 (m, 6H), 7.23-7.19 (m, 2H), 6.87 (d, J=2.1 Hz, 1H), 3.40 (s, 2H), 2.72 (s, 2H), 1.14 (s, 9H), 0.89 (s, 6H).

Step 3

To a mixture of 1-(5-bromo-1H-indol-3-yl)-3-((tert-butyldiphenylsilyl)oxy)-2,2-dimethylpropan-1-one (1.5 g, 2.9 mmol) and 12 (731 mg, 2.9 mmol) in THF (15 mL) at rt was added AgOTf (888 mg, 3.5 mmol). The mixture was stirred at rt for 2 h, then diluted with EtOAc (200 mL) and washed with saturated $Na_2S_2O_3$ (100 mL), dried over anhydrous $Na_2SO_4$ and filtered. The filtrate was concentrated under reduced pressure and the residue was purified by silica gel column chromatography to give 5-bromo-3-(3-((tert-butyldiphenylsilyl)oxy)-2,2-dimethylpropyl)-2-iodo-1H-indole (900 mg, 72% yield) as a solid. $^1H$ NMR (400 MHz, DMSO-$d_6$) δ 11.70 (s, 1H), 7.68 (d, J=1.3 Hz, 1H), 7.64-7.62 (m, 4H), 7.46-7.43 (m, 6H), 7.24-7.22 (d, 1H), 7.14-7.12 (dd, J=8.6, 1.6 Hz, 1H), 3.48 (s, 2H), 2.63 (s, 2H), 1.08 (s, 9H), 0.88 (s, 6H).

Step 4

To a stirred mixture of HCOOH (66.3 g, 1.44 mol) in TEA (728 g, 7.2 mol) at 0° C. under an atmosphere of Ar was added (4S,5S)-2-chloro-2-methyl-1-(4-methylbenzenesulfonyl)-4,5-diphenyl-1,3-diaza-2-ruthenacyclopentane cymene (3.9 g, 6.0 mmol) portion-wise. The mixture was heated to 40° C. and stirred for 15 min, then cooled to rt and 1-(3-bromopyridin-2-yl)ethanone (120 g, 600 mmol) added in portions. The mixture was heated to 40° C. and stirred for an additional 2 h, then the solvent was concentrated under reduced pressure. Brine (2 L) was added to the residue, the mixture was extracted with EtOAc (4×700 mL), dried over anhydrous $Na_2SO_4$ and filtered. The filtrate was concentrated under reduced pressure and the residue was purified by silica gel column chromatography to give (1S)-1-(3-bromopyridin-2-yl)ethanol (100 g, 74% yield) as an oil. LCMS (ESI): m/z [M+H] calc'd for $C_7H_8BrNO$ 201.1. found 201.9.

Step 5

To a stirred mixture of (1S)-1-(3-bromopyridin-2-yl)ethanol (100 g, 495 mmol) in DMF (1 L) at 0° C. was added NaH, 60% dispersion in oil (14.25 g, 594 mmol) in portions. The mixture was stirred at 0° C. for 1 h. MeI (140.5 g, 990 mmol) was added dropwise at 0° C. and the mixture was allowed to warm to rt and stirred for 2 h. The mixture was cooled to 0° C. and saturated $NH_4Cl$ (5 L) was added. The mixture was extracted with EtOAc (3×1.5 L), dried over anhydrous $Na_2SO_4$ and filtered. The filtrate was concentrated under reduced pressure and the residue was purified by silica gel column chromatography to give 3-bromo-2-[(1S)-1-methoxyethyl]pyridine (90 g, 75% yield) as an oil. LCMS (ESI): m/z [M+H] calc'd for $C_8H_{10}BrNO$ 215.0. found 215.9.

Step 6

To a stirred mixture of 3-bromo-2-[(1S)-1-methoxyethyl]pyridine (90 g, 417 mmol) and Pd(dppf)$Cl_2$ (30.5 g, 41.7 mmol) in toluene (900 mL) at rt under an atmosphere of Ar was added bis(pinacolato)diboron (127 g, 500 mmol) and KOAc (81.8 g, 833 mmol) in portions. The mixture was heated to 100° C. and stirred for 3 h. The filtrate was concentrated under reduced pressure and the residue was purified by $Al_2O_3$ column chromatography to give 2-[(1S)-1-methoxyethyl]-3-(4,4,5,5-tetramethyl-1,3,2-dioxaborolan-2-yl)pyridine (100 g, 63% yield) as a semi-solid. LCMS (ESI): m/z [M+H] calc'd for $C_{14}H_{22}BNO_3$ 263.2. found 264.1.

Step 7

To a stirred mixture of 5-bromo-3-[3-[(tert-butyldiphenylsilyl)oxy]-2,2-dimethylpropyl]-2-iodo-1H-indole (140 g, 217 mmol) and 2-[(1S)-1-methoxyethyl]-3-(4,4,5,5-tetramethyl-1,3,2-dioxaborolan-2-yl)pyridine (100 g, 380 mmol) in 1,4-dioxane (1.4 L) at rt under an atmosphere of Ar was added $K_2CO_3$ (74.8 g, 541 mmol), Pd(dppf$Cl_2$ (15.9 g, 21.7 mmol) and $H_2O$ (280 mL) in portions. The mixture was heated to 85° C. and stirred for 4 h, then cooled, $H_2O$ (5 L) added and the mixture extracted with EtOAc (3×2 L). The combined organic layers were washed with brine (2×1 L), dried over anhydrous $Na_2SO_4$ and filtered. The filtrate was concentrated under reduced pressure and the residue was purified by silica gel column chromatography to give 5-bromo-3-[3-[(tert-butyldiphenylsilyl)oxy]-2,2-dimethylpropyl]-2-[2-[(1S)-1-methoxyethyl]pyridin-3-yl]-1H-indole (71 g, 45% yield) as a solid. LCMS (ESI): m/z [M+H] calc'd for $C_{37}H_{43}BrN_2O_2Si$ 654.2. found 655.1.

Step 8

To a stirred mixture of 5-bromo-3-[3-[(tert-butyldiphenylsilyl)oxy]-2,2-dimethylpropyl]-2-[2-[(1S)-1-methoxyethyl]pyridin-3-yl]-1H-indole (71 g, 108 mmol) in DMF (0.8 L) at 0° C. under an atmosphere of N2 was added $Cs_2CO_3$ (70.6 g, 217 mmol) and EtI (33.8 g, 217 mmol) in portions. The mixture was warmed to rt and stirred for 16 h then $H_2O$ (4 L) added and the mixture extracted with EtOAc (3×1.5 L). The combined organic layers were washed with brine (2×1 L), dried over anhydrous $Na_2SO_4$ and filtered. The filtrate was concentrated under reduced pressure and the residue was purified by silica gel column chromatography to give 5-bromo-3-[3-[(tert-butyldiphenylsilyl)oxy]-2,2-dimethylpropyl]-1-ethyl-2-[2-[(1S)-1-methoxyethyl]pyridin-3-yl]indole (66 g, 80% yield) as an oil. LCMS (ESI): m/z [M+H] calc'd for $C_{39}H_{47}BrN_2O_2Si$ 682.3. found 683.3.

Step 9

To a stirred mixture of TBAF (172.6 g, 660 mmol) in THF (660 mL) at rt under an atmosphere of N2 was added 5-bromo-3-[3-[(tert-butyldiphenylsilyl)oxy]-2,2-dimethylpropyl]-1-ethyl-2-[2-[(1S)-1-methoxyethyl]pyridin-3-yl]indole (66 g, 97 mmol) in portions. The mixture was heated to 50° C. and stirred for 16 h, cooled, diluted with $H_2O$ (5 L) and extracted with EtOAc (3×1.5 L). The combined organic layers were washed with brine (2×1 L), dried over anhydrous $Na_2SO_4$ and filtered. Alter filtration, the filtrate was concentrated under reduced pressure. The filtrate was concentrated under reduced pressure and the residue was purified by silica gel column chromatography to give two atropisomers of 3-(5-bromo-1-ethyl-2-(2-((S)-1-methoxyethyl)pyridin-3-yl)-1H-indol-3-yl)-2,2-dimethylpropan-1-ol (as single atropisomers) both as solids. (Combined 30 g, 62% yield) both as a solid. LCMS (ESI): m/z [M+H] calc'd for $C_{23}H_{29}BrN_2O_2$ 444.1. found 445.1.

Intermediate 1. Alternative Synthesis Through Fisher Indole Route

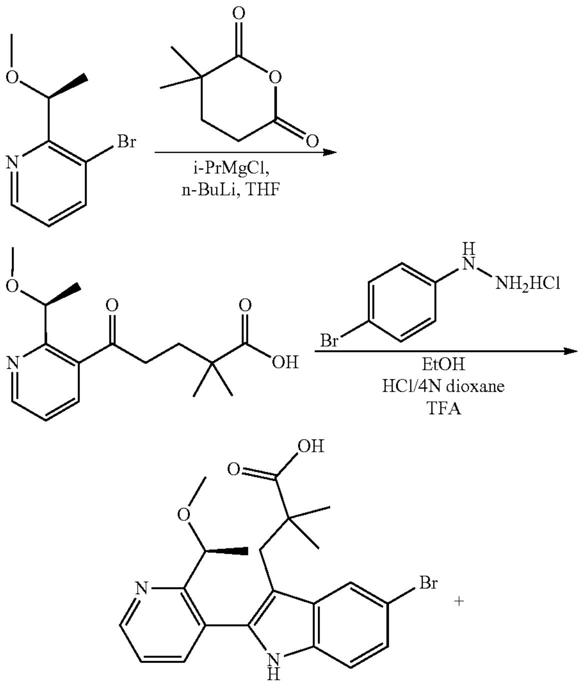

-continued

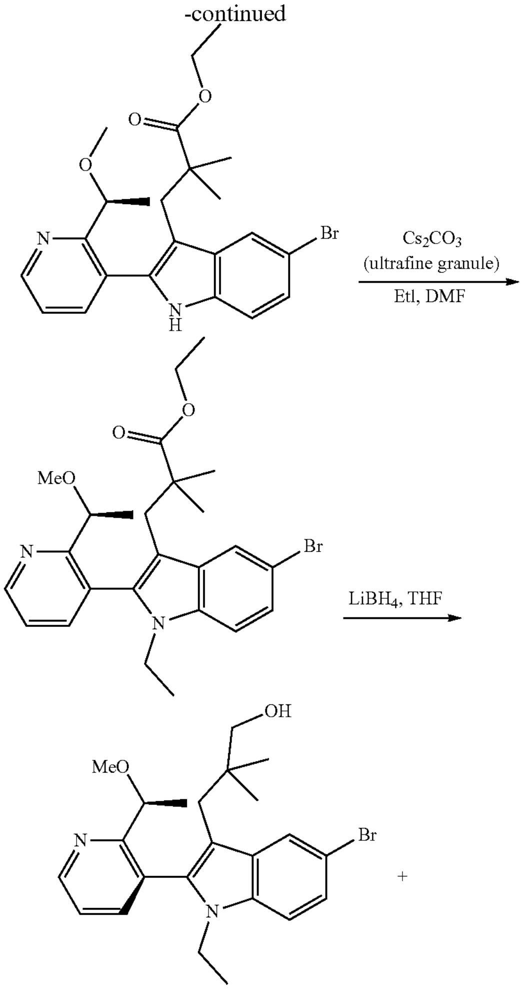

Intermediate 1

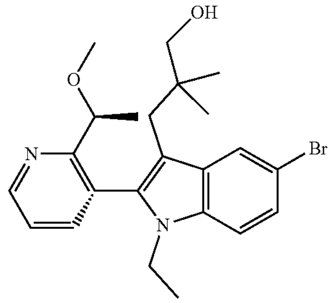

Step 1

To a mixture of i-PrMgCl (2M in in THF, 0.5 L) at −10° C. under an atmosphere of N2 was added n-BuLi, 2.5 M in hexane (333 mL, 833 mmol) dropwise over 15 min. The mixture was stirred for 30 min at −10° C. then 3-bromo-2-[(1S)-1-methoxyethyl]pyridine (180 g, 833 mmol) in THF (0.5 L) added dropwise over 30 min at −10° C. The resulting mixture was warmed to −5° C. and stirred for 1 h, then 3,3-dimethyloxane-2,6-dione (118 g, 833 mmol) in THF (1.2 L) was added dropwise over 30 min at −5° C. The mixture was warmed to 0° C. and stirred for 1.5 h, then quenched with the addition of pre-cooled 4M HCl in 1,4-dioxane (0.6 L) at 0° C. to adjust pH~5. The mixture was diluted with ice-water (3 L) and extracted with EtOAc (3×2.5 L). The combined organic layers were dried over anhydrous $Na_2SO_4$, filtered, the filtrate was concentrated under reduced pressure and the residue was purified by silica gel column chromatography to give 5-[2-[(1S)-1-methoxyethyl]pyridin-3-yl]-2,2-dimethyl-5-oxopentanoic acid (87 g, 34% yield) as a solid. LCMS (ESI): m/z [M+H] calc'd for $C_{15}H_2NO_4$ 279.2. found 280.1.

Step 2

To a mixture of 5-[2-[(1S)-1-methoxyethyl]pyridin-3-yl]-2,2-dimethyl-5-oxopentanoic acid (78 g, 279 mmol) in EtOH (0.78 L) at rt under an atmosphere of N was added (4-bromophenyl)hydrazine HCl salt (68.7 g, 307 mmol) in portions. The mixture was heated to 85° C. and stirred for 2 h, cooled to rt, then 4M HCl in 1,4-dioxane (69.8 mL, 279 mmol) added dropwise. The mixture was heated to 85° C. and stirred for an additional 3 h, then concentrated under reduced pressure and the residue was dissolved in TFA (0.78 L). The mixture was heated to 60 and stirred for 1.5, concentrated under reduced pressure and the residue adjusted to pH~5 with saturated $NaHCO_3$, then extracted with EtOAc (3×1.5 L). The combined organic layers were dried over anhydrous $Na_2SO_4$, filtered, the filtrate concentrated under reduced pressure and the residue was purified by silica gel column chromatography to give 3-(5-bromo-2-[2-[(1S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (78 g, crude). LCMS (ESI): m/z [M+H] calc'd for $C_{21}H_{23}BrN_2O_3$ 430.1 and $C_{23}H_{27}BrN_2O_3$ 458.1. found 431.1 and 459.1.

Step 3

To a mixture of 3-(5-bromo-2-[2-[(1S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (198 g, 459 mmol) in DMF (1.8 L) at 0° C. under an atmosphere of $N_2$ was added $Cs_2CO_3$ (449 g, 1.38 mol) in portions. EtI (215 g, 1.38 mmol) in DMF (200 mL) was then added dropwise at 0° C. The mixture was warmed to rt and stirred for 4 h then diluted with brine (5 L) and extracted with EtOAc (3×2.5 L). The combined organic layers were washed with brine (2×1.5 L), dried over anhydrous $Na_2SO_4$ and filtered. The filtrate was concentrated under reduced pressure and the residue was purified by silica gel column chromatography to give ethyl 3-(5-bromo-1-ethyl-2-[2-[(1S)-1-methoxyethyl]pyridin-3-yl]indol-3-yl)-2,2-dimethylpropanoate (160 g, 57% yield) as a solid. LCMS (ESI): m/z [M+H] calc'd for $C_{25}H_{31}BrN_2O_3$ 486.2. found 487.2.

Step 4

To a mixture of ethyl 3-(5-bromo-1-ethyl-2-[2-[(1S)-1-methoxyethyl]pyridin-3-yl]indol-3-yl)-2,2-dimethylpropanoate (160 g, 328 mmol) in THF (1.6 L) at 0° C. under an atmosphere of $N_2$ was added $LiBH_4$ (28.6 g, 1.3 mol). The mixture was heated to 60° C. for 16 h, cooled, and quenched with pre-cooled (0° C.) aqueous $NH_4Cl$ (5 L). The mixture was extracted with EtOAc (3×2 L) and the combined organic layers were washed with brine (2×1 L), dried over anhydrous $Na_2SO_4$ and filtered. The filtrate was concentrated under reduced pressure and the residue was purified by silica gel column chromatography to give to two atropisomers of 3-(5-bromo-1-ethyl-2-(2-((S)-1-methoxyethyl)pyridin-3-yl)-1H-indol-3-yl)-2,2-dimethylpropan-1-ol (as single atropisomers) (60 g, 38% yield) and (40 g, 26% yield) both as solids. LCMS (ESI): m/z [M+H] calc'd for $C_{23}H_{29}BrN_2O_2$ 444.1. found 445.2.

Intermediate 2. Synthesis of tert-butyl (($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-1H-8-oxa-2(4,2)-thiazola-1(5,3)-indola-6(1,3)-pyridazinacycloundecaphane-4-yl)carbamate

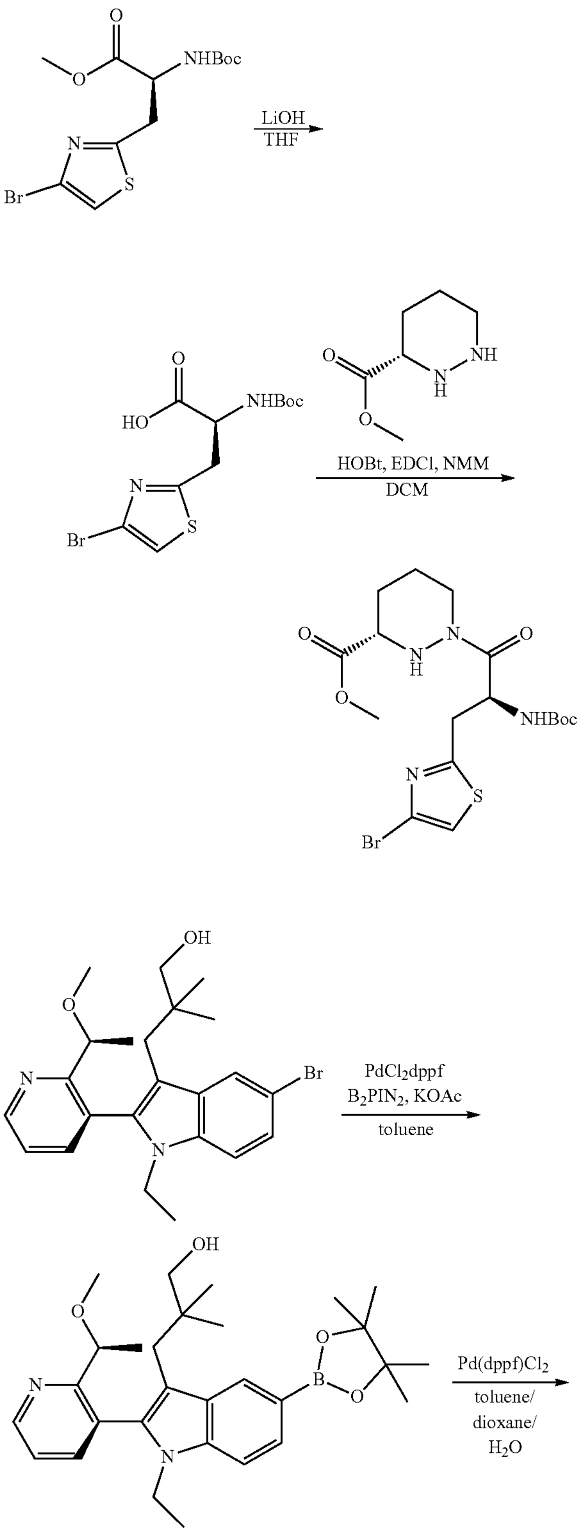

-continued

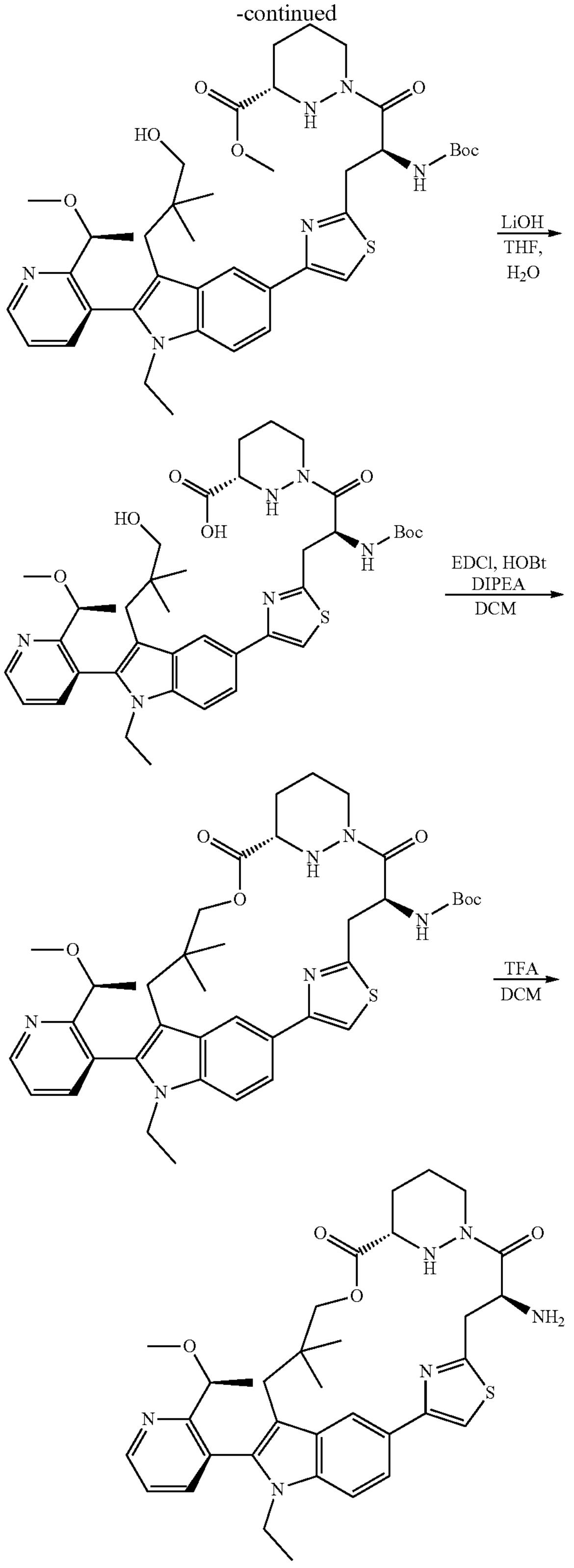

Intermediate 2

Step 1

To a solution of methyl (2S)-3-(4-bromo-1,3-thiazol-2-yl)-2-[(tert-butoxycarbonyl)amino]propanoate (110 g, 301.2 mmol) in THF (500 mL) and $H_2O$ (200 mL) at room temperature was added LiOH (21.64 g, 903.6 mmol). The solution was stirred for 1 h and was then concentrated under reduced pressure. The residue was adjusted to pH 6 with 1 M HCl and then extracted with DCM (3×500 mL). The combined organic layers were, dried over $Na_2SO_4$, filtered, and concentrated under reduced pressure to give (S)-3-(4-bromothiazol-2-yl)-2-((tert-butoxycarbonyl)amino)propanoic acid (108 g, crude). LCMS (ESI): m/z [M+H] calc'd for $C_{11}H_{16}BrN_2O_4S$ 351.0. found 351.0.

Step 2

To a solution of (S)-3-(4-bromothiazol-2-yl)-2-((tert-butoxycarbonyl)amino)propanoic acid (70 g, 199.3 mmol) in DCM (500 mL) at 0° C. was added methyl (3S)-1,2-diazinane-3-carboxylate bis(trifluoroacetic acid) salt (111.28 g, 298.96 mmol), NMM (219.12 mL. 1993.0 mmol), EDCI (76.41 g, 398.6 mmol) and HOBt (5.39 g, 39.89 mmol). The solution was warmed to room temperature and stirred for 1 h. The reaction was then quenched with $H_2O$ (500 mL) and was extracted with EtOAc (3×500 mL). The combined organic layers were dried over $Na_2SO_4$, filtered, and concentrated under reduced pressured. The residue was purified by silica gel column chromatography to give methyl (S)-1-((S)-3-(4-bromothiazol-2-yl)-2-((tert-butoxycarbonyl)amino)propanoyl)hexahydropyridazine-3-carboxylate (88.1 g, 93% yield). LCMS (ESI): m/z [M+H] calc'd for $C_{17}H_{26}BrN_4O_5S$ 477.1. found 477.1.

Step 3

To a solution of 3-(5-bromo-1-ethyl-2-(2-((S)-1-methoxyethyl)pyridin-3-yl)-1H-indol-3-yl)-2,2-dimethylpropan-1-ol (60 g, 134.7 mmol) in toluene (500 mL) at room temperature was added bis(pinacolato)diboron (51.31 g, 202.1 mmol), Pd(dppf)$Cl_2$ (9.86 g, 13.4 mmol), and KOAc (26.44 g, 269 mmol). The reaction mixture was then heated to 90° C. and stirred for 2 h. The reaction solution was then cooled to room temperature and concentrated under reduced pressure. The residue was purified by silica gel column chromatography to give (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (60.6 g, 94% yield). LCMS (ESI): m/z [M+H] calc'd for $C_{29}H_{42}BN_2O_4$ 493.32. found 493.3.

Step 4

To a solution of (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (30 g, 60.9 mmol) in toluene (600 mL), dioxane (200 mL), and $H_2O$ (200 mL) at room temperature was added methyl (S)-1-((S)-3-(4-bromothiazol-2-yl)-2-((tert-butoxycarbonyl)amino)propanoyl)hexahydropyridazine-3-carboxylate (43.62 g, 91.4 mmol), $K_3PO_4$ (32.23 g, 152.3 mmol) and Pd(dppf)$Cl_2$ (8.91 g, 12.18 mmol). The resulting solution was heated to 70° C. and stirred overnight. The reaction mixture was then cooled to room temperature and was quenched with $H_2O$ (200 mL). The mixture was extracted with EtOAc and the combined organic layers were dried over $Na_2SO_4$, filtered, and concentrated under reduced pressure. The residue was purified by silica gel column chromatography to give methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylate (39.7 g, 85% yield). LCMS (ESI): m/z [M+H] calc'd for $C_{40}H_{55}N_6O_7S$ 763.4. found 763.3.

Step 5

To a solution of methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)

thiazol-2-yl)propanoyl)hexahydropyridazine-3-carboxylate (39.7 g, 52.0 mmol) in THF (400 mL) and $H_2O$ (100 mL) at room temperature was added LiOH·$H_2O$ (3.74 g, 156.2 mmol). The mixture was stirred for 1.5 h and was then concentrated under reduced pressure. The residue was acidified to pH 6 with 1 M HCl and extracted with DCM (3×1000 mL). The combined organic layers were dried over $Na_2SO_4$, filtered, and concentrated under reduced pressure to give (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylic acid (37.9 g, crude). LCMS (ESI): m/z [M+H] calc'd for $C_{39}H_{53}N_6O_7S$ 749.4. found 749.4.

Step 6

To a solution of (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylic acid (37.9 g, 50.6 mmol), HOBt (34.19 g, 253.0 mmol) and DIPEA (264.4 mL, 1518 mmol) in DCM (4 L) at 0° C. was added EDC (271.63 g, 1416.9 mmol). The resulting mixture was warmed to room temperature and stirred overnight. The reaction mixture was then quenched with $H_2O$ and washed with 1 M HCl (4×1 L). The organic layer was separated and concentrated under reduced pressure. The residue was purified by silica gel column chromatography to give tert-butyl ((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1H-8-oxa-2(4,2)-thiazola-1(5,3)-indola-6(1,3)-pyridazinacycloundecaphane-4-yl)carbamate (30 g, 81% yield). LCMS (ESI): m/z [M+H] calc'd for $C_{39}H_{51}N_6O_6S$ 731.4. found 731.3.

Step 7

To a solution of tert-butyl ((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate (6 g, 8.21 mmol) in DCM (60 mL) at 0° C. was added TFA (30 mL). The mixture was stirred for 1 h and was then concentrated under reduced pressure to give (6$^3$S,4S,Z)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione (7.0 g, crude). LCMS (ESI): m/z [M+H] calc'd for $C_{34}H_{42}N_6O_4S$ 631.3. found: 630.3.

Intermediate 3. Synthesis of tert-butyl ((6$^3$S,4S,Z)-10,10-dimethyl-5,7-dioxo-12-(4,4,5,5-tetramethyl-1,3,2-dioxaborolan-2-yl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate

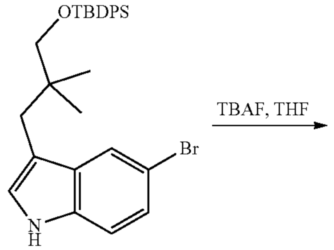

-continued

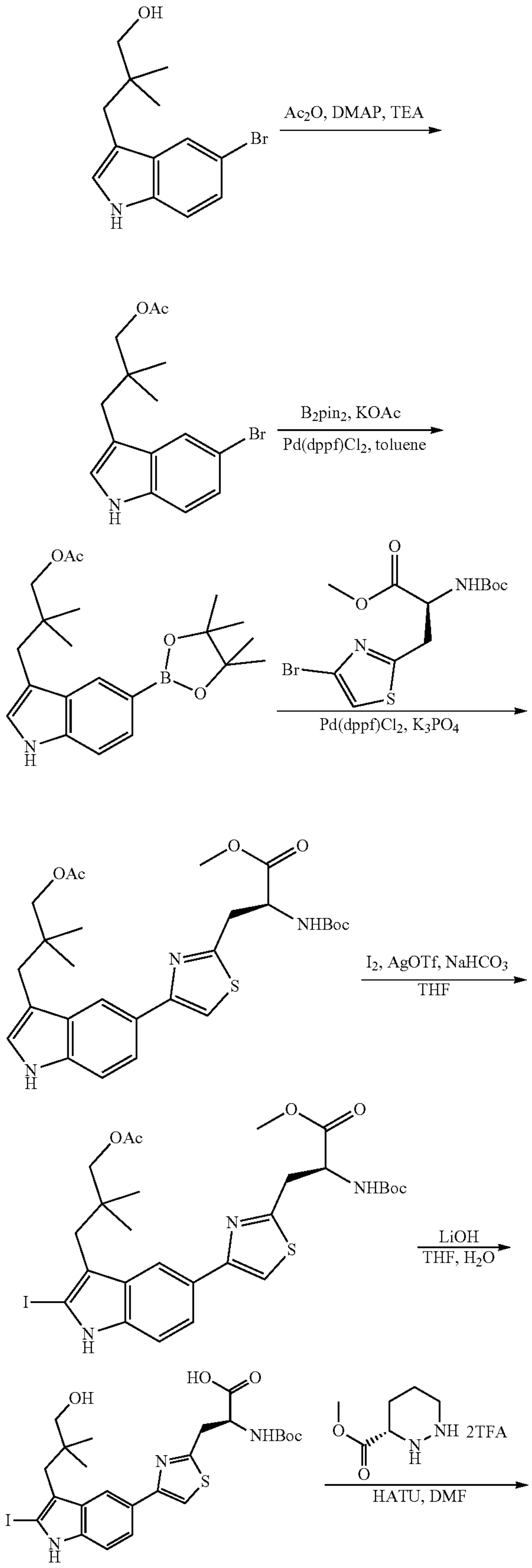

-continued

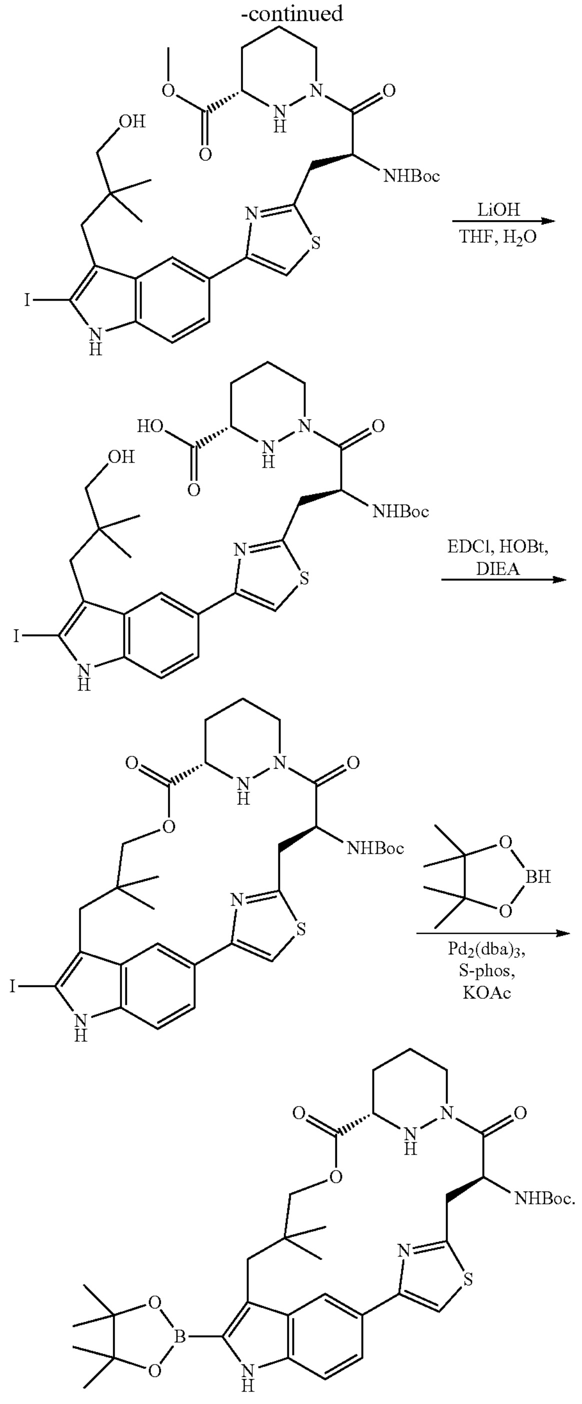

Intermediate 3

Step 1

To a stirred solution of 5-bromo-3-[3-[(tert-butyldiphenylsilyl)oxy]-2,2-dimethylpropyl]-1H-indole (100 g, 192.0 mmol) in THF (1000 mL) were added TBAF (261.17 g, 998.8 mmol) in portion at room temperature. The resulting mixture was stirred for 16 h at 50° C. The resulting mixture was concentrated under reduced pressure. The resulting mixture was extracted with EtOAc. (2 L). The combined organic layers were washed with water (6 L), dried over anhydrous $Na_2SO_4$. After filtration, the filtrate was concentrated under reduced pressure. The residue was purified by silica gel column chromatography, eluted with PE/EtOAc (3:1) to afford 3-(5-bromo-1H-indol-3-yl)-2,2-dimethylpropan-1-ol (54 g, 96.63%). LCMS (ESI): m/z [M+H] calc'd for $C_{13}H_{16}BrNO$ 281.0. found 282.0.

Step 2

To a stirred solution of 3-(5-bromo-1H-indol-3-yl)-2,2-dimethylpropan-1-ol (54 g, 191.3 mmol) in DCM (300 mL) were added TEA (58.09 g, 574.1 mmol) and $Ac_2O$ (18.95 g, 185.6 mmol) and DMAP (1.17 g, 9.5 mmol) dropwise at 0° C. The resulting mixture was washed with water (3×500 mL), dried over anhydrous $Na_2SO_4$. After filtration, the filtrate was concentrated under reduced pressure. This resulted in 3-(5-bromo-1H-indol-3-yl)-2,2-dimethylpropyl acetate (54 g, 80.6%) as a yellow solid. The crude product was used in the next step directly without further purification. LCMS (ESI): m/z [M+H] calc'd for $C_{15}H_{18}BrNO_2$ 323.0. found 324.0.

Step 3

To a stirred solution of 3-(5-bromo-1H-indol-3-yl)-2,2-dimethylpropyl acetate (54 g, 166.5 mmol) in toluene (600 mL) were added KOAc (40.87 g, 416.3 mmol) and $B_2pin_2$ (105.76 g, 416.3 mmol) and $Pd(dppf)Cl_2$ (12.19 g, 16.6 mmol) in portions at room temperature under argon atmosphere. The resulting mixture was stirred for 3 h at 90° C. under argon atmosphere. The resulting mixture was concentrated under reduced pressure. The resulting mixture was extracted with EtOAc (1 L). The combined organic layers were washed with water (3×1 L), dried over anhydrous $Na_2SO_4$. After filtration, the filtrate was concentrated under reduced pressure. The residue was purified by silica gel column chromatography, eluted with PE/EtOAc (3:1) to afford 2,2-dimethyl-3-[5-(4,4,5,5-tetramethyl-1,3,2-dioxaborolan-2-yl)-1H-indol-3-yl]propyl acetate borane (55 g, 76.57%) as a yellow solid. LCMS (ESI): m/z [M+H] calc'd for $C_{21}H_{30}BNO_4$ 371.2. found 372.2.

Step 4

To a stirred solution of 2,2-dimethyl-3-[5-(4,4,5,5-tetramethyl-1,3,2-dioxaborolan-2-yl)-1H-indol-3-yl]propyl acetate (54 g, 145.443 mmol) and methyl (2S)-3-(4-bromo-1,3-thiazol-2-yl)-2-[(tert-butoxycarbonyl)amino]propanoate (79.68 g, 218.1 mmol) and $K_3PO_4$ (77.18 g, 363.6 mmol) in toluene (330 mL) and dioxane (110 mL) and $H_2O$ (110 mL) were added $Pd(dppf)Cl_2$ (10.64 g, 14.5 mmol) in portions at room temperature under argon atmosphere. The resulting mixture was stirred for 36 h at 70° C. under argon atmosphere. The resulting mixture was concentrated under vacuum. The resulting mixture was extracted with EtOAc (3 L). The combined organic layers were washed with water (3×2 L), dried over anhydrous $Na_2SO_4$. After filtration, the filtrate was concentrated under reduced pressure. The residue was purified by silica gel column chromatography, eluted with PE/EtOAc (1:1) to afford methyl (2S)-3-(4-[3-[3-(acetyloxy)-2,2-dimethylpropyl]-1H-indol-5-yl]-1,3-thiazol-2-yl)-2-[(tert-butoxycarbonyl)amino]propanoate (54 g, 60.78%) as a yellow oil. LCMS (ESI): m/z [M+H] calc'd for $C_{27}H_{35}N_3O_{6S}$ 529.2. found 530.2.

Step 5

To a stirred solution of methyl (2S)-3-(4-[3-[3-(acetyloxy)-2,2-dimethylpropyl]-1H-indol-5-yl]-1,3-thiazol-2-yl)-2-[(tert-butoxycarbonyl)amino]propanoate (54 g, 101.954 mmol) in THF (450 mL) were added $NaHCO_3$ (10.28 g, 122.3 mmol) and AgOTf (31.44 g, 122.3 mmol) dropwise at 0° C. To the stirred solution was added 12 (23.29 g, 91.6 mmol) in THF (100 mL) dropwise at 0° C. The resulting mixture was stirred for 15 min at 0° C. The reaction was quenched with sat. Na2S203 (aq.) at 0° C. The resulting mixture was extracted with EtOAc (1 L). The combined organic layers were washed with water (3 L), dried over anhydrous $Na_2SO_4$. After filtration, the filtrate was concentrated under reduced pressure. The residue was purified by silica gel column chromatography, eluted with PE/EtOAc (5:1) to afford methyl (2S)-3-(4-[3-[3-(acetyloxy)-2,2-dimethylpropyl]-2-iodo-1H-indol-5-yl]-1,3-thiazol-2-yl)-2-[(tert-butoxycarbonyl)mino]propanoate (40 g, 53.80%) as a yellow solid. LCMS (ESI): m/z [M+H] calc'd for $C_{27}H_{34}IN_3O_6S$ 655.1. found 656.1.

Step 6

To a stirred solution of methyl (2S)-3-(4-[3-[3-(acetyloxy)-2,2-dimethylpropyl]-2-iodo-1H-indol-5-yl]-1,3-thiazol-2-yl)-2-[(tert-butoxycarbonyl)amino]propanoate (40 g, 61.01 mmol) in THF (300 mL) and $H_2O$ (100 mL) were added LiOH (4.38 g, 183.05 mmol) dropwise at 0° C. The resulting mixture was stirred for overnight at room temperature. The residue was acidified to pH 6 with conc. HCl. The resulting mixture was extracted with EtOAc (500 mL). The combined organic layers were washed with water (3×500 mL), dried over anhydrous $Na_2SO_4$. After filtration, the filtrate was concentrated under reduced pressure. This resulted in (2S)-2-[(tert-butoxycarbonyl)amino]-3-[4-[3-(3-hydroxy-2,2-dimethylpropyl)-2-iodo-1H-indol-5-yl]-1,3-thiazol-2-yl]propanoic acid (40 g, crude) as a yellow oil. The crude product was used in the next step directly without further purification. LCMS (ESI): m/z [M+H] calc'd for $C_{24}H_{30}IN_3O_5S$ 599.1.1. found 600.1.

Step 7

To a stirred solution of (2S)-2-[(tert-butoxycarbonyl)amino]-3-[4-[3-(3-hydroxy-2,2-dimethylpropyl)-2-iodo-1H-indol-5-yl]-1,3-thiazol-2-yl]propanoic acid (40 g, 66.72 mmol) and methyl (3S)-1,2-diazinane-3-carboxylate (28.86 g, 200.17 mmol) and HOBT (1.8 g, 13.35 mmol) and DIEA (172.47 g, 1334.5 mmol) in DCM (350 mL) were added EDCI (31.98 g, 166.8 mmol) dropwise at 0° C. The resulting mixture was stirred for overnight at room temperature under nitrogen atmosphere. The resulting mixture was washed with water (1.5 L), dried over anhydrous $Na_2SO_4$. After filtration, the filtrate was concentrated under reduced pressure. The residue was purified by silica gel column chromatography, eluted with PE/EtOAc (1:1) to afford methyl (3S)-1-[(2S)-2-[(tert-butoxycarbonyl)amino]-3-[4-[3-(3-hydroxy-2,2-dimethylpropyl)-2-iodo-1H-indol-5-yl]-1,3-thiazol-2-yl]propanoyl]-1,2-diazinane-3-carboxylate (28 g, 43.9%) as a yellow oil. LCMS (ESI): m/z [M+H] calc'd for $C_{30}H_{40}IN_5O_6S$ 725.1.1. found 726.1.

Step 8

To a stirred solution of methyl (3S)-1-[(2S)-2-[(tert-butoxycarbonyl)amino]-3-[4-[3-(3-hydroxy-2,2-dimethylpropyl)-2-iodo-1H-indol-5-yl]-1,3-thiazol-2-yl]propanoyl]-1,2-diazinane-3-carboxylate (28 g, 38.5 mmol) in THF (240 mL) were added LiOH (2.77 g, 115.7 mmol) in $H_2O$ (80 mL) dropwise at 0° C. The resulting mixture was stirred for 2 h at room temperature. The mixture was acidified to pH 6 with conc. HCl. The resulting mixture was extracted with EtOAc (300 mL). The combined organic layers were washed with water (3×300 mL), dried over anhydrous $Na_2SO_4$. After filtration, the filtrate was concentrated under reduced pressure. This resulted in (3S)-1-[(2S)-2-[(tert-butoxycarbonyl)amino]-3-[4-[3-(3-hydroxy-2,2-dimethylpropyl)-2-iodo-1H-indol-5-yl]-1,3-thiazol-2-yl]propanoyl]-1,2-diazinane-3-carboxylic acid (25 g, crude) as a yellow oil. The crude product was used in the next step directly without further purification. LCMS (ESI): m/z [M+H] calc'd for $C_{29}H_{38}IN_5O_6S$ 711.1. found 712.2.

Step 9

To a stirred solution of (3S)-1-[(2S)-2-[tert-butoxycarbonyl)amino]-3-[4-[3-(3-hydroxy-2,2-dimethylpropyl)-2-iodo-1H-indol-5-yl]-1,3-thiazol-2-yl]propanoyl]-1,2-diazinane-3-carboxylic acid (25 g, 35.13 mmol) and HOBT (23.74 g, 175.6 mmol) and DIPEA (136.21 g, 1053.9 mmol) in DCM (2 L) were added EDCI (188.5 g, 983.6 mmol) in portions at 0° C. The resulting mixture was stirred for overnight at room temperature under nitrogen atmosphere. The resulting mixture was washed with water (6 L), dried over anhydrous $Na_2SO_4$. After filtration, the filtrate was concentrated under reduced pressure. The residue was purified by silica gel column chromatography, eluted with PE/EtOAc (2:1) to afford tert-butyl (($6^3$S,4S,Z)-$1^2$-iodo-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (13 g, 45.88%) as a yellow solid. LCMS (ESI): m/z [M+H] calc'd for $C_{29}H_{36}IN_5O_5S$ 693.1. found 694.0.

Step 10

To a stirred mixture of tert-butyl (($6^3$S,4S,Z)-$1^2$-iodo-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (13 g, 18.7 mmol) and KOAc (6.44 g, 65.6 mmol) and s-Phos (2.31 g, 5.62 mmol) in toluene (120 mL) were added $Pd_2(dba)_3$ (2.06 g, 2.25 mmol) in portions at room temperature under argon atmosphere. To the stirred solution were added 4,4,5,5-tetramethyl-1,3,2-dioxaborolane (17.99 g, 140.5 mmol) dropwise at 0° C. under argon atmosphere. The resulting mixture was stirred for 3 h at 60° C. under argon atmosphere. The reaction was quenched with sat. $NH_4Cl$ (ag.) at 0° C. The resulting mixture was concentrated under vacuum. The resulting mixture was extracted with EtOAc (200 mL). The combined organic layers were washed with water (3×300 mL), dried over anhydrous $Na_2SO_4$. After filtration, the filtrate was concentrated under reduced pressure. The residue was purified by silica gel column chromatography, eluted with PE/EtOAc (3:1) to afford tert-butyl (($6^3$S,4S,Z)-10,10-dimethyl-5,7-dioxo-$1^2$-(4,4,5,5-tetramethyl-1,3,2-dioxaborolan-2-yl)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (10 g, 68.6% yield) as a yellow solid. LCMS (ESI): m/z [M+H] calc'd for $C_{35}H_{48}BN_5O_7S$ 693.3. found 694.4.

Intermediate 4. Synthesis of (S)-3-bromo-5-iodo-2-(1-methoxyethyl) pyridine

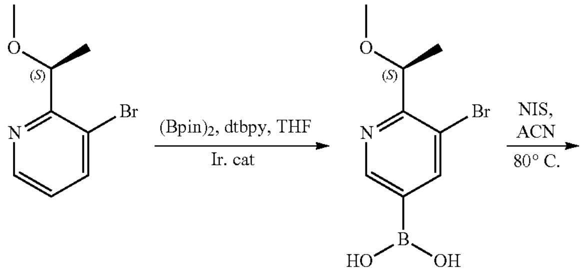

-continued

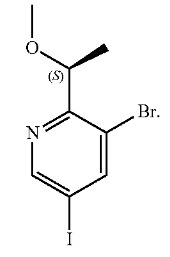

Intermediate 4

Step 1

To a stirred solution of 3-bromo-2-[(1 S1-methoxyethyl] pyridine (80.00 g, 370.24 mmol, 1.00 equiv) and bis(pinacolato)diboron (141.03 g, 555.3 mmol, 1.50 equiv) in THF (320 mL) was added dtbpy (14.91 g, 55.5 mmol) and Chloro(1,5-cyclooctadiene)iridium(I) dimer (7.46 g, 11.1 mmol) under argon atmosphere. The resulting mixture was stirred for 16 h at 75° C. under argon atmosphere. The mixture was concentrated under reduced pressure. The resulting mixture was dissolved in EtOAc (200 mL) and the mixture was adjusted to pH 10 with $Na_2CO_3$ (40 g) and NaOH (10 g) (mass 4:1) in water (600 mL).

The aqueous layer was extracted with EtOAc (800 mL). The aqueous phase was acidified to pH=6 with HCl (6 N) to precipitate the desired solid to afford 5-bromo-6-[(1S)-1-methoxyethyl]pyridin-3-ylboronic acid (50 g, 52.0% yield) as a light-yellow solid. LCMS (ESI): m/z [M+H] calc'd for $C_8H_{11}BBrNO_3$ 259.0. found 260.0.

Step 2

To a stirred solution of 5-bromo-6-[(1S)-1-methoxyethyl] pyridin-3-ylboronic acid (23.00 g, 88.5 mmol) in ACN (230 mL) were added NIS (49.78 g, 221.2 mmol) at room temperature under argon atmosphere. The resulting mixture was stirred for overnight at 80° C. under argon atmosphere. The resulting mixture was concentrated under reduced pressure. The resulting mixture was dissolved in DCM (2.1 L) and washed with $Na_2S2O_3$ (3×500 mL). The organic layer was dried over anhydrous $Na_2SO_4$.

After filtration, the filtrate was concentrated under reduced pressure. The residue was purified by silica gel column chromatography to afford (S)-3-bromo-5-iodo-2-(1-methoxyethyl)pyridine (20 g, 66.0% yield). LCMS (ESI): m/z [M+H] calc'd for $C_8H_9BrINO$ 340.9. found 341.7.

Intermediate 5. Synthesis of tert-butyl (($6^3$S,4S,Z)-11-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-1H-8-oxa-2(4,2)-thiazola-1(5,3)-indola-6(1,3)-pyridazinacycloundecaphane-4-yl)carbamate

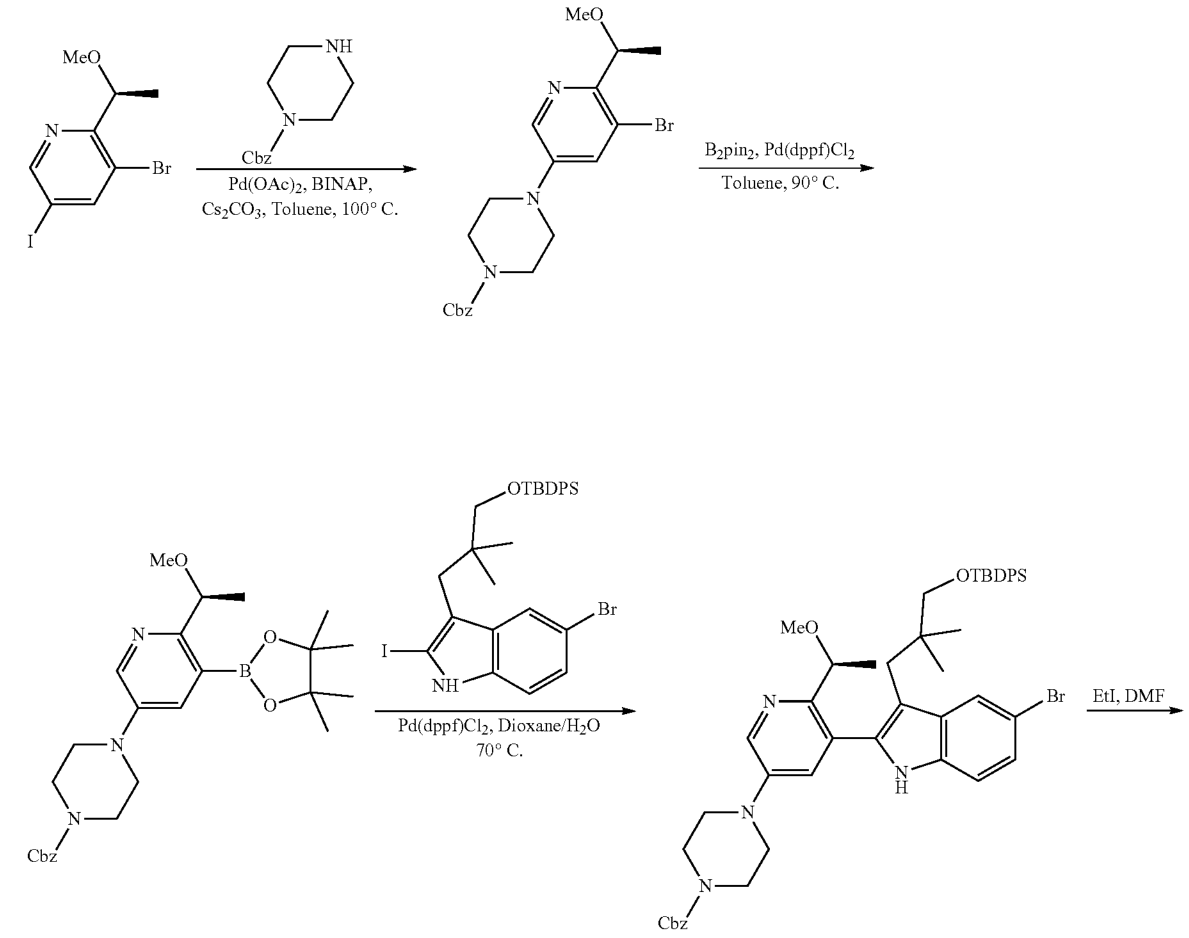

-continued
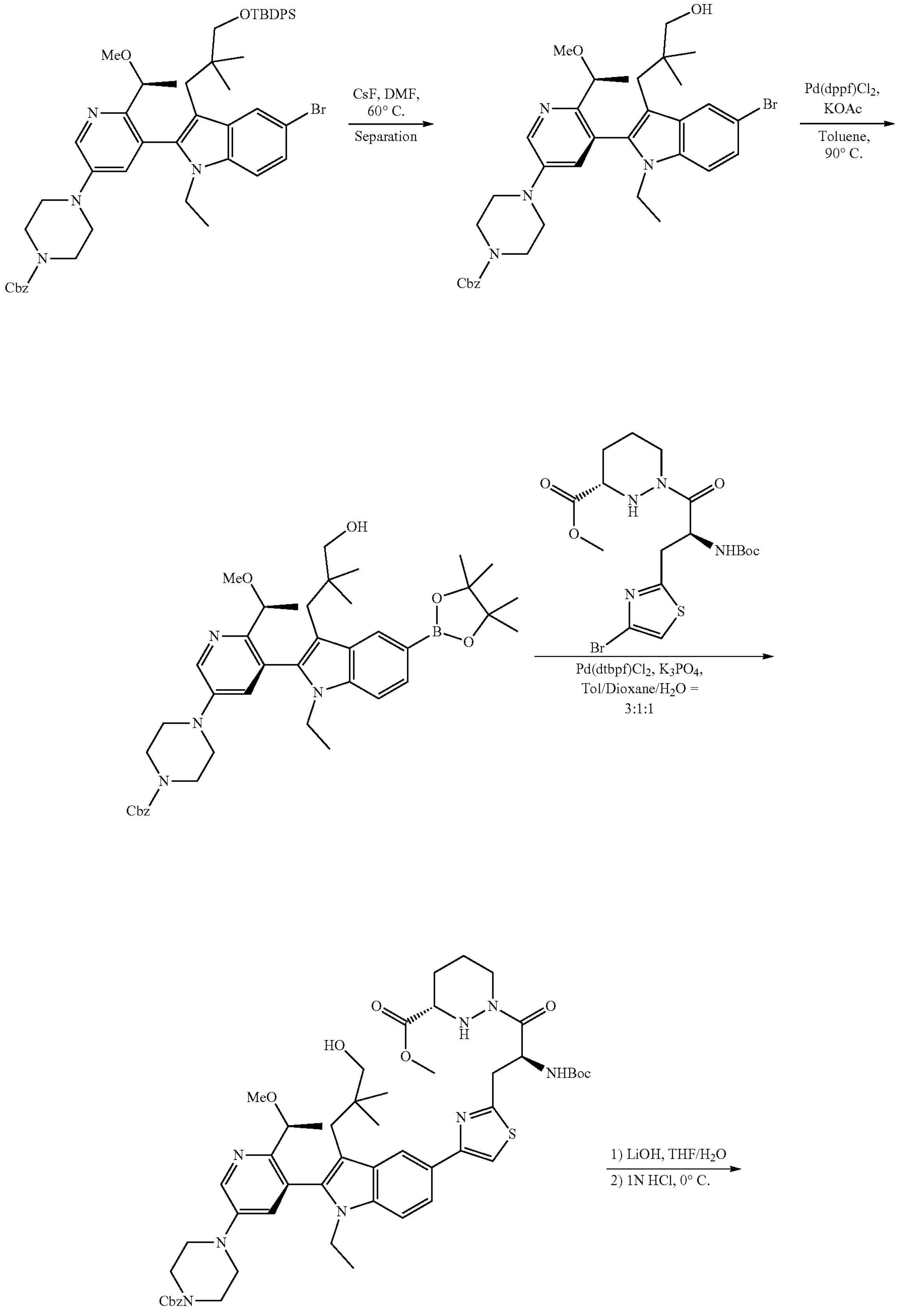

-continued
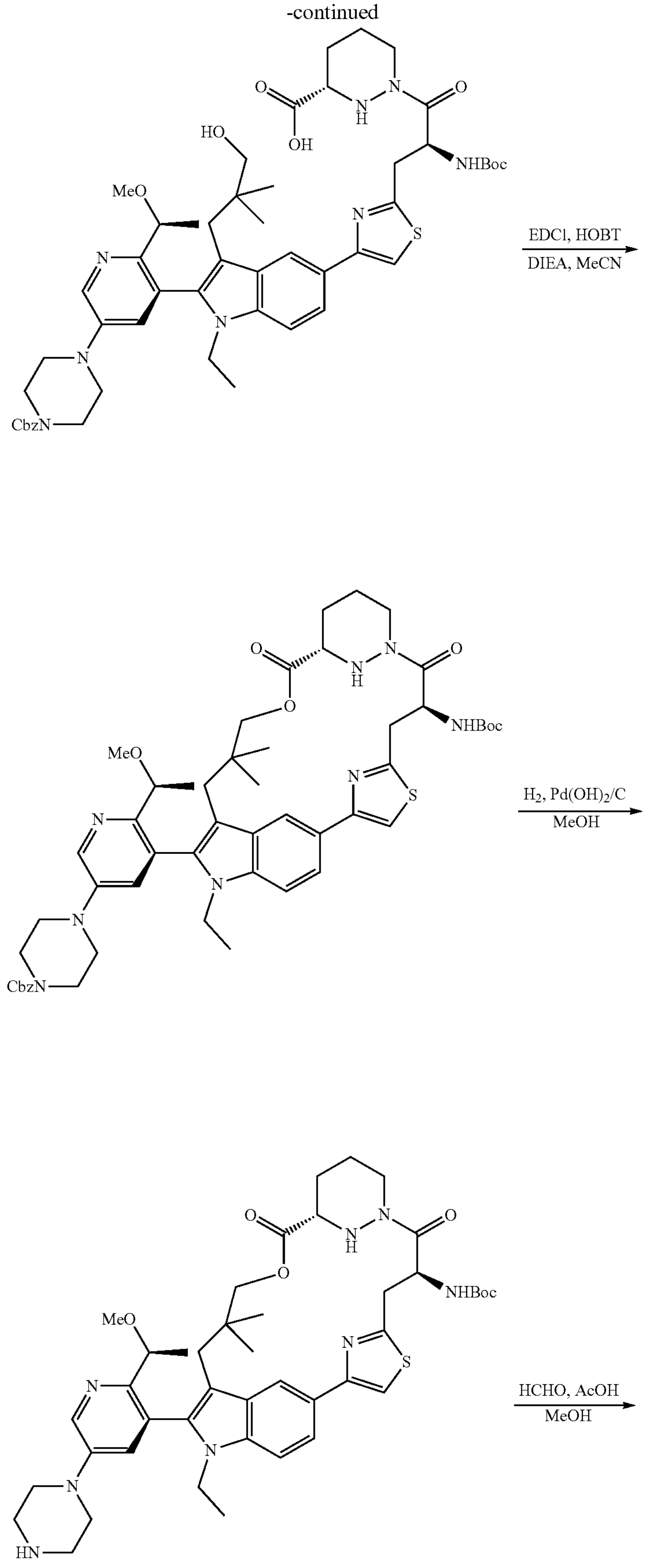

-continued

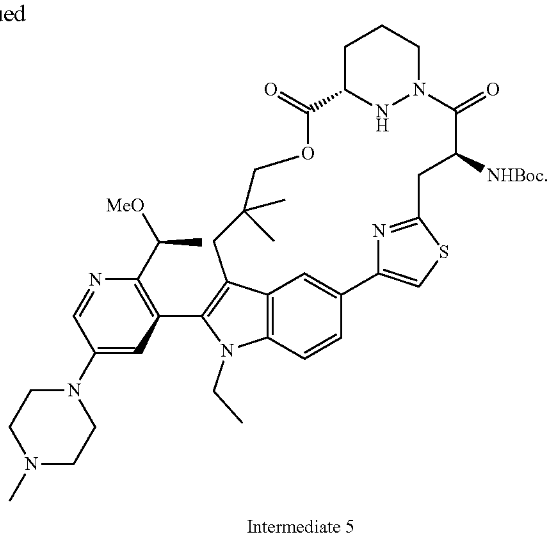

Intermediate 5

Step 1

Into a 3 L 3-necked round-bottom flask purged and maintained with an inert atmosphere of argon, was placed 3-bromo-5-iodo-2-[(1S)-1-methoxyethyl]pyridine (147 g, 429.8 mmol) benzyl piperazine-1-carboxylate (94.69 g, 429.8 mmol), $Pd(OAc)_2$ (4.83 g, 21.4 mmol), BINAP (5.35 g, 8.6 mmcl), $Cs_2CO_3$ (350.14 g, 1074.6 mmol), toluene (1 L). The resulting solution was stirred for overnight at 100° C. in an oil bath. The reaction mixture was cooled to 25° C. after reaction completed. The resulting mixture was concentrated under reduced pressure. The residue was applied onto a silica gel column with ethyl acetate/hexane (1:1). Removal of solvent under reduced pressure gave benzyl (S)-4-(5-bromo-6-(1-methoxyethyl)pyridin-3-yl)piperazine-1-carboxylate (135 g, 65.1% yield) as a dark yellow solid. LCMS (ESI): m/z [M+H] calc'd for $C_{20}H_{24}BrN_3O_3$ 433.1. found 434.1.

Step 2

Into a 3-L 3-necked round-bottom flask purged and maintained with an inert atmosphere of argon, was placed benzyl 4-[5-bromo-6-[(1S)-1-methoxyethyl]pyridin-3-yl]piperazine-1-carboxylate (135 g, 310.8 mmol), bis(pinacolato) diboron (86.82 g, 341.9 mmol), $Pd(dppf)Cl_2$ (22.74 g, 31.0 mmol), KOAc (76.26 g, 777.5 mmol), Toluene (1 L). The resulting solution was stirred for 2 days at 90° C. in an oil bath. The reaction mixture was cooled to 25° C. The resulting mixture was concentrated under vacuum. The residue was applied onto a neutral alumina column with ethyl acetate/hexane (1:3). Removal of solvent under reduced pressure gave benzyl (S)-4-(6-(1-methoxyethyl)-5-(4,4,5,5-tetramethyl-1,3,2-dioxaborolan-2-yl)pyridin-3-yl) piperazine-1-carboxylate (167 g, crude) as a dark yellow solid. LCMS (ESI): m/z [M+H] calc'd for $C_{26}H_{36}BN_3O_5$ 481.3. found 482.1.

Step 3

Into a 3-L 3-necked round-bottom flask purged and maintained with an inert atmosphere of argon, was placed (S)-4-(6-(1-methoxyethyl)-5-(4,4,5,5-tetramethyl-1,3,2-dioxaborolan-2-yl)pyridin-3-yl)piperazine-1-carboxylate (167 g, 346.9 mmol), 5-bromo-3-[3-[(tert-butyldiphenylsilyl)oxy]-2,2-dimethylpropyl]-2-iodo-1H-indole (224.27 g, 346.9 mmol), $Pd(dppf)Cl_2$ (25.38 g, 34.6 mmol), dioxane (600 mL), $H_2O$ (200 mL), $KSPO_4$ (184.09 g, 867.2 mmol), Toluene (200 mL). The resulting solution was stirred for overnight at 70° C. in an oil bath. The reaction mixture was cooled to 25° C. after reaction completed. The resulting mixture was concentrated under vacuum. The residue was applied onto a silica gel column with ethyl acetate/hexane (1:1). Removal of solvent under reduced pressure gave benzyl (S)-4-(5-(5-bromo-3-(3-((tert-butyldiphenylsilyl) oxy)-2,2-dimethylpropyl)-1H-indol-2-yl)-6-(1-methoxyethyl)pyridin-3-yl)piperazine-1-carboxylate (146 g, 48.1% yield) as a yellow solid. LCMS (ESI): m/z [M+H] calc'd for $C_{49}H_{57}BrN_4O_4Si$ 872.3. found 873.3.

Step 4

To a stirred mixture of benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (146 g, 167.0 mmol) and $Cs_2CO_3$ (163.28 g, 501.1 mmol) in DMF (1200 mL) was added $C_2H_5I$ (52.11 g, 334.0 mmol) in portions at 0° C. under $N_2$ atmosphere. The final reaction mixture was stirred at 25° C. for 12 h. Desired product could be detected by LCMS. The resulting mixture was diluted with EA (1 L) and washed with brine (3×1.5 L). The organic layers were dried over anhydrous $Na_2SO_4$. After filtration, the filtrate was concentrated under reduced pressure to give benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate (143 g, crude) as a yellow solid that was used directly for next step without further purification. LCMS (ESI): m/z [M+H] calc'd for $C_{51}H_{61}BrN_4O_4Si$ 900.4. found 901.4.

Step 5

To a stirred mixture of benzyl benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate (143 g, 158.5 mmol) in DMF (1250 mL) was added CsF (72.24 g, 475.5 mmol). Then the reaction mixture was stirred at 60° C. for 2 days under $N_2$ atmosphere. Desired product could be detected by LCMS. The resulting mixture was diluted with EA (1 L) and washed with brine (3×1 L). Then the organic phase was concentrated under reduced pressure. The residue was purified by silica gel column chromatography, eluted with PE/EA (1/3) to afford two atropisomers of benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate A (38 g, 36% yield, RT=1.677 min in 3 min LCMS (0.1% FA)) and B (34 g, 34% yield, RT=1.578 min in 3 min LCMS (0.1% FA)) both as yellow solid. LCMS (ESI): m/z [M+H] calc'd for $C_{35}H_{43}BrN_4O_4$ 663.2. found 662.2.

Step 6

Into a 500-mL 3-necked round-bottom flask purged and maintained with an inert atmosphere of nitrogen, was placed benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate A (14 g, 21.1 mmol), bis(pinacolato)diboron (5.89 g, 23.21 mmol), Pd(dppf)$Cl_2$ (1.54 g, 2.1 mmol), KOAc (5.18 g, 52.7 mmol), Toluene (150 mL). The resulting solution was stirred for 5 h at 90° C. in an oil bath. The reaction mixture was cooled to 25° C. The resulting mixture was concentrated under vacuum. The residue was purified by silica gel column chromatography, eluted with PE/EA (1/3) to give benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (12 g, 76.0% yield) as a yellow solid. LCMS (ESI): m/z [M+H] calc'd for $C_{41}H_{55}BN_4O_6$ 710.4. found 711.3.

Step 7

Into a 250-mL round-bottom flask purged and maintained with an inert atmosphere of argon, was placed benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (10.8 g, 15.2 mmol), methyl (3S)-1-[(2S)-3-(4-bromo-1,3-thiazol-2-yl)-2-[(tert-butoxycarbonyl)amino]propanoyl]-1,2-diazinane-3-carboxylate (7.98 g, 16.7 mmol), Pd(dtbpf)$Cl_2$ (0.99 g, 1.52 mmol), $K_3PO_4$ (8.06 g, 37.9 mmol), Toluene (60 mL), dioxane (20 mL), $H_2O$ (20 mL). The resulting solution was stirred for 3 h at 70° C. in an oil bath. The reaction mixture was cooled to 25° C. The resulting solution was extracted with EtOAc (2×50 mL) and concentrated under reduced pressure. The residue was applied onto a silica gel column with ethyl acetate/hexane (10:1). Removal of solvent to give methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylate (8 g, 50.9% yield) as a yellow solid. LCMS (ESI): m/z [M+H] calc'd for $C_{52}H_{68}N_8O_9S$ 980.5. found 980.9.

Step 8

To a stirred mixture of methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylate (12 g, 12.23 mmol) in THF (100 mL)/$H_2O$ (100 mL) was added LiOH (2.45 g, 61.1 mmol) under $N_2$ atmosphere and the resulting mixture was stirred for 2 h at 25° C. Desired product could be detected by LCMS. THF was concentrated under reduced pressure. The pH of aqueous phase was acidified to 5 with HCL (1N) at 0° C. The aqueous layer was extracted with DCM (3×100 ml). The organic phase was concentrated under reduced pressure to give (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylic acid (10 g, 84.5% yield) as a light yellow solid. LCMS (ESI): m/z [M+H] calc'd for $C_{51}H_{66}N_8O_9S$ 966.5. found 967.0.

Step 9

Into a 3-L round-bottom flask purged and maintained with an inert atmosphere of nitrogen, was placed (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylic acid (18 g, 18.61 mmol), ACN (1.8 L), DIEA (96.21 g, 744.4 mmol), EDCI (107.03 g, 558.3 mmol), HOBT (25.15 g, 186.1 mmol). The resulting solution was stirred for overnight at 25° C. The resulting mixture was concentrated under vacuum after reaction completed. The resulting solution was diluted with DCM (1 L). The resulting mixture was washed with HCl (3×1 L, 1N aqueous). The resulting mixture was washed with water (3×1 L). Then the organic layer was concentrated, the residue was applied onto a silica gel column with ethyl acetate/hexane (1:1). Removal of solvent under reduced pressure gave benzyl 4-(5-(($6^3$S,4S,Z)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)piperazine-1-carboxylate (10.4 g, 54.8% yield) as a light yellow solid. LCMS (ESI): m/z [M+H] calc'd for $C_{51}H_{64}N_8O_8S$ 948.5. found 949.3.

Step 10

Into a 250-mL round-bottom flask purged and maintained with an inert atmosphere of nitrogen, was placed benzyl 4-(5-(($6^3$S,4S,Z)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)piperazine-1-carboxylate (10.40 g, 10.9 mmol), Pd$(OH)_2$/C (5 g, 46.9 mmol), MeOH (100 mL). The resulting solution was stirred for 3 h at 25° C. under 2 atm $H_2$ atmosphere. The solids were filtered out and the filter cake was washed with MeOH (3×100 mL). Then combined organic phase was concentrated under reduced pressure to give tert-butyl (($6^3$S,4S,Z)-11-ethyl-$1^2$-(2-((S)-1-methoxyethyl)-5-(piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (8.5 g, 90.4% yield) as a light yellow solid. LCMS (ESI): m/z [M+H] calc'd for $C_{43}H_{64}N_8O_8S$ 814.4. found 815.3.

Step 11

Into a 1000-mL round-bottom flask purged and maintained with an inert atmosphere of nitrogen, was placed tert-butyl (($6^3$S,4S,Z)-11-ethyl-$1^2$-(2-((S)-1-methoxyethyl)-5-(piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (8.5 g, 10.4 mmol), MeOH (100 mL), AcOH (1.88 g, 31.2 mmol) and stirred for 15 mins. Then HCHO (1.88 g, 23.15 mmol, 37% aqueous solution) and $NaBH_3CN$ (788 mg, 12.5 mmol) was added at 25° C. The resulting solution was stirred for 3 h at 25° C. The resulting mixture was quenched with 100 mL water and concentrated under reduced pressure to remove MeOH.

The resulting solution was diluted with 300 mL of DCM. The resulting mixture was washed with water (3×100 mL). Removal of solvent gave tert-butyl (($6^3$S,4S,Z)-1-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (8.2 g, 90.1% yield) as a yellow solid. LCMS (ESI): m/z [M+H] calc'd for $C_{44}H_{60}N_8O_6S$ 828.4. found 829.3.

Example A120. (1S,2S)N-(($6^3$S,4S,Z)-$1^1$-ethyl-$1^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methylcyclopropane-1-carboxamide
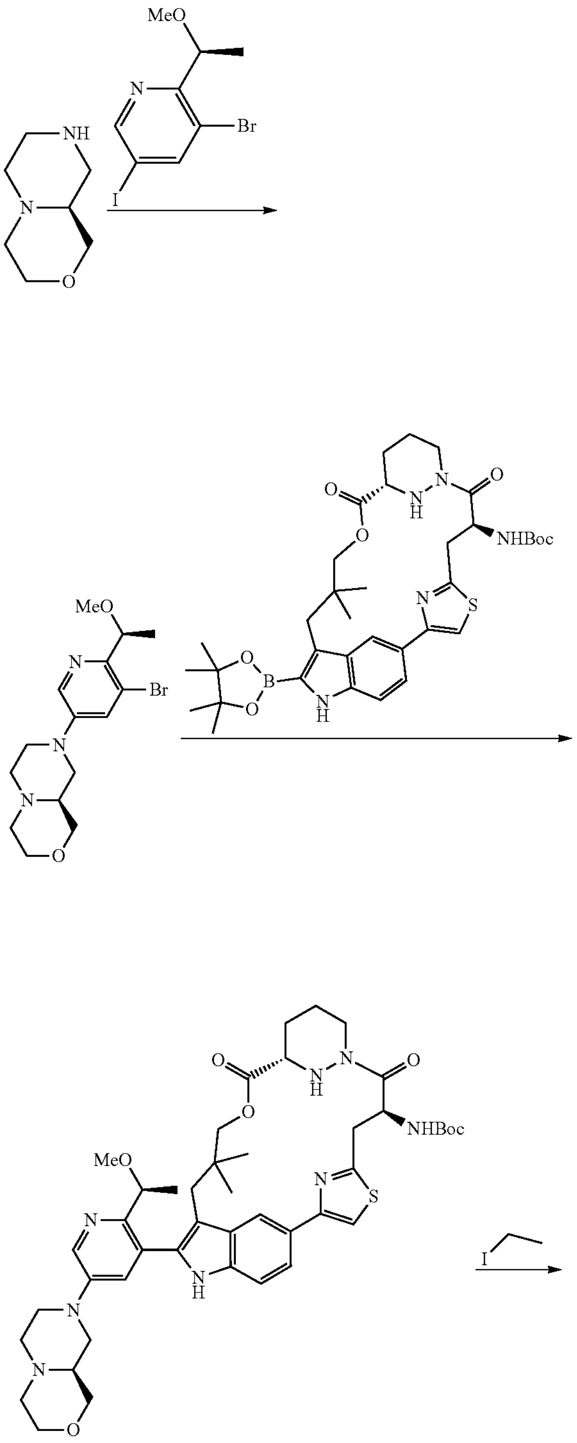
-continued
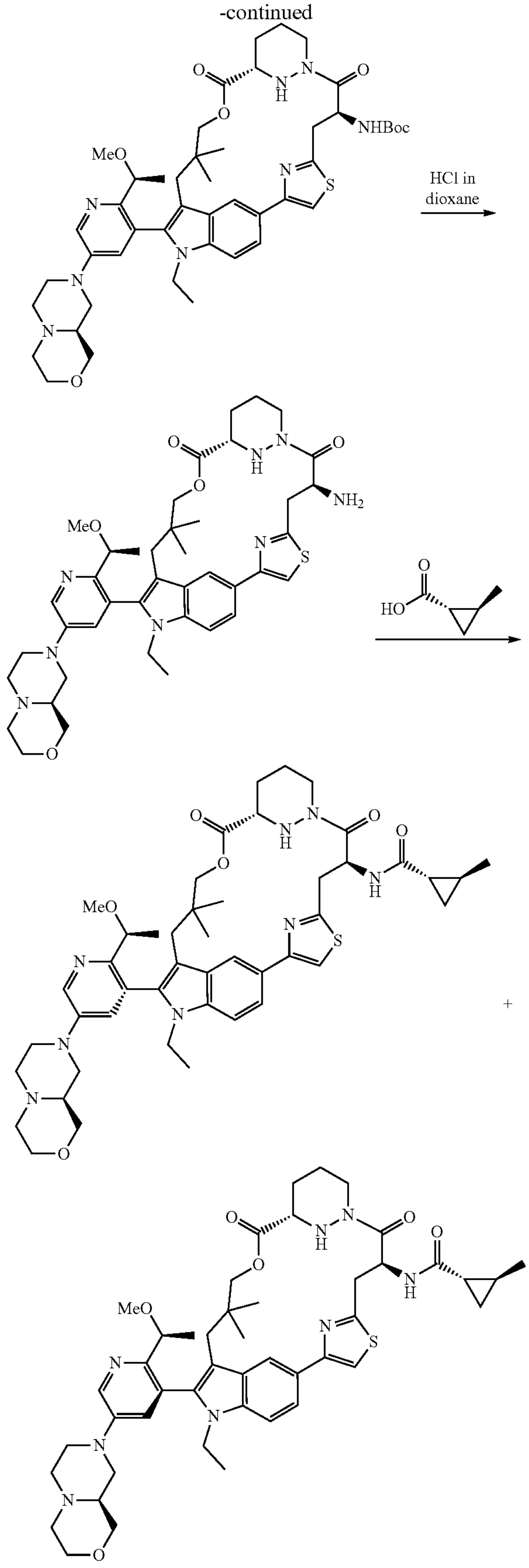

Step 1

To a stirred solution of 3-bromo-5-iodo-2-[(1S)-1-methoxyethyl]pyridine (1 g, 2.92 mmol) (S)-octahydropyrazino[2,1-c][1,4]oxazine (498.9 mg, 3.1 mmol) and Potassium tert-butoxide (656.25 mg, 5.8 mmol) in Toluene (15 mL) were added $Pd_2(dba)_3$ (53.55 mg, 0.06 mmol) and XantPhos (169.2 mg, 0.29 mmol) at room temperature under nitrogen atmosphere. The resulting mixture was stirred for 3 h at 100° C. under nitrogen atmosphere. After completion of reaction, the solution was concentrated under reduced pressure. The residue was purified by reverse flash chromatography (conditions: column, C18 silica gel; mobile phase, ACN in water (0.05% TFA), 0% to 100% gradient in 40 min; detector, UV 254 nm) to afford (S)-8-(5-bromo-6-((S)-1-methoxyethyl)pyridin-3-yl)octahydropyrazino[2,1-c][1,4]oxazine (670 mg, 57.2% yield) as a yellow solid. LCMS (ESI): m/z [M+H] calc'd for $C_{15}H_{22}BrN_3O_2$ 355.1. found 356.1.

Step 2

To a mixture of (S)-8-(5-bromo-6-((S)-1-methoxyethyl)pyridin-3-yl)octahydropyrazino[2,1-c][1,4]oxazine (670 mg, 1.88 mmol), Intermediate 3 (1.56 g, 2.26 mmol) and $K_2CO_3$ (779.74 mg, 5.6 mmol) in Toluene (9 mL), $H_2O$ (3 mL) and 1,4-dioxane (3 mL) was added Pd(dppf)$Cl_2$ (137.61 mg, 0.19 mmol) at room temperature under nitrogen atmosphere. The resulting mixture was stirred for overnight at 65° C. under nitrogen atmosphere. After completion of reaction, the solution was concentrated under reduced pressure. The residue was purified by reverse flash chromatography (conditions: column, C18 silica gel; mobile phase, ACN in water (0.05% TFA), 0% to 100% gradient in 30 min; detector, UV 254 nm) to afford tert-butyl (($6^3$S,4S, Z)-$1^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (1.4 g, 88.3% yield) as a white solid. LCMS (ESI): m/z [M+H] calc'd for $C_{44}H_{58}N_8O_7S$ 842.4. found 843.2.

Step 3

To a stirred mixture of tert-butyl (($6^3$S,4S, Z)-$1^2$-(5-((S)-hexahydropyrazino[2,1-c][1,4]oxazin-8(1H-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-1H-8-oxa-2(4,2)-thiazola-1(5,3)-indola-6(1,3)-pyridazinacycloundecaphane-4-yl)carbamate (1.4 g. 1.66 mmol) and $Cs_2CO_3$ (1.62 g, 4.97 mmol) in DMF (10 mL) was added ethyl iodide (0.39 g, 2.5 mmol) dropwise at 0° C. The resulting mixture was stirred for 2 h at room temperature. After completion of reaction, the solution was concentrated under reduced pressure. The residue was purified by reverse flash chromatography (conditions: column, C18 silica gel; mobile phase, ACN in water (0.05% TFA), 0% to 100% gradient in 30 min; detector, UV 254 nm) to afford tert-butyl (($6^3$S,4S, Z)-$1^1$-ethyl-$1^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (800 mg, 49.7% yield) as a brown yellow solid. LCMS (ESI): m/z [M+H] calc'd for $C_{46}H_{62}N_8O_7S$ 870.4. found 871.2.

Step 4

Into a 50 mL round-bottom flask were added tert-butyl (($6^3$, 4S, Z)-$1^1$-ethyl-$1^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (250 mg, 0.29 mmol) and HCl (4M in 1,4-dioxane, 10 mL) at 0° C. The resulting mixture was stirred for 1 h at room temperature. The resulting mixture was concentrated. The resulting mixture was diluted with 30 mL of dichloromethane and 20 mL saturated $NaHCO_3$ aqueous solution. The organic phase was washed twice with 30 mL brine. Removal of solvent under reduced pressure resulted in ($6^3$S,4S,Z)-4-amino-$1^1$-ethyl-$1^2$-(5-((S)-hexahydropyrazino[2,1-c][1,4]oxazin-8(1H)-yl)-2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (170.00 mg, crude) as a brown solid. LCMS (ESI): m/z [M+H] calc'd for $C_{41}H_{54}N_8O_5S$ 770.4. found 771.2.

Step 5

To a stirred solution of ($6^3$S,4S,Z)-4-amino-$1^1$-ethyl-$1^2$-(5-((S)-hexahydropyrazino[2,1-c][1,4]oxazin-8(1H)-yl)-2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (170 mg, 0.22 mmol) in DMF (8 mL) were added DIEA (2.8 g, 22 mmol), (1S,2S)-2-methylcyclopropane-1-carboxylic acid (33 mg, 0.33 mmol) and HATU (125 mg, 0.33 mmol) at 0° C. The resulting mixture was stirred for 2 h at room temperature. After completion of reaction, the solution was concentrated under reduced pressure. The crude product was purified by Prep-HPLC to afford 50 mg racemated product. The racemate was purified by Prep-CHIRAL-HPLC with the following conditions (Column: CHIRAL ART Cellulose-SB, 2*25 cm, 5 um; Mobile Phase A: MtBE (10 mM $NH_3$-MeOH), Mobile Phase B: EtOH; Flow rate: 20 mL/min; Gradient: 50% B to 50% B in 7 min; 275/210 nm) to afford two atropisomers of (1S,2S)—N-(($6^3$S,4S,Z)-$1^1$-ethyl-$1^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methylcyclopropane-1-carboxamide (as single atropisomer) (10.7 mg, 5.1% yield) and (6 mg, 3.03%) both as white solid. LCMS (ESI): m/z [M+H] calc'd for $C_{46}H_{60}N_8O_6S$ 852.3. found 853.5. Isomer 1. $^1$H NMR (400 MHz, DMSO-d6) δ 8.53 (d, 2H), 8.46 (d, 1H), 7.79 (s, 1H), 7.71 (d, 1H), 7.51 (d, 1H), 7.38 (d, 1H), 5.55 (t, 1H), 5.05 (d, 1H), 4.22 (t, 2H), 3.99-3.80 (m, 4H), 3.82-3.59 (m, 5H), 3.54 (d, 2H), 3.39 (d, 1H), 3.14 (t, 2H), 3.07 (s, 3H), 2.99 (s, 1H), 2.81 (t, 3H), 2.67 (d, 1H), 2.44-2.34 (m, 2H), 2.30 (s, 1H), 2.21-2.07 (n, 2H), 1.80 (s, 2H), 1.51 (s, 2H), 1.21 (d, 4H), 1.15-0.93 (m, 7H), 0.87 (s, 3H), 0.65 (m, 2H), 0.52 (s, 4H). Isomer 2. $^1$H NMR (400 MHz, DMSO-d6) δ 8.54-8.39 (m, 3H), 7.79 (s, 1H), 7.75-7.67 (m, 1H), 7.55 (d, 1H), 7.22 (d, 1H), 5.56 (t, 1H), 5.07 (d, 1H), 4.34-4.09 (m, 5H), 3.83-3.62 (m, 4H), 3.55 (d, 3H), 3.21 (s, 3H), 3.14 (d, 2H), 2.94-2.64 (m, 5H), 2.46-2.36 (m, 2H), 2.32-2.15 (m, 3H), 2.08 (d, 1H), 1.79 (s, 2H), 1.49 (s, 2H), 1.33 (d, 3H), 1.25 (d, 1H), 1.06 (s, 4H), 0.90 (d, 7H), 0.54 (d, 1H), 0.34 (s, 3H).

Example A14. N-[(7S,13S,19M)-21-ethyl-20-{2-[(1S)-1-methoxyethyl]pyridin-3-yl}-17,17-dimethyl-8,14-dioxo-15-oxa-4-thia-9,21,27,28-tetraazapentacyclo[17.5.21$^{2,6}$.1$^{9,13}$.0$^{22,26}$]octacosa-1(25),2,5(28),19,22(26),23-hexaen-7-yl]azetidine-3-carboxamide

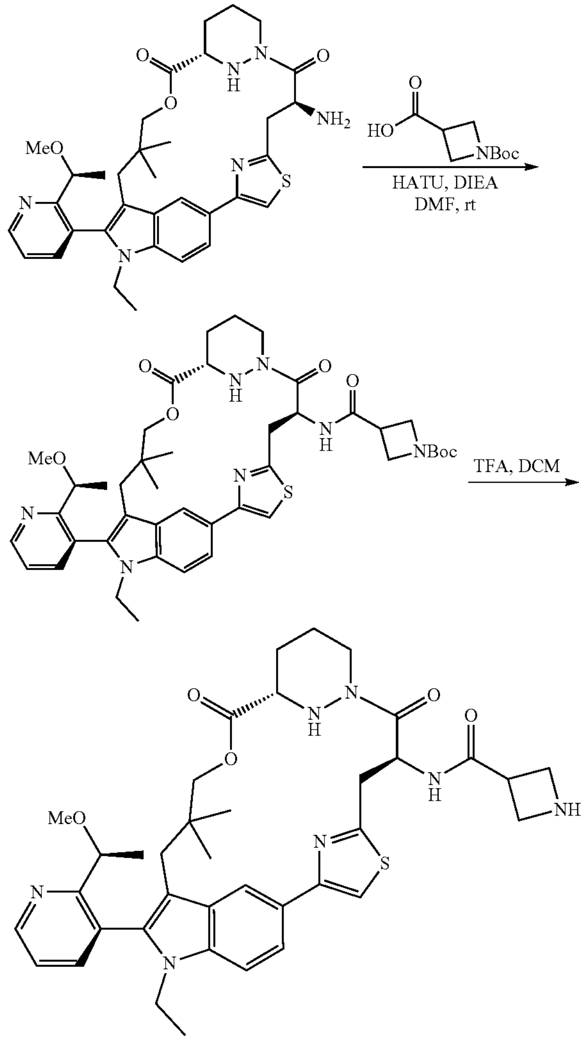

Step 1

To a stirred solution of (6$^{3}$S,4S,Z)-4-amino-1$^{1}$-ethyl-1$^{2}$-(2-((S)-1-methoxyethyl)pyridin-3-yl)-10,10-dimethyl-6$^{1}$,6$^{2}$,6$^{3}$,6$^{4}$,6$^{5}$,6$^{6}$-hexahydro-1H-8-oxa-2(4,2)-thiazola-1(5,3)-indola-6(1,3)-pyridazinacycloundecaphane-5,7-dione (450.00 mg, 0.71 mmol, 1.00 equiv) and 1-(tert-butoxycarbonyl)azetidine-3-carboxylic acid (215.3 mg, 1.07 mmol) in DMF (5.00 mL) were added DIEA (460.99 mg, 3.5 mmol) and HATU (379.7 mg, 1 mmol) in portions at room temperature under $N_2$ atmosphere until the reaction was complete by LCMS. The resulting mixture was extracted with EtOAc (3×20 mL) and the combined organic layers were washed with brine (2×20 mL), dried over anhydrous $Na_2SO_4$. After filtration, the filtrate was concentrated under reduced pressure and the resulting residue was purified by silica gel column chromatography to afford tert-butyl 3-(((6$^{3}$S,4S,Z)-1$^{1}$-ethyl-1$^{2}$-(2-((S)-1-methoxyethyl)pyridin-3-yl)-10,10-dimethyl-5,7-dioxo-6$^{1}$,6$^{2}$,6$^{3}$,6$^{4}$,6$^{5}$,6$^{6}$-hexahydro-1$^{1}$H-8-oxa-2(4,2)-thiazola-1(5,3)-indola-6(1,3)-pyridazinacycloundecaphane-4-yl)carbamoyl)azetidine-1-carboxylate (520 mg, 90%) as a yellow solid. LCMS (ESI): m/z [M+H] calc'd for $C_{43}H_{55}N_7O_7S$ ESI-MS 813.4. found: 814.4.

Step 2

To a solution of tert-butyl 3-(((6$^{3}$S,4S,Z)-1$^{1}$-ethyl-1$^{2}$-(2-((S)-1-methoxyethyl)pyridin-3-yl)-10,10-dimethyl-5,7-dioxo-6$^{1}$,6$^{2}$,6$^{3}$,6$^{4}$,6$^{5}$,6$^{6}$-hexahydro-1$^{1}$H-8-oxa-2(4,2)-thiazola-1(5,3)-indola-6(1,3)-pyridazinacycloundecaphane-4-yl)carbamoyl)azetidine-1-carboxylate (170.00 mg, 0.21 mmol) in DCM (1.6 mL) was added TFA (0.4 mL, 5.3 mmol) dropwised at 0° C. It was stirred for 2 h at room temperature under $N_2$ atmosphere and then concentrated under reduced pressure. The crude product was purified by Prep-HPLC to afford N-[(7S,13S,19M)-21-ethyl-20-{2-[(1S)-1-methoxyethyl]pyridin-3-yl}-17,17-dimethyl-8,14-dioxo-5-oxa-4-thia-9,21,27,28-tetraazapentacyclo[17.5.2.1$^{2,5}$.1$^{9,13}$.0$^{2,26}$]octacosa-1(25),2,5(28),19,22(26),23-hexaen-7-yl]azetidine-3-carboxamide (44.7 mg, 30% yield) as a white solid.

LCMS (ESI): m/z [M+H] calc'd for $C_{38}H_{47}N_7O_5S$ 713.3. found 714.1.

Example A99. (1S,2S)—N-((6$^{1}$S,4S,Z)-1$^{1}$-ethyl-1$^{2}$-(2-((S)-1-methoxyethyl)-5-(4-methylpiperazin-1-yl)pyridin-3-yl)-10,10-dimethyl-5,7-dioxo-6$^{1}$,6$^{2}$,6$^{3}$,6$^{4}$,6$^{5}$,6$^{6}$-hexahydro-1$^{1}$H-8-oxa-2(4,2)-thiazola-1(5,3)-indola-6(1,3)-pyridazinacycloundecaphane-4-yl)-2-phenylcyclopropane-1-carboxamide

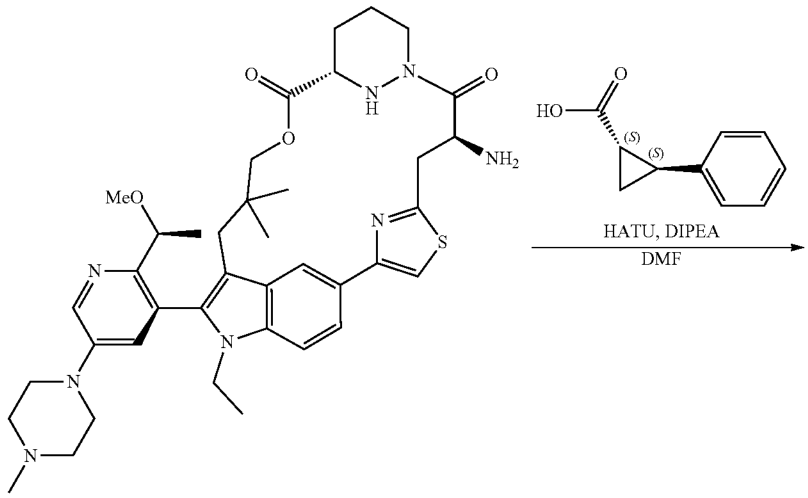

Intermediate 5

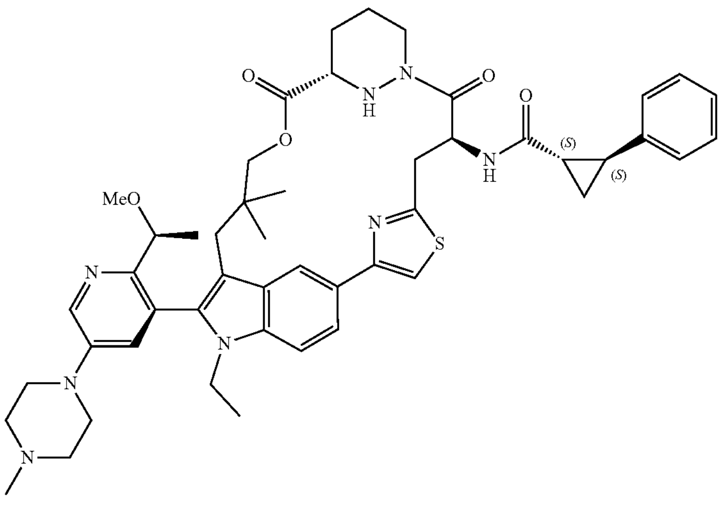

To a solution of tert-butyl (($6^3$S,4S,Z)-11-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate_(50.0 mg, 0.069 mmol), (1S,2S)-2-phenylcyclopropane-1-carboxylic acid (16.69 mg, 0.103 mmol), and DIPEA (44.32 mg, 0.343 mmol) in DMF (0.50 mL) at 0° C. was added HATU (78.24 mg, 0.206 mmol). The resulting mixture was warmed to room temperature and stirred for 3 h. The crude product was purified by prep-HPLC to give (1S,2S)—N-(($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-phenylcyclopropane-1-carboxamide (34 mg, 51% yield) as an off-white solid. LCMS (ESI): m/z [M+H] calc'd for $C_{49}H_{60}N_8O_5S$ 873.5. found 874.1.

Example A121. Synthesis of (1S,2S)—N-(($6^3$S,4S,Z)-$1^1$-ethyl-$1^2$-(2-((S)-1-methoxyethyl)-5-(4-(2-methoxyethyl)piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methylcyclopropane-1-carboxamide
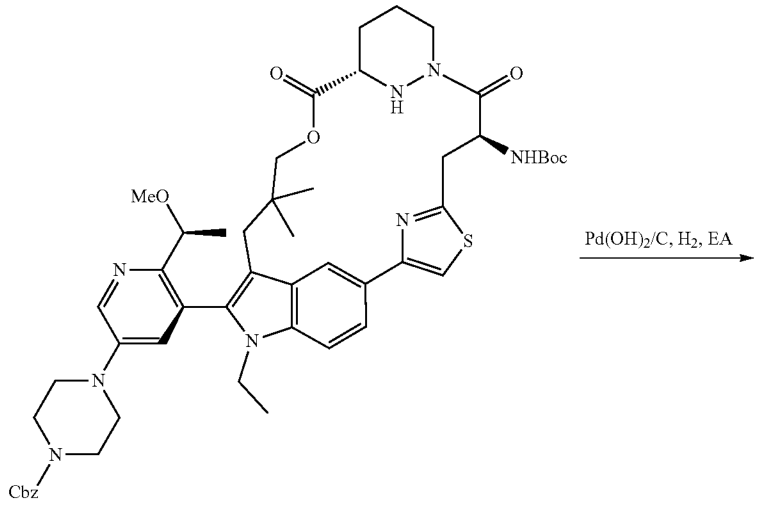
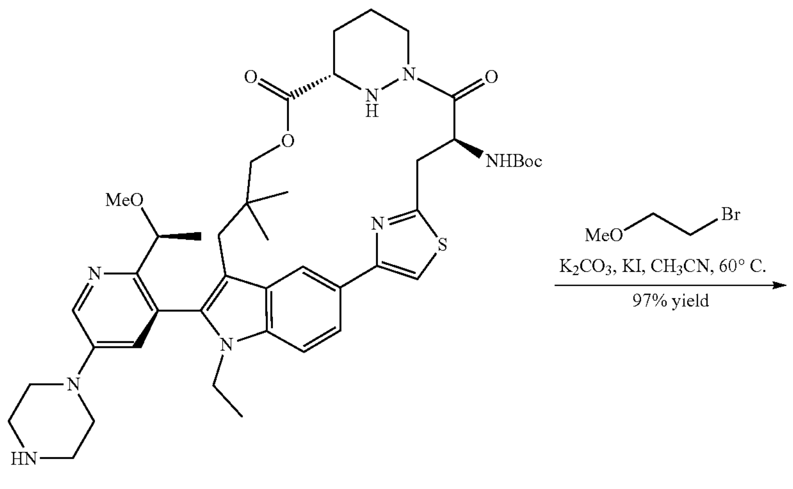

-continued
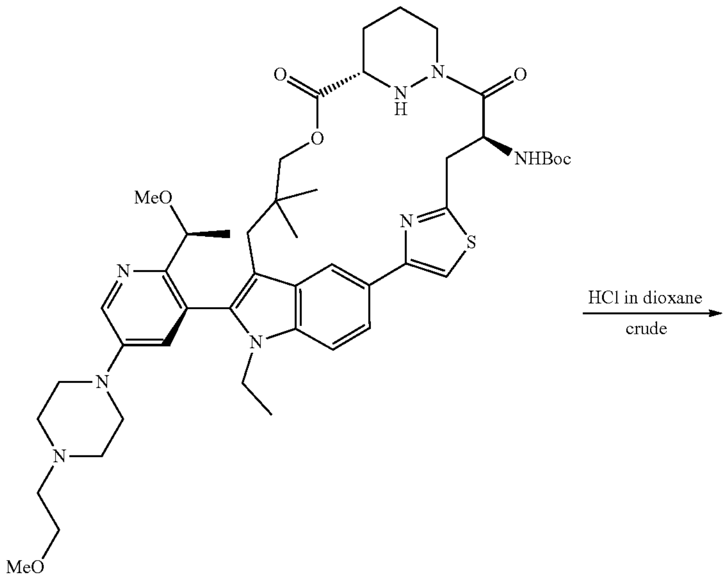
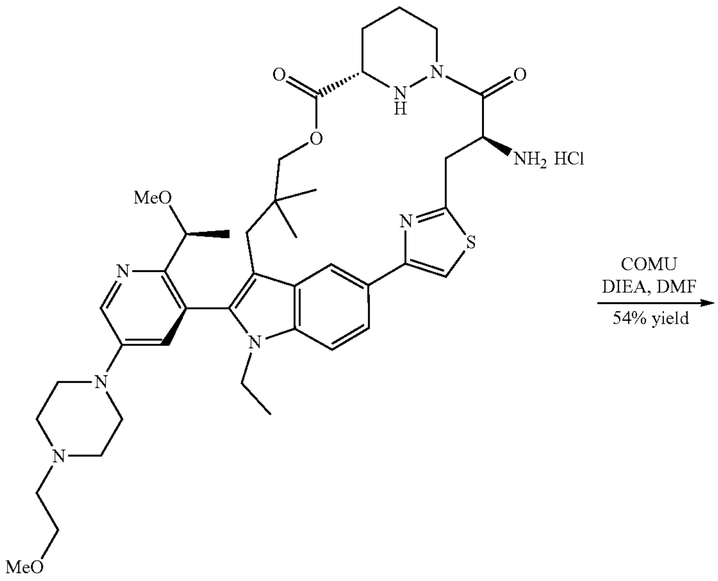

-continued

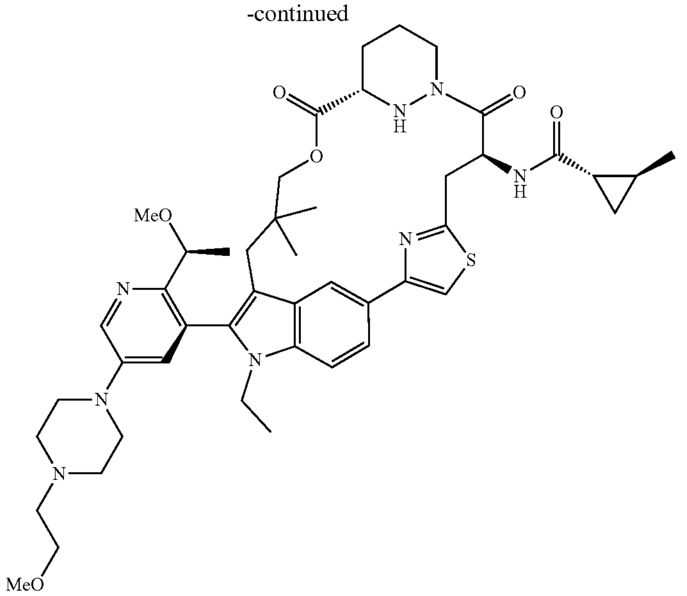

Step 1

A mixture of benzyl 4-(5-(($6^3$S,4S,Z)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-12-yl)-6-((S)-1-methoxyethyl)pyridin-3-yl)piperazine-1-carboxylate (380 mg, 0.4 mmol) in EtOAc (10 mL) was added $Pd(OH)_2$/C (600 mg, 20 mol %) was hydrogenated at rt overnight. The mixture was filtered through a pad of Celite® and the filtrate was concentrated under reduced pressure to give tert-butyl (($6^3$S,4S,Z)-$1^1$-ethyl-$1^2$-(2-((S)-1-methoxyethyl)-5-(piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)- pyridazinacycloundecaphane-4-yl)carbamate (310 mg, crude) as a solid, LCMS (ESI): m/z [M+H] calc'd for $C_{43}H_{58}N_8O_6S$ 814.4. found 815.5.

Step 2

To a mixture of tert-butyl (($6^3$S,4S,Z)-$1^1$-ethyl-$1^2$-(2-((S)-1-methoxyethyl)-5-(piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2 (4,2)-thiazola-1(5,3)-indola-6(1,3)-pyridazinacycloundecaphane-4-yl)carbamate (300 mg, 0.37 mmol) and 1-bromo-2-methoxyethane (56 mg, 0.41 mmol) in MeCN (10 mL) at rt was added KI (61 mg, 0.37 mmol) and $K_2CO_3$ (51 mg, 0.37 mmol) in portions. The mixture was heated to 60° C. and stirred for 2 h, then diluted with $H_2O$ (5 mL). The residue was purified by preparative-HPLC to give tert-butyl (($6^3$S,4S,Z)-$1^1$-ethyl-$1^2$-(2-((S)-1-methoxyethyl)-5-(4-(2-methoxyethyl)piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (310 mg, 97% yield) as a solid. LCMS (ESI): m/z [M+H] calc'd for $C_{46}H_{64}N_8O_7S$ 872.5. found 873.6.

Step 3

A mixture of tert-butyl (($6^3$S,4S,Z)-$1^1$-ethyl-$1^2$-(2-((S)-1-methoxyethyl)-5-(4-(2-methoxyethyl)piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (300 mg, 0.34 mmol) in 4 M HCl in 1,4-dioxane, (10 mL) was stirred at rt for 1 h, then concentrated under reduced pressure to give ($6^3$S,4S,Z)-4-amino-$1^1$-ethyl-12-(2-((S)-1-methoxyethyl)-5-(4-(2-methoxyethyl)piperazin-1-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione HCl salt (315 mg, crude) as a solid, which was used directly in the next step without further purification. LCMS (ESI): m/z [M+H] calc'd for $C_{41}H_{56}N_8O_5S$ 772.4. found 773.3.

Step 4

A mixture of ($6^3$S,4S,Z)-4-amino-$1^1$-ethyl-$1^2$-(2-((S)-1-methoxyethyl)-5-(4-(2-methoxyethyl)piperazin-1-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione HCl salt (300 mg, 0.39 mmol) and (1S,2S)-2-methylcyclopropane-1-carboxylic acid (97 mg, 0.97 mmol) in DMF (5 mL) at 0° C. was added DIPEA (1.00 g, 7.77 mmol) dropwise, then COMU (249 mg, 0.58 mmol) in portions. The mixture was allowed to warm to rt and stirred for 2 h, then concentrated under reduced pressure and the residue was purified by preparative-HPLC to give (1S,2S)—N-(($6^3$S,4S,Z)-$1^1$-ethyl-$1^2$-(2-((S)-1-methoxyethyl)-5-(4-(2-methoxyethyl)piperazin-1-yl) pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methylcyclopropane-1-carboxamide (178 mg, 54% yield) as a solid. LCMS (ESI): m/z [M+H] calc'd for $C_{46}H_{62}N_8O_6S$ 854.5. found 855.5; $^1$H NMR (400 MHz, DMSO-$d_6$) δ 8.55-8.46 (m, 2H), 7.80 (d, J=3.1 Hz, 1H), 7.77-7.70 (m, 1H), 7.57 (d, J=8.6 Hz, 1H), 7.40 (d, J=2.8 Hz, 1H), 5.55 (d, J=9.2 Hz, 1H), 4.37-4.09 (m, 6H), 4.00 (s, 2H), 3.83-3.71 (m, 2H), 3.57 (s, 3H), 3.38 (t, J=4.8 Hz, 2H), 3.32 (d, J=2.5 Hz, 4H), 3.22 (s, 7H), 3.20-3.11 (m, 1H), 2.94 (d, J=14.4 Hz, 1H), 2.76 (t, J=11.4 Hz, 1H), 2.44 (d, J=14.2 Hz, 1H), 2.07 (d, J=12.0 Hz, 1H), 1.80 (s, 2H), 1.60-1.47 (m, 2H), 1.34 (d, J=6.1 Hz, 3H), 1.07 (d, J=1.8 Hz, 4H), 0.95-0.82 (m, 7H), 0.55 (d, J=7.4 Hz, 1H), 0.35 (s, 3H).

Example A157. Synthesis of (1S,2S)—N-(($6^3$S,4S,Z)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$^1$H-8-oxa-2(4,2)-thiazola-1(5,3)-indola-6(1,3)-pyridazinacycloundecaphane-4-yl)-2-methylcyclopropane-1-carboxamide

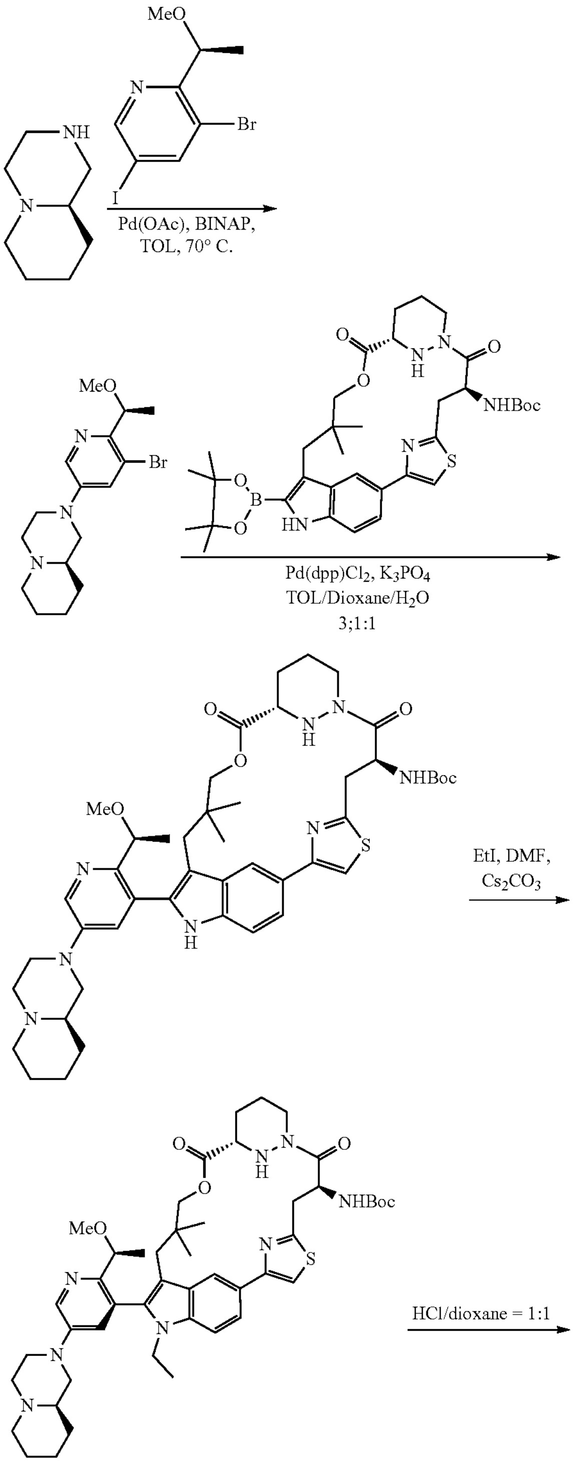

-continued

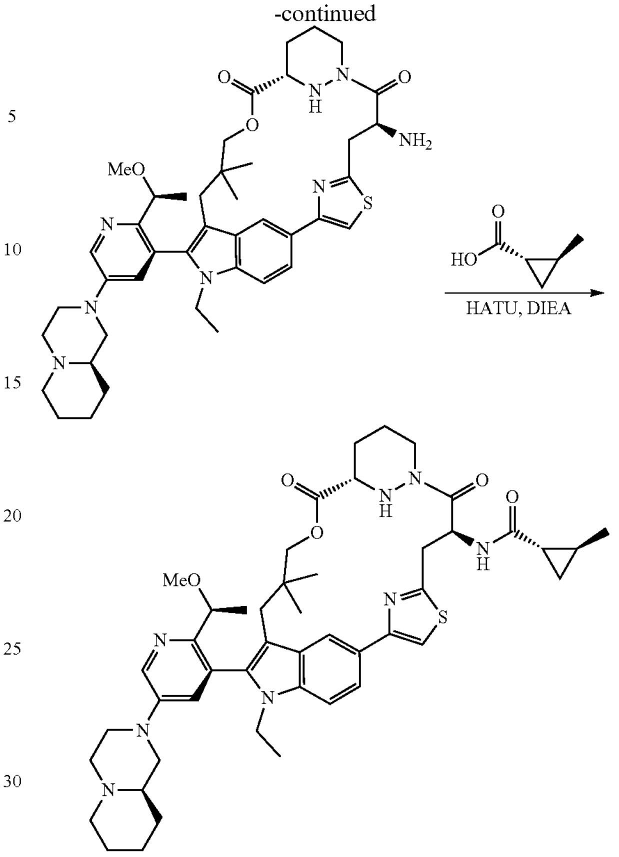

Step 1

5-[(9aR)-octahydropyrido[1,2-a]pyrazin-2-yl]-3-bromo-2-[(1S)-1-methoxyethyl]pyridine was synthesized in a manner similar to (S)-8-(5-bromo-6-((S)-1-methoxyethyl)pyridin-3-yl)octahydropyrazino[2,1-c][1,4]oxazine except (S)-octahydropyrazino[2,1-c][1,4]oxazine was substituted with (S)-octahydropyrazino[2,1-c][1,4]oxazine (1.5 g, 60% yield) as a solid. LCMS (ESI): m/z [M+H] calc'd for $C_{16}H_{24}BrN_3O$ 353.1. found 354.1.

Step 2

Tert-butyl (($6^3$S,4S,Z)-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate was synthesized in a manner similar to tert-butyl (($6^3$S,4S,Z)-$1^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)- pyridazinacycloundecaphane-4-yl)carbamate except (S)-8-(5-bromo-6-((S)-1-methoxyethyl)pyridin-3-yl)octahydropyrazino[2,1-c][1,4] oxazine was substituted with 5-[(9aR)-octahydropyrido[1,2-a]pyrazin-2-yl]-3-bromo-2-[(1S)-1-methoxyethyl]pyridine and $K_2CO_3$ was substituted with $K_3PO_4$ to give (800 mg, 83% yield) as an oil. LCMS (ESI): m/z [M+H] calc'd for $C_{45}H_{60}N_8O_6S$ 840.4. found 841.4.

Step 3

Tert-butyl (($6^3$S,4S,Z)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate was synthesized in a manner similar to tert-butyl ((6$^3$S,4S,Z)-1$^1$-ethyl-1$^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-oxa-2(4,2)-thiazola-1(5,3)-indola-6(1,3)-pyridazinacycloundecaphane-4-yl)carbamate except tert-butyl ((6$^3$S,4S,Z)-1$^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate was substituted with tert-butyl ((6$^3$S4S,Z)-12-(2-((S)-1-methoxyethyl)-5-((R)-octahydro-2H-pyrido[1,2-a]pyrazin-2-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate to give (220 mg, 27% yield) as a solid. LCMS (ESI): m/z [M+H] calc'd for $C_{47}H_{64}N_8O_8S$ 868.5. found 869.5.

Step 4

A mixture of tert-butyl ((6$^3$S,4S,Z)-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate (220 mg, 0.25 mmol) in 1,4-dioxane (2 mL) at 0° C. was added 4M HCl in 1,4-dioxane (1 mL). The mixture was stirred at 0° C. for 1 h then concentrated under reduced pressure to give (6$^3$S,4S,Z)-4-amino-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione (220 mg, crude) as a solid. LCMS (ESI): m/z [M+H] calc'd for $C_{42}H_{56}N_8O_4S$ 768.4. found 769.4.

Step 5

(1S,2S)—N-((6$^3$S,4S,Z)-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-2-methylcyclopropane-1-carboxamide was synthesized in a manner similar to (1S,2S)—N-((6$^3$S,4S,Z)-1$^1$-ethyl-1$^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-2-methylcyclopropane-1-carboxamide except (6$^3$S,4S,Z)-4-amino-1$^1$-ethyl-1$^2$-(5-((S)-hexahydropyrazino[2,1-c][1,4]oxazin-8(1H)-yl)-2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione HCl salt was substituted with (6$^3$S,4S,Z)-4-amino-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione to give (13 mg, 8% yield) as a solid. LCMS (ESI): m/z [M+H] calc'd for $C_{47}H_{62}N_8O_5S$ 850.5. found 851.6: $^1$H NMR (400 MHz, DMSO-$d_6$) δ 8.53-8.41 (m, 3H), 7.79 (s, 1H), 7.72-7.70 (m, 1H), 7.55-7.30 (m, 1H), 7.20-7.10 (m, 1H), 5.56-5.46 (m, 1H), 5.08-5.00 (m, 1H), 4.39-4.04 (m, 5H), 3.72-7.62 (m, 2H), 3.57-3.47 (m, 2H), 3.21-3.11 (m, 3H), 3.15-3.08 (m, 1H), 2.94 (m, 1H), 2.79-2.69 (m, 4H), 2.45-2.35 (m, 3H), 2.24-2.22 (m, 1H), 2.08-2.00 (m, 1H), 2.01-1.88 (m, 2H), 1.81-1.65 (m, 3H), 1.59 (d, J=12.1 Hz, 2H), 1.54-1.38 (m, 2H), 1.33-1.30 m, 3H), 1.28-1.12 (m, 3H), 1.06-0.86 (m, 4H), 0.96-0.79 (m, 6H), 0.55-0.50 (m, 1H), 0.34 (s, 3H).

Example A214. Synthesis of (1S,2S)—N-((6$^1$S,4S,Z)-1$^1$(2-cyanopropan-2-yl)-10,10-dimethyl-1$^1$-(2-(4-methylpiperazin-1-yl)pyridin-4-yl)-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-2-methylcyclopropane-1-carboxamide

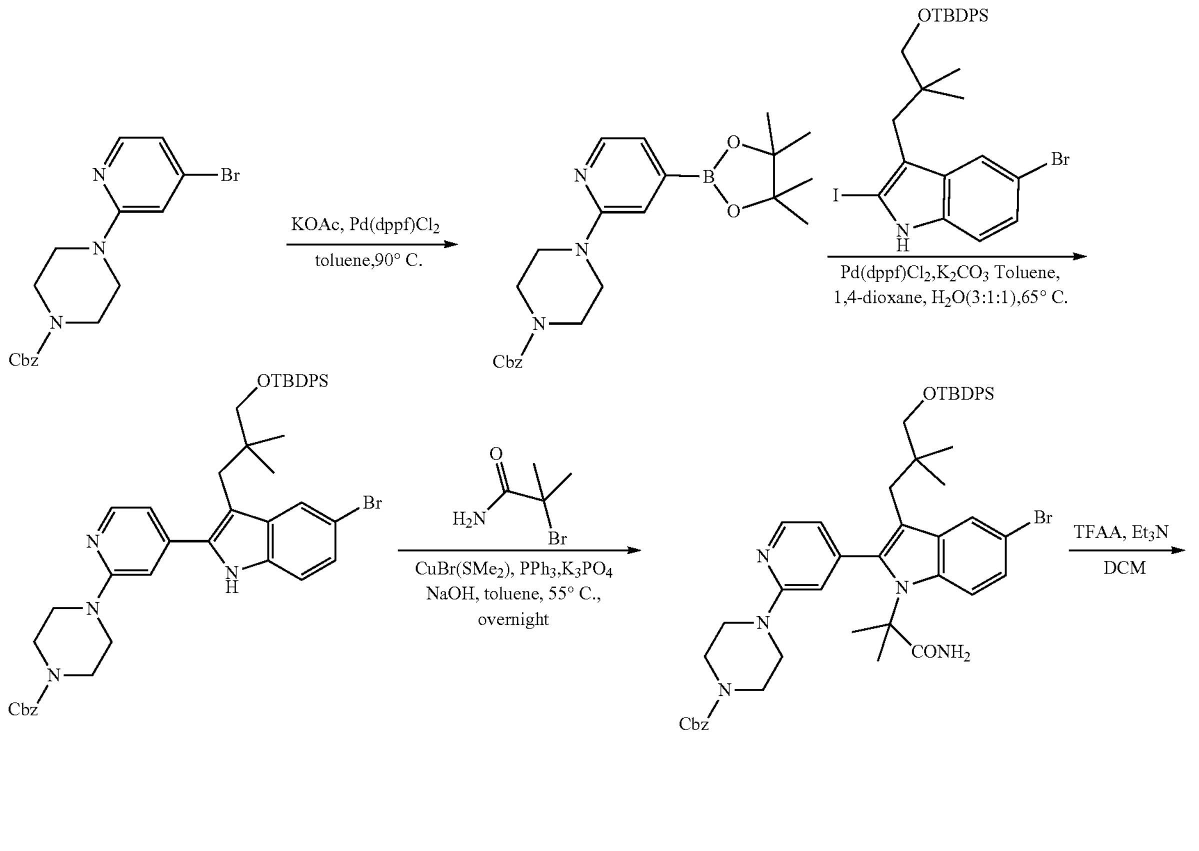

-continued
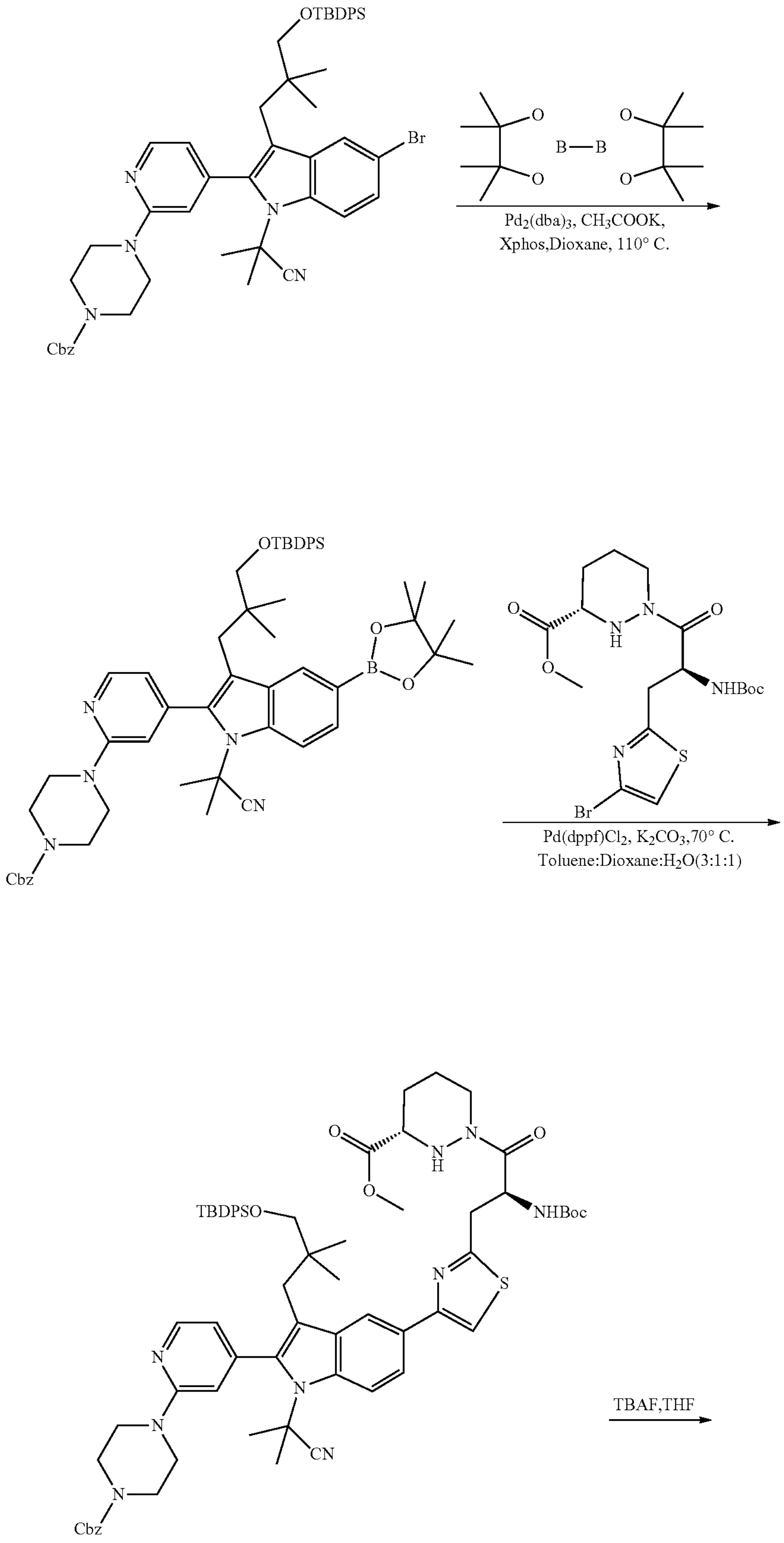

-continued
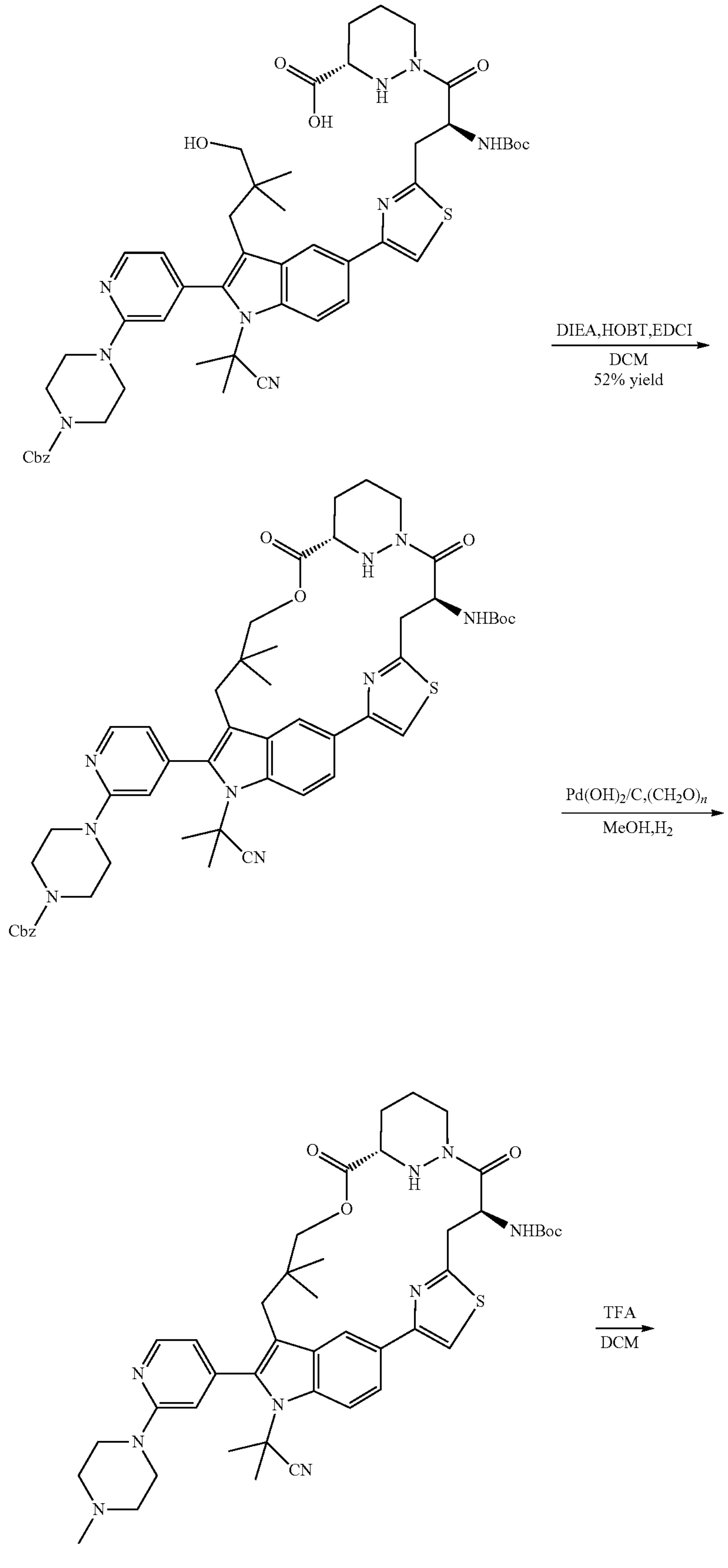

-continued

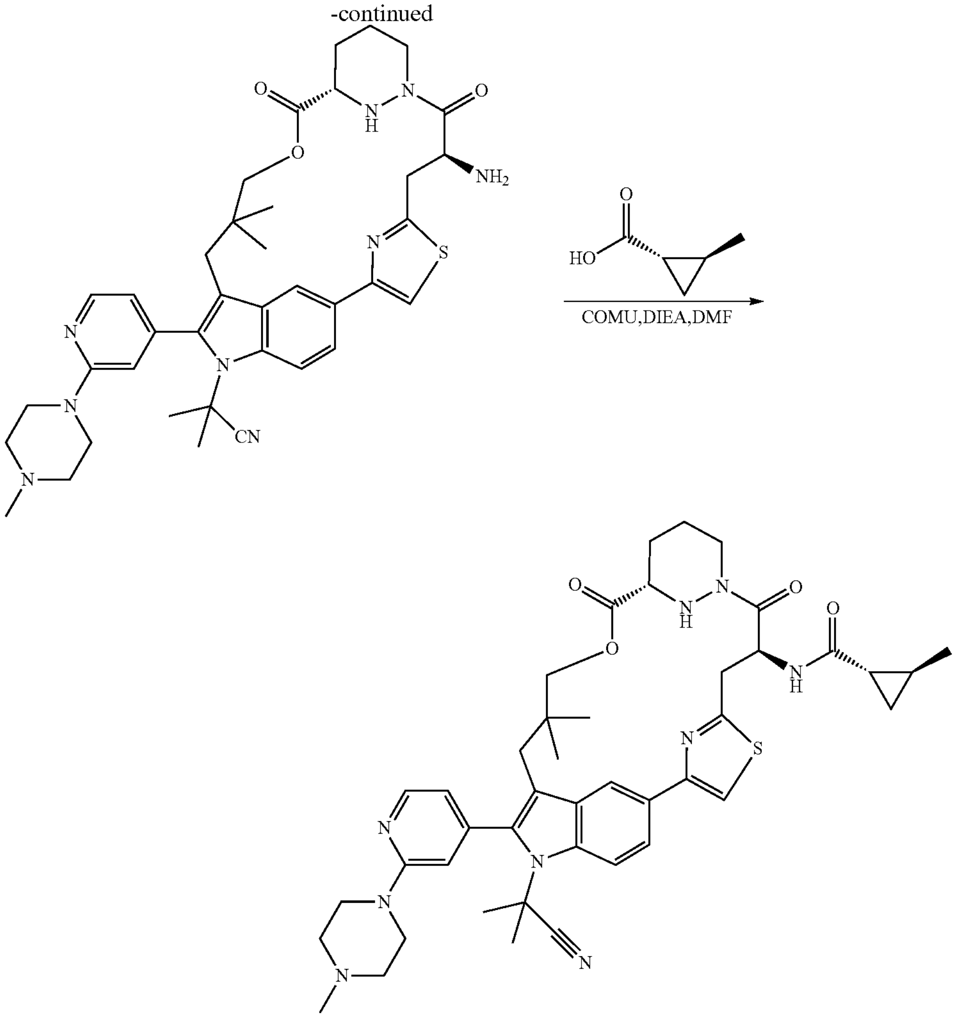

Step 1

A mixture of benzyl 4-(4-bromopyridin-2-yl)piperazine-1-carboxylate (8.09 g, 21.5 mmol), bis(pinacolato)diboron (8.19 g, 32.3 mmol), KOAc (6.33 g, 64.5 mmol), Pd(dppf)$Cl_2$ (0.79 g, 1.1 mmol) in toluene (100 mL) under an atmosphere of Ar was heated to 90° C. and stirred for 2 h. The mixture was concentrated under vacuum, $H_2O$ (50 mL) was added to the residue and the mixture was extracted with EtOAc (2×100 mL). The combined organic layers were washed with brine (2×100 mL), dried, filtered and the filtrate concentrated under reduced pressure to give benzyl 4-[4-(4,4,5,5-tetramethyl-1,3,2-dioxaborolan-2-yl)pyridin-2-yl]piperazine-1-carboxylate (9.2 g, 100% yield) as a solid. LCMS (ESI): m/z [M+H] calc'd for $C_{23}H_{30}BN_3O_4$ 423.2. found 424.2.

Step 2

A mixture of benzyl 4-[4-(4,4,5,5-tetramethyl-1,3,2-dioxaborolan-2-yl)pyridin-2-yl]piperazine-1-carboxylate (5.00 g, 11.8 mmol), 5-bromo-3-[3-[(tert-butyldiphenylsilyl)oxy]-2,2-dimethylpropyl]-2-iodo-1H-indole (7.64 g, 11.8 mmol), Pd(dppf)$Cl_2$ (0.86 g, 1.2 mmol), $K_2CO_3$ (6.27 g, 45.4 mmol) in toluene (45 mL), 1,4-dioxane (15 mL), $H_2O$ (15 mL) under an atmosphere of $N_2$ was heated to 70° C. and stirred for 2 h. $H_2O$ (50 mL) was added and the mixture was extracted with EtOAc (2×50 mL). The combined organic layers were dried over anhydrous $Na_2SO_4$ and filtered. The filtrate was concentrated under reduced pressure and the residue was purified by silica gel column chromatography to give benzyl 4-[4-(5-bromo-3-[3-[(tert-butyldiphenylsilyl)oxy]-2,2-dimethylpropyl]-1H-indol-2-yl)pyridin-2-yl]piperazine-1-carboxylate (4.9 g, 51% yield) as solid. LCMS (ESI): m/z [M+H] calc'd for $C_{46}H_{51}BrN_4O_3Si$ 814.3. found 815.4.

Step 3

A mixture of benzyl 4-[4-(5-bromo-3-[3-[(tert-butyldiphenylsilyl)oxy]-2,2-dimethylpropyl]-1H-indol-2-yl)pyridin-2-yl]piperazine-1-carboxylate (4.5 g, 5.5 mmol), 2-bromo-2-methylpropanamide (2.75 g, 16.6 mmol), $K_3PO_4$ (2.34 g, 11.0 mmol), NaOH (0.57 g, 14.3 mmol), $Ph_3P$ (0.29 g, 1.1 mmol), copper bromide-dimethyl sulfide (0.23 g, 1.1 mmol) in toluene (50 mL) under an atmosphere of $N_2$ was heated to 45° C. and stirred for 2 days. $H_2O$ (50 mL) was added and the mixture was extracted with EtOAc (2×50 mL). The combined organic layers were washed with brine (2×50 mL), dried over $Na_2SO_4$ and filtered. The filtrate was concentrated under reduced pressure and the residue was purified by silica gel column chromatography to give benzyl 4-[4-(5-bromo-3-[3-[(tert-butyldiphenylsilyl)oxy]-2,2-dimethylpropyl]-1-(1-carbamoyl-1-methylethyl)indol-2-yl)pyridin-2-yl]piperazine-1-carboxylate (1.5 g, 30% yield) as a solid. LCMS (ESI): m/z [M+H] calc'd for $C_{50}H_{58}BrN_5O_4Si$ 899.3. found 900.4.

Step 4

A mixture of benzyl 4-[4-(5-bromo-3-[3-[(tert-butyldiphenylsilyl)oxy]-2,2-dimethylpropyl]-1-(1-carbamoyl-1-methylethyl)indol-2-yl)pyridin-2-yl]piperazine-1-carboxylate (1.40 g, 1.6 mmol), $Et_3N$ (0.47 g, 4.7 mmol) and TFAA (0.65 g, 3.1 mmol) in DCM (20 mL), 3 equiv) was stirred at rt for 2 h. $H_2O$ (20 mL) was added and the mixture was extracted with DCM (2×20 mL). The combined organic layers were washed with brine (2×50 mL), dried over $Na_2SO_4$ and filtered. The filtrate was concentrated under reduced pressure to give benzyl 4-[4-(5-bromo-3-[3-[(tert-butyldiphenylsilyl)oxy]-2,2-dimethylpropyl]-1-(1-cyano-1-methylethyl)indol-2-yl)pyridin-2-yl]piperazine-1-carboxylate (1.3 g, 95% yield) as a solid. LCMS (ESI): m/z [M+H] calc'd for $C_{50}H_{58}BrN_5O_3Si$ 881.3. found 882.4.

Step 5

A mixture of benzyl 4-[4-(5-bromo-3-[3-[(tert-butyldiphenylsilyl)oxy]-2,2-dimethylpropyl]-1-(1-cyano-1-methylethyl)indol-2-yl)pyridin-2-yl]piperazine-1-carboxylate (1.50 g, 1.7 mmol), bis(pinacolato)diboron (5.21 g, 20.5 mmol), $Pd_2(dba)_3$ (0.38 g, 0.4 mmol), KOAc (1.21 g, 12.3 mmol), X-Phos (0.20 g, 0.4 mmol) in 1,4-dioxane (25 mL) under an atmosphere of $N_2$ was heated to 110° C. and stirred for 2 h. $H_2O$ (25 ml) was added and the mixture was extracted with EtOAc (2×25 mL). The combined organic layers were washed with brine (2×25 mL), dried over $Na_2SO_4$ and filtered. The filtrate was concentrated under reduced pressure and the residue was purified by silica gel column chromatography to give benzyl 4-[4-(3-[3-[(tert-butyldiphenylsilyl)oxy]-2,2-dimethylpropyl]-1-(1-cyano-1-methylethyl)-5-(4,4,5,5-tetramethyl-1,3,2-dioxaborolan-2-yl)indol-2-yl)pyridin-2-yl]piperazine-1-carboxylate (1.6 g, 94% yield) as an oil. LCMS (ESI): m/z [M+H] calc'd for $C_{56}H_{68}BN_5O_5Si$ 929.5. found 930.4.

Step 6

A mixture of benzyl 4-[4-(3-[3-[(tert-butyldiphenylsilyl)oxy]-2,2-dimethylpropyl]-1-(1-cyano-1-methylethyl)-5-(4,4,5,5-tetramethyl-1,3,2-dioxaborolan-2-yl)indol-2-yl)pyridin-2-yl]piperazine-1-carboxylate (1.60 g, 1.7 mmol), methyl (3S)-1-[(2S)-3-(4-bromo-1,3-thiazol-2-yl)-2-[(tert-butoxycarbonyl)amino]propanoyl]-1,2-diazinane-3-carboxylate (0.82 g, 1.7 mmol), $K_2CO_3$ (0.79 g, 5.8 mmol), $Pd(dppf)Cl_2$ (0.13 g, 0.17 mmol) in toluene (12 mL), 1,4-dioxane (4 mL) and $H_2O$ (4 mL) under an atmosphere of $N_2$ was heated to 70° C. and stirred for 5 h. $H_2O$ (30 mL) was added and the mixture was extracted with EtOAc (2×30 mL). The combined organic layers were washed with brine (2×30 mL), dried over $Na_2SO_4$ and filtered. The filtrate was concentrated under reduced pressure and the residue was purified by silica gel column chromatography to give benzyl 4-[4-(5-[2-[(2S)-2-[(tert-butoxycarbonyl)amino]-3-[(3S)-3-(methoxycarbonyl)-1,2-diazinan-1-yl]-3-oxopropyl]-1,3-thiazol-4-yl]-3-[3-[(tert-butyldiphenylsilyl)oxy]-2,2-dimethylpropyl]-1-(1-cyano-1-methylethyl)indol-2-yl)pyridin-2-yl]piperazine-1-carboxylate (650 mg, 31% yield) as an oil. LCMS (ESI): m/z [M+H] calc'd for $C_{67}H_{81}N_9O_6SSi$ 1199.6. found 1200.5.

Step 7

To a mixture of benzyl 4-[4-(5-[2-[(2S)-2-[(tert-butoxycarbonyl)amino]-3-[(3S)-3-(methoxycarbonyl)-1,2-diazinan-1-yl]-3-oxopropyl]-1,3-thiazol-4-yl]-3-[3-[(tert-butyldiphenylsilyl)oxy]-2,2-dimethylpropyl]-1-(1-cyano-1-methylethyl)indol-2-yl)pyridin-2-yl]piperazine-1-carboxylate (650 mg, 0.54 mmol) in THF (15 mL) under an atmosphere of $N_2$ was added TBAF (1.42 g, 5.4 mmol). The mixture was stirred at rt overnight then the mixture adjusted to pH~6 with 1M HCl and extracted with EtOAc (2×50 mL). The combined organic layers were washed with brine (2×50 mL), dried over $Na_2SO_4$ and filtered. The filtrate was concentrated under reduced pressure and the residue was purified by silica gel column chromatography to give (3S)-1-[(2S)-3-[4-[2-(2-[4-[(benzyloxy)carbonyl]piperazin-1-yl]pyridin-4-yl)-1-(1-cyano-1-methylethyl)-3-(3-hydroxy-2,2-dimethylpropyl)indol-5-yl]-1,3-thiazol-2-yl]-2-[(tert-butoxycarbonyl)amino]propanoyl]-1,2-diazinane-3-carboxylic acid (370 mg, 72% yield) as a solid. LCMS (ESI): m/z [M+H] calc'd for $C_{50}H_{61}N_9O_8S$ 947.4. found 948.5.

Step 8

A mixture of (3S)-1-[(2S)-3-[4-[2-(2-[4-[(benzyloxy)carbonyl]piperazin-1-yl]pyridin-4-yl)-1-(1-cyano-1-methylethyl)-3-(3-hydroxy-2,2-dimethylpropyl)indol-5-yl]-1,3-thiazol-2-yl]-2-[(tert-butoxycarbonyl)amino]propanoyl]-1,2-diazinane-3-carboxylic acid (370 mg, 0.39 mmol), DIPEA (1.51 g, 11.7 mmol), HOBT (264 mg, 1.95 mmol), EDCI (2.09 g, 10.9 mmol) in DCM (370 mL) was stirred at it overnight. $H_2O$ (100 mL) was added and the mixture was extracted with EtOAc (2×100 mL). The combined organic layers were washed with brine (2×100 mL), dried over $Na_2SO_4$, filtered and the filtrate concentrated under reduced pressure to give benzyl 4-(4-(($6^3$S,4S,Z)-4-((tert-butoxycarbonyl)amino)-$1^1$-(2-cyanopropan-2-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-12-yl)pyridin-2-yl)piperazine-1-carboxylate (187 mg, 52% yield) as a solid. LCMS (ESI): m/z [M+H] calc'd for $C_{50}H_{59}N_9O_7S$ 929.4. found 930.8.

Step 9

A mixture of benzyl 4-(4-(($6^3$S,4S,Z)-4-((tert-butoxycarbonyl)amino)-$1^1$-(2-cyanopropan-2-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)- pyridazinacycloundecaphane-12-yl)pyridin-2-yl)piperazine-1-carboxylate (170 mg, 0.18 mmol), paraformaldehyde (165 mg, 1.8 mmol), $Pd(OH)_2/C$ (170 mg, 1.2 mmol) in MeOH (25 mL) was stirred under an atmosphere of $H_2$ overnight. The mixture was filtered and the filtrate was concentrated under reduced pressure to give tert-butyl (($6^3$S,4S,Z)-$1^1$-(2-cyanopropan-2-yl)-10,10-dimethyl-$1^2$-(2-(4-methylpiperazin-1-yl)pyridin-4-yl)-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (110 mg, 74% yield) as a solid. LCMS (ESI): m/z [M+H] calc'd for $C_{43}H_{55}N_9O_5S$ 809.4. found 810.9, Step 10

A mixture of tert-butyl (($6^3$S,4S,Z)-$1^1$-(2-cyanopropan-2-yl)-10,10-dimethyl-$1^2$-(2-(4-methylpiperazin-1-yl)pyridin-4-yl)-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (110 mg, 0.14 mmol) and TFA (5.0 mL, 67.3 mmol) in DCM (5 mL) was stirred at rt for 1 h, then concentrated under reduced pressure to give 2-(($6^3$S,4S,Z)-4-amino-10,10-dimethyl-$1^2$-(2-(4-methylpiperazin-1-yl)pyridin-4-yl)-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^1$-yl)-2-methylpropanenitrile (96 mg, 100% yield) as an oil. LCMS (ESI): m/z [M+H] calc'd for $C_{38}H_{47}N_9O_3S$ 709.4. found 710.5.

Step 11

A mixture of 2-(($6^3$S,4S,Z)-4-amino-10,10-dimethyl-$1^2$-(2-(4-methylpiperazin-1-yl)pyridin-4-yl)-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^1$-yl)-2-methylpropanenitrile (110 mg, 0.16 mmol), (1S,2S)-2-methylcyclopropane-1-carboxylic acid (47 mg, 0.47 mmol), COMU (66 mg, 0.16 mmol), DIPEA (1.00 g, 7.75 mmol) in DMF (5 mL) was stirred at rt for 2 h. $H_2O$ (10 mL) was added and the mixture was extracted with EtOAc (2×10 mL). The combined organic layers were washed with brine (2×10 mL), dried over $Na_2SO_4$ and filtered. The filtrate was concentrated under reduced pressure and the residue was purified by preparative-HPLC to give (1S,2S)—N-(($6^3$S,4S,Z)-$1^1$-(2-cyanopropan-2-yl)-10,10-dimethyl-$1^2$-(2-(4-methylpiperazin-1-yl)pyridin-4-yl)-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methylcyclopropane-1-carboxamide (21 mg, 17% yield) as a solid. LCMS (ESI): m/z [M+H] calc'd for $C_{43}H_{53}N_9OAS$ 791.4. found 792.4; $^1$H-NMR (400 MHz, DMSO-$d_6$) δ 8.51 (d, J=7.1 Hz, 2H), 8.21 (d, J=5.0 Hz, 1H), 8.16 (d, J=5.0 Hz, 1H), 7.89 (d, J=1.8 Hz, 1H), 7.83 (d, J=1.5 Hz, 2H), 7.06 (s, 1H), 6.96 (s, 1H), 6.74-6.68 (m, 1H), 5.54 (q, J=8.6 Hz, 1H), 5.04 (d, J=12.2 Hz, 1H), 4.20 (q, J=12.4 Hz, 2H), 3.66 (dd, J=16.0, 10.9 Hz, 1H), 3.55 (s, 5H), 3.50 (d, J=10.9 Hz, 1H), 3.35 (s, 1H), 3.15 (dd, J=14.8, 9.2 Hz, 1H), 2.93 (dd, J=14.4, 6.3 Hz, 1H), 2.77 (s, 1H), 2.38 (dd, J=10.9, 5.5 Hz, 4H), 2.20 (d, J=5.3 Hz, 3H), 2.09 (s, 1H), 2.06 (s, 1H), 2.09-1.99 (m, 3H), 1.82-1.51 (d, J=4.0 Hz, 4H), 1.07 (s, 4H), 0.90-0.86 (d, J=3.0 Hz, 4H), 0.55 (d, J=6.8 Hz, 1H), 0.47-0.38 (m, 3H).

Examples A221 and A222. Synthesis of (1S,2S)-2-(difluoromethyl)-N-(($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl) cyclopropane-1-carboxamide and (1R,2R)-2-(difluoromethyl)-N-(($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl) cyclopropane-1-carboxamide

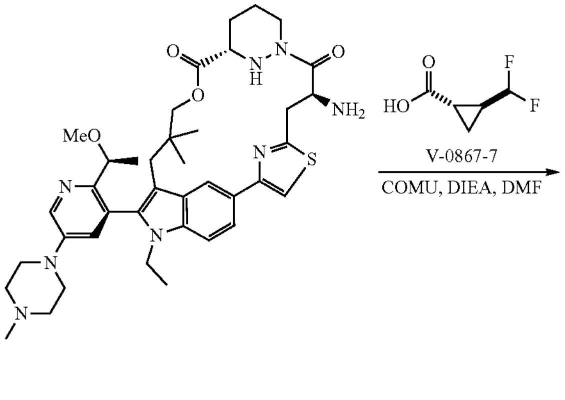

-continued

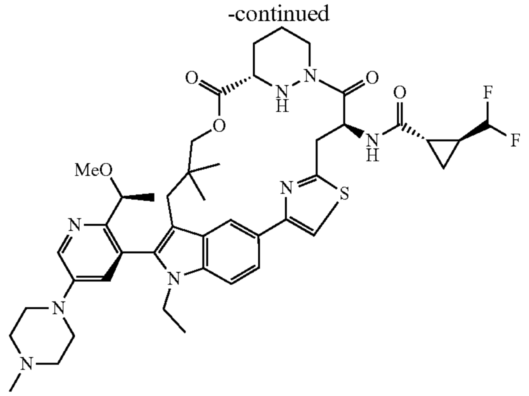

+

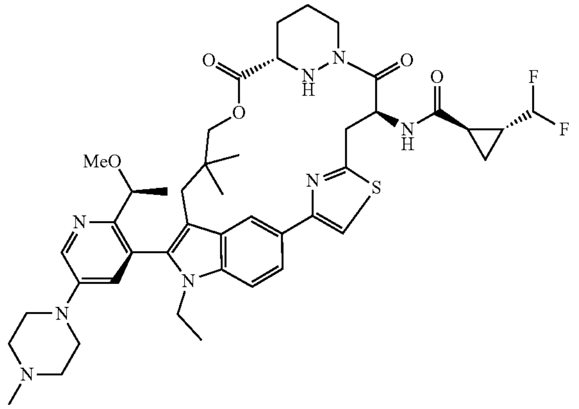

Step 1

To a mixture of ($6^3$S,4S,Z)-4-amino-$1^1$-ethyl-$1^2$-(2-((S)-1-methoxyethyl)-5-(4-methylpiperazin-1-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1 (5,3)-indola-6(1,3)-pyridazinacycloundecaphane-5,7-dione (200 mg, 0.27 mmol) and trans-2-(difluoromethyl)cyclopropane-1-carboxylic acid (56 mg, 0.41 mmol) in DMF (8 mL) at 00° C. was added DIPEA (177 mg, 1.37 mmol) dropwise, followed by COMU (235 mg, 0.55 mmol). The mixture was allowed to warm to rt and stirred for 1 h, then diluted with EtOAc (10 mL) and $H_2O$ (50 mL). The aqueous and organic layers were separated and the aqueous layer was extracted with EtOAc (3×10 mL). The combined organic layers were washed with brine (2×10 mL), dried over anhydrous $Na_2SO_4$ and filtered. The filtrate was concentrated under reduced pressure and the residue was purified by preparative-HPLC to give (1S,2S)-2-(difluoromethyl)-N-(($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)cyclopropane-1-carboxamide (32 mg, 27% yield) and (1R,2R)-2-(difluoromethyl)-N-(($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-1H-8-oxa-2(4,2)-thiazola-1(5,3)-indola-6(1,3)-pyridazinacycloundecaphane- 4-yl)cyclopropane-1-carboxamide (31 mg, 27% yield) both as solids. LCMS (ESI): m/z [M+H] calc'd for $C_{44}H_{56}F_2N_8O_5S$ 846.4. found 847.3; $^1$H NMR (400 MHz, DMSO-$d_6$) δ 8.80 (s, 1H), 8.46 (dd, J=13.4, 2.2 Hz, 2H), 7.83 (s, 2H), 7.73 (dd, J=8.7, 1.6 Hz, 1H), 7.56 (d, J=8.6 Hz, 1H), 7.23 (d, J=2.8 Hz, 1H), 5.95 (d, J=5.3 Hz, 1H), 5.57 (t, J=9.1 Hz, 1H), 5.12 (d, J=12.2 Hz, 1H), 4.14 (d, J=6.4 Hz, 5H), 3.57 (s, 2H), 3.21 (s, 4H), 2.93

(d, J=14.3 Hz, 2H), 2.78-2.68 (m, 1H), 2.67 (p, J=1.9 Hz, 3H), 2.46-2.28 (m, 3H), 2.25 (s, 2H), 2.17-1.92 (m, 2H), 1.79 (s, 2H), 1.66 (dt, J=9.7, 5.0 Hz, 1H), 1.51 (t, J=9.0 Hz, 1H), 1.33 (d, J=6.1 Hz, 4H), 1.24 (d, J=5.6 Hz, 2H), 0.96 (s, 1H), 0.95-0.72 (m, 6H), 0.35 (s, 3H) and LCMS (ESI): m/z [M+H] calc'd for $C_{44}H_{56}F_2N_8O_5S$ 846.4. found 847.3; $^1H$ NMR (400 MHz, DMSO-$d_6$) δ 8.87 (d, J=9.0 Hz, 1H), 8.46 (dd, J=11.3, 2.2 Hz, 2H), 7.80 (s, 2H), 7.73 (dd, J=8.7, 1.6 Hz, 1H), 7.56 (d, J=8.7 Hz, 1H), 7.23 (d, J=2.9 Hz, 1H), 6.09 (d, J=5.1 Hz, 1H), 5.94 (d, J=5.1 Hz, 1H), 5.80 (d, J=5.2 Hz, 1H), 5.59 (t, J=9.1 Hz, 1H), 5.13 (d, J=12.2 Hz, 1H), 4.50-4.06 (m, 5H), 3.57 (s, 2H), 3.21 (s, 4H), 2.93 (d, J=14.1 Hz, 2H), 2.67 (p, J=1.9 Hz, 4H), 2.39-2.15 (m, 4H), 2.17-1.82 (m, 2H), 1.77 (d, J=16.1 Hz, 2H), 1.44 (d, J=43.3 Hz, 1H), 1.35-1.24 (m, 4H), 1.15-0.91 (m, 2H), 0.91 (s, 6H), 0.34 (s, 3H).

Example A173. Synthesis of (2S)—N-(($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$^1$H-8-oxa-2(4,2)-thiazola-1(5,3)-indola-6(1,3)-pyridazinacycloundecaphane-4-yl)-2,4-dimethylpiperazine-1-carboxamide

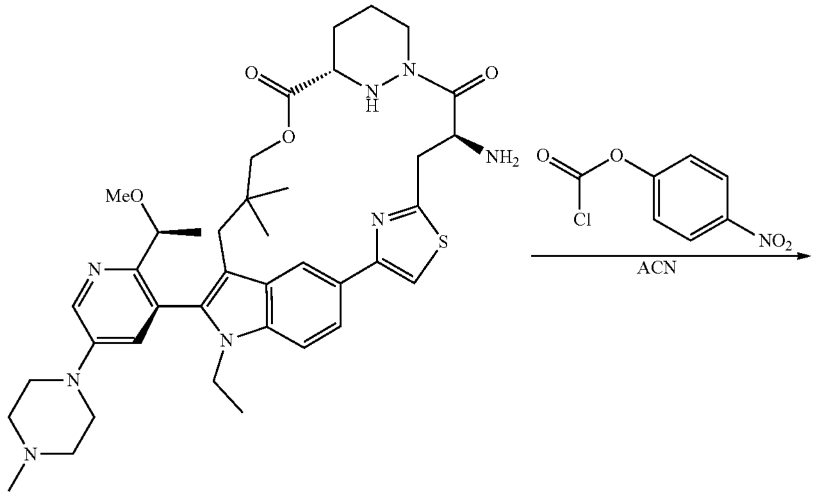

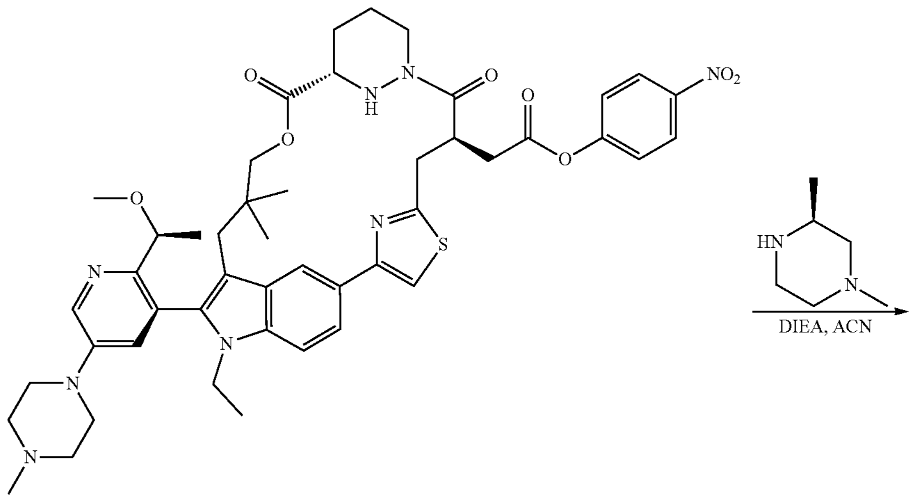

-continued

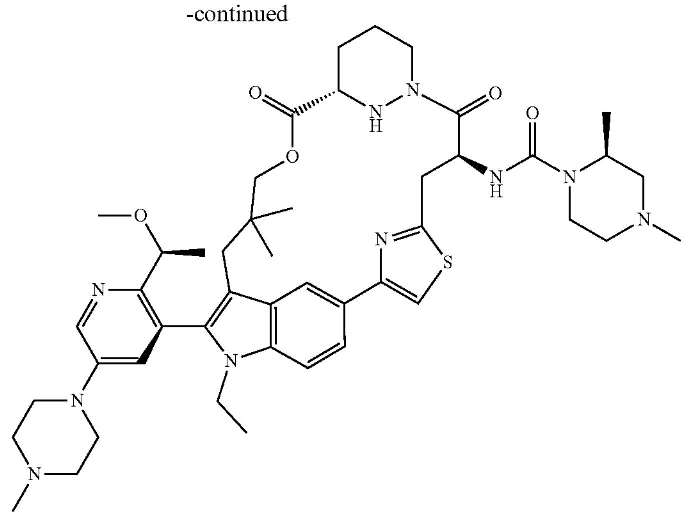

Step 1

To a mixture of (6³S,4S,Z)-4-amino-1¹-ethyl-1²-(2-((S)-1-methoxyethyl)-5-(4-methylpiperazin-1-yl)pyridin-3-yl)-10,10-dimethyl-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione (80 mg, 0.11 mmol) in DCM (6 mL) at 0° C. was added pyridine (2 mL), then 4-nitrophenyl carbonochloridate (55 mg, 0.28 mmol) in portions. The mixture was allowed to warm to rt and stirred for 1 h at room temperature, then washed with 1M $NaHSO_4$ (10 mL) and $H_2O$ (10 mL). The organic layer was concentrated under reduced pressure. to give 4-nitrophenyl ((6³S,4S,Z)-1¹-ethyl-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)carbamate (98 mg, crude) as a solid. LCMS (ESI): m/z [M+H] calc'd for $C_{46}H_{55}N_9O_8S$ 893.4. found 894.2.

Step 2

To a mixture of 4-nitrophenyl ((6³S,4S,Z)-1¹-ethyl-1²-(2-((S)-1-methoxyethyl)-5-(4-methylpiperazin-1-yl)pyridin-3-yl)-10,10-di-oxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)carbamate (98 mg, 0.11 mmol) and (S)-1,3-dimethylpiperazine (63 mg, 0.55 mmol) in ACN (5 mL) at 0° C. was added DIPEA (43 mg, 0.33 mmol) in ACN (2 mL. The crude product was purified by preparative-HPLC to give (2S)—N-((6³S,4S,Z)-1¹-ethyl-12-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-2,4-dimethylpiperazine-1-carboxamide (13 mg, 13% yield) as a solid. LCMS (ESI): m/z [M+H] calc'd for $C_{46}H_{64}N_{10}O_5S$ 868.5. found 869.3; ¹H NMR (400 MHz, DMSO-$d_6$) δ 8.47 (s, 2H), 7.80 (s, 1H), 7.73 (s, 1H), 7.55 (s, 1H), 7.23 (s, 1H), 6.81-6.70 (m, 1H), 5.33-5.25 (m, 1H), 4.99 (s, 1H), 4.40-3.97 (m, 6H), 3.72 (s, 1H), 3.61-3.47 (m, 3H), 3.31-3.22 (m, 8H), 3.02-2.72 (m, 5H), 2.66 (s, 1H), 2.60-2.51 (m, 3H), 2.49-2.37 (m, 2H), 2.35-2.13 (m, 6H), 2.12-1.97 (m, 2H), 1.95-1.66 (m, 3H), 1.55 (s, 1H), 1.33 (s, 3H), 1.27-1.19 (m, 4H), 0.99-0.82 (m, 6H), 0.33 (s, 3H).

Example A225. Synthesis of (1S,2S)—N-((6³S,3S,4S,Z)-3-ethoxy-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-2-methylcyclopropane-1-carboxamide

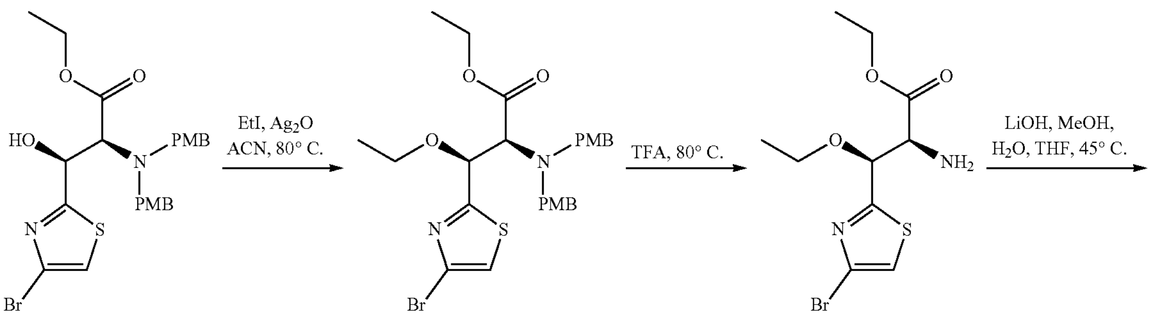

-continued
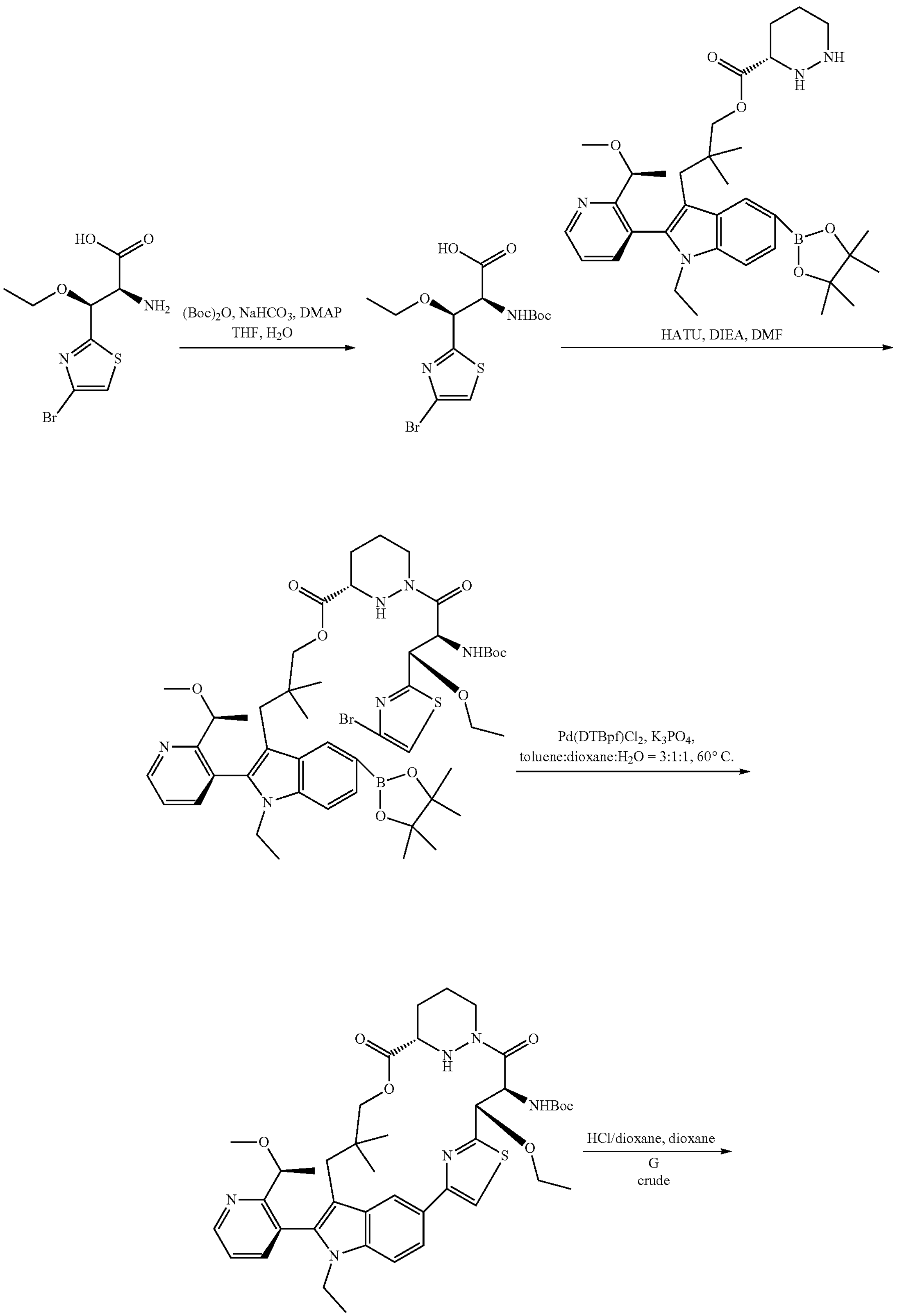

-continued

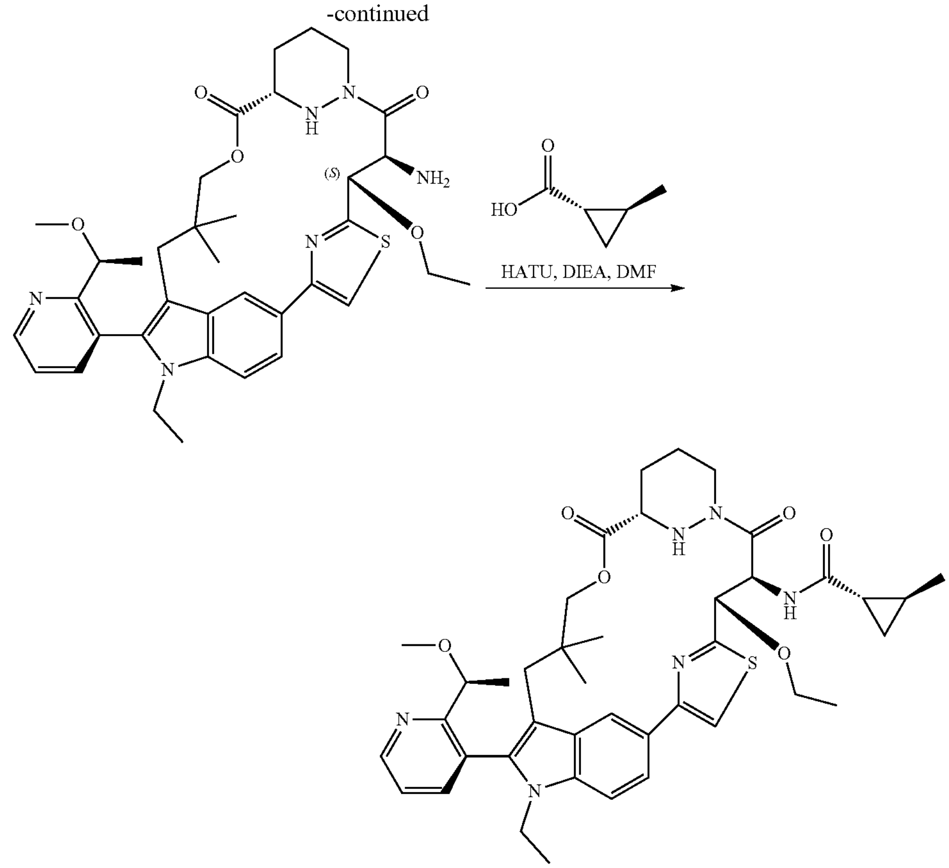

Step 1

To a mixture of ethyl (2S,3S)-2-[bis[(4-methoxyphenyl) methyl]amino]-3-(4-bromo-1,3-thiazol-2-yl)-3-hydroxypropanoate (1.00 g, 1.9 mmol) and $Ag_2O$ (433 g, 18.7 mmol) in ACN (10 mL at 0° C. under an atmosphere of $N_2$ was added ethyl iodide (2.91 g, 18.7 mmol) dropwise. The mixture was heated to 80° C. and stirred for 4 h, then filtered and the filter cake was washed with ACN (3x5 mL). The filtrate was concentrated under reduced pressure and the residue was purified by silica gel column chromatography to give ethyl (2S,3S-2-[bis[(4-methoxyphenyl)methyl]amino]-3-(4-bromo-1,3-thiazol-2-yl)-3-ethoxypropanoate (557 mg, 53% yield) as an oil. LCMS (ESI): m/z [M+H] calc'd for $C_{26}H_{31}BrN_2O_5S$ 562.1. found 563.2.

Step 2

Into a 40 mL sealed tube were added ethyl (2S,3S)-2-[bis[(4-methoxyphenyl)methyl]amino]-3-(4-bromo-1,3-thiazol-2-yl)-3-ethoxypropanoate (530 mg) and TFA (10 mL) Linder an atmosphere of $N_2$. The mixture was heated to 860° C. and stirred overnight, then concentrated under reduced pressure to give ethyl (2S,3S)-2-amino-3-(4-bromo-1,3-thiazol-2-yl)-3-ethoxypropanoate that was used directly in the next step without further purification. LCMS (ESI): m/z [M+H] calc'd for $C_{10}H_{15}BrN_2O_3S$ 322.0. found 323.0.

Step 3

A mixture of ethyl (2S,3S)-2-amino-3-(4-bromo-1,3-thiazol-2-yl)-3-ethoxypropanoate (890 mg, 2.8 mmol), $LiOH{\cdot}H_2O$ (1.16 g, 27.6 mmol), MeOH (6 mL), THF (2 mL) and $H_2O$ (2 ml) was stirred at 45° C. for 2 h. The mixture was concentrated under reduced pressure to give (2S,3S)-2-amino-3-(4-bromo-1,3-thiazol-2-yl)-3-ethoxypropanoic acid (that was used directly in the next step without further purification. LCMS (ESI): m/z [M+H] calc'd for $C_8H_{11}BrN_2O_3S$ 294.0. found 294.9.

Step 4

To a mixture of (2S,3S)-2-amino-3-(4-bromo-1,3-thiazol-2-yl)-3-ethoxypropanoic acid (890 mg, 3.0 mmol), $NaHCO_3$ (507 mg, 6.0 mmol) and DMAP (37 mg, 0.3 mmol) in $THF/H_2O$ (1:1) at 0° C. was added $(Boc)_2O$ (1.97 g, 9.0 mmol). The mixture was warmed to rt and stirred overnight then concentrated under reduced pressure to remove THF and the residue was acidified to pH~6 with HCl. The mixture was extracted with EtOAc (3x5 mL) and the combined organic layers were dried over anhydrous $Na_2SO_4$ and filtered. The filtrate was concentrated under reduced pressure and the residue was purified by silica gel column chromatography to give (2S,3S)-3-(4-bromo-1,3-thiazol-2-yl)-2-[(tert-butoxycarbonyl)amino]-3-ethoxypropanoic acid (369 mg, 31% yield) as a solid. LCMS (ESI): m/z [M+H] calc'd for $C_{13}H_{19}BrN_2O_5S$ 394.0. found 395.0.

Step 5

To a mixture of 3-(1-ethyl-2-(2-((S)-1-methoxyethyl) pyridin-3-yl)-5-(4,4,5,5-tetramethyl-1,3,2-dioxaborolan-2-yl)-1H-indol-3-yl)-2,2-dimethylpropyl-(S)-hexahydropyridazine-3-carboxylate (584 mg, 0.91 mmol) and (2S,3S)-3-(4-bromo-1,3-thiazol-2-yl)-2-[(tert-butoxycarbonyl) amino]-3-ethoxypropanoic acid (360 mg, 0.91 mmol) in DMF at 0° C. was added DIPEA (1.59 mL, 9.1 mmol) and HATU (693 mg, 1.8 mmol). The mixture was allowed to warm to it and stirred for 1 h at room temperature, then cooled to 0° C. and H2O added. The mixture was extracted with EtOAc (2x5 mL) and the combined organic layers were washed with brine (3×10 mL), dried over anhydrous $Na_2SO_4$ and filtered. The filtrate was concentrated under reduced pressure and the residue was purified by silica gel column chromatography to give 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (S)-1-((2S,3S)-3-(4-bromothiazol-2-yl)-2-((tert-butoxycarbonyl)amino)-3-ethoxypropanoyl)hexahydropyridazine-3-carboxylate (410 mg, 46%) yield as a solid. LCMS (ESI): m/z [M+H] calc'd for $C_{47}H_{66}BBrN_8O_9S$ 980.4. found 981.3.

Step 6

Into a 50 mL Schlenk tube were added 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (S)-1-((2S,3S)-3-(4-bromothiazol-2-yl)-2-((tert-butoxycarbonyl)amino)-3-ethoxypropanoyl)hexahydropyridazine-3-carboxylate (390 mg, 0.4 mmol), $Pd(DTBpf)Cl_2$ (78 mg, 0.12 mmol), $K_3PO_4$ (211 mg, 1.0 mmol), toluene (9 mL), 1,4-dioxane (3 mL) and $H_2O$ (3 mL) under an atmosphere of Ar. The mixture was heated to 60° C. and stirred for 1 h, then extracted with EtOAc (3×15 mL). The combined organic layers were dried over anhydrous $Na_2SO_4$, filtered, the filtrate was concentrated under reduced pressure and the residue was purified by silica gel column chromatography to give tert-butyl (($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (96 mg, 31% yield) as a solid. LCMS (ESI): m/z [M+H] calc'd for $C_{41}H_{54}N_6O_7S$ 774.4. found 775.4.

Step 7

A mixture of tert-butyl (($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1 (5,3)-indola-6(1,3)- pyridazinacycloundecaphane-4-yl)carbamate (92 mg, 0.12 mmol), HCl in 1,4-dioxane (2.5 mL) and 1,4-dioxane (2.5 mL) was stirred at rt for 1 h. The mixture was concentrated under reduced pressure to give tert-butyl (($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (100 mg), which was used directly in the next step without further purification. LCMS (ESI): m/z [M+H] calc'd for $C_{36}H_{46}N_6O_5S$ 674.3. found 675.3.

Step 8

To a mixture of tert-butyl (($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2 (4,2)-thiazola-1(5,3)-indola-6(1,3)-pyridazinacycloundecaphane-4-yl)carbamate (90 mg, 0.13 mmol) and (1S,2S)-2-methylcyclopropane-1-carboxylic acid (27 mg, 0.27 mmol) in DMF at 0° C. was added DIPEA (172 mg, 1.3 mmol) and HATU (101 mg, 0.27 mmol). The mixture was allowed to warm to rt and stirred for 1 h, then cooled to 0° C., $H_2O$ added and the mixture extracted with EtOAc (2×5 mL). The combined organic layers were washed with brine (3×20 mL), dried over anhydrous $Na_2SO_4$ and filtered. The filtrate was concentrated under reduced pressure and the residue was purified by preparative-HPLC to give (1S,2S)—N-(($6^3$S,3S,4S,Z)-3-ethoxy-1-ethyl-12-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methylcyclopropane-1-carboxamide (21 mg, 21% yield) as a solid. LCMS (ESI): m/z [M+H] calc'd for $C_{41}H_{52}N_6O_6S$ 756.4. found 757.6: $^1$H NMR (400 MHz, DMSO-$d_6$) δ 8.76 (dd, J=4.8, 1.7 Hz, 1H), 8.50 (s, 1H), 7.91 (s, 1H), 7.84-7.71 (m, 3H), 7.61-7.56 (m, 1H), 7.55-7.50 (m, 1H), 5.91-5.85 (m, 1H), 5.20-5.14 (m, 1H), 4.92 (s, 1H), 4.36-4.21 (m, 3H), 4.17-4.07 (m, 2H), 3.68-3.56 (m, 3H), 3.54-3.46 (m, 1H), 3.22 (s, 3H), 2.90-2.73 (m, 2H), 2.09-2.03 (m, 1H), 1.88-1.73 (m, 3H), 1.55-1.43 (m, 1H), 1.37 (d, J=6.0 Hz, 3H), 1.20 (t, J=6.9 Hz, 3H), 1.04 (s, 4H), 0.93-0.71 (m, 7H), 0.51 (d, J=6.3 Hz, 1H), 0.38 (s, 3H).

Example A227. Synthesis of (1R,2R,3S)—N-(($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide

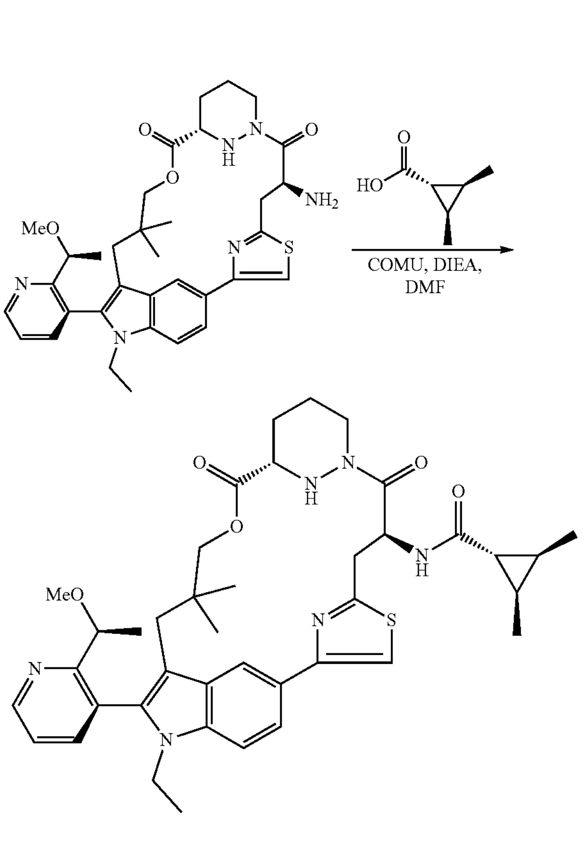

Step 1

To a mixture of ($6^3$S,4S, Z)-4-amino-$1^1$-ethyl-1-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6 (1,3)-pyridazinacycloundecaphane-5,7-dione (126 mg, 0.20 mmol) and (1R,2R,3S)-2,3-dimethylcyclopropane-1-carboxylic acid (34 mg, 0.30 mmol) in DMF (5 mL) at 0° C. was added DIPEA (129 mg, 1.0 mmol) and COMU (171 mg, 0.4 mmol). The mixture was warmed to rt and stirred for 1 h, then diluted with EtOAc (20 mL) and $H_2O$ (20 mL). The aqueous layer was extracted with EtOAc (3×10 mL) and the combined organic layers were washed with brine (2×10 mL), dried over anhydrous $Na_2SO_4$ and filtered. The filtrate was concentrated under reduced pressure and the residue was purified by preparative-HPLC to give (1R,2R,3S)—N-(($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)- pyridazinacycloundecaphane-4-yl)-2,3-dimethylcyclopropane-1-carboxamide (29 mg, 25% yield) as a solid. LCMS (ESI): m/z [M+H] calc'd for $C_{40}H_{50}N_6O_5S$ 726.4. found 727.3; $^1$H NMR (400 MHz, DMSO-$d_6$) δ 8.75 (dd, J=4.8, 1.7 Hz, 1H), 8.49 (d, J=1.6 Hz, 1H), 8.40 (d, J=9.0 Hz, 1H), 7.82 (s, 3H), 7.58 (d, J=8.6 Hz, 1H), 7.52 (dd, J=7.7, 4.7 Hz, 1H), 5.56 (t, J=9.0 Hz, 1H), 5.07 (d, J=12.2 Hz, 1H), 4.44-3.99 (m, 5H), 3.57 (s, 1H), 3.25 (s, 1H), 3.16 (d, J=9.3 Hz, 3H), 2.94 (d, J=14.3 Hz, 1H), 2.81-2.70 (m, 1H), 2.67 (p, J=1.9 Hz, 1H), 2.44-2.27 (m, 1H), 2.16-2.01 (m, 1H), 1.78 (s, 2H), 1.53 (s, 1H), 1.37 (d, J=6.0 Hz, 3H), 1.26-1.13 (m, 3H), 1.07 (dd, J=9.4, 5.4 Hz, 6H), 0.93-0.77 (m, 6H), 0.32 (s, 3H).

Example A372. Synthesis of (1r,2R,3S)—N-(($2^2$R,$6^3$S,4S)-1-ethyl-$1^2$-(2-((S)-1-methoxyethyl)pyridin-3-yl)-$2^2$-(methoxymethyl)-10,10-dimethyl-5,7-dioxo-$2^1$,$2^2$,$2^3$,$2^6$,$6^1$,$6^2$,$6^3$,$6^4$,$6^5$,$6^6$-decahydro-$^1$H-8-oxa-1(5,3)-indola-6(1,3)-pyridazina-2(5,1)-pyridinacycloundecaphane-4-yl)-2,3-dimethylcyclopropane-1-carboxamide

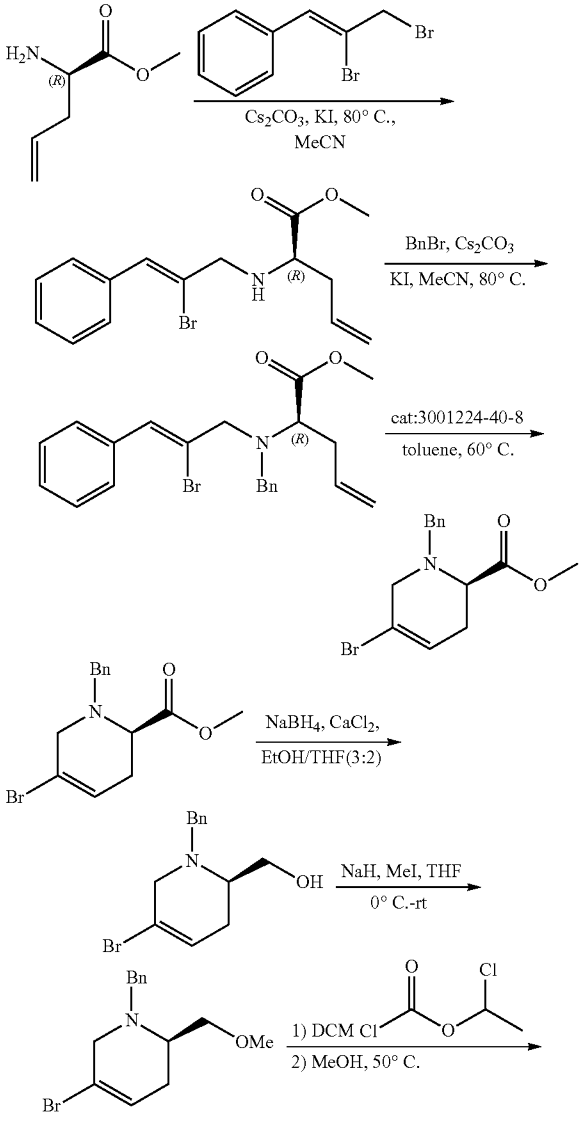

-continued

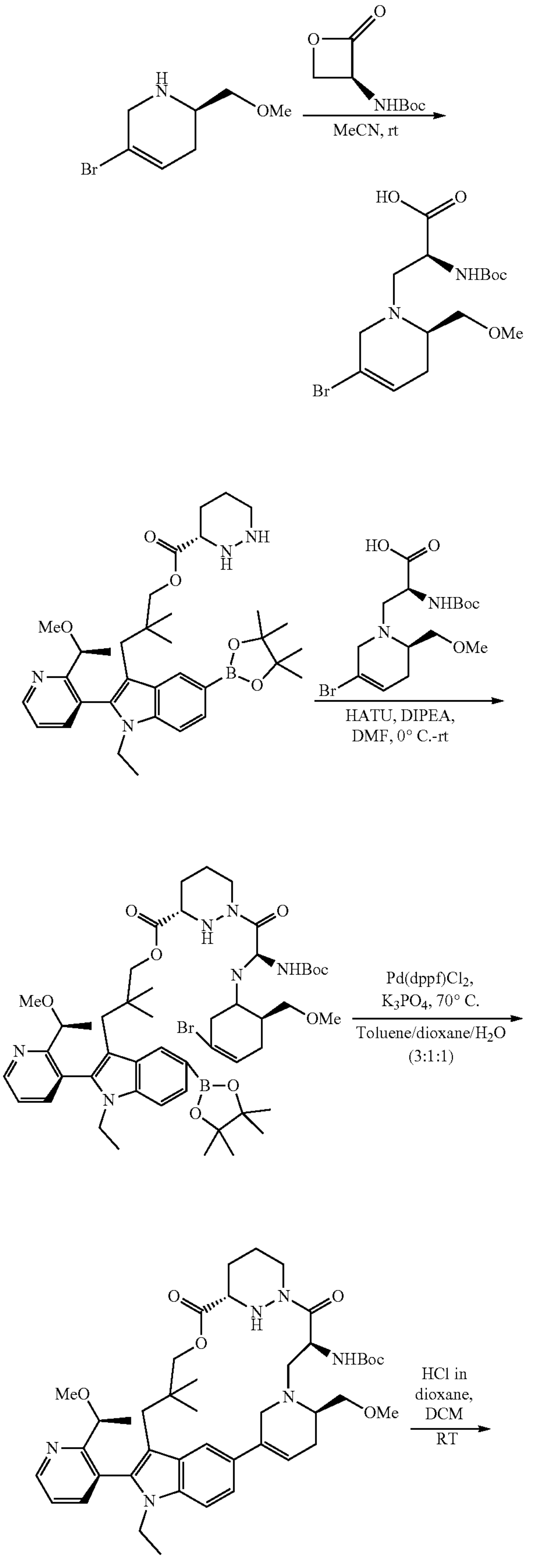

-continued

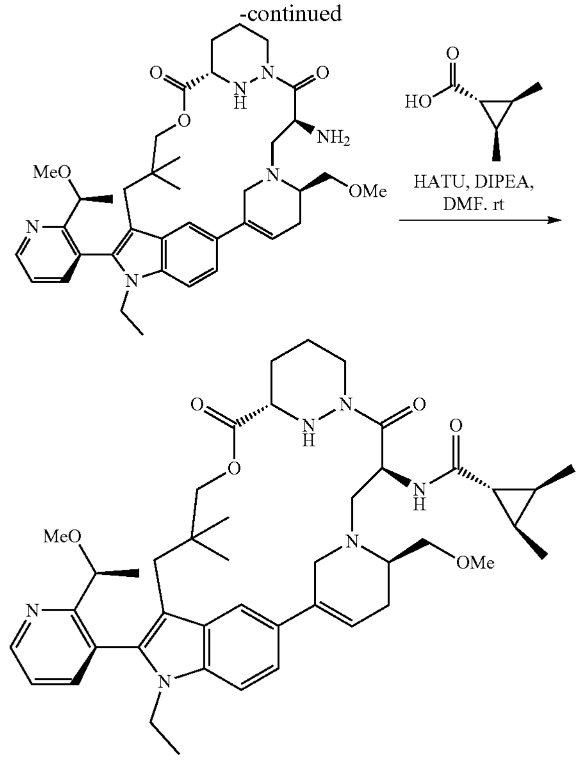

Step 1.

To a mixture of methyl (R')-2-aminopent-4-enoate (8.0 g, 36.5 mmol) and (Z)-(2,3-dibromoprop-1-en-1-yl)benzene (15.1 g, 54.8 mmol) in MECN (80 mL) under an atmosphere of $N_2$ was added $Cs_2CO_3$ (35.7 g, 109.6 mmol) and KI (12.13 g, 73.1 mmol) in portions. The mixture was heated to 80° C. and stirred overnight, then filtered and the filter cake was washed with MeCN (3×20 mL). The filtrate was concentrated under reduced pressure and the residue was purified by silica gel column chromatography to give methyl (R,Z)-2-((2-bromo-3-phenylallyl)amino)pent-4-enoate (12.0 g, 91% yield) as an oil. LCMS (ESI): m/z $[M+H]^+$ calc'd for $C_{15}H_{18}BrNO_2$ 323.1. found 324.1.

Step 2.

To a mixture of methyl (R,Z)-2-((2-bromo-3-phenylallyl) amino)pent-4-enoate (12.0 g, 37.0 mmol) and BnBr (12.66 g, 74.0 mmol) in MeCN (120 mL) under an atmosphere of $N_2$ was added $Cs_2CO_3$ (24.12 g, 74.0 mmol) and KI (6.14 g, 37.0 mmol) in portions. The mixture was stirred at room temperature overnight, then filtered and the filter cake was washed with MeCN (3×20 mL). The filtrate was concentrated under reduced pressure and the residue was purified by silica gel column chromatography to give methyl (R,Z)-2-(benzyl(2-bromo-3-phenylallyl)amino)pent-4-enoate (6.0 g, 35% yield) as an oil. LCMS (ESI): m/z $[M+H]^+$ calc'd for $C_{22}H_{24}BrNO_2$ 415.1. found 416.1 [for $^{81}Br$].

Step 3.

To a mixture of methyl (R,Z)-2-(benzyl(2-bromo-3-phenylallyl)amino)pent-4-enoate (5.8 g, 14.0 mmol) and [1,3-bis(2,4,6-trimethylphenyl)imidazolidin-2-ylidene]dichloro [[2-(propan-2-yloxy)phenyl]methylidene]ruthenium (2.63 g, 4.2 mmol) in toluene (580 mL) under an atmosphere of Ar was heated to 60° C. and stirred for 30 min. The mixture was concentrated under reduced pressure and the residue was purified by preparative-HPLC to give methyl (R)-1-benzyl-5-bromo-1,2,3,6-tetrahydropyridine-2-carboxylate (17 g, 77% yield) as an oil. LCMS (ESI): m/z $[M+H]^+$ calc'd for $C_{14}H_{16}BrNO_2$ 309.0. found 310.1.

Step 4.

To a mixture of methyl (R)-1-benzyl-5-bromo-1,2,3,6-tetrahydropyridine-2-carboxylate (3.7 g, 11.9 mmol) and $CaCl_2$ (2.65 g, 23.9 mmol) in EtOH (22 mL) and THF (15 mL) at 0° C. under an atmosphere of $N_2$ was added $NaBH_4$ (1.80 g, 47.7 mmol) in portions. The mixture was warmed to room temperature and stirred for 2 h, then cooled to 0° C., and MeOH and $H_2O$ were added. The mixture was extracted with DCM (2×50 mL), dried over anhydrous $Na_2SO_4$ and filtered. The filtrate was concentrated under reduced pressure and the residue was purified by preparative HPLC to give (R)-(1-benzyl-5-bromo-1,2,3,6-tetrahydropyridin-2-yl) methanol (2.8 g, 75% yield) as a solid. LCMS (ESI): m/z $[M+H]^+$ calc'd for $C_{13}H_{16}BrNO$ 281.0. found 282.3.

Step 5.

To a mixture of (R)-(1-benzyl-5-bromo-1,2,3,6-tetrahydropyridin-2-yl)methanol (1.0 g, 3.5 mmol) in THF (10 mL) at 0° C. was added NaH, 60% dispersion in oil (0.26 g, 10.6 mmol). The mixture was stirred for 15 min, then MeI (0.75 g 5.3 mmol) was added and the mixture was allowed to warm to room temperature and stirred for 1 h. The mixture was cooled to 0° C., saturated $NH_4Cl$ was added and the mixture was extracted with EtOAc (2×20 mL). The combined organic layers were dried over anhydrous $Na_2SO_4$, filtered, the filtrate was concentrated under reduced pressure and the residue was purified by preparative-HPLC to give (R)-1-benzyl-5-bromo-2-(methoxymethyl)-1,2,3,6-tetrahydropyridine (1.0 g, 86% yield) as a solid. LCMS (ESI): m/z $[M+H]^+$ calc'd for $C_{14}H_{16}BrNO$ 295.1. found 296.2.

Step 6.

A mixture of (R)-1-benzyl-5-bromo-2-(methoxymethyl)-1,2,3,6-tetrahydropyridine (1.0 g, 3.4 mmol) and 1-chloroethyl chloroformate (2 mL, 14.0 mmol) in DCM (10 mL) under an atmosphere of $N_2$ was stirred at room temperature overnight. The mixture was washed with brine (2×10 mL) and the combined aqueous layers were extracted with DCM (10 mL). The combined organic layers were dried over anhydrous $Na_2SO_4$, filtered and the filtrate was concentrated under reduced pressure. The residue was dissolved in MeOH (10 mL), the mixture was heated to 50° C. under an atmosphere of $N_2$ and stirred for 2 h, then concentrated under reduced pressure and the residue was purified by preparative-HPLC to give (R)-5-bromo-2-(methoxymethyl)-1,2,3,6-tetrahydropyridine (500 mg, 72% yield) as an oil. LCMS (ESI): m/z $[M+H]^+$ calc'd for $C_7H_{12}BrNO$ 205.0. found 206.1.

Step 7.

To a mixture of (R)-5-bromo-2-(methoxymethyl)-1,2,3,6-tetrahydropyridine (600 mg, 2.9 mmol) and tert-butyl N-[(3S)-2-oxooxetan-3-yl]carbamate (382 mg, 2.0 mmol) in MeCN (6 mL) Linder an atmosphere of NW was stirred overnight. The mixture was concentrated under reduced pressure and the residue was purified by preparative-HPLC to give (S)-3-((R)-5-bromo-2-(methoxymethyl)-3,6-dihydropyridin-1(2H)-yl)-2-((tert-butoxycarbonyl)amino)propanoic acid (500 mg, 39% yield) as a solid. LCMS (ESI): m/z $[M+H]^+$ calc'd for $C_{15}H_{25}BrN_2O$ 392.1. found 393.1.

Step 8.

To a mixture of 3-(1-ethyl-2-(2-((S)-1-methoxyethyl) pyridin-3-yl)-5-(4,4,5,5-tetramethyl-1,3,2-dioxaborolan-2-yl)-1H-indol-3-yl)-2,2-dimethylpropyl (S)-hexahydropyridazine-3-carboxylate (1.25 g, 2.07 mmol) and (S)-3-((R)-5-bromo-2-(methoxymethyl)-3,6-dihydropyridin-1(2H)-yl)-2-((tert-butoxycarbonyl)amino)propanoic acid (0.49 g, 1.24 mmol) and DIPEA (2.67 g, 20.7 mmol) in DMF (15 mL) under an atmosphere of $N_2$ was added HATU (0.79 g, 2.07 mmol) in portions. The mixture was warmed to room temperature and stirred for 1 h, then $H_2O$ added and the mixture was extracted with EtOAc (50 mL). The organic layer was washed with brine (3×50 mL), dried over anhydrous $Na_2SO_4$ and filtered. The filtrate was concentrated under reduced pressure and the residue was purified by silica gel column chromatography to give 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (S)-1-((S)-3-((R)-5-bromo-2-(methoxymethyl)-3,6-dihydropyridin-1(2H)-yl)-2-((tert-butoxycarbonyl)amino)propanoyl)hexahydropyridazine-3-carboxylate (880 mg, 39% yield) as a solid. LCMS (ESI): m/z $[M+H]^+$ calc'd for $C_{49}H_{72}BBrN_6O_9$ 980.5. found 981.4 [for $^{81}Br$].

Step 9.

To a mixture of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (S)-1-((S)-3-((R)-5-bromo-2-(methoxymethyl)-3,6-dihydropyridin-1(2H)-yl)-2-((tert-butoxycarbonyl)amino)propanoyl)hexahydropyridazine-3-carboxylate (850 mg, 0.87 mmol) and $K_3PO_4$ (460 mg, 2.17 mmol) in toluene (4.5 mL), 1,4-dioxane (1.5 mL) and $H_2O$ (1.5 mL) under an atmosphere of $N_2$ was added $Pd(dppf)Cl_2$ (64 mg, 0.09 mmol) in portions. The mixture was heated to 70° C. and stirred for 3 h at 70° C., then concentrated under reduced pressure and the residue was purified by silica gel column chromatography to give tert-butyl (($2^2$R,$6^3$S,4S)-$1^1$-ethyl-$1^2$-(2-((S)-1-methoxyethyl)pyridin-3-yl)-$2^2$-(methoxymethyl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)carbamate (220 mg, 30% yield) as a solid. LCMS (ESI): m/z $[M+H]^+$ calc'd for $C_{43}H_{60}N_6O_7$, 772.5. found 773.4.

Step 10.

A mixture of tert-butyl (($2^2$R,$6^3$S,4S)-$1^1$-ethyl-$1^2$-(2-((S)-1-methoxyethyl)pyridin-3-yl)-$2^2$-(methoxymethyl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)carbamate (100 mg, 0.13 mmol) and HCl in 1,4-dioxane (2 mL) in DCM (2 mL) was stirred at room temperature for 1 h. The mixture was concentrated under reduced pressure to give ($2^2$R,$6^3$S,4S)-4-amino-1-ethyl-$1^2$-(2-((S)-1-methoxyethyl)pyridin-3-yl)-$2^2$-(methoxymethyl)-10,10-dimethyl-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-5,7-dione (119 rig) as a solid, that was used directly in the next step without further purification.

Step 11.

To a mixture of ($2^2$R,$6^3$S,4S)-4-amino-$1^1$-ethyl-12-(2-((S)-1-methoxyethyl)pyridin-3-yl)-$2^2$-(methoxymethyl)-10,10-dimethyl-$2^1$,$2^2$,$2^3$,$2^6$,$6^1$,$6^2$,$6^3$,$6^4$,$6^5$,$6^6$-decahydro-1H-8-oxa-1(5,3)-indola-6(1,3)-pyridazina-2(5,1)-pyridinacycloundecaphane-5,7-dione (20 mg, 0.18 mmol), (1r,2R,3S)-2,3-dimethylcyclopropanecarboxylic acid, and DIPEA (114 mg, 0.89 mmol) in DMF (2 mL) was added HATU (81 mg, 0.21 mmol) in portions. The mixture was stirred at room temperature for 1 h, then purified by preparative-HPLC to give (1r,2R,3S)—N-(($2^2$R,$6^3$S,4S)-$1^1$-ethyl-$1^2$-(2-((S)-1-methoxyethyl)pyridin-3-yl)-$2^2$-(methoxymethyl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)-2,3-dimethylcyclopropane-1-carboxamide (24 mg, 18% yield) as a solid. LCMS (ESI): m/z $[M+H]^+$ calc'd for $C_{44}H_{60}N_6O_6$ 768.5. found 769.2; $^1H$ NMR (400 MHz, DMSO-$d_6$) δ 8.90-8.65 (m, 1H), 810-7.95 (m, 1H), 7.90-7.75 (m, 1H), 7.57-7.45 (m, 3H), 7.40 (s, 1H), 6.26 (s, 1H), 5.65-5.50 (m, 1H), 5.45-5.30 (m, 1H), 4.39-4.25 (m, 1H), 4.24-4.20 (m, 1H), 4.19-4.10 (m, 1H), 4.09-4.00 (m, 1H), 3.88-3.76 (m, 1H), 3.73-3.62 (m, 2H), 3.62-3.55 (m, 2H), 3.26 (s, 5H), 3.14-3.00 (m, 2H), 2.96-2.87 (m, 1H), 2.79-2.70 (m, 5H), 2.43 (s, 1H), 2.15-2.06 (m, 2H), 1.95-1.86 (m, 1H), 1.86-1.72 (m, 1H), 1.58-1.49 (m, 2H), 1.40-1.30 (m, 3H), 1.10-1.00 (m, 6H), 0.99-0.90 (m, 6H), 0.82 (s, 3H), 0.52 (s, 3H).

Example A373. Synthesis of (1r,2R,3S)—N-(($6^3$S,4S,Z)-$1^2$-(5-(1-(2-(dimethylamino)ethyl)-4-hydroxypiperidin-4-yl)-2-((S)-1-methoxyethyl)pyridin-3-yl)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide

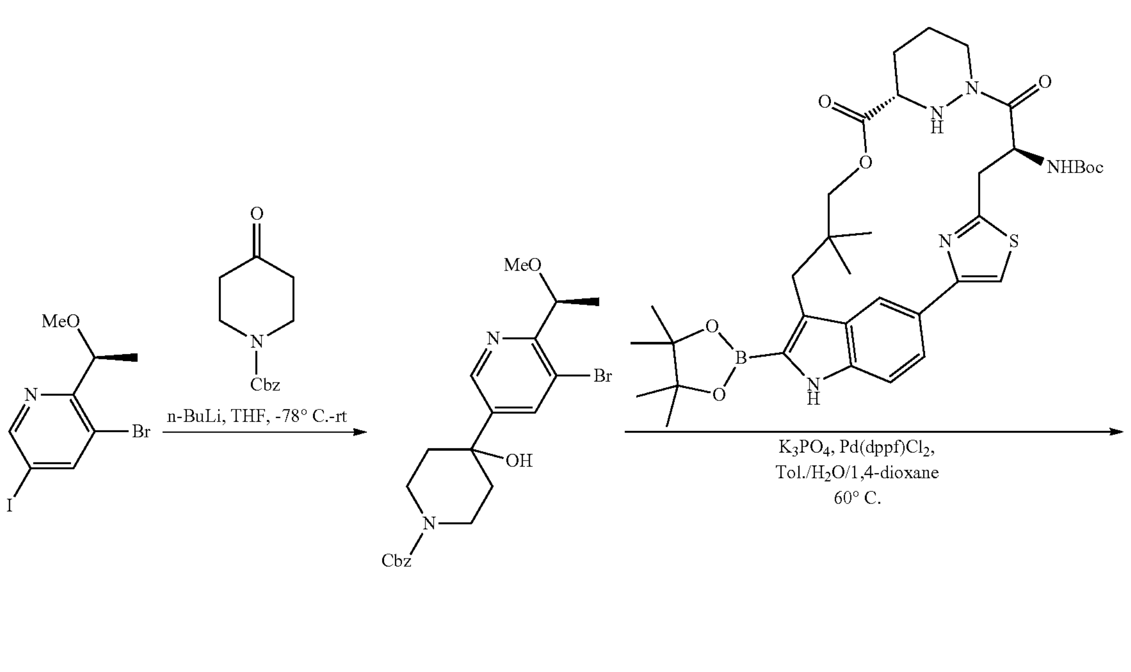

-continued
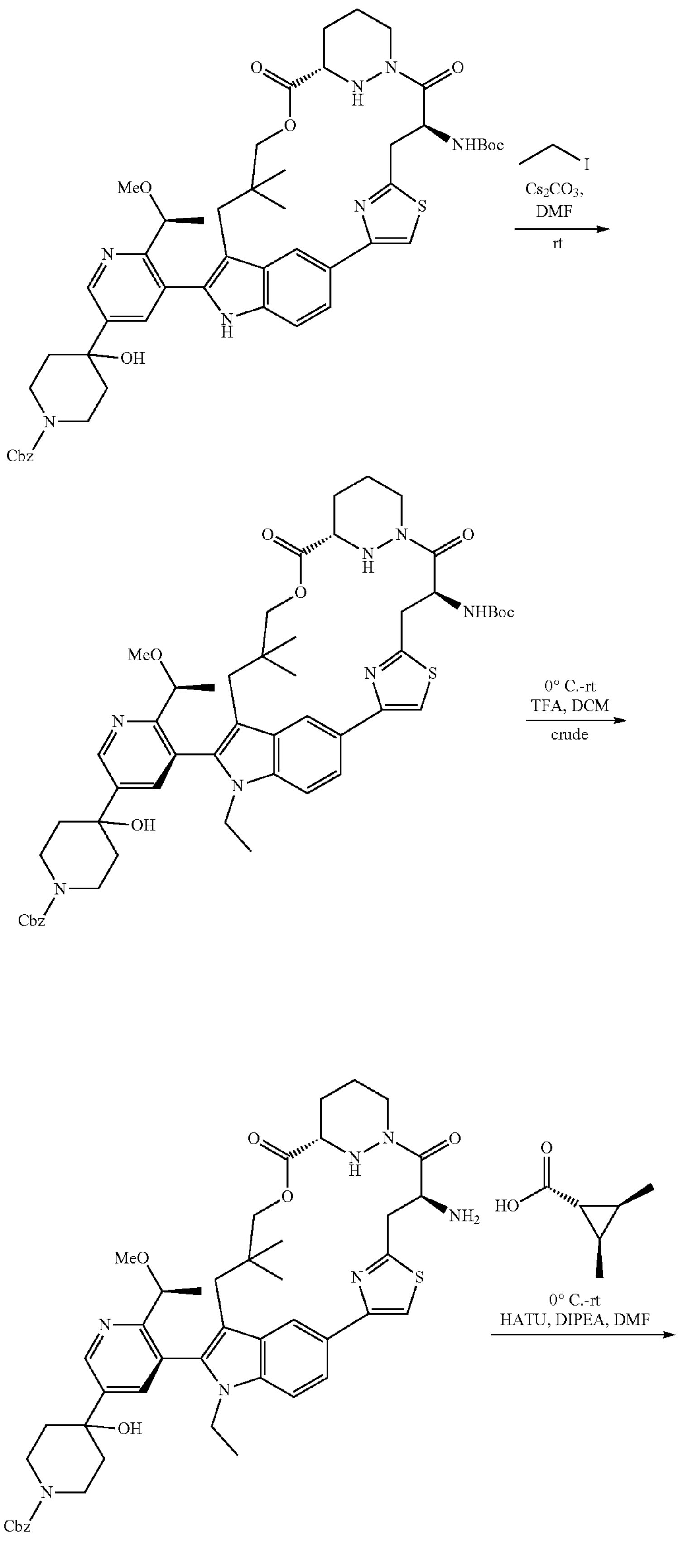

-continued
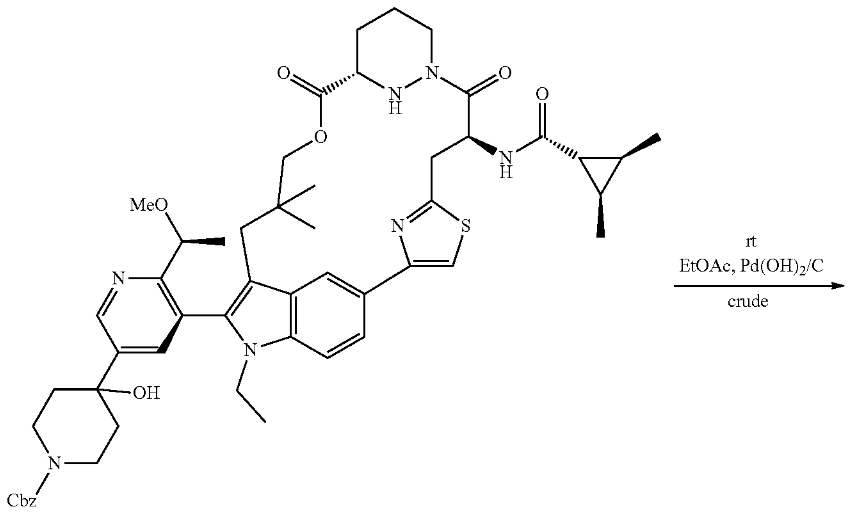
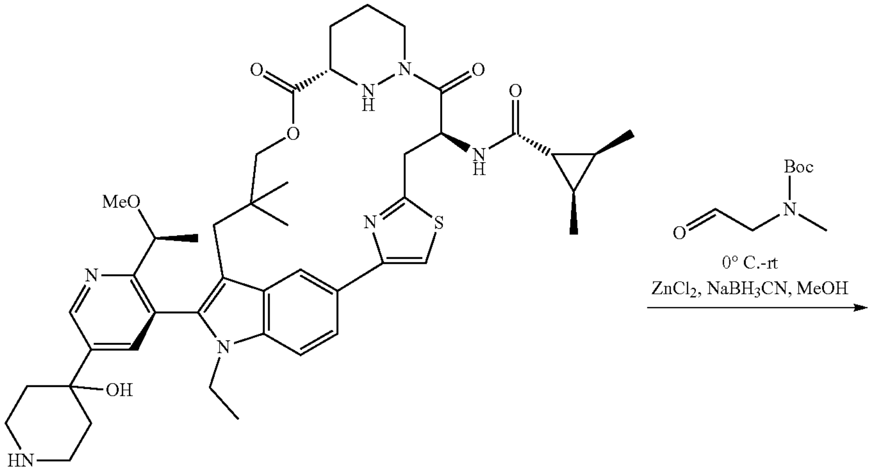
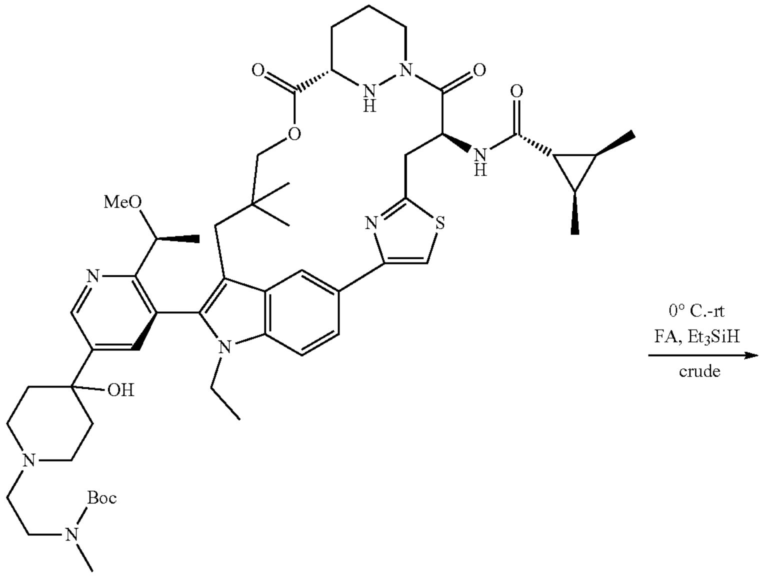

-continued

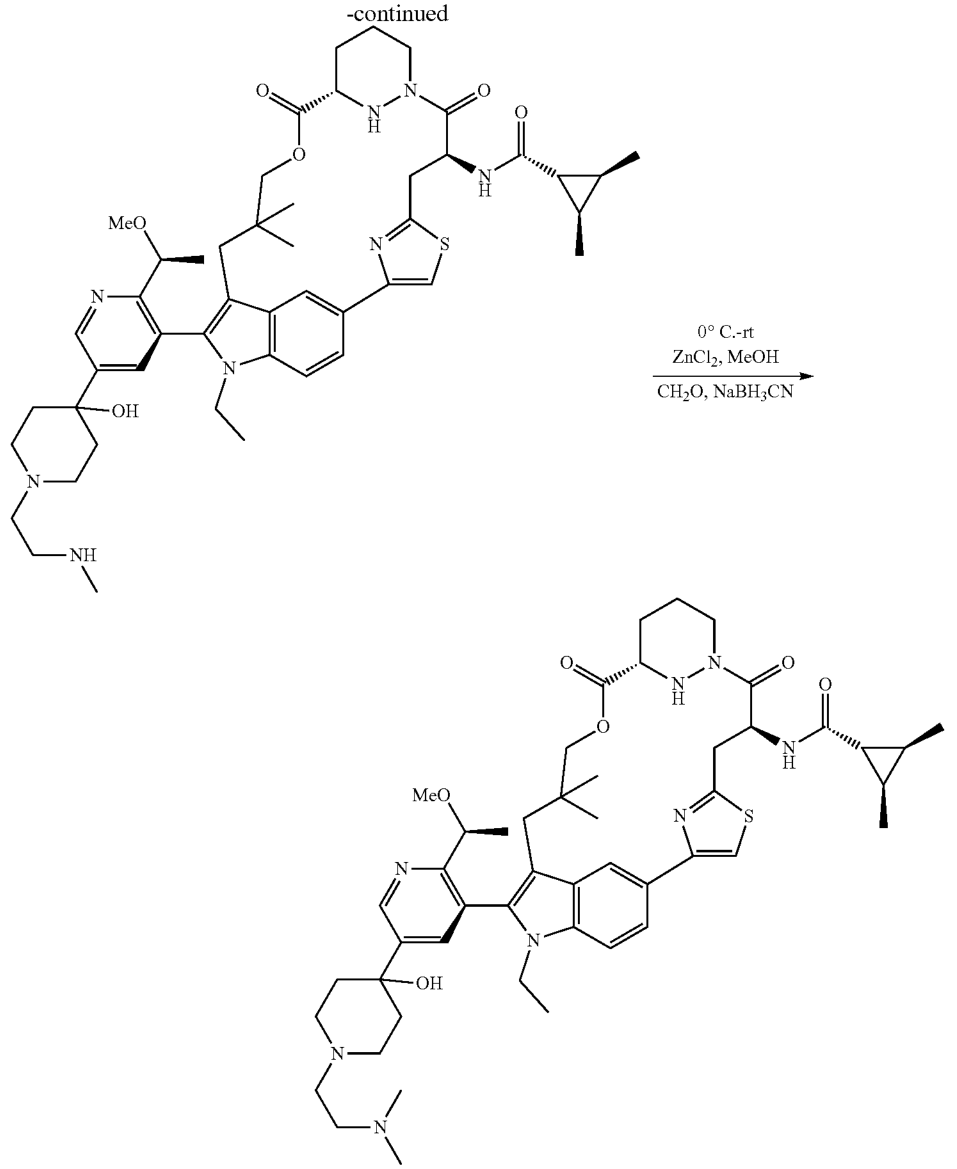

Step 1.

To a mixture of (S)-3-bromo-5-iodo-2-(1-methoxyethyl)pyridine (5.0 g, 14.6 mmol) in THF (40 mL) at −78° C. under an atmosphere of $N_2$ was added n-BuLi in hexanes (5.85 mL, 14.6 mmol) dropwise. The mixture was stirred at −78° C. for 1 h, then benzyl 4-oxopiperidine-1-carboxylate (6.82 g, 29.2 mmol) was added. The mixture was allowed to warm to 6° C. Saturated $NH_4Cl$ (3 mL) was added, the mixture was diluted with $H_2O$ (20 mL) and extracted with EtOAc (3x20 mL). The combined organic layers were dried over anhydrous $Na_2SO_4$, filtered, the filtrate was concentrated under reduced pressure and the residue was purified by silica gel column chromatography to give benzyl (S)-4-(5-bromo-6-(1-methoxyethyl)pyridin-3-yl)-4-hydroxypiperidine-1-carboxylate (800 mg, 12% yield) as a solid. LCMS (ESI): m/z $[M+H]^+$ calc'd for $C_{21}H_{25}BrN_2O_4$ 448.1. found 449.2.

Step 2.

To a mixture of tert-butyl (($6^3$S,4S,Z)-10,10-dimethyl-5,7-dioxo-12-(4,4,5,5-tetramethyl-1,3,2-dioxaborolan-2-yl)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl) carbamate (500 mg, 0.72 mmol) and benzyl (S)-4-(5-bromo-6-(1-methoxyethyl)pyridin-3-yl)-4-hydroxypiperidine-1-carboxylate (648 mg, 1.4 mmol) in toluene (9 mL), $H_2O$ (3 mL) and 1,4-dioxane (3 mL) under an atmosphere of $N_2$ was added $K_3PO_4$ (459 mg, 2.16 mmol) and Pd(dppf)$Cl_2$·$CH_2Cl_2$ (59 mg, 0.07 mmol) in portions. The mixture was heated to 60° C. and stirred for 4 h, then diluted with $H_2O$ (10 mL) and extracted with EtOAc (3x10 mL). The combined organic layers were dried over anhydrous $Na_2SO_4$, filtered, the filtrate was concentrated under reduced pressure and the residue was purified by silica gel column chromatography to give benzyl 4-(5-(($6^3$S,4S,Z)-4-((tert-butoxycarbonyl)amino)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidine-1-carboxylate (1.16 g, 75% yield) as a solid. LCMS (ESI): m/z $[M+H]^+$ calc'd for $C_{50}H_{61}N_7O_9S$ 935.4. found 936.4.

Step 3.

To a mixture of benzyl 4-(5-(($6^3$S,4S,Z)-4-((tert-butoxycarbonyl)amino)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidine-1-carboxylate (1.1 g, 1.18 mmol) and $Cs_2CO_3$ (1.91 g, 5.88 mmol) in DMF (15 mL) at 0° C. was added iodoethane (0.64 g, 4.1 mmol) dropwise.

The mixture was warmed to room temperature and stirred for 2 h, then diluted with $H_2O$ (15 mL) and extracted with EtOAc (3×20 mL). The combined organic layers were dried over anhydrous $Na_2SO_4$, filtered, the filtrate was concentrated under reduced pressure and the residue was purified by preparative-TLC to give benzyl 4-(5-(($6^3$S,4S,Z)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidine-1-carboxylate (110 mg, 9% yield) as a solid. LCMS (ESI): m/z $[M+H]^+$ calc'd for $C_{52}H_{65}N_7O_9S$ 963.5. found 964.4.

Step 4.

To a mixture of benzyl 4-(5-(($6^3$S,4S,Z)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidine-1-carboxylate (110 mg, 0.11 mmol) in DCM (3 mL) at 0° C. was added TFA (1 mL) dropwise. The mixture was warmed to room temperature and stirred for 1.5 h, then concentrated under reduced pressure to give benzyl 4-(5-(($6^3$S,4S,Z)-4-amino-$1^1$-ethyl-10,10-dimethyl-5,7-dioxo-$6^1$,$6^2$$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidine-1-carboxylate (120 mg) as a solid. LCMS (ESI): m/z $[M+H]^+$ calc'd for $C_{47}H_{57}N_7O_7S$ 863.4. found 864.5.

Step 5.

To a mixture of benzyl 4-(5-(($6^3$S,4S,Z)-4-amino-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidine-1-carboxylate (120 mg, 0.14 mmol) and (1R,2R,3S)-2,3-dimethylcyclopropane-1-carboxylic acid (32 mg, 0.28 mmol) in DMF (4 mL) at 0° C. was added DIPEA (180 mg, 1.39 mmol) and HATU (158 mg, 0.42 mmol) in portions. The mixture was warmed to room temperature and stirred for 2 h, then diluted with $H_2O$ (10 mL) and extracted with EtOAc (3×10 mL). The combined organic layers were dried over anhydrous $Na_2SO_4$. After filtration, the filtrate was concentrated under reduced pressure. The residue was purified by reverse flash chromatography with the following conditions: column, C18 silica gel; mobile phase, MECN in water (0.05% TFA), 0% to 100% gradient in 300 min; detector, UV 254 nm. To afford benzyl 4-(5-(($6^3$S,4S,Z)-4-((1r,2R,3S)-2,3-dimethylcyclopropane-1-carboxamido)-$1^1$-ethyl-10,10-dimethyl-5,7-dioxo-$6^1$,$6^2$,$6^3$,$6^4$,$6^5$,$6^6$-hexahydro-11H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidine-1-carboxylate (120 mg, 89% yield) as a brown solid. LCMS (ESI): m/z $[M+H]^+$ calc'd for $C_{53}H_{65}N_7O_8S$ 959.4. found 960.4.

Step 6.

A mixture of benzyl 4-(5-(($6^3$S,4S,Z)-4-((1r,2R,3S)-2,3-dimethylcyclopropane-1-carboxamido)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidine-1-carboxylate (120 mg, 0.13 mmol) and $Pd(OH)_2$, 30% on carbon (80 mg, 0.25 mmol) in EtOAc (2 mL) was stirred under an atmosphere of $H_2$ overnight. The mixture was filtered, the filter cake was washed with MeOH (3×8 mL) and the filtrate was concentrated under reduced pressure to give (1r,2R,3S)—N-((6S,4S,Z)-11-ethyl-12-(5-(4-hydroxypiperidin-4-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (45 mg) as an oil. LCMS (ESI): m/z $[M+H]^+$ calc'd for $C_{45}H_{59}N_7O_6S$ 825.4. found 826.4.

Step 7.

To a mixture of (1r,2R,3S)—N-(($6^3$S,4S,Z)-$1^1$-ethyl-$1^2$-(5-(4-hydroxypiperidin-4-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (50 mg, 0.06 mmol) and tert-butyl N-methyl-N-(2-oxoethyl)carbamate (52 mg, 0.31 mmol) in MeOH (2 mL) at 0° C. was added $ZnCl_2$ (83 mg, 0.61 mmol) in portions. The mixture was warmed to room temperature and stirred for 30 min, then cooled to 0° C. and $NaBH_3CN$ (11 mg, 0.18 mmol) added in portions. The mixture was warmed to room temperature and stirred for 2 h, then the residue was purified by preparative-HPLC to give tert-butyl (2-(4-(5-(($6^3$S,4S,Z)-4-((1r,2R,3S)-2,3-dimethylcyclopropane-1-carboxamido)-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidin-1-yl)ethyl)(methyl)carbamate (30 mg, 50% yield) as a yellow oil. LCMS (ESI): m/z $[M+H]^+$ calc'd for $C_{53}H_{74}N_8O_8S$ 982.5. found 983.6.

Step 8.

To a mixture of tert-butyl (2-(4-(5-(($6^3$S,4S,Z)-4-((1r,2R,3S)-2,3-dimethylcyclopropane-1-carboxamido)-1-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-4-hydroxypiperidin-1-yl)ethyl)(methyl)carbamate (30 mg, 0.03 mmol) in FA (1.5 mL) at 0° C. was added $Et_3SiH$ (18 mg, 0.16 mmol). The mixture was warmed to room temperature and stirred for 40 min, then concentrated under reduced pressure to give (1r,2R,3S)—N-(($6^3$S,4S,Z)-$1^1$-ethyl-$1^2$-(5-(4-hydroxy-1-(2-(methylamino)ethyl)piperidin-4-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-1H-8-oxa-2(4,2)-thiazola-1(5,3)-indola-6(1,3)-pyridazinacycloundecaphane-4-yl)-2,3-dimethylcyclopropane-1-carboxamide (25 mg) as a solid, which was used directly in the next step without further purification. LCMS (ESI): m/z $[M+H]^+$ calc'd for $C_{48}H_{66}N_8O_6S$ 882.5. found 883.6.

Step 9.

To a mixture of (1r,2R,3S)—N-(($6^3$S,4S,Z)-11-ethyl-$1^2$-(5-(4-hydroxy-1-(2-(methylamino)ethyl)piperidin-4-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (30 mg, 0.03 mmol) and formaldehyde (31 mg, 1.0 mmol) in MeOH (3 ml) at 0° C. was added $ZnCl_2$ (46 mg, 0.34 mmol) in portions. The mixture was warmed to room temperature and stirred for 30 min, then cooled to 0° C. and $NaBH_3CN$ (6.4 mg, 0.10 mmol) was added in portions. The mixture was warmed to room temperature and stirred for 2 h, then purified by preparative-HPLC to give (1r,2R,3S)—N-((63S, 4S,Z)-$1^2$-(5-(1-(2-(dimethylamino)ethyl)-4-hydroxypiperidin-4-yl)-2-((S)-1-methoxyethyl)pyridin-3-yl)-$1^1$-ethyl-10, 10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-11-carboxamide (0.7 mg, 2% yield) as a solid. LCMS (ESI): m/z $[M+H]^+$ calc'd for $C_{49}H_{68}N^8O^6S$ 896.5. found 897.4; $^1H$ NMR (400 MHz, DMSO-$d_6$) δ 8.83 (d, J=2.3 Hz, 1H), 8.49 (d, J=1.6 Hz, 1H), 8.38 (d, J=9.1 Hz, 2H), 7.81 (s, 1H), 7.78-7.68 (m, 2H), 7.57 (d, J=8.7 Hz, 1H), 5.57 (t, J=9.3 Hz, 11H), 5.06 (d, J=12.1 Hz, 1H), 4.36-4.07 (m, 6H), 3.56 (s, 2H), 3.24 (s, 3H), 3.18-3.11 (m, 1H), 2.93 (d, J=14.5 Hz, 1H), 2.75-2.60 (m, 2H), 2.43 (d, J=11.4 Hz, 4H), 2.37 (s, 2H), 2.15 (s, 7H), 2.02 (d, J=16.7 Hz, 4H), 1.78 (s, 2H), 1.66 (d, J=12.6 Hz, 2H), 1.50 (s, 1H), 1.36 (d, J=6.1 Hz, 3H), 1.24 (s, 1H), 1.16 (s, 2H), 1.15-0.93 (m, 6H), 0.92-0.63 (m, 6H), 0.31 (s, 3H).

Example A387. Synthesis of (1r,2R,3S)—N-(($6^3$S, 3S,4S,Z)-3-(2,2-difluoroethoxy)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4, 2)-thiazola-1(5,3)-indola-6(1,3)-pyridazinacycloundecaphane-4-yl)-2,3-dimethylcyclopropane-1-carboxamide

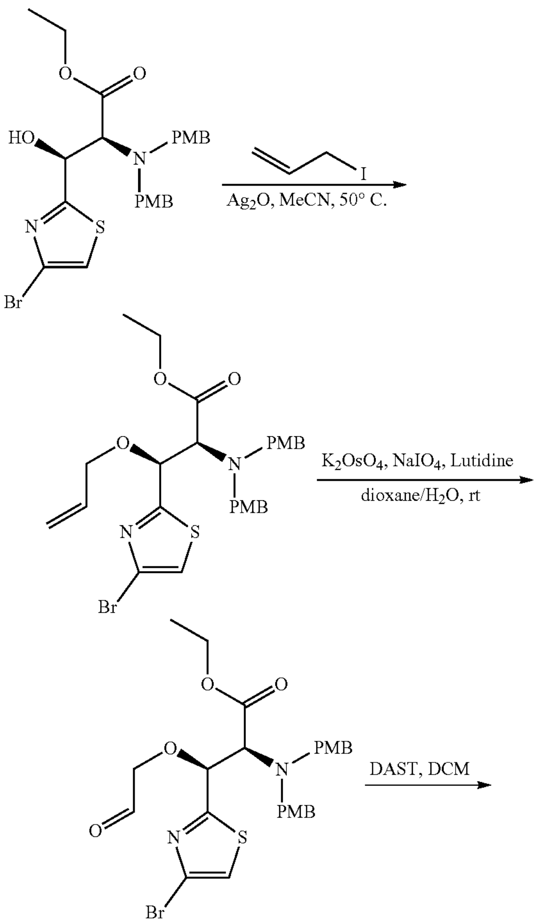

-continued

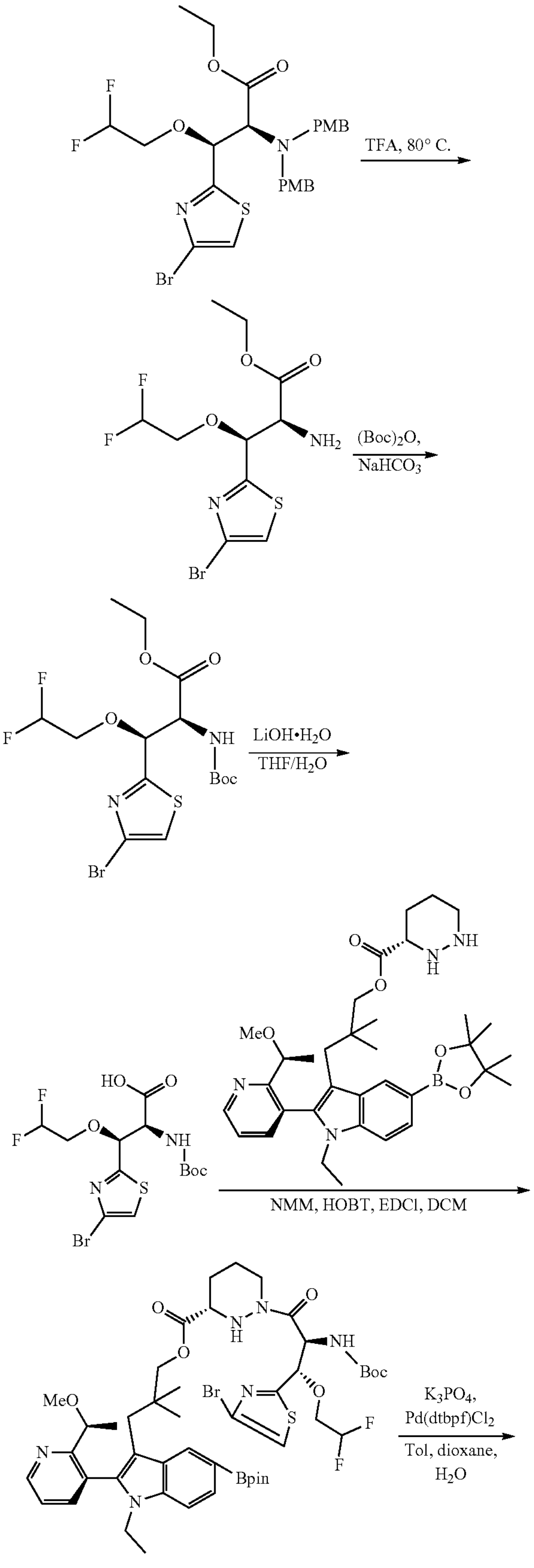

-continued

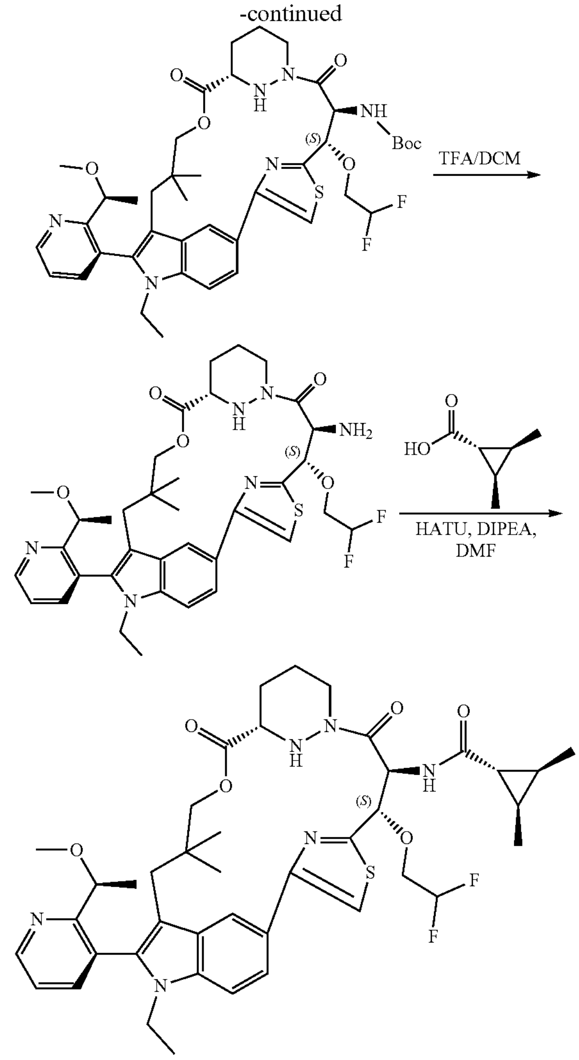

Step 1.

To a mixture of ethyl (2S,3S)-2-(bis(4-methoxybenzyl) amino)-3-(4-bromothiazol-2-yl)-3-hydroxypropanoate (1.0 g, 1.7 mmol) in MeCN (10 m) at room temperature under an atmosphere of $N_2$ was added $Ag_2O$ (2.17 g, 9.4 mmol) and allyl iodide (1.57 g, 9.36 mmol). The resulting mixture was heated to 60° C. and stirred for 16 h, then filtered, and the filter cake was washed with EtOAc (3×20 mL).

The filtrate was concentrated under reduced pressure and the residue was purified by silica gel column chromatography to give ethyl (2S,3S)-3-(allyloxy)-2-(bis(4-methoxybenzyl)amino)-3-(4-bromothiazol-2-yl)propanoate (1.0 g, 93% yield) as a solid. LCMS (ESI): m/z $[M+H]^+$ calc'd for $C_{27}H_{31}BrN_2O_5S$ 574.1 & 576.1. found 575.1 & 577.1.

Step 2.

To a mixture of ethyl (2S,3S)-3-(allyloxy)-2-(bis(4-methoxybenzyl)amino)-3-(4-bromothiazol-2-yl)propanoate (1.0 g. 1.7 mmol) in 1,4-dioxane (10 mL) and $H_2O$ (10 mL) at 0° C. was added 2,6-lutidine (0.37 g, 3.48 mmol) and $K_2OsO_4 \cdot 2H_2O$ (0.03 g, 0.09 mmol). The mixture was stirred at 0° C. for 15 min then $NaIO_4$ (1.49 g, 695 mmol) was added in portions. The mixture was warmed to room temperature and stirred for 2.5 h, then diluted with $H_2O$ (50 mL) and extracted with EtOAc (3×50 mL). The combined organic layers were washed with brine (2×50 mL), dried over anhydrous $Na_2SO_4$, filtered and the filtrate was concentrated under reduced pressure to give ethyl (2S,3S)-2-(bis(4-methoxybenzyl)amino)-3-(4-bromothiazol-2-yl)-3-(2-oxoethoxy)propanoate (1.2 g) as an oil, which was used directly in the next step without further purification. LCMS (ESI): m/z $[M+H]^+$ calc'd for $C_{26}H_{29}BrN_2O_6S$ 576.1 & 578.1. found 577.4 & 579.4.

Step 3.

To a mixture of ethyl (2S,3S)-2-(bis(4-methoxybenzyl) amino)-3-(4-bromothiazol-2-yl)-3-(2-oxoethoxy)propanoate (1.2 g, 2.1 mmol) in DCM (20 mL) at −15° C. under an atmosphere of $N_2$ was added DAST (0.37 g, 2.3 mmol) dropwise. The mixture was warmed to room temperature and stirred for 1.5 h, then re-cooled to 0° C. and further DAST (0.37 g, 2.3 mmol) added dropwise. The mixture was warmed to room temperature and stirred for 1 h, then cooled to 0° C. and saturated $NH_4Cl$ (2 mL) added. The mixture was diluted with $H_2O$ (20 mL) and extracted with DCM (3×20 mL). The combined organic layers were washed with brine (2×50 mL), dried over anhydrous $Na_2SO_4$ and filtered. The filtrate was concentrated under reduced pressure and the residue was purified by preparative-TLC to give ethyl (2S, 3S)-2-(bis(4-methoxybenzyl)amino)-3-(4-bromothiazol-2-yl)-3-(2,2-difluoroethoxy)propanoate (270 mg, 22% yield) as an oil. LCMS (ESI): m/z $[M+H]^+$ calc'd for $C_{26}H_{29}BrF_2N_2O_5S$ 598.1 & 600.1. found 599.1 & 601.1.

Step 4.

A mixture of ethyl (2S,3S)-2-(bis(4-methoxybenzyl) amino)-3-(4-bromothiazol-2-yl)-3-(2,2-difluoroethoxy)propanoate (240 mg, 0.40 mmol) in TFA (3 mL) was heated to 80° C. and stirred for 8 h, then concentrated under reduced pressure to give ethyl (2S,3S)-2-amino-3-(4-bromothiazol-2-yl)-3-(2,2-difluoroethoxy)propanoate (245 mg) as an oil, that was used directly in the next step without further purification. LCMS (ESI): m/z $[M+H]^+$ calc'd for $C_{10}H_{31}BrF_2N_2O_3S$ 358.0 & 360.0. found 359.0 & 361.0.

Step 5.

To a mixture of ethyl (2S,3S)-2-amino-3-(4-bromothiazol-2-yl)-3-(2,2-difluoroethoxy)propanoate (230 mg, 0.64 mmol) and $NaHCO_3$ (108 mg, 1.29 mmol) in $H_2O$ (0.9 mL) and THF (3 mL) was added $(Boc)_2O$ (147 mg, 0.67 mmol). The mixture was stirred at room temperature overnight, then diluted with $H_2O$ (10 mL) and extracted with EtOAc (3×10 mL). The combined organic layers were washed with brine (3×20 mL), dried over anhydrous $Na_2SO_4$ and filtered. The filtrate was concentrated under reduced pressure and the residue was purified by preparative-TLC to give ethyl (2S, 3S)-3-(4-bromothiazol-2-yl)-2-((tert-butoxycarbonyl) amino)-3-(2,2-difluoroethoxy)propanoate (145 mg, 49% yield) as a solid. LCMS (ESI): m/z $[M+H]^+$ calc'd for $C_{15}H_{21}BrF_2N_2O_5S$ 458.0 & 460.0. found 459.0 & 461.0.

Step 6.

To a mixture of ethyl (2S,3S)-3-(4-bromothiazol-2-yl)-2-((tert-butoxycarbonyl)amino)-3-(2,2-difluoroethoxy)propanoate (140 mg, 0.31 mmol) in THF (1.5 mL) at 0° C. was added $LiOH \cdot H_2O$ (64 mg, 1.53 mmol) in $H_2O$ (1.5 mL) dropwise. The mixture was warmed to room temperature and stirred for 1 h, then acidified to pH~5 with aqueous HCl, then extracted with EtOAc (3×10 mL). The combined organic layers were washed with brine (3×20 mL), dried over anhydrous $Na_2SO_4$, filtered and the filtrate was concentrated under reduced pressure to give (2S,3S)-3-(4-bromothiazol-2-yl)-2-((tert-butoxycarbonyl)amino)-3-(2,2-difluoroethoxy)propanoic acid (100 mg) as an oil. LCMS (ESI): m/z $[M+H]^+$ calc'd for $C_{13}H_{17}BrF_2N_2O_5S$ 430.0 & 432.0. found 431.0 & 433.0.

Step 7.

To a mixture of 3-(1-ethyl-2-(2-((S)-1-methoxyethyl) pyridin-3-yl)-5-(4,4,5,5-tetramethyl-1,3,2-dioxaborolan-2-yl)-1H-indol-3-yl)-2,2-dimethylpropyl-(S)-hexahydro-pyridazine-3-carboxylate (134 mg, 0.22 mmol) and NMM (335 mg, 3.32 mmol) in DCM (6 mL) at 0° C. under an atmosphere of $N_2$ was added (2S,3S)-3-(4-bromothiazol-2-yl)-2-((ter-butoxycarbonyl)amino)-3-(2,2-difluoroethoxy) propanoic acid (95 mg, 0.22 mmol) and HOET (6 mg, 0.04 mmol) and EDCI (85 mg, 0.44 mmol). The mixture was warmed to room temperature and stirred overnight, then diluted with $H_2O$ (10 mL) and extracted with DCM (3×10 mL). The combined organic layers were washed with brine (3×20 mL), dried over anhydrous $Na_2SO_4$ and filtered. The filtrate was concentrated under reduced pressure and the residue was purified by preparative-TLC to give 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl-(S)-1-((2S,3S)-3-(4-bromothiazol-2-yl)-2-((tert-butoxycarbonyl)amino)-3-(2,2-difluoroethoxy)propanoyl) hexahydropyridazine-3-carboxylate (70 mg, 36% yield) as a solid. LCMS (ESI): m/z $[M+H]^+$ calc'd for $C_{47}H_{64}BBrF_2N_6O_9S$ 1016.4 & 1018.4. found 1017.3 & 1019.4.

Step 8.

To a mixture of mixture of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl-(S)-1-((2S,3S)-3-(4-bromothiazol-2-yl)-2-((tert-butoxycarbonyl) amino)-3-(2,2-difluoroethoxy)propanoyl) hexahydropyridazine-3-carboxylate (50 mg, 0.05 mmol) and $K_3PO_4$ (31 mg, 0.15 mmol) in toluene (3 mL), 1,4-dioxane (1 mL) and $H_2O$ (1 mL) under an atmosphere of $N_2$ was added Pd(DtBPF)$Cl_2$ (13 mg, 0.02 mmol) in portions. The mixture was heated to 60° C. and stirred for 1 h, then was extracted with EtOAc (3×10 mL). The combined organic layers were washed with brine (3×20 mL), dried over anhydrous $Na_2SO_4$ and filtered. The filtrate was concentrated under reduced pressure and the residue was purified by preparative-TLC to give tert-butyl (($6^3$S,3S,4S,Z)-3-(2,2-difluoroethoxy)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (27 mg, 59% yield) as a solid. LCMS (ESI): m/z $[M+H]^+$ calc'd for $C_{41}H_{52}F_2N_6O_7S$ 810.4. found 811.4.

Step 9.

To a mixture tert-butyl (($6^3$S,3S,4S,Z)-3-(2,2-difluoroethoxy)-$1^1$-ethyl-$1^2$-(2-((S)-1-methoxyethyl)pyridin-3-yl)-10, 10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (25 mg, 0.02 mmol) in DCM (1.5 mL) at 0° C. was added TFA (0.5 mL) dropwise. The mixture was warmed to room temperature and stirred for 1 h, then concentrated under reduced pressure to give ($6^3$S,3S,4S,Z)-4-amino-3-(2,2-difluoroethoxy)-$1^1$-ethyl-12-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (25 mg) as a solid, which was used directly in the next step without further purification. LCMS (ESI): m/z $[M+H]^+$ calc'd for $C_{36}H_{44}F_2N_8O_5S$ 710.3. found 711.3.

Step 10.

To a mixture of ($6^3$S,3S,4S,Z)-4-amino-3-(2,2-difluoroethoxy)-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (25 mg, 0.04 mmol) and (1r,2R,3S)-2,3-dimethylcyclopropane-1-carboxylic acid (6 mg, 0.05 mmol) in DMF (1 mL) at 0° C. under an atmosphere of $N_2$ was added DIPEA (45 mg, 0.35 mmol) and HATU (27 mg, 0.07 mmol) in portions. The mixture was warmed to room temperature and stirred for 2 h, then $H_2O$ (10 mL) added and the mixture was extracted with EtOAc (3×10 mL). The combined organic layers were washed with brine (3×20 mL), dried over anhydrous $Na_2SO_4$ and filtered. The filtrate was concentrated under reduced pressure and the residue was purified by preparative-HPLC to give (1r,2R, 3S)—N-(($6^3$S,3S,4S,Z)-3-(2,2-difluoroethoxy)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (3.3 mg, 12% yield) as a solid. LCMS (ESI): m/z $[M+H]^+$ calc'd for $C_{42}H_{52}F_2N_6O_6S$ 806.4. found 807.2; $^1$H NMR (400 MHz, DMSO-$d_6$) δ 8.95-8.70 (m, 1H), 8.50 (s, 1H), 8.13 (s, 1H), 7.95 (s, 1H), 7.88-7.79 (m, 2H), 7.76 (d, J=8.6 Hz, 1H), 7.59 (d, J=8.7 Hz, 1H), 7.54 (dd, J=7.7, 4.8 Hz, 1H), 7.27-6.88 (m, 1H), 6.36-6.04 (m, 1H), 5.97 (d, J=9.9 Hz, 1H), 5.20 (d, J=12.8 Hz, 2H), 4.25 (dd, J=20.3, 10.5 Hz, 4H), 4.14-3.92 (m, 2H), 3.92-3.73 (m, 1H), 3.59 (q, J=10.9 Hz, 2H), 3.20 (s, 3H), 2.81 (d, J=13.7 Hz, 2H), 2.12-1.93 (m, 1H), 1.78 (d, J=23.7 Hz, 2H), 1.59-1.45 (m, 2H), 1.38 (d, J=6.1 Hz, 3H), 1.21 (d, J=20.3 Hz, 1H), 1.16-1.01 (m, 7H), 0.95-0.73 (m, 6H), 0.43 (s, 3H).

Example A389. Synthesis of (1r,2R,3S)—N-(($6^3$S, 3S,4S,Z)-3-ethoxy-$1^1$-ethyl-$1^2$-(2-((S)-1-methoxy-ethyl)-5-((8S,9aS)-octahydropyrido[2,1-c][1,4] oxazin-8-yl)pyridin-3-yl)-10,10-dimethyl-5,7-dioxo-$6^1$,$6^2$,$6^3$,$6^4$,$6^5$,$6^6$-hexahydro-$^1$H-8-oxa-2(4,2)-thiazola-1(5,3)-indola-6(1,3)-pyridazinacycloundecaphane-4-yl)-2,3-dimethylcyclopropane-1-carboxamide

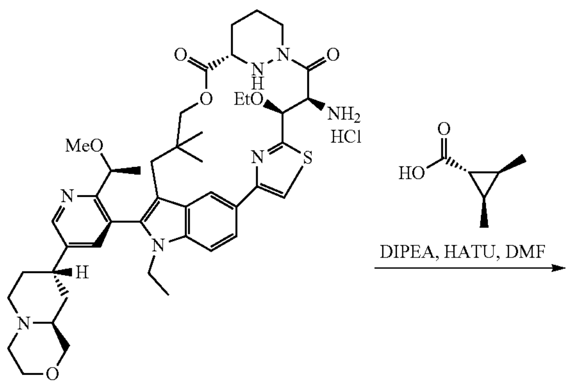

-continued

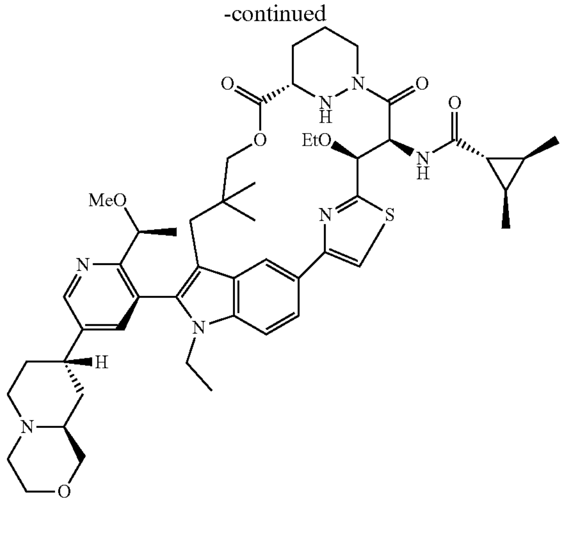

Step 1.

To a mixture of ($6^3$S,3S,4S,Z)-4-amino-3-ethoxy-$1^1$-ethyl-$1^2$-(2-((S)-1-methoxyethyl)-5-((8S,9aS)-octahydropyrido[2,1-c][1,4]oxazin-8-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione HCl salt (90 mg, 0.11 mmol) and (1R,2R,3S)-2,3-dimethylcyclopropane-1-carboxylic acid (19 mg, 0.17 mmol) in DMF (3 mL) at 0° C. was added DIPEA (429 mg, 3.3 mmol) and HATU (63 mg, 0.17 mmol) in portions. The mixture was warmed to room temperature and stirred for 2 h, then diluted with $H_2O$ (10 mL) and the mixture was extracted with EtOAc (2×10 mL). The combined organic layers were washed with brine (3×10 mL), then concentrated under reduced pressure and the residue was purified by preparative-HPLC to give (1r,2R,3S)—N-(($6^3$S,3S,4S,Z)-3-ethoxy-$1^1$-ethyl-$1^2$-(2-((S)-1-methoxyethyl)-5-((8S,9aS)-octahydropyrido[2,1-c][1,4]oxazin-8-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (13.8 mg, 13% yield) as a solid. LCMS (ESI): m/z $[M+H]^+$ calc'd for $C_{50}H_{67}N_7O_7S$ 909.5. found 910.7; $^1H$ NMR (400 MHz, DMSO-$d_6$) δ 8.77 (s, 1H), 8.50 (s, 1H), 7.93 (s, 1H), 7.83-7.51 (m, 4H), 5.96-5.77 (m, 1H), 5.17 (d, J=11.5 Hz, 1H), 4.92 (s, 1H), 4.45-4.03 (m, 5H), 3.57 (ddd, J=34.6, 24.2, 13.9 Hz, 8H), 3.23 (d, J=8.3 Hz, 4H), 3.08 (d, J=10.4 Hz, 2H), 2.84 (d, J=45.9 Hz, 3H), 2.67 (s, 2H), 2.23 (s, 2H), 2.17-2.01 (m, 7H), 1.81 (s, 3H), 1.53 (s, 4H), 1.45-1.30 (m, 4H), 124 (s, 1H), 1.16 (td, J=7.0, 1.9 Hz, 4H), 1.06 (dd, J=12.1, 5.1 Hz, 6H), 0.97-0.76 (m, 8H), 0.38 (s, 3H).

Example A390. Synthesis of (1r,2R,3S)—N-(($6^3$S,3S,4S,Z)-3-ethoxy-$1^1$-ethyl-$1^2$-(2-((S)-1-methoxyethyl)-5-((8R,9aS)-octahydropyrido[2,1-c][1,4]oxazin-8-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide

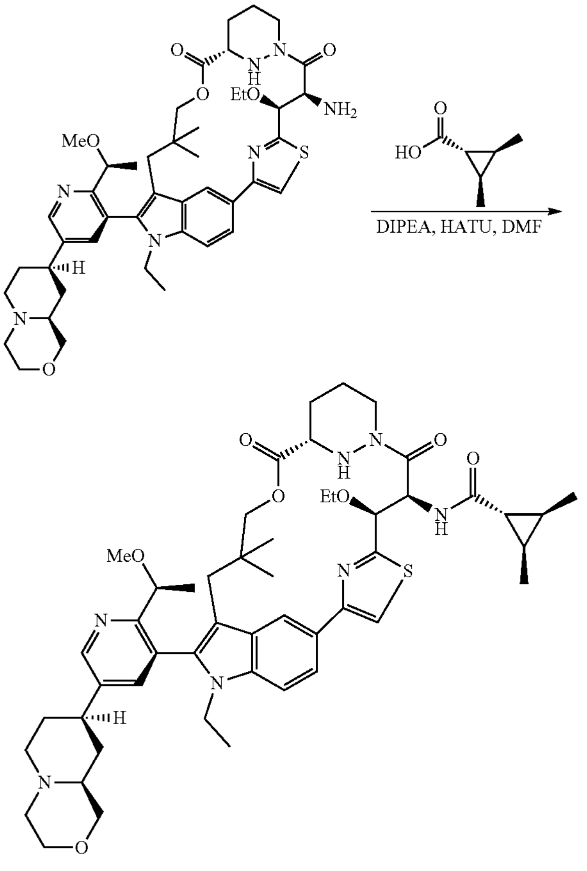

Step 1.

To a mixture of ($6^3$S,3S,4S,Z)-4-amino-3-ethoxy-$1^1$-ethyl-$1^2$-(2-((S)-1-methoxyethyl)-5-((8R,9aS)-octahydropyrido[2,1-c][1,4]oxazin-8-yl)pyridin-3-yl)-10,10Q-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (100 mg, 0.12 mmol) and (1R,2R,3S)-2,3-dimethylcyclopropane-1-carboxylic acid (21 mg, 0.18 mmol) in DMF (3 mL) at −10° C. under an atmosphere of $N_2$ was added DIPEA (476 mg, 3.7 mmol) and HATU (56 mg, 0.15 mmol, 1.2 equiv) in portions. The mixture was stirred at −10° C. for 1.5 h, then diluted with brine (5 mL) and extracted with EtOAc (3×10 mL). The combined organic layers were washed with brine (3×10 mL), dried over anhydrous $Na_2SO_4$ and the filtered. The filtrate was concentrated under reduced pressure and the residue was purified by preparative-HPLC to give (1r,2R,3S)—N-(($6^3$S,3S,4S,Z)-3-ethoxy-$1^1$-ethyl-$1^2$-(2-((S)-1-methoxyethyl)-5-((8R,9aS)-octahydropyrido[2,1-c][1,4]oxazin-8-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (22 mg, 20% yield) as a solid. LCMS (ESI): m/z $[M+H]^+$ calc'd for $C_{50}H_{67}N_7O_7S$ 909.5. found 910.7; $^1$H NMR (400 MHz, DMSO-$d_6$) δ 8.65 (d, J=2.1 Hz, 1H), 8.49 (s, 1H), 7.92 (s, 1H), 7.74 (d, J=8.5 Hz, 1H), 7.68-7.54 (m, 3H), 5.88 (d, J=9.8 Hz, 1H), 5.17 (d, J=12.1 Hz, 1H), 4.93 (s, 1H), 436-3.99 (m, 5H), 3.80-3.43 (m, 7H), 3.24-3.05 (m, 4H), 2.92-2.72 (m, 4H), 2.70-2.59 (m, 1H), 2.28-1.99 (m, 5H), 1.89-1.59 (m, 6H), 1.52 (q, J=8.2, 6.3 Hz, 2H), 1.42-1.22 (m, 5H), 1.20-099 (m, 12H), 0.86 (d, J=25.0 Hz, 7H), 0.39 (s, 3H).

Example A391. Synthesis of (1r,2R,3S)—N-(($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)-2,3-dimethylcyclopropane-1-carboxamide

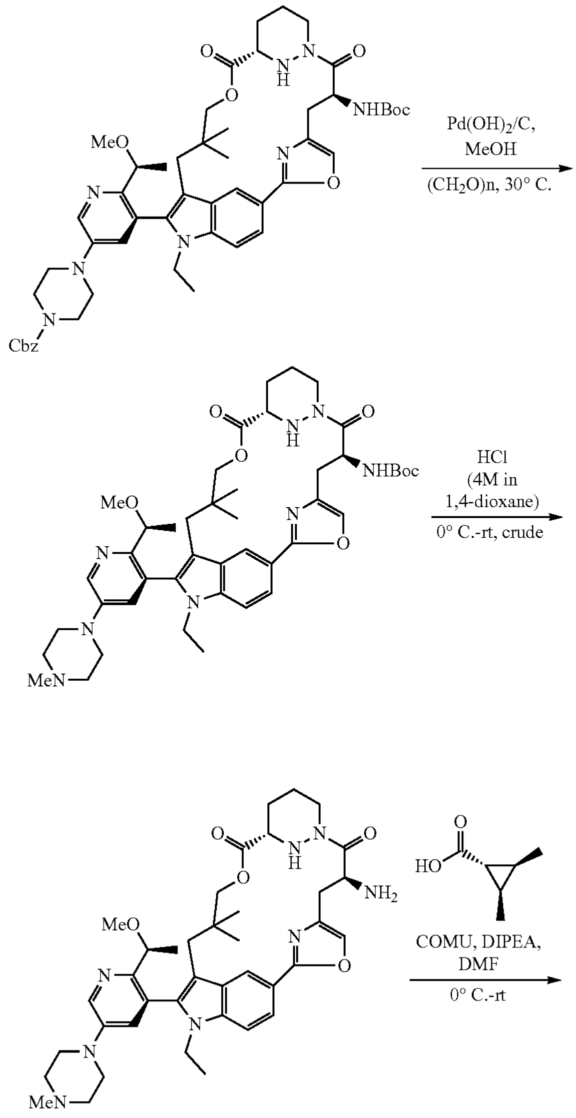

-continued

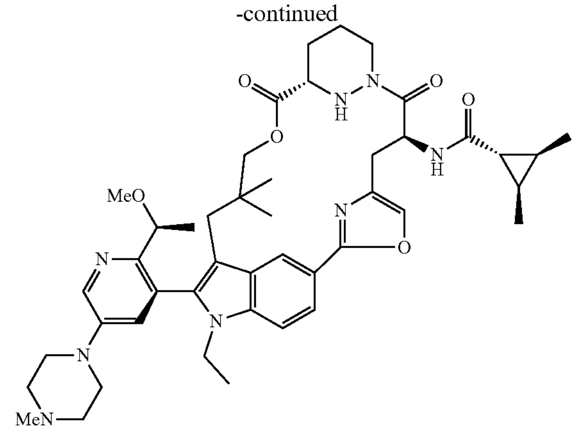

Step 1.

A mixture of benzyl 4-(5-(($6^3$S,4S,Z)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-$1^2$-yl)-6-((S)-1-methoxyethyl)pyridin-3-yl)piperazine-1-carboxylate (150 mg, 0.16 mmol), paraformaldehyde (36 mg, 0.81 mmol) and $Pd(OH)_2$, 30% weight on carbon (151 mg, 0.32 mmol) in MeOH (3 mL) was hydrogenated at 30° C. for 2 h. The mixture was filtered through a pad of Celite and the filtrate was concentrated under reduced pressure to give tert-butyl (($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)carbamate (134 mg) as a solid. LCMS (ESI): m/z $[M+H]^+$ calc'd for $C_{44}H_{60}N_8O_7$ 812.5. found 813.4.

Step 2.

To a mixture of tert-butyl (($6^3$S,4S,Z)-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)carbamate (134 mg, 0.17 mmol) in DCM (1.5 mL) at 0° C. was added TFA (1.50 mL) in portions. The mixture was warmed to room temperature and stirred for 2 h, then concentrated under reduced pressure to give ($6^3$S,4S,Z)-4-amino-$1^1$-ethyl-$1^2$-(2-((S)-1-methoxyethyl)-5-(4-methylpiperazin-1-yl)pyridin-3-yl)-10,10-dimethyl-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-5,7-dione (318 mg) as an oil. LCMS (ESI): m/z $[M+H]^+$ calc'd for $C_{39}H_{52}N_8O_5$ 712.4. found 713.4.

Step 3.

To a mixture of ($6^3$S,4S,Z)-4-amino-$1^1$-ethyl-$1^2$-(2-((S)-1-methoxyethyl)-5-(4-methylpiperazin-1-yl)pyridin-3-yl)-10,10-dimethyl-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-5,7-dione (130 mg, 0.18 mmol), (1R,2R,3S)-2,3-dimethylcyclopropane-1-carboxylic acid (42 mg, 0.36 mmol) and DIPEA (236 mg, 1.8 mmol) in DMF (2 mL) at 0° C. was added COMU (117 mg, 0.27 mmol) in portions. The mixture was warmed to room temperature and stirred for 2 h, then the residue was purified by preparative-HPLC to give (1r,2R,3S)—N-(($6^3$S,4S,Z)-$1^1$-ethyl-A2-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)-2,3-dimethylcyclopropane-1-carboxamide (28 mg, 19% yield)

as a solid. LCMS (ESI): m/z $[M+H]^+$ calc'd for $C_{45}H_{60}N_8O_6$ 808.5. found 809.8; $^1H$ NMR (300 MHz, DMSO-$d_6$) δ 8.66-8.45 (m, 2H), 8.29 (d, J=8.0 Hz, 1H), 7.88 (s, 1H), 7.74 (d, J=9.4 Hz, 2H), 7.30 (s, 1H), 5.81 (s, 1H), 5.00 (d, J=11.7 Hz, 1H), 4.53-4.06 (nm, 5H), 3.77-3.59 (m, 2H), 3.34 (s, 4H), 3.21 (s, 3H), 305-2.61 (m, 5H), 2.52 (s, 4H), 2.28 (s, 3H), 2.05 (s, 1H), 1.83 (s, 1H), 1.56 (s, 2H), 1.48-1.32 (m, 3H), 1.30-0.98 (m, 12H), 0.93 (s, 3H), 0.46 (s, 3H).

Example A396. Synthesis of (2S)—N-(($6^3$S,3S,4S,Z)-3-ethoxy-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-((R)-1-hydroxyethyl)azetidine-1-carboxamide

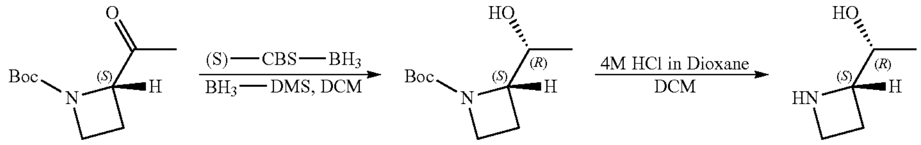

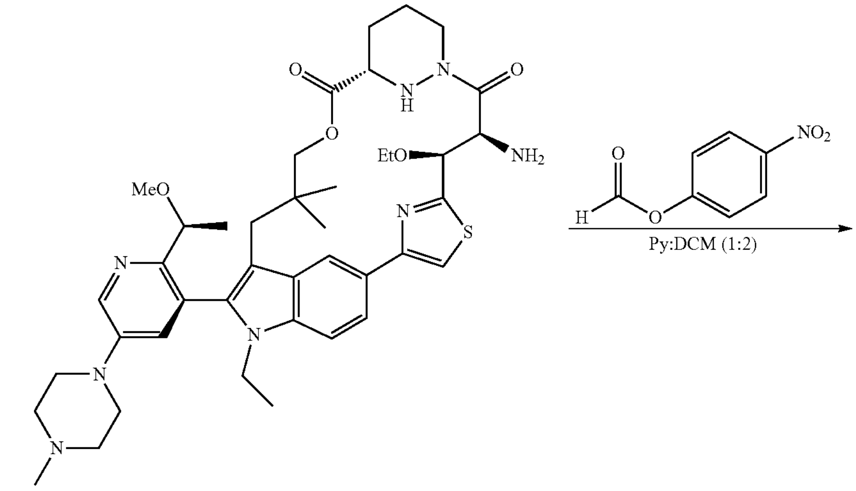

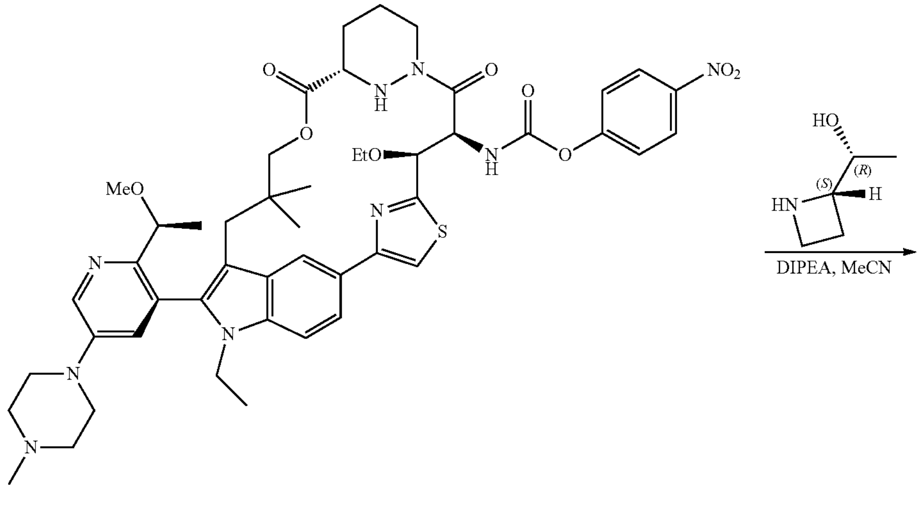

-continued

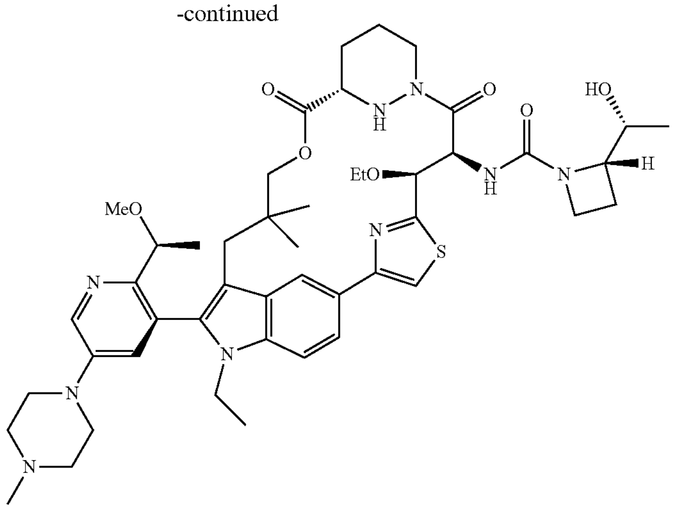

Step 1.

To a mixture of tert-butyl (S)-2-acetylazetidine-1-carboxylate (543 mg, 1.96 mmol) in DCM (330 mL) at room temperature under an atmosphere of $N_2$ was added $BH_3$-$Me_2S$ (2.48 g, 32.6 mmol). To the above mixture was added tert-butyl (2S)-2-acetylazetidine-1-carboxylate [*Org. Lett.* 2019, 22, 9981-9984—see Supporting Information](2.6 g, 13.0 mmol) dropwise over 10 min. The resulting mixture was stirred for additional 2 h at room temperature. The reaction was monitored by LCMS. The reaction was quenched with MeOH at 0° C. and was concentrated under reduced pressure. The residue was purified by silica gel column chromatography to give tert-butyl (S)-2-((R)-1-hydroxyethyl)azetidine-1-carboxylate (1.1 g, 42% yield) as an oil. LCMS (ESI): m/z [M−$C_4H_8$+H]r calc'd for $C_6H_{11}NO_3$ 145.1. found 146.1.

Step 2.

To a mixture of tert-butyl (S)-2-((R)-1-hydroxyethyl) azetidine-1-carboxylate (300 mg, 1.49 mmol) in DCM (5 mL) at 0° C. was added 4M HCl in 1,4-dioxane (5 mL). The mixture was stirred until completion, then concentrated under reduced pressure to give (R)-1-((S)-azetidin-2-yl) ethan-1-ol (310 mg) as a solid, which was used directly in the next step without further purification. LCMS (ESI): m/z $[M+H]^+$ calc'd for $C_5H_{11}NO$ 101.1. found 102.2.

Step 3.

To a mixture of ($6^3$S,3S,4S,Z)-4-amino-3-ethoxy-$1^1$-ethyl-$1^2$-(2-((S)-1-methoxyethyl)-5-(4-methylpiperazin-1-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (150 mg, 0.19 mmol), pyridine (1 mL), and DCM (2 mL) at 0° C. was added 4-nitrophenyl chloroformate (65 mg, 0.39 mmol). The mixture was warmed to room temperature and stirred for 4 h, then concentrated under reduced pressure to give 4-nitrophenyl (($6^3$S,3S,4S,Z)-3-ethoxy-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (crude) as an oil, which was used directly in the next step without further purification. LCMS (ESI): m/z $[M+H]^+$ calc'd for $C_{48}H_{59}N_9O_9S$ 937.4. found 938.3.

Step 4.

To a mixture of 4-nitrophenyl (($6^3$S,3S,4S,Z)-3-ethoxy-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (195 mg, 0.21 mmol) and (R)-1-((S)-azetidin-2-yl)ethan-1-ol (285 mg, 2.8 mmol) in MeCN (2 mL) at 0° C. was added DIPEA (403 mg, 3.1 mmol) dropwise. The mixture was warmed to room temperature and stirred for 1 h. The residue was purified by preparative-HPLC to give (2S)—N-(($6^3$S,3S,4S,Z)-3-ethoxy-$1^1$-ethyl-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-((R)-1-hydroxyethyl)azetidine-1-carboxamide (4.8 mg, 3%) as a solid. LCMS (ESI): m/z $[M+H]^+$ calc'd for $C_{47}H_{59}N_9O_7S$ 899.5. found 900.9; $^1$H NMR (400 MHz, DMSO-$d_6$) δ 8.52-8.45 (m, 2H), 7.91 (s, 1H), 7.76-7.72 (m, 1H), 7.58-7.53 (m, 1H), 7.22 (s, 1H), 6.73-6.68 (m, 1H), 5.54-5.50 (m, 1H), 5.31-5.26 (m, 1H), 5.16-5.12 (m, 1H), 4.91 (s, 1H), 4.30-4.24 (m, 3H), 4.16-4.04 (m, 3H), 3.84-3.67 (m, 2H), 3.69-3.41 (m, 5H), 3.28-3.23 (m, 4H), 3.16 (s, 3H), 2.84-2.79 (m, 2H), 2.48-2.44 (m, 4H), 2.23-2.21 (m, 4H), 2.08-2.05 (m, 1H), 1.93-1.89 (m, 1H), 1.79-1.77 (m, 2H), 1.54-1.52 (m, 1H), 1.36-1.33 (m, 3H), 1.26-1.16 (m, 4H), 1.13-1.10 (m, 3H), 1.00-0.73 (m, 6H), 0.43 (s, 2H).

Examples A424 and A441. Synthesis of (1R,2R,3S)—N-(($2^3$S,$6^3$S,4S)-$1^1$-ethyl-$2^3$-hydroxy-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)-2,3-dimethylcyclopropane-1-carboxamide and (1R,2R,3S)—N-(($2^3$R,6S,4S)-$1^1$-ethyl-$2^3$-hydroxy-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)-2,3-dimethylcyclopropane-1-carboxamide

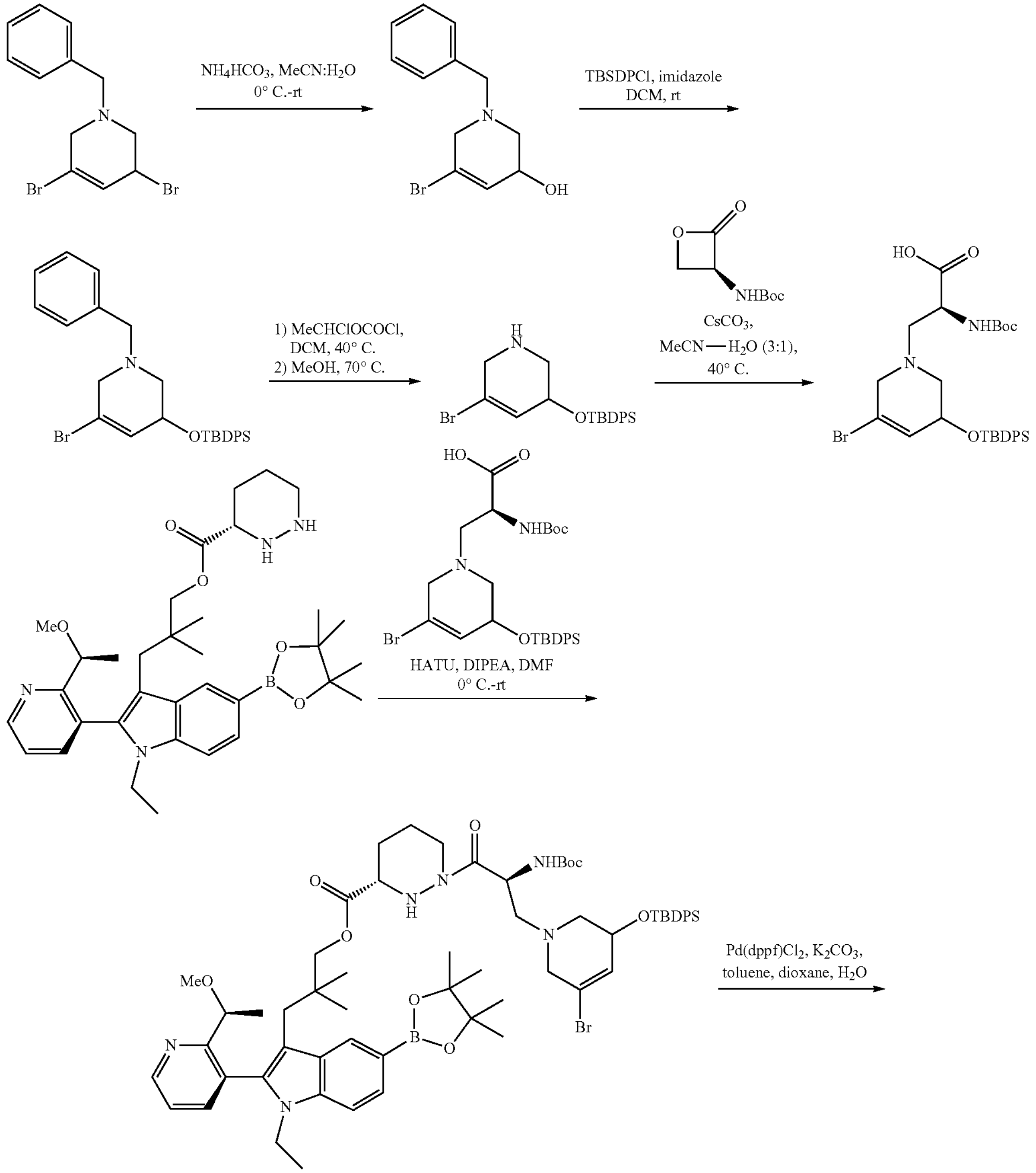

-continued
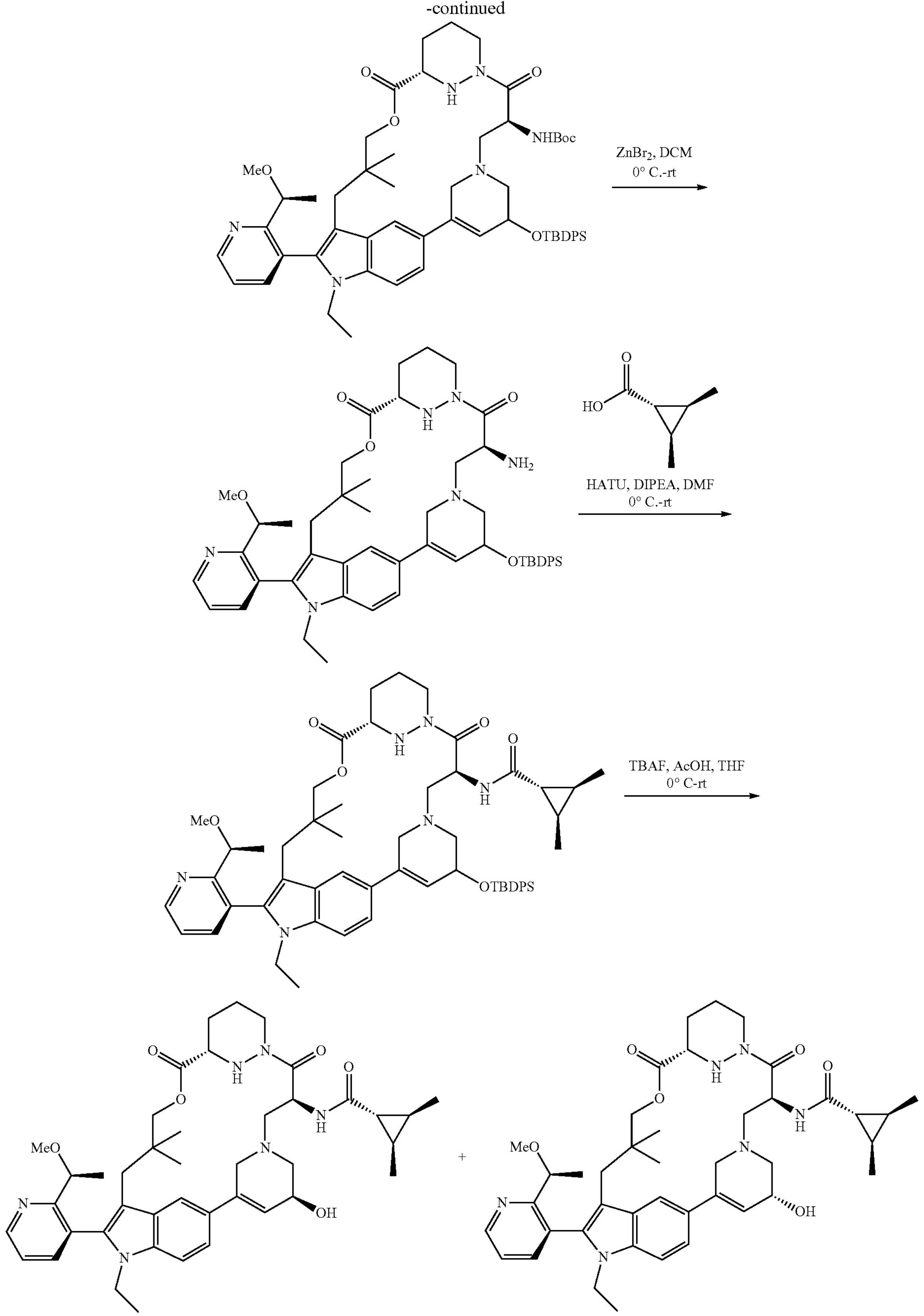

Step 1.

To a mixture of 1-benzyl-3,5-dibromo-1,2,3,6-tetrahydropyridine (40.0 q, 120.8 mmol) in MeCN (900 mL) and $H_2O$ (600 mL at 0° C. was added $NH_4HCO_3$ (14.33 g, 181.2 mmol). The mixture was warmed to room temperature and stirred for 16 h, then concentrated under reduced pressure and the residue was purified by reverse-phase silica gel column chromatography to give 1-benzyl-5-bromo-1,2,3,6-tetrahydropyridin-3-ol (16.0 g. 49% yield) as an oil. LCMS (ESI): m/z $[M+H]^+$ calc'd for $C_{12}H_{14}BrNO$ 267.0. found 268.1.

Step 2.

To a mixture of 1-benzyl-5-bromo-1,2,3,6-tetrahydropyridin-3-ol (15.0 g, 55.9 mmol) in DCM (150 mL) was added TBDPSCl (23.1 g, 83.9 mmol) and imidazole (7.62 g, 111.9 mmol) under an atmosphere of $N_2$ for 16 h. $H_2O$ was added and the mixture and was extracted with EtOAc (3×300 mL). The combined organic layers were washed with brine (3×300 mL); dried over anhydrous $Na_2SO_4$ and filtered. The filtrate was concentrated under reduced pressure and the residue was purified by reverse-phase silica gel column chromatography to give 1-benzyl-5-bromo-3-((tert-butyldiphenylsilyl)oxy)-1,2,3,6-tetrahydropyridine (15.0 g, 53% yield) as an oil. LCMS (ESI): m/z $[M+H]^+$ calc'd for $C_{28}H_{32}BrNOSi$ 505.1. found 506.2.

Step 3.

To a mixture of 1-benzyl-5-bromo-3-((tert-butyldiphenylsilyl)oxy)-1,2,3,6-tetrahydropyridine (15.0 g, 29.6 mmol) in DCM (150 mL) at 0° C. was added 2-chloroethyl chloroformate (16.93 g, 118.5 mmol). The mixture was warmed to 40° C. and was stirred for 4 h, then diluted with $H_2O$ and the mixture was extracted with EtOAc (2×300 mL). The combined organic layers were washed with brine (2×300 mL), dried over anhydrous $Na_2SO_4$ and filtered. The filtrate was concentrated under reduced pressure and the residue was dissolved in MeOH (150 mL). The mixture was heated to 70° C. and stirred for 2 h, then the combined organic layers were washed with $NaHCO_3$ (2×300 mL), dried over anhydrous $Na_2SO_4$ and filtered. The filtrate was concentrated under reduced pressure and the residue was purified by reverse-phase silica gel column chromatography to give 5-bromo-3-((tert-butyldiphenylsilyl)oxy)-1,2,3,6-tetrahydropyridine (9.0 g, 73% yield) as an oil. LCMS (ESI): m/z $[M+H]^+$ calc'd for $C_{21}H_{26}BrNOSi$ 417.1. found 418.0 [for $^{81}Br$].

Step 4.

To a mixture of 5-bromo-3-((tert-butyldiphenylsilyl)oxy)-1,2,3,6-tetrahydropyridine (6.0 g, 14.4 mmol) in MeCN (60 mL) and $H_2O$ (60 mL) at 0° C. was added tert-butyl (S)-(2-oxooxetan-3-yl)carbamate (2.97 g, 15.9 mmol) and $Cs_2CO_3$ (11.74 g, 36.0 mmol). The mixture was warmed to 40° C. and stirred for 16 h, then extracted with EtOAc (2×100 mL). The combined organic layers were washed with brine (3×200 mL), dried over anhydrous $Na_2SO_4$ and filtered. The filtrate was concentrated under reduced pressure and the residue was purified by reverse-phase silica gel column chromatography to give (2S)-3-(5-bromo-3-((tert-butyldiphenylsilyl)oxy)-3,6-dihydropyridin-1(2H)-yl)-2-((tert-butoxycarbonyl)amino)propanoic acid (4.0 g, 46% yield) as a solid. LCMS (ESI): m/z $[M+H]^+$ calc'd for $C_{29}H_{39}BrN_2O_5Si$ 602.2. found 603.1.

Step 5.

To a mixture of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (S)-hexahydropyridazine-3-carboxylate (1.0 g, 1.7 mmol) in DMF (10 mL) at 0° C. was added DIPEA (1.07 g, 8.3 mmol), (2S)-3-(5-bromo-3-((tert-butyldiphenylsilyl)oxy)-3,6-dihydropyridin-1(2H)-yl)-2-((tert-butoxycarbonyl)amino)propanoic acid (749 mg, 1.24 mmol) and HATU (1.26 g, 3.3 mmol). The mixture was stirred at 0° C. for 2 h, then diluted with $H_2O$, and the mixture was extracted with EtOAc (3×100 mL). The combined organic layers were washed with brine (3×100 mL), dried over anhydrous $Na_2SO_4$ and filtered. The filtrate was concentrated under reduced pressure and the residue was purified by preparative-TLC to give 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl-(3S)-1-((2S)-3-(5-bromo-3-((tert-butyldiphenylsilyl)oxy)-3,6-dihydropyridin-1(2H)-yl)-2-((tert-butoxycarbonyl)amino)propanoyl)hexahydropyridazine-3-carboxylate (1.2 g, 61% yield) as an oil. LCMS (ESI): m/z $[M+H]^+$ calc'd for $C_{63}H_{86}BBrN_6O_9Si$ 1188.6. found 1189.4.

Step 6.

To a mixture of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl-(3S)-1-((2S)-3-(5-bromo-3-(tert-butyldiphenylsilyl)oxy)-3,6-dihydropyridin-1(2H)-yl)-2-((tert-butoxycarbonyl)amino)propanoyl)hexahydropyridazine-3-carboxylate (1.2 g, 1.0 mmol) in toluene (30 mL), 1,4-dioxane (10 mL) and $H_2O$ (10 mL) was added $K_2CO_3$ (418 mg, 3.0 mmol) and $Pd(dppf)Cl_2$ (74 mg, 0.1 mmol). The mixture was heated to 65° C. and stirred for 2 h, then diluted with $H_2O$, and the mixture was extracted with EtOAc (2×100 mL). The combined organic layers were washed with brine (2×100 mL), dried over anhydrous $Na_2SO_4$ and filtered. The filtrate was concentrated under reduced pressure and the residue was purified by preparative-TLC to give tert-butyl (($6^3$S,4S)-$2^3$-((tert-butyldiphenylsilyl)oxy)-$1^1$-ethyl-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)- pyridinacycloundecaphane-4-yl)carbamate (420 mg, 42% yield) as an oil. LCMS (ESI): m/z $[M+H]^+$ calc'd for $C_{57}H_{74}N_6O_7Si$ 982.5. found 984.1.

Step 7.

To a mixture of tert-butyl (($6^{3}$'S,4S)-$2^3$-((tert-butyldiphenylsilyl)oxy)-$1^1$-ethyl-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)carbamate (420 mg, 0.43 mmol) in DCM (10 mL) at 0° C. was added $ZnBr_2$ (481 mg, 2.14 mmol). The mixture was warmed to room temperature and stirred for 16 h, then filtered, and the filter cake was washed with EtOAc (3×20 mL). The filtrate was concentrated under reduced pressure to give ($6^3$S,4S)-4-amino-$2^3$-((tert-butyldiphenylsilyl)oxy)-$1^1$-ethyl-$1'^2$-(2-((S)-1-methoxyethyl)pyridin-3-yl)-10,10-dimethyl-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)- pyridinacycloundecaphane-5,7-dione (400 mg) which was used directly in the next step without further purification. LCMS (ESI): m/z $[M+H]^+$ calc'd for $C_{52}H_{66}N_6O_5Si$ 882.5. found 883.6.

Step 8.

To a mixture of ($6^3$S,4S)-4-amino-$2^3$-((tert-butyldiphenylsilyl)oxy)-$1^1$-ethyl-$1^2$-(2-((S)-1-methoxyethyl)pyridin-3-yl)-10,10-dimethyl-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-5,7-dione (380 mg, 0.43 mmol) in DMF (4 mL) at 0° C. was added DIPEA (556 mg, 4.3 mmol), (1R,2R,3S)-2,3-dimethylcyclopropane-1-carboxylic acid (74 mg, 0.65 mmol) and HATU (327 mg, 0.86 mmol). The mixture was stirred at 0° C. for 2 h, then diluted with $H_2O$, and the mixture was extracted with EtOAc (3×50 mL). The combined organic layers were washed with brine (3×50 mL), dried over anhydrous $Na_2SO_6$ and filtered. The filtrate was concentrated under reduced pressure and the residue was purified by preparative-TLC to give (1R,2R,3S)—N-(($6^3$S,4S)-$2^3$-((tert-butyldiphenylsilyl)oxy)-$1^1$-ethyl-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)- pyridinacycloundecaphane-4-yl)-2,3-dimethylcyclopropane-1-carboxamide (190 mg, 45% yield) as a solid. LCMS (ESI): m/z $[M+H]^+$ calc'd for $C_{58}H_{74}N_6O_6Si$ 978.5. found 979.7.

Step 9.

To a mixture of (1R,2R,3S)—N-(($6^3$S,4S)-$2^3$-((tert-butyldiphenylsilyl)oxy)-$1^1$-ethyl-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)-2,3-dimethylcyclopropane-1-carboxamide (190 mg, 0.19 mmol) in THF (4 mL) at 0° C. was added TBAF (811 mg, 3.1 mmol) and AcOH (1 mg, 0.02 mmol). The mixture was warmed to room temperature and stirred for 16 h, then diluted with $H_2O$, and the mixture was extracted with EtOAc (3×50 mL). The combined organic layers were washed with brine (3×50 mL), dried over anhydrous $Na_2SO_4$ and filtered. The filtrate was concentrated under reduced pressure and the residue was purified by preparative-HPLC to give (1R,2R,3S)—N-(($2^3$S,$6^3$S,4S)-$1^1$-ethyl-$2^3$-hydroxy-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)-2,3-dimethylcyclopropane-1-carboxamide (26 mg, 13% yield) and (1R,2R,3S)—N-(($2^3$R,$6^3$S,4S)-$1^1$-ethyl-$2^3$-hydroxy-$1^2$-(2-((S)-1-methoxyethyl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)-2,3-dimethylcyclopropane-1-carboxamide (11 mg, 8% yield) both as solids. LCMS (ESI): m/z $[M+H]^+$ calc'd for $C_{42}H_{56}N_6O_6$ 740.4. found 741.3; $^1H$ NMR (400 MHz, DMSO-$d_6$) δ 8.76 (dd, J=4.8, 1.7 Hz, 1H), 8.07 (d, J=8.4 Hz, 1H), 7.88 (dd, J=7.8, 1.8 Hz, 1H), 7.61-7.55 (m, 1H), 7.55-7.47 (m, 2H), 7.42 (s, 1H), 6.24 (s, 1H), 5.66 (d, J=12.2 Hz, 1H), 5.59 (t, J=9.1 Hz, 1H), 4.91 (d, J=6.7 Hz, 1H), 4.40-4.26 (m, 2H), 4.13 (q, J=6.2 Hz, 1H), 4.08-3.96 (m, 2H), 3.88-3.78 (m, 1H), 3.72 (t, J=11.5 Hz, 1H), 3.64 (q, J=11.0 Hz, 2H), 3.11 (d, J=14.2 Hz, 1H), 2.96 (dt, J=14.4, 7.1 Hz, 2H), 2.80 (d, J=23.8 Hz, 6H), 2.15 (t, J=9.5 Hz, 1H), 2.06 (d, J=8.6 Hz, 1H), 1.94 (d, J=11.0 Hz, 1H), 1.84-1.73 (m, 1H), 1.66-1.51 (m, 2H), 1.41 (d, J=6.2 Hz, 3H), 1.24 (s, 1H), 1.19-1.05 (m, 7H), 1.05-0.96 (m, 6H), 0.88 (s, 3H), 0.48 (s, 3H) and LCMS (ESI): m/z $[M+H]^+$ calc'd for $C_{42}H_{56}N_6O_6$ 740.4. found 741.4; $^1H$ NMR (400 MHz, DMSO-$d_6$) δ 8.76 (dd, J=4.7, 1.8 Hz, 1H), 8.12 (d, J=8.5 Hz, 1H), 7.85 (dd, J=7.8, 1.7 Hz, 1H), 7.51 (q, J=4.5 Hz, 3H), 7.45 (s, 1H), 6.19 (s, 1H), 5.70 (t, J=8.7 Hz, 1H), 5.49 (s, 1H), 4.72 (d, J=6.4 Hz, 1H), 4.31 (d, J=12.7 Hz, 1H), 4.18 (d, J=6.2 Hz, 2H), 4.14-4.06 (m, 1H), 3.99-3.68 (m, 3H), 3.61 (d, J=11.0 Hz, 1H), 3.53 (d, J=10.9 Hz, 1H), 3.14 (d, J=15.8 Hz, 1H), 2.94 (s, 3H), 2.92-2.83 (m, 2H), 2.73 (d, J=14.1 Hz, 3H), 2.33 (q, J=1.8 Hz, 1H), 1.95 (d, J=10.5 Hz, 1H), 1.77 (d, J=10.6 Hz, 1H), 1.64-1.48 (m, 2H), 1.40 (d, J=6.2 Hz, 3H), 1.24 (s, 1H), 1.19-0.95 (m, 12H), 0.85 (s, 1H), 0.72 (s, 3H), 0.58 (s, 3H).

Example A437. Synthesis of (2S,6S)—N-(($6^3$S,3S,4S,Z)-3-(2-(dimethylamino)ethoxy)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,4,6-trimethylpiperazine-1-carboxamide

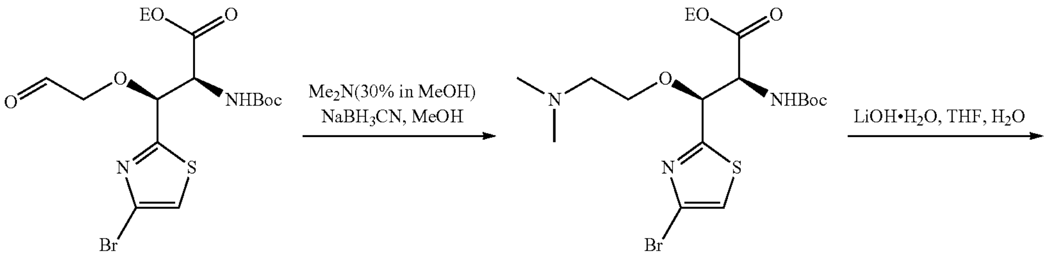

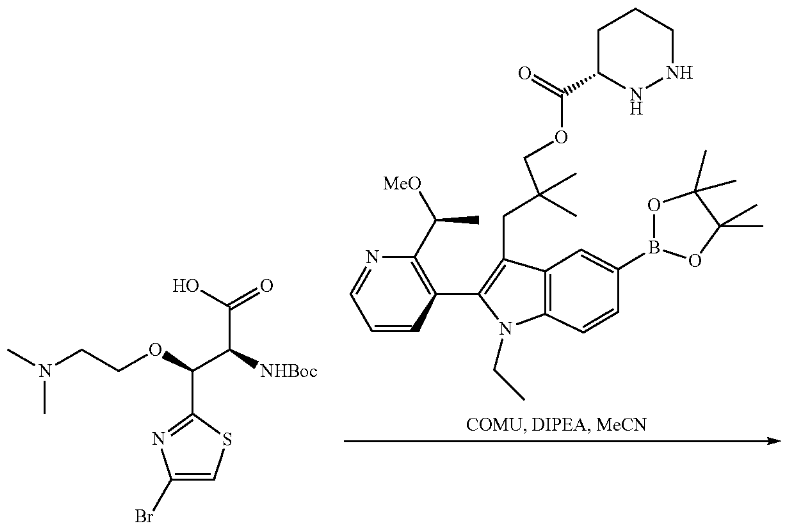

-continued
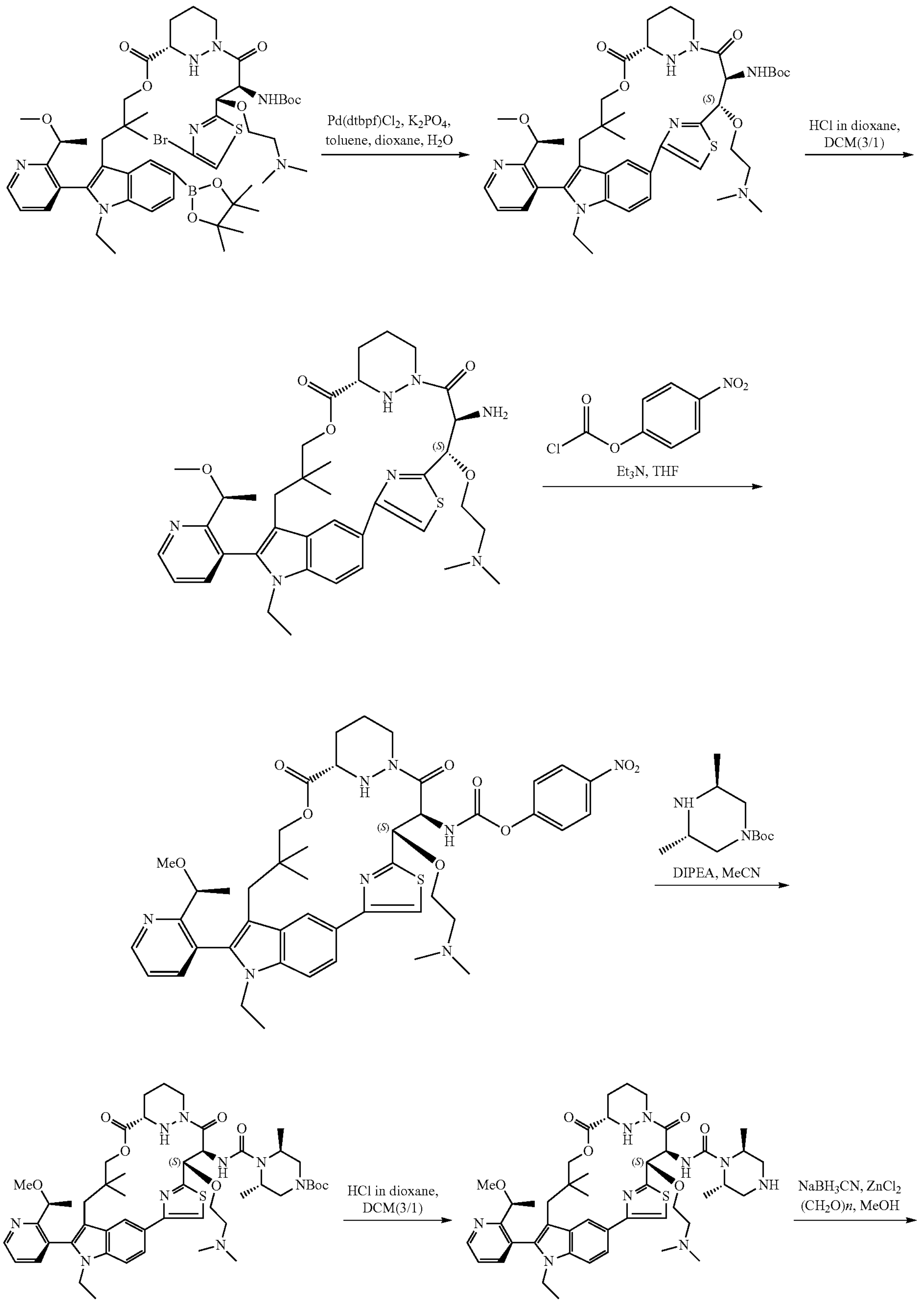

-continued

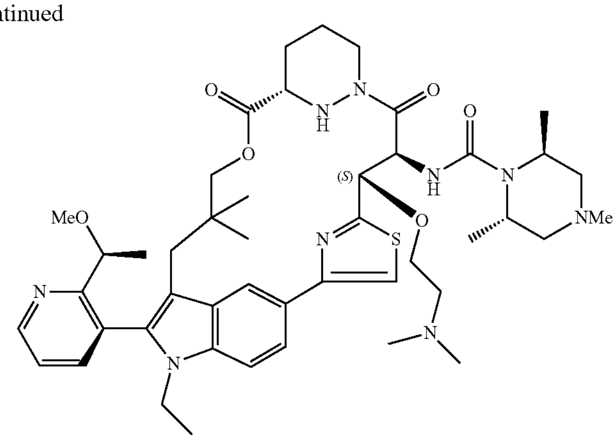

Step 1.

To a mixture of ethyl (2S,3S)-3-(4-bromothiazol-2-yl)-2-((tert-butoxycarbonyl)amino)-3-(2-oxoethoxy)propanoate (0.31 g, 6.9 mmol) and dimethylamine, 30% in MeOH (865 mg, 8.5 mmol in MeOH (20 mL) at 0° C. was added $NaBH_3CN$ (1.08 g, 17.2 ml mmole over 2 min. The mixture was stirred at rt, then diluted with $H_2O$ (30 mL) and extracted with EtOAc (3×20 mL). The combined organic layers were washed with $H_2O$ (4×10 mL), dried over anhydrous $Na_2SO_4$ and filtered. The filtrate was (dimethylamino) ethoxy)propanoate (1.2 g, 45% yield) as an oil. LCMS (ESI): m/z $[M+H]^+$ calc'd for $C_{17}H_{28}BrN_3O_5S$ 467.1. found 468.2.

Step 2.

To a mixture of ethyl (2S,3S)-3-(4-bromothiazol-2-yl)-2-((tert-butoxycarbonyl)amino)-3-(2-(dimethylamino)ethoxy) propanoate (1.25 g, 2.68 mmol) in THF (9 mL) at 0° C. under an atmosphere of $N_2$ was added 1M LiOH (8.0 mL, 8.0 mmol) dropwise. The mixture was stirred at 0° C. for 2 h, then acidified to pH~6 with 1M HCl, then extracted with EtOAc (3×50 mL). The combined organic layers were washed with brine (3×10 mL), dried over anhydrous $Na_2SO_4$, filtered and the filtrate was concentrated under reduced pressure to give (2S,3S)-3-(4-bromothiazol-2-yl)-2-((tert-butoxycarbonyl)amino)-3-(2-(dimethylamino) ethoxy)propanoic acid (600 mg, 51% yield) as an oil. LCMS (ESI): m/z $[M+H]^+$ calc'd for $C_{15}H_{24}BrN_3O_5S$ 439.1. found 440.3 [for $^{81}Br$].

Step 3.

A mixture of (2S,3S)-3-(4-bromothiazol-2-yl)-2-((tert-butoxycarbonyl)amino)-3-(2-(dimethylamino)ethoxy)propanoic acid (570 mg, 1.3 mmol), 2-{[(2M)-1-ethyl-2-{2-[(1S)-1-methoxyethyl]pyridin-3-yl}-5-(4,4,5,5-tetramethyl-1,3,2-dioxaborolan-2-yl)indol-3-yl]methyl}-2-methylpropyl (3S)-1,2-diazinane-3-carboxylate (1.18 g, 1.95 mmol) and DIPEA (5.04 g, 39.0 mmol) in MECN (6 mL) at 0° C. under an atmosphere of $N_2$ was stirred for 5 min, then HATU (593 mg, 1.56 mmol) was added in portions over 2 min. The mixture was warmed to room temperature and stirred for 4 h, then diluted with $H_2O$ (30 mL) and extracted with EtOAc (3×20 mL). The combined organic layers were washed with $H_2O$ (3×10 mL), dried over anhydrous $Na_2SO_4$ and filtered. The filtrate was concentrated under reduced pressure and the residue was purified by preparative-TLC to give 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl-(S)-1-((2S,3S)-3-(4-bromothiazol-2-yl)-2-((tert-butoxycarbonyl)amino)-3-(2-(dimethylamino)ethoxy)propanoyl) hexahydropyridazine-3-carboxylate (580 mg, 44% yield) as a solid. LCMS (ESI): m/z $[M+H]^+$ calc'd for $C_{49}H_{71}BBrN_7O_9S$ 1025.4. found 1026.5 [for $^{81}Br$].

Step 4.

To a mixture of 3-(1-ethyl-2-(2-((S)-1-methoxyethyl) pyridin-3-yl)-5-(4,4,5,5-tetramethyl-1,3,2-dioxaborolan-2-yl)-1H-indol-3-yl)-2,2-dimethylpropyl-(S)-1-((2S,3S)-3-(4-bromothiazol-2-yl)-2-((tert-butoxycarbonyl)amino)-3-(2-(dimethylamino)ethoxy)propanoyl)hexahydropyridazine-3-carboxylate (580 mg, 0.57 mmol) and $K_3PO_4$ (300 mg, 1.42 mmol) in toluene (6 mL), 1,4-dioxane (2 mL) and $H_2O$ (2 mL) under an atmosphere of Ar was added Pd(dtbpf)$Cl_2$. The mixture was heated to 60° C. and stirred for 4 h, then diluted with $H_2O$ (30 mL), and the mixture was extracted with EtOAc (3×30 mL). The combined organic layers were washed with brine (3×10 mL), dried over anhydrous $Na_2SO_4$ and filtered. The filtrate was concentrated under reduced pressure and the residue was purified by preparative-TLC to give (2S,6S)—N-(($6^3$S,3S,4S,Z)-3-(2-(dimethylamino) ethoxy)-$1^1$-ethyl-$1^2$-(2-((S)-1-m ethoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,4,6-trimethylpiperazine-1-carboxamide (230 mg, 50% yield) as a solid. LCMS (ESI): m/z $[M+H]^+$ calc'd for $C_{43}H_{59}N_7O_7S$ 817.4. found 818.4.

Step 5.

To a mixture of tert-butyl (($6^3$S,3S,4S,Z)-3-(2-(dimethylamino)ethoxy)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (230 mg, 0.28 mmol) in DCM (3 mL) at 0° C. under an atmosphere of $N_2$ was added HCl in 1,4-dioxane (1 mL). The mixture was warmed to room temperature and stirred for 2 h, then concentrated under reduced pressure, toluene (30 mL) was added to the residue, and the mixture was concentrated under reduced pressure to give ($6^3$S,3S,4S,Z)-4-amino-3-(2-(dimethylamino)ethoxy)-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (200 mg) as a solid, which was used directly in the next step without further purification. LCMS (ESI): m/z $[M+H]^+$ calc'd for $C_{38}H_{51}N_7O_5S$ 717.4. found 718.7.

Step 6.

To a mixture of (6$^3$S,3S,4S,Z)-4-amino-3-(2-(dimethylamino)ethoxy)-1$^1$-ethyl-12-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione (200 mg, 0.28 mmol) in THF (2 mL) at 0° C. was added $NEt_3$ (85 mg, 0.84 mmol) dropwise over 1 min. The mixture was stirred at 0° C. for 5 min, then 4-nitrophenyl chloroformate (56 mg, 0.28 mmol) was added over 1 min. The mixture was warmed to room temperature and stirred for 4 h and the mixture was concentrated under reduced pressure to give 4-nitrophenyl ((6$^3$S,3S,4S,Z)-3-(2-(dimethylamino)ethoxy)-1$^1$-ethyl-12-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)- pyridazinacycloundecaphane-4-yl)carbamate (250 mg) as a solid, that was used directly in the next step without further purification.

Step 7.

To a mixture of 4-nitrophenyl ((6$^3$S,3S,4S,Z)-3-(2-(dimethylamino)ethoxy)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate (200 mg, 0.23 mmol) in MeCN (2 mL) at 0° C. was added DIPEA (88 mg, 0.68 mmol) dropwise. The mixture was stirred at 0° C. for 2 min, then tert-butyl (3S,5S)-3,5-dimethylpiperazine-1-carboxylate (97 mg, 0.45 mmol) was added dropwise. The mixture was warmed to room temperature and stirred overnight, then diluted with $H_2O$ (3 mL), and the mixture was extracted with EtOAc (3×10 mL). The combined organic layers were washed with brine (3×10 mL), dried over anhydrous $Na_2SO_4$ and filtered. The filtrate was concentrated under reduced pressure and the residue was purified by preparative-TLC to give tert-butyl (3S,5S)-4-(((6$^3$S,3S,4S,Z)-3-(2-(dimethylamino)ethoxy)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamoyl)-3,5-dimethylpiperazine-1-carboxylate (50 mg, 23% yield) as a solid. LCMS (ESI): m/z $[M+H]^+$ calc'd for $C_{50}H_{71}N_9O_8S$ 957.5. found 958.9.

Step 8.

To a mixture of tert-butyl (3S,5S)-4-(((6$^3$S,3S,4S,Z)-3-(2-(dimethylamino)ethoxy)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1H-8-oxa-2(4,2)-thiazola-1(5,3)-indola-6(1,3)-pyridazinacycloundecaphane-4-yl)carbamoyl)-3,5-dimethylpiperazine-1-carboxylate (50 mg, 0.05 mmol) in DCM (3 mL) at 0° C. under an atmosphere of N was added HCl in 1,4-dioxane (1 mL) dropwise. The mixture was warmed to room temperature and stirred for 2 h, then concentrated under reduced pressure, toluene (30 mL) was added to the residue and the mixture was concentrated under reduced pressure to give (2S,6S)—N-((6$^3$S,3S,4S,Z)-3-(2-(dimethylamino)ethoxy)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1H-8-oxa-2(4,2)-thiazola-1(5,3)-indola-6(1,3)-pyridazinacycloundecaphane-4-yl)-2,6-dimethylpiperazine-1-carboxamide (50 mg) as a solid, that was used directly in the next step without further purification.

Step 9.

To a mixture of (2S,6S)—N-((6$^3$S,3S,4S,Z)-3-(2-(dimethylamino)ethoxy)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-2,6-dimethylpiperazine-1-carboxamide (40 mg, 0.05 mmol) and MeOH at 0° C. was added paraformaldehyde (11 mg, 0.24 mmol) in portions, followed by $NaBH_3CN$ (4.4 mg, 0.07 mmol) in portions. The mixture was warmed to room temperature and stirred overnight, then diluted with $H_2O$ (5 mL) and extracted with EtOAc (3×10 mL). The combined organic layers were washed with $H_2O$ (3×10 mL), dried over anhydrous $Na_2SO_4$ and filtered. The filtrate was concentrated under reduced pressure and the residue was purified by preparative-HPLC to give (2S,6S)—N-((6$^3$S,3S,4S,Z)-3-(2-(dimethylamino)ethoxy)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-2,4,6-trimethylpiperazine-1-carboxamide (3.3 mg, 8% yield) as a solid. LCMS (ESI): m/z $[M+H]^+$ calc'd for $C_{46}H_{65}N_9O_6S$ 871.5. found 872.3; $^1H$ NMR (400 MHz, DMSO-$d_6$) δ 8.74-8.64 (dd, J=4.7, 1.6 Hz, 1H), 8.49-8.36 (s, 1H), 7.91-7.81 (s, 1H), 7.79-7.71 (d, J=7.7 Hz, 1H), 7.71-7.63 (d, J=8.6 Hz, 1H), 7.56-7.47 (s, 1H), 7.47-7.36 (dd, J=7.7, 4.7 Hz, 1H), 6.32-6.21 (d, J=9.9 Hz, 1H), 5.55-5.46 (s, 1H), 5.19-5.11 (s, 1H), 5.04-4.97 (s, 1H), 4.45-3.94 (m, 6H), 3.67-3.36 (m, 11H), 3.23 (s, 3H), 3.11 (s, 3H), 2.78-2.75 (m, 2H), 2.40-2.34 (m, 3H), 2.15 (s, 6H), 2.11-2.04 (m, 6H), 1.75 (s, 2H), 1.59-1.41 (m, 1H), 1.30 (d, J=6.0 Hz, 3H), 1.13 (s, 1H), 1.12 (d, J=6.1 Hz, 6H), 0.80 (d, J=28.4 Hz, 6H), 0.57-0.12 (s, 3H).

Example A438. Synthesis of (1r,2R,3S)—N-((6$^3$S,3S,4S,Z)-3-ethoxy-1$^1$-(2-isopropoxyethyl)-1$^2$-(2-((S)-1-methoxyethyl)-5-(4-methylpiperazin-1-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-2,3-dimethylcyclopropane-1-carboxamide

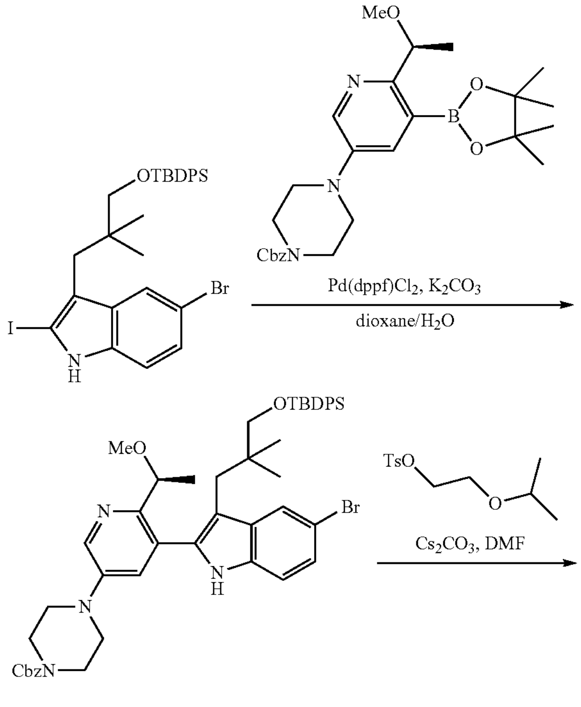

-continued
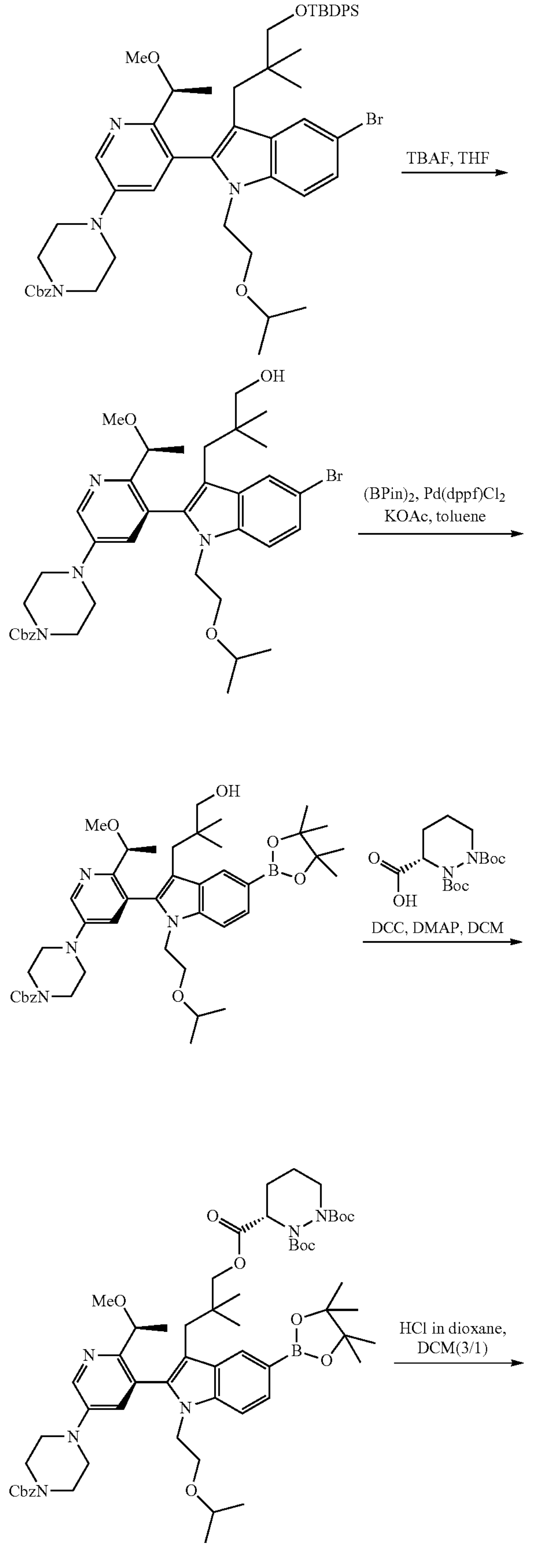
-continued
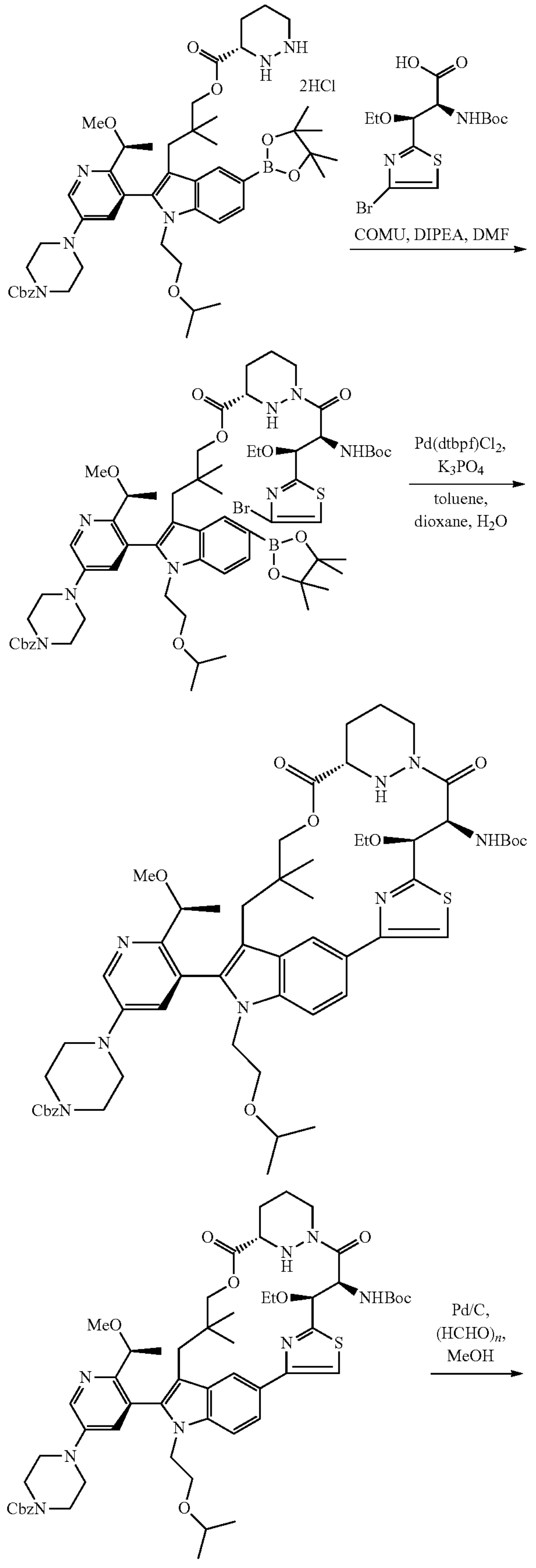

-continued

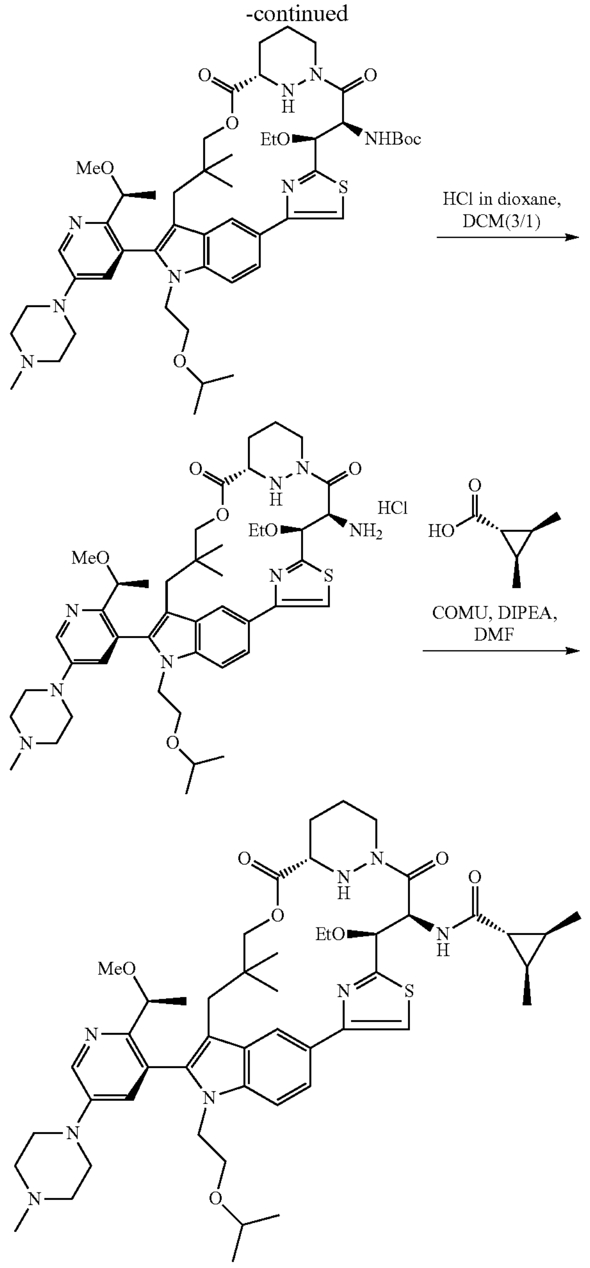

Step 1.

To a mixture of 5-bromo-3-{3-[(tert-butyidiphenylsilyl)oxy]-2,2-dimethylpropyl}-2)iodo-1H-indole (22.0 g, 34.0 mmol) and benzyl 4-[6-(methoxymethyl)-5-(4,4,5,5-tetramethyl-1,3,2-dioxaborolan-2-yl)-pyridin-3-yl]piperazine-1-carboxylate (19.1 g, 40.8 mmol) in 4-dioxane (400 mL) and $H_2O$ (80 mL) under an atmosphere of $N_2$ was added Pd(dppf)$Cl_2$ (2.49 g, 3.4 mmol) and $K_2CO_3$ (11.76 g, 85.1 mmol) in portions. The mixture was heated to 70° C. and stirred for 16 h, then $H_2O$ added, and the mixture was extracted with EtOAc (3×200 mL). The combined organic layers were washed with brine (3×100 mL), dried over anhydrous $Na_2SO_4$ and filtered. The filtrate was concentrated under reduced pressure and the residue was purified by silica gel column chromatography to give benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (20 g, 67% yield) as a solid. LCMS (ESI): m/z $[M+H]^+$ calc'd for $C_{49}H_{57}BrN_4O_4Si$ 874.3. found 875.5.

Step 2.

To a mixture of benzyl (S)-4-(5-(5-bromo-3-(3-((tert-butyldiphenylsilyloxy)-2,2-dimethylpropyl)-1H-indol-2-yl)-6-(1-methoxyethyl)pyridin-3-yl)piperazine-1-carboxylate (23.0 g, 26.3 mmol) and 2-isopropoxyethyl 4-methylbenzenesulfonate (13.6 g, 52.6 mmol) in DMF (300 mL) under an atmosphere of $N_2$ was added $Cs_2CO_3$ (25.72 g, 79.0 mmol) in portions. The mixture was heated to 60° C. and stirred for 2, then diluted with brine (100 mL) and extracted with EtOAc (3×200 mL). The combined organic layers were washed with brine (3×200 mL), dried over anhydrous $Na_2SO_4$ and filtered. The filtrate was concentrated under reduced pressure and the residue was purified by silica gel column chromatography to give benzyl (S)-4-(5-(5-bromo-3-(3-((tert-butyldiphenylsilyl)oxy)-2,2-dimethylpropyl)-1-(2-isopropoxyethyl)-1H-indol-2-yl)-6-(1-methoxyethyl)pyridin-3-yl)piperazine-1-carboxylate (19.2 g, 76% yield) as a solid. LCMS (ESI): m/z $[M+H]^+$ calc'd for $C_{54}H_{67}BrN_4O_5Si$ 960.4. found 961.4 [for $^{81}Br$].

Step 3.

To a mixture of benzyl (S)-4-(5-(5-bromo-3-(3-((tert-butyldiphenylsilyl)oxy)-2,2-dimethylpropyl)-1-(2-isopropoxyethyl)-1H-indol-2-yl)-6-(1-methoxyethyl)pyridin-3-yl)piperazine-1-carboxylate (3.0 g, 3.1 mmol) in THF (30 mL) at 0° C. under an atmosphere of $N_2$ was added TBAF, 1M in THF (15.6 mL, 15.6 mmol) in portions. The mixture was heated to 45° C. and stirred overnight, then diluted with brine (30 mL) and extracted with EtOAc (3×100 mL). The combined organic layers were washed with brine (3×50 mL), dried over anhydrous $Na_2SO_4$ and filtered. The filtrate was concentrated under reduced pressure and the residue was purified by silica gel column chromatography to give benzyl (S)-4-(5-(5-bromo-3-(3-hydroxy-2,2-dimethylpropyl)-1-(2-isopropoxyethyl)-1H-indol-2-yl)-6-(1-methoxyethyl)pyridin-3-yl)piperazine-1-carboxylate (1.19 g, 53% yield) as a solid. LCMS (ESI): m/z $[M+H]^+$ calc'd for $C_{38}H_{49}BrN_4O_5$ 720.3. found 721.3.

Step 4.

To a mixture of benzyl (S)-4-(5-(5-bromo-3-(3-hydroxy-2,2-dimethylpropyl)-1-(2-isopropoxyethyl)-1H-indol-2-yl)-6-(1-methoxyethyl)pyridin-3-yl)piperazine-1-carboxylate (1.09 g, 1.51 mmol) and bis(pinacolato)diboron (0.58 g, 2.27 mmol) in toluene (11 mL) under an atmosphere of $N_2$ was added Pd(dppf)$Cl_2$ (0.11 g, 0.15 mmol) and KOAc (037 g, 3.78 mmol) in portions. The mixture was heated to 80° C. and stirred for 2 h, then diluted with brine (10 mL) and extracted with EtOAc (3×20 mL). The combined organic layers were washed with brine (3×20 mL), dried over anhydrous $Na_2SO_4$ and filtered.

The filtrate was concentrated under reduced pressure and the residue was purified by silica gel column chromatography to give benzyl (S)-4-(5-(3-(3-hydroxy-2,2-dimethylpropyl)-1-(2-isopropoxyethyl)-5-(4,4,5,5-tetramethyl-1,3,2-dioxaborolan-2-yl)-1H-indol-2-yl)-6-(1-methoxyethyl) pyridin-3-yl)piperazine-1-carboxylate (1.0 g, 86% yield) as a solid. LCMS (ESI): m/z $[M+H]^+$ calc'd for $C_{44}H_{61}BN_4O_7$ 768.5. found 769.7.

Step 5.

To a mixture of benzyl (S)-4-(5-(3-(3-hydroxy-2,2-dimethylpropyl)-1-(2-isopropoxyethyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (1.0 g, 1.3 mmol) and (3S)-1,2-bis(tert-butoxycarbonyl)-1,2-diazinane-3-carboxylic acid (0.64 g, 2.0 mmol) in DCM (10 mL) at 0°

C. under an atmosphere of $N_2$ was added DMAP (0.24 g, 2.0 mmol) and DCC (0.40 g, 2.0 mmol) in portions. The mixture was warmed to room temperature and stirred overnight, then diluted with brine (20 mL) and extracted with DCM (3×50 mL). The combined organic layers were washed with brine (3×20 mL), dried over anhydrous $Na_2SO_4$ and filtered. The filtrate was concentrated under reduced pressure and the residue was purified by silica gel column chromatography to give 3-(3-(2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)-2,2-dimethylpropyl)1,2-di-tert-butyl-(S)-tetrahydropyridazine-1,2,3-tricarboxylate (108 g, 77% yield) as a solid. LCMS (ESI): m/z $[M+H]^+$ calc'd for $C_{59}H_{85}BN_5O_{12}$ 1080.6. found 1081.7.

Step 6.

To a mixture of 3-(3-(2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)-2,2-dimethylpropyl)1,2-di-tert-butyl-(S)-tetrahydropyridazine-1,2,3-tricarboxylate (1.0 g, 0.9 mmol) in DCM (3 mL) at 0° C. under an atmosphere of $N_2$ was added HCl in 1,4-dioxane (9 mL) in portions. The mixture was warmed to room temperature and stirred for 6 h, then diluted with toluene (30 mL) and concentrated under reduced pressure to give 3-(2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)-2,2-dimethylpropyl-(S)-hexahydropyridazine-3-carboxylate bis hydrochloride (1.0 g) as a solid. LCMS (ESI): m/z $[M+H]^+$ calc'd for $C_{49}H_{69}BN_6O_8$ 880.5. found 881.5.

Step 7.

To a mixture of 3-(2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)-2,2-dimethylpropyl-(S)-hexahydropyridazine-3-carboxylate bis hydrochloride (1.0 g, 1.1 mmol) and (2S,3S)-3-(4-bromo-1,3-thiazol-2-yl)-2-[(tert-butoxycarbonyl)amino]-3-ethoxypropanoic acid (0.54 g, 1.36 mmol) in DMF (10 mL) at 0° C. under an atmosphere of $N_2$ was added DIPEA (4.40 g, 34.1 mmol) and (Z)-(ethyl cyano({[(dimethyliminiumyl)(morpholin-4-yl)methoxy]imino})formate); hexafluorophosphate (0.53 g, 1.3 mmol) in portions. The mixture was stirred at 0° C. for 1 h, then diluted with brine (30 mL) and extracted with EtOAc (3×50 mL). The combined organic layers were washed with brine (3×30 mL), dried over anhydrous $Na_2SO_4$ and filtered. The filtrate was concentrated under reduced pressure and the residue was purified by preparative-TLC to give 3-(2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)-2,2-dimethylpropyl-(S)-1-((2S,3S)-3-(4-bromothiazol-2-yl)-2-((tert-butoxycarbonyl)amino)-3-ethoxypropanoyl)hexahydropyridazine-3-carboxylate (1.0 g, 70% yield) as a solid. LCMS (ESI): m/z $[M+H]^+$ calc'd for $C_{62}H_{86}BBrN_6O_{12}S$ 1258.5. found 1259.5.

Step 8.

To a mixture of 3-(2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)-2,2-dimethylpropyl-(S)-1-((2S,3S)-3-(4-bromothiazol-2-yl)-2-((tert-butoxycarbonyl)amino)-3-ethoxypropanoyl)hexahydropyridazine-3-carboxylate (1.0 g, 0.8 mmol) in toluene (30 mL), 1,4-dioxane (10 mL) and $H_2O$ (10 mL) under an atmosphere of $N_2$ was added $Pd(dtbpf)Cl_2$ (0.16 g, 0.24 mmol) and $K_3PO_4$ (0.42 g, 2.0 mmol) in portions. The mixture was heated to 65° C. and stirred for 2 h, then diluted with $H_2O$ and extracted with EtOAc (3×50 mL). The combined organic layers were washed with brine (3×50 mL), dried over anhydrous $Na_2SO_4$ and filtered. The filtrate was concentrated under reduced pressure and the residue was purified by preparative-TLC to give benzyl 4-(5-(($6^3$S,3S,4S,Z)-4-((tert-butoxycarbonyl)amino)-3-ethoxy-$1^1$-(2-isopropoxyethyl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)piperazine-1-carboxylate (370 mg, 44% yield) as a solid. LCMS (ESI): m/z $[M+H]^+$ calc'd for $C_{56}H_{74}N_8O_{10}S$ 1050.5. found 1051.9.

Step 9.

To a mixture of benzyl 4-(5-(($6^3$S,3S,4S,Z)-4-((tert-butoxycarbonyl)amino)-3-ethoxy-$1^1$-(2-isopropoxyethyl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)piperazine-1-carboxylate (340 mg, 0.32 mmol) in MeOH (5 mL) was added paraformaldehyde (49 mg, 1.6 mmol) and Pd/C (34 mg, 0.32 mmol) in portions. The mixture was stirred under an atmosphere of $H_2$ overnight, then filtered through a pad of Celite and the filter cake was washed with MeOH (3×20 mL). The filtrate was concentrated under reduced pressure and the residue was purified by preparative-TLC to give tert-butyl (($6^3$S,3S,4S,Z)-3-ethoxy-$1^1$-(2-isopropoxyethyl)-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (240 mg, 80% yield) as a solid. LCMS (ESI): m/z $[M+H]^+$ calc'd for $C_{49}H_{70}N_8O_8S$ 930.5. found 931.5.

Step 10.

To a mixture of tert-butyl (($6^3$S,3S,4S,Z)-3-ethoxy-$1^1$-(2-isopropoxyethyl)-$1^2$-2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (240 mg, 0.26 mmol) in DCM (2 mL) at 0° C. under an atmosphere of $N_2$ was added HCl in 1,4-dioxane (6 mL) in portions. The mixture was stirred at 0° C. for 1 h, then diluted with toluene (20 mL) and concentrated under reduced pressure to give ($6^3$S,3S,4S,Z)-4-amino-3-ethoxy-$1^1$-(2-isopropoxyethyl)-$1^2$-(2-((S)-1-methoxyethyl)-5-(4-methylpiperazin-1-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione HCl salt (240 mg) as a solid. LCMS (ESI): m/z $[M+H]^+$ calc'd for $C_{44}H_{62}N_8O_6S$ 830.5. found 831.4.

Step 11.

To a mixture of ($6^3$S,3S,4S,Z)-4-amino-3-ethoxy-$1^1$-(2-isopropoxyethyl)-$1^2$-(2-((S)-1-methoxyethyl)-5-(4-methylpiperazin-1-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione HCl salt (100 mg, 0.12 mmol) and (1R,2R,3S)-2,3-dimethylcyclopropane-1-carboxylic acid (21 mg, 0.18 mmol) in DMF (5 mL) at 0° C. under an atmosphere of $N_2$ was added DIPEA (467 mg, 3.6 mmol) and (Z)-(ethyl cyano({[(dimethyliminiumyl)(morpholin-4-yl)methoxy]imino})formate); hexafluorophate (62 mg, 0.14 mmol) in portions. The mixture was stirred at 0° C. for 1 h, then diluted with brine (5 mL) and extracted with EtOAc (3×5 mL). The combined organic layers were washed with brine (3×15 mL), dried over anhydrous $Na_2SO_4$ and filtered. The filtrate was concentrated under reduced pressure and the residue was purified by (1r,2R,3S)—N-(($6^3$S,3S,4S,Z)-3-ethoxy-$1^1$-(2-isopropoxyethyl)-12-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (38 mg, 34% yield) as a solid. LCMS (ESI): m/z $[M+H]^+$ calc'd for $C_{50}H_{70}N_8O_7S$ 926.5. found 927.5; $^1H$ NMR (400 MHz, DMSO-$d_6$) δ 8.52-8.42 (m, 2H), 7.91 (s, 1H), 7.72 (dd, J=8.5, 1.6 Hz, 1H), 7.61 (dd, J=18.7, 9.2 Hz, 2H), 7.21 (d, J=2.9 Hz, 1H), 5.88 (d, J=9.8 Hz, 1H), 5.19 (d, J=12.2 Hz, 1H), 4.92 (s, 1H), 4.41-4.02 (m, 5H), 3.73-3.47 (m, 4H), 3.25 (q, J=4.1, 2.7 Hz, 8H), 3.13 (s, 3H), 2.78 (t, J=11.3 Hz, 2H), 2.49-2.39 (m, 6H), 2.22 (s, 4H), 2.11-1.96 (m, 1H), 1.78 (d, J=29.7 Hz, 3H), 1.51 (s, 3H), 1.32 (d, J=6.1 Hz, 4H), 1.24 (d, J=2.8 Hz, 1H), 1.20-0.97 (m, 12H), 0.84 (dd, J=23.4, 6.0 Hz, 10H), 0.44 (s, 3H).

Example A449. Synthesis of (1r,2R,3S)—N-(($6^3$S,3S,4S,Z)-3-ethoxy-$1^1$-ethyl-$1^2$-(2-((S)-1-methoxyethyl)-5-(1-(oxetan-3-yl)piperidin-4-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide

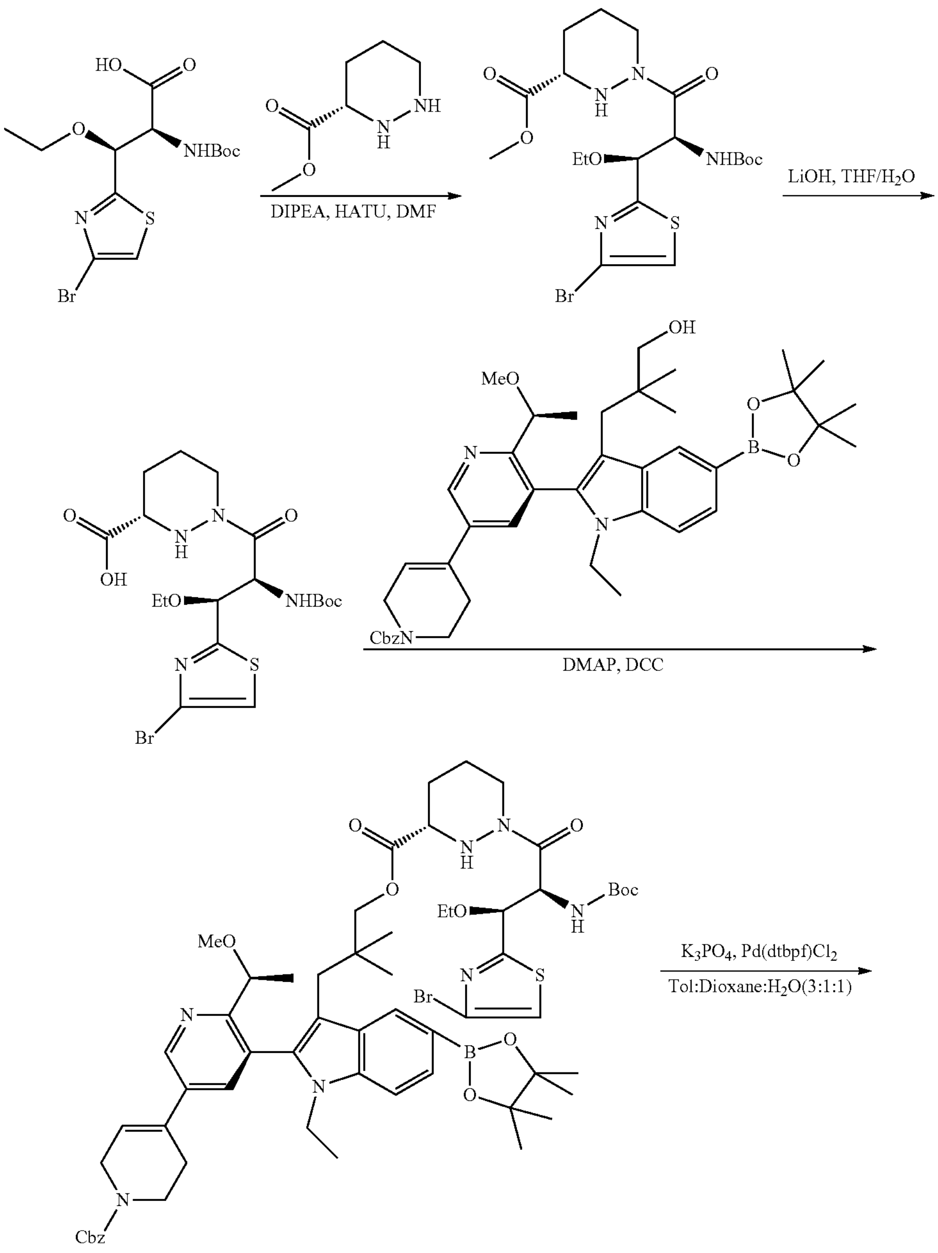

-continued
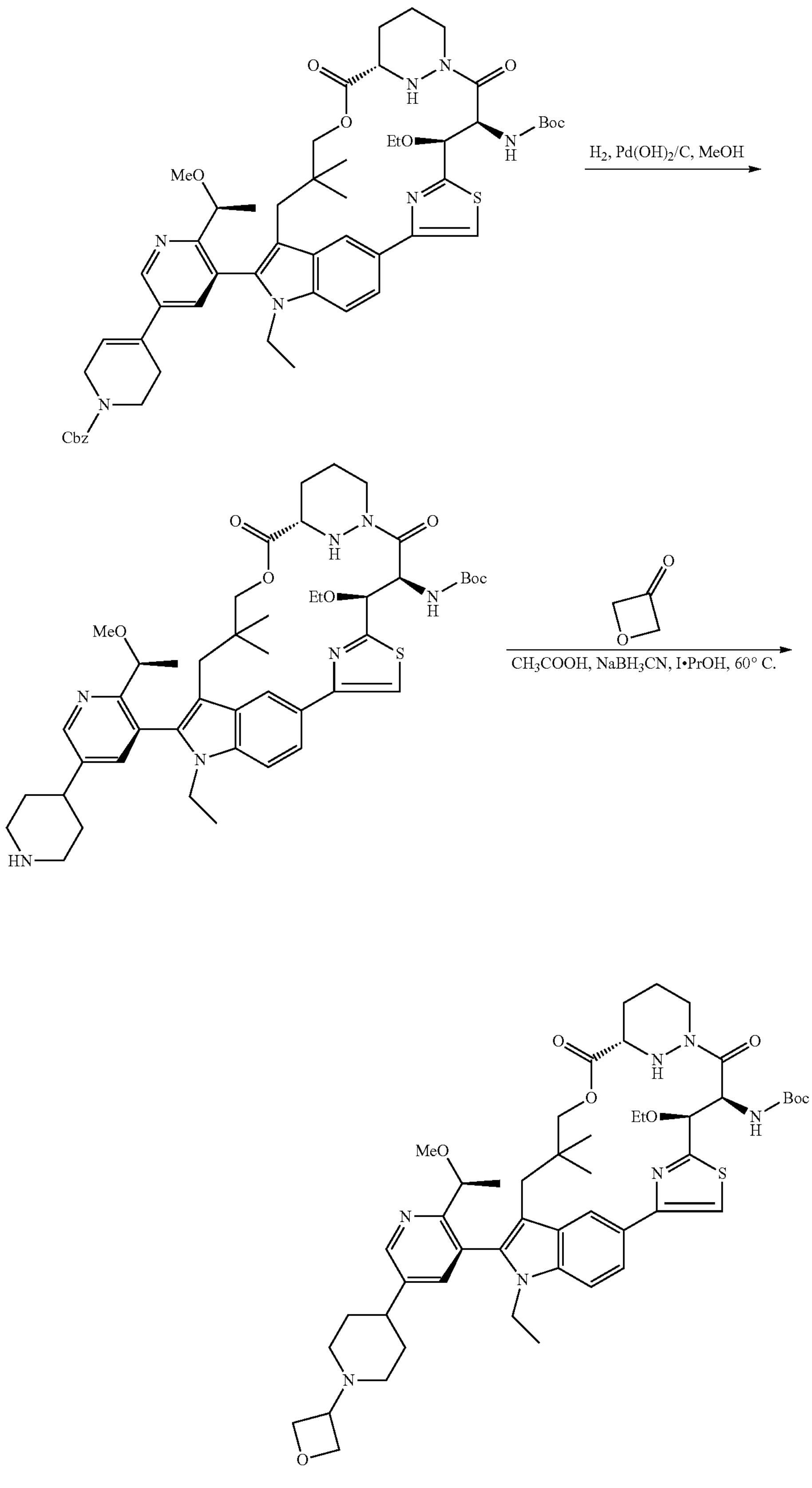

-continued
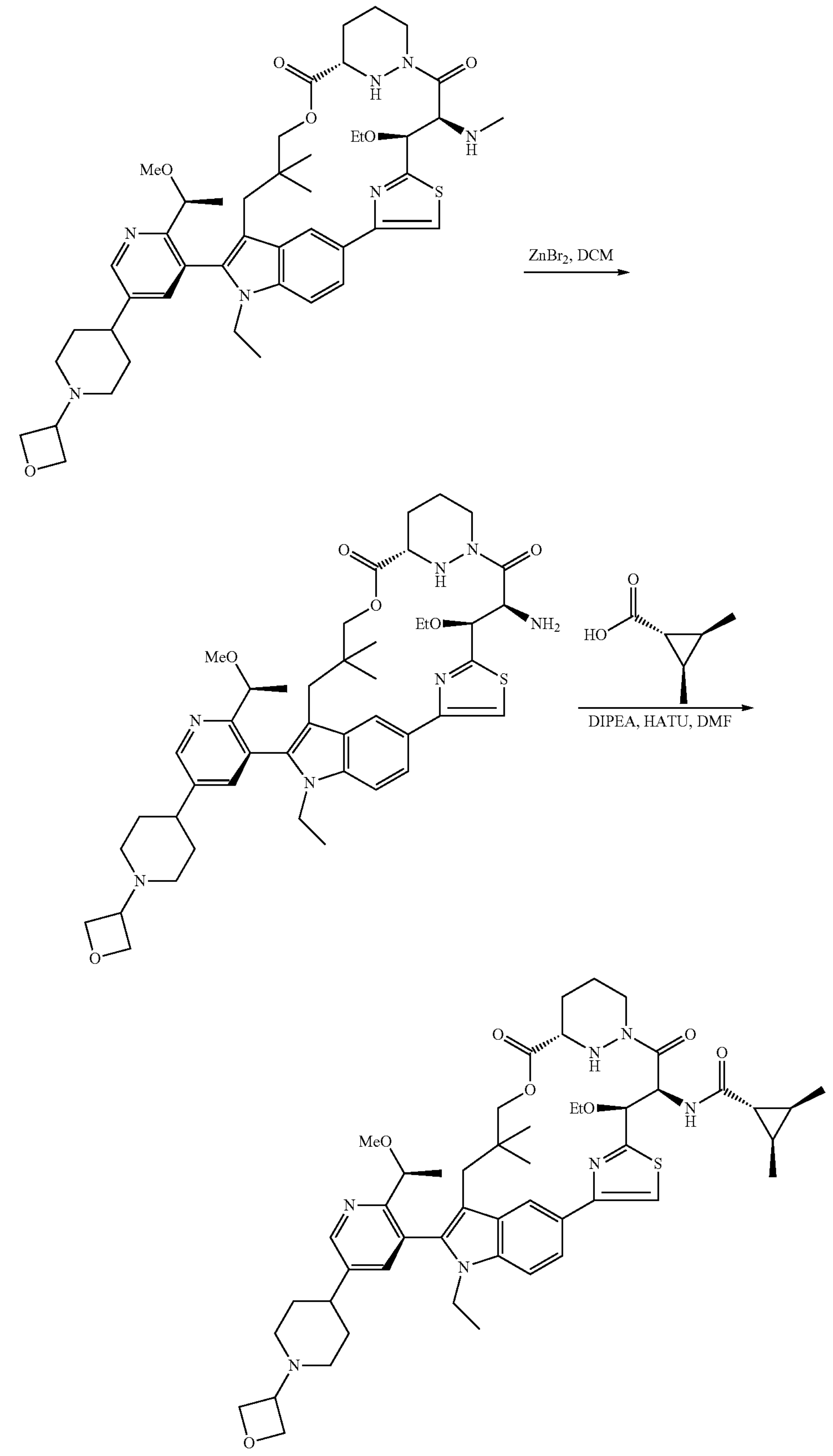

Step 1.

A mixture of (2S,3S)-3-(4-bromothiazol-2-yl)-2-((tert-butoxycarbonyl)amino)-3-ethoxypropanoic acid (1.11 g, 7.7 mmol) and DIPEA (4.95 g, 38.3 mmol) in DMF (20 mL) was stirred at room temperature for 5 min, then (2S,3S)-3-(4-bromo-1,3-thiazol-2-yl)-2-[(tert-butoxycarbonyl)amino]-3-ethoxypropanoic acid (1.52 g, 3.8 mmol) and HATU (2.91 g, 7.7 mmol) were added. When the reaction was complete by LCMS, it was cooled to 0° C., diluted with $H_2O$ and extracted with EtOAc (50 mL). The organic layer was washed with brine (3×100 mL), dried over anhydrous $Na_2SO_4$ and filtered. The filtrate was concentrated under reduced pressure and the residue was purified by silica gel column chromatography to give methyl (S)-1-((2S,3S)-3-(4-bromothiazol-2-yl)-2-((tert-butoxycarbonyl)amino)-3-ethoxypropanoyl) hexahydropyridazine-3-carboxylate (1.56 g, 78% yield). LCMS (ESI): m/z $[M+H]^+$ calc'd for $C_{19}H_{29}BrN_4O_6S$ 522.1. found 523.1 [for $^{81}Br$].

Step 2.

A mixture of methyl (3S)-1-[(2S,3S)-3-(4-bromo-1,3-thiazol-2-yl)-2-[(tert-butoxycarbonyl)amino]-3-ethoxypropanoyl]-1,2-diazinane-3-carboxylate (1.56 g, 3.0 mmol), $LiOH·H_2O$ (0.63 g, 15.0 mmol), THF (5 mL) and $H_2O$ (5 mL) at room temperature was stirred until complete by LCMS. The mixture was acidified to pH~7 with 1 N HCl was extracted with EtOAc (3×100 mL). The combined organic layers were dried over anhydrous $Na_2SO_4$, filtered, and the filtrate was concentrated under reduced pressure to give (3S)-1-[(2S,3S)-3-(4-bromo-1,3-thiazol-2-yl)-2-[(tert-butoxycarbonyl)amino]-3-ethoxypropanoyl]-1,2-diazinane-3-carboxylic acid (1.3 g), which was used directly in the next step without further purification. LCMS (ESI): m/z $[M+H]^+$ calc'd for $C_{19}H_{29}BrN_4O_6S$ 506.1. found 507.1.

Step 3.

A mixture of (3S)-1-[(2S,3S)-3-(4-bromo-1,3-thiazol-2-yl)-2-[(tert-butoxycarbonyl)amino]-3-ethoxypropanoyl]-1,2-diazinane-3-carboxylic acid (600 mg, 1.18 mmol), benzyl (5M)-5-[1-ethyl-3-(3-hydroxy-2,2-dimethylpropyl)-5-(4,4,5,5-tetramethyl-1,3,2-dioxaborolan-2-yl)indol-2-yl]-6-[(1S)-1-methoxyethyl]-3',6'-dihydro-2'H-[3,4'-bipyridine]-1'-carboxylate (754 mg, 1.1 mmol), DMAP (29 mg, 0.24 mmol), DCC (488 mg, 2.37 mmol) and DCM (15 mL) at room temperature until deemed complete by LCMS. The mixture was diluted with DCM (100 mL) and washed with $H_2O$ (100 mL), then the aqueous layer was extracted with DCM (3×100 mL). The combined organic layers were dried over anhydrous $Na_2SO_4$, filtered, the filtrate was concentrated under reduced pressure and the residue was purified by silica gel column chromatography to give benzyl (5M)-5-(3-{3-[(3S)-1-[(2S,3S)-3-(4-bromo-1,3-thiazol-2-yl)-2-[(tert-butoxycarbonyl)amino]-3-ethoxypropanoyl]-1,2-diazinane-3-carbonyloxy]-2,2-dimethylpropyl}-1-ethyl-5-(4,4,5,5-tetramethyl-1,3,2-dioxaborolan-2-yl)indol-2-yl)-6-[(1S)-1-methoxyethyl]-3',6'-dihydro-2'H-[3,4'-bipyridine]-1'-carboxylate (735 mg, 52% yield) as an oil. LCMS (ESI): m/z $[M+H]^+$ calc'd for $C_{60}H_{79}BBrN_7O_{11}S$ 1195.5. found 1196.4.

Step 4.

A mixture of benzyl (5M)-5-(3-{3-[(3S)-1-[(2S,3S)-3-(4-bromo-1,3-thiazol-2-yl)-2-[(tert-butoxycarbonyl)amino]-3-ethoxypropanoyl]-1,2-diazinane-3-carbonyloxy]-2,2-dimethylpropyl}-1-ethyl-5-(4,4,5,5-tetramethyl-1,3,2-dioxaborolan-2-yl)indol-2-yl)-6-[(1)-1-methoxyethyl]-3',6'-dihydro-2'H-[3,4'-bipyridine]-1'-carboxylate (725 mg, 0.61 mmol), $K_3PO_4$ (322 mg, 1.52 mmol), Pd(DtBPF)$Cl_2$ (79 mg, 0.12 mmol), toluene (9 mL), 1,4-dioxane (3 mL) and $H_2O$ (3 mL) under an atmosphere of $N_2$ was heated to 70° C. and stirred for 1 h at 70° C. The mixture was diluted with $H_2O$ (50 mL) and extracted with EtOAc (3×100 mL). The combined organic layers were dried over anhydrous $Na_2SO_4$, filtered, the filtrate was concentrated under reduced pressure and the residue was purified by silica gel column chromatography to give benzyl 5-(($6^3$S,3S,4S,Z)-4-((tert-butoxycarbonyl)amino)-3-ethoxy-1-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)-3',6'-dihydro-[3,4'-bipyridine]-1'(2'H)-carboxylate (233 mg, 39% yield) as a an oil. LCMS (ESI): m/z $[M+H]^+$ calc'd for $C_{54}H_{57}N_7O_9S$ 989.5. found 990.6.

Step 5.

A mixture of benzyl 5-(($6^3$S,3S,4S,Z)-4-((tert-butoxycarbonyl)amino)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)-3',6'-dihydro-[3,4-bipyridine]-1'(2'H)-carboxylate (223 mg, 0.23 mmol) and $Pd(OH)_2$/C (200 mg, 1.4 mmol) in MeOH (2 mL) was stirred under an atmosphere of $H_2$ until deemed complete by LCMS. The mixture was filtered, and the filter cake was washed with MeOH (3×20 mL). The filtrate was concentrated under reduced pressure to give tert-butyl (($6^3$S,3S,4S,Z)-3-ethoxy-$1^1$-ethyl-$1^2$-(2-((S)-1-methoxyethyl)-5-(piperidin-4-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (192 mg) as a solid, that was used in the next step without further purification. LCMS (ESI): m/z $[M+H]^+$ calc'd for $C_{46}H_{63}N_7O_7S$ 875.5. found 858.4.

Step 6.

A mixture of tert-butyl (($6^3$S,3S,4S,Z)-3-ethoxy-$1^1$-ethyl-$1^2$-(2-((S)-1-methoxyethyl)-5-(piperidin-4-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (80 mg, 0.09 mmol), 3-oxetanone (134 mg, 1.86 mmol), AcOH (56 mg, 0.93 mmol) and $NaBH_3CN$ (59 mg, 0.93 mmol) in $^i$PrOH (2 mL) at room temperature was stirred until deemed complete by LCMS. The mixture was cooled to 0° C. quenched with saturated $NaHCO_3$ and extracted with EtOAc (3×30 mL). The combined organic layers were dried over anhydrous $Na_2SO_4$, filtered, the filtrate was concentrated under reduced pressure and the residue was purified by silica gel column chromatography to give tert-butyl (($6^3$S,3S,4S,Z)-3-ethoxy-$1^1$-ethyl-$1^2$-(2-((S)-1-methoxyethyl)-5-(1-(oxetan-3-yl)piperidin-4-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (30 mg, 35% yield) as a an oil. LCMS (ESI): m/z $[M+H]^+$ calc'd for $C_{49}H_{67}N_7O_8S$ 913.5. found 914.4.

Step 7.

A mixture of tert-butyl (($6^3$S,3S,4S,Z)-3-ethoxy-$1^1$-ethyl-$1^2$-(2-((S)-1-methoxyethyl)-5-(1-(oxetan-3-yl)piperidin-4-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (40 mg, 0.05 mmol), $ZnBr_2$ (55 mg, 0.24 mmol) and DCM (1 mL) was stirred at room temperature until deemed complete by LCMS. The mixture was filtered, the filter cake was washed with DCM (3×10 mL), and the filtrate was concentrated under reduced pressure to give ($6^3$S,3S,4S,Z)-4-amino-3-ethoxy-$1^1$-ethyl-$1^2$-(2-((S)-1-methoxyethyl)-5-(1-(oxetan-3-yl)piperidin-4-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)- indola-6(1,3)-pyridazinacycloundecaphane-5,7-dione as (crude) an oil, which was used directly in the next step without further purification. LCMS (ESI): m/z $[M+H]^+$ calc'd for $C_{44}H_{59}N_7O_6S$ 813.4. found 814.8.

Step 8.

To a mixture of ($6^3$S,3S,4S,Z)-4-amino-3-ethoxy-$1^1$-ethyl-$1^2$-(2-((S)-1-methoxyethyl)-5-(1-(oxetan-3-yl)piperidin-4-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione as (40 mg, 0.05 mmol) in DMF (2 mL) at room temperature was added DIPEA (64 mg, 0.49 mmol), (1R,2R,3S)-2,3-dimethylcyclopropane-1-carboxylic acid (6 mg, 0.05 mmol) and HATU (37 mg, 01 mmol) in portions. The mixture was stirred until deemed complete by LCMS. The mixture was diluted with $H_2O$ (10 mL), extracted with EtOAc (50 mL), the organic layer was washed with brine (3×50 mL), dried over anhydrous $Na_2SO_4$ and filtered. The filtrate was concentrated under reduced pressure and the residue was purified by preparative-HPLC to give (1r,2R,3S)—N-(($6^3$S,3S,4S,Z)-3-ethoxy-$1^1$-ethyl-$1^2$-(2-((S)-1-methoxyethyl)-5-(1-(oxetan-3-yl)piperidin-4-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (3.5 mg, 8% yield) as a solid. LCMS (ESI): m/z $[M+H]^+$ calc'd for $C_{50}H_{67}N_7O_7S$ 909.5. found 910.8; $^1H$ NMR (400 MHz, $CD_3OD$) δ 8.66-8.52 (m, 2H), 7.82-7.72 (m, 2H), 7.67 (s, 1H), 7.53-7.44 (m, 1H), 5.99 (s, 1H), 4.78-4.68 (m, 4H), 4.71-4.54 (m, 10H), 4.48-4.39 (m, 1H), 4.36-4.02 (m, 4H), 3.75-3.68 (m, 1H), 3.68-3.64 (m, 3H), 3.02-2.97 (m, 3H), 2.91-2.80 (m, 2H), 2.65-2.63 (m, 1H), 2.24-2.12 (m, 3H), 2.03-2.00 (m, 4H), 1.93-1.72 (m, 3H), 1.69-1.55 (m, 1H), 1.47-1.23 (m, 6H), 1.16-1.13 (m, 5H) 1.06-0.85 (m, 5H), 0.50 (s, 3H).

Example A451. Synthesis of (1S,2S)—N-(($6^3$S,3S,4S,Z)-$1^1$-ethyl-$1^2$-(2-((S)-1-methoxyethyl)pyridin-3-yl)-10,10-dimethyl-3-((1-methylpiperidin-4-yl)methoxy)-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methylcyclopropane-1-carboxamide

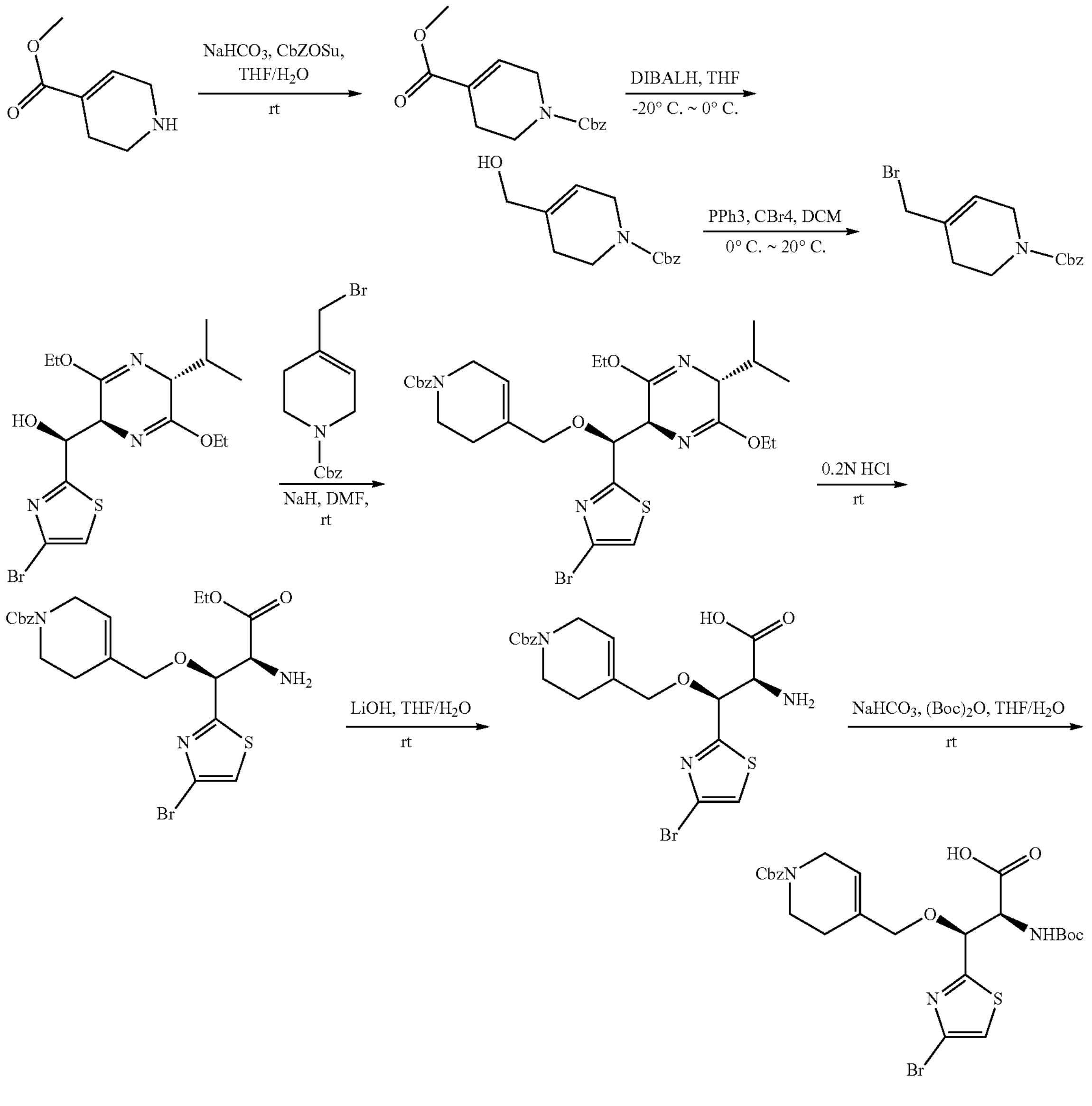

-continued
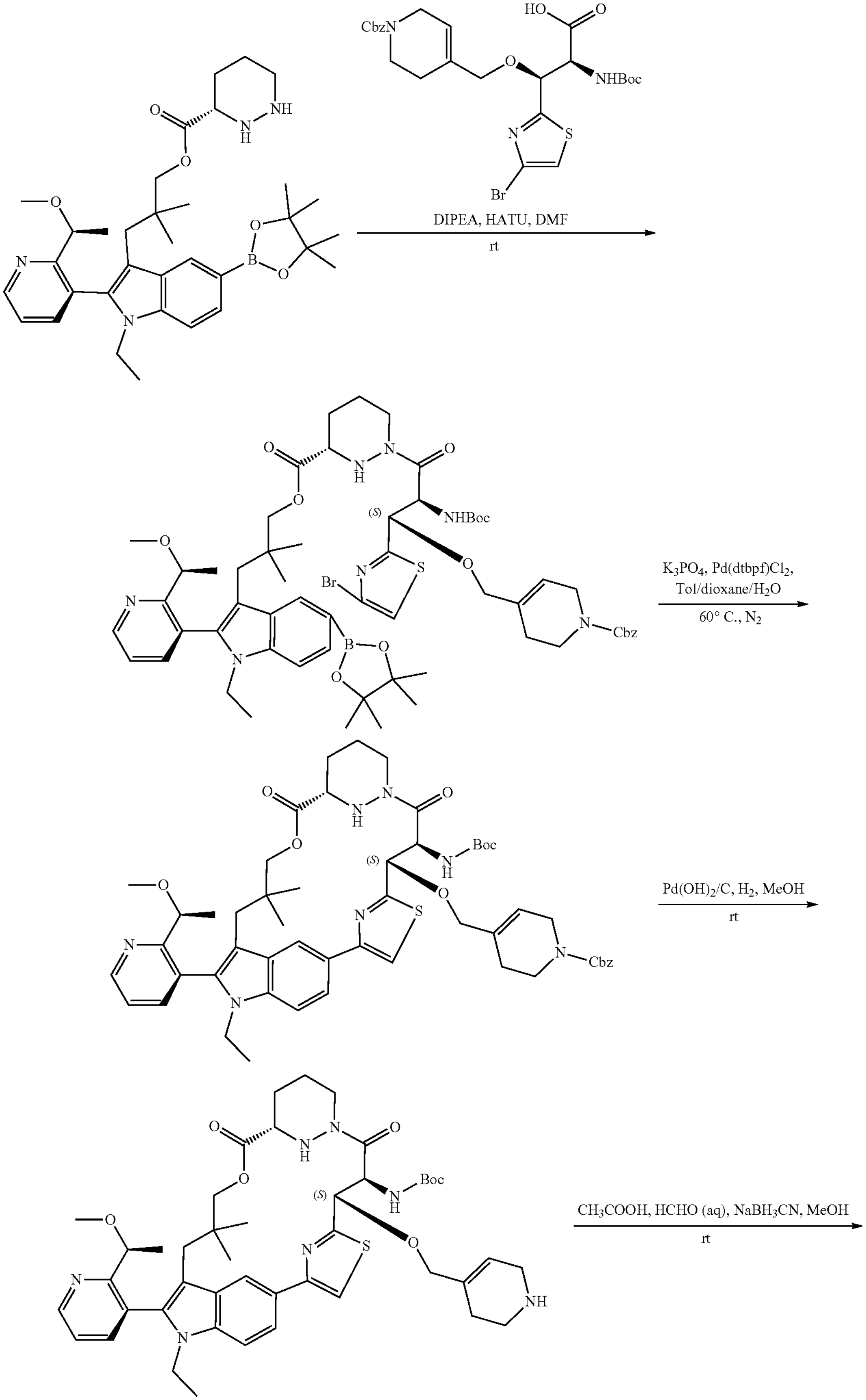

-continued

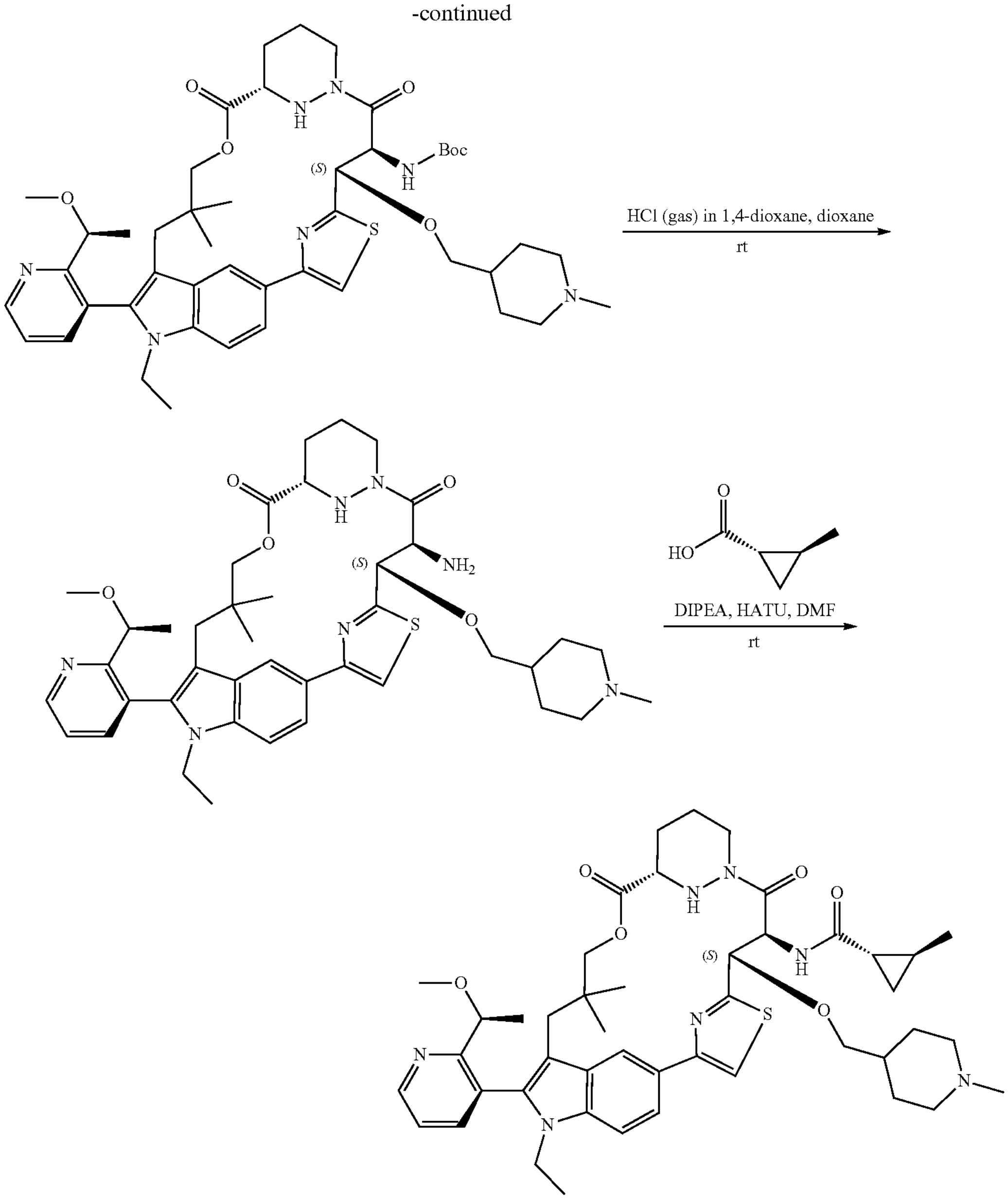

Step 1.

To a mixture of methyl 1,2,3,6-tetrahydropyridine-4-carboxylate (10.0 g, 70.8 mmol) and $NaHCO_3$ (29.75 g, 354.2 mol) in THF (50 mL) and $H_2O$ (50 mL was added CbzOSu (26.48 g, 106.3 mmol) in portions. The mixture was stirred at room temperature for 2 h, then washed with $H_2O$ (3×100 mL) and the combined aqueous layers were extracted with EtOAc (3×100 mL). The combined organic layers were concentrated under reduced pressure and the residue was purified by silica gel column chromatography to give 1-benzyl 4-methyl 3,6-dihydropyridine-1,4(2H)-dicarboxylate as an oil LCMS (ESI): m/z $[M+H]^+$ calc'd for $C_{15}H_{17}NO_4$ 275.1. found 276.1.

Step 2.

To a mixture of 1-benzyl 4-methyl 3,6-dihydropyridine-1,4(2H)-dicarboxylate (8.0 g, 29.1 mmol) in THF at −20° C. under an atmosphere of $N_2$ was added DIBAL-H (80 mL, 0.80 mmol) dropwise. The mixture was stirred at −20° C. for 2 h. then warmed to room temperature and quenched with saturated $NH_4Cl$. The aqueous layer was extracted with EtOAc (2×100 mL) and the combined organic layers were concentrated under reduced pressure. The residue was purified by reverse-phase silica gel column chromatography to give benzyl 4-(hydroxymethyl)-3,6-dihydropyridine-1 (2H-carboxylate (2.3 g 32% yield) as an oil. LCMS (ESI): m/z $[M+H]^+$ calc'd for $C_{14}H_{17}NO_3$ 247.1; found 248.2

Step 3.

To a mixture of benzyl 4-(hydroxymethyl)-3,6-dihydropyridine-1(2H)-carboxylate (2.3 g, 93 mml) and $PPh_3$ (2.93 g, 11.2 mmol) in DCM at 0° C. was added $CBr_4$ (3.70 g, 11.2 mmol) dropwise. The mixture was stirred at room temperature until completion, then quenched with saturated $NH_4Cl$. The aqueous layer was extracted with EtOAc (2×30 mL), the combined organic layers were concentrated under, reduced pressure and the residue was purified by silica gel column chromatography to give benzyl 4-(bromomethyl)-3,6-dihydropyridine-1(2M-carboxylate (2.1 g, 7:3% yield) as an oil. LCMS (ESI): m/z $[M+H]^+$ calc'd for $C_{14}H_{16}BrNO_2$ 309.0. found 310.0.

Step 4.

To a mixture of (S)-(4-bromothiazol-2-yl) ((2S,5R)-3,6-diethoxy-5-isopropyl-2,5-dihydropyrazin-2-yl)methanol (1.37 g, 3.39 mmol) in DMF (20 mL) at 0° C. was added NaH (0.16 g, 6.78 mmol) in portions. The mixture was stirred at 0° C. for 1 h, then benzyl 4-(bromomethyl)-3,6-dihydropyridine-1(2H-carboxylate (2.10 g, 6.78 mmol) was added. The mixture was warmed to room temperature and stirred for 2 h, then diluted with saturated $NH_4Cl$ (100 mL), and the mixture was extracted with EtOAc (2×30 mL). The combined organic layers were concentrated under reduced pressure and the residue was purified by silica gel column chromatography to give benzyl 4-(((S)-(4-bromothiazol-2-yl)((2S,5R)-3,6-diethoxy-5-isopropyl-2,5-dihydropyrazin-2-yl)methoxy)methyl)-3,6-dihydropyridine-1(2H-carboxylate (1.75 g, 82% yield) as an oil. LCMS (ESI): m/z $[M+H]^+$ calc'd for $C_{29}H_{27}BrN_4O_5S$ 632.2. found 633.2.

Step 5.

To a mixture of benzyl 4-(((S)-(4-bromothiazol-2-yl)((2S,5R)-3,6-diethoxy-5-isopropyl-2,5-dihydropyrazin-2-yl) methoxy)methyl)-3,6-dihydropyridine-1(2H-carboxylate (1.75 g, 2.76 mmol) in THF (40 mL) and MECN (16 mL) at 0° C. was added 0.02M HCl (35 mL, 0.7 mmol) dropwise. The mixture was warmed to room temperature and stirred overnight, then quenched with saturated $NaHCO_3$ and extracted with EtOAc (2×100 mL). The combined organic layers were concentrated under reduced pressure and the residue was purified by silica gel column chromatography to give benzyl 4-(((1S,2S)-2-amino-1-(4-bromothiazol-2-yl)-3-ethoxy-3-oxopropoxy)methyl)-3,6-dihydropyridine-1(2H)-carboxylate (1.15 g, 79% yield) as an oil. LCMS (ESI): m/z $[M+H]^+$ calc'd for $C_{22}H_{26}BrN_3O_5S$ 523.1. found 524.2.

Step 6.

A mixture of benzyl 4-(((1S,2S)-2-amino-1-(4-bromothiazol-2-yl)-3-ethoxy-3-oxopropoxy)methyl)-3,6-dihydropyridine-1(2H)-carboxylate (1.15 g, 2.19 mmol) and LiOH (0.21 g, 8.77 mmol) in THF (50 mL) and $H_2O$ (50 mL) was stirred at room temperature for 1 h, then acidified to pH~4 with 1M HCl. The mixture was then used directly in the next step without further purification. LCMS (ESI): m/z $[M+H]^+$ calc'd for $C_{20}H_{22}BrN_3O_5S$ 497.0. found 497.9 [for $^{81}$Br].

Step 7.

To the above mixture was added $NaHCO_3$ (0.97 g, 11.59 mmol) and $(Boc)_2O$ (1.01 g, 4.63 mmol). The mixture was stirred at room temperature overnight, then extracted with DCM (3×20 mL). The aqueous layer was acidified to pH~4 with 1M HCl and extracted with EtOAc (3×30 mL). The combined organic layers were concentrated under reduced pressure to give (2S,3S)-3-((1-((benzyloxy)carbonyl)-1,2,3,6-tetrahydropyridin-4-yl)methoxy)-3-(4-bromothiazol-2-yl)-2-((tert-butoxycarbonyl)amino)propanoic acid (1.1 g, 79% yield) as an oil. LCMS (ESI): m/z $[M+H]^+$ calc'd for $C_{25}H_{30}BrN_3O_7S$ 597.1. found 598.0 [for $^{81}$Br].

Step 8.

To a mixture of 3-(1-ethyl-2-(2-((S)-1-methoxyethyl) pyridin-3-yl)-5-(4,4,5,5-tetramethyl-1,3,2-dioxaborolan-2-yl)-1H-indol-3-yl)-2,2-dimethylpropyl (S)-hexahydropyridazine-3-carboxylate (1.5 g, 2.5 mmol) and (2S,3S)-3-((1-((benzyloxy)carbonyl)-1,2,3,6-tetrahydropyridin-4-yl) methoxy)-3-(4-bromothiazol-2-yl)-2-((tert-butoxycarbonyl) amino)propanoic acid (1.48 g, 2.5 mmol) in DMF was added DIPEA (3.21 g, 24.8 mmol) and HATU (1.89 g, 4.96 mmol) in portions. The mixture was stirred at room temperature for 2 h, then washed with $H_2O$ (3×30 mL). The combined aqueous layers were extracted with EtOAc (3×30 mL), the combined organic layers were concentrated under reduced pressure and the residue was purified by silica gel column chromatography to give 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl-(S)-1-((2S,3S)-3-((1-((benzyloxy)carbonyl)-1,2,3,6-tetrahydropyridin-4-yl)methoxy)-3-(4-bromothiazol-2-yl)-2-((tert-butoxycarbonyl)amino)propanoyl)hexahydropyridazine-3-carboxylate (1.0 g, 34% yield) as an oil. LCMS (ESI): m/z $[M+H]^+$ calc'd for $C_{59}H_{77}BBrN_7O_{11}S$ 1183.5. found 1184.3 [for $^{81}$Br].

Step 9.

To a mixture of 3-(1-ethyl-2-(2-((S)-1-methoxyethyl) pyridin-3-yl)-5-(4,4,5,5-tetramethyl-1,3,2-dioxaborolan-2-yl)-1H-indol-3-yl)-2,2-dimethylpropyl-(S)-1-((2S,3S)-3-((1-((benzyloxy)carbonyl)-1,2,3,6-tetrahydropyridin-4-yl) methoxy)-3-(4-bromothiazol-2-yl)-2-((tert-butoxycarbonyl) amino)propanoyl)hexahydropyridazine-3-carboxylate (1.0 g, 0.85 mmol) and $K_3PO_4$ (0.45 g, 2.11 mmol) in toluene, dioxane and $H_2O$ under an atmosphere of $N_2$ was added $Pd(dtbpf)Cl_2$ (0.11 g, 0.17 mmol) in portions. The mixture was heated to 60° C. and stirred for 2 h, then washed with $H_2O$ (3×30 mL) and the combined aqueous layers extracted with EtOAc (3×30 mL). The combined organic layers were concentrated under reduced pressure and the residue was purified by silica gel column chromatography to give benzyl 4-(((($6^3$S,3S,4S,Z)-4-((tert-butoxycarbonyl)amino)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-3-yl)oxy)methyl)-3,6-dihydropyridine-1(2H)-carboxylate (260 mg, 32% yield) as an oil. LCMS (ESI): m/z $[M+H]^+$ calc'd for $C_{53}H_{65}N_7O_9S$ 975.5. found 976.6.

Step 10.

A mixture of benzyl 4-(((($6^3$S3S,4S,Z)-4-((tert-butoxycarbonyl)amino)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-3-yl)oxy)methyl)-3,6-dihydropyridine-1(2H)-carboxylate (260 mg, 0.27 mmol) and $Pd(OH)_2$, 20% on carbon (0.26 g) in MeOH (3 mL) was stirred under an atmosphere of $H_2$ (balloon) at room temperature for 1 h. The mixture was filtered through a pad of Celite pad and the filtrate was concentrated under reduced pressure to give tert-butyl (($6^3$S,3S,4S,Z)-$1^1$-ethyl-$1^2$-(2-((S)-1-methoxyethyl)pyridin-3-yl)-10,10-dimethyl-5,7-dioxo-3-(piperidin-4-ylmethoxy)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (230 mg, 72% yield) as an oil. LCMS (ESI): m/z $[M+H]^+$ calc'd for $C_{45}H_{61}N_7O_7S$ 843.4. found 844.3.

Step 11.

To a mixture of tert-butyl (($6^3$S,3S,4S,Z)-$1^1$-ethyl-$1^2$-(2-((S)-1-methoxyethyl)pyridin-3-yl)-10,10-dimethyl-5,7-dioxo-3-(piperidin-4-ylmethoxy)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (230 mg, 0.27 mmol) and AcOH (49 mg, 0.82 mmol) in MeOH was added paraformaldehyde (49 mg, 1.6 mmol) and $NaBH_3CN$ (86 mg, 1.36 mmol) in portions. The mixture was stirred at room temperature for 2 h, then diluted with $H_2O$ and extracted with EtOAc (3×20 mL). The combined organic layers were concentrated under reduced pressure and the residue was purified by silica gel column chromatography to give tert-butyl (($6^3$S,3S,4S, Z)-$1^1$-ethyl-$1^2$-(2-((S)-1-methoxyethyl)

pyridin-3-yl)-10,10-dimethyl-3-((1-methylpiperidin-4-yl)methoxy)-5,7-dioxo-$6^1$,$6^2$,$6^3$,$6^4$,$6^5$,$6^6$-hexahydro-1H-8-oxa-2(4,2)-thiazola-1(5,3)-indola-6(1,3)-pyridazinacycloundecaphane-4-yl)carbamate (280 mg, 81% yield) as a an oil. LCMS (ESI): m/z $[M+H]^+$ calc'd for $C_{46}H_{53}N_7O_7S$ 857.5. found 858.4.

Step 12.

A mixture of tert-butyl (($6^3$S,3S,4S, Z)-$1^1$-ethyl-$1^2$-(2-((S)$_1$-methoxyethyl)pyridin-3-yl)-10,10-dimethyl-3-((1-methylpiperidin-4-yl)methoxy)-5,7-dioxo-$6^1$,$6^2$,$6^3$,$6^4$,$6^5$,$6^6$-hexahydro-1H-8-oxa-2(4,2)-thiazola-1(5,3)-indola-6(1,3)-pyridazinacycloundecaphane-4-yl)carbamate (280 mg, 0.33 mmol) and HCl in 1,4-dioxane (3 mL) in 1,4-dioxane was stirred at room temperature for 1 h. The mixture was concentrated under reduced pressure to give ($6^3$S,3S,4S,Z)-4-amino-$1^1$-ethyl-$1^2$-(2-((S)-1-methoxyethyl)pyridin-3-yl)-10,10-dimethyl-3-((1-methylpiperidin-4-yl)methoxy)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione as an oil. LCMS (ESI): m/z $[M+H]^+$ calc'd for $C_{41}H_{56}N_7O_5S$ 757.4. found 758.5.

Step 13.

To a mixture of ($6^3$S,3S,4S,Z)-4-amino-$1^1$-ethyl-$1^2$-(2-((S)-1-methoxyethyl)pyridin-3-yl)-10,10-dimethyl-3-((1-methylpiperidin-4-yl)methoxy)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (265 mg, 0.35 mmol) and (1S,2S)-2-methylcyclopropane-1-carboxylic acid (35 mg, 0.35 mmol) in DMF was added DIPEA (904 mg, 7.0 mmol) in portions. The mixture was stirred at room temperature for 2 h, then washed with $H_2O$ (3×20 mL). The combined aqueous layers were extracted with EtOAc (2×20 mL) and the combined organic layers were concentrated under reduced pressure and the residue was purified by silica gel column chromatography to give (1S,2S)—N-(($6^3$S,3S,4S,Z)-$1^1$-ethyl-$1^2$-(2-((S)-1-methoxyethyl)pyridin-3-yl)-10,10-dimethyl-3-((1-methylpiperidin-4-yl)methoxy)-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methylcyclopropane-1-carboxamide (24 mg, 8% yield) as a solid. LCMS (ESI): m/z $[M+H]^+$ calc'd for $C_{46}H_{61}N_7O_6S$ 839.4. found 840.4; $^1$H NMR (300 MHz, DMSO-$d_6$) δ 8.83-8.64 (m, 1H), 8.56-8.43 (m, 1H), 8.00-7.89 (m, 1H), 7.81-7.73 (m, 3H), 7.63-7.53 (m, 2H), 5.93-5.85 (m, 1H), 5.20-5.12 (m, 1H), 4.90 (s, 1H), 4.32-4.13 (m, 5H), 3.68-3.60 (m, 2H), 3.26-3.22 (m, 5H), 2.95-2.83 (m, 1H), 2.79-2.72 (m, 3H), 2.49-2.46 (m, 1H), 2.20-2.10 (s, 3H), 2.09-2.01 (m, 1H), 1.93-1.72 (m, 6H), 1.70-1.45 (m, 3H), 1.41-1.30 (m, 3H), 1.21-0.99 (m, 7H), 0.98-0.87 (m, 8H), 0.60-0.50 (m, 1H), 0.35 (s, 3H).

Example A457. Synthesis of (1r,2R,3S)—N-(($6^3$S,4S,Z)-$1^2$-(2-((S)-1-methoxyethyl)pyridin-3-yl)-10,10-dimethyl-5,7-dioxo-$1^1$-(2-((tetrahydro-2H-pyran-4-yl)oxy)ethyl)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide

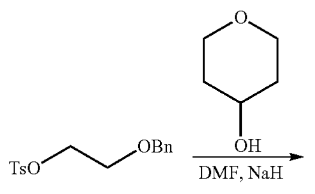

-continued

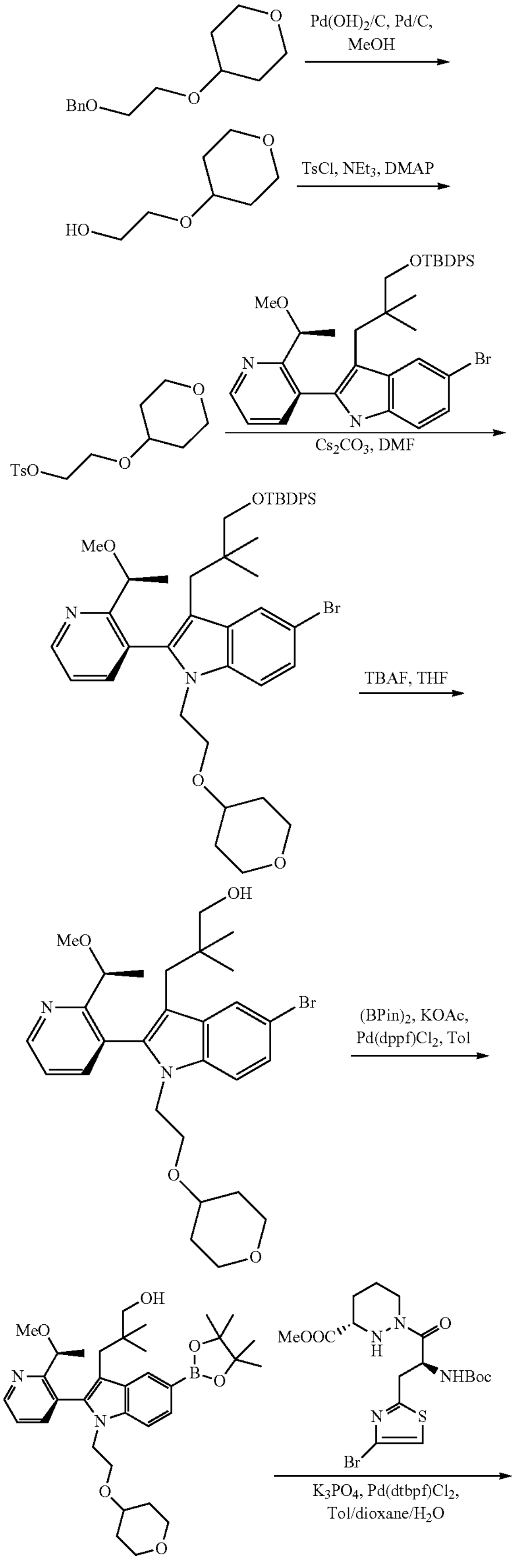

-continued

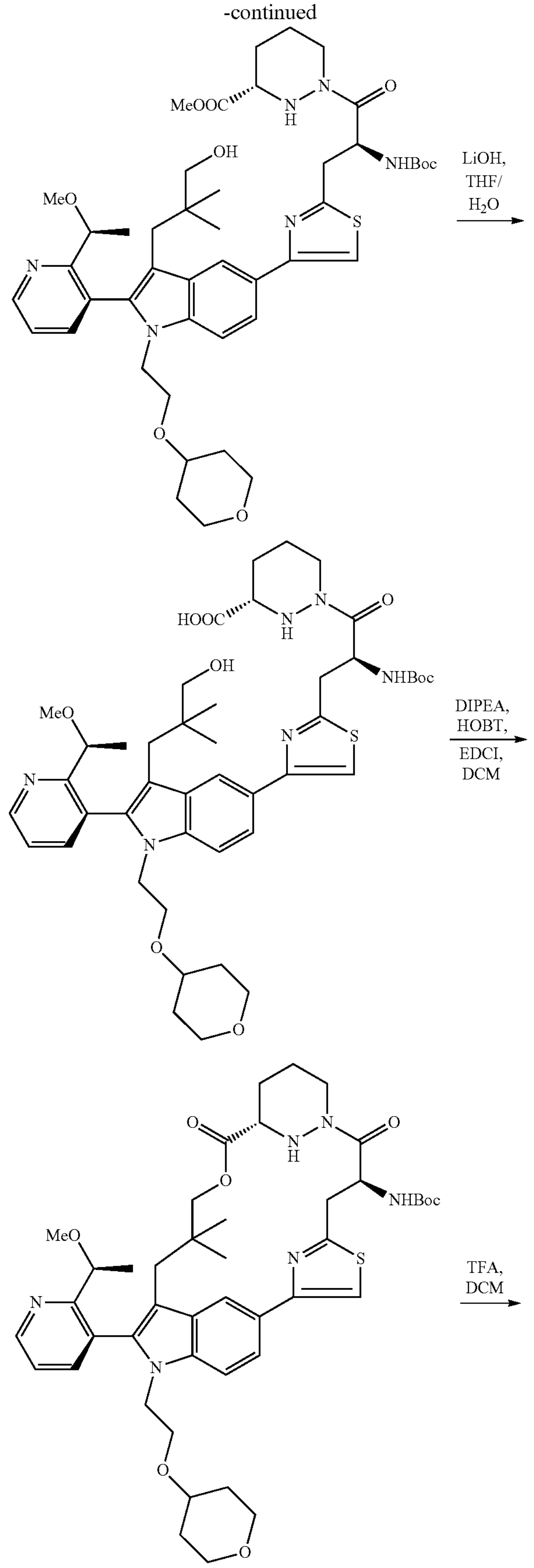

-continued

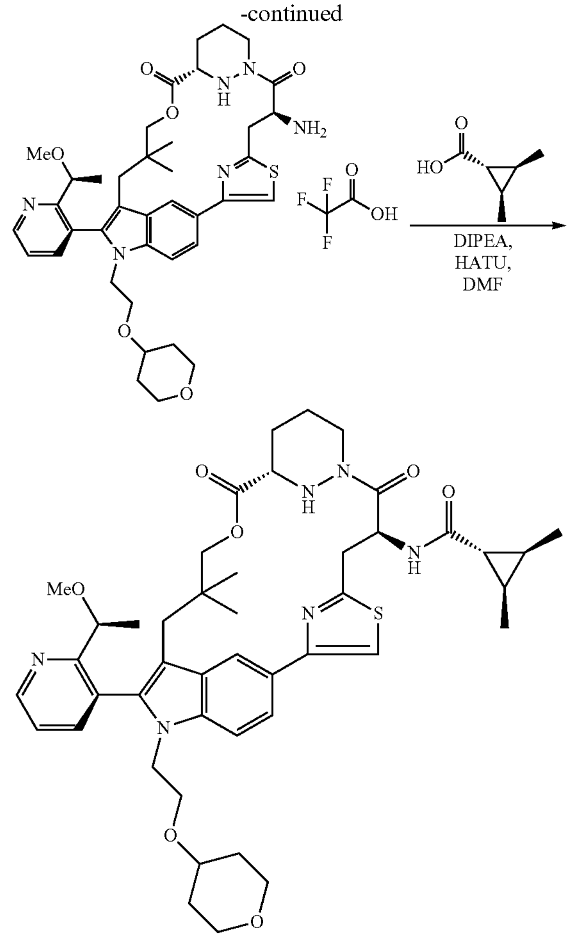

Step 1.

To a mixture of (S)-5-bromo-3-(3-((tert-butyldiphenylsilyl)oxy)-2,2-dimethylpropyl)-2-(2-(1-methoxyethyl)pyridin-3-yl)-1H-indole (3.0 g, 4.6 mmol) and 2-((tetrahydro-2H-pyran-4-yl)oxy)ethyl 4-methylbenzenesulfonate (2.06 g, 6.9 mmol) in DMF (20 mL) at 0° C. under an atmosphere of $N_2$ was added $Cs_2CO_3$ (3.73 g, 11.4 mmol) in portions. The mixture was heated to 65° C. and stirred overnight, then diluted with $H_2O$ (50 mL) and extracted with EtOAc (3×50 mL). The combined organic layers were washed with brine (3×50 mL), dried over anhydrous $Na_2SO_4$ and filtered. The filtrate was concentrated under reduced pressure and the residue was purified by silica gel column chromatography to give (S)-5-bromo-3-(3-((tert-butyldiphenylsilyl)oxy)-2,2-dimethylpropyl)-2-(2-(1-methoxyethyl)pyridin-3-yl)-1-(2-((tetrahydro-2H-pyran-4-yl)oxy)ethyl)-1H-indole (2.3 g, 64% yield) as a solid. LCMS (ESI): m/z $[M+H]^+$ calc'd for $C_{44}H_{55}BrN_2O_4Si$ 784.3. found 785.2.

Step 2.

To a mixture of (S)-5-bromo-3-(3-((tert-butyldiphenylsilyl)oxy)-2,2-dimethylpropyl)-2-(2-(1-methoxyethyl)pyridin-3-yl)-1-(2-((tetrahydro-2H-pyran-4-yl)oxy)ethyl)-1H-indole (2.3 g, 2.9 mmol) in THF (20 mL) at 0° C. under an atmosphere of $N_2$ was added TBAF, 1 M in THF (14.67 mL, 14.7 mmol) in portions. The mixture was heated to 45° C. and stirred for 6 h, then diluted with $H_2O$ and extracted with EtOAc (3×30 mL). The combined organic layers were washed with brine (3×30 mL), dried over anhydrous $Na_2SO_4$ and filtered. The filtrate was concentrated under reduced pressure and the residue was purified by preparative-TLC to give (S)-3-(5-bromo-2-(2-(1-methoxyethyl)pyridin-3-yl)-1-

(2-((tetrahydro-2H-pyran-4-yl)oxy)ethyl)-1H-indol-3-yl)-2,2-dimethylpropan-1-ol (690 mg, 43% yield) as a solid. LCMS (ESI): m/z [M+H]$^+$ calc'd for $C_{28}H_{37}BrN_2O_4$ 546.2. found 546.9.

Step 3.

To a mixture of (S)-3-(5-bromo-2-(2-(1-methoxyethyl)pyridin-3-yl)-1-(2-((tetrahydro-2H-pyran-4-yl)oxy)ethyl)-1H-indol-3-yl)-2,2-dimethylpropan-1-ol (690 mg, 1.3 mmol) and $(Bpin)_2$ (643 mg, 2.5 mmol) in toluene (7 mL) under an atmosphere of Ar was added KOAc (372 mg, 3.8 mmol) and $Pd(dppf)Cl_2$ (93 mg, 0.13 mmol) in portions. The mixture was heated to 80° C. and stirred for 2.5 h, then diluted with $H_2O$ (20 mL) and extracted with EtOAc (3×20 mL). The combined organic layers were washed with brine (3×30 mL), dried over anhydrous $Na_2SO_4$ and filtered. The filtrate was concentrated under reduced pressure and the residue was purified by preparative-TLC to give (S)-3-(2-(2-(1-methoxyethyl)pyridin-3-yl)-1-(2-((tetrahydro-2H-pyran-4-yl)oxy)ethyl)-5-(4,4,5,5-tetramethyl-1,3,2-dioxaborolan-2-yl)-1H-indol-3-yl)-2,2-dimethylpropan-1-ol (700 mg, 93% yield) as a solid. LCMS (ESI): m/z [M+H]$^+$ calc'd for $C_{34}H_{49}BN_2O_6$ 592.4. found 593.1.

Step 4.

To a mixture of (S)-3-(2-(2-(1-methoxyethyl)pyridin-3-yl)-1-(2-((tetrahydro-2H-pyran-4-yl)oxy)ethyl)-5-(4,4,5,5-tetramethyl-1,3,2-dioxaborolan-2-yl)-1H-indol-3-yl)-2,2-dimethylpropan-1-ol (670 mg, 1.13 mmol) and Pd(DtBPF)$Cl_2$ (147 mg, 0.23 mmol) in toluene (3 mL), 1,4-dioxane (1 mL) and $H_2O$ (1 mL) under an atmosphere of Ar was added methyl (S)-1-((S)-3-(4-bromothiazol-2-yl)-2-((tert-butoxycarbonyl)amino)propanoyl)hexahydropyridazine-3-carboxylate (648 mg, 1.36 mmol) and $K_3PO_4$ (720 mg, 3.39 mmol) in portions. The mixture was heated to 60° C. and stirred for 3 h, then diluted with $H_2O$ (10 mL) and extracted with EtOAc (3×10 mL). The combined organic layers were washed with brine (3×10 mL), dried over anhydrous $Na_2SO_4$ and filtered. The filtrate was concentrated under reduced pressure and the residue was purified by preparative-TLC to give methyl (S)-1-((S)-2-((tert-butoxycarbonyl)amino)-3-(4-(3-(3-hydroxy-2,2-dimethylpropyl)-2-(2-((S)-1-methoxyethyl)pyridin-3-yl)-1-(2-((tetrahydro-2H-pyran-4-yl)oxy)ethyl)-1H-indol-5-yl)thiazol-2-yl)propanoyl)hexahydropyridazine-3-carboxylate (680 mg, 70% yield) as a solid. LCMS (ESI): m/z [M+H]$^+$ calc'd for $C_{45}H_{62}N_6O_9S$ 862.4. found 863.1.

Step 5.

To a mixture of methyl (S)-1-((S)-2-((tert-butoxycarbonyl)amino)-3-(4-(3-(3-hydroxy-2,2-dimethylpropyl)-2-(2-((S)-1-methoxyethyl)pyridin-3-yl)-1-(2-((tetrahydro-2H-pyran-4-yl)oxy)ethyl)-1H-indol-5-yl)thiazol-2-yl)propanoyl)hexahydropyridazine-3-carboxylate (300 mg, 0.35 mmol) in THF (6 mL) at 0° C. under an atmosphere of $N_2$ was added 1M LiOH (1.74 mL, 1.74 mmol) in portions. When the reaction was deemed complete by LCMS the mixture was acidified to pH~6 with 1M HCl, then extracted with EtOAc (3×50 mL). The combined organic layers were washed with brine (2×20 mL), dried over anhydrous $Na_2SO_4$, filtered and the filtrate was concentrated under reduced pressure to give (S)-1-((S)-2-((tert-butoxycarbonyl)amino)-3-(4-(3-(3-hydroxy-2,2-dimethylpropyl)-2-(2-((S)-1-methoxyethyl)pyridin-3-yl)-1-(2-((tetrahydro-2H-pyran-4-yl)oxy)ethyl)-1H-indol-5-yl)thiazol-2-yl)propanoyl)hexahydropyridazine-3-carboxylic acid (280 mg) as a solid, which was used directly in the next step without further purification. LCMS (ESI): m/z [M+H]$^+$ calc'd for $C_{44}H_{60}N_6O_9S$ 848.4. found 849.4.

Step 6.

To a mixture of (S)-1-((S)-2-((tert-butoxycarbonyl)amino)-3-(4-(3-(3-hydroxy-2,2-dimethylpropyl)-2-(2-((S)-1-methoxyethyl)pyridin-3-yl)-1-(2-((tetrahydr-2H-pyran-4-yl)oxy)ethyl)-1H-indol-5-yl)thiazol-2-yl)propanoyl)hexahydropyridazine-3-carboxylic acid (300 mg, 0.35 mmol) and DIPEA (457 mg, 3.5 mmol) in DCM (50 mL) at 0° C. under an atmosphere of $N_2$ was added HOST (477 mg, 3.5 mmol) and EDCI (2.03 g, 10.6 mmol) in portions. The mixture was warmed to room temperature and stirred overnight, then washed with $H_2O$ (50 mL) and the aqueous layer was extracted with DCM (3×50 mL). The combined organic layers were washed with brine (3×100 mL), dried over anhydrous $Na_2SO_4$ and filtered. The filtrate was concentrated under reduced pressure and the residue was purified by preparative-TLC to give tert-butyl (($6^3$S,4S,Z)-$1^2$-(2-((S)-1-methoxyethyl)pyridin-3-yl)-10,10-dimethyl-5,7-dioxo-$1^1$-(2-((tetrahydro-2H-pyran-4-yl)oxy)ethyl)-$6^1$,$6^2$,$6^3$,$6^4$,$6^5$,$6^6$-hexahydro-$1^1$H-8-oxa-2(4,2)-thiazola-1(5,3)-indola-6(1,3)- pyridazinacycloundecaphane-4-yl)carbamate (200 mg, 68% yield) as a solid. LCMS (ESI): m/z [M+H]$^+$ calc'd for $C_{44}H_{58}N_6O_8S$ 830.4. found 831.3.

Step 7.

To a mixture of tert-butyl (($6^3$S,4S,Z)-$1^2$-(2-((S)-1-methoxyethyl)pyridin-3-yl)-10,10-dimethyl-5,7-dioxo-$1^1$-(2-((tetrahydro-2H-pyran-4-yl)oxy)ethyl)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (90 mg, 0.11 mmol) in DCM (1 mL) at 0° C. under an atmosphere of $N_2$ was added TFA (1 mL) in portions. The mixture was stirred at 0° C. for 1.5 h, then concentrated under reduced pressure to give ($6^3$S,4S,Z)-4-amino-$1^2$-(2-((S)-1-methoxyethyl)pyridin-3-yl)-10,10-dimethyl-$1^1$-(2-((tetrahydro-2H-pyran-4-yl)oxy)ethyl)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione TFA salt (80 mg) as an oil, that was used directly in the next step without further purification. LCMS (ESI): m/z [M+H]$^+$ calc'd for $C_{39}H_{50}N_6O_6S$ 730.4. found 731.4.

Step 8.

To a mixture of ($6^3$S,4S,Z)-4-amino-$1^2$-(2-((S)-1-methoxyethyl)pyridin-3-yl)-10,10-dimethyl-$1^1$-(2-((tetrahydro-2H-pyran-4-yl)oxy)ethyl)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione TFA salt (90 mg, 0.12 mmol) and (1r,2R,3S)-2,3-dimethylcyclopropane-1-carboxylic acid (17 mg, 0.15 mmol) at 0° C. under an atmosphere of $N_2$ was added DIPEA (318 mg, 2.5 mmol) and HATU (56 mg, 0.15 mmol) in portions. The mixture was stirred at 0° C. for 1 h, then washed with $H_2O$ (1 mL) and extracted with EtOAc (3×30 mL). The combined organic layers were washed with brine (30 mL), dried over anhydrous $Na_2SO_4$ and filtered. The filtrate was concentrated under reduced pressure and the residue was purified by preparative-HPLC to give (1r,2R,3S)—N-(($6^3$S,4S,Z)-$1^2$-(2-((S)-1-methoxyethyl)pyridin-3-yl)-10,10-dimethyl-5,7-dioxo-$1^1$-(2-((tetrahydro-2H-pyran-4-yl)oxy)ethyl)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (17 mg, 17% yield) as a solid. LCMS (ESI): m/z [M+H]$^+$ calc'd for $C_{45}H_{58}N_6O_7S$ 826.4. found 827.6; $^1$H NMR (400 MHz, DMSO-$d_6$) δ 8.74 (dd, J=4.7, 1.8 Hz, 1H), 8.48 (d, J=1.6 Hz, 1H), 8.39 (d, J=9.0 Hz, 1H), 7.81 (s, 1H), 7.74 (ddd, J=10.5, 8.2, 1.8 Hz, 2H), 7.61 (d, J=8.7 Hz, 1H), 7.51 (dd, J=7.7, 4.7 Hz, 1H), 5.56 (t, J=9.0 Hz, 1H), 5.07 (d, J=12.1 Hz, 1H), 4.46 (dt, J=14.9, 5.3 Hz, 1H), 4.32-4.09 (m, 4H), 3.62-3.47 (m, 4H), 3.34-3.30 (m, 1H), 3.30-3.28 (m, 1H), 3.26 (s, 3H), 3.21-3.04 (m, 4H), 2.94 (d, J=14.3 Hz, 1H), 2.83-2.68 (m, 1H), 2.46-2.43 (m, 1H), 2.16-2.05 (m, 1H), 1.76 (d, J=20.9 Hz, 2H), 1.51 (d, J=13.5 Hz, 3H), 1.36 (d, J=6.1 Hz, 3H), 1.30-1.09 (m, 3H), 1.13-0.98 (m, 8H), 0.88 (s, 3H), 0.32 (s, 3H).

Example A459. Synthesis of (2S)—N-(($6^3$S,3S,4S,Z)-3-ethoxy-$1^1$-(2-isopropoxyethyl)-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-(methoxymethyl)azetidine-1-carboxamide
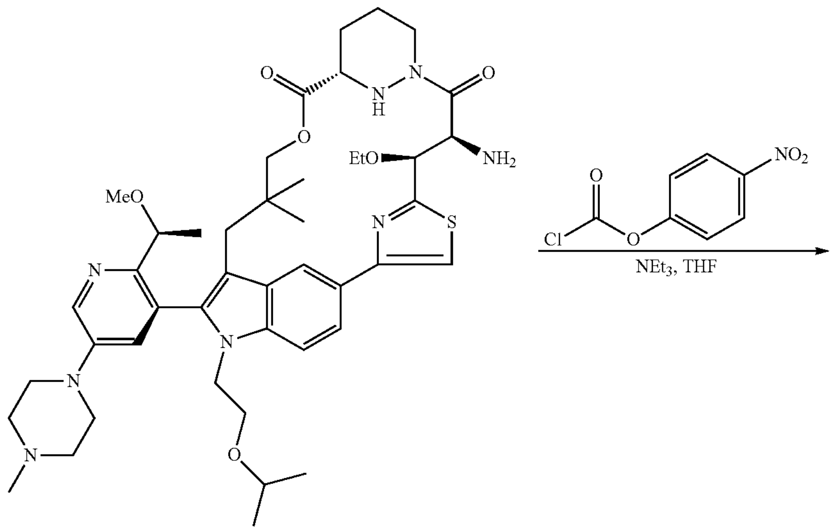
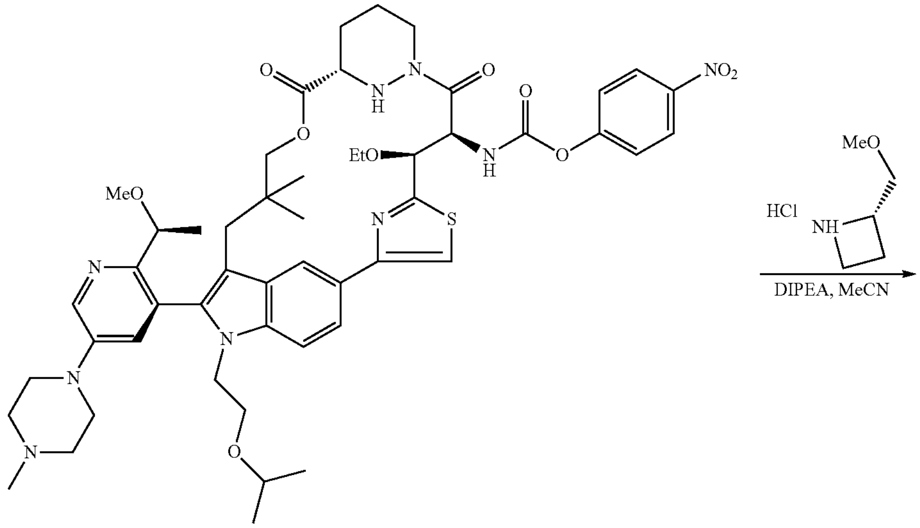

-continued

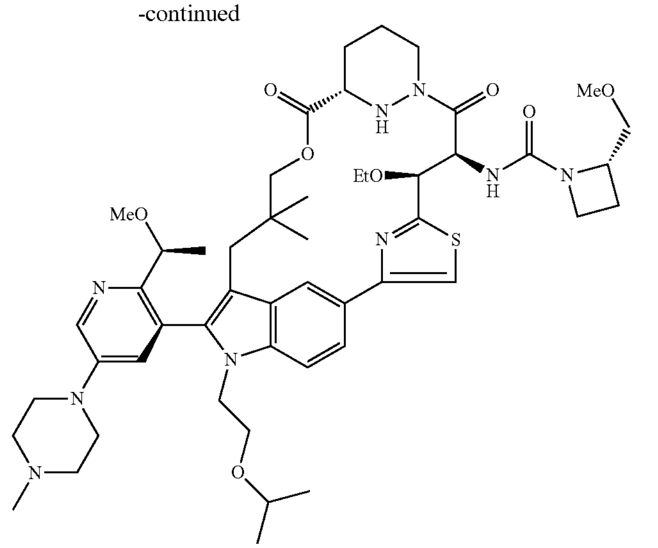

Step 1.

A mixture of ($6^3$S,3S,4S,Z)-4-amino-3-ethoxy-$1^1$-(2-isopropoxyethyl)-$1^2$-(2-((S)-1-methoxyethyl)-5-(4-methylpiperazin-1-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (170 mg, 0.21 mmol) in THF (6 mL) at 0° C. under an atmosphere of $N_2$ was added TEA (62 mg, 0.62 mmol) and 4-nitrophenyl chloroformate (62 mg, 0.31 mmol) in portions. The mixture was warmed to room temperature and stirred for 4 h, then concentrated under reduced pressure to give 4-nitrophenyl (($6^3$S,3S,4S,Z)-3-ethoxy-11-(2-isopropoxyethyl)-12-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (200 mg) as a solid, which was used directly in the next step without further purification.

Step 2.

To a mixture of 4-nitrophenyl (($6^3$S,3S,4S,Z)-3-ethoxy-$1^1$-(2-isopropoxyethyl)-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (150 mg, 0.15 mmol) in MeCN (8 mL) at 0° C. under an atmosphere of NW was added DIPEA (78 mg, 0.60 rnmnol) and (2S)-2-(methoxymethyl)azetidine HCl salt (46 mg, 0.45 mmol) in portions. The mixture was warmed to room temperature and stirred overnight, then the mixture was diluted with brine (10 mL) and extracted with EtOAc (3×20 mL). The combined organic layers were washed with brine (3×20 mL), dried over anhydrous $Na_2SO_4$ and filtered. The filtrate was concentrated under reduced pressure and the residue was purified by preparative-HPLC to give (2S)—N-(($6^3$S,3S,4S,Z)-3-ethoxy-$1^1$-(2-isopropoxyethyl)-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-1H-8-oxa-2(4,2)-thiazola-1 (5,3)-indola-6(1,3)-pyridazinacycloundecaphane-4-yl)-2-(methoxymethyl) azetidine-1-carboxamide (56 mg, 39% yield) as a solid. LCMS (ESI): m/z $[M+H]^+$ calc'd for $C_{50}H_{71}N_9O_8S$ 957.5. found 958.4; $^1$H NMR (400 MHz, DMSO-$d_6$) δ 8.47 (dd, J=14.9, 2.2 Hz, 2H), 7.91 (s, 1H), 7.74 (dd, J=8.6, 1.6 Hz, 1H), 7.59 (d, J=8.7 Hz, 1H), 7.21 (s, 1H), 6.83 (d, J=10.2 Hz, 1H), 5.51 (d, J=10.2 Hz, 1H), 5.16 (d, J=12.0 Hz, 1H), 4.90 (s, 1H), 4.37 (s, 2H), 4.27-4.00 (m, 4H), 3.71 (q, J=8.4 Hz, 1H), 3.65-3.54 (m, 5H), 3.50 (q, J=9.4, 8.4 Hz, 2H), 3.43 (s, 3H), 3.40 (s, 2H), 3.30 (s, 1H), 3.29-3.20 (m, 4H), 3.13 (s, 3H), 2.90-2.72 (m, 2H), 2.67 (s, 1H), 2.43 (s, 2H), 2.23 (s, 4H), 2.05 (d, J=12.0 Hz, 1H), 1.82 (dd, J=23.8, 13.9 Hz, 3H), 1.52 (d, J=12.1 Hz, 1H), 1.33 (d, J=6.1 Hz, 3H), 1.13 (t, J=7.0 Hz, 3H), 0.93-0.84 (m, 6H), 0.81 (d, J=6.1 Hz, 3H), 0.44 (s, 3H).

Example A460. Synthesis of (2R)—N-((6[3]S,3S,4S,Z)-3-ethoxy-1[1]-(2-isopropoxyethyl)-1[2]-(2-((S)-1-methoxyethyl)-5-(4-methylpiperazin-1-yl)pyridin-3-yl)-10,10-dimethyl-5,7-dioxo-6[1],6[2],6[3],6[4],6[5],6[6]-hexahydro-1[1]H-8-oxa-2(4,2)-thiazola-1(5,3)-indola-6(1,3)-pyridazinacycloundecaphane-4-yl)-2-methylazetidine-1-carboxamide

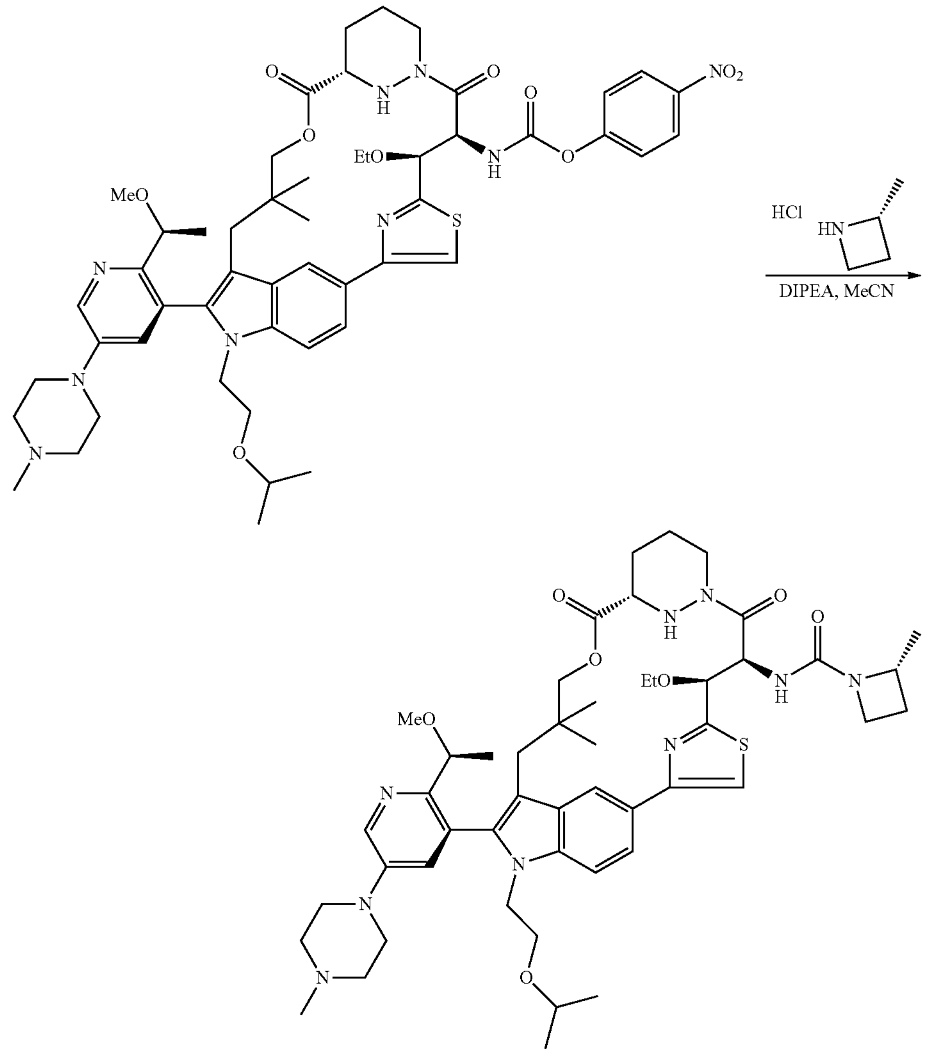

Step 1.

To a mixture of 4-nitrophenyl ((6[3]S,3S,4S,Z)-3-ethoxy-1[1]-(2-isopropoxyethyl)-1[2]-(2-((S)-1-methoxyethyl)-5-(4-methylpiperazin-1-yl)pyridin-3-yl)-10,10-dimethyl-5,7-dioxo-6[1],6[2],6[3],6[4],6[5],6[6]-hexahydro-1[1]H-8-oxa-2(4,2)-thiazola-1(5,3)-indola-6(1,3)-pyridazinacycloundecaphane-4-yl)carbamate (150 mg, 0.15 mmol) in MECN (8 mL) at 0° C. under an atmosphere of $N_2$ was added DIPEA (78 mg, 0.60 mmol) and (2R)-2-methylazetidine (32 mg, 0.45 mmol) in portions. The mixture was warmed to room temperature and stirred overnight, then diluted with brine (10 mL) and extracted with EtOAc (3×20 mL).

The combined organic layers were washed with brine (3×20 mL), dried over anhydrous $Na_2SO_4$ and filtered. The filtrate was concentrated under reduced pressure and the residue was purified by preparative-HPLC to give (2R)—N-((6[3]S,3S,4S,Z)-3-ethoxy-1[1]-(2-isopropoxyethyl)-1[2]-(2-((S)-1-methoxyethyl)-5-(4-methylpiperazin-1-yl)pyridin-3-yl)-10,10-dimethyl-5,7-dioxo-6[1],6[2],6[3],6[4],6[5],6[6]-hexahydro-1[1]H-8-oxa-2(4,2)-thiazola-1(5,3)-indola-6(1,3)-pyridazinacycloundecaphane-4-yl)-2-methylazetidine-1-carboxamide (57 mg, 41% yield) as a solid. LCMS (ESI): m/z $[M+H]^+$ calc'd for $C_{49}H_{69}N_9O_7S$ 927.5. found 928.4; $^1H$ NMR (400 MHz, DMSO-$d_6$) δ 8.53-8.40 (m, 2H), 7.93 (s, 1H), 7.78-7.69 (m, 1H), 7.59 (d, J=8.6 Hz, 1H), 7.21 (s, 1H), 5.56 (d, J=10.2 Hz, 1H), 5.21 (d, J=12.1 Hz, 1H), 5.12 (d, J=10.2 Hz, 1H), 4.91 (s, 1H), 4.35 (d, J=13.9 Hz, 1H), 4.27-4.12 (m, 4H), 4.08 (d, J=6.1 Hz, 1H), 3.75 (t, J=7.4 Hz, 2H), 3.65-3.46 (m, 4H), 3.30 (s, 2H), 3.29 (s, 1H), 3.26 (d, J=5.9 Hz, 5H), 3.13 (s, 3H), 2.79 (d, J=13.5 Hz, 2H), 2.60 (s, 2H), 2.45 (p, J=1.9 Hz, 4H), 2.22 (s, 3H), 2.06 (d, J=12.1 Hz, 1H), 1.82 (s, 3H), 1.54-1.49 (m, 1H), 1.34 (dd, J=14.9, 6.2 Hz, 6H), 1.13 (t, J=7.0 Hz, 3H), 0.87 (t, J=6.8 Hz, 6H), 0.81 (d, J=6.0 Hz, 3H), 0.44 (s, 3H).

Example A476. Synthesis of (1R,2R,3S)—N-((3'S,3'S,4'S,Z)-3'-ethoxy-1'-(2-isopropoxyethyl)-2'-(2-((S)-1-methoxyethyl)-5-(4-methylpiperazin-1-yl)pyridin-3-yl)-5',7'-dioxospiro[cyclopropane-1,10'-8-oxa-2(4,2)-thiazola-1(5,3)-indola-6(1,3)-pyridazinacycloundecaphan]-4'-yl)-2,3-dimethylcyclopropane-1-carboxamide and (1R,2R,3S)—N-((3'S,3'S,4'S,Z)-3'-ethoxy-1'-2-isopropoxyethyl)-2'-(2-((S)-1-methoxyethyl)-5-(4-methylpiperazin-1-yl)pyridin-3-yl)-5',7'-dioxospiro[cyclopropane-1,10'-8-oxa-2(4,2)-thiazola-1(5,3)-indola-6(1,3)-pyridazinacycloundecaphan]-4'-yl)-2,3-dimethylcyclopropane-1-carboxamide

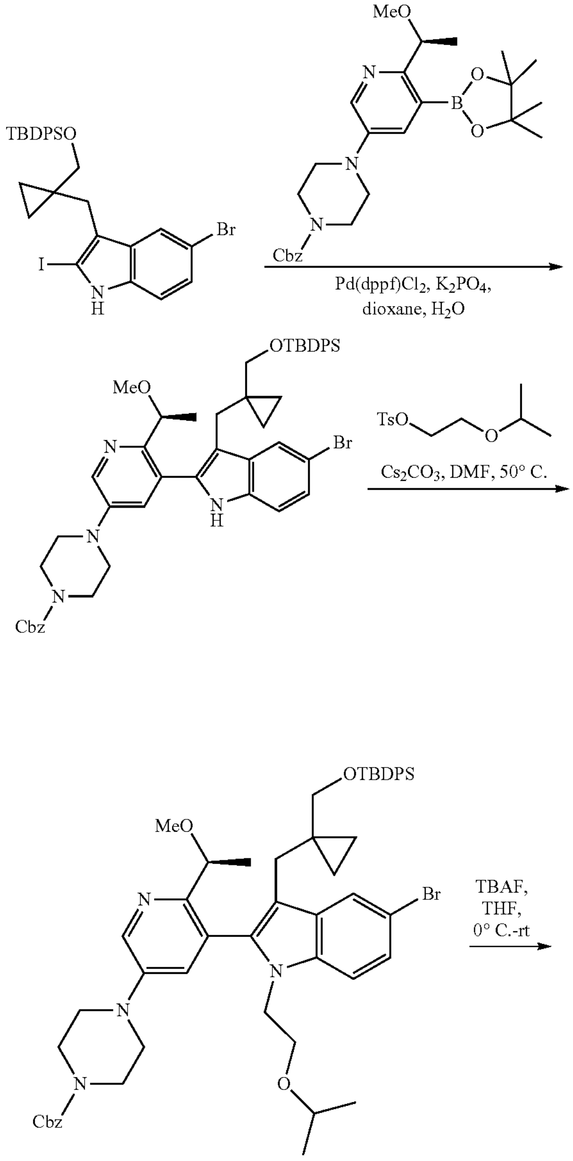

-continued

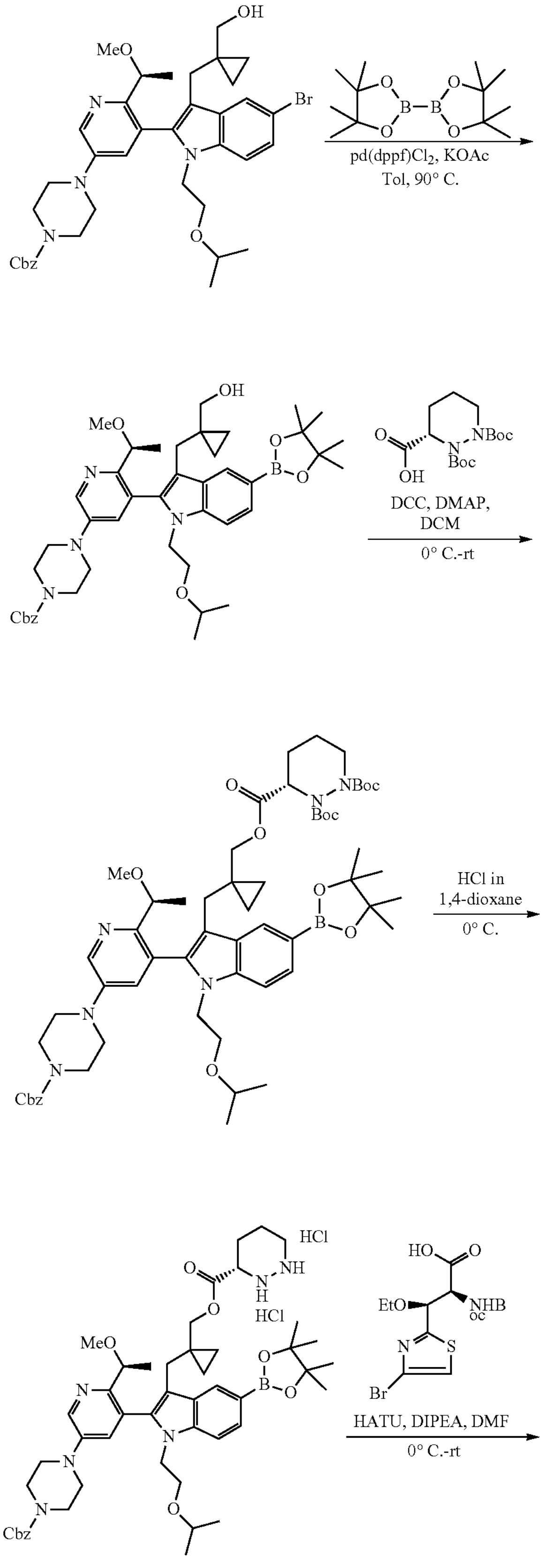

-continued

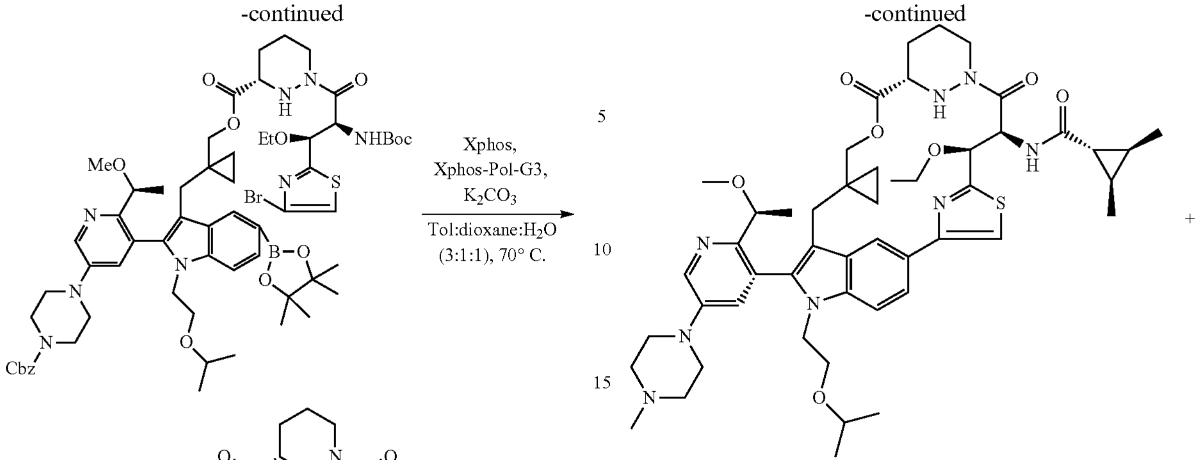

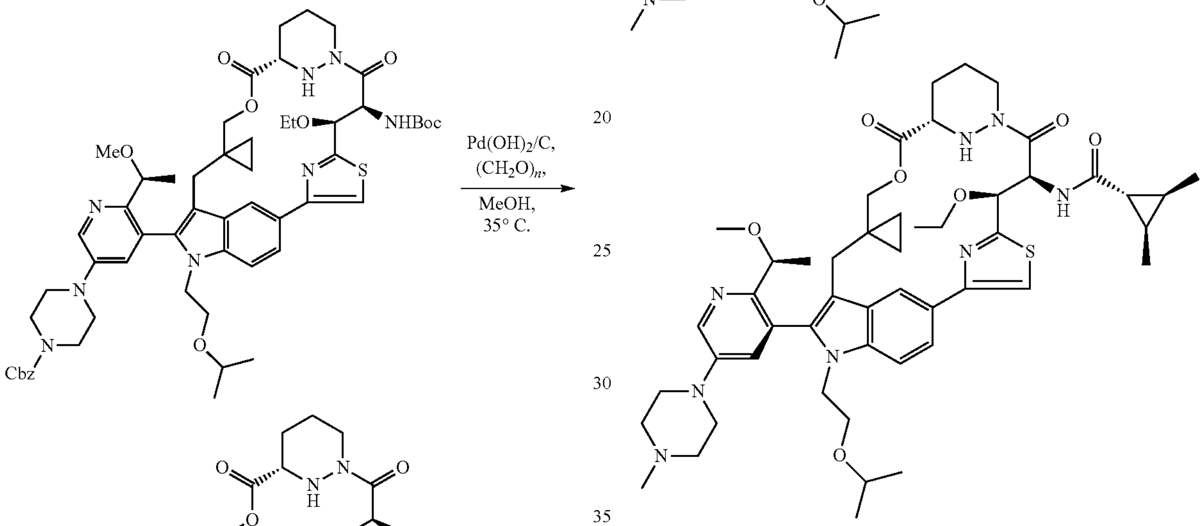

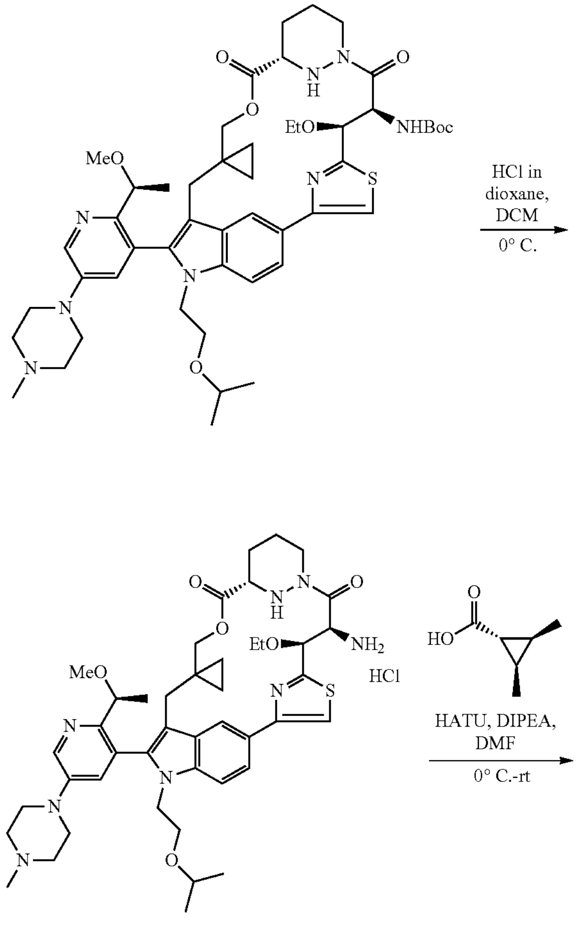

Step 1.

To a mixture of 5-bromo-3-(1-(((tert-butyldiphenylsilyl)oxy)methyl)cyclopropyl)methyl)-2-iodo-1H-indole (6.1 g, 9.5 mmol) and benzyl (S)-4-(6-(1-methoxyethyl)-5-(4,4,5,5-tetramethyl-1,3,2-dioxaborolan-2-yl)pyridin-3-yl)piperazine-1-carboxylate (4.56 g, 9.5 mmol) in 1,4-dioxane (120 mL) and $H_2O$ (20 mL) under an atmosphere of $N_2$ was added Pd(dppf)$Cl_2$ (1.04 g, 1.4 mmol) and $K_3PO_4$ (4.02 g, 18.9 mmol) in portions. The mixture was heated to 65° C. and stirred for 3 h, then extracted with EtOAc (3×100 ml). The combined organic layers were washed with brine (3×100 mL); dried over anhydrous $Na_2SO_4$ and filtered. The filtrate was concentrated under reduced pressure and the residue was purified by silica gel column chromatography to give benzyl (S)-4-(5-(5-bromo-3-((1-(((tert-butyldiphenylsilyl)oxy)methyl)cyclopropyl)methyl)-1H-indol-2-yl)-6-(1-methoxyethyl)pyridin-3-yl)piperazine-1-carboxylate (4.7 g, 57% yield) as a solid. LCMS (ESI): m/z $[M+H]^+$ calc'd for $C_{49}H_{55}BrN_4O_4Si$ 870.3. found 871.5.

Step 2.

To a mixture of benzyl (S)-4-(5-(5-bromo-3-((1-(((tert-butyldiphenylsilyl)oxy)methyl)cyclopropyl)methyl)-1H-indol-2-yl)-6-(1-methoxyethyl)pyridin-3-yl)piperazine-1-carboxylate (4.6 g, 5.3 mmol) in DMF (50 mL) at 0° C. was added 2-isopropoxyethyl 4-methylbenzenesulfonate (2.04 g, 7.9 mmol) and $Cs_2CO_3$ (5.16 g, 15.8 mmol). The mixture was heated to 50° C. and stirred for 2 h, then diluted with $H_2O$ and extracted with EtOAc (2×100 mL). The combined organic layers were washed with brine (3×100 mL), dried over anhydrous $Na_2SO_4$ and filtered. The filtrate was concentrated under reduced pressure and the residue was purified by reverse-phase silica gel column chromatography to give benzyl (S)-4-(5-(5-bromo-3-((1-(((tert-butyldiphenylsilyl)oxy)methyl)cyclopropyl)methyl)-1-(2-isopropoxyethyl)-1H-indol-2-yl)-6-(1-methoxyethyl)pyridin-3-yl)piperazine-1-carboxylate (4.5 g, 89% yield) as an oil. LCMS (ESI): m/z $[M+H]^+$ calc'd for $C_{54}H_{65}BrN_4O_5Si$ 956.4. found 957.2.

Step 3.

To a mixture of benzyl (S)-4-(5-(5-bromo-3-((1-(((tert-butyldiphenylsilyl)oxy)methyl)cyclopropyl)methyl)-1-(2-isopropoxyethyl)-1H-indol-2-yl)-6-(1-methoxyethyl)pyridin-3-yl)piperazine-1-carboxylate (3.2 g, 3.3 mmol) in THF (32 mL) at 0° C. was added TBAF (13.1 g, 50.1 mmol). The mixture was warmed to room temperature and stirred for 16 h, then diluted with $H_2O$ and extracted with EtOAc (2×100 mL). The combined organic layers were washed with brine (3×100 mL), dried over anhydrous $Na_2SO_4$ and filtered. The filtrate was concentrated under reduced pressure and the residue was purified by reverse-phase silica gel column chromatography to give benzyl (S)-4-(5-(5-bromo-3-((1-(hydroxymethyl)cyclopropyl)methyl)-1-(2-isopropoxyethyl)-1H-indol-2-yl)-6-(1-methoxyethyl)pyridin-3-yl)piperazine-1-carboxylate (1.84 g, 77% yield) as an oil. LCMS (ESI): m/z $[M+H]^+$ calc'd for $C_{38}H_{47}BrN_4O_5$, 718.3. found 719.2.

Step 4.

To a mixture of benzyl (S)-4-(5-(5-bromo-3-((1-(hydroxymethyl)cyclopropyl)methyl)-1-(2-isopropoxyethyl)-1H-indol-2-yl)-6-(1-methoxyethyl)pyridin-3-yl)piperazine-1-carboxylate (1.7 g, 2.4 mmol) in toluene (20 mL) at 0° C. under an atmosphere of Ar was added 4,4,4',4',5,5,5',5'-octamethyl-2,2'-bi(1,3,2-dioxaborolane) (1.80 g, 7.1 mmol), KOAc (580 mg, 5.9 mmol) and $Pd(dppf)Cl_2$ (346 mg, 0.47 mmol). The mixture was heated to 90° C. and stirred for 3 h, then diluted with $H_2O$ and extracted with EtOAc (2×50 mL). The combined organic layers were washed with brine (2×50 mL), dried over anhydrous $Na_2SO_4$ and filtered. The filtrate was concentrated under reduced pressure and the residue was purified by reverse-phase silica gel column chromatography to give benzyl (S)-4-(5-(3-((1-(hydroxymethyl)cyclopropyl)methyl)-1-(2-isopropoxyethyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (1.4 g, 77% yield) as a solid. LCMS (ESI): m/z $[M+H]^+$ calc'd for $C_{44}H_{59}BN_4O_7$ 766.5. found 767.4.

Step 5.

To a mixture of benzyl (S)-4-(5-(3-((1-(hydroxymethyl)cyclopropyl)methyl)-1-(2-isopropoxyethyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (1.4 g, 1.8 mmol) in DCM (20 mL) at 0° C. was added (S)-1,2-bis(tert-butoxycarbonyl)hexahydropyridazine-3-carboxylic acid (664 mg, 2.0 mmol), DCC (490 mg, 2.4 mmol) and DMAP (45 mg, 0.37 mmol). The mixture was warmed to room temperature and stirred for 16 h, then diluted with $H_2O$ and extracted with EtOAc (2×100 mL). The combined organic layers were washed with brine (2×100 mL), dried over anhydrous $Na_2SO_4$ and filtered. The filtrate was concentrated under reduced pressure and the residue was purified by reverse-phase silica gel column chromatography to give 3-((1-((2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)methyl)cyclopropyl)methyl) 1,2-di-tert-butyl (S)-tetrahydropyridazine-1,2,3-tricarboxylate (1.2 g, 61% yield) as an oil. LCMS (ESI): m/z $[M+H]^+$ calc'd for $C_{59}H_{83}BN_6O_{12}$ 1078.6. found 1079.5.

Step 6.

A mixture of 3-((1-((2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)methyl)cyclopropyl)methyl) 1,2-di-tert-butyl (S)-tetrahydropyridazine-1,2,3-tricarboxylate (1.2 g, 1.1 mmol) in HCl in 1,4-dioxane (15 mL) at 0° C. was stirred for 2 h, then concentrated under reduced pressure to give (1-((2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)methyl)cyclopropyl)methyl (S)-hexahydropyridazine-3-carboxylate (1.25 g), which was used directly in the next step without further purification. LCMS (ESI): m/z $[M+H]^+$ calc'd for $C_{49}H_{67}BN_6O_8$ 878.5. found 879.4.

Step 7.

To a mixture of (1-((2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)methyl)cyclopropyl)methyl (S)-hexahydropyridazine-3-carboxylate (1.0 g, 1.1 mmol) in DMF (15 mL) at 0° C. was added DIPEA (1.47 g, 11.4 mmol) and (2S,3S)-3-(4-bromothiazol-2-yl)-2-((tert-butoxycarbonyl)amino)-3-ethoxypropanoic acid (675 mg, 1.7 mmol), followed by HATU (865 mg, 2.3 mmol). The mixture was stirred at 0° C. for 2 h, then diluted with $H_2O$ and extracted with EtOAc (2×100 mL). The combined organic layers were washed with brine (2×100 mL), dried over anhydrous $Na_2SO_4$ and filtered. The filtrate was concentrated under reduced pressure and the residue was purified by preparative-TLC to give (1-((2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)methyl)cyclopropyl)methyl (S)-1-((2S,3S)-3-(4-bromothiazol-2-yl)-2-((tert-butoxycarbonyl)amino)-3-ethoxypropanoyl)hexahydropyridazine-3-carboxylate (730 mg, 51% yield) as an oil. LCMS (ESI): m/z $[M+H]^+$ calc'd for $C_{82}H_{84}BBrN_8O_{12}S$ 1254.5. found 1255.4.

Step 8.

To a mixture of (1-((2-(5-(4-((benzyloxy)carbonyl)piperazin-1-yl)-2-((S)-1-methoxyethyl)pyridin-3-yl)-1-(2-isopropoxyethyl)-5-(4,4,5,5-tetramethyl-1,3,2-dioxaborolan-2-yl)-1H-indol-3-yl)methyl)cyclopropyl)methyl (S)-1-((2S,3S)-3-(4-bromothiazol-2-yl)-2-((tert-butoxycarbonyl)amino)-3-ethoxypropanoyl)hexahydropyridazine-3-carboxylate (700 mg, 0.56 mmol) in toluene (12 mL), 1,4-dioxane (4 mL) and $H_2O$ (4 mL) at 0° C. under an atmosphere of Ar was added XPhos (53 mg, 0.11 mmol), $KSPO_4$ (296 mg, 1.39 mmol) and XPho-Pd-G3 (47 mg, 0.06 mmol). The mixture was heated to 65° C. and stirred for 2 h, then diluted with $H_2O$ and extracted with EtOAc (2×50 mL). The combined organic layers were washed with brine (2×50 mL), dried over anhydrous $Na_2SO_4$ and filtered. The filtrate was concentrated under reduced pressure and the residue was purified by preparative-TLC to give benzyl 4-(5-((3'S,3'S,4'S,Z)-4'-((tert-butoxycarbonyl)amino)-3-ethoxy-1-(2-isopropoxyethyl)-5',7'-dioxospiro[cyclopropane-1,10'-8-oxa-2(4,2)-thiazola-1(5,3)-indola-6(1,3)-pyridazinacycloundecaphan]-2'-yl)-6-((S)-1-methoxyethyl)pyridin-3-yl)piperazine-1-carboxylate (160 mg, 27% yield) as an oil. LCMS (ESI): m/z $[M+H]^+$ calc'd for $C_{56}H_{72}N_8O_{10}S$ 1048.5. found 1049.3.

Step 9.

To a mixture of benzyl 4-(5-((3'S,3'S,4'S,Z)-4'-((tert-butoxycarbonyl)amino)-3'-ethoxy-1'-(2-isopropoxyethyl)-5',7'-dioxospiro[cyclopropane-1,10'-8-oxa-2(4,2)-thiazola-1(5,3)-indola-6(1,3)-pyridazinacycloundecaphan]-2'-yl)-6-((S)-1-methoxyethyl)pyridin-3-yl)piperazine-1-carboxylate (160 mg, 0.15 mmol) in MeOH (3 mL) at 0° C. was added methoxymethanol amine (34 mg, 0.76 mmol) and Pd(OH)$_{21}$C (171 mg, 1.2 mmol). The mixture was placed under an atmosphere of $H_2$, heated to 35° C. and stirred for 4 h, then filtered, and the filter cake was washed with MeOH (2×50 mL). The filtrate was concentrated under reduced pressure to give tert-butyl ((3'S,3'S,4S,Z)-3'-ethoxy-1'-(2-isopropoxyethyl)-2'-(2-((S)-1-methoxyethyl)-5-(4-methylpiperazin-1-yl)pyridin-3-yl)-5',7'-dioxospiro[cyclopropane-1,10'-8-oxa-2(4,2)-thiazola-1(5,3)-indola-6(1,3)-pyridazinacycloundecaphan]-4'-yl)carbamate (100 mg), which was used directly in the next step without further purification. LCMS (ESI): m/z $[M+H]^+$ calc'd for $C_{49}H_{68}N_8O_8S$ 928.5. found 929.4.

Step 10.

To a mixture of tert-butyl ((3'S,3'S,4'S,Z)-3'-ethoxy-1'-(2-isopropoxyethyl)-2'-(2-((S)-1-methoxyethyl)-5-(4-methylpiperazin-1-yl)pyridin-3-yl)-5',7'-dioxospiro[cyclopropane-1,10'-8-oxa-2(4,2)-thiazola-1(5,3)-indola-6(1,3)-pyridazinacycloundecaphan]-4'-yl)carbamate (100 mg, 0.11 mmol) in DCM (1 mL) at 0° C. was added HCl in 1,4-dioxane (1 mL). The mixture was stirred at 0° C. for 2 h, then concentrated under reduced pressure to give (3S,3S,4'S,Z)-4'-amino-3-ethoxy-1'-(2-isopropoxyethyl)-2'-(2-((S)-1-methoxyethyl)-5-(4-methylpiperazin-yl)pyridin-3-yl)spiro[cyclopropane-1,10'-8-oxa-2(4,2)-thiazola-1(5,3)-indola-6(1,3)-pyridazinacycloundecaphane]-5',7'-dione (110 mg), which was used directly in the next step without further purification. LCMS (ESI): m/z $[M+H]^+$ calc'd for $C_{44}H_{60}N_8O_6S$ 828.4. found 829.4.

Step 11.

To a mixture of (3'S,3'S,4'S,Z)-4'-amino-3'-ethoxy-1'-(2-isopropoxyethyl)-2'-(2-((S)-1-methoxyethyl)-5-(4-methylpiperazin-1-yl)pyridin-3-yl)spiro[cyclopropane-1,10'-8-oxa-2(4,2)-thiazola-1(5,3)-indola-6(1,3)-pyridazinacycloundecaphane]-5',7'-dione (100 mg, 0.12 mmol) in DMF (2 mL) at 0° C. was added DIPEA (78 mg, 0.61 mmol), (1R,2R,3S)-2,3-dimethylcyclopropane-1-carboxylic acid (21 mg, 0.18 mmol) and HATU (92 mg, 0.24 mmol). The mixture was stirred at 0° C. for 2 h, then diluted with $H_2O$ and extracted with EtOAc (2×30 mL). The combined organic layers were washed with brine (2×30 mL), dried over anhydrous $Na_2SO_4$ and filtered. The filtrate was concentrated under reduced pressure and the residue was purified by preparative-HPLC to give (1R,2R,3S)—N-((3'S,3'S,4'S,Z)-3'-ethoxy-1'-(2-isopropoxyethyl)-2'-(2-((S)-1-methoxyethyl)-5-(4-methylpiperazin-1-yl)pyridin-3-yl)-5',7'-dioxospiro[cyclopropane-1,10'-8-oxa-2(4,2)-thiazola-1(5,3)-indola-6(1,3)-pyridazinacycloundecaphan]-4'-yl)-2,3-dimethylcyclopropane-1-carboxamide (7 mg, 6% yield) and (1R,2R,3S)—N-((3'S,3'S,4'S,Z)-3'-ethoxy-1'-(2-isopropoxyethyl)-2'-(2-((S)-1-methoxyethyl)-5-(4-methylpiperazin-1-yl)pyridin-3-yl)-5',7-dioxospiro[cyclopropane-1,10'-8-oxa-2(4,2)-thiazola-1(5,3)-indola-6(1,3)-pyridazinacycloundecaphan]-4'-yl)-2,3-dimethylcyclopropane-1-carboxamide (13 mg, 12% yield), both as solids. LCMS (ESI): m/z $[M+H]^+$ calc'd for $C_{50}H_{68}N_8O_7S$ 924.5. found 925.5; $^1H$ NMR (400 MHz, DMSO-$d_6$) δ 8.50 (d, J=1.5 Hz, 1H), 8.42 (d, J=3.0 Hz, 1H), 7.91 (s, 1H), 7.71 (d, J=8.6 Hz, 1H), 7.64 (d, J=10.1 Hz, 1H), 7.58 (d, J=8.6 Hz, 1H), 7.25 (d, J=2.8 Hz, 1H), 6.55 (s, 1H), 5.77 (d, J=10.1 Hz, 1H), 5.04 (d, J=12.3 Hz, 1H), 4.92 (s, 1H), 4.37-4.28 (m, 1H), 4.22 (d, J=10.9 Hz, 1H), 4.18-4.08 (nm, 3H), 3.98 (dd, J=12.2, 6.1 Hz, 3H), 3.65-3.58 (m, 6H), 3.36-3.20 (m, 6H), 3.17 (d, J=5.2 Hz, 2H), 2.98 (s, 3H), 2.45 (s, 6H), 2.39-2.30 (m, 3H), 2.10-1.89 (m, 3H), 1.86-1.66 (m, 3H), 1.51 (d, J=3.8 Hz, 2H), 1.36 (d, J=6.2 Hz, 3H), 1.24 (s, 1H), 1.16 (t, J=7.0 Hz, 5H), 1.08 (d, J=5.5 Hz, 3H), 1.04 (d, J=5.5 Hz, 3H), 0.91 (d, J=6.1 Hz, 3H), 0.86 (d, J=6.1 Hz, 4H) and LCMS (ESI): m/z $[M+H]^+$ calc'd for $C_{50}H_{68}N_8O_7S$ 924.5. found 925.5; $^1H$ NMR (400 MHz, DMSO-$d_6$) δ 8.52 (s, 1H), 8.47 (d, J=3.1 Hz, 1H), 7.76-7.71 (m, 1H), 7.67 (d, J=10.2 Hz, 1H), 7.57 (d, J=8.5 Hz, 1H), 7.37 (d, J=3.2 Hz, 1H), 5.76 (d, J=10.1 Hz, 1H), 5.03 (d, J=12.3 Hz, 1H), 4.92 (s, 1H), 4.15 (dd, J=27.1, 12.3 Hz, 1H), 3.83 (d, J=6.2 Hz, 3H), 3.54 (dd, J=17.3, 6.9 Hz, 1H), 3.44 (d, J=6.7 Hz, 3H), 3.34-3.26 (m, 9H), 2.92 (s, 3H), 2.47-2.41 (m, 7H), 2.37-2.31 (m, 3H), 2.23 (s, 1H), 1.94-1.77 (m, 3H), 1.55 (s, 2H), 1.24 (d, J=6.4 Hz, 4H), 1.15 (t, J=6.9 Hz, 5H), 1.09 (d, J=5.7 Hz, 3H), 1.04 (d, J=5.7 Hz, 3H), 0.95 (d, J=6.1 Hz, 3H), 0.86 (d, J=6.1 Hz, 3H), 0.50-0.42 (m, 1H), 0.33 (s, 2H), 0.14-0.06 (m, 1H).

Example A483. Synthesis of (1r,2R,3S)—N-(($6^3$S,3S,4S,Z)-$1^2$(5-((1R,5S,7s)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide

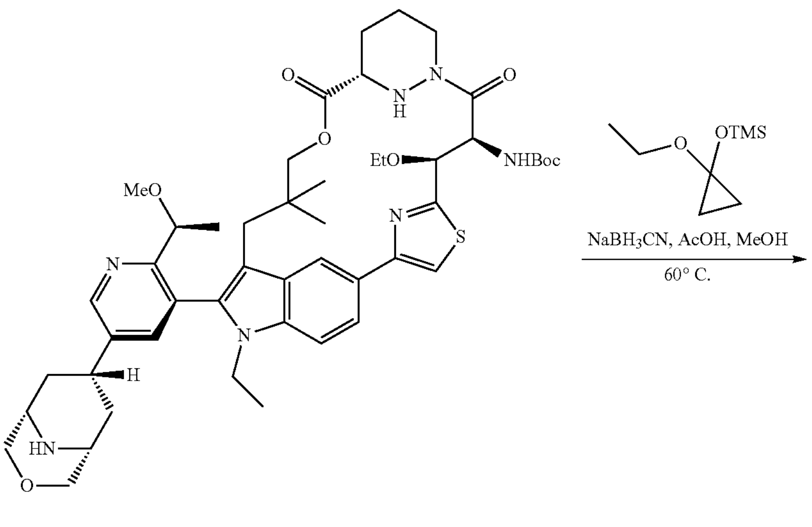

-continued
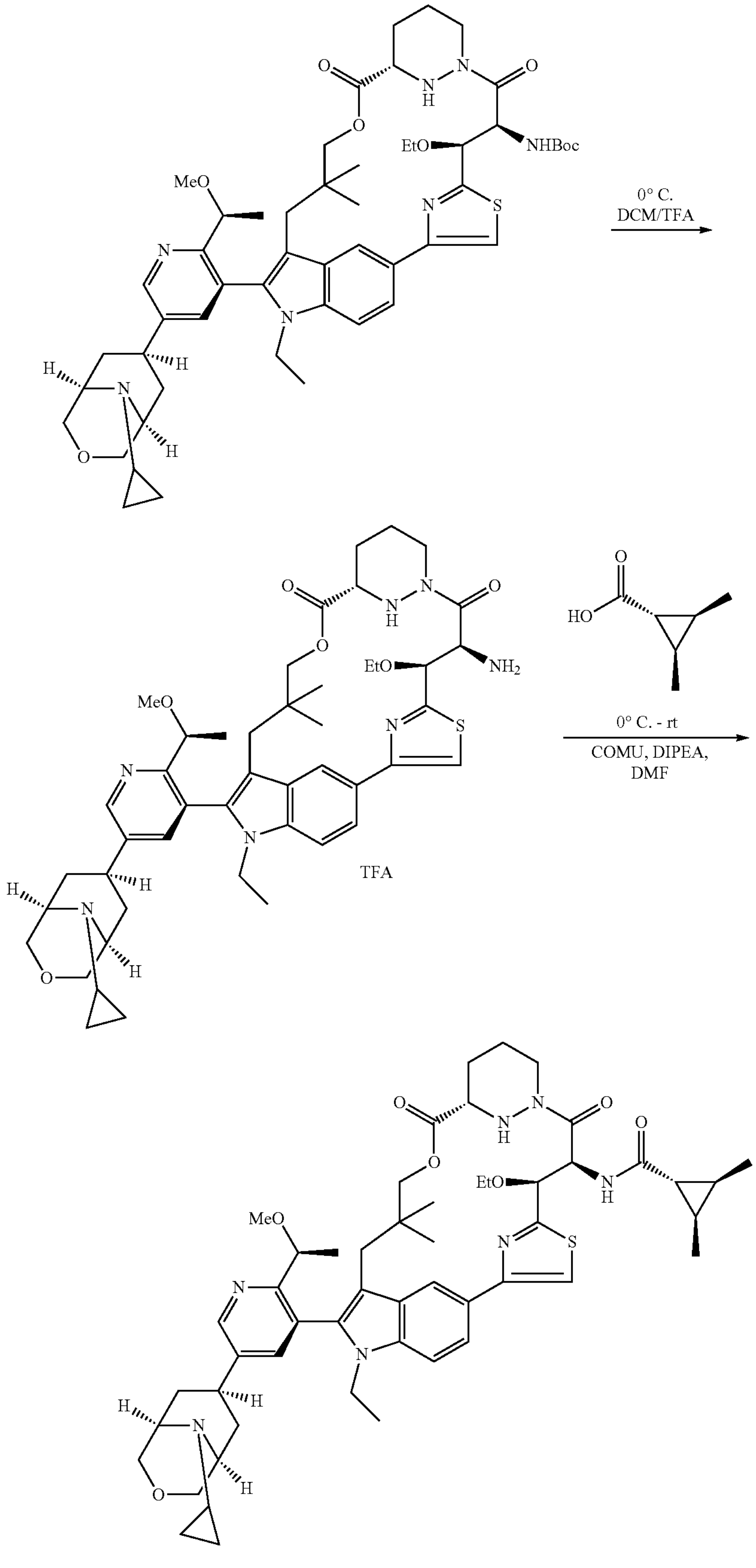

Step 1.

To a mixture of tert-butyl (($6^3$S,3S,4S,Z)-$1^2$-(5-(1R,5S,7s)-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (50% purity; 500 mg, 0.28 mmol) and (1-ethoxycyclopropoxy)trimethylsilane (968 mg, 5.6 mmol) in MeOH (2 mL) at 0° C. was added AcOH (83 mg, 1.39 mmol) and $NaBH_3CN$ (87 mg, 1.39 mmol) in portions. The mixture was warmed to 60° C. and stirred for 2 h, then concentrated under reduced pressure. The residue purified by silica gel column chromatography to give tert-butyl (($6^3$S,3S,4S,Z)-$1^2$-(5-(1R,5S,7s)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (80 mg, 30% yield) as a solid. LCMS (ESI): m/z $[M+H]^+$ calc'd for $C_{51}H_{69}N_7O_8S$ 939.5. found 940.6.

Step 2.

A mixture of tert-butyl (($6^3$S,3S,4S,Z)-$1^2$-(5-((1R,5S,7s)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (80 mg, 0.09 mmol) and TFA (0.4 mL) in DCM (2 mL) at 0° C. was stirred for 1 h, then concentrated under reduced pressure to give ($6^3$S,3S,4S,Z)-4-amino-$1^2$-(5-((1R,5S,7s)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)- pyridazinacycloundecaphane-5,7-dione as a TFA salt (180 mg) as an oil. LCMS (ESI): m/z $[M+H]^+$ calc'd for $C_{46}H_{61}N_7O_3S$ 839.4. found 840.4.

Step 3.

To a mixture of ($6^3$S,3S,4S,Z)-4-amino-12-(5-((1R,5S,7s)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-$6^1$,$6^2$,$6^3$,$6^4$,$6^5$,$6^6$-hexahydro-1H-8-oxa-2(4,2)-thiazola-1(5,3)-indola-6(1,3)-pyridazinacycloundecaphane-5,7-dione (180 mg, 0.21 mmol) and (1R,2R,3S)-2,3-dimethylcyclopropane-1-carboxylic acid (49 mg, 0.43 mmol) in DMF (3 mL) at 0° C. was added DIPEA (277 mg, 2.14 mmol) and COMU (184 mg, 0.43 mmol) in portions. The mixture was warmed to room temperature and stirred for 2 h. The residue was purified by preparative-HPLC to give (1r,2R,3S)—N-(($6^3$S,3S,4S,Z)-$1^2$-(5-(1R,5S,7s)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (23 mg, 11% yield) as a solid. LCMS (ESI): m/z $[M+H]^+$ calc'd for $C_{52}H_{69}N_7O_7S$ 935.5. found 936.4; $^1$H NMR (300 MHz, DMSO-$d_6$) δ 8.74 (d, J=2.2 Hz, 1H), 8.56 (s, 1H), 7.98 (s, 1H), 7.81 (d, J=8.6 Hz, 1H), 7.74-7.56 (m, 3H), 5.94 (d, J=9.7 Hz, 1H), 5.23 (d, J=12.4 Hz, 1H), 5.00 (s, 1H), 4.42-4.08 (m, 5H), 3.92 (d, J=10.9 Hz, 2H), 3.90-3.65 (m, 6H) 3.57-3.46 (m, 2H), 3.26 (s, 4H), 3.02 (d, J=10.1 Hz, 2H), 2.89 (m, 2H), 2.67 (m, 1H), 2.35 (s, 2H), 2.13 (d, J=10.5 Hz, 1H), 1.85 (d, J=13.6 Hz, 3H), 1.59 (s, 2H), 1.43 (d, J=6.1 Hz, 3H), 1.42-1.30 (m, 2H), 1.28-1.08 (m, 12H), 1.10-0.98 (m, 7H), 0.55 (d, J=6.0 Hz, 2H), 0.45 (s, 2H), 0.39 (s, 2H).

Example A484. Synthesis of ($6^3$S,3S,4S,Z)-4-amino-3-ethoxy-$1^1$-ethyl-$1^2$-(2-((S)-1-methoxyethyl)-5-((1R,5S,7s)-9-(oxetan-3-yl)-3-oxa-9-azabicyclo[3.3.1]nonan-7-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione

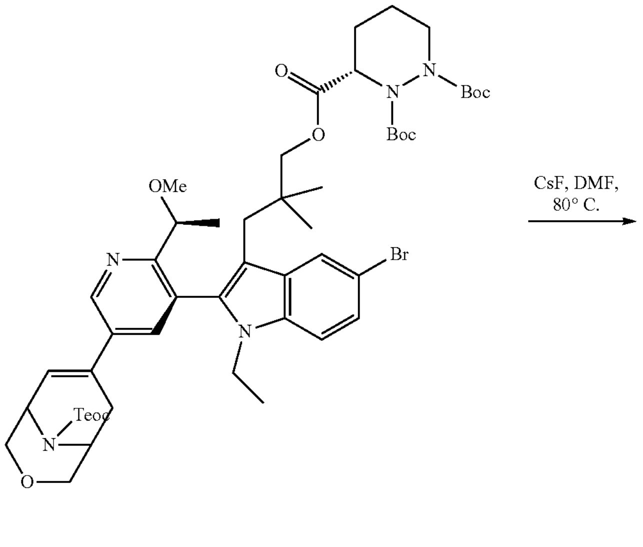

-continued
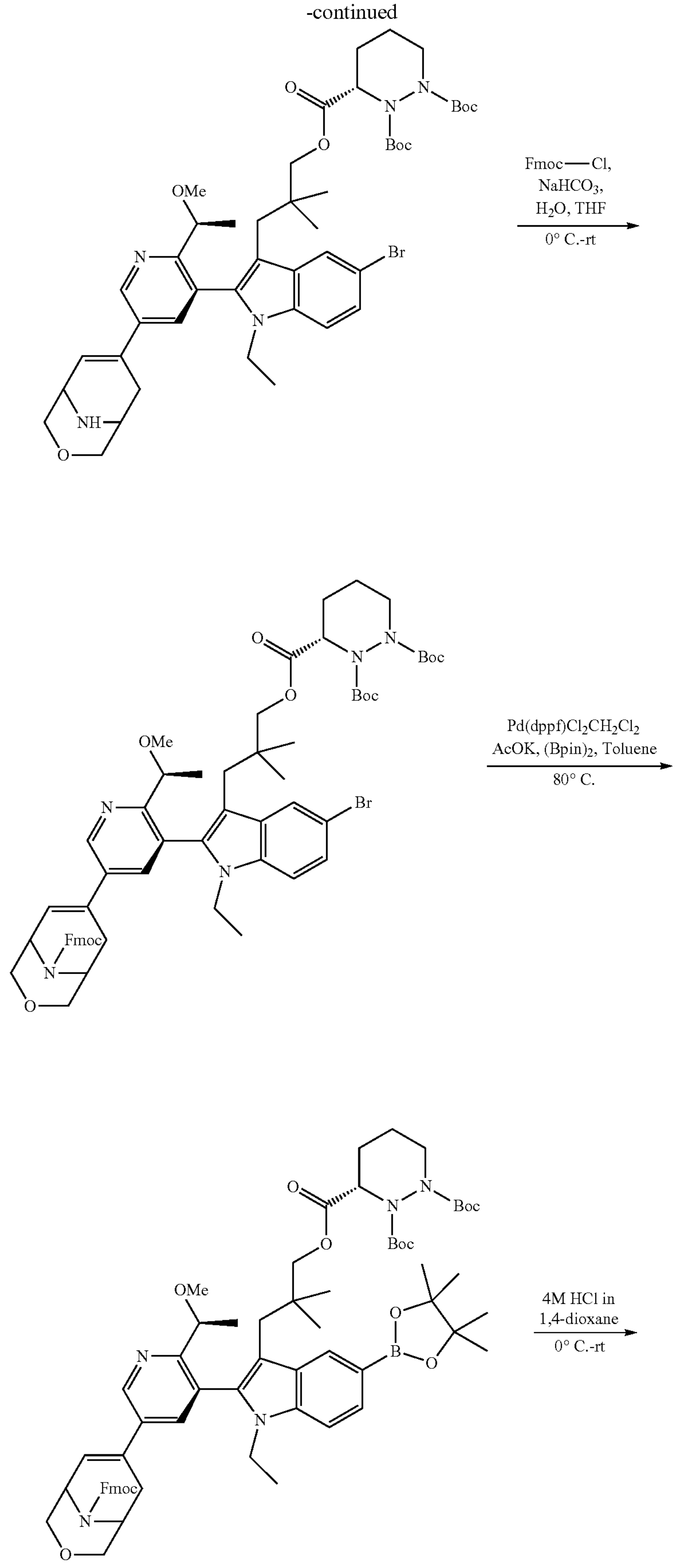

-continued
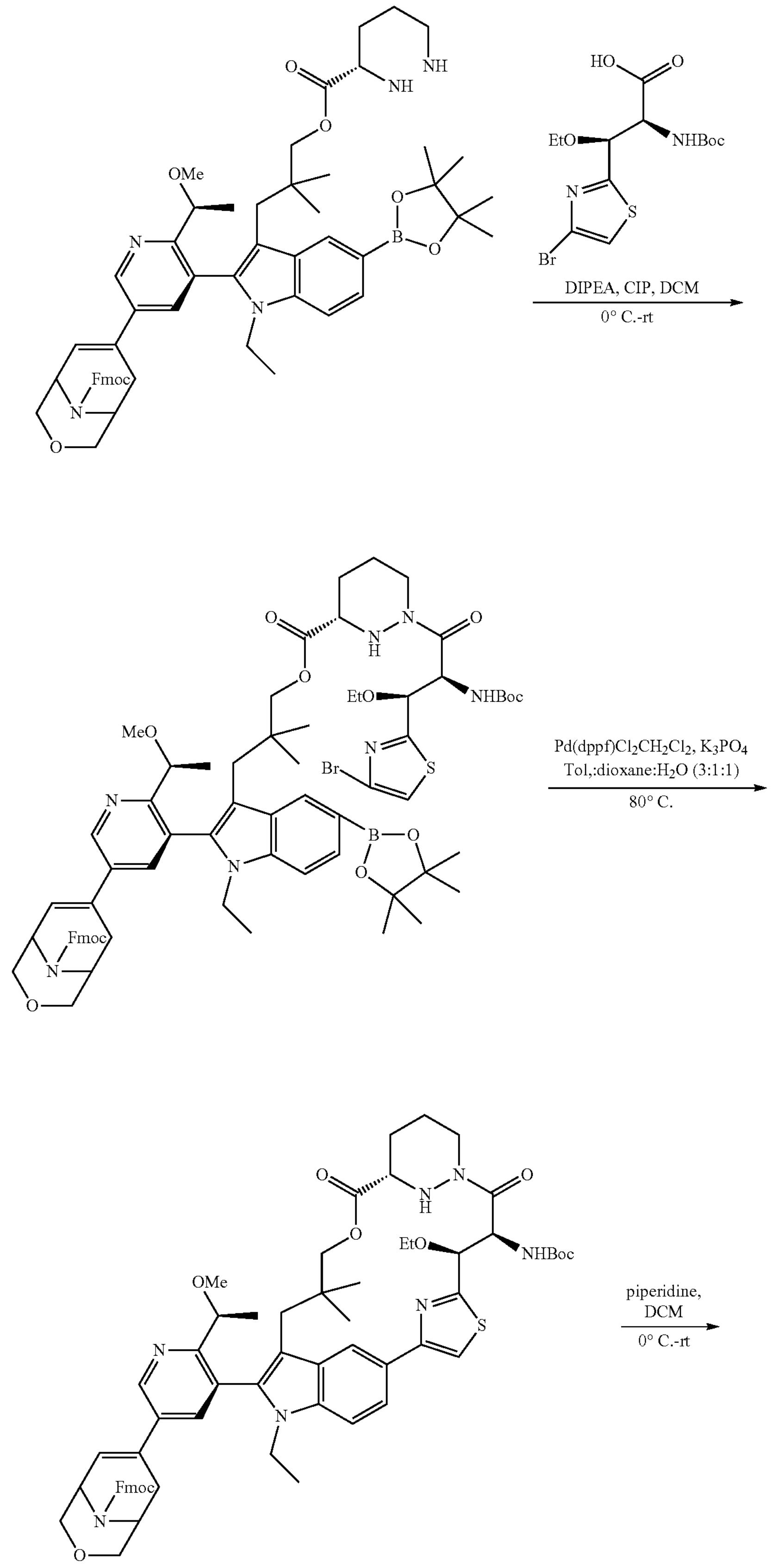

-continued
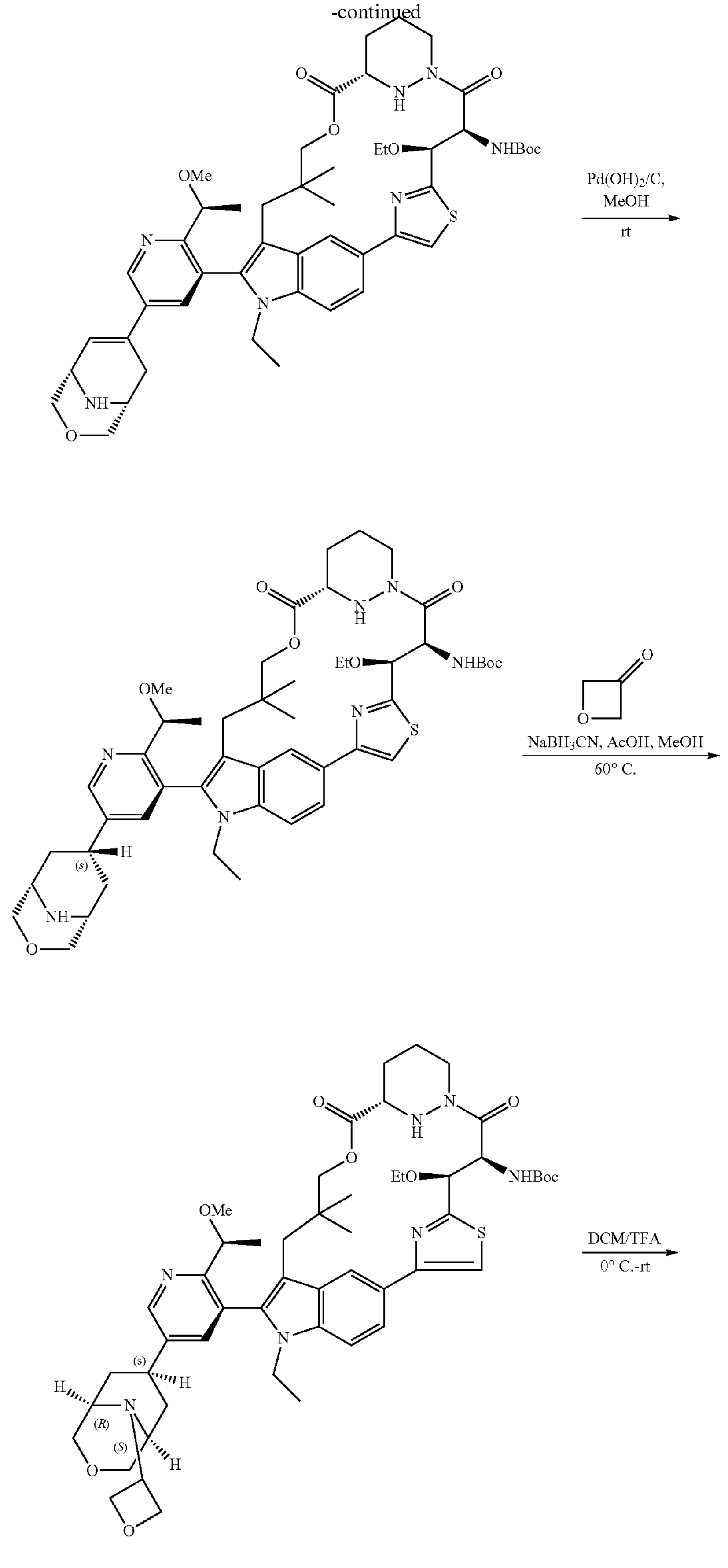

-continued

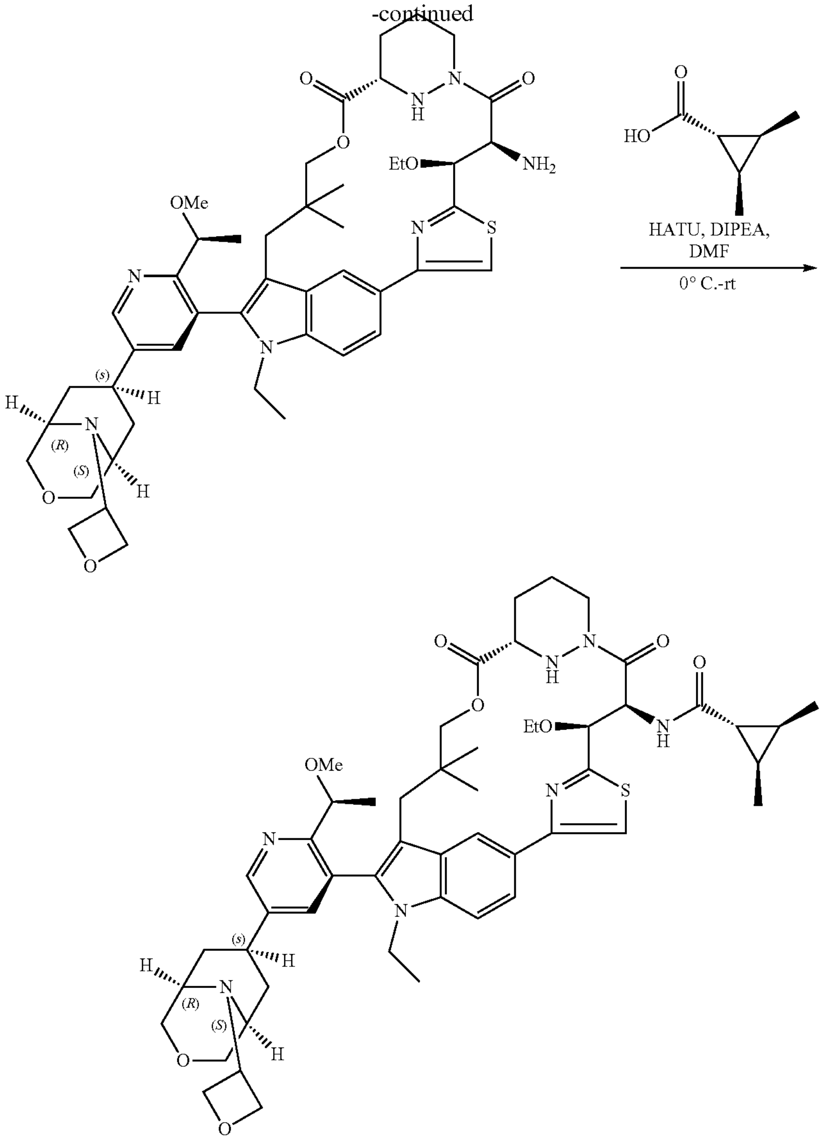

Step 1.

A mixture of 3-(3-(5-bromo-1-ethyl-2-(2-((S)-1-methoxyethyl)-5-(9-((2,2,2-trichloroethoxy)carbonyl)-3-oxa-9-azabicyclo[3.3.1]non-6-en-7-yl)pyridin-3-yl)-1H-indol-3-yl)-2,2-dimethylpropyl)-1,2-di-tert-butyl-(3S)-tetrahydropyridazine-1,2,3-tricarboxylate (6.57 g, 6.22 mmol) and CsF (4.72 g, 31.1 mmol) in DMF (50 mL) was heated to 30° C. and stirred for 2 h, then diluted with $H_2O$ (3×200 mL) and extracted with EtOAc (200 mL). The organic layer was concentrated under reduced pressure to give 3-(3-(2-(5-(3-oxa-9-azabicyclo[3.3.1]non-6-en-7-yl)-2-((S)-1-methoxyethyl)pyridin-3-yl)-5-bromo-1-ethyl-1H-indol-3-yl)-2,2-dimethylpropyl)-1,2-di-tert-butyl-(3S)-tetrahydropyridazine-1,2,3-tricarboxylate (5.83 g) as a solid. LCMS (ESI): m/z $[M+H]^+$ calc'd for $C_{45}H_{62}BrN_5O_8$ 879.4 & 881.4. found 880.1 & 882.1.

Step 2.

To a mixture of 3-(3-(2-(5-(3-oxa-9-azabicyclo[3.3.1]non-6-en-7-yl)-2-((S)-1-methoxyethyl)pyridin-3-yl)-5-bromo-1-ethyl-1H-indol-3-yl)-2,2-dimethylpropyl)-1,2-di-tert-butyl-(3S)-tetrahydropyridazine-1,2,3-tricarboxylate (5.83 g, 6.62 mmol) and $NaHCO_3$ (2.78 g, 33.1 mmol) in $H_2O$ (20 mL) and THF (20 mL) at 0° C. was added 9H-fluoren-9-ylmethyl chloroformate (2.57 g, 9.93 mmol) in portions. The mixture was warmed to room temperature and stirred overnight, then extracted with EtOAc (3×50 mL). The combined organic layers were dried over anhydrous $Na_2SO_4$, filtered, the filtrate was concentrated under reduced pressure and the residue was purified by silica gel column chromatography to give 3-(3-(2-(5-(9-(((9H-fluoren-9-yl)methoxy)carbonyl)-3-oxa-9-azabicyclo[3.3.1]non-6-en-7-yl)-2-((S)-1-methoxyethyl)pyridin-3-yl)-5-bromo-1-ethyl-1H-indol-3-yl)-2,2-dimethylpropyl)1,2-di-tert-butyl(3S)-tetrahydropyridazine-1,2,3-tricarboxylate (6.63 g, 90% yield) as a solid. LCMS (ESI): m/z $[M+H]^+$ calc'd for $C_{60}H_{72}BrN_5O_{10}$ 1101.5 & 1103.4. found 1102.4 & 1104.4.

Step 3.

To a mixture of 3-(3-(2-(5-(9-(((9H-fluoren-9-yl)methoxy)carbonyl)-3-oxa-9-azabicyclo[3.3.1]non-6-en-7-yl)-2-((S)-1-methoxyethyl)pyridin-3-yl)-5-bromo-1-ethyl-1H-indol-3-yl)-2,2-dimethylpropyl)1,2-di-tert-butyl(3S)-tetrahydropyridazine-1,2,3-tricarboxylate (6.4 g, 5.8 mmol)

and bis(pinacolato)diboron (2.21 g, 8.7 mmol) in toluene (25 mL) under an atmosphere of $N_2$ was added AcOK (1.42 g, 14.5 mmol) and Pd(dppf)$Cl_2CH_2Cl_2$ (0.47 g, 0.58 mmol) in portions. The mixture was heated to 80° C. and stirred for 3 h, then concentrated under reduced pressure and the residue was purified by silica gel column chromatography to give 3-(3-(2-(5-(9-(((9H-fluoren-9-yl)methoxy)carbonyl)-3-oxa-9-azabicyclo[3.3.1]non-6-en-7-yl)-2-((S)-1-methoxyethyl)pyridin-3-yl)-1-ethyl-5-(4,4,5,5-tetramethyl-1,3,2-dioxaborolan-2-yl)-1H-indol-3-yl)-2,2-dimethylpropyl) 1,2-di-tert-butyl (3S)-tetrahydropyridazine-1,2,3-tricarboxylate (4.9 g, 73% yield) as a solid. LCMS (ESI): m/z $[M+H]^+$ calc'd for $C_{66}H_{84}BN_5O_{12}$ 1149.6. found 1150.8.

Step 4.

To 3-(3-(2-(5-(9-(((9H-fluoren-9-yl)methoxy)carbonyl)-3-oxa-9-azabicyclo[3.3.1]non-6-en-7-yl)-2-((S)-1-methoxyethyl)pyridin-3-yl)-1-ethyl-5-(4,4,5,5-tetramethyl-1,3,2-dioxaborolan-2-yl)-1H-indol-3-yl)-2,2-dimethylpropyl) 1,2-di-tert-butyl (3S)-tetrahydropyridazine-1,2,3-tricarboxylate (4.9 g, 4.3 mmol) was added HCl in 1,4-dioxane (15 mL) at 0° C. The mixture was warmed to room temperature and stirred for 5 h, then concentrated under reduced pressure to give (9H-fluoren-9-yl)methyl-7-(5-(1-ethyl-3-(3-(((S)-hexahydropyridazine-3-carbonyl)oxy)-2,2-dimethylpropyl)-5-(4,4,5,5-tetramethyl-1,3,2-dioxaborolan-2-yl)-1H-indol-2-yl)-6-((S)-1-methoxyethyl)pyridin-3-yl)-3-oxa-9-azabicyclo[3.3.1]non-6-ene-9-carboxylate (4.9 g) as a solid, that was used directly in the next step without further purification. LCMS (ESI): m/z $[M+H]^+$ calc'd for $C_{56}H_{68}BN_5O_3$ 949.5. found 950.5.

Step 5.

To a mixture of (9H-fluoren-9-yl)methyl-7-(5-(1-ethyl-3-(3-(((S)-hexahydropyridazine-3-carbonyl)oxy)-2,2-dimethylpropyl)-5-(4,4,5,5-tetramethyl-1,3,2-dioxaborolan-2-yl)-1H-indol-2-yl)-6-((S)-1-methoxyethyl)pyridin-3-yl)-3-oxa-9-azabicyclo[3.3.1]non-6-ene-9-carboxylate (4.8 g, 5.1 mmol) and (2S,3S)-3-(4-bromo-1,3-thiazol-2-yl)-2-[(tert-butoxycarbonyl)amino]-3-ethoxypropanoic acid (3.00 g, 7.6 mmol) in DCM (30 mL) at 0° C. was added DIPEA (6.53 g, 50.5 mmol) and CIP (4.22 g, 15.2 mmol) in portions. The mixture was warmed to room temperature and stirred for 3 h, then concentrated under reduced pressure and the residue was purified by silica gel column chromatography to give (9H-fluoren-9-yl)methyl 7-(5-(3-(3-(((S)-1-((2S,3S)-3-(4-bromothiazol-2-yl)-2-((tert-butoxycarbonyl)amino)-3-ethoxypropanoyl)hexahydropyridazine-3-carbonyl)oxy)-2,2-dimethylpropyl)-1-ethyl-5-(4,4,5,5-tetramethyl-1,3,2-dioxaborolan-2-yl)-1H-indol-2-yl)-6-((S)-1-methoxyethyl)pyridin-3-yl)-3-oxa-9-azabicyclo[3.3.1]non-6-ene-9-carboxylate (5.5 g, 82% yield) as a solid. LCMS (ESI): m/z $[M+H]^+$ calc'd for $C_{69}H_{85}BBrN_7O_{12}S$ 1325.5 & 1327.5. found 1326.5 & 1328.5.

Step 6.

To a mixture of (9H-fluoren-9-yl)methyl 7-(5-(3-(3-(((S)-1-((2S,3S)-3-(4-bromothiazol-2-yl)-2-((tert-butoxycarbonyl)amino)-3-ethoxypropanoyl)hexahydropyridazine-3-carbonyl)oxy)-2,2-dimethylpropyl)-1-ethyl-5-(4,4,5,5-tetramethyl-1,3,2-dioxaborolan-2-yl)-1H-indol-2-yl)-6-((S)-1-methoxyethyl)pyridin-3-yl)-3-oxa-9-azabicyclo[3.3.1]non-6-ene-9-carboxylate (5.5 g, 4.1 mmol) and $K_3PO_4$ (2.20 g, 10.4 mmol) in toluene (12 mL), dioxane (4 mL) and $H_2O$ (4 mL) under an atmosphere of $N_2$ was added Pd(dppf)$Cl_2$ DCM (034 g, 0.41 mmol) in portions. The mixture was heated to 80° C. and stirred for 3 h, then filtered and the filter cake was washed with EtOAc (3×10 mL) and $H_2O$ (10 mL). The filtrate was partioned and the aqueous layer was extracted with EtOAc (3×20 mL). The combined organic layers were dried over anhydrous $Na_2SO_4$, filtered, the filtrate was concentrated under reduced pressure and the residue was purified by silica gel column chromatography to give (9H-fluoren-9-yl)methyl-7-(5-(($6^3$S,3S,4S,Z)-4-((tert-butoxycarbonyl)amino)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-12-yl)-6-((S)-1-methoxyethyl)pyridin-3-yl)-3-oxa-9-azabicyclo[3.3.1]non-6-ene-9-carboxylate (2.3 g, 49% yield) as a solid. LCMS (ESI): m/z $[M+H]^+$ calc'd for $C_{63}H_{73}N_7O_{10}S$ 1119.5. found 1120.3.

Step 7.

To a mixture of (9H-fluoren-9-yl)methyl-7-(5-(($6^3$S,3S,4S,Z)-4-((tert-butoxycarbonyl)amino)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-12-yl)-6-((S)-1-methoxyethyl)pyridin-3-yl)-3-oxa-9-azabicyclo[3.3.1]non-6-ene-9-carboxylate (2.3 g, 2.1 mmol) and piperidine (0.87 g, 10.3 mmol) in DCM (10 mL) was stirred at room temperature for 3 h, then concentrated under reduced pressure to give tert-butyl(($6^3$S,3S,4S,Z)-$1^2$-(5-((1R,5S)-3-oxa-9-azabicyclo[3.3.1]non-6-en-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$^1$H-8-oxa-2(4,2)-thiazola-1(5,3)-indola-6(1,3)-pyridazinacycloundecaphane-4-yl) carbamate (2.3 g) as an oil. LCMS (ESI): m/z $[M+H]^+$ calc'd for $C_{48}H_{63}N_7O_8S$ 897.5. found 898.9.

Step 8.

A mixture of tert-butyl (($6^3$S,3S,4S,Z)-$1^2$-(5-((1R,5S)-3-oxa-9-azabicyclo[3.3.1]non-6-en-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (2.3 g, 2.6 mmol) and $Pd(OH)_2$, 20% on carbon (2.30 g, 3.3 mmol) in MeOH (10 mL) was hydrogenated (balloon) at room temperature for 2 h. The mixture was filtered through a pad of Celite and the filtrate was concentrated under reduced pressure to give tert-butyl (($6^3$S,3S,4S,Z)-12-(5-((1R,5S,7s)-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (23 g) as an oil, which was used directly in the next step without further purification. LCMS (ESI): m/z $[M+H]^+$ calc'd for $C_{48}H_{65}N_7O_8S$ 899.5. found 901.0.

Step 9.

To a mixture of tert-butyl (($6^3$S,3S,4S,Z)-$1^2$-(5-((1R,5S,7s)-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (480 mg, 0.53 mmol) and 3-oxetanone (154 mg, 2.1 mmol) in MeOH (4 mL) at 0° C. was added AcOH (320 mg, 5.3 mmol) dropwise. The mixture was warmed to room temperature and stirred for 30 min, then the mixture was re-cooled to 0° C. and $NaBH_3CN$ (101 mg, 1.6 mmol) was added in portions. The mixture was heated to 60° C. and stirred for 2 h, then concentrated under reduced pressure and the residue was purified by silica gel column chromatography to give tert-butyl ((6$^3$S,3S,4S,Z)-3-ethoxy-1$^1$-ethyl-1$^2$-(2-((S)-1-methoxyethyl)-5-((1R,5S,7s)-9-(oxetan-3-yl)-3-oxa-9-azabicyclo[3.3.1]nonan-7-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate (200 mg, 39% yield) as a solid. LCMS (ESI): m/z [M+H]$^+$ calc'd for $C_{51}H_{69}N_7O_9S$ 955.5. found 956.7.

Step 10.

To a mixture of tert-butyl ((6$^3$S,3S,4S,Z)-3-ethoxy-1$^1$-ethyl-1$^2$-(2-((S)-1-methoxyethyl)-5-((1R,5S,7s)-9-(oxetan-3-yl)-3-oxa-9-azabicyclo[3.3.1]nonan-7-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate (200 mg, 0.21 mmol) in DCM (2 mL) at 0° C. was added TFA (0.4 mL) dropwise. The mixture was warmed to room temperature and stirred for 1 h, then concentrated under reduced pressure to give (6$^3$S,3S,4S,Z)-4-amino-3-ethoxy-1$^1$-ethyl-1$^2$-(2-((S)-1-methoxyethyl)-5-((1R,5S,7s)-9-(oxetan-3-yl)-3-oxa-9-azabicyclo[3.3.1]nonan-7-yl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione (220 mg) as a solid. LCMS (ESI): m/z [M+H]$^+$ calc'd for $C_{48}H_{61}N_7O_7S$ 855.4. found 856.6.

Step 11.

To a mixture of (6$^3$S,3S,4S,Z)-4-amino-3-ethoxy-1$^1$-ethyl-1$^2$-(2-((S)-1-methoxyethyl)-5-((1R,5S,7s)-9-(oxetan-3-yl)-3-oxa-9-azabicyclo[3.3.1]nonan-7-yl)pyridin-3-yl)-10,10-dimethyl-6$^1$,6$^2$,6$^3$,6$^4$,6$^5$,6$^6$-hexahydro-1H-8-oxa-2(4,2)-thiazola-1 (5,3)-indola-6(1,3)-pyridazinacycloundecaphane-5,7-dione (220 mg, 0.26 mmol) and (1r,2R,3S)-2,3-dimethylcyclopropane-1-carboxylic acid (59 mg, 0.51 mmol) in DMF (3 mL) at 0° C. under an atmosphere of $N_2$ was added DIPEA (332 mg, 2.57 mmol) and HATU (293 mg, 0.77 mmol) in portions. The mixture was warmed to room temperature and stirred for 2 h, then purified by preparative-HPLC to give (1r,2R,3S)—N-((6$^3$S,3S,4S,Z)-3-ethoxy-1$^1$-ethyl-1$^2$-(2-((S)-1-methoxyethyl)-5-((1R,5S,7s)-9-(oxetan-3-yl)-3-oxa-9-azabicyclo [3.3.1]nonan-7-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-2,3-dimethylcyclopropane-1-carboxamide (67 mg, 27% yield) as a solid. LCMS (ESI): m/z [M+H]$^+$ calc'd for $C_{52}H_{69}N_7O_8S$ 951.5. found 952.5; $^1$H NMR (400 MHz, DMSO-$d_6$) δ 8.79 (s, 1H), 8.50 (d, J=1.6 Hz, 1H), 7.92 (s, 1H), 7.79-7.72 (m, 2H), 7.65 (d, J=9.9 Hz, 1H), 7.58 (d, J=8.7 Hz, 1H), 5.86 (d, J=9.9 Hz, 1H), 5.15 (d, J=12.3 Hz, 2H), 4.91 (s, 1H), 4.74 (s, 4H), 4.37-4.20 (m, 3H), 4.18-4.05 (m, 3H), 3.92 (s, 3H), 3.57 (d, J=3.5 Hz, 5H), 3.51-3.44 (m, 7H), 3.22 (s, 3H), 2.90-2.74 (m, 2H), 2.55 (s, 2H), 2.39 (s, 2H), 2.06 (d, J=12.3 Hz, 1H), 1.78 (d, J=29.9 Hz, 2H), 1.56-1.47 (m, 2H), 1.37 (d, J=6.1 Hz, 3H), 1.16 (t, J=7.0 Hz, 5H), 1.11-0.94 (n, 7H), 0.93-0.77 (m, 6H), 0.36 (s, 3H).

Example A496. Synthesis of (1S,2S)—N-((6$^3$S,3S,4S,Z)-3-(dimethylamino)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1H-8-oxa-2(4,2)-thiazola-1(5,3)-indola-6(1,3)-pyridazinacycloundecaphane-4-yl)-2-methylcyclopropane-1-carboxamide

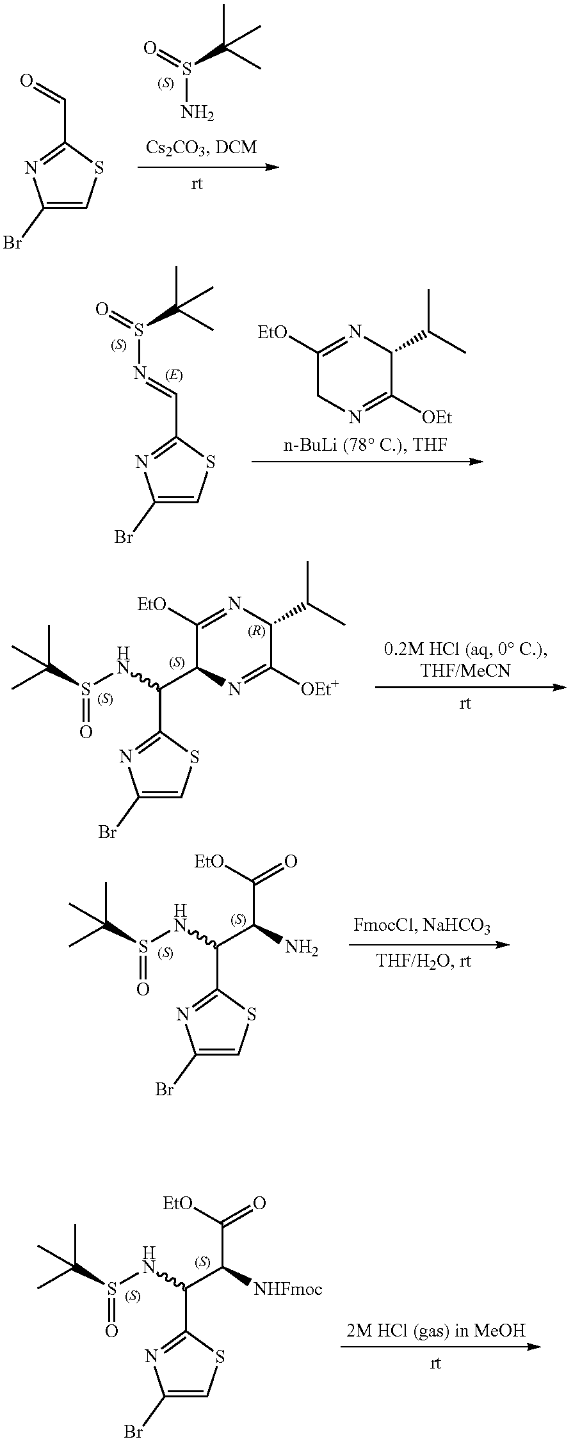

-continued

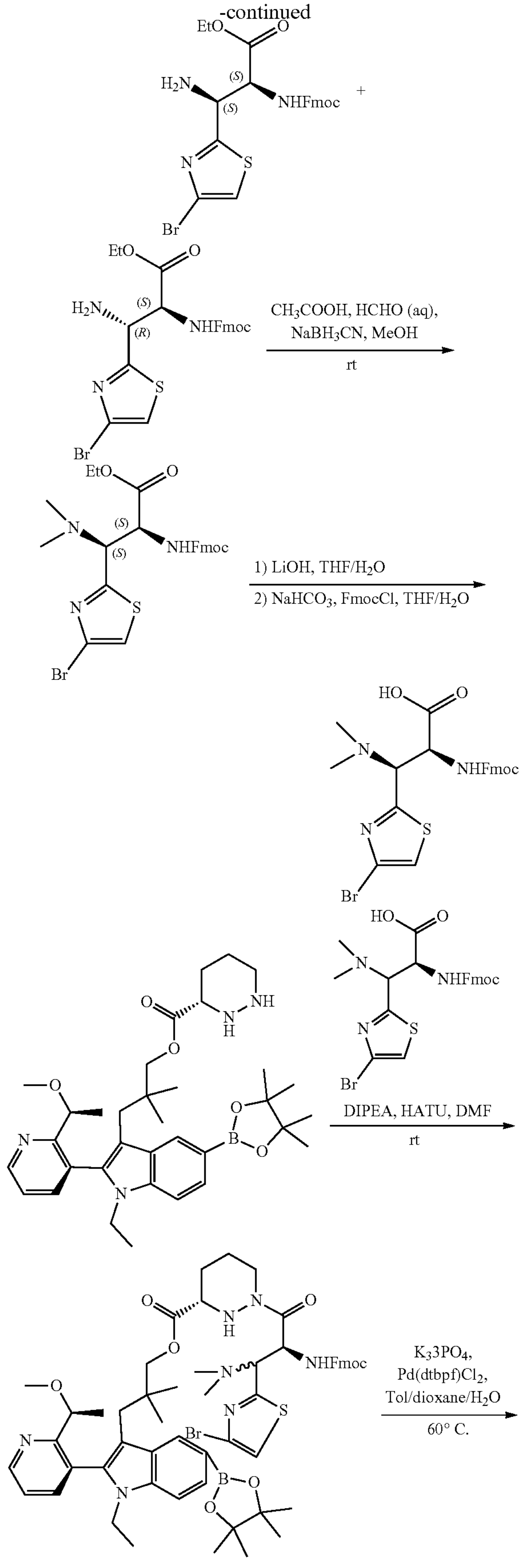

-continued

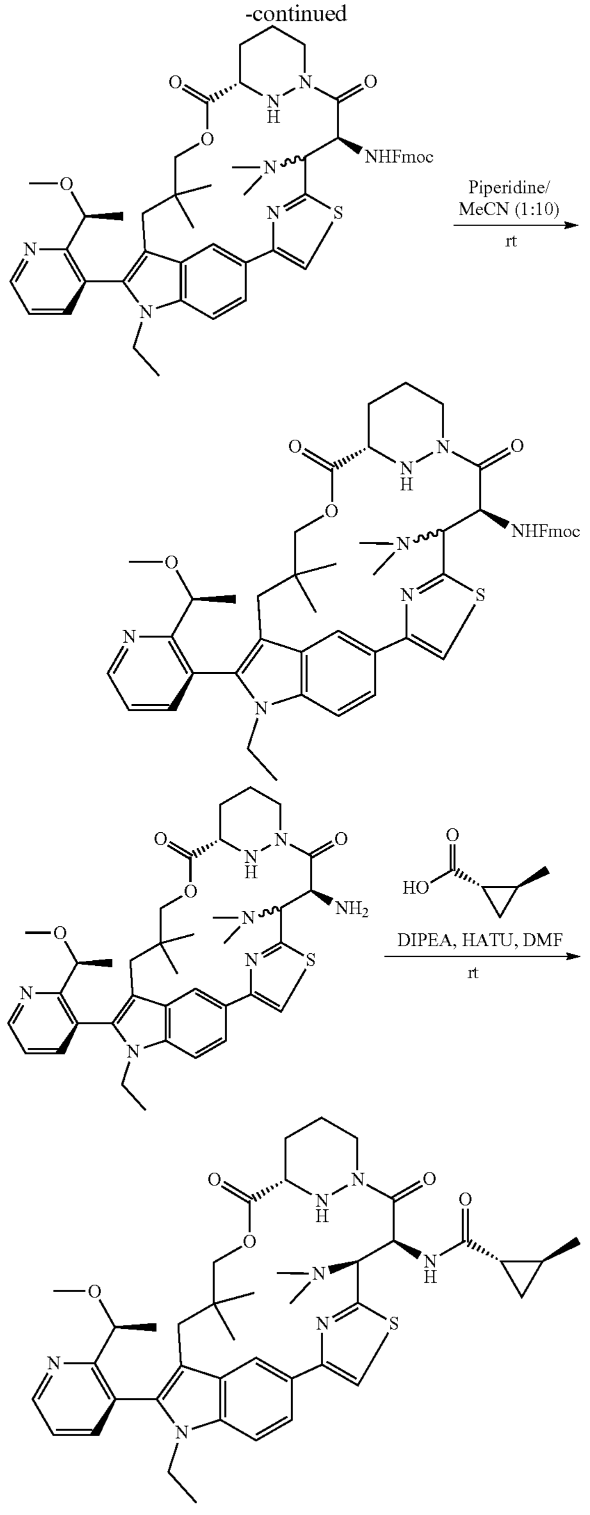

Step 1.

To a mixture of 4-bromothiazole-2-carbaldehyde (15.0 g, 78.1 mmol) and (S)-2-methylpropane-2-sulfinamide (9.47 g, 78.1 mmol) in DCM was added $Cs_2CO_3$ (50.90 g, 156.2 mmol) in portions. The mixture was stirred at room temperature for 2 h, then filtered and the filter cake was washed with DCM (3×20 mL). The filtrate was concentrated under reduced pressure and the residue was purified by silica gel column chromatography to give (S,E)-N-((4-bromothiazol- 2-yl)methylene)-2-methylpropane-2-sulfinamide (26 g, 97% yield) as an oil. LCMS (ESI): m/z $[M+H]^+$ calc'd for $C_8H_{11}BrN_2OS_2$ 294.0; found 294.8.

Step 2.

To a mixture of (R)-3,6-diethoxy-2-isopropyl-2,5-dihydropyrazine (20.57 g, 96.9 mmol) in THF at −78° C. under an atmosphere of N2 was treated with n-BuLi in hexanes (20.5 mL, 105.7 mmol). The mixture was stirred at −78° C. for 30 min, then (S,E)-N-((4-bromothiazol-2-yl)methylene)-2-methylpropane-2-sulfinamide (26.0 g, 88.1 mmol) was added dropwise. The mixture was stirred at −78° C. for 2 h, then warmed to 0° C. and quenched with saturated $NaHCO_3$. The aqueous layer was extracted with EtOAc (3×500 mL), the combined organic layers were concentrated under reduced pressure and the residue was purified by silica gel column chromatography to give (S)—N—((S)-(4-bromothiazol-2-yl)((2S,5R)-3,6-diethoxy-5-isopropyl-2,5-dihydropyrazin-2-yl)methyl)-2-methylpropane-2-sulfinamide (32.0 g, 72% yield) as an oil. LCMS (ESI): m/z $[M+H]^+$ calc'd for $C_{19}H_{31}BrN_4O_3S_2$ 506.1; found 507.0.

Step 3.

To a mixture of (S)—N—((S)-(4-bromothiazol-2-yl)((2S,5R)-3,6-diethoxy-5-isopropyl-2,5-dihydropyrazin-2-yl)methyl)-2-methylpropane-2-sulfinamide (32.0 g, 63.0 mmol) in THF (1 L) and MECN (640 mL) at 0° C. was added 0.2M HCl (790 mL) dropwise. The mixture was warmed to room temperature and stirred overnight, then quenched by the addition of saturated $NaHCO_3$ and extracted with EtOAc (3×500 mL). The combined organic layers were concentrated under reduced pressure and the residue was purified by silica gel column chromatography to give ethyl (2S,3S)-2-amino-3-(4-bromothiazol-2-yl)-3-(((S)-tert-butylsulfinyl)amino)propanoate (18.0 g, 72% yield) as an oil. LCMS (ESI): m/z $[M+H]^+$ calc'd for $C_{12}H_{20}BrN_3O_3S_2$ 397.0; found 398.1.

Step 4.

To a mixture of ethyl (2S,3S)-2-amino-3-(4-bromothiazol-2-yl)-3-(((S)-tert-butylsulfinyl)amino)propanoate (15.0 g, 37.7 mmol) and $NaHCO_3$ (15.82 g, 188.3 mmol) in THF (100 mL) and H2O (100 mL) was added FmocCl (11.69 g, 45.2 mmol) in portions. The mixture was stirred at room temperature for 2 h, then washed with H2O (3×100 mL). The aqueous layer was extracted with EtOAc (3×100 mL), the combined organic layers were concentrated under reduced pressure and the residue was purified by silica gel column chromatography to give ethyl (2S,3S)-2-((((9H-fluoren-9-yl)methoxy)carbonyl)amino)-3-(4-bromothiazol-2-yl)-3-(((S)-tert-butylsulfinyl)amino)propanoate (20.0 g, 86% yield) as an oil. LCMS (ESI): m/z $[M+H]^+$ calc'd for $C_{27}H_{30}BrN_3O_5S_2$ 619.1; found 620.0.

Step 5.

A mixture of ethyl (2S,3S)-2-((((9H-fluoren-9-yl)methoxy)carbonyl)amino)-3-(4-bromothiazol-2-yl)-3-(((S)-tert-butylsulfinyl)amino)propanoate (20.0 g, 32.2 mmol) and 4M HCl in MeOH (150 mL) was stirred at room temperature for 2 h. The mixture was concentrated under reduced pressure and the residue was purified by reverse-phase silica gel column chromatography to give ethyl (2S,3S)-2-((((9H-fluoren-9-yl)methoxy)carbonyl)amino)-3-amino-3-(4-bromothiazol-2-yl)propanoate (7.5 g, 45% yield) as an oil. LCMS (ESI): m/z $[M+H]^+$ calc'd for $C_{23}H_{22}BrN_3O_4S$ 515.1; found 516.0.

Step 6.

To a mixture of ethyl (2S,3S)-2-((((9H-fluoren-9-yl)methoxy)carbonyl)amino)-3-amino-3-(4-bromothiazol-2-yl)propanoate (1.2 g, 2.3 mmol) and AcOH (419 mg, 7.0 mmol) in MeOH (20 mL) was added HCHO, 37% aqueous solution (419 mg, 13.9 mmol) and $NaBH_3CN$ (730 mg, 11.6 mmol) in portions. The mixture was stirred at room temperature for 2 h, then diluted with $H_2O$ and extracted with EtOAc (3×200 mL). The combined organic layers were concentrated under reduced pressure and the residue was purified by silica gel column chromatography to give ethyl (2S,3S)-2-((((9H-fluoren-9-yl)methoxy)carbonyl)amino)-3-(4-bromothiazol-2-yl)-3-(dimethylamino)propanoate (990 mg, 78% yield) as an oil. LCMS (ESI): m/z $[M+H]^+$ calc'd for $C_{25}H_{26}BrN_3O_4S$ 543.1; found 543.8.

Step 7.

A mixture of ethyl (2S,3S)-2-((((9H-fluoren-9-yl)methoxy)carbonyl)amino)-3-(4-bromothiazol-2-yl)-3-(dimethylamino)propanoate (990 mg, 1.8 mmol) and $LiOH \cdot H_2O$ (174 mg, 7.3 mmol) in THF (50 mL) and $H_2O$ (50 mL) was stirred at room temperature for 1 h, then acidified to pH~5 with 1M HCl. The mixture was used directly in the next step without further purification.

Step 8.

To the above mixture was added $NaHCO_3$ (764 mg, 9.1 mmol) and FmocCl (565 mg, 9.1 mmol) in portions. The mixture was stirred at room temperature overnight, then washed with $H_2O$ (3×300 mL) and the combined aqueous layers were extracted with EtOAc (3×30 mL). The combined organic layers were concentrated under reduced pressure and the residue was purified by silica gel column chromatography to give (2S,3S)-2-((((9H-fluoren-9-yl)methoxy)carbonyl)amino)-3-(4-bromothiazol-2-yl)-3-(dimethylamino)propanoic acid (320 mg, 60% yield) as a solid. LCMS (ESI): m/z $[M+H]^+$ calc'd for $C_{23}H_{22}BrN_3O_4S$ 515.1; found 516.0.

Step 9.

To a mixture of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl (S)-hexahydropyridazine-3-carboxylate (450 mg, 0.74 mmol) and DIPEA (1.60 g, 12.4 mmol) in DMF (30 mL) was added (2S)-2-((((9H-fluoren-9-yl)methoxy)carbonyl)amino)-3-(4-bromothiazol-2-yl)-3-(dimethylamino)propanoic acid (320 mg, 0.62 mmol) and HATU (471 mg, 1.24 mmol) in portions. The mixture was stirred at room temperature for 1 h, then washed with $H_2O$ (3×30 mL) and the combined aqueous layers were extracted with EtOAc (3×30 mL). The combined organic layers were concentrated under reduced pressure and the residue was purified by silica gel column chromatography to give 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl-(3S)-1-((2S)-2-((((9H-fluoren-9-yl)methoxy)carbonyl)amino)-3-(4-bromothiazol-2-yl)-3-(dimethylamino)propanoyl)hexahydropyridazine-3-carboxylate (450 mg, 66% yield) as a solid. LCMS (ESI): m/z $[M+H]^+$ calc'd for $C_{57}H_{69}BBrN_7O_8S$ 1101.4; found 1102.5.

Step 10.

To a mixture of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl-(3S)-1-((2S)-2-((((9H-fluoren-9-yl)methoxy)carbonyl)amino)-3-(4-bromothiazol-2-yl)-3-(dimethylamino)propanoyl)hexahydropyridazine-3-carboxylate (450 mg, 0.41 mmol) and $K_3PO_4$ (217 mg, 1.0 mmol) in toluene (9 mL), 1,4-dioxane (3 mL) and $H_2O$ (3 mL) under an atmosphere of N2 was added $Pd(dtbpf)Cl_2$ (53 mg, 0.08 mmol) in portions. The mixture was heated to 60° C. and stirred for 1 h, then washed with $H_2O$ (3×20 mL) and the combined aqueous layers extracted with EtOAc (3×20 mL). The combined organic layers were concentrated under reduced pressure and the residue was purified by silica gel column chromatography to give (9H-fluoren-9-yl)methyl(($6^3$S,4S,Z)-3-(dimethylamino)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (70 mg, 19% yield) as an oil. LCMS (ESI): m/z $[M+H]^+$ calc'd for $C_{51}H_{57}N_7O_6S$ 895.4; found 896.3.

Step 11.

A mixture of (9H-fluoren-9-yl)methyl(($6^3$S,4S,Z)-3-(dimethylamino)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (70 mg, 0.08 mmol) and piperidine (0.2 mL) in MECN (2 mL) was stirred at room temperature for 1 h. The mixture was concentrated under reduced pressure to give ($6^3$S,4S,Z)-4-amino-3-(dimethylamino)-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (60 mg, 71% yield) as an oil, which was used directly in the next step without further purification. LCMS (ESI): m/z $[M+H]^+$ calc'd for $C_6H_{47}N_7O_4S$ 673.3. found 674.1.

Step 12.

To a mixture of ($6^3$S,4S,Z)-4-amino-3-(dimethylamino)-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (60 mg, 0.09 mmol) and (1S,2S)-2-methylcyclopropane-1-carboxylic acid (9 mg, 0.09 mmol) in DMF (5 mL) was added DIPEA (230 mg, 1.78 mmol) and HATU (68 mg, 0.18 mmol) in portions. The mixture was stirred at room temperature for 1 h, then diluted with $H_2O$ and extracted with EtOAc (2×20 mL). The combined organic layers were washed with $H_2O$ (3×20 mL), dried over anhydrous $Na_2SO_4$ and filtered. The filtrate was concentrated under reduced pressure and the residue was purified by preparative-HPLC to give (1S,2S)—N-(($6^3$S,3S,4S,Z)-3-(dimethylamino)-$1^1$-ethyl-12-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methylcyclopropane-1-carboxamide (3.6 mg, 5% yield) as a solid. LCMS (ESI): m/z $[M+H]^+$ calc'd for $C_{41}H_{53}N_7O_5S$ 755.4; found 756.4; $^1$H NMR (400 MHz, $CD_3OD$) δ 8.66-8.62 (m, 1H), 8.44-8.39 (m, 1H), 7.86-7.79 (m, 1H), 7.63-7.54 (m, 2H), 7.48-7.43 (m, 1H), 7.41-7.37 (m, 1H), 6.01-5.94 (m, 1H), 4.26-3.95 (m, 6H), 3.94-3.81 (m, 2H), 3.47-3.38 (m, 1H), 3.07 (s, 3H), 2.80-2.72 (m, 1H), 2.67-2.58 (m, 1H), 2.55-2.45 (m, 1H), 2.38-2.13 (s, 6H), 1.91 (s, 2H), 1.63-1.40 (m, 3H), 1.39-1.32 (m, 3H), 1.29-1.08 (m, 7H), 1.06-0.91 (m, 8H), 0.84-0.75 (m, 1H), 0.69-0.41 (m, 7H).

Example A502. Synthesis of (1r,2R,3S)—N-(($6^3$S,3S,4S,Z)-3-ethoxy-$1^1$-ethyl-$1^2$-(2-((S)-1-methoxyethyl)-5-((1R,5S,7r)-9-(oxetan-3-yl)-3-oxa-9-azabicyclo[3.3.1]nonan-7-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide

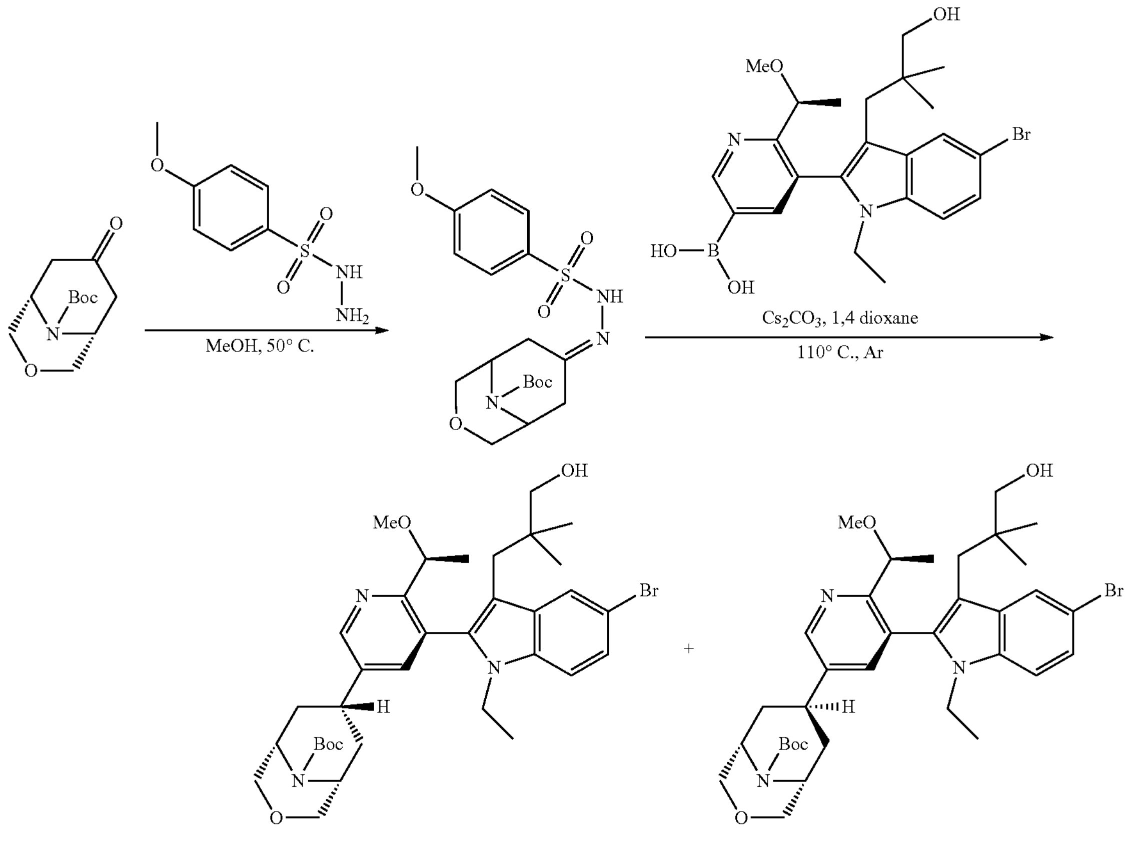

-continued
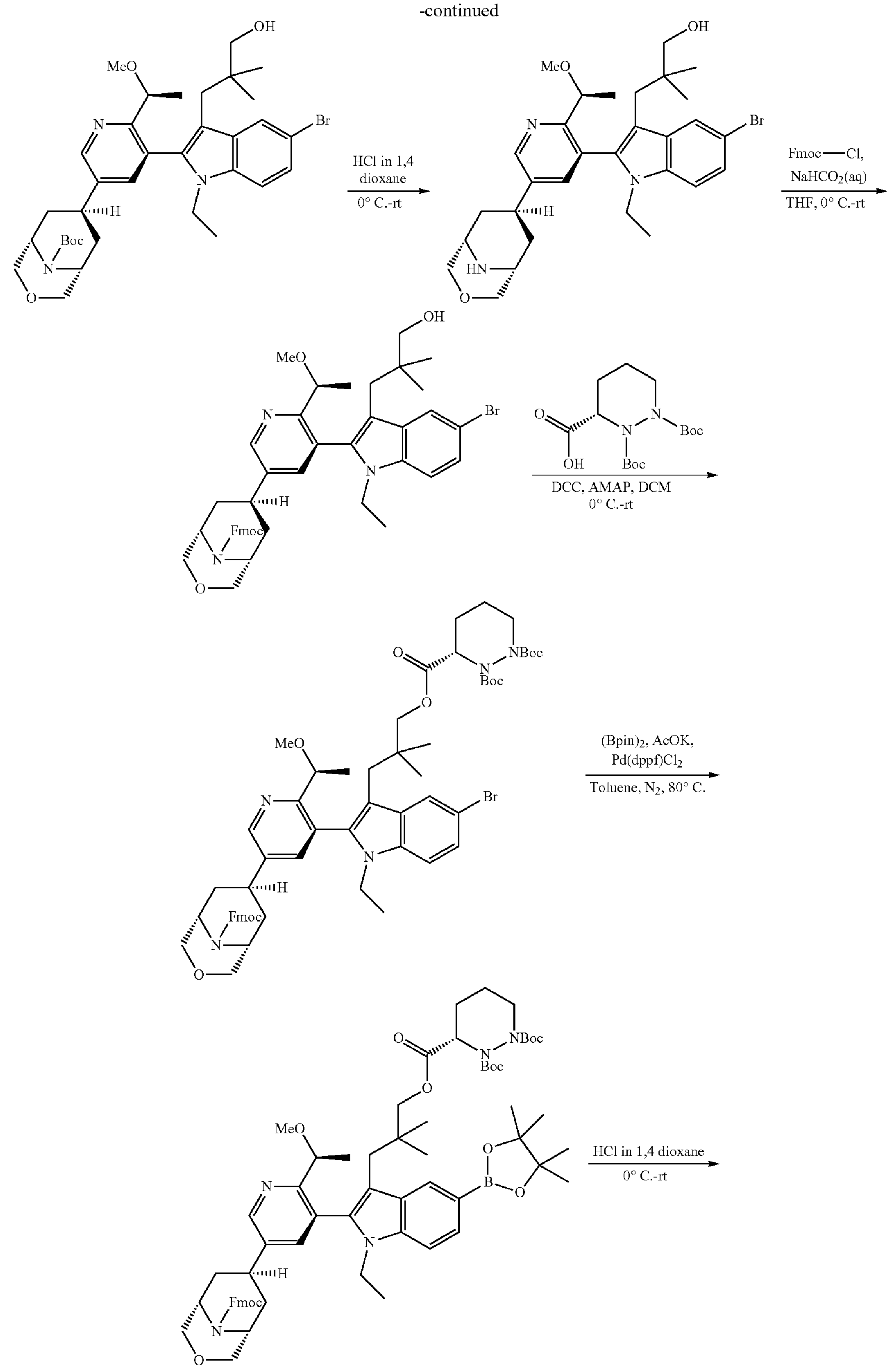

-continued
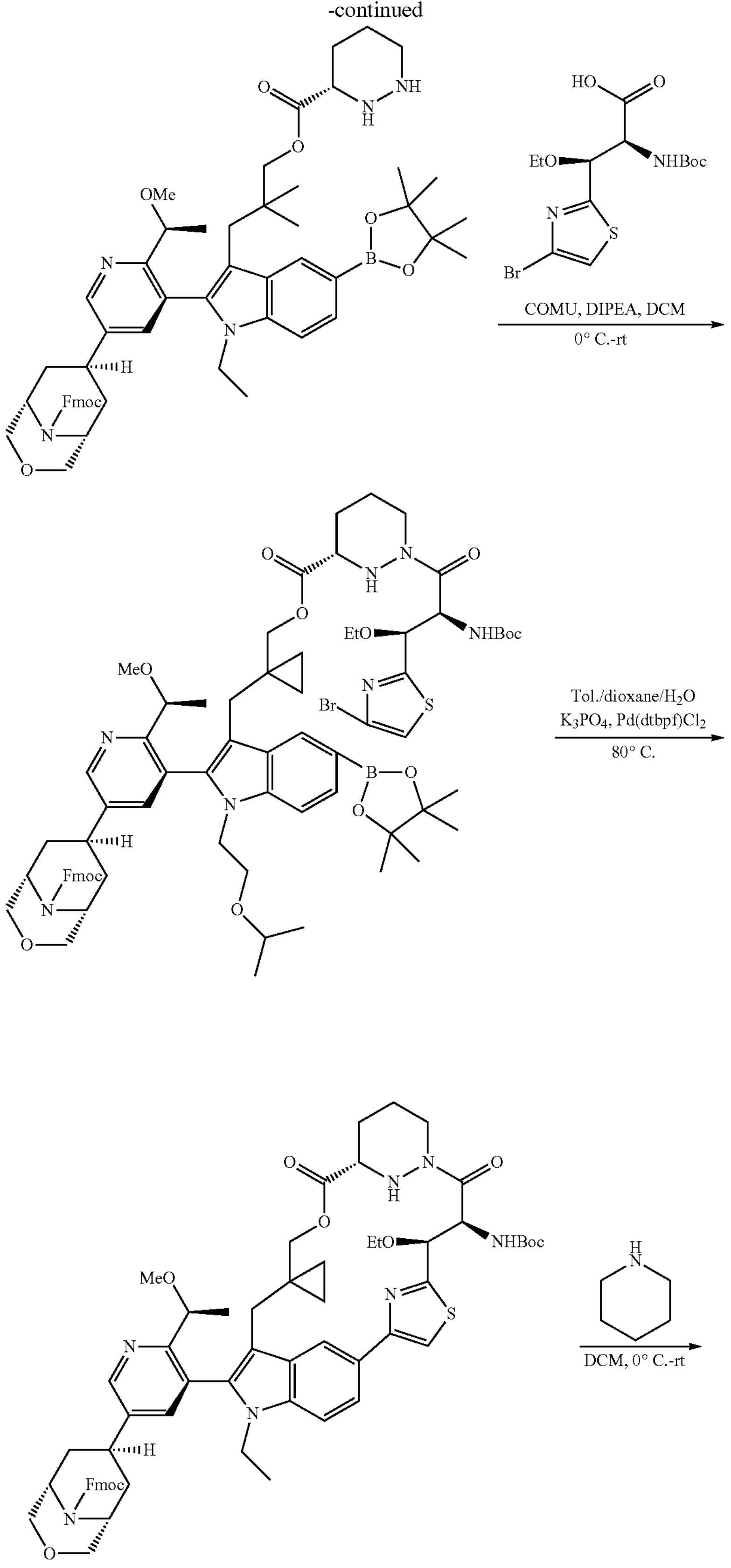

-continued
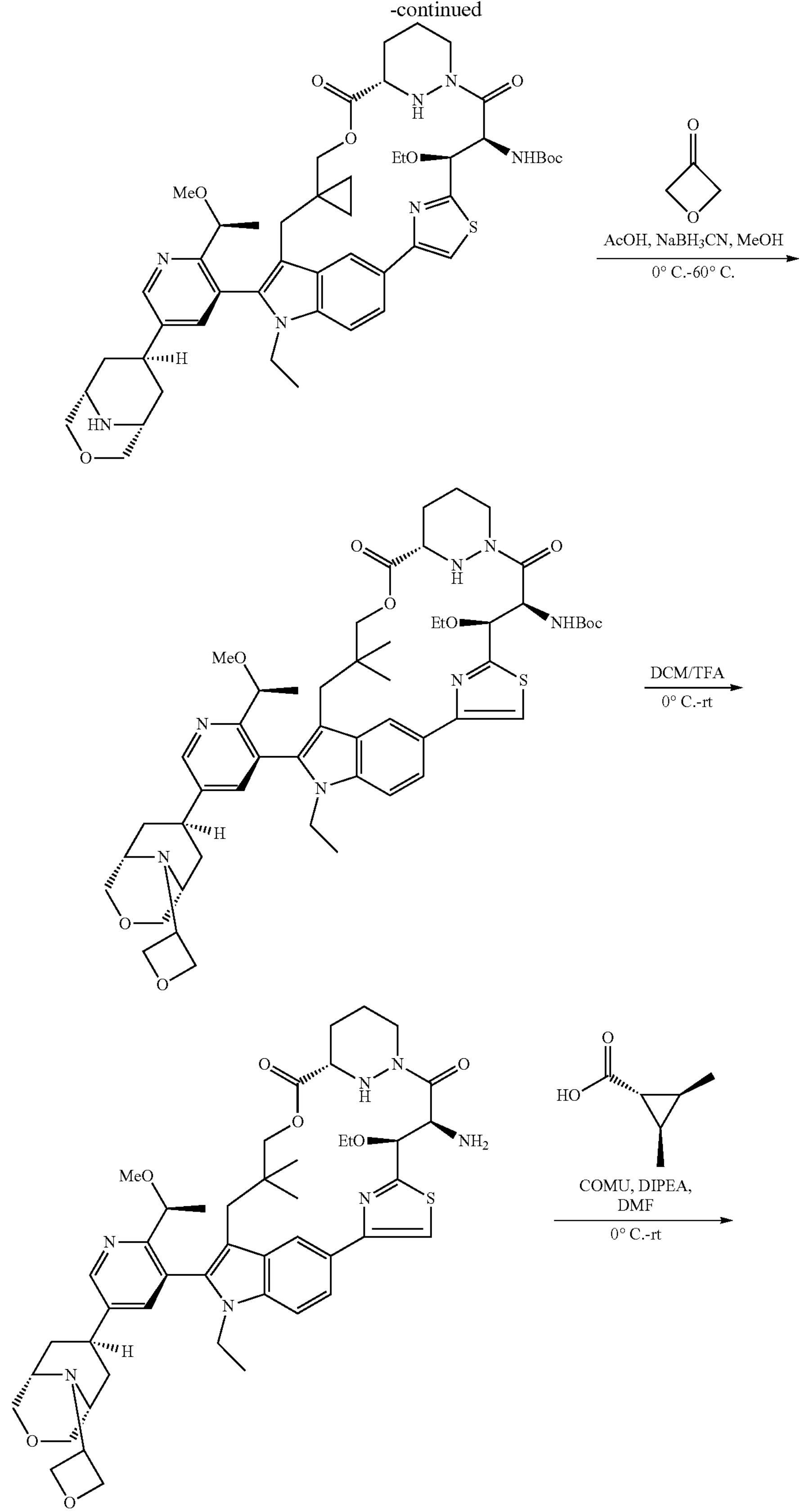

-continued

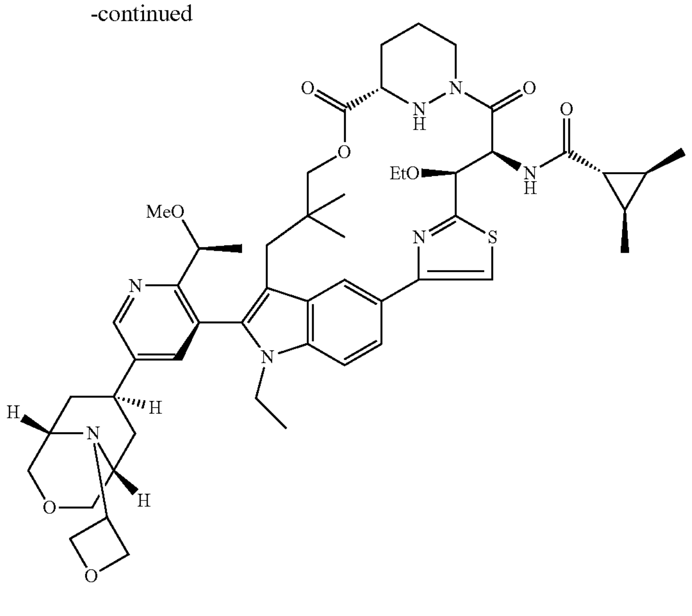

Step 1.

To a mixture of tert-butyl (1R,5S)-7-oxo-3-oxa-9-azabicyclo[3.3.1]nonane-9-carboxylate (9.00 g, 37.3 mmol) in MeOH (90 mL) was added 4-methoxybenzenesulfonohydrazide (9.05 g, 44.8 mmol). The mixture was heated to 50° C. and stirred for 16 h, then concentrated under reduced pressure to give tert-butyl 7-(2-((4-methoxyphenyl)sulfonyl)hydrazineylidene)-3-oxa-9-azabicyclo[3.3.1]nonane-9-carboxylate (15.0 g) as a solid, which was used directly in the next step without further purification. LCMS (ESI): m/z $[M+H]^+$ calc'd for $C_{19}H_{27}N_3O_6S$ 425.2; found 426.3.

Step 2.

A mixture of tert-butyl 7-(2-((4-methoxyphenyl)sulfonyl)hydrazineylidene)-3-oxa-9-azabicyclo[3.3.1]nonane-9-carboxylate (12.2 g, 28.7 mmol), (S)-(5-(5-bromo-1-ethyl-3-(3-hydroxy-2,2-dimethylpropyl)-1H-indol-2-yl)-6-(1-methoxyethyl)pyridin-3-yl)boronic acid (21.0 g, 43.0 mmol) and $Cs_2CO_3$ (14.0 g, 43.0 mmol) in 1,4-dioxane (120 mL) under an atmosphere of Ar was heated to 110° C. and stirred for 16 h. The mixture was concentrated under reduced pressure and the residue was purified by silica gel column chromatography and chiral-HPLC to give tert-butyl (1R,5S,7s)-7-(5-(5-bromo-1-ethyl-3-(3-hydroxy-2,2-dimethylpropyl)-1H-indol-2-yl)-6-((S)-1-methoxyethyl)pyridin-3-yl)-3-oxa-9-azabicyclo[3.3.1]nonane-9-carboxylate (3.3 g, 17% yield; RT=1.98 min) as solid and tert-butyl (1R,5S,7r)-7-(5-(5-bromo-1-ethyl-3-(3-hydroxy-2,2-dimethylpropyl)-1H-indol-2-yl)-6-((S)-1-methoxyethyl)pyridin-3-yl)-3-oxa-9-azabicyclo[3.3.1]nonane-9-carboxylate (4.5 g, 23% yield, RT=2.16 min) as a solid.

Step 3.

To tert-butyl (1R,5S)-7-(5-(5-bromo-1-ethyl-3-(3-hydroxy-2,2-dimethylpropyl)-1H-indol-2-yl)-6-((S)-1-methoxyethyl)pyridin-3-yl)-3-oxa-9-azabicyclo[3.3.1]nonane-9-carboxylate (4.49 g, 6.7 mmol) was added HCl in 1,4-dioxane (40 mL, 10.0 mmol) at 0° C. The mixture was warmed to room temperature and stirred for 1 h, then concentrated under reduced pressure to give 3-(2-(5-((1R,5S,7r)-3-oxa-9-azabicyclo[3.3.1]nonan-7-yl)-2-((S)-1-methoxyethyl)pyridin-3-yl)-5-bromo-1-ethyl-H-indol-3-yl)-2,2-dimethylpropan-1-ol (4.5 g, 92% yield) as a solid, which was used directly in the next step without further purification. LCMS (ESI): m/z $[M+H]^+$ calc'd for $C_{30}H_{40}BrN_3O_3$ 569.2; found 570.3.

Step 4.

To a mixture of 3-(2-(5-((1R,5S,7r)-3-oxa-9-azabicyclo[3.3.1]nonan-7-yl)-2-((S)-1-methoxyethyl)pyridin-3-yl)-5-bromo-1-ethyl-1H-indol-3-yl)-2,2-dimethylpropan-1-ol (4.49 g, 7.87 mmol) in THF (20 mL) at 0° C. was added 9H-fluoren-9-ylmethyl chloroformate (3.05 g, 11.8 mmol) in aqueous $NaHCO_3$ (20 mL) dropwise. The mixture was warmed to room temperature and stirred for 2 h, then extracted with EtOAc (3×20 mL). The combined organic layers were washed with $H_2O$ (2×20 mL), dried over anhydrous $Na_2SO_4$ and filtered. The filtrate was concentrated under reduced pressure and the residue was purified by silica gel column chromatography to give (9H-fluoren-9-yl)methyl (1R,5S,7r)-7-(5-(5-bromo-1-ethyl-3-(3-hydroxy-2,2-dimethylpropyl)-1H-indol-2-yl)-6-((S)-1-methoxyethyl)pyridin-3-yl)-3-oxa-9-azabicyclo[3.3.1]nonane-9-carboxylate (5.8 g, 92% yield) as a solid. LCMS (ESI): m/z $[M+H]^+$ calc'd for $C_{45}H_{50}BrN_3O_5$ 793.3; found 794.3 [for $^{81}Br$].

Step 5.

To a mixture of (9H-fluoren-9-yl)methyl (1R,5S,7r)-7-(5-(5-bromo-1-ethyl-3-(3-hydroxy-2,2-dimethylpropyl)-1H-indol-2-yl)-6-((S)-1-methoxyethyl)pyridin-3-yl)-3-oxa-9-azabicyclo[3.3.1]nonane-9-carboxylate (5.8 g, 7.3 mmol) and (S)-1,2-bis(tert-butoxycarbonyl)hexahydropyridazine-3-carboxylic acid (4.83 g, 14.6 mmol) in DCM (50 mL) at 0° C. was added DMAP (0.38 g, 3.1 mmol) and DCC (2.55 g, 12.4 mmol) in portions. The mixture was warmed to room temperature and stirred for 2 h, then filtered and the filter cake was washed with DCM (3×30 mL). The filtrate was concentrated under reduced pressure and the residue was purified by silica gel column chromatography to give 3-(3-(2-(5-((1R,5S,7r)-9-(((9H-fluoren-9-yl) methoxy)carbonyl)-3-oxa-9-azabicyclo[3.3.1]nonan-7-yl)-2-((S)-1-methoxyethyl)pyridin-3-yl)-5-bromo-1-ethyl-1H-indol-3-yl)-2,2-dimethylpropyl)1,2-di-tert-butyl-(S)-tetrahydropyridazine-1,2,3-tricarboxylate (7.6 g) as a solid. LCMS (ESI): m/z $[M+H]^+$ calc'd for $C_{60}H_{74}BrN_5O_{10}$ 1105.5; found 1106.4 [for $^{81}Br$].

Step 6.

To a mixture of 3-(3-(2-(5-((1R,5S,7r)-9-(((9H-fluoren-9-yl) methoxy)carbonyl)-3-oxa-9-azabicyclo[3.3.1]nonan-7-yl)-2-((S)-1-methoxyethyl)pyridin-3-yl)-5-bromo-1-ethyl-1H-indol-3-yl)-2,2-dimethylpropyl)1,2-di-tert-butyl-(S)-tetrahydropyridazine-1,2,3-tricarboxylate (7.4 g, 6.7 mmol) and bis(pinacolato)diboron (8.50 g, 33.5 mmol) in toluene (70 mL) under an atmosphere of $N_2$ was added AcOK (2.63 g, 26.8 mmol) and $Pd(dppf)Cl_2CH_2C_2$ (1.09 g, 1.34 mmol). The mixture was heated to 80° C. and stirred for 3 h, then concentrated under reduced pressure. The residue was purified by silica gel column chromatography to give 3-(3-(2-(5-((1R,5S,7r)-9-(((9H-fluoren-9-yl)methoxy)carbonyl)-3-oxa-9-azabicyclo[3.3.1]nonan-7-yl)-2-((S)-1-methoxyethyl)pyridin-3-yl)-1-ethyl-5-(4,4,5,5-tetramethyl-1,3,2-dioxaborolan-2-yl)-1H-indol-3-yl)-2,2-dimethylpropyl)1,2-di-tert-butyl-(S)-tetrahydropyridazine-1,2,3-tricarboxylate (6.9 g, 89% yield) as a solid. LCMS (ESI): m/z $[M+H]^+$ calc'd for $C_{66}H_{86}BN_5O_{12}$ 1151.6. found 1152.6.

Step 7.

To 3-(3-(2-(5-((1R,5S,7r)-9-(((9H-fluoren-9-yl)methoxy) carbonyl)-3-oxa-9-azabicyclo[3.3.1]nonan-7-yl)-2-((S)-1-methoxyethyl)pyridin-3-yl)-1-ethyl-5-(4,4,5,5-tetramethyl-1,3,2-dioxaborolan-2-yl)-1H-indol-3-yl)-2,2-dimethylpropyl)1,2-di-tert-butyl-(S)-tetrahydropyridazine-1,2,3-tricarboxylate (6.9 g, 6.0 mmol) was added HCl in 1,4-dioxane (60 mL) at 0° C. The mixture was warmed to room temperature and was stirred for 4 h, then concentrated under reduced pressure to give (9H-fluoren-9-yl)methyl(1R, 5S,7r)-7-(5-(1-ethyl-3-(3-(((S)-hexahydropyridazine-3-carbonyl)oxy)-2,2-dimethylpropyl)-5-(4,4,5,5-tetramethyl-1,3, 2-dioxaborolan-2-yl)-1H-indol-2-yl)-6-((S)-1-methoxyethyl)pyridin-3-yl)-3-oxa-9-azabicyclo[3.3.1] nonane-9-carboxylate (6.47 g) as a solid. LCMS (ESI): m/z $[M+H]^+$ calc'd for $C_{56}H_{70}BN_5O_8$ 951.5; found 952.6.

Step 8.

To a mixture of (9H-fluoren-9-yl)methyl(1R,5S,7r)-7-(5-(1-ethyl-3-(3-(((S)-hexahydropyridazine-3-carbonyl)oxy)-2,2-dimethylpropyl)-5-(4,4,5,5-tetramethyl-1,3,2-dioxaborolan-2-yl)-1H-indol-2-yl)-6-((S)-1-methoxyethyl) pyridin-3-yl)-3-oxa-9-azabicyclo[3.3.1]nonane-9-carboxylate (6.45 g, 6.78 mmol) and (2S,3S)-3-(4-bromothiazol-2-yl)-2-((tert-butoxycarbonyl)amino)-3-ethoxypropanoic acid (3.21 g, 8.13 mmol) in DCM (60 mL) at 0° C. was added DIPEA (8.76 g, 67.8 mmol) and COMU (3.48 g, 8.1 mmol) in portions. The mixture was warmed to room temperature and stirred for 2 h, then concentrated under reduced pressure and the residue was purified by silica gel column chromatography to give (9H-fluoren-9-yl) methyl (1R,5S,7r)-7-(5-(3-(3-(((S)-1-((2S,3S)-3-(4-bromothiazol-2-yl)-2-((tert-butoxycarbonyl)amino)-3-ethoxypropanoyl)hexahydropyridazine-3-carbonyl)oxy)-2,2-dimethylpropyl)-1-ethyl-5-(4,4,5,5-tetramethyl-1,3,2-dioxaborolan-2-yl)-1H-indol-2-yl)-6-((S)-1-methoxyethyl) pyridin-3-yl)-3-oxa-9-azabicyclo[3.3.1]nonane-9-carboxylate (6.9 g, 76% yield) as a solid. LCMS (ESI): m/z $[M+H]^+$ calc'd for $C_{69}H_{87}BBrN_7O_{12}S$ 1329.5; found 1330.5.

Step 9.

To a mixture of (9H-fluoren-9-yl)methyl (1R,5S,7r)-7-(5-(3-(3-(((S)-1-((2S,3S)-3-(4-bromothiazol-2-yl)-2-((tert-butoxycarbonyl)amino)-3-ethoxypropanoyl)hexahydro-pyridazine-3-carbonyl)oxy)-2,2-dimethylpropyl)-1-ethyl-5-(4,4,5,5-tetramethyl-1,3,2-dioxaborolan-2-yl)-1H-indol-2-yl)-6-((S)-1-methoxyethyl)pyridin-3-yl)-3-oxa-9-azabicyclo[3.3.1]nonane-9-carboxylate (6.9 g, 5.2 mmol) in toluene (300 mL), 1,4-dioxane (100 mL) and $H_2O$ (100 mL) under an atmosphere of $N_2$ was added $K_3PO_4$ (3.31 g, 15.6 mmol) and $Pd(DtBPF)Cl_2$ (0.42 g, 0.52 mmol). The mixture was heated to 80° C. and stirred for 3 h, then concentrated under reduced pressure and the residue was purified by silica gel column chromatography to give (9H-fluoren-9-yl) methyl(1R,5S,7r)-7-(5-(($6^3$S,3S,4S,Z)-4-((tert-butoxycarbonyl)amino)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl)pyridin-3-yl)-3-oxa-9-azabicyclo[3.3.1]nonane-9-carboxylate (3.8 g, 65% yield) as a solid. LCMS (ESI): m/z $[M+H]^+$ calc'd for $C_{63}H_{75}N_7O_{10}S$ 1121.5; found 1123.3.

Step 10.

To a mixture of (9H-fluoren-9-yl)methyl(1R,5S,7r)-7-(5-(($6^3$S,3S,4S,Z)-4-((tert-butoxycarbonyl)amino)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-$1^2$-yl)-6-((S)-1-methoxyethyl) pyridin-3-yl)-3-oxa-9-azabicyclo[3.3.1]nonane-9-carboxylate (3.8 g, 3.4 mmol) in DCM (40 mL) at 0° C. was added piperidine (1.44 g, 16.9 mmol) dropwise. The mixture was warmed to room temperature and stirred for 5 h, then concentrated under reduced pressure to give tert-butyl (($6^3$S, 3S,4S,Z)-$1^2$-(5-((1R,5S,7r)-3-oxa-9-azabicyclo[3.3.1] nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (4.7 g) as a solid, which was used directly in the next step without further purification. LCMS (ESI): m/z $[M+H]^+$ calc'd for $C_{48}H_{65}N_7O_8S$ 899.5; found 900.6.

Step 11.

To a mixture of tert-butyl (($6^3$S,3S,4S,Z)-$1^2$-(5-((1R,5S, 7r)-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2 (4,2)-thiazola-1(5,3)-indola-6(1,3)-pyridazinacycloundecaphane-4-yl)carbamate (1.12 g, 15.6 mmol) in MeOH (2 mL) at 0° C. was added AcOH (467 mg, 7.8 mmol). The mixture was stirred for 30 min, then $NaBH_3CN$ (147 mg, 2.33 mmol) was added, and the mixture was heated to 60° C. and stirred for 3 h.

The mixture was concentrated under reduced pressure and the residue was purified by silica gel column chromatography to give tert-butyl (($6^3$S,3S,4S,Z)-3-ethoxy-$1^1$-ethyl-$1^2$-(2-((S)-1-methoxyethyl)-5-((1R,5S,7r)-9-(oxetan-3-yl)-3-oxa-9-azabicyclo[3.3.1]nonan-7-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (251 mg, 33% yield) as a solid. LCMS (ESI): m/z $[M+H]^+$ calc'd for $C_{51}H_{69}N_7O_9S$ 955.5. found 956.5.

Step 12.

To a mixture of tert-butyl (($6^3$S,3S,4S,Z)-3-ethoxy-$1^1$-ethyl-$1^2$-(2-((S)-1-methoxyethyl)-5-((1R,5S,7r)-9-(oxetan-3-yl)-3-oxa-9-azabicyclo[3.3.1]nonan-7-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (250 mg, 0.26 mmol) in DCM (2 mL) at 0° C. was added TFA (0.4 mL). The mixture was warmed to room temperature and stirred for 30 min, then concentrated under reduced pressure to give ($6^3$S,3S,4S,Z)-4-amino-3-ethoxy-$1^1$-ethyl-$1^2$-(2-((S)-1-methoxyethyl)-5-((1R,5S,7r)-9-(oxetan-3-yl)-3-oxa-9-azabicyclo[3.3.1]nonan-7-yl)pyridin-3-yl)-10,10-dimethyl- $6^1,6^2,6^3,6^4,6^5,6^6$-hexahydro-$1^1$H-8-oxa-2(4,2)-thiazola-1(5,3)-indola-6(1,3)-pyridazinacycloundecaphane-5,7-dione (310 mg) as a solid, that was used directly in the next step without further purification. LCMS (ESI): m/z $[M+H]^+$ calc'd for $C_{46}H_{61}N_7O_7S$ 855.4. found 856.5.

Step 13.

To a mixture of ($6^3$S,3S,4S,Z)-4-amino-3-ethoxy-$1^1$-ethyl-$1^2$-(2-((S)-1-methoxyethyl)-5-((1R,5S,7r)-9-(oxetan-3-yl)-3-oxa-9-azabicyclo[3.3.1]nonan-7-yl)pyridin-3-yl)-10,10-dimethyl-$6^1,6^2,6^3,6^4,6^5,6^6$-hexahydro-$1^1$H-8-oxa-2(4,2)-thiazola-1(5,3)-indola-6(1,3)-pyridazinacycloundecaphane-5,7-dione (310 mg, 0.36 mmol) and (1r,2R,3S)-2,3-dimethylcyclopropane-1-carboxylic acid (62 mg, 0.54 mmol) in DMF (3 mL) at 0° C. was added DIPEA (468 mg, 3.62 mmol) and COMU (155 mg, 0.36 mmol) in portions. The mixture was warmed to room temperature and stirred for 1 h, then purified by preparative-HPLC to give (1r,2R,3S)—N-(($6^3$S,3S,4S,Z)-3-ethoxy-$1^1$-ethyl-$1^2$-(2-((S)-1-methoxyethyl)-5-((1R,5S,7r)-9-(oxetan-3-yl)-3-oxa-9-azabicyclo[3.3.1]nonan-7-yl)pyridin-3-yl)-10,10-dimethyl-5,7-dioxo-$6^1,6^2,6^3,6^4,6^5,6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (113 mg, 32% yield) as a solid. LCMS (ESI): m/z $[M+H]^+$ calc'd for $C_{52}H_{69}N_7O_8S$ 951.5; found 952.5; $^1$H NMR (300 MHz, DMSO-$d_6$) δ 8.66 (d, J=2.1 Hz, 1H), 8.51 (s, 1H), 7.92 (s, 1H), 7.76 (d, J=8.4 Hz, 2H), 7.61 (dd, J=15.3, 9.2 Hz, 2H), 5.88 (d, J=9.9 Hz, 1H), 5.18 (d, J=11.6 Hz, 1H), 4.93 (s, 1H), 4.59-4.41 (m, 3H), 4.32 (s, 2H), 4.24 (d, J=6.2 Hz, 2H), 4.13 (s, 3H), 3.82 (d, J=11.0 Hz, 4H), 3.69-3.49 (m, 4H), 3.19 (s, 3H), 2.84-2.74 (s, 2H), 2.64 (s, 2H), 2.10-1.94 (m, 3H), 1.76 (s, 4H), 1.53 (s, 1H), 1.37 (d, J=6.1 Hz, 3H), 1.24 (s, 1H), 1.19 (d, J=7.0 Hz, 3H), 1.15 (s, 2H), 1.07 (d, J=7.2 Hz, 6H), 0.93 (t, J=7.0 Hz, 3H), 0.84 (s, 3H), 0.41 (s, 3H).

Example A503. Synthesis of (1r,2R,3S)—N-(($6^3$S,3S,4S,Z)-$1^2$-(5-((1R,5S,7r)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1,6^2,6^3,6^4,6^5,6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide

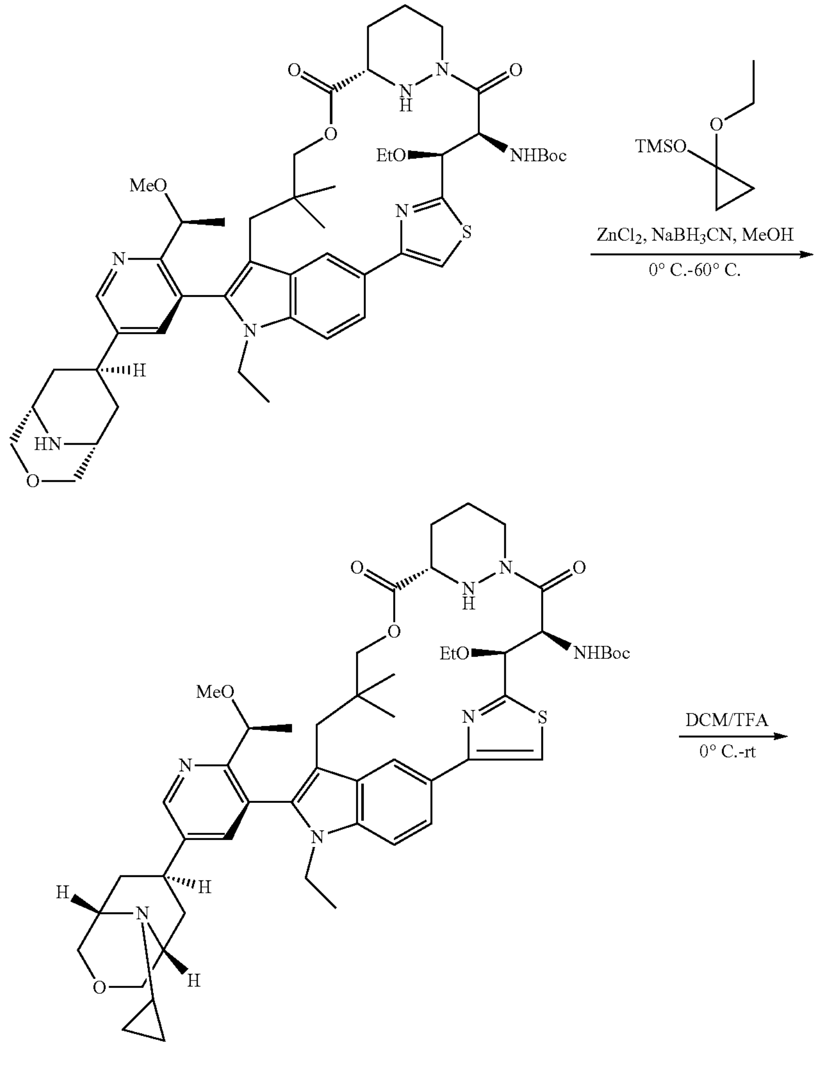

-continued

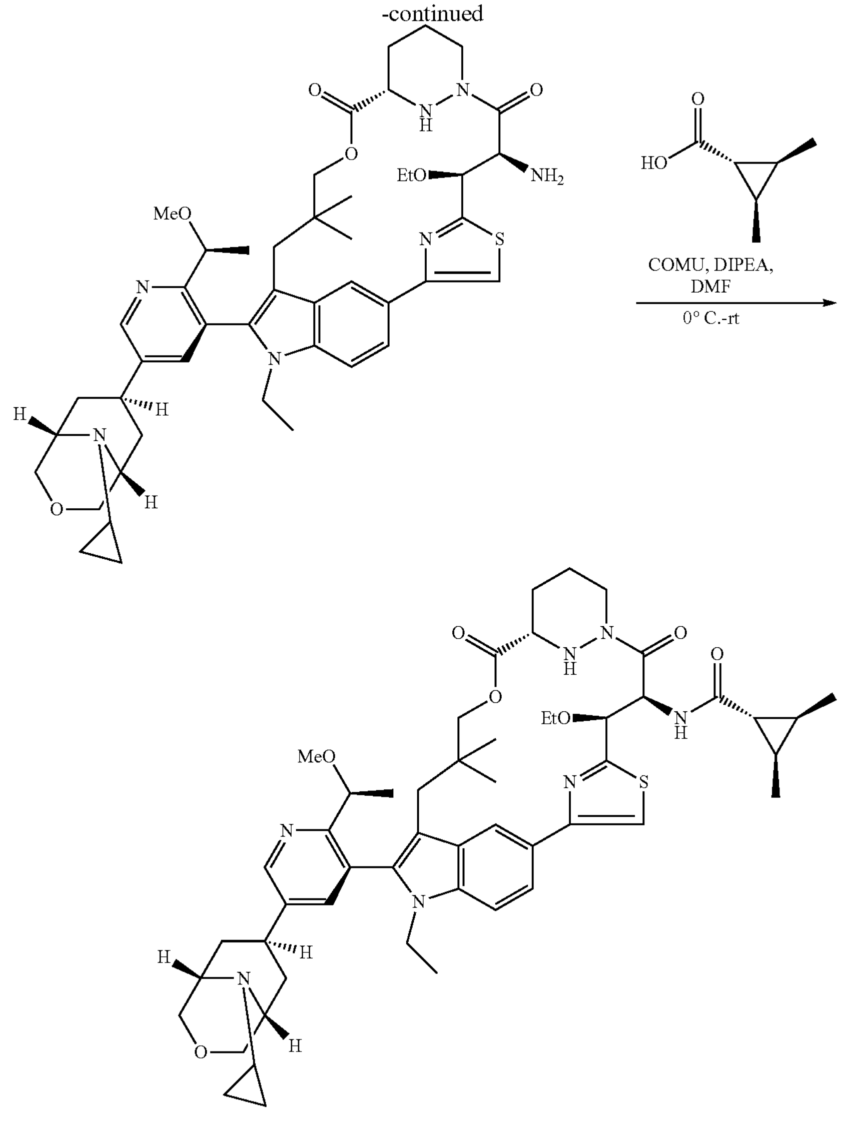

Step 1.

To a mixture of tert-butyl (($6^3$S,3S,4S,Z)-$1^2$-(5-((1R,5S,7r)-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (300 mg, 0.33 mmol) and (1-ethoxycyclopropoxy)trimethylsilane (1.16 g, 6.6 mmol) in MeOH (1.5 mL) at 0° C. was added AcOH (200 mg, 3.3 mmol) dropwise. The mixture was stirred at 0° C. for 30 min, then $NaBH_3CN$ (105 mg, 1.67 mmol) was added, the mixture was heated to 60° C. and stirred for 2 h. The residue was purified by silica gel column chromatography to give tert-butyl (($6^3$S,3S,4S,Z)-$1^2$-(5-((1R,5S,7r)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (235 mg, 75% yield) as a solid. LCMS (ESI): m/z $[M+H]^+$ calc'd for $C_{51}H_{69}N_7O_6S$ 939.5; found 940.3.

Step 2.

To a mixture of tert-butyl (($6^3$S,3S,4S,Z)-12-(5-((1R,5S,7r)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (230 mg, 0.25 mmol) in DCM (2 mL) at 0° C. was added TFA (0.4 mL) dropwise. The mixture was warmed to room temperature and stirred for 1 h, then concentrated under reduced pressure to give ($6^3$S,3S,4S,Z)-4-amino-12-(5-((1R,5S,7r)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (340 mg) as a solid. LCMS (ESI): m/z $[M+H]^+$ calc'd for $C_{46}H_{61}N_7O_6S$ 839.4; found 840.5.

Step 3.

To a mixture of ($6^3$S,3S,4S,Z)-4-amino-12-(5-((1R,5S,7r)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-$6^1$,$6^2$,$6^3$,$6^4$,$6^5$,$6^6$-hexahydro-$1^1$H-8-oxa-2(4,2)- thiazola-1(5,3)-indola-6(1,3)-pyridazinacycloundecaphane-5,7-dione (200 mg, 0.24 mmol) and (1r,2R,3S)-2,3-dimethylcyclopropane-1-carboxylic acid (41 mg, 0.36 mmol) in DMF (2 mL) at 0° C. was added DIPEA (308 mg, 2.4 mmol) and COMU (102 mg, 0.24 mmol) in portions. The mixture was warmed to room temperature and stirred for 1 h, then purified by preparative-HPLC to give (1r,2R,3S)—N-(($6^3$S,3S,4S,Z)-12-(5-((1R,5S,7r)-9-cyclopropyl-3-oxa-9-azabicyclo[3.3.1]nonan-7-yl)-2-((S)-1-methoxyethyl)pyridin-3-yl)-3-ethoxy-$1^1$-ethyl-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2,3-dimethylcyclopropane-1-carboxamide (78 mg, 35% yield) as a solid. LCMS (ESI): m/z $[M+H]^+$ calc'd for $C_{52}H_{69}N_7O_7S$ 935.5; found 936.4; $^1$H NMR (300 MHz, DMSO-$d_6$) δ 8.73 (m, 1H), 8.50 (m, 1H), 7.93 (s, 1H), 7.82-7.53 (m, 3H), 5.88 (d, J=9.8 Hz, 1H), 5.22 (d, J=9.7 Hz, 1H), 4.92 (s, 2H), 4.55-3.86 (m, 14H), 3.84-3.37 (m, 7H), 3.21 (s, 3H), 2.81 (d, J=12.3 Hz, 2H), 2.32 (s, 3H), 2.02 (d, 1H), 1.82 (s, 2H), 1.53 (t, J=3.9 Hz, 2H), 1.38 (d, J=6.0 Hz, 3H), 1.12 (dt, J=34.8, 6.3 Hz, 13H), 0.86 (s, 7H), 0.55 (s, 3H).

Example A504. Synthesis of presumed (1S,2R,3S)—N-(($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methyl-3-(pyrimidin-4-yl)cyclopropane-1-carboxamide

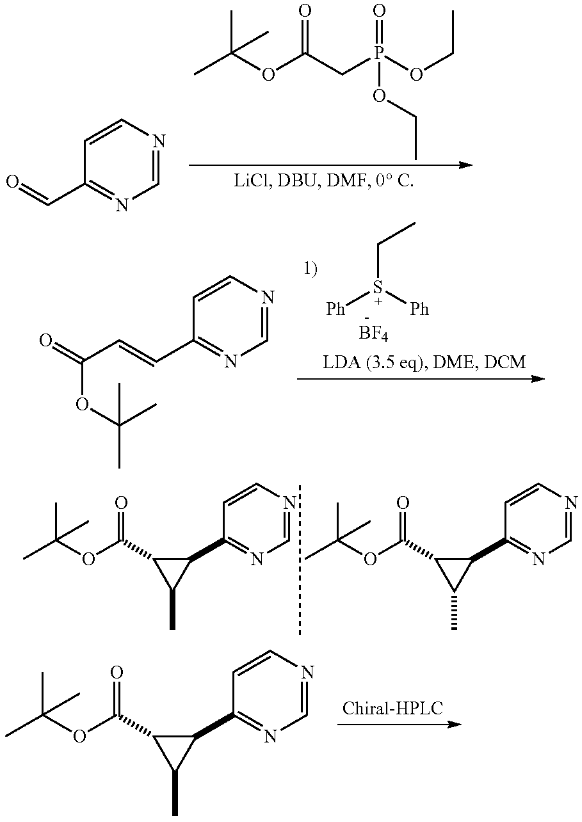

-continued

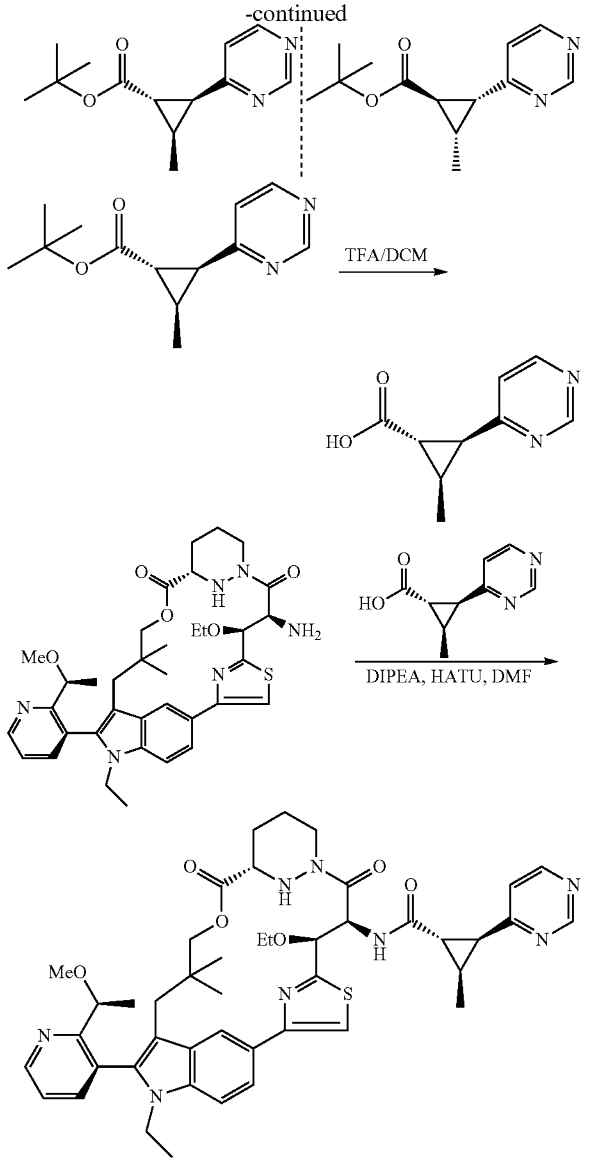

Step 1.

To a mixture of LiCl (0.31 g, 7.4 mmol) and pyrimidine-4-carbaldehyde (1.0 g, 9.3 mmol) in DMF at 0° C. was added DBU (1.69 g, 11.1 mmol) and tert-butyl 2-(diethoxyphosphoryl)acetate (2.80 g, 11.1 mmol) dropwise. The mixture was warmed to room temperature and stirred for 1 h at room temperature, then cooled to 0° C., quenched with saturated $NH_4Cl$ and extracted with EtOAc (200 mL). The organic layer was washed with brine (3×200 mL) and concentrated under reduced pressure. The residue was purified by silica gel column chromatography to give tert-butyl (E)-3-(pyrimidin-4-yl)acrylate (1.0 g, 52% yield) as a solid. LCMS (ESI): m/z $[M+H]^+$ calc'd for $C_{11}H_{14}N_2O_2$ 206.1. found 207.1.

Step 2.

To a mixture ethyldiphenylsulfanium tetrafluoroborate (2.2 g, 10.2 mmol) in DME and DCM (10:1) at −60° C. under an atmosphere of $N_2$ was treated with LDA, 2M in THF (6.0 mL, 12.0 mmol) for 0.5 h. The mixture was warmed to room temperature and tert-butyl (E)-3-(pyrimidin-4-yl)acrylate (700 mg, 3.4 mmol) was added dropwise.

The mixture was stirred at room temperature 1 h, then quenched with saturated $NH_4Cl$ and extracted with EtOAc (3×100 mL). The combined organic layers were concentrated under reduced pressure and the residue was purified by preparative-HPLC to give 2-methyl-3-(pyrimidin-4-yl) cyclopropane-1-carboxylic acid (160 mg, 20% yield) as a solid. LCMS (ESI): m/z [M+H]) calc'd for $C_{13}H_{18}N_2O_2$ 234.1. found 235.1: $^1$H NMR (300 MHz, $CDCl_3$) δ 9.10 (s, 1H), 8.63 (s, 1H), 7,33 (s, 1H), 2.66 (dd, J=9.7, 4.7 Hz, 1H), 2.46 (dd, J=5.7, 4.7 Hz, 1H), 2.06-1.78 (m, 1H), 1.47 (s, 9H), 1.13 (d, J=6.4 Hz, 3H).

A racemic mixture of the above compound was separated by chiral-HPLC to give (55 mg, single diastereomer of unknown absolute configuration, RT=6.2 min) as a solid and (61 mg, single diastereomer of unknown absolute configuration, RT=7.3 min).

Step 3.

A mixture of tert-butyl (1S,2R,3S)-2-methyl-3-(pyrimidin-4-yl)cyclopropane-1-carboxylate (50 mg, 0.21 mmol, single diastereomer of unknown absolute configuration; RT=6.2 min) and TFA (5 mL, 67.3 mmol) in DCM was stirred at room temperature for 1 h, then concentrated under reduced pressure to give (1S,2R,3S)-2-methyl-3-(pyrimidin-4-yl)cyclopropane-1-carboxylic acid, that was used directly in the next step without further purification (single diastereomer of unknown absolute configuration). LCMS (ESI): m/z $[M+H]^+$ calc'd for $C_9H_{10}N_2O_2$ 178.0. found 179.1.

Step 4.

To a mixture of (1S,2R,3S)-2-methyl-3-(pyrimidin-4-yl) cyclopropane-1-carboxylic acid (53 mg, 0.3 mmol) and DIPEA (192 mg, 1.48 mmol) in DMF at room temperature under an atmosphere of $N_2$ was added ($6^3$S,3S,4S,Z)-4-amino-3-ethoxy-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1 (5,3)-indola-6(1,3)-pyridazinacycloundecaphane-5,7-dione (100 mg, 0.15 mmol) and HATU (113 mg, 0.3 mmol). The mixture was stirred at room temperature for 1 h, then diluted with EtOAc (100 mL) and washed with brine (3×100 mL). The organic layer was concentrated under reduced pressure and the residue was purified by preparative-HPLC to give (1S,2R,3S)—N-(($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1 (5,3)-indola-6(1,3)-pyridazinacycloundecaphane-4-yl)-2-methyl-3-(pyrimidin-4-yl)cyclopropane-1-carboxamide (19 mg, 15% yield; single diastereomer of unknown absolute configuration) as a solid. LCMS (ESI): m/z $[M+H]^+$ calc'd for $C_{45}H_{54}N_8O_6S$ 834.4. found 835.2; $^1$H NMR (300 MHz, DMSO-$d_6$) δ 9.09 (s, 1H), 8.82-8.71 (m, 1H), 8.66 (m, 1H), 8.51 (s, 1H), 8.23-8.22 (m, 1H), 7.94 (s, 1H), 7.87-7.65 (m, 2H), 7.63-7.30 (m, 3H), 5.89-5.76 (m, 1H), 5.19-5.15 (m, 1H), 4.95 (s, 1H), 4.28-4.13 (m, 5H), 3.79-3.52 (m, 7H), 3.42-3.31 (m, 3H), 2.83 (s, 2H), 2.08 (s, 1H), 1.78 (s, 3H), 1.38-1.34 (m, 3H), 1.31-1.20 (m, 6H), 0.88-0.78 (m, 6H), 0.41 (s, 3H).

Example A505. Synthesis of presumed (1R,2S,3R)—N-(($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methyl-3-(pyrimidin-4-yl)cyclopropane-1-carboxamide

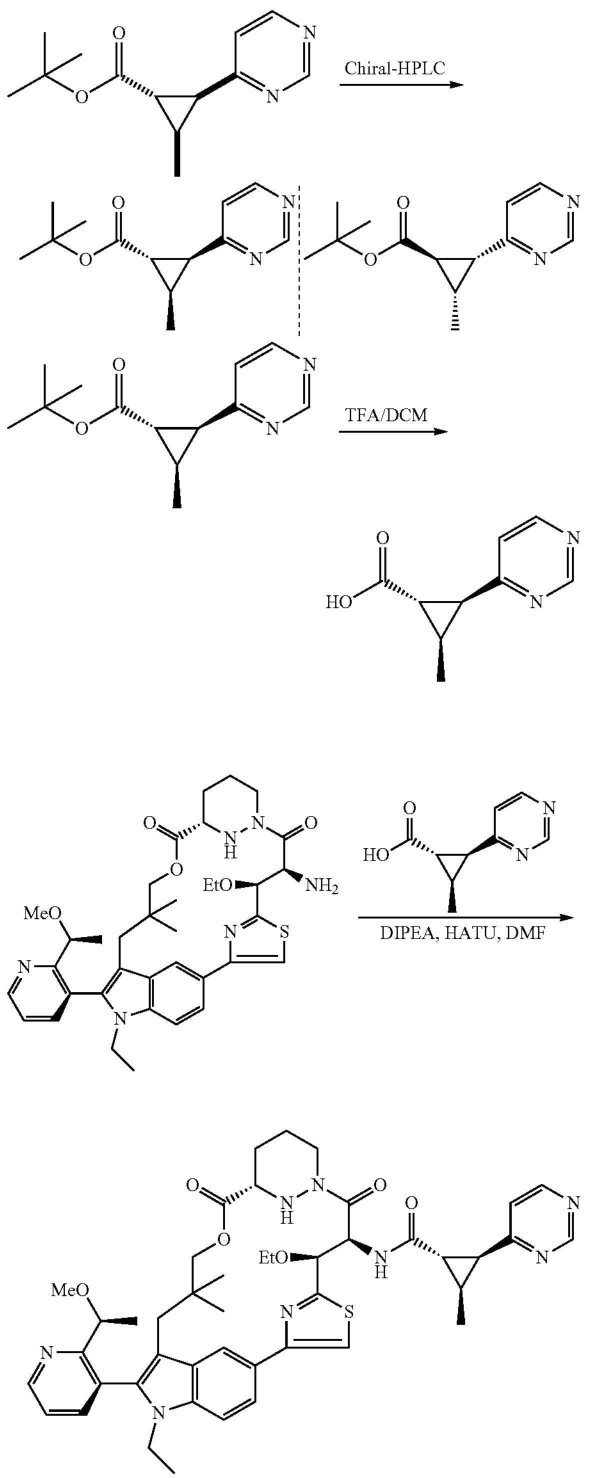

Step 1.

A racemic mixture of the starting cyclopropane was separated by chiral HPLC [condition (Column: CHIRALPAK IF, 2×25 cm, 5 μM; Mobile Phase A: Hexane (10 mM $NH_3$-MeOH), Mobile Phase B: IPA-HPLC; Flow rate: 20 mL/min; Gradient: 5% B to 5% B in 10 min; Wave Length: 252/220 nm; RT1 (min): 6.2; RT2 (min): 7.3; Sample Solvent: MeOH:DCM=1:1; Injection Volume: 0.2 mL; Number Of Runs: 11)]. Product A (single diastereomer of unknown absolute configuration, 55 mg, RT=6.2 min) as white solid; Product B (single diastereomer of unknown absolute configuration, 61 mg, RT=7.3 min).

Step 2.

A mixture of presumed tert-butyl (1R,2S,3R)-2-methyl-3-(pyrimidin-4-yl)cyclopropane-1-carboxylate (single diastereomer of unknown absolute configuration, 50 mg, 0.21 mmol) and TFA (5 mL, 67.3 mmol) in DCM was stirred at room temperature for 1 h, then concentrated under reduced pressure to give presumed (1R,2S,3R)-2-methyl-3-(pyrimidin-4-yl)cyclopropane-1-carboxylic acid (single diastereomer of unknown absolute configuration). LCMS (ESI): m/z $[M+H]^+$ calc'd for $C_9H_{10}N_2O_2$ 178.0. found 179.1.

Step 3.

To a mixture of (1R,2S,3R)-2-methyl-3-(pyrimidin-4-yl) cyclopropane-1-carboxylic acid (53 mg, 0.3 mmol) and DIPEA (192 mg, 1.48 mmol) in DMF at room temperature under an atmosphere of $N_2$ was added ($6^3$S,3S,4S,Z)-4-amino-3-ethoxy-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-1H-8-oxa-2(4,2)-thiazola-1(5,3)-indola-6(1,3)-pyridazinacycloundecaphane-5,7-dione (100 mg, 0.15 mmol) and HATU (113 mg, 0.3 mmol). The mixture was stirred at room temperature for 1 h, then diluted with EtOAc (100 mL) and washed with brine (3×100 mL). The organic layer was concentrated under reduced pressure and the residue was purified by preparative-HPLC to give (1R,2S,3R)—N-(($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methyl-3-(pyrimidin-4-yl)cyclopropane-1-carboxamide (single diastereomer of unknown absolute configuration, 29 mg, 19% yield) as a solid. LCMS (ESI): m/z $[M+H]^+$ calc'd for $C_{45}H_{54}N_8O_6S$ 834.4. found 835.2; $^1H$ NMR (300 MHz, DMSO-$d_6$) δ 9.10 (s, 1H), 8.83-8.78 (m, 1H), 8.71 (m, 1H), 8.54 (s, 1H), 8.29-8.24 (m, 1H), 7.98 (s, 1H), 7.88-7.78 (m, 2H), 7.74-7.69 (m, 1H), 7.67-7.35 (m, 3H), 5.85-5.72 (m, 1H), 5.19-5.12 (m, 1H), 4.93 (s, 1H), 4.30-4.22 (m, 5H), 3.80-3.60 (m, 7H), 3.46-3.38 (m, 3H), 2.88 (s, 1H), 2.75-2.56 (m, 1H), 2.18 (s, 1H), 1.88 (s, 1H), 1.71-1.56 (m, 2H), 1.48-1.24 (m, 3H), 1.28-1.22 (m, 3H), 1.19-1.02 (m, 3H), 0.98-0.88 (m, 6H), 0.44 (s, 3H).

Example A506 & A507. Synthesis of presumed (1R,2S,3R)—N-(($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$^1$H-8-oxa-2(4,2)-thiazola-1(5,3)-indola-6(1,3)-pyridazinacycloundecaphane-4-yl)-2-methyl-3-(1-methyl-1H-imidazol-4-yl)cyclopropane-1-carboxamide and (1R,2S,3R)—N-(($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methyl-3-(1-methyl-1H-imidazol-4-yl)cyclopropane-1-carboxamide

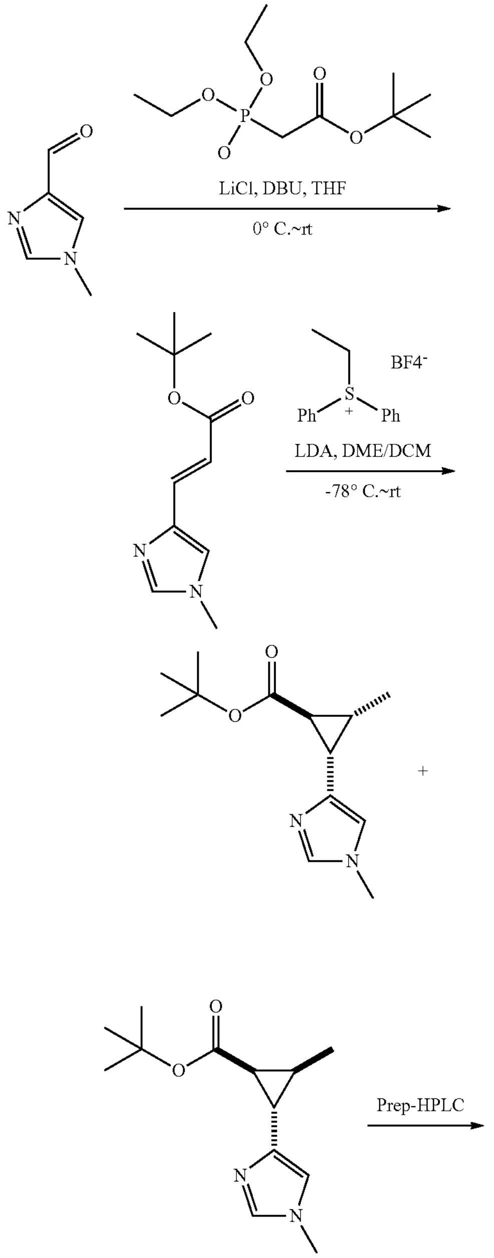

-continued

-continued

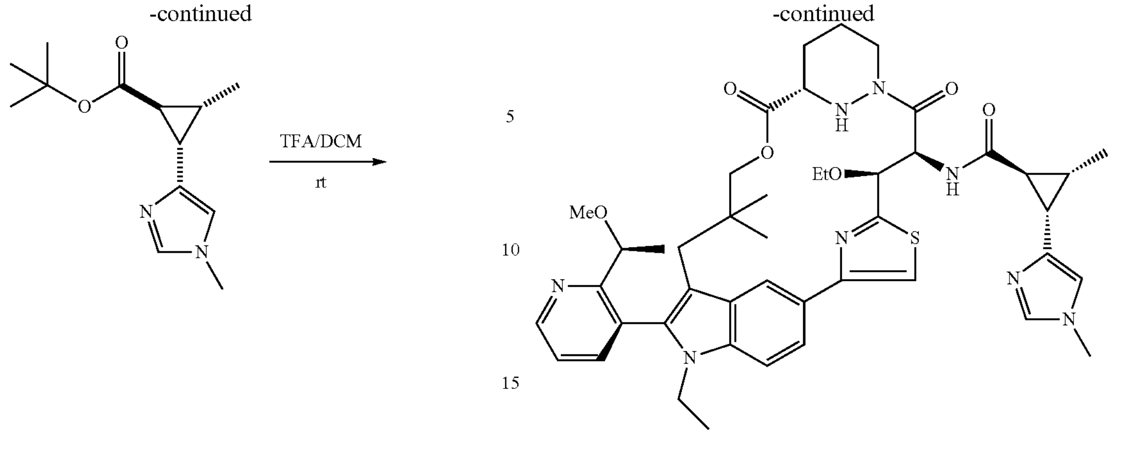

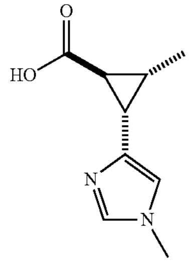

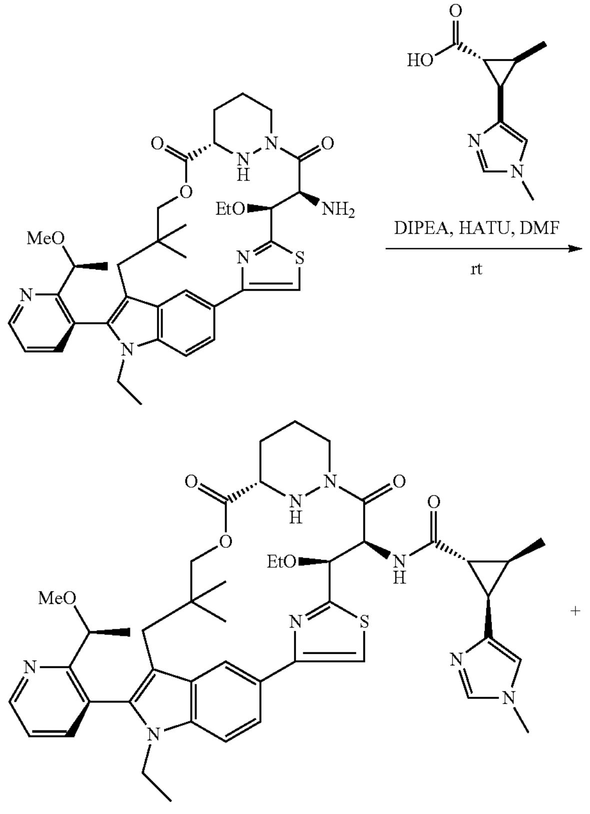

+

Step 1.

To a mixture of 1-methyl-1H-imidazole-4-carbaldehyde (1.9 g, 17.3 mmol) and LiCl (0.95 g, 22.4 mmol) in THF (10 mL) at 0° C. were added tert-butyl 2-(diethoxyphosphoryl) acetate (5.66 g, 22.4 mmol) and DBU (2.63 g, 17.3 mmol) in portions. The mixture was allowed to warm to room temperature and stirred for 2 h then the mixture was washed $H_2O$ (2×30 mL). The combined aqueous layers were extracted with EtOAc (3×30 mL) and the combined organic layers were dried and filtered. The filtrate was concentrated under reduced pressure and the residue was purified by silica gel column chromatography to give tert-butyl (E)-3-(i-methyl-1H-imidazol-4-yl)acrylate (3 g, 84% yield) as an oil. LCMS (ESI): m/z $[M+H]^+$ calc'd for $C_{11}H_{16}N_2O_2$ 208.1. found 209.1.

Step 2.

To a mixture of ethyldiphenylsulfonium tetrafluoroborate (2.18 g, 7.2 mmol) in DCM:DME (1:10) at −60° C. under an atmosphere of $N_2$ was treated with 2M LDA in THF (12 mL, 24 mmol) for 30 min, followed by the addition of tert-butyl (E)-3-(1-methyl-1H-imidazol-4-yl)acrylate (500 mg, 2.4 mmol) in portions. The mixture was warmed to room temperature and stirred for 2 h, then quenched with saturated $NH_4Cl$ and extracted with EtOAc (3×50 mL). The combined organic layers were dried. The residue was purified by preparative-HPLC to give tert-butyl (1S,2R,3S)-2-methyl-3-(1-methyl-1H-imidazol-4-yl)cyclopropane-1-carboxylate (200 mg, 35% yield of a single diastereomer of unknown absolute configuration) and tert-butyl (1S,2S,3S)-2-methyl-3-(1-methyl-1H-imidazol-4-yl)cyclopropane-1-carboxylate (110 mg, 19% yield of a single diastereomer of unknown absolute configuration), as an oil. LCMS (ESI): m/z $[M+H]^+$ calc'd for $C_{13}H_{20}N_2O_2$ 236.2. found 236.9.

Step 3.

A mixture of presumed tert-butyl (1S,2R,3S)-2-methyl-3-(1-methyl-1H-imidazol-4-yl)cyclopropane-1-carboxylate (70 mg, 0.3 mmol) and TFA (1 mL) in DCM was stirred at room temperature for 2 h, then concentrated under reduced pressure to give (1S,2R,3S)-2-methyl-3-(1-methyl-1H-imidazol-4-yl)cyclopropane-1-carboxylic acid as an oil, which was used directly in the next step without further purification. LCMS (ESI): m/z $[M+H]^+$ calc'd for $C_9H_{12}N_2O_2$ 180.1. found 181.3.

Step 4.

To a mixture of ($6^3$S,3S,4S, Z)-4-amino-3-ethoxy-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione (122 mg, 0.18 mmol) and tert-butyl (1S,2R,3S)-2-methyl-3-(1-methyl-1H-imidazol-4-yl)cyclopropane-1-carboxylate (65 mg, 0.36 mmol) in DMF (10 mL) at room temperature was added DIPEA (467 mg, 3.6 mmol) and HATU (76 mg, 0.2 mmol) in portions. The mixture was irradiated under microwave radiation for 2 h at room temperature. The mixture was extracted with EtOAc (2×20 mL) and the combined organic layers were washed with $H_2O$ (3×20 mL), dried over anhydrous $Na_2SO_4$ and filtered. The filtrate was concentrated under reduced pressure and the residue was purified by preparative-HPLC to give (1R,2S,3R)—N-(($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)-2-methyl-3-(1-methyl-1H-imidazol-4-yl)cyclopropane-1-carboxamide (34 mg, 21%, diastereomer of unknown absolute configuration RT=1.00 min) as a solid and (1R,2S,3R)—N-(($6^3$S,3S,4S,Z)-3-ethoxy-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)- pyridazinacycloundecaphane-4-yl)-2-methyl-3-(1-methyl-1H-imidazol-4-yl)cyclopropane-1-carboxamide (36 mg, 22%, single diastereomer of unknown absolute configuration RT=1.07 min) as a solid. Data for first diastereomer (RT=1.00 min): LCMS (ESI): m/z $[M+H]^+$ calc'd for $C_{45}H_{56}N_8O_6S$ 836.4. found 837.1; $^1H$ NMR (400 MHz, $CD_3OD$) δ 8.74-8.69 (m, 1H), 8.63-8.60 (m, 1H), 7.86-7.80 (m, 1H), 7.73-7.68 (m, 1H), 7.63 (s, 1H), 7.56-7.45 (m, 3H), 6.94 (s, 1H), 6.01 (s, 1H), 5.04-5.01 (m, 1H), 4.50-4.41 (m, 1H), 4.38-4.33 (m, 1H), 4.29-4.20 (m, 2H), 4.15-4.06 (m, 1H), 3.76-3.73 (m, 2H), 3.72-3.68 (m, 3H), 3.66-3.58 (m, 2H), 3.32-3.27 (m, 3H), 3.05-2.95 (m, 1H), 2.86-2.78 (m, 1H), 2.66-2.61 (m, 1H), 2.49-2.41 (m, 1H), 2.24-2.16 (m, 1H), 2.11-2.06 (m, 1H), 2.02-1.92 (m, 1H), 1.87-1.77 (m, 1H), 1.69-1.52 (m, 3H), 1.46-1.41 (m, 3H), 1.38-1.15 (m, 11H), 1.04-0.81 (m, 13H), 0.50 (s, 3H). Data for second diastereomer (RT=1.07 min): LCMS (ESI): m/z $[M+H]^+$ calc'd for $C_{45}H_{56}N_8O_6S$ 836.4. found 837.1; $^1H$ NMR (400 MHz, $CD_3OD$) δ 8.74-8.67 (m, 1H), 8.63-8.60 (m, 1H), 7.86-7.80 (m, 1H), 7.73-7.68 (m, 1H), 7.63 (s, 1H), 7.56-7.45 (m, 3H), 6.94 (s, 1H), 6.01 (s, 1H), 5.04-5.01 (m, 1H), 4.50-4.41 (m, 1H), 4.38-4.33 (m, 1H), 4.29-4.20 (m, 2H), 4.15-4.06 (m, 1H), 3.76-3.73 (m, 2H), 3.72-3.68 (m, 3H), 3.66-3.58 (m, 2H), 3.32-3.27 (m, 3H), 3.05-2.95 (m, 1H), 2.86-2.78 (m, 1H), 2.66-2.61 (m, 1H), 2.49-2.41 (m, 1H), 2.24-2.16 (m, 1H), 2.11-2.06 (m, 1H), 2.02-1.92 (m, 3H), 1.87-1.77 (m, 3H), 1.68-1.53 (m, 4H), 1.46-1.41 (m, 11H), 1.38-1.15 (m, 3H), 1.04-0.81 (m, 10H), 0.50 (s, 3H).

The following table of compounds were prepared using the aforementioned methods or variations thereof, as would be known to those of skill in the art.

TABLE 4

Exemplary Compounds Prepared by Methods of the Present Invention

| Ex # | LCMS (ESI): m/z [M + H] Found |
|---|---|
| A1 | 799.2 |
| A2 | 827.5 |
| A3 | 827.5 |
| A4 | 809.5 |
| A5 | 757.4 |
| A6 | 757.4 |
| A7 | 756.4 |
| A8 | 784.2 |
| A9 | 770.2 |
| A10 | 836.2 |

TABLE 4-continued

Exemplary Compounds Prepared by Methods of the Present Invention

| Ex # | LCMS (ESI): m/z [M + H] Found |
|---|---|
| A11 | 836.3 |
| A12 | 738.3 |
| A13 | 738.3 |
| A14 | 714.1 |
| A15 | 853.4 |
| A16 | 853.2 |
| A17 | 869.2 |
| A18 | 869.2 |
| A19 | 880.3 |
| A20 | 826.2 |
| A21 | 894.1 |
| A22 | 840.2 |
| A23 | 757.4 |
| A24 | 820.2 |
| A25 | 800.3 |
| A26 | 786.4 |
| A27 | 786.4 |
| A28 | 875.6 |
| A29 | 865.5 |
| A30 | 823.5 |
| A31 | 823.5 |
| A32 | 853.5 |
| A33 | 853.5 |
| A34 | 806.8 |
| A35 | 757.7 |
| A36 | 811.7 |
| A37 | 763.7 |
| A38 | 820.4 |
| A39 | 800.5 |
| A40 | 882.2 |
| A41 | 881.9 |
| A42 | 804.6 |
| A43 | 804.6 |
| A44 | 798.2 |
| A45 | 798.2 |
| A46 | 784.3 |
| A47 | 796.4 |
| A48 | 796.4 |
| A49 | 768.4 |
| A50 | 818.2 |
| A51 | 796.2 |
| A52 | 785.2 |
| A53 | 837.5 |
| A54 | 837.6 |
| A55 | 841.5 |
| A56 | 861.2 |
| A57 | 833.1 |
| A58 | 881.4 |
| A59 | 827.2 |
| A60 | 776.7 |
| A61 | 776.7 |
| A62 | 776.7 |
| A63 | 776.7 |
| A64 | 757.7 |
| A65 | 775.7 |
| A66 | 713.6 |
| A67 | 769.7 |
| A68 | 749.7 |
| A69 | 803.7 |
| A70 | 803.7 |
| A71 | 770.7 |
| A72 | 770.8 |
| A73 | 790.8 |
| A74 | 790.8 |
| A75 | 787.7 |
| A76 | 787.8 |
| A77 | 782.8 |
| A78 | 777.8 |
| A79 | 777.8 |
| A80 | 776.7 |
| A81 | 776.37 |
| A82 | 771.8 |
| A83 | 771.8 |
| A84 | 770 |
| A85 | 758.7 |

TABLE 4-continued

| Exemplary Compounds Prepared by Methods of the Present Invention | |
|---|---|
| Ex # | LCMS (ESI): m/z [M + H] Found |
| A86 | 757.7 |
| A87 | 755.7 |
| A88 | 738.7 |
| A89 | 738.7 |
| A90 | 741.7 |
| A91 | 725.7 |
| A92 | 738.7 |
| A93 | 724.7 |
| A94 | 743.7 |
| A95 | 729.8 |
| A96 | 759.5 |
| A97 | 759.4 |
| A98 | 867.9 |
| A99 | 874.1 |
| A100 | 815.9 |
| A101 | 768.5 |
| A102 | 743.4 |
| A103 | 756.5 |
| A104 | 771.5 |
| A105 | 801.6 |
| A106 | 771.2 |
| A107 | 797.6 |
| A108 | 724.4 |
| A109 | 724.4 |
| A110 | 800.4 |
| A111 | 784.4 |
| A112 | 784.4 |
| A113 | 796.4 |
| A114 | 784.4 |
| A115 | 791.4 |
| A116 | 791.4 |
| A117 | 743.4 |
| A118 | 825.5 |
| A119 | 825.5 |
| A120 | 853.5 |
| A121 | 855.5 |
| A122 | 811.5 |
| A123 | 811.6 |
| A124 | 865.5 |
| A125 | 724.3 |
| A126 | 867.4 |
| A127 | 813.5 |
| A128 | 713.2 |
| A129 | 742.3 |
| A130 | 742.3 |
| A131 | 757.3 |
| A132 | 772.4 |
| A133 | 738.3 |
| A134 | 738.3 |
| A135 | 836.3 |
| A136 | 836.2 |
| A137 | 770.2 |
| A138 | 784.2 |
| A139 | 756.4 |
| A140 | 757.4 |
| A141 | 757.4 |
| A142 | 770.4 |
| A143 | 809.5 |
| A144 | 827.5 |
| A145 | 827.5 |
| A146 | 400.4 |
| A147 | 835.5 |
| A148 | 835.5 |
| A149 | 862.6 |
| A150 | 862.5 |
| A151 | 804 |
| A152 | 804.5 |
| A153 | 818.5 |
| A154 | 818.5 |
| A155 | 756.4 |
| A156 | 799.4 |
| A157 | 851.6 |
| A158 | 771 |
| A159 | 812.5 |
| A160 | 850.6 |

TABLE 4-continued

| Exemplary Compounds Prepared by Methods of the Present Invention | |
|---|---|
| Ex # | LCMS (ESI): m/z [M + H] Found |
| A161 | 892.6 |
| A162 | 743.4 |
| A163 | 856.5 |
| A164 | 711.4 |
| A165 | 795.8 |
| A166 | 875.6 |
| A167 | 823.5 |
| A168 | 837.7 |
| A169 | 825.6 |
| A170 | 822.5 |
| A171 | 822.7 |
| A172 | 822.5 |
| A173 | 869.3 |
| A174 | 917.7 |
| A175 | 917.7 |
| A176 | 746.4 |
| A177 | 728.2 |
| A178 | 730.2 |
| A179 | 852.4 |
| A180 | 850.5 |
| A181 | 886.6 |
| A182 | 829 |
| A183 | 829 |
| A184 | 852.1 |
| A185 | 727.2 |
| A186 | 727.2 |
| A187 | 924.6 |
| A188 | 924.6 |
| A189 | 856.6 |
| A190 | 765.7 |
| A191 | 756.8 |
| A192 | 760.8 |
| A193 | 790.8 |
| A194 | 742.7 |
| A195 | 742.6 |
| A196 | 742.4 |
| A197 | 742.9 |
| A198 | 783 |
| A199 | 864.6 |
| A200 | 864.5 |
| A201 | 904.7 |
| A202 | 891.7 |
| A203 | 898.9 |
| A204 | 790.4 |
| A205 | 823.7 |
| A206 | 823.8 |
| A207 | 841.6 |
| A208 | 841.6 |
| A209 | 853.8 |
| A210 | 764.4 |
| A211 | 764.3 |
| A212 | 772.3 |
| A213 | 861.6 |
| A214 | 792.8 |
| A215 | 911.7 |
| A216 | 783.6 |
| A217 | 772.7 |
| A218 | 758.4 |
| A219 | 757.9 |
| A220 | 839.7 |
| A221 | 847.3 |
| A222 | 847.3 |
| A223 | 837 |
| A224 | 772.6 |
| A225 | 757.6 |
| A226 | 800.6 |
| A227 | 727.3 |
| A228 | 870.7 |
| A229 | 810.7 |
| A230 | 839.9 |
| A231 | 867.7 |
| A232 | 773.3 |
| A233 | 727.3 |
| A234 | 727.4 |
| A235 | 852.6 |

TABLE 4-continued

Exemplary Compounds Prepared by Methods of the Present Invention

| Ex # | LCMS (ESI): m/z [M + H] Found |
|---|---|
| A236 | 792.6 |
| A237 | 852.9 |
| A238 | 852.8 |
| A239 | 850.6 |
| A240 | 906.6 |
| A241 | 797.6 |
| A242 | 829.6 |
| A243 | 898.7 |
| A244 | 912.7 |
| A245 | 756.2 |
| A246 | 769.6 |
| A247 | 811.6 |
| A248 | 866.6 |
| A249 | 866.7 |
| A250 | 866.8 |
| A251 | 891.4 |
| A252 | 825.7 |
| A253 | 825.5 |
| A254 | 825.6 |
| A255 | 825.8 |
| A256 | 770.3 |
| A257 | 883.8 |
| A258 | 854.7 |
| A259 | 853.5 |
| A260 | 890.5 |
| A261 | 873.6 |
| A262 | 873.6 |
| A263 | 837.3 |
| A264 | 881.7 |
| A265 | 865.3 |
| A266 | 865.5 |
| A267 | 865.1 |
| A268 | 813.7 |
| A269 | 867.4 |
| A270 | 772.5 |
| A271 | 913.7 |
| A272 | 899.7 |
| A273 | 867.5 |
| A274 | 851.7 |
| A275 | 811.7 |
| A276 | 891.3 |
| A277 | 907.5 |
| A278 | 897.6 |
| A279 | 843.8 |
| A280 | 856.7 |
| A281 | 857.7 |
| A282 | 965.6 |
| A283 | 965.5 |
| A284 | 805.4 |
| A285 | 768.5 |
| A286 | 850.9 |
| A287 | 909.6 |
| A288 | 925.8 |
| A289 | 855.6 |
| A290 | 855.6 |
| A291 | 755.2 |
| A292 | 755.2 |
| A293 | 811.8 |
| A294 | 793.6 |
| A295 | 384.9 |
| A296 | 770.6 |
| A297 | 899.7 |
| A298 | 906.8 |
| A299 | 905.5 |
| A300 | 865.5 |
| A301 | 869.6 |
| A302 | 869.4 |
| A303 | 785.5 |
| A304 | 935.4 |
| A305 | 901 |
| A306 | 901 |
| A307 | 757.4 |
| A308 | 741.4 |
| A309 | 771.4 |
| A310 | 804.7 |

TABLE 4-continued

Exemplary Compounds Prepared by Methods of the Present Invention

| Ex # | LCMS (ESI): m/z [M + H] Found |
|---|---|
| A311 | 889.7 |
| A312 | 910.5 |
| A313 | 752.4 |
| A314 | 887.4 |
| A315 | 887.5 |
| A316 | 869.5 |
| A317 | 869.5 |
| A318 | 839.7 |
| A319 | 839.6 |
| A320 | 783.8 |
| A321 | 841.8 |
| A322 | 785.3 |
| A323 | 799.4 |
| A324 | 979.6 |
| A325 | 755.1 |
| A326 | 755.1 |
| A327 | 855.9 |
| A328 | 853.6 |
| A329 | 763 |
| A330 | 763 |
| A331 | 855.5 |
| A332 | 854.5 |
| A333 | 885.9 |
| A334 | 813.5 |
| A335 | 870.7 |
| A336 | 785.4 |
| A337 | 769.5 |
| A338 | 809.9 |
| A339 | 799.6 |
| A340 | 739.6 |
| A341 | 743.5 |
| A342 | 852.7 |
| A343 | 852.7 |
| A344 | 820.4 |
| A345 | 820.4 |
| A346 | 732.6 |
| A347 | 732.6 |
| A348 | 730.6 |
| A349 | 730.3 |
| A350 | 747.5 |
| A351 | 745.3 |
| A352 | 745.3 |
| A353 | 833.8 |
| A354 | 870.8 |
| A355 | 743.5 |
| A356 | 738.5 |
| A357 | 783.4 |
| A358 | 744.5 |
| A359 | 758.6 |
| A360 | 758.6 |
| A361 | 728.4 |
| A362 | 747.6 |
| A363 | 747.5 |
| A364 | 745.6 |
| A365 | 731.6 |
| A366 | 807.4 |
| A367 | 789.4 |
| A368 | 746.5 |
| A369 | 747.4 |
| A370 | 827.4 |
| A371 | 842.0 |
| A372 | 769.2 |
| A373 | 897.4 |
| A374 | 778.3 |
| A375 | 806.4 |
| A376 | 758.4 |
| A377 | 871 |
| A378 | 760.5 |
| A379 | 760.35 |
| A380 | 760.5 |
| A381 | 784.4 |
| A382 | 758.5 |
| A383 | 733.4 |
| A384 | 825.3 |
| A385 | 741.2 |

TABLE 4-continued

Exemplary Compounds Prepared by Methods of the Present Invention

| Ex # | LCMS (ESI): m/z [M + H] Found |
|---|---|
| A386 | 741.2 |
| A387 | 807.5 |
| A388 | 840.3 |
| A389 | 910.7 |
| A390 | 910.4 |
| A391 | 809.8 |
| A392 | 768.6 |
| A393 | 768.5 |
| A394 | 770.6 |
| A395 | 770.6 |
| A396 | 900.9 |
| A397 | 886.2 |
| A398 | 774.3 |
| A399 | 744.6 |
| A400 | 743.6 |
| A401 | 918.6 |
| A402 | 825.6 |
| A403 | 803.5 |
| A404 | 803.5 |
| A405 | 826.25 |
| A406 | 856.7 |
| A407 | 745.4 |
| A408 | 881.9 |
| A409 | 753.6 |
| A410 | 911.8 |
| A411 | 885.9 |
| A412 | 760.6 |
| A413 | 784.3 |
| A414 | 741.4 |
| A415 | 769.5 |
| A416 | 829.7 |
| A417 | 820.4 |
| A418 | 866.8 |
| A419 | 755.3 |
| A420 | 755.3 |
| A421 | 856.7 |
| A422 | 739.5 |
| A423 | 740.4 |
| A424 | 741.4 |
| A425 | 763.2 |
| A426 | 941.8 |
| A427 | 941.3 |
| A428 | 910.7 |
| A429 | 899.2 |
| A430 | 742.3 |
| A431 | 756.6 |
| A432 | 756.6 |
| A433 | 898.9 |
| A434 | 885.4 |
| A435 | 746.6 |
| A436 | 757.3 |
| A437 | 872.3 |
| A438 | 927.9 |
| A439 | 820.2 |
| A440 | 828.3 |
| A441 | 828.2 |
| A442 | 866.5 |
| A443 | 763.3 |
| A444 | 738.1 |
| A445 | 770.2 |
| A446 | 756.7 |
| A447 | 742.7 |
| A448 | 813.6 |
| A449 | 910.8 |
| A450 | 976.9 |
| A451 | 840.7 |
| A452 | 856.4 |
| A453 | 838.7 |
| A454 | 838.4 |
| A455 | 799.4 |
| A456 | 813.6 |
| A457 | 827.6 |
| A458 | 771.2 |
| A459 | 958.4 |
| A460 | 928.4 |

TABLE 4-continued

Exemplary Compounds Prepared by Methods of the Present Invention

| Ex # | LCMS (ESI): m/z [M + H] Found |
|---|---|
| A461 | 894.8 |
| A462 | 813.5 |
| A463 | 820.7 |
| A464 | 771.6 |
| A465 | 771.6 |
| A466 | 757.7 |
| A467 | 856.35 |
| A468 | 771.3 |
| A469 | 756.3 |
| A470 | 745.4 |
| A471 | 754.5 |
| A472 | 742.2 |
| A473 | 785.5 |
| A474 | 799.5 |
| A475 | 925.5 |
| A476 | 925.4 |
| A477 | 870.3 |
| A478 | 840.6 |
| A479 | 837.6 |
| A480 | 837.6 |
| A481 | 932.4 |
| A482 | 932.4 |
| A483 | 936.4 |
| A484 | 952.5 |
| A485 | 784.3 |
| A486 | 757.5 |
| A487 | 771.5 |
| A488 | 757.2 |
| A489 | 757.25 |
| A490 | 800.3 |
| A491 | 790.4 |
| A492 | 790.6 |
| A493 | 858.3 |
| A494 | 850.5 |
| A495 | 850.4 |
| A496 | 756.4 |
| A497 | 910.4 |
| A498 | 790.3 |
| A499 | 790.3 |
| A500 | 911.8 |
| A501 | 911.8 |
| A502 | 952.5 |
| A503 | 936.4 |
| A504 | 835.2 |
| A505 | 835.2 |
| A506 | 837.4 |
| A507 | 837.3 |
| A508 | 854.6 |
| A509 | 868.6 |
| A510 | 883.7 |
| A511 | 898.4 |
| A512 | 897.8 |
| A513 | 897.8 |
| A514 | 787.7 |
| A515 | 883.5 |
| A516 | 883.55 |
| A517 | 844.3 |
| A518 | 828.35 |
| A519 | 770.3 |
| A520 | 1004.3 |
| A521 | 968.9 |
| A522 | 835.5 |
| A523 | 821.3 |
| A524 | 811.5 |
| A525 | 793.4 |
| A526 | 755.2 |
| A527 | 796.6 |
| A528 | 796.3 |
| A529 | 812.5 |
| A530 | 812.3 |
| A531 | 840.2 |
| A532 | 840.2 |
| A533 | 824.2 |
| A534 | 824.2 |
| A535 | 884.3 |

TABLE 4-continued

Exemplary Compounds Prepared by Methods of the Present Invention

| Ex # | LCMS (ESI): m/z [M + H] Found |
|---|---|
| A536 | 884.3 |
| A537 | 884.25 |
| A538 | 946.3 |
| A539 | 1047.6 |
| A540 | 996.9 |
| A541 | 997.0 |
| A542 | 837.3 |
| A543 | 849.3 |
| A544 | 783.3 |
| A545 | 756.6 |
| A546 | 835.7 |
| A547 | 835.4 |
| A548 | 884.3 |
| A549 | 910.3 |
| A550 | 910.7 |
| A551 | 853.8 |
| A552 | 823.3 |
| A553 | 769.3 |
| A554 | 742.5 |
| A555 | 953.8 |
| A556 | 739.3 |
| A557 | 799.2 |
| A558 | 887.6 |
| A559 | 887.6 |
| A560 | 952.5 |
| A561 | 968.35 |
| A562 | 968.8 |
| A563 | 1011.7 |
| A564 | 995.3 |
| A565 | 1035.7 |
| A566 | 826.5 |
| A567 | 826.6 |
| A568 | 886.7 |
| A569 | 938.8 |
| A570 | 1032.4 |
| A571 | 1032.3 |
| A572 | 828.4 |
| A573 | 824.2 |
| A574 | 834.3 |
| A575 | 875.2 |
| A576 | 824.3 |
| A577 | 959.4 |
| A578 | 959.4 |
| A579 | 868.5 |
| A580 | 868.6 |
| A581 | 879.25 |
| A582 | 879.6 |
| A583 | 866.4 |
| A584 | 896.2 |
| A585 | 833.3 |
| A586 | 887.4 |
| A587 | 887.4 |
| A588 | 894.4 |
| A589 | 812.3 |
| A590 | 812.3 |
| A591 | 1031.7 |
| A592 | 1010.5 |
| A593 | 996.6 |
| A594 | 1010.4 |
| A595 | 868.6 |
| A596 | 858.5 |
| A597 | 865.2 |
| A598 | 918.6 |
| A599 | 868.6 |
| A600 | 868.25 |
| A601 | 872.3 |
| A602 | 879.6 |
| A603 | 884.6 |
| A604 | 884.4 |
| A605 | 884.7 |
| A606 | 880.2 |
| A607 | 896.7 |
| A608 | 904.3 |

In Vitro and In Vivo Experiments:

Potency Assay: pERK

The purpose of this assay was to measure the ability of test compounds to inhibit K-Ras in cells. Activated K-Ras induces increased phosphorylation of ERK at Threonine 202 and Tyrosine 204 (pERK). This procedure measures a decrease in cellular pERK in response to test compounds. The procedure described below in NCI-H358 cells is applicable to K-Ras G12C.

Note: this protocol may be executed substituting other cell lines to characterize inhibitors of other RAS variants, including, for example, AsPC-1 (K-Ras G12D), Capan-1 (K-Ras G12V), NCI-H1355 (K-Ras G13C), Hs 766T (K-Ras Q61H), NCI-H2347 or KU-19-19 (N-Ras Q61R), or SK-MEL-30 (N-Ras Q61K).

NCI-H358 cells were grown and maintained using media and procedures recommended by the ATCC. On the day prior to compound addition, cells were plated in 384-well cell culture plates (40 μl/well) and grown overnight in a 37° C., 5% CO2 incubator. Test compounds were prepared in 10, 3-fold dilutions in DMSO, with a high concentration of 10 mM. On day of assay, 40 nl of test compound was added to each well of cell culture plate using an Echo550 liquid handler (LabCyteÆ). Concentrations of test compound were tested in duplicate. After compound addition, the plates are shaken for 15 seconds at 300 rpm, centrifuged, and cells were incubated 4 hours at 37° C., 5% CO2. Following incubation, culture medium was removed and cells were washed once with phosphate buffered saline.

In some experiments, cellular pERK level was determined using the AlphaLISA SureFire Ultra p-ERK1/2 Assay Kit (PerkinElmer). Cells were lysed in 25 μl lysis buffer, with shaking at 600 RPM at room temperature. Lysate (10 μl) was transferred to a 384-well Opti-plate (PerkinElmer) and 5 μl acceptor mix was added. After a 2-hour incubation in the dark, 5 μl donor mix was added, plate was sealed and incubated 2 hours at room temperature. Signal was read on an Envision plate reader (PerkinElmer) using standard AlphaLISA settings. Analysis of raw data was carried out either a) in Excel (Microsoft) and Prism (GraphPad). Signal was plotted vs. the decadal logarithm of compound concentration, and $IC_{50}$ was determined by fitting a 4-parameter sigmoidal concentration response model or b) using Genedata Screener (Genedata). Normalized signal was plotted vs the decadal logarithm of compounds concentration, and IC50 was determined by fitting a 4-parameter sigmoidal concentration response model.

In other experiments, cellular pERK was determined by In-Cell Western. Following compound treatment, cells were washed twice with 200 μl tris buffered saline (TBS) and fixed for 15 minutes with 150 μl 4% paraformaldehyde in TES. Fixed cells were washed 4 times for 5 minutes with TBS containing 0.1% Triton X-100 (TBST) and then blocked with 100 μl Odyssey blocking buffer (LI-COR) for 60 minutes at room temperature. Primary antibody (pERK, CST-4370, Cell Signaling Technology) was diluted 1:200 in blocking buffer, and 50 μl was added to each well and incubated overnight at 4° C. Cells were washed 4 times for 5 minutes with TEST. Secondary antibody (IR-800CW rabbit, LI-COR, diluted 1:800) and DNA stain DRAQ5 (LI-COR, diluted 1:2000) were added and incubated 1-2 hours at room temperature. Cells were washed 4 times for 5 minutes with TBST. Plates were scanned on a Li—COR Odyssey CLx Imager. Analysis of raw data was carried out in Excel (Microsoft) and Prism (GraphPad). Signal was plotted vs. the decadal logarithm of compound concentration, and $IC_{50}$ was determined by fitting a 4-parameter sigmoidal concentration response model.

All compounds A001-A608 herein exhibit an IC50 of 2 μM or less in an AsPC-1 (K-Ras G12D) pERK potency assay and/or a Capan-1 (K-Ras G12V) pERK potency assay. About 40% of compounds A001-A608 were measured in a H358 K-Ras G12C context: of those that were measured, >99% had an IC50 of 2 uM or under. About 40% of compounds A001-A608 were measured in a H1975 K-Ras WT context: of those that were measured, >96% had an IC50 of 2 uM or under.

Disruption of B-Raf Ras-binding Domain ($BRAF^{RBD}$) Interaction with K-Ras by Compounds of the Invention Note—The following protocol describes a procedure for monitoring disruption of K-Ras G12C (GMP-PNP) binding to $BRAF^{RBD}$ by a compound of the invention. This protocol may also be executed substituting other Ras proteins or nucleotides.

The purpose of this biochemical assay was to measure the ability of test compounds to facilitate ternary complex formation between a nucleotide-loaded K-Ras isoform and Cyclophilin A; the resulting ternary complex disrupts binding to a $BRAF^{RBD}$ construct, inhibiting K-Ras signaling through a RAF effector. Data was reported as IC50 values.

In assay buffer containing 25 mM HEPES pH 7.3, 0.002% Tween20, 0.1% BSA, 100 mM NaCl and 5 mM $MgCl_2$, tagless Cyclophilin A, His6-K-Ras-GMPPNP, and GST-$BRAF^{RBD}$ were combined in a 384-well assay plate at final concentrations of 25 μM, 12.5 nM and 50 nM, respectively. Compound was present in plate wells as a 10-point 3-fold dilution series starting at a final concentration of 30 μM. After incubation at 25° C. for 3 hours, a mixture of Anti-His Eu—W1024 and anti-GST allophycocyanin was then added to assay sample wells at final concentrations of 10 nM and 50 nM, respectively, and the reaction incubated for an additional 1.5 hours. TR-FRET signal was read on a microplate reader (Ex 320 nm, Em 665/615 nm). Compounds that facilitate disruption of a K-Ras:RAF complex were identified as those eliciting a decrease in the TR-FRET ratio relative to DMSO control wells.

Over 95% of compounds A001-A608 were measured in a K-Ras G12D context using the Ras-Raf assay: of those that were measured, >80% had an IC50 of 2 uM or under. Over 95% of compounds A001-A608 were measured in a K-Ras G12V: of those that were measured, >90% had an IC50 of 2 uM or under. Over 95% of compounds A001-A608 were measured in a K-Ras WT context using the Ras-Raf assay: of those that were measured, >85% had an IC50 of 2 uM or under. Over 95% of compounds A001-A608 were measured in a K-Ras G12C context: of those that were measured, >90% had an IC50 of 2 uM or under. Over 95% of compounds A001-A608 were measured in a K-Ras G13C context: of those that were measured, >90% had an IC50 of 2 uM or under.

Determination of Cell Viability in RAS Mutant Cancer Cell Lines

Protocol: CellTiter-GloÆCell Viability Assay

Note—The following protocol describes a procedure for monitoring cell viability of KRAS mutant cancer cell lines in response to a compound of the invention. Other RAS isoforms may be employed, though the number of cells to be seeded will vary based on cell line used.

The purpose of this cellular assay was to determine the effects of test compounds on the proliferation of three human cancer cell lines (NCI-H358 (KRAS G12C), AsPC-1 (KRAS G12D), Capan-1 (KRAS G12V)) over a 5-day treatment period by quantifying the amount of ATP present at endpoint using the CellTiter-GloÆ2.0 Reagent (Promega).

Cells were seeded at 250 cells/well in 40 μl of growth medium in 384-well assay plates and incubated overnight in a humidified atmosphere of 5% $CO_2$ at 37° C. On the day of the assay, test compounds were prepared in 9, 3-fold dilutions in DMSO, with a high concentration of 1 or 10 mM as appropriate. The test compounds (40 nl) are directly dispensed to each well of cell culture plate using an Echo550 liquid handler (LabCyteÆ). The plates were shaken for 15 seconds at 300 rpm, centrifuged, and incubated in a humidified atmosphere of 5% $CO_2$ at 37° C. for 5 days. On day 5, assay plates and their contents were equilibrated to room temperature for approximately 30 minutes. CellTiter-GloÆ2.0 Reagent (25 μl) was added, and plate contents were mixed for 2 minutes on an orbital shaker before incubation at room temperature for 10 minutes. Luminescence was measured using the PerkinElmer Enspire. Data was normalized by the following: (Sample signal/Avg. DMSO)*100. The data was fit using a four-parameter logistic fit.

Over 95% of compounds A001-A608 were measured using the CTG assay in an H358 (K-Ras G12C) cell line: of those that were measured, >90% had an IC50 of 2 uM or under. Over 80% of compounds A001-A608 were measured in an AsPC-1 (K-Ras G12D) cell line: of those that were measured, >90% had an IC50 of 2 uM or under. Over 80% of compounds A001-A608 were measured in a Capan-1 (K-Ras G12V) cell line: of those that were measured, >90% had an IC50 of 2 uM or under.

Compound A, a Representative Inhibitor of the Present Invention, Drives Regressions of $KRAS^{G12D}$ Tumors in Vivo Methods: Effects of Compound A on tumor cell growth in vivo were evaluated in the human pancreatic adenocarcinoma HPAC $KRAS^{G12D/wt}$ xenograft model using female BALB/c nude mice (6-8 weeks old). Mice were implanted with HPAC tumor cells in PBS (3×106 cells/mouse) subcutaneously in the flank. Once tumors reached an average size of ~150 $mm^3$, mice were randomized to treatment groups to start the administration of test articles or vehicle. Compound A was administered by oral gavage once every other day (po q2d). Body weight and tumor volume (using calipers) was measured twice weekly until study endpoints.

Results: Single-agent Compound A administered at 50 mg/kg po and 100 mg/kg po every other day led to complete regression of all tumors in each group (complete regression defined as >85% tumor regression from baseline) at the end of treatment (Day 38 after treatment started) in the HPAC CDX model with heterozygous $KRAS^{G12D}$ (FIG. 1A). The anti-tumor activity of both tested doses of Compound A was statistically significant compared with control group (***p<0.001, ordinary One-way ANOVA with multiple comparisons via a post-hoc Tukey's test).

Compound A, a Representative Inhibitor of the Present Invention, Regulates RAS Pathway and Drives Regressions of $KRAS^{G12V}$ Tumors in Vivo Methods: Effects of Compound A on blood and tumor pharmacokinetics (PK), pharmacodynamics (PD), and tumor cell growth were evaluated in vivo in the human non-small cell lung cancer (NSCLC) NCI-H441 $KRAS^{G12V/wt}$ xenograft model using female BALB/c nude mice (6-8 weeks old). Mice were implanted with NCI-H441 tumor cells (2×106 cells/mouse) in 50% media, 50% Matrigel, subcutaneously in the flank. For PK/PD, animals were grouped out when tumors were ~400 $mm^3$ and animals were treated with a single dose of Compound A at 10, 25 or 50 mg/kg by oral gavage. For PK/PD n=3 measurements per timepoint.

Once tumors reached an average size of ~155 $mm^3$, mice were randomized to treatment groups to start the administration of test articles or vehicle. In NCI-H441 Compound A was administered by oral gavage once daily (po qd) at 10 or 25 mg/kg. Body weight and tumor volume (using calipers) was measured twice weekly until study endpoints.

Figure 1B:
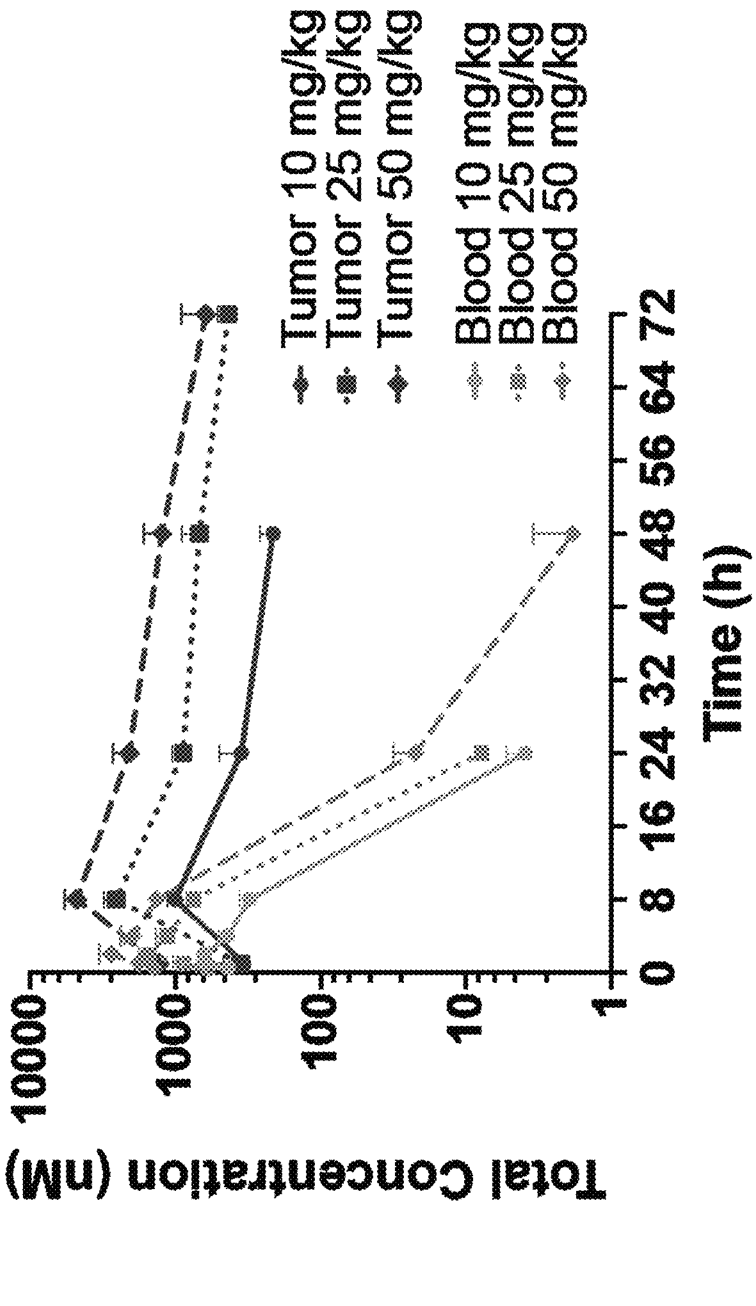
FIG. 1B is a graph demonstrating dose-dependent exposure of Compound A, a Ras inhibitor disclosed herein, in blood and tumor samples from BALB/c nude mice (6-8 weeks old, human non-small cell lung cancer (NSCLC) NCI-H441 $KRAS^{G12D/wt}$ xenograft model), monitored through 72 hours following dose. Pharmacokinetics were analyzed based on total concentration (nM) of Compound A in tumors or blood, following a single oral gavage dose of Compound A at 10, 25 or 50 mg/kg to 72 hours. At each time point, tumor or blood was sampled from n=3 animals.
Figure 1C:
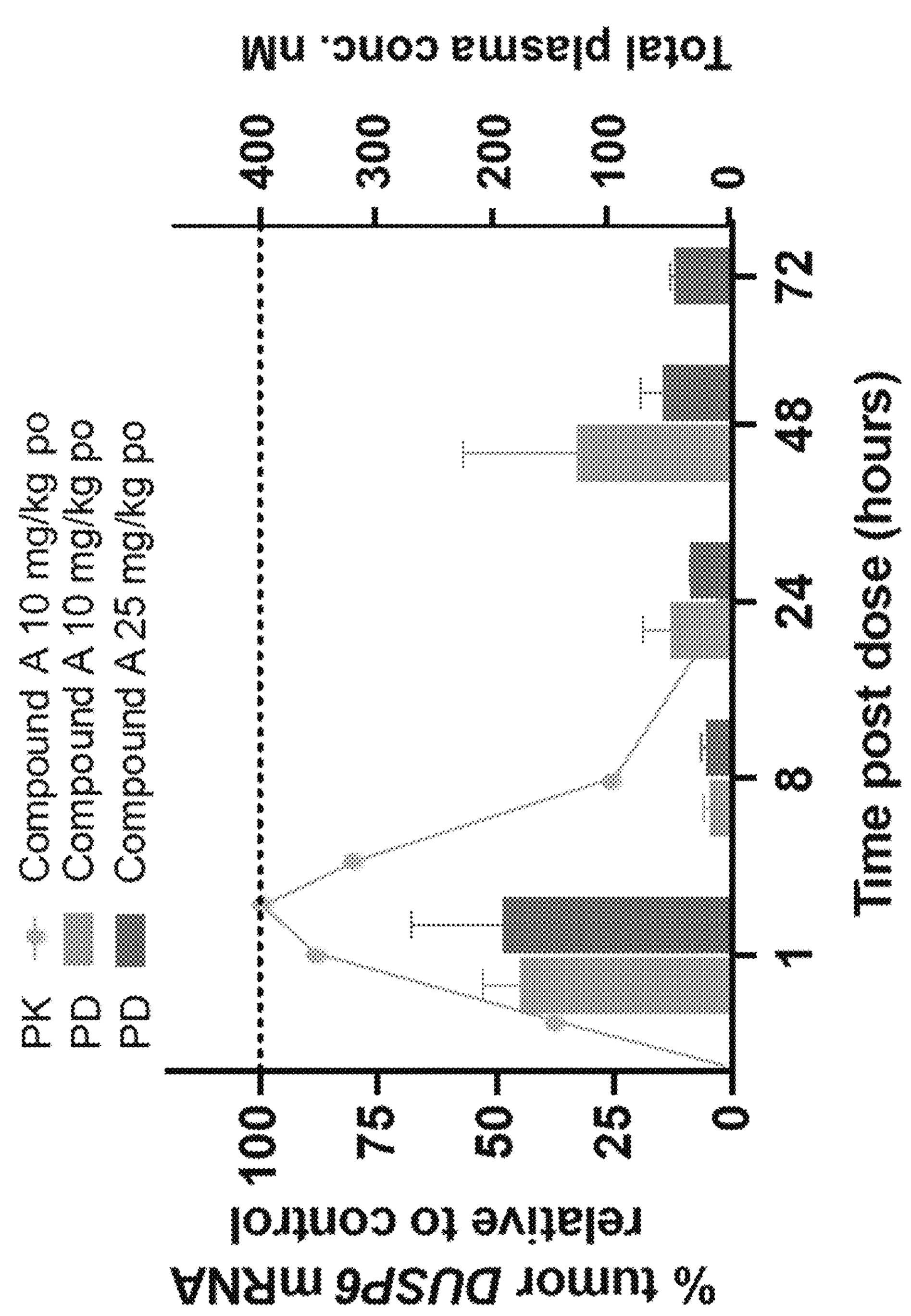
FIG. 1C is a graph showing PK (10 mg/kg, po) and PD (% tumor DUSP relative to control, 10 and 25 mg/kg, po) in naÔe animals treated with a single dose of Compound A, a Ras inhibitor disclosed herein.

Results: Pharmacokinetics were analyzed based on total concentration (nM) of Compound A in tumors or blood, following a single oral gavage dose of Compound A at 10, 25 or 50 mg/kg, monitored through 72 hours following dose. Compound A exhibited dose-dependent exposure in blood and tumor samples. Compound A treated at 25 mg/kg or 50 mg/kg doses was detectable in tumors through 72 hours following treatment (FIG. 1B). PK from naive animals treated with a single dose of Compound A delivered at 10 mg/kg demonstrates maximum exposure of at 2 hours (FIG. 1C). Tumor DUSP6 demonstrates modulation of DUSP6, a marker of RAS pathway activity for 72 hours following single dose administration (FIG. 1C).

Figure 1D:
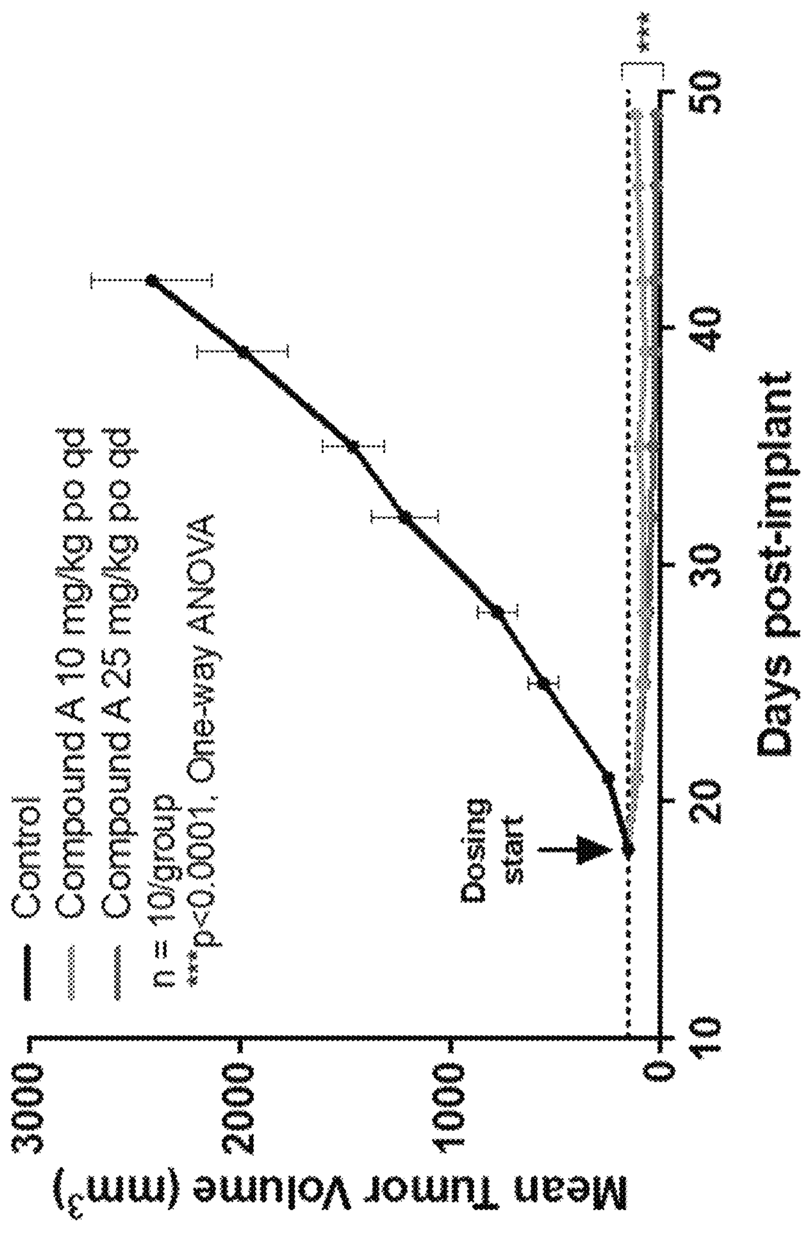
FIG. 1D is a graph demonstrating the in vivo efficacy of Compound A, a Ras inhibitor disclosed herein, in the NCI-H441 CDX model with heterozygous $KRAS^{G12V}$. NCI-H441 cells were implanted in 50% Matrigel. Animals were randomized and treatment was initiated at average tumor volume of ~155 $mm^3$. Animals were dosed with Compound A 10 or 25 mg/kg po qd or Control for 32 days. All dose levels were tolerated. n=10/group. ***$p<0.0001$ by one-way ANOVA.
Figure 1E:
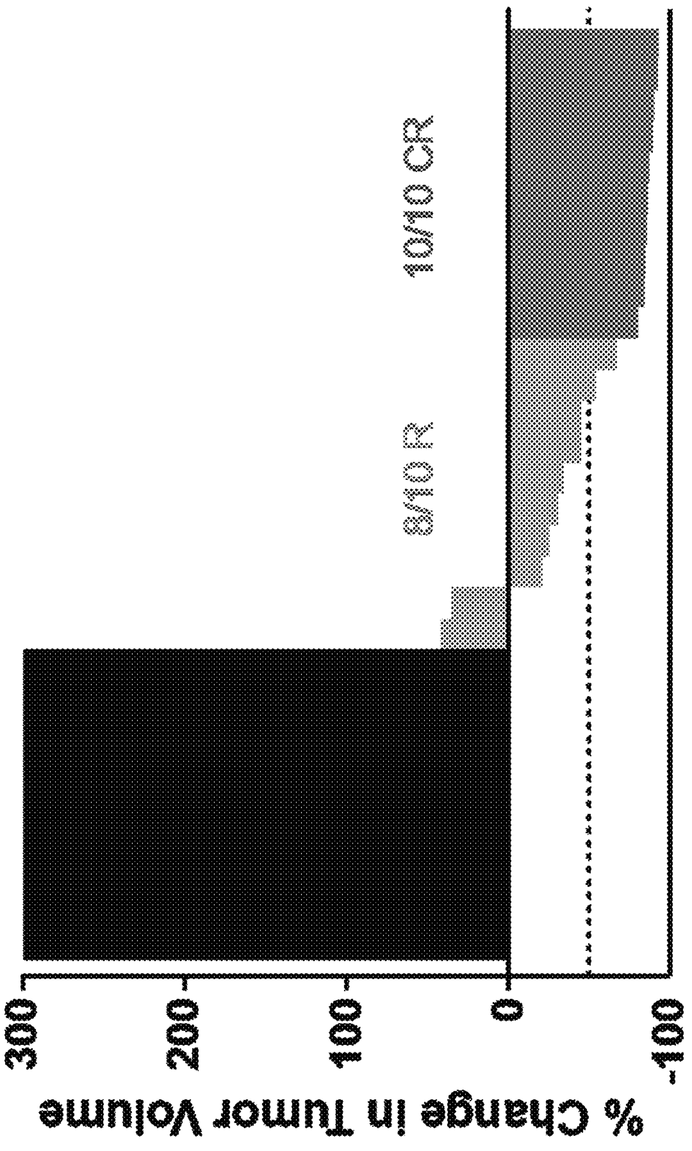
FIG. 1E shows end of study responses for Compound A, a KRAS(ON) inhibitor disclosed herein, in the NCI-H441 CDX model with heterozygous $KRAS^{G12V}$. NCI-H441 end of study tumors were graphed as % change in tumor volume compared to volume at treatment initiation. R (regressions) =number of regressions>10% from initial. CR (complete response)=number of regressions>80% from initial. Each animal represented as a separate bar.
Figure 1F:
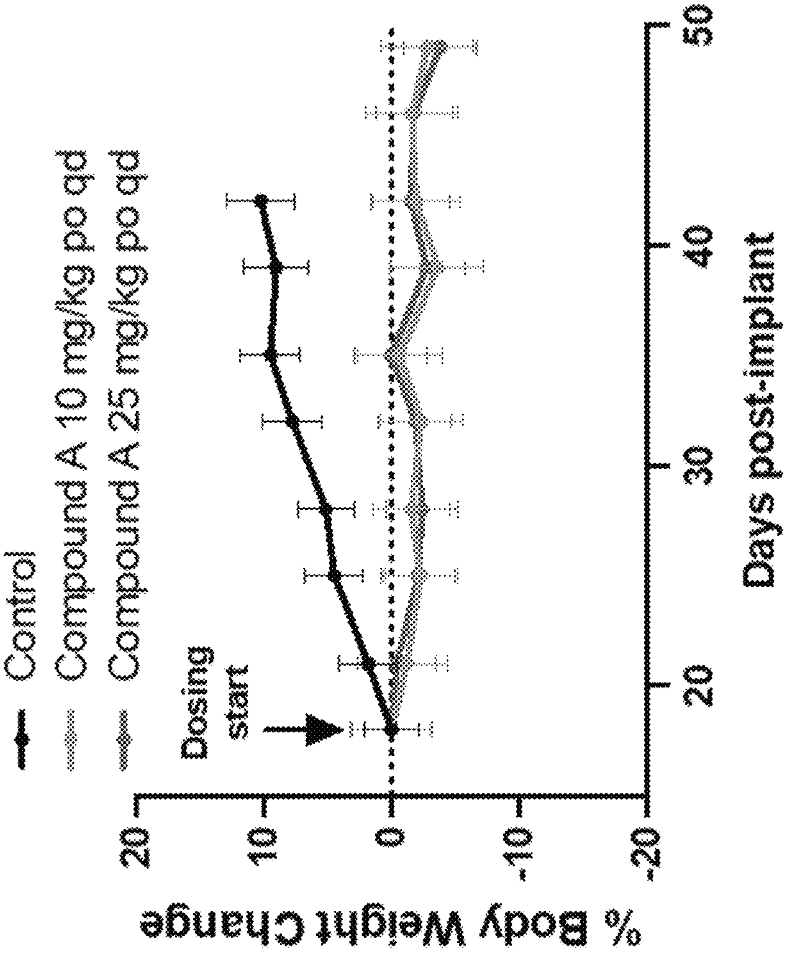
FIG. 1F shows % body weight change in animals treated with Compound A, a KRAS(ON) inhibitor disclosed herein, (in the NCI-H441 CDX model with heterozygous $KRAS^{G12V}$). NCI-H441 cell-derived xenografts were measured twice weekly by caliper measurements. Body weight change graphed as percentage of animals starting body weight.

Single-agent Compound A administered to NCI-H441 tumor bearing animals, treated at 10 mg/kg po qd led to regressions (reductions in tumor volume>10% from initial) in all animals. Treated at 25 mg/kg po qd, Compound A led to complete regression of all tumors (complete regression defined as >85% tumor regression from baseline) at the end of treatment (Day 38 after treatment started) in the NCI-H441 CDX model with heterozygous $KRAS^{G12V}$ (FIG. 1D, FIG. 1E). The anti-tumor activity of Compound A was statistically significant compared with control group (*p<0.0001, ordinary One-way ANOVA with multiple comparisons via a post-hoc Tukey's test). Treatments were well tolerated by body weight measurements (FIG. 1**F).

Compound A, a Representative Inhibitor of the Present Invention, Drives Regressions of $KRAS^{G12V}$ Pancreatic Ductal Adenocarcinoma and Colorectal Tumors in Vivo Methods: Effects of Compound A on tumor cell growth in vivo were evaluated in the human pancreatic adenocarcinoma Capan-2 $KRAS^{G12V/wt}$ and colorectal SW403 $KRAS^{G12V/wt}$ xenograft models using female BALB/c nude mice (6-8 weeks old). Mice were implanted with Capan-2 tumor cells (4×106 (media/Matrigel) cells/mouse), or SW403 tumor cells (1×107 cells/mouse) in 50% PBS, 50% Matrigel, subcutaneously in the flank. Once tumors reached an average size of ~160-170 $mm^3$, mice were randomized to treatment groups to start the administration of test articles or vehicle. In Capan-2, Compound A was administered by oral gavage once daily (po qd) at 10 or 25 mg/kg. In SW403 CDX, Compound A was administered by oral gavage once daily (po qd) at 25 mg/kg or every other day (q2d) at 50 mg/kg. Body weight and tumor volume (using calipers) was measured twice weekly until study endpoints.

Figure 2A:
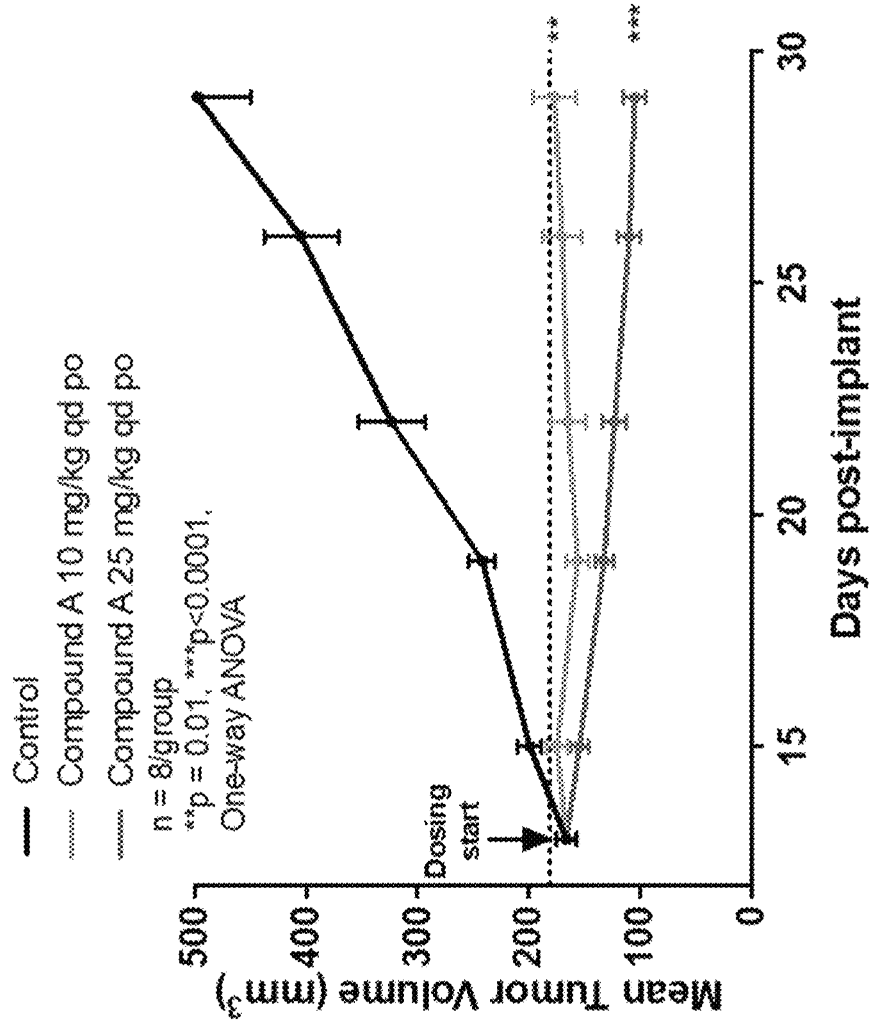
FIG. 2A is a graph demonstrating in vivo efficacy of Compound A, a KRAS(ON) inhibitor disclosed herein, in the human pancreatic Capan-2 CDX xenograft model with heterozygous $KRAS^{G12V}$ using female BALB/c nude mice. The graph shows tumor volume ($mm^3$) vs. days post-implant of the mouse xenograft model. Capan-2 cells were implanted in 50% Matrigel. Animals were randomized and treatment was initiated at average tumor volume of ~166 $mm^3$. Animals were dosed with Compound A 10 mg/kg po qd or 25 mg/kg po q2d or Control for 28 days. All dose levels were tolerated. n=8/group. $p=0.01$, *$p<0.0001$ by one-way ANOVA.
Figure 2B:
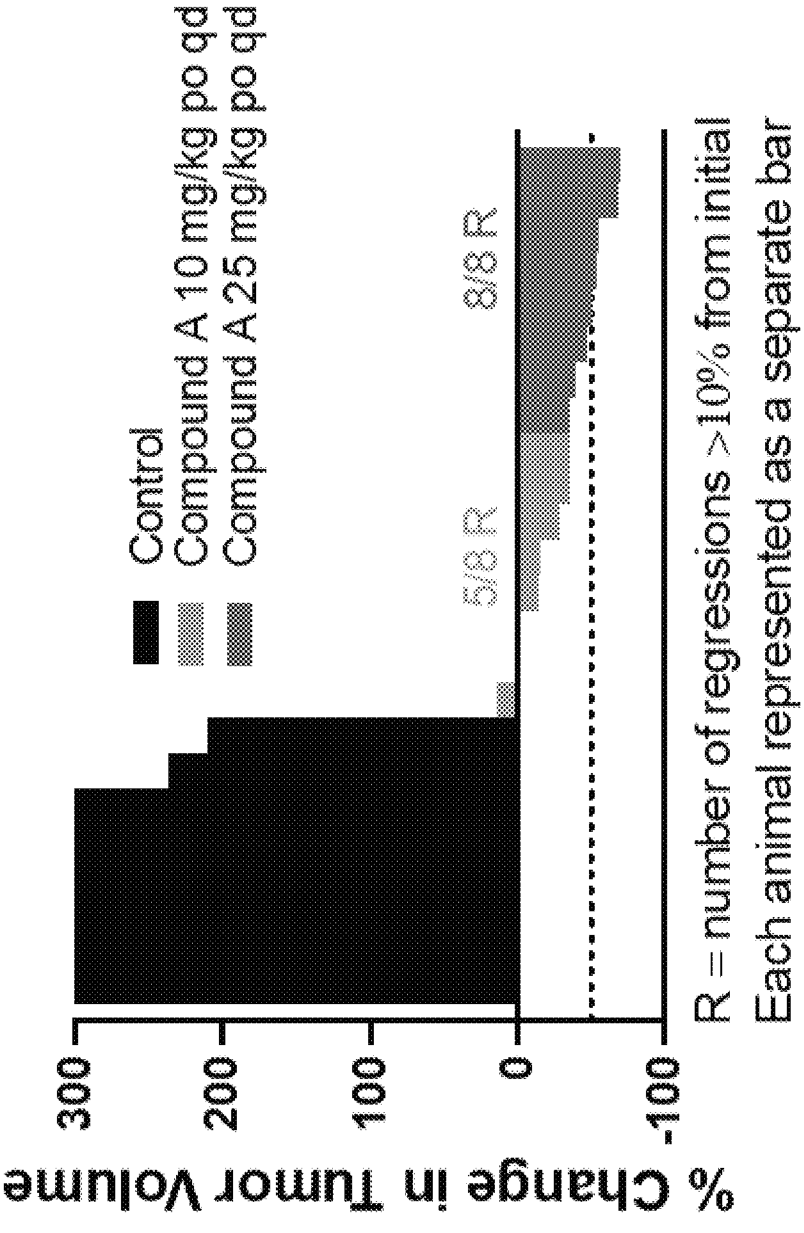
FIG. 2B shows end of study responses for Compound A, a KRAS(ON) inhibitor disclosed herein, in the human pancreatic Capan-2 CDX xenograft model with heterozygous $KRAS^{G12V}$. Capan-2 end of study tumors were graphed as % change in tumor volume compared to volume at treatment initiation. R (regressions)=number of regressions>10% from initial. Each animal represented as a separate bar.
Figure 2C:
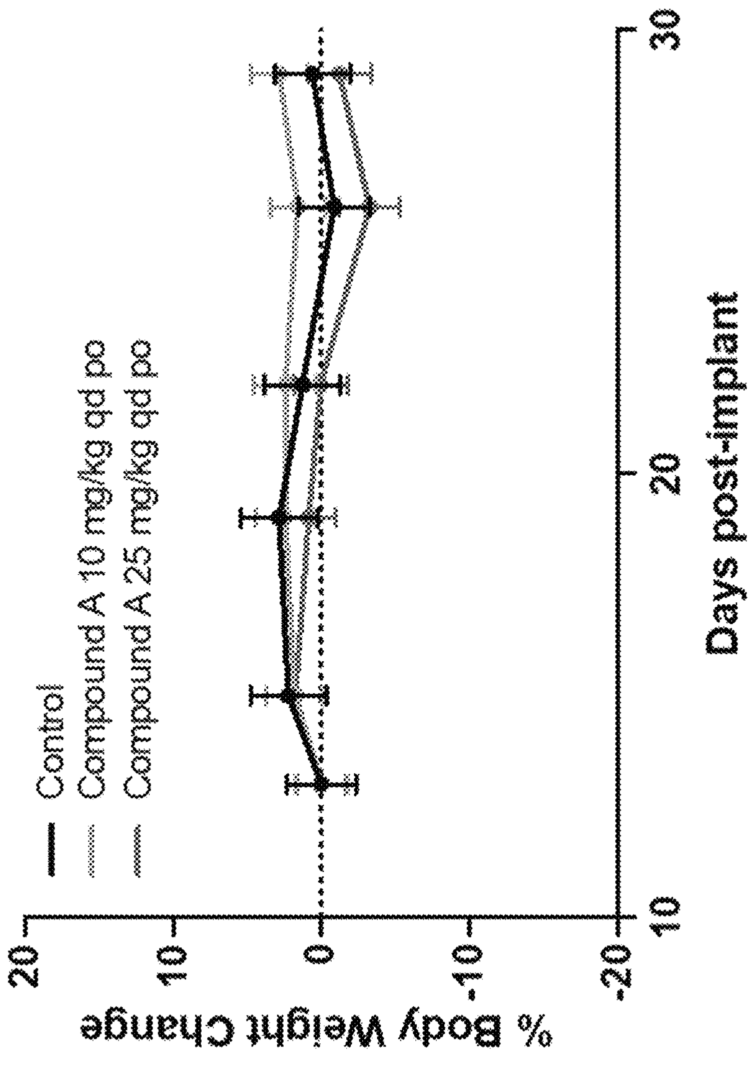
FIG. 2C shows % body weight change in animals treated with Compound A, a KRAS(ON) inhibitor disclosed herein, in the human pancreatic Capan-2 CDX xenograft model with heterozygous $KRAS^{G12V}$. Capan-2 cell-derived xenografts were measured twice weekly by caliper measurements. Body weight change graphed as percentage of animals starting body weight.
Figure 2D:
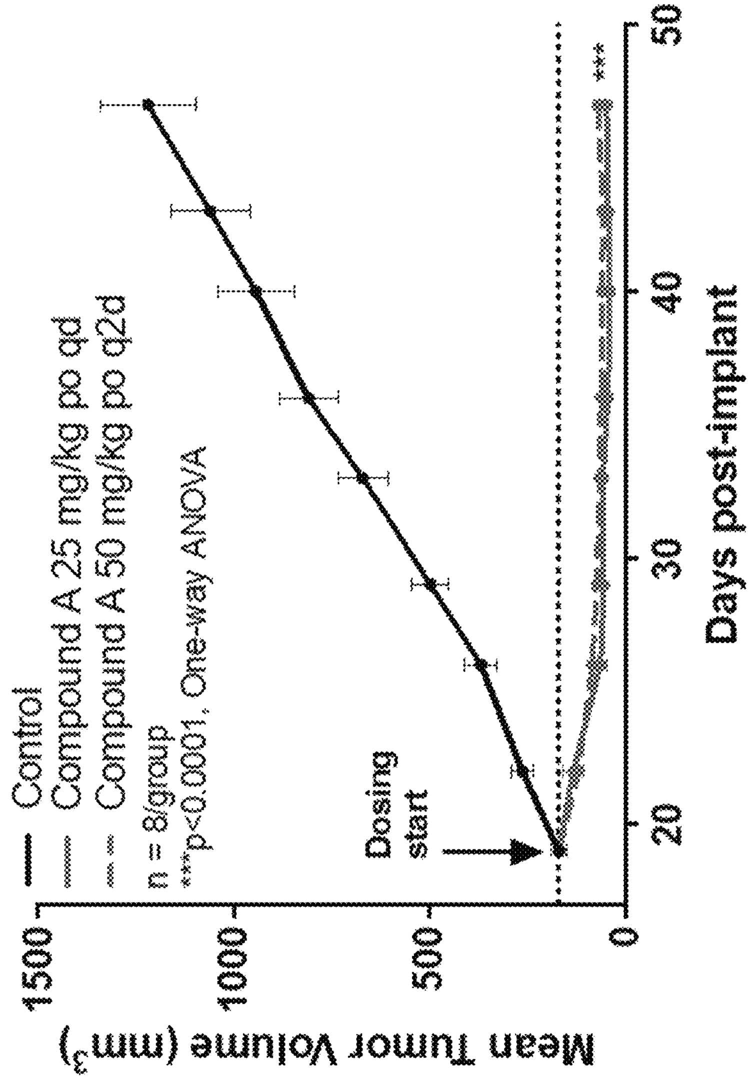
FIG. 2D is a graph demonstrating in vivo efficacy of Compound A, a KRAS(ON) inhibitor disclosed herein, in the human colorectal SW403 $KRAS^{G12V/wt}$ xenograft model using female BALB/c nude mice. The graph shows tumor volume ($mm^3$) vs. days post-implant of the mouse xenograft model. SW403 cells were implanted in 50% Matrigel. Animals were randomized and treatment was initiated at average tumor volume of ~171 $mm^3$. Animals were dosed with Compound A 25 mg/kg po qd or 50 mg/kg po q2d or Control for 28 days. All dose levels were tolerated. n=8/group. ***$p<0.0001$ by one-way ANOVA.
Figure 2E:
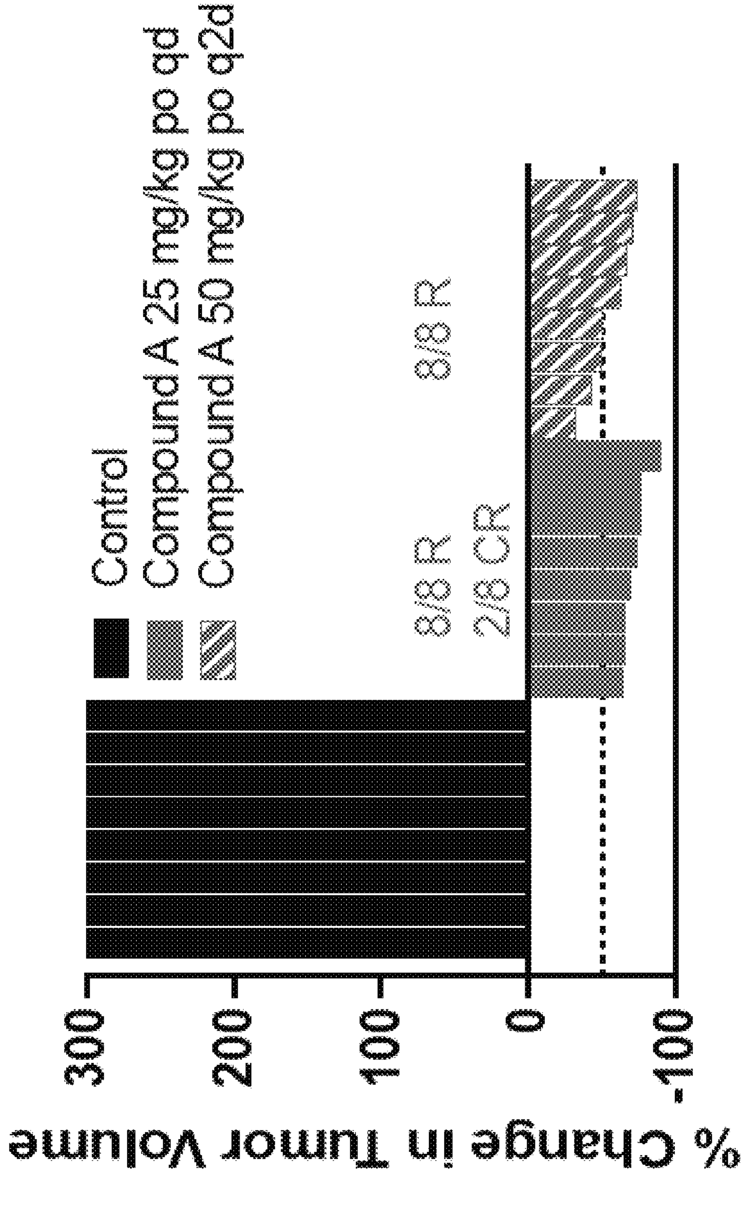
FIG. 2E shows end of study responses for Compound A, a KRAS(ON) inhibitor disclosed herein, in the human colorectal SW403 $KRAS^{G12V/wt}$ xenograft model. SW403 end of study tumors were graphed as % change in tumor volume compared to volume at treatment initiation. R (regressions)=number of regressions>10% from initial. CR (complete response)=number of regressions>80% from initial. Each animal represented as a separate bar.
Figure 2F:
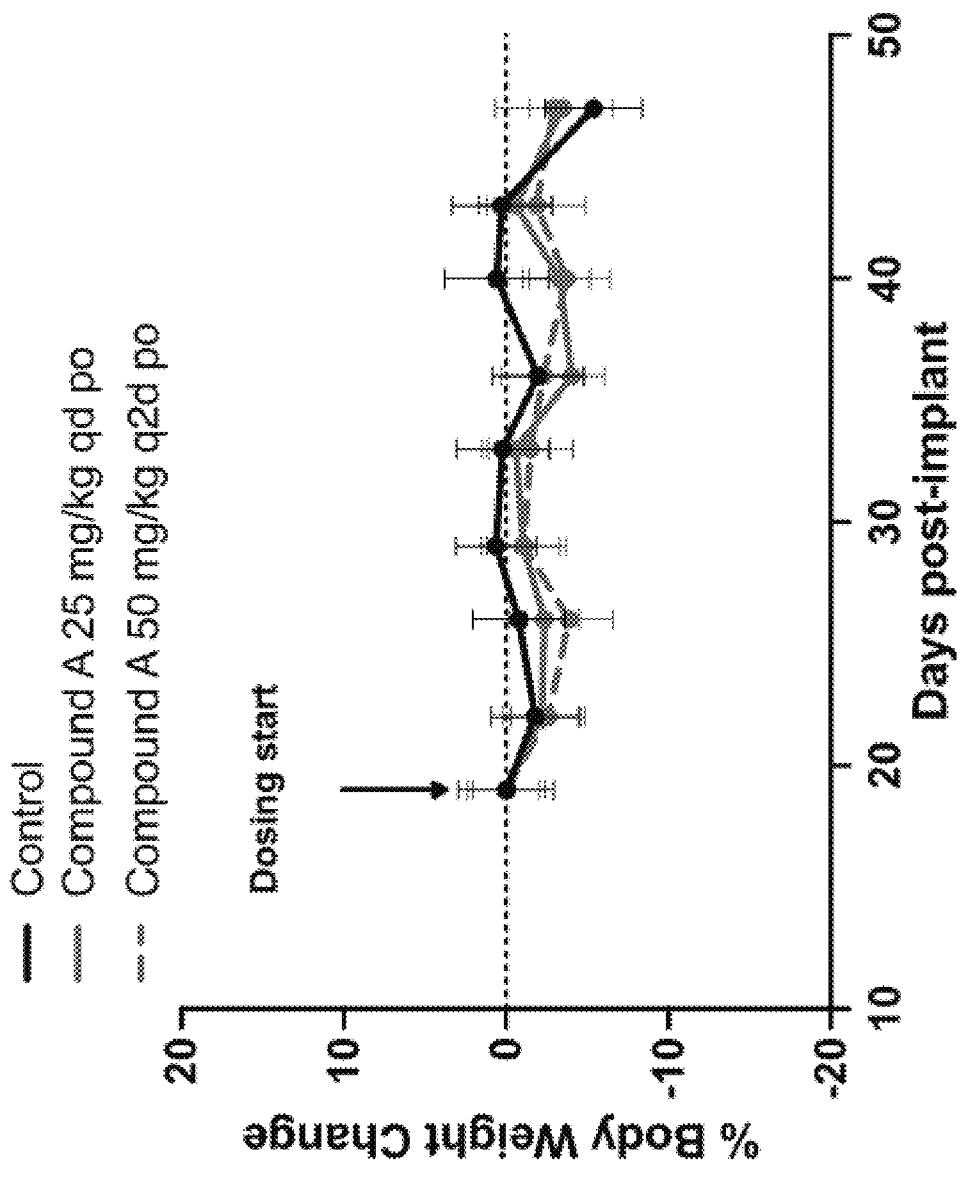
FIG. 2F shows % body weight change in animals treated with Compound A, a KRAS(ON) inhibitor disclosed herein, in the human colorectal SW403 $KRAS^{G12V/wt}$ xenograft model. SW403 cell-derived xenografts were measured twice weekly by caliper measurements. Body weight change graphed as percentage of animals starting body weight.

Results: Single-agent Compound A administered to Capan-2 tumor bearing animals, treated at 10 mg/kg po qd led to 5/8 regressions, and 25 mg·kg po qd led to 8/8 regressions at the end of treatment (Day 38 after treatment started) in the Capan-2 CDX model with heterozygous $KRAS^{G}12V$ (FIG. 2A, FIG. 2B). The anti-tumor activity of Compound A was statistically significant compared with control group (p<001 *p<0.0001, ordinary One-way ANOVA with multiple comparisons via a post-hoc Tukey's test). Treatments were well tolerated by body weight measurements (FIG. 2C). In SW403 CDX model, single-agent Compound A administered at 25 mg/kg po daily or 50 mg/kg po q2d led to significant tumor growth inhibition in all tumors through the end of treatment (Day 35 after treatment started). Compound A treatment at 25 mg/kg po qd drove regressions in 8/8 tumors, and 2/8 CR's (FIG. 2D, FIG. 2E). Compound A treatment at 50 mg/kg po q2d drove regressions in 8/8 tumors. The anti-tumor activity of Compound A was statistically significant compared with control group (*p<0.0001, ordinary One-way ANOVA with multiple comparisons via a post-hoc Tukey's test). Treatments were well tolerated by body weight measurements (FIG. 2**F).

Compound A Exhibits Potent in Vivo Inhibition of Multiple RAS-Driven Cancer Cell Lines Compounds A, B, and C Exhibit Potent in Vitro Inhibition of Multiple RAS-Driven Cancer Cell Lines Methods: Potency of in vitro cell proliferation inhibition of Capan-1 ($KRAS^{G12V}$), NCI-H358 ($KRAS^{G12C}$), AsPC-1 ($KRAS^{G12D}$), HCT116 ($KRAS^{G13D}$), SK-MEL-30 ($NRAS^{Q61K}$), NCI-H1975 ($EGFR^{T790M/L858R}$), and/or A375 ($BRAF^{V600E}$) cells exposed to Compounds A, B, or C for 120 hours. Cells were seeded in growth medium in 384-well assay plates and incubated overnight in a humidified atmosphere of 5% $CO_2$ at 37° C. The following day, cells were exposed to a 9-concentration 3-fold serial dilution of Compound A, B, or C at a starting assay concentration of 0.1 μM, 1 μM, or 10 μM as appropriate. After 5 days of incubation, CellTiter-GloÆ2.0 Reagent was added to assay plates and luminescence measured. Data were normalized to the mean signal of DMSO-treated cells, and IC50 values were estimated using a four-parameter concentration response model.

Figure 3A:
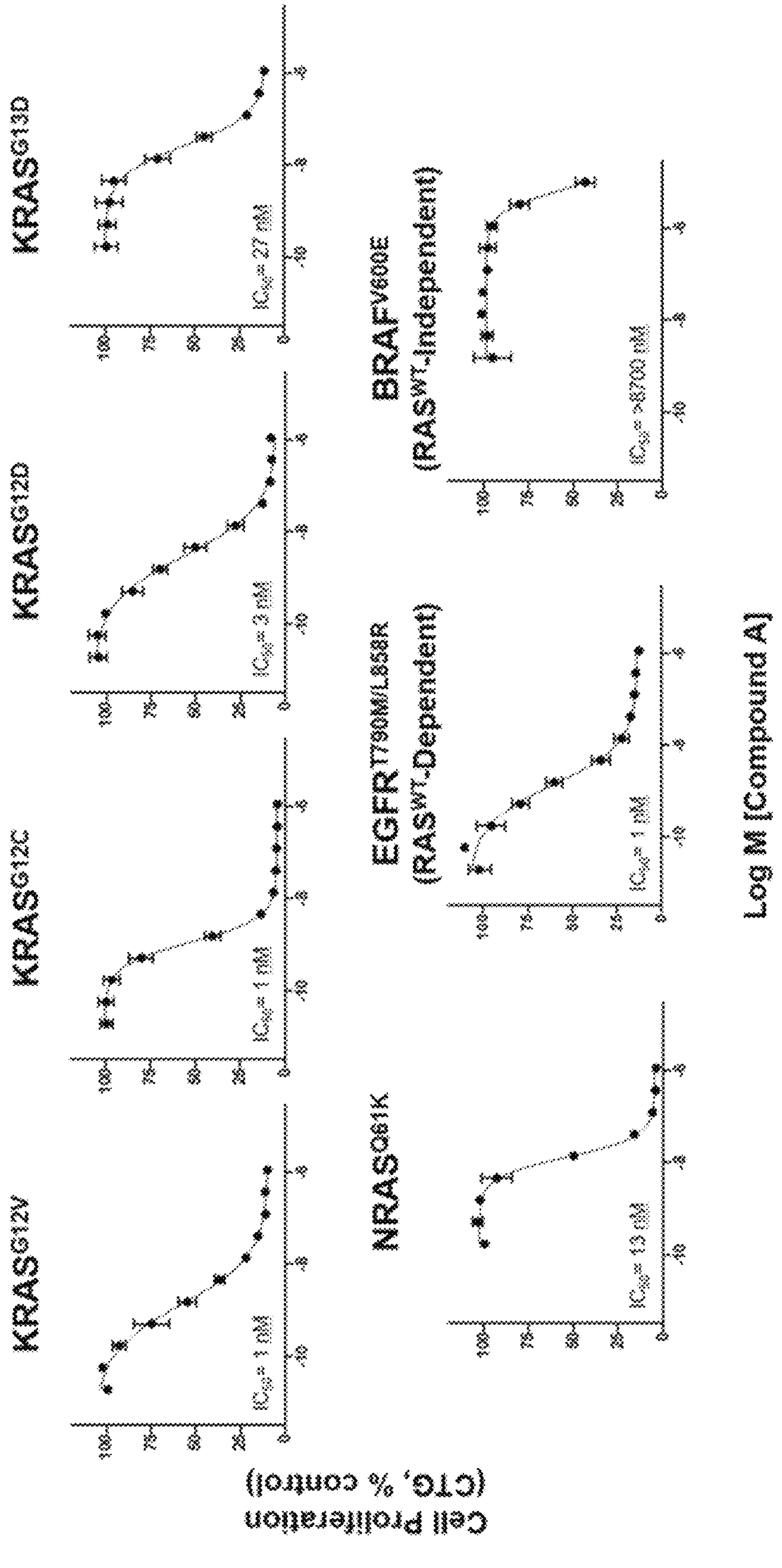
FIG. 3A demonstrates in vitro efficacy of Compound A, a KRAS(ON) inhibitor disclosed herein, in multiple RAS-driven cancer cell lines. Each graph shows cell proliferation (% relative to control) vs. log M [Compound A]. Potency of in vitro cell proliferation inhibition of Capan-1 ($KRAS^{G12V}$), NCI-H358 ($KRAS^{G12C}$), AsPC-1 ($KRAS^{G12D}$), HCT116 ($KRAS^{G13D}$), SK-MEL-30 ($NRAS^{Q61K}$), NCI-H1975 ($EGFR^{T790M/L858R}$), and A375 ($BRAF^{V600E}$) cells exposed to Compound A for 120 hours.
Figure 3B:
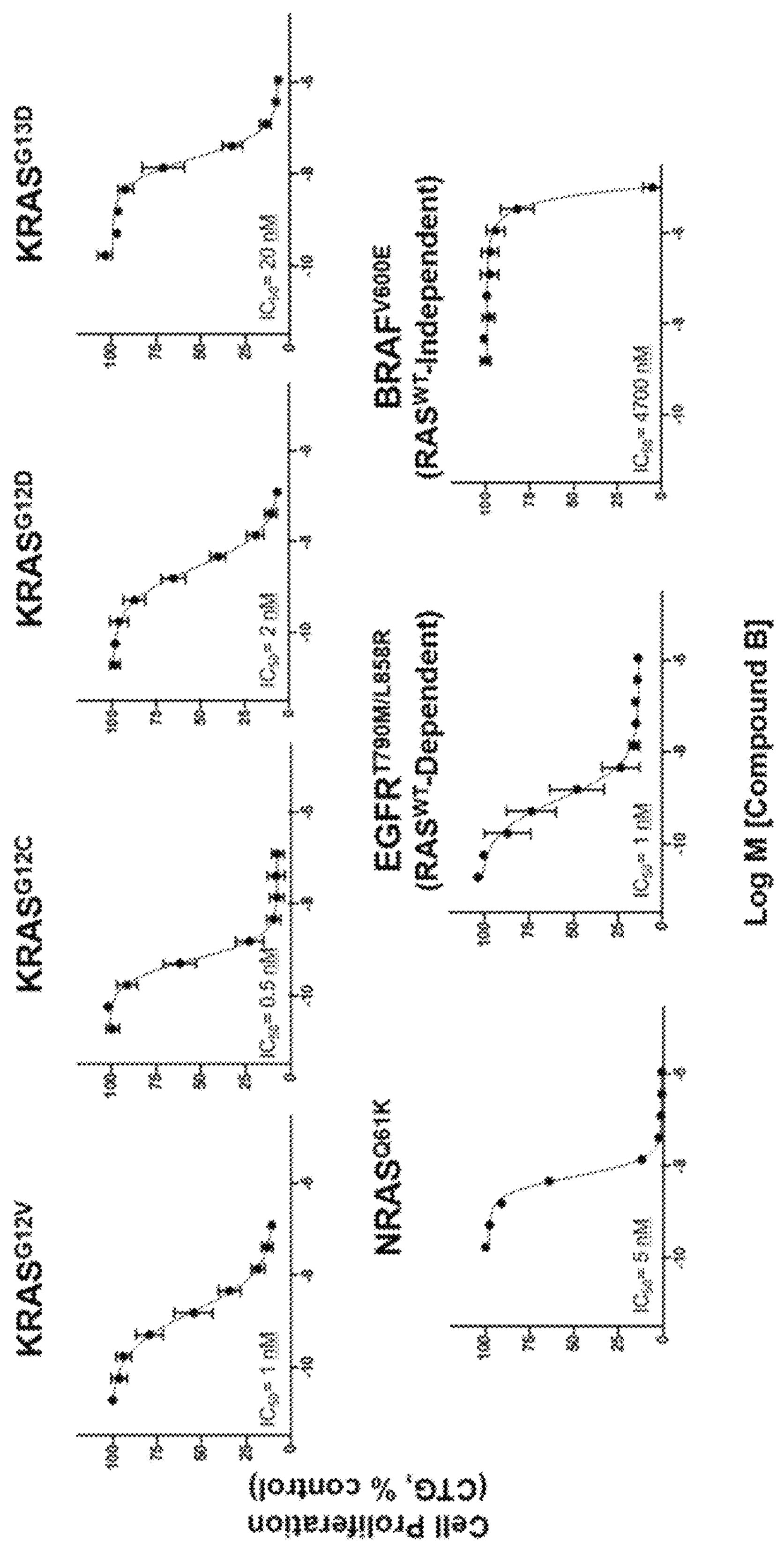
FIG. 3B demonstrates in vitro efficacy of Compound B, a KRAS(ON) inhibitor disclosed herein, in multiple RAS-driven cancer cell lines. Each graph shows cell proliferation (% relative to control) vs. log M [Compound B]. Potency of in vitro cell proliferation inhibition of Capan-1 ($KRAS^{G12V}$), NCI-H358 ($KRAS^{G12C}$), AsPC-1 ($KRAS^{G12D}$), HCT116 ($KRAS^{G13D}$), SK-MEL-30 ($NRAS^{C61K}$), NCI-H1975 ($EGFR^{T790M/L858R}$), and A375 ($BRAF^{V600E}$) cells exposed to Compound B for 120 hours.
Figure 3C:
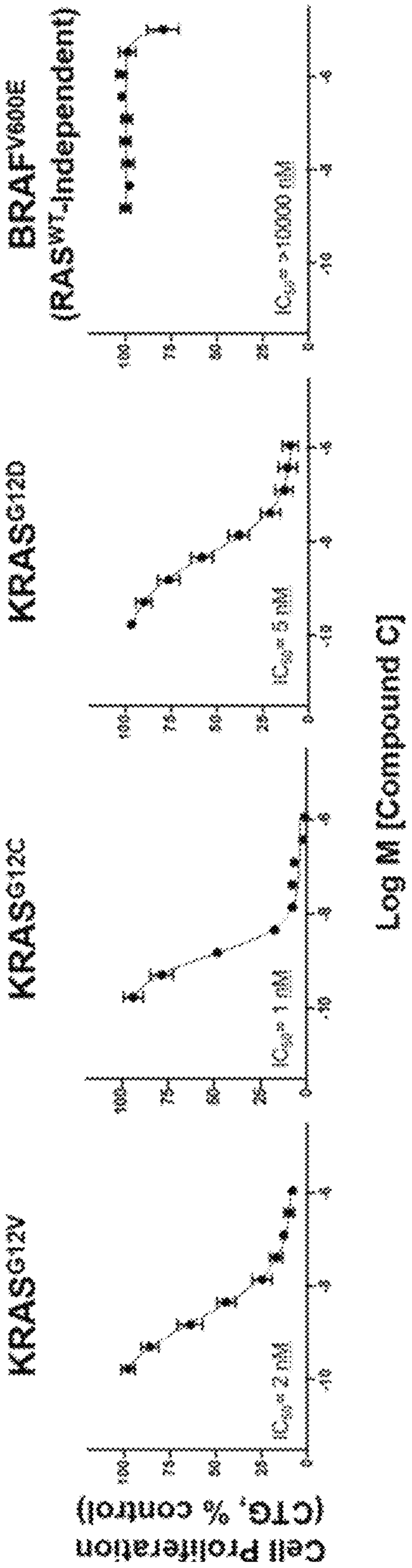
FIG. 3C demonstrates in vitro efficacy of Compound C, a KRAS(ON) inhibitor disclosed herein, in multiple RAS-driven cancer cell lines. Each graph shows cell proliferation (% relative to control) vs. log M [Compound C]. Potency of in vitro cell proliferation inhibition of Capan-1 ($KRAS^{G12V}$), NCI-H358 ($KRAS^{G12C}$), AsPC-1 ($KRAS^{G12D}$), and A375 ($BRAF^{V600E}$) cells exposed to Compound C for 120 hours.

Results: Compounds A, B, and C inhibited cell proliferation in RAS-driven lines (FIG. 3A, FIG. 3B, and FIG. 3C). Compound A IC50s for RAS-Driven cancer cell lines are as follows: Capan-1 ($KRAS^{G12V}$)=1 nM, NCI-H358 ($KRAS^{G12C}$)=1 nM, AsPC-1 ($KRAS^{G12D}$)=3 nM, HCT116 ($KRAS^{G13D}$)=27 nM, SK-MEL-30 ($NRAS^{Q61K}$)=13 nM, NCI-H1975 ($EGFR^{T790M/L858R}$)=1 nM. Compound B IC50s for RAS-Driven cancer cell lines are as follows: Capan-1 ($KRAS^{G12V}$)=1 nM, NCI-H358 ($KRAS^{G12C}$)=0.5 nM, AsPC-1 ($KRAS^{G12D}$)=2 nM, HCT116 ($KRAS^{G13D}$)=20 nM, SK-MEL-30 ($NRAS^{Q61K}$)=5 nM, NCI-H1975 ($EGFR^{T790M/L858R}$)=1 nM. Compound C IC50s for RAS-Driven cancer cell lines are as follows: Capan-1 ($KRAS^{G12V}$)=2 nM, NCI-H358 ($KRAS^{G12C}$)=1 nM, AsPC-1 ($KRAS^{G12D}$)=5 nM. RAS WT-Independent cell line A375 ($BRAF^{V600E}$) was not sensitive to Compound A, B, or C treatment with IC50s>8700 nM, 4700 nM, and >10000 nM, respectively.

Compound A, a Representative Inhibitor of the Present Invention, Drives Regressions of $KRAS^{G12D}$ Tumors in Vivo Methods: Effects of Compound A on tumor cell growth in vivo were evaluated in the human pancreatic adenocarcinoma HPAC $KRAS^{G12D/wt}$ and colorectal GP2d $KRAS^{G12D/wt}$ xenograft models using female BALB/c nude mice (6-8 weeks old). Mice were implanted with HPAC tumor cells (3×106 cells/mouse), or GP2d tumor cells (2×106 cells/mouse) in 50% PBS, 50% Matrigel, subcutaneously in the flank. Once tumors reached an average size of ~150 $mm^3$, mice were randomized to treatment groups to start the administration of test articles or vehicle. Compound A was administered by oral gavage once daily (po qd) at 25 mg/kg. Body weight and tumor volume (using calipers) was measured twice weekly until study endpoints.

Figure 4A:
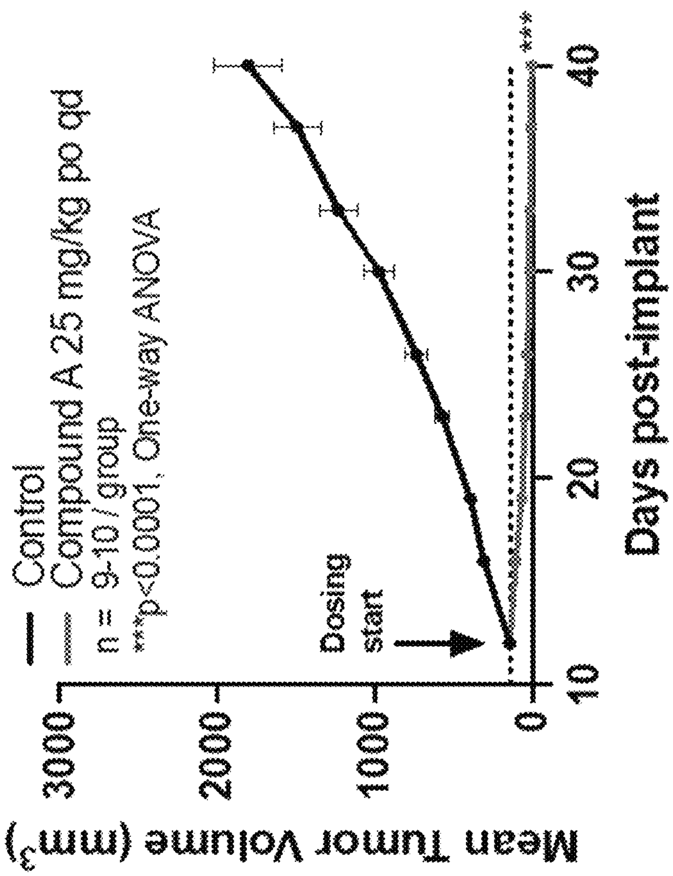
FIG. 4A demonstrates in vivo efficacy of Compound A (25 mg/kg po qd), a KRAS(ON) inhibitor disclosed herein, in the human pancreatic adenocarcinoma HPAC $KRAS^{G12D/wt}$ xenograft model using female BALB/c nude mice. The graph shows tumor volume ($mm^3$) vs. days post-implant of the mouse xenograft model. HPAC cells were implanted in 50% Matrigel. Animals were randomized and treatment was initiated at average tumor volume of ~142 $mm^3$. Animals were dosed with Compound A 25 mg/kg po qd or Control for 28 days. Dose level was tolerated. n=9-10/group. ***p<0, 0001 by one-way ANOVA.
Figure 4B:
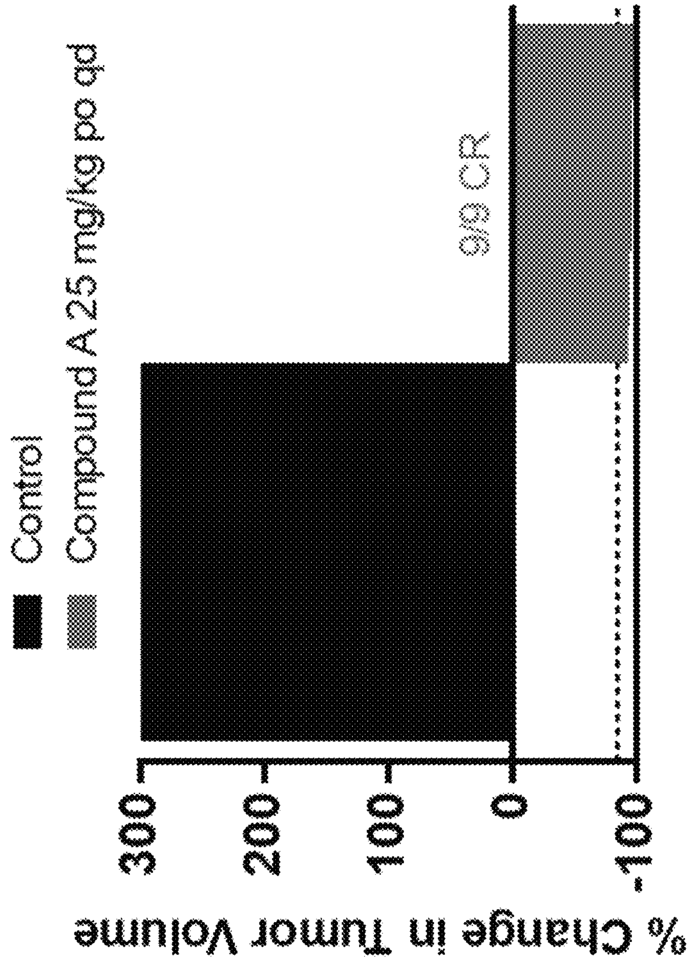
FIG. 4B shows end of study responses for Compound A, a KRAS(ON) inhibitor disclosed herein, in the human pancreatic adenocarcinoma HPAC $KRAS^{G12D/wt}$ xenograft model. HPAC end of study tumors were graphed as % change in tumor volume compared to volume at treatment initiation. CR (complete response)=number of regressions>80% from initial. Each animal represented as a separate bar.
Figure 4C:
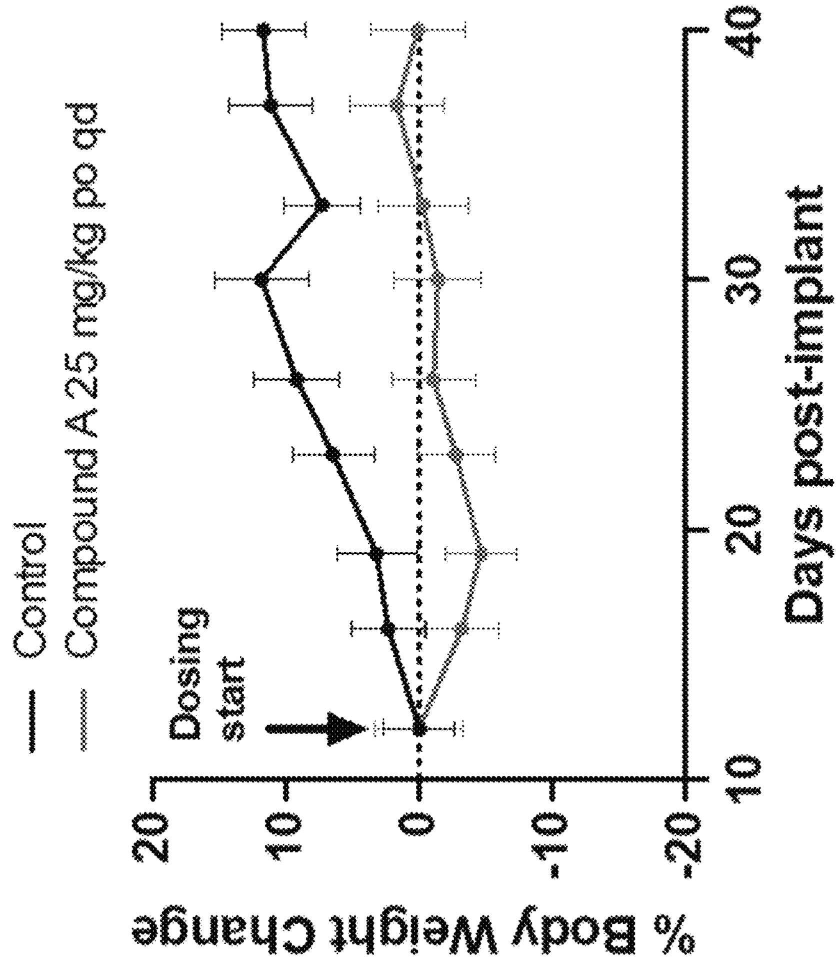
FIG. 4C shows % body weight change in animals treated with Compound A, a KRAS(ON) inhibitor disclosed herein, in the human pancreatic adenocarcinoma HPAC $KRAS^{G12D/wt}$ xenograft model. HPAC cell-derived xenografts were measured twice weekly by caliper measurements. Body weight change graphed as percentage of animals starting body weight.
Figure 4D:
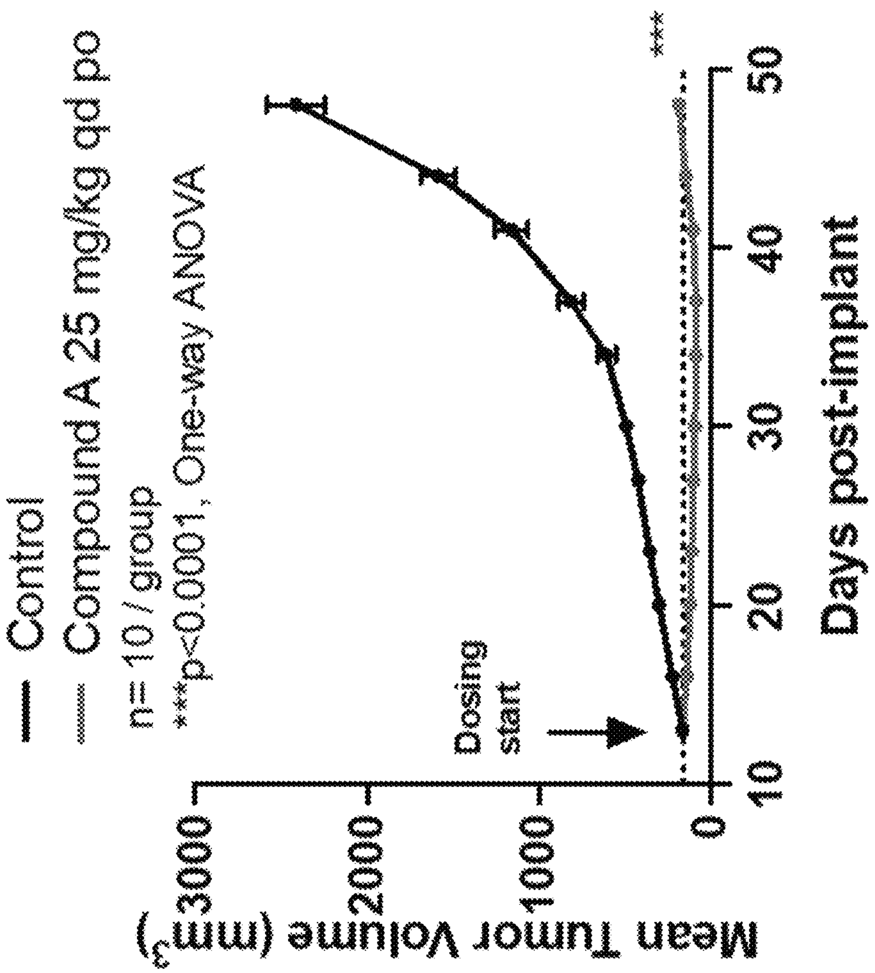
FIG. 4D demonstrates in vivo efficacy of Compound A, a KRAS(ON) inhibitor disclosed herein, in the human colorectal GP2d $KRAS^{G12D/wt}$ xenograft model using female BALB/c nude mice. The graph shows tumor volume ($mm^3$) vs. days post-implant of the mouse xenograft model. GP2d cells were implanted in 50% Matrigel. Animals were randomized and treatment was initiated at average tumor volume of ~154 $mm^3$. Animals were dosed with Compound A 25 mg/kg po qd or Control for 28 days. Dose level was tolerated. n=10/group. ***p<0.0001 by one-way ANOVA.
Figure 4E:
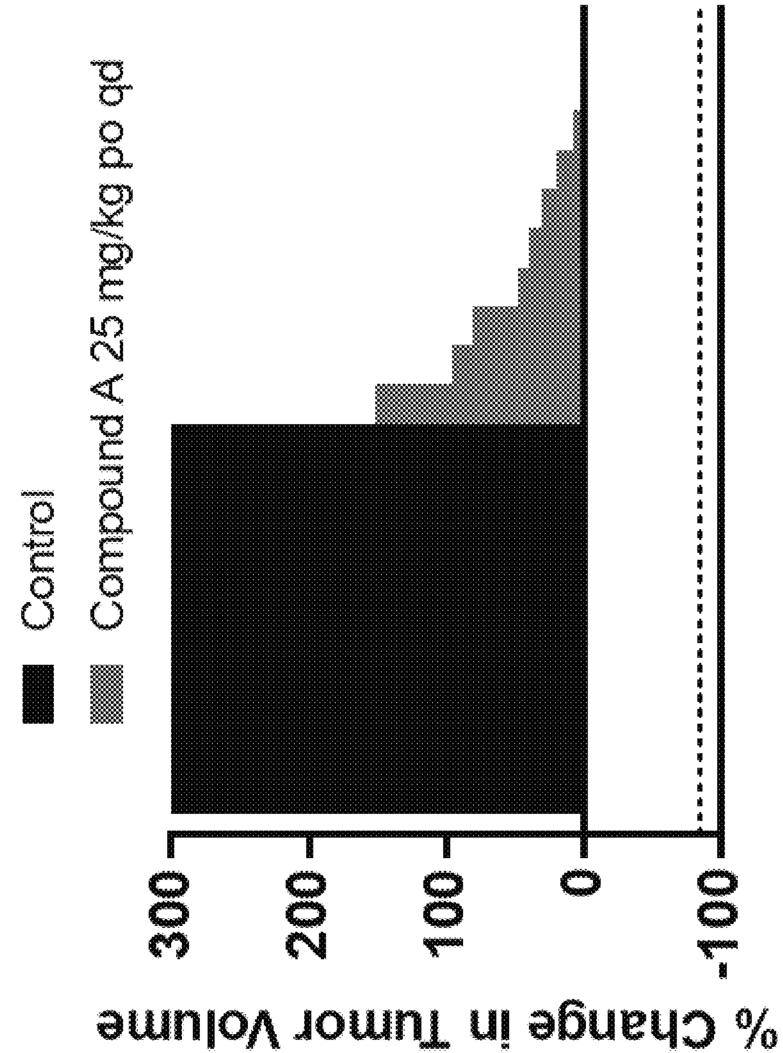
FIG. 4E shows end of study responses for Compound A, a KRAS(ON) inhibitor disclosed herein, in the human colorectal GP2d $KRAS^{G12D/wt}$ xenograft model. GP2d end of study tumors were graphed as % change in tumor volume compared to volume at treatment initiation. Each animal represented as a separate bar.
Figure 4F:
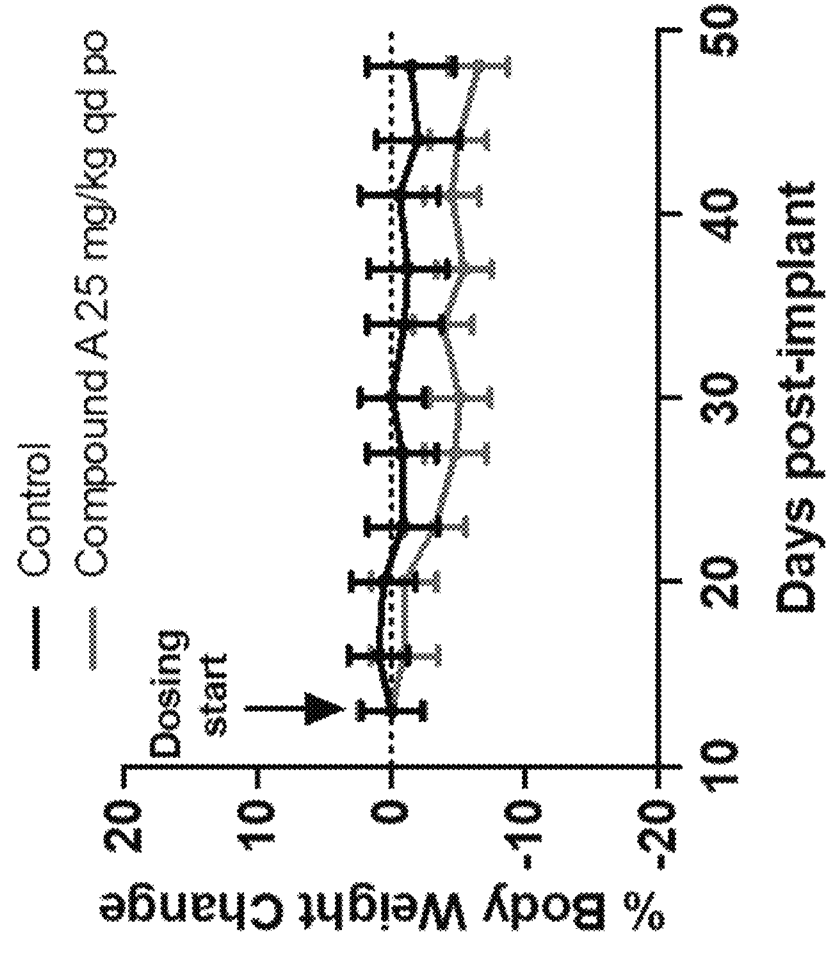
FIG. 4F shows % body weight change in animals treated with Compound A, a KRAS(ON) inhibitor disclosed herein, in the human colorectal GP2d $KRAS^{G12D/wt}$ xenograft model. GP2d cell-derived xenografts were measured twice weekly by caliper measurements. Body weight change graphed as percentage of animals starting body weight.

Results: Single-agent Compound A administered at 25 mg/kg po daily led to complete regression of all tumors (complete regression defined as >85% tumor regression from baseline) at the end of treatment (Day 38 after treatment started) in the HPAC CDX model with heterozygous $KRAS^{G12D}$ (FIG. 4A, FIG. 4B). The anti-tumor activity of Compound A was statistically significant compared with control group (*p<0.0001, ordinary One-way ANOVA with multiple comparisons via a post-hoc Tukey's test). Treatments were well tolerated by body weight measurements (FIG. 4C). In Gp2d CDX model, single-agent Compound A administered at 25 mg/kg po daily led to significant tumor growth inhibition in all tumors through the end of treatment (Day 35 after treatment started) (FIG. 4D, FIG. 4E). The anti-tumor activity of Compound A was statistically significant compared with control group (*p<0.0001, ordinary One-way ANOVA with multiple comparisons via a post-hoc Tukey's test). Treatments were well tolerated by body weight measurements (FIG. 4F).

Compound A Down-Regulates Immune Checkpoint Proteins in NCI-H358, SW900, and Capan-2 Cells In Vitro Methods: To assess the effect of Compound A on checkpoint molecule expression in vitro, NC—H358, SW900 or Capan-2 cells (5e4 cells/well) were seeded in a 96-well plate and after 24 hours treated with a five-fold dilution of Compound A in the presence of 250 pg/ml IFNγ. The plates were incubated for 48 hours at 37° C. and 5% $CO_2$. The cells were detached with 0.25% Trypsin, incubated for 15 minutes in PBS containing Fixable Blue Dead Cell Stain (Invitrogen) and subsequently incubated with FITC anti-human CD274 (PD-L1), PerCP/Cyanine5.5 anti-human CD155 (PVR) and Brilliant Violet 605 anti-human CD73 (Biolegend) for 30 minutes on ice. The cells were washed twice with staining buffer (PBS/2% FCS) before flow cytometric acquisition on a Cytek Aurora instrument. The analysis was performed using the SpectroFlo and FlowJo v10 software.

Figure 5A:
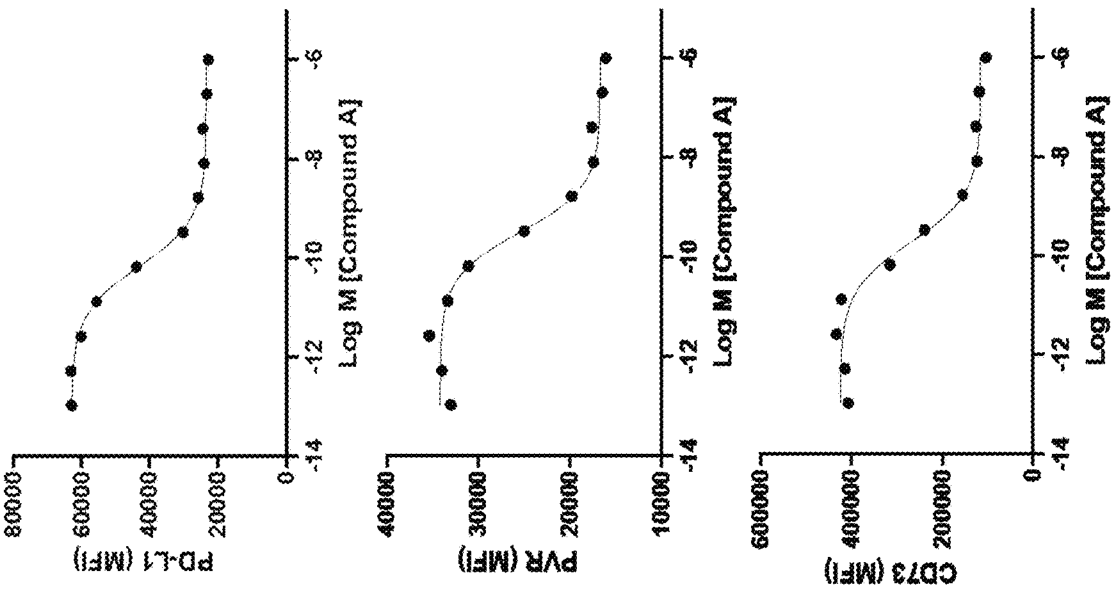
FIG. 5A demonstrates in vitro efficacy of Compound A, a KRAS(ON) inhibitor disclosed herein, in down-regulating immune checkpoint proteins in NCI-H358 $KRAS^{G12D/wt}$ Cells in Vitro.
Figure 5B:
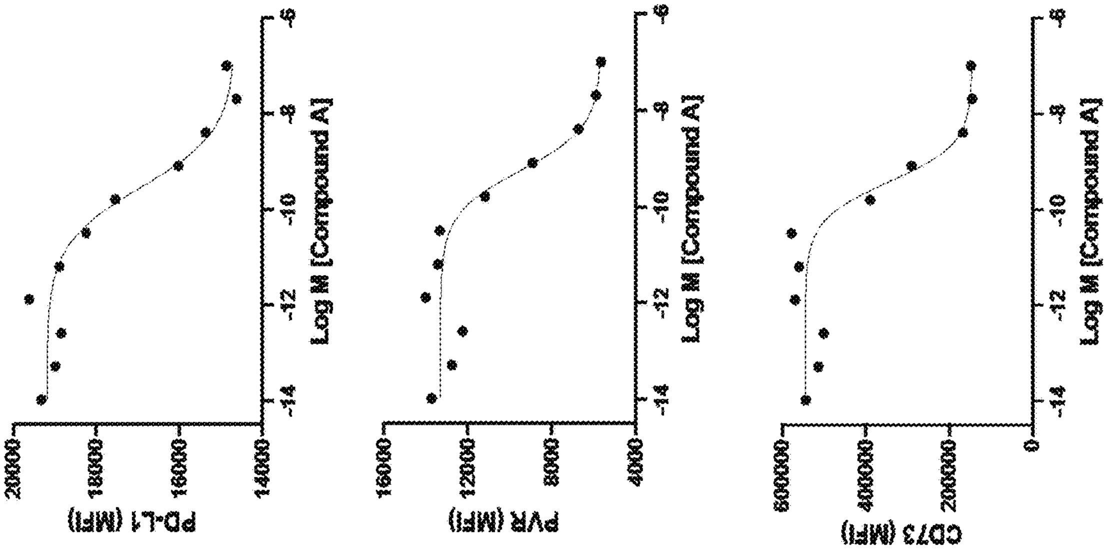
FIG. 5B demonstrates in vitro efficacy of Compound A, a KRAS(ON) inhibitor disclosed herein, in down-regulating immune checkpoint proteins in SW900 $KRAS^{G12C}$ Cells in Vitro.
Figure 5C:
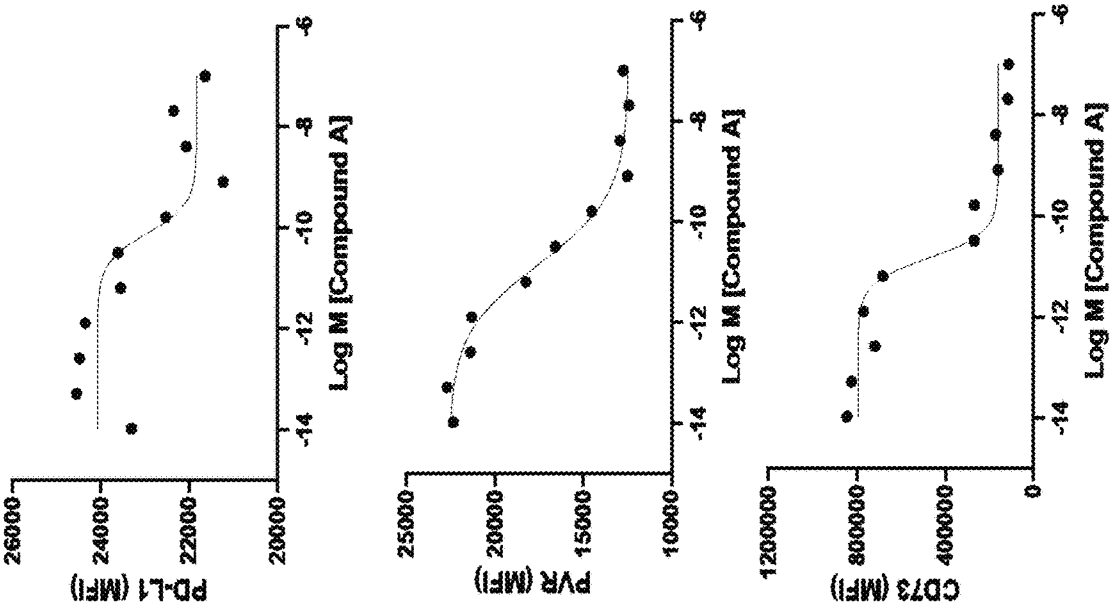
FIG. 5C demonstrates in vitro efficacy of Compound A, a KRAS(ON) inhibitor disclosed herein, in down-regulating immune checkpoint proteins in Capan-2 $KRAS^{G12C}$ Cells in Vitro.

Results: Compound A produced a concentration-dependent 2- to 5-fold decrease of PD-L1, PVR and CD73 on NCI-H358 (FIG. 5A), SW900 (FIG. 5B), or Capan-2 (FIG. 5C) cells in vitro. Down-regulation of these proteins is predicted to transform the immuno-suppressive tumor immune microenvironment in favor of anti-tumor immunity (Rothlin et al JITC 2020).

Figures 6A, 6B:
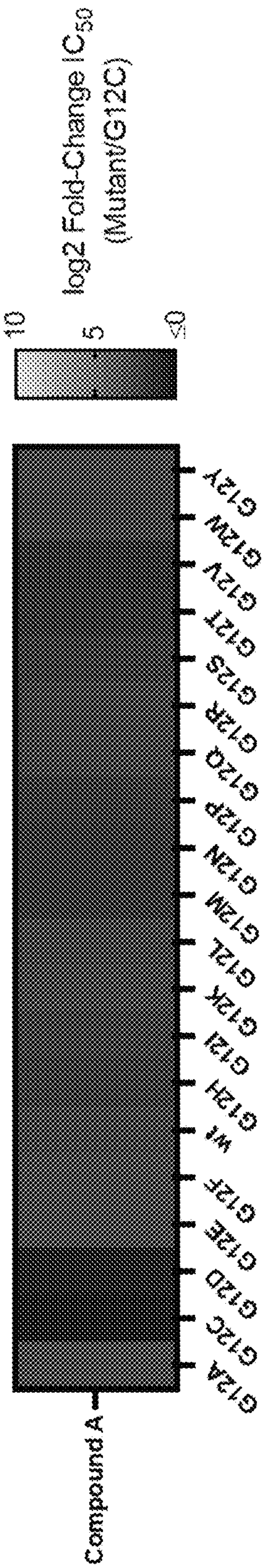
FIGS. 6A-6B demonstrate that Compound A, a KRAS (ON) inhibitor disclosed herein, is active against RAS oncogene switching mutations observed in $KRAS^{C12C}$ (OFF) resistance.

Compound A, a KRAS(ON) Inhibitor Disclosed Herein, is Active Against RAS Oncogene Switching Mutations FIG. 6A is a heatmap representing cellular RAS/RAF disruption assay results regarding various KRAS mutations in the presence of different RAS inhibitors (Compound A, a KRAS(ON) inhibitor disclosed herein, and $KRAS^{G12C}$ (OFF) inhibitors MRTX849 (adagrasib) and AMG 510 (sotorasib)).

Plasmids expressing nanoluciferase-tagged mutant KRAS4B and halo-tagged RAF1 (residues 51-149) were co-transfected into U2OS cells and incubated for 24 hours. Plasmids encoding the relevant mutation were generated by New England Biolabs Q5 site-directed mutagenesis. Transfected cells were reseeded at 25000 cells/well in 96-well plates in assay media (OptiMEM+4% FBS+100 nM HaloTag NanoBRET 618 Ligand) and incubated overnight. Promega Vivazine Nano-Glo substrate was added according to manufacturer's instructions. Compounds were added at concentrations ranging from 0 to 10 μM and incubated for 1 hour. The luminescence signal was measured at 460 nm and 618 nm and the BRET ratio was calculated as the 618 nm signal divided by the 460 nm signal. The BRET ratios were fit to a standard sigmoidal dose response function and the IC50 values were used to calculate the Log 2(Fold-Change) relative to $KRAS^{G12C}$. FIG. 6B shows the IC50 value associated with each colored bar of the heatmap.

Compound A Drives Regressions of a Syngeneic KRAS G12C Tumor Model In Vivo and Synergizes with Anti-PD-1

Methods: Effects of Compound A on tumor cell growth in vivo were evaluated in the murine syngeneic eCT26 $KRAS^{G12C/G12C}$ $ABCB1^{-/-}$ I20 model using female Balb/c (6-8 weeks old). Mice were implanted with tumor cells (5×106 cells/mouse) in RPMI medium without supplements subcutaneously in the upper right flank. Once tumors reached an average size of ~100 $mm^3$, mice were randomized to treatment groups to start the administration of test articles or vehicle. Compound A was administered by oral gavage once daily (po qd) at 25 mg/kg. InVivoMAb anti-mouse PD-1 (CD279) antibody (Clone RMP1-14 from BioXCell) and inVivoMAb rat IgG2a isotype control (Clone 2A3 from BioXCell) were administered at 10 mg/kg by intraperitoneal injection biweekly (ip biw). Body weight and tumor volume (using calipers) was measured twice weekly until study endpoints.

Figure 7A:
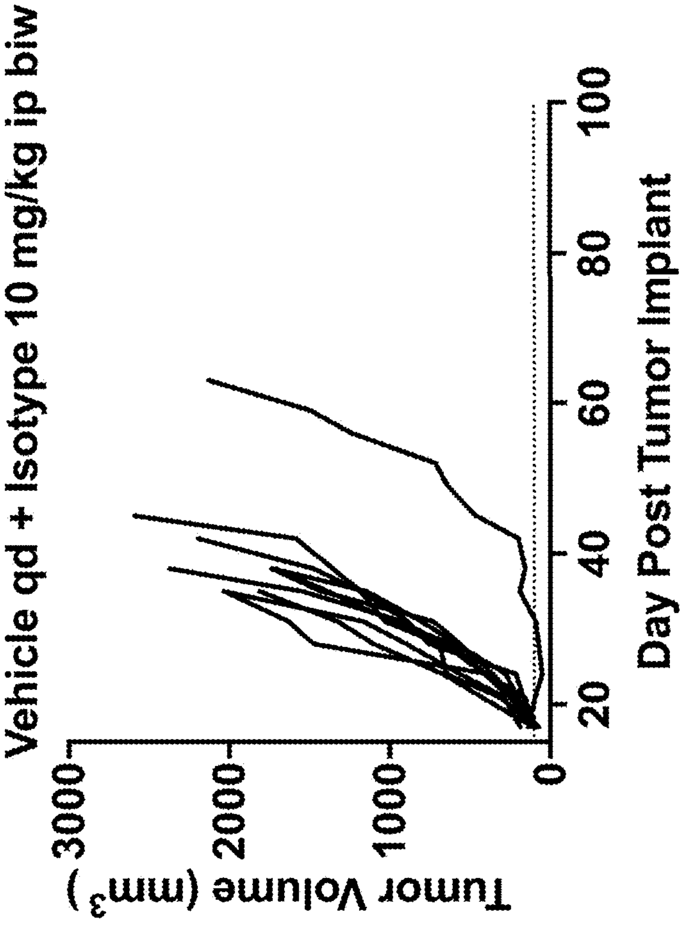
FIGS. 7A-7D demonstrate that Compound A, a KRAS (ON) inhibitor disclosed herein, drives regressions of a syngeneic $KRAS^{G12C}$ tumor model in vivo and synergizes with anti-PD-1. eCT26 (CRC, $KRAS^{G12C/G12C}$ $ABCB1^{-/-}$) I20 tumor growth in individual mice treated with: vehicle and Isotype (FIG. 7A); anti-PD-1 (FIG. 7B); Compound A (FIG. 7C); and Compound A+anti-PD-1 (FIG. 7D).
Figure 7B:
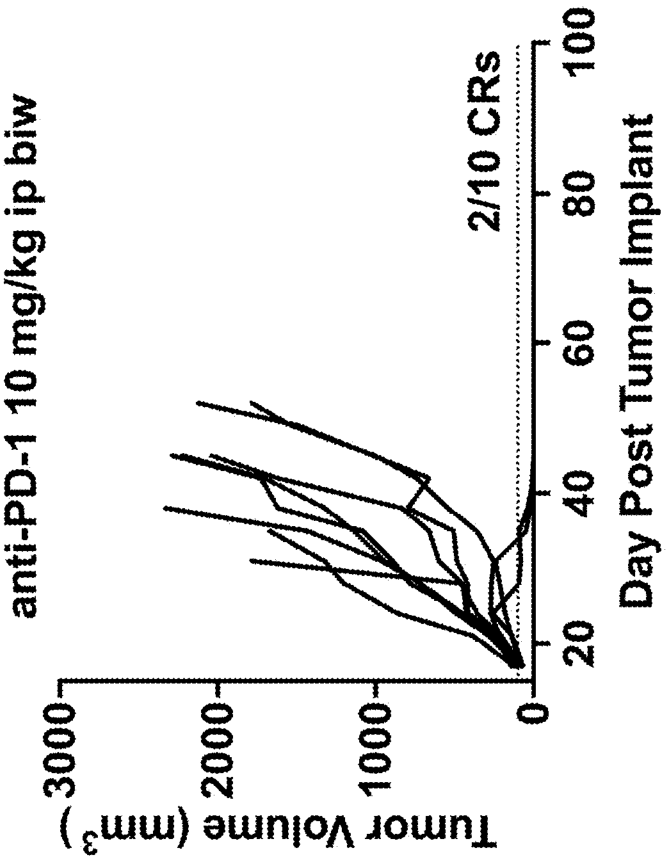
Figure 7C:
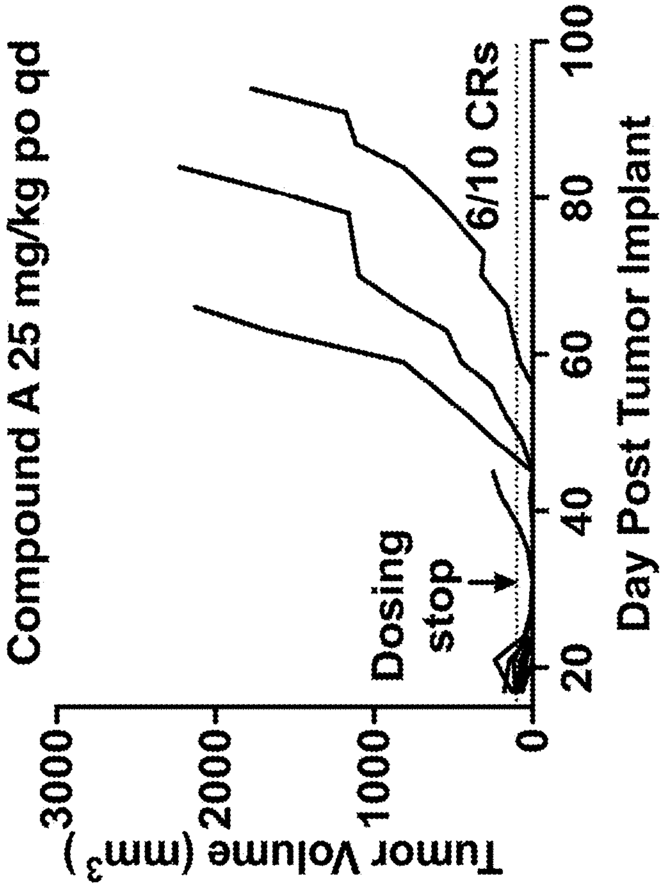
Figure 7D:
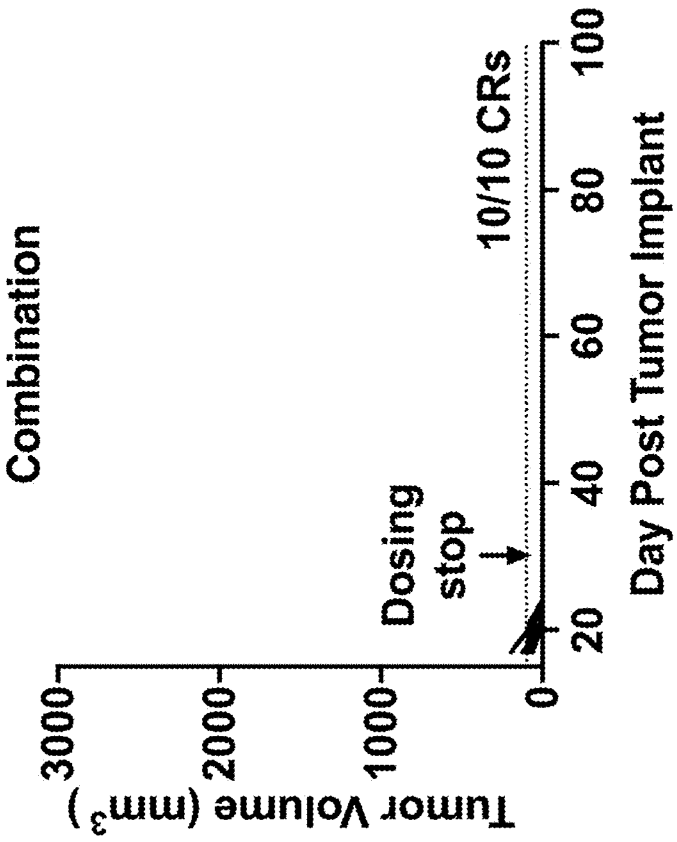
Figure 8:
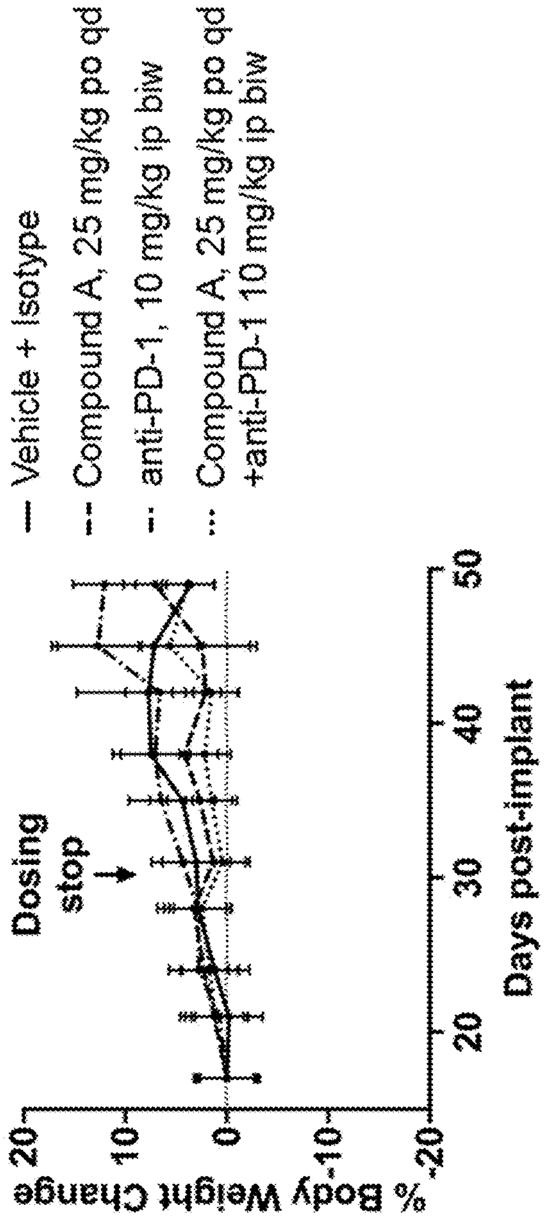
FIG. 8 demonstrates that Compound A, a KRAS(ON) inhibitor disclosed herein, in combination with anti-PD-1 is well tolerated in vivo in the eCT26 (CRC, $KRAS^{G12C/G12C}$ ABCB1$^{-/-}$ I20 model. Body weight change graphed as percentage of animals starting body weight.

Results: Single-agent Compound A and the combination with anti-PD-1 led to complete regression of all tumors at day 14 after treatment start (FIGS. 7C and 7D). The administration of Compound A was ceased at that time in the monotherapy and combination groups. Anti-PD-1 and isotype control were administered for 21 days. FIG. 7A shows the isotype control results. In the anti-PD-1 monotherapy group, 2/10 tumors achieved complete regressions (FIG. 7B). Tumor regrowth was observed in 4/10 mice treated with single agent Compound A and 0/10 mice treated with Compound A in combination with anti-PD-1 (FIGS. 7C and 7D). Treatments were well tolerated by body weight measurements (FIG. 8). One animal in the group treated with Compound A monotherapy was found dead at day 14 after dosing stop.

Compound A Modulates the Immune Tumor Microenvironment in Favor of Anti-Tumor Immunity In Vivo Methods: eCT26 $KRAS^{G12C/G12C}$ $ABCB1^{-/-}$ I20 tumors were removed 24 hours post the last dose after 4 days of treatment. Tumor tissue was minced, processed with the Miltenyi Biotec Mouse Tumor Dissociation Kit, and homogenized with the gentleMACS™ Dissociator. The cell suspension was incubated at 4-C for 30 minutes with Mouse BD Fc Block (Clone 2.4G2 from BD Pharmingen), 10 minutes with Blue Dead Cell Stain Kit (from Invitrogen) and 30 min in cell staining buffer. Antibodies used targeted CD45 (Clone 30-F11 from BD Biosciences), CD19 (Clone 1D3 from BD Biosciences), CD3ε (145-2C11 from Biolegend), CD8b (Clone H35-17.2 from BD Biosciences), CD4 (Clone GK1.5 from Biolegend), F4/80 (Clone BM8 from Biolegend), Ly-6G (Clone 1A8 from BD Biosciences), Ly-6C (Clone HK1.4 from Biolegend), I-A/I-E (Clone M5/114.15.2 from BD Biosciences) and CD206 (Clone C068C2 from Biolegend).

The eCT26 $KRAS^{G12C/G12C}$ $ABCB1^{-/-}$ cell line was engineered from the murine CT26 homozygous $KRAS^{G12D}$ tumor cell line (purchased from American Type Culture Collection). Both $KRAS^{G12D}$ alleles were replaced with $KRAS^{G12C}$ using CRISPR technology at Synthego. The following donor sequence GCCTGCTGAAAATGACT-GAGTATAAACTTGTGATGGTTG-GAGCTTGTGGCGTAGGCAAGAGCGCCTT GACGA-TACAGCTAATTCAGAATCA (SEQ ID NO: 1) and guide RNA sequence AUGGUUGGAGCUGAUGGCGU (SEQ ID NO: 2) were utilized. Additionally, the P-glycoprotein drug transporter was knocked out using the guide RNA sequences corresponding to TAAGTGGGAGCGC-CACTCCA (SEQ ID NO: 3) and CCAAACACCAGCAT-CAAGAG (SEQ ID NO: 4), targeting the Abcb1a and Abcb1b genes. The homozygous G12C mutation and the ABCB1 knock out was confirmed by Sanger sequencing in the clone 120. This clone was used for in vivo experiments.

Figure 9A:
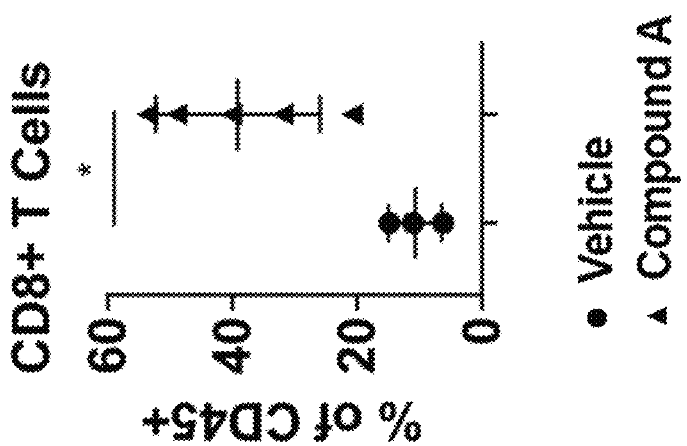
FIGS. 9A, 9B and 9C demonstrates that Compound A, a KRAS(ON) inhibitor disclosed herein, modulates the immune tumor microenvironment in favor of anti-tumor immunity in vivo. Flow cytometric immunophenotyping of eCT26 (CRC, KRAS$^{G12C/G12C}$ ABCB1$^{-/-)}$ $^{I}$20 tumors treated for 4 days with vehicle or Compound A 25 mg/kg qd. Symbols represent individual tumors. Average starting tumor volume was ~188 mm$^3$ for the vehicle group and ~586 mm$^3$ for Compound A treated group. Single-agent Compound A resulted in an increase of CD8+ T-cells (FIG. 9A). Compound A also led to a decrease in M2 macrophages (FIG. 9B) and monocytic MDSCs (FIG. 5C). Data are mean+/−SD; *$p<0.05$, **$p<0.01$ by two-sided Student's t-test.
Figure 9B:
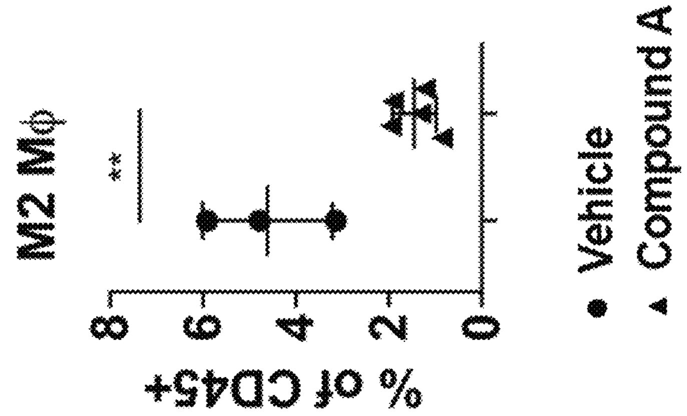
Figure 9C:
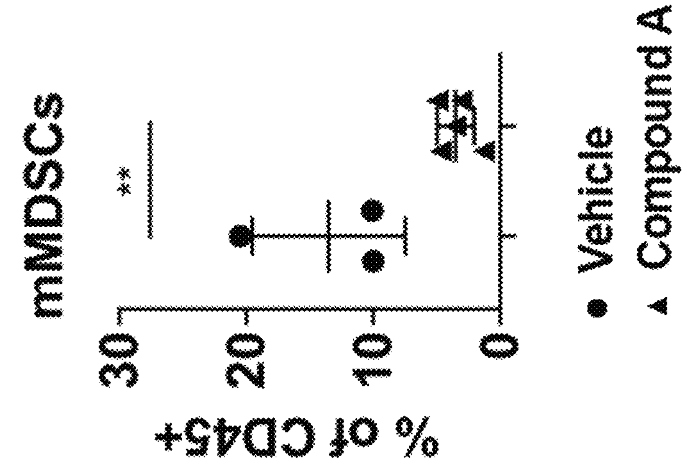

Results: Single-agent Compound A resulted in an increase of CD8+ T-cells (FIG. 9A). Compound A also led to a decrease in M2 macrophages (FIG. 9B) and monocytic MDSCs (FIG. 9C). *p<0.05, **p<0.01 by two-tailed Student's t-test.

Compound A Exhibits Significant Anti-Tumor Activity in $KRAS^{G12X}$ Tumor Models In Vivo Methods: Effects of Compound A treatment on the growth of mutant KRAS-driven xenograft models of human NSCLC or PDAC in vivo was evaluated in a panel of representative CDX and PDX models in female immune-deficient mice. Mice were implanted with tumor cells or fragments subcutaneously in the flank. Once tumors reached an average size of ~150-200 $mm^3$, mice were randomized to treatment groups to start the administration of test articles or vehicle. Compound A was orally administered at 25 mg/kg once daily. Body weight and tumor volume (using calipers) was measured twice weekly until study endpoints. Responses were assessed as % change from baseline tumor volume after 21-42 days of treatment; study duration was based on controls reaching maximal tumor burden as an endpoint.

Figure 10A:
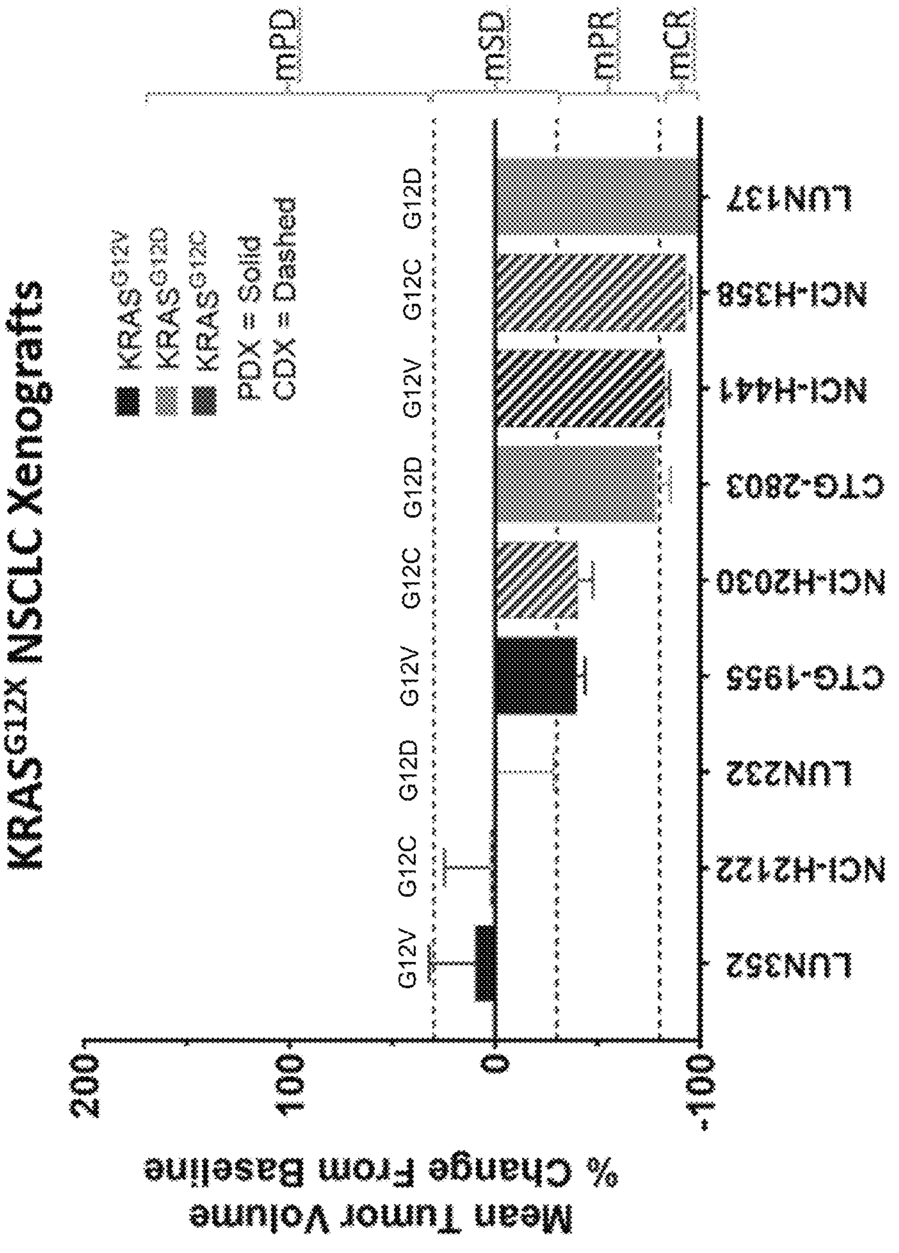
FIGS. 10A and 10B demonstrate that Compound A, a KRAS(ON) inhibitor disclosed herein, exhibits significant anti-tumor activity in KRAS$^{G12X}$ tumor models of human NSCLC (FIG. 10A) or PDAC (FIG. 10B) in vivo.
Figure 10B:
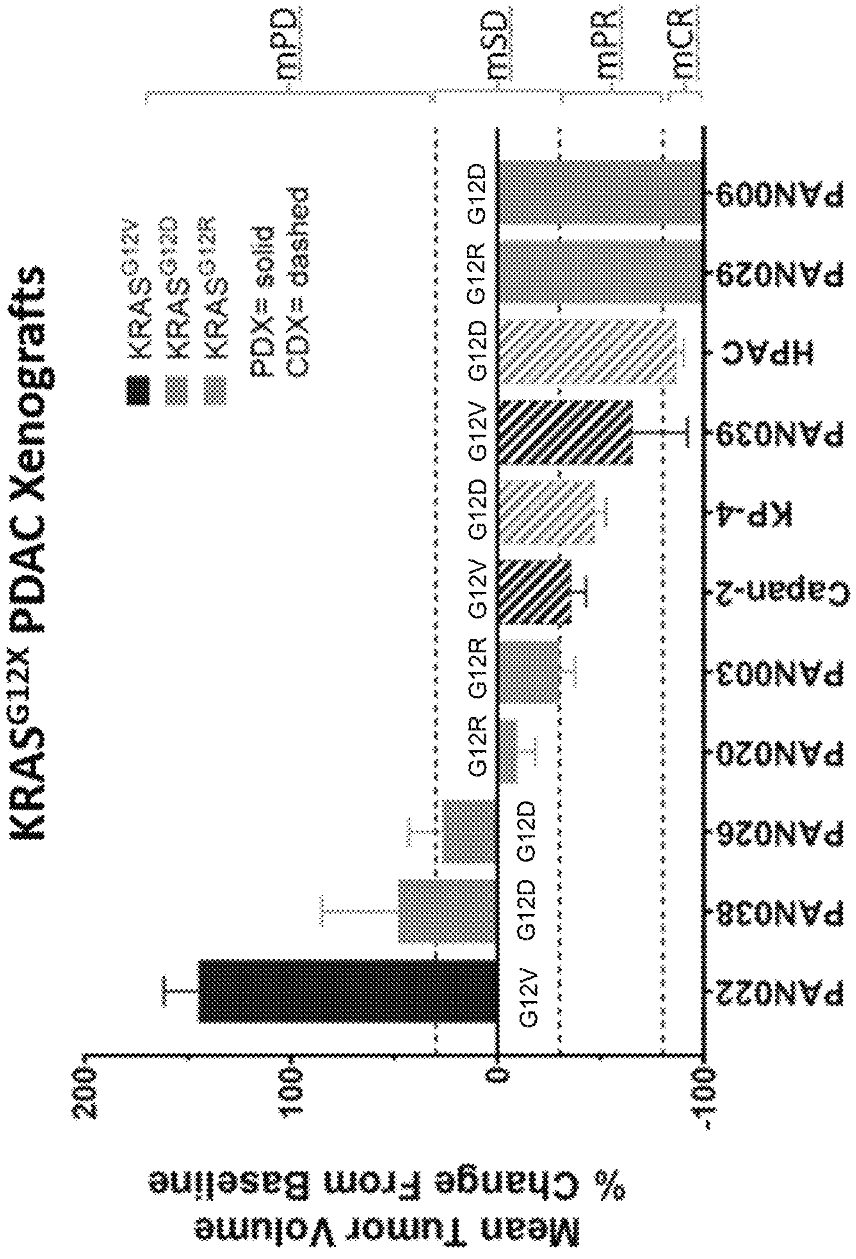

Results: Single-agent Compound A administered at 25 mg/kg po daily led to tumor regressions in the majority of KRAS mutant models examined here (FIGS. 10A and 10B). A small minority of models did not exhibit tumor regressions but showed significant tumor growth inhibition as compared to controls (not shown).

Compound A Significantly Extends Time to Tumor Doubling Across Xenograft Models

Methods: The impact of Compound A treatment on the growth of xenograft tumor models with RAS pathway aberrations (either mutations in K, H, or NRA S or upstream or downstream of RAS) in vivo was evaluated in a panel of representative CDX and PDX models in female immune-deficient mice. Mice were implanted with tumor cells or fragments subcutaneously in the flank. Once tumors reached an average size of ~150-200 $mm^3$, mice were randomized to treatment groups to start the administration of test articles or vehicle. Compound A was orally administered at 25 mg/kg once daily. Body weight and tumor volume (using calipers) was measured twice weekly until study endpoints. Responses were assessed via a survival analysis of time to progression with progression defined % change from baseline tumor volume within 28 days of treatment.

Figure 11:
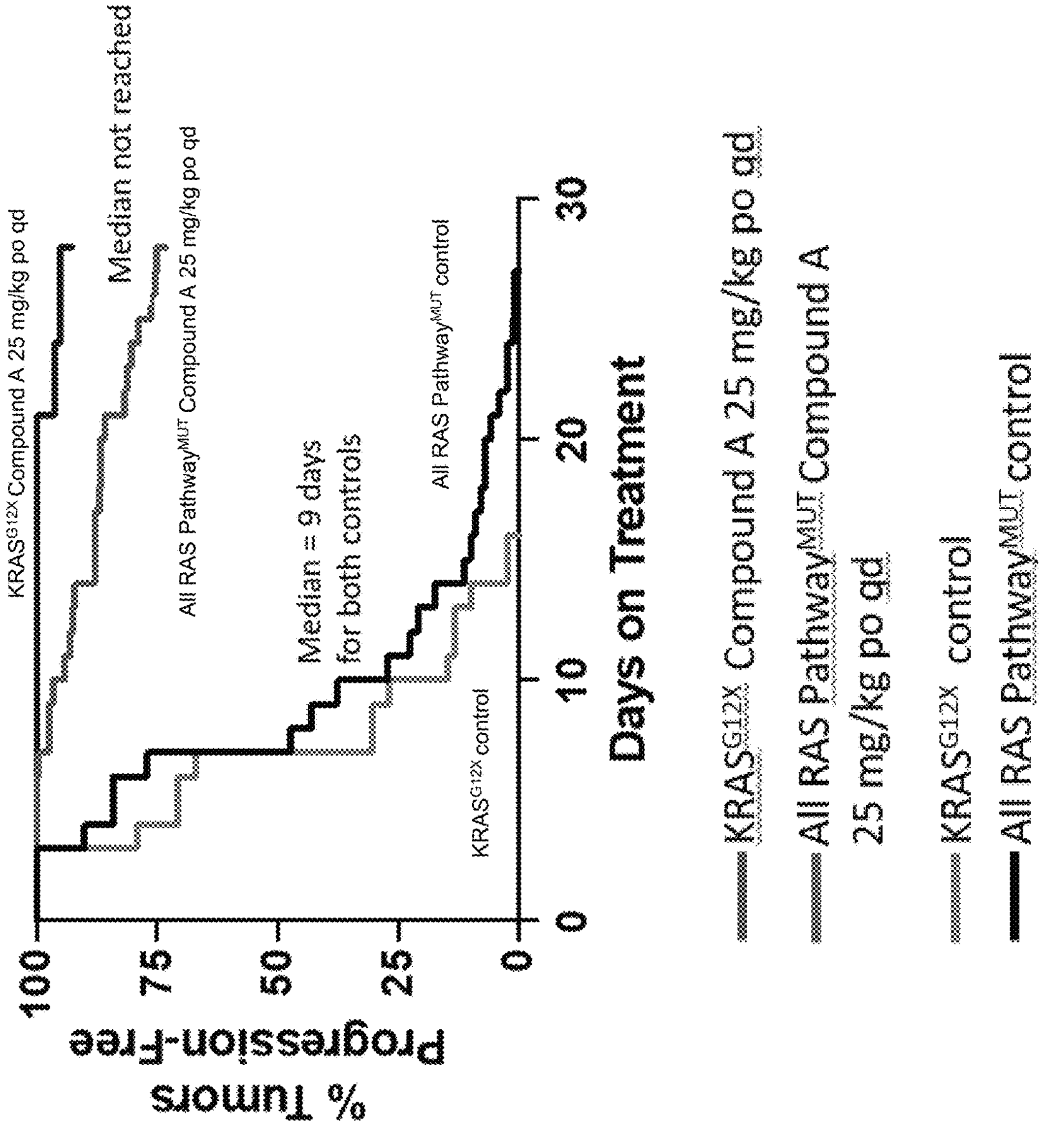
FIG. 11 demonstrates that Compound A, a KRAS(ON) inhibitor disclosed herein, extends time to tumor doubling across xenograft models. $p<0.0001$ by Log-rank test (control vs treated). KRAS$^{G12X}$: n=154; other RAS and RAS pathway mutations: n=86; All RAS Pathway$^{MUT}$ includes both groups: n=240. Progression defined as tumor doubling from baseline over 28 days.

Results: Single-agent Compound A administered at 25 mg/kg po daily led to a significant delay in time to tumor doubling in all the CDX and PDX xenograft models tested as compared to controls (p<0.0001 assessed via a Log-Rank test) with the population not reaching a median time in the 28-day interval of this study (FIG. 11). Interestingly, when time to tumor doubling was examined in the subset of models with a specific $KRAS^{G12X}$ mutation, a further delay in time to tumor doubling models was observed in this subset, which was significantly differentiated from the overall model population (p<0.005 via a Log-Rank test). These data indicate that tumors with $KRAS^{G12X}$ mutation may be more susceptible to Compound A treatment as compared to tumors with other RAS pathway aberrations. Thus, these preclinical findings implicate $KRAS^{G12X}$ mutation as an enrichment biomarker for patient enrollment in the context of RMC-Compound treatment in the clinical setting.

Compounds A, B and D Drive Regressions of $KRAS^{G12V}$ Tumors In Vivo

Methods: The effects of compounds A, B and D on tumor cell growth in vivo were evaluated in the NCI-H441 $KRAS^{G12V/wt}$ xenograft model of human non-small cell lung carcinoma using female BALB/c nude mice (6-8 weeks old). Mice were implanted with tumor cells in PBS ($3\times10^6$ cells/mouse) subcutaneously in the flank. Once tumors reached an average size of ~200 $mm^3$, mice were randomized to treatment groups to start the administration of test articles or vehicle. Compounds were administered orally once daily. Body weight and tumor volume (using calipers) was measured twice weekly until study endpoints.

Figure 12A:
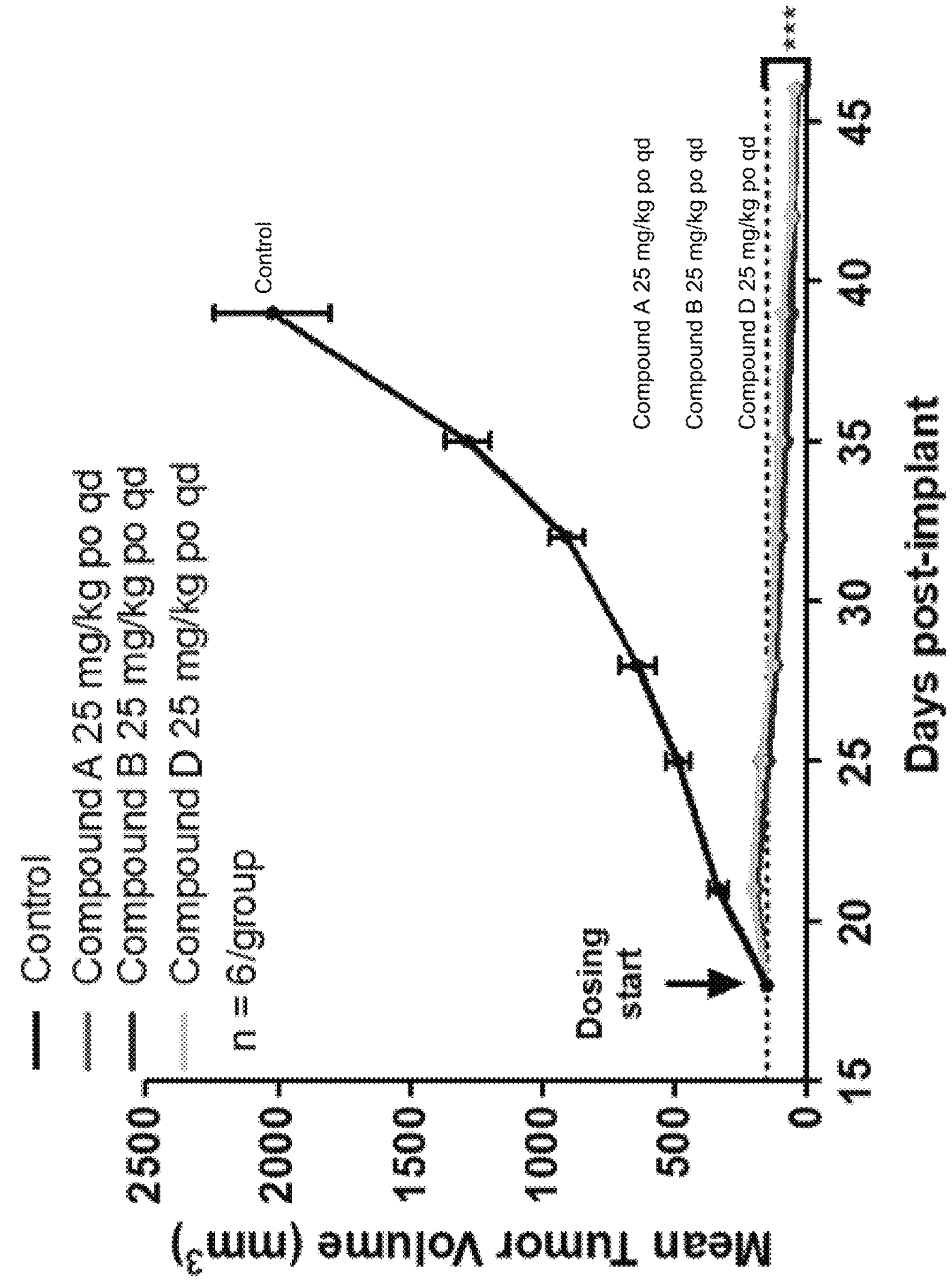
FIGS. 12A, 12B and 12C demonstrate that Compounds A, B and D, KRAS(ON) inhibitors disclosed herein, drive regressions of KRAS$^{G12V}$ tumors in vivo, as measured by mean tumor volume (FIG. 12A), % body weight change (FIG. 12B), and % change in tumor volume (FIG. 12C). n=6/group. ***$p<0.001$. All treatments well tolerated as assessed by body weight.
Figure 12B:
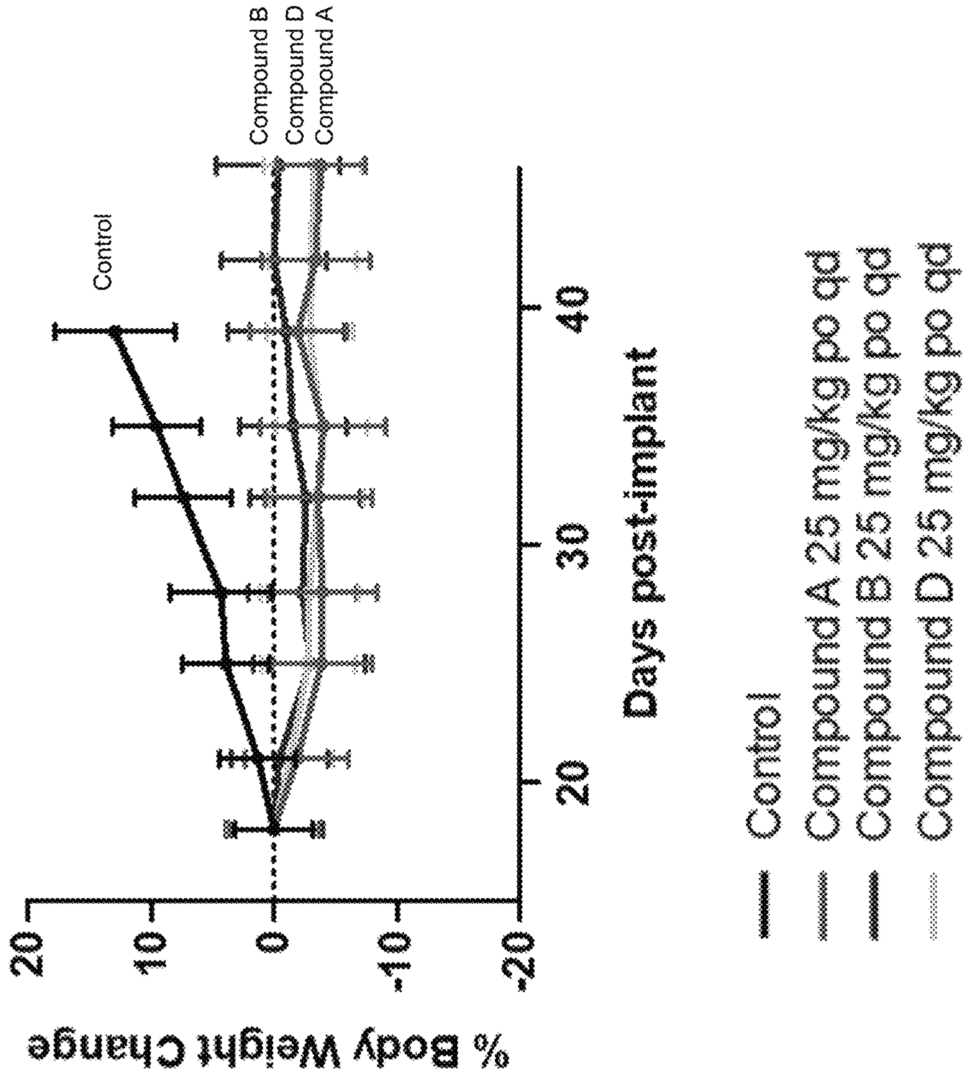
Figure 12C:
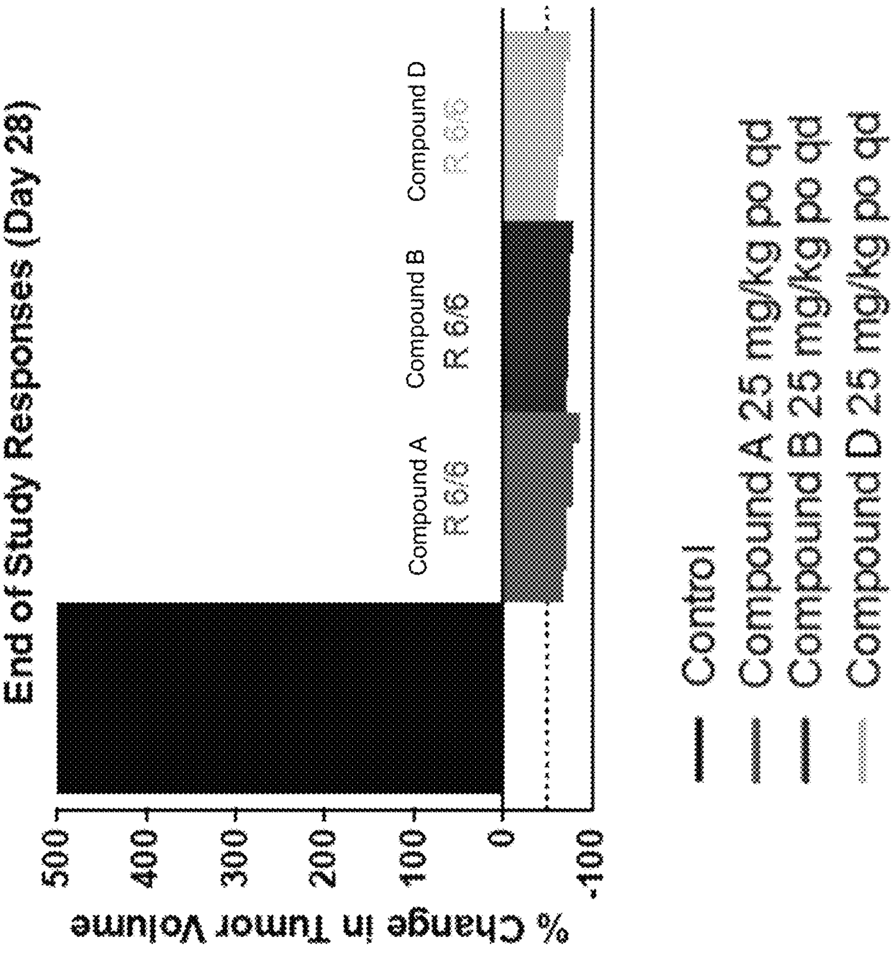

Results: Daily oral administration of each agent at 25 mg/kg led to the regression of all tumors in each treatment group at the end of treatment (Day 28 after treatment started) in this model (FIG. 12A, FIG. 12B, FIG. 12C). The anti-tumor activity of each agent was statistically significant compared with control group (***p<0.001, ordinary One-way ANOVA with multiple comparisons via a post-hoc Tukey's test).

Compounds A, B and D Deeply and Durably Inhibit RAS Pathway Signaling In Vivo

Methods: The NCI-H441 $KRAS^{G12V/wt}$ xenograft model of human non-small cell lung carcinoma was used for a single-dose PKPD study. Compounds A, B and D were administered orally at 25 mg/kg. The treatment groups with sample collections at various time points were summarized in Table 5 below. Tumor samples were collected to assess RAS/ERK signaling pathway modulation by measuring the mRNA level of human DUSP6 in qPCR assay.

TABLE 5

Summary of treatment groups, doses, and time points for single-dose PD study using NCI-H441 tumors

| Compound/group | Dose/Regimen | PD, n = 3/time point |
|---|---|---|
| Vehicle control | 10 ml/kg po | 1 h, 24 h |
| Compound A | 25 mg/kg po | 1 h, 8 h, 24 h, 48 h |
| Compound B | 25 mg/kg po | 1 h, 8 h, 24 h, 48 h |
| Compound D | 25 mg/kg po | 1 h, 8 h, 24 h, 48 h |

Figure 13A:
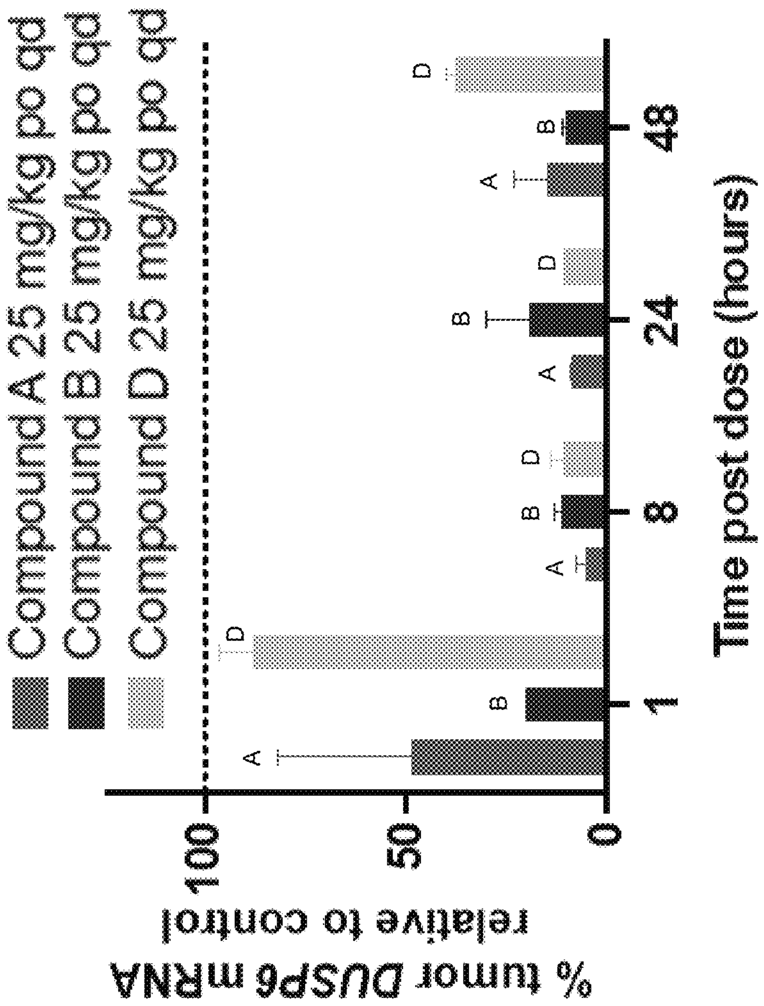
FIGS. 13A and 13B show PD (FIG. 13A) and PK (FIG. 13B) results demonstrating that Compounds A, B and D, KRAS(ON) inhibitors disclosed herein, deeply and durably inhibit RAS pathway signaling in vivo. Single dose experiment; all doses well tolerated.
Figure 13B:
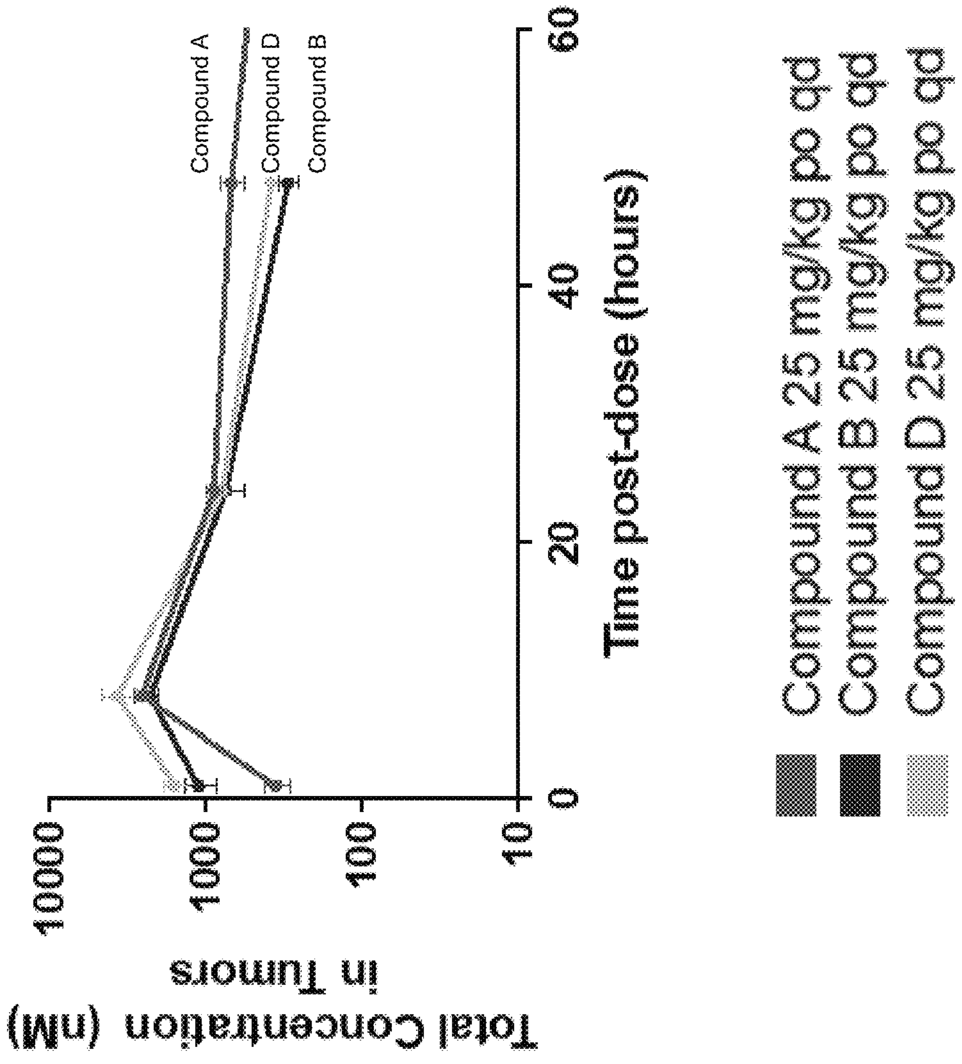

Results: All treatments led to inhibition of DUSP6 mRNA levels in tumors at all time points tested, indicating strong MAPK pathway modulation (FIG. 13A). And the inhibitory effects of each compound on DUSP6 mRNA levels are durable even 48 hours after drug administration, consistent with the durable pharmacokinetic profile observed in the blood (FIG. 13B).

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features set forth herein.

All publications, patents and patent applications are herein incorporated by reference in their entirety to the same extent as if each individual publication, patent or patent application was specifically and individually indicated to be incorporated by reference in its entirety.

The invention claimed is:

1. A compound having the structure of:

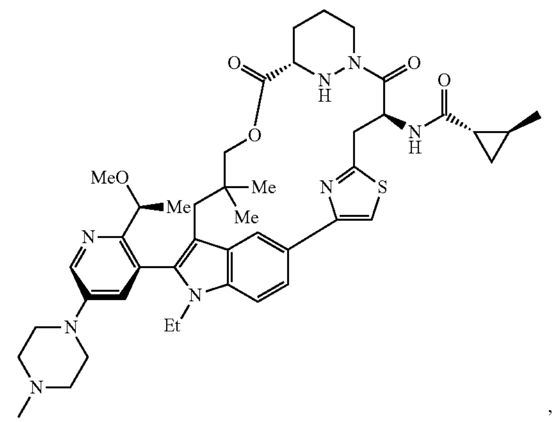

, or a pharmaceutically acceptable salt thereof, wherein at least one hydrogen atom of the compound is replaced by deuterium.

2. A pharmaceutical composition comprising a compound of claim 1, or a pharmaceutically acceptable salt thereof, and a pharmaceutically acceptable excipient or carrier.

* * * * *